United States Patent
Anantanarayan et al.

(10) Patent No.: US 6,423,713 B1
(45) Date of Patent: Jul. 23, 2002

(54) SUBSTITUTED PYRAZOLES AS P38 KINASE INHIBITORS

(75) Inventors: Ashok Anantanarayan, Hainesville; Michael Clare, Skokie; Paul W. Collins, Deerfield; Joyce Zuowu Crich, Glenview, all of IL (US); Rajesh Devraj, Ballwin; Daniel L. Flynn, Clarkson Valley, both of MO (US); Lifeng Geng, Skokie, IL (US); Matthew J. Graneto; Cathleen E. Hanau, both of Chesterfield, MO (US); Gunnar J. Hanson, Skokie, IL (US); Susan J. Hartmann, Kirkwood; Michael Hepperle, St. Charles, both of MO (US); He Huang, Chicago, IL (US); Francis J. Koszyk, Prospect Heights, IL (US); Shuyuan Liao, Glen Ellyn, IL (US); Suzanne Metz, Chesterfield, MO (US); Richard A. Partis, Evanston, IL (US); Thao D. Perry, Chesterfield, MO (US); Shashidhar N. Rao, St. Louis, MO (US); Shaun Raj Selness, Chesterfield, MO (US); Michael S. South, St. Louis, MO (US); Michael A. Stealey, Libertyville, IL (US); John Jeffrey Talley, St. Louis; Michael L. Vazquez, Ballwin, both of MO (US); Richard M. Weier, Lake Bluff, IL (US); Xiangdong Xi, Evanston, IL (US); Ish K. Khanna, Libertyville, IL (US); Yi Yu, Skokie, IL (US)

(73) Assignee: G. D. Searle & Company, Skokie, IL (US)

(*) Notice: Subject to any disclaimer, the term of this patent is extended or adjusted under 35 U.S.C. 154(b) by 0 days.

(21) Appl. No.: 09/918,481

(22) Filed: Jul. 31, 2001

Related U.S. Application Data

(60) Division of application No. 09/196,623, filed on Nov. 20, 1998, which is a continuation-in-part of application No. 09/083,670, filed on May 22, 1998, now abandoned.
(60) Provisional application No. 60/047,570, filed on May 22, 1997.

(51) Int. Cl.[7] .................. A61K 31/496; A61K 31/4523; C07D 401/04; C07D 401/14; C07D 413/02
(52) U.S. Cl. .............................. 514/235.8; 514/253.01; 514/254.05; 514/319; 514/341; 544/124; 544/364; 546/206; 546/256; 546/275.4
(58) Field of Search ........................ 514/253.01, 254.05, 514/319, 341, 235.8; 544/124, 364; 546/206, 256, 275.4

(56) References Cited

U.S. PATENT DOCUMENTS

| | | | |
|---|---|---|---|
| 3,254,093 A | 5/1966 | Huisgen et al. | 260/295 |
| 3,984,431 A | 10/1976 | Guérémy et al. | 260/310 |
| 4,000,281 A | 12/1976 | Beiler et al. | 424/263 |
| 5,134,142 A | 7/1992 | Matsuo et al. | 514/255 |
| 5,486,534 A | 1/1996 | Lee et al. | |
| 5,559,137 A | 9/1996 | Adams et al. | 514/341 |
| 5,589,439 A | 12/1996 | Goto et al. | 504/261 |

FOREIGN PATENT DOCUMENTS

| | | |
|---|---|---|
| EP | 0 115 640 A2 | 12/1983 |
| EP | 0 418 845 A | 3/1991 |
| EP | 0 515 041 A2 | 11/1992 |
| EP | 0 531 901 A2 | 3/1993 |
| JP | 4-145081 | 5/1992 |
| JP | 5-17470 | 1/1993 |
| JP | 5-345772 | 12/1993 |
| JP | 8-183787 | 7/1996 |
| WO | WO 83/00330 | 2/1983 |
| WO | WO 92/19615 | 11/1992 |
| WO | WO 95/06036 | 3/1995 |
| WO | WO 95/22545 A1 | 8/1995 |
| WO | WO 96/03385 A1 | 2/1996 |
| WO | WO 96/21452 | 7/1996 |
| WO | WO 97/01551 | 1/1997 |

OTHER PUBLICATIONS

Bauer, V.J. et al., "4–3(5)–Pyrazolyl Pyridinium Salts. A New Class Of Hypoglycemic Agents", J. Med. Chem., vol. 11; pp. 981–4, (Sep. 1968).

Cativeila, C. et al., "On the Synthesis Of 3(5)–(Carbomethoxy)–4–hetarylpyrazoles", J. Heterocycl. Chem., vol. 25; pp. 851–855 (May–Jun. 1988).

Fischer, U. et al., "1,3–Dipolar Additions To 7–Methylthieno [2,3–c]pyridine 1,1–dioxide", Helv. Chim. Acta ; vol. 63(6), No. 180, pp. 1719–27, (1980).

Popova, A. N. et al., "Synthesis Of 4–(Pyrazol–4–yl)–Substituted Salts Of Pyrylium And Pyridines", Chemical Abstracts, vol. 098, No. 1, Jan. 3, 1983, Abstract No. 004498.

(List continued on next page.)

Primary Examiner—T. A. Solola
(74) Attorney, Agent, or Firm—Harness, Dickey & Pierce, P.L.C.

(57) ABSTRACT

A class of pyrazole derivatives is described for use in treating p38 kinase mediated disorders. Compounds of particular interest are defined by Formula IA (IA)

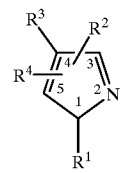

wherein $R^1$, $R^2$, $R^3$ and $R^4$ are as described in the specification.

88 Claims, No Drawings

OTHER PUBLICATIONS

Laszlo, S.E. et al., "Pyrroles And Other Heterocycles As Inhibitors Of p38 Kinase", *Bioorganic & Medicinal Chemistry Letters 8*, pp. 2689–2694, 1998.

Dannhardt G. et al., "ω–Aminopropyl–pyrazole durch Ringtransformation von Enaminonen der Pyrrolidinreihe", Arch. Pharm., vol. 321, No. 1, pp. 17–19, 1988.

Moerck R.E. et al., "Pyrazole Addition To $\Delta^1$–Azirines, Structure of Purported 2:1 Adducts of $\Delta^1$–Azirines With sym–Tetrazines", J.Chem. Soc., Chem. Commun., No. 19, pp. 782–783, 1974.

Zheng–Nian Huang, "Synthesis and Biological Actitivies of 1–(substituted pyrazol–4–yl)–1,2,4–triazoles", *Chemical Abstracts*, vol. 124, No. 23, Abstract No. 317062d, 1996.

Chemical Abstracts, 13$^{th}$ Chemical Substance Index 1992–1996, Book 51, pp. 546–555.

Zhengming, Li et al., "Syntheses of Di–heterocyclic Compounds; Pyrazolylimidazoles And Isoxazolylimadazoles", *Heteroatom. Chem.*, vol. 9, No. 3, pp. 317–320, 1998.

Zheng–Nian Huang, "The Reaction Of α–OXO–α–Triazolyketene Dithioacetal With Amines, Hydrazine And Cuanidine", Chinese Chemical Letters, vol. 5, No. 1, pp. 31–34, 1994.

SUBSTITUTED PYRAZOLES AS P38 KINASE INHIBITORS

CROSS-REFERENCE TO RELATED APPLICATION

This application is a divisional application of U.S. application Ser. No. 09/196,623, filed Nov. 20, 1998, now allowed which is a continuation-in-part application of U.S. application Ser. No. 09/083,670, filed May 22, 1998, abandoned which claims priority from U.S. Provisional Patent Application Ser. No. 60/047,570 filed May 22, 1997.

FIELD OF THE INVENTION

This invention relates to a novel group of pyrazole compounds, compositions and methods for treating p38 kinase mediated disorders.

BACKGROUND OF THE INVENTION

Mitogen-activated protein kinases (MAP) is a family of proline-directed serine/threonine kinases that activate their substrates by dual phosphorylation. The kinases are activated by a variety of signals including nutritional and osmotic stress, UV light, growth factors, endotoxin and inflammatory cytokines. The p38 MAP kinase group is a MAP family of various isoforms, including p38α, p38β and p38γ, and is responsible for phosphorylating and activating transcription factors (e.g. ATF2, CHOP and MEF2C) as well as other kinases (e.g. MAPKAP-2 and MAPKAP-3). The p38 isoforms are activated by bacterial lipopolysaccharide, physical and chemical stress and by pro-inflammatory cytokines, including tumor necrosis factor (TNF-α) and interleukin-1 (IL-1). The products of the p38 phosphorylation mediate the production of inflammatory cytokines, including TNF and IL-1, and cyclooxygenase-2.

TNF-α is a cytokine produced primarily by activated monocytes and macrophages. Excessive or unregulated TNF production has been implicated in mediating a number of diseases. Recent studies indicate that TNF has a causative role in the pathogenesis of rheumatoid arthritis. Additional studies demonstrate that inhibition of TNF has broad application in the treatment of inflammation, inflammatory bowel disease, multiple sclerosis and asthma.

TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpesvirus-6 (HHV-6), human herpesvirus-7 (HHV-7), human herpesvirus-8 (HHV-8), pseudorabies and rhinotracheitis, among others.

IL-8 is another pro-inflammatory cytokine, which is produced by mononuclear cells, fibroblasts, endothelial cells, and keratinocytes, and is associated with conditions including inflammation.

IL-1 is produced by activated monocytes and macrophages and is involved in the inflammatory response. IL-1 plays a role in many pathophysiological responses including rheumatoid arthritis, fever and reduction of bone resorption.

TNF, IL-1 and IL-8 affect a wide variety of cells and tissues and are important inflammatory mediators of a wide variety of disease states and conditions. The inhibition of these cytokines by inhibition of the p38 kinase is of benefit in controlling, reducing and alleviating many of these disease states.

Various pyrazoles have previously been described. U.S. Pat. No. 4,000,281, to Beiler and Binon, describes 4,5-aryl/heteroaryl substituted pyrazoles with antiviral activity against both RNA and DNA viruses such as myxoviruses, adenoviruses, rhinoviruses, and various viruses of the herpes group. WO 92/19615, published Nov. 12, 1992, describes pyrazoles as novel fungicides. U. S. Pat. No. 3,984,431, to Cueremy and Renault, describes derivatives of pyrazole-5-acetic acid as having anti-inflammatory activity. Specifically, [1-isobutyl-3,4-diphenyl-1H-pyrazol-5-yl] acetic acid is described. U. S. Pat. No. 3,245,093 to Hinsgen et al, describes a process for preparing pyrazoles. WO 83/00330, published Feb. 3, 1983, describes a new process for the preparation of diphenyl-3,4-methyl-5-pyrazole derivatives. WO 95/06036, published Mar. 2, 1995, describes a process for preparing pyrazole derivatives. U.S. Pat. No. 5,589,439, to T. Goto, et al., describes tetrazole derivatives and their use as herbicides. EP 515,041 describes pyrimidyl substituted pyrazole derivatives as novel agricultural fungicides. Japanese Patent 4,145,081 describes pyrazolecarboxylic acid derivatives as herbicides. Japanese Patent 5,345,772 describes novel pyrazole derivatives as inhibiting acetylcholinesterase.

Pyrazoles have been described for use in the treatment of inflammation. Japanese Patent 5,017,470 describes synthesis of pyrazole derivatives as anti-inflammatory, anti-rheumatic, anti-bacterial and anti-viral drugs. EP 115640, published Dec. 30, 1983, describes 4-imidazolyl-pyrazole derivatives as inhibitors of thromboxane synthesis. 3-(4-Isopropyl-1-methylcyclohex-1-yl)-4-(imidazol-1-yl)-1H-pyrazole is specifically described. WO 97/01551, published Jan. 16, 1997, describes pyrazole compounds as adenosine antagonists. 4-(3-Oxo-2,3-dihydropyridazin-6-yl)-3-phenylpyrazole is specifically described. U.S. Pat. No. 5,134,142, to Matsuo et al. describes 1,5-diaryl pyrazoles as having anti-inflammatory activity.

U.S. Pat. No. 5,559,137 to Adams et al, describes novel pyrazoles (1,3,4,-substituted) as inhibitors of cytokines used in the treatment of cytokine diseases. Specifically, 3-(4-fluorophenyl)-1-(4-methylsulfinylphenyl)-4-(4-pyridyl)-5H-pyrazole is described. WO 96/03385, published Feb. 8, 1996, describes 3,4-substituted pyrazoles, as having anti-inflammatory activity. Specifically, 3-methylsulfonylphenyl-4-aryl-pyrazoles and 3-aminosulfonylphenyl-4-aryl-pyrazoles are described.

Laszlo et al., *Bioorg. Med. Chem. Letters*, 8 (1998) 2689-2694, describes certain furans, pyrroles and pyrazolones, particularly 3-pyridyl-2,5-diaryl-pyrroles, as inhibitors of p38 kinase.

The invention's pyrazolyl compounds are found to show usefulness as p38 kinase inhibitors.

DESCRIPTION OF THE INVENTION

A class of substituted pyrazolyl compounds useful in treating p38 mediated disorders is defined by Formula IA:

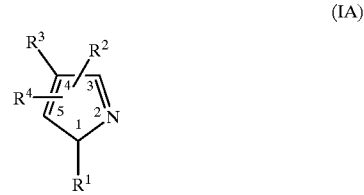

wherein $R^1$ is selected from hydrido, hydroxy, alkyl, cycloalkyl, alkenyl, cycloalkenyl, alkynyl, aryl, heterocyclyl, cycloalkylalkylene, cycloalkenylalkylene, heterocyclylalkylene, haloalkyl, haloalkenyl, haloalkynyl, hydroxyalkyl, hydroxyalkenyl, hydroxyalkynyl, aralkyl, aralkenyl, aralkynyl, arylheterocyclyl, carboxy, carboxyalkyl, alkoxyalkyl, alkenoxyalkyl, alkynoxyalkyl, aryloxyalkyl, alkoxyaryl, heterocyclyloxyalkyl, alkoxyalkoxy, mercaptoalkyl, alkylthioalkylene, alkenylthioalkylene, alkylthioalkenylene, amino, aminoalkyl, alkylamino, alkenylamino, alkynylamino, arylamino, heterocyclylamino, alkylsulfinyl, alkenylsulfinyl, alkynylsulfinyl, arylsulfinyl, heterocyclylsulfinyl, alkylsulfonyl, alkenylsulfonyl, alkynylsulfonyl, arylsulfonyl, heterocyclylsulfonyl, alkylaminoalkylene, alkylsulfonylalkylene, acyl, acyloxycarbonyl, alkoxycarbonylalkylene, aryloxycarbonylalkylene, heterocyclyloxycarbonylalkylene, alkoxycarbonylarylene, aryloxycarbonylarylene, heterocyclyloxycarbonylarylene, alkylcarbonylalkylene, arylcarbonylalkylene, heterocyclylcarbonylalkylene, alkylcarbonylarylene, arylcarbonylarylene, heterocyclylcarbonylarylene, alkylcarbonyloxyalkylene, arylcarbonyloxyalkylene, heterocyclylcarbonyloxyalkylene, alkylcarbonyloxyarylene, arylcarbonyloxyarylene, and heterocyclylcarbonyloxyarylene; or $R^1$ has the formula

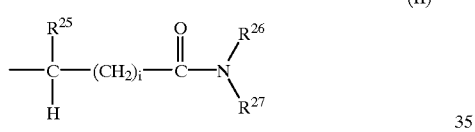

(II)

wherein:

i is an integer from 0 to 9;

$R^{25}$ is selected from hydrogen, alkyl, aralkyl, heterocyclylalkyl, alkoxyalkylene, aryloxyalkylene, aminoalkyl, alkylaminoalkyl, arylaminoalkyl, alkylcarbonylalkylene, arylcarbonylalkylene, and heterocyclcarbonylaminoalkylene; and $R^{26}$ is selected from hydrogen, alkyl, alkenyl, alkynyl, cycloalkylalkylene, aralkyl, alkoxycarbonylalkylene, and alkylaminoalkyl; and $R^{27}$ is selected from alkyl, cycloalkyl, alkynyl, aryl, heterocyclyl, aralkyl, cycloalkylalkylene, cycloalkenylalkylene, cycloalkylarylene, cycloalkylcycloalkyl, heterocyclylalkylene, alkylarylene, alkylaralkyl, aralkylarylene, alkylheterocyclyl, alkylheterocyclylalkylene, alkylheterocyclylarylene, aralkylheterocyclyl, alkoxyalkylene, alkoxyarylene, alkoxyaralkyl, alkoxyheterocyclyl, alkoxyalkoxyarylene, aryloxyarylene, aralkoxyarylene, alkoxyheterocyclylalkylene, aryloxyalkoxyarylene, alkoxycarbonylalkylene, alkoxycarbonylheterocyclyl, alkoxycarbonylheterocyclylcarbonylalkylene, aminoalkyl, alkylaminoalkylene, arylaminocarbonylalkylene, alkoxyarylaminocarbonylalkylene, aminocarbonylalkylene, arylaminocarbonylalkylene, alkylaminocarbonylalkylene, arylcarbonylalkylene, alkoxycarbonylarylene, aryloxycarbonylarylene, alkylaryloxycarbonylarylene, arylcarbonylarylene, alkylarylcarbonylarylene, alkoxycarbonylheterocyclylarylene, alkoxycarbonylalkoxyarylene, heterocyclylcarbonylalkylarylene, alkylthioalkylene, cycloalkylthioalkylene, alkylthioarylene, aralkylthioarylene, heterocyclylthioarylene, arylthioalklylarylene, arylsulfonylaminoalkylene, alkylsulfonylarylene, alkylaminosulfonylarylene; wherein said alkyl, cycloalkyl, aryl, heterocyclyl, aralkyl, heterocyclylalkylene, alkylheterocyclylarylene, alkoxyarylene, aryloxyarylene, arylaminocarbonylalkylene, aryloxycarbonylarylene, arylcarbonylarylene, alkylthioarylene, heterocyclylthioarylene, arylthioalklylarylene, and alkylsulfonylarylene groups are optionally substituted with one or more radicals independently selected from alkyl, halo, haloalkyl, alkoxy, keto, amino, nitro, and cyano; or $R^{27}$ is —$CHR^{28}R^{29}$ wherein $R^{28}$ is alkoxycarbonyl, and $R^{29}$ is selected from aralkyl, aralkoxyalkylene, heterocyclylalkylene, alkylheterocyclylalkylene, alkoxycarbonylalkylene, alkylthioalkylene, and aralkylthioalkylene; wherein said aralkyl and heterocylcyl groups are optionally substituted with one or more radicals independently selected from alkyl and nitro; or $R^{26}$ and $R^{27}$ together with the nitrogen atom to which they are attached form a heterocycle, wherein said heterocycle is optionally substituted with one or more radicals independently selected from alkyl, aryl, heterocyclyl, heterocyclylalkylene, alkylheterocyclylalkylene, aryloxyalkylene, alkoxyarylene, alkylaryloxyalkylene, alkylcarbonyl, alkoxycarbonyl, aralkoxycarbonyl, alkylamino and alkoxycarbonylamino; wherein said aryl, heterocyclylalkylene and aryloxyalkylene radicals are optionally substituted with one or more radicals independently selected from halogen, alkyl and alkoxy; and $R^2$ is selected from hydrido, halogen, mercapto, alkyl, alkenyl, alkynyl, aryl, heterocyclyl, haloalkyl, hydroxyalkyl, aralkyl, alkylheterocyclyl, heterocyclylalkyl, heterocyclylheterocyclyl, heterocyclylalkylheterocyclyl, alkylamino, alkenylamino, alkynylamino, arylamino, aryl(hydroxyalkyl)amino, heterocyclylamino, heterocyclylalkylamino, aralkylamino, N-alkyl-N-alkynyl-amino, aminoalkyl, aminoaryl, aminoalkylamino, aminocarbonylalkylene, arylaminoalkylene, alkylaminoalkylene, arylaminoarylene, alkylaminoarylene, alkylaminoalkylamino, alkylcarbonylaminoalkylene, aminoalkylcarbonylaminoalkylene, alkylaminoalkylcarbonylamino, cycloalkyl, cycloalkenyl, aminoalkylthio, alkylaminocarbonylalkylthio, alkylaminoalkylaminocarbonylalkylthio, alkoxy, heterocyclyloxy, alkylthio, cyanoalkylthio, alkenylthio, alkynylthio, carboxyalkylthio, arylthio, heterocyclylthio, alkoxycarbonylalkylthio, alkylsulfinyl, alkylsulfonyl, carboxy, carboxyalkyl, alkoxyalkyl, alkoxyalkylthio, carboxycycloalkyl, carboxycycloalkenyl, carboxyalkylamino, alkoxycarbonyl, heterocyclylcarbonyl, alkoxycarbonylalkyl, alkoxycarbonylalkylamino, alkoxycarbonylheterocyclyl, alkoxycarbonylheterocyclylcarbonyl, alkoxyalkylamino, alkoxycarbonylaminoalkylene, alkoxycarbonylaminoalkoxy, alkoxycarbonylaminoalkylamino, heterocyclylsulfonyl, aralkythio, heterocyclylalkylthio, aminoalkoxy, cyanoalkoxy, carboxyalkoxy, aryloxy, aralkoxy, alkenyloxy, alkynyloxy, and heterocyclylalkyloxy; wherein the aryl, heterocyclyl, heterocyclylalkyl, cycloalkyl and cycloalkenyl groups are optionally substituted with one or more radicals independently selected from halo, keto, amino, alkyl, alkenyl, alkynyl, aryl, heterocyclyl, aralkyl, heterocyclylalkyl, epoxyalkyl, amino(hydroxyalkyl) carboxy, alkoxy, aryloxy, aralkoxy, haloalkyl, alkylamino, alkynylamino, alkylaminoalkylamino, heterocyclylalkylamino, alkylcarbonyl, alkoxycarbonyl, alkylsulfonyl, arylsulfonyl, and aralkylsulfonyl; or $R^2$ is $R^{200}$-heterocyclyl-$R^{201}$, $R^{200}$-aryl-$R^{201}$, or $R^{200}$-cycloalkyl-$R^{201}$ wherein:

$R^{200}$ is selected from:
—$(CR^{202}R^{203})$—;
—C(O)—;
—C(O)—$(CH_2)_y$—;
—C(O)—O—$(CH_2)_y$;
—$(CH_2)_y$—C(O)—;
—O—$(CH_2)_y$C(O)—;
—$NR^{202}$—;
—$NR^{202}$—$(CH_2)_y$—;
—$(CH_2)_y$—$NR^{202}$—;
—$(CH_2)_y$—$NR^{202}$—$(CH_2)_z$—;
—$(CH_2)_y$—C(O)—$NR^{202}$—$(CH_2)_z$—;
—$(CH_2)_y$—$NR^{202}$—C(O)—$(CH_2)_z$—;
$(CH_2)_y$—$NR^{202}$—C(O)—$NR^{203}$—$(CH_2)_z$—;
—$S(O)_x$—$(CR^{202}R^{203})_y$—;
—$(CR^{202}R^{203})_y$—$S(O)_x$—;
—$S(O)_x$—$(CR^{202}R^{203})_y$—O—;
—$S(O)_x$—$(CR^{202}R^{203})_y$—C(O)—;
—O—$(CH_2)_y$—;
—$(CH_2)_y$—O—;
—S—;
—O—;
or $R^{200}$ represents a bond;

$R^{201}$ represents one or more radicals selected from the group consisting of hydrido, halogen, hydroxy, carboxy, keto, alkyl, hydroxyalkyl, haloalkyl, cycloalkyl, alkenyl, alkynyl, aryl, heterocyclyl, aralkyl, heterocyclylalkylene, alkylcarbonyl, hydroxyalkylcarbonyl, cycloalkylcarbonyl, arylcarbonyl, haloarylcarbonyl, alkoxy, alkoxyalkylene, alkoxyarylene, alkoxycarbonyl, carboxyalkylcarbonyl, alkoxyalkylcarbonyl, heterocyclylalkylcarbonyl, alkylsulfonyl, alkylsulfonylalkylene, amino, aminoalkyl, alkylamino, aralkylamino, alkylaminoalkylene, aminocarbonyl, alkylcarbonylamino, alkylcarbonylaminoalkylene, alkylaminoalkylcarbonyl, alkylaminoalkylcarbonylamino, aminoalkylcarbonylaminoalkyl, alkoxycarbonylamino, alkoxyalkylcarbonylamino, alkoxycarbonylaminoalkylene, alkylimidocarbonyl, amidino, alkylamidino, aralkylamidino, guanidino, guanidinoalkylene, or alkylsulfonylamino; and $R^{202}$ and $R^{203}$ are independently selected from hydrido, alkyl, aryl and aralkyl; and y and z are independently 0, 1, 2, 3, 4, 5 or 6 wherein y+z is less than or equal to 6; and z is 0, 1 or 2; or $R^2$ is —$NHCR^{204}R^{205}$ wherein $R^{204}$ is alkylaminoalkylene, and $R^{205}$ is aryl; or $R^2$ is —$C(NR^{206})R^{207}$ wherein $R^{206}$ is selected from hydrogen and hydroxy, and $R^{207}$ is selected from alkyl, aryl and aralkyl; or $R^2$ has the formula:

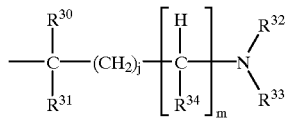

(III)

wherein:
j is an integer from 0 to 8; and
m is 0 or 1; and $R^{30}$ and $R^{31}$ are independently selected from hydrogen, alkyl, aryl, heterocyclyl, aralkyl, heterocyclylalkylene, aminoalkyl, alkylaminoalkyl, aminocarbonylalkyl, alkoxyalkyl, and alkylcarbonyloxyalkyl; and $R^{32}$ is selected from hydrogen, alkyl, aralkyl, heterocyclylalkyl, alkoxyalkylene, aryloxyalkylene, aminoalkyl, alkylaminoalkyl, arylaminoalkyl, alkylcarbonylalkylene, arylcarbonylalkylene, and heterocyclylcarbonylaminoalkylene;

$R^{33}$ is selected from hydrogen, alkyl, —$C(O)R^{35}$, —$C(O)OR^{35}$, —$SO_2R^{36}$, —$C(O)NR^{37}R^{38}$, and —$SO_2NR^{39}R^{40}$, wherein $R^{35}$, $R^{36}$, $R^{37}$, $R^{38}$, $R^{39}$ and $R^{40}$ are independently selected from hydrocarbon, heterosubstituted hydrocarbon and heterocyclyl; and $R^{34}$ is selected from hydrogen, alkyl, aminocarbonyl, alkylaminocarbonyl, and arylaminocarbonyl; or $R^2$ is —$CR^{41}R^{42}$ wherein $R^{41}$ is aryl, and $R^{42}$ is hydroxy; and $R^3$ is selected from pyridinyl, pyrimidinyl, quinolinyl, purinyl, maleimidyl, pyridonyl, thiazolyl, thiazolylalkyl, thiazolylamino,

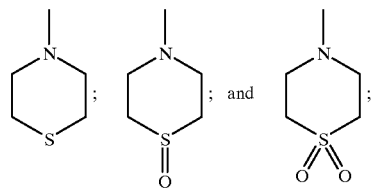

wherein the $R^3$ pyridinyl, pyrimidinyl, quinolinyl, purinyl, maleimidyl, pyridonyl, thiazolyl, thiazolylalkyl, thiazolylamino,

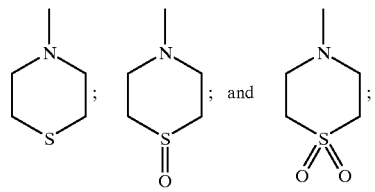

groups are optionally substituted with one or more radicals independently selected from halo, keto, alkyl, aralkyl, aralkenyl, arylheterocyclyl, carboxy, carboxyalkyl, alkoxy, aryloxy, alkylthio, arylthio, alkylsulfinyl, arylsulfinyl, alkylsulfonyl, arylsulfonyl, aralkoxy, heterocyclylalkoxy, amino, alkylamino, alkenylamino, alkynylamino, cycloalkylamino, cycloalkenylamino, arylamino, haloarylamino, heterocyclylamino, aminocarbonyl, cyano, hydroxy, hydroxyalkyl, alkoxyalkylene, alkenoxyalkylene, aryloxyalkyl, alkoxyalkylamino, alkylaminoalkoxy, alkoxycarbonyl, aryloxycarbonyl, heterocyclyloxycarbonyl, alkoxycarbonylamino, alkoxyarylamino, alkoxyaralkylamino, aminosulfinyl, aminosulfonyl, alkylsulfonylamino, alkylaminoalkylamino, hydroxyalkylamino, aralkylamino, aryl(hydroxyalkyl)amino, alkylaminoalkylaminoalkylamino, alkylheterocyclylamino, heterocyclylalkylamino, alkylheterocyclylalkylamino, aralkylheterocyclylamino, heterocyclylheterocyclylalkylamino, alkoxycarbonylheterocyclylamino, nitro, alkylaminocarbonyl, alkylcarbonylamino, haloalkylsulfonyl, aminoalkyl, haloalkyl, alkylcarbonyl, hydrazinyl, alkylhydrazinyl, arylhydrazinyl, or —NR$^{44}$R$^{45}$ wherein R$^{44}$ is alkylcarbonyl or amino, and R$^{45}$ is alkyl or aralkyl; and R$^4$ is selected from hydrido, alkyl, alkenyl, alkynyl, cycloalkyl, cycloalkenyl, aryl, and heterocyclyl, wherein R$^4$ is optionally substituted with one or more radicals independently selected from halo, alkyl, alkenyl, alkynyl, aryl, heterocyclyl, alkylthio, arylthio, alkylthioalkylene, arylthioalkylene, alkylsulfinyl, alkylsulfinylalkylene, arylsulfinylalkylene, alkylsulfonyl, alkylsulfonylalkylene, arylsulfonylalkylene, alkoxy, aryloxy, aralkoxy, aminocarbonyl, alkylaminocarbonyl, arylaminocarbonyl, alkoxycarbonyl, aryloxycarbonyl, haloalkyl, amino, cyano, nitro, alkylamino, arylamino, alkylaminoalkylene, arylaminoalkylene, aminoalkylamino, and hydroxy;

provided R$^3$ is not 2-pyridinyl when R$^4$ is a phenyl ring containing a 2-hydroxy substituent and when R$^1$ is hydrido; and further provided R$^2$ is selected from aryl, heterocyclyl, unsubstituted cycloalkyl and cycloalkenyl when R$^4$ is hydrido; and further provided that R$^4$ is not methylsulfonylphenyl or aminosulfonylphenyl; and further provided that R$^1$ is not methylsulfonylphenyl; or a pharmaceutically-acceptable salt or tautomer thereof.

In a subclass of interest, R$^2$ is as defined above, and

R$^1$ is selected from hydrido, alkyl, cycloalkyl, alkenyl, cycloalkenyl, alkynyl, cycloalkylalkylene, cycloalkenylalkylene, heterocyclylalkylene, haloalkyl, haloalkenyl, haloalkynyl, hydroxyalkyl, hydroxyalkenyl, hydroxyalkynyl, aralkyl, aralkenyl, aralkynyl, arylheterocyclyl, carboxy, carboxyalkyl, alkoxyalkyl, alkenoxyalkyl, alkynoxyalkyl, aryloxyalkyl, heterocyclyloxyalkyl, alkoxyalkoxy, mercaptoalkyl, alkylthioalkylene, alkenylthioalkylene, alkylthioalkenylene, amino, aminoalkyl, alkylamino, alkenylamino, alkynylamino, arylamino, heterocyclylamino, alkylsulfinyl, alkenylsulfinyl, alkynylsulfinyl, arylsulfinyl, heterocyclylsulfinyl, alkylsulfonyl, alkenylsulfonyl, alkynylsulfonyl, arylsulfonyl, heterocyclylsulfonyl, alkylaminoalkylene, alkylsulfonylalkylene, acyl, acyloxycarbonyl, alkoxycarbonylalkylene, aryloxycarbonylalkylene, heterocyclyloxycarbonylalkylene, alkylcarbonylalkylene, arylcarbonylalkylene, heterocyclylcarbonylalkylene, alkylcarbonyloxyalkylene, arylcarbonyloxyalkylene, heterocyclylcarbonyloxyalkylene, alkylcarbonyloxyarylene, arylcarbonyloxyarylene, and heterocyclylcarbonyloxyarylene; or R$^1$ has the formula

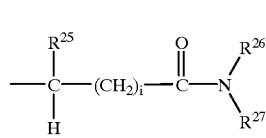

(II)

wherein:

i is an integer from 0 to 9;

R$^{25}$ is selected from hydrogen, alkyl, aralkyl, heterocyclylalkyl, alkoxyalkylene, aryloxyalkylene, aminoalkyl, alkylaminoalkyl, arylaminoalkyl, alkylcarbonylalkylene, arylcarbonylalkylene, and heterocyclylcarbonylaminoalkylene; and R$^{26}$ is selected from hydrogen, alkyl, alkenyl, alkynyl, cycloalkylalkylene, aralkyl, alkoxycarbonylalkylene, and alkylaminoalkyl; and R$^{27}$ is selected from alkyl, cycloalkyl, alkynyl, aryl, heterocyclyl, aralkyl, cycloalkylalkylene, cycloalkenylalkylene, cycloalkylarylene, cycloalkylcycloalkyl, heterocyclylalkylene, alkylarylene, alkylaralkyl, aralkylarylene, alkylheterocyclyl, alkylheterocyclylalkylene, alkylheterocyclylarylene, aralkylheterocyclyl, alkoxyalkylene, alkoxyarylene, alkoxyaralkyl, alkoxyheterocyclyl, alkoxyalkoxyarylene, aryloxyarylene, aralkoxyarylene, alkoxyheterocyclylalkylene, aryloxyalkoxyarylene, alkoxycarbonylalkylene, alkoxycarbonylheterocyclyl, alkoxycarbonylheterocyclylcarbonylalkylene, aminoalkyl, alkylaminoalkylene, arylaminocarbonylalkylene, alkoxyarylaminocarbonylalkylene, aminocarbonylalkylene, arylaminocarbonylalkylene, alkylaminocarbonylalkylene, arylcarbonylalkylene, alkoxycarbonylarylene, aryloxycarbonylarylene, alkylaryloxycarbonylarylene, arylcarbonylarylene, alkylarylcarbonylarylene, alkoxycarbonylheterocyclylarylene, alkoxycarbonylalkoxylarylene, heterocyclylcarbonylalkylarylene, alkylthioalkylene, cycloalkylthioalkylene, alkylthioarylene, aralkylthioarylene, heterocyclylthioarylene, arylthioalklylarylene, arylsulfonylaminoalkylene, alkylsulfonylarylene, alkylaminosulfonylarylene; wherein said alkyl, cycloalkyl, aryl, heterocyclyl, aralkyl, heterocyclylalkylene, alkylheterocyclylarylene, alkoxyarylene, aryloxyarylene, arylaminocarbonylalkylene, aryloxycarbonylarylene, arylcarbonylarylene, alkylthioarylene, heterocyclylthioarylene, arylthioalklylarylene, and alkylsulfonylarylene groups are optionally substituted with one or more radicals independently selected from alkyl, halo, haloalkyl, alkoxy, keto, amino, nitro, and cyano; or R$^{27}$ is —CHR$^{28}$R$^{29}$ wherein R$^{28}$ is alkoxycarbonyl, and R$^{29}$ is selected from aralkyl, aralkoxyalkylene, heterocyclylalkylene, alkylheterocyclylalkylene, alkoxycarbonylalkylene, alkylthioalkylene, and aralkylthioalkylene; wherein said aralkyl and heterocylcyl groups are optionally substituted with one or more radicals independently selected from alkyl and nitro; or $R^{26}$ and $R^{27}$ together with the nitrogen atom to which they are attached form a heterocycle, wherein said heterocycle is optionally substituted with one or more radicals independently selected from alkyl, aryl, heterocyclyl, heterocyclylalkylene, alkylheterocyclylalkylene, aryloxyalkylene, alkoxyarylene, alkylaryloxyalkylene, alkylcarbonyl, alkoxycarbonyl, aralkoxycarbonyl, alkylamino and alkoxycarbonylamino; wherein said aryl, heterocyclylalkylene and aryloxyalkylene radicals are optionally substituted with one or more radicals independently selected from halogen, alkyl and alkoxy; and $R^3$ is selected from pyridinyl, pyrimidinyl, quinolinyl, purinyl, maleimidyl, pyridonyl, thiazolyl, thiazolylalkyl, thiazolylamino,

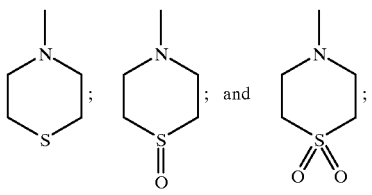

wherein the $R^3$ pyridinyl, pyrimidinyl, quinolinyl, purinyl, maleimidyl, pyridonyl, thiazolyl, thiazolylalkyl, thiazolylamino,

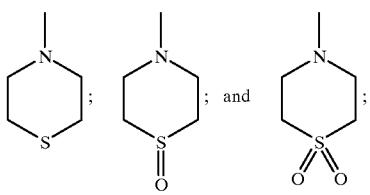

groups are optionally substituted with one or more radicals independently selected from halo, keto, alkyl, aralkyl, aralkenyl, arylheterocyclyl, carboxy, carboxyalkyl, alkoxy, aryloxy, alkylthio, arylthio, alkylsulfinyl, arylsulfinyl, arylsulfonyl, aralkoxy, heterocyclylalkoxy, amino, alkylamino, alkenylamino, alkynylamino, cycloalkylamino, cycloalkenylamino, arylamino, haloarylamino, heterocyclylamino, aminocarbonyl, cyano, hydroxy, hydroxyalkyl, alkoxyalkylene, alkenoxyalkylene, aryloxyalkyl, alkoxyalkylamino, alkylaminoalkoxy, alkoxycarbonyl, aryloxycarbonyl, heterocyclyloxycarbonyl, alkoxycarbonylamino, alkoxyarylamino, alkoxyaralkylamino, aminosulfinyl, alkylsulfonylamino, alkylaminoalkylamino, hydroxyalkylamino, aralkylamino, aryl(hydroxyalkyl)amino, alkylaminoalkylaminoalkylamino, alkylheterocyclylamino, heterocyclylalkylamino, alkylheterocyclylalkylamino, aralkylheterocyclylamino, heterocyclylheterocyclylalkylamino, alkoxycarbonylheterocyclylamino, nitro, alkylaminocarbonyl, alkylcarbonylamino, aminoalkyl, haloalkyl, alkylcarbonyl, hydrazinyl, alkylhydrazinyl, arylhydrazinyl, or —NR$^{44}$R$^{45}$ wherein R$^{44}$ is alkylcarbonyl or amino, and R$^{45}$ is alkyl or aralkyl; and $R^4$ is selected from hydrido, alkyl, alkenyl, alkynyl, cycloalkyl, cycloalkenyl, aryl, and heterocyclyl, wherein R$^4$ is optionally substituted with one or more radicals independently selected from halo, alkyl, alkenyl, alkynyl, aryl, heterocyclyl, alkylthio, arylthio, alkylthioalkylene, arylthioalkylene, alkylsulfinyl, alkylsulfinylalkylene, arylsulfinylalkylene, alkylsulfonylalkylene, arylsulfonylalkylene, alkoxy, aryloxy, aralkoxy, aminocarbonyl, alkylaminocarbonyl, arylaminocarbonyl, alkoxycarbonyl, aryloxycarbonyl, haloalkyl, amino, cyano, nitro, alkylamino, arylamino, alkylaminoalkylene, arylaminoalkylene, aminoalkylamino, and hydroxy; or a pharmaceutically-acceptable salt or tautomer thereof.

A subclass of compounds useful in treating p38 mediated disorders is defined by Formula I:

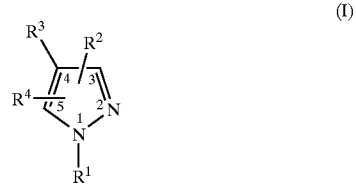

(I)

wherein $R^1$ is selected from hydrido, alkyl, cycloalkyl, alkenyl, cycloalkenyl, alkynyl, aryl, heterocyclyl, cycloalkylalkylene, cycloalkenylalkylene, heterocyclylalkylene, haloalkyl, haloalkenyl, haloalkynyl, hydroxyalkyl, hydroxyalkenyl, hydroxyalkynyl, aralkyl, aralkenyl, aralkynyl, arylheterocyclyl, carboxy, carboxyalkyl, alkoxyalkyl, alkenoxyalkyl, alkynoxyalkyl, aryloxyalkyl, heterocyclyloxyalkyl, alkoxyalkoxy, mercaptoalkyl, alkylthioalkylene, alkenylthioalkylene, alkylthioalkenylene, amino, aminoalkyl, alkylamino, alkenylamino, alkynylamino, arylamino, heterocyclylamino, alkylsulfinyl, alkenylsulfinyl, alkynylsulfinyl, arylsulfinyl, heterocyclylsulfinyl, alkylsulfonyl, alkenylsulfonyl, alkynylsulfonyl, arylsulfonyl, heterocyclylsulfonyl, alkylaminoalkylene, alkylsulfonylalkylene, acyl, acyloxycarbonyl, alkoxycarbonylalkylene, aryloxycarbonylalkylene, heterocyclyloxycarbonylalkylene, alkoxycarbonylarylene, aryloxycarbonylarylene, heterocyclyloxycarbonylarylene, alkylcarbonylalkylene, arylcarbonylalkylene, heterocyclylcarbonylalkylene, alkylcarbonylarylene, arylcarbonylarylene, heterocyclylcarbonylarylene, alkylcarbonyloxyalkylene, arylcarbonyloxyalkylene, heterocyclylcarbonyloxyalkylene, alkylcarbonyloxyarylene, arylcarbonyloxyarylene, and heterocyclylcarbonyloxyarylene; or $R^1$ has the formula

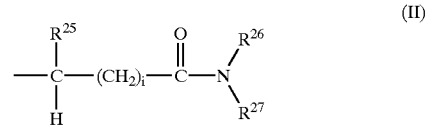

(II)

wherein:
i is an integer from 0 to 9;
$R^{25}$ is selected from hydrogen, alkyl, aralkyl, heterocyclylalkyl, alkoxyalkylene, aryloxyalkylene, aminoalkyl, alkylaminoalkyl, arylaminoalkyl, alkylcarbonylalkylene, arylcarbonylalkylene, and heterocyclylcarbonylaminoalkylene; and R²⁶ is selected from hydrogen, alkyl, alkenyl, alkynyl, cycloalkylalkylene, aralkyl, alkoxycarbonylalkylene, and alkylaminoalkyl; and R²⁷ is selected from alkyl, cycloalkyl, alkynyl, aryl, heterocyclyl, aralkyl, cycloalkylalkylene, cycloalkenylalkylene, cycloalkylarylene, cycloalkylcycloalkyl, heterocyclylalkylene, alkylarylene, alkylaralkyl, aralkylarylene, alkylheterocyclyl, alkylheterocyclylalkylene, alkylheterocyclylarylene, aralkylheterocyclyl, alkoxyalkylene, alkoxyarylene, alkoxyaralkyl, alkoxyheterocyclyl, alkoxyalkoxyarylene, aryloxyarylene, aralkoxyarylene, alkoxyheterocyclylalkylene, aryloxyalkoxyarylene, alkoxycarbonylalkylene, alkoxycarbonylheterocyclyl, alkoxycarbonylheterocyclylcarbonylalkylene, aminoalkyl, alkylaminoalkylene, arylaminocarbonylalkylene, alkoxyarylaminocarbonylalkylene, aminocarbonylalkylene, arylaminocarbonylalkylene, alkylaminocarbonylalkylene, arylcarbonylalkylene, alkoxycarbonylarylene, aryloxycarbonylarylene, alkylaryloxycarbonylarylene, arylcarbonylarylene, alkylarylcarbonylarylene, alkoxycarbonylheterocyclylarylene, alkoxycarbonylalkoxylarylene, heterocyclylcarbonylalkylarylene, alkylthioalkylene, cycloalkylthioalkylene, alkylthioarylene, aralkylthioarylene, heterocyclylthioarylene, arylthioalklylarylene, arylsulfonylaminoalkylene, alkylsulfonylarylene, alkylaminosulfonylarylene; wherein said alkyl, cycloalkyl, aryl, heterocyclyl, aralkyl, heterocyclylalkylene, alkylheterocyclylarylene, alkoxyarylene, aryloxyarylene, arylaminocarbonylalkylene, aryloxycarbonylarylene, arylcarbonylarylene, alkylthioarylene, heterocyclylthioarylene, arylthioalklylarylene, and alkylsulfonylarylene groups are optionally substituted with one or more radicals independently selected from alkyl, halo, haloalkyl, alkoxy, keto, amino, nitro, and cyano; or R²⁷ is —CHR²⁸R²⁹ wherein R²⁸ is alkoxycarbonyl, and R²⁹ is selected from aralkyl, aralkoxyalkylene, heterocyclylalkylene, alkylheterocyclylalkylene, alkoxycarbonylalkylene, alkylthioalkylene, and aralkylthioalkylene; wherein said aralkyl and heterocylcyl groups are optionally substituted with one or more radicals independently selected from alkyl and nitro; or R²⁶ and R²⁷ together with the nitrogen atom to which they are attached form a heterocycle, wherein said heterocycle is optionally substituted with one or more radicals independently selected from alkyl, aryl, heterocyclyl, heterocyclylalkylene, alkylheterocyclylalkylene, aryloxyalkylene, alkoxyarylene, alkylaryloxyalkylene, alkylcarbonyl, alkoxycarbonyl, aralkoxycarbonyl, alkylamino and alkoxycarbonylamino; wherein said aryl, heterocyclylalkylene and aryloxyalkylene radicals are optionally substituted with one or more radicals independently selected from halogen, alkyl and alkoxy; and R² is selected from hydrido, halogen, alkyl, alkenyl, alkynyl, aryl, heterocyclyl, haloalkyl, hydroxyalkyl, aralkyl, alkylheterocyclyl, heterocyclylalkyl, alkylamino, alkenylamino, alkynylamino, arylamino, heterocyclylamino, heterocyclylalkylamino, aralkylamino, aminoalkyl, aminoaryl, aminoalkylamino, arylaminoalkylene, alkylaminoalkylene, arylaminoarylene, alkylaminoarylene, alkylaminoalkylamino, cycloalkyl, cycloalkenyl, alkoxy, heterocyclyloxy, alkylthio, arylthio, heterocyclylthio, carboxy, carboxyalkyl, carboxycycloalkyl, carboxycycloalkenyl, carboxyalkylamino, alkoxycarbonyl, heterocyclylcarbonyl, alkoxycarbonylalkyl, alkoxycarbonylheterocyclyl, alkoxycarbonylheterocyclylcarbonyl, alkoxyalkylamino, alkoxycarbonylaminoalkylamino, and heterocyclylsulfonyl; wherein the aryl, heterocyclyl, heterocyclylalkyl, cycloalkyl and cycloalkenyl groups are optionally substituted with one or more radicals independently selected from halo, keto, amino, alkyl, alkenyl, alkynyl, aryl, heterocyclyl, aralkyl, heterocyclylalkyl, epoxyalkyl, amino (hydroxyalkyl) carboxy, alkoxy, aryloxy, aralkoxy, haloalkyl, alkylamino, alkynylamino, alkylaminoalkylamino, heterocyclylalkylamino, alkylcarbonyl, alkoxycarbonyl, alkylsulfonyl, arylsulfonyl, and aralkylsulfonyl; or R² has the formula:

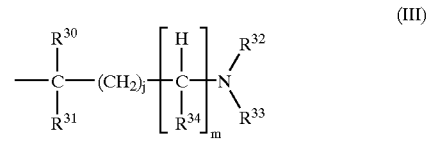

(III)

wherein:
j is an integer from 0 to 8; and
m is 0 or 1; and

R³⁰ and R³¹ are independently selected from hydrogen, alkyl, aryl, heterocyclyl, aralkyl, heterocyclylalkylene, aminoalkyl, alkylaminoalkyl, aminocarbonylalkyl, alkoxyalkyl, and alkylcarbonyloxyalkyl; and R³² is selected from hydrogen, alkyl, aralkyl, heterocyclylalkyl, alkoxyalkylene, aryloxyalkylene, aminoalkyl, alkylaminoalkyl, arylaminoalkyl, alkylcarbonylalkylene, arylcarbonylalkylene, and heterocyclylcarbonylaminoalkylene;

R³³ is selected from hydrogen, alkyl, —C(O)R³⁵, —C(O)OR³⁵, —SO₂R³⁶, —C(O)NR³⁷R³⁸, and —SO₂NR³⁹R⁴⁰, wherein R³⁵, R³⁶, R³⁷, R³⁸, R³⁹ and R⁴⁰ are independently selected from hydrocarbon, heterosubstituted hydrocarbon and heterocyclyl; and R³⁴ is selected from hydrogen, alkyl, aminocarbonyl, alkylaminocarbonyl, and arylaminocarbonyl; or R² is —CR⁴¹R⁴² wherein R⁴¹ is aryl, and R⁴² is hydroxy; and R³ is selected from pyridinyl, pyrimidinyl, quinolinyl, purinyl,

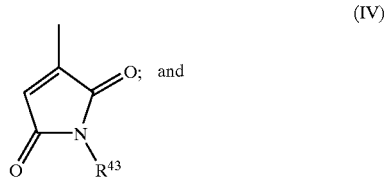

(IV)

O; and

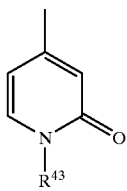

(V)

wherein $R^{43}$ is selected from hydrogen, alkyl, aminoalkyl, alkoxyalkyl, alkenoxyalkyl, and aryloxyalkyl; and wherein the $R^3$ pyridinyl, pyrimidinyl, quinolinyl and purinyl groups are optionally substituted with one or more radicals independently selected from halo, alkyl, aralkyl, aralkenyl, arylheterocyclyl, carboxy, carboxyalkyl, alkoxy, aryloxy, alkylthio, arylthio, alkylsulfinyl, arylsulfinyl, alkylsulfonyl, arylsulfonyl, aralkoxy, heterocyclylalkoxy, amino, alkylamino, alkenylamino, alkynylamino, cycloalkylamino, cycloalkenylamino, arylamino, heterocyclylamino, aminocarbonyl, cyano, hydroxy, hydroxyalkyl, alkoxycarbonyl, aryloxycarbonyl, heterocyclyloxycarbonyl, alkoxycarbonylamino, alkoxyaralkylamino, aminosulfinyl, aminosulfonyl, alkylaminoalkylamino, hydroxyalkylamino, aralkylamino, heterocyclylalkylamino, aralkylheterocyclylamino, nitro, alkylaminocarbonyl, alkylcarbonylamino, halosulfonyl, aminoalkyl, haloalkyl, alkylcarbonyl, hydrazinyl, alkylhydrazinyl, arylhydrazinyl, or —$NR^{44}R^{45}$ wherein $R^{44}$ is alkylcarbonyl or amino, and $R^{45}$ is alkyl or aralkyl; and $R^4$ is selected from hydrido, alkyl, alkenyl, alkynyl, cycloalkyl, cycloalkenyl, aryl, and heterocyclyl, wherein $R^4$ is optionally substituted with one or more radicals independently selected from halo, alkyl, alkenyl, alkynyl, aryl, heterocyclyl, alkylthio, arylthio, alkylthioalkylene, arylthioalkylene, alkylsulfinyl, alkylsulfinylalkylene, arylsulfinylalkylene, alkylsulfonyl, alkylsulfonylalkylene, arylsulfonylalkylene, alkoxy, aryloxy, aralkoxy, aminocarbonyl, alkylaminocarbonyl, arylaminocarbonyl, alkoxycarbonyl, aryloxycarbonyl, haloalkyl, amino, cyano, nitro, alkylamino, arylamino, alkylaminoalkylene, arylaminoalkylene, aminoalkylamino, and hydroxy;

provided $R^3$ is not 2-pyridinyl when $R^4$ is a phenyl ring containing a 2-hydroxy substituent and when $R^1$ is hydrido; further provided $R^2$ is selected from aryl, heterocyclyl, unsubstituted cycloalkyl and cycloalkenyl when $R^4$ is hydrido; and further provided $R^4$ is not methylsulfonylphenyl; or a pharmaceutically-acceptable salt or tautomer thereof.

Compounds of Formula I and/or IA would be useful for, but not limited to, the treatment of any disorder or disease state in a human, or other mammal, which is exacerbated or caused by excessive or unregulated TNF or p38 kinase production by such mammal. Accordingly, the present invention provides a method of treating a cytokine-mediated disease which comprises administering an effective cytokine-interfering amount of a compound of Formula I and/or 1A or a pharmaceutically acceptable salt thereof.

Compounds of Formula I and/or IA would be useful for, but not limited to, the treatment of inflammation in a subject, and for use as antipyretics for the treatment of fever. Compounds of the invention would be useful to treat arthritis, including but not limited to, rheumatoid arthritis, spondyloarthropathies, gouty arthritis, osteoarthritis, systemic lupus erythematosus and juvenile arthritis, osteoarthritis, gouty arthritis and other arthritic conditions. Such compounds would be useful for the treatment of pulmonary disorders or lung inflammation, including adult respiratory distress syndrome, pulmonary sarcoisosis, asthma, silicosis, and chronic pulmonary inflammatory disease. The compounds are also useful for the treatment of viral and bacterial infections, including sepsis, septic shock, gram negative sepsis, malaria, meningitis, cachexia secondary to infection or malignancy, cachexia secondary to acquired immune deficiency syndrome (AIDS), AIDS, ARC (AIDS related complex), pneumonia, and herpesvirus. The compounds are also useful for the treatment of bone resorption diseases, such as osteoporosis, endotoxic shock, toxic shock syndrome, reperfusion injury, autoimmune disease including graft vs. host reaction and allograft rejections, cardiovascular diseases including atherosclerosis, thrombosis, congestive heart failure, and cardiac reperfusion injury, renal reperfusion injury, liver disease and nephritis, and myalgias due to infection. The compounds are also useful for the treatment of influenza, multiple sclerosis, cancer, diabetes, systemic lupus erthrematosis (SLE), skin-related conditions such as psoriasis, eczema, burns, dermatitis, keloid formation, scar tissue formation, and angiogenic disorders. Compounds of the invention also would be useful to treat gastrointestinal conditions such as inflammatory bowel disease, Crohn's disease, gastritis, irritable bowel syndrome and ulcerative colitis. The compounds would also be useful in the treatment of ophthalmic diseases, such as retinitis, retinopathies, uveitis, ocular photophobia, and of acute injury to the eye tissue. Compounds of the invention also would be useful for treatment of angiogenesis, including neoplasia; metastasis; ophthalmological conditions such as corneal graft rejection, ocular neovascularization, retinal neovascularization including neovascularization following injury or infection, diabetic retinopathy, retrolental fibroplasia and neovascular glaucoma; ulcerative diseases such as gastric ulcer; pathological, but non-malignant, conditions such as hemaginomas, including invantile hemaginomas, angiofibroma of the nasopharynx and avascular necrosis of bone; diabetic nephropathy and cardiomyopathy; and disorders of the female reproductive system such as endometriosis. The compounds of the invention may also be useful for preventing the production of cyclooxygenase-2.

Besides being useful for human treatment, these compounds are also useful for veterinary treatment of companion animals, exotic animals and farm animals, including mammals, rodents, and the like. More preferred animals include horses, dogs, and cats.

The present compounds may also be used in co-therapies, partially or completely, in place of other conventional anti-inflammatories, such as together with steroids, cyclooxygenase-2 inhibitors, DMARD's, immunosuppressive agents, NSAIDS, 5-lipoxygenase inhibitors, $LTB_4$ antagonists and $LTA_4$ hydrolase inhibitors.

As used herein, the term "TNF mediated disorder" refers to any and all disorders and disease states in which TNF plays a role, either by control of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disorder mediated by TNF.

As used herein, the term "p38 mediated disorder" refers to any and all disorders and disease states in which p38 plays a role, either by control of p38 itself, or by p38 causing another factor to be released, such as but not limited to IL-1, IL-6 or IL-8. A disease state in which, for instance, IL-1 is a major component, and whose production or action, is exacerbated or secreted in response to p38, would therefore be considered a disorder mediated by p38.

As TNF-β has close structural homology with TNF-α (also known as cachectin) and since each induces similar biologic responses and binds to the same cellular receptor, the synthesis of both TNF-α and TNF-β are inhibited by the compounds of the present invention and thus are herein referred to collectively as "TNF" unless specifically delineated otherwise.

A preferred class of compounds consists of those compounds of Formula I wherein $R^1$ is selected from hydrido, lower alkyl, lower cycloalkyl, lower alkenyl, lower alkynyl, lower heterocyclyl, lower cycloalkylalkylene, lower haloalkyl, lower hydroxyalkyl, lower aralkyl, lower alkoxyalkyl, lower mercaptoalkyl, lower alkylthioalkylene, amino, lower alkylamino, lower arylamino, lower alkylaminoalkylene, and lower heterocyclylalkylene; or $R^1$ has the formula

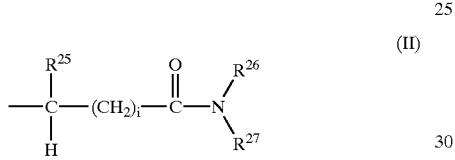

(II)

wherein:
i is 0, 1 or 2; and $R^{25}$ is selected from hydrogen, lower alkyl, lower phenylalkyl, lower heterocyclylalkyl, lower alkoxyalkylene, lower phenoxyalkylene, lower aminoalkyl, lower alkylaminoalkyl, lower phenoxyaminoalkyl, lower alkylcarbonylalkylene, lower phenoxycarbonylalkylene, and lower heterocyclylcarbonylaminoalkylene; and $R^{26}$ is selected from hydrogen, lower alkyl, lower alkenyl, lower alkynyl, lower cycloalkylalkylene, lower phenylalkyl, lower alkoxycarbonylalkylene, and lower alkylaminoalkyl; and $R^{27}$ is selected from lower alkyl, lower cycloalkyl, lower alkynyl, aryl selected from phenyl, biphenyl and naphthyl, lower heterocyclyl, lower phenylalkyl, lower cycloalkylalkylene, lower cycloalkenylalkylene, lower cycloalkylarylene, lower cycloalkylcycloalkyl, lower heterocyclylalkylene, lower alkylphenylene, lower alkylphenylalkyl, lower phenylalkylphenylene, lower alkylheterocyclyl, lower alkylheterocyclylalkylene, lower alkylheterocyclylphenylene, lower phenylalkylheterocyclyl, lower alkoxyalkylene, lower alkoxyphenylene, lower alkoxyphenylalkyl, lower alkoxyheterocyclyl, lower alkoxyalkoxyphenylene, lower phenoxyphenylene, lower phenylalkoxyphenylene, lower alkoxyheterocyclylalkylene, lower phenoxyalkoxyphenylene, lower alkoxycarbonylalkylene, lower alkoxycarbonylheterocyclyl, lower alkoxycarbonylheterocyclylcarbonylalkylene, lower aminoalkyl, lower alkylaminoalkylene, lower phenylaminocarbonylalkylene, lower alkoxyphenylaminocarbonylalkylene, lower aminocarbonylalkylene, arylaminocarbonylalkylene, lower alkylaminocarbonylalkylene, lower phenylcarbonylalkylene, lower alkoxycarbonylphenylene, lower phenoxycarbonylphenylene, lower alkylphenoxycarbonylphenylene, lower phenylcarbonylphenylene, lower alkylphenylcarbonylphenylene, lower alkoxycarbonylheterocyclylphenylene, lower alkoxycarbonylalkoxylphenylene, lower heterocyclylcarbonylalkylphenylene, lower alkylthioalkylene, cycloalkylthioalkylene, lower alkylthiophenylene, lower phenylalkylthiophenylene, lower heterocyclylthiophenylene, lower phenylthioalklylphenylene, lower phenylsulfonylaminoalkylene, lower alkylsulfonylphenylene, lower alkylaminosulfonylphenylene; wherein said lower alkyl, lower cycloalkyl, aryl selected from phenyl, biphenyl and naphthyl, lower heterocyclyl, lower phenylalkyl, lower heterocyclylalkylene, lower alkylheterocyclylphenylene, lower alkoxyphenylene, lower phenoxyphenylene, lower phenylaminocarbonylalkylene, lower phenoxycarbonylphenylene, lower phenylcarbonylphenylene, lower alkylthiophenylene, lower heterocyclylthiophenylene, lower phenylthioalklylphenylene, and lower alkylsulfonylphenylene groups are optionally substituted with one or more radicals independently selected from lower alkyl, halo, lower haloalkyl, lower alkoxy, keto, amino, nitro, and cyano; or $R^{27}$ is —$CHR^{46}R^{47}$ wherein $R^{46}$ is lower alkoxycarbonyl, and $R^{47}$ is selected from lower phenylalkyl, lower phenylalkoxyalkylene, lower heterocyclylalkylene, lower alkylheterocyclylalkylene, lower alkoxycarbonylalkylene, lower alkylthioalkylene, and lower phenylalkylthioalkylene; wherein said phenylalkyl and heterocylcyl groups are optionally substituted with one or more radicals independently selected from lower alkyl and nitro; or $R^{26}$ and $R^{27}$ together with the nitrogen atom to which they are attached form a 4–8 membered ring heterocycle, wherein said heterocycle is optionally substituted with one or more radicals independently selected from lower alkyl, aryl selected from phenyl, biphenyl and naphthyl, heterocyclyl, heterocyclylalkylene, lower alkylheterocyclylalkylene, lower phenoxyalkylene, lower alkoxyphenylene, lower alkylphenoxyalkylene, lower alkylcarbonyl, lower alkoxycarbonyl, lower phenylalkoxycarbonyl, lower alkylamino and lower alkoxycarbonylamino; wherein said aryl selected from phenyl, biphenyl and naphthyl, lower heterocyclylalkylene and lower phenoxyalkylene radicals are optionally substituted with one or more radicals independently selected from halogen, lower alkyl and lower alkoxy; and $R^2$ is selected from hydrido, halogen, lower alkyl, aryl selected from phenyl, biphenyl, and naphthyl, lower haloalkyl, lower hydroxyalkyl, 5- or 6-membered heterocyclyl, lower alkylheterocyclyl, lower heterocyclylalkyl, lower alkylamino, lower alkynylamino, phenylamino, lower heterocyclylamino, lower heterocyclylalkylamino, lower phenylalkylamino, lower aminoalkyl, lower aminoalkylamino, lower alkylaminoalkylamino, lower cycloalkyl, lower alkenyl, lower alkoxycarbonylalkyl, lower cycloalkenyl, lower carboxyalkylamino, lower alkoxycarbonyl, lower heterocyclylcarbonyl, lower alkoxycarbonylheterocyclyl, lower alkoxycarbonylheterocyclylcarbonyl, alkoxycarbonylalkyl, lower alkoxyalkylamino, lower alkoxycarbonylaminoalkylamino, lower heterocyclylsulfonyl, lower heterocyclyloxy, and lower heterocyclylthio; wherein the aryl, heterocylyl, heterocylylalkyl, cycloalkyl, and cycloalkenyl groups are optionally substituted with one or more radicals independently selected from halo, keto, lower alkyl, lower alkynyl, phenyl, 5- or 6-membered heterocyclyl, lower phenylalkyl, lower heterocyclylalkyl, lower epoxyalkyl, carboxy, lower alkoxy, lower aryloxy, lower phenylalkoxy, lower haloalkyl, lower alkylamino, lower alkylaminoalkylamino, lower alkynylamino, lower amino(hydroxyalkyl), lower heterocyclylalkylamino, lower alkylcarbonyl, lower alkoxycarbonyl, lower alkylsulfonyl, lower phenylalkylsulfonyl, and phenylsulfonyl; or $R^2$ has the formula:

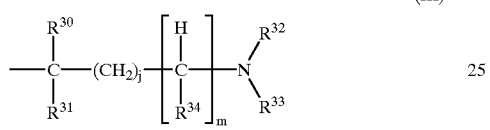

(III)

wherein:
j is 0, 1 or 2; and
m is 0;

$R^{30}$ and $R^{31}$ are independently selected from hydrogen, alkyl, aryl, heterocyclyl, aralkyl, heterocyclylalkylene, aminoalkyl, alkylaminoalkyl, aminocarbonylalkyl, alkoxyalkyl, and alkylcarbonyloxyalkyl; and $R^{32}$ is selected from hydrogen, alkyl, aralkyl, heterocyclylalkyl, alkoxyalkylene, aryloxyalkylene, aminoalkyl, alkylaminoalkyl, arylaminoalkyl, alkylcarbonylalkylene, arylcarbonylalkylene, and heterocyclylcarbonylaminoalkylene; and $R^{33}$ is selected from hydrogen, alkyl, —C(O)$R^{35}$, —C(O)O$R^{35}$, —SO$_2$$R^{36}$, —C(O)NR$^{37}$R$^{38}$, and —SO$_2$NR$^{39}$R$^{40}$;

wherein $R^{35}$ is selected from alkyl, cycloalkyl, haloalkyl, alkenyl, aryl, heterocyclyl, aralkyl, arylcycloalkyl, cycloalkenylalkylene, heterocyclylalkylene, alkylarylene, alkylheterocyclyl, arylarylene, arylheterocyclyl, alkoxy, alkenoxy, alkoxyalkylene, alkoxyaralkyl, alkoxyarylene, aryloxyalkylene, aralkoxyalkylene, cycloalkyloxyalkylene, alkoxycarbonyl, heterocyclylcarbonyl, alkylcarbonyloxyalkylene, alkylcarbonyloxyarylene, alkoxycarbonylalkylene, alkoxycarbonylarylene, aralkoxycarbonylheterocyclyl, alkylcarbonylheterocyclyl, arylcarbonyloxyalkylarylene, and alkylthioalkylene; wherein said aryl, heterocyclyl, aralkyl, alkylarylene, arylheterocyclyl, alkoxyarylene, aryloxyalkylene, cycloalkoxyalkylene, alkoxycarbonylalkylene, and alkylcarbonylheterocyclyl groups are optionally substituted with one or more radicals independently selected from alkyl, halo, haloalkyl, alkoxy, haloalkoxy, keto, amino, nitro, and cyano; or $R^{35}$ is CHR$^{48}$R$^{49}$ wherein $R^{48}$ is arylsulfonylamino or alkylarylsulfonylamino, and $R^{49}$ is selected from aralkyl, amino, alkylamino, and aralkylamino; or $R^{35}$ is —NR$^{50}$R$^{51}$ wherein $R^{50}$ is alkyl, and $R^{51}$ is aryl; and wherein $R^{36}$ is selected from alkyl, haloalkyl, aryl, heterocyclyl, cycloalkylalkylene, alkylarylene, alkenylarylene, arylarylene, aralkyl, aralkenyl, heterocyclylheterocyclyl, carboxyarylene, alkoxyarylene, alkoxycarbonylarylene, alkylcarbonylaminoarylene, alkylcarbonylaminoheterocyclyl, arylcarbonylaminoalkylheterocyclyl, alkylaminoarylene, alkylamino, alkylaminoarylene, alkylsulfonylarylene, alkylsulfonylaralkyl, and arylsulfonylheterocyclyl; wherein said aryl, heterocyclyl, cycloalkylalkylene, aralkyl, alkylcarbonylaminoheterocyclyl, and alkylsulfonylarylene groups are optionally substituted with one or more radicals independently selected from alkyl, halo, hydroxy, haloalkyl, alkoxy, haloalkoxy, keto, amino, nitro, and cyano; and wherein $R^{37}$ is selected from hydrogen and alkyl; and wherein $R^{38}$ is selected from hydrogen, alkyl, alkenyl, aryl, heterocyclyl, aralkyl, alkylarylene, arylcycloalkyl, arylarylene, cycloalkylalkylene, heterocyclylalkylene, alkylheterocyclylalkylene, aralkylheterocyclyl, alkoxyalkylene, alkoxyarylene, aryloxyarylene, arylcarbonyl, alkoxycarbonyl, alkoxycarbonylalkylene, alkoxycarbonylarylene, alkylcarbonylcarbonylalkylene, alkylaminoalkylene, alkylaminoaralkyl, alkylcarbonylaminoalkylene, alkylthioarylene, alkylsulfonylaralkyl, and aminosulfonylaralkyl; wherein said aryl, heterocyclyl, aralkyl, and heterocyclylalkylene groups are optionally substituted with one or more radicals independently selected from alkyl, halo, hydroxy, haloalkyl, alkoxy, haloalkoxy, keto, amino, nitro, and cyano; or $R^{38}$ is —CR$^{52}$R$^{53}$ wherein $R^{52}$ is alkoxycarbonyl, and $R^{53}$ is alkylthioalkylene; or $R^{37}$ and $R^{38}$ together with the nitrogen atom to which they are attached form a heterocycle; and $R^{39}$ and $R^{40}$ have the same definition as $R^{26}$ and $R^{27}$ in claim 1; or $R^2$ is —CR$^{54}$R$^{55}$ wherein $R^{54}$ is phenyl and $R^{55}$ is hydroxy; or $R^2$ is selected from the group consisting of

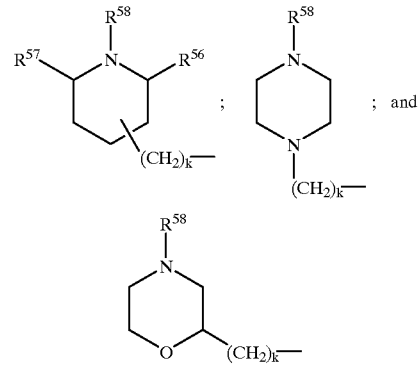

wherein
k is an integer from 0 to 3; and
$R^{56}$ is hydrogen or lower alkyl; and
$R^{57}$ is hydrogen or lower alkyl; or
$R^{56}$ and $R^{57}$ form a lower alkylene bridge; and R⁵⁸ is selected from hydrogen, alkyl, aralkyl, aryl, heterocyclyl, heterocyclylalkyl, alkoxycarbonyl, alkylsulfonyl, aralkylsulfonyl, arylsulfonyl, —C(O)R⁵⁹, —SO₂R⁶⁰, and —C(O)NHR⁶¹;

wherein R⁵⁹ is selected from alkyl, haloalkyl, cycloalkyl, aryl, heterocyclyl, alkylarylene, aralkyl, alkylheterocyclyl, alkoxy, alkenoxy, aralkoxy, alkoxyalkylene, alkoxyarylene, alkoxyaralkyl; wherein said aryl, heterocyclyl, and aralkyl groups are optionally substituted with one or more radicals independently selected from alkyl, halo, hydroxy, haloalkyl, alkoxy, haloalkoxy, keto, amino, nitro, and cyano; and wherein R⁶⁰ is selected from alkyl, aryl, heterocyclyl, alkylarylene, alkylheterocyclyl, aralkyl, heterocyclylheterocyclyl, alkoxyarylene, alkylamino, alkylaminoarylene, alkylsulfonylarylene, and arylsulfonylheterocyclyl; wherein said aryl, heterocyclyl, and aralkyl groups are optionally substituted with one or more radicals independently selected from alkyl, halo, hydroxy, haloalkyl, alkoxy, haloalkoxy, keto, amino, nitro, and cyano; and wherein R⁶¹ is selected from alkyl, aryl, alkylarylene, and alkoxyarylene; wherein said aryl group is optionally substituted with one or more radicals independently selected from alkyl, halo, hydroxy, haloalkyl, alkoxy, haloalkoxy, keto, amino, nitro, and cyano; and R³ is selected from pyridinyl, pyrimidinyl, quinolinyl, purinyl, and

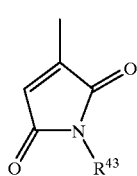

(IV)

wherein R⁴³ is selected from hydrogen, lower alkyl, lower aminoalkyl, lower alkoxyalkyl, lower alkenoxyalkyl and lower aryloxyalkyl; and wherein the R³ pyridinyl, pyrimidinyl, quinolinyl and purinyl groups are optionally substituted with one or more radicals independently selected from lower alkylthio, lower alkylsulfonyl, aminosulfonyl, halo, lower alkyl, lower aralkyl, lower phenylalkenyl, lower phenylheterocyclyl, carboxy, lower alkylsulfinyl, cyano, lower alkoxycarbonyl, aminocarbonyl, lower alkylcarbonylamino, lower haloalkyl, hydroxy, lower alkoxy, amino, lower cycloalkylamino, lower alkylamino, lower alkenylamino, lower alkynylamino, lower aminoalkyl, arylamino, lower aralkylamino, nitro, halosulfonyl, lower alkylcarbonyl, lower alkoxycarbonylamino, lower alkoxyphenylalkylamino, lower alkylaminoalkylamino, lower hydroxyalkylamino, lower heterocyclylamino, lower heterocyclylalkylamino, lower phenylalkylheterocyclylamino, lower alkylaminocarbonyl, lower alkoxyphenylalkylamino, hydrazinyl, lower alkylhydrazinyl, or —NR⁶²R⁶³ wherein R⁶² is lower alkylcarbonyl or amino, and R⁶³ is lower alkyl or lower phenylalkyl; and R⁴ is selected from hydrido, lower cycloalkyl, lower cycloalkenyl, aryl selected from phenyl, biphenyl, and naphthyl, and 5- or 6- membered heterocyclyl; wherein the lower cycloalkyl, lower cycloalkenyl, aryl and 5–10 membered heterocyclyl groups of R⁴ are optionally substituted with one or more radicals independently selected from lower alkylthio, lower alkylsulfonyl, lower alkylsulfinyl, halo, lower alkyl, lower alkynyl, lower alkoxy, lower aryloxy, lower aralkoxy, lower heterocyclyl, lower haloalkyl, amino, cyano, nitro, lower alkylamino, and hydroxy; or a pharmaceutically-acceptable salt or tautomer thereof.

A class of compounds of particular interest consists of these compounds of Formula I wherein R¹ is selected from hydrido, methyl, ethyl, propyl, isopropyl, tert-butyl, isobutyl, fluoromethyl, difluoromethyl, trifluoromethyl, chloromethyl, dichloromethyl, trichloroethyl, pentafluoroethyl, heptafluoropropyl, difluorochloromethyl, dichlorofluoromethyl, difluoroethyl, difluoropropyl, dichloroethyl, dichloropropyl, ethenyl, propenyl, ethynyl, propargyl, 1-propynyl, 2-propynyl, piperidinyl, piperazinyl, morpholinyl, benzyl, phenylethyl, morpholinylmethyl, morpholinylethyl, pyrrolidinylmethyl, piperazinylmethyl, piperidinylmethyl, pyridinylmethyl, thienylmethyl, methoxymethyl, ethoxymethyl, amino, methylamino, dimethylamino, phenylamino, methylaminomethyl, dimethylaminomethyl, methylaminoethyl, dimethylaminoethyl, ethylaminoethyl, diethylaminoethyl, cyclopropyl, cyclopentyl, cyclohexyl, cyclohexylmethyl, hydroxymethyl, hydroxyethyl, mercaptomethyl, and methylthiomethyl; and R² is selected from hydrido, chloro, fluoro, bromo, methyl, ethyl, propyl, isopropyl, tert-butyl, isobutyl, phenyl, biphenyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxymethyl, hydroxyethyl, pyridinyl, isothiazolyl, isoxazolyl, thienyl, thiazolyl, oxazolyl, pyrimidinyl, quinolyl, isoquinolinyl, imidazolyl, benzimidazolyl, furyl, pyrazinyl, piperidinyl, piperazinyl, morpholinyl, N-methylpiperazinyl, methoxycarbonylethyl, ethoxycarbonylethyl, N-methylamino, N,N-dimethylamino, N-ethylamino, N,N-diethylamino, N-n-propylamino, N,N-dimethylamino, N-methyl-N-phenylamino, N-phenylamino, piperadinylamino, N-benzylamino, N-propargylamino, cyclopropyl, cyclobutyl, cyclopentyl, cyclohexyl, cyclopropenyl, cyclobutenyl, cyclopentenyl, cyclohexenyl, cyclohexadienyl, aminomethyl, aminoethyl, aminoethylamino, aminopropylamino, N,N-dimethylaminoethylamino, N,N-dimethylaminopropylamino, morpholinylethylamino, morpholinylpropylamino, carboxymethylamino, methoxyethylamino, methoxycarbonyl, ethoxycarbonyl, propoxycarbonyl, 1,1-dimethylethoxycarbonyl, 1,1-dimethylethoxycarbonylaminoethylamino, 1,1-dimethylethoxycarbonylaminopropylamino, piperazinylcarbonyl, and 1,1-dimethylethoxycarbonylpiperazinylcarbonyl; wherein the aryl, heteroaryl, cycloalkyl and cycloalkenyl groups are optionally substituted with one or more radicals independently selected from fluoro, chloro, bromo, keto, methyl, ethyl, isopropyl, tert-butyl, isobutyl, benzyl, carboxy, methoxy, ethoxy, phenoxy, benzyloxy, trifluoromethyl, fluoromethyl, difluoromethyl, dimethylamino, methoxycarbonyl, ethoxycarbonyl, and 1,1-dimethylethylcarbonyl; or $R^2$ is —$CR^{54}R^{55}$ wherein $R^{54}$ is phenyl and $R^{55}$ is hydroxy; and $R^3$ is selected from pyridinyl, pyrimidinyl, and purinyl; wherein $R^3$ is optionally substituted with one or more radicals independently selected from methylthio, methylsulfinyl, methylsulfonyl, fluoro, chloro, bromo, aminosulfonyl, methyl, ethyl, isopropyl, tert-butyl, isobutyl, cyano, methoxycarbonyl, ethoxycarbonyl, aminocarbonyl, methylcarbonylamino, trifluoromethyl, difluoromethyl, fluoromethyl, trichloromethyl, dichloromethyl, chloromethyl, hydroxy, fluorophenylmethyl, fluorophenylethyl, chlorophenylmethyl, chlorophenylethyl, fluorophenylethenyl, chlorophenylethenyl, fluorophenylpyrazolyl, chlorophenylpyrazolyl, carboxy, methoxy, ethoxy, propyloxy, n-butoxy, methylamino, ethylamino, dimethylamino, diethylamino, 2-methylbutylamino, propargylamino, aminomethyl, aminoethyl, N-methyl-N-phenylamino, phenylamino, diphenylamino, benzylamino, phenethylamino, cyclopropylamino, nitro, chlorosulfonyl, amino, methylcarbonyl, methoxycarbonylamino, ethoxycarbonylamino, methoxyphenylmethylamino, N,N-dimethylaminoethylamino, hydroxypropylamino, hydroxyethylamino, imidazolylethylamino, morpholinylethylamino, (1-ethyl-2-hydroxy) ethylamino, piperidinylamino, pyridinylmethylamino, phenylmethylpiperidinylamino, phenylmethylamino, fluorophenylmethylamino, fluorophenylethylamino, methylaminocarbonyl, ethylaminocarbonyl, methylcarbonyl, methoxyphenylmethylamino, hydrazinyl, 1-methyl-hydrazinyl, or —$NR^{62}R^{63}$ wherein $R^{62}$ is methylcarbonyl or amino, and $R^{63}$ is methyl, ethyl or phenylmethyl; and $R^4$ is selected from hydrido, cyclopropyl, cyclobutyl, cyclopentyl, cyclohexyl, cyclopropylenyl, cyclobutenyl, cyclopentenyl, cyclohexenyl, cyclohexadienyl, phenyl, biphenyl, morpholinyl, pyrrolidinyl, piperazinyl, piperidinyl, pyridinyl, thienyl, isothiazolyl, isoxazolyl, thiazolyl, oxazolyl, pyrimidinyl, quinolyl, isoquinolinyl, imidazolyl, benzimidazolyl, furyl, pyrazinyl, dihydropyranyl, dihydropyridinyl, dihydrofuryl, tetrahydropyranyl, tetrahydrofuryl, benzofuryl, dihydrobenzofuryl, and benzodioxolyl; wherein the cycloalkyl, cycloalkenyl, aryl and heterocyclyl groups of $R^4$ are optionally substituted with one or more radicals independently selected from methylthio, methylsulfinyl, methylsulfonyl, fluoro, chloro, bromo, methyl, ethyl, isopropyl, tert-butyl, isobutyl, ethynyl, methoxy, ethoxy, phenoxy, benzyloxy, trifluoromethyl, fluoromethyl, difluoromethyl, amino, cyano, nitro, dimethylamino, and hydroxy; or a pharmaceutically-acceptable salt or tautomer thereof.

Another class of compounds of particular interest consists of these compounds of Formula I wherein $R^1$ is hydrido, methyl, ethyl, propargyl, hydroxyethyl, dimethylaminoethyl, diethylaminoethyl or morpholinylethyl;

$R^2$ is selected from hydrido, methyl, ethyl, propyl, phenyl, trifluoromethyl, methoxycarbonylethyl, N,N-dimethylamino, N-phenylamino, piperidinyl, piperazinyl, pyridinyl, N-methylpiperazinyl, and piperazinylamino; wherein the phenyl, piperidinyl, and pyridinyl groups are optionally substituted with one or more radicals independently selected from fluoro, chloro, bromo, methyl, ethyl, and trifluoromethyl;

$R^3$ is selected from pyridinyl, pyrimidinyl or quinolinyl; wherein $R^3$ is optionally substituted with one or more radicals independently selected from fluoro, bromo, methyl, cyano, methoxycarbonyl, aminocarbonyl, benzyl, phenethyl, acetyl, hydroxyl, methoxy, dimethylamino, benzylamino, phenethylamino, aminomethyl, amino, hydroxy, and methylcarbonyl;

$R^4$ is selected from phenyl, quinolyl, biphenyl, pyridinyl, thienyl, furyl, dihydropyranyl, benzofuryl, dihydrobenzofuryl, and benzodioxolyl; wherein the cycloalkyl, cycloalkenyl, aryl and heterocyclyl groups of $R^4$ are optionally substituted with one or more radicals independently selected from methylthio, fluoro, chloro, bromo, methyl, ethyl, methoxy, ethoxy, phenoxy, benzyloxy, trifluoromethyl, nitro, dimethylamino, and hydroxy; or a pharmaceutically-acceptable salt or tautomer thereof.

A class of compounds of specific interest consists of those compounds of Formula I wherein $R^1$ is hydrido or methyl;

$R^2$ is selected from hydrido, methyl or ethyl;

$R^3$ is selected from pyridinyl, pyrimidinyl or quinolinyl; wherein $R^3$ is optionally substituted with one or more radicals independently selected from fluoro, bromo, methyl, cyano, methoxycarbonyl, aminocarbonyl, benzyl, phenethyl, acetyl, hydroxyl, methoxy, dimethylamino, benzylamino, phenethylamino, aminomethyl, amino, hydroxy, and methylcarbonyl;

$R^4$ is selected from phenyl which is optionally substituted with one or more radicals independently selected from methylthio, fluoro, chloro, bromo, methyl, ethyl, methoxy, ethoxy, phenoxy, benzyloxy, trifluoromethyl, nitro, dimethylamino, and hydroxy; or a pharmaceutically-acceptable salt or tautomer thereof.

Still another class of compounds of particular interest consists of those compounds of Formula I wherein $R^1$ is selected from hydrido, methyl, ethyl, propyl, isopropyl, tert-butyl, isobutyl, fluoromethyl, difluoromethyl, trifluoromethyl, chloromethyl, dichloromethyl, trichloroethyl, pentafluoroethyl, heptafluoropropyl, difluorochloromethyl, dichlorofluoromethyl, difluoroethyl, difluoropropyl, dichloroethyl, dichloropropyl, ethenyl, propenyl, ethynyl, propargyl, 1-propynyl, 2-propynyl, piperidinyl, piperazinyl, morpholinyl, benzyl, phenylethyl, morpholinylmethyl, morpholinylethyl, pyrrolidinylmethyl, piperazinylmethyl, piperidinylmethyl, pyridinylmethyl, thienylmethyl, methoxymethyl, ethoxymethyl, amino, methylamino, dimethylamino, phenylamino, methylaminomethyl, dimethylaminomethyl, methylaminoethyl, dimethylaminoethyl, ethylaminoethyl, diethylaminoethyl, cyclopropyl, cyclopentyl, cyclohexyl, cyclohexylmethyl, hydroxymethyl, hydroxyethyl, mercaptomethyl, and methylthiomethyl; and $R^2$ has the formula:

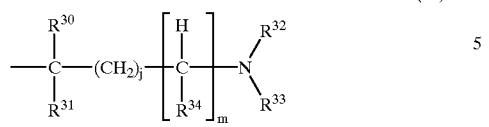

(III)

wherein:
j is 0, 1 or 2; and
m is 0; and
$R^{30}$ and $R^{31}$ are independently selected from hydrogen and lower alkyl;
$R^{32}$ is selected from hydrogen, lower alkyl, lower phenylalkyl, lower heterocyclylalkyl, lower alkoxyalkylene, aryloxyalkylene, aminoalkyl, lower alkylaminoalkyl, lower phenylaminoalkyl, lower alkylcarbonylalkylene, lower phenylcarbonylalkylene, and lower heterocyclylcarbonylaminoalkylene;
$R^{33}$ is selected from hydrogen, lower alkyl, —C(O)$R^{35}$, —C(O)O$R^{35}$, —SO$_2$$R^{36}$, —C(O)N$R^{37}$$R^{38}$, and —SO$_2$N$R^{39}$$R^{40}$;
wherein $R^{35}$ is selected from lower alkyl, lower cycloalkyl, lower haloalkyl, lower alkenyl, aryl selected from phenyl, biphenyl and naphthyl, lower heterocyclyl, lower phenylalkyl, lower phenylcycloalkyl, lower cycloalkenylalkylene, lower heterocyclylalkylene, lower alkylphenylene, lower alkylheterocyclyl, phenylphenylene, lower phenylheterocyclyl, lower alkoxy, lower alkenoxy, lower alkoxyalkylene, lower alkoxyphenylalkyl, lower alkoxyphenylene, lower phenoxyalkylene, lower phenylalkoxyalkylene, lower cycloalkyloxyalkylene, lower alkoxycarbonyl, lower heterocyclylcarbonyl, lower alkylcarbonyloxyalkylene, lower alkylcarbonyloxyphenylene, lower alkoxycarbonylalkylene, lower alkoxycarbonylphenylene, lower phenylalkoxycarbonylheterocyclyl, lower alkylcarbonylheterocyclyl, lower phenylcarbonyloxyalkylphenylene, and lower alkylthioalkylene; wherein said aryl selected from phenyl, biphenyl and naphthyl, lower heterocyclyl, lower phenylalkyl, lower alkylphenylene, lower phenylheterocyclyl, lower alkoxyphenylene, lower phenoxyalkylene, lower cycloalkoxyalkylene, lower alkoxycarbonylalkylene, and lower alkylcarbonylheterocyclyl groups are optionally substituted with one or more radicals independently selected from lower alkyl, halo, lower haloalkyl, lower alkoxy, lower haloalkoxy, keto, amino, nitro, and cyano; or
$R^{35}$ is CH$R^{48}$$R^{49}$ wherein $R^{48}$ is phenylsulfonylamino or lower alkylphenylsulfonylamino, and $R^{49}$ is selected from lower phenylalkyl, amino, lower alkylamino, and lower phenylalkylamino; or
$R^{35}$ is —N$R^{50}$$R^{51}$ wherein $R^{50}$ is lower alkyl, and $R^{51}$ is aryl selected from phenyl, biphenyl and naphthyl; and
wherein $R^{36}$ is selected from lower alkyl, lower haloalkyl, aryl selected from phenyl, biphenyl and naphthyl, lower heterocyclyl, lower cycloalkylalkylene, lower alkylphenylene, lower alkenylphenylene, phenylphenylene, lower phenylalkyl, lower phenylalkenyl, lower heterocyclylheterocyclyl, carboxyphenylene, lower alkoxyphenylene, lower alkoxycarbonylphenylene, lower alkylcarbonylaminophenylene, lower alkylcarbonylaminoheterocyclyl, lower phenylcarbonylaminoalkylheterocyclyl, lower alkylaminophenylene, lower alkylamino, lower alkylaminophenylene, lower alkylsulfonylphenylene, lower alkylsulfonylphenylalkyl, and lower phenylsulfonylheterocyclyl; wherein said aryl selected from phenyl, biphenyl and naphthyl, lower heterocyclyl, lower cycloalkylalkylene, lower phenylalkyl, lower alkylcarbonylaminoheterocyclyl, and lower alkylsulfonylphenylene groups are optionally substituted with one or more radicals independently selected from lower alkyl, halo, hydroxy, lower haloalkyl, lower alkoxy, lower haloalkoxy, keto, amino, nitro, and cyano; and
wherein $R^{37}$ is selected from hydrogen and lower alkyl; and
wherein $R^{38}$ is selected from hydrogen, lower alkyl, lower alkenyl, aryl selected from phenyl, biphenyl and naphthyl, lower heterocyclyl, lower phenylalkyl, lower alkylphenylene, lower phenylcycloalkyl, phenylphenylene, lower cycloalkylalkylene, lower heterocyclylalkylene, lower alkylheterocyclylalkylene, lower phenylalkylheterocyclyl, lower alkoxyalkylene, lower alkoxyphenylene, lower phenoxyphenylene, phenylcarbonyl, lower alkoxycarbonyl, lower alkoxycarbonylalkylene, lower alkoxycarbonylphenylene, lower alkylcarbonylcarbonylalkylene, lower alkylaminoalkylene, lower alkylaminophenylalkyl, lower alkylcarbonylaminoalkylene, lower alkylthiophenylene, lower alkylsulfonylphenylalkyl, and lower aminosulfonylphenylalkyl; wherein said aryl selected from phenyl, biphenyl and naphthyl, lower heterocyclyl, lower phenylalkyl, and lower heterocyclylalkylene groups are optionally substituted with one or more radicals independently selected from lower alkyl, halo, hydroxy, lower haloalkyl, lower alkoxy, lower haloalkoxy, keto, amino, nitro, and cyano; or
$R^{38}$ is —C$R^{52}$$R^{53}$ wherein $R_{52}$ is lower alkoxycarbonyl, and $R_{53}$ is lower alkylthioalkylene; or
$R^{37}$ and $R^{38}$ together with the nitrogen atom to which they are attached form a 4–8 membered ring heterocycle;
$R^{39}$ and $R^{40}$ have the same definition as $R^{26}$ and $R^{27}$ in claim 2; or
$R^2$ is selected from the group consisting of

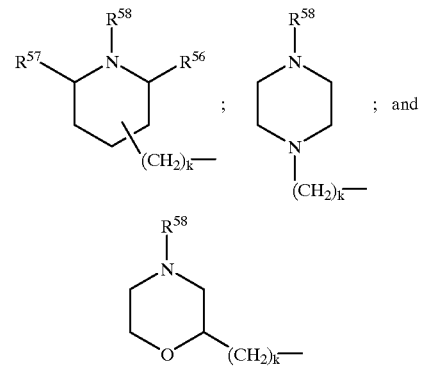

wherein
k is an integer from 0 to 2; and
$R^{56}$ is hydrogen or lower alkyl; and
$R^{57}$ is hydrogen or lower alkyl; and $R^{58}$ is selected from hydrogen, lower alkyl, lower phenylalkyl, aryl selected from phenyl, biphenyl and naphthyl, lower heterocyclyl, lower heterocyclylalkyl, lower alkoxycarbonyl, lower alkylsulfonyl, lower phenylalkylsulfonyl, lower phenylsulfonyl, —C(O) $R^{59}$, —SO$_2$R$^{60}$, and —C(O)NHR$^{61}$;

wherein $R^{59}$ is selected from lower alkyl, lower haloalkyl, lower cycloalkyl, aryl selected from phenyl, biphenyl and naphthyl, lower heterocyclyl, lower alkylphenylene, lower phenylalkyl, lower alkylheterocyclyl, lower alkoxy, lower alkenoxy, loewr phenylalkoxy, lower alkoxyalkylene, lower alkoxyphenylene, lower alkoxyphenylalkyl; wherein said aryl selected from phenyl, biphenyl and naphthyl, lower heterocyclyl, and lower phenylalkyl groups are optionally substituted with one or more radicals independently selected from lower alkyl, halo, hydroxy, lower haloalkyl, lower alkoxy, lower haloalkoxy, keto, amino, nitro, and cyano; and wherein $R^{60}$ is selected from lower alkyl, aryl selected from phenyl, biphenyl and naphthyl, lower heterocyclyl, lower alkylphenylene, lower alkylheterocyclyl, lower phenylalkyl, lower heterocyclylheterocyclyl, lower alkoxyphenylene, lower alkylamino, lower alkylaminophenylene, lower alkylsulfonylphenylene, and lower phenylsulfonylheterocyclyl; wherein said aryl selected from phenyl, biphenyl and naphthyl, lower heterocyclyl, and lower phenylalkyl groups are optionally substituted with one or more radicals independently selected from lower alkyl, halo, hydroxy, lower haloalkyl, lower alkoxy, lower haloalkoxy, keto, amino, nitro, and cyano; and wherein $R^{61}$ is selected from lower alkyl, aryl selected from phenyl, biphenyl and napthyl, lower alkylphenylene, and lower alkoxyphenylene; wherein said aryl group is optionally substituted with one or more radicals independently selected from lower alkyl, halo, hydroxy, lower haloalkyl, lower alkoxy, lower haloalkoxy, keto, amino, nitro, and cyano; and $R^3$ is selected from pyridinyl, pyrimidinyl, and purinyl; wherein $R^3$ is optionally substituted with one or more radicals independently selected from methylthio, methylsulfinyl, methylsulfonyl, fluoro, chloro, bromo, aminosulfonyl, methyl, ethyl, isopropyl, tert-butyl, isobutyl, cyano, methoxycarbonyl, ethoxycarbonyl, aminocarbonyl, methylcarbonylamino, trifluoromethyl, difluoromethyl, fluoromethyl, trichloromethyl, dichloromethyl, chloromethyl, hydroxy, fluorophenylmethyl, fluorophenylethyl, chlorophenylmethyl, chlorophenylethyl, fluorophenylethenyl, chlorophenylethenyl, fluorophenylpyrazolyl, chlorophenylpyrazolyl, carboxy, methoxy, ethoxy, propyloxy, n-butoxy, methylamino, ethylamino, dimethylamino, diethylamino, 2-methylbutylamino, propargylamino, aminomethyl, aminoethyl, N-methyl-N-phenylamino, phenylamino, diphenylamino, benzylamino, phenethylamino, cyclopropylamino, nitro, chlorosulfonyl, amino, methylcarbonyl, methoxycarbonylamino, ethoxycarbonylamino, methoxyphenylmethylamino, N,N-dimethylaminoethylamino, hydroxypropylamino, hydroxyethylamino, imidazolylethylamino, morpholinylethylamino, (1-ethyl-2-hydroxy) ethylamino, piperidinylamino, pyridinylmethylamino, phenylmethylpiperidinylamino, phenylmethylamino, fluorophenylmethylamino, fluorophenylethylamino, methylaminocarbonyl, ethylaminocarbonyl, methylcarbonyl, methoxyphenylmethylamino, hydrazinyl, 1-methyl-hydrazinyl, or —NR$^{62}$R$^{63}$ wherein $R^{62}$ is methylcarbonyl or amino, and $R^{63}$ is methyl, ethyl or phenylmethyl; and $R^4$ is selected from hydrido, cyclopropyl, cyclobutyl, cyclopentyl, cyclohexyl, cyclopropylenyl, cyclobutenyl, cyclopentenyl, cyclohexenyl, cyclohexadienyl, phenyl, biphenyl, morpholinyl, pyrrolidinyl, piperazinyl, piperidinyl, pyridinyl, thienyl, isothiazolyl, isoxazolyl, thiazolyl, oxazolyl, pyrimidinyl, quinolyl, isoquinolinyl, imidazolyl, benzimidazolyl, furyl, pyrazinyl, dihydropyranyl, dihydropyridinyl, dihydrofuryl, tetrahydropyranyl, tetrahydrofuryl, benzofuryl, dihydrobenzofuryl, and benzodioxolyl; wherein the cycloalkyl, cycloalkenyl, aryl and heterocyclyl groups of $R^4$ are optionally substituted with one or more radicals independently selected from methylthio, methylsulfinyl, methylsulfonyl, fluoro, chloro, bromo, methyl, ethyl, isopropyl, tert-butyl, isobutyl, ethynyl, methoxy, ethoxy, phenoxy, benzyloxy, trifluoromethyl, fluoromethyl, difluoromethyl, amino, cyano, nitro, dimethylamino, and hydroxy; or a pharmaceutically-acceptable salt or tautomer thereof.

Still another class of compounds of particular interest consists of those compounds of Formula I wherein $R^1$ is hydrido, methyl, ethyl, propargyl, hydroxyethyl, dimethylaminoethyl, diethylaminoethyl or morpholinylethyl;

$R^2$ has the formula:

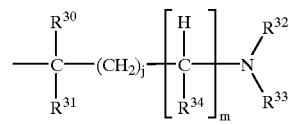

(III)

wherein:

j is 0, 1 or 2; and m is 0; and $R^{30}$ is hydrogen; and $R^{31}$ is selected from hydrogen and lower alkyl; and $R^{32}$ is selected from hydrogen and lower alkyl; and $R^{33}$ is selected from lower alkyl, —C(O)R$^{35}$, —C(O)OR$^{35}$, —SO$_2$R$^{36}$, —C(O)NR$^{37}$R$^{38}$, and —SO$_2$NR$^{39}$R$^{40}$;

wherein $R^{35}$ is selected from lower alkyl, lower cycloalkyl, phenyl, lower heterocyclyl, lower alkylphenylene, lower alkoxy, lower alkenoxy, lower alkoxyalkylene, lower phenoxyalkylene, and lower phenylalkoxyalkylene; wherein said phenyl and lower phenoxyalkylene groups are optionally substituted with one or more radicals independently selected from lower alkyl, halo, and lower haloalkyl; and wherein $R^{36}$ is selected from lower alkyl, phenyl, lower heterocyclyl, lower alkylphenylene, phenylphenylene, lower phenylalkyl, lower alkylheterocyclyl, lower heterocyclylheterocyclyl, lower alkoxyphenylene, and lower alkylamino; wherein said phenyl and lower heterocyclyl groups are optionally substituted with one or more radicals independently selected from lower alkyl, halo, hydroxy, lower haloalkyl, lower alkoxy, lower haloalkoxy, keto, amino, nitro, and cyano; and wherein $R^{37}$ is hydrogen; and wherein $R^{38}$ is selected from lower alkyl, phenyl, and lower alkylphenylene;

wherein $R^{39}$ and $R^{40}$ have the same definition as $R^{26}$ and $R^{27}$ in claim 2; or $R^2$ is selected from the group consisting of

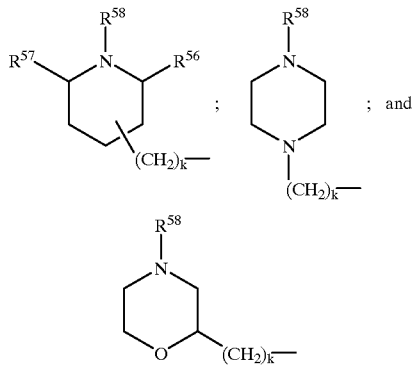

wherein k is an integer from 0 or 1; and $R^{56}$ is hydrogen; and $R^{57}$ is hydrogen; and $R^{58}$ is selected from —C(O)$R^{59}$ and —SO$_2$$R^{60}$;

wherein $R^{59}$ is selected from lower alkyl, lower cycloalkyl, phenyl, lower alkylphenylene, and lower alkoxyalkylene; wherein said phenyl group is optionally substituted with one or more radicals independently selected from lower alkyl, halo, hydroxy, lower haloalkyl, lower alkoxy, lower haloalkoxy, keto, amino, nitro, and cyano; and wherein $R^{60}$ is selected from lower alkyl; and $R^3$ is selected from pyridinyl, pyrimidinyl or quinolinyl; wherein $R^3$ is optionally substituted with one or more radicals independently selected from fluoro, bromo, methyl, cyano, methoxycarbonyl, aminocarbonyl, benzyl, phenethyl, acetyl, hydroxyl, methoxy, dimethylamino, benzylamino, phenethylamino, aminomethyl, amino, hydroxy, and methylcarbonyl; and $R^4$ is selected from phenyl, quinolyl, biphenyl, pyridinyl, thienyl, furyl, dihydropyranyl, benzofuryl, dihydrobenzofuryl, and benzodioxolyl; wherein the cycloalkyl, cycloalkenyl, aryl and heterocyclyl groups of $R^4$ are optionally substituted with one or more radicals independently selected from methylthio, fluoro, chloro, bromo, methyl, ethyl, methoxy, ethoxy, phenoxy, benzyloxy, trifluoromethyl, nitro, dimethylamino, and hydroxy; or a pharmaceutically-acceptable salt or tautomer thereof.

Still another class of compounds of specific interest consists of those compounds of Formula I wherein $R^1$ is hydrido or methyl; and $R^3$ is selected from pyridinyl, pyrimidinyl or quinolinyl; wherein $R^3$ is optionally substituted with one or more radicals independently selected from fluoro, bromo, methyl, cyano, methoxycarbonyl, aminocarbonyl, benzyl, phenethyl, acetyl, hydroxyl, methoxy, dimethylamino, benzylamino, phenethylamino, aminomethyl, amino, hydroxy, and methylcarbonyl; and $R^4$ is selected from phenyl which is optionally substituted with one or more radicals independently selected from methylthio, fluoro, chloro, bromo, methyl, ethyl, methoxy, ethoxy, phenoxy, benzyloxy, trifluoromethyl, nitro, dimethylamino, and hydroxy; or a pharmaceutically-acceptable salt or tautomer thereof.

In one embodiment of the present invention, the compounds of Formula I and/or 1A satisfy one or more of the following conditions:

$R^1$ is hydrido or lower alkyl; more preferably, $R^1$ is hydrido or methyl; and still more preferably, $R^1$ is hydrido;

$R^2$ is hydrido or lower alkyl; more preferably, $R^2$ is hydrido or methyl; and still more preferably, $R^2$ is hydrido;

$R^2$ comprises a piperidinyl, piperazinyl or cyclohexyl moiety;

$R^3$ is substituted or unsubstituted pyridinyl; and preferably, the pyridinyl is a 4-pyridinyl; or $R^4$ is substituted or unsubstituted phenyl; and preferably, $R^4$ is phenyl substituted with halo.

In addition, where $R^3$ is substituted pyrimidinyl, preferably at least one $R^3$ substitutent is attached to the carbon atom positioned between two nitrogen atoms of the pyrimidinyl ring.

A family of specific compounds of particular interest within Formula I and/or 1A consists of compounds, tautomers and pharmaceutically-acceptable salts thereof as follows:

4-[5-(3-fluoro-4-methoxyphenyl)-3-methyl-1H-pyrazol-4-yl]pyridine;

4-(3-methyl-5-phenyl-1H-pyrazol-4-yl)pyridine;

4-[5-methyl-3-(2-methylphenyl)-1H-pyrazol-4-yl]pyridine;

4-[3-(4-fluorophenyl)-5-methyl-1H-pyrazol-4-yl]pyridine;

4-[5-methyl-3-(4-methylphenyl)-1H-pyrazol-4-yl]pyridine;

4-[5-methyl-3-[4-(methylthio)phenyl]-1H-pyrazol-4-yl]pyridine;

4-[3-(4-chlorohpenyl)-5-methyl-1H-pyrazol-4-yl]pyridine;

4-[3-methyl-5-(3-methylphenyl)-1H-pyrazol-4-yl]pyridine;

4-[5-(2,5-dimethylphenyl)-3-methyl-1H-pyrazol-4yl]pyridine;

4-[5-(1,3-benzodioxol-5-yl)-3-methyl-1H-pyrazol-4-yl]pyridine;

4-[3-methyl-5-(4-phenoxyphenyl)-1H-pyrazol-4-yl]pyridine;

4-[5-[(1,1'-biphenyl)-4-yl]-3-methyl-1H-pyrazol-4-yl]pyridine;

4-[3-methyl-5-[3-(phenoxyphenyl)-1H-pyrazol-4-yl]pyridine;

4-[3-methyl-5-[3-(phenylmethoxy)phenyl]-1H-pyrazol-4-yl]pyridine;

4-[3-methyl-5-[2-(phenylmethoxy)phenyl]-1H-pyrazol-4-yl]pyridine;

2-[3-methyl-4-(4-pyridinyl)-1H-pyrazol-4-yl]phenol;

3-[3-methyl-4-(4-pyridinyl)-1H-pyrazol-4-yl]phenol;

1-hydroxy-4-(3-methyl-5-phenyl-1H-pyrazol-4-yl]pyridinium;

5-(4-fluorophenyl)-N,N-dimethyl-4-(4-pyridinyl)-1H-pyrazol-3-amine;

5-(4-fluorophenyl)-N-phenyl-4-(4-pyridinyl)-1H-pyrazol-3-amine;

4-[5-(4-fluorophenyl)-3-phenyl-1H-pyrazol-4-yl]pyridine;

4-[5-(3-methylphenyl)-3-(trifluoromethyl)-1H-pyrazol-4-yl]pyridine;

4-[3-(4-fluorophenyl)-4-(4-pyridinyl)-1H-pyrazol-5-yl]pyridine;

4-(5-cyclohexyl)-3-methyl-1H-pyrazol-4-yl)pyridine;

4-[5-(3-fluoro-5-methoxyphenyl)-3-methyl-1H-pyrazol-4-yl]pyridine;

4-[5-(3-methylphenyl)-3-propyl-1H-pyrazol-4-yl]pyridine;
4-[(3-methyl-5-phenyl-1H-pyrazol-4-yl)methyl]pyridine;
4-[3,5-bis(3-methylphenyl)-1H-pyrazol-4-yl]pyridine;
4-[4-methyl-2-(2-trifluorophenyl)-1H-pyrazol-4-yl]
pyridine;
4-[3-(2-chlorophenyl)-5-methyl-1H-pyrazol-4-yl]pyridine;
4-[5-methyl-3-(2,4-dimethylphenyl)-1H-pyrazol-4-yl]
pyridine;
4-[5-(4-chlorophenyl)-1,3-dimethyl-1H-pyrazol-4-yl]
pyridine;
4-[3-(3-fluoro-2-methylphenyl)-5-methyl-1H-pyrazol-4-yl]
pyridine;
4-[3-(3,5-dimethylphenyl)-5-methyl-1H-pyrazol-4-yl]
pyridine;
4-[3-(3,5-dimethoxyphenyl)-5-methyl-1H-pyrazol-4-yl]
pyridine;
4-[5-methyl-3-(3-nitrophenyl)-1H-pyrazol-4-yl]pyridine;
N,N-dimethyl-4-[5-methyl-4-(4-pyridinyl)-1H-pyrazol-3yl]
benzenamine;
4-[3-(2,3-dihydrobenzofuran-5-yl)-5-methyl-1H-pyrazol-4-
yl]pyridine;
4-[3-(4-bromophenyl)-5-methyl-1H-pyrazol-4-yl]pyridine;
4-[3-(2-fluorophenyl)-5-methyl-1H-pyrazol-4-yl]pyridine;
4-[3-(3-fluorophenyl)-5-methyl-1H-pyrazol-4-yl]pyridine;
4-[3-methyl-5-[3-(trifluoromethyl)phenyl]-1H-pyrazol-4-
yl]pyridine;
4-(3-ethyl-4-phenyl-1H-pyrazol-4-yl)pyridine;
4-[5-(3-methoxyphenyl)-3-methyl-1H-pyrazol-4-
yl}pyridine;
4-[3-ethyl-5-(3-methylphenyl)-1H-pyrazol-4-yl]pyridine;
4-[5-(3,4-difluorophenyl)-3-methyl-1H-pyrazol-4-yl]
pyridine;
4-[5-(3-ethoxyphenyl)-3-methyl-1H-pyrazol-4-yl]pyridine;
4-[3-methyl-5-[4-(trifluoromethyl)phenyl]-1H-pyrazol-4-
yl]pyridine;
4-[3-methyl-5-(3-thienyl)-1H-pyrazol-4-yl]pyridine;
4-[5-(2,4-dichlorophenyl)-3-methyl-1H-pyrazol-4-yl]
pyridine;
4-[5-(3-chlorophenyl)-3-methyl-1H-pyrazol-4-yl]pyridine;
4-[5-(3-chloro-4-methoxyphenyl)-3-methyl-1H-pyrazol-4-
yl]pyridine;
ethyl 3-(4-chlorophenyl)-4-(4-pyridinyl)-1H-pyrazole-5-
propanoate;
4-[3-(4-fluorophenyl)-1-methyl-pyrazol-4-yl]pyridine;
5-[5-(3-chlorophenyl)-3-methyl-1H-pyrazol-4-yl]
pyrimidin-2-amine;
5-[3-methyl-5-(3-methylphenyl)-1H-pyrazol-4-yl]
pyrimidin-2-amine;
5-[3-methyl-5-(2-methylphenyl)-1H-pyrazol-4-yl]
pyrimidin-2-amine;
5-[5-(4-chlorophenyl)-3-methyl-1H-pyrazol-4-yl]
pyrimidin-2-amine;
5-[5-(4-fluorophenyl)-3-methyl-1H-pyrazol-4-yl]
pyrimidin-2-amine;
5-[5-(4-methoxyphenyl)-3-methyl-1H-pyrazol-4-yl]
pyrimidin-2-amine;
5-[5-(3-chlorophenyl)-3-methyl-1H-pyrazol-4-yl]pyridin-2-
amine;
4-[5-(3-chlorophenyl)-3-methyl-1H-pyrazol-4-yl]pyridin-2-
amine;
4-[5-(3-methylphenyl)-3-methyl-1H-pyrazol-4-yl]pyridin-
2-amine;
4-[5-(2-methylphenyl)-3-methyl-1H-pyrazol-4-yl]pyridin-
2-amine;
4-[5-(4-chlorophenyl)-3-methyl-1H-pyrazol-4-yl]pyridin-2-
amine;
4-[5-(4-fluorophenyl)-3-methyl-1H-pyrazol-4-yl]pyridin-2-
amine;
4-[5-(4-methoxyphenyl)-3-methyl-1H-pyrazol-4-yl]
pyridin-2-amine;
5-[5-(3-chlorophenyl)-3-methyl-1H-pyrazol-4-yl]-2-
methoxypyridine;
2-methoxy-5-[3-methyl-5-(3-methylphenyl)-1H-pyrazol-4-
yl]pyridine;
2-methoxy-5-[5-(4-methoxyphenyl)-3-methyl-1H-pyrazol-
4-yl]pyridine;
4-[5-(3-chlorophenyl)-3-methyl-1H-pyrazol-4-yl]-2-
methoxypyridine;
2-methoxy-4-[3-methyl-5-(3-methylphenyl)-1H-pyrazol-4-
yl]pyridine;
2-methoxy-4-[3-methyl-5-(2-methylphenyl)-1H-pyrazol-4-
yl]pyridine;
4-[5-(4-chlorophenyl)-3-methyl-1H-pyrazol-4-yl]-2-
methoxypyridine;
4-[5-(4-fluorophenyl)-3-methyl-1H-pyrazol-4-yl-2-
methoxypyridine;
2-methoxy-4-[3-methyl-5-(4-methylphenyl)-1H-pyrazol-4-
yl]pyridine;
5-[5-(3-chlorophenyl)-3-methyl-1H-pyrazol-4-yl]pyridin-2-
ol;
4-[5-(3-chlorophenyl)-3-methyl-1H-pyrazol-4-yl]pyridin-2-
ol;
4-[5-(3-methylphenyl)-3-methyl-1H-pyrazol-4-yl]pyridin-
2-ol;
4-[5-(2-methylphenyl)-3-methyl-1H-pyrazol-4-yl]pyridin-
2-ol;
4-[5-(4-chlorophenyl)-3-methyl-1H-pyrazol-4-yl]pyridin-2-
ol;
4-[5-(4-fluorophenyl)-3-methyl-1H-pyrazol-4-yl]pyridin-2-
ol;
4-[5-(4-methoxyphenyl)-3-methyl-1H-pyrazol-4-yl]
pyridin-2-ol;
5-[5-(3-chlorophenyl)-3-methyl-1H-pyrazol-4-yl]pyridine-
2-methanamine;
4-[5-(3-chlorophenyl)-3-methyl-1H-pyrazol-4-yl]pyridine-
2-methanamine;
4-[5-(3-methylphenyl)-3-methyl-1H-pyrazol-4-yl]pyridine-
2-methanamine;
4-[5-(2-methylphenyl)-3-methyl-1H-pyrazol-4-yl]pyridine-
2-methanamine;
4-[5-(4-chlorophenyl)-3-methyl-1H-pyrazol-4-yl]pyridine-
2-methanamine;
4-[5-(4-fluorophenyl)-3-methyl-1H-pyrazol-4-yl]pyridine-
2-methanamine;
4-[5-(4-methoxyphenyl)-3-methyl-1H-pyrazol-4-yl]
pyridine-2-methanamine;
5-[5-(3-chlorophenyl)-3-methyl-1H-pyrazol-4-yl]pyridine-
2-carboxamide;
4-[5-(3-chlorophenyl)-3-methyl-1H-pyrazol-4-yl]pyridine-
2-carboxamide;
4-[5-(3-methylphenyl)-3-methyl-1H-pyrazol-4-yl]pyridine-
2-carboxamide;
4-[5-(2-methylphenyl)-3-methyl-1H-pyrazol-4-yl]pyridine-
2-carboxamide;
4-[5-(4-chlorophenyl)-3-methyl-1H-pyrazol-4-yl]pyridine-
2-carboxamide;
4-[5-(4-fluorophenyl)-3-methyl-1H-pyrazol-4-yl]pyridine-
2-carboxamide;
4-[5-(4-methoxyphenyl)-3-methyl-1H-pyrazol-4-yl]
pyridine-2-carboxamide;
4-[5-(3-fluoro-4-methoxyphenyl)-3-methyl-1H-pyrazol-4-
yl]pyridine;
4-[5-(4-fluoro-3-methoxyphenyl)-3-methyl-1H-pyrazol-4-
yl]pyridine;
4-[5-(4-chloro-3-methoxyphenyl)-3-methyl-1H-pyrazol-4-
yl]pyridine;

4-[5-(2,3-dihydrobenzofuran-6-yl)-3-methyl-1H-pyrazol-4-yl]pyridine;
4-[5-(benzofuran-6-yl)-3-methyl-1H-pyrazol-4-yl]pyridine;
4-[5-(3-fluoro-5-methoxyphenyl)-3-methyl-1H-pyrazol-4-yl]pyridine;
4-[5-(3-chloro-5-methoxyphenyl)-3-methyl-1H-pyrazol-4-yl]pyridine;
4-[5-(1-cyclohexyen-1-yl)-3-methyl-1H-pyrazol-4-yl]pyridine;
4-[5-(1,3-cyclohexadien-1-yl)-3-methyl-1H-pyrazol-4-yl]pyridine;
4-[5-(5,6-dihydro-2H-pyran-4-yl)-3-methyl-1H-pyrazol-4-yl]pyridine;
4-(5-cyclohexyl-3-methyl-1H-pyrazol-4-yl)pyridine;
4-[5-(4-methoxy-3-methylphenyl)-3-methyl-1H-pyrazol-4-yl]pyridine;
4-[5-(3-methoxy-4-methylphenyl)-3-methyl-1H-pyrazol-4-yl]pyridine;
4-[5-(3-methoxy-5-methylphenyl)-3-methyl-1H-pyrazol-4-yl]pyridine;
4-[5-(3-furyl)-3-methyl-1H-pyrazol-4-yl]pyridine;
2-methyl-4-(3-methyl-5-phenyl-1H-pyrazol-4-yl)pyridine;
2-methoxy-4-(3-methyl-5-phenyl-1H-pyrazol-4-yl)pyridine;
methyl 4-(3-methyl-5-phenyl-1H-pyrazol-4-yl)pyridine-2-carboxylate;
4-(3-methyl-5-phenyl-1H-pyrazol-4-yl)pyridine-2-carboxamide;
1-[4-(3-methyl-5-phenyl-1H-pyrazol-4-yl)pyridin-2-yl]ethanone;
N,N-dimethyl-4-(3-methyl-5-phenyl-1H-pyrazol-2-yl)pyridin-2-amine;
3-methyl-4-(3-methyl-5-phenyl-1H-pyrazol-4-yl)pyridine;
3-methoxy-4-(3-methyl-5-phenyl-1H-pyrazol-4-yl)pyridine;
methyl 4-(3-methyl-5-phenyl-1H-pyrazol-4yl)pyridine-3-carboxylate;
4-(3-methyl-5-phenyl-1H-pyrazol-4-yl)pyridine-3-carboxamide;
1-[4-(3-methyl-5-phenyl-1H-pyrazol-4-yl)pyridin-3-yl]ethanone;
3-bromo-4-(3-methyl-5-phenyl-1H-pyrazol-4-yl)pyridine;
N,N-dimethyl-4-(3-methyl-5-phenyl-1H-pyrazol-2-yl)pyridin-3-amine;
2-methyl-4-(3-methyl-5-phenyl-1H-pyrazol-4-yl)pyrimidine;
4-(3-methyl-5-phenyl-1H-pyrazol-4-yl)pyrimidine;
2-methoxy-4-(3-methyl-5-phenyl-1H-pyrazol-4-yl)pyrimidine;
4-(3-methyl-5-phenyl-1H-pyrazol-4-yl)pyrimidin-2-amine;
N,N-dimethyl-4-(3-methyl-5-phenyl-1H-pyrazol-4-yl)pyrimidin-2-amine;
4-(5,6-dihydro-2H-pyran-4-yl)-3-methyl-5-phenyl-1H-pyrazole;
3-methyl-5-phenyl-4-(3-thienyl)-1H-pyrazole;
4-(3-furyl)-3-methyl-5-phenyl-1H-pyrazole;
3-methyl-5-phenyl-4-(2-thienyl)-1H-pyrazole;
4-(2-furyl)-3-methyl-5-phenyl-1H-pyrazole;
4-(3-isothiazolyl)-3-methyl-5-phenyl-1H-pyrazole
4-(3-isoxazolyl)-3-methyl-5-phenyl-1H-pyrazole;
4-(5-isothiazolyl)-3-methyl-5-phenyl-1H-pyrazole;
4-(5-isoxazolyl)-3-methyl-5-phenyl-1H-pyrazole;
3-methyl-5-phenyl-4-(5-thiazolyl)-1H-pyrazole;
3-methyl-4-(5-oxazolyl)-5-phenyl-1H-pyrazole;
4-[3-(4-fluorophenyl)-1H-pyrazol-4-yl]pyridine;
2-methyl-4-[3-(3-methylphenyl)-1H-pyrazol-4-yl]pyridine;
4-(1-methyl-3-phenyl-1H-pyrazol-4-yl)pyridine;
4-(3-phenyl-1H-pyrazol-4-yl)pyridine;
2-methyl-4-(3-phenyl-1H-pyrazol-4-yl)pyridine;
4-[3-(3-chorophenyl)--methyl-pyrazol-4-yl]pyridine;
4-[3-(4-chlorophenyl)-1-methyl-pyrazol-4-yl]pyridine;
4-[3-(3-chlorophenyl)-1H-pyrazol-4-yl]pyridine;
4-[3-(4-chlorophenyl)-1H-pyrazol-4-yl]pyridine;
4-[3-(3-chlorophenyl)-1H-pyrazol-4-yl]-2-methylpyridine;
4-[3-(3-fluorophenyl)-1-methyl-1H-pyrazol-4-yl]pyridine;
4-[3-(3-fluorophenyl)-1H-pyrazol-4-yl]pyridine;
4-[3-(3-chlorophenyl)-1-methyl-pyrazol-4-yl]-2-methylpyridine;
5-(4-chlorophenyl)-N-phenyl-4-(4-pyridinyl)-1H-pyrazol-3-amine;
5-(4-chlorophenyl)-N-methyl-4-(4-pyridinyl)-1H-pyrazol-3-amine;
5-(4-chlorophenyl)-N,N-dimethyl-4-(4-pyridinyl)-1H-pyrazol-3-amine dihydrate;
5-(3-fluorophenyl)-N,N-dimethyl-4-(4-pyridinyl)-1H-pyrazol-3-amine;
N,N-dimethyl-5-(3-methylphenyl)-4-(4-pyridinyl)-1H-pyrazol-3-amine;
N-methyl-5-(3-methylphenyl)-4-(4-pyridinyl)-1H-pyrazol-3-amine;
N-ethyl-5-(3-methylphenyl)-4-(4-pyridinyl)-1H-pyrazol-3-amine;
N,N-diethyl-5-(3-methylphenyl)-4-(4-pyridinyl)-1H-pyrazol-3-amine;
5-(4-chlorophenyl)-N,N-diethyl-4-(4-pyridinyl)-1H-pyrazol-3-amine;
4-[5-(4-chlorophenyl)-4-(4-pyridinyl)-1H-pyrazol-3-yl]morpholine;
5-(4-chlorophenyl)-N-propyl-4-(4-pyridinyl)-1H-pyrazol-3-amine;
5-(4-chlorophenyl)-N-(phenylmethyl)-4-(4-pyridinyl)-1H-pyrazol-3-amine hydrate (2:1);
5-(4-chlorophenyl)-N-(2-methoxyethyl)-4-(4-pyridinyl)-1H-pyrazol-3-amine monohydrate;
1,1-dimethylethyl 4-[5-(4-chlorophenyl)-4-(4-pyridinyl)-1H-pyrazol-3-yl-1-piperazinecarboxylate;
1-[5-(4-chlorophenyl)-4-(4-pyridinyl)-1H-pyrazol-3-yl]piperazine trihydrochloride;
1-[5-(4-chlorophenyl)-4-(4-pyridinyl)-1H-pyrazol-3-yl]-4-methylpiperazine;
1,1-dimethylethyl 4-[5-(4-fluorophenyl)-4-(4-pyridinyl)-1H-pyrazol-3-yl]-1-piperazinecarboxylate;
1-[5-(4-fluorophenyl)-4-(4-pyridinyl)-1H-pyrazol-3-yl]piperazine trihydrochloride;
1-[5-(4-chlorophenyl)-4-(4-pyridinyl)-1H-pyrazol-3-yl]piperazine;
N-[5-(4-chlorophenyl)-4-[2-(phenylmethyl)aminol-4-pyridinyl]-1H-pyrazol-3-yl-1,3-propanediamine, trihydrochloride;
1-[5-(4-chlorophenyl)-4-(4-pyridinyl)-1H-pyrazol-3-yl)-4-(phenylmethyl)piperazine;
4-[3-(4-fluorophenyl)-5-(1-piperazinyl)-1H-pyrazol-4 -yl]pyrimidine, dihydrochloride;
1,1-dimethylethyl [3-[[5-(4-chlorophenyl)-4-(4-pyridinyl)-1H-pyrazol-3-yl]amino]propyl]carbamate;
N-[5-[4-chlorophenyl)-4-(4-pyridinyl)-1H-pyrazol-3-yl]-1,3-propanediamine, trihydrochloride monohydrate;
1,1-dimethylethyl [2-[[5-(4-chlorophenyl)-4-(4-pyridinyl)-1H-pyrazol-3-yl]amino]ethyl]carbamate;
1,1-dimethylethyl 4-[5-(4-chlorophenyl)-1-(2-hydroxyethyl)-4-(4-pyridinyl)-1H-pyrazol-3-yl]-1-piperazinecarboxylate;
1,1-dimethylethyl 4-[5-(4-fluorophenyl)-4-(4-pyrimidinyl)-1H-pyrazol-3-yl]-1-piperazinecarboxylate;

1,1-dimethylethyl [3-[[5-(4-chlorophenyl)-4-(2-fluoro-4-pyridinyl)-1H-pyrazol-3-yl]amino]propyl]carbamate;
1-[5-(4-chlorophenyl)-4-(4-pyridinyl)-1H-pyrazol-3-yl]-4-ethylpiperazine;
N-[5-(4-chlorophenyl)-4-(4-pyridinyl)-1H-pyrazol-3-yl]-1,2-ethanediamine;
4-[3-(2,6-difluorophenyl)-5-methyl-1H-pyrazol-4-yl]pyridine;
4-[3-(3-ethylphenyl)-5-methyl-1H-pyrazol-4-yl]pyridine;
4-[3-(3-chlorophenyl)-5-ethyl-1H-pyrazol-4-yl]pyridine;
4-[3-ethyl-5-(3-ethylphenyl)-1H-pyrazol-4-yl]pyridine;
4-[3-(4-chlorophenyl)-5-(1-methylethyl)-1H-pyrazol-4-yl]pyridine;
4-[3-cyclopropyl-5-(4-fluorophenyl)-1H-pyrazol-4-yl]pyridine;
4-[3-(4-fluorophenyl)-5-(trifluoromethyl)-1H-pyrazol-4-yl]pyridine;
4-[5-(cyclopropyl-3-(4-(fluorophenyl)-1-methyl-1H-pyrazol-4-yl]pyridine;
5-cyclopropyl-3-(4-fluorophenyl)-4-(4-pyridinyl)-1H-pyrazole-1-ethanol;
3-(4-fluorophenyl)-5-(2-methoxy-4-pyridinyl)-4-(4-pyridinyl)-1H-pyrazole-1-ethanol;
4-[3-(4-fluorophenyl)-1-(2-hydroxyethyl)-4-(4-pyridinyl)-1H-pyrazol-5-yl]-2(1H)-pyridinone;
1-acetyl-4-[3-(4-fluorophenyl)-1-(2-hydroxyethyl)-4-(4-pyridinyl)-1H-pyrazol-5-yl]-2(1H)-pyridinone;
Ethyl 2-[3-(4-fluorophenyl)-1-(2-hydroxyethyl)-4-(4-pyridinyl)-1H-pyrazol-5-yl]cyclopropanecarboxylate;
2-[3-(4-fluorophenyl)-1-(2-hydroxyethyl)-4-(4-pyridinyl)-1H-pyrazol-5-yl]cyclopropanecarboxylic acid;
3-(4-fluorophenyl)-5-(4-imidazolyl)-4-(4-pyridinyl)-1H-pyrazole-1-ethanol;
4-[3-(4-chloro-3-methylphenyl)-1H-pyrazol-4-yl]pyridine
5-(4-fluorophenyl)-4-(4-pyridinyl)-1H-pyrazole-3-carboxylic acid;
5-(4-fluorophenyl)-4-(4-pyridinyl)-1H-pyrazole-3-methanol;
1-[[5-(4-fluorophenyl)-4-(4-pyridinyl)-1H-pyrazol-3-yl]carbonyl]piperazine;
1,1-dimethylethyl 4-[[5-(4-fluorophenyl)-4-(4-pyridinyl)-1H-pyrazol-3-yl]carbonyl]-1-piperazinecarboxylate;
4-(1,5-dimethyl-3-phenyl-1H-pyrazol-4-yl)pyridine;
4-(1,3-dimethyl-5-phenyl-1H-pyrazol-4-yl)pyridine;
4-[3-(4-chlorophenyl)-1,5-dimethyl-1H-pyrazol-4-yl]pyridine;
4-[5-(4-chlorophenyl)-1,3-dimethyl-1H-pyrazol-4-yl]pyridine;
4-[5-ethyl-1-methyl-3-(3-methylphenyl)-1H-pyrazol-4-yl]pyridine;
4-[3-ethyl-1-methyl-5-(3-methylphenyl)-1H-pyrazol-4-yl]pyridine;
4-[3-(4-chlorophenyl)-1-ethyl-5-methyl-1H-pyrazol-4-yl]pyridine;
4-[3-(4-chlorophenyl)-2-ethyl-5-methyl-1H-pyrazol-4-yl]pyridine;
4-[3-(4-fluorophenyl)-1H-pyrazol-4-yl]pyridine;
4-[3-(2-chlorophenyl)-1H-pyrazol-4-yl]pyridine;
3-(4-fluorophenyl)-4-(4-pyridinyl)-1H-pyrazole-1-ethanol;
3-(4-fluorophenyl)-4-(4-pyrimidinyl)-1H-pyrazole-1-ethanol;
4-[3-(4-fluorophenyl)-1-methyl-1H-pyrazol-4-yl]pyridine;
2-[[4-[3-(4-fluorophenyl)-1H-pyrazol-4-yl]-2-pyridinyl]amino]-1-butanol;
4-[5-bromo-3-(4-fluorophenyl)-1-methyl-1H-pyrazol-4-yl]pyridine;
4-[3-(4-fluorophenyl)-1H-pyrazol-4-yl]-2-pyridinecarbonitrile;
4-[2-[3-(4-fluorophenyl)-4-(4-pyridinyl)-1H-pyrazol-1-yl]ethyl]morpholine;
3-(4-fluorophenyl)-1-methyl-α-phenyl-4-(4-pyridinyl)-1H-pyrazole-5-methanol;
N-(5-(4-fluorophenyl)-4-(4-pyridinyl)-1H-pyrazol-3-yl]-4-morpholineethanamine;
4-[3-(3-chlorophenyl)-1H-pyrazol-4-yl]-2(1H)-pyridinone hydrazone;
4-[3-(3-chlorophenyl)-1H-pyrazol-4-yl]-N-(phenylmethyl)-2-pyridinamine;
4-[3-(3-chlorophenyl)-1H-pyrazol-4-yl]-N-(phenylethyl)-2-pyridinamine;
4-[3-(3-chlorophenyl)-1H-pyrazol-4-yl]-N-ethyl-2-pyridinamine;
4-(3-(4-fluorophenyl)-1H-pyrazol-4-yl]-2-pyridinecarboxamide;
Methyl 4-[3-(4-fluorophenyl)-1H-pyrazol-4-yl]-2-pyridinecarboxylate;
4-[3-(4-fluorophenyl)-1H-pyrazol-4-yl]-N-methyl-2-pyridinecarboxamide;
4-[3-(4-fluorophenyl)-1H-pyrazol-4-yl]-2-pyridinecarboxylic acid;
4-[3-(3-fluorophenyl)-1H-pyrazol-4-yl]pyridine;
4-[3-(1,3-benzodioxol-5-yl)-1H-pyrazol-4-yl]pyridine4-[3-(3-fluorophenyl)-1-methyl-1H-pyrazol-4-yl]pyridine;
4-[3-(4-chlorophenyl)-1H-pyrazol-4-yl]pyridine;
4-[3-(1,3-benzodioxol-5-y)-1-methyl-1H-pyrazol-4-yl]pyridine;
4-[3-(4-chlorophenyl)-1-methyl-1H-pyrazol-4-yl]pyridine;
4-[3-(3-chlorophenyl)-1-methyl-1H-pyrazol-4-yl]-2-methylpyridine;
4-[5-(3-chlorophenyl)-1-methyl-1H-pyrazol-4-yl]-2-methyl]pyridine;
4-[3-(3-chlorophenyl)-1-methyl-1H-pyrazol-4-yl]pyridine;
4-[5-(3-chlorophenyl)-1-methyl-1H-pyrazol-4-yl]pyridine;
2-methyl-4-[1-methyl-3-(3-methylphenyl)-1H-pyrazol-4-yl]pyridine;
2-methyl-4-[1-methyl-5-(3-methylphenyl)-1H-pyrazol-4-yl]pyridine;
4-(3-phenyl-1H-pyrazol-4-yl)pyridine;
4-[3-[3-(trifluoromethyl)phenyl]-1H-pyrazol-4-yl]pyridine;
4-[1-methyl-3-[3-(trifluoromethyl)phenyl]-1H-pyrazol-4-yl]pyridine;
4-[3-(3,4-difluorophenyl)-1H-pyrazol-4-yl]pyridine;
4-[3-(4-chlorophenyl)-1H-pyrazol-4-yl]-2-fluoropyridine;
4-[3-(4-bromophenyl)-1H-pyrazol-4yl]pyridine;
4-[3-(3,4-difluorophenyl)-1-methyl-1H-pyrazol-4-yl]pyridine;
4-[3-(4-bromophenyl)-1-methyl-1H-pyrazol-4-yl]pyridine;
(E)-4-[3-(4-fluorophenyl)-1H-pyrazol-4-yl]-2-(2-phenylethenyl)pyridine;
(S)-4-[3-(4-chlorophenyl)-1H-pyrazol-4-yl]-N-(2-methylbutyl)-2-pyridinamine;
4-[3-(4-chlorophenyl)-1H-pyrazol-4-yl]-N-[(4-methoxyphenyl)methyl]-2-pyridinamine;
N-[4-[3-(4-chlorophenyl)-1H-pyrazol-4-yl]-2-pyridinyl]-2-pyridinemethanamine;
N-[4-[3-(4-fluorophenyl)-1H-pyrazol-4-yl]-2-pyridinyl]-2-pyridinemethanamine;
2-fluoro-4-[3-(4-fluorophenyl)-1H-pyrazol-4-yl]pyridine;
4-[3-(4-iodophenyl)-1H-pyrazol-4-yl]pyridine;
4-[3-(4-iodophenyl)-1-methyl-1H-pyrazol-4-yl]pyridine;
4-[1-methyl-3-[4-(trifluoromethyl)phenyl]-1H-pyrazol-4-yl]pyridine;
N-[1-(4-fluorophenyl)ethyl]-4-[3-(4-fluorophenyl)-1H-pyrazol-4-yl]-2-pyridinamine;
N-[(3-fluorophenyl)methyl]-4-[3-(4-fluorophenyl)-1H-pyrazol-4-yl]-2-pyridinamine;

4-[3-(4-fluorophenyl)-1-methyl-1H-pyrazol-4-yl]-2-(1-methylhydrazino)pyridine;
2-fluoro-4-[3-(4-fluorophenyl)-1-methyl-1H-pyrazol-4-yl]pyridine;
4-[3-(3,4-difluorophenyl)-1H-pyrazol-4-yl]-2-fluoro-pyridine;
4-[3-(4-fluorophenyl)-1H-pyrazol-4-yl-3-methyl]pyridine;
4-[3-(4-fluorophenyl)-1-methyl-1H-pyrazol-4-yl]-3-methyl-pyridine;
4-[3-(3,4-difluorophenyl)-1-methyl-1H-pyrazol-4-yl]-2-fluoropyridine;
3-(4-fluorophenyl)-N,N-dimethyl-4-(4-pyridinyl)-1H-pyrazole-1-ethanamine;
2-[2-(4-fluorophenyl)ethyl]-4-[3-(4-fluorophenyl)-1-methyl-1H-pyrazol-4-yl]pyridine;
4-[3-(4-fluorophenyl)-1H-pyrazol-4-yl]-N-[1-(phenylmethyl)-4-piperidinyl]-2-pyridinamine;
N'-[4-[3-(4-fluorophenyl)-1H-pyrazol-4-yl]-2-pyridinyl]-N,N-dimethyl-1,2-ethanediamine;
2,4-bis[3-(4-fluorophenyl)-1H-pyrazol-4-yl]pyridine;
N-[4-[3-(4-fluorophenyl)-1H-pyrazol-4-yl]-2-pyridinyl]-4-morpholineethanamine;
3-(4-fluorophenyl)-4-(2-fluoro-4-pyridinyl)-1H-pyrazole-1-ethanol;
4-[3-(4-fluorophenyl)-1H-pyrazol-4-yl]-N-[2-(1H-imidazol-1-yl)ethyl]-2-pyridinamine;
4-[2-[3-(4-fluorophenyl)-4-(2-fluoro-4-pyridinyl)-1H-pyrazol-1-yl]ethyl]morpholine;
(E)-3-(4-fluorophenyl)-4-[2-[2-(4-fluorophenyl)ethenyl]-4-pyridinyl]-1H-pyrazole-1-ethanol;
3-(4-fluorophenyl)-4-(2-fluoro-4-pyridinyl)-N,N-dimethyl-1H-pyrazole-1-ethanamine;
3-(4-fluorophenyl)-4-[2-[2-(4-fluorophenyl)ethyl]-4-pyridinyl]-1H-pyrazole-1-ethanol;
4-[1-[2-(dimethylamino)ethyl]-3-(4-fluorophenyl)-1H-pyrazol-4-yl]-N,N-dimethyl-2-pyridinamine;
4-[1-[2-(dimethylamino)ethyl]-3-(4-fluorophenyl)-1H-pyrazol-4-yl]-N-[(4-fluorophenyl)methyl]-2-pyridinamine;
3-(4-fluorophenyl)-4-[2-[2-(4-fluorophenyl)ethyl]-4-pyridinyl]-N,N-dimethyl-1H-pyrazole-1-ethanamine;
N-[(4-fluorophenyl)methyl]-4-[3(or 5)-(4-fluorophenyl)-1-[[2-(4-morpholinyl)ethyl]-1H-pyrazol-4-yl]-2-pyridinamine;
4-[3-(4-fluorophenyl)-1H-pyrazol-4-yl]-N-4-piperadinyl-2-pyridinamine;
N,N-diethyl-3-(4-fluorophenyl)-4-(2-fluoro-4-pyridinyl)-1H-pyrazole-1-ethanamine;
4-[1-[2-(diethylamino)ethyl]-3-(4-fluorophenyl)-1H-pyrazol-4-yl]-N-[(4-fluorophenyl)methyl]-2-pyridinamine;
2-[[4-[3-(4-(fluorophenyl)-1H-pyrazol-4-yl]-2-pyridinyl]amino]ethanol;
2-[[4-[3-(4-fluorophenyl)-1-methyl-1H-pyrazol-4-yl]-2-pyridinyl]amino]ethanol;
3-[[4-[3-(4-fluorophenyl)-1H-pyrazol-4-yl]-2-pyridinyl]amino]-1-propanol;
3-(4-fluorophenyl)-4-[2-[[(4-fluorophenyl)methyl]amino]-4-pyridinyl]-1H-pyrazole-1-ethanol;
5-(4-fluorophenyl)-4-[2-[[(4-fluorophenyl)methyl]amino]-4-pyridinyl]-1H-pyrazole-1-ethanol;
N,N-diethyl-3-(4-fluorophenyl)-4-(4-pyridinyl)-1H-pyrazole-1-ethanamine;
N-[(4-fluorophenyl)methyl]-4-[3-(4-fluorophenyl)-1-[2-(4-morpholinyl)ethyl]-1H-pyrazol-4-yl]-2-pyridinamine;
N-[5-(4-fluorophenyl)-4-(4-pyridinyl)-1H-pyrazol-3-yl]-4-morpholinepropanamine;

N'-[5-(4-fluorophenyl)-4-(4-pyridinyl)-1H-pyrazol-3-yl]-N,N-dimethyl-1,3-propanediamine;
5-(4-fluorophenyl)-N-2-propynyl-4-(4-pyridinyl)-1H-pyrazol-3-amine;
3-(4-fluorophenyl)-4-[2-[[(4-fluorophenyl)methyl]amino]-4-pyridinyl]-1H-pyrazole-1-ethanol;
5-(4-fluorophenyl)-4-[2-[[(4-fluorophenyl)methyl]amino]-4-pyridinyl]-1H-pyrazole-1-ethanol;
4-[3-[(4-fluorophenyl)-1H-pyrazol-4-yl]quinoline;
N-[5-(4-fluorophenyl)-4-(4-pyridinyl)-1H-pyrazol-3-yl] glycine methyl ester;
N-[5-(4-fluorophenyl)-4-(4-pyridinyl)-1H-pyrazol-3-yl] glycine;
4-[3-(4-fluorophenyl)-1-(2-propynyl)-1H-pyrazol-4-yl] pyridine;
4-[5-(4-fluorophenyl)-1-(2-propynyl)-1H-pyrazol-4-yl] pyridine;
4,4'-(1H-pyrazole-3,4-diyl)bis[pyridine];
4-[3-(3,4-dichlorophenyl)-1H-pyrazol-4-yl]pyridine;
N-[5-(4-chlorophenyl)-4-(4-pyridinyl)-1H-pyrazol-3-yl]-4-piperidinamine;
2-Chloro-4-[3-(4-fluorophenyl)-1H-pyrazol-4-yl]pyrimidine;
4-[3-(4-fluorophenyl)-1H-pyrazol-4-yl]-2 (1H)-pyrimidinone hydrazone;
4-[3-(4-fluorophenyl)-1H-pyrazol-4-yl]-N,N-dimethyl-2-pyrimidinamine;
4-[3-(4-fluorophenyl)-1H-pyrazol-4-yl]-N-methyl-2-pyrimidinamine;
4-[3-(4-fluorophenyl)-1H-pyrazol-4-yl]-N-(phenylmethyl)-2-pyrimidinamine;
N-cyclopropyl-4-[3-(4-fluorophenyl)-1H-pyrazol-4-yl]-2-pyrimidinamine;
4-[3-(4-fluorophenyl)-1H-pyrazol-4-yl]-N-[(4-methoxyphenyl)methyl]-2-pyrimidinamine;
4-[3-(4-fluorophenyl)-1H-pyrazol-4-yl]-2-pyrimidinamine;
N-[4-[3-(4-fluorophenyl)-1H-pyrazol-4-yl]-2-pyrimidinyl]-N-(phenylmethyl)acetamide;
Ethyl [4-[3-(4-fluorophenyl)-1H-pyrazol-4-yl]-2-pyrimidinyl]carbamate;
4-[3-(3-methylphenyl)-1H-pyrazol-4-yl]pyrimidine;
4-[3-(4-chlorophenyl)-1H-pyrazol-4-yl]pyrimidine;
4-[3-(3-fluorophenyl)-1H-pyrazol-4-yl]pyrimidine;
4-[3-(4-fluorophenyl)-1H-pyrazol-4-yl]pyrimidine;
1-[5-(4-chlorophenyl)-4-(4-pyridinyl)-1H-pyrazol-3-yl]-4-cyclopropylpiperazine;
1-[5-(4-fluorophenyl)-4-(4-pyridinyl)-1H-pyrazol-3-yl]-4-methylpiperazine, dihydrate;
methyl 4-[5-(4-chlorophenyl)-4-(4-pyridinyl)-1H-pyrazol-3-yl]-1-piperazinecarboxylate, monohydrate;
4-[5-(4-chlorophenyl)-4-(4-pyridinyl)-1H-pyrazol-3-yl]-γ-oxo-1-piperazinebutanoic acid, dihydrate;
4-[5-(4-chlorophenyl)-4-(4-pyridinyl)-1H-pyrazol-3-yl]-γ-oxo-1-piperazinebutanoic acid, monosodium salt dihydrate;
1-[5-(4-chlorophenyl)-4-(4-pyridinyl)-1H-pyrazol-3-yl]-4-(methylsulfonyl)piperazine, monohydrate;
1-[5-(4-chlorophenyl)-4-(4-pyridinyl)-1-(2-propynyl)-1H-pyrazol-3-yl]piperazine, trihydrochloride monohydrate;
4-[3-(4-fluorophenyl)-5-(1H-imidazol-4-yl)-1-(4-methoxyphenyl)-1H-pyrazol-4-yl]pyridine;
4-[3-(4-fluorophenyl)-1H-pyazol-4-yl]-N-2-propynyl-2-pyrimidinamine;
N-(2-fluorophenyl)-4-[3-(4-fluorophenyl)-1H-pyrazol-4-yl]-2-pyrimidinamine;
4-[3-(4-fluorophenyl)-1H-pyrazol-4-yl]-N-(2-methoxyphenyl)-2-pyrimidinamine;

1-[5-(3-chlorophenyl)-4-(4-pyridinyl)-1H-pyrazol-3-yl]-4-methylpiperazine;
N-[5-(4-fluorophenyl)-4-(4-pyridinyl)-1H-pyrazol-3-yl]-4-piperidinamine, trihydrochloride;
N-[5-(4-fluorophenyl)-4-(pyridinyl)-1H-pyrazol-3-yl]-1-methyl-4-piperidinamine;
ethyl 4-[[5-(4-fluorophenyl)-4-(4-pyridinyl)-1H-pyrazol-3-yl]amino]-1-piperidinecarboxylate, monohydrate;
1-[5-(4-chlorophenyl)-4-(4-pyridinyl)-1H-pyrazol-3-yl]-4-(2-methoxyphenyl)piperazine;
1-[5-(4-chlorophenyl)-4-(4-pyridinyl)-1H-pyrazol-3-yl]-4-phenylpiperazine;
N-[5-(4-chlorophenyl)-4-(4-pyridinyl)-1H-pyrazol-3-yl]-1-methyl-4-piperidinamine;
1-[5-(4-chlorophenyl)-4-(4-pyridinyl)-1H-pyrazol-3-yl]-4-(2-propynyl)piperazine;
1-[5-(4-chlorophenyl)-4-(4-pyridinyl)-1H-pyrazol-3-yl]piperazine;
1,1-dimethylethyl [3-[[5-(4-chlorophenyl)-4-(2-[(phenylmethyl)amino]-4-pyridinyl-1H-pyrazol-3-yl]amino]propyl]carbamate;
1,1-dimethylethyl 4-[5-(4-chlorophenyl)-4-(2-fluoro-4-pyridinyl)-1H-pyrazol-3-yl]-1-piperazinecarboxylate;
ethyl 4-[[5-(4-chlorophenyl)-4-(4-pyridinyl)-1H-pyrazol-3-yl]amino]-1-piperidinecarboxylate;
1-(4-chlorophenyl)-2-(1,3-dithietan-2-ylidene)-2-(4-pyridinyl)ethanone;
4-[3-(4-fluorophenyl)-5-[(1-methyl-4-piperidinyl)methyl]-1H-pyrazol-4-yl]pyridine;
1,1-dimethylethyl 4-[[5-(4-fluorophenyl)-4-(4-pyridinyl)-1H-pyrazol-3-yl]carbonyl]-1-piperazinecarboxylate;
1-[[5-(4-fluorophenyl)-4-(4-pyridinyl)-1H-pyrazol-3-yl]methyl]-4-methylpiperazine;
1-[[5-(4-fluorophenyl)-4-(4-pyridinyl)-1H-pyrazol-3-yl]methyl]-4-piperazine;
4-[3-(4-fluorophenyl)-5-(4-piperidinylmethyl)-1H-pyrazol-4-yl]pyridine;
N-[5-(4-chlorophenyl)-4-(4-pyridinyl)-3H-pyrazol-3-yl]-4-piperidineamine, trihydrochloride, monohydrate;
N-[5-(4-chlorophenyl)-4-(4-pyridinyl)-1H-pyrazol-3-yl]-4-N,1-dimethyl-4-piperidinamine, dihydrate
1-[2-[5-(4-chlorophenyl)-4-(4-pyridinyl)-1H-pyrazol-3-yl]ethyl]piperazine;
1-[2-[5-(4-chlorophenyl)-4-(4-pyridinyl)-1H-pyrazol-3-yl]ethyl]-4-methylpiperazine;
1-[2-[5-(4-fluorophenyl)-4-(4-pyridinyl)-1H-pyrazol-3-yl]ethyl]piperazine;
1-[2-[5-(4-fluorophenyl)-4-(4-pyridinyl)-1H-pyrazol-3-yl]ethyl]-4-methylpiperazine;
1-[[5-(4-chlorophenyl)-4-(4-pyridinyl)-1H-pyrazol-3-yl]methyl]piperazine;
1-[[5-(4-chlorophenyl)-4-(4-pyridinyl)-1H-pyrazol-3-yl]methyl]-4-methylpiperazine;
4-[5-(4-chlorophenyl)-4-(4-pyridinyl)-1H-pyrazol-3-yl]-1-piperazineethanol;
4-[5-(4-chlorophenyl)-4-(4-pyridinyl)-1H-pyrazol-3-yl]-1-piperazineethanamine;
4-[5-[4-fluorophenyl)-4-(4-pyridinyl)-1H-pyrazol-3-yl]-1-piperazineethanol;
4-[5-(4-fluorophenyl)-4-(4-pyridinyl)-1H-pyrazol-3-yl]-1-piperazineethanamine;
1-[5-(4-chlorophenyl)-4-(4-pyridinyl)-1H-pyrazol-3-yl]-3,5-dimethylpiperazine;
4-[5-(4-chlorophenyl)-4-(4-pyridinyl)-1H-pyrazol-3-yl]-1,2,6-trimethylpiperazine;
1-[5-(4-fluorophenyl)-4-(4-pyridinyl)-1H-pyrazol-3-yl]-3,5-dimethylpiperazine;
4-[5-(4-fluorophenyl)-4-(4-pyridinyl)-1H-pyrazol-3-yl]-1,2,6-trimethylpiperazine;
1-[5-(4-chlorophenyl)-4-(4-pyridinyl)-1H-pyrazol-3-yl]-3-methylpiperazine;
4-[5-(4-chlorophenyl)-4-(4-pyridinyl)-1H-pyrazol-3-yl]-1,2-dimethylpiperazine;
1-[5-(4-fluorophneyl)-4-(4-pyridinyl)-1H-pyrazol-3-yl]-3-methylpiperazine;
4-[5-(4-fluorophenyl)-4-(4-pyridinyl)-1H-pyrazol-3-yl]-1,2-dimethylpiperazine;
5-(4-chlorophenyl)-4-(4-pyridinyl)-N-3-pyrrolidinyl-1H-pyrazol-3-amine;
5-(4-chlorophenyl)-N-(1-methyl-3-pyrrolidinyl)-4-(4-pyridinyl)-1H-pyrazol-3-amine;
5-(4-fluorophenyl)-4-(4-pyridinyl)-N-3-pyrrolidinyl-1H-pyrazol-3-amine;
5-(4-fluorophenyl)-N-(1-methyl-3-pyrrolidinyl)-4-(4-pyridinyl)-1H-pyrazol-3-amine;
1-[5-(4-chlorophenyl)-4-(4-pyridinyl)-1H-pyrazol-3-yl]-3-pyrrolidinamine;
1-[5-(4-chlorophenyl)-4-(4-pyridinyl)-1H-pyrazol-3-yl]-N,N-dimethyl-3-pyrrolidinamine;
1-[5-(4-fluorophenyl)-4-(4-pyridinyl)-1H-pyrazol-3-yl]-3-pyrrolidinamine;
1-[5-(4-fluorophenyl)-4-(4-pyridinyl)-1H-pyrazol-3-yl]-N,N-dimethyl-3-pyrrolidinamine;
5-(4-chlorophenyl)-N-[(1-ethyl-2-pyrrolidinyl)methyl]-4-(4-pyridinyl)-1H-pyrazol-3-amine;
5-(4-fluorophenyl)-N-[(1-ethyl-2-pyrrolidinyl)methyl]-4-(4-pyridinyl)-1H-pyrazol-3-amine;
N-[5-(4-chlorophenyl)-4-(4-pyridinyl)-1H-pyrazol-3-yl]-3-piperidinamine;
N-[5-(4-chlorophenyl)-4-(4-pyridinyl)-1H-pyrazol-3-yl]-1-methyl-3-piperidinamine;
N-[5-(4-fluorophenyl)-4-(4-pyridinyl)-1H-pyrazol-3-yl]-3-piperidinamine;
N-[5-(4-fluorophenyl)-4-(4-pyridinyl)-1H-pyrazol-3-yl]-1-methyl-3-piperidinamine;
4-[5-(4-chlorophenyl)-4-(4-pyridinyl)-1H-pyrazol-3-yl]-2-piperazinemethanol;
4-[5-(4-chlorophenyl)-4-(4-pyridinyl)-1H-pyrazol-3-yl]-2-piperazinemethanamine;
4-[5-(4-chlorophenyl)-4-(4-pyridinyl)-1H-pyrazol-3-yl]-1-methyl-2-piperazinemethanol;
4-[5-(4-chlorophenyl)-4-(4-pyridinyl)-1H-pyrazol-3-yl]-1-methyl-2-piperazinemethanamine;
4-[5-(4-fluorophenyl)-4-(4-pyridinyl)-1H-pyrazol-3-yl]-2-piperazinemethanol;
4-[5-(4-fluorophenyl)-4-(4-pyridinyl)-1H-pyrazol-3-yl]-2-piperazinemethanamine;
4-[5-(4-fluorophenyl)-4-(4-pyridinyl)-1H-pyrazol-3-yl]-1-methyl-2-piperazinemethanol;
4-[5-(4-fluorophenyl)-4-(4-pyridinyl)-1H-pyrazol-3-yl]-1-methyl-2-piperazinemethanamine;
4-[3-(4-chlorophenyl)-5-(4-methyl-1-piperazinyl)-1H-pyrazol-4-yl]-N-methyl-2-pyrimidinamine;
4-[3-(4-fluorophenyl)-5-(4-methyl-1-piperazinyl)-1H-pyrazol-4-yl]-N-methyl-2-pyrimidinamine;
1-[[5-(4-chlorophenyl)-4-(4-pyridinyl)-1H-pyrazol-3-yl]methyl]-4-piperidinol;
1-[[5-(4-fluorophenyl)-4-(4-pyridinyl)-1H-pyrazol-3-yl]methyl]-4-piperidinol;
4-[3-(4-chlorophenyl)-5-(4-methyl-1-piperazinyl)-1H-pyrazol-4-yl]pyrimidine;
4-[3-(4-fluorophenyl)-5-(4-methyl-1-piperazinyl)-1H-pyrazol-4-yl]pyrimidine;
4-[5-(4-chlorophenyl)-4-(4-pyridinyl)-1H-pyrazol-3-yl]-2-piperazinecarboxylic acid;

ethyl 4-[5[-(4-chlorophenyl)-4-(4-pyridinyl)-1H-pyrazol-3-yl]-2-piperazinecarboxylate;
4-[5-(4-chlorophenyl)-4-(4-pyridinyl)-1H-pyrazol-3-yl-1-methyl-2-piperazinecarboxylic acid;
ethyl 4-[5-(4-chlorophenyl)-4-(4-pyridinyl)-1H-pyrazol-3-yl]-1-methyl-2-piperazinecarboxylate;
4-[5-(4-chlorophenyl)-4-(4-pyridinyl)-1H-pyrazol-3-yl]-1-methyl-2-piperazinecarboxamide;
4-[5-(4-chlorophenyl)-4-(4-pyridinyl)-1H-pyrazol-3-yl]-2-piperazinecarboxamide;
4-[5-(4-fluorophenyl)-4-(4-pyridinyl)-1H-pyrazol-3-yl]-2-piperazinecarboxylic acid;
ethyl 4-[5-(4-fluorophenyl)-4-(4-pyridinyl)-1H-pyrazol-3-yl]-2-piperazinecarboxylate;
4-[5-(4-fluorophenyl)-4-(4-pyridinyl)-1H-pyrazol-3-yl]-2-piperazinecarboxamide;
4-[5-(4-fluorophenyl)-4-(4-pyridinyl)-1H-pyrazol-3-yl]-1-methyl-2-piperazinecarboxylic acid;
ethyl 4-[5-(4-fluorophenyl)-4-(4-pyridinyl)-1H-pyrazol-3-yl]-1-methyl-2-piperazinecarboxylate;
4-[5-(4-fluorophenyl)-4-(4-pyridinyl)-1H-pyrazol-3-yl]-1-methyl-2-piperazinecarboxamide;
N-[5-(4-chlorophenyl)-4-(4-pyridinyl)-1H-pyrazol-3-yl]-1-ethyl-4-piperidinamine;
N-[5-(4-chlorophenyl)-4-(4-pyridinyl)-1H-pyrazol-3-yl]-1-(phenylmethyl)-4-piperidinamine;
1-acetyl-N-[5-(4-chlorophenyl)-4-(4-pyridinyl)-1H-pyrazol-3-yl]-4-piperidinamine;
N-[5-(4-chlorophenyl)-4-(4-pyridinyl)-1H-pyrazol-3-yl]-1-(2-propynyl)-4-piperidinamine;
N-[5-(4-chlorophenyl)-4-(4-pyridinyl)-1H-pyrazol-3-yl]-1-cyclopropyl-4-piperidinamine;
N-[5-(4-chlorophenyl)-4-(4-pyridinyl)-1H-pyrazol-3-yl]-1-(methoxyacetyl)-4-piperidinamine;
N-[5-(4-chlorophenyl)-4-(4-pyridinyl)-1H-pyrazol-3-yl]-1-(methylethyl)-4-piperidinamine;
N-[5-(4-chlorophenyl)-4-(4-pyridinyl)-1H-pyrazol-3-yl]-1-propyl-4-piperidinamine;
ethyl 4-[[5-(4-chlorophenyl)-4-(4-pyridinyl)-1H-pyrazol-3-yl]amino]-1-piperidinecarboxylate;
5-(4-fluorophenyl)-N-methyl-N-2-propynyl-4-(4-pyridinyl)-1H-pyrazol-3-amine;
(βR)-β-[[4-[3-(4-fluorophenyl)-1H-pyrazol-4-yl]-2-pyridinyl]amino]benzene ethanol;
(βS)-β-[[4-[3-(4-fluorophenyl)-1H-pyrazol-4-yl]-2-pyridinyl]amino]benzene propanol;
(βS)-β-[[4-[3-(4-fluorophenyl)-1H-pyrazol-4-yl]-2-pyridinyl]amino]benzene ethanol;
(βR)-β-[[4-[3-(4-fluorophenyl)-1H-pyrazol-4-yl]-2-pyridinyl]amino]benzene propanol;
N-[2-(1-ethyl-2-piperidinyl)ethyl]-4-[3-(4-fluorophenyl)-1H-pyrazol-4-yl]-2-pyridinamine;
N2,N2-diethyl-N1-[4-[3-(4-fluorophenyl)-1H-pyrazol-4-yl]-2-pyridinyl]-1-phenyl-1,2-ethanediamine;
N-(1-ethyl-4-piperidinyl)-4-[3-(4-fluorophenyl)-1H-pyrazol-4-yl]-2-pyridinamine;
4-[3-(4-fluorophenyl)-1H-pyrazol-4-yl]-N-(4-piperidinylmethyl)-2-pyridinamine;
2-[[4-[3-(4-fluorophenyl)-1H-pyrazol-4-yl]-2-pyridinyl]amino]-3-methyl-1-butanol;
(2S)-2-[[4-[3-(4-fluorophenyl)-1H-pyrazol-4-yl]-2-pyridinyl]amino]-4-methyl-1-pentanol;
N1,N1-diethyl-N4-[4-[3-(4-fluorophenyl)-1H-pyrazol-4-yl]-2-pyrimidinyl]-1,4-pentanediamine;
(2R)-1-[[4-[3-(4-fluorophenyl)-1H-pyrazol-4-yl]-2-pyridinyl]amino]-2-propanol;
N4-[4-[3-(4-chlorophenyl)-1H-pyrazol-4-yl]-2-pyridinyl]-N1,N1-diethyl-1,4-pentanediamine;
(2S)-1-[[4-[3-(4-fluorophenyl)-1H-pyrazol-4-yl]-2-pyridinyl]amino]-2-propanol;
1-[5-(3,4-dichlorophenyl)-4-(4-pyridinyl)-1H-pyrazol-3-yl]-4-methylpiperazine;
4-[3-(4-fluorophenyl)-1H-pyrazol-4-yl]-N-[2-(1-piperidinyl)ethyl]-2-pyridinamine;
N,N-diethyl-N'-[4-[3-(4-fluorophenyl)-1H-pyrazol-4-yl]-2-pyridinyl]-1,2-ethanediamine;
4-[3-(4-fluorophenyl)-1-(2-propenyl)-1H-pyrazol-4-yl]pyridine, monohydrochloride;
8-[5-(4-fluorophenyl)-4-(4-pyridinyl)-1H-pyrazol-3-yl]-1,4-dioxa-8-azaspiro[4.5]decane;
1-[5-(4-fluorophenyl)-4-(4-pyridinyl)-1H-pyrazol-3-yl]-4-piperidinone;
1-[5-(4-fluorophenyl)-4-(4-pyridinyl)-1H-pyrazol-3-yl]-4-piperidinol;
1-[5-(4-fluorophenyl)-4-(4-pyridinyl)-1H-pyrazol-3-yl]-1,2,3,6-hexahydropyridine;
1-[5-(4-fluorophenyl)-4-(4-pyridinyl)-1H-pyrazol-3-yl]-N,N-dimethyl-4-piperidinamine, trihydrochloride;
1-[5-(4-fluorophenyl)-4-(4-pyridinyl)-1H-pyrazol-3-yl]-4-piperidinamine, trihydrochloride;
4-[3-(4-fluorophenyl)-5-(4-(1-pyrrolidinyl)-1-piperidinyl]-1H-pyrazol-4-yl]pyridine, trihydrochloride;
ethyl 4-[[4-[3-(4-fluorophenyl)-1H-pyrazol-4-yl]-2-pyridinyl]amino]-1-piperidinecarboxylate;
1-methyl-4-[5-phenyl-4-(4-pyridinyl)-1H-pyrazol-3-yl]piperazine;
1-[5-(3,4-difluorophenyl)-4-(4-pyridinyl)-1H-pyrazol-3-yl]-4-methylpiperazine;
4-[5-(4-fluorophenyl)-4-(4-pyridinyl)-1H-pyrazol-3-yl]morpholine;
N1,N1-diethyl-N4-[4-[3-(4-fluorophenyl)-1H-pyrazol-4-yl]-2-pyridinyl]-1,4-pentanediamine;
4-[3-(4-fluorophenyl)-1H-pyrazol-4-yl]-N-[3-(2-methyl-1-piperidinyl)propyl]-2-pyridinamine;
ethyl 4-(5-phenyl-4-(4-pyridinyl)-1H-pyrazol-3-yl]-1-piperazinecarboxylate;
N,N-diethyl-N'-[5-(4-fluorophenyl)-4-(4-pyridinyl)-1H-pyrazol-3-yl]-1,3-propanediamine;
N1,N1,-diethyl-N4-[5-(4-fluorophenyl)-4-(4-pyridinyl)-1H-pyrazol-3-yl]-1,4-pentanediamine;
N-[4-[3-(4-fluorophenyl)-1H-pyrazol-4-yl]-2-pyridinyl]-4-methyl-1-piperazinepropanamine(2E)-2-butenedioate (1:1);
N-(2-[1,4'-bipiperidin]-1'-ylethyl)-4-[3-(4-fluorophenyl)-1H-pyrazol-4-yl]-2-pyridinamine;
N-[2-[[4-[3-(4-fluorophenyl)-1H-pyrazol-4-yl-2-pyridinyl]amino]ethyl]-N,N',N'-trimethyl-1,3-propanediamine;
N,N,N"-triethyl-N'-[2-[[4-[3-(4-fluorophenyl)-1H-pyrazol-4-yl]-2-pyridinylamino]ethyl]-1,3-propanediamine;
3-[[4-[3-(4-fluorophenyl)-1H-pyrazol-4-yl]-2-pyridinyl]amino]-1,2-propanediol;
trans-4-[[4-[3-(4-fluorophenyl)-1H-pyrazol-4-yl]-2-pyridinyl]amino]cyclohexanol;
4-[[4-[3-(4-fluorophenyl)-1H-pyrazol-4-yl]-2-pyridinyl]amino]cyclohexanone; and
1-[5-(4-fluorophenyl)-4-(4-pyridinyl)-1H-pyrazol-3-yl]-N,N-diethyl-4-piperidinamine, trihydrochloride.

Within Formula I there is another subclass of compounds of high interest represented by Formula IX:

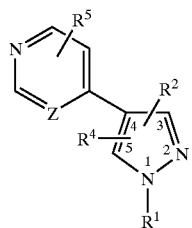

(IX)

wherein
Z represents a carbon atom or a nitrogen atom; and
$R^1$ is selected from hydrido, lower alkyl, lower hydroxyalkyl, lower alkynyl, lower heterocycyl, lower aralkyl, lower aminoalkyl and lower alkylaminoalkyl; and
$R^2$ is selected from hydrido, lower alkyl, aryl selected from phenyl, biphenyl, and naphthyl, 5- or 6-membered heterocyclyl selected from piperidinyl, piperazinyl, imidazolyl, pyridinyl and morpholinyl, lower haloalkyl, lower hydroxyalkyl, lower alkoxycarbonyl, lower alkylamino, lower alkylaminoalkyl, phenylamino, lower aralkyl, lower aralkylamino, lower alkylaminoalkylamino, lower aminoalkyl, lower aminoalkylamino, lower alkynylamino, lower heterocyclylamino, lower heterocyclylalkyl, lower heterocyclylalkylamino, lower alkylheterocyclyl, lower carboxycycloalkyl, lower carboxyalkylamino, lower alkoxyalkylamino, lower alkoxycarbonylaminoalkylamino, lower heterocyclylcarbonyl, lower alkoxycarbonylheterocyclyl, and lower alkoxycarbonylheterocyclylcarbonyl; wherein the aryl and heteroaryl groups are optionally substituted with one or more radicals independently selected from halo, lower alkyl, keto, aralkyl, carboxy, lower alkylaminoalkylamino, lower alkynylamino, lower heterocyclylalkylamino, lower alkylcarbonyl and lower alkoxycarbonyl; or
$R^2$ is —$CR^{54}R^{55}$ wherein $R^{54}$ is phenyl and $R^{55}$ is hydroxy; and
$R^4$ is selected from hydrido, lower cycloalkyl, lower cycloalkenyl, lower cycloalkyldienyl, 5- or 6-membered heterocyclyl, and aryl selected from phenyl, biphenyl, naphthyl; wherein $R^4$ is optionally substituted at a substitutable position with one or more radicals independently selected from halo, lower alkyl, lower alkoxy, aryloxy, lower aralkoxy, lower haloalkyl, lower alkylthio, lower alkylamino, nitro, hydroxy; and
$R^5$ is selected from halo, amino, cyano, aminocarbonyl, lower alkyl, lower alkoxy, hydroxy, lower aminoalkyl, lower aralkyl, lower aralkyloxy, lower aralkylamino, lower alkoxycarbonyl, lower alkylamino, lower alkylcarbonyl, lower aralkenyl, lower arylheterocyclyl, carboxy, lower cycloalkylamino, lower alkoxycarbonylamino, lower alkoxyaralkylamino, lower alkylaminoalkylamino, lower heterocyclylamino, lower heterocyclylalkylamino, lower aralkylheterocyclylamino, lower alkylaminocarbonyl, lower alkylcarbonyl, lower alkoxyaralkylamino, hydrazinyl, and lower alkylhydrazinyl, or —$NR^{62}R^{63}$ wherein $R^{62}$ is lower alkylcarbonyl or amino, and $R^{63}$ is lower alkyl or lower phenylalkyl; or
a pharmaceutically-acceptable salt or tautomer thereof.
A preferred class of compounds consists of those compounds of Formula IX
$R^1$ is selected from hydrido, methyl, ethyl, hydroxyethyl and propargyl; and
$R^2$ is selected from hydrido, methyl, ethyl, propyl, phenyl, trifluoromethyl, hydroxyethyl, methoxycarbonylethyl, ethoxycarbonylethyl, N-methylamino, N,N-dimethylamino, N-ethylamino, N,N-diethylamino, N-propylamino, N-phenylamino, aminomethyl, aminoethyl, aminoethylamino, aminopropylamino, propargylamino, benzylamino, dimethylaminopropylamino, morpholinylpropylamino, morpholinylethylamino, piperidinyl, piperazinyl, imidazolyl, morpholinyl, pyridinyl, carboxymethylamino, methoxyethylamino, (1,1-dimethyl)ethylcarbonyl, (1,1-dimethyl)ethylcarbonylaminopropylamino, (1,1-dimethyl)ethylcarbonylaminoethylamino, piperazinylcarbonyl, 1,1-dimethyl-ethylpiperazinylcarbonyl; wherein the phenyl, piperidinyl, piperazinyl, imidazolyl, morpholinyl, and pyridinyl groups are optionally substituted with one or more radicals independently selected from fluoro, chloro, bromo, keto, methyl, ethyl, trifluoromethyl, benzyl, methoxy, methoxycarbonyl, ethoxycarbonyl and (1,1-dimethyl)ethoxycarbonyl; and
$R^4$ is selected from cyclohexyl, cyclohexenyl, cyclohexadienyl, phenyl, quinolyl, biphenyl, pyridinyl, thienyl, furyl, dihydropyranyl, benzofuryl, dihydrobenzofuryl, and benzodioxolyl; wherein $R^4$ is optionally substituted with one or more radicals independently selected from methylthio, fluoro, chloro, bromo, methyl, ethyl, methoxy, ethoxy, phenoxy, benzyloxy, trifluoromethyl, nitro, dimethylamino, and hydroxy; and
$R^5$ is selected from fluoro, chloro, bromo, methyl, fluorophenylethyl, fluorophenylethenyl, fluorophenylpyrazolyl, cyano, methoxycarbonyl, aminocarbonyl, acetyl, hydroxy, carboxy, methoxy, methylamino, dimethylamino, 2-methylbutylamino, ethylamino, dimethylaminoethylamino, hydroxypropylamino, hydroxyethylamino, imidazolylamino, morpholinylethylamino, (1-ethyl-2-hydroxy)ethylamino, piperidinylamino, pyridinylmethylamino, phenylmethylpiperidinylamino, aminomethyl, cyclopropylamino, amino, hydroxy, methylcarbonyl, ethoxycarbonylamino, methoxyphenylmethylamino, phenylmethylamino, fluorophenylmethylamino, fluorophenylethylamino, methylaminocarbonyl, methylcarbonyl, hydrazinyl, and 1-methylhydrazinyl, or —$NR^{62}R^{63}$ wherein $R^{62}$ is methylcarbonyl or amino, and $R^{63}$ is methyl or benzyl; or
a pharmaceutically-acceptable salt or tautomer thereof.
Within Formula I there is another subclass of compounds of high interest represented by Formula X:

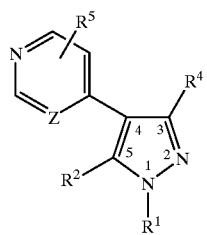

(X)

wherein

Z represents a carbon atom or a nitrogen atom; and $R^1$ is selected from lower alkyl, lower hydroxyalkyl, lower alkynyl, lower aminoalkyl and lower alkylaminoalkyl; and $R^2$ is selected from hydrido, lower alkyl, aryl selected from phenyl, biphenyl, and naphthyl, 5- or 6-membered heterocyclyl selected from piperidinyl, piperazinyl, imidazolyl, pyridinyl and morpholinyl, lower haloalkyl, lower hydroxyalkyl, lower alkoxycarbonyl, lower alkylamino, lower alkylaminoalkyl, phenylamino, lower aralkyl, lower aralkylamino, lower alkylaminoalkylamino, lower aminoalkyl, lower aminoalkylamino, lower alkynylamino, lower heterocyclylamino, lower heterocyclylalkyl, lower heterocyclylalkylamino, lower alkylheterocyclyl, lower carboxycycloalkyl, lower carboxyalkylamino, lower alkoxyalkylamino, lower alkoxycarbonylaminoalkylamino, lower heterocyclylcarbonyl, lower alkoxycarbonylheterocyclyl, and lower alkoxycarbonylheterocyclylcarbonyl; wherein the aryl and heteroaryl groups are optionally substituted with one or more radicals independently selected from halo, lower alkyl, keto, aralkyl, carboxy, lower alkylaminoalkylamino, lower alkynylamino, lower heterocyclylalkylamino, lower alkylcarbonyl and lower alkoxycarbonyl; or $R^2$ is —$CR^{54}R^{55}$ wherein $R^{54}$ is phenyl and $R^{55}$ is hydroxy; and $R^4$ is selected from 5- or 6-membered heteroaryl, and aryl selected from phenyl, biphenyl, and naphthyl; wherein $R^4$ is optionally substituted with one or more radicals independently selected from halo, lower alkyl, lower alkoxy, aryloxy, lower aralkoxy, lower haloalkyl, lower alkylthio, lower alkylamino, nitro, hydroxy; and $R^5$ is selected from halo, amino, cyano, aminocarbonyl, lower alkyl, lower alkoxy, hydroxy, lower aminoalkyl, lower aralkyl, lower aralkyloxy, lower aralkylamino, lower alkoxycarbonyl, lower alkylamino, lower alkylcarbonyl, lower aralkenyl, lower arylheterocyclyl, carboxy, lower cycloalkylamino, lower alkoxycarbonylamino, lower alkoxyaralkylamino, lower alkylaminoalkylamino, lower heterocyclylamino, lower heterocyclylalkylamino, lower aralkylheterocyclylamino, lower alkylaminocarbonyl, lower alkylcarbonyl, lower alkoxyaralkylamino, hydrazinyl, and lower alkylhydrazinyl, or —$NR^{62}R^{63}$ wherein $R^{62}$ is lower alkylcarbonyl or amino, and $R^{63}$ is lower alkyl or lower phenylalkyl; or a pharmaceutically-acceptable salt or tautomer thereof.

A preferred class of compounds consists of those compounds of Formula X $R^1$ is selected from methyl, ethyl, hydroxyethyl and propargyl; and $R^2$ is selected from methyl, ethyl, propyl, phenyl, trifluoromethyl, hydroxyethyl, methoxycarbonylethyl, ethoxycarbonylethyl, N-methylamino, N,N-dimethylamino, N-ethylamino, N,N-diethylamino, N-propylamino, N-phenylamino, aminomethyl, aminoethyl, aminoethylamino, aminopropylamino, propargylamino, benzylamino, piperadinylamino, dimethylaminoethylamino, dimethylaminopropylamino, morpholinylpropylamino, morpholinylethylamino, piperidinyl, piperazinyl, imidazolyl, morpholinyl, pyridinyl, N-methylpiperazinyl, carboxymethylamino, methoxyethylamino, (1,1-dimethyl)ethylcarbonyl, (1,1-dimethyl)ethylcarbonylaminopropylamino, (1,1-dimethyl)ethylcarbonylaminoethylamino, piperazinylcarbonyl, and 1,1-dimethyl-ethylpiperazinylcarbonyl; wherein the phenyl, piperidinyl, piperazinyl, imidazolyl, morpholinyl, and pyridinyl groups are optionally substituted with one or more radicals independently selected from fluoro, chloro, bromo, keto, methyl, ethyl, trifluoromethyl, benzyl, methoxy, methoxycarbonyl, ethoxycarbonyl and (1,1-dimethyl)ethoxycarbonyl; and $R^4$ is selected from phenyl, quinolyl, biphenyl, pyridinyl, thienyl, furyl, dihydropyranyl, benzofuryl, dihydrobenzofuryl, and benzodioxolyl; wherein $R^4$ is optionally substituted with one or more radicals independently selected from methylthio, fluoro, chloro, bromo, methyl, ethyl, methoxy, ethoxy, phenoxy, benzyloxy, trifluoromethyl, nitro, dimethylamino, and hydroxy; and $R^5$ is selected from fluoro, chloro, bromo, methyl, fluorophenylethyl, fluorophenylethenyl, fluorophenylpyrazolyl, cyano, methoxycarbonyl, aminocarbonyl, acetyl, hydroxy, carboxy, methoxy, methylamino, dimethylamino, 2-methylbutylamino, ethylamino, dimethylaminoethylamino, hydroxypropylamino, hydroxyethylamino, propargylamino, imidazolylamino, morpholinylethylamino, (1-ethyl-2-hydroxy)ethylamino, piperidinylamino, pyridinylmethylamino, phenylmethylpiperidinylamino, aminomethyl, cyclopropylamino, amino, hydroxy, methylcarbonyl, ethoxycarbonylamino, methoxyphenylmethylamino, phenylmethylamino, fluorophenylmethylamino, fluorophenylethylamino, methylaminocarbonyl, methylcarbonyl, hydrazinyl, and 1-methylhydrazinyl, or $NR^{62}R^{63}$ wherein $R^{62}$ is methylcarbonyl or amino, and $R^{63}$ is methyl or benzyl; or a pharmaceutically-acceptable salt or tautomer thereof.

Within Formula I there is another subclass of compounds of high interest represented by Formula XI:

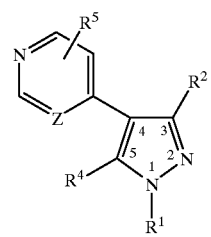

(XI)

wherein

Z represents a carbon atom or a nitrogen atom; and $R^1$ is selected from lower alkyl, lower hydroxyalkyl, lower alkynyl, lower aminoalkyl and lower alkylaminoalkyl; and $R^2$ is selected from hydrido, lower alkyl, aryl selected from phenyl, biphenyl, and naphthyl, 5- or 6-membered heterocyclyl selected from piperidinyl, piperazinyl, imidazolyl, pyridinyl and morpholinyl, lower haloalkyl, lower hydroxyalkyl, lower alkoxycarbonyl, lower alkylamino, lower alkylaminoalkyl, phenylamino, lower aralkyl, lower aralkylamino, lower alkylaminoalkylamino, lower aminoalkyl, lower aminoalkylamino, lower alkynylamino, lower heterocyclylamino, lower heterocyclylalkyl, lower heterocyclylalkylamino, lower alkylheterocyclyl, lower carboxycycloalkyl, lower carboxyalkylamino, lower alkoxyalkylamino, lower alkoxycarbonylaminoalkylamino, lower heterocyclylcarbonyl, lower alkoxycarbonylheterocyclyl, and lower alkoxycarbonylheterocyclylcarbonyl; wherein the aryl and heteroaryl groups are optionally substituted with one or more radicals independently selected from halo, lower alkyl, keto, aralkyl, carboxy, lower alkylaminoalkylamino, lower alkynylamino, lower heterocyclylalkylamino, lower alkylcarbonyl and lower alkoxycarbonyl; or $R^2$ is $-CR^{54}R^{55}$ wherein $R^{54}$ is phenyl and $R^{55}$ is hydroxy; and $R^4$ is selected from 5- or 6-membered heteroaryl, and aryl selected from phenyl, biphenyl, and naphthyl; wherein $R^4$ is optionally substituted with one or more radicals independently selected from halo, lower alkyl, lower alkoxy, aryloxy, lower aralkoxy, lower haloalkyl, lower alkylthio, lower alkylamino, nitro, hydroxy; and $R^5$ is selected from halo, amino, cyano, aminocarbonyl, lower alkyl, lower alkoxy, hydroxy, lower aminoalkyl, lower aralkyl, lower aralkyloxy, lower aralkylamino, lower alkoxycarbonyl, lower alkylamino, lower alkylcarbonyl, lower aralkenyl, lower arylheterocyclyl, carboxy, lower cycloalkylamino, lower alkoxycarbonylamino, lower alkoxyaralkylamino, lower alkylaminoalkylamino, lower heterocyclylamino, lower heterocyclylalkylamino, lower aralkylheterocyclylamino, lower alkylaminocarbonyl, lower alkylcarbonyl, lower alkoxyaralkylamino, hydrazinyl, and lower alkylhydrazinyl, or $-NR^{62}R^{63}$ wherein $R^{62}$ is lower alkylcarbonyl or amino, and $R^{63}$ is lower alkyl or lower phenylalkyl; or a pharmaceutically-acceptable salt or tautomer thereof.

A preferred class of compounds consists of those compounds of Formula XI $R^1$ is selected from methyl, ethyl, hydroxyethyl and propargyl; and $R^2$ is selected from methyl, ethyl, propyl, phenyl, trifluoromethyl, hydroxyethyl, methoxycarbonylethyl, ethoxycarbonylethyl, N-methylamino, N,N-dimethylamino, N-ethylamino, N,N-diethylamino, N-propylamino, N-phenylamino, aminomethyl, aminoethyl, aminoethylamino, aminopropylamino, propargylamino, benzylamino, dimethylaminopropylamino, morpholinylpropylamino, morpholinylethylamino, piperidinyl, piperazinyl, imidazolyl, morpholinyl, pyridinyl, carboxymethylamino, methoxyethylamino, (1,1-dimethyl)ethylcarbonyl, (1,1-dimethyl)ethylcarbonylaminopropylamino, (1,1-dimethyl)ethylcarbonylaminoethylamino, piperazinylcarbonyl, 1,1-dimethylethylpiperazinylcarbonyl; wherein the phenyl, piperidinyl, piperazinyl, imidazolyl, morpholinyl, and pyridinyl groups are optionally substituted with one or more radicals independently selected from fluoro, chloro, bromo, keto, methyl, ethyl, trifluoromethyl, benzyl, methoxy, methoxycarbonyl, ethoxycarbonyl and (1,1-dimethyl)ethoxycarbonyl;

$R^4$ is selected from phenyl, quinolyl, biphenyl, pyridinyl, thienyl, furyl, dihydropyranyl, benzofuryl, dihydrobenzofuryl, and benzodioxolyl; wherein $R^4$ is optionally substituted with one or more radicals independently selected from methylthio, fluoro, chloro, bromo, methyl, ethyl, methoxy, ethoxy, phenoxy, benzyloxy, trifluoromethyl, nitro, dimethylamino, and hydroxy; and $R^5$ is selected from fluoro, chloro, bromo, methyl, fluorophenylethyl, fluorophenylethenyl, fluorophenylpyrazolyl, cyano, methoxycarbonyl, aminocarbonyl, acetyl, hydroxy, carboxy, methoxy, methylamino, dimethylamino, 2-methylbutylamino, ethylamino, dimethylaminoethylamino, hydroxypropylamino, hydroxyethylamino, imidazolylamino, morpholinylethylamino, (1-ethyl-2-hydroxy)ethylamino, piperidinylamino, pyridinylmethylamino, phenylmethylpiperidinylamino, aminomethyl, cyclopropylamino, amino, hydroxy, methylcarbonyl, ethoxycarbonylamino, methoxyphenylmethylamino, phenylmethylamino, fluorophenylmethylamino, fluorophenylethylamino, methylaminocarbonyl, methylcarbonyl, hydrazinyl, and 1-methylhydrazinyl, or $-N^{62}R^{63}$ wherein $R^{62}$ is methylcarbonyl or amino, and $R^{63}$ is methyl or benzyl; or a pharmaceutically-acceptable salt or tautomer thereof.

A preferred class of compounds consists of those compounds of Formula IX wherein Z represents a carbon atom or a nitrogen atom; and $R^1$ is selected from hydrido, lower alkyl, lower hydroxyalkyl, lower alkynyl, lower aminoalkyl and lower alkylaminoalkyl; and $R^2$ is selected from hydrido, lower alkyl, aryl selected from phenyl, biphenyl, and naphthyl, 5- or 6-membered heterocyclyl selected from piperidinyl, piperazinyl, imidazolyl, pyridinyl and morpholinyl, lower haloalkyl, lower hydroxyalkyl, lower alkoxycarbonyl, lower alkylamino, lower alkylaminoalkyl, phenylamino, lower aralkyl, lower aralkylamino, lower alkylaminoalkylamino, lower aminoalkyl, lower aminoalkylamino, lower alkynylamino, lower heterocyclylamino, lower heterocyclylalkyl, lower heterocyclylalkylamino, lower alkylheterocyclyl, lower carboxycycloalkyl, lower carboxyalkylamino, lower alkoxyalkylamino, lower alkoxycarbonylaminoalkylamino, lower heterocyclylcarbonyl, lower alkoxycarbonylheterocyclyl, and lower alkoxycarbonylheterocyclylcarbonyl; wherein the aryl and heteroaryl groups are optionally substituted with one or more radicals independently selected from halo, lower alkyl, keto, aralkyl, carboxy, lower alkylaminoalkylamino, lower alkynylamino, lower heterocyclylalkylamino, lower alkylcarbonyl and lower alkoxycarbonyl; or $R^2$ is $-CR^{54}R^{55}$ wherein $R^{54}$ is phenyl and $R^{55}$ is hydroxy; and $R^4$ is phenyl that is optionally substituted with one or more radicals independently selected from halo, lower alkyl, lower alkoxy, aryloxy, lower aralkoxy, lower haloalkyl, lower alkylthio, lower alkylamino, nitro, hydroxy; and $R^5$ is selected from halo, amino, cyano, aminocarbonyl, lower alkyl, lower alkoxy, hydroxy, lower aminoalkyl, lower aralkyl, lower aralkyloxy, lower aralkylamino, lower alkoxycarbonyl, lower alkylamino, lower alkylcarbonyl, lower aralkenyl, lower arylheterocyclyl, carboxy, lower cycloalkylamino, lower alkoxycarbonylamino, lower alkoxyaralkylamino, lower alkylaminoalkylamino, lower heterocyclylamino, lower heterocyclylalkylamino, lower aralkylheterocyclylamino, lower alkylaminocarbonyl, lower alkylcarbonyl, lower alkoxyaralkylamino, hydrazinyl, and lower alkylhydrazinyl, or —$NR^{62}R^{63}$ wherein $R^{62}$ is lower alkylcarbonyl or amino, and $R^{63}$ is lower alkyl or lower phenylalkyl; or a pharmaceutically-acceptable salt or tautomer thereof.

A class of compounds of specific interest consists of those compounds of Formula IX wherein $R^1$ is selected from hydrido, methyl, ethyl, hydroxyethyl and propargyl;

$R^2$ is selected from methyl, ethyl, propyl, phenyl, trifluoromethyl, hydroxyethyl, methoxycarbonylethyl, ethoxycarbonylethyl, N-methylamino, N,N-dimethylamino, N-ethylamino, N,N-diethylamino, N-propylamino, N-phenylamino, aminomethyl, aminoethyl, aminoethylamino, aminopropylamino, propargylamino, benzylamino, dimethylaminopropylamino, morpholinylpropylamino, morpholinylethylamino, piperidinyl, piperazinyl, imidazolyl, morpholinyl, pyridinyl, carboxymethylamino, methoxyethylamino, (1,1-dimethyl)ethylcarbonyl, (1,1-dimethyl)ethylcarbonylaminopropylamino, (1,1-dimethyl)ethylcarbonylaminoethylamino, piperazinylcarbonyl, 1,1-dimethyl-ethylpiperazinylcarbonyl; wherein the phenyl, piperidinyl, piperazinyl, imidazolyl, morpholinyl, and pyridinyl groups are optionally substituted with one or more radicals independently selected from fluoro, chloro, bromo, keto, methyl, ethyl, trifluoromethyl, benzyl, methoxy, methoxycarbonyl, ethoxycarbonyl and (1,1-dimethyl)ethoxycarbonyl;

$R^4$ is phenyl that is optionally substituted with one or more radicals independently selected from methylthio, fluoro, chloro, bromo, methyl, ethyl, methoxy, ethoxy, phenoxy, benzyloxy, trifluoromethyl, nitro, dimethylamino, and hydroxy; and $R^5$ is selected from fluoro, chloro, bromo, methyl, fluorophenylethyl, fluorophenylethenyl, fluorophenylpyrazolyl, cyano, methoxycarbonyl, aminocarbonyl, acetyl, hydroxy, carboxy, methoxy, methylamino, dimethylamino, 2-methylbutylamino, ethylamino, dimethylaminoethylamino, hydroxypropylamino, hydroxyethylamino, imidazolylamino, morpholinylethylamino, (1-ethyl-2-hydroxy)ethylamino, piperidinylamino, pyridinylmethylamino, phenylmethylpiperidinylamino, aminomethyl, cyclopropylamino, amino, hydroxy, methylcarbonyl, ethoxycarbonylamino, methoxyphenylmethylamino, phenylmethylamino, fluorophenylmethylamino, fluorophenylethylamino, methylaminocarbonyl, methylcarbonyl, hydrazinyl, and 1-methylhydrazinyl, or —$NR^{62}R^{63}$ wherein $R^{62}$ is methylcarbonyl or amino, and $R^{63}$ is methyl or benzyl; or a pharmaceutically-acceptable salt or tautomer thereof.

Another class of compounds of specific interest consists of those compounds of Formula IX wherein Z represents a carbon atom or a nitrogen atom; and $R^1$ is selected from hydrido, lower alkyl, lower hydroxyalkyl and lower alkynyl; and $R^2$ is selected from hydrido and lower alkyl; and $R^4$ is selected from phenyl and benzodioxolyl; wherein phenyl is optionally substituted with one or more halo radicals; and $R^5$ is selected from hydrido, halo and alkylhydrazinyl; or a pharmaceutically-acceptable salt or tautomer thereof.

Still another class of compounds of specific interest consists of those compounds of Formula IX wherein Z represents a carbon atom; and $R^1$ is selected from hydrido, methyl, hydroxyethyl, propargyl; and $R^2$ is hydrido; and $R^4$ is selected from phenyl and benzodioxolyl; wherein phenyl is optionally substituted with one or more radicals independently selected from chloro, fluoro and bromo; and $R^5$ is selected from hydrido, fluoro, and 1-methylhydrazinyl; or a pharmaceutically-acceptable salt or tautomer thereof.

A preferred class of compounds of specific interest consists of those compounds of Formula IX wherein Z represents a carbon atom; and $R^1$ is selected from hydrido and methyl; and $R^2$ is hydrido; and $R^4$ is selected from phenyl that is optionally substituted with one or more radicals independently selected from chloro, fluoro and bromo; and $R^5$ is selected from hydrido and fluoro; or a pharmaceutically-acceptable salt or tautomer thereof.

Within Formula IA there is another subclass of compounds of interest represented by Formula IXA:

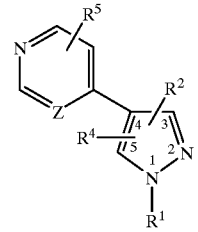

(IXA)

wherein

Z represents a carbon atom or a nitrogen atom; and $R^1$ is selected from hydrido, lower alkyl, lower hydroxyalkyl, lower alkynyl, lower aralkyl, lower aminoalkyl and lower alkylarninoalkyl; and $R^2$ is selected from hydrido, lower alkylamino, lower alkynylamino, arylamino, lower aralkylamino, lower heterocyclylalkylamino, lower aminoalkylamino, lower alkylaminoalkylamino, lower hydroxyalkylamino, lower carboxyalkylamino, and lower alkoxyalkylamino, lower alkoxycarbonylaminoalkylamino, wherein the aryl group is optionally substituted with one or more radicals independently selected from halo, keto, lower alkyl, aralkyl, carboxy, lower alkoxy, lower alkylaminoalkylamino, lower alkynylamino, lower heterocyclylalkylamino, lower alkylcarbonyl and lower alkoxycarbonyl; or $R^2$ is $R^{200}$-heterocyclyl-$R^{201}$ or $R^{200}$-cycloalkyl-$R^{201}$ wherein:

$R^{200}$ is selected from:
—$(CR^{202}R^{203})_y$—;
—$NR^{202}$—;
—$NR^{202}$—$(CH_2)_y$—;
—$(CH_2)_y$—$NR^{202}$—;
—O—$(CH_2)_y$—;
—$(CH_2)_y$—O—;
—S—;
—O—;

or $R^{200}$ represents a bond;

$R^{201}$ represents one or more radicals selected from the group consisting of hydrido, halogen, hydroxy, carboxy, keto, lower alkyl, lower hydroxyalkyl, lower haloalkyl, lower cycloalkyl, lower alkenyl, lower alkynyl, aryl, heterocyclyl, lower aralkyl, lower heterocyclylalkylene, lower alkylcarbonyl, lower hydroxyalkylcarbonyl, lower cycloalkylcarbonyl, arylcarbonyl, haloarylcarbonyl, lower alkoxy, lower alkoxyalkylene, lower alkoxyarylene, lower alkoxycarbonyl, lower carboxyalkylcarbonyl, lower alkoxyalkylcarbonyl, lower heterocyclylalkylcarbonyl, lower alkylsulfonyl, lower alkylsulfonylalkylene, amino, lower aminoalkyl, lower alkylamino, lower aralkylamino, lower alkylaminoalkylene, aminocarbonyl, lower alkylcarbonylamino, lower alkylcarbonylaminoalkylene, lower alkylaminoalkylcarbonyl, lower alkylaminoalkylcarbonylamino, lower aminoalkylcarbonylaminoalkyl, lower alkoxycarbonylamino, lower alkoxyalkylcarbonylamino, lower alkoxycarbonylaminoalkylene, lower alkylimidocarbonyl, amidino, lower alkylamidino, lower aralkylamidino, guanidino, lower guanidinoalkylene, and lower alkylsulfonylamino; and $R^{202}$ and $R^{203}$ are independently selected from hydrido, lower alkyl, aryl and lower aralkyl; and y is 0, 1, 2 or 3; and $R^4$ is selected from aryl selected from phenyl, biphenyl, naphthyl, wherein said aryl is optionally substituted at a substitutable position with one or more radicals independently selected from halo, lower alkyl, lower alkoxy, aryloxy, lower aralkoxy, lower haloalkyl, lower alkylthio, lower alkylamino, nitro, and hydroxy; and $R^5$ is selected from hydrido, halo, amino, cyano, aminocarbonyl, lower alkyl, lower alkoxy, hydroxy, lower aminoalkyl, lower aralkyl, lower aralkyloxy, lower aralkylamino, lower alkoxycarbonyl, lower alkylamino, lower hydroxyalkylamino, lower alkylcarbonyl, lower aralkenyl, lower arylheterocyclyl, carboxy, lower cycloalkylamino, lower hydroxycycloalkylamino, lower alkoxycarbonylamino, lower alkoxyaralkylamino, lower alkylaminoalkylamino, lower heterocyclylamino, lower heterocyclylalkylamino, lower aralkylheterocyclylamino, lower alkylaminocarbonyl, lower alkylcarbonyl, lower alkoxyaralkylamino, hydrazinyl, and lower alkylhydrazinyl, or —$NR^{62}R^{63}$ wherein $R^{62}$ is lower alkylcarbonyl or amino, and $R^{63}$ is lower alkyl or lower phenylalkyl; or a pharmaceutically-acceptable salt or tautomer thereof.

When the substituent at the 4-position of the pyrazole ring is a substituted pyridinyl, at least one of the substituents preferably is attached to a ring carbon atom adjacent the nitrogen heteroatom of the pyridine ring. When the substituent at the 4-position of the pyrazole ring is a substituted pyrimidinyl, at least one of the substituents preferably is attached to the carbon ring atom between the nitrogen heteroatoms of the pyrimidine ring. When $R^2$ comprises a substituted piperidinyl or piperazinyl moiety, at least one of the substituents preferably is attached to the distal nitrogen heteroatom or to a carbon ring atom adjacent to the distal nitrogen heteroatom of the piperidine or piperazine ring.

A subclass of compounds of specific interest consists of those compounds of Formula IXA wherein:

$R^1$ is selected from hydrido, methyl, ethyl, hydroxyethyl and propargyl; and $R^2$ is selected from hydrido, N-methylamino, N,N-dimethylamino, N-ethylamino, N,N-diethylamino, N-propylamino, N,N-dipropylamino, N-butylamino, N-propargylamino, N-phenylamino, N-benzylamino, aminoethylamino, aminopropylamino, aminobutylamino, methylaminoethylamino, dimethylaminoethylamino, ethylaminoethylamino, diethylaminoethylamino, methylaminopropylamino, dimethylaminopropylamino, ethylaminopropylamino, diethylaminopropylamino, morpholinylmethylamino, morpholinylethylamino, morpholinylpropylamino, piperidinylmethylamino, piperidinylethylamino, piperidinylpropylamino, piperazinylmethylamino, piperazinylethylamino, piperazinylpropylamino, carboxymethylamino, carboxyethylamino, methoxyethylamino, ethoxyethylamino, ethoxymethylamino, (1,1-dimethyl)ethylcarbonylaminopropylamino, and (1,1-dimethyl)ethylcarbonylaminoethylamino, wherein the phenyl, morpholinyl, piperidinyl, and piperazinyl groups are optionally substituted with one or more radicals independently selected from fluoro, chloro, bromo, keto, methyl, ethyl, trifluoromethyl, benzyl, methoxy, ethyoxy, methoxycarbonyl, ethoxycarbonyl and (1,1-dimethyl)ethoxycarbonyl; and $R^2$ is $R^{200}$-piperidinyl-$R^{201}$, $R^{200}$-piperazinyl-$R^{201}$, or $R^{200}$-cyclohexyl-$R^{201}$ wherein:

$R^{200}$ is selected from:
—$(CR^{202}R^{203})_y$—;
—$NR^{202}$—;
—S—;
—O—;

or $R^{200}$ represents a bond;

$R^{201}$ represents one or more radicals selected from the group consisting of hydrido, chloro, fluoro, bromo, iodo, hydroxy, carboxy, keto, methyl, ethyl, propyl, butyl, hydroxymethyl, hydroxyethyl, hydroxypropyl, hydroxybutyl, (1-hydroxy-1,1-dimethyl)ethyl, chloromethyl, chloroethyl, chloropropyl, chlorobutyl, fluoromethyl, fluoroethyl, fluoropropyl, fluorobutyl, cyclopropyl, cyclobutyl, cyclopentyl, cyclohexyl, ethenyl, propenyl, butenyl, ethynyl, propynyl, propargyl, butynyl, phenyl, benzyl, piperidinyl, piperazinyl, morpholinyl, piperidinylmethylene, piperazinylmethylene, morpholinylmethylene, methoxy, ethoxy, propoxy, butoxy, methoxymethylene, methoxyethylene, methoxypropylene, ethoxyethylene, ethoxypropylene, propoxyethylene, propoxypropylene, methoxyphenylene, ethoxyphenylene, propoxyphenylene, methylcarbonyl, ethylcarbonyl, propylcarbonyl, cyclopropylcarbonyl, cyclobutylcarbonyl, cyclopentylcarbonyl, cyclohexylcarbonyl, benzoyl, chlorobenzoyl, fluorobenzoyl, hydroxymethylcarbonyl, hydroxyethylcarbonyl, hydroxypropylcarbonyl, carboxymethylcarbonyl, carboxyethylcarbonyl, carboxypropylcarbonyl, methoxymethylcarbonyl, methoxyethylcarbonyl, methoxypropylcarbonyl, ethoxymethylcarbonyl, ethoxyethylcarbonyl, ethoxypropylcarbonyl, propoxymethylcarbonyl, propoxyethylcarbonyl, propoxypropylcarbonyl, methoxyphenylcarbonyl, ethoxyphenylcarbonyl, propoxyphenylcarbonyl, piperidinylmethylcarbonyl, piperazinylmethylcarbonyl, morpholinylcarbonyl, methylsulfonyl, ethylsulfonyl, methylsulfonylmethylene, amino, aminomethyl, aminoethyl, aminopropyl, N-methylamino, N,N-dimethylamino, N-ethylamino, N,N-diethylamino, N-propylamino, N,N-dipropylamino, phenylamino, benzylamino, methylaminomethylene, ethylaminomethylene, methylaminoethylene, ethylaminoethylene, aminocarbonyl, methylcarbonylamino, ethylcarbonylamino, methylaminomethylcarbonyl, ethylaminomethylcarbonyl, methylcarbonylaminomethylene, ethylcarbonylaminomethylene, aminomethylcarbonylaminocarbonylmethylene, methoxycarbonylamino, ethoxycarbonylamino, methoxymethylcarbonylamino, methoxyethylcarbonylamino, ethoxymethylcarbonylamino, ethoxyethylcarbonylamino, methoxycarbonylaminomethylene, ethoxycarbonylaminomethylene, methylimidocarbonyl, ethylimidocarbonyl, amidino, methylamidino, methylamidino, benzylamidino, guanidino, guanidinomethylene, guanidinoethylene, and methylsulfonylamino; and $R^{202}$ and $R^{203}$ are independently selected from hydrido, methyl, ethyl, propyl, butyl, phenyl and benzyl; and y is 0, 1 or 2; and $R^4$ is phenyl, wherein said phenyl is optionally substituted with one or more radicals independently selected from methylthio, fluoro, chloro, bromo, iodo, methyl, ethyl, methoxy, ethoxy, phenoxy, benzyloxy, trifluoromethyl, nitro, dimethylamino, and hydroxy; and $R^5$ is selected from hydrido, fluoro, chloro, bromo, iodo, hydroxy, methyl, ethyl, propyl, benzyl, fluorophenylethyl, fluorophenylethenyl, fluorophenylpyrazolyl, cyano, carboxy, methoxy, methoxycarbonyl, aminocarbonyl, acetyl, methylamino, dimethylamino, 2-methylbutylamino, ethylamino, dimethylaminoethylamino, hydroxyethylamino, hydroxypropylamino, hydroxybutylamino, hydroxycyclopropylamino, hydroxycyclobutylamino, hydroxycyclopentylamino, hydroxycyclohexylamino, imidazolylamino, morpholinylethylamino, (1-ethyl-2-hydroxy)ethylamino, piperidinylamino, pyridinylmethylamino, phenylmethylpiperidinylamino, aminomethyl, cyclopropylamino, amino, hydroxy, ethoxycarbonylamino, methoxyphenylmethylamino, phenylmethylamino, fluorophenylmethylamino, fluorophenylethylamino, methylaminoethylamino, dimethylaminoethylamino, methylaminopropylamino, dimethylaminopropylamino, methylaminobutylamino, dimethylaminobutylamino, methylaminopentylamino, dimethylaminopentylamino, ethylaminoethylamino, diethylaminoethylamino, ethylaminopropylamino, diethylaminopropylamino, ethylaminobutylamino, diethylaminobutylamino, ethylaminopentylamino, methylaminocarbonyl, methylcarbonyl, ethylcarbonyl, hydrazinyl, and 1-methylhydrazinyl, or —NR$^{62}$R$^{63}$ wherein R$^{62}$ is methylcarbonyl or amino, and R$^{63}$ is methyl or benzyl; or a pharmaceutically-acceptable salt or tautomer thereof.

Within Formula IXA there is another subclass of compounds of interest represented by Formula XA:

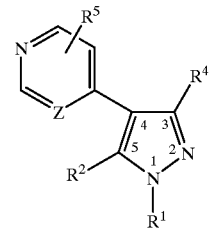

(XA)

wherein:

$R^1$ is selected from hydrido, methyl, ethyl, hydroxyethyl and propargyl; and $R^2$ is selected from hydrido, N-methylamino, N,N-dimethylamino, N-ethylamino, N,N-diethylamino, N-propylamino, N,N-dipropylamino, N-butylamino, N-propargylamino, N-phenylamino, N-benzylamino, aminoethylamino, aminopropylamino, aminobutylamino, methylaminoethylamino, dimethylaminoethylamino, ethylaminoethylamino, diethylaminoethylamino, methylaminopropylamino, dimethylaminopropylamino, ethylaminopropylamino, diethylaminopropylamino, morpholinylmethylamino, morpholinylethylamino, morpholinylpropylamino, piperidinylmethylamino, piperidinylethylamino, piperidinylpropylamino, piperazinylmethylamino, piperazinylethylamino, and piperazinylpropylamino, wherein the phenyl, morpholinyl, piperidinyl, and piperazinyl groups are optionally substituted with one or more radicals independently selected from fluoro, chloro, bromo, keto, methyl, ethyl, trifluoromethyl, benzyl, and methoxy; and $R^4$ is phenyl, wherein said phenyl is optionally substituted with one or more radicals independently selected from fluoro, chloro, methyl, ethyl, methoxy and ethoxy; and $R^5$ is selected from hydrido, fluoro, chloro, bromo, hydroxy, methyl, ethyl, propyl, benzyl, cyano, carboxy, methoxy, methoxycarbonyl, aminocarbonyl, acetyl, methylamino, dimethylamino, 2-methylbutylamino, ethylamino, dimethylaminoethylamino, hydroxyethylamino, hydroxypropylamino, hydroxybutylamino, hydroxycyclopropylamino, hydroxycyclobutylamino, hydroxycyclopentylamino, hydroxycyclohexylamino, imidazolylamino, morpholinylethylamino, (1-ethyl-2-hydroxy)ethylamino, piperidinylamino, pyridinylmethylamino, phenylmethylpiperidinylamino, aminomethyl, cyclopropylamino, amino, hydroxy, ethoxycarbonylamino, methoxyphenylmethylamino, phenylmethylamino, fluorophenylmethylamino, fluorophenylethylamino, methylaminoethylamino, dimethylaminoethylamino, methylaminopropylamino, dimethylaminopropylamino, methylaminobutylamino, dimethylaminobutylamino, methylaminopentylamino, dimethylaminopentylamino, ethylaminoethylamino, diethylaminoethylamino, ethylaminopropylamino, diethylaminopropylamino, ethylaminobutylamino, diethylaminobutylamino, ethylaminopentylamino, methylaminocarbonyl, methylcarbonyl, and ethylcarbonyl; or a pharmaceutically-acceptable salt or tautomer thereof.

A subclass of compounds of particular interest consists of those compounds of Formula XA wherein:

$R^1$ is selected from hydrido, methyl, ethyl, hydroxyethyl and propargyl; and $R^2$ is selected from hydrido, methylaminopropylamino, dimethylaminopropylamino, ethylaminopropylamino, diethylaminopropylamino, morpholinylmethylamino, morpholinylethylamino, morpholinylpropylamino, wherein the phenyl and morpholinyl groups are optionally substituted with one or more radicals independently selected from fluoro, chloro, bromo, methyl, ethyl, and methoxy; and $R^4$ is phenyl, wherein said phenyl is optionally substituted with one or more radicals independently selected from fluoro, chloro, methyl, ethyl, methoxy and ethoxy; and $R^5$ is selected from hydrido, fluoro, chloro, bromo, hydroxy, methyl, ethyl, cyano, carboxy, methoxy, methoxycarbonyl, aminocarbonyl, acetyl, methylamino, dimethylamino, ethylamino, dimethylaminoethylamino, hydroxyethylamino, hydroxypropylamino, hydroxybutylamino, hydroxycyclopropylamino, hydroxycyclobutylamino, hydroxycyclopentylamino, hydroxycyclohexylamino, (1-ethyl-2-hydroxy)ethylamino, aminomethyl, cyclopropylamino, amino, ethoxycarbonylamino, methoxyphenylmethylamino, phenylmethylamino, fluorophenylmethylamino, fluorophenylethylamino, methylaminoethylamino, dimethylaminoethylamino, methylaminopropylamino, dimethylaminopropylamino, methylaminobutylamino, dimethylaminobutylamino, methylaminopentylamino, dimethylaminopentylamino, ethylaminoethylamino, diethylaminoethylamino, ethylaminopropylamino, diethylaminopropylamino, ethylaminobutylamino, diethylaminobutylamino, ethylaminopentylamino, methylaminocarbonyl, methylcarbonyl, and ethylcarbonyl; or a pharmaceutically-acceptable salt or tautomer thereof.

A subclass of compounds of specific interest consists of those compounds of Formula XA wherein:

$R^1$ is hydrido; and $R^2$ is selected from hydrido, methylaminopropylamino, dimethylaminopropylamino, ethylaminopropylamino, diethylaminopropylamino, morpholinylmethylamino, morpholinylethylamino, and morpholinylpropylamino; and $R^4$ is phenyl, wherein said phenyl is optionally substituted with one or more radicals independently selected from fluoro, chloro, methyl, and methoxy; and $R^5$ is selected from hydrido, methylamino, dimethylamino, ethylamino, dimethylaminoethylamino, hydroxypropylamino, hydroxyethylamino, hydroxypropylamino, hydroxybutylamino, hydroxycyclopropylamino, hydroxycyclobutylamino, hydroxycyclopentylamino, hydroxycyclohexylamino, (1-ethyl-2-hydroxy)ethylamino, aminomethyl, cyclopropylamino, amino, dimethylaminoethylamino, dimethylaminopropylamino, dimethylaminobutylamino, dimethylaminopentylamino, diethylaminoethylamino, diethylaminopropylamino, diethylaminobutylamino, and diethylaminopentylamino; or a pharmaceutically-acceptable salt or tautomer thereof.

A subclass of compounds of high interest consists of those compounds of Formula XA wherein:

$R^1$ is selected hydrido; and $R^2$ is selected from hydrido, dimethylaminopropylamino, diethylaminopropylamino, morpholinylethylamino, and morpholinylpropylamino; and $R^4$ is phenyl, wherein said phenyl is optionally substituted with one or more radicals independently selected from fluoro, chloro, methyl, and methoxy; and $R^5$ is selected from hydrido, hydroxypropylamino, hydroxycyclohexylamino, diethylaminoethylamino; or a pharmaceutically-acceptable salt or tautomer thereof.

Within Formula IA there is another subclass of compounds of interest represented by Formula XA:

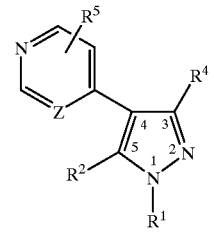

(XA)

$R^1$ is selected from hydrido, methyl, ethyl, hydroxyethyl and propargyl; and $R^2$ is $R^{200}$-piperidinyl-$R^{201}$ wherein:

$R^{200}$ is selected from:
—$(CR^{202}R^{203})_y$—;
—$NR^{202}$—;
—S—;
—O—;

or $R^{200}$ represents a bond;

$R^{201}$ represents one or more radicals selected from the group consisting of hydrido, chloro, fluoro, bromo, iodo, hydroxy, carboxy, keto, methyl, ethyl, propyl, butyl, hydroxymethyl, hydroxyethyl, hydroxypropyl, hydroxybutyl, (1-hydroxy-1,1-dimethyl)ethyl, chloromethyl, chloroethyl, chloropropyl, chlorobutyl, fluoromethyl, fluoroethyl, fluoropropyl, fluorobutyl, cyclopropyl, cyclobutyl, cyclopentyl, cyclohexyl, ethenyl, propenyl, butenyl, ethynyl, propynyl, propargyl, butynyl, phenyl, benzyl, piperidinyl, piperazinyl, morpholinyl, piperidinylmethylene, piperazinylmethylene, morpholinylmethylene, methoxy, ethoxy, propoxy, butoxy, methoxymethylene, methoxyethylene, methoxypropylene, ethoxyethylene, ethoxypropylene, propoxyethylene, propoxypropylene, methoxyphenylene, ethoxyphenylene, propoxyphenylene, methylcarbonyl, ethylcarbonyl, propylcarbonyl, cyclopropylcarbonyl, cyclobutylcarbonyl, cyclopentylcarbonyl, cyclohexylcarbonyl, benzoyl, chlorobenzoyl, fluorobenzoyl, hydroxymethylcarbonyl, hydroxyethylcarbonyl, hydroxypropylcarbonyl, carboxymethylcarbonyl, carboxyethylcarbonyl, carboxypropylcarbonyl, methoxymethylcarbonyl, methoxyethylcarbonyl, methoxypropylcarbonyl, ethoxymethylcarbonyl, ethoxyethylcarbonyl, ethoxypropylcarbonyl, propoxymethylcarbonyl, propoxyethylcarbonyl, propoxypropylcarbonyl, methoxyphenylcarbonyl, ethoxyphenylcarbonyl, propoxyphenylcarbonyl, piperidinylmethylcarbonyl, piperazinylmethylcarbonyl, morpholinylcarbonyl, methylsulfonyl, ethylsulfonyl, methylsulfonylmethylene, amino, aminomethyl, aminoethyl, aminopropyl, N-methylamino, N,N-dimethylamino, N-ethylamino, N,N-diethylamino, N-propylamino, N,N-dipropylamino, phenylamino, benzylamino, methylaminomethylene, ethylaminomethylene, methylaminoethylene, ethylaminoethylene, aminocarbonyl, methylcarbonylamino, ethylcarbonylamino, methylaminomethylcarbonyl, ethylaminomethylcarbonyl, methylcarbonylaminomethylene, ethylcarbonylaminomethylene, aminomethylcarbonylaminocarbonylmethylene, methoxycarbonylamino, ethoxycarbonylamino, methoxymethylcarbonylamino, methoxyethylcarbonylamino, ethoxymethylcarbonylamino, ethoxyethylcarbonylamino, methoxycarbonylaminomethylene, ethoxycarbonylaminomethylene, methylimidocarbonyl, ethylimidocarbonyl, amidino, methylamidino, methylamidino, benzylamidino, guanidino, guanidinomethylene, guanidinoethylene, and methylsulfonylamino; and $R^{202}$ and $R^{203}$ are independently selected from hydrido, methyl, ethyl, propyl, butyl, phenyl and benzyl; and y is 0, 1 or 2; and $R^4$ is phenyl, wherein said phenyl is optionally substituted with one or more radicals independently selected from fluoro, chloro, methyl, ethyl, methoxy and ethoxy; and $R^5$ is selected from hydrido, fluoro, chloro, bromo, hydroxy, methyl, ethyl, propyl, benzyl, cyano, carboxy, methoxy, methoxycarbonyl, aminocarbonyl, acetyl, methylamino, dimethylamino, 2-methylbutylamino, ethylamino, dimethylaminoethylamino, hydroxyethylamino, hydroxypropylamino, hydroxybutylamino, hydroxycyclopropylamino, hydroxycyclobutylamino, hydroxycyclopentylamino, hydroxycyclohexylamino, imidazolylamino, morpholinylethylamino, (1-ethyl-2-hydroxy) ethylamino, piperidinylamino, pyridinylmethylamino, phenylmethylpiperidinylamino, aminomethyl, cyclopropylamino, amino, hydroxy, ethoxycarbonylamino, methoxyphenylmethylamino, phenylmethylamino, fluorophenylmethylamino, fluorophenylethylamino, methylaminoethylamino, dimethylaminoethylamino, methylaminopropylamino, dimethylaminopropylamino, methylaminobutylamino, dimethylaminobutylamino, methylaminopentylamino, dimethylaminopentylamino, ethylaminoethylamino, diethylaminoethylamino, ethylaminopropylamino, diethylaminopropylamino, ethylaminobutylamino, diethylaminobutylamino, ethylaminopentylamino, methylaminocarbonyl, methylcarbonyl, and ethylcarbonyl; or a pharmaceutically-acceptable salt or tautomer thereof.

A subclass of compounds of particular interest consists of those compounds of Formula XA wherein:

$R^1$ is selected from hydrido, methyl, ethyl, hydroxyethyl and propargyl; and $R^2$ is $R^{200}$-piperidinyl-$R^{201}$ wherein:

$R^{200}$ is selected from:
  methylene;
  —$NR^{202}$—;
  —S—;
  —O—;
or $R^{200}$ represents a bond;

$R^{201}$ represents one or more radicals selected from the group consisting of hydrido, chloro, fluoro, hydroxy, carboxy, keto, methyl, ethyl, propyl, hydroxymethyl, hydroxyethyl, hydroxypropyl, (1-hydroxy-1,1-dimethyl)ethyl, chloromethyl, chloroethyl, chloropropyl, fluoromethyl, fluororoethyl, fluoropropyl, phenyl, benzyl, piperidinyl, piperazinyl, morpholinyl, piperidinylmethylene, piperazinylmethylene, morpholinylmethylene, methoxy, ethoxy, propoxy, methoxymethyl, methoxyethyl, methoxypropyl, ethoxyethyl, ethoxypropyl, propoxyethyl, propoxypropyl, methoxyphenyl, ethoxyphenyl, propoxyphenyl, methylcarbonyl, ethylcarbonyl, propylcarbonyl, hydroxymethylcarbonyl, hydroxyethylcarbonyl, carboxymethylcarbonyl, carboxyethylcarbonyl, methoxymethylcarbonyl, methoxyethylcarbonyl, methoxypropylcarbonyl, ethoxymethylcarbonyl, ethoxyethylcarbonyl, ethoxypropylcarbonyl, propoxymethylcarbonyl, propoxyethylcarbonyl, propoxypropylcarbonyl, methoxyphenylcarbonyl, ethoxyphenylcarbonyl, propoxyphenylcarbonyl, methylsulfonyl, ethylsulfonyl, methylsulfonylmethylene, amino, aminomethyl, aminoethyl, aminopropyl, N-methylamino, N,N-dimethylamino, N-ethylamino, N,N-diethylamino, N-propylamino, N,N-dipropylamino, N-benzylamino, methylaminomethylene, aminocarbonyl, methoxycarbonylamino, ethoxycarbonylamino, or methylsulfonylamino; and $R^{202}$ is selected from hydrido, methyl, ethyl, phenyl and benzyl; and $R^4$ is phenyl, wherein said phenyl is optionally substituted with one or more radicals independently selected from fluoro, chloro, methyl, ethyl, methoxy and ethoxy; and $R^5$ is selected from hydrido, fluoro, chloro, bromo, hydroxy, methyl, ethyl, cyano, carboxy, methoxy, methoxycarbonyl, aminocarbonyl, acetyl, methylamino, dimethylamino, ethylamino, dimethylaminoethylamino, hydroxyethylamino, hydroxypropylamino, hydroxybutylamino, hydroxycyclopropylamino, hydroxycyclobutylamino, hydroxycyclopentylamino, hydroxycyclohexylamino, (1-ethyl-2-hydroxy)ethylamino, aminomethyl, cyclopropylamino, amino, ethoxycarbonylamino, methoxyphenylmethylamino, phenylmethylamino, fluorophenylmethylamino, fluorophenylethylamino, methylaminoethylamino, dimethylaminoethylamino, methylaminopropylamino, dimethylaminopropylamino, methylaminobutylamino, dimethylaminobutylamino, methylaminopentylamino, dimethylaminopentylamino, ethylaminoethylamino, diethylaminoethylamino, ethylaminopropylamino, diethylaminopropylamino, ethylaminobutylamino, diethylaminobutylamino, ethylaminopentylamino, methylaminocarbonyl, methylcarbonyl, and ethylcarbonyl; or a pharmaceutically-acceptable salt or tautomer thereof.

A subclass of compounds of specific interest consists of those compounds of Formula XA wherein:

$R^1$ is hydrido; and
$R^2$ is $R^{200}$-piperidinyl-$R^{201}$ wherein:
$R^{200}$ is selected from:
  methylene;
  —$NR^{202}$—;
  —S—;
  —O—;
or $R^{200}$ represents a bond;

$R^{201}$ represents one or more radicals selected from the group consisting of hydrido, hydroxy, methyl, ethyl, propyl, hydroxymethyl, hydroxyethyl, hydroxypropyl, methoxymethyl, methoxyethyl, methoxypropyl, ethoxyethyl, ethoxypropyl, propoxyethyl, propoxypropyl, methoxyphenyl, ethoxyphenyl, propoxyphenyl, methylcarbonyl, ethylcarbonyl, propylcarbonyl, hydroxymethylcarbonyl, hydroxyethylcarbonyl, carboxymethylcarbonyl, carboxyethylcarbonyl, methoxymethylcarbonyl, methoxyethylcarbonyl, ethoxymethylcarbonyl, ethoxyethylcarbonyl, methoxyphenylcarbonyl, ethoxyphenylcarbonyl, methylsulfonyl, ethylsulfonyl, amino, aminomethyl, aminoethyl, aminopropyl, N-methylamino, N,N-dimethylamino, N-ethylamino, N,N-diethylamino, N-propylamino, N,N-dipropylamino, N-benzylamino, methylaminomethylene, aminocarbonyl, methoxycarbonylamino, and ethoxycarbonylamino; and $R^{202}$ is selected from hydrido, methyl phenyl and benzyl; and $R^4$ is phenyl, wherein said phenyl is optionally substituted with one or more radicals independently selected from fluoro, chloro, methyl, and methoxy; and $R^5$ is selected from hydrido, methylamino, dimethylamino, 2-methylbutylamino, ethylamino, dimethylaminoethylamino, hydroxypropylamino, hydroxyethylamino, hydroxypropylamino, hydroxybutylamino, hydroxycyclopropylamino, hydroxycyclobutylamino, hydroxycyclopentylamino, hydroxycyclohexylamino, (1-ethyl-2-hydroxy)ethylamino, aminomethyl, cyclopropylamino, amino, dimethylaminoethylamino, dimethylaminopropylamino, dimethylaminobutylamino, dimethylaminopentylamino, diethylaminoethylamino, diethylaminopropylamino, diethylaminobutylamino, and diethylaminopentylamino; or p1 a pharmaceutically-acceptable salt or tautomer thereof.

A subclass of compounds of high interest consists of those compounds of Formula XA wherein:

$R^1$ is hydrido; and
$R^2$ is $R^{200}$-piperidinyl-$R^{201}$ wherein:
$R^{200}$ is selected from:
  methylene;
  $NR^{202}$—;
  —S—;
  —O—;
or $R^{200}$ represents a bond;

$R^{201}$ represents one or more radicals selected from the group consisting of hydrido, methyl, methoxyethyl, methylcarbonyl, hydroxymethylcarbonyl, methoxymethylcarbonyl, methylsulfonyl, amino, N,N-dimethylamino, and N,N-diethylamino; and $R^{202}$ is selected from hydrido and methyl; and $R^4$ is phenyl, wherein said phenyl is optionally substituted with one or more radicals independently selected from fluoro, chloro, methyl, and methoxy; and $R^5$ is selected from hydrido, hydroxypropylamino, hydroxycyclohexylamino, diethylaminoethylamino; or a pharmaceutically-acceptable salt or tautomer thereof.

Within Formula IXA there is another subclass of compounds of interest represented by Formula XA:

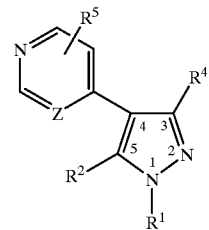

(XA)

$R^1$ is selected from hydrido, methyl, ethyl, hydroxyethyl and propargyl; and
$R^2$ is $R^{200}$-piperazinyl-$R^{201}$ wherein:
$R^{200}$ is selected from:
  —$(CR^{202}R^{203})_y$—;
  —$NR^{202}$—;
  —S—;
  —O—;
or $R^{200}$ represents a bond;

$R^{201}$ represents one or more radicals selected from the group consisting of hydrido, chloro, fluoro, bromo, iodo, hydroxy, carboxy, keto, methyl, ethyl, propyl, butyl, hydroxymethyl, hydroxyethyl, hydroxypropyl, hydroxybutyl, (1-hydroxy-1,1-dimethyl)ethyl, chloromethyl, chloroethyl, chloropropyl, chlorobutyl, fluoromethyl, fluoroethyl, fluoropropyl, fluorobutyl, cyclopropyl, cyclobutyl, cyclopentyl, cyclohexyl, ethenyl, propenyl, butenyl, ethynyl, propynyl, propargyl, butynyl, phenyl, benzyl, piperidinyl, piperazinyl, morpholinyl, piperidinylmethylene, piperazinylmethylene, morpholinylmethylene, methoxy, ethoxy, propoxy, butoxy, methoxymethylene, methoxyethylene, methoxypropylene, ethoxyethylene, ethoxypropylene, propoxyethylene, propoxypropylene, methoxyphenylene, ethoxyphenylene, propoxyphenylene, methylcarbonyl, ethylcarbonyl, propylcarbonyl, cyclopropylcarbonyl, cyclobutylcarbonyl, cyclopentylcarbonyl, cyclohexylcarbonyl, benzoyl, chlorobenzoyl, fluorobenzoyl, hydroxymethylcarbonyl, hydroxyethylcarbonyl, hydroxypropylcarbonyl, carboxymethylcarbonyl, carboxyethylcarbonyl, carboxypropylcarbonyl, methoxymethylcarbonyl, methoxyethylcarbonyl, methoxypropylcarbonyl, ethoxymethylcarbonyl, ethoxyethylcarbonyl, ethoxypropylcarbonyl, propoxymethylcarbonyl, propoxyethylcarbonyl, propoxypropylcarbonyl, methoxyphenylcarbonyl, ethoxyphenylcarbonyl, propoxyphenylcarbonyl, piperidinylmethylcarbonyl, piperazinylmethylcarbonyl, morpholinylcarbonyl, methylsulfonyl, ethylsulfonyl, methylsulfonylmethylene, amino, aminomethyl, aminoethyl, aminopropyl, N-methylamino, N,N-dimethylamino, N-ethylamino, N,N-diethylamino, N-propylamino, N,N-dipropylamino, phenylamino, benzylamino, methylaminomethylene, ethylaminomethylene, methylaminoethylene, ethylaminoethylene, aminocarbonyl, methylcarbonylamino, ethylcarbonylamino, methylaminomethylcarbonyl, ethylaminomethylcarbonyl, methylcarbonylaminomethylene, ethylcarbonylaminomethylene, aminomethylcarbonylaminocarbonylmethylene, methoxycarbonylamino, ethoxycarbonylamino, methoxymethylcarbonylamino, methoxyethylcarbonylamino, ethoxymethylcarbonylamino, ethoxyethylcarbonylamino, methoxycarbonylaminomethylene, ethoxycarbonylaminomethylene, methylimidocarbonyl, ethylimidocarbonyl, amidino, methylamidino, methylamidino, benzylamidino, guanidino, guanidinomethylene, guanidinoethylene, and methylsulfonylamino; and $R^{202}$ and $R^{203}$ are independently selected from hydrido, methyl, ethyl, propyl, butyl, phenyl and benzyl; and y is 0, 1 or 2; and $R^4$ is phenyl, wherein said phenyl is optionally substituted with one or more radicals independently selected from fluoro, chloro, methyl, ethyl, methoxy and ethoxy; and $R^5$ is selected from hydrido, fluoro, chloro, bromo, hydroxy, methyl, ethyl, propyl, benzyl, cyano, carboxy, methoxy, methoxycarbonyl, aminocarbonyl, acetyl, methylamino, dimethylamino, 2-methylbutylamino, ethylamino, dimethylaminoethylamino, hydroxyethylamino, hydroxypropylamino, hydroxybutylamino, hydroxycyclopropylamino, hydroxycyclobutylamino, hydroxycyclopentylamino, hydroxycyclohexylamino, imidazolylamino, morpholinylethylamino, (1-ethyl-2-hydroxy)ethylamino, piperidinylamino, pyridinylmethylamino, phenylmethylpiperidinylamino, aminomethyl, cyclopropylamino, amino, hydroxy, ethoxycarbonylamino, methoxyphenylmethylamino, phenylmethylamino, fluorophenylmethylamino fluorophenylethylamino, methylaminoethylamino, dimethylaminoethylamino, methylaminopropylamino, dimethylaminopropylamino, methylaminobutylamino, dimethylaminobutylamino, methylaminopentylamino, dimethylaminopentylamino, ethylaminoethylamino, diethylaminoethylamino, ethylaminopropylamino, diethylaminopropylamino, ethylaminobutylamino, diethylaminobutylamino, ethylaminopentylamino, methylaminocarbonyl, methylcarbonyl, and ethylcarbonyl; or a pharmaceutically-acceptable salt or tautomer thereof.

A subclass of compounds of particular interest consists of those compounds of Formula XA wherein:

$R^1$ is selected from hydrido, methyl, ethyl, hydroxyethyl and propargyl; and $R^2$ is $R^{200}$-piperazinyl-$R^{201}$ wherein:

$R^{200}$ is selected from:

—(CR$^{202}$R$^{203}$)—;
—NR$^{202}$—;
—S—;
—O—;
or $R^{200}$ represents a bond;

$R^{201}$ represents one or more radicals selected from the group consisting of hydrido, chloro, fluoro, bromo, hydroxy, carboxy, keto, methyl, ethyl, propyl, hydroxymethyl, hydroxyethyl, hydroxypropyl, (1-hydroxy-1,1-dimethyl)ethyl, chloromethyl, chloroethyl, chloropropyl, fluoromethyl, fluoroethyl, fluoropropyl, cyclopropyl, cyclobutyl, cyclopentyl, cyclohexyl, ethenyl, propenyl, butenyl, ethynyl, propynyl, propargyl, phenyl, benzyl, piperidinyl, piperazinyl, morpholinyl, piperidinylmethylene, piperazinylmethylene, morpholinylmethylene, methoxy, ethoxy, propoxy, methoxymethylene, methoxyethylene, ethoxyethylene, methoxyphenylene, ethoxyphenylene, methylcarbonyl, ethylcarbonyl, propylcarbonyl, cyclopropylcarbonyl, cyclobutylcarbonyl, cyclopentylcarbonyl, cyclohexylcarbonyl, benzoyl, chlorobenzoyl, fluorobenzoyl, hydroxymethylcarbonyl, hydroxyethylcarbonyl, hydroxypropylcarbonyl, carboxymethylcarbonyl, carboxyethylcarbonyl, carboxypropylcarbonyl, methoxymethylcarbonyl, methoxyethylcarbonyl, methoxypropylcarbonyl, ethoxymethylcarbonyl, ethoxyethylcarbonyl, ethoxypropylcarbonyl, propoxymethylcarbonyl, propoxyethylcarbonyl, propoxypropylcarbonyl, methoxyphenylcarbonyl, ethoxyphenylcarbonyl, propoxyphenylcarbonyl, piperidinylmethylcarbonyl, piperazinylmethylcarbonyl, morpholinylcarbonyl, methylsulfonyl, ethylsulfonyl, methylsulfonylmethylene, amino, aminomethyl, aminoethyl, aminopropyl, N-methylamino, N,N-dimethylamino, N-ethylamino, N,N-diethylamino, N-propylamino, N,N-dipropylamino, phenylamino, benzylamino, methylaminomethylene, ethylaminomethylene, methylaminoethylene, ethylaminoethylene, aminocarbonyl, methylcarbonylamino, ethylcarbonylamino, methylaminomethylcarbonyl, ethylaminomethylcarbonyl, methylcarbonylaminomethylene, ethylcarbonylaminomethylene, aminomethylcarbonylaminocarbonylmethylene, methoxycarbonylamino, ethoxycarbonylamino, methoxymethylcarbonylamino, methoxyethylcarbonylamino, ethoxymethylcarbonylamino, ethoxyethylcarbonylamino, methoxycarbonylaminomethylene, ethoxycarbonylaminomethylene, and methylsulfonylamino; and $R^{202}$ and $R^{203}$ are independently selected from hydrido, methyl, ethyl, phenyl and benzyl; and y is 0, 1 or 2; and $R^4$ is phenyl, wherein said phenyl is optionally substituted with one or more radicals independently selected from fluoro, chloro, methyl, ethyl, methoxy and ethoxy; and $R^5$ is selected from hydrido, fluoro, chloro, bromo, hydroxy, methyl, ethyl, cyano, carboxy, methoxy, methoxycarbonyl, aminocarbonyl, acetyl, methylamino, dimethylamino, ethylamino, dimethylaminoethylamino, hydroxyethylamino, hydroxypropylamino, hydroxybutylamino, hydroxycyclopropylamino, hydroxycyclobutylamino, hydroxycyclopentylamino, hydroxycyclohexylamino, (1-ethyl-2-hydroxy)ethylamino, aminomethyl, cyclopropylamino, amino, ethoxycarbonylamino, methoxyphenylmethylamino, phenylmethylamino, fluorophenylmethylamino, fluorophenylethylamino, methylaminoethylamino, dimethylaminoethylamino, methylaminopropylamino, dimethylaminopropylamino, methylaminobutylamino, dimethylaminobutylamino, methylaminopentylamino, dimethylaminopentylamino, ethylaminoethylamino, diethylaminoethylamino, ethylaminopropylamino, diethylaminopropylamino, ethylaminobutylamino, diethylaminobutylamino, ethylaminopentylamino, methylaminocarbonyl, methylcarbonyl, and ethylcarbonyl; or a pharmaceutically-acceptable salt or tautomer thereof.

A subclass of compounds of specific interest consists of those compounds of Formula XA wherein:

$R^1$ is hydrido; and
$R^2$ is $R^{200}$-piperazinyl-$R^{201}$ wherein:
$R^{200}$ is selected from:
  methylene;
  —$NR^{202}$—;
  —S—;
  —O—;
or $R^{200}$ represents a bond;
$R^{202}$ represents one or more radicals selected from the group consisting of hydrido, methyl, ethyl, propyl, cyclopropyl, cyclobutyl, cyclopentyl, cyclohexyl, ethynyl, propynyl, propargyl, phenyl, benzyl, piperidinyl, piperazinyl, and morpholinyl; and
$R^{202}$ is selected from hydrido, methyl, ethyl, phenyl and benzyl; and
y is 0, 1 or 2; and
$R^4$ is phenyl, wherein said phenyl is optionally substituted with one or more radicals independently selected from fluoro, chloro, methyl, and methoxy; and
$R^5$ is selected from hydrido, methylamino, dimethylamino, 2-methylbutylamino, ethylamino, dimethylaminoethylamino, hydroxypropylamino, hydroxyethylamino, hydroxypropylamino, hydroxybutylamino, hydroxycyclopropylamino, hydroxycyclobutylamino, hydroxycyclopentylamino, hydroxycyclohexylamino, (1-ethyl-2-hydroxy)ethylamino, aminomethyl, cyclopropylamino, amino, dimethylaminoethylamino, dimethylaminopropylamino, dimethylaminobutylamino, dimethylaminopentylamino, diethylaminoethylamino, diethylaminopropylamino, diethylaminobutylamino, and diethylaminopentylamino; or a pharmaceutically-acceptable salt or tautomer thereof.

A subclass of compounds of high interest consists of those compounds of Formula XA wherein:

$R^1$ is hydrido; and
$R^2$ is $R^{200}$-piperazinyl-$R^{201}$ wherein:
$R^{200}$ is selected from:
  methylene;
  —$NR^{202}$—;
  —S—;
  —O—;
or $R^{200}$ represents a bond;
$R^{201}$ represents one or more radicals selected from the group consisting of hydrido, methyl, cyclopropyl, propargyl, and benzyl; and $R^{202}$ is selected from hydrido and methyl; and
$R^4$ is phenyl, wherein said phenyl is optionally substituted with one or more radicals independently selected from fluoro, chloro, methyl, and methoxy; and
$R^5$ is selected from hydrido, hydroxypropylamino, hydroxycyclohexylamino, and diethylaminoethylamino; or a pharmaceutically-acceptable salt or tautomer thereof.

Within Formula IA there is another subclass of compounds of interest represented by Formula XA:

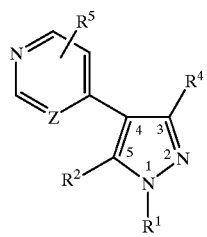

(XA)

$R^1$ is selected from hydrido, methyl, ethyl, hydroxyethyl and propargyl; and
$R^2$ is $R^{200}$-cyclohexyl-$R^{201}$ wherein:
$R^{200}$ is selected from:
  —$(CR^{202}R^{203})_y$—;
  —$NR^{202}$—;
  —S—;
  —O—;
or $R^{200}$ represents a bond;
$R^{201}$ represents one or more radicals selected from the group consisting of hydrido, chloro, fluoro, bromo, iodo, hydroxy, carboxy, keto, methyl, ethyl, propyl, butyl, hydroxymethyl, hydroxyethyl, hydroxypropyl, hydroxybutyl, (1-hydroxy-1,1-dimethyl)ethyl, chloromethyl, chloroethyl, chloropropyl, chlorobutyl, fluoromethyl, fluoroethyl, fluoropropyl, fluorobutyl, cyclopropyl, cyclobutyl, cyclopentyl, cyclohexyl, ethenyl, propenyl, butenyl, ethynyl, propynyl, propargyl, butynyl, phenyl, benzyl, piperidinyl, piperazinyl, morpholinyl, piperidinylmethylene, piperazinylmethylene, morpholinylmethylene, methoxy, ethoxy, propoxy, butoxy, methoxymethylene, methoxyethylene, methoxypropylene, ethoxyethylene, ethoxypropylene, propoxyethylene, propoxypropylene, methoxyphenylene, ethoxyphenylene, propoxyphenylene, methylcarbonyl, ethylcarbonyl, propylcarbonyl, cyclopropylcarbonyl, cyclobutylcarbonyl, cyclopentylcarbonyl, cyclohexylcarbonyl, benzoyl, chlorobenzoyl, fluorobenzoyl, hydroxymethylcarbonyl, hydroxyethylcarbonyl, hydroxypropylcarbonyl, carboxymethylcarbonyl, carboxyethylcarbonyl, carboxypropylcarbonyl, methoxymethylcarbonyl, methoxyethylcarbonyl, methoxypropylcarbonyl, ethoxymethylcarbonyl, ethoxyethylcarbonyl, ethoxypropylcarbonyl, propoxymethylcarbonyl, propoxyethylcarbonyl, propoxypropylcarbonyl, methoxyphenylcarbonyl, ethoxyphenylcarbonyl, propoxyphenylcarbonyl, piperidinylmethylcarbonyl, piperazinylmethylcarbonyl, morpholinylcarbonyl, methylsulfonyl, ethylsulfonyl, methylsulfonylmethylene, amino, aminomethyl, aminoethyl, aminopropyl, N-methylamino, N,N-dimethylamino, N-ethylamino, N,N-diethylamino, N-propylamino, N,N-dipropylamino, phenylamino, benzylamino, methylaminomethylene, ethylaminomethylene, methylaminoethylene, ethylaminoethylene, aminocarbonyl, methylcarbonylamino, ethylcarbonylamino, methylaminomethylcarbonyl, ethylaminomethylcarbonyl, methylcarbonylaminomethylene, ethylcarbonylaminomethylene, aminomethylcarbonylaminocarbonylmethylene, methoxycarbonylamino, ethoxycarbonylamino, methoxymethylcarbonylamino, methoxyethylcarbonylamino, ethoxymethylcarbonylamino, ethoxyethylcarbonylamino, methoxycarbonylaminomethylene, ethoxycarbonylaminomethylene, methylimidocarbonyl, ethylimidocarbonyl, amidino, methylamidino, methylamidino, benzylamidino, guanidino, guanidinomethylene, guanidinoethylene, and methylsulfonylamino; and $R^{202}$ and $R^{203}$ are independently selected from hydrido, methyl, ethyl, propyl, butyl, phenyl and benzyl; and y is 0, 1 or 2; and $R^4$ is phenyl, wherein said phenyl is optionally substituted with one or more radicals independently selected from fluoro, chloro, methyl, ethyl, methoxy and ethoxy; and $R^5$ is selected from hydrido, fluoro, chloro, bromo, hydroxy, methyl, ethyl, propyl, benzyl, cyano, carboxy, methoxy, methoxycarbonyl, aminocarbonyl, acetyl, methylamino, dimethylamino, 2-methylbutylamino, ethylamino, dimethylaminoethylamino, hydroxyethylamino, hydroxypropylamino, hydroxybutylamino, hydroxycyclopropylamino, hydroxycyclobutylamino, hydroxycyclopentylamino, hydroxycyclohexylamino, imidazolylamino, morpholinylethylamino, (1-ethyl-2-hydroxy)ethylamino, piperidinylamino, pyridinylmethylamino, phenylmethylpiperidinylamino, aminomethyl, cyclopropylamino, amino, hydroxy, ethoxycarbonylamino, methoxyphenylmethylamino, phenylmethylamino, fluorophenylmethylamino, fluorophenylethylamino, methylaminoethylamino, dimethylaminoethylamino, methylaminopropylamino, dimethylaminopropylamino, methylaminobutylamino, dimethylaminobutylamino, methylaminopentylamino, dimethylaminopentylamino, ethylaminoethylamino, diethylaminoethylamino, ethylaminopropylamino, diethylaminopropylamino, ethylaminobutylamino, diethylaminobutylamino, ethylaminopentylamino, methylaminocarbonyl, methylcarbonyl, and ethylcarbonyl; or a pharmaceutically-acceptable salt or tautomer thereof.

A subclass of compounds of particular interest consists of those compounds of Formula XA wherein:

$R^1$ is selected from hydrido, methyl, ethyl, hydroxyethyl and propargyl; and $R^2$ is $R^{200}$-cyclohexyl-$R^{201}$ wherein:

$R^{200}$ is selected from:
—(CR$^{202}$R$^{203}$)$_y$—;
—NR$^{202}$—;
—S—;
—O—;

or $R^{200}$ represents a bond;

$R^{201}$ represents one or more radicals selected from the group consisting of hydrido, chloro, fluoro, bromo, hydroxy, carboxy, keto, methyl, ethyl, propyl, hydroxymethyl, hydroxyethyl, hydroxypropyl, (1-hydroxy-1,1-dimethyl)ethyl, chloromethyl, chloroethyl, chloropropyl, fluoromethyl, fluoroethyl, fluoropropyl, cyclopropyl, cyclobutyl, cyclopentyl, cyclohexyl, phenyl, benzyl, piperidinyl, piperazinyl, morpholinyl, piperidinylmethylene, piperazinylmethylene, morpholinylmethylene, methoxy, ethoxy, propoxy, methoxymethylene, methoxyethylene, methoxypropylene, ethoxyethylene, ethoxypropylene, propoxyethylene, propoxypropylene, methoxyphenylene, ethoxyphenylene, propoxyphenylene, methylcarbonyl, ethylcarbonyl, propylcarbonyl, cyclopropylcarbonyl, cyclobutylcarbonyl, cyclopentylcarbonyl, cyclohexylcarbonyl, benzoyl, chlorobenzoyl, fluorobenzoyl, hydroxymethylcarbonyl, hydroxyethylcarbonyl, hydroxypropylcarbonyl, carboxymethylcarbonyl, carboxyethylcarbonyl, carboxypropylcarbonyl, methoxymethylcarbonyl, methoxyethylcarbonyl, methoxypropylcarbonyl, ethoxymethylcarbonyl, ethoxyethylcarbonyl, ethoxypropylcarbonyl, propoxymethylcarbonyl, propoxyethylcarbonyl, propoxypropylcarbonyl, methoxyphenylcarbonyl, ethoxyphenylcarbonyl, propoxyphenylcarbonyl, piperidinylmethylcarbonyl, piperazinylmethylcarbonyl, morpholinylcarbonyl, methylsulfonyl, ethylsulfonyl, methylsulfonylmethylene, amino, aminomethyl, aminoethyl, aminopropyl, N-methylamino, N,N-dimethylamino, N-ethylamino, N,N-diethylamino, N-propylamino, N,N-dipropylamino, phenylamino, benzylamino, methylaminomethylene, ethylaminomethylene, methylaminoethylene, ethylaminoethylene, aminocarbonyl, methylcarbonylamino, ethylcarbonylamino, methylaminomethylcarbonyl, ethylaminomethylcarbonyl, methylcarbonylaminomethylene, ethylcarbonylaminomethylene, aminomethylcarbonylaminocarbonylmethylene, methoxycarbonylamino, ethoxycarbonylamino, methoxymethylcarbonylamino, methoxyethylcarbonylamino, ethoxymethylcarbonylamino, ethoxyethylcarbonylamino, methoxycarbonylaminomethylene, and ethoxycarbonylaminomethylene; and $R^{202}$ and $R^{203}$ are independently selected from hydrido, methyl, ethyl, phenyl and benzyl; and y is 0, 1 or 2; and $R^4$ is phenyl, wherein said phenyl is optionally substituted with one or more radicals independently selected from fluoro, chloro, methyl, ethyl, methoxy and ethoxy; and $R^5$ is selected from hydrido, fluoro, chloro, bromo, hydroxy, methyl, ethyl, cyano, carboxy, methoxy, methoxycarbonyl, aminocarbonyl, acetyl, methylamino, dimethylamino, ethylamino, dimethylaminoethylamino, hydroxyethylamino, hydroxypropylamino, hydroxybutylamino, hydroxycyclopropylamino, hydroxycyclobutylamino, hydroxycyclopentylamino, hydroxycyclohexylamino, (1-ethyl-2-hydroxy)ethylamino, aminomethyl, cyclopropylamino, amino, ethoxycarbonylamino, methoxyphenylmethylamino, phenylmethylamino, fluorophenylmethylamino, fluorophenylethylamino, methylaminoethylamino, dimethylaminoethylamino, methylaminopropylamino,
dimethylaminopropylamino, methylaminobutylamino,
dimethylaminobutylamino, methylaminopentylamino,
dimethylaminopentylamino, ethylaminoethylamino,
diethylaminoethylamino, ethylaminopropylamino,
diethylaminopropylamino, ethylaminobutylamino,
diethylaminobutylamino, ethylaminopentylamino,
methylaminocarbonyl, methylcarbonyl, and ethylcarbonyl; or a pharmaceutically-acceptable salt or tautomer thereof.

A subclass of compounds of specific interest consists of those compounds of Formula XA wherein:

$R^1$ is hydrido; and $R^2$ is $R^{200}$-cyclohexyl-$R^{201}$ wherein:

$R^{200}$ is selected from:
  methylene;
  —$NR^{202}$—;
  —S—
  —O—;
or $R^{200}$ represents a bond;

$R^{201}$ represents one or more radicals selected from the group consisting of hydrido, amino, aminomethyl, aminoethyl, aminopropyl, N-methylamino, N,N-dimethylamino, N-ethylamino, N,N-diethylamino, N-propylamino, N,N-dipropylamino, phenylamino, benzylamino, methylaminomethylene, ethylaminomethylene, methylaminoethylene, ethylaminoethylene, aminocarbonyl, methylcarbonylamino, ethylcarbonylamino, methylaminomethylcarbonyl, ethylaminomethylcarbonyl, methylcarbonylaminomethylene, ethylcarbonylaminomethylene, aminomethylcarbonylaminocarbonylmethylene, methoxycarbonylamino, ethoxycarbonylamino, methoxymethylcarbonylamino, methoxyethylcarbonylamino, ethoxymethylcarbonylamino, ethoxyethylcarbonylamino, methoxycarbonylaminomethylene, and ethoxycarbonylaminomethylene; and $R^{202}$ is selected from hydrido, methyl, phenyl and benzyl; and $R^4$ is phenyl, wherein said phenyl is optionally substituted with one or more radicals independently selected from fluoro, chloro, methyl, and methoxy; and $R^5$ is selected from hydrido, methylamino, dimethylamino, 2-methylbutylamino, ethylamino, dimethylaminoethylamino, hydroxypropylamino, hydroxyethylamino, hydroxypropylamino, hydroxybutylamino, hydroxycyclopropylamino, hydroxycyclobutylamino, hydroxycyclopentylamino, hydroxycyclohexylamino, (1-ethyl-2-hydroxy) ethylamino, aminomethyl, cyclopropylamino, amino, dimethylaminoethylamino, dimethylaminopropylamino, dimethylaminobutylamino, dimethylaminopentylamino, diethylaminoethylamino, diethylaminopropylamino, diethylaminobutylamino, and diethylaminopentylamino; or a pharmaceutically-acceptable salt or tautomer thereof.

A subclass of compounds of high interest consists of those compounds of Formula XA wherein:

$R^1$ is hydrido; and $R^2$ is $R^{200}$-cyclohexyl-$R^{201}$ wherein:

$R^{200}$ is selected from:
  methylene;
  —$NR^{202}$—;
  —S—;
  —O—;
or $R^{200}$ represents a bond;

$R^{201}$ represents one or more radicals selected from the group consisting of amino, aminomethyl, N,N-dimethylamino, and N-isopropylamino; and $R^{202}$ is selected from hydrido and methyl; and $R^4$ is phenyl, wherein said phenyl is optionally substituted with one or more radicals independently selected from fluoro, chloro, methyl, and methoxy; and $R^5$ is selected from hydrido, hydroxypropylamino, hydroxycyclohexylamino, and diethylaminoethylamino; or a pharmaceutically-acceptable salt or tautomer thereof.

Within Formula IA is another subclass of compounds of interest wherein:

$R^1$ is selected from hydrido, hydroxy, alkyl, cycloalkyl, alkenyl, cycloalkenyl, alkynyl, aryl, heterocyclyl, cycloalkylalkylene, cycloalkenylalkylene, heterocyclylalkylene, haloalkyl, haloalkenyl, haloalkynyl, hydroxyalkyl, hydroxyalkenyl, hydroxyalkynyl, aralkyl, aralkenyl, aralkynyl, arylheterocyclyl, carboxy, carboxyalkyl, alkoxyalkyl, alkenoxyalkyl, alkynoxyalkyl, aryloxyalkyl, alkoxyaryl, heterocyclyloxyalkyl, alkoxyalkoxy, mercaptoalkyl, alkylthioalkylene, alkenylthioalkylene, alkylthioalkenylene, amino, aminoalkyl, alkylamino, alkenylamino, alkynylamino, arylamino, heterocyclylamino, alkylsulfinyl, alkenylsulfinyl, alkynylsulfinyl, arylsulfinyl, heterocyclylsulfinyl, alkylsulfonyl, alkenylsulfonyl, alkynylsulfonyl, arylsulfonyl, heterocyclylsulfonyl, alkylaminoalkylene, alkylsulfonylalkylene, acyl, acyloxycarbonyl, alkoxycarbonylalkylene, aryloxycarbonylalkylene, heterocyclyloxycarbonylalkylene, alkoxycarbonylarylene, aryloxycarbonylarylene, heterocyclyloxycarbonylarylene, alkylcarbonylalkylene, arylcarbonylalkylene, heterocyclylcarbonylalkylene, alkylcarbonylarylene, arylcarbonylarylene, heterocyclylcarbonylarylene, alkylcarbonyloxyalkylene, arylcarbonyloxyalkylene, heterocyclylcarbonyloxyalkylene, alkylcarbonyloxyarylene, arylcarbonyloxyarylene, and heterocyclylcarbonyloxyarylene; or $R^1$ has the formula

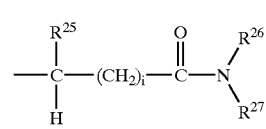

(II)

wherein:
  i is an integer from 0 to 9;
  $R^{25}$ is selected from hydrogen, alkyl, aralkyl, heterocyclylalkyl, alkoxyalkylene, aryloxyalkylene, aminoalkyl, alkylaminoalkyl, arylaminoalkyl, alkylcarbonylalkylene, arylcarbonylalkylene, and heterocyclylcarbonylaminoalkylene; and
  $R^{26}$ is selected from hydrogen, alkyl, alkenyl, alkynyl, cycloalkylalkylene, aralkyl, alkoxycarbonylalkylene, and alkylaminoalkyl; and $R^{27}$ is selected from alkyl, cycloalkyl, alkynyl, aryl, heterocyclyl, aralkyl, cycloalkylalkylene, cycloalkenylalkylene, cycloalkylarylene, cycloalkylcycloalkyl, heterocyclylalkylene, alkylarylene, alkylaralkyl, aralkylarylene, alkylheterocyclyl, alkylheterocyclylalkylene, alkylheterocyclylarylene, aralkylheterocyclyl, alkoxyalkylene, alkoxyarylene, alkoxyaralkyl, alkoxyheterocyclyl, alkoxyalkoxyarylene, aryloxyarylene, aralkoxyarylene, alkoxyheterocyclylalkylene, aryloxyalkoxyarylene, alkoxycarbonylalkylene, alkoxycarbonylheterocyclyl, alkoxycarbonylheterocyclylcarbonylalkylene, aminoalkyl, alkylaminoalkylene, arylaminocarbonylalkylene, alkoxyarylaminocarbonylalkylene, aminocarbonylalkylene, arylaminocarbonylalkylene, alkylaminocarbonylalkylene, arylcarbonylalkylene, alkoxycarbonylarylene, aryloxycarbonylarylene, alkylaryloxycarbonylarylene, arylcarbonylarylene, alkylarylcarbonylarylene, alkoxycarbonylheterocyclylarylene, alkoxycarbonylalkoxylarylene, heterocyclylcarbonylalkylarylene, alkylthioalkylene, cycloalkylthioalkylene, alkylthioarylene, aralkylthioarylene, heterocyclylthioarylene, arylthioalklylarylene, arylsulfonylaminoalkylene, alkylsulfonylarylene, alkylaminosulfonylarylene; wherein said alkyl, cycloalkyl, aryl, heterocyclyl, aralkyl, heterocyclylalkylene, alkylheterocyclylarylene, alkoxyarylene, aryloxyarylene, arylaminocarbonylalkylene, aryloxycarbonylarylene, arylcarbonylarylene, alkylthioarylene, heterocyclylthioarylene, arylthioalklylarylene, and alkylsulfonylarylene groups are optionally substituted with one or more radicals independently selected from alkyl, halo, haloalkyl, alkoxy, keto, amino, nitro, and cyano; or $R^{27}$ is —$CHR^{28}R^{29}$ wherein $R^{28}$ is alkoxycarbonyl, and $R^{29}$ is selected from aralkyl, aralkoxyalkylene, heterocyclylalkylene, alkylheterocyclylalkylene, alkoxycarbonylalkylene, alkylthioalkylene, and aralkylthioalkylene; wherein said aralkyl and heterocylcyl groups are optionally substituted with one or more radicals independently selected from alkyl and nitro; or $R^{26}$ and $R^{27}$ together with the nitrogen atom to which they are attached form a heterocycle, wherein said heterocycle is optionally substituted with one or more radicals independently selected from alkyl, aryl, heterocyclyl, heterocyclylalkylene, alkylheterocyclylalkylene, aryloxyalkylene, alkoxyarylene, alkylaryloxyalkylene, alkylcarbonyl, alkoxycarbonyl, aralkoxycarbonyl, alkylamino and alkoxycarbonylamino; wherein said aryl, heterocyclylalkylene and aryloxyalkylene radicals are optionally substituted with one or more radicals independently selected from halogen, alkyl and alkoxy; and $R^2$ is selected from mercapto, heterocyclylheterocyclyl, heterocyclylalkylheterocyclyl, N-alkyl-N-alkynylamino, aminocarbonylalkylene, alkylcarbonylaminoalkylene, aminoalkylcarbonylaminoalkylene, alkylaminoalkylcarbonylamino, aminoalkylthio, alkylaminocarbonylalkylthio, alkylaminoalkylaminocarbonylalkylthio, cyanoalkylthio, alkenylthio, alkynylthio, carboxyalkylthio, alkoxycarbonylalkylthio, alkylsulfinyl, alkylsulfonyl, alkoxycarbonylalkylamino, alkoxycarbonylaminoalkylene, alkoxycarbonylaminoalkoxy, aralkythio, heterocyclylalkylthio, aminoalkoxy, cyanoalkoxy, carboxyalkoxy, aryloxy, aralkoxy, alkenyloxy, alkynyloxy, and heterocyclylalkyloxy; wherein the aryl, heterocyclyl, heterocyclylalkyl, cycloalkyl and cycloalkenyl groups are optionally substituted with one or more radicals independently selected from halo, keto, amino, alkyl, alkenyl, alkynyl, aryl, heterocyclyl, aralkyl, heterocyclylalkyl, epoxyalkyl, amino (hydroxyalkyl)carboxy, alkoxy, aryloxy, aralkoxy, haloalkyl, alkylamino, alkynylamino, alkylaminoalkylamino, heterocyclylalkylamino, alkylcarbonyl, alkoxycarbonyl, alkylsulfonyl, arylsulfonyl, and aralkylsulfonyl; or $R^2$ is $R^{200}$-heterocyclyl-$R^{201}$, $R^{200}$-aryl-$R^{201}$, or $R^{200}$-cycloalkyl-$R^{201}$ wherein:

$R^{200}$ is selected from:
—$(CR^{202}R^{203})$—;
—$C(O)$—;
—$C(O)$—$(CH_2)_y$—;
—$C(O)$—$O$—$(CH_2)_y$—;
—$(CH_2)_y$—$C(O)$—;
—$O$—$(CH_2)_y$—$C(O)$—;
—$NR^{202}$—;
—$NR^{202}$—$(CH_2)_y$—;
—$(CH_2)_y$—$NR^{202}$—;
—$(CH_2)_y$—$NR^{202}$—$(CH_2)_z$—;
—$(CH_2)_y$—$C(O)$—$NR^{202}$—$(CH_2)_z$—;
—$(CH_2)_y$—$NR^{202}$—$C(O)$—$(CH_2)_z$—;
—$(CH_2)_y$—$NR^{202}$—$C(O)$—$NR^{203}$—$(CH_2)_z$—;
—$S(O)_x$—$(CR^{202}R^{203})_y$—;
—$(CR^{202}R^{203})_y$—$S(O)_x$—;
—$S(O)_x$—$(CR^{202}R^{203})_y$—$O$—;
—$S(O)_x$—$(CR^{202}R^{203})_y$—$C(O)$—;
—$O$—$(CH_2)_y$—;
—$(CH_2)_y$—$O$—;
—$S$—;
—$O$—;

or $R^{200}$ represents a bond;

$R^{201}$ represents one or more radicals selected from the group consisting of hydrido, halogen, hydroxy, carboxy, keto, alkyl, hydroxyalkyl, haloalkyl, cycloalkyl, alkenyl, alkynyl, aryl, heterocyclyl, aralkyl, heterocyclylalkylene, alkylcarbonyl, hydroxyalkylcarbonyl, cycloalkylcarbonyl, arylcarbonyl, haloarylcarbonyl, alkoxy, alkoxyalkylene, alkoxyarylene, alkoxycarbonyl, carboxyalkylcarbonyl, alkoxyalkylcarbonyl, heterocyclylalkylcarbonyl, alkylsulfonyl, alkylsulfonylalkylene, amino, aminoalkyl, alkylamino, aralkylamino, alkylaminoalkylene, aminocarbonyl, alkylcarbonylamino, alkylcarbonylaminoalkylene, alkylaminoalkylcarbonyl, alkylaminoalkylcarbonylamino, aminoalkylcarbonylaminoalkyl, alkoxycarbonylamino, alkoxyalkylcarbonylamino, alkoxycarbonylaminoalkylene, alkylimidocarbonyl, amidino, alkylamidino, aralkylamidino, guanidino, guanidinoalkylene, or alkylsulfonylamino; and $R^{202}$ and $R^{203}$ are independently selected from hydrido, alkyl, aryl and aralkyl; and y and z are independently 0, 1, 2, 3, 4, 5 or 6 wherein y+z is less than or equal to 6; and z is 0, 1 or 2; or $R^2$ is —$NHCR^{204}R^{205}$ wherein $R^{204}$ is alkylaminoalkylene, and $R^{205}$ is aryl; or $R^2$ is —$C(NR^{206})R^{207}$ wherein $R^{206}$ is selected from hydrogen and hydroxy, and $R^{207}$ is selected from alkyl, aryl and aralkyl; and $R^3$ is selected from pyridinyl, pyrimidinyl, quinolinyl, purinyl, maleimidyl, pyridonyl, thiazolyl, thiazolylalkyl, thiazolylamino,

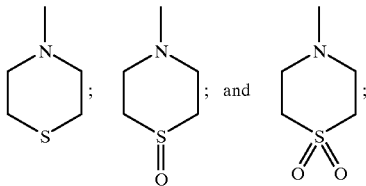

wherein the $R^3$ pyridinyl, pyrimidinyl, quinolinyl, purinyl, maleimidyl, pyridonyl, thiazolyl, thiazolylalkyl, thiazolylamino,

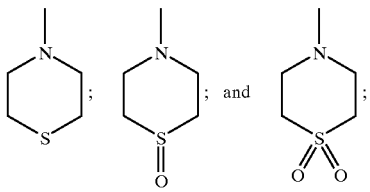

groups are optionally substituted with one or more radicals independently selected from halo, keto, alkyl, aralkyl, aralkenyl, arylheterocyclyl, carboxy, carboxyalkyl, alkoxy, aryloxy, alkylthio, arylthio, alkylsulfinyl, arylsulfinyl, alkylsulfonyl, arylsulfonyl, aralkoxy, heterocyclylalkoxy, amino, alkylamino, alkenylamino, alkynylamino, cycloalkylamino, cycloalkenylamino, arylamino, haloarylamino, heterocyclylamino, aminocarbonyl, cyano, hydroxy, hydroxyalkyl, alkoxyalkylene, alkenoxyalkylene, aryloxyalkyl, alkoxyalkylamino, alkylaminoalkoxy, alkoxycarbonyl, aryloxycarbonyl, heterocyclyloxycarbonyl, alkoxycarbonylamino, alkoxyarylamino, alkoxyaralkylamino, aminosulfinyl, aminosulfonyl, alkylsulfonylamino, alkylaminoalkylamino, hydroxyalkylamino, aralkylamino, aryl(hydroxyalkyl) amino, alkylaminoalkylaminoalkylamino, alkylheterocyclylamino, heterocyclylalkylamino, alkylheterocyclylalkylamino, aralkylheterocyclylamino, heterocyclylheterocyclylalkylamino, alkoxycarbonylheterocyclylamino, nitro, alkylaminocarbonyl, alkylcarbonylamino, halosulfonyl, aminoalkyl, haloalkyl, alkylcarbonyl, hydrazinyl, alkylhydrazinyl, arylhydrazinyl, or —$NR^{44}R^{45}$ wherein $R^{44}$ is alkylcarbonyl or amino, and $R^{45}$ is alkyl or aralkyl; and $R^4$ is selected from hydrido, alkyl, alkenyl, alkynyl, cycloalkyl, cycloalkenyl, aryl, and heterocyclyl, wherein $R^4$ is optionally substituted with one or more radicals independently selected from halo, alkyl, alkenyl, alkynyl, aryl, heterocyclyl, alkylthio, arylthio, alkylthioalkylene, arylthioalkylene, alkylsulfinyl, alkylsulfinylalkylene, arylsulfinylalkylene, alkylsulfonyl, alkylsulfonylalkylene, arylsulfonylalkylene, alkoxy, aryloxy, aralkoxy, aminocarbonyl, alkylaminocarbonyl, arylaminocarbonyl, alkoxycarbonyl, aryloxycarbonyl, haloalkyl, amino, cyano, nitro, alkylamino, arylamino, alkylaminoalkylene, arylaminoalkylene, aminoalkylamino, and hydroxy; or a pharmaceutically-acceptable salt or tautomer thereof.

Within Formula IA is another subclass of compounds of interest wherein:

$R^1$ is selected from hydrido, hydroxy, alkyl, cycloalkyl, alkenyl, cycloalkenyl, alkynyl, aryl, heterocyclyl, cycloalkylalkylene, cycloalkenylalkylene, heterocyclylalkylene, haloalkyl, haloalkenyl, haloalkynyl, hydroxyalkyl, hydroxyalkenyl, hydroxyalkynyl, aralkyl, aralkenyl, aralkynyl, arylheterocyclyl, carboxy, carboxyalkyl, alkoxyalkyl, alkenoxyalkyl, alkynoxyalkyl, aryloxyalkyl, alkoxyaryl, heterocyclyloxyalkyl, alkoxyalkoxy, mercaptoalkyl, alkylthioalkylene, alkenylthioalkylene, alkylthioalkenylene, amino, aminoalkyl, alkylamino, alkenylamino, alkynylamino, arylamino, heterocyclylamino, alkylsulfinyl, alkenylsulfinyl, alkynylsulfinyl, arylsulfinyl, heterocyclylsulfinyl, alkylsulfonyl, alkenylsulfonyl, alkynylsulfonyl, arylsulfonyl, heterocyclylsulfonyl, alkylaminoalkylene, alkylsulfonylalkylene, acyl, acyloxycarbonyl, alkoxycarbonylalkylene, aryloxycarbonylalkylene, heterocyclyloxycarbonylalkylene, alkoxycarbonylarylene, aryloxycarbonylarylene, heterocyclyloxycarbonylarylene, alkylcarbonylalkylene, arylcarbonylalkylene, heterocyclylcarbonylalkylene, alkylcarbonylarylene, arylcarbonylarylene, heterocyclylcarbonylarylene, alkylcarbonyloxyalkylene, arylcarbonyloxyalkylene, heterocyclylcarbonyloxyalkylene, alkylcarbonyloxyarylene, arylcarbonyloxyarylene, and heterocyclylcarbonyloxyarylene; or $R^1$ has the formula

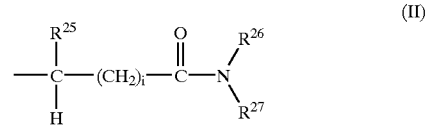

(II)

wherein:

i is an integer from 0 to 9;

$R^{25}$ is selected from hydrogen, alkyl, aralkyl, heterocyclylalkyl, alkoxyalkylene, aryloxyalkylene, aminoalkyl, alkylaminoalkyl, arylaminoalkyl, alkylcarbonylalkylene, arylcarbonylalkylene, and heterocyclylcarbonylaminoalkylene; and $R^{26}$ is selected from hydrogen, alkyl, alkenyl, alkynyl, cycloalkylalkylene, aralkyl, alkoxycarbonylalkylene, and alkylaminoalkyl; and $R^{27}$ is selected from alkyl, cycloalkyl, alkynyl, aryl, heterocyclyl, aralkyl, cycloalkylalkylene, cycloalkenylalkylene, cycloalkylarylene, cycloalkylcycloalkyl, heterocyclylalkylene, alkylarylene, alkylaralkyl, aralkylarylene, alkylheterocyclyl, alkylheterocyclylalkylene, alkylheterocyclylarylene, aralkylheterocyclyl, alkoxyalkylene, alkoxyarylene, alkoxyaralkyl, alkoxyheterocyclyl, alkoxyalkoxyarylene, aryloxyarylene, aralkoxyarylene, alkoxyheterocyclylalkylene, aryloxyalkoxyarylene, alkoxycarbonylalkylene, alkoxycarbonylheterocyclyl, alkoxycarbonylheterocyclylcarbonylalkylene, aminoalkyl, alkylaminoalkylene, arylaminocarbonylalkylene, alkoxyarylaminocarbonylalkylene, aminocarbonylalkylene, arylaminocarbonylalkylene, alkylaminocarbonylalkylene, arylcarbonylalkylene, alkoxycarbonylarylene, aryloxycarbonylarylene, alkylaryloxycarbonylarylene, arylcarbonylarylene, alkylarylcarbonylarylene, alkoxycarbonylheterocyclylarylene, alkoxycarbonylalkoxylarylene, heterocyclylcarbonylalkylarylene, alkylthioalkylene, cycloalkylthioalkylene, alkylthioarylene, aralkylthioarylene, heterocyclylthioarylene, arylthioalklylarylene, arylsulfonylaminoalkylene, alkylsulfonylarylene, alkylaminosulfonylarylene; wherein said alkyl, cycloalkyl, aryl, heterocyclyl, aralkyl, heterocyclylalkylene, alkylheterocyclylarylene, alkoxyarylene, aryloxyarylene, arylaminocarbonylalkylene, aryloxycarbonylarylene, arylcarbonylarylene, alkylthioarylene, heterocyclylthioarylene, arylthioalklylarylene, and alkylsulfonylarylene groups are optionally substituted with one or more radicals independently selected from alkyl, halo, haloalkyl, alkoxy, keto, amino, nitro, and cyano; or $R^{27}$ is —$CHR^{28}R^{29}$ wherein $R^{28}$ is alkoxycarbonyl, and $R^{29}$ is selected from aralkyl, aralkoxyalkylene, heterocyclylalkylene, alkylheterocyclylalkylene, alkoxycarbonylalkylene, alkylthioalkylene, and aralkylthioalkylene; wherein said aralkyl and heterocylcyl groups are optionally substituted with one or more radicals independently selected from alkyl and nitro; or $R^{26}$ and $R^{27}$ together with the nitrogen atom to which they are attached form a heterocycle, wherein said heterocycle is optionally substituted with one or more radicals independently selected from alkyl, aryl, heterocyclyl, heterocyclylalkylene, alkylheterocyclylalkylene, aryloxyalkylene, alkoxyarylene, alkylaryloxyalkylene, alkylcarbonyl, alkoxycarbonyl, aralkoxycarbonyl, alkylamino and alkoxycarbonylamino; wherein said aryl, heterocyclylalkylene and aryloxyalkylene radicals are optionally substituted with one or more radicals independently selected from halogen, alkyl and alkoxy; and $R^2$ is selected from hydrido, halogen, mercapto, alkyl, alkenyl, alkynyl, aryl, heterocyclyl, haloalkyl, hydroxyalkyl, aralkyl, alkylheterocyclyl, heterocyclylalkyl, heterocyclylheterocyclyl, heterocyclylalkylheterocyclyl, alkylamino, alkenylamino, alkynylamino, arylamino, aryl(hydroxyalkyl)amino, heterocyclylamino, heterocyclylalkylamino, aralkylamino, N-alkyl-N-alkynyl-amino, aminoalkyl, aminoaryl, aminoalkylamino, aminocarbonylalkylene, arylaminoalkylene, alkylaminoalkylene, arylaminoarylene, alkylaminoarylene, alkylaminoalkylamino, alkylcarbonylaminoalkylene, aminoalkylcarbonylaminoalkylene, alkylaminoalkylcarbonylamino, cycloalkyl, cycloalkenyl, aminoalkylthio, alkylaminocarbonylalkylthio, alkylaminoalkylaminocarbonylalkylthio, alkoxy, heterocyclyloxy, alkylthio, cyanoalkylthio, alkenylthio, alkynylthio, carboxyalkylthio, arylthio, heterocyclylthio, alkoxycarbonylalkylthio, alkylsulfinyl, alkylsulfonyl, carboxy, carboxyalkyl, alkoxyalkyl, alkoxyalkylthio, carboxycycloalkyl, carboxycycloalkenyl, carboxyalkylamino, alkoxycarbonyl, heterocyclylcarbonyl, alkoxycarbonylalkyl, alkoxycarbonylalkylamino, alkoxycarbonylheterocyclyl, alkoxycarbonylheterocyclylcarbonyl, alkoxyalkylamino, alkoxycarbonylaminoalkylene, alkoxycarbonylaminoalkoxy, alkoxycarbonylaminoalkylamino, heterocyclylsulfonyl, aralkythio, heterocyclylalkylthio, aminoalkoxy, cyanoalkoxy, carboxyalkoxy, aryloxy, aralkoxy, alkenyloxy, alkynyloxy, and heterocyclylkyloxy; wherein the aryl, heterocyclyl, heterocyclylalkyl, cycloalkyl and cycloalkenyl groups are optionally substituted with one or more radicals independently selected from halo, keto, amino, alkyl, alkenyl, alkynyl, aryl, heterocyclyl, aralkyl, heterocyclylalkyl, epoxyalkyl, amino(hydroxyalkyl) carboxy, alkoxy, aryloxy, aralkoxy, haloalkyl, alkylamino, alkynylamino, alkylaminoalkylamino, heterocyclylalkylamino, alkylcarbonyl, alkoxycarbonyl, alkylsulfonyl, arylsulfonyl, and aralkylsulfonyl; or $R^2$ is $R^{200}$-heterocyclyl-$R^{201}$, $R^{200}$-aryl-$R^{201}$, or $R^{200}$-cycloalkyl-$R^{201}$ wherein:

$R^{200}$ is selected from:
—$(CR^{202}R^{203})_y$—;
—$C(O)$—;
—$C(O)$—$(CH_2)_y$—;
—$C(O)$—$O$—$(CH_2)_y$—;
—$(CH_2)_y$—$C(O)$—;
—$O$—$(CH_2)_y$—$C(O)$—;
—$NR^{202}$—;
—$NR^{202}$—$(CH_2)_y$—;
—$(CH_2)_y$—$NR^{202}$—;
—$(CH_2)_y$—$NR^{202}$—$(CH_2)_z$—;
—$(CH_2)_y$—$C(O)$—$NR^{202}$—$(CH_2)_z$—;
—$(CH_2)_y$—$NR^{202}$—$C(O)$—$(CH_2)_z$—;
—$(CH_2)_y$—$NR^{202}$—$C(O)NR^{203}$—$(CH_2)$—;
—$S(O)_x$—$(CR^{202}R^{203})_y$—;
—$(CR^{202}R^{203})_y$—$S(O)_x$—;
—$S(O)_x$—$(CR^{202}R^{203})_y$—$O$—;
—$S(O)_x$—$(CR^{202}R^{203})_y$—$C(O)$—;
—$O$—$(CH_2)_y$—;
—$(CH_2)_y$—$O$—;
—$O$—;
or $R^{200}$ represents a bond;

$R^{201}$ represents one or more radicals selected from the group consisting of hydrido, halogen, hydroxy, carboxy, keto, alkyl, hydroxyalkyl, haloalkyl, cycloalkyl, alkenyl, alkynyl, aryl, heterocyclyl, aralkyl, heterocyclylalkylene, alkylcarbonyl, hydroxyalkylcarbonyl, cycloalkylcarbonyl, arylcarbonyl, haloarylcarbonyl, alkoxy, alkoxyalkylene, alkoxyarylene, alkoxycarbonyl, carboxyalkylcarbonyl, alkoxyalkylcarbonyl, heterocyclylalkylcarbonyl, alkylsulfonyl, alkylsulfonylalkylene, amino, aminoalkyl, alkylamino, aralkylamino, alkylaminoalkylene, aminocarbonyl, alkylcarbonylamino, alkylcarbonylaminoalkylene, alkylaminoalkylcarbonyl, alkylaminoalkylcarbonylamino, aminoalkylcarbonylaminoalkyl, alkoxycarbonylamino, alkoxyalkylcarbonylamino, alkoxycarbonylaminoalkylene, alkylimidocarbonyl, amidino, alkylamidino, aralkylamidino, guanidino, guanidinoalkylene, or alkylsulfonylamino; and $R^{202}$ and $R^{203}$ are independently selected from hydrido, alkyl, aryl and aralkyl; and y and z are independently 0, 1, 2, 3, 4, 5 or 6 wherein y+z is less than or equal to 6; and
z is 0, 1 or 2; or
$R^2$ is —NHCR$^{204}$R$^{205}$ wherein R$^{204}$ is alkylaminoalkylene, and R$^{205}$ is aryl; or
$R^2$ is —C(NR$^{206}$)R$^{207}$ wherein R$^{206}$ is selected from hydrogen and hydroxy, and R$^{207}$ is selected from alkyl, aryl and aralkyl; or
$R^2$ has the formula:

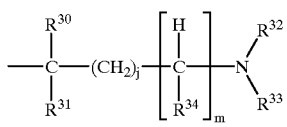
(III)

wherein:
j is an an integer from 0 to 8; and
m is 0 or 1; and
$R^{30}$ and $R^{31}$ are independently selected from hydrogen, alkyl, aryl, heterocyclyl, aralkyl, heterocyclylalkylene, aminoalkyl, alkylaminoalkyl, aminocarbonylalkyl, alkoxyalkyl, and alkylcarbonyloxyalkyl; and
$R^{32}$ is selected from hydrogen, alkyl, aralkyl, heterocyclylalkyl, alkoxyalkylene, aryloxyalkylene, aminoalkyl, alkylaminoalkyl, arylaminoalkyl, alkylcarbonylalkylene, arylcarbonylalkylene, and heterocyclylcarbonylaminoalkylene;
$R^{33}$ is selected from hydrogen, alkyl, —C(O)R$^{35}$, —C(O)OR$^{35}$, —SO$_2$R$^{36}$, —C(O)R$^{37}$, R$^{38}$, and —SO$_2$NR$^{39}$R$^{40}$, wherein R$^{35}$, R$^{36}$, R$^{37}$, R$^{38}$, R$^{39}$ and R$^{40}$ are independently selected from hydrocarbon, heterosubstituted hydrocarbon and heterocyclyl; and
$R^{34}$ is selected from hydrogen, alkyl, aminocarbonyl, alkylaminocarbonyl, and arylaminocarbonyl; or
$R^2$ is —CR$^{41}$R$^{42}$ wherein R$^{41}$ is aryl, and R$^{42}$ is hydroxy; and
$R^3$ is selected from pyridinyl, pyrimidinyl, quinolinyl purinyl, maleimidyl, pyridonyl, thiazolyl, thiazolylalkyl, thiazolylamino,

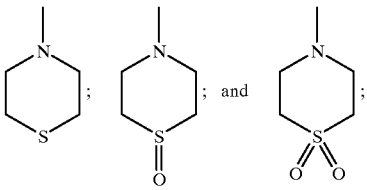

wherein the $R_3$ pyridinyl, pyrimidinyl, quinolinyl, purinyl, maleimidyl, pyridonyl, thiazolyl, thiazolylalkyl, thiazolylamino,

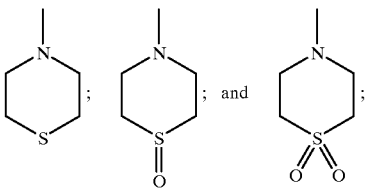

groups are substituted with one or more radicals independently selected from keto, haloarylamino, alkoxyalkylene, alkenoxyalkylene, aryloxyalkyl, alkoxyalkyl amino, alkylaminoalkoxy, alkoxyaryl amino, alkylsulfonylamino, aryl (hydroxyalkyl) amino, alkylaminoalkylaminoalkylamino, alkylheterocyclylamino, alkylheterocyclylalkyl amino, heterocyclylheterocyclylalkylamino, and alkoxycarbonylheterocyclylamino; and
$R^4$ is selected from hydrido, alkyl, alkenyl, alkynyl, cycloalkyl, cycloalkenyl, aryl, and heterocyclyl, wherein $R^4$ is optionally substituted with one or more radicals independently selected from halo, alkyl, alkenyl, alkynyl, aryl, heterocyclyl, alkylthio, arylthio, alkylthioalkylene, arylthioalkylene, alkylsulfinyl, alkylsulfinylalkylene, arylsulfinylalkylene, alkylsulfonyl, alkylsulfonylalkylene, arylsulfonylalkylene, alkoxy, aryloxy, aralkoxy, aminocarbonyl, alkylaminocarbonyl, arylaminocarbonyl, alkoxycarbonyl, aryloxycarbonyl, haloalkyl, amino, cyano, nitro, alkylamino, arylamino, alkylaminoalkylene, arylaminoalkylene, aminoalkylamino, and hydroxy; or
a pharmaceutically-acceptable salt or tautomer thereof.

Within Formula IA is another subclass of compounds of interest wherein:
$R^1$ is selected from hydrido, hydroxy, alkyl, cycloalkyl, alkenyl, cycloalkenyl, alkynyl, aryl, heterocyclyl, cycloalkylalkylene, cycloalkenylalkylene, heterocyclylalkylene, haloalkyl, haloalkenyl, haloalkynyl, hydroxyalkyl, hydroxyalkenyl, hydroxyalkynyl, aralkyl, aralkenyl, aralkynyl, arylheterocyclyl, carboxy, carboxyalkyl, alkoxyalkyl, alkenoxyalkyl, alkynoxyalkyl, aryloxyalkyl, alkoxyaryl, heterocyclyloxyalkyl, alkoxyalkoxy, mercaptoalkyl, alkylthioalkylene, alkenylthioalkylene, alkylthioalkenylene, amino, aminoalkyl, alkylamino, alkenylamino, alkynylamino, arylamino, heterocyclylamino, alkylsulfinyl, alkenylsulfinyl, alkynylsulfinyl, arylsulfinyl, heterocyclylsulfinyl, alkylsulfonyl, alkenylsulfonyl, alkynylsulfonyl, arylsulfonyl, heterocyclylsulfonyl, alkylaminoalkylene, alkylsulfonylalkylene, acyl, acyloxycarbonyl, alkoxycarbonylalkylene, aryloxycarbonylalkylene, heterocyclyloxycarbonylalkylene, alkoxycarbonylarylene, aryloxycarbonylarylene, heterocyclyloxycarbonylarylene, alkylcarbonylalkylene, arylcarbonylalkylene, heterocyclylcarbonylalkylene, alkylcarbonylarylene, arylcarbonylarylene, heterocyclylcarbonylarylene, alkylcarbonyloxyalkylene, arylcarbonyloxyalkylene, heterocyclylcarbonyloxyalkylene, alkylcarbonyloxyarylene, arylcarbonyloxyarylene, and heterocyclylcarbonyloxyarylene; or
$R^1$ has the formula

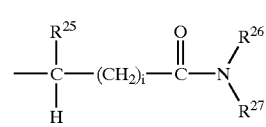
(II)

wherein:
i is an integer from 0 to 9;
$R^{25}$ is selected from hydrogen, alkyl, aralkyl, heterocyclylalkyl, alkoxyalkylene, aryloxyalkylene, aminoalkyl, alkylaminoalkyl, arylaminoalkyl, alkylcarbonylalkylene, arylcarbonylalkylene, and heterocyclylcarbonylaminoalkylene; and $R^{26}$ is selected from hydrogen, alkyl, alkenyl, alkynyl, cycloalkylalkylene, aralkyl, alkoxycarbonylalkylene, and alkylaminoalkyl; and $R^{27}$ is selected from alkyl, cycloalkyl, alkynyl, aryl, heterocyclyl, aralkyl, cycloalkylalkylene, cycloalkenylalkylene, cycloalkylarylene, cycloalkylcycloalkyl, heterocyclylalkylene, alkylarylene, alkylaralkyl, aralkylarylene, alkylheterocyclyl, alkylheterocyclylalkylene, alkylheterocyclylarylene, aralkylheterocyclyl, alkoxyalkylene, alkoxyarylene, alkoxyaralkyl, alkoxyheterocyclyl, alkoxyalkoxyarylene, aryloxyarylene, aralkoxyarylene, alkoxyheterocyclylalkylene, aryloxyalkoxyarylene, alkoxycarbonylalkylene, alkoxycarbonylheterocyclyl, alkoxycarbonylheterocyclylcarbonylalkylene, aminoalkyl, alkylaminoalkylene, arylaminocarbonylalkylene, alkoxyarylaminocarbonylalkylene, aminocarbonylalkylene, arylaminocarbonylalkylene, alkylaminocarbonylalkylene, arylcarbonylalkylene, alkoxycarbonylarylene, aryloxycarbonylarylene, alkylaryloxycarbonylarylene, arylcarbonylarylene, alkylarylcarbonylarylene, alkoxycarbonylheterocyclylarylene, alkoxycarbonylalkoxyarylene, heterocyclylcarbonylalkylarylene, alkylthioalkylene, cycloalkylthioalkylene, alkylthioarylene, aralkylthioarylene, heterocyclylthioarylene, arylthioalklylarylene, arylsulfonylaminoalkylene, alkylsulfonylarylene, alkylaminosulfonylarylene; wherein said alkyl, cycloalkyl, aryl, heterocyclyl, aralkyl, heterocyclylalkylene, alkylheterocyclylarylene, alkoxyarylene, aryloxyarylene, arylaminocarbonylalkylene, aryloxycarbonylarylene, arylcarbonylarylene, alkylthioarylene, heterocyclylthioarylene, arylthioalklylarylene, and alkylsulfonylarylene groups are optionally substituted with one or more radicals independently selected from alkyl, halo, haloalkyl, alkoxy, keto, amino, nitro, and cyano; or $R^{27}$ is —CHR$^{28}$R$^{29}$ wherein $R^{28}$ is alkoxycarbonyl, and $R^{29}$ is selected from aralkyl, aralkoxyalkylene, heterocyclylalkylene, alkylheterocyclylalkylene, alkoxycarbonylalkylene, alkylthioalkylene, and aralkylthioalkylene; wherein said aralkyl and heterocylcyl groups are optionally substituted with one or more radicals independently selected from alkyl and nitro; or $R^{26}$ and $R^{27}$ together with the nitrogen atom to which they are attached form a heterocycle, wherein said heterocycle is optionally substituted with one or more radicals independently selected from alkyl, aryl, heterocyclyl, heterocyclylalkylene, alkylheterocyclylalkylene, aryloxyalkylene, alkoxyarylene, alkylaryloxyalkylene, alkylcarbonyl, alkoxycarbonyl, aralkoxycarbonyl, alkylamino and alkoxycarbonylamino; wherein said aryl, heterocyclylalkylene and aryloxyalkylene radicals are optionally substituted with one or more radicals independently selected from halogen, alkyl and alkoxy; and $R^2$ is selected from hydrido, halogen, mercapto, alkyl, alkenyl, alkynyl, aryl, heterocyclyl, haloalkyl, hydroxyalkyl, aralkyl, alkylheterocyclyl, heterocyclylalkyl, heterocyclylheterocyclyl, heterocyclylalkylheterocyclyl, alkylamino, alkenylamino, alkynylamino, arylamino, aryl(hydroxyalkyl)amino, heterocyclylamino, heterocyclylalkylamino, aralkylamino, N-alkyl-N-alkynyl-amino, aminoalkyl, aminoaryl, aminoalkylamino, aminocarbonylalkylene, arylaminoalkylene, alkylaminoalkylene, arylaminoarylene, alkylaminoarylene, alkylaminoalkylamino, alkylcarbonylaminoalkylene, aminoalkylcarbonylaminoalkylene, alkylaminoalkylcarbonylamino, cycloalkyl, cycloalkenyl, aminoalkylthio, alkylaminocarbonylalkylthio, alkylaminoalkylaminocarbonylalkylthio, alkoxy, heterocyclyloxy, alkylthio, cyanoalkylthio, alkenylthio, alkynylthio, carboxyalkylthio, arylthio, heterocyclylthio, alkoxycarbonylalkylthio, alkylsulfinyl, alkylsulfonyl, carboxy, carboxyalkyl, alkoxyalkyl, alkoxyalkylthio, carboxycycloalkyl, carboxycycloalkenyl, carboxyalkylamino, alkoxycarbonyl, heterocyclylcarbonyl, alkoxycarbonylalkyl, alkoxycarbonylalkylamino, alkoxycarbonylheterocyclyl, alkoxycarbonylheterocyclylcarbonyl, alkoxyalkylamino, alkoxycarbonylaminoalkylene, alkoxycarbonylaminoalkoxy, alkoxycarbonylaminoalkylamino, heterocyclylsulfonyl, aralkythio, heterocyclylalkylthio, aminoalkoxy, cyanoalkoxy, carboxyalkoxy, aryloxy, aralkoxy, alkenyloxy, alkynyloxy, and heterocyclylalkyloxy; wherein the aryl, heterocyclyl, heterocyclylalkyl, cycloalkyl and cycloalkenyl groups are optionally substituted with one or more radicals independently selected from halo, keto, amino, alkyl, alkenyl, alkynyl, aryl, heterocyclyl, aralkyl, heterocyclylalkyl, epoxyalkyl, amino(hydroxyalkyl) carboxy, alkoxy, aryloxy, aralkoxy, haloalkyl, alkylamino, alkynylamino, alkylaminoalkylamino, heterocyclylalkylamino, alkylcarbonyl, alkoxycarbonyl, alkylsulfonyl, arylsulfonyl, and aralkylsulfonyl; or $R^2$ is $R^{200}$-heterocyclyl-$R^{201}$, $R^{200}$-aryl-$R^{201}$, or $R^{200}$-cycloalkyl-$R^{201}$ wherein:

$R^{200}$ is selected from:
—(CR$^{202}$R$^{203}$)$_y$—;
—C(O)—;
—C(O)—(CH$_2$)$_y$—;
—C(O)—O—(CH$_2$)$_y$—;
—(CH$_2$)$_y$—C(O)—;
—O—(CH$_2$)$_y$—C(O)—;
—NR$^{202}$—;
—NR$^{202}$—(CH$_2$)$_y$—;
—(CH$_2$)$_y$—NR$^{202}$—;
—(CH$_2$)$_y$—NR$^{202}$—(CH$_2$)$_z$—;
—(CH$_2$)$_y$—C(O)—NR$^{202}$—(CH$_2$)$_z$—;
—(CH$_2$)$_y$—NR$^{202}$—C(O)—(CH$_2$)$_z$—;
—(CH$_2$)$_y$—NR$^{202}$—C(O)—NR$^{203}$—(CH$_2$)$_z$—;
—S(O)$_x$—(CR$^{202}$R$^{203}$)$_y$—;
—(CR$^{202}$R$^{203}$)$_y$—S(O)$_x$—;
—S(O)$_x$—(CR$^{202}$R$^{203}$)$_y$—O—;
—S(O)$_x$—(CR$^{202}$R$^{203}$)$_y$—C(O)—;
—O—(CH$_2$)$_y$—;
—(CH$_2$)$_y$—O—;
—S—;
—O—;

or $R^{200}$ represents a bond;

$R^{201}$ represents one or more radicals selected from the group consisting of hydrido, halogen, hydroxy, carboxy, keto, alkyl, hydroxyalkyl, haloalkyl, cycloalkyl, alkenyl, alkynyl, aryl, heterocyclyl, aralkyl, heterocyclylalkylene, alkylcarbonyl, hydroxyalkylcarbonyl, cycloalkylcarbonyl, arylcarbonyl, haloarylcarbonyl, alkoxy, alkoxyalkylene, alkoxyarylene, alkoxycarbonyl, carboxyalkylcarbonyl, alkoxyalkylcarbonyl, heterocyclylalkylcarbonyl, alkylsulfonyl, alkylsulfonylalkylene, amino, aminoalkyl, alkylamino, aralkylamino, alkylaminoalkylene, aminocarbonyl, alkylcarbonylamino, alkylcarbonylaminoalkylene, alkylaminoalkylcarbonyl, alkylaminoalkylcarbonylamino, aminoalkylcarbonylaminoalkyl, alkoxycarbonylamino, alkoxyalkylcarbonylamino, alkoxycarbonylaminoalkylene, alkylimidocarbonyl, amidino, alkylamidino, aralkylamidino, guanidino, guanidinoalkylene, or alkylsulfonylamino; and $R^{202}$ and $R^{203}$ are independently selected from hydrido, alkyl, aryl and aralkyl; and y and z are independently 0, 1, 2, 3, 4, 5 or 6 wherein y+z is less than or equal to 6; and z is 0, 1 or 2; or $R^2$ is $-NHCR^{204}R^{205}$ wherein $R^{204}$ is alkylaminoalkylene, and $R^{205}$ is aryl; or $R^2$ is $-C(NR^{206})R^{207}$ wherein $R^{206}$ is selected from hydrogen and hydroxy, and $R^{207}$ is selected from alkyl, aryl and aralkyl; or $R^2$ has the formula:

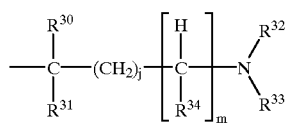

(III)

wherein:
j is an integer from 0 to 8; and
m is 0 or 1; and $R^{30}$ and $R^{31}$ are independently selected from hydrogen, alkyl, aryl, heterocyclyl, aralkyl, heterocyclylalkylene, aminoalkyl, alkylaminoalkyl, aminocarbonylalkyl, alkoxyalkyl, and alkylcarbonyloxyalkyl; and $R^{32}$ is selected from hydrogen, alkyl, aralkyl, heterocyclylalkyl, alkoxyalkylene, aryloxyalkylene, aminoalkyl, alkylaminoalkyl, arylaminoalkyl, alkylcarbonylalkylene, arylcarbonylalkylene, and heterocyclylcarbonylaminoalkylene;

$R^{33}$ is selected from hydrogen, alkyl, $-C(O)R^{35}$, $-C(O)OR^{35}$, $-SO_2R^{36}{}_1$, $-C(O)NR^{37}R^{38}$, and $-SO_2NR^{39}R^{40}$, wherein $R^{35}$, $R^{36}$, $R^{37}$, $R^{38}$, $R^{39}$ and $R^{40}$ are independently selected from hydrocarbon, heterosubstituted hydrocarbon and heterocyclyl; and $R^{34}$ is selected from hydrogen, alkyl, aminocarbonyl, alkylaminocarbonyl, and arylaminocarbonyl; or $R^2$ is $-CR^{41}R^{42}$ wherein $R^{41}$ is aryl, and $R^{42}$ is hydroxy; and $R^3$ is selected from maleimidyl, pyridonyl, thiazolyl, thiazolylalkyl, thiazolylamino,

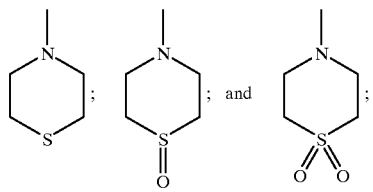

wherein the $R^3$ maleimidyl, pyridonyl, thiazolyl, thiazolylalkyl, thiazolylamino,

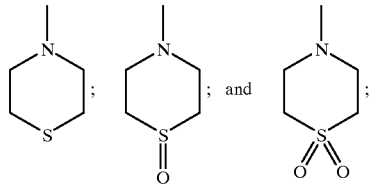

groups are optionally substituted with one or more radicals independently selected from halo, keto, alkyl, aralkyl, aralkenyl, arylheterocyclyl, carboxy, carboxyalkyl, alkoxy, aryloxy, alkylthio, arylthio, alkylsulfinyl, arylsulfinyl, alkylsulfonyl, arylsulfonyl, aralkoxy, heterocyclylalkoxy, amino, alkylamino, alkenylamino, alkynylamino, cycloalkylamino, cycloalkenylamino, arylamino, haloarylamino, heterocyclylamino, aminocarbonyl, cyano, hydroxy, hydroxyalkyl, alkoxyalkylene, alkenoxyalkylene, aryloxyalkyl, alkoxyalkylamino, alkylaminoalkoxy, alkoxycarbonyl, aryloxycarbonyl, heterocyclyloxycarbonyl, alkoxycarbonylamino, alkoxyarylamino, alkoxyaralkylamino, aminosulfinyl, aminosulfonyl, alkylsulfonylamino, alkylaminoalkylamino, hydroxyalkylamino, aralkylamino, aryl(hydroxyalkyl)amino, alkylaminoalkylaminoalkylamino, alkylheterocyclylamino, heterocyclylalkylamino, alkylheterocyclylalkylamino, aralkylheterocyclylamino, heterocyclylheterocyclylalkylamino, alkoxycarbonylheterocyclylamino, nitro, alkylaminocarbonyl, alkylcarbonylamino, halosulfonyl, aminoalkyl, haloalkyl, alkylcarbonyl, hydrazinyl, alkylhydrazinyl, arylhydrazinyl, or $-NR^{44}R^{45}$ wherein $R^{44}$ is alkylcarbonyl or amino, and $R^{45}$ is alkyl or aralkyl; and $R^4$ is selected from hydrido, alkyl, alkenyl, alkynyl, cycloalkyl, cycloalkenyl, aryl, and heterocyclyl, wherein $R^4$ is optionally substituted with one or more radicals independently selected from halo, alkyl, alkenyl, alkynyl, aryl, heterocyclyl, alkylthio, arylthio, alkylthioalkylene, arylthioalkylene, alkylsulfinyl, alkylsulfinylalkylene, arylsulfinylalkylene, alkylsulfonyl, alkylsulfonylalkylene, arylsulfonylalkylene, alkoxy, aryloxy, aralkoxy, aminocarbonyl, alkylaminocarbonyl, arylaminocarbonyl, alkoxycarbonyl, aryloxycarbonyl, haloalkyl, amino, cyano, nitro, alkylamino, arylamino, alkylaminoalkylene, arylaminoalkylene, aminoalkylamino, and hydroxy;

provided that $R^3$ is other than maleimidyl or pyridonyl having the structures:

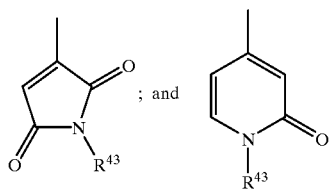

respectively, wherein R$^{43}$ is selected from hydrogen, alkyl, aminoalkyl, alkoxyalkyl, alkenoxyalkyl, and aryloxyalkyl; or a pharmaceutically-acceptable salt or tautomer thereof.

The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. Where used, either alone or within other terms such as "haloalkyl", "alkylsulfonyl", "alkoxyalkyl" and "hydroxyalkyl", "cyanoalkyl" and "mercaptoalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about six carbon atoms. Examples of alkenyl radicals include ethenyl, allyl, propenyl, butenyl and 4-methylbutenyl. The terms "alkenyl" and "lower alkenyl", embrace radicals having "cis" and "trans" orientations, or alternatively, "E" and "Z" orientations. The term "alkynyl" embraces linear or branched radicals having at least one carbon-carbon triple bond of two to about twenty carbon atoms or, preferably, two to about twelve carbon atoms. More preferred alkynyl radicals are "lower alkynyl" radicals having two to about six carbon atoms. Examples of alkynyl radicals include propargyl, 1-propynyl, 2-propynyl, 1-butyne, 2-butynyl and 1-pentynyl. The term "cycloalkyl" embraces saturated carbocyclic radicals having three to about twelve carbon atoms. The term "cycloalkyl" embraces saturated carbocyclic radicals having three to about twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl. The term "cycloalkylalkylene" embraces alkyl radicals substituted with a cycloalkyl radical. More preferred cycloalkylalkylene radicals are "lower cycloalkylalkylene" which embrace lower alkyl radicals substituted with a lower cycloalkyl radical as defined above. Examples of such radicals include cyclopropylmethyl, cyclobutylmethyl, cyclopentylmethyl and cyclohexylmethyl. The term "cycloalkenyl" embraces partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having one to six carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The terms "alkoxy" and "alkyloxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" embraces alkyl radicals having one or more alkoxy radicals attached to the alkyl radical, that is, to form monoalkoxyalkyl and dialkoxyalkyl radicals. The "alkoxy" radicals may be further substituted with one or more halo atoms, such as fluoro, chloro or bromo, to provide haloalkoxy radicals. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. Aryl moieties may also be substituted at a substitutable position with one or more substituents selected independently from halo, alkyl, alkenyl, alkynyl, aryl, heterocyclyl, alkylthio, arylthio, alkylthioalkylene, arylthioalkylene, alkylsulfinyl, alkylsulfinylalkylene, arylsulfinylalkylene, alkylsulfonyl, alkylsulfonylalkylene, arylsulfonylalkylene, alkoxy, aryloxy, aralkoxy, aminocarbonyl, alkylaminocarbonyl, arylaminocarbonyl, alkoxycarbonyl, aryloxycarbonyl, haloalkyl, amino, cyano, nitro, alkylamino, arylamino, alkylaminoalkylene, arylaminoalkylene, aminoalkylamino, hydroxy, alkoxyalkyl, carboxyalkyl, alkoxycarbonylalkyl, aminocarbonylalkylene, acyl, carboxy, and aralkoxycarbonyl. The term "heterocyclyl" embraces saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heteroaryl" embraces unsaturated heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b] pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like. The term "heterocycle" also embraces radicals where heterocyclyl radicals are fused with aryl or cycloalkyl radicals. Examples of such fused bicyclic radicals include benzofuran, benzothiophene, and the like. Said "heterocyclyl group" may have 1 to 3 substituents such as alkyl, hydroxyl, halo, alkoxy, oxo, amino, alkylthio and alkylamino. The term "heterocyclylalkylene" embraces heterocyclyl-substituted alkyl radicals. More preferred heterocyclylalkylene radicals are "lower heterocyclylalkylene" radicals having one to six carbon atoms and a heterocyclyl radicals. The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "alkylthioalkylene" embraces radicals containing an alkylthio radical attached through the divalent sulfur atom to an alkyl radical of one to about ten carbon atoms. More preferred alkylthioalkylene radicals are "lower alkylthioalkylene" radicals having alkyl radicals of one to six carbon atoms. Examples of such lower alkylthioalkylene radicals include methylthiomethyl. The term "alkylsulfinyl" embraces radicals containing a linear or branched alkyl radical, of one to about ten carbon atoms, attached to a divalent —S(=O)— radical. More preferred alkylsulfinyl radicals are "lower alkylsulfinyl" radicals having alkyl radicals of one to six carbon atoms. Examples of such lower alkylsulfinyl radicals include methylsulfinyl, ethylsulfinyl, butylsulfinyl and hexylsulfinyl. The term "sulfonyl", whether used alone or linked to other terms such as "alkylsulfonyl", "halosulfonyl" denotes a divalent radical, —SO$_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals may be further substituted with one or more halo atoms, such as fluoro, chloro or bromo, to provide haloalkylsulfonyl radicals. The term "halosulfonyl" embraces halo radicals attached to a sulfonyl radical. Examples of such halosulfonyl radicals include chlorosulfonyl, and bromosulfonyl. The terms "sulfamyl", "aminosulfonyl" and "sulfonamidyl" denote NH$_2$O$_2$S—. The term "acyl" denotes a radical provided by the residue after removal of hydroxyl from an organic acid. Examples of such acyl radicals include alkanoyl and aroyl radicals. Examples of such alkanoyl radicals include formyl, acetyl, propionyl, butyryl, isobutyryl, valeryl, isovaleryl, pivaloyl, hexanoyl, and radicals formed from succinic, glycolic, gluconic, lactic, malic, tartaric, citric, ascorbic, glucuronic, maleic, fumaric, pyruvic, mandelic, pantothenic, β-hydroxybutyric, galactaric and galacturonic acids. The term "carbonyl", whether used alone or with other terms, such as "alkoxycarbonyl", denotes —(C=O)—. The terms "carboxy" or "carboxyl", whether used alone or with other terms, such as "carboxyalkyl", denotes —CO$_2$H. The term "carboxyalkyl" embraces alkyl radicals substituted with a carboxy radical. More preferred are "lower carboxyalkyl" which embrace lower alkyl radicals as defined above, and may be additionally substituted on the alkyl radical with halo. Examples of such lower carboxyalkyl radicals include carboxymethyl, carboxyethyl and carboxypropyl. The term "alkoxycarbonyl" means a radical containing an alkoxy radical, as defined above, attached via an oxygen atom to a carbonyl radical. More preferred are "lower alkoxycarbonyl" radicals with alkyl portions having one to six carbons. Examples of such lower alkoxycarbonyl (ester) radicals include substituted or unsubstituted methoxycarbonyl, ethoxycarbonyl, propoxycarbonyl, butoxycarbonyl and hexyloxycarbonyl. The term "alkoxycarbonylalkyl" embraces alkyl radicals substituted with a alkoxycarbonyl radical as defined above. More preferred are "lower alkoxycarbonylalkyl" radicals with alkyl portions having one to six carbons. Examples of such lower alkoxycarbonylalkyl radicals include substituted or unsubstituted methoxycarbonylmethyl, ethoxycarbonylmethyl, methoxycarbonyl-ethyl and ethoxycarbonylethyl. The term "alkylcarbonyl", includes radicals having alkyl, hydroxylalkyl, radicals, as defined herein, attached to a carbonyl radical. Examples of such radicals include substituted or unsubstituted methylcarbonyl, ethylcarbonyl, propylcarbonyl, butylcarbonyl, pentylcarbonyl, hydroxymethylcarbonyl, hydroxyethylcarbonyl. The term "aralkyl" embraces aryl-substituted alkyl radicals such as benzyl, diphenylmethyl, triphenylmethyl, phenylethyl, and diphenylethyl. The aryl in said aralkyl may be additionally substituted with one or more substituents selected independently from halo, alkyl, alkoxy, halkoalkyl, haloalkoxy, amino and nitro. The terms benzyl and phenylmethyl are interchangeable. The term "heterocyclylalkylene" embraces saturated and partially unsaturated heterocyclyl-substituted alkyl radicals (also can be called heterocycloalkylalkylene and heterocycloalkenylalkylene correspondingly), such as pyrrolidinylmethyl, and heteroaryl-substituted alkyl radicals (also can be called heteroarylalkylene), such as pyridylmethyl, quinolylmethyl, thienylmethyl, furylethyl, and quinolylethyl. The heteroaryl in said heteroaralkyl may be additionally substituted with halo, alkyl, alkoxy, halkoalkyl and haloalkoxy. The term "aryloxy" embraces aryl radicals attached through an oxygen atom to other radicals. The term "aralkoxy" embraces aralkyl radicals attached through an oxygen atom to other radicals. The term "aminoalkyl" embraces alkyl radicals substituted with amino radicals. More preferred are "lower aminoalkyl" radicals. Examples of such radicals include aminomethyl, aminoethyl, and the like. The term "alkylamino" denotes amino groups which are substituted with one or two alkyl radicals. Preferred are "lower alkylamino" radicals having alkyl portions having one to six carbon atoms. Suitable lower alkylamino may be monosubstituted N-alkylamino or disubstituted N,N-alkylamino, such as N-methylamino, N-ethylamino, N,N-dimethylamino, N,N-diethylamino or the like. The term "arylamino" denotes amino groups which are substituted with one or two aryl radicals, such as N-phenylamino. The "arylamino" radicals may be further substituted on the aryl ring portion of the radical. The term "aminocarbonyl" denotes an amide group of the formula —C(=O)NH$_2$. The term "alkylaminocarbonyl" denotes an aminocarbonyl group which has been substituted with one or two alkyl radicals on the amino nitrogen atom. Preferred are "N-alkylaminocarbonyl" and "N,N-dialkylaminocarbonyl" radicals. More preferred are "lower N-alkylaminocarbonyl" and "lower N,N-dialkylaminocarbonyl" radicals with lower alkyl portions as defined above. The term "alkylcarbonylamino" embraces amino groups which are substituted with one alkylcarbonyl radicals. More preferred alkylcarbonylamino radicals are "lower alkylcarbonylamino" having lower alkylcarbonyl radicals as defined above attached to amino radicals. The term "alkylaminoalkylene" embraces radicals having one or more alkyl radicals attached to an aminoalkyl radical.

The "hydrocarbon" moieties described herein are organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Preferably, these moieties comprise 1 to 20 carbon atoms.

The heterosubstituted hydrocarbon moieties described herein are hydrocarbon moieties which are substituted with at least one atom other than carbon, including moieties in which a carbon chain atom is substituted with a hetero atom such as nitrogen, oxygen, sulfur, or a halogen atom. These substituents include lower alkoxy such as methoxy, ethoxy, butoxy; halogen such as chloro or fluoro; ethers; acetals; ketals; esters; heterocyclyl such as furyl or thienyl; alkanoxy; hydroxy; protected hydroxy; acyl; acyloxy; nitro; cyano; amino; and amido.

The additional terms used to describe the substituents of the pyrazole ring and not specifically defined herein are defined in a similar manner to that illustrated in the above definitions. As above, more preferred substituents are those containing "lower" radicals. Unless otherwise defined to contrary, the term "lower" as used in this application means that each alkyl radical of a pyrazole ring substituent comprising one or more alkyl radicals has one to about six carbon atoms; each alkenyl radical of a pyrazole ring substituent comprising one or more alkenyl radicals has two to about six carbon atoms; each alkynyl radical of a pyrazole ring substituent comprising one or more alkynyl radicals has two to about six carbon atoms; each cycloalkyl or cycloalkenyl radical of a pyrazole ring substituent comprising one or more cycloalkyl and/or cycloalkenyl radicals is a 3 to 8 membered ring cycloalkyl or cycloalkenyl radical, respectively; each aryl radical of a pyrazole ring substituent comprising one or more aryl radicals is a monocyclic aryl radical; and each heterocyclyl radical of a pyrazole ring substituent comprising one or more heterocyclyl radicals is a 4–8 membered ring heterocyclyl.

The present invention comprises the tautomeric forms of compounds of Formulae I and IX (as well as the compounds of Formulae (IA and IXA). As illustrated below, the pyrazoles of Formula I and I' are magnetically and structurally equivalent because of the prototropic tautomeric nature of the hydrogen:

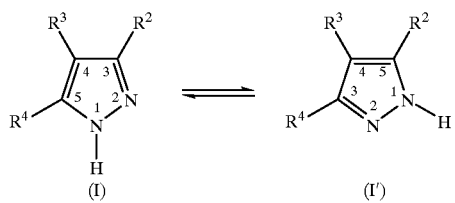

The present invention also comprises compounds of Formula I, IA, IX, IXA, X, XA and XI having one or more asymmetric carbons. It is known to those skilled in the art that those pyrazoles of the present invention having asymmetric carbon atoms may exist in diastereomeric, racemic, or optically active forms. All of these forms are contemplated within the scope of this invention. More specifically, the present invention includes enantiomers, diastereomers, racemic mixtures, and other mixtures thereof.

The present invention comprises a pharmaceutical composition for the treatment of a TNF mediated disorder, a p38 kinase mediated disorder, inflammation, and/or arthritis, comprising a therapeutically-effective amount of a compound of Formula I and/or IA, or a therapeutically-acceptable salt or tautomer thereof, in association with at least one pharmaceutically-acceptable carrier, adjuvant or diluent.

The present invention further encompasses substituted pyrazoles that specifically bind to the ATP binding site of p38 kinase. Without being held to a particular theory, applicants hypothesize that these substituted pyrazoles interact with p38 kinase as set forth below. As the substituent at the 3-position of the pyrazole ring approaches the ATP binding site of p38 kinase, a hydrophobic cavity in the p38 kinase forms around the 3-position substituent at the binding site. This hydrophobic cavity is believed to form as the 3-position substituent binds to a specific peptide sequence of the enzyme. In particular, it is believed to bind to the sidechains of Lys$_{52}$, Glu$_{69}$, Leu$_{73}$, Ile$_{82}$, Leu$_{84}$, Leu$_{101}$ and the methyl group of the Thr$_{103}$ sidechain of p38 kinase at the ATP binding site (wherein the numbering scheme corresponds to the numbering scheme conventionally used for ERK-2). Where the 3-position substituent is aryl or heteroaryl, such aryl or heteroaryl may be further substituted. It is hypothesized that such ring substituents may be beneficial in preventing hydroxylation or further metabolism of the ring.

The substituent at the 4-position of the pyrazole ring is one that is a partial mimic of the adenine ring of ATP, although it may be further elaborated. Preferably, it is a planar substituent terminated by a suitable hydrogen bond acceptor functionality. It is hypothesized that this acceptor hydrogen bonds to the backbone N—H of the Met$_{106}$ residue while one edge of this substituent is in contact with bulk solvent.

Substitution at the 5-position of the pyrazole ring is well tolerated and can provide increased potency and selectivity. It is hypothesized that such substituents extend out in the direction of the bulk solvent and that suitable polar functionality placed at its terminus can interact with the sidechain of Asp[109], leading to increased potency and selectivity.

Similarly, substitution on the nitrogen atom at the 1- or 2-position of the pyrazole ring is well tolerated and can provide increased potency. It is hypothesized that a hydrogen substituent attached to one of the ring nitrogen atoms is hydrogen bonded to $Asp_{165}$. Preferably, the nitrogen atom at the 2-position is double bonded to the carbon atom at the 3-position of the pyrazole while the nitrogen atom at the 1-position of the pyrazole is available for substitution with hydrogen or other substituents.

The 5-position substituent and the 1- or 2-position substituent of the pyrazole can be selected so as to improve the physical characteristics, especially aqueous solubility and drug delivery performance, of the substituted pyrazole. Preferably, however, these substituents each have a molecular weight less than about 360 atomic mass units. More preferably, these substituents each have a molecular weight less than about less than about 250 atomic mass units. Still more preferably, these substituents have a combined molecular weight less than about 360 atomic mass units.

A class of substituted pyrazoles of particular interest consists of those compounds having the formula:

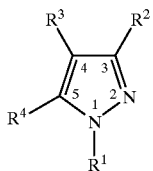

(XII)

wherein
- $R^1$ is a hydrocarbyl, heterosubstituted hydrocarbyl or heterocyclyl radical having a molecular weight less than about 360 atomic mass units; and
- $R^2$ is a hydrocarbyl, heterosubstituted hydrocarbyl or heterocyclyl radical that binds with p38 kinase at said ATP binding site of p38 kinase; and
- $R^3$ is a hydrocarbyl, heterosubstituted hydrocarbyl or heterocyclyl radical having a hydrogen bond acceptor functionality; and
- $R^4$ is a hydrocarbyl, heterosubstituted hydrocarbyl or heterocyclyl radical having a molecular weight less than about 360 atomic mass units;
- provided $R^3$ is not 2-pyridinyl when $R^4$ is a phenyl ring containing a 2-hydroxy substituent and when $R^1$ is hydrido; further provided $R^2$ is selected from aryl, heterocyclyl, unsubstituted cycloalkyl and cycloalkenyl when $R^4$ is hydrido; and further provided $R^4$ is not methylsulfonylphenyl; or
- a pharmaceutically-acceptable salt or tautomer thereof.

In this embodiment of the invention, one or more of $R^1$, $R^2$, $R^3$ and $R^4$ preferably are selected from the corresponding groups of the compounds of Formula I and/or IA. More preferably, $R^3$ is an optionally substituted pyridinyl or pyrimidinyl, $R^4$ is a halo substituted phenyl, and $R^1$ and $R^2$ have the definitions set forth immediately above.

A class of substituted pyrazoles of particular interest consists of those compounds of Formula XI wherein
- $R^1$ is a hydrocarbyl, heterosubstituted hydrocarbyl or heterocyclyl radical having a molecular weight less than about 360 atomic mass units; and
- $R^2$ is a hydrocarbyl, heterosubstituted hydrocarbyl or heterocyclyl radical wherein said radical binds with $Lys_{52}$, $Glu_{69}$, $Leu_{73}$, $Ile_{82}$, $Leu_{84}$, $Leu_{101}$, and $Thr_{103}$ sidechains at said ATP binding site of p38 kinase, said radical being substantially disposed within a hydrophobic cavity formed during said binding by p38 kinase at the ATP binding site; and
- $R^3$ is a hydrocarbyl, heterosubstituted hydrocarbyl or heterocyclyl radical having a hydrogen bond acceptor functionality that hydrogen bonds with the N—H backbone of $Met_{106}$ of p38 kinase; and
- $R^4$ is a hydrocarbyl, heterosubstituted hydrocarbyl or heterocyclyl radical having a molecular weight less than about 360 atomic mass units.

The present invention also comprises a therapeutic method of treating a TNF mediated disorder, a p38 kinase mediated disorder, inflammation and/or arthritis in a subject, the method comprising treating a subject having or susceptible to such disorder or condition with a therapeutically-effective amount of a compound of Formula I and/or IA.

For example, in one embodiment the present invention comprises a therapeutic method of treating a TNF mediated disorder, a p38 kinase mediated disorder, inflammation and/or arthritis in a subject, the method comprising treating a subject having or susceptible to such disorder or condition with a therapeutically-effective amount of a compound of Formula I

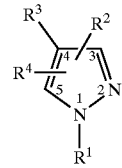

(I)

wherein
- $R^1$ is selected from hydrido, alkyl, cycloalkyl, alkenyl, cycloalkenyl, alkynyl, aryl, heterocyclyl, cycloalkylalkylene, cycloalkenylalkylene, heterocyclylalkylene, haloalkyl, haloalkenyl, haloalkynyl, hydroxyalkyl, hydroxyalkenyl, hydroxyalkynyl, aralkyl, aralkenyl, aralkynyl, arylheterocyclyl, carboxy, carboxyalkyl, alkoxyalkyl, alkenoxyalkyl, alkynoxyalkyl, aryloxyalkyl, heterocyclyloxyalkyl, alkoxyalkoxy, mercaptoalkyl, alkylthioalkylene, alkenylthioalkylene, alkylthioalkenylene, amino, aminoalkyl, alkylamino, alkenylamino, alkynylamino, arylamino, heterocyclylamino, alkylsulfinyl, alkenylsulfinyl, alkynylsulfinyl, arylsulfinyl, heterocyclylsulfinyl, alkylsulfonyl, alkenylsulfonyl, alkynylsulfonyl, arylsulfonyl, heterocyclylsulfonyl, alkylaminoalkylene, alkylsulfonylalkylene, acyl, acyloxycarbonyl, alkoxycarbonylalkylene, aryloxycarbonylalkylene, heterocyclyloxycarbonylalkylene, alkoxycarbonylarylene, aryloxycarbonylarylene, heterocyclyloxycarbonylarylene, alkylcarbonylalkylene, arylcarbonylalkylene, heterocyclylcarbonylalkylene, alkylcarbonylarylene, arylcarbonylarylene, heterocyclylcarbonylarylene, alkylcarbonyloxyalkylene, arylcarbonyloxyalkylene, heterocyclylcarbonyloxyalkylene, alkylcarbonyloxyarylene, arylcarbonyloxyarylene, and heterocyclylcarbonyloxyarylene; or $R^1$ has the formula

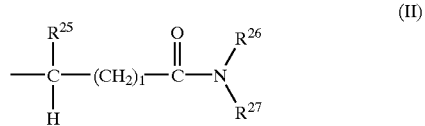

(II)

wherein:

i is an integer from 0 to 9;

$R^{25}$ is selected from hydrogen, alkyl, aralkyl, heterocyclylalkyl, alkoxyalkylene, aryloxyalkylene, aminoalkyl, alkylaminoalkyl, arylaminoalkyl, alkylcarbonylalkylene, arylcarbonylalkylene, and heterocyclylcarbonylaminoalkylene; and $R^{26}$ is selected from hydrogen, alkyl, alkenyl, alkynyl, cycloalkylalkylene, aralkyl, alkoxycarbonylalkylene, and alkylaminoalkyl; and $R^{27}$ is selected from alkyl, cycloalkyl, alkynyl, aryl, heterocyclyl, aralkyl, cycloalkylalkylene, cycloalkenylalkylene, cycloalkylarylene, cycloalkylcycloalkyl, heterocyclylalkylene, alkylarylene, alkylaralkyl, aralkylarylene, alkylheterocyclyl, alkylheterocyclylalkylene, alkylheterocyclylarylene, aralkylheterocyclyl, alkoxyalkylene, alkoxyarylene, alkoxyaralkyl, alkoxyheterocyclyl, alkoxyalkoxyarylene, aryloxyarylene, aralkoxyarylene, alkoxyheterocyclylalkylene, aryloxyalkoxyarylene, alkoxycarbonylalkylene, alkoxycarbonylheterocyclyl, alkoxycarbonylheterocyclylcarbonylalkylene, aminoalkyl, alkylaminoalkylene, arylaminocarbonylalkylene, alkoxyarylaminocarbonylalkylene, aminocarbonylalkylene, arylaminocarbonylalkylene, alkylaminocarbonylalkylene, arylcarbonylalkylene, alkoxycarbonylarylene, aryloxycarbonylarylene, alkylaryloxycarbonylarylene, arylcarbonylarylene, alkylarylcarbonylarylene, alkoxycarbonylheterocyclylarylene, alkoxycarbonylalkoxylarylene, heterocyclylcarbonylalkylarylene, alkylthioalkylene, cycloalkylthioalkylene, alkylthioarylene, aralkylthioarylene, heterocyclylthioarylene, arylthioalklylarylene, arylsulfonylaminoalkylene, alkylsulfonylarylene, alkylaminosulfonylarylene; wherein said alkyl, cycloalkyl, aryl, heterocyclyl, aralkyl, heterocyclylalkylene, alkylheterocyclylarylene, alkoxyarylene, aryloxyarylene, arylaminocarbonylalkylene, aryloxycarbonylarylene, arylcarbonylarylene, alkylthioarylene, heterocyclylthioarylene, arylthioalklylarylene, and alkylsulfonylarylene groups are optionally substituted with one or more radicals independently selected from alkyl, halo, haloalkyl, alkoxy, keto, amino, nitro, and cyano; or $R^{27}$ is —$CHR^{28}R^{29}$ wherein $R^{28}$ is alkoxycarbonyl, and $R^{29}$ is selected from aralkyl, aralkoxyalkylene, heterocyclylalkylene, alkylheterocyclylalkylene, alkoxycarbonylalkylene, alkylthioalkylene, and aralkylthioalkylene; wherein said aralkyl and heterocylcyl groups are optionally substituted with one or more radicals independently selected from alkyl and nitro; or $R^{26}$ and $R^{27}$ together with the nitrogen atom to which they are attached form a heterocycle, wherein said heterocycle is optionally substituted with one or more radicals independently selected from alkyl, aryl, heterocyclyl, heterocyclylalkylene, alkylheterocyclylalkylene, aryloxyalkylene, alkoxyarylene, alkylaryloxyalkylene, alkylcarbonyl, alkoxycarbonyl, aralkoxycarbonyl, alkylamino and alkoxycarbonylamino; wherein said aryl, heterocyclylalkylene and aryloxyalkylene radicals are optionally substituted with one or more radicals independently selected from halogen, alkyl and alkoxy; and $R^2$ is selected from hydrido, halogen, alkyl, alkenyl, alkynyl, aryl, heterocyclyl, haloalkyl, hydroxyalkyl, aralkyl, alkylheterocyclyl, heterocyclylalkyl, alkylamino, alkenylamino, alkynylamino, arylamino, heterocyclylamino, heterocyclylalkylamino, aralkylamino, aminoalkyl, aminoaryl, aminoalkylamino, arylaminoalkylene, alkylaminoalkylene, arylaminoarylene, alkylaminoarylene, alkylaminoalkylamino, cycloalkyl, cycloalkenyl, alkoxy, heterocyclyloxy, alkylthio, arylthio, heterocyclylthio, carboxy, carboxyalkyl, carboxycycloalkyl, carboxycycloalkenyl, carboxyalkylamino, alkoxycarbonyl, heterocyclylcarbonyl, alkoxycarbonylalkyl, alkoxycarbonylheterocyclyl, alkoxycarbonylheterocyclylcarbonyl, alkoxyalkylamino, alkoxycarbonylaminoalkylamino, and heterocyclylsulfonyl; wherein the aryl, heterocyclyl, heterocyclylalkyl, cycloalkyl and cycloalkenyl groups are optionally substituted with one or more radicals independently selected from halo, keto, amino, alkyl, alkenyl, alkynyl, aryl, heterocyclyl, aralkyl, heterocyclylalkyl, epoxyalkyl, amino (hydroxyalkyl) carboxy, alkoxy, aryloxy, aralkoxy, haloalkyl, alkylamino, alkynylamino, alkylaminoalkylamino, heterocyclylalkylamino, alkylcarbonyl, alkoxycarbonyl, alkylsulfonyl, arylsulfonyl, and aralkylsulfonyl; or $R^2$ has the formula:

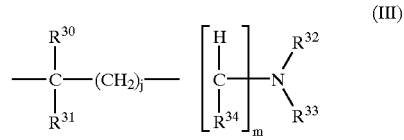

(III)

wherein:

j is an integer from 0 to 8; and m is 0 or 1; and $R^{30}$ and $R^{31}$ are independently selected from hydrogen, alkyl, aryl, heterocyclyl, aralkyl, heterocyclylalkylene, aminoalkyl, alkylaminoalkyl, aminocarbonylalkyl, alkoxyalkyl, and alkylcarbonyloxyalkyl; and $R^{32}$ is selected from hydrogen, alkyl, aralkyl, heterocyclylalkyl, alkoxyalkylene, aryloxyalkylene, aminoalkyl, alkylaminoalkyl, arylaminoalkyl, alkylcarbonylalkylene, arylcarbonylalkylene, and heterocyclylcarbonylaminoalkylene;

$R^{33}$ is selected from hydrogen, alkyl, —$C(O)R^{35}$, —$C(O)OR^{35}$, —$SO_2R^{36}$, —$C(O)NR^{37}R^{38}$, and —$SO_2NR^{39}R^{40}$, wherein $R^{35}$, $R^{36}$, $R^{37}$, $R^{38}$, $R^{39}$ and $R^{40}$ are independently selected from hydrocarbon, heterosubstituted hydrocarbon and heterocyclyl; and $R^{34}$ is selected from hydrogen, alkyl, aminocarbonyl, alkylaminocarbonyl, and arylaminocarbonyl; or $R^2$ is —$CR^{41}R^{42}$ wherein $R^{41}$ is aryl, and $R^{42}$ is hydroxy; and $R^3$ is selected from pyridinyl, pyrimidinyl, quinolinyl, purinyl,

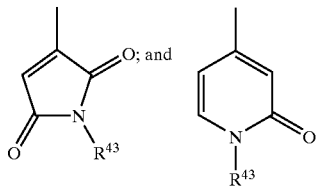

wherein $R^{43}$ is selected from hydrogen, alkyl, aminoalkyl, alkoxyalkyl, alkenoxyalkyl, and aryloxyalkyl; and wherein the $R^3$ pyridinyl, pyrimidinyl, quinolinyl and purinyl groups are optionally substituted with one or more radicals independently selected from halo, alkyl, aralkyl, aralkenyl, arylheterocyclyl, carboxy, carboxyalkyl, alkoxy, aryloxy, alkylthio, arylthio, alkylsulfinyl, arylsulfinyl, alkylsulfonyl, arylsulfonyl, aralkoxy, heterocyclylalkoxy, amino, alkylamino, alkenylamino, alkynylamino, cycloalkylamino, cycloalkenylamino, arylamino, heterocyclylamino, aminocarbonyl, cyano, hydroxy, hydroxyalkyl, alkoxycarbonyl, aryloxycarbonyl, heterocyclyloxycarbonyl, alkoxycarbonylamino, alkoxyaralkylamino, aminosulfinyl, aminosulfonyl, alkylaminoalkylamino, hydroxyalkylamino, aralkylamino, heterocyclylalkylamino, aralkylheterocyclylamino, nitro, alkylaminocarbonyl, alkylcarbonylamino, halosulfonyl, aminoalkyl, haloalkyl, alkylcarbonyl, hydrazinyl, alkylhydrazinyl, arylhydrazinyl, or —$NR^{44}R^{45}$ wherein $R^{44}$ is alkylcarbonyl or amino, and $R^{45}$ is alkyl or aralkyl; and $R^4$ is selected from hydrido, alkyl, alkenyl, alkynyl, cycloalkyl, cycloalkenyl, aryl, and heterocyclyl, wherein $R^4$ is optionally substituted with one or more radicals independently selected from halo, alkyl, alkenyl, alkynyl, aryl, heterocyclyl, alkylthio, arylthio, alkylthioalkylene, arylthioalkylene, alkylsulfinyl, alkylsulfinylalkylene, arylsulfinylalkylene, alkylsulfonyl, alkylsulfonylalkylene, arylsulfonylalkylene, alkoxy, aryloxy, aralkoxy, aminocarbonyl, alkylaminocarbonyl, arylaminocarbonyl, alkoxycarbonyl, aryloxycarbonyl, haloalkyl, amino, cyano, nitro, alkylamino, arylamino, alkylaminoalkylene, arylaminoalkylene, aminoalkylamino, and hydroxy;

provided $R^3$ is not 2-pyridinyl when $R^4$ is a phenyl ring containing a 2-hydroxy substituent and when $R^1$ is hydrido; further provided $R^2$ is selected from aryl, heterocyclyl, unsubstituted cycloalkyl and cycloalkenyl when $R^4$ is hydrido; and further provided $R^4$ is not methylsulfonylphenyl; or a pharmaceutically-acceptable salt or tautomer thereof.

The present invention also is directed to the use of the compounds of Formula I and/or IA in the preparation of medicaments useful in the treatment and/or prophylaxis of p38 kinase mediated conditions and disorders.

Also included in the family of compounds of Formulae I and/or IA are the pharmaceutically-acceptable salts and prodrugs thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formulae I and/or IA may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclyl, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, β-hydroxybutyric, galactaric and galacturonic acid. Suitable pharmaceutically-acceptable base addition salts of compounds of Formula I and/or IA include metallic salts and organic salts. More preferred metallic salts include, but are not limited to appropriate alkali metal (group Ia) salts, alkaline earth metal (group IIa) salts and other physiological acceptable metals. Such salts can be made from aluminum, calcium, lithium, magnesium, potassium, sodium and zinc. Preferred organic salts can be made from tertiary amines and quaternary ammonium salts, including in part, tromethamine, diethylamine, N,N'-dibenzylethylenediamine, chloroprocaine, choline, diethanolamine, ethylenediamine, meglumine (N-methylglucamine) and procaine. All of these salts may be prepared by conventional means from the corresponding compound of Formulae I and/or IA by reacting, for example, the appropriate acid or base with the compound of Formulae I and/or IA.

The present invention additionally comprises a class of compounds defined by Formula XX:

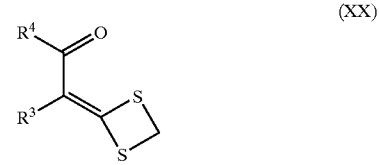

wherein $R^3$ and $R^4$ are as defined for the compounds of Formulae I and/or IA. Also included in the family of compounds of Formula XX are the pharmaceutically-acceptable salts and prodrugs thereof.

The compounds of Formula XX are useful as intermediates in the preparation of the compounds of Formulae I and/or IA. In addition, the compounds of Formula XX themselves have been found to show usefulness as p38 kinase inhibitors. These compounds are useful for the prophylaxis and treatment of the same p38 kinase mediated disorders and conditions as the compounds of formulae I and/or IA. Accordingly, the present invention provides a method of treating a cytokine-mediated disease which comprises administering an effective cytokine-interfering amount of a compound of Formula XX or a pharmaceutically acceptable salt or prodrug thereof.

The present invention further comprises a pharmaceutical composition for the treatment of a TNF mediated disorder, a p38 kinase mediated disorder, inflammation, and/or arthritis, comprising a therapeutically-effective amount of a compound of Formula XX, or a therapeutically-acceptable salt or prodrug thereof, in association with at least one pharmaceutically-acceptable carrier, adjuvant or diluent.

General Synthetic Procedures

The compounds of the invention can be prepared according to the following procedures of Schemes I–XXIX wherein $R^1$, $R^2$, $R^3$, $R^4$, $R^5$ and $Ar^1$ are as previously defined for the compounds of Formula I, IX, X and XI except where expressly noted.

SCHEME I

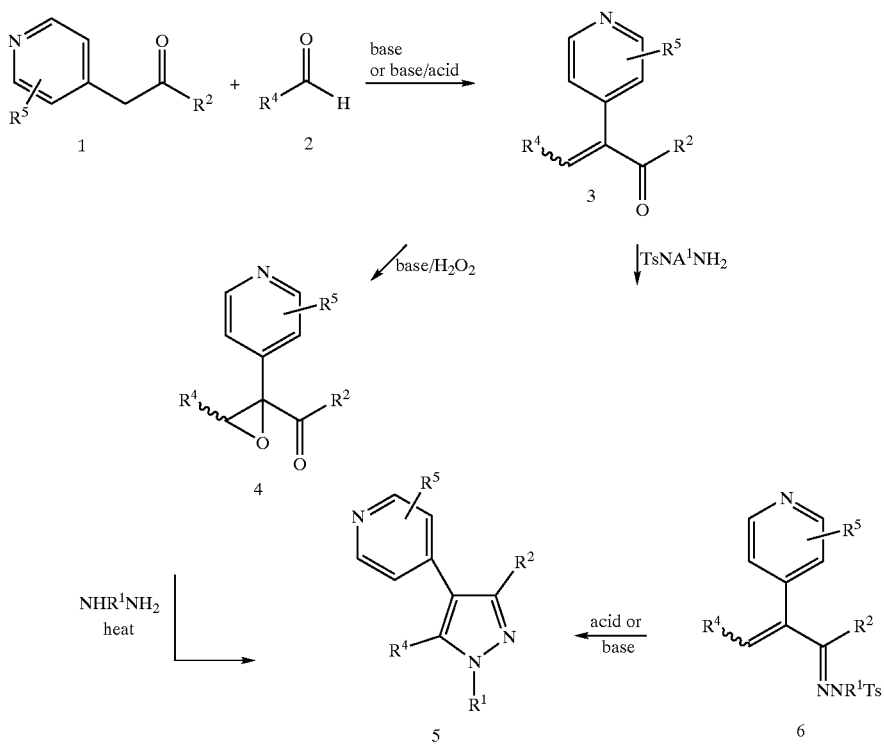

Scheme I shows the synthesis of pyrazole 5 by two routes. Condensation of the pyridylmethyl ketone 1 with aldehyde 2 in the presence of a base, such as piperdine, in a solvent, such as toluene or benzene, either in the absence or the presence of acetic acid at reflux, provides the α,β-unsaturated ketone 3. In route 1, ketone 3 is first converted to epoxide 4, such as by treatment with hydrogen peroxide solution at room temperature, in the presence of base such as sodium hydroxide. Treatment of epoxide 4 with hydrazine in ethanol or other suitable solvent at a temperature ranging up to reflux, yields pyrazole 5. In route 2, ketone 3 is condensed directly with tosyl hydrazide in the presence of an acid such as acetic acid, at reflux, to provide pyrazole 5. Alternatively, the intermediate tosyl hydrazone 6 may be isolated, conversion of it to pyrazole 5 is effected by treatment with a base, such as potassium hydroxide, in a suitable solvent, such as ethylene glycol, at a temperature ranging from 25° C. up to 150° C.

SCHEME II

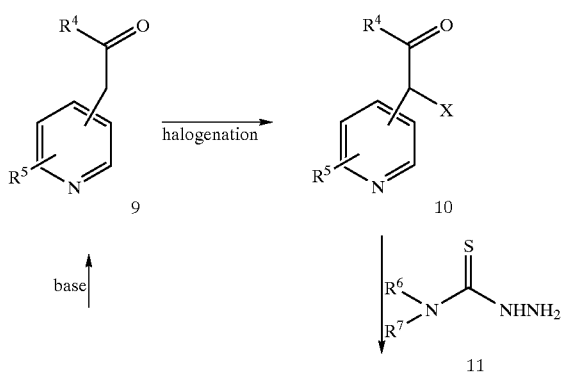

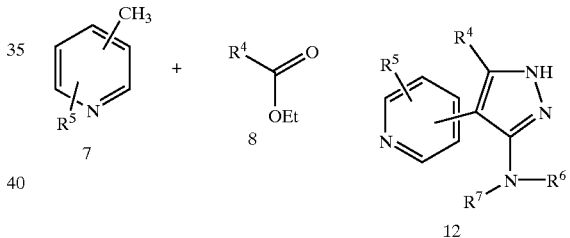

Scheme II shows the synthesis of pyrazole 12 of the present invention. The treatment of pyridine derivative 7 with ester 8 in the presence of a base, such as sodium bis(trimethylsilyl)amide, in a suitable solvent, such as tetrahydrofuran, gives ketone 9. Treatment of ketone 9 or a hydrohalide salt of ketone 9 with a halogenating agent, such as bromine, N-bromosuccinimide or N-chlorosuccinimide, in suitable solvents, such as acetic acid, methylene chloride, methanol, or combinations thereof, forms the a-halogenated ketone 10 (wherein X is halo). Examples of suitable hydrohalide salts include the hydrochloride and hydrobromide salts. Reaction of haloketone 10 with thiosemicarbazide 11 (where $R^6$ and $R^7$ can be hydrido, lower alkyl, phenyl, heterocyclyl and the like or where $R^6$ and $R^7$ form a heterocyclyl ring optionally containing an additional heteroatom) provides pyrazole 12. Examples of suitable solvents for this reaction are ethanol and dimethylformamide. The reaction may be carried out in the presence or absence of base or acid at temperatures ranging from room temperature to 100° C.

Thiosemicarbazides which are not commercially available may be conveniently prepared by one skilled in the art by first reacting an appropriate amine with carbon disulfide in the presence of a base, followed by treatment with an alkylating agent such as methyl iodide. Treatment of the resultant alkyl dithiocarbamate with hydrazine results in the desired thiosemicarbazide. This chemistry is further described in E. Lieber and R. C. Orlowski, *J. Org. Chem.*, Vol. 22, p. 88 (1957). An alternative approach is to add hydrazine to appropriately substituted thiocyanates as described by Y. Nomoto et al., *Chem. Pharm. Bull.*, Vol. 39, p. 86 (1991). The Lieber and Nomoto publications are incorporated herein by reference.

Where Compound 12 contains a second derivatizable nitrogen atom, a wide range of substituents may be placed on that atom by methods known to those skilled in the art. For example, in cases where $R^6$ and $R^7$ together with the nitrogen atom to which they are attached comprise a piperazine ring, the distal nitrogen of that ring may be, for example, (i) methylated by reaction with formic acid and formaldehyde; (ii) propargylated by reaction with propargyl bromide in a suitable solvent such as dimethylformamide in the presence of a suitable base such as potassium carbonate; (iii) acylated or sulfonylated by reaction with a suitable acyl or sulfonyl derivative in pyridine; or (iv) cyclopropanated by reaction with [1(1-ethoxycyclopropyl)oxy]trimethylsilane using sodium cyanoborohydride in the presence of acetic acid.

Additionally, one of the nitrogen atoms of the pyrazole ring optionally may be alkylated by reaction with an alkyl halide, such as propargyl bromide, in the presence of a strong base such as sodium hydride.

hydrazide 16, which is then reacted with acyl halide or anhydride 17 at low temperature to provide acyl hydrazone 18. Upon heating at a temperature up to 200° C., acyl hydrazone 18 is converted to pyrazole 19. In Route 2, acyl hydrazone 18 is formed directly by reaction of ketone 13 with acyl hydrazide 15, formed by reaction of hydrazine with a carboxylic acid ester, at room temperature. Heating acyl hydrazone 18 as above then provides pyrazole 19. In Route 3, ketone 13 is treated with acyl hydrazide 15 at a suitable temperature, ranging from room temperature to about 200° C., to give pyrazole 19 directly. Alternatively, this condensation may be carried out in an acidic solvent, such as acetic acid, or in a solvent containing acetic acid.

SCHEME IV

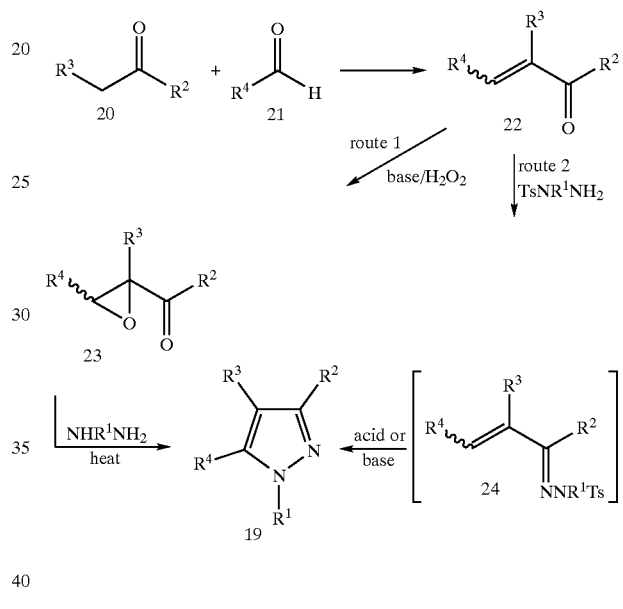

SCHEME III

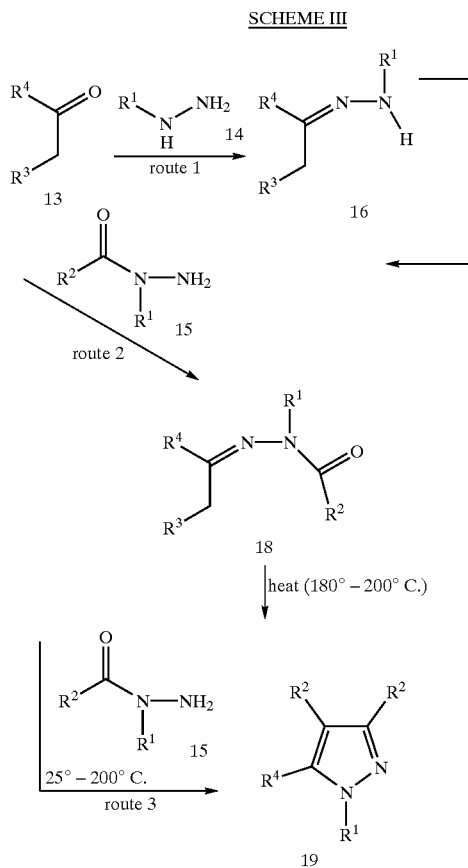

Scheme III shows the synthesis of pyrazole 19 in more general form by three routes. In Route 1, ketone 13 is condensed with hydrazine 14 to give the substituted Synthetic Scheme IV describes the preparation of pyrazole 19.

SCHEME V

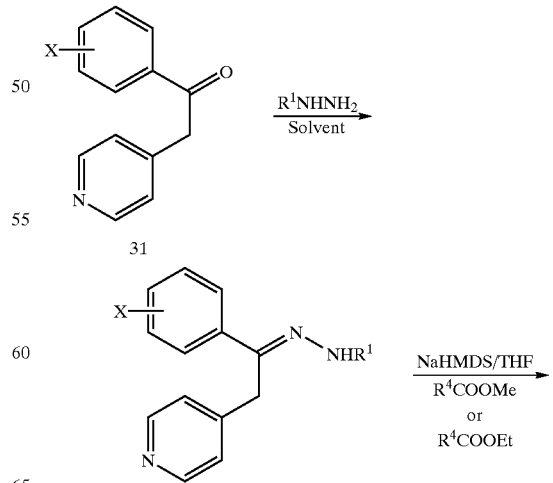

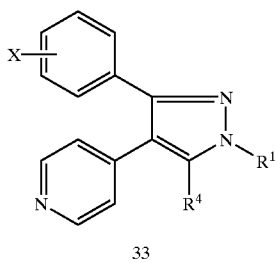

33

X = halyl, alkyl
R¹ = Me, CH₂CH₂OH
R⁴ = cyclopropyl, 4-pyridyl, 4-imidazolyl

Scheme V shows the two step synthesis of the 3-substituted 4-pyridyl-5-arylpyrazoles 33 of the present invention by cyclization of hydrazone dianions with carboxylates. In step 1, the reaction of substituted pyridylmethyl ketones 31 (prepared, for example, as later described in Scheme IX) with hydrazines in the presence of solvents such as ethanol gives ketohydrazones 32. Examples of suitable hydrazines include, but are not limited to, phenylhydrazine and p-methoxyphenylhydrazine. In step 2, the hydrazones 32 are treated with two equivalents of a base such as sodium bis(trimethylsilyl)amide in a suitable solvent such as tetrahydrofuran to generate dianions. This reaction may be carried out at temperatures of about 0° C. or lower. In the same step, the dianions then are condensed with esters such as methyl isonicotinate, methyl cyclopropanecarboxylate, to give the desired pyrazoles 33. It may be necessary to treat the product from this step with a dehydrating agent, such as a mineral acid, to produce the target pyrazole in some instances.

Scheme VI shows an alternative method for synthesizing pyrazoles which are unsubstituted at the 5 position of the ring. In accordance with this method, a heteroarylmethyl ketone 34 is synthesized by first treating a heteroarylmethane with a strong base such as lithium hexamethyldisilazide or lithium diisopropylamide. Examples of suitable heteroarylmethanes are 4-methylpyridine, 4-methylpyrimidine, 2,4-dimethylpyridine, 2-chloro-4-methylpyrimidine, 2-chloro-4-methylpyridine and 2-fluoro-4-methylpyridine. The resulting heteroarylmethyl lithium species is then reacted with a substituted benzoate ester to produce ketone 34. Examples of suitable benzoate esters are methyl and ethyl p-fluorobenzoate and ethyl and methyl p-chlorobenzoate. Ketone 34 is converted to the aminomethylene derivative 35 by reaction with an aminomethylenating agent such as dimethylformamide dimethyl acetal or tert-butoxybis(dimethylamino)methane. Ketone 35 is converted to pyrazole 36 by treatment with hydrazine.

A modification of this synthetic route serves to regioselectively synthesize pyrazole 38 which contains a substituted nitrogen at position 1 of the ring. Ketone 34 is first converted to hydrazone 37 by reaction with the appropriate substituted hydrazine. Examples of suitable hydrazines are N-methylhydrazine and N-(2-hydroxyethyl)hydrazine. Reaction of hydrazone 37 with an aminomethylenating agent produces pyrazole 38. Examples of suitable aminomethylenating agents include dimethylformamide dimethyl acetal and tert-butoxybis(dimethylamino)methane.

In cases where the $R^3$ substituent of pyrazoles 36 and 38 bears a leaving group such as a displaceable halogen, subsequent treatment with an amine produces an aminosubstituted heteroaromatic derivative. Examples of such amines include benzylamine, cyclopropylamine and ammonia. The leaving group may also be replaced with other nucleophiles such as mercaptides and alkoxides. Examples of substitutable $R^3$ groups include, but are not limited to, 2-chloropyridinyl and 2-bromopyridinyl groups.

SCHEME VI

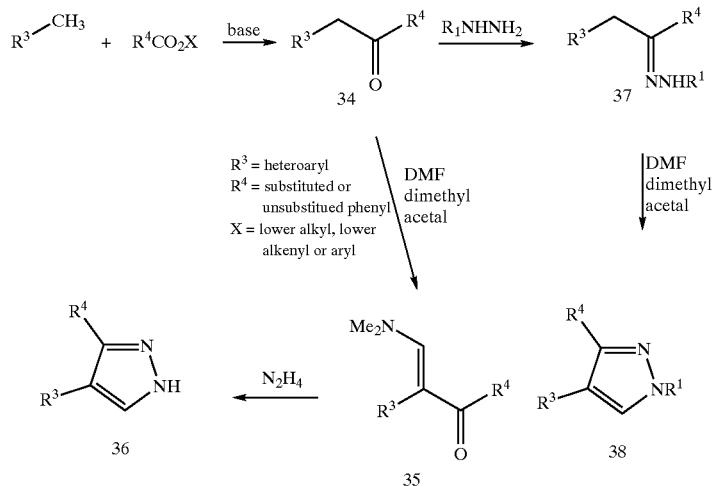

SCHEME VII

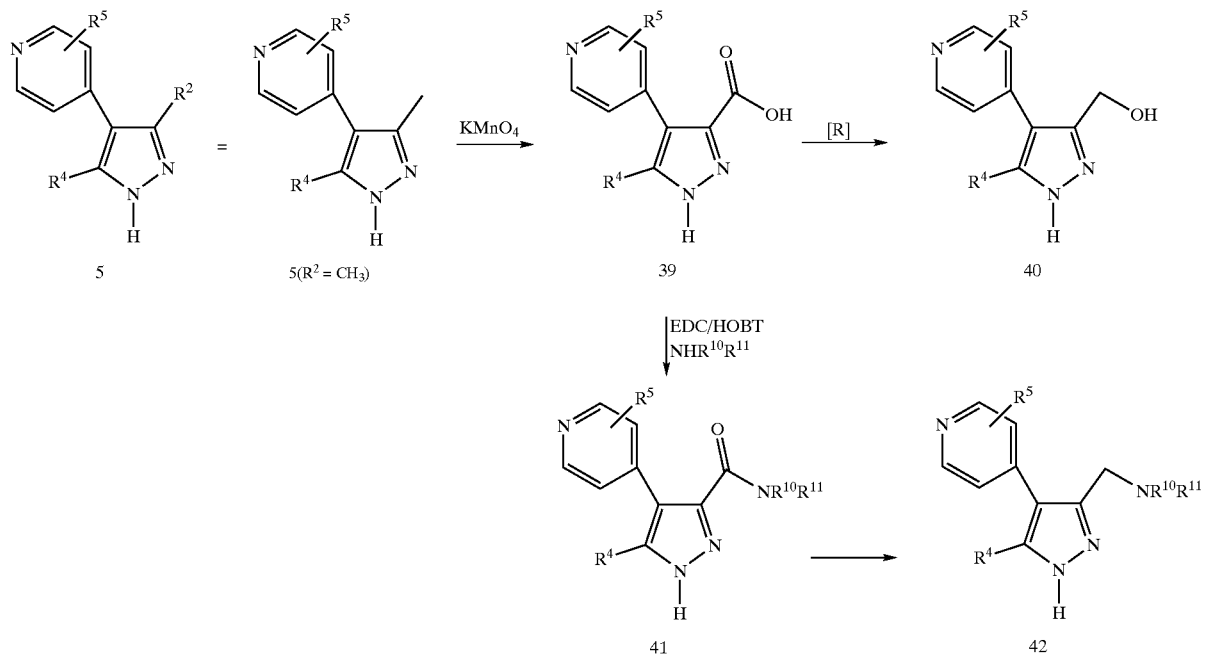

Scheme VII describes the preparation of derivatives from pyrazole 5 (prepared in accordance with Scheme I) when $R^2$=$CH_3$. Oxidation of pyrazole 5 gives carboxylic acid 39, which is then reduced to hydroxymethyl compound 40, or coupled with amine $NR^{10}R^{11}$ (wherein $R^{10}$ and $R^{11}$ are independently selected, for example, from hydrogen, alkyl and aryl, or together with the nitrogen atom to which they are attached form a 4–8 membered ring that may contain one or more additional heteroatoms selected from oxygen, nitrogen or sulfur) to form amide 41 followed by reduction to generate amine derivative 42.

Scheme VIII illustrates the synthesis of pyrazoles 44 and 45 from pyrazole 43. The alkylation of the ring nitrogen atoms of pyrazole 43 can be accomplished using conventional techniques. Treatment of pyrazole 43 with an appropriate base (for example, sodium hydride) followed by treatment with an alkyl halide (for example, $CH_3I$) yields a mixture of isomers 44 and 45.

SCHEME VIII / SCHEME IX

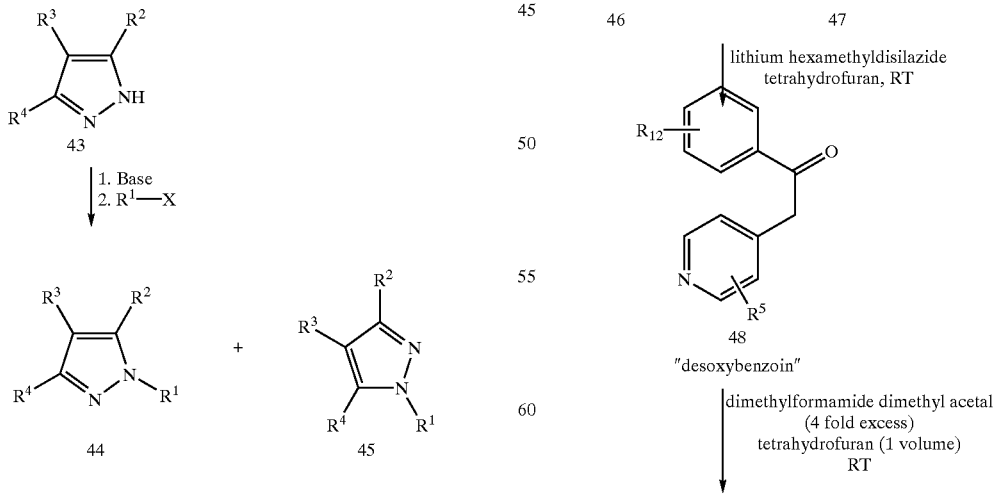

-continued

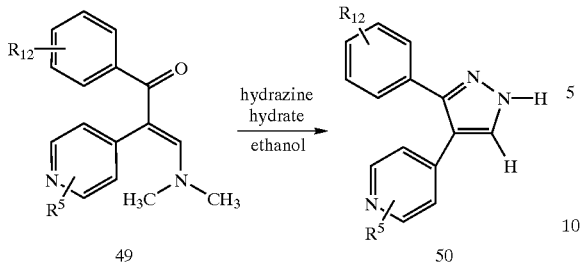

49 → 50

Scheme IX illustrates the synthesis of 3-aryl-4-pyridyl-pyrazoles of the present invention. Benzoate 46 is reacted with pyridine 47 in the presence of a strong base, such as an alkali metal hexamethyldisilazide (preferably sodium hexamethyldisilazide or lithium hexamethyldisilazide), in a suitable solvent, such as tetrahydrofuran, to give desoxybenzoin 48. Desoxybenzoin 48 is then converted to ketone 49 by treatment with an excess of dimethylformamide dimethyl acetal. Ketone 49 is then reacted with hydrazine hydrate in a suitable solvent such as ethanol to yield pyrazole 50. In Scheme IX, $R^{12}$ represents one or more radicals independently selected from the optional substituents previously defined for $R^4$. Preferably, $R^{12}$ is hydrogen, alkyl, halo, trifluoromethyl, methoxy or cyano, or represents methylenedioxy.

The 3-aryl-4-pyrimidinyl-pyrazoles of the present invention can be synthesized in the manner of Scheme IX by replacing pyridine 47 with the corresponding pyrimidine. In a similar manner, Schemes X through XVII can be employed to synthesize 3-aryl-4-pyrimidinyl-pyrimidines corresponding to the 3-aryl-4-pyrimidinyl-pyrazoles shown in those schemes.

SCHEME X

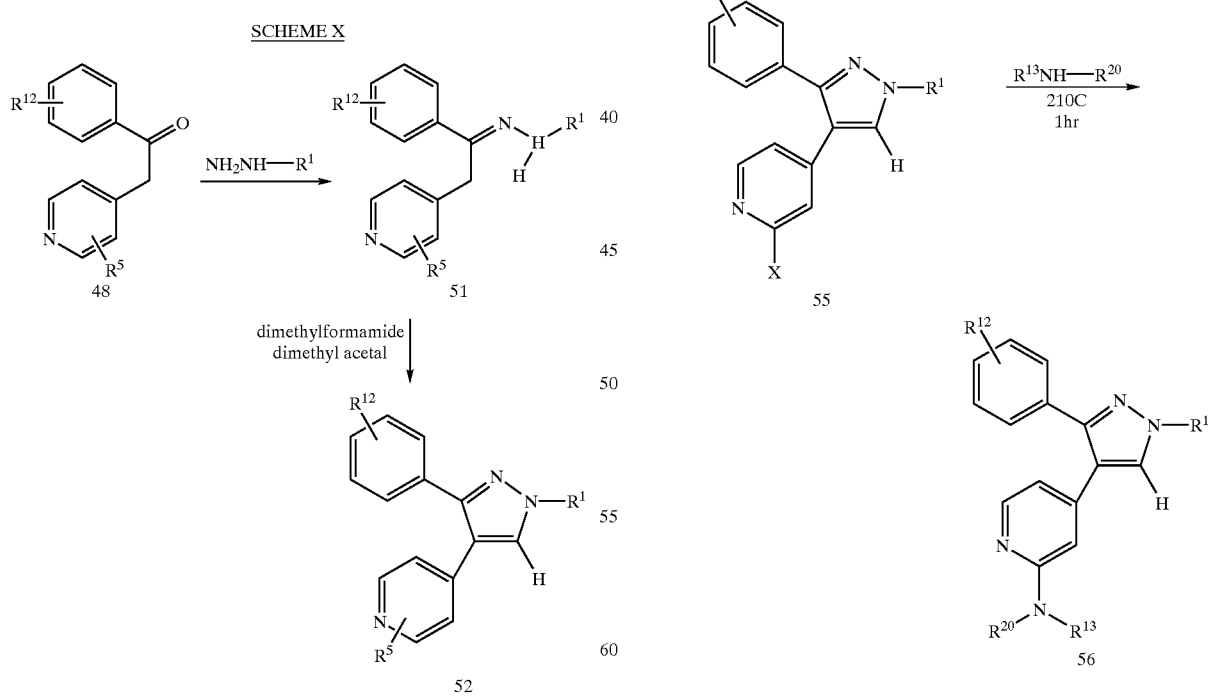

Scheme X illustrates one variation of Scheme IX that can be used to synthesize 3-aryl-4-pyridyl-pyrazoles that are further substituted on the nitrogen atom at position 1 of the pyrazole ring. If desoxybenzoin 48 (prepared in accordance with Scheme IX) instead is first converted to hydrazone 51 by treatment with hydrazine and hydrazone 51 is then treated with dimethylformamide dimethyl acetal, then the resulting product is pyrazole 52.

Schemes XI through XVIII illustrate further modifications that can be made to Scheme IX to synthesize other 3-aryl-4-pyridyl-pyrazoles having alternative substituents.

SCHEME XI

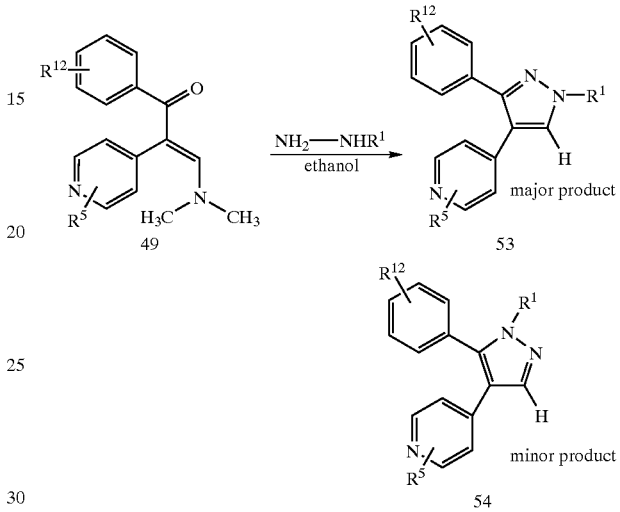

SCHEME XII

In Scheme XII, X is chloro, fluoro or bromo; $R^{13}$ is, for example, hydrogen, alkyl, phenyl, aralkyl, heteroarylalkyl, amino or alkylamino; and $R_{20}$, is, for example, hydrogen or alkyl.

SCHEME XIII
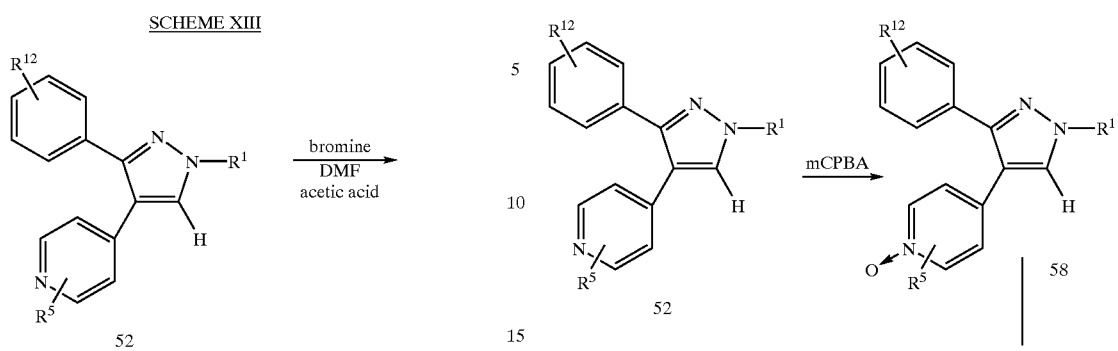
SCHEME XIV
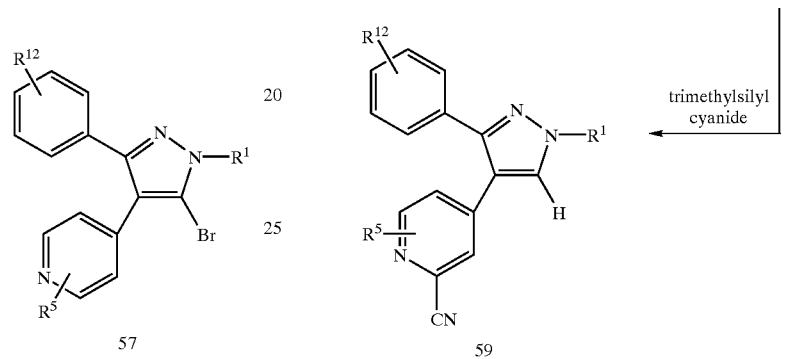
SCHEME XV
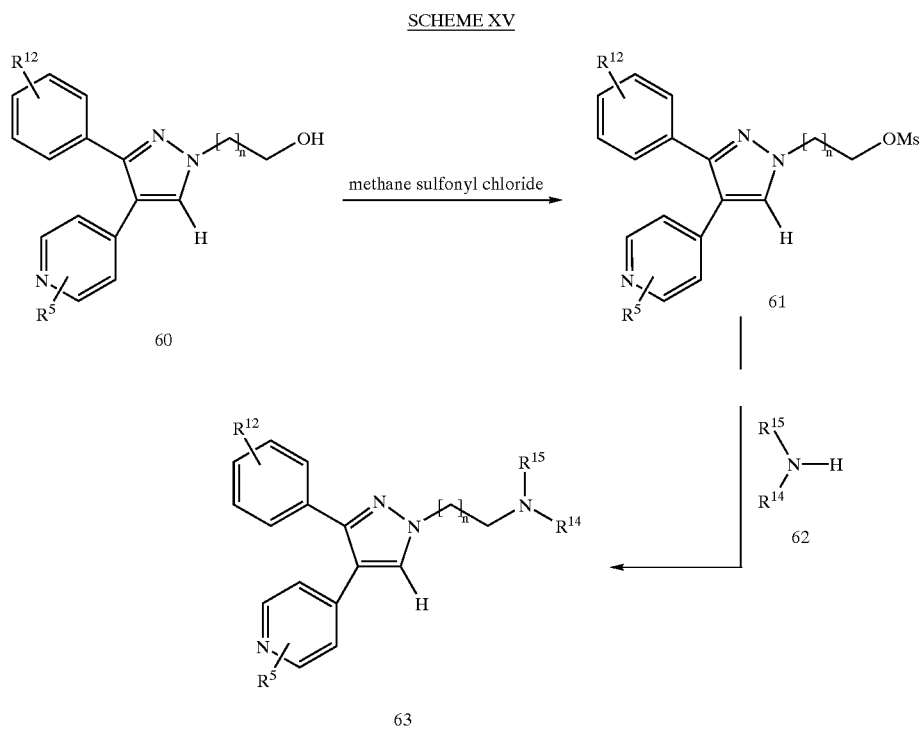

In Scheme XV, n is 1, 2, 3, 4 or 5; and $R^{14}$ and $R^{15}$ are independently selected from, for example, hydrogen, alkyl or aryl, or together with the nitrogen atom to which they are attached form a 4–7 membered ring that may contain one or more additional heteroatoms selected from oxygen, nitrogen or sulfur.

SCHEME XVI

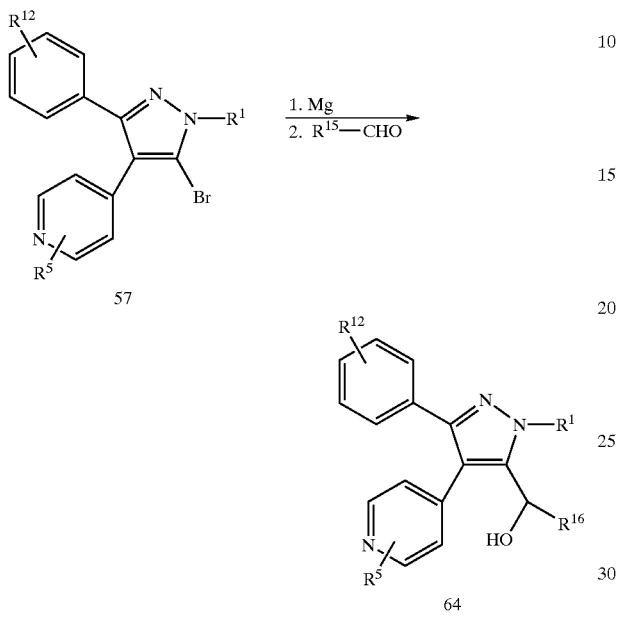

In Scheme XVI, $R^{16}$ is selected, for example, from hydrogen, alkyl and phenyl.

SCHEME XVII

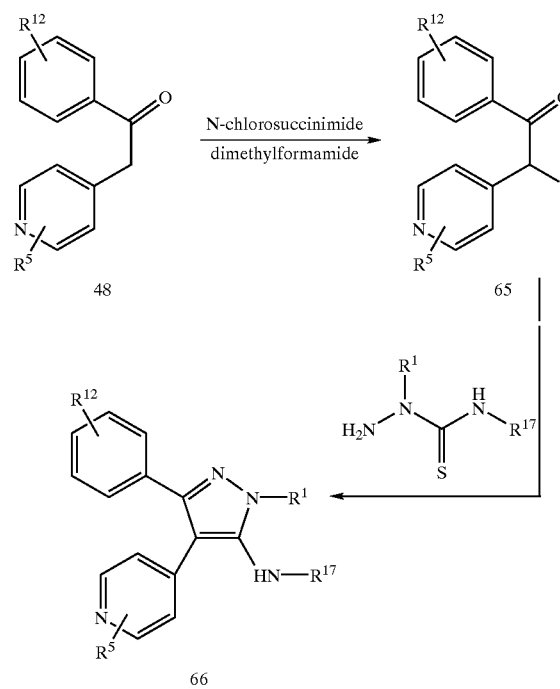

In Scheme XVII, $R^{17}$ is selected, for example, from alkyl, phenylalkyl and heterocyclylalkyl.

SCHEME XVIII

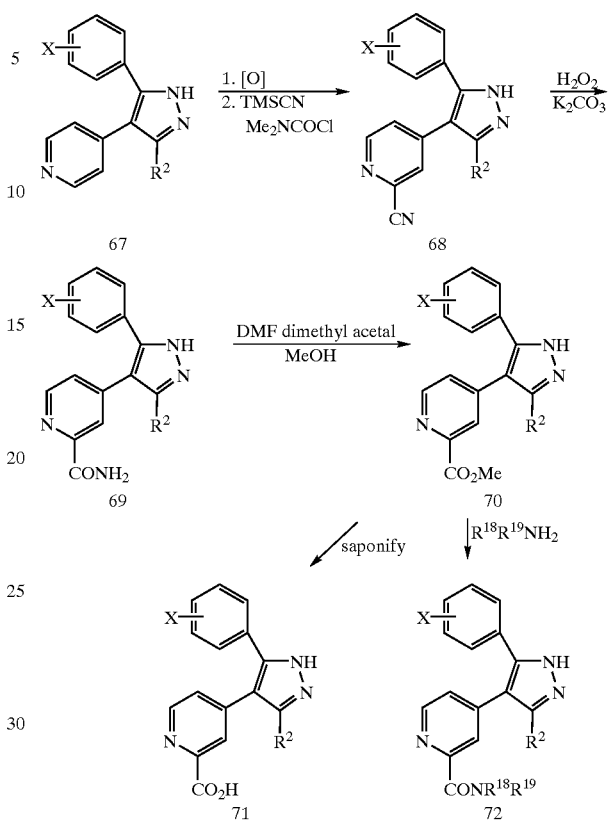

Compounds wherein the 2-position of the pyridine ring is substituted by a carboxyl group or a carboxyl derivative may be synthesized according to the procedures outline in Scheme XVIII. The starting pyridyl pyrazole 67 is converted to the 2-cyano derivative 68 by first conversion to its pyridine N-oxide by reaction with an oxidizing agent such as m-chloroperoxybenzoic acid. Treatment of the pyridine N-oxide with trimethylsilyl cyanide followed by dimethylcarbamoyl chloride produces the 2-cyano compound 68. Compound 68 is converted to its carboxamide 69 by reaction with hydrogen peroxide in the presence of a suitable base. Examples of suitable bases include potassium carbonate and potassium bicarbonate. Carboxamide 69 is converted to its methyl ester 70 by reaction with dimethylformamide dimethyl acetal in methanol. The ester 70 is converted to its carboxylic acid 71 by saponification. Typical saponification conditions include reaction with a base such as sodium hydroxide or potassium hydroxide in a suitable solvent such as ethanol or ethanol and water or methanol and water or the like. Ester 70 is also convertible to substituted amide 72 by treatment with a desired amine, such as methylamine at a suitable temperature. Temperatures may range from room temperature to 180° C. In Scheme XVIII, $R^{18}$ and $R^{19}$ are independently selected, for example, from hydrogen, alkyl and aryl, or together with the nitrogen atom to which they are attached form a 4–8 membered ring that may contain one or more additional heteroatoms selected from oxygen, nitrogen or sulfur.

SCHEME XIX

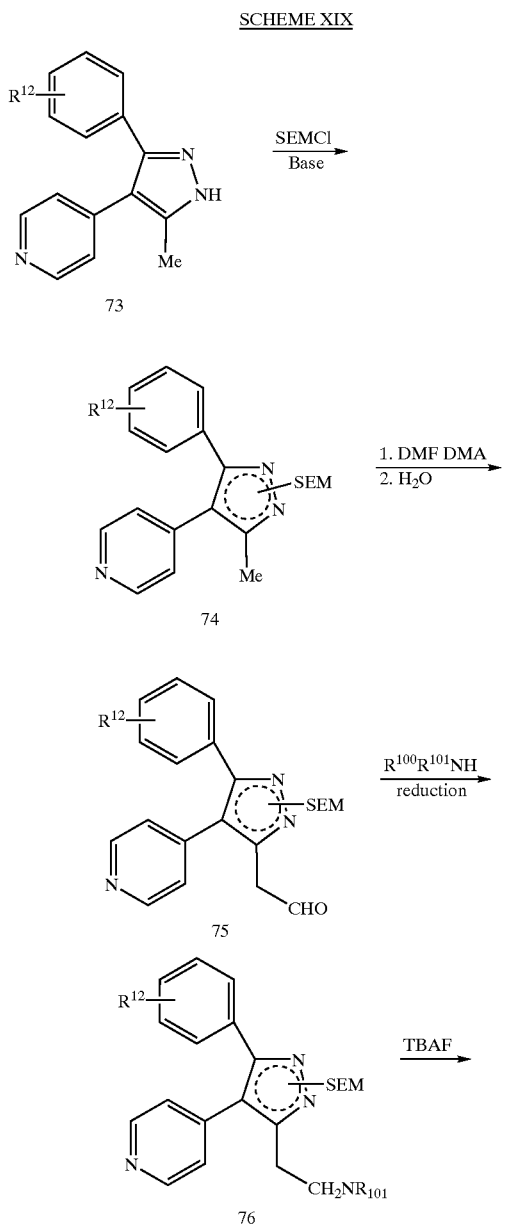

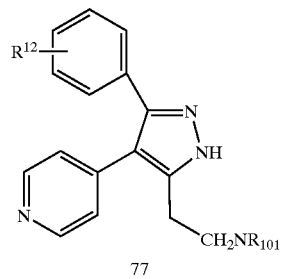

The synthesis of compound 77, wherein the amino group is extended two methylene units from the pyrazole ring is illustrated in Scheme XIX above. Reaction of pyrazole 73 with a protecting reagent such as 2-(trimethylsilyl) ethoxymethyl chloride (SEM-Cl) in the presence of a base such as sodium hydride yields protected pyrazole 74. This reaction results in a mixture of regioisomers wherein the 2-(trimethylsilyl)-ethoxymethyl (SEM) group may be attached to either of the nitrogen atoms of the pyrazole ring. Alternatively, protecting reagents such as 2-methoxyethoxymethyl chloride (MEMCl) also may be used.

Reaction of compound 74 with a suitable derivative of dimethyl formamide, followed by exposure to water, leads to aldehyde 75. Examples of suitable derivatives of dimethylformamide include tert.-butoxybis(dimethylamino)methane and dimethylformamide dimethyl acetal. One skilled in the art will understand that this leads to the formation of a reactive vinyl amine as an intermediate. The reaction may be carried out in the reagent itself or in the presence of dimethylformamide as solvent. Suitable reaction temperatures range from about 50° C. to about 153° C. The contacting of the intermediate vinyl amine with water may be carried out in solution in a suitable solvent such as methanol, ethanol, acetone, or dioxane. Alternatively, a solution of the vinyl amine in a suitable solvent may be contacted with hydrated silica gel.

Aldehyde 75 may be reductively aminated to amine 76 by reaction with the desired amine in the presence of a reducing agent. Typical reducing agents include sodium cyanoborohydride, sodium borohydride or hydrogen in the presence of a catalyst, such as a palladium/carbon catalyst or a Raney nickel catalyst, either at atmospheric pressure or in a pressurized system. An acid catalyst such as acetic acid or dilute hydrochloric acid may also be employed. The reaction may be run at ambient temperature or may be heated.

Pyrazole 77 is obtained by removal of the pyrazole nitrogen protecting group. The deprotection reaction employed will depend upon the specific protecting group removed. A 2-(trimethylsilyl)ethoxymethyl group can be removed, for example, by reaction of amine 76 with tetrabutylammonium fluoride while a 2-methoxyethoxymethyl group can be removed, for example, by acid hydrolysis.

SCHEME XX

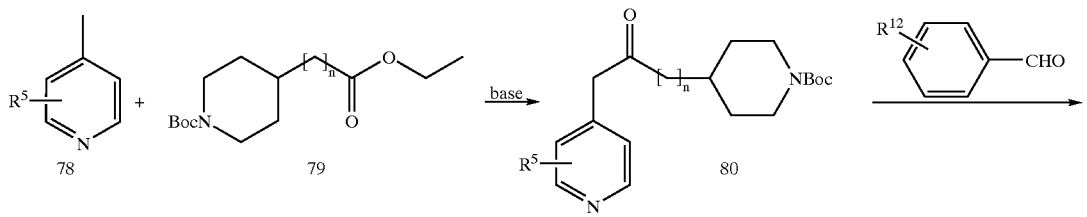

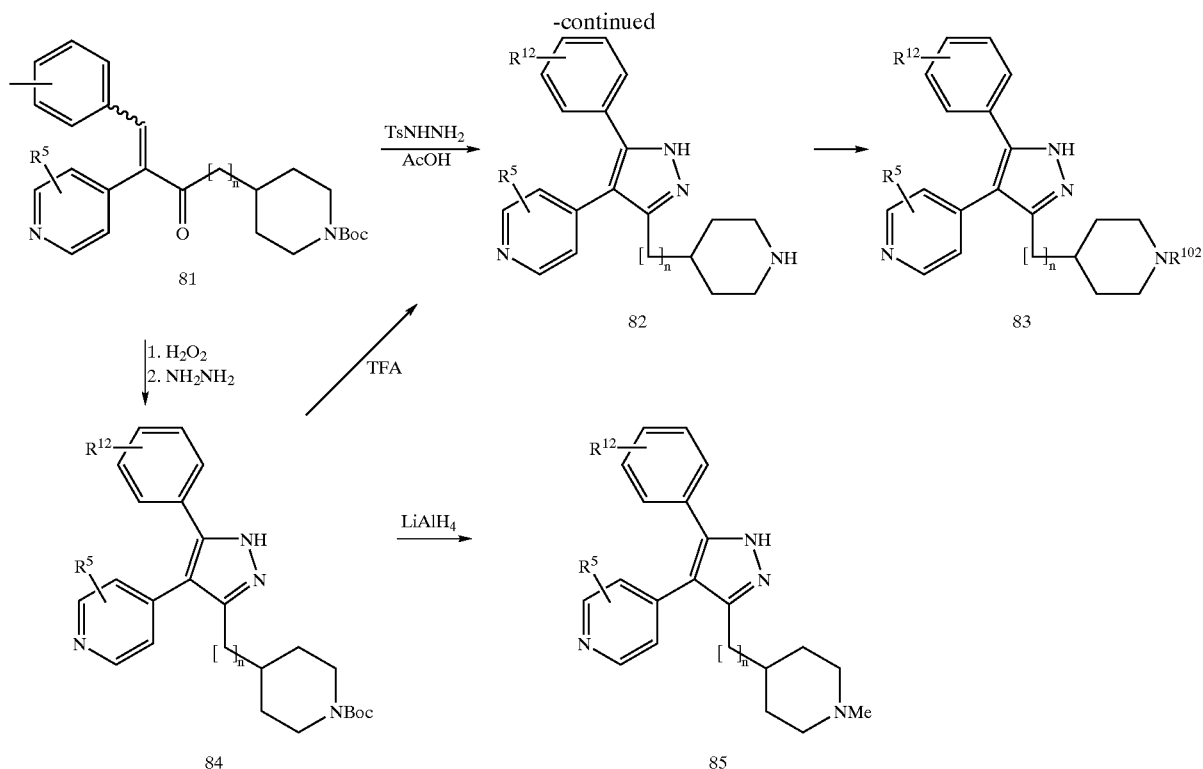

Scheme XX shows the syntheses of pyrazole 82 and its derivatives 83 and 85. A substituted 4-picoline 78 is condensed with ethyl ester derivative 79 in the presence of a base such as lithium diisopropylamide to give ketone derivative 80. An example of a suitable picoline is 4-picoline. Suitable ethyl ester derivatives include ethyl 4-piperidinylacetate (Compound 79, n=1). Ester 79 may be synthesized, for example, by hydrogenation of ethyl 4-pyridylacetate and protection of the resulting piperidine nitrogen as the tert.-butoxycarbonyl (Boc) derivative by reaction with tert.-butoxycarbonyl chloride. The hydrogenation may be carried out, for example, at pressures from atmospheric to 100 psi. Suitable catalysts include 5% platinum on carbon. The presence of an acid such as hydrochloric acid may also improve reaction performance.

Treatment of 80 with a substituted benzaldehyde provides unsaturated ketone 81. Pyrazole 82 may be synthesized by treatment of 81 with p-toluenesulfonylhydrazide in the presence of acetic acid. During this reaction, the protecting tert.-butoxycarbonyl group is removed. Derivatization of pyrazole 82 by appropriate methods as described in Scheme II for analogous piperazine derivatives gives various pyrazole derivatives 83.

Alternatively, unsaturated ketone 81 can be converted to pyrazole 84 by first reaction with hydrogen peroxide in the presence of sodium or postassium hydroxide, followed by reaction with hydrazine. Using trifluoroacetic acid, the tert.-butoxycarbonyl group may be removed from pyrazole 84 to give pyrazole 82.

Alternatively, the tert.-butoxycarbonyl group of 84 may be reduced with a reagent such as lithium aluminum hydride to provide the methyl derivative 85.

SCHEME XXI

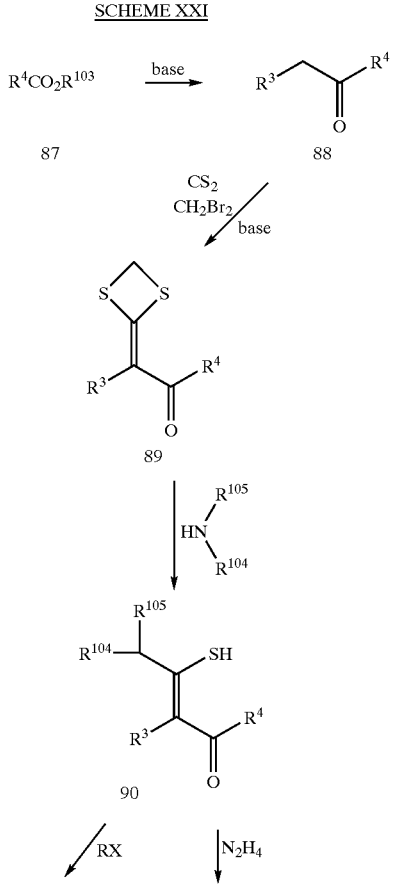

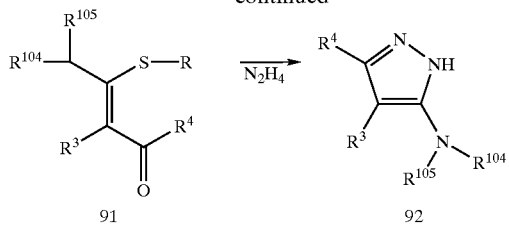

Scheme XXI shows the synthesis of pyrazoles 92. Treatment of compound 86 with ester 87 in the presence of a base, such as sodium bis(trimethylsilyl)amide, in a suitable solvent such as tetrahydrofuran, gives ketone 88. Substituent $R^3$ is typically heteroaryl, preferably pyridinyl or pyrimidinyl, and more preferably 4-pyridinyl. Substituent $R^4$ is typically aryl, substituted aryl, heteroaryl, substituted heteroaryl, alkyl or aralkyl, and is preferably a substituted phenyl. $R^{103}$ can be, for example, lower alkyl.

Treatment of ketone 88 with carbon disulfide, dibromomethane, and a base such as potassium carbonate in a suitable solvent such as acetone gives dithietane 89. Other suitable bases include, but are not limited to, carbonates such as sodium carbonate, tertiary amines such as triethylamine or diazabicycloundecane (DBU), and alkoxides such as potassium tert-butoxide. Other suitable solvents include, but are not limited to, low molecular weight ketones, methyl ethyl ketone, tetrahydrofuran, glyme, acetonitrile, dimethylformamide, dimethylsulfoxide, dichloromethane, benzene, substituted benzenes and toluene.

Dithietane 89 may be reacted with an appropriate amine, with or without heating, in an acceptable solvent such as toluene or acetonitrile to make thioamide 90. Thioamide 90 is treated with hydrazine or a substituted hydrazine in an appropriate solvent such as tetrahydrofuran or an alcohol, with or without heating, to produce pyrazole 92 and/or its tautomer.

Alternatively, thioamide 90 can be reacted with an alkyl halide or a sulphonic acid ester to yield substituted thioamide 91. Substituted thioamide 91 is treated with hydrazine or a substituted hydrazine in an appropriate solvent such as tetrahydrofuran or an alcohol, with or without heating, to produce pyrazole 92 or its tautomer.

$R^{104}$ and $R^{105}$ can be independent radicals or can form a hererocyclyl ring that is optionally substituted and/or contains an additional heteroatom.

SCHEME XXII

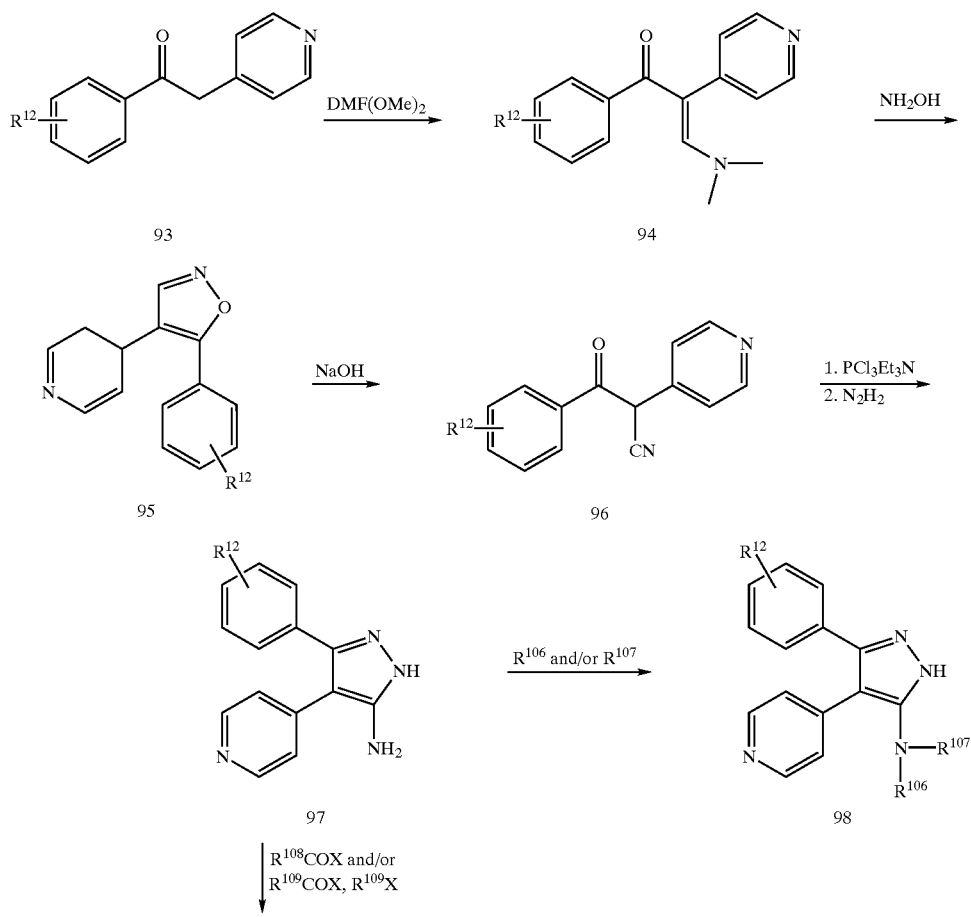

-continued

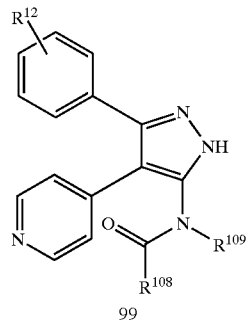

99

Scheme XXII shows the synthesis of substituted 5-amino pyrazoles 98 and 99. Desoxybenzoin 93 (prepared, for example, as illustrated in Scheme IX, supra, or Example C-1, infra) is reacted with an aminomethylenating agent, such as N,N-dimethylformamide dimethyl acetal, to form aminomethylene ketone 94. Aminomethylene ketone 94 is converted to isoxazole 95 by treatment with a hydroxylamine in a suitable solvent such as ethanol. Isoxazole 95 is treated with a base, such as dilute aqueous sodium hydroxide, to form cyanoketone 96. Cyanoketone 96 is then reacted with a chlorinating agent, such as phosphorous trichloride, to form a vinyl chloride which is then treated with hydrazine hydrate (or a substituted hydrazine hydrate) to form amino pyrazole 97. Amino pyrazole 97 can be reacted further with a variety of alkyl halides, such as methyl bromoacetate, bromoacetonitrile, and chloroethylamine, to form the appropriate mono- or disubstituted, cyclic or acyclic amino pyrazole 98. Typical $R^{106}$ and $R^{107}$ substituents include, for example, hydrogen and alkyl. In addition, amino pyrazole 97 can be reacted further with a variety of acylating agents, such as benzyliminodiacetic acid and N,N-dimethylglycine, to give the corresponding mono- or disubstituted, cyclic or acyclic amide or imide 99. Typical $R^{108}$ and $R^{109}$ substituents include, for example, hydrogen, alkyl and acyl.

SCHEME XXIII

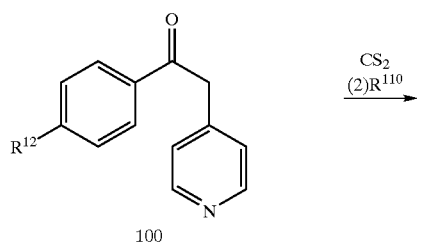

100

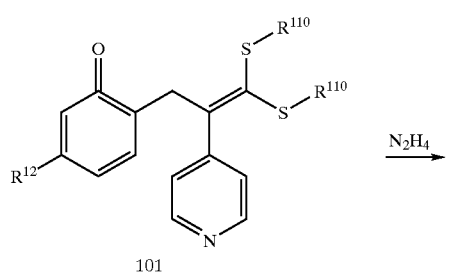

101

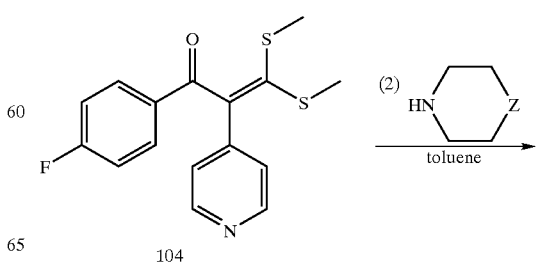

102

103

Scheme XXIII shows the synthesis of sulfoxide/sulfone 103. Ketone 100, wherein X is preferably halo such as fluoro or chloro, in a solvent, such as tetrahydrofuran, is treated with a suitable base, such as sodium hydride or potassium t-butoxide, to yield an enolate intermediate. The enolate intermediate is reacted with carbon disulfide and then alkylated with an appropriate alkylating agent, such as methyl iodide, benzyl bromide, or trimethylsilylchloride, to form dithioketene acetal 101. Dithioketene acetal 101 can be cyclized to pyrazole 102 using hydrazine, or its hydrate (or a substituted hydrazine or its hydrate), in a suitable solvent, such as tetrahydrofuran or ethanol. Pyrazole 102 is then treated with an oxidizing agent, such as potassium peroxymonosulfate, ammonium persulfate, or 3-chloroperoxybenzoic acid, to generate sulfoxide 103 (n=1) and/or sulfone 103 (n=2).

SCHEME XXIV

104

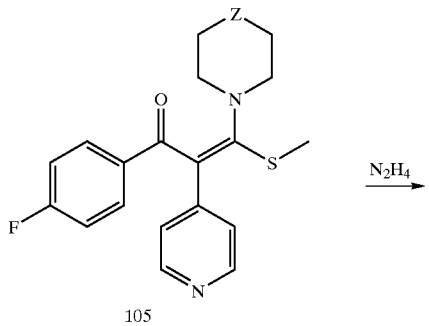

105

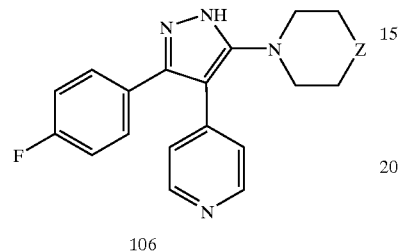

106

Scheme XXIV shows the synthesis of pyrazole 106. Dithioketene acetal 104 in a suitable solvent, such as toluene, is combined with a secondary amine, wherein Z is preferably S or —NCH$_3$, and heated to about 80–110° C. After the solution has been heated for several hours, any insoluble bis substituted material may be removed by filtration. Mono substituted product 105 is then reacted with hydrazine, or its hydrate (or a substituted hydrazine or its hydrate), in a solvent, such as tetrahydrofuran or ethanol, at ambient up to reflux temperatures, to form pyrazole 106.

SCHEME XXV

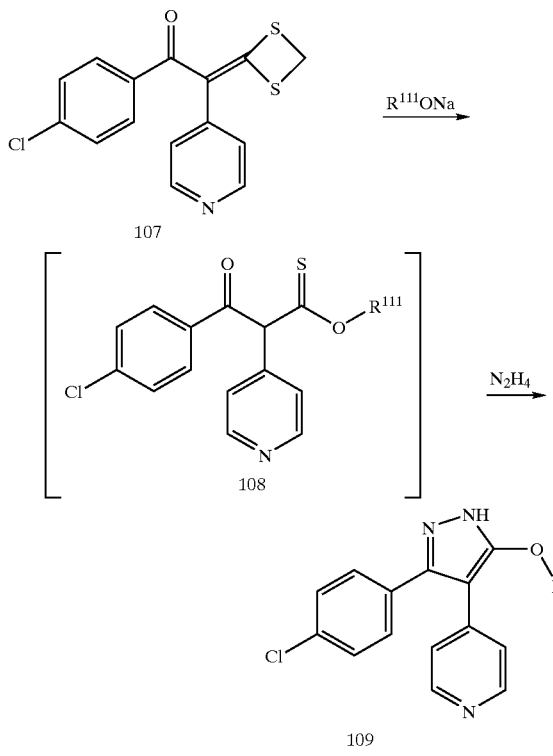

Scheme XXV shows the synthesis of pyrazole 109. Dithietane 107 is added to a solution of a sodium or potassium alkoxide in tetrahydrofuran. The alkoxide may be generated by treating an alcohol, in tetrahydrofuran, with a suitable base, such as sodium hydride, sodium hexamethyldisilazide, or potassium hexamethyldisilazide. The reaction mixture is stirred from 4 to 72 hours at room temperature. The resulting thionoester 108 is reacted with hydrazine, or its hydrate (or a substituted hydrazine or its hydrate), in ethanol, methanol, or tetrahydrofuran at room temperature for about 2–18 hours to generate pyrazole 109.

SCHEME XXVI

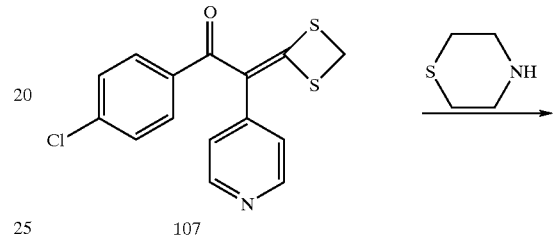

107

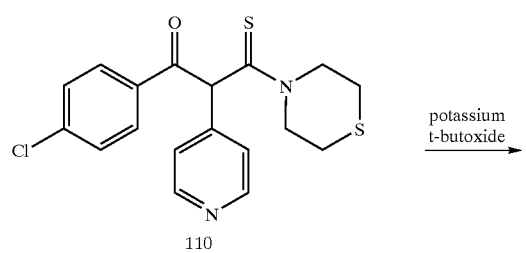

110

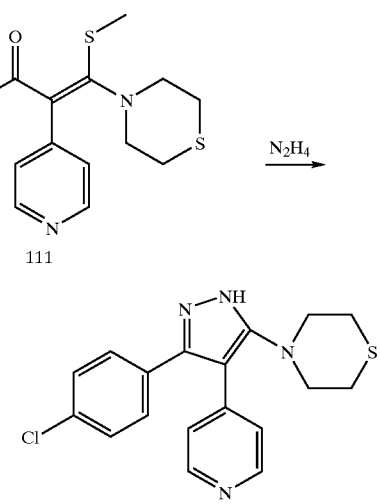

111

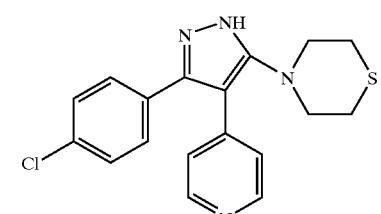

112

Scheme XXVI shows the synthesis of pyrazole 112. To dithietane 107 in a suitable solvent, such as toluene, is added an amine, such as thiomorpholine and heated to about 80–110° C., to form thioamide 110. Thioamide 110 may be isolated or used directly in the next reaction step. To thioamide 110 in tetrahydrofuran is added a suitable base, such as potassium t-butoxide, and the resulting thiol anion alkylated with iodomethane to form alkylated thioamide 111. Alkylated thioamide 111 can be cyclized with hydrazine (or substituted hydrazine), in a solvent, such as tetrahydrofuran or ethanol, to generate pyrazole 112.

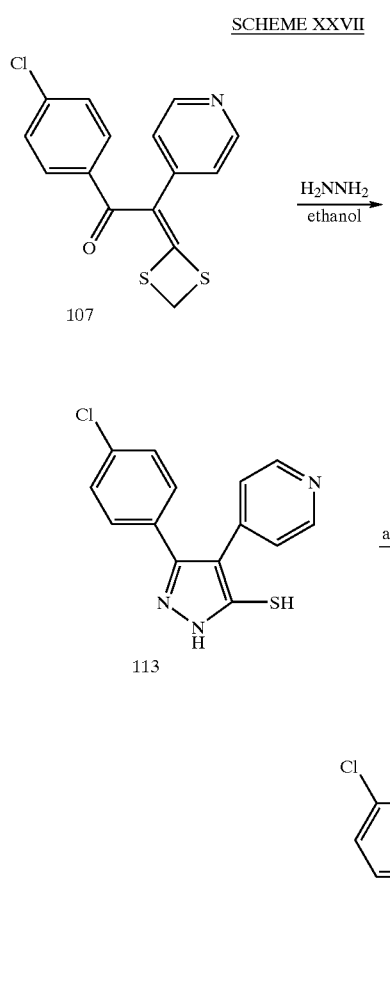

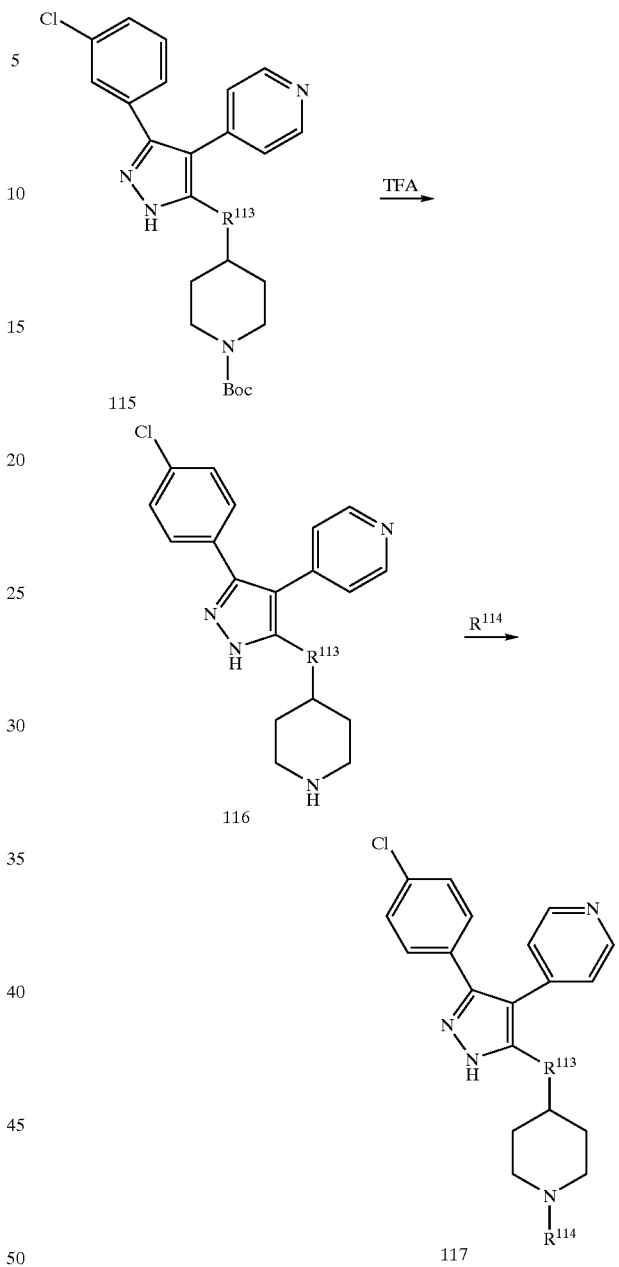

Scheme XXVII shows the synthesis of pyrazole 114. Dithietane 107 in a suitable solvent, such as tetrahydrofuran or ethanol, is reacted with hydrazine, or its hydrate (or a substituted hydrazine or its hydrate), at room temperature up to the reflux temperature of the solvent to generate thiopyrazole 113. The thiol group of thiopyrazole 113 may be alkylated with a variety of alkylating agents, such as alkyl halides or Michael acceptors, including, but not limited to, methyl chloroacetate, ethyl acrylate, and benzyl bromide, in the presence of a suitable base such as potassium carbonate, sodium ethoxide or triethylamine, in a solvent such as dimethylformamide or ethanol to generate pyrazole 114.

Scheme XXVIII shows the synthesis of pyrazole 117. Pyrazoles containing acid labile amine protecting groups, such as pyrazole 115, may be treated with a suitable acid catalyst, such as trifluoroacetic acid in dichloromethane or HCl in ethanol or dioxane to yield amine 116. Amine 116 can then be acylated or alkylated by methods known to one of ordinary skill in the art, such as reacting amine 116 with a reagent such as acetyl chloride or methyl iodide in the presence of a suitable base, such as potassium carbonate or triethylamine. In addition, N-methylation can be performed directly, using formaldehyde and formic acid in ethanol/water at reflux to give pyrazole 117 wherein $R^{114}$ is methyl.

SCHEME XXIX

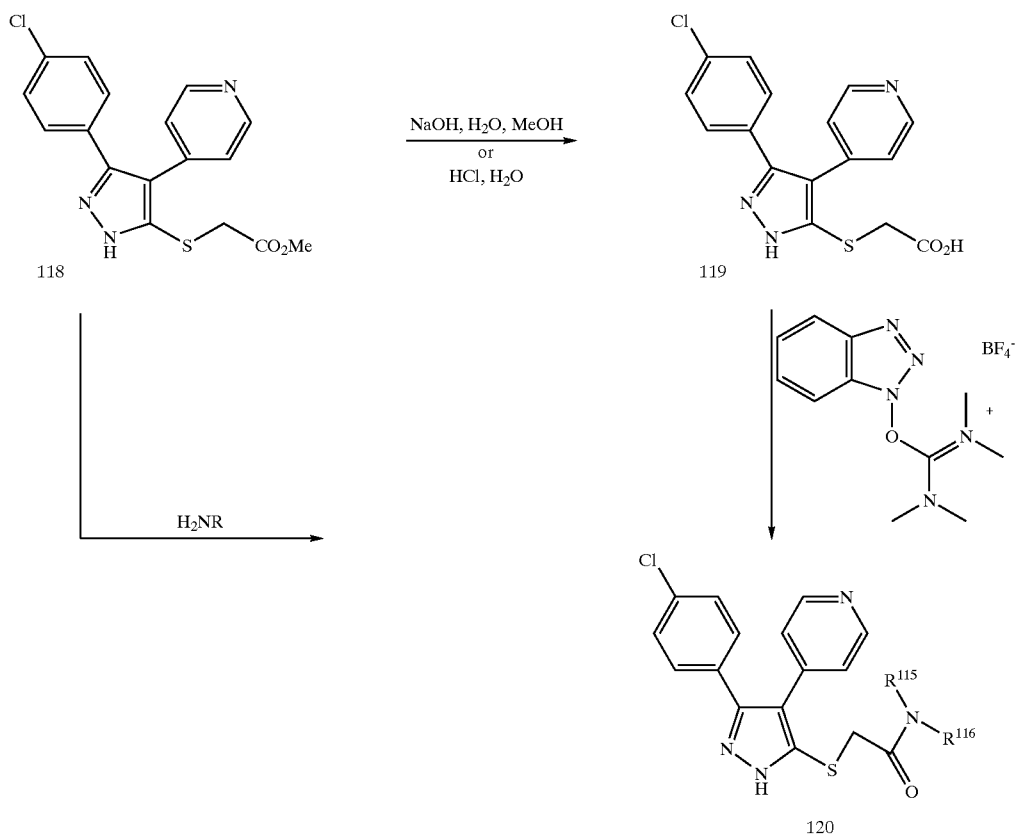

Scheme XXIX shows the synthesis of pyrazole 120. Pyrazoles containing base labile esters, such as pyrazole 118, may be treated with a suitable base, such as, sodium hydroxide to generate free acid 119. Acid 119 can then be aminated by methods known to one of ordinary skill in the art, such as treating acid 119 with a suitable coupling reagent, such as 1-(3-dimethylaminopropyl)3-ethylcarbodiimide hydrochloride or O-benzotriazole-1-yl-N,N,N',N'-tetramethyluronium tetrafluoroborate, with or without catalysts, such as 1-hydroxybenzotriazole or N-hydroxysuccinimide, and an appropriate amine. In addition, amidation can be performed directly, by treating the methyl ester with an appropriate amine, for example N-methylpiperazine, in a suitable solvent such as dimethylformamide or methanol, at a temperature from room temperature up to reflux to generate pyrazole 120.

The following examples contain detailed descriptions of the methods of preparation of compounds of Formulas I, IA, XI, X, XI, and XX. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. All compounds showed NMR spectra consistent with their assigned structures. In some cases, the assigned structures were confirmed by nuclear Overhauser effect (NOE) experiments.

The following abbreviations are used:
HCl—hydrochloric acid
MgSO$_4$—magnesium sulfate
Na$_2$SO$_4$—sodium sulfate
NaIO$_4$—sodium periodate
NaHSO$_3$—sodium bisulfite
NaOH—sodium hydroxide
KOH—potassium hydroxide
P$_2$O$_5$—phosphorus pentoxide
Me—methyl
Et—ethyl
MeOH—methanol
EtOH—ethanol
HOAc (or AcOH)—acetic acid
EtOAc—ethyl acetate
H$_2$O—water
H$_2$O$_2$—hydrogen peroxide
CH$_2$Cl$_2$—methylene chloride
K$_2$CO$_3$—potassium carbonate
KMnO$_4$—potassium permanganate
NaHMDS—sodium hexamethyldisilazide
DMF—dimethylformamide
EDC—1-(3-dimethylaminopropyl)3-ethylcarbodiimide hydrochloride
HOBT—1-hydroxybenzotriazole
mCPBA—3-chloroperoxybenzoic acid
Ts—tosyl
TMSCN—trimethylsilyl cyanide
Me$_2$NCOCl—N,N-dimethylcarbamoyl chloride
SEM-Cl—2-(trimethylsilyl)ethoxymethyl chloride
h—hour

119 hr—hour
min—minutes
THF—tetrahydrofuran
TLC—thin layer chromatography
DSC—differential scanning calorimetry
b.p.—boiling point
m.p.—melting point
eq—equivalent
RT—room temperature
DMF DMA—dimethylformamide dimethyl acetal
TBAF—tetrabutylammonium fluoride
Boc—tert.-butoxycarbonyl
DBU—diazabicycloundecane
DMF(OMe)$_2$—N,N-dimethylformamide dimethyl acetal
Et$_3$N—triethylamine
TMSCl—trimethylsilylchloride
TFA—trifluoroacetic acid
TBTU—O-benzotriazole-1-yl-N,N,N',N'-tetramethyluronium tetrafluoroborate
psi—pounds per square inch
ESHRMS—electron spray high resolution mass spectroscopy

EXAMPLE A-1

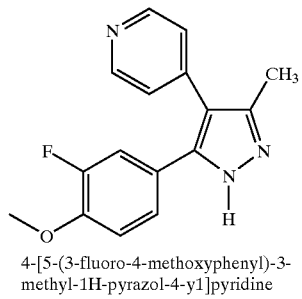

4-[5-(3-fluoro-4-methoxyphenyl)-3-methyl-1H-pyrazol-4-yl]pyridine

Step 1: Preparation of 4-(3-fluoro-4-methoxylphenyl)-3-pyridyl-3-butene-2-one

A solution of 4-pyridylacetone (1.0 g, 7.4 mmol), 3-fluoro-p-anisaldehyde (1.25 g, 8.1 mmol), and piperidine (0.13 g, 1.5 mmol) in toluene (50 ml) was heated to reflux. After 18 hours, the reaction was cooled to room temperature and the solvent was removed under reduced pressure. The crude product (3.0 g) was purified by column chromatography (silica gel, 65:35 ethyl acetate/hexane) to give 4-(3-fluoro-4-methoxylphenyl)-3-pyridyl-3-butene-2-one as a pale yellow solid (1.60 g, 80%).

Step 2: Preparation of 4-[5-(3-fluoro-4-methoxyphenyl)-3-methyl-1H-pyrazol-4-yl]pyridine To a solution of 3-pyridyl-4-(3-fluoro-4-methoxylphenyl)-3-butene-2-one (step 1) (0.99 g, 3.65 mmol) in acetic acid (25 ml), p-toluenesulfonyl hydrazide (0.68 g, 3.65 mol) was added. The reaction solution was heated to reflux for 6 hours. Acetic acid was removed by distillation from the reaction solution. The resulting residue was diluted with CH$_2$Cl$_2$ (150 ml), washed with H$_2$O (2×100 ml), dried (Na$_2$SO$_4$), filtered, and concentrated. The crude product (1.5 g) was purified by chromatography (silica gel, ethyl acetate) to give 4-[5-(3-fluoro-4-methoxyphenyl)-3-methyl-1H-pyrazol-4-yl]pyridine as a pale yellow solid (213 mg, 20.7%): Anal. Calc'd for C$_{16}$H$_{14}$N$_3$OF.0.1 H$_2$O: C, 67.41; H, 5.02; N, 14.74. Found: C, 67.37; H, 4.88; N, 14.35.

EXAMPLE A-2

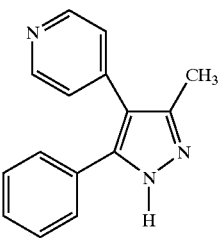

4-(3-methyl-5-phenyl-1H-pyrazol-4-yl)pyridine

Step 1: Preparation of 4-pyridylacetone

4-Pyridylacetone was prepared according to the method of Ippolito et al, U.S. Pat. No. 4,681,944.

Step 2: Preparation of 4-phenyl-3-(4-pyridyl)-3-butene-2-one

Using the procedure of Example A-1, step 1, 4-pyridylacetone (step 1) (1 g, 7.4 mmol) was condensed with benzaldehyde (790 mg, 7.4 mmol) in benzene (15 mL) containing piperidine (50 mg) at reflux. The desired 4-phenyl-3-(4-pyridyl)-3-butene-2-one (1.3 g, 78%) was obtained as a crystalline solid: m.p. 101–103° C. Anal. Calc'd for C$_{15}$H$_{13}$NO (223.28): C, 80.69; H, 5.87; N, 6.27. Found: C, 80.59; H, 5.79; N, 6.18.

Step 3: Preparation of 4-phenyl-3-(4-pyridyl)-3,4-epoxy-2-butanone

Using the procedure of Example A-1, step 2, a solution of 4-phenyl-3-(4-pyridyl)-3-butene-2-one (step 2) (1.25 g, 5.6 mmol) in methanol (20 ml) was treated with 30% aqueous hydrogen peroxide (1 ml) in the presence of sodium hydroxide (230 mg, 5.7 mmol). The crude product was purified by chromatography (silica gel, 1:1 ethyl acetate/hexane) to give 4-phenyl-3-(4-pyridyl)-3,4-epoxy-2-butanone (270 mg, 20%).

Step 4: Preparation of 4-(3-methyl-5-phenyl-1H-pyrazol-4-yl)pyridine

Using the procedure of Example A-1, step 3, a solution of 4-phenyl-3-(4-pyridyl)-3,4-epoxy-2-butanone (step 3) (250 mg, 1 mmol) in ethanol (15 ml) was treated with anhydrous hydrazine (50 mg, 1.5 mmol) and heated to reflux for 4 hours. The crude product was purified by chromatography (silica gel, 1:1 acetone/hexane). The product was recrystallized from ethyl acetate and hexane to give 4-(3-methyl-5-phenyl-1H-pyrazol-4-yl)pyridine (81 mg, 35%) as a crystalline solid: m. p. 212–214° C. Anal. Calc'd for C$_{15}$H$_{13}$N$_3$ (235.29): C, 76.57; H, 5.57; N, 17.86. Found: C, 76.49; H, 5.42; N, 17.39.

EXAMPLE A-3

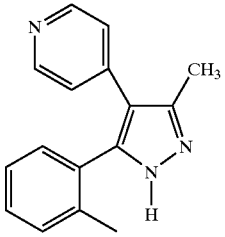

4-[5-methyl-3-(2-methylphenyl)-1H-pyrazol-4-yl]pyridine

Step 1: Preparation of 4-(2-methylphenyl)-3-(4-pyridyl)-3-butene-2-one

A solution of 4-pyrridylacetone (Example A-5, step 1) (0.75 g, 5.56 mmol), o-tolualdehyde (0.73 g, 5.56 mmol) and piperidine (100 mg) in toluene (50 ml) was heated to reflux. Water generated during the reaction was removed by a Dean-Stark trap. After heating at reflux for 5 hours, the reaction mixture was stirred at room temperature for 15 hours. The mixture was concentrated to an orange color oily residue. The crude ketone was purified by chromatography to give 4-(2-methylphenyl)-3-(4-pyridyl)-3-butene-2-one: Anal. Calc'd for $C_{16}H_{15}NO$ (237.30): C, 80.98; H, 6.37; N, 5.90. Found: C, 80.78; H, 6.61; N, 5.85.

Step 2: Preparation of 4-(2-methylphenyl)-3-(4-pyridyl)-3,4-eyoxy-2-butanone

To a solution of 4-(2-methylphenyl)-3-(4-pyridyl)-3-butene-2-one (step 1) (1.0 g, 4.2 mmol) in methyl alcohol (18 ml), a solution of $H_2O_2$ (30% by wt.) (0.95 g, 8.4 mmol) and sodium hydroxide (0.18 g 4.6 mmol) in water (4 ml) was added. The reaction was stirred at room temperature for 70 hours. After methyl alcohol was removed, water (25 ml) and ethyl acetate (100 ml) were added and the two phase mixture was stirred for 30 minutes. The layers were separated, and the aqueous layer was washed with ethyl acetate (100 ml). The combined organic layer was dried with $Na_2SO_4$, filtered and concentrated to give an oil. 4-(2-Methylphenyl)-3-(4-pyridyl)-3,4-epoxy-2-butanone was isolated from the oil residue by chromatography.

Step 3: Preparation of 4-[5-methyl-3-(2-methylphenyl)1H-pyrazol-4-yl]pyridine

A solution of 4-(2-methylphenyl)-3-(4-pyridyl)-3,4-epoxy-2-butanone (step 2) (0.11 g, 0.434 mmol) and hydrazine hydrate (0.043 g, 0.868 mmol) in ethyl alcohol (50 ml) was heated at reflux for 20 hours. The solvent was removed and the resulting residue was purified by chromatography to give 4-[5-methyl-3-(2-methylphenyl)-1 H-pyrazol-4-yl]pyridine: Anal. Calc'd for $C_{16}H_{15}N_3$ (249.32): C, 77.08; H, 6.06; N, 16.85. Found: C, 76.66; H, 5.91; N, 16.84.

EXAMPLE A-4

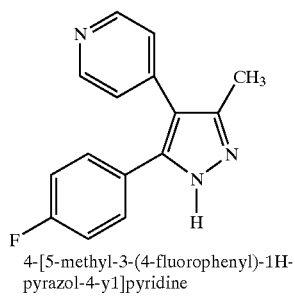

4-[5-methyl-3-(4-fluorophenyl)-1H-pyrazol-4-yl]pyridine

By following the method of Example A-3 and substituting p-fluorobenzaldehyde for o-tolualdehyde, the titled compound was prepared: Anal. Calc'd for $C_{15}H_{12}N_3F+0.1\ H_2O$: (249.32): C, 70.63; H, 4.82; N, 16.47. Found: C, 70.63; H, 4.78; N, 16.40.

EXAMPLE A-5

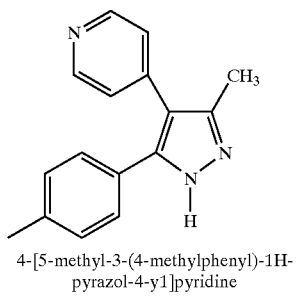

4-[5-methyl-3-(4-methylphenyl)-1H-pyrazol-4-yl]pyridine

By following the method of Example A-3 (with one minor modification: in Step 2, the preparation of the intermediate epoxide was accomplished at 0–10° C. for 1 hour, and the reaction was quenched by being partitioned between water, containing 2 eq. sodium bisulfite, and ethyl acetate) and substituting p-tolualdehyde for o-tolualdehyde, the titled product was isolated: Anal. Calc'd for $C_{16}H_{15}N_3$ (249.32): C, 77.08; H, 6.06; N, 16.85. Found: C, 76.97; H, 6.09; N, 16.90.

EXAMPLE A-6

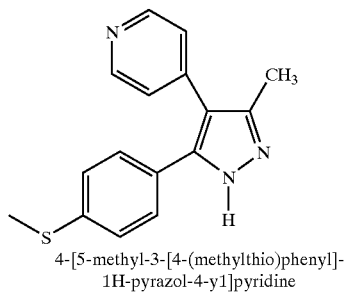

4-[5-methyl-3-[4-(methylthio)phenyl]-1H-pyrazol-4-yl]pyridine

By following the method of Example A-5 and substituting 4-(methylthio)benzaldehyde for p-tolualdehyde, the titled product was prepared: Anal. Calc'd for $C_{16}H_{15}H_3S$ (281.38): C, 68.30; H, 5.37; N, 14.93. Found: C, 68.34; H, 5.09; N, 14.78.

EXAMPLE A-7

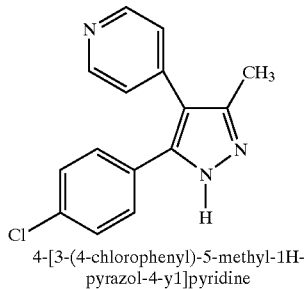

4-[3-(4-chlorophenyl)-5-methyl-1H-pyrazol-4-yl]pyridine

By following the method of Example A-5 and substituting p-chlorobenzaldehyde for p-tolualdehyde, the titled product was obtained. Anal. Calc'd for $C_{15}H_{12}H_3Cl$ (269.77): C, 66.79; H, 4.48; N, 15.58. Found: C, 66.43; H, 4.44; N, 15.78.

EXAMPLE A-8

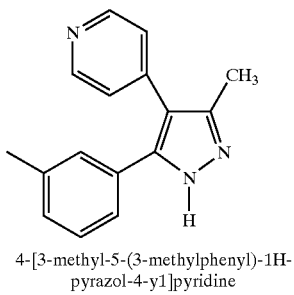

4-[3-methyl-5-(3-methylphenyl)-1H-pyrazol-4-yl]pyridine

By following the method of Example A-5 and substituting m-tolualdehyde for p-tolualdehyde, the titled product was obtained: Anal. Calc'd for $C_{16}H_{15}N_3+0.2H_2O$: C, 75.98; H, 6.14; N, 16.61. Found: C, 76.06; H, 6.05; N, 16.38.

EXAMPLE A-9

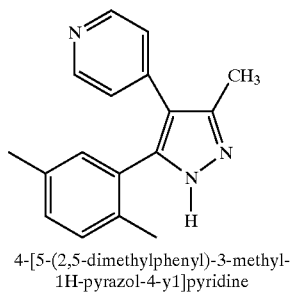

4-[5-(2,5-dimethylphenyl)-3-methyl-1H-pyrazol-4-yl]pyridine

By following the method of Example A-5 and substituting 2,5-dimethylbenzaldehyde for p-tolualdehyde, the titled product was obtained: Anal. Calc'd for $C_{17}H_{17}N_3+0.1H_2O$: C, 77.01; H, 6.54;N, 15.85. Found: C, 76.96; H, 6.81; N, 15.51.

EXAMPLE A-10

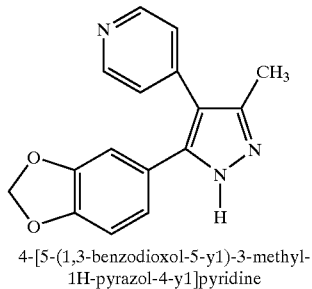

4-[5-(1,3-benzodioxol-5-yl)-3-methyl-1H-pyrazol-4-yl]pyridine

4-Pyridylacetone (1.5 g, 12 mmol), piperonal (1.6 g, 10.6 mmol), acetic acid (110 mg, 1.8 mmol), and piperidine (110 mg, 1.3 mmol) were dissolved in toluene (30 mL) and heated for 2 hours at reflux in a flask equipped with a Dean-Stark trap. The solution was cooled to room temperature, and ethyl acetate was added to precipitate a solid, which was collected on a filter plate (1.25 g). A sample (500 mg) of this solid was heated with p-toluensulfonyl hydrazide (348 mg, 1.81 mmol) in acetic acid (5 mL) at 80° C. for 1 hour. The reaction was heated to reflux for 1 hour. The reaction was cooled to room temperature and the solvent was evaporated. The residue was dissolved in ethyl acetate, washed with 5% aqueous potassium carbonate, and water. The organic layer was dried (MgSO$_4$), filtered and evaporated to obtain a yellow solid. This solid was triturated with methylene chloride, yielding 4-[5-(1,3-benzodioxol-5-yl)-3-methyl-1H-pyrazol-4-yl]pyridine which was collected on a filter plate (220 mg, 42% yield). Anal. Calc'd for $C_{16}H_{13}H_3O_2$: C, 68.81; H, 4.69; N, 15.04. Found: C, 68.02; H, 4.54; N, 14.76. MS (M$^+$H): 280 (base peak).

EXAMPLE A-11

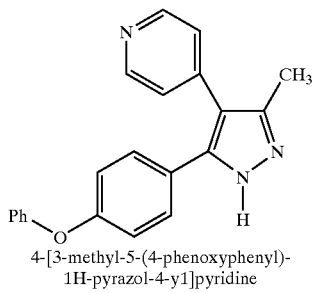

4-[3-methyl-5-(4-phenoxyphenyl)-1H-pyrazol-4-yl]pyridine

4-Pyridylacetone (1.5 g, 12 mmol), 4-phenoxybenzoldehyde 92.1 g, 10.6 mmol), acetic acid (110 mg, 1.8 mmol), and piperidine (110 mg, 1.3 mmol) were dissolved in toluene (30 mL) and heated for 2 hours at reflux in a flask equipped with a Dean-Stark trap. The solution was cooled to room temperature and ethyl acetate was added to precipitate a solid, which was collected on a filter plate. A sample (223 mg) of this solid was heated with p-toluensulfonyl hydrazide (348 mg, 1.81 mmol) in ethylene glycol with potassium hydroxide (77 mg) at 110° C. for 0.5 hour. The work up procedure was the same as that in Example A-10. 4-[3-Methyl-5-(4-phenoxyphenyl)-1H-pyrazol-4-yl]pyridine was obtained (100 mg, 66% yield): Anal. Calc'd for $C_{21}H_{17}H_3O+0.1\ H_2O$: C, 76.62; H, 5.27; N, 12.76. Found: C, 76.37; H, 5.19; N, 12.64. MS (M$^+$H): 328 (base peak).

EXAMPLE A-12

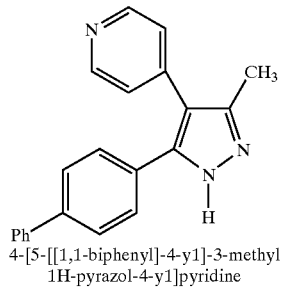

4-[5-[[1,1-biphenyl]-4-yl]-3-methyl 1H-pyrazol-4-yl]pyridine

The same procedure as for the preparation of Example A-10 was used, substituting 4-formylbiphenyl in place of piperonal, to give 4-[5-[(1,1'-biphenyl)-4-yl]-3-methyl-1H-pyrazol-4-yl]pyridine as a white solid: MS (M$^+$H): 312 (base peak).

EXAMPLE A-13

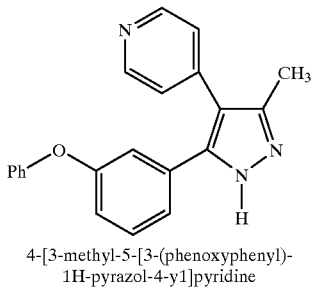

4-[3-methyl-5-[3-(phenoxyphenyl)-
1H-pyrazol-4-yl]pyridine

The same procedure for the preparation of Example A-10 was used, substituting 3-phenoxybenzaldehyde in place of piperonal, to give 4-[3-methyl-5-[3-(phenoxyphenyl)-1H-pyrazol-4-yl]pyridine as a white solid.

EXAMPLE A-14

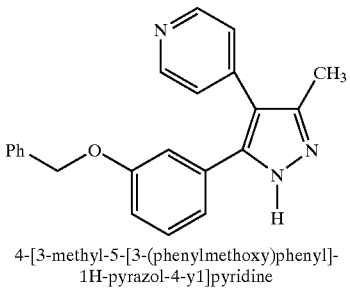

4-[3-methyl-5-[3-(phenylmethoxy)phenyl]-
1H-pyrazol-4-yl]pyridine

The same procedure for the preparation of Example A-10 was used, substituting 3-benzyloxybenzaldehyde in place of piperonal, to give 4-[3-methyl-5-[3-(phenylmethoxy)phenyl]-1H-pyrazol-4-yl]pyridine as a white solid: MS (M$^+$H): 342 (base peak).

EXAMPLE A-15

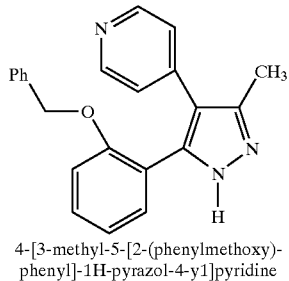

4-[3-methyl-5-[2-(phenylmethoxy)-
phenyl]-1H-pyrazol-4-yl]pyridine

The same procedure for the preparation of Example A-10 was used, substituting 2-benzyloxybenzaldehyde in place of piperonal, to give 4-[3-methyl-5-[2-(phenylmethyloxy)phenyl]-1H-pyrazol-4-yl]pyridine. MS (M$^+$H): 342 (base peak).

EXAMPLE A-16

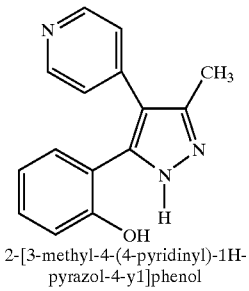

2-[3-methyl-4-(4-pyridinyl)-1H-
pyrazol-4-yl]phenol

The same procedure for the preparation of Example A-10 was used, substituting 2-hydroxybenzaldehyde in place of piperonal, to give 2-[3-methyl-4-(4-pyridinyl)-1H-pyrazol-4-yl]phenol: MS (M$^+$H): 252 (base peak).

EXAMPLE A-17

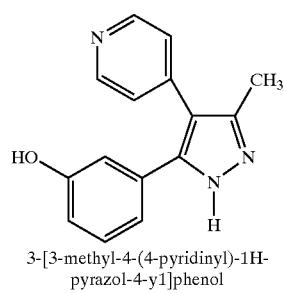

3-[3-methyl-4-(4-pyridinyl)-1H-
pyrazol-4-yl]phenol

The same procedure for the preparation of Example was used, substituting 3-hydroxybenzaldehyde in place of piperonal, to give 3-[3-methyl-4-(4-pyridinyl)-1H-pyrazol-4-yl]phenol: MS (M$^+$H): 252 (base peak).

EXAMPLE A-18

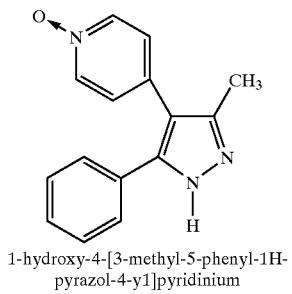

1-hydroxy-4-[3-methyl-5-phenyl-1H-
pyrazol-4-yl]pyridinium

To a solution of 4-(3-methyl-5-phenyl-1H-pyrazol-4-yl)pyridine (Example A-2) (2.06 g, 8.76 mmol) in a mixture of CH$_2$Cl$_2$ (10 mL) and MeOH (20 mL), was added 3-chloroperoxybenzoic acid (57~86%) (2.65 g, 8.76 mmol). The reaction was stirred at room temperature for 2 h, quenched with K$_2$CO$_3$ solution (25%, 15 mL), and concentrated. The resulting residue was partitioned between EtOAc (2.0 L) and H$_2$O (500 mL). The organic layer was separated, washed with H$_2$O (500 mL), dried over MgSO$_4$, filtered and concentrated to give 1-hydroxy-4-[3-methyl-5-phenyl-1H-pyrazol-4-yl]pyridinium (1.12 g, 54.5%): MS (M+H): 252 (base peak).

EXAMPLE A-19

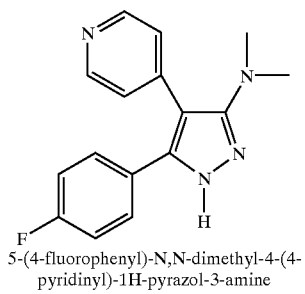

5-(4-fluorophenyl)-N,N-dimethyl-4-(4-pyridinyl)-1H-pyrazol-3-amine

Step 1: Preparation of 1-fluoro-4-(4'-pyridylacetyl)benzene

To a solution of sodium bis(trimethylsilyl)amide (200 mL, 1.0 M in THF) at 0° C. was added a solution of 4-picoline (18.6 g, 0.20 mol) in dry THF (200 mL) over 30 minutes. The reaction mixture was stirred at 0–10° C. for another 30 minutes, then was added to a solution of ethyl 4-fluorobenzoate (16.8 g, 0.10 mol) in dry THF (200 mL) at such a rate that the internal temperature didn't exceed 15° C. After the addition, the resulting yellow suspension was stirred at room temperature for 3 hours. Water (600 mL) was added and the aqueous phase was extracted with ethyl acetate (3×200 mL). The combined organic layers were washed with brine, dried over magnesium sulfate and filtered. The filtrate was concentrated in vacuo to give 1-fluoro-4-(4'-pyridylacetyl)benzene (19.9 g, 92%) as an oil which solidified upon standing: m.p.: 90–91° C.; Anal. Calc'd for $C_{13}H_{10}FNO$: C, 72.55; H, 4.68; N, 6.51. Found: C, 72.07; H, 4.66; N, 6.62.

Step 2: Preparation of 1-fluoro-4-(4'-pyridylbromoacetyl)benzene

To a solution of 1-fluoro-4-(4'-pyridylacetyl)benzene (step 1) (10.0 g, 0.046 mol) in acetic acid (200 mL) was added a solution of bromine (8.2 g, 0.052 mol) in acetic acid (20 mL) dropwise. The reaction mixture was stirred at room temperature overnight. After the solvent was removed, the residue was triturated with ethyl acetate. A yellow solid formed, which was filtered and air-dried to give 1-fluoro-4-(4'-pyridylbromacetyl)benzene (14.5 g). The compound was used in next step without further purification.

Step 3: Preparation of 5-(4-fluorophenyl)-N,N-dimethyl-4-(4-pyridinyl)-1H-pyrazol-3-amine A mixture of 1-fluoro-4-(4'-pyridylbromacetyl)-benzene (step 2) (3.8 g, 0.01 mol) and 4,4-dimethylamino-3-thiosemicarbazide (1.2 g, 0.01 mol) in ethanol (10 mL) was heated at reflux for 30 minutes. The dark green solution was cooled and poured into water (100 mL). The aqueous phase was extracted with methylene chloride (100 mL). The combined organic layers were washed with brine, dried over magnesium sulfate, filtered, and concentrated. The resulting residue was purified by chromatography (silica gel, ethyl acetate) to give 0.3 g 5-(4-fluorophenyl)-N,N-dimethyl-4-(4-pyridinyl)-1H-pyrazol-3-amine (0.3 g, 11%) as a light yellow solid: m.p.: 245–247° C. Anal. Calc'd for $C_{16}H_{15}FN_4$: C, 68.07; H, 5.36; N, 19.84. Found: C, 68.00; H, 5.37; N, 19.61.

EXAMPLE A-20

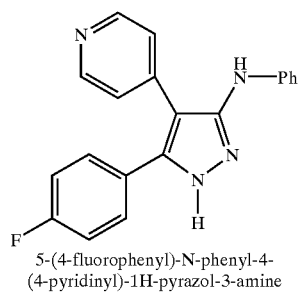

5-(4-fluorophenyl)-N-phenyl-4-(4-pyridinyl)-1H-pyrazol-3-amine 5-(4-Fluorophenyl)-N-phenyl-4-(4-pyridinyl)-1H-pyrazol-3-amine was prepared by the same procedure as described for Example A-19: m.p. 218–219° C. Anal. Calc'd for $C_{20}H_{15}FN_4$+0.1 $H_2O$: C, 72.33; H, 4.61; N, 16.87. Found: C, 72.16; H, 4.56; N, 16.77.

EXAMPLE A-21

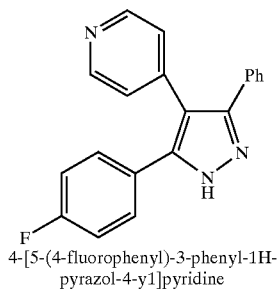

4-[5-(4-fluorophenyl)-3-phenyl-1H-pyrazol-4-yl]pyridine

Step 1: Preparation of 1-fluoro-4-(4Õ-pyridylacetyl)benzene N-benzoylhydrazone

To a solution of benzoic hydrazide (1.36 g, 0.01 mol) in THF (20 mL) was added 1-fluoro-4-(4'-pyridylacetyl)benzene (2.15 g, 0.011 mol) in one portion followed by a drop of conc. HCl. The reaction mixture was stirred at room temperature overnight. There was white precipitate formed, which was filtered, washed with ether and air-dried to give 1-fluoro-4-(4'-pyridylacetyl)benzene N-benzoylhydrazone (2.90 g, 79%) as a mixture of cis and trans (ratio, 1:9) isomers.

Step 2: Preparation of 4-[5-(4-fluorophenyl)-3-phenyl-1H-pyrazol-4-yl]pyridine

1-Fluoro-4-(4'-pyridylacetyl)benzene N-benzoylhydrazone (step 1) (0.50 g, 1.5 mmol) was heated at 180° C. under $N_2$ for 15 minutes, then cooled. The resulting solid was purified by chromatography (silica gel, 1:1 ethyl acetate/hexane) to give 4-[5-(4-fluorophenyl)-3-phenyl-1H-pyrazol-4-yl]pyridine (0.25 g, 53%) as a pale yellow solid: m.p.: 265–267° C. Anal. Calc'd for $C_{20}H_{14}FN_3$+0.25 $H_2O$: C, 75.10; H. 4.57; N, 13.14. Found: C, 74.98; H, 4.49; N, 12.87.

EXAMPLE A-22

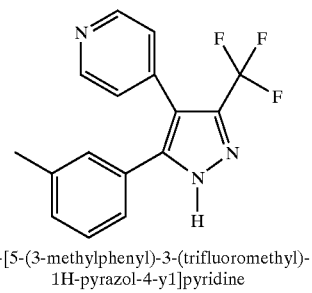

4-[5-(3-methylphenyl)-3-(trifluoromethyl)-
1H-pyrazol-4-yl]pyridine

Step 1: Preparation of 3-(4'-pyridylacetyl)toluene
3-(4'-Pyridylacetyl)toluene was prepared by the same method as described for Example A-19, step 1 in 70% yield.
Step 2: Preparation of trifluoroacetyl hydrazide
A mixture of ethyl trifluoroacetate (14.2 g, 0.10 mol) and hydrazine hydrate (5.54 g, 0.11 mol) in ethanol (25 mL) was heated at reflux for 6 hours. Solvent was removed and the resulting residue was dried in vacuum to give trifluoroacetyl hydrazide (12.3 g, 96%) as a clear oil which solidified upon standing.
Step 3: Preparation of 4-[5-(3-methylphenyl)-3-(trifluoromethyl)-1H-pyrazol-4-yl]pyridine
A mixture of 3-(4'-pyridylacetyl)toluene (2.11 g, 0.01 mol) and trifluoroacetyl hydrazide (step 2) (1.0 g, 0.01 mol) was heated at 200° C. under $N_2$ for 15 minutes. The crude residue was purified by chromatography (silica gel, 35:65 ethyl acetate/hexane) to give 4-[5-(3-methylphenyl)-3-(trifluoromethyl)-1H-pyrazol-4-yl]pyridine (0.56 g) as a white solid: m.p. 237–239° C. Anal. Calc'd for $C_{16}H_{12}F_3N_3$: C, 63.36; H, 3.99; N, 13.85. Found: C, 63.6; H, 4.00; N, 13.70.

EXAMPLE A-23

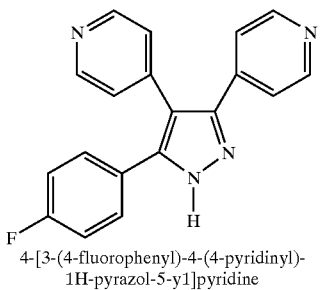

4-[3-(4-fluorophenyl)-4-(4-pyridinyl)-
1H-pyrazol-5-yl]pyridine

A mixture of 1-fluoro-4-(4'-pyridylacetyl)benzene (1.0 g, 4.6 mmol) and isonicotinic hydrazide (0.63 g, 4.6 mmol) in THF (25 mL) was heated to dissolution and then evaporated to dryness. The resulting solid was heated first to 140° C., which caused a phase change, and subsequently melted on further heating until 180° C. whereupon a solid crystallized out. The reaction was immediately cooled, diluted with 10% HCl (50 mL) and washed with chloroform. The aqueous layer was neutralized with bicarbonate and a tan colored solid was precipitated out. The solid was purified by treatment with activated carbon (Darco®) in boiling MeOH (100 mL), followed by filtration and concentration, to give 4-[3-(4-fluorophenyl)-4-(4-pyridinyl)-1H-pyrazol-5-yl]pyridine (1.05 g, 69%) as a shiny tan solid: m.p. 304° C. (DSC). Mass (MH$^+$) 137 (100%). Anal. Calc'd for $C_{19}H_{13}N_4F.1/4H_2O$: C, 71.13; H, 4.24; N, 17.46. Found: C, 70.88; H, 3.87; N, 17.38.

EXAMPLE A-24

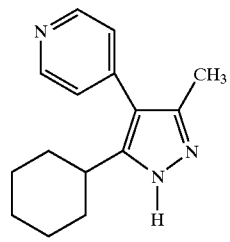

4-(5-cyclohexyl)-3-methyl-1H-pyrazol-4-yl)pyridine

Step 1: Preparation of 4-cyclohexyl-3-pyridyl-3-butene-2-one

4-Cyclohexyl-3-pyridyl-3-butene-2-one was prepared by the method of Example A-1, step 1 by replacing of 3-fluoro-p-anisaldehyde with cyclohexanecarboxaldehyde.

Step 2: Preparation of 4-(-cyclohexyl)-3-methyl-1H-pyrazol-4-yl)pyridine 4-(5-Cyclohexyl)-3-methyl-1H-pyrazol-4-yl)pyridine was prepared by the method for Example A-1, step 2, by replacing 4-(3-fluoro-4-methoxylphenyl)-3-pyridyl-3-butene-2-one with 4-cyclohexyl-3-pyridyl-3-butene-2-one (step 1): Anal. Calc'd for $C_{15}H_{19}H_3$:C, 73.56; Ha 7.98; N. 17.16. Found: C, 73.72; H. 7.91; N. 19.98.

EXAMPLE A-25

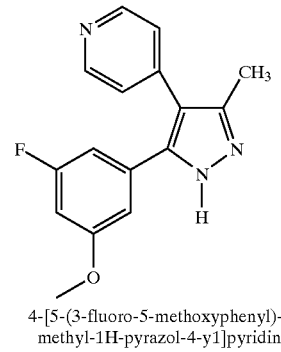

4-[5-(3-fluoro-5-methoxyphenyl)-3-
methyl-1H-pyrazol-4-yl]pyridine

4-{5-(3-Fluoro-5-methoxyphenyl)-3-methyl-3-methyl-1H-pyrazol-4-yl}pyridine was prepared by the method of Example A-1, steps 1 and 2 by replacing 3-fluoro-p-anisaldehyde with 3-fluoro-m-anisaldehyde: Anal. Calc'd for $C_{16}H_{14}N_3OF$: C, 67.83; H, 4.98; N, 14.83. Found: C, 67.68, H, 4.92; N, 14.92.

The following examples (No 26–55) listed in Table 1 were prepared by the procedures described above:

TABLE 1

| No A- | R¹ | R² | R³ | R⁴ |
|---|---|---|---|---|
| 26 | H | -CH₂-CH(-)-CH₂-CH₃ | 4-pyridyl | 3-methylphenyl |
| 27 | H | -CH₃ | 4-pyridyl | phenyl |
| 28 | H | 3-methylphenyl | 4-pyridyl | 3-methylphenyl |
| 29 | H | 2-(trifluoromethyl)phenyl | 4-pyridyl | -CH₃ |
| 30 | H | -CH₃ | 4-pyridyl | 2-chlorophenyl |
| 31 | H | -CH₃ | 4-pyridyl | 2,4-dimethylphenyl |
| 32 | -CH₃ | -CH₃ | 4-pyridyl | 4-chlorophenyl |
| 33 | H | -CH₃ | 4-pyridyl | 2-methyl-3-fluorophenyl |
| 34 | H | -CH₃ | 4-pyridyl | 3,5-dimethylphenyl |
| 35 | H | -CH₃ | 4-pyridyl | 3,4-dimethoxyphenyl |

TABLE 1-continued

| 36 | H | sec-butyl (CH(CH3)CH2CH3-like: -CH2-CH(CH3)-CH2-) | 4-pyridyl | 3-nitrophenyl |
| 37 | H | -CH3 | 4-pyridyl | 4-(N,N-dimethylamino)phenyl |
| 38 | H | chroman-6-yl | 4-pyridyl | -CH3 |
| 39 | H | 4-bromophenyl | 4-pyridyl | -CH3 |
| 40 | H | 2-fluorophenyl | 4-pyridyl | -CH3 |
| 41 | H | -CH3 | 4-pyridyl | 3-fluorophenyl |
| 42 | H | -CH3 | 4-pyridyl | 3-trifluoromethylphenyl |
| 43 | H | -CH2CH3 | 4-pyridyl | phenyl |
| 44 | H | -CH3 | 4-pyridyl | 3-methoxyphenyl |
| 45 | H | -CH2CH3 | 4-pyridyl | 3-methylphenyl |

TABLE 1-continued
| 46 | H | 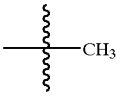 | 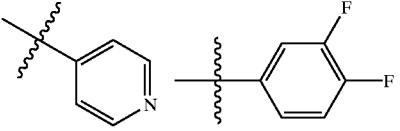 | 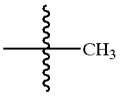 |
| 47 | H | 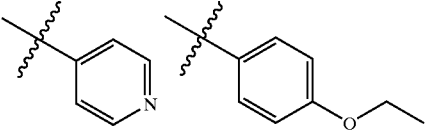 | 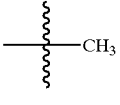 | 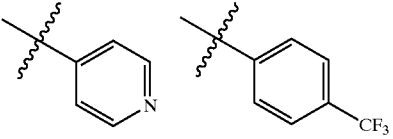 |
| 48 | H | 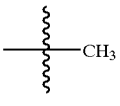 | 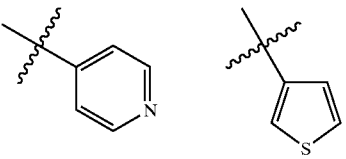 | 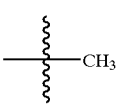 |
| 49 | H | 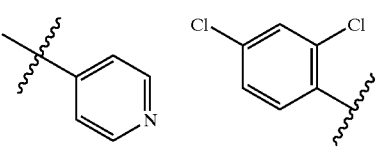 | 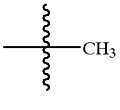 | 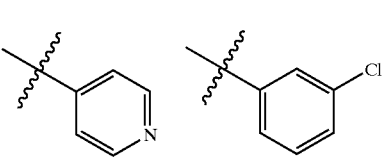 |
| 50 | H | 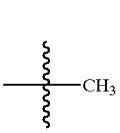 | 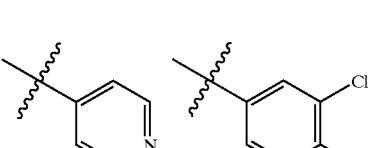 | 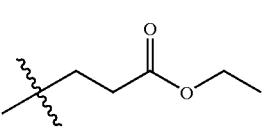 |
| 51 | H | | | |
| 52 | H | | | |
| 53 | H | 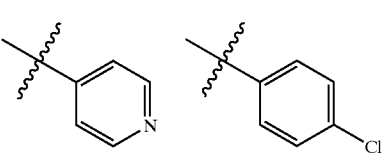 | | |

TABLE 1-continued

| 54 | —C(CH₃)— | 4-fluorophenyl | 4-pyridyl | H |
| 55 | H | 4-fluorophenyl | 4-pyridyl | H |

| No A- | m. p. or DSC(° C.) | Anal. Calc'd Formula | Anal. Calc'd (calcd/found) C | H | N |
|---|---|---|---|---|---|
| 26 | 185–186 | $C_{18}H_{19}N_3$ | 77.95/77.51 | 6.90/6.93 | 15.15/14.73 |
| 27 | 142–144 | $C_{16}H_{15}N_3$ | 75.71/75.69 | 6.16/6.11 | 16.55/16.49 |
| 28 | 240–242 | $C_{22}H_{19}N_3 \cdot 0.25H_2O$ | 80.09/79.74 | 5.96/5.90 | 12.74/13.01 |
| 29 | 228.8 | $C_{16}H_{12}N_3F_3$ | 63.36/63.28 | 3.99/3.73 | 13.85/13.69 |
| 30 | 189.6 | $C_{15}H_{12}N_3Cl \cdot 0.15H_2O$ | 66.13/65.98 | 4.55/4.31 | 15.42/15.74 |
| 31 | 171.6 | $C_{17}H_{17}N_3 \cdot 0.2H_2O$ | 76.49/76.69 | 6.57/6.53 | 15.74/15.61 |
| 32 | 88.6 | $C_{16}H_{14}N_3Cl$ | 67.72/67.35 | 4.97/5.29 | 14.81/15.02 |
| 33 | 188.8 | $C_{16}H_{14}N_3F$ | 71.89/71.72 | 5.28/5.45 | 15.72/15.77 |
| 34 | 215.7 | $C_{17}H_{17}N_3$ | 77.54/77.24 | 6.51/6.80 | 15.96/15.71 |
| 35 | 201.4 | $C_{17}H_{17}N_3O_2 \cdot 0.25H_2O$ | 68.10/67.92 | 5.88/5.65 | 14.01/13.65 |
| 36 | 210.7 | $C_{15}H_{12}N_4O_2 \cdot 0.25H_2O$ | 63.26/63.59 | 4.42/4.39 | 19.67/19.31 |
| 37 | 252.5 | $C_{17}H_{18}N_4$ | 73.35/72.61 | 6.52/6.79 | 20.13/19.59 |
| 38 | 196.3 | $C_{17}H_{15}N_3O$ | 73.63/73.43 | 5.45/5.46 | 15.15/15.19 |
| 39 | 252.8 | $C_{15}H_{12}N_3Br$ | 57.34/57.09 | 3.85/3.79 | 13.37/13.06 |
| 40 | 198.5 | $C_{15}H_{12}N_3F$ | 71.13/71.23 | 4.78/5.01 | 16.59/16.76 |
| 41 | 225.6 | $C_{15}H_{12}N_3F_3$ | 71.13/70.74 | 4.78/4.66 | 16.59/16.44 |
| 42 | 219.5 | $C_{16}H_{12}F_3N_3$ | 63.36/63.19 | 3.99/4.07 | 13.85/13.38 |
| 43 | 227.7 | $C_{16}H_{15}N_3 \cdot 0.1H_2O$ | 76.53/76.53 | 6.10/6.20 | 16.73/16.49 |
| 44 | 175.6 | $C_{16}H_{15}N_3O \cdot 0.15H_2O$ | 71.70/71.92 | 5.75/5.76 | 15.68/15.29 |
| 45 | — | $C_{17}H_{19}N_3$ | 77.54/77.13 | 6.51/6.28 | 15.96/15.69 |
| 46 | 412.1 | $C_{15}H_{11}N_3F_2$ | 66.42/66.12 | 4.09/3.86 | 15.49/15.25 |
| 47 | 168.5 | $C_{17}H_{17}N_3O \cdot 0.15H_2O$ | 72.40/72.39 | 6.18/5.87 | 14.90/14.50 |
| 48 | 211.2 | $C_{16}H_{12}N_3F_3 \cdot 0.2H_2O$ | 62.62/62.64 | 4.07/4.06 | 13.69/13.35 |
| 49 | — | $C_{13}H_{11}N_3S$ | 64.71/64.44 | 4.59/4.58 | 17.41/17.27 |
| 50 | 189.2 | $C_{15}H_{11}N_3Cl_2$ | 59.23/59.22 | 3.65/3.24 | 13.81/13.81 |
| 51 | 211.7 | $C_{15}H_{12}N_3Cl \cdot 0.15H_2O$ | 66.13/66.33 | 4.55/4.62 | 15.42/15.05 |
| 52 | 219.8 | $C_{16}H_{14}N_3Cl$ | 64.11/63.85 | 4.71/4.69 | 14.02/13.93 |
| 53 | 163.4 | $C_{19}H_{17}N_3O_2Cl$ | 64.32/63.98 | 4.83/5.08 | 11.84/11.80 |
| 54 | — | $C_{15}H_{12}N_3F \cdot 0.2H_2O$ | 70.15/70.18 | 4.86/4.60 | 16.35/16.47 |
| 55 | — | $C_{14}H_{10}N_3F$ | 70.28/69.97 | 4.21/3.84 | 17.56/17.53 |

The following pyrazoles could be prepared by the procedures described above:

EXAMPLE A-56

5-[5-(3-chlorophenyl)-3-methyl-1H-pyrazol-4-yl]pyrimidin-2-amine;

EXAMPLE A-57

5-[3-methyl-5-(3-methylphenyl)-1H-pyrazol-4-yl]pyrimidin-2-amine;

EXAMPLE A-58

5-[3-methyl-5-(2-methylphenyl)-1H-pyrazol-4-yl]pyrimidin-2-amine;

EXAMPLE A-59

5-[5-(4-chlorophenyl)-3-methyl-1H-pyrazol-4-yl]pyrimidin-2-amine;

EXAMPLE A-60

5-[5-(4-fluorophenyl)-3-methyl-1H-pyrazol-4-yl]pyrimidin-2-amine;

EXAMPLE A-61

5-[5-(4-methoxyphenyl)-3-methyl-1H-pyrazol-4-yl]pyrimidin-2-amine;

EXAMPLE A-62

5-[5-(3-chlorophenyl)-3-methyl-1H-pyrazol-4-yl]pyridin-2-amine;

EXAMPLE A-63

4-[5-(3-chlorophenyl)-3-methyl-1H-pyrazol-4-yl]pyridin-2-amine;

EXAMPLE A-64

4-[5-(3-methylphenyl)-3-methyl-1H-pyrazol-4-yl]pyridin-2-amine;

EXAMPLE A-65

4-[5-(2-methylphenyl)-3-methyl-1H-pyrazol-4-yl]pyridin-2-amine;

EXAMPLE A-66
4-[5-(4-chlorophenyl)-3-methyl-1H-pyrazol-4-yl]
pyridin-2-amine;
EXAMPLE A-67
4-[5-(4-fluorophenyl)-3-methyl-1H-pyrazol-4-yl]
pyridin-2-amine;
EXAMPLE A-68
4-[5-(4-methoxyphenyl)-3-methyl-1H-pyrazol-4-yl]
pyridin-2-amine;
EXAMPLE A-69
5-[5-(3-chlorophenyl)-3-methyl-1H-pyrazol-4-yl]-2-
methoxypyridine;
EXAMPLE A-70
2-methoxy-5-[3-methyl-5-(3-methylphenyl)-1H-
pyrazol-4-yl]pyridine;
EXAMPLE A-71
2-methoxy-5-[5-(4-methoxyphenyl)-3-methyl-1H-
pyrazol-4-yl]pyridine;
EXAMPLE A-72
4-[5-(3-chlorophenyl)-3-methyl-1H-pyrazol-4-yl]-2-
methoxypyridine;
EXAMPLE A-73
2-methoxy-4-[3-methyl-5-(3-methylphenyl)-1H-
pyrazol-4-yl]pyridine;
EXAMPLE A-74
2-methoxy-4-[3-methyl-5-(2-methylphenyl)-1H-
pyrazol-4-yl]pyridine;
EXAMPLE A-75
4-[5-(4-chlorophenyl)-3-methyl-1H-pyrazol-4-yl]-2-
methoxypyridine;
EXAMPLE A-76
4-[5-(4-fluorophenyl)-3-methyl-1H-pyrazol-4-yl]-2-
methoxypyridine;
EXAMPLE A-77
2-methoxy-4-[3-methyl-5-(4-methylphenyl)-1H-
pyrazol-4-yl]pyridine;
EXAMPLE A-78
5-[5-(3-chlorophenyl)-3-methyl-1H-pyrazol-4-yl]
pyridin-2-ol;
EXAMPLE A-79
4-[5-(3-chlorophenyl)-3-methyl-1H-pyrazol-4-yl]
pyridin-2-ol;
EXAMPLE A-80
4-[5-(3-methylphenyl)-3-methyl-1H-pyrazol-4-yl]
pyridin-2-ol;
EXAMPLE A-81
4-[5-(2-methylphenyl)-3-methyl-1H-pyrazol-4-yl]
pyridin-2-ol;
EXAMPLE A-82
4-[5-(4-chlorophenyl)-3-methyl-1H-pyrazol-4-yl]
pyridin-2-ol;
EXAMPLE A-83
4-[5-(4-fluorophenyl)-3-methyl-1H-pyrazol-4-yl]
pyridin-2-ol;
EXAMPLE A-84
4-[5-(4-methoxyphenyl)-3-methyl-1H-pyrazol-4-yl]
pyridin-2-ol;
EXAMPLE A-85
5-[5-(3-chlorophenyl)-3-methyl-1H-pyrazol-4-yl]
pyridine-2-methanamine;
EXAMPLE A-86
4-[5-(3-chlorophenyl)-3-methyl-1H-pyrazol-4-yl]
pyridine-2-methanamine;
EXAMPLE A-87
4-[5-(3-methylphenyl)-3-methyl-1H-pyrazol-4-yl]
pyridine-2-methanamine;
EXAMPLE A-88
4-[5-(2-methylphenyl)-3-methyl-1H-pyrazol-4-yl]
pyridine-2-methanamine;
EXAMPLE A-89
4-[5-(4-chlorophenyl)-3-methyl-1H-pyrazol-4-yl]
pyridine-2-methanamine;
EXAMPLE A-90
4-[5-(4-fluorophenyl)-3-methyl-1H-pyrazol-4-yl]
pyridine-2-methanamine;
EXAMPLE A-91
4-[5-(4-methoxyphenyl)-3-methyl-1H-pyrazol-4-yl)
pyridine-2-methanamine;
EXAMPLE A-92
5-[5-(3-chlorophenyl)-3-methyl-1H-pyrazol-4-yl]
pyridine-2-carboxamide;
EXAMPLE A-93
4-[5-(3-chlorophenyl)-3-methyl-1H-pyrazol-4-yl]
pyridine-2-carboxamide;
EXAMPLE A-94
4-[5-(3-methylphenyl)-3-methyl-1H-pyrazol-4-yl]
pyridine-2-carboxamide;
EXAMPLE A-95
4-[5-(2-methylphenyl)-3-methyl-1H-pyrazol-4-yl]
pyridine-2-carboxamide;
EXAMPLE A-96
4-[5-(4-chlorophenyl)-3-methyl-1H-pyrazol-4-yl)
pyridine-2-carboxamide;
EXAMPLE A-97
4-[5-(4-fluorophenyl)-3-methyl-1H-pyrazol-4-yl]
pyridine-2-carboxamide;
EXAMPLE A-98
4-[5-(4-methoxyphenyl)-3-methyl-1H-pyrazol-4-yl]
pyridine-2-carboxamide;
EXAMPLE A-99
4-[5-(3-fluoro-4-methoxyphenyl)-3-methyl-1H-
pyrazol-4-yl]pyridine;
EXAMPLE A-100
4-[5-(4-fluoro-3-methoxyphenyl)-3-methyl-1H-
pyrazol-4-yl]pyridine;
EXAMPLE A-101
4-[5-(4-chloro-3-methoxyphenyl)-3-methyl-1H-
pyrazol-4-yl]pyridine;
EXAMPLE A-102
4-[5-(2,3-dihydrobenzofuran-6-yl)-3-methyl-1H-
pyrazol-4-yl]pyridine;
EXAMPLE A-103
4-[5-(benzofuran-6-yl)-3-methyl-1H-pyrazol-4-yl]
pyridine;
EXAMPLE A-104
4-[5-(3-fluoro-5-methoxyphenyl)-3-methyl-1H-
pyrazol-4-yl]pyridine;
EXAMPLE A-105
4-[5-(3-chloro-5-methoxyphenyl)-3-methyl-1H-
pyrazol-4-yl]pyridine;
EXAMPLE A-106
4-[5-(1-cyclohexyen-1-yl)-3-methyl-1H-pyrazol-4-
yl]pyridine;
EXAMPLE A-107
4-[5-(1,3-cyclohexadien-1-yl)-3-methyl-1H-pyrazol-
4-yl]pyridine;

EXAMPLE A-108

4-[5-(5,6-dihydro-2H-pyran-4-yl)-3-methyl-1H-pyrazol-4-yl]pyridine;

EXAMPLE A-109

4-(5-cyclohexyl-3-methyl-1H-pyrazol-4-yl)pyridine;

EXAMPLE A-110

4-[5-(4-methoxy-3-methylphenyl)-3-methyl-1H-pyrazol-4-yl]pyridine;

EXAMPLE A-111

4-[5-(3-methoxy-4-methylphenyl)-3-methyl-1H-pyrazol-4-yl]pyridine;

EXAMPLE A-112

4-[5-(3-methoxy-5-methylphenyl)-3-methyl-1H-pyrazol-4-yl]pyridine;

EXAMPLE A-113

4-[5-(3-furanyl)-3-methyl-1H-pyrazol-4-yl]pyridine;

EXAMPLE A-114

2-methyl-4-(3-methyl-5-phenyl-1H-pyrazol-4-yl)pyridine;

EXAMPLE A-115

2-methoxy-4-(3-methyl-5-phenyl-1H-pyrazol-4-yl)pyridine;

EXAMPLE A-116 methyl 4-(3-methyl-5-phenyl-1H-pyrazol-4-yl)pyridine-2-carboxylate;

EXAMPLE A-117

4-(3-methyl-5-phenyl-1H-pyrazol-4-yl)pyridine-2-carboxamide;

EXAMPLE A-118

1-[4-(3-methyl-5-phenyl-1H-pyrazol-4-yl)pyridin-2-yl]ethanone;

EXAMPLE A-119

N,N-dimethyl-4-(3-methyl-5-phenyl-1H-pyrazol-2-yl)pyridin-2-amine;

EXAMPLE A-120

3-methyl-4-(3-methyl-5-phenyl-1H-pyrazol-4-yl)pyridine;

EXAMPLE A-121

3-methoxy-4-(3-methyl-5-phenyl-1H-pyrazol-4-yl)pyridine;

EXAMPLE A-122 methyl 4-(3-methyl-5-phenyl-1H-pyrazol-4-yl)pyridine-3-carboxylate;

EXAMPLE A-123

4-(3-methyl-5-phenyl-1H-pyrazol-4-yl)pyridine-3-carboxamide;

EXAMPLE A-124

1-[4-(3-methyl-5-phenyl-1H-pyrazol-4-yl)pyridin-3-yl]ethanone;

EXAMPLE A-125

3-bromo-4-(3-methyl-5-phenyl-1H-pyrazol-4-yl)pyridine;

EXAMPLE A-126

N,N-dimethyl-4-(3-methyl-5-phenyl-1H-pyrazol-2-yl)pyridin-3-amine;

EXAMPLE A-127

2-methyl-4-(3-methyl-5-phenyl-1H-pyrazol-4-yl)pyrimidine;

EXAMPLE A-128

4-(3-methyl-5-phenyl-1H-pyrazol-4-yl)pyrimidine;

EXAMPLE A-129

2-methoxy-4-(3-methyl-5-phenyl-1H-pyrazol-4-yl)pyrimidine;

EXAMPLE A-130

4-(3-methyl-5-phenyl-1H-pyrazol-4-yl)pyrimidin-2-amine;

EXAMPLE A-131

N,N-dimethyl-4-(3-methyl-5-phenyl-1H-pyrazol-4-yl)pyrimidin-2-amine;

EXAMPLE A-132

4-(5,6-dihydro-2H-pyran-4-yl)-3-methyl-5-phenyl-1H-pyrazole;

EXAMPLE A-133

3-methyl-5-phenyl-4-(3-thienyl)-1H-pyrazole;

EXAMPLE A-134

4-(3-furanyl)-3-methyl-5-phenyl-1H-pyrazole;

EXAMPLE A-135

3-methyl-5-phenyl-4-(2-thienyl)-1H-pyrazole;

EXAMPLE A-136

4-(2-furanyl)-3-methyl-5-phenyl-1H-pyrazole;

EXAMPLE A-137

4-(3-isothiazolyl)-3-methyl-5-phenyl-1H-pyrazole;

EXAMPLE A-138

4-(3-isoxazolyl)-3-methyl-5-phenyl-1H-pyrazole;

EXAMPLE A-139

4-(5-isothiazolyl)-3-methyl-5-phenyl-1H-pyrazole;

EXAMPLE A-140

4-(5-isoxazolyl)-3-methyl-5-phenyl-1H-pyrazole;

EXAMPLE A-141

3-methyl-5-phenyl-4-(5-thiazolyl)-1H-pyrazole;

EXAMPLE A-142

3-methyl-4-(5-oxazolyl)-5-phenyl-1H-pyrazole;

EXAMPLE A-143

2-methyl-4-[3-(3-methylphenyl)-1H-pyrazol-4-yl]pyridine;

EXAMPLE A-144

4-(1-methyl-3-phenyl-1H-pyrazol-4-yl)pyridine;

EXAMPLE A-145

4-(3-phenyl-1H-pyrazol-4-yl)pyridine;

EXAMPLE A-146

2-methyl-4-(3-phenyl-1H-pyrazol-4-yl)pyridine;

EXAMPLE A-147

4-[3-(3-chlorophenyl)-1-methyl-pyrazol-4-yl]pyridine;

EXAMPLE A-148

4-[3-(4-chlorophenyl)-1-methyl-pyrazol-4-yl]pyridine;

EXAMPLE A-149

4-[3-(3-chlorophenyl)-1H-pyrazol-4-yl]pyridine;

EXAMPLE A-150

4-[3-(4-chlorophenyl)-1H-pyrazol-4-yl]pyridine;

EXAMPLE A-151

4-[3-(3-chlorophenyl)-1H-pyrazol-4-yl]-2-methylpyridine;

EXAMPLE A-152

4-[3-(3-fluorophenyl)-1-methyl-1H-pyrazol-4-yl]pyridine;

EXAMPLE A-153

4-[3-(3-fluorophenyl)-1H-pyrazol-4-yl]pyridine; and

EXAMPLE A-154

4-[3-(3-chlorophenyl)-1-methyl-pyrazol-4-yl]-2-methylpyridine.

The compounds of Examples A-155 through A-172 were synthesized in accordance with the chemistry described above (particularly Scheme II) and illustrated by many of the previously disclosed Examples by selection of the corresponding starting reagents:

EXAMPLE A-155

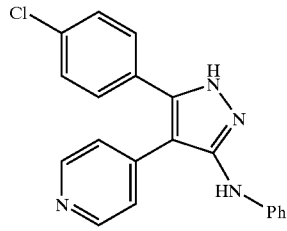

5-(4-chlorophenyl)-N-phenyl-4-(4-pyridinyl)-1H-pyrazol-3-amine: DSC 261° C. Anal. Calc'd for $C_{20}H_{15}ClN_4$+0.25 $H_2O$ (MW 351.32): C, 68.38, H. 4.30, N, 15.95. Found: C, 68.25, H, 4.41, N, 15.74.

EXAMPLE A-156

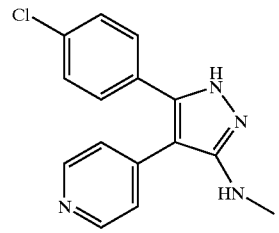

5-(4-chlorophenyl)-N-methyl-4-(4-pyridinyl)-1H-pyrazol-3-amine: DSC 260° C. Anal. Calc'd for $C_{15}H_{13}ClN_4$+0.125 $H_2O$ (MW 287.00): C, 62.77, H, 4.57, N, 19.52. Found: C, 62.78, H, 4.33, N, 19.22.

EXAMPLE A-157

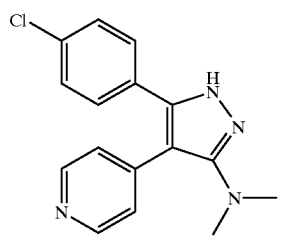

5-(4-chlorophenyl)-N,N-dimethyl-4-(4-pyridinyl)-1H-pyrazol-3-amine dihydrate: DSC 230° C. Anal. Calc'd for $C_{16}H_{15}ClN_4$+2 $H_2O$ (MW 334.81): C, 57.40, H, 4.52, N, 16.73. Found: C, 57.72, H, 4.85, N, 16.54.

EXAMPLE A-158

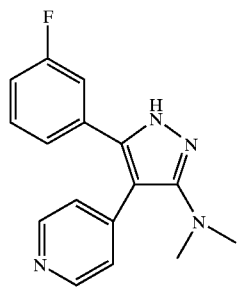

5-(3-fluorophenyl)-N,N-dimethyl-4-(4-pyridinyl)-1H-pyrazol-3-amine: DSC 227° C. Anal. Calc'd for $C_{16}H_{15}FN_4$+0.125 $H_2O$ (MW 284.57): C, 67.53, H, 5.31, N, 19.69. Found: C, 67.60, H, 5.20, N, 19.84.

EXAMPLE A-159

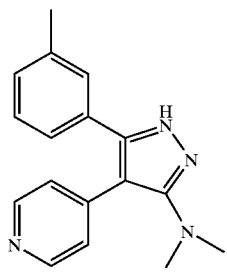

N,N-dimethyl-5-(3-methylphenyl)-4-(4-pyridinyl)-1H-pyrazol-3-amine: DSC 222° C. Anal. Calc'd for $C_{17}H_{18}N_4$+ 0.25 $H_2O$ (MW 282.86): C, 72.19, H, 6.41, N, 19.81. Found: C, 71.99, H, 6.46, N, 19.90.

EXAMPLE A-160

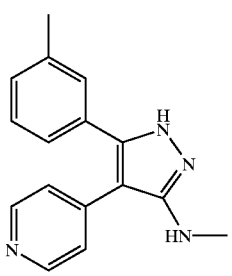

N-methyl-5-(3-methylphenyl)-4-(4-pyridinyl)-1H-pyrazol-3-amine: DSC 226° C. Anal. Calc'd for $C_{16}H_{16}N_4$+ 0.125 $H_2O$ (MW 266.58): C, 72.09, H, 6.05, N, 21.02. Found: C, 72.12, H, 6.12, N, 20.83.

EXAMPLE A-161

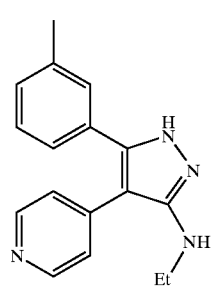

N-ethyl-5-(3-methylphenyl)-4-(4-pyridinyl)-1H-pyrazol-3-amine: DSC 227° C. Anal. Calc'd for $C_{17}H_{18}N_4$+0.125 $H_2O$ (MW 280.61): C, 72.77, H, 6.47, N, 19.97. Found: C, 72.63, H, 6.40, N, 19.73.

EXAMPLE A-162

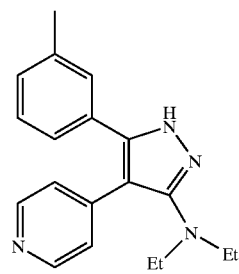

N,N-diethyl-5-(3-methylphenyl)-4-(4-pyridinyl)-1H-pyrazol-3-amine: DSC 234° C. Anal. Calc'd for $C_{19}H_{22}N_4$ (MW 306.41): C, 74.48, H, 7.24, N, 18.29. Found: C, 74.12, H, 7.18, N, 18.13.

EXAMPLE A-163

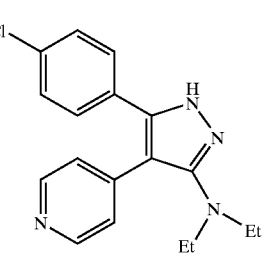

5-(4-chlorophenyl)-N,N-diethyl-4-(4-pyridinyl)-1H-pyrazol-3-amine: m.p. 260–261° C. Anal. Calc'd for $C_{18}H_{19}ClN_4$ (MW 326.83): C, 66.15, H, 5.86, N, 17.14. Found: C, 66.03, H, 5.72, N, 17.23.˙[

EXAMPLE A-164

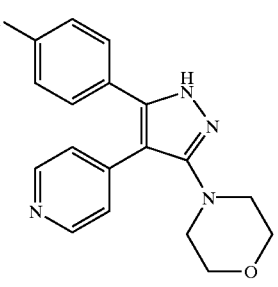

4-[5-(4-chlorophenyl)-4-(4-pyridinyl)-1H-pyrazol-3-yl] morpholine: DSC 279° C. Anal. Calc'd for $C_{18}H_{17}ClN_4O$+ 0.25 $H_2O$ (MW 345.32): C, 62.61, H, 4.96, N, 16.23. Found: C, 62.52, H, 4.77, N, 16.52.

EXAMPLE A-165

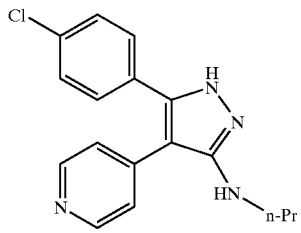

5-(4-chlorophenyl)-N-propyl-4-(4-pyridinyl)-1H-pyrazol-3-amine: DSC 244° C. Anal. Calc'd for $C_{17}H_{17}ClN_4+0.125\ H_2O$ (MW 315.06): C, 64.81, H, 5.44, N, 17.78. Found: C, 64.94, H, 5.43, N, 17.78.

EXAMPLE A-166

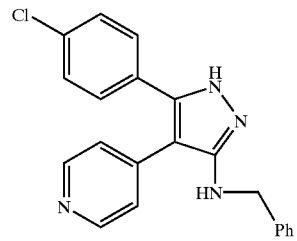

Isolated as 5-(4-chlorophenyl)-N-(phenylmethyl)-4-(4-pyridinyl)-1H-pyrazol-3-amine hydrate (2:1): DSC 237° C. Anal. Calc'd for $C_{12}H_{17}ClN_4+0.5\ H_2O$ (MW 369.86): C, 68.20, H, 4.63, N, 15.15. Found: C, 68.09, H, 4.55, N, 15.15.

EXAMPLE A-167

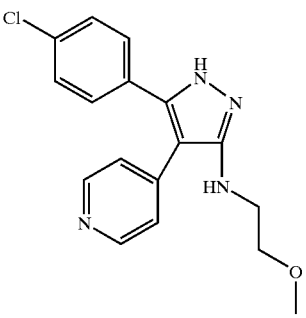

Isolated as 5-(4-chlorophenyl)-N-(2-methoxyethyl)-4-(4-pyridinyl)-1H-pyrazol-3-amine monohydrate: DSC 223° C. Anal. Calc'd for $C_{17}H_{17}ClN_4O+H_2O$ (MW 346.82): C, 58.87, H, 4.94, N, 16.15. Found: C, 58.59, H, 4.79, N, 16.02.

EXAMPLE A-168

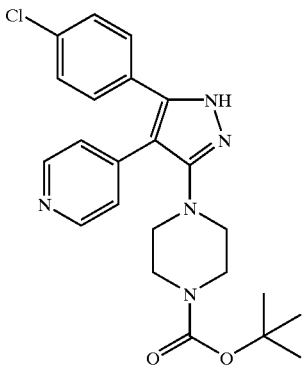

1,1-dimethylethyl 4-[5-(4-chlorophenyl)-4-(4-pyridinyl)-1H-pyrazol-3-yl]-1-piperazinecarboxylate: DSC 251° C. Anal. Calc'd for $C_{23}H_{26}ClN_5O$ (MW 439.95): C, 62.79, H, 5.96, N, 15.92. Found: C, 62.40, H, 5.82, N, 15.82.

EXAMPLE A-169

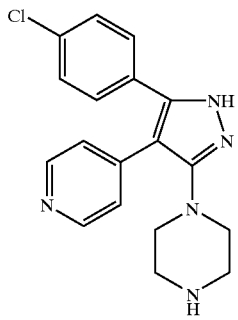

Isolated as 1-[5-(4-chlorophenyl)-4-(4-pyridinyl)-1H-pyrazol-3-yl]piperazine trihydrochloride: DSC 99° C. Anal. Calc'd for $C_{18}H_{18}ClN_4+3\ HCl$ (MW 449.21): C, 48.13, H, 4.71, N, 15.59. Found: C, 47.76, H, 5.07, N, 15.51.

EXAMPLE A-170

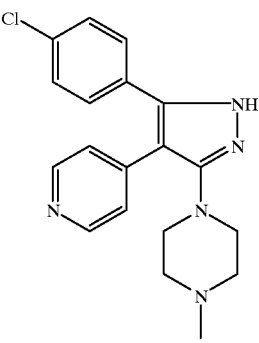

1-[5-(4-chlorophenyl)-4-(4-pyridinyl)-1H-pyrazol-3-yl)-4-methylpiperazine: m.p. 247–249° C. Anal. Calc'd for $C_{19}H_{20}ClN_5+0.75$ $H_2O$ (MW 367.33): C, 62.12, H, 5.49, N, 19.06. Found: C, 62.45, H, 5.86, N, 19.32.

EXAMPLE A-171

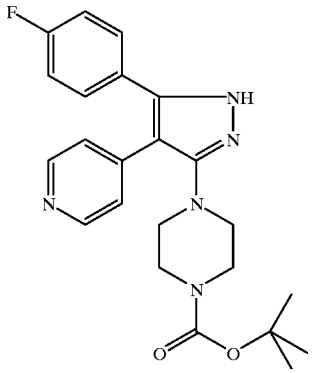

1,1-dimethylethyl 4-[5-(4-fluorophenyl)-4-(4-pyridinyl)-1H-pyrazol-3-yl]-1-piperazinecarboxylate: m.p. 243–244° C. Anal. Calc'd for $C_{23}H_{26}FN_5O_2+0.5$ $CH_3CH_2CO_2CH_2CH_3$ (MW 467.55): C, 64.22, H, 6.47, N, 14.98. Found: C, 63.90, H, 6.61, N, 14.88.

EXAMPLE A-172

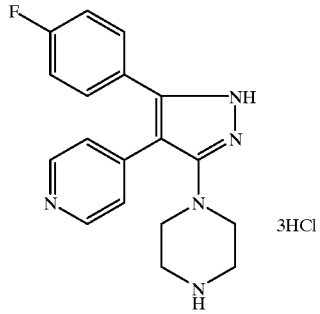

1-[5-(4-fluorophenyl)-4-(4-pyridinyl)-1H-pyrazol-3-yl] piperazine trihydrochloride: m.p. 204–206° C. Anal. Calc'd for $C_{18}H_{18}FN_5+3$ $HCl+0.5$ $H_2O$ (MW 441.77): C, 48.94, H, 4.79, N, 15.85. Found: C, 48.66, H, 4.88, N, 15.50.

1-[5-(4-chlorophenyl)-4-(4-pyridinyl)-1H-pyrazol-3-yl] piperazine: m.p. 264–265° C. Anal. Calc'd for $C_{18}H_{18}ClN_5+0.125$ $H_2O$ (MW 342.08): C, 63.20, H, 5.30, N, 20.47. Found: C, 63.04, H, 5.36, N, 20.33.

Additional compounds that were synthesized in accordance with the chemistry described in Scheme II by selection of the corresponding starting reagents further include the compounds disclosed in Table 2.

TABLE 2

| Example | General Procedure | Formula | Microanalysis | | | | | | DSC deg C. |
|---|---|---|---|---|---|---|---|---|---|
| | | | C calc | C found | H calc | H found | N calc | N found | |
| A-173 | Sch. II | C24H25ClN6·3HCl·1.5H2O | 50.63 | 50.58 | 4.96 | 5.03 | 14.76 | 14.68 | 182 |
| A-174 | Sch. II | C25H24ClN5·0.125H2O | 69.47 | 69.33 | 5.60 | 5.56 | 16.20 | 16.11 | 259 |
| A-175 | Scb. II | C17H17FN6·1.25H2O | 48.64 | 48.45 | 4.56 | 4.86 | 20.02 | 20.24 | 82 |
| A-176 | Sch. II | C22H26ClN5O2 | 61.75 | 61.57 | 6.12 | 6.04 | 16.37 | 16.34 | 217 |
| A-177 | Sch. II | C17H18ClN5·3HCl·H2O | 44.85 | 44.96 | 4.65 | 4.87 | 15.38 | 15.17 | 220 |
| A-178 | Sch. II | C21H24ClN5O2·0.125H2O | 60.61 | 60.51 | 5.81 | 5.81 | 16.83 | 16.64 | 232 |
| A-179 | Sch. II | C25H30 ClN5O3 | 62.04 | 61.76 | 6.25 | 6.25 | 14.47 | 14.37 | 220 |
| A-180 | Sch. II | C22H25 FN6O2·0.5H2O | 60.96 | 60.86 | 5.81 | 6.21 | 19.39 | 19.47 | N.D. |
| A-181 | Sch. II | C22H25 ClFN5O2 | 59.26 | 58.98 | 5.65 | 5.55 | 15.71 | 15.36 | 210 |
| A-182 | Sch. II | C20H22ClN5·0.75H2O | 62.98 | 62.97 | 5.81 | 5.64 | 18.36 | 17.83 | 271 |
| A-183 | Sch. II | C16H19Cl4N5·3HCl | 45.41 | 45.37 | 4.53 | 4.74 | | | 120 |

EXAMPLE A-173

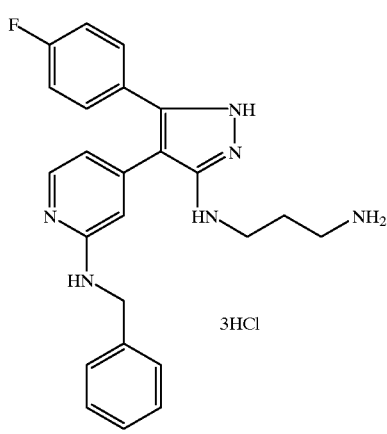

N-[5-(4-chlorophenyl)-4-[2-(phenylmethyl)amino]-
4-pyridinyl]-1H-pyrazol-3-yl]-1,3-propanediamine,
trihydrochloride

EXAMPLE A-174

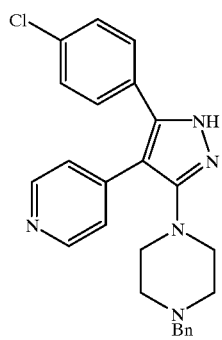

1-[5-(4-chlorophenyl)-4-(4-pyridinyl)-1H-pyrazol-3-
yl]-4-(phenylmethyl)piperazine

EXAMPLE A-175

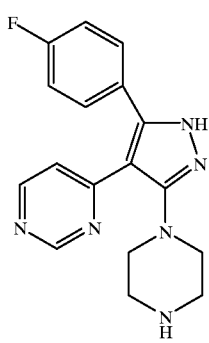

Isolated as 4-[3-(4-fluorophenyl)-5-(1-piperazinyl)-
1H-pyrazol-4-yl]pyrimidine, dihydrochloride

EXAMPLE A-176

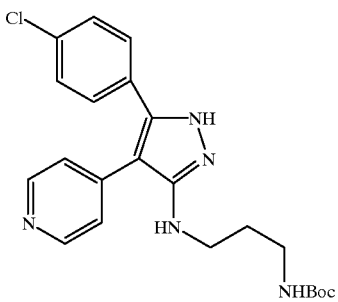

1,1-dimethylethyl [3-[[5-(4-chlorophenyl)-4-(4-
pyridinyl)-1H-pyrazol-3-yl]amino]propyl]carbamate

EXAMPLE A-177

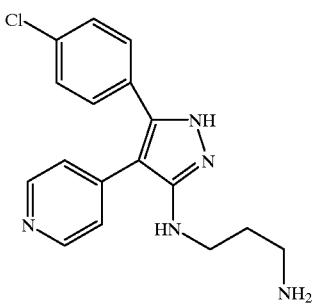

Isolated as N-[5-[4-chlorophenyl)-4-(4-pyridinyl)-
1H-pyrazol-3-yl]-1,3-propanediamine,
trihydrochloride monohydrate

EXAMPLE A-178

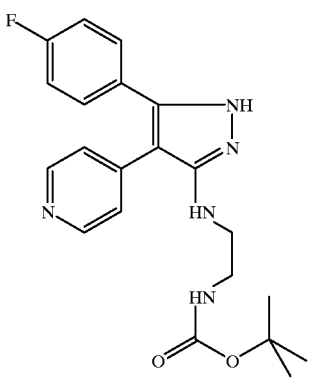

-continued

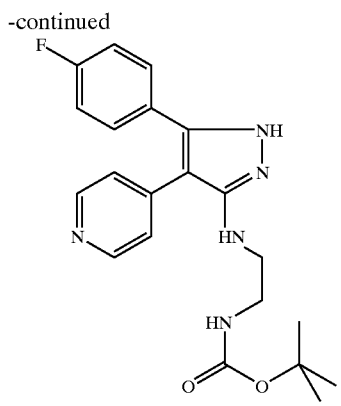

1,1-dimethylethyl [2-[[5-(4-chlorophenyl)-4-(4-pyridinyl)-1H-pyrazol-3-yl]amino]ethyl]carbamate

EXAMPLE A-179

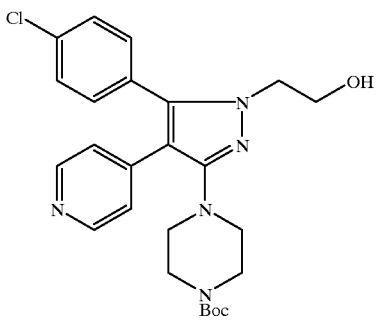

1,1-dimethyle thyl 4-[5-(4-chlorophenyl)-1-(2-hydroxyethyl)-4-(4-pyridinyl)-1H-pyrazol-3-yl]-1-piperazinecarboxylate

EXAMPLE A-180

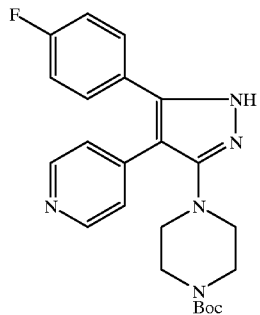

1,1-dimethylethyl 4-[5-(4-fluorophenyl)-4-(4-pyrimidinyl)-1H-pyrazol-3-yl]-1-piperazinecarboxylate

EXAMPLE A-181

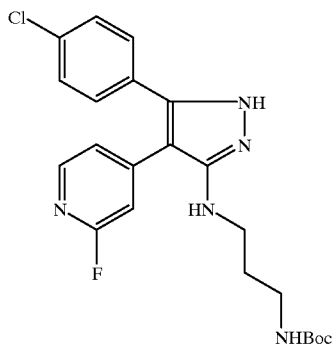

1,1-dimethylethyl [3-[[5-(4-chlorophenyl)-4-(2-fluoro-4-pyridinyl)-1H-pyrazol-3-yl]amino]propyl] carbamate

EXAMPLE A-182

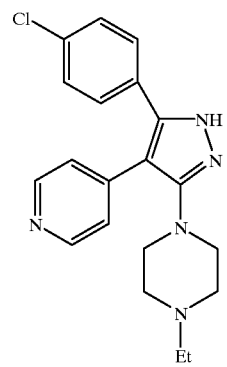

1-[5-(4-chlorophenyl)-4-(4-pyridinyl)-1H-pyrazol-3-yl]-4-ethylpiperazine

EXAMPLE A-183

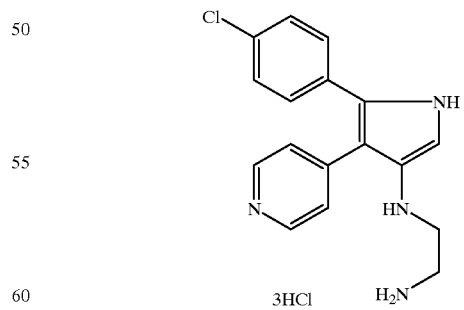

N-[5-(4-chlorophenyl)-4-(4-pyridinyl)-1H-pyrazol-3-yl]-1,2-ethanediamine

The compounds of Examples A-184 through A-189 were synthesized in accordance with the chemistry described above (particularly in Schemes I and IV) and illustrated by the previously disclosed Examples by selection of the corresponding starting reagents:

EXAMPLE A-184

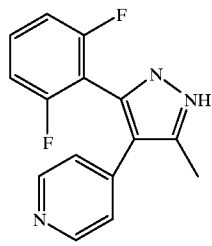

4-[3-(2,6-difluorophenyl)-5-methyl-1H-pyrazol-4-yl]pyridine: Anal. Calc'd for $C_{15}H_{11}F_2N_3$: C, 66.42; H, 4.09; N, 15.49. Found: C, 66.20; H, 3.94; N, 15.16; m.p. 236.67° C.

EXAMPLE A-185

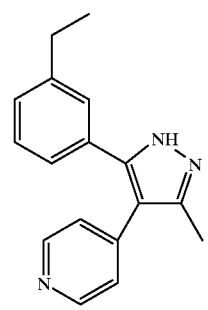

4-[3-(3-ethylphenyl)-5-methyl-1H-pyrazol-4-yl]pyridine: Anal. Calc'd for $C_{17}H_{17}N_3$: C, 77.54; H, 6.51; N, 15.96. Found; C, 77.16; H, 6.27; N, 15.69. m.p. (DSC): 189.25° C.

EXAMPLE A-186

4-[3-(3-chlorophenyl)-5-ethyl-1H-pyrazol-4-yl]pyridine: Anal Calc'd for $C_{16}H_{14}ClN_3 \cdot 0.1$ mole $H_2$): C, 67.15; H, 4.91; N, 14.33. Found: C, 66.95; H, 5.00; N, 14.36. DSC: 176.18° C.

EXAMPLE A-187

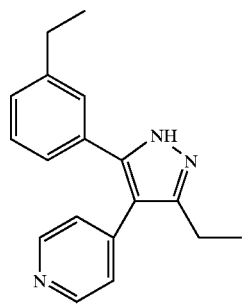

4-[3-ethyl-5-(3-ethylphenyl)-1H-pyrazol-4-yl]pyridine: Anal. Calc'd for $C_{18}H_{19}N_3 \cdot 0.1$ mole $H_2$): C, 77.44; H, 6.93; N, 15.05. Found: C, 77.39; H, 6.94; N, 14.93. m.p. (DSC): 192.66° C.

EXAMPLE A-188

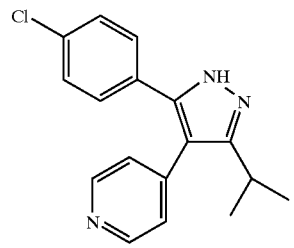

4-[3-(4-chlorophenyl)-5-(1-methylethyl)-1H-pyrazol-4-yl]pyridine: Anal. Calc'd for $C_{17}H_{16}ClN_2 \cdot 0.4M$ EtOAc: C, 67.08; H, 5.81; N, 12.62. Found: C, 67.40; H, 6.15; N, 12.34.

EXAMPLE A-189

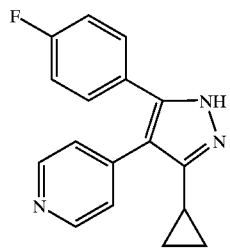

4-[3-cyclopropyl-5-(4-fluorophenyl)-1H-pyrazol-4-yl]pyridine: Anal. Calc'd for $C_{17}H_{14}FN_3$: C, 73.1; H, 5.05; N, 15.04. Found: C, 73.23; H, 4.89; N, 14.63; m.p.: 239–240° C.

The compound of Example A-190 was synthesized in accordance with the chemistry described above (particularly in Scheme III) and illustrated by the previously disclosed Examples by selection of the corresponding starting reagents:

EXAMPLE A-190

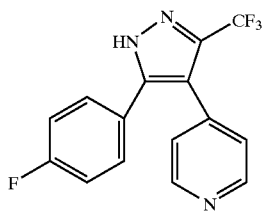

4-[3-(4-fluorophenyl)-5-(trifluoromethyl)-1H-pyrazol-4-yl]pyridine

This compound was prepared by the same procedure as described for Example A-22 by replacing 3-(4'-pyridylacetyl)toluene with 1-fluoro-4-(4'-pyridylacetyl)benzene (prepared as set forth in Example A-19).

Anal. Calc'd for $C_{15}H_9F_4N_3$: C, 58.64; H, 2.95; N, 13.68. Found: C, 58.57; H, 3.07; N, 13.31. m.p. (DSC): 281.94° C.

The compounds of Examples A-191 through A-198 were synthesized in accordance with the chemistry described above (particularly in Scheme V) by selection of the corresponding starting reagents:

EXAMPLE A-191

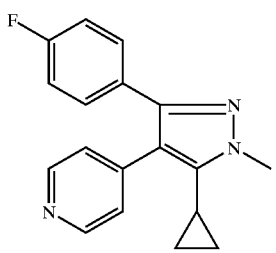

4-[5-(cyclopropyl-3-(4-(fluorophenyl)-1-methyl-1H-pyrazol-4-yl]pyridine

Step 1: Preparation of 1-(4-fluorophenyl)-2-(4-pyridinyl)ethanone methylhydrazone

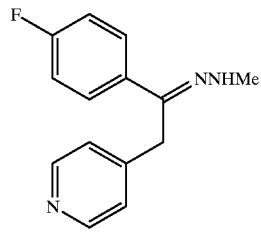

1-(4-fluorophenyl)-2-(4-pyridinyl)ethanone methylhydrazone

To a solution of 4-fluorobenzoyl-4'-pyridinyl methane (8.60 g, 0.04 mol) and methyl hydrazine (2.14 g, 0.044 mol) in 50 mL of ethanol was added two drops of concentrated sulfuric acid. The reaction mixture was stirred at room temperature overnight. After the removal of solvent, the residue was partitioned between ethyl acetate and water. The organic layer was washed with saturated sodium carbonate solution, washed with brine, and dried over magnesium sulfate. The filtrate was concentrated and the crude product was recrystallized from diethyl ether and hexane to afford 7.5 g of a yellow solid product (77% yield), 1-(4-fluorophenyl)-2-(4-pyridinyl)ethanone methylhydrazone.

Step 2: Preparation of 4-[5-(cyclopropyl-3-(4-(fluorophenyl)-1-methyl-1H-pyrazol-4-yl]pyridine To a solution of sodium hexamethyldisilazide (5.5 mL, 1.0 M in THF) at 0° C. was added a solution of the compound prepared in step 1 (0.67 g, 0.0028 mol) in 10 mL of dry THF dropwise. The dark brown solution was stirred at this temperature for 30 minutes. Then a solution of methyl cyclopropanecarboxylate (0.34 g, 0.0034 mol) in 5 mL of dry THF was added. The reaction mixture was allowed to warm up to room temperature and stirred for 3 hours. Water was added and the aqueous phase was extracted with ethyl acetate. The organic layer was washed with brine, dried over magnesium sulfate and filtered. The filtrate was concentrated and purified by chromatography on silica gel (ethyl acetate/hexane/acetone, 10:9:1) to give 0.45 g of product, 4-[5-(cyclopropyl-3-(4-(fluorophenyl)-1-methyl-1H-pyrazol-4-yl]pyridine, as a light yellow solid (55% yield), mp: 129–130° C.; $^1$H NMR (CDCL$_3$): δ8.53 (m, 2H), 7.32 (m, 2H), 7.14 (m, 2H), 6.97 (m, 2H), 4.00 (s, 3H), 1.83 (m, 1H), 0.95 (m, 2H), 0.36 (m, 2H); Anal. Calc'd For $C_{18}H_{16}FN_3$: C, 73.70; H, 5.50; N, 14.32. Found: C, 73.63; H, 5.57; N, 14.08.

EXAMPLE A-192

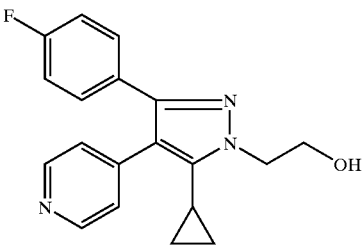

5-cyclopropyl-3-(4-fluorophenyl)-4-(4-pyridinyl)-1H-pyrazole-1-ethanol

Step 1: Preparation of 1-(4-fluorophenyl)-2-(4-pyridinyl)ethanone(2-hydroxyethyl)hydrazone

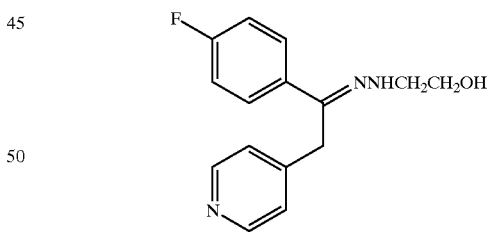

1-(4-fluorophenyl)-2-(4-pyridinyl)ethanone(2-hydroxyethyl)hydrazone

To a flask containing hydroxyethyl hydrazine (3.4 g, 0.04 mol) at 80° C. was added 4-fluorobenzoyl-4'-pyridinyl methane (8.6 g, 0.04 mol) portionwise. The yellow oil was stirred at this temperature overnight. The cooled reaction mixture was dissolved with hot ethyl acetate and then triturated with hexane to give 8.9 g of product, 1-(4-fluorophenyl)-2-(4-pyridinyl)ethanone(2-hydroxyethyl)hydrazone, as a yellow crystal (81%), mp: 122–123° C.

Step 2: Preparation of 1-(4-fluorophenyl)-2-(4-pyridinyl)ethanone[2-[[(1,1-dimethylethyl)dimethylsilyl]oxy]ethyl]hydrazone

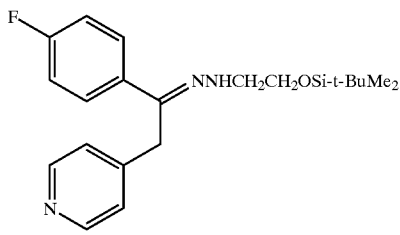

1-(4-fluorophenyl)-2-(4-pyridinyl)ethanone
[2-[[(1,1-dimthylethyl)dimethyisllyl]oxy]ethyl]hydrazone To a solution of the 1-(4-fluorophenyl)-2-(4-pyridinyl)ethanone(2-hydroxyethyl)hydrazone prepared in step 1 (2.73 g, 0.01 mol) and (1,1-dimethylethyl)dimethylsilyl chloride (1.5 g, 0.01 mol) in 25 mL of DMF was added imidazole portionwise. The reaction mixture was stirred at room temperature overnight. Water was added and extracted with ethyl acetate, the organic layer was washed with water, washed with brine, dried over magnesium sulfate and filtered. The filtrate was concentrated to give 3.8 g of crude product, 1-(4-fluorophenyl)-2-(4-pyridinyl)ethanone(2-[[(1,1-dimethylethyl)dimethylsilyl]oxy]ethyl]hydrazone, as a yellow oil that was used in the next step without further purification.

Step 3: 5-cyclopropyl-1-[2-[[(1,1-dimethylethyl)dimethylsilyl]oxy]ethyl]-3,4-diphenyl-1H-pyrazole

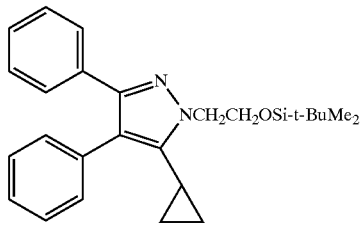

5-cyclopropyl-1-[2-[[(1,1-dimethylethyl)dimethylsllyl]oxy]ethyl]-3,4-diphenyl-1h-pyrazole To a solution of sodium hexamethyldisilazide (4.2 mL, 1.0 M in THF) at 0° C. was added a solution of the compound prepared in step 2 (0.78 g, 0.002 mol) in 10 mL of dry THF dropwise. The dark brown solution was stirred at this temperature for 30 minutes. Then a solution of methyl cyclopropanecarboxylate (0.27 g, 0.0026 mol) in 5 mL of dry THF was added. The reaction mixture was allowed to warm up to room temperature and stirred for 3 hours. Water was added and the aqueous phase was extracted with ethyl acetate. The organic layer was washed with brine, dried over magnesium sulfate and filtered. The filtrate was concentrated and purified by chromatography on silica gel (ethyl acetate/hexane, 3:7) to give 0.30 g of product, 5-cyclopropyl-1-[2-[[(1,1-dimethylethyl)dimethylsilyl]oxy]ethyl]-3,4-diphenyl-1H-pyrazole, as a light yellow oil (35% yield), $^1$H NMR (CDCL$_3$): δ8.53 (m, 2H), 7.32 (m, 2H), 7.14 (d, J=5.6 Hz, 2H), 6.97 (m, 2H), 4.47 (t, J=4.8 Hz, 2H), 4.14 (t, J=4.8 Hz, 2H), 1.93 (m, 1H), 0.95 (m, 2H), 0.87 (s, 9H), 0.41(m, 2H); Anal. Calc'd For C$_{25}$H$_{32}$FN$_3$OSi: C, 68.61; H, 7.37; N, 9.60. Found: C, 68.39; H, 7.81; N, 9.23.

Step 4: Preparation of 5-cyclopropyl-3-(4-fluorophenyl)-4-(4-pyridinyl)-1H-pyrazole-1-ethanol To a solution of the compound prepared in step 3 (0.27 g, 0.00062 mol) in 5 mL of THF was added tetrabutylammonium fluoride (1.9 mL of 1.0 M THF solution) at room temperature. After 1 hour, water was added and extracted with ethyl acetate. The organic layer was washed with brine, dried over magnesium sulfate and filtered. The filtrate was concentrated and purified by chromatography on silica gel (ethyl acetate/hexane, 9:1) to give 0.16 g of product, 5-cyclopropyl-3-(4-fluorophenyl)-4-(4-pyridinyl)-1H-pyrazole-1-ethanol, as a pale yellow solid, mp: 155–157° C.; $^1$H NMR (CDCL$_3$): δ8.53 (br s, 2H), 7.32 (m, 2H), 7.14 (d, J=5.6 Hz, 2H), 6.97 (m, 2H), 4.42 (t, J=4.8 Hz, 2H), 4.14 (t, J=4.8 Hz, 2H), 1.83 (m, 1H), 0.93 (m, 2H), 0.35(m, 2H); Anal. Calc'd For C$_{19}$H$_{18}$FN$_3$O: C, 70.57; H, 5.61; N, 12.99. Found: C, 70.46; H, 5.87; N, 12.84.

EXAMPLE A-193

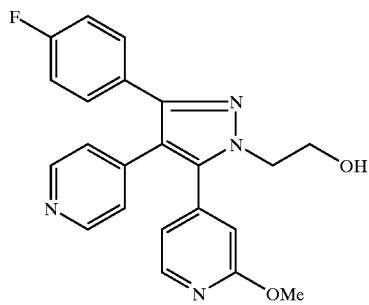

3-(4-fluorophenyl)-5-(2-methoxy-4-pyridinyl)-4-(4-pyridinyl)-1H-pyrazole-1-ethanol To a solution of sodium hexamethyldisilazide (7.4 mL, 1.0 M in THF) at 0° C. was added a solution of the compound prepared in step 2 of Example A-192 (1.25 g, 0.0034 mol) in 15 mL of dry THF dropwise. The dark brown solution was stirred at this temperature for 30 minutes. Then a solution of methyl 4-(2-methoxy)pyridinecarboxylate (0.0.59 g, 0.0035 mol) in 5 mL of dry THF was added. The reaction mixture was allowed to warm up to room temperature and stirred for 3 hours. Water was added and the aqueous phase was extracted with ethyl acetate. The organic layer was washed with brine, dried over magnesium sulfate and filtered. The filtrate was concentrated and purified by chromatography on silica gel (ethyl acetate/hexane, 1:1) to give 0.28 g of product, 3-(4-fluorophenyl)-5-(2-methoxy-4-pyridinyl)-4-(4-pyridinyl)-1H-pyrazole-1-ethanol, as a yellow solid, mp: 168–169° C.; $^1$H NMR (CDCL$_3$): δ8.42 (m, 2H), 8.20 (dd, J=0.7, 5.2 Hz, 1H), 7.37 (m, 2H), 7.02 (m, 2H), 6.95 (m, 2H), 6.71 (dd, J=1.4, 5.2 Hz, 1H), 6.66 (t, J=0.7 Hz, 1H), 4.20 (m, 2H), 4.14 (m, 2H), 3.95 (s, 3H); Anal. Calc'd for C$_{22}$H$_{19}$FN$_4$O$_2$: C, 67.86; H, 4.91; N, 14.35. Found: C, 67.46; H, 5.08; N, 14.03.

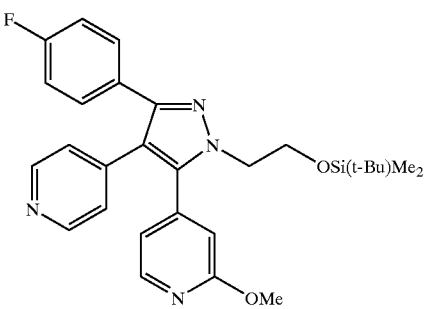

4-[1-[2-[[(1,1-dimethylethyl)dimethylsilyl]-oxy]ethyl]-3-(4-fluorophenyl-4-(4-pyridinyl)-1H-pyrazol-5-yl]-2-methoxypyridine A second compound, 4-[1-[2-[[(1,1-dimethylethyl)dimethylsilyl]oxy]ethyl]-3-(4-fluorophenyl-4-(4-pyridinyl)-

1H-pyrazol-5-yl]-2-methoxypyridine also was isolated from the above reaction as a yellow oil by chromatography. $^{1}$H NMR (CDCL$_{3}$): δ8.45 (m, 2H), 8.20 (m, 1H), 7.40 (m, 2H), 7.04 (m, 2H), 6.93 (m, 2H), 6.81 (m, 2H), 4.24 (m, 2H), 4.14 (m, 2H), 3.98 (s, 3H), 0.83 (s, 9H), 0.02 (s, 6H).

EXAMPLE A-194

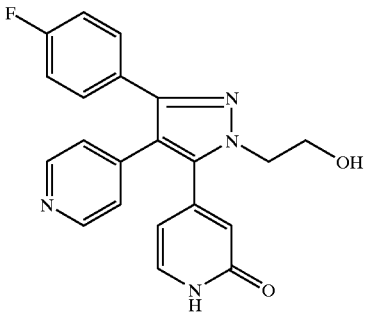

4-[3-(4-fluorophenyl)-1-(2-hydroxyethyl)-4-(4-pyridinyl)-1H-pyrazol-5-yl]-2(1H)-pyridinone To a solution of 3-(4-fluorophenyl)-5-(2-methoxy-4-pyridinyl)-4-(4-pyridinyl)-1H-pyrazole-1-ethanol (0.28 g, 0.0006 mol) in 5 mL of acetic acid was added 3 mL of 48% hydrobromic acid. The reaction mixture was heated at reflux for 3 hour. The cooled mixture was then treated with water, basified with ammonium hydroxide and extracted with ethyl acetate. The organic layer was washed with brine, dried over magnesium sulfate and filtered. The filtrate was concentrated and purified by chromatography on silica gel (MeOH/CH$_{2}$Cl$_{2}$/NH4OH, 5:94:1) to give 0.07 g of product, 4-[3-(4-fluorophenyl)-1-(2-hydroxyethyl)-4-(4-pyridinyl)-1H-pyrazol-5-yl]-2(1H)-pyridinone, as a yellow solid (32% yield), mp: 250–251° C.; $^{1}$H NMR (DMSO-d$_{6}$): δ11.74 (s, 1H), 8.45 (d, J=5.0 Hz, 2H), 7.35 (m, 3H), 7.16 (m, 2H), 7.03 (d, J=5.0 Hz, 2H), 6.37 (s, 1H), 6.05 (d, J=5.2 Hz, 1H), 5.0 (m, 1H), 4.13 (m, 2H), 3.81 (m, 2H); Anal. Calc'd for C$_{21}$H$_{17}$FN$_{4}$O$_{2}$.0.2 H$_{2}$): C, 66.06; H, 4.65; N, 14.67. Found: C, 66.31; H, 4.49; N, 14.27.

EXAMPLE A-195

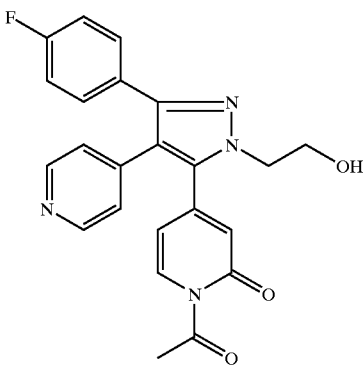

1-acetyl-4-[3-(4-fluorophenyl)-1-(2-hydroxyethyl)-4-(4-pyridinyl)-1H-pyrazol-5-yl]-2(1H)-pyridinone 1-acetyl-4-[3-(4-fluorophenyl)-1-(2-hydroxyethyl)-4-(4-pyridinyl)-1H-pyrazol-5-yl]-2(1H)-pyridinone was obtained as a byproduct of the reaction of Example A-194 in the form of a yellow solid (38% yield), mp: 220–221° C.; $^{1}$H NMR (CDCl$_{3}$): δ8.50 (m, 2H), 7.39 (m, 3H), 7.02 (m, 4H), 6.59 (m, 1H) 6.08 (dd, J=1.4, 5.2 Hz, 1H), 4.52 (t, J=6.0 Hz, 2H), 4.43 (t, J=6.0 Hz, 2H), 2.04 (s,3H); Anal. Calc'd for C$_{23}$H$_{19}$FN$_{4}$O$_{3}$.0.3 H$_{2}$): C, 65.46; H, 4.63; N, 13.28. Found: C, 65.09; H, 4.64; N, 12.99.

EXAMPLE A-196

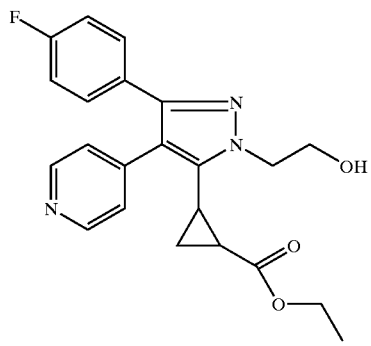

Ethyl 2-[3-(4-fluorophenyl)-1-(2-hydroxyethyl)-4-(4-pyridinyl)-1H-pyrazol-5-yl]cyclopropanecarboxylate To a solution of sodium hexamethyldisilazide (17.0 mL, 1.0 M in THF) at 0° C. was added a solution of the compound prepared in step 1 of Example A-192 (1.37 g, 0.005 mol) in 20 mL of dry THF dropwise. The dark brown solution was stirred at this temperature for 30 minutes. Then a solution of diethyl 1,2-cyclopropanedicarboxylate (1.12 g, 0.006 mol) in 10 mL of dry THF was added. The reaction mixture was allowed to warm up to room temperature and stirred for 2 hours. Water was added and the aqueous phase was extracted with ethyl acetate. The organic layer was washed with brine, dried over magnesium sulfate and filtered. The filtrate was concentrated and purified by chromatography on silica gel (ethyl acetate/hexane, 8:2) to give 0.18 g of product, ethyl 2-[3-(4-fluorophenyl)-1-(2-hydroxyethyl)-4-(4-pyridinyl)-1H-pyrazol-5-yl]cyclopropanecarboxylate, as a light yellow oil (35% yield), $^{1}$H NMR (CDCL$_{3}$): δ8.55 (m, 2H), 7.32 (m, 2H), 7.11 (m, 2H), 6.97 (m, 2H), 4.38 (m,2H), 4.16 (m, 4H), 2.47 (m, 1H), 1.53 (m, 2H), 1.26 (t, J=7.0 Hz, 3H), (m, 2H), 0.90 (m, 2H); Anal. Calc'd for C$_{22}$H$_{22}$FN$_{3}$O$_{3}$.0.25 H$_{2}$): C, 66.07; H, 5.67; N, 10.51 Found: C, 65.89; H, 5.80; N, 9.95.

EXAMPLE A-197

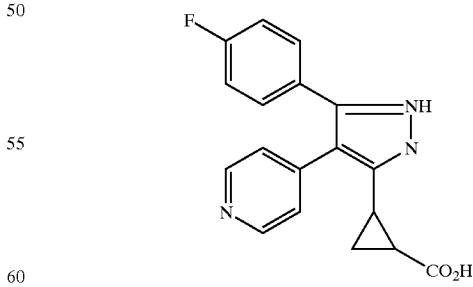

2-[3-(4-fluorophenyl)-1-(2-hydroxyethyl)-4-(4-pyridinyl)-1H-pyrazol-5-yl]cyclopropanecarboxylic acid To a solution of ethyl 2-[3-(4-fluorophenyl)-1-(2-hydroxyethyl)-4-(4-pyridinyl)-1H-pyrazol-5-yl]

cyclopropanecarboxylate prepared in accordance with Example A-196 (0.21 g, 0.00045 mol) in 10 mL of methanol was added a solution of sodium hydroxide (0.09 g, 0.0022 mol) in 2 mL of water. The reaction mixture was stirred at reflux for 6 hours. After the solvent was removed, the residue was dissolved with 10 mL of 1N HCl and stirred for 30 minutes. The pH was then adjusted to 5–6 by addition of 1N sodium hydroxide solution and then extracted with ethyl acetate. The organic layer was washed with brine, dried over magnesium and filtered. The filtrate was concentrated and the crude was purified by recrystallization from ethanol and ether to give 0.1 g of product, 2-[3-(4-fluorophenyl)-1-(2-hydroxyethyl)-4-(4-pyridinyl)-1H-pyrazol-5-yl] cyclopropanecarboxylic acid, as a white solid (60% yield), mp: 253–255° C.; $^1$H NMR (CD$_3$OD): δ8.46 (m, 2H), 7.32 (m, 2H), 7.25 (m, 2H), 7.04 (m, 2H), 4.39 (t, J=5.0 Hz, 2H), 4.03 (m, 2H), 2.60 (m, 1H), 1.51 (m, 2H), 0.97 (m, 2H); Anal. Calc'd For C$_{20}$H$_{18}$FN$_3$O$_3$: C, 65.39; H, 4.94; N, 11.44. Found: C, 64.92; H, 4.77; N, 11.20.

EXAMPLE A-198

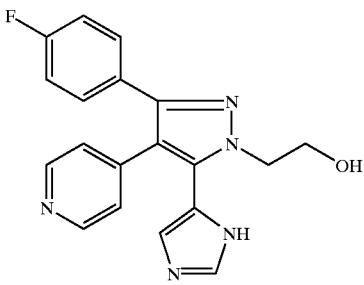

3-(4-fluorophenyl)-5-(4-imidazolyl)-4-(4-pyridinyl)-1H-pyrazole-1-ethanol

Step 1: Preparation of methyl 1-[[2-(trimethylsilyl)-ethoxy]methyl]-1H-pyrrole-3-carboxylate

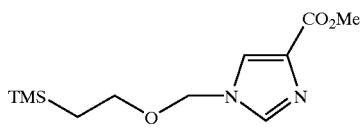

methyl 1-[[2-(trimethylsilyl)ethoxy]methyl]-1H-pyrrole-3-carboxylate

To a suspension of sodium hydride (1.0 g, 0.025 mol) in 50 mL of DMF was added methyl 4-imidazolecarboxylate (2.95 g, 0.023 mol) portionwise at room temperature. The mixture was stirred at room temperature for 0.5 hours. Then SEM-Cl (4.17 g, 0.025 mol) was added dropwise over 5 minutes. The reaction mixture was stirred for 4 hours and quenched by adding water. The aqueous phase was extracted with ethyl acetate and the organic layer was washed with brine, dried over magnesium sulfate and filtered. The filtrate was concentrated and the crude was purified by chromatography on silica gel (ethyl acetate/hexane, 8:2) to give 4.0 g of the major regioisomer as a clear oil.

Step 2: Preparation of 4-[1-[2-[[(1,1-dimethylethyl) dimethylsilyl]oxy]ethyl]-3-(4-fluorophenyl-5-[1-[[(2-trimethysilyl)ethoxy]methyl-1H-imidizol-4-yl-1H-pyrazol-4-yl]pyridine

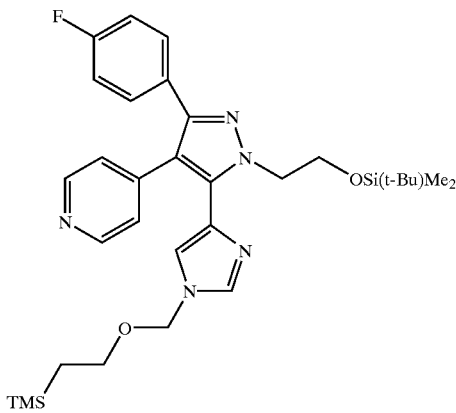

4-[1-[2[[(1,1-dimethylethyl)dimethylsilyl]-oxy] ethyl]-3-(4-fluorophenyl)-5-[1-[[2-trimethylsilyl) ethoxy]methyl]-1H-imidazol-4-yl]-1H-pyrazol-4-yl] pyridine To a solution of sodium hexamethyldisilazide (4.5 mL, 1.0 M in THF) at 0° C. under Ar was added a solution of the compound prepared in step 2 of Example A-192 (0.8 g, 0.002 mol) in 10 mL of dry THF dropwise. The dark brown solution was stirred at this temperature for 30 minutes. Then a solution of the compound prepared in step 1 of the present Example (0.54 g, 0.0021 mol) in 5 mL of dry THF was added. The reaction mixture was allowed to warm up to room temperature and stirred for 1 hour. Water was added and the aqueous phase was extracted with ethyl acetate. The organic layer was washed with brine, dried over magnesium sulfate and filtered. The filtrate was concentrated and purified by chromatography on silica gel (ethyl acetate/hexane, 8:2) to give 0.98 g of product as a light yellow oil which solidified upon standing (91% yield), mp: 79–80° C.; $^1$H NMR (CDCL$_3$): δ8.48 (d, J=6.0 Hz, 2H), 7.68 (d, J=1.3 Hz, 1H), 7.38 (d, J=6.0 Hz, 2H), 7.10 (m, 2H), 7.00 (m, 2H), 6.93 (d, J=1.3 Hz , 1H), 5.25 (s, 2H), 4.53 (t, J=6.0 Hz, 2H), 4.12 (t, J=6.0 Hz, 2H), 3.84 (t, J=8.0 Hz , 2H), 0.92 (t, J=8.0 Hz, 2H), 0.84 (s, 9H), 0.021 (s, 18H); Anal. Calc'd For C$_{31}$H$_{44}$FN$_5$O$_2$Si$_2$: C, 62.70; H, 7.47; N, 11.79. Found: C, 62.98; H, 7.74; N, 11.88.

Step 3: Preparation of 3-(4-fluorophenyl)-5-(4-imidazolyl)-4-(4-pyridinyl)-1H-pyrazole-1-ethanol To a solution of the compound prepared in step 2 of the present Example (0.54 g, 0.001 mol) in 10 mL of THF was added a solution of tetrabutylammonium fluoride (1.0 M in THF). After the mixture was heated at reflux for 3 hours, the solvent was removed and the residue was partitioned between ethyl acetate and water. The organic layer was washed with brine, dried over magnesium sulfate and filtered. The filtrate was concentrated and the crude product was purified on silica gel (methylene chloride/methanol, 95:5) to give 0.22 g of the product, 3-(4-fluorophenyl)-5-(4-imidazolyl)-4-(4-pyridinyl)-1H-pyrazole-1-ethanol, as a white solid (63% yield), mp: 227–228° C.; $^1$H NMR (DMSO-d$_6$): δ8.45 (m, 2H), 7.83 (s, 1H), 7.35 (m, 2H), 7.15 (m, 4H), 7.09 (s, 1H), 5.20 (br s, 1H), 4.32 (s, 2H), 3.81 (m, 2H); Anal. Calc'd For C$_{19}$H$_{16}$FN$_5$O: C, 65.32; H, 4.62; N, 20.05. Found: C, 64.98; H, 4.55; N, 19.79.

The compound of Example A-199 was synthesized in accordance with the chemistry described above (particularly in Scheme VI) by selection of the corresponding starting reagents:

EXAMPLE A-199

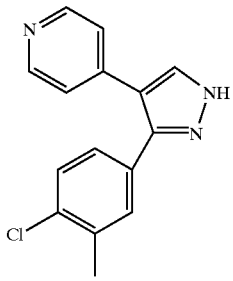

4-[3-(4-chloro-3-methylphenyl)-1H-pyrazol-4-yl]pyridine

Anal. Calc'd for $C_{15}H_{12}N_3Cl$ (269.74): C, 66.79; H, 4.48; N, 15.58. Found: C, 66.57; H. 4.15; N, 15.54. m.p. (DSC): 198.17° C.

The compounds of Examples A-200 through A-202 were synthesized in accordance with the chemistry described above (particularly in Scheme VII) by selection of the corresponding starting reagents:

EXAMPLE A-200

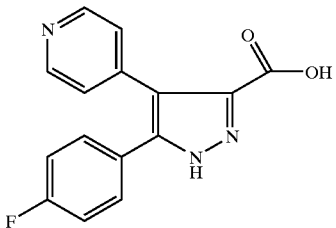

5-(4-fluorophenyl)-4-(4-pyridinyl)-1H-pyrazole-3-carboxylic acid

A mixture of 4-[3-(4-fluorophenyl)-5-methyl-1H-pyrazol-4-yl]pyridine prepared as set forth in Example A-4 (5.83 g, 24.0909 mmol) and potassium permanganate (7.6916 g, 48.1818 mmol) in water (7.5 ml) and tert-butanol (10 ml) was heated at reflux for 6 hours (or until all the potassium permanganate was consumed). The mixture was then stirred at room temperature overnight and then diluted with water (150 ml). Manganese dioxide was removed from the mixture by filtration. The filtrate was extracted with ethyl acetate to remove unreacted starting material. The aqueous layer was acidified with 1N HCl to increase the pH to about 6. A white precipitate formed, was collected by filtration, washed with water, and dried in a vacuum oven to give 5-(4-fluorophenyl)-4-(4-pyridinyl)-1H-pyrazole-3-carboxylic acid (isolated as the monohydrate salt) (2.9777 g, 43.7%). Anal. Calc'd for $C_{15}H_{10}N_3FO_2.H_2O$ (283+18): C, 59.80; H, 4.01; N, 13.95; Found: C, 59.48; H, 3.26; N, 13.65. MS (MH$^{3o}$): 284 (base peak)

EXAMPLE A-201

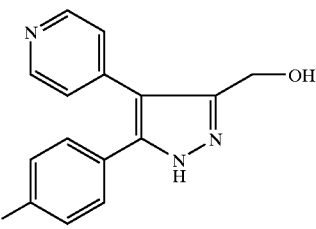

5-(4-fluorophenyl)-4-(4-pyridinyl)-1H-pyrazole-3-methanol

To a suspension of 5-(4-fluorophenyl)-4-(4-pyridinyl)-1H-pyrazole-3-carboxylic acid, monohydrate prepared in accordance with Example A-200 (0.526 g, 2.0 mmol) in dry THF (15 ml) at reflux under nitrogen, a solution of 1N lithium aluminum hydride in THF (4.0 ml, 4.0 mmol) was added dropwise over 15 minutes. A precipitate formed. The mixture was boiled for an additional hour. Excess lithium aluminum hydride was then decomposed by cautiously adding a solution of 4N potassium hydroxide in water (0.5 ml). Upon hydrolysis, a white salt precipitated. After the addition was complete, the mixture was heated at reflux for 15 minutes. The hot solution was filtered by suction through a Buchner funnel, and remaining product was extracted from the precipitate by refluxing with THF (15 ml) for 1 hour, followed again by suction filtration. The combined filtrates were concentrated under reduced pressure. The resulting residue was taken into ethyl acetate, washed with water and brine, dried over $MgSO_4$ to give a crude product (0.45 g). Recrystallization of the crude product from methanol gave 5-(4-fluorophenyl)-4-(4-pyridinyl)-1H-pyrazole-3-methanol (0.2808 g, 56.5%). DSC: 260.26° C.; Anal. Calc'd for $C_{15}H_{12}N_3FO$ (269): C, 66.91; H, 4.49; N, 15.60; Found: C, 66.07; H, 4.63; N, 15.20. MS (MH$^+$): 270 (base peak)

EXAMPLE A-202

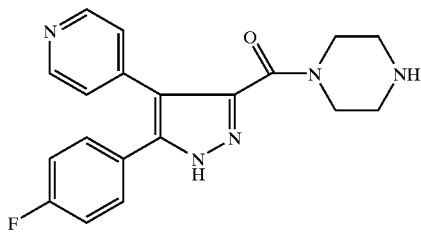

1-[[5-(4-fluorophenyl)-4-(4-pyridinyl)-1H-pyrazol-3-yl]carbonyl]piperazine

Step 1: Preparation of 1,1-dimethylethyl 4-[[5-(4-fluorophenyl)-4-(4-pyridinyl)-1H-pyrazol-3-yl]carbonyl]-1-piperazinecarboxylate

167

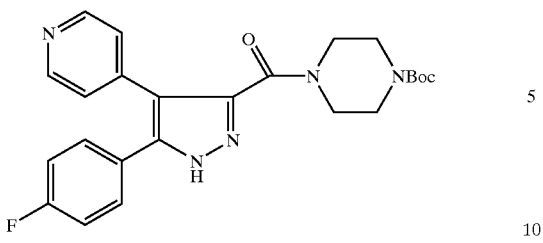

To a solution of 5-(4-fluorophenyl)-4-(4-pyridinyl)-1H-pyrazole-3-carboxylic acid, monohydrate prepared in accordance with Example A-200 (0.9905 g, 3.5 mmol) and 1-hydroxybenzotriazole (0.4824 g, 3.57 mmol) in DMF (20 ml) at 0° C. under nitrogen, 1-(3-dimethylaminopropyl)3-ethylcarbodiimide hydrochloride (0.6984 g, 3.57 mmol, Aldrich Chemical Co.) was added. The solution was stirred at 0° C. under nitrogen for 1 hour then 1-butoxycarbonylpiperazine (0.6585 g, 3.5 mmol) was added followed by N-methylmorpholine (0.40 ml, 3.6 mmol). The reaction was stirred from 0° C. to room temperature overnight. After 19 hours, the solvent was removed under reduced pressure, and resulting residue was diluted with ethyl acetate, washed with saturated $NaHCO_3$ solution, water and brine, and dried over $MgSO_4$. After filtration, the solvent was removed under reduced pressure to give a crude product (1.7595 g). 1,1-Dimethylethyl 4-[[5-(4-fluorophenyl)-4-(4-pyridinyl)-1H-pyrazol-3-yl]carbonyl]-1-piperazinecarboxylate (1.2372 g, 78.4%) was obtained by chromatography. Anal. Calc'd for $C_{24}H_{26}N_5O_3F$. (451): C, 63.85; H, 5.80; N, 15.51; Found: C, 63.75; H, 5.71; N, 15.16. MS (MH$^+$): 452 (base peak).

Step 2: Preparation of 1-[[5-(4-fluorophenyl)-4-(4-pyridinyl)-1H-pyrazol-3-yl]carbonyl]piperazine bis (trifluoroacetate), monohydrate A solution of the compound prepared in step 1 (0.1804 g, 0.4 mmol) in methylene chloride (1.0 ml) and TFA (0.3 ml) was stirred at room temperature under nitrogen for 2 hours. The solvent was removed under reduced pressure and TFA was chased by methylene chloride and methanol. The resulting colorless oily residue was dried in a vacuum oven overnight to give 1-[[5-(4-fluorophenyl)-4-(4-pyridinyl)-1H-pyrazol-3-yl]carbonyl]piperazine (isolated as the bis (trifluoroacetate), monohydrate salt) (0.2400g, 100%) as a white solid. Anal. Calc'd for $C_{19}H_{18}N_5OF.2CF_3COOH.H_2O$ (351+228+18): C, 46.24; H, 3.71; N, 11.72; Found: C, 45.87; H, 3.43; N, 11.45. MS (MH$^+$): 352 (base peak).

The compounds of Examples A-203 through A-206 were synthesized in accordance with the chemistry described above (particularly in Scheme VIII) by selection of the corresponding starting reagents:

EXAMPLE A-203

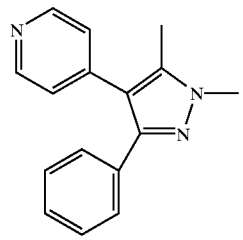

168

4-(15-dimethyl-3-phenyl-1H-pyrazol-4-yl)pyridine

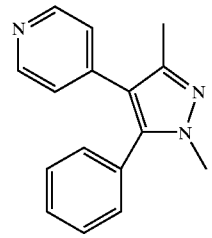

4-(1,3-dimethyl-5-phenyl-1H-pyrazol-4-yl]pyridine

A 60% dispersion of sodium hydride (41 mg, 0.00172 moles) (prewashed with hexane) in mineral oil (69 mg) was added with 5 ml of dioxane to a stirred solution of 4-(3-methyl-5-phenyl-1H-pyrazol-4-yl)pyridine (200 mg, 0.00086 moles) (prepared as set forth in Example A-2) in 50 ml of dioxane. After 3 hours a solution of $CH_3I$ (122 mg, 0.00086 mole) in 10 ml dioxane was added and the mixture was stirred at room temperature for 20 hours. The mixture was concentrated to a solid. The products were partitioned between water (15 ml) and ethyl acetate (50 ml). The organic layer was dried over $Na_2SO_4$, filtered and concentrated to a solid. The products were purified and separated by radial chromatography. NMR (NOE experiments) showed that the first component off the column (the minor component) was 4-(1,3-dimethyl-5-phenyl-1H-pyrazol-4-yl]pyridine, and the second material off the column was 4-(1,5-dimethyl-3-phenyl-1H-pyrazol-4-yl)pyridine.

Major isomer (4-(1,5-dimethyl-3-phenyl-1H-pyrazol-4-yl)pyridine): m.p.: 94–99° C. Anal. calc'd for $C_{16}H_{15}N_3.0.1MH_2O$: C, 77.08; H, 6.06; N, 16.85. Found: C, 76.59; H, 5.70; N, 16.62

EXAMPLE A-204

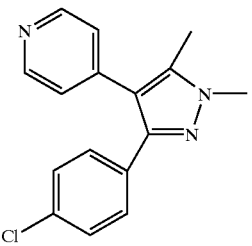

4-[3-(4-chlorophenyl)-1,5-dimethyl-1H-pyrazol-4-yl]pyridine

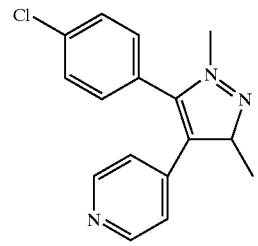

4-[5-(4-chlorophenyl)-1,3-dimethyl-1H-pyrazol-4-yl]pyridine (the compound of Example A-32)

4-[3-(4-chlorophenyl)-1,5-dimethyl-1H-pyrazol-4-yl] pyridine and 4-[5-(4-chlorophenyl)-1,3-dimethyl-1H- pyrazol-4-yl]pyridine were prepared by the same procedure as described for Example A-203 by replacing 4-(3-methyl-5-phenyl-1H-pyrazol-4-yl)pyridine with 4-(3-(4-chlorophenyl)-5-methyl-1H-pyrazol-4-yl)pyridine (prepared as set forth in Example A-7).

Major Isomer (4-[3-(4-chlorophenyl)-1,5-dimethyl-1H-pyrazol-4-yl]pyridine): Anal. calc'd for $C_{16}H_{14}N_3Cl$ (283.76): C, 67.72; H, 4.97; N, 14.81; Found: C, 67.45; H, 4.71; N, 14.63. m.p. (DSC): 190.67° C.

Minor Isomer (4-[5-(4-chlorophenyl)-1,3-dimethyl-1H-pyrazol-4-yl]pyridine): m.p.: 82–88° C. Anal. calc'd for $C_{16}H_{14}N_3Cl$: C, 67.72; H, 4.97; N, 14.81; Found: C, 67.56; H, 4.96; N, 14.73.

EXAMPLE A-205

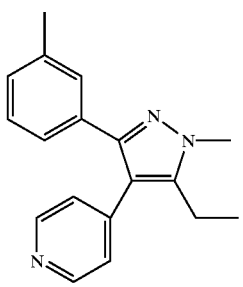

4-[5-ethyl-1-methyl-3-(3-methylphenyl)1H-pyrazol-4-yl]pyridine

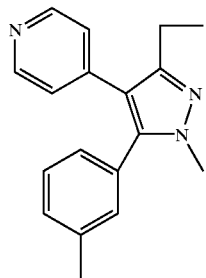

4-[3-ethyl-1-methyl-5-(3-methyphenyl)-1H-pyrazol-4-yl]pyridine

4-[5-ethyl-1-methyl-3-(3-methylphenyl)-1H-pyrazol-4-yl]pyridine and 4-[3-ethyl-1-methyl-5-(3-methylphenyl)-1H-pyrazol-4-yl]pyridine were prepared by the same procedure as described for Example A-203 by replacing 4-(3-methyl-5-phenyl-1H-pyrazol-4-yl)pyridine with 4-(3-(4-methylphenyl)-5-ethyl-1H-pyrazol-4-yl)pyridine (prepared as set forth in Example A-45).

Major Isomer (4-[5-ethyl-1-methyl-3-(3-methylphenyl)-1H-pyrazol-4-yl]pyridine): Anal. Calc'd for $C_{18}H_{19}NO_3 \cdot 0.45\ MH_2O$: C, 75.73; H, 7.03; N, 14.77. Found: C, 76.03; H, 6.87 N, 14.28.

Minor Isomer (4-[3-ethyl-1-methyl-5-(3-methylphenyl)-1H-pyrazol-4-yl]pyridine): Anal. Calc'd for $C_{18}H_{19}NO_3 \cdot 0.30MH_2O$: C, 76.46; H, 6.99; N, 14.86. Found: C, 76.58; H, 6.98; N, 14.63.

EXAMPLE A-206

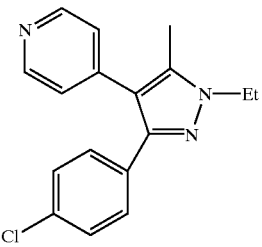

4-[3-(4-chlorophenyl)-1-ethyl-5-methyl-1H-pyrazol-4-yl]pyridine: Anal. Calc'd for $C_{17}H_{16}N_3Cl$ (297.79): C, 68.57; H, 5.42; N, 14.11. Found: C, 68.33; H, 5.27; N, 14.08; m.p. (DSC) 164.36° C.

EXAMPLE A-207

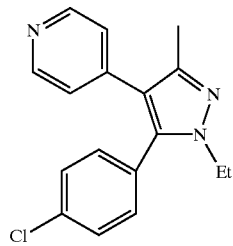

4-[3-(4-chlorophenyl)-2-ethyl-5-methyl-1H-pyrazol-4-yl]pyridine: Anal. Calc'd for $C_{17}H_{16}N_3Cl$ (297.79): C, 68.57; H, 5.42; N, 14.11. Found: C, 68.25; H, 5.36; N, 13.74; m.p. (DSC) 153.46° C.

The compounds of Examples A-208 and A-209 were prepared in accordance with the chemistry described above (particularly in Scheme IX):

EXAMPLE A-208

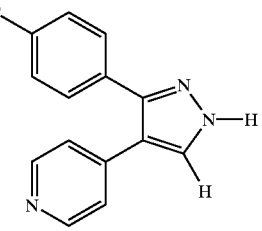

4-[3-(4-fluorophenyl)-1H-pyrazol-4-yl]pyridine
Step 1: Preparation of 4-fluorobenzoyl-4'-pyridyl methane To a mixture of 4-picoline (32.6 g, 0.35 moles) and ethyl-4-fluorobenzoate (50.45g, 0.3 moles), maintained at 20° C., was added lithium bis(trimethylsilylamide) (600 mL (1M)) in a steady but rapid stream so as to maintain ambient temperature. The initial yellow solution turned into a suspension which was then stirred for an additional 2 hours. Toluene (250 mL) was added and the mixture cooled to 0° C. The reaction mixture was quenched with concentrated HCl at 0° C. to lower the pH to about 7. The organic layer was separated and the aqueous layer re-extracted with of toluene (100 mL). The organic layer was dried (sodium sulfate) and concentrated, to furnish a yellow solid which on trituration with hexanes (200 mL) provided the pure desoxybenzoin, 4-fluorobenzoyl-4'-pyridyl methane, in 90% yield (58g). ¹H NMR was consistent with the proposed structure.

Step 2

To a suspension of the desoxybenzoin prepared in step 1 (30 g, 0.14 moles) in tetrahydrofuran (50 mL) was added dimethylformamide dimethyl acetal (50 mL) and the mixture stirred at ambient temperature for two days. The solution was then concentrated to dryness and the solid paste obtained was triturated with hexanes (150 mL) to furnish a yellow solid which was of sufficient purity (as determined by NMR) and was used for the next step without additional purification. Yield: 33.9 g (90%). ¹H NMR was consistent with the proposed structure.

Step 3

The vinyl amine prepared in step 2 (33.9 g, 0.1255 moles) was dissolved in 125 mL of ethanol and cooled to 0° C. Hydrazine hydrate (8.0 g of anhydrous or 16.0 g. of hydrate, 0.25 moles) was then added in one portion. The mixture was stirred well and allowed to warm up to ambient temperature for a total reaction time of 3 hours. The mixture was concentrated and taken up in 200 mL of chloroform. After washing with water (100 mL), the organic layer was extracted with 150 mL of 10% HCl. The water layer was then treated with 0.5 g of activated charcoal at 70° C. for 10 minutes, filtered through celite and neutralized cautiously to pH 7–8 with vigorous stirring and cooling (20% sodium hydroxide was used). The fine off-white precipitate was filtered and dried to give 4-[3-(4-fluorophenyl)-1H-pyrazol-4-yl]pyridine. Yield: 27.3 g. (91%). Mass spectrum: m/z= 240. ¹H NMR was consistent with the proposed structure. Anal. calc'd for $C_{14}H_{10}FN_3$: C, 70.28; H, 4.21; N, 17.56. Found: C, 70.11; H, 4.33; N, 17.61.

EXAMPLE A-209

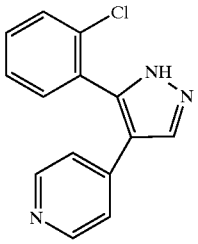

4-[3-(2-chlorophenyl)-1H-pyrazol-4-yl]pyridine

This compound was prepared by the same procedure described for Example A-208 using the corresponding starting reagents.

Anal. Calc'd for $C_{14}H_{10}ClN_3$: C, 65.76; H, 3.94; N, 16.43. Found: C, 65.22; H, 3.91; N, 16.50. m.p. (DSC): 208.46

The compounds of Examples A-210 and A-211 illustrate were prepared in accordance with the chemistry described above (particularly in Scheme X):

EXAMPLE A-210

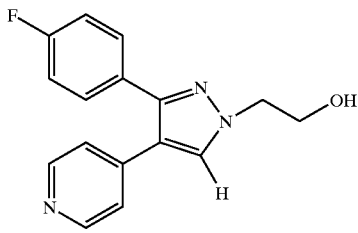

3-(4-fluorophenyl)-4-(4-pyridinyl)-1H-pyrazole-1-ethanol

The desoxybenzoin prepared in step 1 of Example A-208, 4-fluorobenzoyl-4'-pyridyl methane, (12.7 g, 0.059 moles) was mixed with 90% hydroxyethyl hydrazine (5.3 g, 0.062 moles) in 30 mL of ethanol containing 0.5 mL of acetic acid in a 500 mL Erlenmeyer flask. After gentle boiling (1 hour), a small sample was evacuated at high vacuum and examined by ¹H NMR to confirm completion of hydrazone formation. On cooling to ambient temperature, the reaction mass solidified to a yellow cake. DMF dimethylacetal (36 mL, 0.27 moles) was then added and the mixture heated to 80 C. for 10 min, at which point all the solids dissolved and a clear yellow viscous solution was obtained. The reaction mixture was immediately allowed to cool slowly to 25° C., and water (20 mL) was added dropwise with stirring, at which point a cloudy yellow oily suspension was obtained. The solution was now warmed to approximately 50–60° C., whereupon the solution turned clear yellow. Slow cooling to ambient temperature with stirring (a crystal seed if available speeds up the process) results in a copious formation of crystals. Suction filtration followed by washing with 10% ethanol-water (50 mL), followed by drying, furnishes 3-(4-fluorophenyl)-4-(4-pyridinyl)-1H-pyrazole-1-ethanol as a light yellow crystalline solid. Re-heating the filtrate to clarity as before, followed by cooling, yields additional product. The third and fourth recovery from the mother liquor on standing overnight furnishes the remaining 3-(4-fluorophenyl)-4-(4-pyridinyl)-1H-pyrazole-1-ethanol. Total yield: {12.3+3.3+0.4+0.4}=16.4 g. (97.6%). Mass spectrum, m/z=284. ¹H NMR was consistent with the proposed structure. Anal. calc'd for $C_{16}H_{14}FN_3O+H_2$): C, 63.78; H, 5.35; N, 13.95. Found: C, 63.55; H, 5.07; N, 13.69.

EXAMPLE A-211

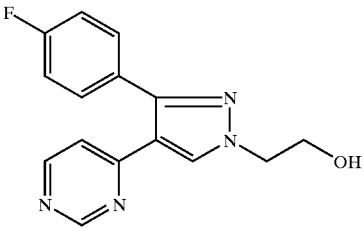

3-(4-fluorophenyl)-4-(4-pyrimidinyl)-1H-pyrazole-1-ethanol

This compound was prepared by the same procedure as described for Example A-210 except that the 4-picoline used to synthesize the desoxybenzoin was replaced with 4-methyl-pyrimidine.

The compound of Example A-212 was prepared in accordance with the chemistry of Scheme XI:

EXAMPLE A-212

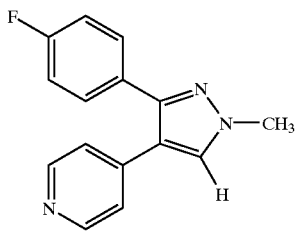

4-[3-(4-fluorophenyl)-1-methyl-1H-pyrazol-4-yl]pyridine

The vinyl amine prepared in Step 2 of Example A-208 (5.0 g, 0.0185 moles) was taken up in ethanol (75mL) and cooled to 0° C. Methyl hydrazine (1.79, 0.037 moles) in ethanol (75 mL) was added in one portion while maintaining the temperature at 0 to 10° C. After 3 hours at ambient temperature the solvent was removed and the residue taken up in methylene chloride (150 mL) and water (100 mL). The organic layer was separated, dried and concentrated to provide the crude regio-isomeric mixture as a light tan colored solid (80:20 by NMR in favor of the title compound). The crude isomeric mixture was taken up in 10% HCl (100 mL) and washed with methylene chloride (100 mL) and the water layer treated with activated charcoal (0.5 g). After filtration through Celite, the solution was neutralized with sodium hydroxide (20%) to pH 8 with good stirring and cooling. The cream colored precipitate was filtered, washed with water and dried. The solid (5 g) was dissolved in hot 10% heptane/toluene (70 mL) and allowed to cool slowly, first to ambient temperature and then to 15° C. Scratching the sides of the flask starts the crystallization process. After 2 hours of standing, the solids formed were filtered, washed with cold 50% toluene/heptane (25 mL) followed by hexane (25 mL) and dried to yield the pure title compound. $^1$H NMR confirmed the structure (including regiochemistry using NOE experiments). Yield: 2.1 g. (45%). Mass spectrum, m/z=254 (base peak). Anal. calc'd for $C_{15}H_{12}FN_3$+0.2 $H_2O$: C, 70.15; H, 4.86; N, 16.4. Found: C, 70.18; H, 4.6; N, 16.47.

The compound of Example A-213 was prepared in accordance with the chemistry of Scheme XII:

EXAMPLE A-213

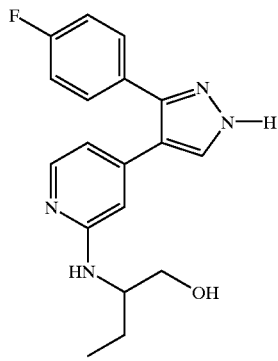

2-[[4-[3-(4-fluorophenyl)-1H-pyrazol-4-yl]-2-pyridinyl]amino]-1-butanol

An intimate mixture of 2-fluoro-pyridinyl pyrazole (0.2 g, (prepared by the same procedure as described for Example A-210 except that the 4-picoline used to synthesize the desoxybenzoin was replaced with 2-fluoro-4-methylpyridine) and (R,S)-2-amino-1-butanol (4 fold molar excess) was heated to 210–220° C. in a sealed vial for 1.5 hours. After cooling to 100° C. the vial was cautiously opened and 5 mL of toluene and 5 mL of water were added and stirred well for 1 hour. The solid obtained, 2-[[4-[3-(4-fluorophenyl)-1H-pyrazol-4-yl]-2-pyridinyl]amino]-1-butanol, was suction-filtered and washed with an additional 5 mL of water followed by toluene and dried. Yield: 190 mg. (71%). Mass spectrum, m/z=343. $^1$H NMR was consistent with the proposed structure.

The compound of Example A-214 was prepared in accordance with the chemistry of Scheme XIII:

EXAMPLE A-214

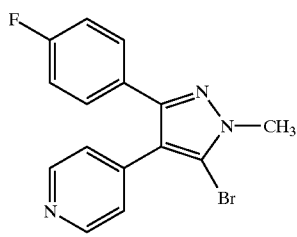

4-[5-bromo-3-(4-fluorophenyl)-1-methyl-1H-pyrazol-4-yl]pyridine

To a solution of 4-[3-(4-fluorophenyl)-1-methyl-1H-pyrazol-4-yl]pyridine (2.7 g, 10.67 mmol) (prepared in accordance with Example A-212) in acetic acid (30 mL) and DMF (13 mL) was added bromine (19.5 g, 122.0 mmol). The solution was heated at 80° C. overnight. TLC indicated that the reaction was complete. The mixture was quenched slowly with $K_2CO_3$ (25 g). When pH was about 5, a precipitate was formed. The precipitate was washed with water (50 mL×5) to give 4-[5-bromo-3-(4-fluorophenyl)-1-methyl-1H-pyrazol-4-yl]pyridine (1.249, 35%): mp 174.38° C.; Mass spectrum m/z=332, 334; $^1$H NMR was consistent with the proposed structure. Anal. Calc'd for $C_{15}H_{11}N_3FBr.0.2\ H_2O$: C, 53.66; H, 3.42; N, 12.51. Found: C, 53.58; H, 3.12; N, 12.43.

The compound of Example A-215 was prepared in accordance with the chemistry of Scheme XIV:

EXAMPLE A-215

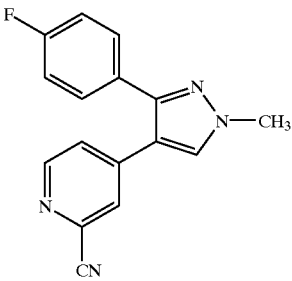

4-[3-(4-fluorophenyl)-1H-pyrazol-4-yl]-2-pyridinecarbonitrile

Step 1

To a solution of 4-[3-(4-fluorophenyl)-1H-pyrazol-4-yl]pyridine (4.3 g, 17.97 mmol) (prepared in accordance with Example A-208) in methanol (100 mL) was added 3-chloroperoxybenzoic acid (5.44 g in 57% purity, 17.97 mmol). The solution was stirred at 25° C. for overnight. The mixture was concentrated. $K_2CO_3$ (10%, 100 mL) was added to the residue. A precipitate was formed, filtered and washed with water (30 mL×3) to give the corresponding N-oxide (3.764 g, 81.66%).

Step 2

To a suspension of the N-oxide prepared in step 1 (0.40 g, 1.567 mmol) in DMF (5 mL) was added trimethysilyl cyanide (0.3 mL, 2.25 mmol). The mixture was stirred for 15 minutes at 25° C. Dimethylcarbamyl chloride (0.8 mL, 8.69 mmol) was added. The mixture was stirred at 25° C. for 2 hours. TLC indicated that the starting materials were gone. The mixture was partitioned into ethyl acetate:water (100 mL:20 mL). The organic layer was washed with $K_2CO_3$ (10%, 20 mL), water (50 mL), brine (50 mL), dried over $MgSO_4$, filtered and concentrated to give 4-[3-(4-fluorophenyl)-1H-pyrazol-4-yl]-2-pyridinecarbonitrile (0.23 g, 56% yield): mp 209.22° C. ; Mass spectrum (chemical ionization): m/z=265; $^1H$ NMR was consistent with the proposed structure. Anal. Calc'd for $C_{15}H_9N_4F.0.2\ H_2$): C, 67.26; H, 3.54; N, 20.92. Found: C, 67.44; H, 3.40; N, 20.69.

The compound of Example A-216 was prepared in accordance with the chemistry of Scheme XV:

EXAMPLE A-216

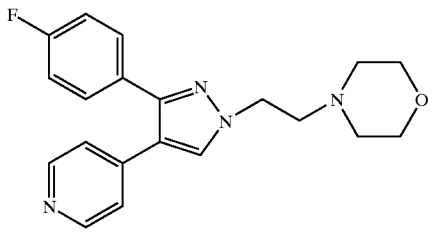

4-[2-[3-(4-fluorophenyl)-4-(4-pyridinyl)-1H-pyrazol-1-yl]ethyl]morpholine

Step 1

3-(4-fluorophenyl)-4-(4-pyridinyl)-1H-pyrazole-1-ethanol (prepared in accordance with Example A-210) (10.0 g, 0.0353 moles) was suspended in pyridine (100 mL) and cooled to 0° C. Methane sulfonyl chloride (4.4 g, 0.0388 moles) was added slowly while maintaining the temperature at 0° C. After stirring overnight at 10° C., chilled water (100 mL) and methylene chloride (150 mL) was added and the two layers separated. The water layer was re-extracted with 100 mL of methylene chloride and the organic layer dried and concentrated to a paste. After drying at high vacuum, a light tan colored cake was obtained which was triturated with ether (75 mL), filtered and dried to furnish a cream colored solid in 79% yield (10.1 g). $^1H$ NMR was consistent with the proposed structure. The compound was used as such for step 2.

Step 2

The mesylate prepared in step 1 (5.0 g, 0.0138 moles) was dissolved in an eight fold excess of morpholine (9.6 g, 0.11 moles) in methanol (50 mL) and heated at reflux for 3 to 4 hours. After an NMR sample confirmed completion, the mixture was concentrated and taken up in methylene chloride (150 mL) and washed with water (100 mL) and then with 75 mL of 5% HCl. The water layer was neutralized to pH 8 and extracted with methylene chloride (100 mL). On drying and concentration a light yellow pasty solid was obtained which was triturated with 25 mL of ether to furnish a solid. Re-crystallization from toluene/hexane provided 4-[2-[3-(4-fluorophenyl)-4-(4-pyridinyl)-1H-pyrazol-1-yl] ethyl]morpholine as a solid. Yield: 4.5 g (86%). Mass spectrum, m/z=353. $^1H$ NMR was consistent with the proposed structure. Anal. calc'd for $C_{20}H_{21}FN_4O$: C, 68.16; H, 6.01; N, 15.90. Found: C, 68.20; H, 6.21; N, 15.80.

The compound of Example A-217 was prepared in accordance with the chemistry of Scheme XVI:

EXAMPLE A-217

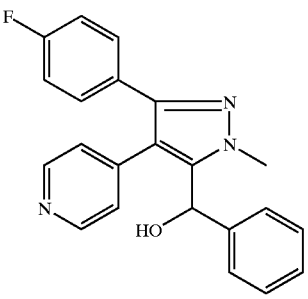

3-(4-fluorophenyl)-1-methyl-α-phenyl-4-(4-pyridinyl)-1H-pyrazole-5-methanol

To solid magnesium (60 mg, 5 mmol) under nitrogen was added a solution of 4-[5-bromo-3-(4-fluorophenyl)-1-methyl-1H-pyrazol-4-yl]pyridine (450 mg, 1.35 mmol) (prepared in accordance with Example A-214) in tetrahydrofuran (7 mL). The mixture was heated at 40° C. for 2 hours. Benzaldehyde (1 mL) was added. The mixture was heated to 45° C. for 2 hours. It was quenched with HCl (10 mL, 1N) and washed with ethyl acetate. The aqueous acid layer was basified and extracted with ethyl acetate. The organic layer was washed with water, brine, dried over $MgSO_4$, filtered and concentrated to give a residue. The residue was purified with a silica gel column to give the title compound (59 mg, 12% yield). MS: m/z=360 (M+1); $^1H$ NMR was consistent with the proposed structure. Anal. Calc'd for $C_{22}H_{18}N_2OF.0.6EtOAC$: C, 71.1; H, 5.6; N, 10.2; Found: C, 70.9; H, 5.47; N, 10.2.

The compound of Example A-218 was prepared in accordance with the chemistry described above (particularly Scheme XVII):

EXAMPLE A-218

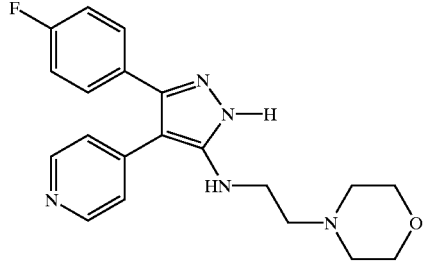

N-[5-(4-fluorophenyl)-4-(4-pyridinyl)-1H-pyrazol-3-yl]-4-morpholineethanamine

The starting desoxybenzoin prepared in step 1 of Example A-208, 4-fluorobenzoyl-4'-pyridyl methane, (1.0 g, 0.0046 moles) was dissolved in 10 mL of DMF and cooled to −10°

C. (dry ice-aqueous isopropanol). N-chlorosuccinimide (0.62 g, 0.0046 moles) was added in one portion while maintaining the temperature at −10° C. After 5 minutes the thiosemicarbazide (0.0046 moles) was added in one portion at 0° C. and allowed to warm to ambient temperature slowly over 1 hour. After stirring overnight, the solvent was removed at high vacuum and water and toluene (25 mL each) added and stirred well. The toluene layer was separated and the water layer (starting pH of 5.5) treated with bicarbonate to pH 8. The fine precipitate formed was filtered and washed with water, toluene and ether. A final trituration with ether (25 mL) furnished an off white solid, N-[5-(4-fluorophenyl)-4-(4-pyridinyl)-1H-pyrazol-3-yl]-4-morpholineethanamine, which was re-filtered and dried. Yield: 0.95 g. (56%). Mass Spec. m/z: 368 (base peak). Anal. Calc'd for $C_{20}H_{22}FN_5O$. C, 65.38; H, 6.04; N, 19.06. Found: C, 64.90; H, 5.92; N, 18.67.

EXAMPLE A-219

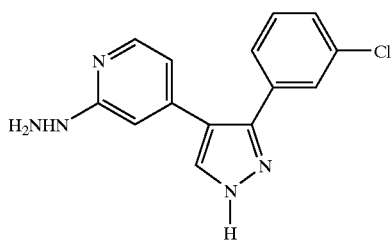

4-[3-(3-chlorophenyl)-1H-pyrazol-4-yl]-2(1H)-pyridinone hydrazone

Step 1: Preparation of (E)-2-(2-bromo-4-pyridinyl)-N,N-dimethylethenamine

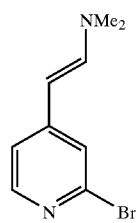

4-Methyl-2-bromopyridine (1.0 g, 5.8 mmol) and t-butoxybis(dimethylamino)methane (5 ml) were heated to 150° C. for 16 hours. 4-Methyl-2-bromopyridine was prepared as set forth in B. Adger et al., *J. Chem. Soc.*, Perkin Trans. 1, pp. 2791–2796 (1988), which is incorporated herein by reference. The contents were evaporated and the residue dissolved in ethyl acetate and washed with water. The organic layer was dried over magnesium sulfate and solvent removed in vacuo to give 1.0 g of (E)-2-(2-bromo-4-pyridinyl)-N,N-dimethylethenamine as an oil suitable for use in step 2.

Step 2: Preparation of (Z)-2-(2-bromo-4-pyridinyl)-1-(3-chlorophenyl)-3-(dimethylamino)-2-propen-1-one

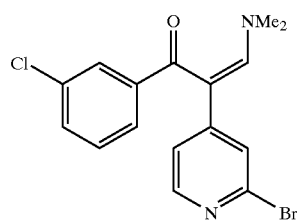

The product from step 1 (1.0 g, 4.4 mmol) was dissolved in methylene chloride (15 ml). Triethylamine (900 mg, 8.8 mmol) was added at 0° C., followed by the addition of 3-chlorobenzoyl chloride (350 mg, 4.5 mmol). The mixture was stirred under nitrogen for 16 hours. Solvent was evaporated in vacuo and the residue was dissolved in ether (25 ml), stirred with magnesium sulfate (500 mg) and silica gel (500 mg), and filtered. Ether was evaporated and the residue was chromatographed on silica gel using mixtures of acetone and methylene chloride as eluents to give 670 mg of the product, (Z)-2-(2-bromo-4-pyridinyl)-1-(3-chlorophenyl)-3-(dimethylamino)-2-propen-1-one, as a glass which was used in step 3 without further purification.

Step 3: Preparation of 2-bromo-4-[3-(3-chlorophenyl)-1H-pyrazol-4-yl]pyridine

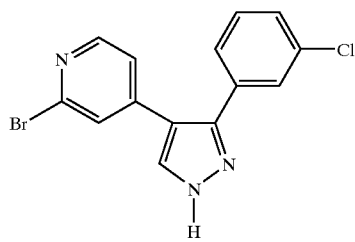

A solution of the product from step 2 (650 mg, 1.8 mmol) and hydrazine monohydrate (100 mg) in ethanol (10 ml) was refluxed for 24 hours. Solvent was evaporated and the residue was chromatographed on silica gel using mixtures of ethyl acetate and toluene as eluents to give 2-bromo-4-[3-(3-chlorophenyl)-1H-pyrazol-4-yl]pyridine (190 mg, 31%) as an oil: Anal. Calc'd for $C_{14}H_9BrClN_3$: C, 50.25; H, 2.71; N, 12.56. Found: C, 50.10; H, 2.60; N, 12.40.

Continued elution with mixtures of ethyl acetate and methanol gave 4-[3-(3-chlorophenyl)-1H-pyrazol-4-yl]-2(1H)-pyridinone hydrazone (190 mg, 36%) as a crystalline solid: m.p. 163–164° C.; MS (M+H)=286. Anal. Calc'd for $C_{14}H_{12}N_5Cl$: C, 58.85; H, 4.23; N, 24.51. Found: C, 58.53; H, 4.28; N, 24.87.

EXAMPLE A-220

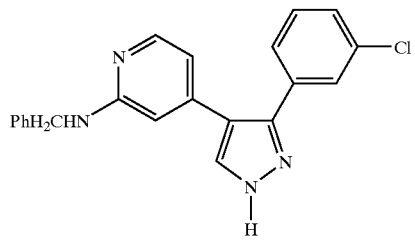

4-[3-(3-chlorophenyl)-1H-pyrazol-4-yl]-N-(phenylmethyl)-2-pyridinamine

A solution of the bromopyridine compound prepared in step 3 of Example A-219 (150 mg, 0.5 mmol) in benzylamine (5 ml) was heated at 175° C. for six hours. After cooling, excess benzylamine was removed by high vacuum distillation and ethyl acetate added to the residue.

After washing the organic phase with water and drying over magnesium sulfate, the solvent was removed in vacuo and the residue chromatographed on silica gel using mixtures of ethyl acetate and toluene to give 4-[3-(3-chlorophenyl)-1H-pyrazol-4-yl]-N-(phenylmethyl)-2-pyridinamine (110 mg, 61%) as a solid, m.p. 179–180° C.

Anal. Calc'd For $C_{21}H_{17}ClN_4$: C, 69.90; H, 4.75; N, 15.53. Found: C, 69.69; H, 4.81; N, 15.11.

EXAMPLE A-221

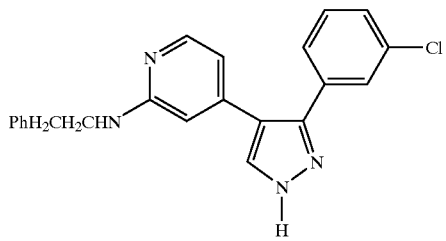

4-[3-(3-chlorophenyl)-1H-pyrazol-4-yl]-N-(phenylethyl)-2-pyridinamine

A solution of the bromopyridine compound prepared in step 3 of Example A-219 (250 mg, 0.75 mmol) in phenethylamine (5 ml) was heated at 175° C. for six hours under a nitrogen atmosphere. The excess amine was distilled off under high vacuum and the residue was dissolved in ethyl acetate and washed with water. After drying over magnesium sulfate and removal of solvent, the residue was chromatographed on silica gel with mixtures of ethyl acetate and toluene to give 4-[3-(3-chlorophenyl)-1H-pyrazol-4-yl]-N-(phenylethyl)-2-pyridinamine (230 mg, 81%) as a solid, m.p. 185–186° C.

Anal. Calc'd For $C_{22}H_{19}ClN_4$: C, 70.49; H, 5.11; N, 14.95. Found: C, 70.29; H, 5.15; N, 14.66.

EXAMPLE A-222

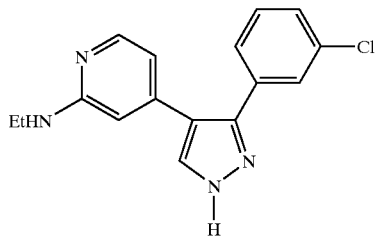

4-[3-(3-chlorophenyl)-1H-pyrazol-4-yl]-N-ethyl-2-pyridinamine

A solution of the bromopyridine compound prepared in step 3 of Example A-219 (300 mg, 0.9 mmol) in ethylamine (3.5 ml) and ethanol (5 ml) as heated at 150° C. in a sealed tube for 9 hours. The solvent was removed in vacuo and the residue chromatographed on silica gel with 70 ethyl acetate/30 toluene to give 4-[3-(3-chlorophenyl)-1H-pyrazol-4-yl]-N-ethyl-2-pyridinamine (125 mg, 46%) as a solid, m.p. 186–187° C.

Anal. Calc'd For $C_{16}H_{15}ClN_4$: C, 64.32; H, 7.06; N, 18.75. Found: C, 64.42; H, 7.01; N, 18.45.

The compounds of Examples A-223 through A-226 were synthesized in accordance with the chemistry described above (particularly in Scheme XVIII) by selection of the corresponding starting reagents:

EXAMPLE A-223

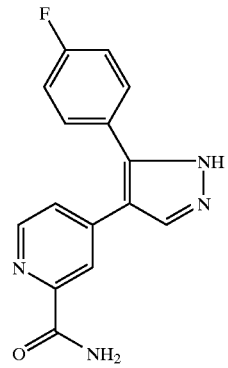

4-[3-(4-fluorophenyl)-1H-pyrazol-4-yl]-2-pyridinecarboxamide

Step 1

To a suspension of 4-[3-(4-fluorophenyl)-1H-pyrazol-4-yl]pyridine (prepared as set forth in Example A-208) (8.8 g, 0.037 mol) in methylene chloride was added m-chloroperoxybenzoic acid (mCPBA) in one portion at room temperature. After stirring for 16 hours, solvent was removed and the residue was treated with saturated sodium bicarbonate solution. The precipitate was filtered, air-dried to give 8.2 g of a product as a white solid (87%), mp: 207–209° C.

Step 2: Preparation of 4-[3-(4-fluorophenyl)-1H-pyrazol-4-yl]-2-pyridinecarbonitrile To a solution of the product of step 1 (5.1 g, 0.02 mol) in 20 mL of DMF was added trimethylsilyl cyanide (2.5 g, 0.025 mol), followed by a solution of N,N-dimethylcarbamoyl chloride (2.7 g, 0.025 mol) in 5 mL of DMF at room temperature. After stirring overnight, the reaction mixture was basified by 200 mL of 10% potassium carbonate water solution. The aqueous phase was extracted with ethyl acetate. The organic layer was washed with brine, dried over magnesium sulfate and filtered. The filtrate was concentrated and the crude was triturated with hexane and filtered to give 4.3 g of 4-[3-(4-fluorophenyl)-1H-pyrazol-4-yl]-2-pyridinecarbonitrile (90%) as a pale yellow solid, mp: 238–239° C.

Step 3: Preparation of 4-[3-(4-fluorophenyl)-1H-pyrazol-4-yl]-2-pyridinecarboxamide To a solution of 4-[3-(4-fluorophenyl)-1H-pyrazol-4-yl]-2-pyridinecarbonitrile from step 2 (0.45 g, 0.0017 mol) in 10 mL of DMSO was added hydrogen peroxide (0.24 mL of 30% aqueous solution, 1.7 mmol) and potassium carbonate (0.04 g, 0.4 mmol) at 0° C. The mixture was stirred for 1 hour while allowing it to warm to room temperature. Water was added and the precipitate was collected by filtration and air-dried to give 0.32 g of 4-[3-(4-fluorophenyl)-1H-pyrazol-4-yl]-2-pyridinecarboxamide as a white solid (67% yield), mp: 230–231° C. Anal. Calc'd for $C_{15}H_{11}FN_4O$: C, 63.83; H, 3.93; N, 19.85. Found C, 63.42; H, 3.66; N, 19.58.

EXAMPLE A-224

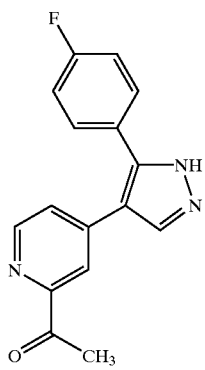

Methyl 4-[3-(4-fluorophenyl)-1H-pyrazol-4-yl]-2-pyridinecarboxylate

To a suspension of 4-[3-(4-fluorophenyl)-1H-pyrazol-4-yl]-2-pyridinecarboxamide prepared as set forth in Example A-223 (2.9 g, 0.01 mol) in 50 mL of methanol was added N,N-dimethylformamide dimethyl acetal (3.67 g, 0.03 mol) dropwise. The reaction mixture was stirred at room temperature overnight and heated at reflux for 4hours. After cooling, the precipitate was collected by filtration and air-dried to give 2.0 g of methyl 4-[3-(4-fluorophenyl)-1H-pyrazol-4-yl]-2-pyridinecarboxylate as a white solid (69% yield), mp: 239–241° C. Anal. Calc'd for $C_{16}H_{12}FN_3O_2$: C, 64.64; H, 4.07; N, 14.13. Found: C, 64.36; H, 4.10; N, 14.27.

EXAMPLE A-225

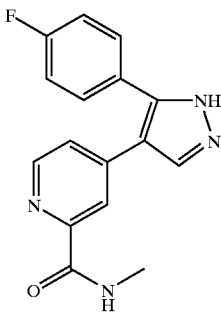

4-[3-(4-fluorophenyl)-1H-pyrazol-4-yl]-N-methyl-2-pyridinecarboxamide

A mixture of methyl 4-[3-(4-fluorophenyl)-1H-pyrazol-4-yl]-2-pyridinecarboxylate prepared as set forth in Example A-224 (0.45 g, 1.5 mmol) and 20 mL of methylamine (40% aqueous solution) was heated at 120° C. in a sealed tube for 16 hours. After cooling, water was added and the aqueous phase was extracted with ethyl acetate. The organic layer was washed with brine, dried over magnesium sulfate and filtered. The filtrate was concentrated to afford 0.4 g of 4-[3-(4-fluorophenyl)-1H-pyrazol-4-yl]-N-methyl-2-pyridinecarboxamide as a white solid, mp: 88–89° C. Anal. Calc'd for $C_{16}H_{13}FN_4O+0.4 H_2O$: C, 63.32; H, 4.58; N, 18.46. Found C, 63.10; H, 4.62; N, 18.35.

EXAMPLE A-226

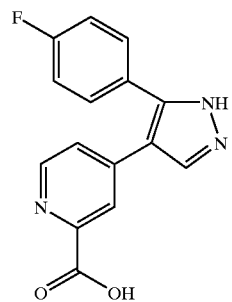

4-[3-(4-fluorophenyl)-1H-pyrazol-4-yl]-2-pyridinecarboxylic acid

To a solution of 4-[3-(4-fluorophenyl)-1H-pyrazol-4-yl]-2-pyridinecarboxylate prepared as set forth in Example A-224 (0.90 g, 0.003 mol) in 10 mL of ethanol was added a solution of sodium hydroxide (0.24 g, 0.006 mol) in 5 mL of water. The reaction mixture was heated at reflux for 10 hours. After the removal of solvent, the residue was dissolved in water and acidified with citric acid solution to pH 5. Then the aqueous phase was extracted with ethyl acetate and the organic phase was dried over magnesium sulfate and concentrated. The crude was purified by treating with ether to give 0.62 g of 4-[3-(4-fluorophenyl)-1H-pyrazol-4-yl]-2-pyridinecarboxylic acid as a white solid (73% yield), mp: 245° C.(dec). Anal Calc'd for $C_{15}H_{10}FN_3O+0.2 H_2O$: C, 62.80; H, 3.65; N, 14.65. Found: C, 62.77; H, 3.42; N, 14,58.

Additional compounds of the present invention which were prepared according to one or more of above reaction schemes (particularly Schemes IX through XVIII) are disclosed in Table 3. The specific synthesis scheme or schemes as well as the mass spectroscopy and elemental analysis results for each compound also are disclosed in Table 3.

TABLE 3

| Example | General Procedure | MS M + 1 | Microanalysis | | | | | | water added | EtOAc added |
|---|---|---|---|---|---|---|---|---|---|---|
| | | | C calc | C found | H calc | H found | N calc | N found | | |
| A-227 | IX | 240 | 69 | 69 | 4.3 | 4.6 | 17.2 | 16.8 | 0.25 | |
| A-228 | IX | 266 | 65.69 | 65.69 | 4.41 | 4.33 | 15.32 | 14.98 | | |
| A-229 | XI | 254 | 70.6 | 70.6 | 4.8 | 4.5 | 16.5 | 16.3 | 0.1 | |
| A-230 | IX | 256 | 65.76 | 65.48 | 3.94 | 3.78 | 16.43 | 16.52 | | |
| A-231 | XI | 280 | 64.18 | 63.95 | 4.39 | 4.31 | 13.86 | 13.90 | | |

TABLE 3-continued

| | | | Microanalysis | | | | | | | |
|---|---|---|---|---|---|---|---|---|---|---|
| Example | General Procedure | MS M + 1 | C calc | C found | H calc | H found | N calc | N found | water added | EtOAc added |
| A-232 | XI | 271 | 66.79 | 66.79 | 4.48 | 4.24 | 15.58 | 15.32 | | |
| A-233 | XI | 284 | 66.9 | 66.8 | 5 | 5 | 14.6 | 14.9 | 0.2 | |
| A-234 | XI | 270 | 65.9 | 65.6 | 4.6 | 4.6 | 15.4 | 15.4 | 0.2 | |
| A-235 | XI | 264 | 77 | 76.7 | 6.5 | 6.5 | 15.8 | 15.7 | 0.1 | |
| A-236 | IX | 221 | 75.38 | 75.44 | 5.06 | 5.1 | 18.84 | 19 | 0.1 | |
| A-237 | IX | 290 | 61.52 | 61.67 | 3.58 | 3.51 | 14.35 | 14.32 | | |
| A-238 | XI | 304 | 63.36 | 63.28 | 3.99 | 3.91 | 13.85 | 13.83 | | |
| A-239 | IX | 258 | 65.37 | 65.39 | 3.53 | 3.52 | 16.33 | 16.31 | | |
| A-240 | IX | 274 | 61.44 | 61.14 | 3.31 | 3.01 | 15.35 | 14.95 | | |
| A-241 | IX | 300 | 56.02 | 55.99 | 3.36 | 3.26 | 14.00 | 14.01 | | |
| A-242 | XI | 272 | 66.42 | 66.41 | 4.09 | 4.04 | 15.49 | 15.32 | | |
| A-243 | XI | 314 | 57.34 | 57.22 | 3.85 | 3.68 | 13.37 | 13.27 | | |
| A-244 | IX | 342 | 76.39 | 76.16 | 4.81 | 4.51 | 12.31 | 12.05 | 0.25 | |
| A-245 | XII | 341 | 64.89 | 64.65 | 6.36 | 6.17 | 15.93 | 15.82 | 0.6 | |
| A-246 | XII | 391 | 66.08 | 66.18 | 5.04 | 5.56 | 14.01 | 12.26 | 0.5 | |
| A-247 | XII | 362 | 64.46 | 64.16 | 4.65 | 4.34 | 18.79 | 18.65 | 0.6 | |
| A-249 | XII | 258 | 64.91 | 64.84 | 3.58 | 3.63 | 16.22 | 15.98 | 0.1 | |
| A-250 | IX | 348 | 48.44 | 48.07 | 2.9 | 2.82 | 12.1 | 12.01 | | |
| A-251 | XI | 362 | 49.88 | 49.89 | 3.35 | 3.51 | 11.63 | 11.54 | | |
| A-252 | XI | 304 | 63.36 | 63.34 | 3.99 | 3.96 | 13.85 | 13.81 | | |
| A-253 | XII | 377 | 68.24 | 68.17 | 5 | 4.71 | 14.47 | 14.34 | 0.6 | |
| A-254 | XII | 363 | 66.31 | 66.12 | 4.77 | 4.31 | 14.73 | 14.6 | 1 | |
| A-215 | XIV | 265 | 67.3 | 67.4 | 3.5 | 3.4 | 20.9 | 20.7 | 0.2 | |
| A-255 | XII | 298 | 64.63 | 64.64 | 5.42 | 5.41 | 23.55 | 23.32 | | |
| A-256 | XI | 272 | 66.42 | 66.58 | 4.09 | 4.26 | 15.49 | 14.78 | | |
| A-257 | IX | 276 | 60.11 | 60.4 | 3.06 | 3.18 | 15.02 | 14.73 | 0.25 | |
| A-258 | IX | 254 | | | | | | | | |
| A-259 | XI | 268 | 71.89 | 71.63 | 5.28 | 5.24 | 15.72 | 15.84 | | |
| A-260 | X | 290 | 62.28 | 62.41 | 3.48 | 3.48 | 14.53 | 14.51 | | |
| A-261 | X, XV | 311 | 69.26 | 69.2 | 6.2 | 6.25 | 17.95 | 17.89 | 0.1 | |
| A-262 | XI | 376 | 72.71 | 72.5 | 5.17 | 4.98 | 11.06 | 10.99 | 0.25 | |
| A-263 | XII | 428 | 70.81 | 70.59 | 6.28 | 6.45 | 15.88 | 15.08 | 0.75 | |
| A-264 | XII | 326 | 63.79 | 63.76 | 6.39 | 6.09 | 20.66 | 20.45 | 0.75 | |
| A-265 | IX | 400 | 66.18 | 66.77 | 4.1 | 4.23 | 16.78 | 15.83 | 1 | |
| A-266 | XII | 368 | 62.32 | 62.38 | 6.28 | 6.5 | 18.17 | 17.56 | 1 | |
| A-267 | XI | 302 | 62.66 | 62.85 | 4.47 | 4.34 | 13.7 | 13.53 | 0.4 | |
| A-268 | XII | 349 | 62.9 | 63.2 | 5.2 | 4.8 | 22.7 | 22.5 | 0.75 | 0.1 |
| A-269 | XI, XV | 371 | 61.85 | 61.84 | 5.71 | 5.24 | 14.42 | 14.17 | 1 | |
| A-270 | XI, XV | 404 | 70.66 | 70.7 | 4.82 | 4.61 | 10.3 | 10.15 | 0.25 | |
| A-271 | XI, XV | 329 | 65.8 | 65.3 | 5.5 | 5.6 | 17.1 | 16.8 | | |
| A-272 | XI | 406 | 69.95 | 70.13 | 5.35 | 5.28 | 10.14 | 9.89 | 0.5 | |
| A-273 | XI | 354 | 66.9 | 67.2 | 6.9 | 6.6 | 19.1 | 18.7 | 0.2 | 0.1 |
| A-274 | XI, XII, XV | 434 | 63.6 | 63.1 | 6.3 | 5.8 | 14.4 | 14 | 2 | 0.2 |
| A-275 | XI, XV | 433 | 70.44 | 70.74 | 6.18 | 6.3 | 12.64 | 12.05 | 0.6 | |
| A-276 | XI, XII, XV | 476 | 65.9 | 66.2 | 6.1 | 6.1 | 13.3 | 13.6 | 0.5 | 0.5 |
| A-277 | XII | 338 | 61.11 | 63.02 | 6.48 | 6.39 | 18.75 | 16.61 | | |
| A-278 | XI, XV | 357 | 64.2 | 63.8 | 6.5 | 6 | 15 | 14.8 | 1 | |
| A-279 | XI, XII, XV | 462 | 67.4 | 67.1 | 6.7 | 6.2 | 13.6 | 13.7 | 0.6 | 0.5 |
| A-280 | XII | 299 | 61.27 | 61.47 | 5.37 | 5.11 | 17.86 | 17.21 | 0.9 | |
| A-281 | XII | 313 | 64.63 | 64.94 | 5.55 | 5.63 | 17.73 | 17.48 | 0.2 | |
| A-282 | XII | 313 | 64.63 | 64.81 | 5.55 | 5.43 | 17.73 | 17.38 | 0.3 | |
| A-283 | XI, XII | 407 | 67.2 | 67 | 5 | 5.2 | 13.6 | 13.2 | 0.25 | |
| A-284 | XI, XV | 339 | 70 | 70.3 | 6.9 | 6.9 | 16.3 | 16.2 | 0.25 | |
| A-285 | XI, XII, XV | 476 | 68.2 | 68.5 | 5.7 | 6.2 | 14.7 | 13.6 | | |
| A-286 | XVII | 382 | 59.77 | 59.69 | 6.81 | 6.56 | 16.6 | 16.65 | 2.25 | |
| A-287 | XVII | 340 | 56.07 | 56.26 | 7.31 | 7.1 | 17.21 | 17.27 | 3.75 | |
| A-288 | XVII | 293 | 69.42 | 69.4 | 4.52 | 4.6 | 19.05 | 19.09 | 0.1 | |
| A-289 | XI, XII | 407 | 68 | 67.5 | 5 | 4.5 | 13.8 | 13.5 | | |
| A-290 | XI, XII | 407 | 64 | 64.5 | 5.3 | 4.9 | 13 | 12.4 | 1.4 | |
| A-291 | IX | 290 | 74.7 | 74.9 | 4.2 | 4.2 | 14.5 | 14.5 | | |
| A-292 | XVII | 326 | 61.22 | 61.46 | 4.77 | 4.53 | 16.8 | 16.97 | 0.4 | |
| A-293 | XVII | 313 | 55.75 | 55.98 | 4.85 | 4.02 | 16.25 | 16.37 | 1.8 | |
| A-294 | XI | 278 | 73.6 | 73.2 | 4.4 | 4.2 | 15.2 | 15 | | |
| A-295 | XI | 278 | 67.9 | 67.7 | 4.9 | 4.3 | 14 | 13.7 | 1.3 | |
| A-296 | IX | | 70.3 | 70.4 | 4.5 | 4.7 | 25.2 | 25.4 | | |
| A-297 | IX | | 57.9 | 57.7 | 3.1 | 2.9 | 14.5 | 14.5 | | |

EXAMPLE A-227

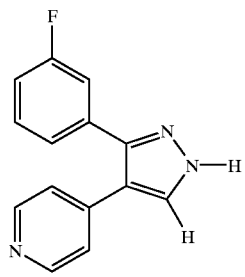

4-[3-(3-fluorophenyl)-1H-pyrazol-4-yl]pyridine

EXAMPLE A-228

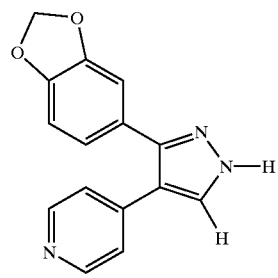

4-[3-(1,3-benzodioxol-5-yl)-1H-pyrazol-4-yl]
pyridine

EXAMPLE A-229

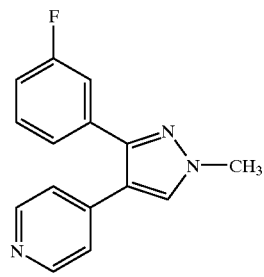

4-[3-(3-fluorophenyl)-1-methyl-1H-pyrazol-4-yl]
pyridine

EXAMPLE A-230

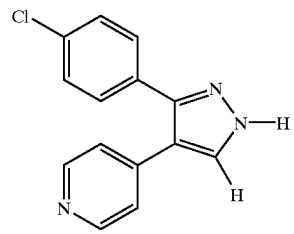

4-[3-(4-chlorophenyl)-1H-pyrazol-4-yl]pyridine

EXAMPLE A-231

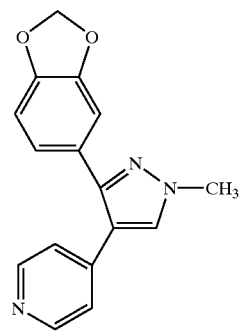

4-[3-(1,3-benzodioxol-5-y)-1-methyl-1H-pyrazol-4-
yl]pyridine

EXAMPLE A-232

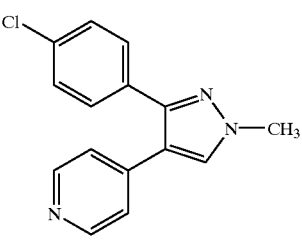

4-[3-(4-chlorophenyl)-1-methyl-1H-pyrazol-4-yl]
pyridine

EXAMPLE A-233

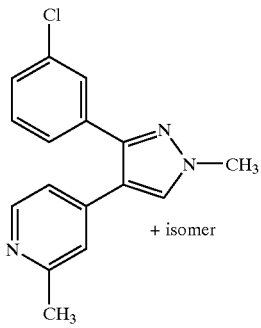

4-[3-(3-chlorophenyl)-1-methyl-1H-pyrazol-4-yl]-2-
methylpyridine and 4-[5-(3-chlorophenyl)-1-methyl-
1H-pyrazol-4-yl]-2-methylpyridine

EXAMPLE A-234

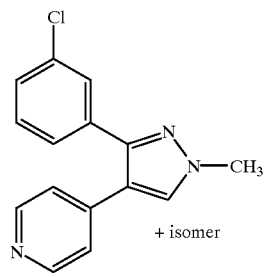

+ isomer

4-[3-(3-chlorophenyl)-1-methyl-1H-pyrazol-4-yl]
pyridine and 4-[5-(3-chlorophenyl)-1-methyl-1H-
pyrazol-4-yl]pyridine

EXAMPLE A-235

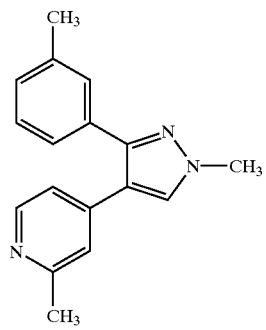

2-methyl-4-[1-methyl-3 (or 5)-(3-methylphenyl)-
1H-pyrazol-4-yl]pyridine

EXAMPLE A-236

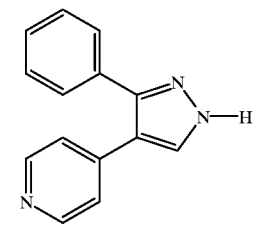

4-(3-phenyl-1H-pyrazol-4-yl)pyridine

EXAMPLE A-237

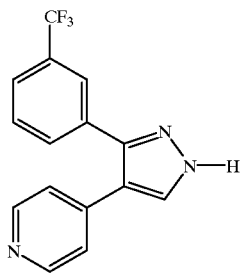

4-[3-[3-(trifluoromethyl)phenyl]-1H-pyrazol-4-yl]
pyridine

EXAMPLE A-238

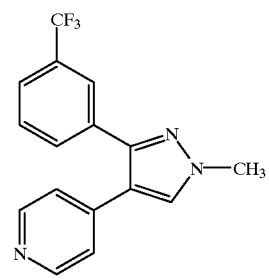

4-[1-methyl-3-[3-(trifluoromethyl)phenyl]-1H-
pyrazol-4-yl]pyridine

EXAMPLE A-239

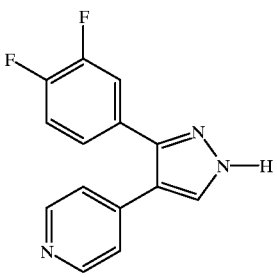

4-[3-(3,4-difluorophenyl)-1H-pyrazol-4-yl]pyridine

EXAMPLE A-240

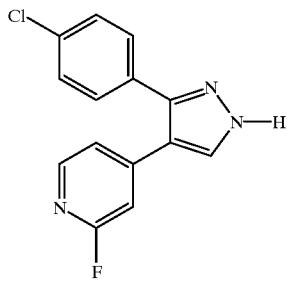

4-[3-(4-chlorophenyl)-1H-pyrazol-4-yl]-2-fluoropyridine

EXAMPLE A-241

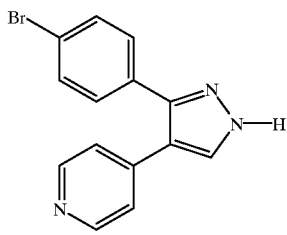

4-[3-(4-bromophenyl)-1H-pyrazol-4yl]pyridine

EXAMPLE A-242

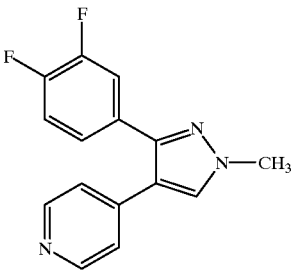

4-[3-(3,4-difluorophenyl)-1-methyl-1H-pyrazol-4-yl]pyridine

EXAMPLE A-243

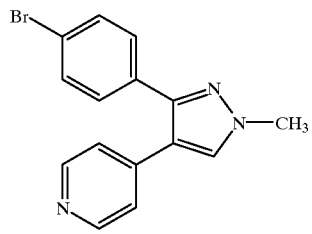

4-[3-(4-bromophenyl)-1-methyl-1H-pyrazol-4-yl]pyridine

EXAMPLE A-244

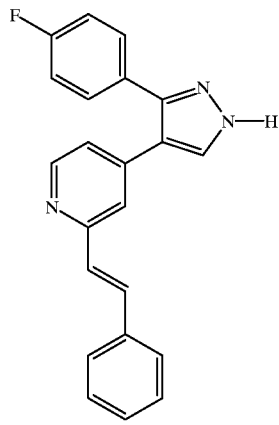

(E)-4-[3-(4-fluorophenyl)-1H-pyrazol-4-yl]-2-(2-phenylethenyl)pyridine

EXAMPLE A-245

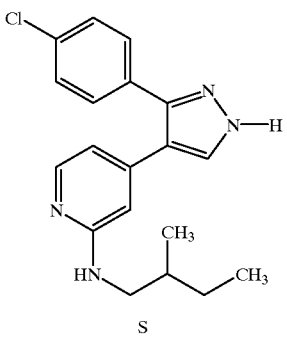

(S)-4-[3-(4-chlorophenyl)-1H-pyrazol-4-yl]-N-(2-methylbutyl)-2-pyridinamine

EXAMPLE A-246

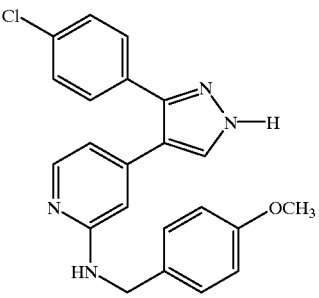

4-[3-(4-chlorophenyl)-1H-pyrazol-4-yl]-N-[(4-methoxy-phenyl)methyl]-2-pyridinamine

EXAMPLE A-247

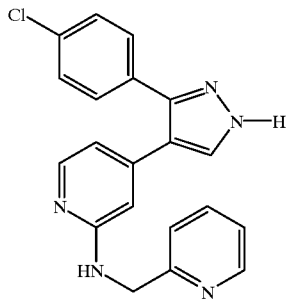

N-[4-[3-(4-chlorophenyl)-1H-pyrazol-4-yl]-2-pyridinyl]-2-pyridinemethanamine

EXAMPLE A-248

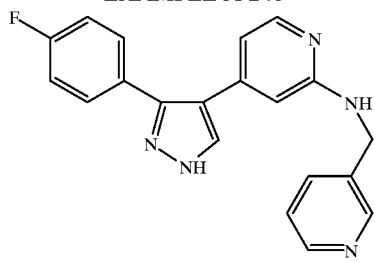

N-[4-[3-(4-fluorophenyl)-1H-pyrazol-4-yl]-2-pyridinyl]-2-pyridinemethanamine

Anal Calc'd: C, 41.12; H, 3.58; N, 9.22. Found: C, 41.74; H, 5.05; N, 11.11.

EXAMPLE A-249

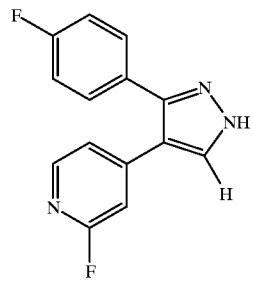

2-fluoro-4-[3-(4-fluorophenyl)-1H-pyrazol-4-yl]pyridine

EXAMPLE A-250

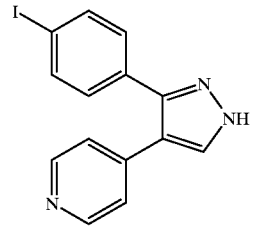

4-[3-(4-iodophenyl)-1H-pyrazol-4-yl]pyridine

EXAMPLE A-251

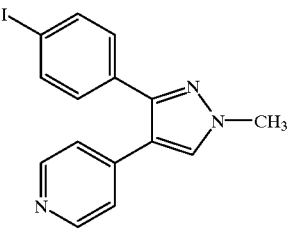

4-[3-(4-iodophenyl)-1-methyl-1H-pyrazol-4-yl]pyridine

EXAMPLE A-252

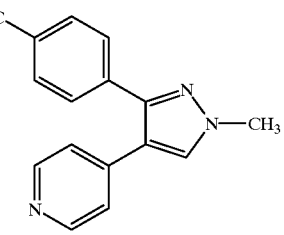

4-[1-methyl-3-[4-(trifluoromethyl)phenyl]-1H-pyrazol-4-yl]pyridine

EXAMPLE A-253

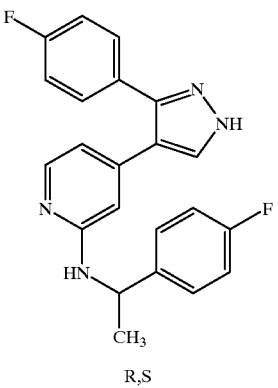

N-[1-(4-fluorophenyl)ethyl]-4-[3-(4-fluorophenyl)-1H-pyrazol-4-yl]-2-pyridinamine

EXAMPLE A-254

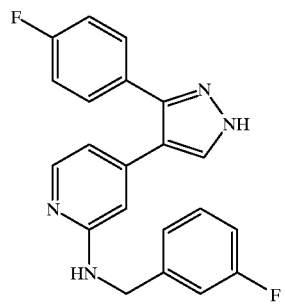

N-[(3-fluorophenyl)methyl]-4-[3-(4-fluorophenyl)-
1H-pyrazol-4-yl]-2-pyridinamine

EXAMPLE A-255

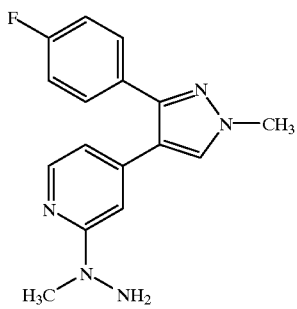

4-[3-(4-fluorophenyl)-1-methyl-1H-pyrazol-4-yl]-2-
(1-methylhydrazino)pyridine

EXAMPLE A-256

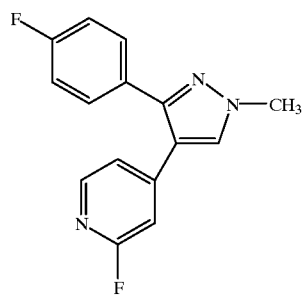

2-fluoro-4-[3-(4-fluorophenyl)-1-methyl-1H-
pyrazol-4-yl]pyridine

EXAMPLE A-257

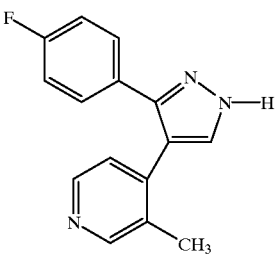

4-[3-(3,4-difluorophenyl)-1H-pyrazol-4-yl]-2-fluoro-
pyridine

EXAMPLE A-258

4-[3-(4-fluorophenyl)-1H-pyrazol-4-yl]-3-
methylpyridine

EXAMPLE A-259

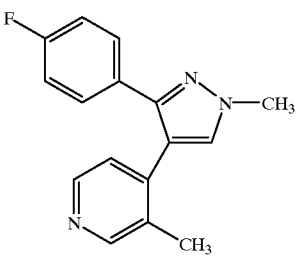

4-[3-(4-fluorophenyl)-1-methyl-1H-pyrazol-4-yl]-3-
methylpyridine

EXAMPLE A-260

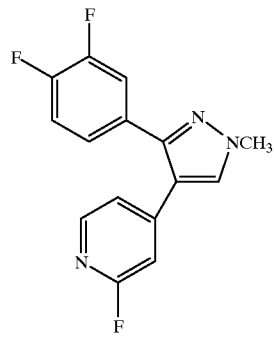

4-[3-(3,4-difluorophenyl)-1-methyl-1H-pyrazol-4-yl]-2-fluoropyridine

EXAMPLE A-261

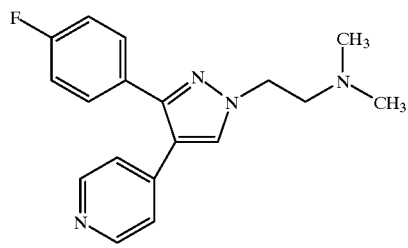

3-(4-fluorophenyl)-N,N-dimethyl-4-(4-pyridinyl)-1H-pyrazole-1-ethanamine

EXAMPLE A-262

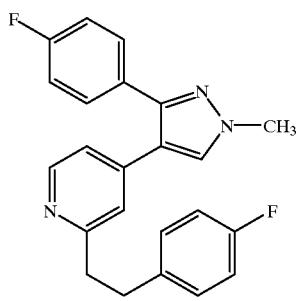

2-[2-(4-fluorophenyl)ethyl]-4-[3-(4-fluorophenyl)-1-methyl-1H-pyrazol-4-yl]pyridine

EXAMPLE A-263

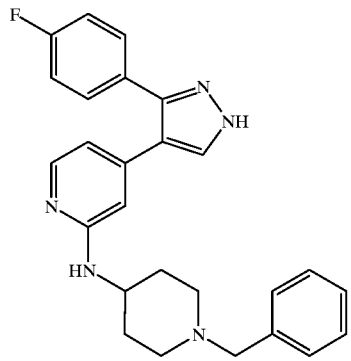

4-[3-(4-fluorophenyl)-1H-pyrazol-4-yl]-N-[1-(phenylmethyl)-4-piperidinyl]-2-pyridinamine

EXAMPLE A-264

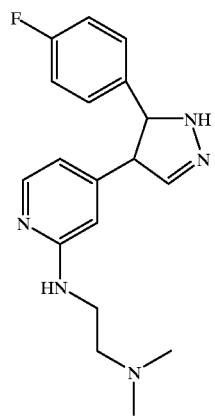

N'-[4-(3-(4-fluorophenyl)-1H-pyrazol-4-yl]-2-pyridinyl]-N,N-dimethyl-1,2-ethanediamine

EXAMPLE A-265

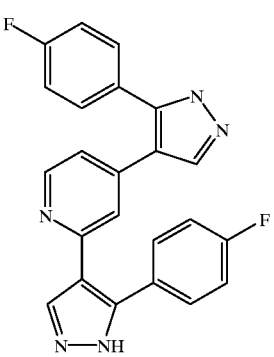

2,4-bis[3-(4-fluorophenyl)-1H-pyrazol-4-yl]pyridine

EXAMPLE A-266

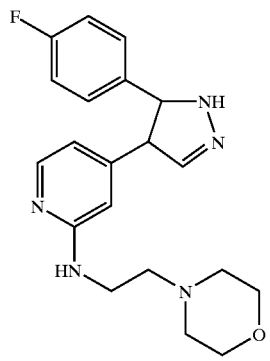

N-[4-[3--4-fluorophenyl)-1H-pyrazol-4-yl]-2-pyridinyl]-4-morpholineethanamine

EXAMPLE A-267

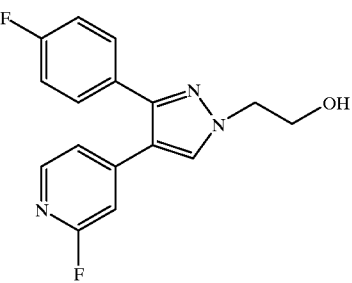

3-(4-fluorophenyl)-4-(2-fluoro-4-pyridinyl)-1H-pyrazole-1-ethanol

EXAMPLE A-268

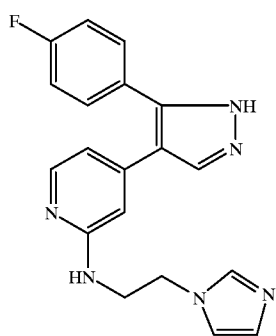

4-[3-(4-fluorophenyl)-1H-pyrazol-4-yl]-N-[2-(1H-imidazol-1-yl)ethyl]-2-pyridinamine

EXAMPLE A-269

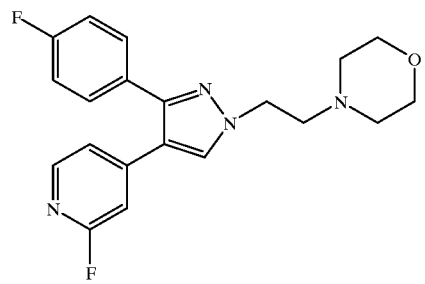

4-[2-[3-(4-fluorophenyl)-4-(2-fluoro-4-pyridinyl)-1H-pyrazol-1-yl]ethyl]morpholine

EXAMPLE A-270

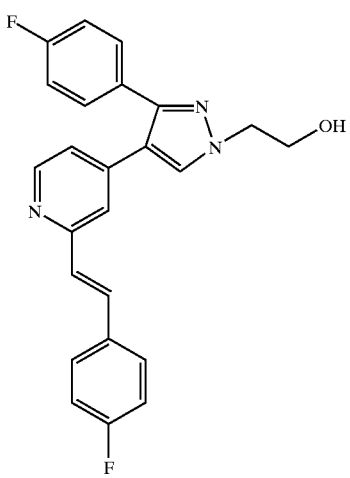

(E)-3-(4-fluorophenyl)-4-[2-[2-(4-fluorophenyl)ethenyl]-4-pyridinyl]-1H-pyrazole-1-ethanol

EXAMPLE A-271

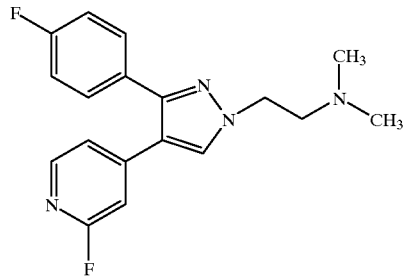

3-(4-fluorophenyl)-4-(2-fluoro-4-pyridinyl)-N,N-dimethyl-1H-pyrazole-1-ethanamine

EXAMPLE A-272

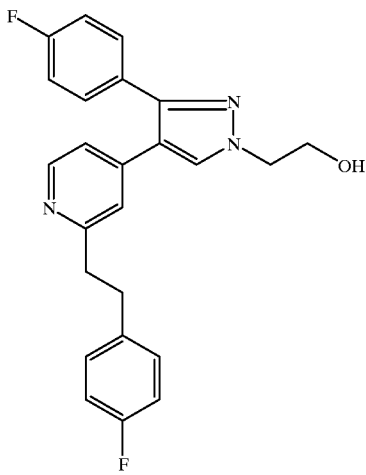

3-(4-fluorophenyl)-4-[2-[2-(4-fluorophenyl)ethyl]-4-pyridinyl]-1H-pyrazole-1-ethanol

EXAMPLE A-273

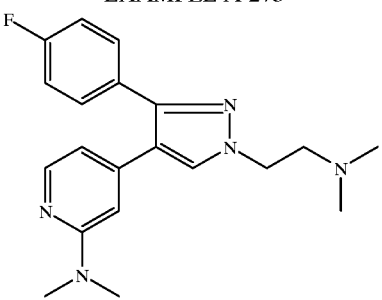

4-[1-[2-(dimethylamino)ethyl]-3-(4-fluorophenyl)-1H-pyrazol-4-yl]-N,N-dimethyl-2-pyridinamine

EXAMPLE A-274

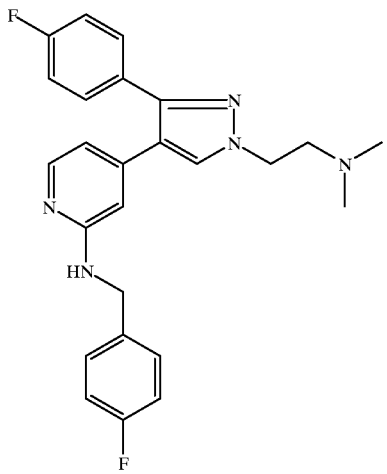

4-[1-[2-(dimethylamino)ethyl]-3-(4-fluorophenyl)-1H-pyrazol-4-yl]-N-[(4-fluorophenyl)methyl]-2-pyridinamine

EXAMPLE A-275

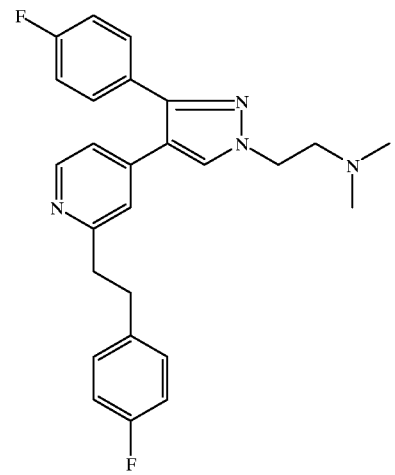

3-(4-fluorophenyl)-4-[2-[2-(4-fluorophenyl)ethyl-4-pyridinyl]-N,N-dimethyl-1H-pyrazole-1-ethanamine

EXAMPLE A-276

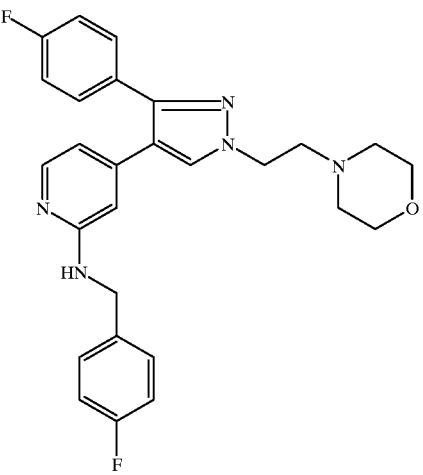

N-(4-fluorophenyl)methyl]-4-[3(or 5)-(4-fluorophenyl)-1-[[2-(4-morpholinyl)ethyl]-1H-pyrazol-4-yl]-2-pyridinamine

EXAMPLE A-277

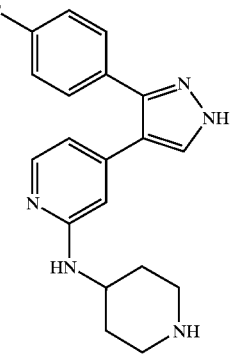

4-[3-(4-fluorophenyl)-1H-pyrazol-4-yl]-N-4-piperadinyl-2-pyridinamnine

EXAMPLE A-278

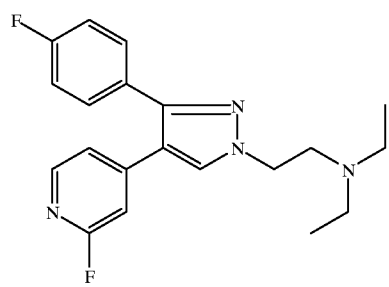

N,N-diethyl-3-(4-fluorophenyl)-4-(2-fluoro-4-pyridinyl)-1H-pyrazole-1-ethanamine

EXAMPLE A-279

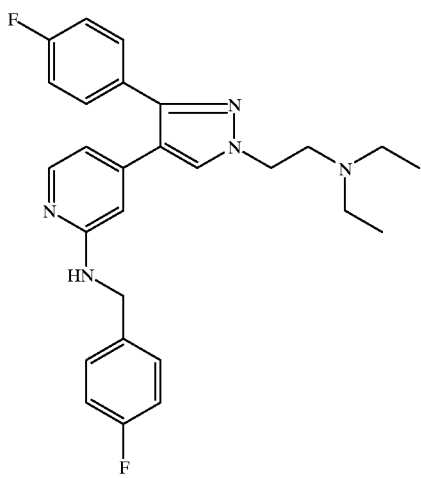

4-[1-[2-(diethylamino)ethyl]-3-(4-fluorophenyl)-1H-pyrazol-4-yl]-N-[(4-fluorophenyl)methyl]-2-pyridinamine

EXAMPLE A-280

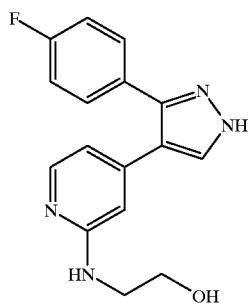

2-[[4-[3-(4-(fluorophenyl)-1H-pyrazol-4-yl]-2-pyridinyl]amino]ethanol

EXAMPLE A-281

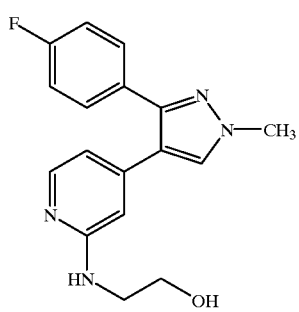

2-[[4-[3-(4-fluorophenyl)-1-methyl-1H-pyrazol-4-yl]-2-pyridinyl]amino]ethanol

EXAMPLE A-282

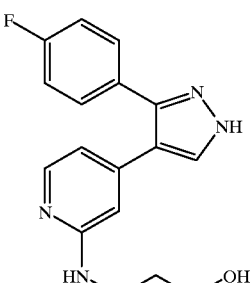

3-[[4-[3-(4-fluorophenyl)-1H-pyrazol-4-yl]-2-pyridinyl]amino]-1-propanol

EXAMPLE A-283

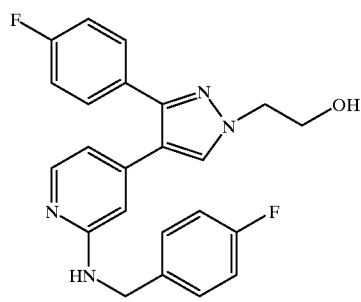

3 (or 5)-(4-fluorophenyl)-4-[2-[[(4-fluorophenyl)methyl]amino]-4-pyridinyl]-1H-pyrazole-1-ethanol

EXAMPLE A-284

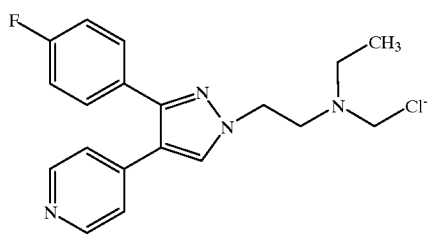

N,N-diethyl-3-(4-fluorophenyl)-4-(4-pyridinyl)-1H-pyrazole-1-ethanamine

EXAMPLE A-285

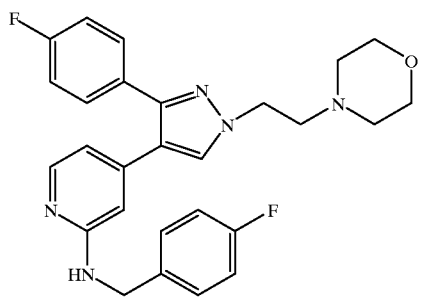

N-[(4-fluorophenyl)methyl]-4-[3-(4-fluorophenyl)-1-[2-(4-morpholinyl)ethyl]-1H-pyrazol-4-yl]-2-pyridinamine

EXAMPLE A-286

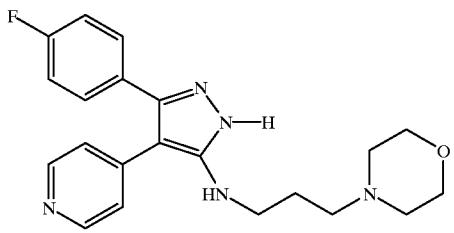

N-[5-(4-fluorophenyl)-4-(4-pyridinyl)-1H-pyrazol-3-yl]-4-morpholinepropanamine

EXAMPLE A-287

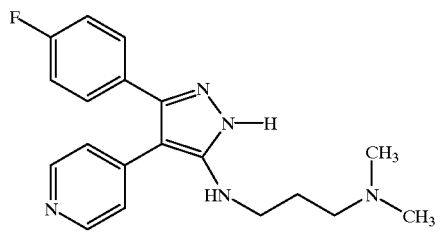

N'-[5-(4-fluorophenyl)-4-(4-pyridinyl)-1H-pyrazol-3-yl]-N,N-dimethyl-1,3-propanediamine

EXAMPLE A-288

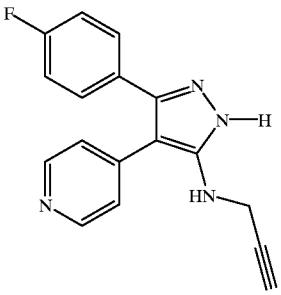

5-(4-fluorophenyl)-N-2-propynyl-4-(4-pyridinyl)-1H-pyrazol-3-amine

EXAMPLE A-289

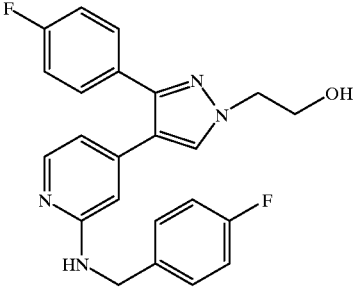

3-(4-fluorophenyl)-4-[2-[[(4-fluorophenyl)methyl]amino]-4-pyridinyl]-1H-pyrazole-1-ethanol

EXAMPLE A-290

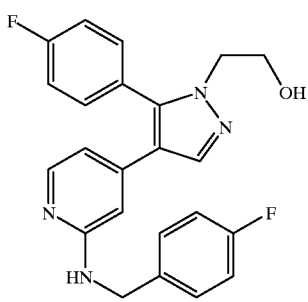

5-(4-fluorophenyl)-4-[2-[[(4-fluorophenyl)methyl]amino]-4-pyridinyl]-1H-pyrazole-1-ethanol

EXAMPLE A-291

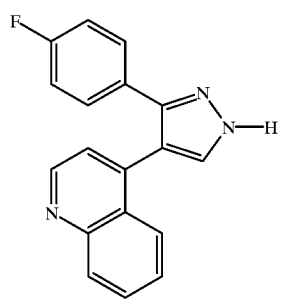

4-[3-[(4-fluorophenyl)-1H-pyrazol-4-yl]quinoline

EXAMPLE A-292

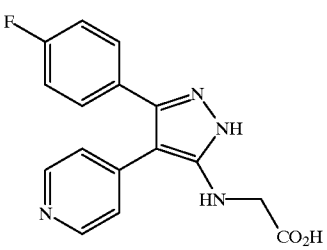

N-[5-(4-fluorophenyl)-4-(4-pyridinyl)-1H-pyrazol-3-yl]glycine methyl ester

EXAMPLE A-293

N-[5-(4-fluorophenyl)-4-(4-pyridinyl)-1H-pyrazol-3-yl]glycine

EXAMPLE A-294

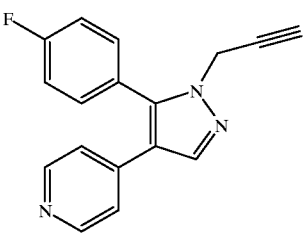

4-[3-(4-fluorophenyl)-1-(2-propynyl)-1H-pyrazol-4-yl]pyridine

EXAMPLE A-295

4-[5-(4-fluorophenyl)-1-(2-propynyl)-1H-pyrazol-4-yl]pyridine

EXAMPLE A-296

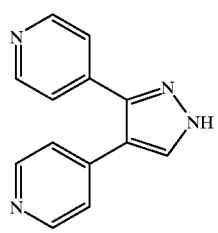

4,4'-(1H-pyrazole-3,4-diyl)bis[pyridine]

EXAMPLE A-297

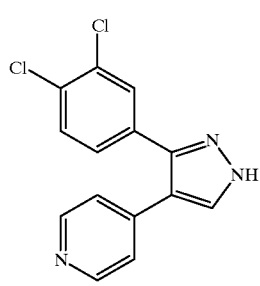

4-[3-(3,4-dichlorophenyl)-1H-pyrazol-4-yl]pyridine

EXAMPLE A-298

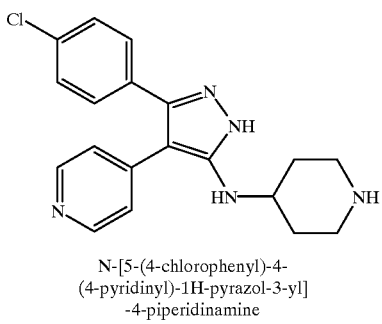

N-[5-(4-chlorophenyl)-4-
(4-pyridinyl)-1H-pyrazol-3-yl]
-4-piperidinamine

The pyrimidine-substituted compounds of Examples A-299 through A-312 were synthesized in accordance with the chemistry described in Schemes I-XVIII by selection of, the corresponding starting reagents:

EXAMPLE A-299

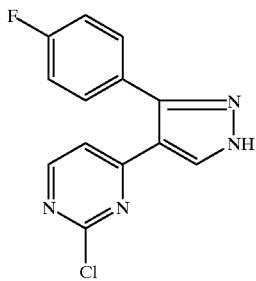

2-Chloro-4-[3-(4-fluorophenyl)-1H-pyrazol-4-yl]
pyrimidine

Step 1

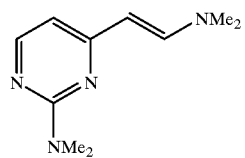

A mixture of 2,6-dichloro-4-methylpyrimidine (5.0 g, 0.031 mol), triethylamine (6.23 g, 0.062 mol) and catalytic amount of 5% Pd/C in 100 mL of THF was hydrogenated on a Parr apparatus under 40 psi at room temperature. After 0.5 hour, the catalyst was filtered and the filtrate was concentrated. The crude was purified by chromatography on silica gel (ethyl acetate/hexane, 3:7) to give 2.36 g of product as a pale yellow crystal (50% yield); mp: 47–49° C.

Step 2: Preparation of 2-(2-chloro-4-pyrimidinyl)-1(4-fluorophenyl)ethanone

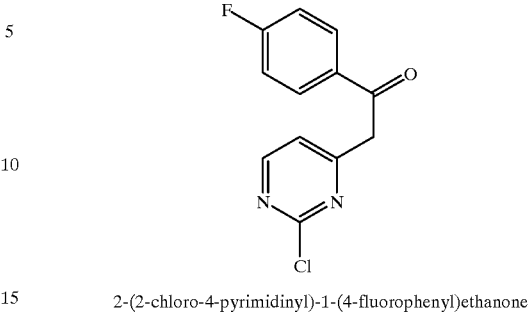

2-(2-chloro-4-pyrimidinyl)-1-(4-fluorophenyl)ethanone

To a solution of lithium diisopropylamide (generated from BuLi (0.045 mol) and diisopropylamine (0.048 mol) in THF) at −78° C. was added a solution of the compound prepared in step 1 (5.5 g, 0.037 mol) in THF slowly over 30 minutes. After 1 hour, a solution of ethyl 4-fluorobenzoate (7.62 g, 0,045 mol) in THF was added and the reaction mixture was stirred overnight and allowed to warm up to room temperature. Water was added and the aqueous phase was extracted with ethyl acetate. Organic layer was washed with brine, dried over magnesium sulfate and filtered. The filtrate was concentrated and the crude product purified by chromatography on silica gel (ethyl acetate/hexane, 3:7) to give 4.78 g of a yellow solid (51% yield), mp: 112–113° C.

Step 3: Preparation of (E)-2-(2-chloro-4-pyrimidinyl)-3-(dimethylamino)-1-(4-fluorophenyl)-2-propen-1-one

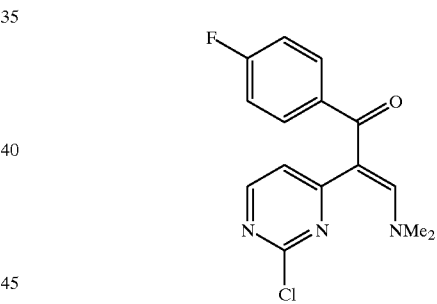

(E)-2-(2-chloro-4-pyrimidinyl)-3-(dimethylamino)-
1-(4-fluorophenyl)-2-propen-1-one A mixture of the compound prepared in step 2 (4.7 g, 0.017 mol) in 100 mL of dimethylformamide dimethyl acetal was stirred at room temperature overnight. Excess dimethylformamide dimethyl acetal was removed under vacuum to give 4.5 g of crude product as a thick brown oil, which was used without further purification.

Step 4: Preparation of 2-chloro-4-[3-(4-fluorophenyl)-1H-pyrazol-4-yl]pyrimidine A solution of the compound prepared in step 3 (4.4 g) and hydrazine hydrate (0.82 g, 0.014 mol) was stirred at room temperature for 6 hours. The yellow precipitate was collected by filtration and air-dried to give 1.85 g of 2-chloro-4-[3-(4-fluorophenyl)-1H-pyrazol-4-yl]pyrimidine as a yellow solid, mp: 204–205° C.; Anal. Calc'd for $C_{13}H_8ClFN_4$: C, 56.84; H, 2.94; N, 20.40; Cl, 12.91. Found: C, 56.43; H, 2.76; N, 20.02; Cl, 12.97.

EXAMPLE A-300

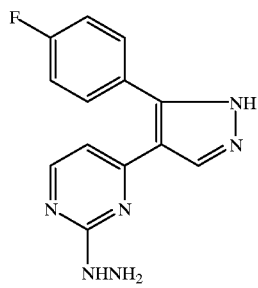

4-[3-(4-fluorophenyl)-1H-pyrazol-4-yl]-2(1H)-pyrimidinone hydrazone

A solution of the compound prepared in step 3 of Example A-299 (1.5 g) and hydrazine hydrate (5 mL) in ethanol was heated at reflux overnight. After the reaction mixture was cooled, the solvent was removed. The residue was partitioned between ethyl acetate and water. The organic phase was washed with brine, dried over magnesium sulfate and filtered. The filtrate was concentrated and the crude product was purified by recrystallization from ethyl acetate and hexane to give 0.5 g of product, 4-[3-(4-fluorophenyl)-1H-pyrazol-4-yl]-2(1H)-pyrimidinone hydrazone, as a pale yellow solid (38% yield), mp: 149–150° C.; Anal. Calc'd for $C_{13}H_{11}FN_6$: C, 57.77; H, 4.10; N, 31.10. Found: C, 57.70; H, 4.31; N, 30.73.

EXAMPLE A-301

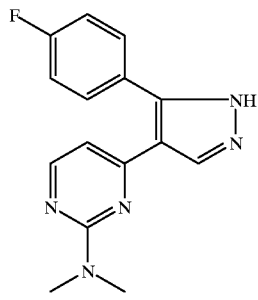

4-[3-(4-fluorophenyl)-1H-pyrazol-4-yl]-N,N-dimethyl-2-pyrimidinamine

Step 1: Preparation of

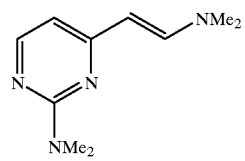

A solution of the compound prepared in step 2 of Example A-299 (3.0 g, 0.02 mol) and tert-butylbis(dimethylamino)methane (10.45 g, 0.06 mol) in 40 mL of DMF was stirred at 110° C. overnight. After the solvent was removed under vacuum, water was added and extracted with ethyl acetate. The organic layer was washed with brine, dried over magnesium sulfate and filtered. The filtrate was concentrated and purified by recrystallization from ethyl acetate and hexane to give 1.23 g of a yellow solid product (32% yield), mp: 76–77° C.; Anal. Calc'd for $C_{10}H_{16}N_4$: C, 62.47; H, 8.39; N, 29.14. Found: C, 62.19; H, 8.58; N, 29.02.

Step 2: Preparation of 4-[3-(4-fluorophenyl)-1H-pyrazol-4-yl]-N,N-dimethyl-2-pyrimidinamine To a solution of the compound prepared in step 1 of the present Example (1.2 g, 0.0064 mol) and triethylamine (0.65 g, 0.0064 mol) in 10 mL of toluene was added 4-fluorobenzoyl chloride dropwise. The mixture was heated at reflux for 10 hours and the solvent was removed. The residue was partitioned between ethyl acetate and water. The organic layer was washed with brine, dried over magnesium sulfate and filtered. The filtrate was concentrated and the crude (1.6 g) was then dissolved in 50 mL of ethanol. The solution was treated with hydrazine hydrate (0.36 g, 0.006 mol) and the mixture was heated at reflux for 2 hours. After ethanol was removed, the residue was partitioned between water and ethyl acetate. The organic phase was washed with brine, dried over magnesium sulfate and filtered. The filtrate was concentrated and the crude was purified by chromatography on silica gel (ethyl acetate/hexane, 1:1) to give 0.6 g of product, 4-[3-(4-fluorophenyl)-1H-pyrazol-4-yl]-N,N-dimethyl-2-pyrimidinamine, as a yellow solid (33% yield), mp: 155–156° C.; Anal. Calc'd for $C_{15}H_{14}FN_5$: C, 63.59; H, 4.98; N, 24.72. Found: C, 63.32; H, 4.92; N, 24.31.

EXAMPLE A-302

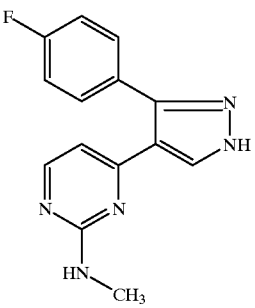

4-[3-(4-fluorophenyl)-1H-pyrazol-4-yl]-N-methyl-2-pyrimidinamine

A suspension of 2-chloro-4-[3-(4-fluorophenyl)-1H-pyrazol-4-yl]pyrimidine prepared in accordance with Example A-299 (0.3 g, 0.0011 mol) in 10 mL of methylamine (40% water solution) was heated in a sealed tube at 100° C. overnight. The mixture was then cooled to room temperature and the precipitate was filtered, air-dried to give 0.2 g of product, 4-[3-(4-fluorophenyl)-1H-pyrazol-4-yl]-N-methyl-2-pyrimidinamine, as a white solid (68% yield), mp: 217–218° C.; Anal Calc'd for $C_{14}H_{12}FN_5$: C, 62.45; H, 4.49; N, 26.01. Found: C, 62.58; H, 4.36; N, 25.90.

EXAMPLE A-303

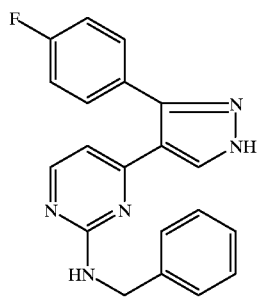

4-[3-(4-fluorophenyl)-1H-pyrazol-4-yl]-N-(phenylmethyl)-2-pyrimidinamine

This compound was synthesize by refluxing 2-chloro-4-[3-(4-fluorophenyl)-1H-pyrazol-4-yl]pyrimidine prepared in accordance with Example A-299 in benzylamine overnight. The product, 4-[3-(4-fluorophenyl)-1H-pyrazol-4-yl]-N-(phenylmethyl)-2-pyrimidinamine, was obtained as a white solid in 95% yield; mp: 216–217° C.; Anal. Calc'd for $C_{20}H_{16}FN_5$: C, 69.55; H, 4.67; N, 20.28. Found: C, 69.73; H, 4.69; N, 19.90.

EXAMPLE A-304

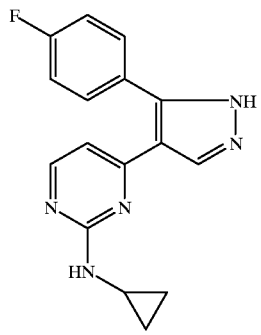

N-cyclopropyl-4-[3-(4-fluorophenyl)-1H-pyrazol-4-yl]-2-pyrimidinamine

This compound was synthesized by stirring 2-chloro-4-[3-(4-fluorophenyl)-1H-pyrazol-4-yl]pyrimidine prepared in accordance with Example A-299 with excess cyclopropylamine in methanol at 50° C. for 12 hours. The product, N-cyclopropyl-4-[3-(4-fluorophenyl)-1H-pyrazol-4-yl]-2-pyrimidinamine, was obtained as a white solid in 26% yield, mp: 203–204° C.; Anal. Calc'd for $C_{16}H_{14}FN_5$: C, 65.07; H, 4.78; N, 23.71. Found: C, 64.42; H, 4.82; N, 23.58.

EXAMPLE A-305

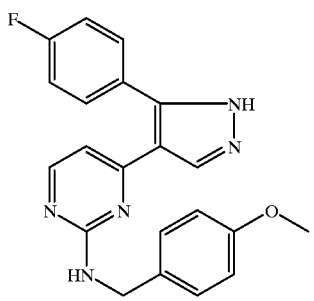

4-[3-(4-fluorophenyl)-1H-pyrazol-4-yl]-N-[(4-methoxyphenyl)methyl]-2-pyrimidinamine This compound was synthesized by refluxing 2-chloro-4-[3-(4-fluorophenyl)-1H-pyrazol-4-yl]pyrimidine prepared in accordance with Example A-299 in 4-methoxybenzylamine overnight. The product, 4-[3-(4-fluorophenyl)-1H-pyrazol-4-yl]-N-[(4-methoxyphenyl)methyl]-2-pyrimidinamine, was obtained as a off-white solid in 80% yield, mp: 183–185° C.; Anal. Calc'd for $C_{21}H_{18}FN_5O$: C, 67.19; H, 4.83, N, 18.66. Found: C, 67.01; H, 5.11; N, 18.93.

EXAMPLE A-306

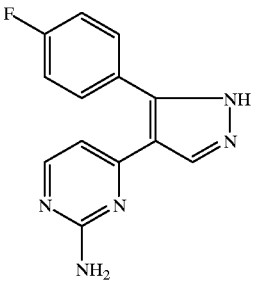

4-[3-(4-fluorophenyl)-1H-pyrazol-4-yl]-2-pyrimidinamine

A solution of 4-[3-(4-fluorophenyl)-1H-pyrazol-4-yl]-N-[(4-methoxyphenyl)methyl]-2-pyrimidinamine prepared in accordance with Example A-305 (0.35 g, 0.00093 mol) in 15 mL of trifluoroacetic acid was heated at reflux for 16 hours. Solvent was removed and the residue was partitioned between ethyl acetate and 1 N ammonia hydroxide. Organic layer was washed with brine, dried over magnesium sulfate and filtered. The filtrate was concentrated and purified by chromatography on silica gel (ethyl acetate) to give 0.14 g of product, 4-[3-(4-fluorophenyl)-1H-pyrazol-4-yl]-2-pyrimidinamine, as a pale yellow solid (59% yield), mp: 273–274° C.; Anal. Calc'd for $C_{13}H_{10}FN_5 \cdot 0.25\ H_2O$: C, 60.11; H, 4.07; N, 26.96. Found: C, 60.15; H, 3.82; N, 26.38.

EXAMPLE A-307

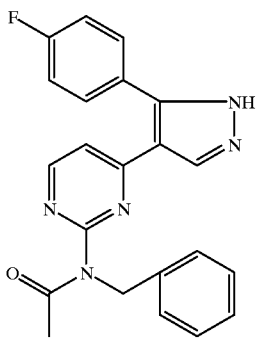

N-[4-[3-(4-fluorophenyl)-1H-pyrazol-4-yl]-2-pyrimidinyl]-N-(phenylmethyl)acetamide To a mixture of 4-[3-(4-fluorophenyl)-1H-pyrazol-4-yl]-N-(phenylmethyl)-2-pyrimidinamine prepared in accordance with Example A-303 (0.15 g, 0.00043 mol), DMAP (0.027 g, 0.00022 mol) and acetic anhydride (0.066 g, 0.00066 mol) in 10 mL of THF was added triethylamine (0.053 g, 0.00052 mol). The solution was stirred at room temperature overnight. After the removal of solvent, the residue was partitioned between ethyl acetate and water. The organic layer was washed with saturated $NaHCO_3$, washed with brine, dried over magnesium sulfate and filtered. The filtrate was concentrated and the crude product was triturated with ether to give 0.1 g of product, N-[4-[3-(4-fluorophenyl)-1H-pyrazol-4-yl]-2-pyrimidinyl]-N-(phenylmethyl)acetamide, as a white solid (60% yield), mp: 176–178° C.; Anal. Calc'd for $C_{22}H_{18}FN_5$: C, 68.21; H, 4.68; N, 18.08. Found: C, 67.67; H, 4.85; N, 17.79.

EXAMPLE A-308

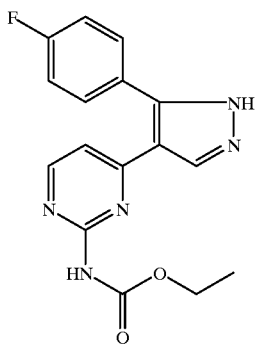

Ethyl [4-[3-(4-fluorophenyl)-1H-pyrazol-4-yl]-2-pyrimidinyl]carbamate

To a suspension of 4-[3-(4-fluorophenyl)-1H-pyrazol-4-yl]-2-pyrimidinamine prepared in accordance with Example A-306 (0.26 g, 0.001 mol) in 5 mL of pyridine was added ethyl chloroformate dropwise. After the addition, the clear solution was stirred at room temperature for 6 hours. Water was added and the aqueous phase was extracted with ethyl acetate. The organic layer was washed with brine, dried over magnesium sulfate and filtered. The filtrate was concentrated and the crude was triturated with ether to give 0.15 g of product, ethyl[4-[3-(4-fluorophenyl)-1H-pyrazol-4-yl]-2-pyrimidinyl]carbamate, as a white solid (46% yield), mp: 163–165° C.; Anal. Calc'd for $C_{16}H_{14}FN_5O_2$: C, 58.71; H, 4.31; N, 21.04. Found: C, 59.22; H, 4.51; N, 21.66.

EXAMPLE A-309

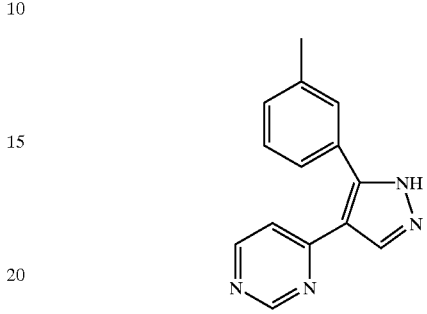

4-[3-(3-methylphenyl)-1H-pyrazol-4-yl]pyrimidine

This compound was prepared by the same procedure as described for Example A-208 except that 1-methyl-3-(4'-pyrimidinylacetyl)benzene (prepared as set forth in Step 1 of Example A-19 from 4-methyl-pyrimidine and methyl 3-methylbenzoate) was used in place of 4-fluorobenzoyl-4-pyridinyl methane.

Anal. Calc'd for $C_{14}H_{12}N_4$ (236.27): C, 71.17; H, 5.12; N, 23.71. Found C, 70.67; H, 5.26; N, 23.53. m.p. (DSC): 151.67° C.

EXAMPLE A-310

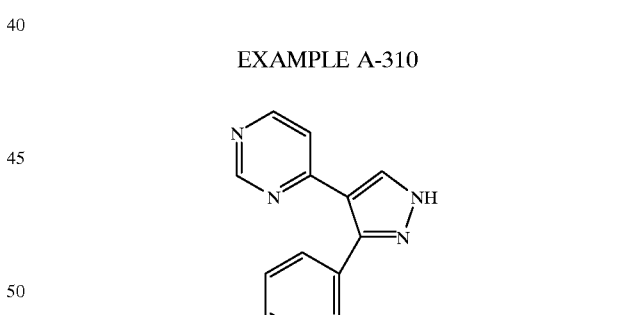

4-[3-(4-chlorophenyl)-1H-pyrazol-4-yl]pyrimidine

This compound was prepared according to the chemistry described in Schemes VI and IX by selection of the corresponding pyrimidine starting material in place of the pyridine starting material.

Anal. Calc'd for $C_{13}H_9N_4Cl.O0.25MH_2$): C, 59.78; H, 3.67; N, 21.45. Found: C, 59.89; H, 3.32; N, 21.56. m.p. (DSC): 218.17° C.

EXAMPLE A-311

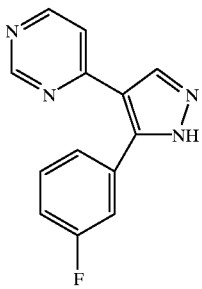

4-[3-(3-fluorophenyl)-1H-pyrazol-4-yl]pyrimidine

This compound was prepared according to the chemistry described in Schemes VI and IX by selection of the corresponding pyrimidine starting material in place of the pyridine starting material.

Anal. Calc'd for $C_{13}H_9N_4F$ (240.24): C, 64.99; H, 3.78; N, 23.22. Found: C, 64.78; H, 3.75; N, 23.31. m.p. (DSC): 168.58° C.

EXAMPLE A-312

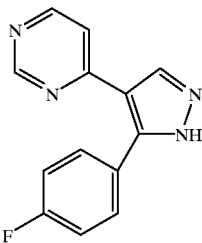

4-[3(4-fluorophenyl)-1H-pyrazol-4-yl]pyrimidine

This compound was prepared according to the chemistry described in Schemes VI and IX by selection of the corresponding pyrimidine starting material in place of the pyridine starting material.

Anal. Calc'd for $C_{13}H_9N_4F$ (240.24): C, 64.99; H, 3.78; N, 23.32. Found: C, 64.94; H, 3.56; N, 23.44. m.p. (DSC): 191.47° C.

EXAMPLE A-313

The compound 1-[[5-(4-fluorophenyl)-4-(4-pyridinyl)-1H-pyrazol-3-yl]methyl]-4-methylpiperazine was prepared in accordance with general synthetic Scheme VII:

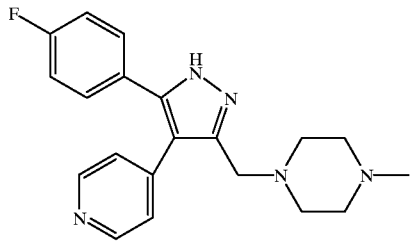

Step 1: Preparation of 5-(4-fluorophenyl)-4-(4-pyridinyl)-1H-pyrazole-3-carboxylic acid, monohydrate

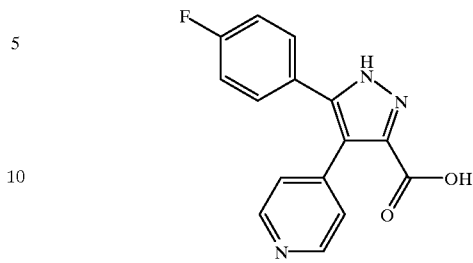

A mixture of 4-[3-(4-fluorophenyl)-5-methyl-1H-pyrazol-4-yl)pyridine (5.8 g, 24.0909 mmol; prepared as set forth in Example A-4) and potassium permanganate (7.6916 g, 48.1818 mmol) in water (7.5 mL) and tert-butanol (10 mL) was heated to reflux at 95 to 100° C. for 6 hours (or until all the potassium permanganate was consumed) and stirred at room temperature overnight. The mixture was diluted with water (150 mL) and filtered to remove manganese dioxide. The aqueous filtrate (pH>10) was extracted with ethyl acetate to remove unreacted starting material. The aqueous layer was acidified with 1N HCl to a pH of about 6.5. A white precipitate was formed. This precipitate was collected by filtration, dried in air, and then dried in a vacuum oven overnight at 50° C. to give 5-(4-fluorophenyl)-4-(4-pyridinyl)-1H-pyrazole-3-carboxylic acid, monohydrate (2.7677 g, 40.6%). The remaining product (0.21 g, 3.1%) was isolated from the mother liquid by reverse phase chromatography. The total isolated yield of 5-(4-fluorophenyl)-4-(4-pyridinyl)-1H-pyrazole-3-carboxylic acid, monohydrate was 43.7%. Anal. Calc'd for $C_{15}H_{10}N_3FO_2 \cdot H_2O$: C, 59.80; H, 4.01; N, 13.95; Found: C, 59.48; H, 3.26; N, 13.65. MS (MH$^+$): 284 (base peak).

Step 2: Preparation of 1,1-dimethylethyl 4-[[5-(4-fluorophenyl)-4-(4-pyridinyl)-1H-pyrazol-3-yl]carbonyl]-1-piperazinecarboxylate

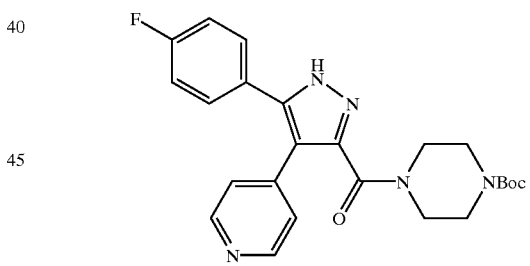

In a solution of 5-(4-fluorophenyl)-4-(4-pyridinyl)-1H-pyrazole-3-carboxylic acid, monohydrate (0.9905 g, 3.5 mmol) from step 1 and 1-hydroxybenzotriazole hydrate (0.4824 g, 3.57 mmol) in dimethylformamide (20 mL) at 0° C. under $N_2$, 1-(3-dimethylaminopropyl)-3-ethylcarbodiimide hydrochloride (0.6983 g, 3.57 mmol) was added. The solution was stirred at 0° C. under $N_2$ for 1 hour, then was added 1-tert.-butoxycarbonylpiperazine (0.6585 g, 3.5 mmol) followed by N-methyl morpholine (0.40 mL, 3.6 mmol). The reaction was stirred from 0° C. to room temperature overnight. The reaction mixture was diluted with ethyl acetate and saturated $NaHCO_3$ solution, extracted. The organic layer was washed with water and brine, and dried over $MGSO_4$. After filtration, the solvent was removed under reduced pressure, and crude product was obtained (1.7595 g). The desired product 1,1-dimethylethyl 4-[[5-(4-fluorophenyl)-4-(4-pyridinyl)-1H-pyrazol-3-yl]carbonyl]-1-piperazinecarboxylate (1.2375 g, 78.4%) was isolated by chromatography (silica gel, 10:90 isopropyl alcohol/ toluene). Anal. Calc'd for $C_{24}H_{26}N_5FO_3$: C, 63.85; H, 5.80; N, 15.51; Found: C, 63.75; H, 5.71; N, 15.16. MS (MH$^+$): 452 (base peak).

Step 3: Preparation of 1-[[5-(4-fluorophenyl)-4-(4-pyridinyl)-1H-pyrazol-3-yl]methyl]-4-methylpiperazine To a suspension of 1,1-dimethylethyl 4-[[5-(4-fluorophenyl)-4-(4-pyridinyl)-1H-pyrazol-3-yl]carbonyl]-1-piperazinecarboxylate (0.451 g, 1.0 mL) in dry tetrahydrofuran (8 mL), 1.0N LiAlH$_4$ in tetrahydrofuran (2.5 mL, 2.5 mmol) was added dropwise at such a rate as to maintain reflux over 15 minutes. Upon the addition, the suspension became a clear light yellow solution, which was kept boiling for an additional 1.5 hours. Excess LiAlH$_4$ was decomposed by cautious addition of a solution of KOH (0.5611 g, 10.0 mmol) in water (3.5 mL). Upon hydrolysis, a white salt precipitated. After the addition was completed, the mixture was heated to reflux for 1 hour. The hot solution was filtered by suction through a buchner funnel. Any remaining product was extracted from the precipitate by refluxing with tetrahydrofuran (10 mL) for 1 hour, followed again by suction filtration. The combined filtrates were concentrated under reduced pressure to give a crude residue, which was then diluted with ethyl acetate and washed with water and brine. The organic layer was dried over MgSO$_4$. After filtration, the solvent was removed under reduced pressure, and a crude product was obtained.

The desired product 1-[[5-(4-fluorophenyl)-4-(4-pyridinyl)-1H-pyrazol-3-yl]methyl]-4-methylpiperazine (0.1509 g, 50.1%) was obtained by chromatography (silica gel, 70:30:1 methanol/ethyl acetate/NH$_4$OH). Anal. Calc'd for $C_{20}H_{22}N_5F.0.6H_2O$: C, 66.32; H. 6.46; N, 19.33; Found: C, 66.31; H, 5.96; N, 18.83. MS (MH$^+$): 352 (base peak)

EXAMPLE A-314

The compound 1-[[5-(4-fluorophenyl)-4-(4-pyridinyl)-1H-pyrazol-3-yl]methyl]-4-piperazine was prepared in accordance with general synthetic Scheme VII:

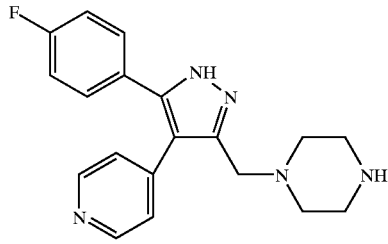

Step 1: Preparation of 1-[[5-(4-fluorophenyl)-4-(4-pyridinyl)-1H-pyrazol-3-yl]carbonyl]piperazine, monhydrate

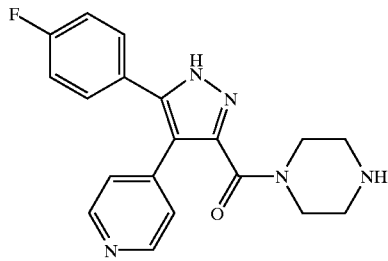

A solution of 1,1-dimethylethyl 4-[[5-(4-fluorophenyl)-4-(4-pyridinyl)-1H-pyrazol-3-yl]carbonyl]-1-piperazinecarboxylate (0.6349 g; 1.4077 mmol; prepared as set forth in step 2 of Example A-313) in methylene chloride (3.5 mL) and TFA (1.1 mL, 14.077 mmol) was stirred at room temperature under N$_2$ for 2 hours. The solvents were removed under reduced pressure, and TFA was chased by methylene chloride and methanol. The resulting colorless oily residue was triturated with methanol. The resulting solid was collected by filtration and dried in a vacuum oven overnight to give the desired product 1-[[5-(4-fluorophenyl)-4-(4-pyridinyl)-1H-pyrazol-3-yl]carbonyl] piperazine, monohydrate (0.7860 g, 96.4%). Anal. Calc'd for $C_{19}H_{18}N_5OF.2TFA H_2O$: C, 46.24; H, 3.71; N, 11.72; Found: C, 45.87; H, 3.43; N. 11.45. MS (MH$^+$): 352 (base peak).

Step 2: Preparation of 1-[[5-(4-fluorophenyl)-4-(4-pyridinyl)-1H-pyrazol-3-yl]methyl]-4-piperazine By following the method of Example A-313, step 3 and substituting of 1-[[5-(4-fluorophenyl)-4-(4-pyridinyl)-1H-pyrazol-3-yl]carbonyl]piperazine, monohydrate (prepared in step 1 of this Example) for 1,1-dimethylethyl 4-[[5-(4-fluorophenyl)-4-(4-pyridinyl)-1H-pyrazol-3-yl]carbonyl]-1-piperazinecarboxylate, the title product 1-[[5-(4-fluorophenyl)-4-(4-pyridinyl)-1H-pyrazol-3-yl]methyl]-4-piperazine was obtained. Anal. Calc'd for $C_{19}H_{20}N_5F.0.75H_2O$: C, 65.03, H, 6.18, N,19.96. Found: C, 65.47, H, 5.83, N,19.35. MS (MH$^+$): 338 (base peak).

EXAMPLE A-315

The compound 4-[3-(4-fluorophenyl)-5-(4-piperidinylmethyl)-1H-pyrazol-4-yl]pyridine was prepared in accordance with general synthetic Scheme XX:

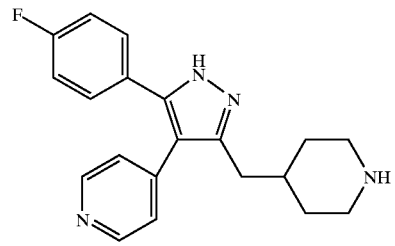

Step 1: Preparation of ethyl 1-[(1,1-dimethylethoxy) carbonyl]-4-1piperidineacetate

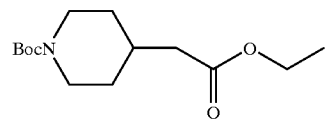

Ethyl 4-pyridyl acetate was converted to 2-(4-piperidinyl) ethyl acetate hydrochloride by hydrogenation (60 psi H$_2$) catalyzed by 5% Pt/C at 40° C. in ethanol and HCl solution. To a solution of 2-(4-piperidinyl)ethyl acetate hydrochloride (21.79 g, 0.105 mol) in tetrahydrofuran (500 mL) at 0° C., triethylamine (32.06 mL, 0.230 mL) was added followed by di-tert-butyldicarbonate (23.21 g, 0.105 mol). The reaction mixture was stirred under N$_2$ from 0° C. to room temperature overnight. After removing tetrahydrofuran, the reaction mixture was diluted with ethanol, washed with saturated NaHCO$_3$, 10% citric acid, water and brine, and dried over MgSO$_4$. After filtration, the solvent was removed under reduced pressure. The resulting oily product was dried under vacuum to give ethyl 1-[(1,1-dimethylethoxy)carbonyl]-4-piperidineacetate (27.37 g, 95.9%). The structure of this product was confirmed by NMR.

Step 2: Preparation of 1,1-dimethylethyl 4-[2-oxo-3-(4-pyridinyl)propyl]-1-piperidinecarboxylate

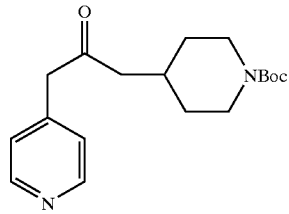

To a solution of diisopropylamide (6.15 mL, 43.91 mmol) in dry tetrahydrofuran (40 mL) at 0° C. was added 2.5 M butyl lithium solution in hexane (16.22 mL, 40.53 mmol) dropwise over 10 minutes. After the addition, the lithium diisopropylamide solution was stirred at 0° C. for 20 minutes, then cooled to −78° C. 4-Picoline (3.98 mL, 40.53 mmol) was added to the above lithium diisopropylamide solution under $N_2$ dropwise over 10 minutes. The resulting solution was stirred at −78° C. under $N_2$ for 1.5 hours, then transferred into a suspension of anhydrous cerium chloride (10.0 g, 40.53 mmol) in tetrahydrofuran (40 mL) at −78° C. under $N_2$. The mixture was stirred at −78° C. under $N_2$ for 2 hours, then a solution of ethyl 1-[(1,1-dimethylethoxy)carbonyl]-4-piperidineacetate (from step 1 of this Example) (10.98 g, 40.53 mmol) in tetrahydrofuran (40 mL) was added slowly for 1 hour. The mixture was stirred under $N_2$ from −78° C. to room temperature overnight. The reaction was quenched with water, diluted with ethyl acetate, and washed with a pH 7 buffer. The organic layer was washed with water and brine. After filtration, the solvent was removed under reduced pressure to give a crude product mixture. The desired product 1,1-dimethylethyl 4-[2-oxo-3-(4-pyridinyl)propyl]-1-piperidinecarboxylate (3.19 g, 25%) was isolated by chromatography (silica gel, 50:50-75:25-100:0 ethyl acetate/hexane).

Step 3: Preparation of 1,1-dimethylethyl 4-[4-(4-fluorophenyl)-2-oxo-3-(4-pyridinyl)-3-butenyl]-1-piperidinecarboxylate

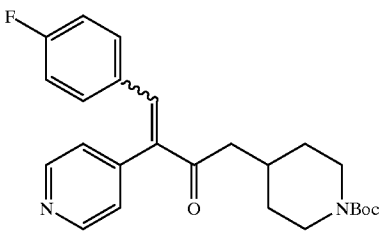

1,1-Dimethylethyl 4-[4-(4-fluorophenyl)-2-oxo-3-(4-pyridinyl)-3-butenyl]-1-piperidinecarboxylate was prepared by the same method as described for step 1 of Example A-1 by replacing 4-pyridylacetone and 3-fluoro-p-anisaldehyde with the ketone of step 2 of the present Example and 4-fluorobenzaldehyde, respectively.

Step 4: Preparation of 1,1-dimethylethyl 4-[2-[3-(4-fluorophenyl)-2-(4-pyridinyl)oxiranyl]-2-oxoethyl]-1-piperidinecarboxylate

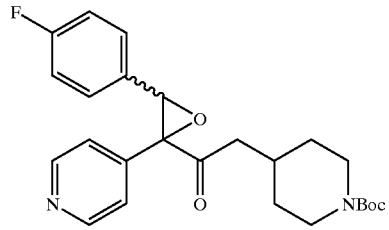

1,1-Dimethylethyl 4-[2-[3-(4-fluorophenyl)-2-(4-pyridinyl)oxiranyl]-2-oxoethyl]-1-piperidinecarboxylate was prepared by the same method as described for step 3 of Example A-2 by replacing 4-phenyl-3-(4-pyridyl)-3-butene-2-one with the α,β unsaturated ketone of step 3 of the present Example.

Step 5: Preparation of 1,1-dimethylethyl 4-[[5-(4-fluorophenyl)-4-(4-pyridinyl)-1H-pyrazol-3-yl]methyl]-1-piperidinecarboxylate

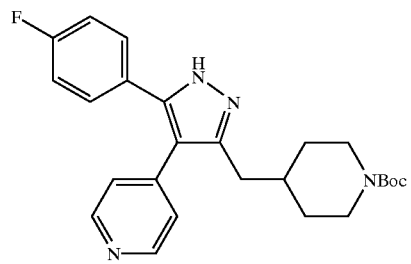

To a solution of 1,1-dimethylethyl 4-[2-[3-(4-fluorophenyl)-2-(4-pyridinyl)oxiranyl]-2-oxoethyl]-1-piperidinecarboxylate prepared in step 4 of this Example (3.45 g, 7.8409 mmol) in ethanol (15 mL), anhydrous hydrazine (0.50 mL, 15.6818 mmol) was added. The reaction was heated to reflux overnight. The reaction solution was cooled to room temperature and ethanol was removed under reduced pressure. The resulting residue was taken into ethyl acetate, washed with water and brine, and dried over $MgSO_4$. After filtration the solvent was removed under reduced pressure. The crude residue was purified by chromatography (silica gel, 2:1-1:1-1:2 hexane/ethyl acetate) to give 1,1-dimethylethyl 4-[[5-(4-fluorophenyl)-4,5-dihydro-4-hydroxy-4-(4-pyridinyl)-1H-pyrazol-3-yl]methyl]-1-piperidinecarboxylate (1.9187 g, 53.9%). This intermediate (1.8611 g, 4.0993 mmol) was dissolved in dry methylene chloride (40 mL) and treated with Martin sulfurane dehydrating reagent (4.13 g, 6.1490 mmol). The reaction solution was stirred at room temperature under $N_2$ overnight, then diluted with ethyl acetate, washed with 1N sodium hydroxide solution, water and brine, dried over $MgSO_4$. After filtration the solvents were removed. The resulting crude product mixture was purified by flash chromatoghaphy (silica gel, 2:1-1:1-1:2 Hexane/ethyl acetate) to give 1,1-dimethylethyl 4-[[5-(4-fluorophenyl)-4-(4-pyridinyl)-1H-pyrazol-3-yl]methyl]-1 -piperidinecarboxylate (0.6964 g, 39%).

Step 6: Preparation of 4-[3-(4-fluorophenyl)-5-(4-piperidinylmethyl)-1H-pyrazol-4-yl]pyridine 4-[3-(4-Fluorophenyl)-5-(4-piperidinylmethyl)-1H-pyrazol-4-yl]pyridine was prepared using the same method as described for Example A-314, step 1 by replacing 1-[[5-

(4-fluorophenyl)-4-(4-pyridinyl)-1H-pyrazol-3-yl]carbonyl]
piperazine, monohydrate with the pyrazole of step 5 of the
present Example. Anal. Calc'd for
$C_{20}H_{21}N_4F \cdot 2TFA \cdot 1.25H_2O$: C, 49.11; H, 4.38; N, 9.54;
Found: C, 48.74; H, 4.02; N, 9.57. MS (MH$^+$): 337 (base peak)

EXAMPLE A-316

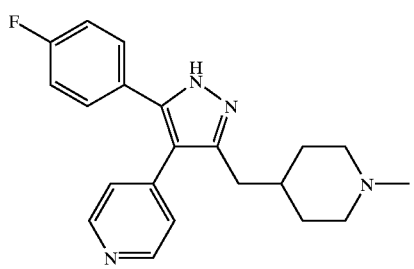

4-[3-(4-fluorophenyl)-5-[(1-methyl-4-piperidinyl)
methyl]-1H-pyrazol-4-yl]pyridine was prepared by the same
method as described for step 3 of Example A-313 by
replacing 1,1-dimethylethyl 4-[[5-(4-fluorophenyl)-4-(4-
pyridinyl)-1H-pyrazol-3-yl]carbonyl]-1-
piperazinecarboxylate with the pyrazole of step 5 of the
present Example. Anal. Calc'd for $C_{21}H_{23}N_4F \cdot 0.2\ H_2O$: C,
71.24; H, 6.66; N, 15.82; Found: C, 71.04; H, 6.54; N, 15.56.
MS (MH$^+$): 351 (base peak).

EXAMPLE A-317

The compound 1-[5-(4-fluorophenyl)-4-(4-pyridinyl)-
1H-pyrazol-3-yl]-4-methylpiperazine, dihydrate was pre-
pared in accordance with general synthetic Scheme II:

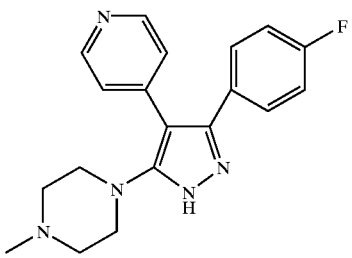

2-(4-Pyridyl)-1-(4-fluorophenyl)ethanone hydrochloride
(5.9 g, 0.023 moles) was dissolved in a methylene chloride/
methanol solution (70/15) at room temperature and
N-chlorosuccinimide (3.25 g, 0.024 moles) was added as a
solid. The mixture was stirred at room temperature for 2.5
hours. N-methylpiperazinylthiosemicarbazide (4.1 g, 0.023
moles) was added as a solid and the mixture was stirred for
3 days at room temperature. The mixture was diluted with
100 mL of methylene chloride and washed with saturated
aqueous sodium bicarbonate solution. The organic phase
was dried (MgSO$_4$) and solvent removed using a rotary
evaporator. The residue was treated with ethyl acetate with
stirring while cooling in an ice bath. The solid formed was
filtered and recrystallized from ethyl acetate with a small
amount of methanol to give 1.7 g (22%) of 1-[5-(4-
fluorophenyl)-4-(4-pyridinyl)-1H-pyrazol-3-yl]-4-
methylpiperazine, dihydrate. Anal. Calc'd. for
$C_{19}H_{20}FN_5 \cdot 2H_2O$: C, 61.11; H, 6.48; N, 18.75. Found: C,
60.59; H, 6.41; N, 18.44. M.p. (DSC) 262–264° C.; MH+=
338.

EXAMPLE A-318

The compound 1-[5-(4-chlorophenyl)-4-(4-pyridinyl)-1-
(2-propynyl)-1H-pyrazol-3-yl]piperazine, trihydrochloride
monohydrate was prepared in accordance with general syn-
thetic Scheme VII:

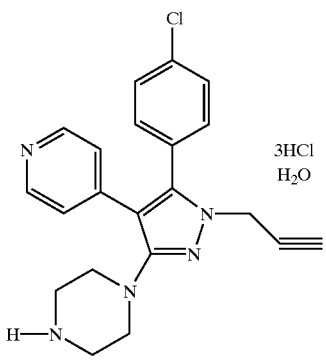

To a mixture of sodium hydride (30 mg, 1.5 mmol) in
dimethylformamide (25 mL) stirred under a nitrogen atmo-
sphere at room temperature was added 3-(4-chlorophenyl)-
4-(4-pyridyl)-5-(4-N-tert.-butoxycarbonylpiperazinyl)
pyrazole (500 mg, 1.1 mmol; prepared as set forth in
Example A-169). After stirring for 1 hour, propargyl bro-
mide (225 mg, 1.5 mmol, 80% solution in toluene) was
added. After stirring for an additional 2 hour at room
temperature, the reaction mixture was poured into water and
extracted with ethyl acetate. The organic layer was dried
with MgSO$_4$, filtered and concentrated in vacuo. The residue
was chromatographed on silica gel using 70% ethyl acetate/
hexane as the eluent to give 110 mg of 3-(4-chlorophenyl)-
4-(4-pyridyl)-5-(4-N-tert.-butoxycarbonylpiperazinyl)
pyrazole (24%), m. p. 204–205° C. Anal. Calc'd. for
$C_{26}H_{28}ClN_5O_2$: C, 65.33; H, 5.90; N, 14.65. Found: C,
65.12; H, 5.81; N, 14.70.

A solution of HCl in methanol (5 mL) was generated by
addition of acetyl chloride (200 mg) to methanol while
cooling (5° C.). 3-(4-Chlorophenyl)-4-(4-pyridyl)-5-(4-N-
tert.-butoxycarbonylpiperazinyl)pyrazole (100 mg, 0.2
mmol) prepared above was added and the reaction stirred in
the cold for one hour. The reaction mixture was concentrated
in vacuo and the residue azeotroped with toluene to give 100
mg of 1-[5-(4-chlorophenyl)-4-(4-pyridinyl)-1-(2-
propynyl)-1H-pyrazol-3-yl]piperazine, trihydrochloride
monohydrate (90%), m.p.=231–233° C. (dec.). Anal. Calc'd.
for $C_{21}H_{20}N_5Cl \cdot 3HCl \cdot H_2O$: C, 49.92; H, 4.99; N, 13.86.
Found: C, 49.71; H, 4.89; N, 13.61.

EXAMPLE A-319

The compound methyl 4-[5-(4-chlorophenyl)-4-(4-
pyridinyl)-1H-pyrazol-3-yl]-1-piperazinecarboxylate,
monohydrate was prepared in accordance with general syn-
thetic Scheme II:

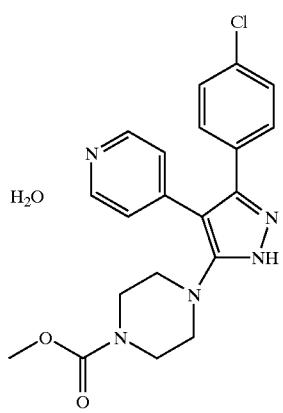

Methyl chloroformate (55 mg) was added to a solution of 3-(4-chlorophenyl)-4-(4-pyridyl)-5-(4-piperazinyl)pyrazole (200 mg, 0.54 mmol; prepared as set forth in Example A-169) and 4-dimethylaminopyridine (5 mg) in pyridine (10 mL). The mixture was stirred at room temperature for 3 hours. Additional methyl chloroformate (30 mg) was added and stirring was continued for 24 hours. The solvent was removed in vacuo. The residue was treated with water and extracted with ethyl acetate. After drying the organic layer (MgSO$_4$), the solvent was blown down to a volume of 10 mL and refrigerated. The resultant crystalline solid was filtered and air dried to give 103 mg (48%) of methyl 4-[5-(4-chlorophenyl)-4-(4-pyridinyl)-1H-pyrazol-3-yl]-1-piperazinecarboxylate, monohydrate, mp 264–265° C. Anal. Calc'd. for $C_{20}H_{20}ClN_5O_2 \cdot H_2O$: C, 57.76; H, 5.33; N, 16.84. Found: C, 57.98; H, 4.89; N, 16.44.

EXAMPLE A-320

The compound 1-[5-(4-chlorophenyl)-4-(4-pyridinyl)-1H-pyrazol-3-yl]-4-(methylsulfonyl)piperazine, monohydrate was prepared in accordance with general synthetic Scheme II:

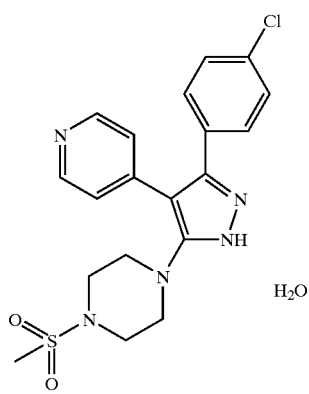

A solution of 3-(4-chlorophenyl)-4-(4-pyridyl)-5-(4-piperazinyl)pyrazole (200 mg; 0.54 mmol; prepared as set forth in Example A-169), methanesulfonyl chloride (75 mg) and 4-dimethylaminopyridine (5 mg) in pyridine was stirred at room temperature for 3 hours. The solvent was removed in vacuo and the residue was treated with water. The resultant crystalline solid was filtered, air dried and recrystallized from methanol and water to give 118 mg (37%) of 1-[5-(4-chlorophenyl)-4-(4-pyridinyl)-1H-pyrazol-3-yl]-4-(methylsulfonyl)piperazine, monohydrate, m.p. 245–248° C. Anal. Calc'd. for $C_{19}H_{20}ClN_5SO_2 \cdot H_2O$: C, 52.35; H, 5.09; N, 16.07. Found: C, 52.18; H, 5.31; N, 16.00.

EXAMPLE A-321

The compounds 4-[5-(4-chlorophenyl)-4-(4-pyridinyl)-1H-pyrazol-3-yl]-γ-oxo-1-piperazinebutanoic acid, dihydrate, and 4-[5-(4-chlorophenyl)-4-(4-pyridinyl)-1H-pyrazol-3-yl]-γ-oxo-1-piperazinebutanoic acid, monosodium salt dihydrate, were prepared in accordance with general synthetic Scheme II:

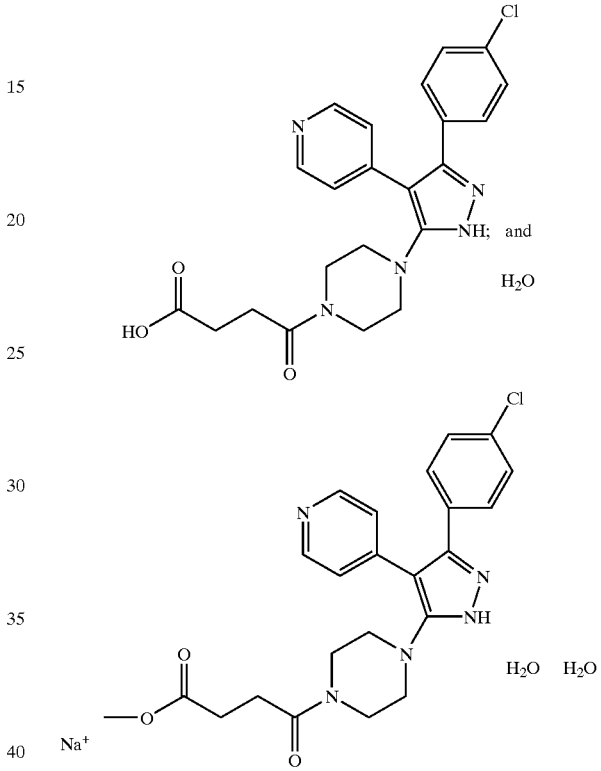

A solution of 3-(4-chlorophenyl)-4-(4-pyridyl)-5-(4-piperzinyl)pyrazole (200 mg; 0.54 mmol; prepared as set forth in Example A-169), succinic anhydride (60 mg, 0.55 mmol) and 4-dimethylaminopyridine (5 mg) was stirred at room temperature for 24 hours. The solvent was removed in vacuo and the residue treated with methanol and water (1:1). The resultant crystalline solid was filtered and air dried to give 170 mg (58%) of 4-[5-(4-chlorophenyl)-4-(4-pyridinyl)-1H-pyrazol-3-yl]-γ-oxo-1-piperazinebutanoic acid, dihydrate, m. p. 281–283° C. (dec.). Anal. Calc'd. for $C_{22}H_{22}ClN_5O_3 \cdot 2H_2O$: C, 55.52; H, 5.51; N, 14.72. Found: C, 55.11; H, 5.20; N, 14.44.

A slurry of 4-[5-(4-chlorophenyl)-4-(4-pyridinyl)-1H-pyrazol-3-yl]-γ-oxo-1-piperazinebutanoic acid, dihydrate (150 mg, 0.31 mmol) from above in methanol (10 mL) was treated with a solution of sodium hydroxide (12 mg, 0.31 mmol) in methanol (2 mL). The reaction was stirred at room temperature for 15 minutes until dissolution was completed. The solvent was removed in vacuo. The residue was treated with tetrahydrofuran and filtered and air dried to give 150 mg (97%) of 4-[5-(4-chlorophenyl)-4-(4-pyridinyl)-1H-pyrazol-3-yl]-γ-oxo-1-piperazinebutanoic acid, monosodium salt dihydrate as a solid. Anal. Calc'd. for $C_{22}H_{21}ClN_5O_3Na \cdot 2H_2O$: C, 53.07; H, 5.06; N, 14.07. Found: C, 52.81; H, 5.11; N, 13.90.

EXAMPLE A-322

The compound 1-[5-(4-chlorophenyl)-4-(4-pyridinyl)-1H-pyrazol-3-yl)-4-cyclopropylpiperazine was prepared in accordance with general synthetic Scheme II:

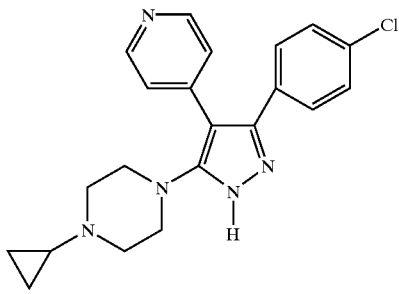

To a solution of 3-(4-chlorophenyl)-4-(4-pyridyl)-5-(4-piperazinyl)pyrazole (1.95 g; 5.8 mmoles; prepared as set forth in Example A-169) and acetic acid (3.6 g, 60 mmol) containing 5A molecular sieves (6 g) was added [(1-ethoxycyclopropyl)oxy]trimethylsilane (6 g, 35 mmol). After stirring for 5 minutes, sodium cyanoborohydride (1.7 g, 26 mmol) was added and the mixture was refluxed under a nitrogen atmosphere for 6 hours. The reaction mixture was filtered hot and the filtrate concentrated in vacuo. Water (50 mL) was added and the solution made basic with 2N sodium hydroxide. The resultant gel was extracted with dichloroethane and the combined organic extracts dried ($MgSO_4$). Evaporation again yielded a gel which was treated with hot methanol. Upon cooling, the product crystallized to give 1.4 g (63%) of 1-[5-(4-chlorophenyl)-4-(4-pyridinyl)-1H-pyrazol-3-yl)-4-cyclopropylpiperazine, m. p. 264–265° C. Anal. Calc'd. for $C_{21}H_{22}ClN_5 \cdot 1.5 H_2O$: C, 61.99; H, 6.19; N, 17.21. Found: C, 62.05; H, 5.81; N, 16.81.

EXAMPLE A-323

The compound 4-[3-(4-fluorophenyl)-5-(1H-imidazol-4-yl)-1-(4-methoxyphenyl)-1H-pyrazol-4-yl]pyridine was prepared in accordance with general synthetic Scheme V:

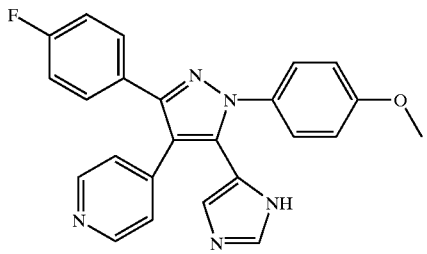

To a suspension of sodium hydride (1.0 g, 0.025 mol) in 50 mL of dimethylformamide was added methyl 4-imidazolecarboxylate (2.95 g, 0.023 mol) portionwise at room temperature. The mixture was stirred at room temperature for 0.5 hour. Then 2-(trimethylsilyl)ethoxymethyl chloride (4.17 g, 0.025 mol) was added dropwise over 5 minutes. The reaction mixture was stirred for 4 hours and quenched by cautiously adding water. The aqueous phase was extracted with ethyl acetate and the organic layer was washed with brine, dried over magnesium sulfate and filtered. The filtrate was concentrated and the crude was purified by chromatography on silica gel using ethyl acetate/hexane (8:2) as the eluent to give 4.0 g of the major regioisomer as a clear oil.

To a solution of 4-fluorobenzoyl-4'-pyridyl methane (8.6 g, 0.04 mol, prepared as set forth in Step 1 of Example A-208) in 150 mL of ethanol was added p-methoxyphenylhydrazine hydrochloride (7.34 g, 0.042 mol), followed by triethylamine (4.05 g, 0.04 mol). The reaction mixture was refluxed for 16 hours. After the removal of solvent, the residue was partitioned between water and ethyl acetate. The organic layer was washed with brine, dried over $MgSO_4$ and filtered. The filtrate was concentrated and the crude residue was purified by recrystallization from ethyl acetate and hexane to give 8.45 g of the product hydrazone as a yellow solid. To a solution of sodium hexamethyldisilazide (9 mL of 1.0 M tetrahydrofuran solution, 0.009 mol) was added a solution of this hydrazone (1.35 g, 0.004 mol) in 10 mL of dry tetrahydrofuran at 0° C. After stirring for 30 minutes at this temperature, a solution of the regioisomer prepared above (1.1 g, 0.0042 mol) in 5 mL of dry tetrahydrofuran was added dropwise. The reaction mixture was stirred for 3 hours at room temperature. Water was added and the aqueous phase was extracted with ethyl acetate. The organic layer was washed with brine, dried over magnesium sulfate and filtered. The filtrate was concentrated and the crude product was purified by chromatography on silica gel using ethyl acetate as the eluent to give 0.74 g of the desired product as an orange solid (34%). Deprotection of the above solid by using tetrabutylammonium fluoride afforded 0.37 g of 4-[3-(4-fluorophenyl)-5-(1H-imidazol-4-yl)-1-(4-methoxyphenyl)-1H-pyrazol-4-yl]pyridine as a yellow solid (75%), mp: 124–126° C. Anal. Calc'd. for $C_{24}H_{18}FN_5O \cdot 0.5 H_2O$: C, 68.56; H, 4.55; N, 16.66. Found: C, 68.44; H, 4.39; N, 16.00.

EXAMPLE A-324

The compound 4-[3-(4-fluorophenyl)-1H-pyazol-4-yl]-N-2-propynyl-2-pyrimidinamine was prepared in accordance with general synthetic Scheme XII:

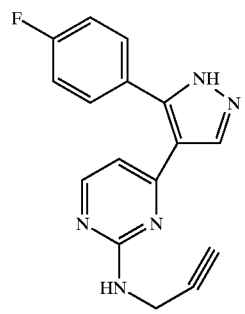

A mixture of 2-chloro-4-[3-(4-fluorophenyl)-1H-pyrazol-4-yl]pyrimidine (0.28 g; 0.001 mol; prepared as set forth in Example A-299) and 10 mL propargylamine was heated at reflux for 16 hour. Excess amine was removed in vacuo and the residue was partitioned between water and ethyl acetate. The organic layer was washed with brine, dried over $MgSO_4$ and filtered. The filtrate was concentrated and the residue purified by chromatography on silica gel using ethyl acetate/hexane (1:1) as the eluent to give 0.21 g of 4-[3-(4-fluorophenyl)-1H-pyazol-4-yl]-N-2-propynyl-2-pyrimidinamine as a pale yellow solid (68% yield), mp: 186–187° C. Anal. Calc'd. for $C_{16}H_{12}FN_5$: C, 65.52; H, 4.12; N, 23.88. Found: C, 64.99; H, 4.15; N, 23.91.

EXAMPLE A-325

The compound N-(2-fluorophenyl)-4-[3-(4-fluorophenyl)-1H-pyrazol-4-yl]-2-pyrimidinamine was prepared in accordance with general synthetic Scheme XII:

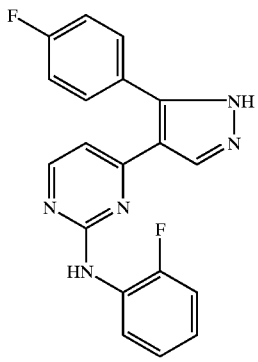

A mixture of 2-chloro-4-[3-(4-fluorophenyl)-1H-pyrazol-4-yl]pyrimidine (0.37 g; 0.0013 mol; prepared as set forth in Example A-299), 7 mL of 2-fluoroaniline and 2 drops of methanol was heated at 180° C. in a sealed tube for 16 hours. Excess amine was removed by vacuum distillation and the residue was treated with ethyl acetate to give 0.35 g of N-(2-fluorophenyl)-4-[3-(4-fluorophenyl)-1H-pyrazol-4-yl]-2-pyrimidinamine as a yellow solid (77%), mp: 239–240° C. Anal. Calc'd. for $C_{19}H_{13}F_2N_5$: C, 65.33; H, 3.75; N, 20.05. Found: C, 64.95; H, 3.80; N, 19.77.

EXAMPLE A-326

The compound 4-[3-(4-fluorophenyl)-1H-pyrazol-4-yl]-N-(2-methoxyphenyl)-2-pyrimidinamine was prepared in accordance with general synthetic Scheme XII:

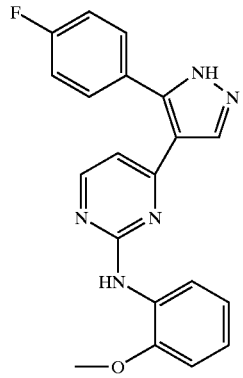

4-[3-(4-Fluorophenyl)-1H-pyrazol-4-yl]-N-(2-methoxyphenyl)-2-pyrimidinamine was synthesized in 41% yield using the same method described for the preparation of N-(2-fluorophenyl)-4-[3-(4-fluorophenyl)-1H-pyrazol-4-yl]-2-pyrimidinamine in Example A-325 using 2-methoxyaniline in place of 2-fluoroaniline; mp: 265° C. (dec.). Anal. Calc'd. for $C_{20}H_{16}FN_5O$: C, 66.47; H, 4.46; N, 19.38. Found: C, 66.70; H, 4.53; N, 19.20.

EXAMPLE A-327

The compound 1-[5-(3-chlorophenyl)-4-(4-pyridinyl)-1H-pyrazol-3-yl]-4-methylpiperazine was prepared in accordance with general synthetic Scheme II:

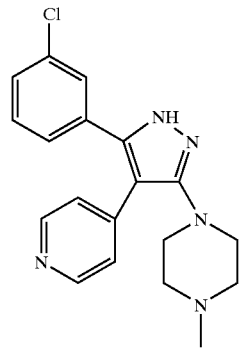

1-[5-(3-Chlorophenyl)-4-(4-pyridinyl)-1H-pyrazol-3-yl]-4-methylpiperazine was synthesized in 12% yield as a pale yellow solid using the same method described for the preparation of 1-[5-(4-chlorophenyl)-4-(4-pyridinyl)-1H-pyrazol-3-yl]-4-methylpiperazine in Example A-170 using 2-(4-pyridyl)-1-(3-chlorophenyl)ethanone in place of 2-(4-pyridyl)-1-(4-chlorophenyl)ethanone; mp: 229–231° C. Anal. Calc'd. for $C_{19}H_{20}ClN_5 \cdot 0.4\ H_2O$: C, 63.21; H, 5.81; N, 19.40. Found: C, 62.85; H, 5.57; N, 19.77.

Additional aminopyrazole compounds that were synthesized in accordance with the chemistry described in Scheme II by selection of the corresponding starting reagents include the compounds disclosed in Table 3-1 below.

TABLE 3-1

| EXAMPLE | FORMULA | MW | Theoretical | | | Found | | | DSC (mp) |
| | | | C | H | N | C | H | N | |
| --- | --- | --- | --- | --- | --- | --- | --- | --- | --- |
| A-328 | $C_{18}H_{18}ClN_5 \cdot 1/8H_2O$ | 342.08 | 63.20 | 5.30 | 20.47 | 63.04 | 5.36 | 20.33 | 199° C. |
| A-329 | $C_{23}H_{33}ClN_6O_2$ | 533.08 | 65.34 | 6.24 | 15.77 | 64.98 | 6.11 | 15.58 | (168–171° C.) |
| A-330 | $C_{23}H_{25}ClN_5O_2$ | 457.94 | 60.33 | 5.50 | 15.29 | 59.97 | 5.52 | 15.17 | (253–255° C.) |
| A-331 | $C_{22}H_{24}ClN_5O_2$ | 425.92 | 62.04 | 5.68 | 16.44 | 61.64 | 5.94 | 16.29 | (273–275° C.) |
| A-332 | $C_{19}H_{23}Cl_4N_5 \cdot H_2O$ | 481.26 | 47.42 | 4.82 | 14.35 | 47.66 | 5.11 | 13.74 | (217–219° C.) |
| A-333 | $C_{21}H_{20}ClN_5 \cdot 2.5H_2O$ | 422.92 | 59.64 | 4.77 | 16.56 | 59.67 | 4.88 | 15.96 | (247° C.) (d) |
| A-334 | $C_{20}H_{22}ClN_5 \cdot 1/4H_2O$ | 372.39 | 64.51 | 5.96 | 18.81 | 64.79 | 5.97 | 18.95 | 242° C. |

TABLE 3-1-continued

| EXAMPLE | FORMULA | MW | Theoretical C | H | N | Found C | H | N | DSC (mp) |
|---|---|---|---|---|---|---|---|---|---|
| A-335 | $C_{24}H_{22}ClN_5 \cdot 3/4H_2O$ | 429.44 | 67.13 | 5.16 | 16.31 | 67.04 | 5.31 | 16.32 | 230° C. |
| A-336 | $C_{25}H_{24}ClN_5O_2 \cdot 1/4H_2O$ | 450.46 | 66.66 | 5.37 | 15.55 | 66.64 | 5.11 | 15.69 | (270–271° C.) |
| A-337 | $C_{22}H_{24}FN_5O_2 \cdot H_2O$ | 427.48 | 61.81 | 5.66 | 16.38 | 61.88 | 5.96 | 16.41 | 249° C. |
| A-338 | $C_{20}H_{22}FN_5 \cdot 1/2H_2O$ | 360.44 | 66.65 | 6.15 | 19.43 | 66.74 | 6.59 | 19.37 | 241° C. |
| A-339 | $C_{19}H_{20}FN_5 \cdot 3HCl \cdot 1/2H_2O$ | 455.79 | 50.07 | 5.09 | 15.30 | 49.87 | 5.47 | 15.30 | (237–239° C.) |

EXAMPLE A-328

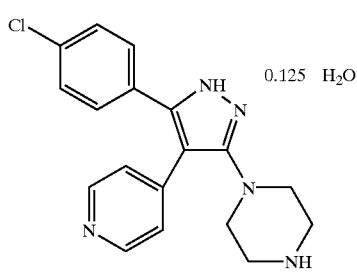

1-[5-(4-chlorophenyl)-4-(4-pyridinyl)-1H-pyrazol-3-yl]piperazine

EXAMPLE A-329

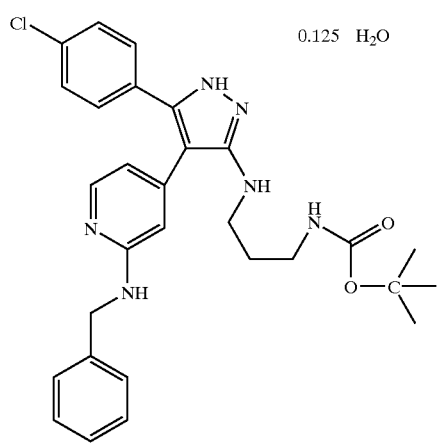

1,1-dimethylethyl [3-[[5-(4-chlorophenyl)-4-[2-[(phenylmethyl)amino]-4-pyridinyl-1H-pyrazol-3-yl]amino]propyl]carbamate

EXAMPLE A-330

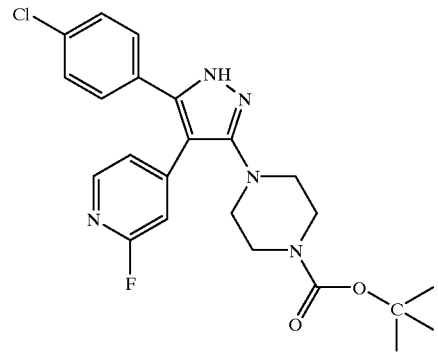

1,1-dimethylethyl 4-[5-(4-chlorophenyl)-4-(2-fluoro-4-pyridinyl)-1H-pyrazol-3-yl]-1-piperazinecarboxylate

EXAMPLE A-331

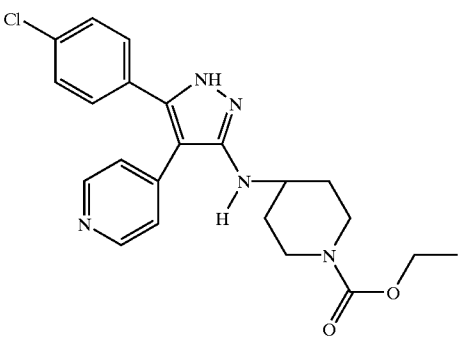

ethyl 4-[[5-(4-chlorophenyl)-4-(4-pyridinyl)-1H-pyrazol-3-yl]amino]-1-piperidinecarboxylate

EXAMPLE A-332

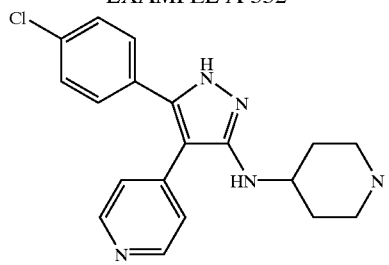

N-[5-(4-chlorophenyl)-4-(4-pyridinyl)-3H-pyrazol-3-yl]-4-piperidineamine, trihydrochloride, monohydrate

EXAMPLE A-333

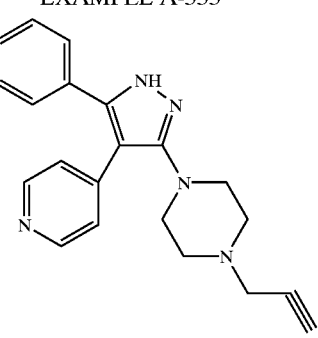

The compound 1-[5-(4-chlorophenyl)-4-(4-pyridinyl)-1H-pyrazol-3-yl]-4-(2-propynyl)piperazine was prepared in accordance with general synthetic Scheme II. To a suspension of of 1-[5-(4-Chlorophenyl)-4-(4-pyridinyl)-1H-pyrazol-3-yl]piperazine (92 mg, 0.27 mmole) in 2 mL of dimethylformamide was added 75 mg (0.54 mmole) of anhydrous potassium carbonate and then 60 microliters of 80% propargyl bromide solution in toluene (containing 64 mg, 0.54 mmole). The resulting mixture was stirred for 30 minutes and then partitioned between ethyl acetate and water. The aqueous layer was further extracted with ethyl acetate, and the combined organic extracts filtered through silica gel using 10% methanol-ethyl acetate as eluent to give, after evaporation of the appropriate fractions, 34 mg of 1-[5-(4-chlorophenyl)-4-(4-pyridinyl)-1H-pyrazol-3-yl]-4-(2-propynyl)piperazine as a pale yellowish solid, m.p. 247° C. (decomp.). Anal. Calc'd. for $C_{21}H_{20}ClN_5 \cdot 2.5H_2O$ (MW 422.92): C, 59.64, H, 4.77, N, 16.56. Found: C, 59.67, H, 4.88, N, 15.96.

EXAMPLE A-334

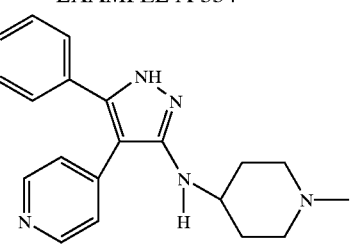

N-[5-(4-chlorophenyl)-4-(4-pyridinyl)-1H-pyrazol-3-yl]-1-methyl-4-piperidinamine

EXAMPLE A-335

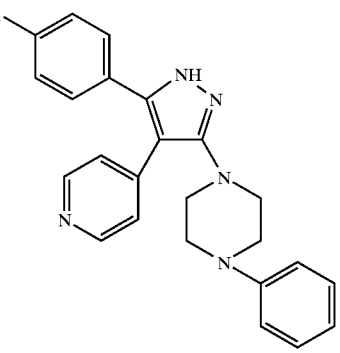

1-[5-(4-chlorophenyl)-4-(4-pyridinyl)-1H-pyrazol-3-yl]-4-phenylpiperazine

EXAMPLE A-336

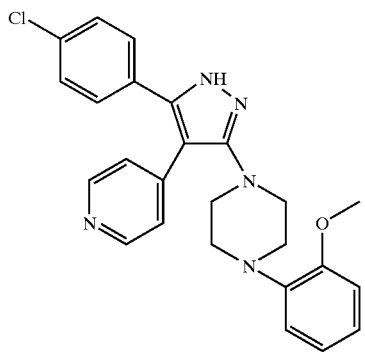

1-[5-(4-chlorophenyl)-4-(4-pyridinyl)-1H-pyrazol-3-yl]-4-(2-methoxyphenyl)piperazine

EXAMPLE A-337

Ethyl 4-[[5-(4-fluorophenyl)-4-(4-pyridinyl)-1H-pyrazol-3-yl]-amino]-1-piperidinecarboxylate, monohydrate

EXAMPLE A-338

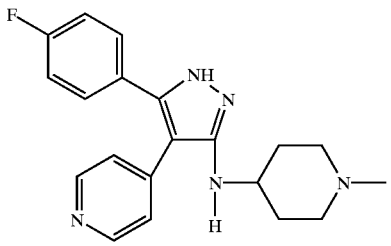

N-[5-(4-fluorophenyl)-4-(pyridinyl)-1H-pyrazol-3-yl]-1-methyl-4-piperidinamine

EXAMPLE A-339

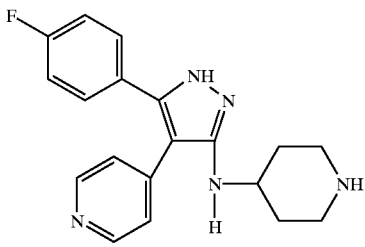

N-[5-(4-fluorophenyl)-4-(4-pyridinyl)-1H-pyrazol-3-yl]-4-piperidinamine, trihydrochloride

EXAMPLE A-340

The compound of Example A-170 was also synthesized in the following manner. 1-[5-(4-Chlorophenyl)-4-(4-pyridinyl)-1H-pyrazol-3-yl]piperazine (12.2 g, 36 mmol, prepared as set forth in Example A-169), 88% formic acid (20 mL), and formaldehyde (37% formalin solution; 44 g, 540 mmol) were combined and stirred at 60° C. for 16 hours under a nitrogen atmosphere. Excess solvent was removed on the rotary evaporator and the residue was dissolved in water (150 mL). The pH was adjusted to 8–9 by addition of solid sodium bicarbonate. The resulting precipitate was filtered and air dried. It was then treated with hot methanol (400 mL), filtered and blown down to a volume of 75 mL, cooled and filtered. After drying in a vacuum oven at 80° C. overnight, there was obtained 8.75 g (68%) of 1-[5-(4-chlorophenyl)-4-(4-pyridinyl)-1H-pyrazol-3-yl]-4-methylpiperazine, m. p. 262–264° C. Anal. Calc'd. for $C_{19}H_{20}N_5Cl$: C, 64.49; H, 5.70; N, 19.79. Found: C, 64.04; H, 5.68; N, 19.63.

The compounds of Examples A-341 through A-345 were synthesized, for example, in accordance with the chemistry described in Scheme XXI by selection of the corresponding starting reagents.

EXAMPLE A-341

The compound of Example A-170 was also synthesized in the following manner:

Step 1: Preparation of 1-(4-chlorophenyl)-2-(1,3-dithietan-2-ylidene)-2-(4-pyridinyl)ethanone To a solution of 2-(4-pyridyl)-1-(4-chlorophenyl) ethanone (70.0 g, 0.3 mol) prepared in a similar manner as the compound of Step 1 of Example A-19, dibromomethane (200 mL) and carbon disulfide (25.9 g, 0.34 mol) in acetone (800 mL) was added potassium carbonate (83.0 g, 0.6 mol). The reaction mixture was stirred at room temperature for 24 hours. An additional two equivalents of potassium carbonate and one equivalent of carbon disulfide was added and the stirring was continued for another 24 hours. Solvent was removed and the residue was partitioned between dichloromethane and water. The organic layer was washed with brine, dried over magnesium sulfate and filtered. The filtrate was concentrated and the crude was stirred with 1000 mL of a mixture of ethyl acetate and ether (1:9) to give 78.4 g of pure product, 1-(4-chlorophenyl)-2-(1,3-dithietan-2-ylidene)-2-(4-pyridinyl)ethanone, as a yellow solid (82%), mp: 177–179° C. Anal. Calc'd. for $C_{15}H_{10}ClNOS_2$: C, 56.33; H, 3.15; N, 4.38. Found: C, 55.80; H, 2.84; N, 4.59.

Step 2: Preparation of 1-[3-(4-chlorophenyl)-3-oxo-2-(4-pyridinyl)-1-thiopropyl]-4-methylpiperazine

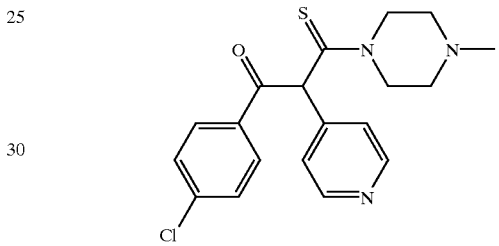

A mixture of 1-(4-chlorophenyl)-2-(1,3-dithietan-2-ylidene)-2-(4-pyridinyl)ethanone (78.3 g, 0.24 mol) and 1-methylpiperazine (75.0 g, 0.73 mol) in 800 mL of toluene was heated at reflux for 2 hours. Solvent and excess 1-methylpiperazine was removed under vacuum and the residue was triturated with a mixture was ethyl acetate and ether (1:3) to give 53.0 g of product, 1-[3-(4-chlorophenyl)-3-oxo-2-(4-pyridinyl)-1-thiopropyl]-4-methylpiperazine, as yellow crystals (60%), mp: 149–151° C. Anal. Calc'd. for $C_{19}H_{20}ClN_3OS$: C, 61.03; H, 5.39; N, 11.24. Found: C, 60.74; H, 5.35; N, 11.14.

Step 3: Preparation of 1-[5-(4-chlorophenyl)-4-(4-pyridinyl)-1H-pyrazol-3-yl]-4-methylpiperazine To a suspension of 1-[3-(4-chlorophenyl)-3-oxo-2-(4-pyridinyl)-1-thiopropyl]-4-methylpiperazine (52.0 g, 0.14 mol) in 500 mL of dry tetrahydrofuran was added anhydrous hydrazine (8.9 g, 0.28 mol) dropwise. The reaction mixture was stirred at room temperature for 16 hours. The pale yellow precipitate was filtered and recrystallized from hot methanol to give 30.2 g of 1-[5-(4-chlorophenyl)-4-(4-pyridinyl)-1H-pyrazol-3-yl]-4-methylpiperazine as a white powder (60%), mp: 267–268° C. Anal. Calc'd. for $C_{19}H_{20}ClN_5$: C, 64.49; H, 5.70; N, 19.79. Found: C, 64.89; H, 5.55; N, 19.99.

EXAMPLE A-342

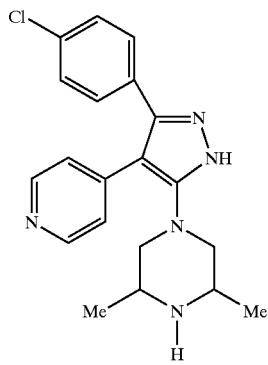

1-[5-(4-chlorophenyl)-4-(4-pyridinyl)-1H-pyrazol-3-yl]-3,5-dimethylpiperazine

A mixture of 1-(4-chlorophenyl)-2-(1,3-dithietan-2-ylidene)-2-(4-pyridinyl)ethanone (3.2 g, 0.01 mol; prepared as set forth in Step 1 of Example A-341) and 2,6-dimethylpiperazine (3.43 g, 0.03 mol) in 35 mL of toluene was heated at reflux for 12 hours. Toluene and excess 2,6-dimethylpiperazine were then removed under vacuum and the crude thiamide produced was used without purification. A solution of the crude thiamide and anhydrous hydrazine (0.65 g, 0.02 mol) in 40 mL of dry tetrahydrofuran was stirred at room temperature overnight. After the removal of tetrahydrofuran, the residue was stirred with a mixture of ethyl acetate and ammonium hydroxide for one hour. The precipitate was filtered and air dried to give 1.6 g of 1-[5-(4-chlorophenyl)-4-(4-pyridinyl)-1H-pyrazol-3-yl]-3,5-dimethylpiperazine as a white solid (43% overall yield), mp: 236–238° C. Anal. Calc'd. for $C_{20}H_{22}ClN_5 \cdot 0.25H_2O$: C, 64.51; H. 6.09; N, 18.81; Cl, 9.52. Found: C, 64.28; H, 5.85; N, 18.70; Cl, 9.67.

EXAMPLE A-343

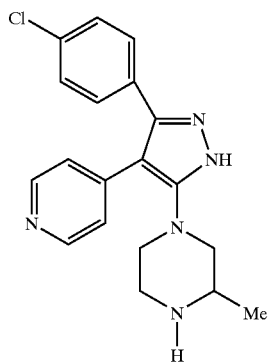

1-[5-(4-chlorophenyl)-4-(4-pyridinyl)-1H-pyrazol-3-yl]-3-methylpiperazine

1-[5-(4-Chlorophenyl)-4-(4-pyridinyl)-1H-pyrazol-3-yl]-3-methylpiperazine was prepared according to the same procedure set forth above in Example A-342 except that 2-methylpiperazine was used in place of 2,6-dimethylpiperazine (4% overall yield), mp: 235–237° C. Anal. Calc'd. for $C_{19}H_{20}ClN_5 \cdot 0.75H_2O$: C, 62.12; H, 5.90; N, 19.06. Found: C, 62.23; H, 5.53; N, 18.80.

EXAMPLE A-344

The compound of Example A-317 was also synthesized in the following manner:

Step 1: Preparation of 1-(4-pyridyl)-1-(methylenedithioketene)-2-(4-fluorophenyl)-ethanone To a solution of 4-fluorobenzoyl-4'-pyridyl methane (70.0 g, 0.3 mol, prepared as set forth in Step 1 of Example A-208) and dibromomethane (125 mL) was added solid anhydrous potassium carbonate (55.0 g, 0.4 mol) portionwise over five minutes. Carbon disulfide (17 g, 0.22 mol) was added dropwise over 15 minutes at room temperature. After stirring for 16 hours under a nitrogen atmosphere, the reaction was incomplete. Additional carbon disulfide (15 g) was added and the reaction mixture was stirred for an additional 24 hours. The reaction mixture was filtered and the potassium carbonate was washed on the filter with methylene chloride. The filtered solid was dissolved in water and extracted with methylene chloride. The extract was combined with the filtrate and dried over magnesium sulfate. The drying agent was filtered and the filtrate concentrated in vacua. The residue was treated with ethyl acetate/ether (1:1), filtered and air dried to give 1-(4-pyridyl)-1-(methylenedithioketene)-2-(4-fluorophenyl)-ethanone (26 g, 86%) as a solid, m.p. 182–183° C.; Anal. Calc'd. for $C_{15}H_{10}FNOS_2$: C, 59.39; H, 3.32; N, 4.62. Found: C, 59.18; H, 3.41; N, 4.49.

Step 2: Preparation of 1-[5-(4-fluorophenyl)-4-(4-pyridinyl)-1H-pyrazol-3-yl]-4-methylipiperazine, dihydrate A mixture of the 1-(4-pyridyl)-1-(methylenedithioketene)-2-(4-fluorophenyl)-ethanone (3 g, 0.01 mol) prepared in Step 1 and 1-methylpiperazine (3 g, 0.03 mol) in 30 mL of toluene was refluxed under a nitrogen atmosphere for three hours. The mixture was cooled and solvent was removed under vacuum. The residue was dissolved in dry tetrahydrofuran (30 mL) and anyhydrous hydrazine (640 mg, 0.02 mol) was added. The reaction mixture was stirred at room temperature for 16 hours and the resulting precipitate was filtered. The precipitate was warmed in methanol and a few drops of concentrated ammonium hydroxide were added. The mixture was filtered hot and the filtrate blown down to half the volume. As the filtrate cooled, a product crystallized and was filtered to give 1.5 g (42%) of 1-[5-(4-fluorophenyl)-4-(4-pyridinyl)-1H-pyrazol-3-yl]-4-methylpiperazine, dihydrate, mp: 238–240° C.; Anal. Calc'd. for $C_{19}H_{20}FN_5 \cdot 2H_2O$: C, 61.11; H, 65.48; N, 18.75. Found: C, 60.79; H, 6.21; N, 18.98.

EXAMPLE A-345

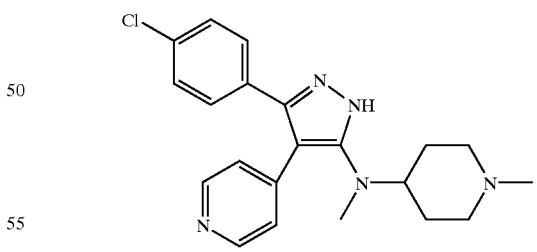

N-[5-(4-chlorophenyl)-4-(4-pyridinyl)-1H-pyrazol-3-yl]-4-N,1-dimethyl-4-piperidinamine, dihydrate Step 1: Preparation of 1-methyl-4-methylaminopiperidine A mixture of 1-methyl-4-piperidone (20 g, 0.18 mol) in methanol:tetrahydrofuran (100 mL, 1:1) and methyl amine (2 M in tetrahydrofuran, 3 mole excess) was placed in a Parr shaker with 5% Pd/C and hydrogenated for two hours at 60 psi and 70° C. The catalyst was filtered and the filtrate concentrated on the rotary evaporator. The crude material was distilled at 44–45° C. at 0.3 mm Hg to give 20 g (87%)

of 1-methyl-4-methylaminopiperidine. Anal. Calc'd for $C_7H_{16}N_2$: C, 65.57; H, 12.58; N, 21.85. Found: C, 65.49; H, 12.44; N: 21,49.

Step 2: Preparation of N-[5-(4-chlorophenyl)-4-(4-pyridinyl)-1H-Pyrazol-3-yl]-4-N,1-dimethyl-4-piperidinamine, dihydrate A solution of 1-(4-chlorophenyl)-2-(1,3-dithietan-2-ylidene)-2-(4-pyridinyl)ethanone (3.2 g, 0.01 mol; prepared as set forth in Step 1 of Example A-341) and 1-methyl-4-methylaminopiperidine (3.8 g, 0.03 mol) in 30 mL of toluene refluxed for six hours under nitrogen. The mixture was cooled and solvent was removed under vacuum. The residue was dissolved in dry tetrahydrofuran (30 mL) and anyhydrous hydrazine (650 mg, 0.02 mol) was added. The reaction mixture was stirred at room temperature under nitrogen for 16 hours. The resulting precipitate was filtered and warmed in methanol and a few drops of concentrated ammonium hydroxide. The mixture was filtered hot and the filtrate blown down to half the volume. As the filtrate cooled, a product separated and was filtered to give 395 of pure N-[5-(4-chlorophenyl)-4-(4-pyridinyl)-1H-pyrazol-3-yl]-4-N,1-dimethyl-4-piperidinamine, dihydrate, m.p. 260–261° C. Anal. Calc'd for $C_{21}H_{24}ClN_5\cdot 2H_2O$: C, 60.35; H, 6.75; N, 16.76. Found: C, 59.89; H, 6.56; N: 16.40.

Additional compounds of the present invention that were prepared according to one or more of above reaction schemes (particularly Schemes IX through XVIII) are disclosed in Table 3-2. The specific synthesis scheme or schemes as well as the mass spectroscopy and elemental analysis results for each compound also are disclosed in Table 3-2.

TABLE 3-2

| Example | General | MS M+ | C Found | C Found | H Calc | H Found | N Calc | N Found | Water Added | EtOAc Added | CHCl₃ Added | Toluene Added | HCl Added |
|---|---|---|---|---|---|---|---|---|---|---|---|---|---|
| A-346 | XII | | | | | | | | | | | | |
| A-347 | XII | 329 | 59.33 | 59.59 | 5.65 | 5.47 | 15.55 | 15.41 | 0.8 | 0.2 | | | |
| A-348 | XII | 439 | 68.46 | 66.59 | 8.04 | 8.48 | 19.16 | 16.17 | | | | | |
| A-349 | XII | 397 | 61.85 | 61.99 | 7.79 | 7.52 | 17.45 | 17.39 | 1.3 | 0.7 | | | |
| A-350 | XII | 449 | 66.29 | 66.75 | 7.60 | 7.68 | 17.84 | 17.00 | 1.25 | | | | |
| A-351 | XII | 352 | 68.36 | 57.51 | 6.31 | 7.31 | 19.93 | 17.17 | | | | | |
| A-352 | XII | 366 | 69.02 | 66.27 | 6.62 | 6.59 | 19.16 | 18.22 | | | | | |
| A-353 | XII | 430 | 69.26 | 71.50 | 7.40 | 6.91 | 18.36 | 14.87 | | | | | |
| A-354 | XII | 355 | 70.48 | 70.12 | 6.80 | 7.15 | 13.99 | 13.91 | | | | 0.5 | |
| A-355 | XII | 341 | 66.73 | 67.09 | 6.29 | 6.77 | 16.04 | 15.78 | | 0.1 | | | |
| A-356 | XVII | 410 | 63.42 | 63.61 | 6.00 | 6.06 | 16.81 | 16.63 | 0.4 | | | | |
| A-357 | XVII | 392 | 54.37 | 53.93 | 5.91 | 6.32 | 13.78 | 14.68 | 0.4 | | | | |
| A-358 | XII | 394 | 70.20 | 68.50 | 7.17 | 7.68 | 17.80 | 16.58 | | | | | |
| A-359 | XVII | 396 | 69.21 | 69.33 | 7.68 | 8.01 | 17.55 | 17.61 | 0.2 | | | | |
| A-360 | XVII | 366 | 50.81 | 50.74 | 5.97 | 5.80 | 14.11 | 14.00 | 1.2 | | | | 3 |
| A-361 | XII | 389 | 71.12 | 68.67 | 5.45 | 5.64 | 14.42 | 12.90 | | | | | |
| A-362 | XII | 375 | 70.57 | 68.54 | 5.12 | 5.39 | 14.96 | 13.90 | | | | | |
| A-363 | XII | 389 | 71.12 | 68.86 | 5.45 | 5.58 | 14.42 | 13.09 | | | | | |
| A-364 | XVII | 368 | 68.31 | 68.39 | 7.15 | 7.49 | 18.97 | 18.93 | 0.1 | | | | |
| A-365 | XVII | 338 | 48.72 | 48.57 | 5.47 | 5.45 | 14.95 | 14.79 | 1.2 | | | | 3 |
| A-366 | XII | 397 | 56.34 | 56.21 | 7.31 | 7.03 | 17.92 | 17.89 | 2 | | | | 1 |
| A-367 | XVII | 321 | 70.25 | 69.83 | 5.43 | 5.62 | 17.25 | 17.82 | 0.25 | | | | |
| A-368 | XII | 313 | 64.66 | 64.28 | 5.73 | 5.62 | 16.76 | 16.93 | | 0.25 | | | |
| A-369 | XII | 412 | 66.76 | 66.60 | 7.36 | 7.61 | 16.93 | 16.74 | 0.1 | | | | |
| A-370 | XII | 313 | 64.66 | 64.36 | 5.73 | 5.59 | 16.76 | 16.82 | | 0.25 | | | |
| A-371 | XVII | | 63.78 | 63.63 | 6.37 | 6.09 | 17.71 | 17.24 | 1 | | | | |
| A-372 | XII | | 68.63 | 68.80 | 7.26 | 7.53 | 17.40 | 17.14 | 0.5 | | | | |
| A-373 | XVII | 389 | 58.10 | 57.99 | 5.00 | 4.88 | 17.83 | 17.48 | 0.25 | | | | |
| A-374 | XII | 354 | 67.97 | 67.23 | 6.84 | 6.81 | 19.81 | 19.38 | | | | | |
| A-375 | XII | 366 | 68.18 | 68.06 | 6.67 | 6.80 | 18.93 | 16.56 | 0.25 | | | | |
| A-376 | XII | 375 | 70.57 | 68.19 | 5.12 | 6.06 | 14.96 | 13.13 | | | | | |
| A-377 | XII | 396 | 64.14 | 64.44 | 6.99 | 6.78 | 16.02 | 16.02 | | | 0.35 | | |
| A-378 | XVII | 337 | 66.42 | 66.44 | 5.22 | 4.91 | 16.31 | 16.27 | 0.4 | | | | |
| A-379 | XVII | 339 | 62.76 | 62.80 | 6.04 | 5.43 | 15.41 | 15.17 | 1.4 | | | | |
| A-380 | XVII | 381 | 63.31 | 63.40 | 5.19 | 5.82 | 14.06 | 13.84 | 1 | | | | 1 |
| A-381 | XVII | 307 | 70.57 | 69.69 | 4.94 | 5.00 | 18.29 | 17.68 | | | | | |
| A-382 | XVII | | | | | | | | | | | | |
| A-383 | XVII | | | | | | | | | | | | |
| A-384 | | 320 | 55.48 | 53.44 | 5.64 | 5.00 | 17.03 | 21.60 | | | | | |
| A-385 | XI | 280 | 52.65 | 52.51 | 5.98 | 5.17 | 10.83 | 11.12 | | | | | |
| A-386 | XII | 351 | 64.96 | 64.77 | 5.82 | 5.34 | 14.85 | 15.03 | 1 | 0.1 | | | |
| A-387 | XII | 353 | 65.29 | 65.62 | 6.32 | 6.14 | 14.64 | 14.47 | 0.7 | 0.2 | | | |
| A-388 | | 394 | 54.93 | 55.34 | 6.21 | 6.79 | 13.93 | 14.01 | | | | | 3 |

EXAMPLE A-346

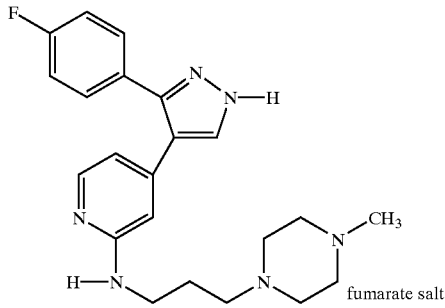

N-[4-[3-(4-fluorophenyl)-1H-pyrazol-4-yl]-2-pyridinyl]-4-methyl-1-piperazinepropanamine(2E)-2-butenedioate (1:1)

EXAMPLE A-347

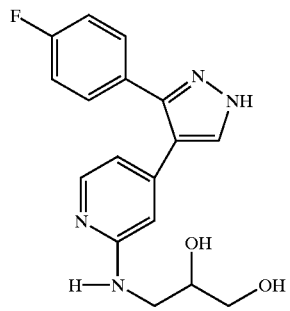

3-[[4-[3-(4-fluorophenyl)-1H-pyrazol-4-yl]-2-pyridinyl]amino]-1,2-propanediol

EXAMPLE A-348

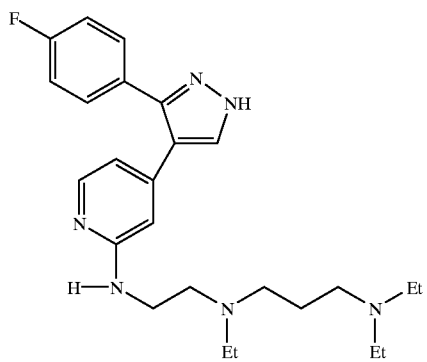

N,N''-triethyl-N'-[2-[[4-[3-(4-fluorophenyl)-1H-pyrazol-4-yl]-2-pyridinyl]amino]ethyl]-1,3-propanediamine;

EXAMPLE A-349

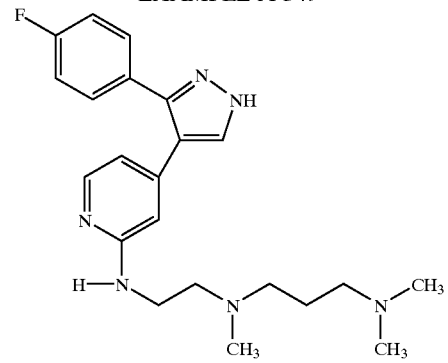

N-[2-[[4-[3-(4-fluorophenyl)-1H-pyrazol-4-yl]-2-pyridinyl]amino]ethyl]-N,N',N'-trimethyl-1,3-propanediamine;

EXAMPLE A-350

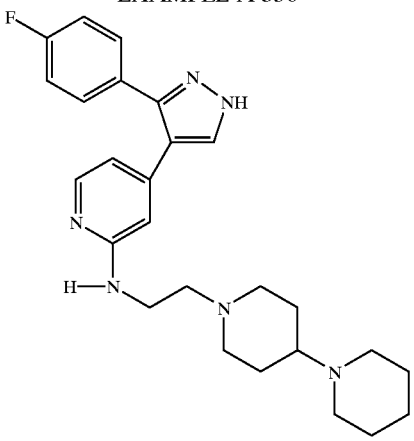

N-(2-[1,4'-bipiperidin]-1'-ylethyl)-4-[3-(4-fluorophenyl)-1H-pyrazol-4-yl]-2-pyridinamine

EXAMPLE A-351

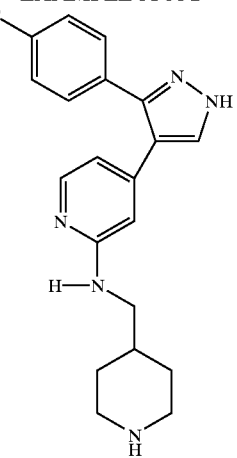

4-[3-(4-fluorophenyl)-1H-pyrazol-4-yl]-N-(4-piperidinylmethyl)-2-pyridinamine

EXAMPLE A-352

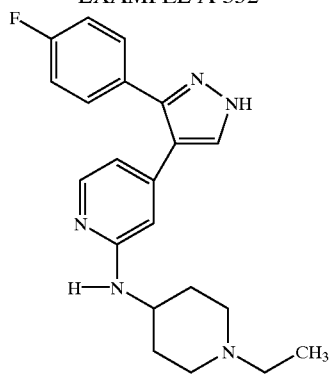

N-(1-ethyl-4-piperidinyl)-4-[3-(4-fluorophenyl)-1H-pyrazol-4-yl]-2-pyridinamine

EXAMPLE A-353

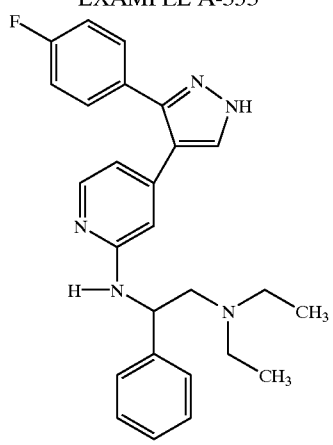

N2,N2-diethyl-N1-[4-[3-(4-fluorophenyl)-1H-pyrazol-4-yl]-2-pyridinyl]-1-phenyl-1,2-ethanediamine

EXAMPLE A-354

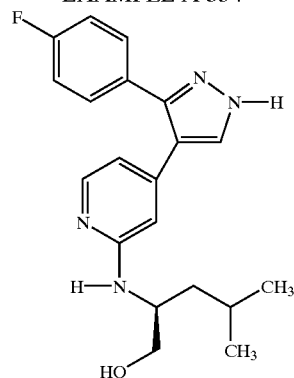

(2S)-2-[[4-[3-(4-fluorophenyl)-1H-pyrazol-4-yl]-2-pyridinyl]amino]-4-methyl-1-pentanol

EXAMPLE A-355

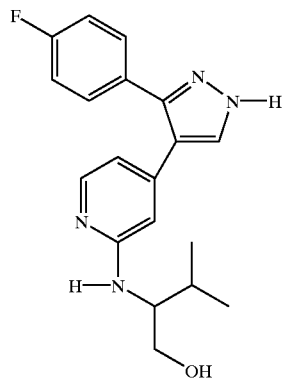

2-[[4-[3-(4-fluorophenyl)-1H-pyrazol-4-yl]-2-pyridinyl]amino]-3-methyl-1-butanol

EXAMPLE A-356

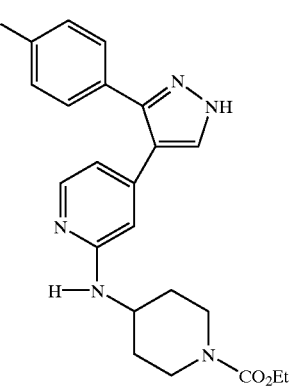

ethyl 4-[[4-[3-(4-fluorophenyl)-1H-pyrazol-4-yl]-2-pyridinyl]amino]-1-piperidinecarboxylate

EXAMPLE A-357

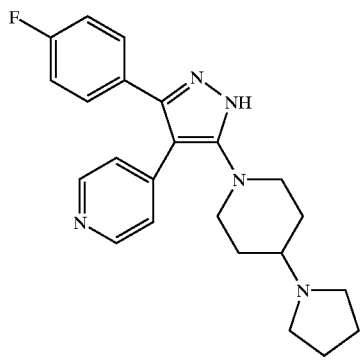

4-[3-(4-fluorophenyl)-5-(4-(1-pyrrolidinyl)-1-piperidinyl]-1H-pyrazol-4-yl]pyridine, trihydrochlaride

EXAMPLE A-358

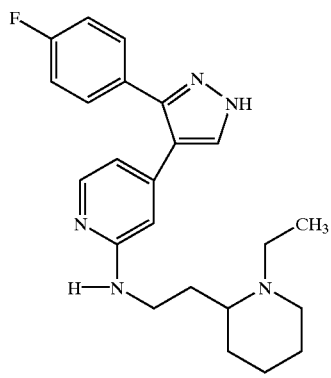

N-[2-(1-ethyl-2-piperidinyl)ethyl]-4-[3-(4-fluorophenyl)-1H-pyrazol-4-yl]-2-pyridinamine

EXAMPLE A-359

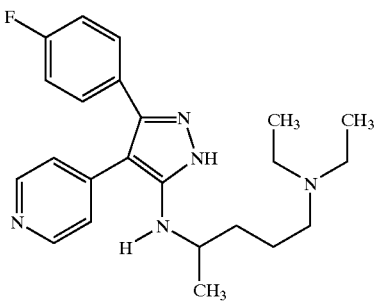

N1,N1,-diethyl-N4-[5-(4-fluorophenyl)-4-(4-pyridinyl)-1H-pyrazol-3-yl]-1,4-pentanediamine

EXAMPLE A-360

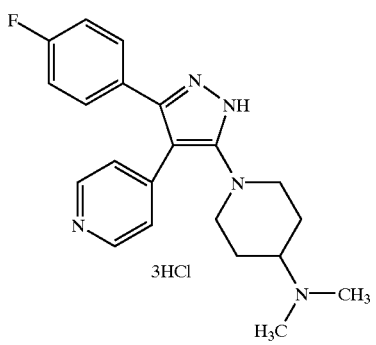

1-[5-(4-flucrophenyl)-4-(4-pyridinyl)-1H-pyrazol-3-yl]-N,N-dimethyl-4-piperidinamine, trihydrochloride

EXAMPLE A-361

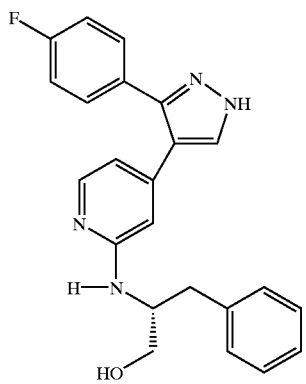

(βR)-β-[[4-[3-(4-fluorophenyl)-1H-pyrazol-4-yl]-2-pyridinyl]amino]benzene propanol

EXAMPLE A-362

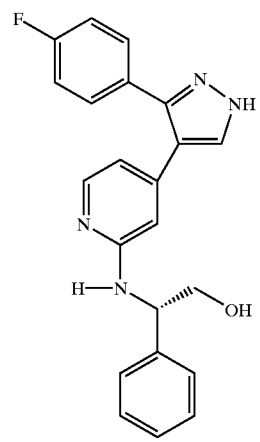

(βS)-β-[[4-[3-(4-fluorophenyl)-1H-pyrazol-4-yl]-2-pyridinyl]amino]benzene ethanol

EXAMPLE A-363

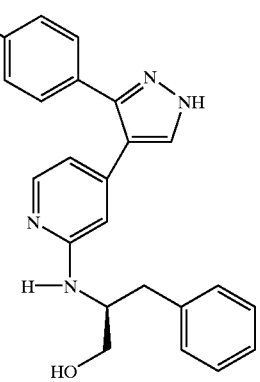

(βS)-β-[[4-[3-(4-fluorophenyl)-1H-pyrazol-4-yl]-2-pyridinyl]amino]benzene propanol

EXAMPLE A-364

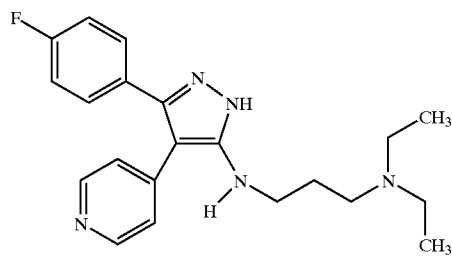

N,N-diethyl-N'-[5-(4-fluorophenyl)-4-(4-pyridinyl)-
1H-pyrazol-3-yl]-1,3-propanediamine

EXAMPLE A-365

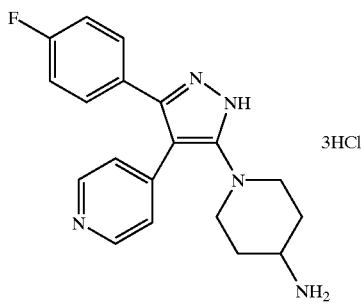

1-[5-(4-fluorophenyl)-4-(4-pyridinyl)-1H-pyrazol-3-
yl]-4-piperidinamine, trihydrochloride

EXAMPLE A-366

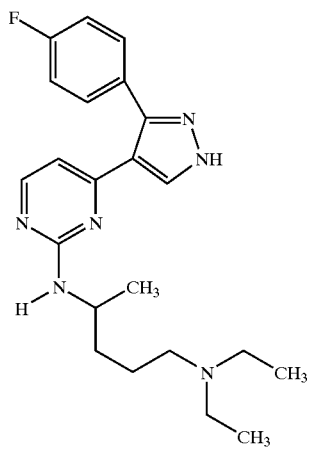

N1,N1-diethyl-N4-[4-[3-(4-fluorophenyl)-1H-
pyrazol-4-yl]-2-pyrimidinyl]-1,4-pentanediamine

EXAMPLE A-367

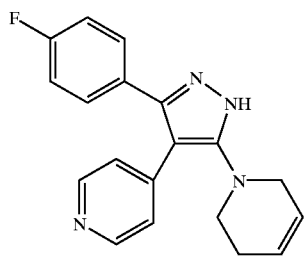

1-[5-(4-fluorophenyl)-4-(4-pyridinyl)-1H-pyrazol-3-
yl]-1,2,3,6-hexahydropyridine

EXAMPLE A-368

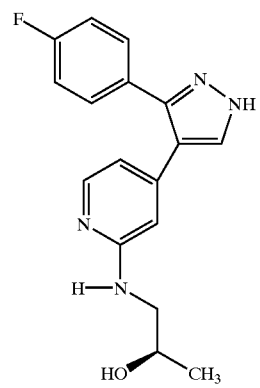

(2R)-1-[[4-[3-(4-fluorophenyl)-1H-pyrazol-4-yl]-2-
pyridinyl]amino]-2-propanol

EXAMPLE A-369

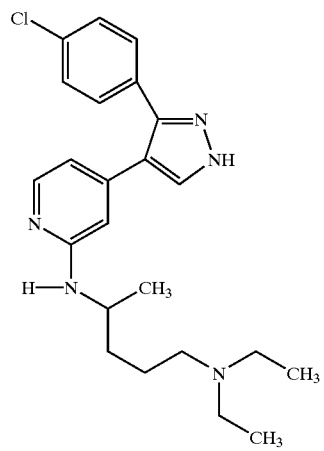

N4-[4-[3-(4-chlorophenyl)-1H-pyrazol-4-yl]-2-
pyridinyl]-N1,N1-diethyl-1,4-pentanediamine

EXAMPLE A-370

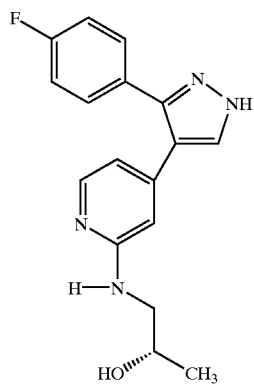

(2S)-1-[[4-[3-(4-fluorophenyl)-1H-pyrazol-4-yl]-2-pyridinyl]amino]-2-propanol

EXAMPLE A-371

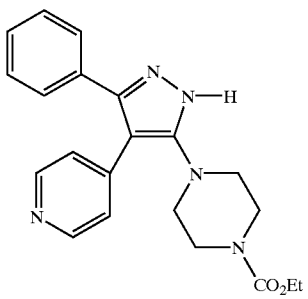

ethyl 4-[5-phenyl-4-(4-pyridinyl)-1H-pyrazol-3-yl]-1-piperazinecarboxylate

EXAMPLE A-372

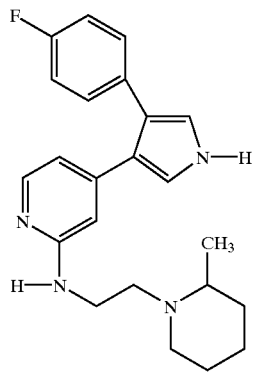

4-[3-(4-fluorophenyl)-1H-pyrazol-4-yl]-N-[3-(2-methyl-1-piperidinyl)propyl]-2-pyridinamine

EXAMPLE A-373

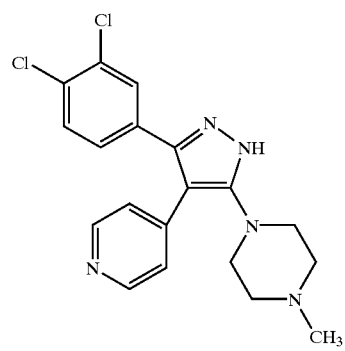

1-[5-(3,4-dichlorophenyl)-4-(4-pyridinyl)-1H-pyrazol-3-yl]-4-methylpiperazine

EXAMPLE A-374

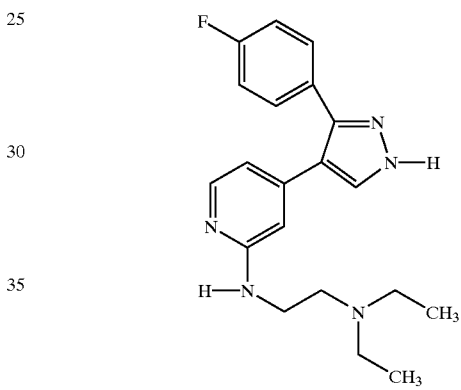

N,N-diethyl-N'-[4-[3-(4-fluorophenyl)-1H-pyrazol-4-yl]-2-pyridinyl]-1,2-ethanediamine

EXAMPLE A-375

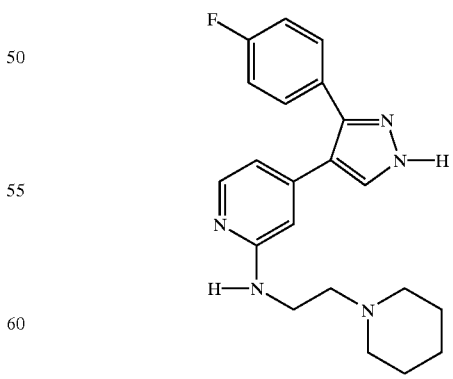

4-[3-(4-fluorophenyl)-1H-pyrazol-4-yl]-N-[2-(1-piperidinyl)ethyl]-2-pyridinamine

EXAMPLE A-376

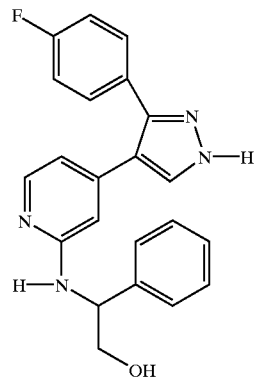

(βR)-β-([4-[3-(4-fluorophenyl)-1H-pyrazol-4-yl-2-pyridinyl]amino]benzene ethanol

EXAMPLE A-377

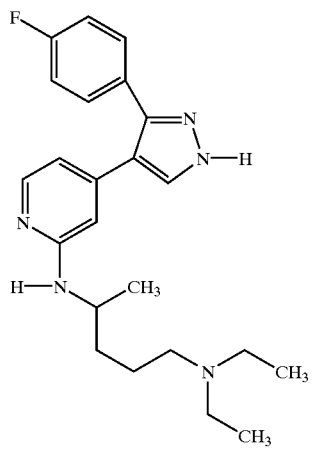

N1,N1-diethyl-N4-[4-[3-(4-fluorophenyl)-1H-pyrazol-4-yl]-2-pyridinyl]-1,4-pentanediamine

EXAMPLE A-378

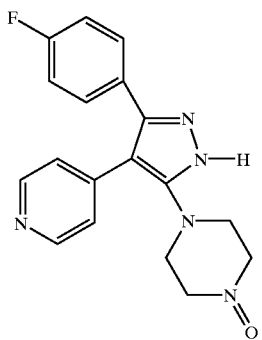

1-[5-(4-fluorophenyl)-4-(4-pyridinyl)-1H-pyrazol-3-yl]-4-piperidinone

EXAMPLE A-379

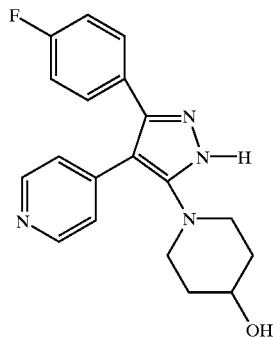

1-[5-(4-fluorophenyl)-4-(4-pyridinyl)-1H-pyrazol-3-yl]-4-piperidinol

EXAMPLE A-380

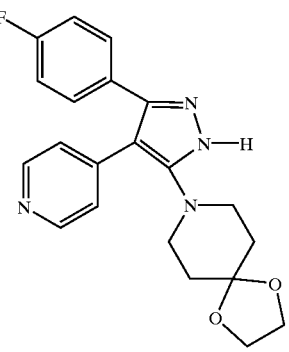

8-(5-(4-fluorophenyl)-4-(4-pyridinyl)-1H-pyrazol-3-yl]-1,4-dioxa-8-azaspiro[4.5]decane;

EXAMPLE A-381

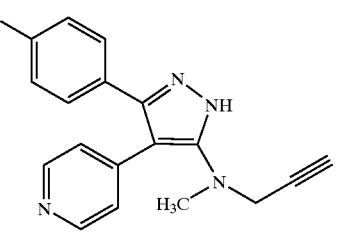

5(4-fluorophenyl)-N-methyl-N-2-propynyl-4-(4-pyridinyl)-1H-pyrazol-3-amine

EXAMPLE A-382

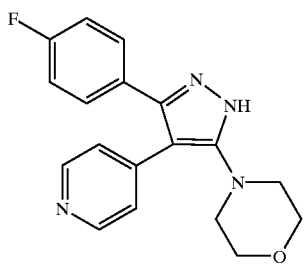

4-[5-(4-fluorophenyl)-4-(4-pyridinyl)-1H-pyrazol-3-yl]morpholine

EXAMPLE A-383

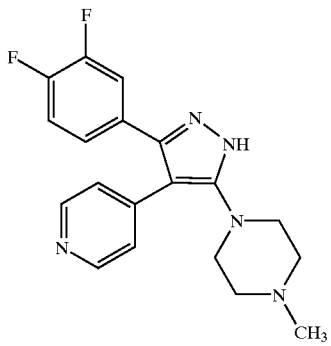

1-[5-(3,4-difluorophenyl)-4-(4-pyridinyl)-1H-pyrazol-3-yl]-4-methylpiperazine

EXAMPLE A-384

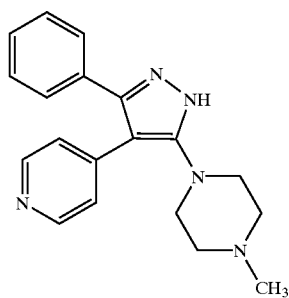

1-methyl-4-[5-phenyl-4-(4-pyridinyl)-1H-pyrazol-3-yl]piperazine

EXAMPLE A-385

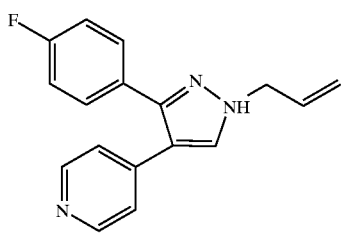

4-[3-(4-fluorophenyl)-1-(2-propenyl)-1H-pyrazol-4-yl]pyridine, monohydrochloride

EXAMPLE A-386

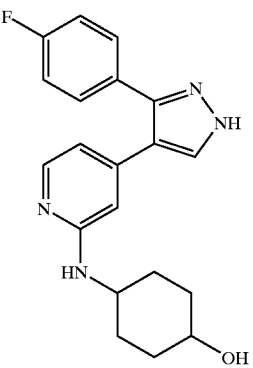

trans-4-[[4-[3-(4-fluorophenyl)-1H-pyrazol-4-yl]-2-pyridinyl]amino]cyclohexanol

EXAMPLE A-387

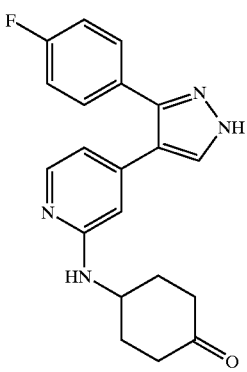

4-[[4-[3-(4-fluorophenyl)-1H-pyrazol-4-yl]-2-pyridinyl]amino]cyclohexanone

EXAMPLE A-388

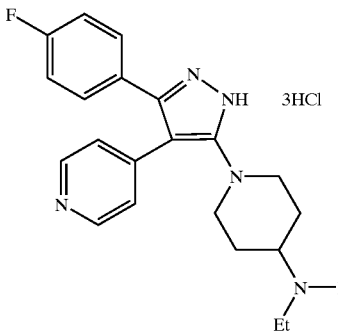

1-[5-(4-fluorophenyl)-4-(4-pyridinyl)-1H-pyrazol-3-yl]-N,N-diethyl-4-piperidinamine, trihydrochloride

EXAMPLE A-389

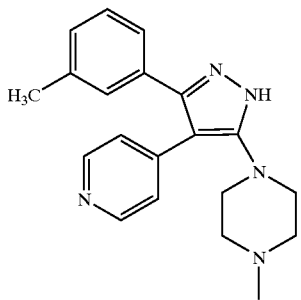

1-[5-(3-tolyl)-4-(4-pyridinyl)-1H-pyrazol-3-yl-4-methylpiperazine

Step 1. Preparation of 1-tolyl-2-(4-pyridyl)ethanone

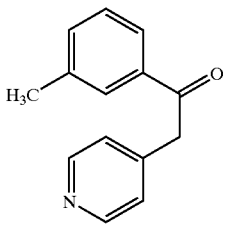

Methyl 3-methylbenzoate (6.0 g, 40 mmol), tetrahydrofuran (50 mL), and 4-picoline (4.1 g, 44 mmol) were stirred at −78° C. under an atmosphere of nitrogen. Sodium (bis) trimethylsilylamide 1.0 M in tetrahydrofuran (88 mL, 88 mmol) was added dropwise. The mixture was allowed to warm to room temperature, stirred for 16 hours and then was poured into saturated aqueous sodium bicarbonate solution. The mixture was then extracted with ethyl acetate (3×50 mL). The combined organics were washed with brine (2×50 mL), dried over magnesium sulfate, and concentrated. The product was recrystallized from ethyl acetate/hexane to yield a light yellow solid (5.7 g, 67%), mp 118.0–119.0° C.; $^1$H NMR (acetone-d6/300 MHz) 8.50 (m, 2H), 7.90 (m, 2H), 7.44 (m, 2H), 7.29 (m, 2H), 4.45 (s, 2H), 2.41 (s, 3H); ESHRMS m/z 212.1067 (M+H, $C_{14}H_{13}NO$ requires 212.1075); Anal. Calc'd for $C_{14}H_{13}NO$: C, 79.59; H, 6.20; N, 6.63. Found: C, 79.54; H, 6.30; N, 6.56.

Step 2. Preparation of 1-(3-tolyl)-2-(1,3-dithietan-2-ylidene)-2-(4-pyridyl)ethanone

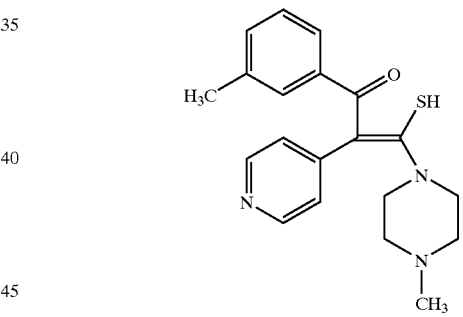

1-tolyl-2-(4-pyridyl)ethanone (4.22 g, 20 mmol), acetone (100 mL), potassium carbonate (8.3 g, 60 mmol), carbon disulfide 4.56 g, 60 mmol), and dibromomethane (10.43 g, 60 mmol) were stirred at room temperature for 16 hours. Water (100 mL) was added and the mixture was extracted with ethyl acetate (3×50 mL). The combined organic extracts were washed with brine (2×50 mL), dried over magnesium sulfate and concentrated. This crude material was purified by either flash column chromatography eluting with ethyl acetate:hexane or crystallization from ethyl acetate/hexane to yield a yellow solid (4.8 g, 80%), mp 178.6–179.2° C.; $^1$H NMR (acetone-d6/300 MHz) 8.47 (m, 2H), 7.08 (m, 6H), 4.37 (s, 2H), 2.21 (s, 3H); ESHRMS m/z 300.0521 (M+H, $C_{16}H_{13}NOS_2$ requires 300.0517); Anal. Calc'd for $C_{16}H_{13}NOS_2$: C, 64.18; H, 4.38; N, 4.68. Found: C, 64.08; H, 4.25; N, 4.62.

Step 3. Preparation of 1-[3-(3-tolyl)-3-oxo-2-(4-pyridinyl)-1-thyiopropyl]-4-methylpiperazine The dithietane compound from step 2 above (3.0 g, 10 mmol), N-methylpiperazine (5.0 g, 50 mmol), and toluene (50 mL) were refluxed using a Dean-Stark apparatus for one to three hours. The reaction was allowed to cool to room temperature and was concentrated to dryness under high vacuum. This thick, oily material was crystallized from ethyl acetate/hexane (2.9 g, 82%), mp 124.8–125.8° C.; $^1$H NMR (acetone-d6/300 MHz) 8.57 (m, 2H), 7.75 (m, 2H), 4.19 (m, 1H), 3.83 (m, 1H), 2.47–2.28 (m, 6H), 2.22 (s, 3H), 2.17 (m, 1H); ESHRMS m/z 354.1669 (M+H, $C_{20}H_{23}N_3OS$ requires 354.1640); Anal. Calc'd for $C_{20}H_{23}N_3OS$: C, 67.96; H, 6.56; N, 11.89. Found: C, 67.79; H, 6.66; N, 11.88.

Step 4. Preparation of 1-[5-(3-tolyl)-4-(4-pyridinyl)-1H-pyrazol-3-yl-4-methylpiperazine The thioamide compound from step 3 above (1.06 g, 3 mmol), tetrahydrofuran (50 mL), and hydrazine (15 mL, 15 mmol, 1.0 M) in tetrahydrofuran were stirred at room temperature for 16 hours. A white solid was collected by filtration. Purification when necessary was by trituration or recrystallization (0.98 g, 97%), mp 261.9–262.0° C.; $^1$H NMR (DMSO-d6/300 MHz) 12.6 (brs, 1H), 8.42 (m, 2H), 7.2 (m, 4H), 7.12 (s, 1H), 7.0 (m, 1H), 2.86 (m, 4H), 2.34 (m, 4H) 2.25 (s, 3H), 2.16 (s, 3H); ESHRMS m/z 334.2049 (M+H, $C_{20}H_{23}N_5$ requires 334.2032); Anal. Calc'd for $C_{20}H_{23}N_5$: C, 72.04; H, 6.95; N, 21.00. Found: C, 71.83; H, 7.06; N, 20.83.

Additional dithietanes and pyrazoles that were synthesized by selection of the corresponding starting reagents in accordance with the chemistry described in Scheme XXI and further illustrated in Example 389 above include compounds A-390 through A-426 disclosed below.

EXAMPLE A-390

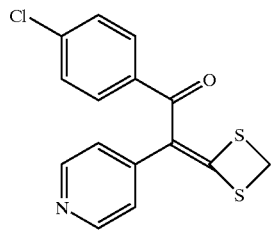

mp 185.3–185.4° C.; $^1$H NMR (acetone-d6/300 MHz) 8.49 (m, 2H), 7.31 (m, 4H), 7.09 (m, 2H), 4.39 (s, 2H); ESHRMS m/z 319.9981 (M+H, $C_{15}H_{10}ClNOS_2$ requires 319.9971); Anal. Calc'd for $C_{15}H_{10}ClNOS_2$: C, 56.33; H, 3.15; N, 4.38. Found: C, 56.47; H, 3.13; N, 4.44.

EXAMPLE A-391

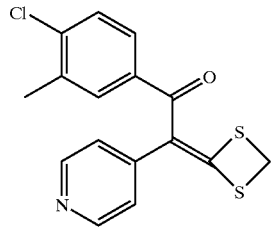

1-(4-chloro-3-methylphenyl)-2-1,3-dithietan-2-ylidene-2-pyridin-4-yl-ethanone mp 164.0–165.0° C.; $^1$H NMR (acetone-d6/300 MHz) 8.49 (m, 2H), 7.25 (m, 2H), 7.0 (m, 3H), 4.38 (s, 2H), 2.24 (s, 3H); ESHRMS m/z 334.0130 (M+H, $C_{16}H_{12}ClNOS_2$ requires 334.0127); Anal. Calc'd for $C_{16}H_{12}ClNOS_2$: C, 57.56; H, 3.62; N, 4.20. Found: C, 57.68; H, 3.67; N, 4.17.

EXAMPLE A-392

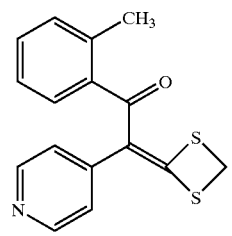

mp 126.5–126.6° C.; $^1$H NMR (acetone-d6/300 MHz) 8.40 (m, 2H), 7.17 (m, 2H), 7.0 (m, 4H), 4.39 (s, 2H), 2.85 (s, 3H); ESHRMS m/z 300.0483 (M+H, $C_{16}H_{13}NOS_2$ requires 300.0517); Anal. Calc'd for $C_{16}H_{13}NOS_2$: C, 64.18; H, 4.38; N, 4.68. Found: C, 64.05; H, 4.27; N, 4.59.

EXAMPLE A-393

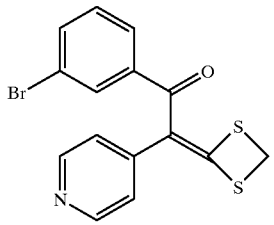

mp 159.6–159.7° C.; $^1$H NMR (acetone-d6/300 MHz) 8.52 (m, 2H), 7.6 (m, 1H), 7.50 (s, 1H), 7.21 (m, 2H), 7.13 (m, 2H), 4.40 (s, 2H); ESHRMS m/z 363.9503 (M+H, $C_{15}H_{10}BrNOS_2$ requires 363.9465); Anal. Calc'd for $C_{15}H_{10}BrNOS_2$: C, 49.46; H, 2.77; N, 3.84. Found: C, 49.51; H, 2.68; N, 3.74.

EXAMPLE A-394

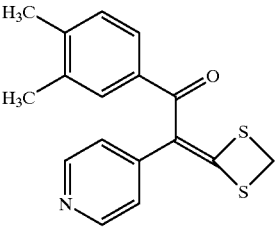

mp 198.8–198.9° C.; $^1$H NMR (acetone-d6/300 MHz) 8.45 (m, 2H), 7.05 (m, 3H), 6.95 (m, 1H), 6.82 (m, 1H), 4.29 (s, 2H), 2.14 (s, 3H), 2.08 (s, 3H); ESHRMS m/z 314.0691 (M+H, $C_{17}H_{15}NOS_2$ requires 314.0673).

EXAMPLE A-395

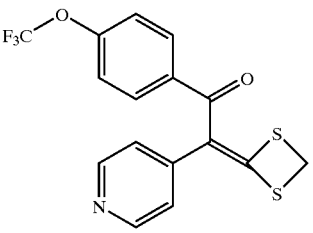

mp 182.6–183.0° C. $^1$H NMR (acetone-d6/300 MHz) 8.50 (m, 2H), 7.42 (d, 2H, J=8.5 Hz), 7.23 (d, 2H, J=8.5 Hz), 7.10 (m, 2H), 4.40 (s, 2H). ESHRMS m/z 370.0173 (M+H, $C_{16}H_{10}F_3NO_2S_2$ requires 370.0183).

EXAMPLE A-396

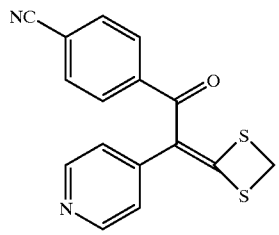

mp 193.3–193.4° C. $^1$H NMR (acetone-d6/300 MHz) 8.49 (m, 2H), 7.69 (d, 2H, J=8.2 Hz), 7.46 (d, 2H, J=8.2 Hz), 7.01 (m, 2H), 4.43 (s, 2H). ESHRMS m/z 311.0327 (M+H, $C_{16}H_{10}N_2OS_2$ requires 311.0313).

EXAMPLE A-397

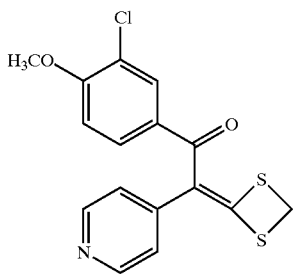

mp 191.5–192.5° C.; $^1$H NMR (CDCl$_3$/300 MHz) 8.55 (dd, 2H, J=4.6, 1.6 Hz), 7.4 (m, 1H), 7.09–7.03 (m, 3H), 6.67 (d, 1H, J=8.7 Hz), 4.17 (s, 2H), 3.86 (s, 3H); ESHRMS m/z 350.0090 (M+H, $C_{16}H_{12}ClNO_2S_2$ requires 350.0076); Anal. Calc'd. for $C_{16}H_{12}ClNO_2S_2$: C, 54.93; H, 3.60; N, 4.00; Cl, 10.13; S, 18.33. Found: C, 54.74; H, 3.60; N, 3.89; Cl, 10.45; S, 18.32.

EXAMPLE A-398

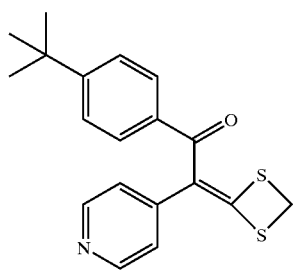

mp 172.1–173.1° C.; $^1$H NMR (CDCl$_3$/300 MHz) 8.51 (dd, 2H, J=4.4, 1.6 Hz), 7.23–7.21 (m, 4H), 7.04 (dd, 2H, J=4.6, 1.6 Hz), 4.17 (s, 2H), 1.25 (s, 9H); ESHRMS m/z 342.1004 (M+H, $C_{19}H_{19}NOS_2$ requires 342.0986); Anal. Calc'd for $C_{19}H_{19}NOS_2$: C, 66.83; H, 5.61; N, 4.10; S, 18.78. Found: C, 66.97; H, 5.89; N, 4.02; S, 18.64.

EXAMPLE A-399

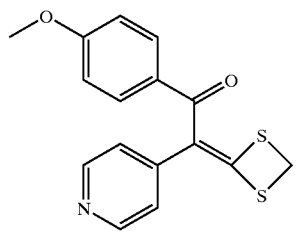

mp 203.0–204.1° C.; $^1$H NMR (CDCl$_3$/300 MHz) 8.52 (dd, 2H, J=4.4, 1.6 Hz), 7.29 (d, 1H, J=6.8 Hz), 7.28 (d, 1H, J=7.0 Hz), 7.05 (dd, 2H, J=4.4, 1.6 Hz), 6.70 (d, 1H, J=6.8 Hz), 6.69 (d, 1H, J=6.8 Hz), 4.17 (s, 2H), 3.79 (s, 3H); ESHRMS m/z 316.0475 (M+H, $C_{16}H_{13}NO_2S_2$ requires 316.0466); Anal. Calc'd. for $C_{16}H_{13}NO_2S_2$: C, 60.93; H, 4.15; N, 4.44; S, 20.33. Found: C, 60.46; H, 4.17; N, 4.37; S, 19.84.

EXAMPLE A-400

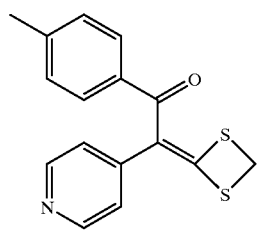

mp 209.1–215.1° C.; $^1$H NMR (CDCl$_3$/300 MHz) 8.50 (dd, 2H, J=4.4, 1.6 Hz), 7.20 (d, 2H, J=8.0 Hz), 7.03–6.99 (m, 4H), 4.18 (s, 2H), 2.30 (s, 3H); ESHRMS m/z 300.0517 (M+H, $C_{16}H_{13}NOS_2$ requires 300.0517); Anal. Calc'd. for $C_{16}H_{13}NOS_2$: C64.18; H, 4.38; N, 4.69; S, 21.42. Found: C, 64.02; H, 4.62; N, 4.54; S, 21.24.

EXAMPLE A-401

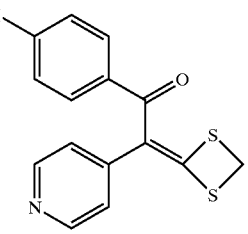

mp 257.6–257.7° C.; $^1$H NMR (CDCl$_3$/300 MHz) 8.51 (dd, 2H, J=4.4, 1.6 Hz), 7.57 (d, 2H, J=8.5 Hz), 7.27–6.99 (m, 4H), 4.18 (s, 2H); ESHRMS m/z 411.9348 (M+H, $C_{15}H_{10}NIOS_2$ requires 411.9327); Anal. Calc'd. for $C_{15}H_{10}NIOS_2$: C, 43.81; H, 2.45; N, 3.41. Found: C, 43.71; H, 2.27; N, 3.41.

EXAMPLE A-402

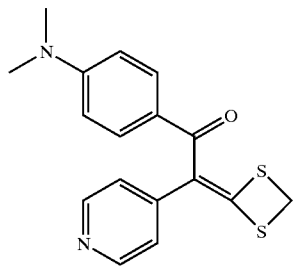

mp 197.3–202.2° C.; $^1$H NMR (CDCl$_3$/300 MHz) 8.53 (dd, 2H, J=4.4, 1.6 Hz), 7.26 (d, 2H, J=9.3 Hz), 7.09 (dd, 2H, J=4.4, 1.6 Hz), 6.43 (d, 2H, J=9.3 Hz), 4.14 (s, 2H), 2.97 (s, 6H); ESHRMS m/z 329.0789 (M+H, C$_{17}$H$_{16}$N$_2$OS$_2$ requires 329.0782); Anal. Calc'd. for C$_{17}$H$_{16}$N$_2$OS$_2$: C, 62.17; H, 4.91; N, 8.53; S, 19.53. Found: C, 61.93; H, 5.12; N, 8.46; S, 19.26.

EXAMPLE A-403

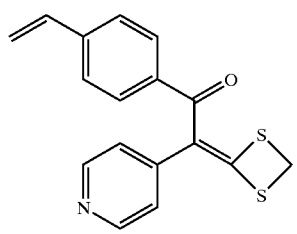

mp 176.6–176.7° C.; $^1$H NMR (CDCl$_3$/300 MHz) 8.51 (dd, 2H, J=4.4, 1.6 Hz), 7.29–7.22 (m, 4H), 7.03(dd, 2H, J=4.4, 1.6 Hz), 6.64 (dd, 1H, J=17.5, 10.9 Hz), 5.76 (d, 1H, J=17.7 Hz), 5.31 (d, 1H, J=10.9 Hz), 4.19 (s, 2H); ESHRMS 312.0513 (M+H, C$_{17}$H$_{13}$NOS$_2$ requires 312.0517); Anal. Calc'd. for C$_{17}$H$_{13}$NOS$_2$: C, 65.56; H, 4.21; N, 4.50. Found: C, 65.75; H, 4.11; N, 4.46.

EXAMPLE A-404

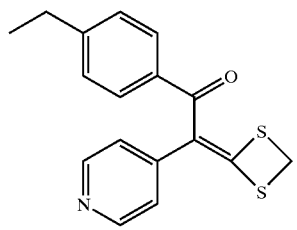

mp 174.8–175.0° C.; $^1$H NMR (CDCl$_3$/300 MHz) 8.50 (dd, 2H, J=4.4, 1.6 Hz), 7.23–7.20 (m, 4H), 7.03 (dd, 2H, J=4.6, 1.6 Hz), 4.17 (s, 2H), 2.59 (q, 2H, J=7.6 Hz), 1.17 (t, 3H, J=7.7 Hz); ESHRMS m/z 314.0677 (M+H, C$_{17}$H$_{15}$NOS$_2$ requires 314.0673); Anal. Calc'd. for C$_{17}$H$_{15}$NOS$_2$: C, 65.14; H, 4.82; N, 4.47. Found: C, 64.90; H, 4.62; N, 4.45.

EXAMPLE A-405

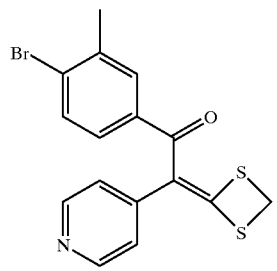

mp 167.1–167.5° C.; $^1$H NMR (CDCl$_3$/300 MHz) 8.52 (dd, 1H, J=4.4, 1.6 Hz), 7.33 (d, 1H, J=8.3 Hz), 7.02–7.00 (m, 3H), 6.87–6.83 (m, 1H), 4.19 (s, 2H), 2.28 (s, 3H); ESHRMS m/z 379.9577 (M+H, C$_{16}$H$_{12}$BrNOS$_2$ requires 379.9622); Anal. Calc'd. for C$_{16}$H$_{12}$BrNOS$_2$: C, 50.80; H, 3.20; N, 3.70. Found: C, 50.69; H, 3.19; N, 3.71.

EXAMPLE A-406

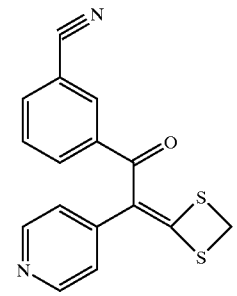

mp 168.6–168.7° C.; $^1$H NMR (CDCl$_3$/300 MHz) 8.54 (dd, 2H, J=4.6, 1.8 Hz), 7.68–7.62 (m 2H), 7.43–7.39 (m, 1H), 7.33–7.28 (m, 1H), 6.99 (dd, 2H, J=4.4, 1.6 Hz), 4.22 (s, 2H); ESHRMS m/z 311.0330 (M+H, C$_{16}$H$_{10}$N$_2$OS$_2$ requires 311.0313); Anal. Calc'd. for C$_{16}$H$_{10}$N$_2$OS$_2$: C, 61.91; H, 3.25; N, 9.02. Found: C, 61.45; H, 3.18; N, 8.91.

EXAMPLE A-407

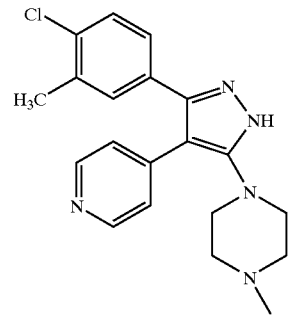

1-[5-(3-methyl-4-chlorophenyl)-4-(4-pyridinyl)-1H-pyrazol-3-yl]-4-methylpiperazine mp 236.7–239.3° C.; $^1$H NMR (DMSO-d6/300 MHz) 12.6 (brs, 1H), 8.45 (m, 2H), 7.41 (m, 1H), 7.26 (m, 3H), 7.0

(m, 1H), 2.86 (m, 4H), 2.35 (m, 4H), 2.27 (s, 3H), 2.16 (s, 3H); ESHRMS m/z 368.4653 (M+H, $C_{20}H_{22}ClN_5$ requires 368.1642).

EXAMPLE A-408

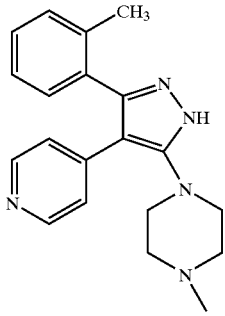

1-[5-(2-tolyl)-4-(4-pyridinyl)-1H-pyrazol-3-yl]-4-methylpiperazine mp 244.0–244.2° C.; $^1$H NMR (acetone-d6/300 MHz) 11.6 (brs, 1H), 8.35 (m, 2H), 7.35 (m, 2H), 7.25 (m, 4H), 3.05 (m, 4H), 2.47 (m, 4H), 2.25 (s, 3H), 2.00 (s, 3H); ESHRMS m/z 334.2018 (M+H, $C_{20}H_{23}N_5$ requires 334.2032); Anal. Calc'd for $C_{20}H_{23}N_5$: C, 72.04; H, 6.95; N, 21.00. Found: C, 72.03; H, 7.00; N. 20.85.

EXAMPLE A-409

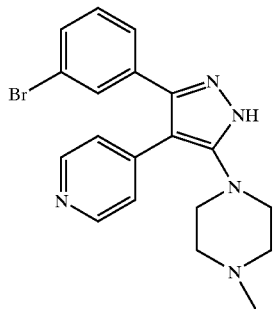

1-[5-(3-bromophenyl)-4-(4-pyridinyl)-1H-pyrazol-3-yl]-4-methylpiperazine mp 222.5–223.4° C.; $^1$H NMR (acetone-d6/300 MHz) 11.8 (brs, 1H), 8.51 (m, 2H), 7.55 (m, 2H), 7.34 (m, 4H), 3.0 (m, 4H), 2.41 (m, 4H), 2.22 (s, 3H); ESHRMS m/z 398.0982 (M+H, $C_{19}H_{20}BrN_5$ requires 398.0980).

EXAMPLE A-410

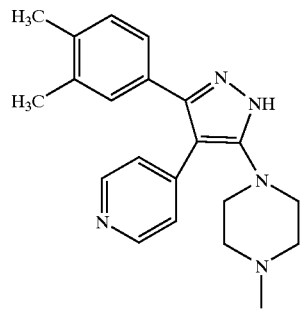

1-(5-(3,4-dimethylphenyl)-4-(4-pyridinyl)-1H-pyrazol-3-yl]-4-methylpiperazine mp 270.9–272.7° C.; $^1$H NMR (DMSO-d6/300 MHz) 12.5 (brs, 1H), 8.41 (m, 2H), 7.24 (m, 2H), 7.26 (m, 3H), 7.10 (m, 2H), 6.92 (m, 1H), 2.86 (m, 4H), 2.38 (m, 4H), 2.21 (s, 3H), 2.19 (s, 3H), 2.16 (s, 3H); ESHRMS m/z 348.2183 (M+H, $C_{21}H_{25}N_5$ requires 348.2188).

EXAMPLE A-411

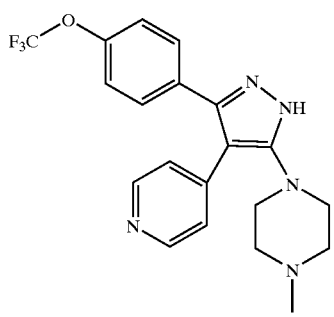

1-[5-(4-trifluoromethoxyphenyl)-4-(4-pyridinyl)-1H-pyrazol-3-yl]-4-methylpiperazine mp 221.0–221.2° C.; $^1$H NMR (DMSO-d6/300 MHz) 12.7 (brs, 1H), 8.45 (m, 2H), 7.38 (s, 4H), 7.24 (m, 2H), 2.86 (m, 4H), 2.34 (m, 4H), 2.16 (s, 3H); ESHRMS m/z 404.1698 (M+H, $C_{20}H_{20}F_3N_5O$ requires 404.1698).

EXAMPLE A-412

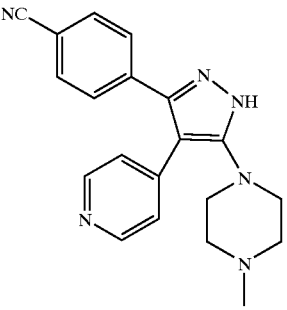

1-[5-(4-cyanophenyl)-4-(4-pyridinyl)-1H-pyrazol-3-yl]-4-methylpiperazine mp>300° C.; $^1$H NMR (DMSO-d6/300 MHz) 12.8 (brs, 1H), 8.47 (m, 2H), 7.83 (m, 2H), 7.42 (m, 2H), 2.88 (m, 4H), 2.39 (m, 4H), 2.20 (s, 3H); ESHRMS m/z 345.1848 (M+H, $C_{20}H_{20}N_6$ requires 345.1828).

EXAMPLE A-413

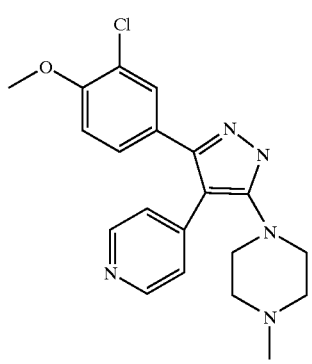

1-[5-(3-chloro-4-methoxyphenyl)-4-(4-pyridinyl-1H-pyrazol-3-yl]-4-methylpiperazine mp 272.7–276.4° C.; $^1$H NMR (DMSO-d6/300 MHz) 8.44 (dd, 2H, J=4.6, 1.6 Hz), 7.32–7.13 (m, 5H), 3.84 (s, 3H), 2.90–2.85 (m, 4H), 2.38–2.35 (m, 4H), 2.16 (s, 3H); ESHRMS m/z 384.1580 (M+H $C_{20}H_{22}ClN_5O$ requires 384.1591).

EXAMPLE A-414

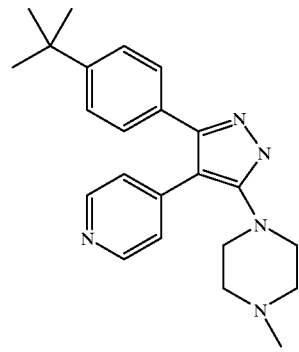

1-[5-(4-tert-butylphenyl)-4-(4-pyridinyl)-1H-pyrazol-3-yl]-4-methylpiperazine mp 243.6–244.3° C.; $^1$H NMR (DMSO-d6/300 MHz) 8.44 (dd, 2H, J=4.6, 1.6, Hz), 7.40 (d, 2H, J=8.3 Hz), 7.28–7.18 (m, 4H), 2.90–2.85 (m, 4=H), 2.38–2.34 (m, 4H), 2.16 (s,3H), 1.26 (s, 9H); ESHRMS m/z 376.2491 (M+H, $C_{23}H_{29}N_5$ requires 376.2501).

EXAMPLE A-415

1-[4-(4-methoxyphenyl)-4-(4-pyridinyl)-1H-pyrazol-3-yl]-4-methylpiperazine mp 259.0–260.2° C.; $^1$H NMR (DMSO-d6/300 MHz) 8.53 (dd, 2H, J=4.4, 1.6 Hz), 7.24 (dd, 2H, J=4.4, 1.6 Hz), 7.18 (d, 2H, J=8.9 Hz), 6.94 (d, 2H, J=8.9 Hz), 3.75 (s, 3H), 2.90–2.85 (m, 4H), 2.39–2.35 (m, 4H), 2.16 (s, 3H); ESHRMS m/z 350.1991 (M+H, $C_{20}H_{23}N_5O$ requires 350.1981); Anal. Calc'd. for $C_{20}H_{23}N_5O$+3.93% H2O: C, 66.04; H, 6.81; N, 19.25. Found: C, 66.01; H, 6.62; N, 19.32.

EXAMPLE A-416

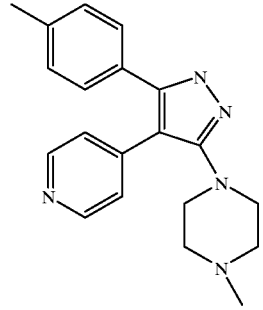

1-[5-(4-methylphenyl)-4-(4-pyridinyl)-1H-pyrazol-3-yl]-4-methylpiperazine mp 243.0–246.8° C.; $^1$H NMR (DMSO-d6/300 MHz) 8.41 (dd, 2H, J=4.6, 1.6 Hz), 7.24 (m, 6H), 2.91–2.86 (m, 4H), 2.40–2.35 (m, 4H), 2.29 (s, 3H), 2.16 (s, 3H); ESHRMS m/z 334.2041 (M+H, $C_{20}H_{23}N_5$ requires 334.2032); Anal. Calc'd for $C_{20}H_{23}N_5$+4.09% H2O: C, 69.10; H, 7.13; N, 20.14. Found: C, 69.10; H, 7.08; N, 20.13.

EXAMPLE A-417

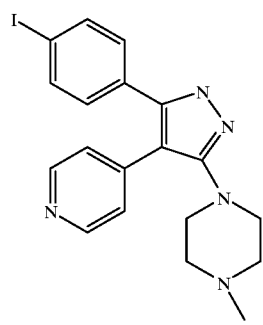

1-[5-(4-iodophenyl)-4-(4-pyridinyl)-1H-pyrazol-3-yl]-4-methylpiperazine mp 265.2–265.8° C.; $^1$H NMR (CD$_3$OD/300 MHz) 8.41 (dd, 2H, J=4.6, 1.6 Hz), 7.76–7.74 (m, 2H), 7.41–7.39 (m, 2H), 7.08–7.05 (m, 2H), 3.08–3.04 (m, 4H), 2.61–2.58 (m, 4H), 2.35 (s, 3H); ESHRMS m/z 446.0847 (M+H, C$_{19}$H$_{20}$IN$_5$ requires 446.0842); Anal. Calc'd. for C$_{19}$H$_{20}$IN$_5$+12.09% H$_2$O: C, 44.60; H, 5.39; N, 13.69. Found: C, 44.50; H, 4.56; N, 13.66.

EXAMPLE A-418

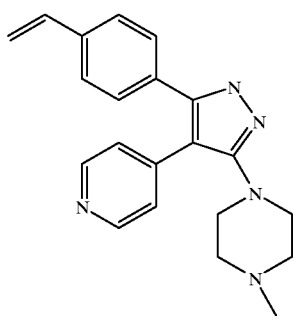

1-[5-(4-ethenylphenyl)-4-(4-pyridinyl)-1H-pyrazol-3-yl]-4-methylpiperazine mp>300° C.; $^1$H NMR (CD$_3$OD/300 MHz) 8.49 (dd, 2H, J=4.6, 1.6 Hz), 7.47–7.44 (m, 4H), 7.26 (d, 2H, J=8.4 Hz), 6.75 (dd, J=17.7, 11.1 Hz), 5.83 (d, 1H, J=17.5 Hz), 5.28 (d, 1H, J=11.1 Hz), 3.07–3.03 (m, 4H), 2.58–2.53 (m, 4H), 2.31 (s, 3H); ESHRMS m/z 346.2034 (M+H, C$_{21}$H$_{23}$N$_5$ requires 346.2032); Anal. Calc'd. for C$_{21}$H$_{23}$N$_5$+2.83% H$_2$O: C, 70.95; H, 6.84; N, 19.70. Found: C, 70.97; H, 6.49; N, 19.54.

EXAMPLE A-419

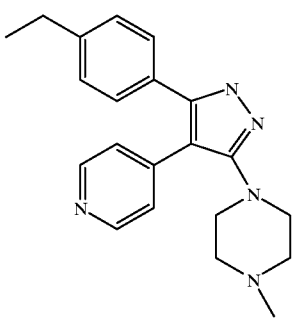

1-[5-(4-ethylphenyl)-4-(4-pyridinyl)-1H-pyrazol-3-yl]-4-methylpiperazine mp 221.6–222.6° C.; $^1$H NMR (CD$_3$OD/300 MHz) 8.38 (dd, 2H, J=4.6, 1.6 Hz), 7.44–7.40 (m, 2H), 7.26–7.19 (m, 4H), 3.06–3.02 (m, 4H), 2.66 (q, 2H, J=7.5 Hz), 2.59–2.54 (m, 4H), 2.32 (s, 3H), 1.23 (t, 3H, J=7.5 Hz); ESHRMS m/z 348.2188 (M+H, C$_{21}$H$_{25}$N$_5$ requires 348.2188); Anal. Calc'd for C$_{21}$H$_{25}$N$_5$+2.59% H$_2$O: C, 70.71; H, 7.35; N, 19.63. Found: C, 70.76; H, 7.40; N, 19.46.

EXAMPLE A-420

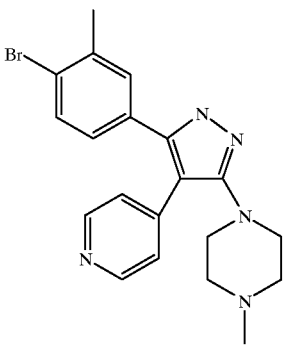

1-[5-(4-bromo-3-methylphenyl)-4-(4-pyrdinyl)-1H-pyrazol-3-yl]-4-methylpiperazine mp 294.7° C. decomp.; $^1$H NMR (CD$_3$OD/300 MHz) 8.41 (dd, 2H, J=4.6, 1.6 Hz), 7.55 (d, 1H, J=8.2 Hz), 7.45–7.42 (m, 2H), 7.27–7.25 (m, 1H), 7.00–6.97 (m 2H), 3.08–3.03 (m, 4H), 2.59–2.54 (m, 4H), 2.35 (s, 3H), 2.31 (s, 3H); ESHRMS m/z 412.1124 (M+H, C$_{20}$H$_{22}$BrN$_5$ requires 412.1137).

EXAMPLE A-421

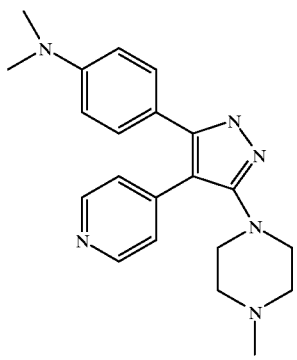

1-[5-(4-dimethylaminophenyl)-4-(4-pyridinyl)-1H-pyrazol-3-yl]-4-methylpiperazine mp>300° C. (decomposed); $^1$H NMR (CD$_3$OD/300 MHz) 8.37 (d, 2H, J=4.6 Hz), 7.44 (d, 2H, J=4.8 Hz), 7.12, (d, 2H, J=8.9 Hz), 6.73 (d, 2H, J=8.7 Hz), 3.04–3.02 (m, 4H), 2.96 (s, 6H), 2.54–2.49 (m, 4H), 2.31 (s, 3H); ESHRMS m/z 363.2266 (M+H, C$_{21}$H$_{26}$N$_6$ requires 363.22972).

EXAMPLE A-422

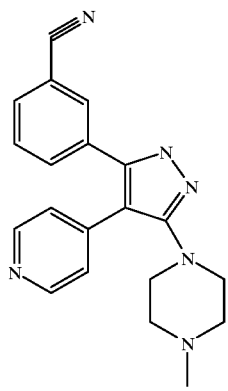

1-[5-(3-cyanophenyl)-4-(4-pyrdinyl)-1H-pyrazol-3-yl]4-methylpiperazine mp 223.4–224.3° C.; $^1$H NMR (CD$_3$OD/300 MHz) 8.44 (dd, 2H, J=4.6, 1.4 Hz), 7.75–7.69 (m, 2H), 7.56–7.54 (m, 2H), 7.40–7.38 (m, 2H), 3.05–3.03 (m, 4H), 2.54–2.49 (m, 4H), 2.53 (s, 3H); ESHRMS m/z 345.1840 (M+H, C$_{20}$H$_{20}$N$_6$ requires 345.1828).

EXAMPLE A-423

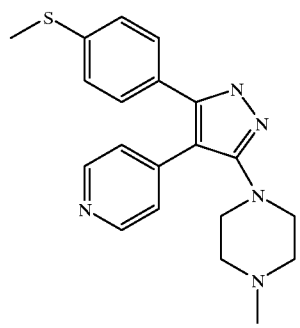

1-[5-(4-thiomethoxyphenyl)-4-(4-pyridinyl)-1H-pyrazol-3-yl-4-methylpiperazine mp 275.6–281.9° C.; $^1$H NMR (CD$_3$OD/300 MHz) 8.44–8.40 (m, 2H), 7.46–7.41 (m, 2H), 7.28–7.23 (m, 4H), 3.04–3.00 (m, 4H), 2.59–2.53 (M, 4H), 2.48 (s, 3H), 2.31 (s, 3H); ESHRMS m/z 366.1777 (M+H, C$_{20}$H$_{23}$N$_5$S requires 366.1752).

EXAMPLE A-424

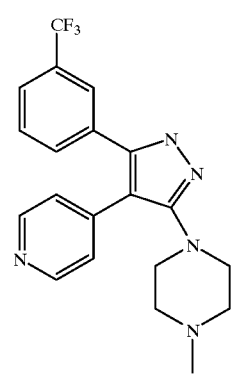

1-[5-(3-trifluoromethylphenyl)-4-(4-pyridinyl-1H-pyrazol-3-yl]-4-methylpiperazine mp 212.6–213.7° C.; $^1$H NMR (CD$_3$OD/300 MHz) 8.43 (d, 2H, J=4.8 Hz), 7.69–7.56 (m, 4H), 7.41 (s, 2H), 3.07–3.04 (m, 4H), 2.56–2.53 (m, 4H), 2.32 (s, 3H); ESHRMS m/z 388.1764 (M+H, C$_{20}$H$_{20}$F$_3$N$_5$ requires 388.1749).

EXAMPLE A-425

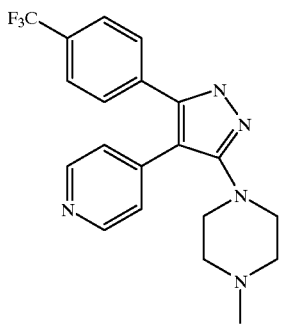

1-[5-(4-trifluoromethylphenyl)-4-(4-pyridinyl-1H-pyrazol-3-yl]-4-methylpiperazine mp 240.5° C. (decomposed); $^1$H NMR (CD$_3$OD/300 MHz) 8.43 (dd, 2H, J=4.6, 1.6 Hz), 7.70–7.67 (m, 2H), 7.51–7.48 (m, 2H), 7.42–7.38 (m 2H), 3.09–3.04 (m, 4H), 2.59–2.53 (m, 4H), 2.31 (s, 3H); ESHRMS m/z 388.1768 (M+H, C$_{20}$H$_{20}$F$_3$N$_5$ requires 388.1749).

EXAMPLE A-426

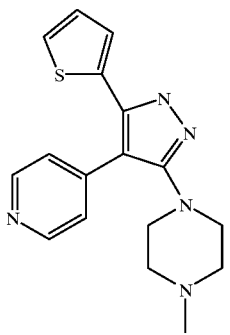

1-[5-(2-thienyl)-4-(4-pyridinyl-1H-pyrazol-3-yl]-4-methylpiperazine mp 199.7° C. (decomposed); $^1$H NMR (CD$_3$OD/300 MHz) 8.44 (d, 2H, J=5.8 Hz), 7.47 (d, 2H, J=5.6 Hz), 7.13–7.07 (m, 3H), 3.04–3.00 (m, 4H), 2.53–2.49 (m, 4H), 2.30 (s, 3H); ESHRMS m/z 326.1454 (M+H, C$_{17}$H$_{19}$N$_5$S requires 326.1439).

EXAMPLE A-427

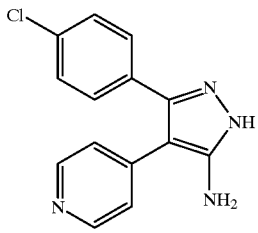

Step 1: Preparation of 3-dimethylamino-1-(4-chlorophenyl)-2-(pyridin-4-yl)-2-propene-1-one A solution of 4-chlorophenyl-2-(pyridin-4-yl)ethan-1-one (20.0 g, 86.4 mmol) and N,N-dimethylformamide dimethylacetal (57.6 mL, 0.43 mole) was heated at 100° C. for 3½ hours. The reaction mixture was concentrated in vacuo, and the residue crystallized from methyl butyl ether to give 3-dimethylamino-1-(4-chlorophenyl)-2-(pyridin-4-yl)-2-propen-1-one (22.80 g, 93%). $^1$H NMR (CDCl$_3$/300 MHz) δ8.52 (d, 2H), 7.38 (d, 2H), 7.29 (d, 2H), 7.08 (d, 2H), 2.83 (s, 6H).

Step 2: Preparation of 5-(4-chlorophenyl)-4-(pyridin-4-yl) isoxazole

A solution of 3-dimethylamino-1-(4-chlorophenyl)-2-(pyridin-4-yl)-2-propen-1-one (22.80 g, 79.7 mmol), hydroxylamine hydrochloride (18.01 g, 0.26 mole), and 150 mL ethanol was heated to reflux for 30 minutes. The reaction mixture was then cooled to room temperature and concentrated in vacuo. The residue was dissolved in 1N hydrochloric acid and then treated with an aqueous saturated solution of sodium bicarbonate. The precipitates were collected by filtration, washed with water and ethanol, and dried to yield 5-(4-chlorophenyl)-4-(pyridin-4-yl)isoxazole (20.50 g, 93%). m.p. 120.8–120.9° C. $^1$H NMR (CDCl$_3$/CD$_3$OD/300 MHz) δ8.53 (d, 2H), 8.46(s, 1H), 7.51(d, 2H), 7.41–7.34 (m, 4H). ESLRMS m/z 257 (M+H). ESHRMS m/z 257.0457 (M+H, C$_{14}$H$_9$N$_2$OCl requires 257.0482).

Step 3: Preparation of 3-(4-chlorophenyl)-3-oxo-2-(pyridin-4-yl) propanenitrile

A solution of 5-(4-chlorophenyl)-4-(pyridin-4-yl) isoxazole (20.5 g, 79.9 mmol) and 150 mL of a 1N sodium hydroxide solution was stirred at 60° C. for 1 hour. The reaction mixture was cooled to room temperature and adjusted to pH 6 with concentrated hydrochloric acid. The precipitates were filtered, washed with water and ethanol, and dried to give 3-(4-chlorophenyl)-3-oxo-2-(pyridin-4-yl) propanenitrile (20.0 g, quantitative yield). m.p. 225.4–234.9° C. $^1$H NMR (CDCl$_3$/CD$_3$OD/300 MHz) δ8.12 (brs, 2H), 7.73–7.59 (m, 5H), 7.30 (d, 3H). ESLRMS m/z 257 (M+H). ESHRMS m/z 257.0481 (M+H, C$_{14}$H$_9$N$_2$OCl requires 257.0482).

Step 4: 5-amino-3-(4-chlorophenyl)-4-(pyridin-4-yl)-pyrazole

A solution of 3-(4-chlorophenyl)-3-oxo-2-(pyridin- 4-yl) propanenitrile (3.50 g, 13.6 mmol) in 40 mL acetonitrile and phosphorous trichloride (14.2 ml, 163 mmol) was stirred at 100° C. for 5 hours. The reaction mixture was concentrated in vacuo, and the residue taken up in toluene and concentrated again. The residue was then taken up in ethanol (150 mL) and treated with anhydrous hydrazine (1.71 mL, 54.4 mmol). The reaction mixture was heated to reflux for 3 hours, cooled, and concentrated in vacuo. The residue was triturated with a mixture of ethanol and dichloromethane (1:4), and filtered. The solid was washed with the ethanol/dichloromethane mixture, and dried to give 5-amino-3-(4-chlorophenyl)-4-(pyridin-4-yl)-pyrazole (2.0 g, 54%): m.p. >300° C. $^1$H NMR (DMSO/300 MHz) δ8.40 (d, 2H), 7.40 (d, 2H), 7.29 (d, 2H), 7.11 (d, 2H), 5.05 (s, 2H). ESLRMS m/z 271 (M+H). ESHRMS m/z 271.0752 (M+H, C$_{14}$H$_{11}$N$_4$Cl requires 271.0750).

EXAMPLE A-428

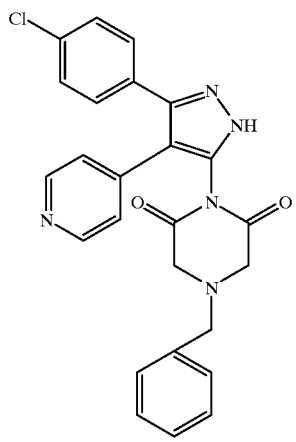

A solution of 1,1'-carbonyldiimidazole (1.19 g, 7.38 mmol) and N-benzyliminodiacetic acid (0.824 g, 3.69 mmol) in dimethylformamide was heated at 75° C. for 30 minutes. To this mixture the 5-amino-3-(4-chlorophenyl)-4-(pyridin-4-yl)-pyrazole (1.0 g, 3.69 mmol) was added, and heating was continued at 75° C. overnight. The white solid was filtered, was washed with diethyl ether, methylene chloride, 5% methanol/methylene chloride, and ethanol, and was dried to give the desired imide as an off-white solid (0.9 g, 53%): m.p. >300° C. $^1$H NMR (DMSO/300 MHz) δ8.53 (m, 2H), 7.5(d, 2H), 7.44–7.16 (m, 7H), 6.98(m, 2H), 3.64 (m, 4H), 3.48 (m, 2H). ESLRMS m/z 458 (M+H). ESHRMS m/z 458.1380 (M+H, $C_{25}H_{20}N_5O_2Cl$ requires 458.1384).

EXAMPLE A-429

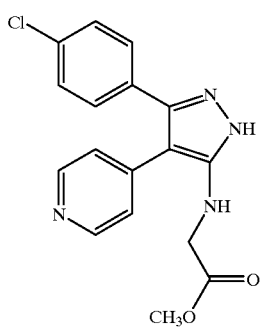

Methyl 2-{[3–94-chlorophenyl)-4-(4-pyridinyl)-1H-pyrazol-5-yl]amino}acetate

A solution of 5-amino-3-(4-chlorophenyl)-4-(pyridin-4-yl)-pyrazole (1.0 g, 3.7 mmol) in dimethylformamide (30 mL) was heated to 95° C. and methyl bromo acetate (0.34 mL, 3.7 mmol) was added dropwise. The resulting solution was stirred at 95° C. for 4 hours, cooled, and concentrated in vacuo to an orange viscous oil (1.79 g). A portion of this product mixture (1.20 g) was crystallized from ethanol and diethyl ether to give methyl 2-{[3-4-chlorophenyl)-4-(4-pyridinyl)-1H-pyrazol-5-yl]amino}acetate as a bright yellow solid (805 mg): m.p. 195.4–196.8° C. $^1$H NMR (CD$_3$OD/300 MHz) δ8.49 (d,2H), 7.68 (d, 2H), 7.44 (m, 4H), 5.37 (s, 2H), 3.84 (s, 3H) ESLRMS m/z 343 (M+H). ESHRMS m/z 343.0975 (M+H, $C_{17}H_{16}N_4O_2Cl$ requires 343.0962).

EXAMPLE A-430

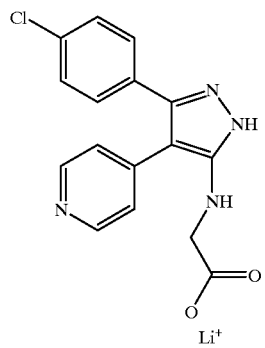

Lithium 2-{[3-4-chlorophenyl)-4-(4-pyridinyl)-1H-pyrazol-5-ylamino}acetate

To a solution of methyl 2-{[3-4-chlorophenyl)-4-(4-pyridinyl)-1H-pyrazol-5-yl]amino}acetate (500 mg, 1.5 mmol) in 15 mL of methanol and 5 mL of water was added lithium hydroxide (189 mg, 4.5 mmol). The reaction mixture was stirred at room temperature for 5 hours. The solvent was removed in vacuo, and the residue taken up in ethanol. The precipitate was filtered and washed with methanol, and the filtrate was concentrated to give lithium 2-{[3-4-chlorophenyl)-4-(4-pyridinyl)-1H-pyrazol-5-yl]amino}acetate as a yellow/orange solid (479 mg, 95%). mp >300° C. $^1$H NMR (CD$_3$OD/300 MHz) δ8.06 (d, 2H), 7.43 (d, 2H), 7.37 (m, 4H), 3.34 (s, 2H). ESLRMS m/z 329 (M+H), 335 (M+Li), 351 (M+Na). ESHRMS m/z 329.0772 (M+H, $C_{16}H_{14}N_4O_2Cl$ requires 329.0805).

EXAMPLE A-431

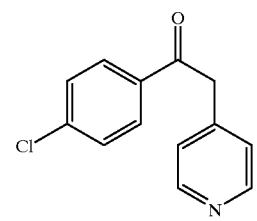

The above 4-chlorophenylketone was prepared according to the procedure used in Step 1 of Example C-1, infra, substituting methyl 4-chlorobenzoate for ethyl 4-fluorobenzoate. Yield; (74%), yellow solid, mp=95.5–97.3° C.; 1H-NMR (DMSO-d6/300 MHz) 8.57 (br d, 2H), 7.92 (d, 2H), 7.46 (d, 2H), 7.20 (d, 2H), 4.28 (s, 2H); ESLRMS m/z 232 (M+H).

EXAMPLE A-432

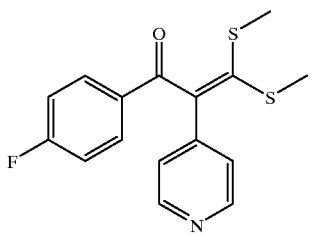

To the ketone (1.0 gm, 4.7 mmol) from Step 1 of Example C-1, infra, in anhydrous tetrahydrofuran (10 mL) was added 1M potassium t-butoxide in tetrahydrofuran (10 mL, 10 mmol). The reaction mixture was stirred for 15 minutes at room temperature, then carbon disulfide (0.31 mL, 5.1 mmol) was added. After several minutes, methyl iodide (0.64 mL, 10.3 mmol) was added and the reaction allowed to stir for 4 hours. The reaction mixture was diluted with saturated sodium bicarbonate solution (25 mL) and extracted twice with ethyl acetate (35 mL). The combined ethyl acetate layers were washed with water (25 mL) and brine (25 mL). The organic solution was dried (MgSO$_4$), filtered and concentrated to an orange oil. The oil solidified on standing. Yield 1.4 gm (94%), mp 80.2–82.1° C.; $^1$H-NMR (CDCl$_3$/300 MHz) 8.59 (d, 2H), 7.96 (m, 2H), 7.38 (m, 2H), 7.14 (m, 2H), 2.33 (s, 3H), 2.23 (s, 3H); Anal. Calc'd for C$_{16}$H$_{14}$FNOS$_2$: C, 60.16; H, 4.42; N, 4.39; S, 20.08. Found: C, 59.89; H, 4.09; N, 4.31; S, 20.14.

EXAMPLE A-433

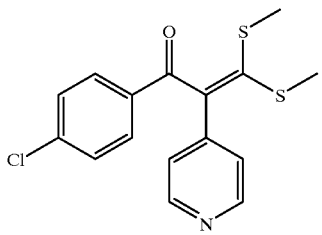

The above compound was prepared in a manner analogous to Example A-432 starting with the product of Example A-431. Crude yield: 100%; mp 87.6–88.2° C.; $^1$H-NMR (CDCl$_3$/300 MHz) 8.60 (d, 2H), 7.87 (d, 2H), 7.44 (d, 2H), 7.37 (m, 2H), 2.33 (s, 3H), 2.22 (s, 3H); ESHRMS m/z 336.0297 (M+H, C$_{16}$H$_{15}$ClNOS$_2$ requires 336.0283); Anal. Calc'd for C$_{16}$H$_{14}$ClNOS$_2$: C, 57.22; H, 4.20; N, 4.17. Found: C, 57.44; H, 3.97; N, 4.04.

EXAMPLE A-434

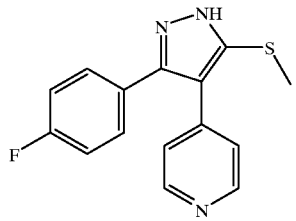

To the compound of Example A-432 (1.4 gm, 4.4 mmol) in ethanol (15 mL) was added 1M hydrazine in acetic acid (5 mL, 5 mmol). The reaction was stirred at room temperature for 18 hours. No reaction had occurred, so additional hydrazine hydrate (1.08 mL, 22 mmol) was added and the reaction heated to reflux for 6 hours. The product began to precipitate from the reaction mixture. The reaction was cooled to room temperature and water was added to precipitate the product. The solid was collected by suction filtration and air dried. Yield: 675 mg (53%). The product was recrystallized from ethanol: 494 mg; mp 249.9–249.9° C.; $^1$H-NMR (DMSO-d6/300 MHz) 13.51 (br s, 1H), 8.50 (d, 2H), 7.34 (m, 2H), 7.23 (m, 2H), 7.16 (m, 2H), 2.43 (s, 3H); ESHRMS m/z 286.0807 (M+H, C$_{15}$H$_{13}$FN$_3$S requires 286.0814); Anal. Calc'd for C$_{15}$H$_{12}$FN$_3$S: C, 63.14; H, 4.24; N, 14.73. Found: C, 63.01; H, 4.43; N, 14.81.

EXAMPLE A-435

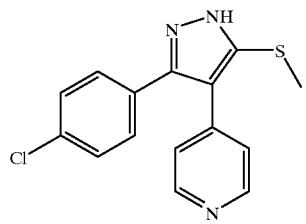

The above compound was made in an analogous manner to Example A-434 starting with the compound of Example A-433. Yield: 750 mg (33%); mp 250.2–250.2° C.; $^1$H NMR (DMSO-d6/300 MHz) 13.57 (br s, 1H), 8.51 (m, 2H), 7.45 (br s, 2H), 7.32 (m, 2H), 7.17 (m, 2H), 2.43 (s, 3H); ESHRMS m/z 302.0537 (M+H, C$_{15}$H$_{13}$ClN$_3$S requires 302.0518); Anal. Calc'd for C$_{15}$H$_{12}$ClN$_3$S: C, 59.70; H, 4.01; N, 13.92. Found: C, 59.56; H, 3.96; N, 13.96.

EXAMPLE A-436

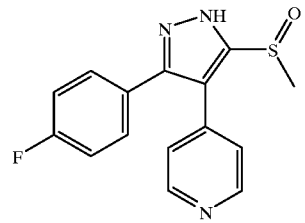

3-(4-fluorophenyl)-4-(methylsulfinyl)-pyridin-4-yl-1H-pyrazole

To the compound of Example A-434 (150 mg, 0.52 mmol) in ethanol (15 mL) was added ammonium persulfate (450 mg, 1.97 mmol). The reaction mixture was stirred at ambient temperature. After several hours an additional amount of ammonium persulfate (450 mg) was added. The reaction mixture was monitored by TLC (silica) using 5% methanol in dichloromethane as the eluting solvent. When the stating material had been consumed, the reaction mixture was quenched with saturated sodium bicarbonate (25 mL) and extracted with ethyl acetate (2×25 mL). The ethyl acetate layers were combined, washed with brine (25 mL) and dried (MgSO$_4$). Filtration and concentration produced a white solid. The solid was triturated with diethyl ether, collected by suction filtration, and air dried. Yield 150 mg (96%), mp 262.9–262.9° C.; $^1$H NMR (DMSO-d6/300 MHz) 14.22 (br s, 1H), 8.56 (d, 2H), 7.42–7.23 (br m, 6H), 2.94 (s, 3H); Anal. Calc'd for $C_{15}H_{12}FN_3OS \cdot 0.25\ H_2O$: C, 58.91; H, 4.12; N, 13.74; Found: C, 58.88; H, 4.17; N, 13.39.

EXAMPLE A-437

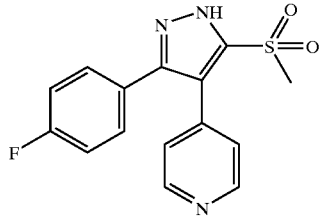

3-(4-fluorophenyl)-5-(methylsulfonyl)-4-pyridin-4-yl-1H-pyrazole

To the compound of Example A-434 (285 mg, 1 mmol) in ethanol (10 mL) was added potassium peroxymonosulfate (2.45 gm, 4 mmol) and water (5 mL). The reaction mixture was stirred at ambient temperature. After 6 hours the reaction mixture was diluted with water (20 mL) and extracted with ethyl acetate (2×30 mL). The ethyl acetate layers were combined, washed with brine (25 mL) and dried ($MgSO_4$). The ethyl acetate did not efficiently extract the product from the aqueous phase, so the aqueous layer was saturated with sodium chloride and extracted with acetonitrile (50 mL). The acetonitrile solution was dried ($MgSO_4$), filtered, and combined with the filtered ethyl acetate solution. The solvents were evaporated and the resulting solid was triturated with a small amount of acetonitrile, collected by suction filtration, and air dried. Yield: 203 mg (64%); mp 297.1->300° C.; $^1$H NMR (DMSO-d6/300 MHz) 14.37 (br s, 1H), 8.54 (m, 2H), 7.29 (m, 6H), 3.26 (s, 3H); Anal. Calc'd for $C_{15}H_{12}FN_3O_2S$: C, 56.77; H, 3.81; N, 13.24. Found: C, 56.52; H, 4.03; N, 13.11.

EXAMPLE A-438

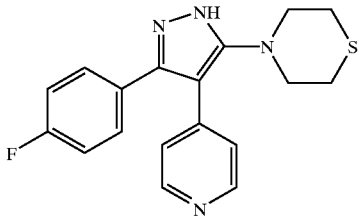

To the compound of Example A-432 (638 mg, 2 mmol) in toluene (6 mL) was added thiomorpholine (502 uL, 5 mmol). The reaction mixture was heated to between 80 and 110° C. After about three hours the bis-thiomorpholine substituted product began to precipitate from the reaction mixture. When the dithioketene acetal had been completely consumed, the reaction mixture was cooled to room temperature and the insoluble bis-thiomorpholine compound removed by filtration. To the toluene solution was added hydrazine hydrate (1 mL) and sufficient ethanol to create a homogeneous solution. The reaction mixture was then stirred at room temperature for 72 hours. The reaction mixture was diluted with ethyl acetate (50 mL) and extracted twice with water (25 mL) and once with brine (25 mL). The organic solution was dried ($MgSO_4$), filtered and concentrated to a reddish solid. The solid was triturated with acetonitrile, collected by suction filtration, and dried in-vacuo. The solid was then suspended in acetonitrile and heated to reflux. Ethyl acetate was then added until the solid almost completely dissolved. A small amount of ethanol was then added and the homogeneous yellow solution concentrated until a solid began to form. Allow to cool to room temperature. Collected a white solid by suction filtration. Yield: 63 mg, (7%); $^1$H NMR (DMSO-d6/300 MHz) 12.65 (br s, 1H), 8.45 (d, 2H), 7.27 (m, 6H), 3.14 (m, 4H), 2.63 (m, 4H). ESLRMS m/z 341 (M+H); ESHRMS m/z 341.1241 (M+H, $C_{18}H_{18}FN_4S$ requires 341.1236).

EXAMPLE A-439

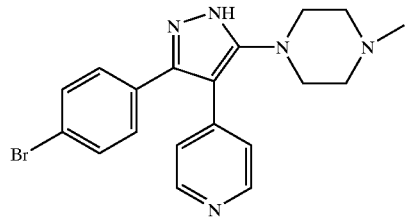

The above compound was prepared in a similar manner to Example A-438 starting with the appropriate dithioketene acetal and N-methylpiperazine. A white solid was obtained, mp 270.2–270.7° C.; $^1$H NMR (DMSO-d6/300 MHz) 12.7 (br s, 1H), 8.47 (m, 2H), 7.57 (m, 2H), 7.21 (m, 2H), 2.85 (m, 4H), 2.34 (m, 4H) 2.15 (s, 3H); ESHRMS 398.0993 (M+H, $C_{19}H_{21}BrN_5$ requires 398.0980).

EXAMPLE A-440

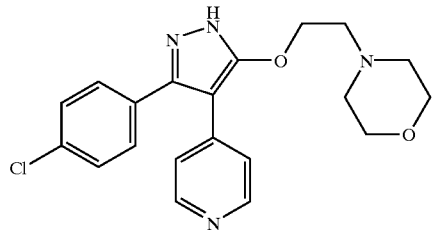

To N-(2-hydroxyethyl)morpholine (363 uL, 3 mmol) in anhydrous tetrahydrofuran (7 mL), under nitrogen, was added 1M sodium hexamethyldisilamide (3 ml, 3 mmol) in tetrahydrofuran at ambient temperature. The reaction mixture was stirred for 15 minutes, then the dithietane prepared as set forth in Step 1 of Example A-341 (636 mg, 2 mmol) was added as a solid. The reaction mixture gradually became dark orange. After about 18 hours at ambient temperature, the reaction was quenched with saturated sodium bicarbonate solution (30 mL) and extracted twice with ethyl acetate (30 mL). The organic solutions were combined and washed with saturated NaCl solution (20 mL), then dried ($MgSO_4$), filtered, and concentrated to an orange oil. The oil was taken up in methanol (10 mL) and reconcentrated to remove any remaining ethyl acetate. The oil was then taken up in methanol (5 mL) and anhydrous hydrazine (69 uL) was added. The reaction mixture was allowed to stir at ambient temperature 18 hours, then quenched with saturated sodium bicarbonate solution (30 mL) and extracted twice with ethyl acetate (30 mL). The organic solutions were combined and washed with water (20 mL) and saturated NaCl solution (20 mL), then dried ($MgSO_4$), filtered, and concentrated to an orange semi-solid. The solid was triturated with acetonitrile (5 mL), collected by suction filtration, washed with acetonitrile and dried in-vacuo. Yield: off-white solid, 114 mg (14.8%); mp 198.9–199.9° C.; ¹H-NMR (DMSO-d6/300 MHz) 12.61 (br s, 1H), 8.41 (d, 2H), 7.52 (d, 2H), 7.38 (d, 2H), 7.21 (d, 2H), 4.33 (t, 2H), 3.54 (m, 4H), 2.70 (t, 2H), 2.44 (m 4H); ESHRMS m/z 385.1444 (M+H, $C_{20}H_{22}ClN_4O_2$ requires 385.1431).

EXAMPLE A-441

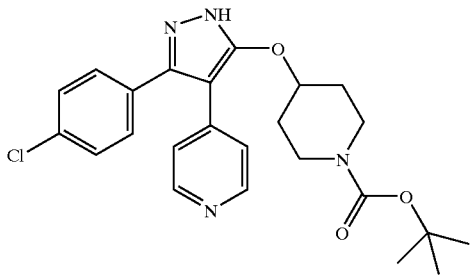

The above compound was prepared in an analogous manner to that of Example A-440, starting with 4-hydroxy-N-t-boc piperidine. Recrystallized from acetone/methanol. Yield: white solid 263 mg (29%); mp 230.1–231.8° C.; 1H-NMR (DMSO-d6/300 MHz) 12.61 (br s, 1H), 8.42 (d, 2H), 7.52 (d, 2H), 7.38 (d, 2H), 7.20 (d, 2H), 4.88 (m, 1H), 3.52 (m, 2H), 3.30 (m, 2H), 1.93 (m, 2H), 1.65 (m, 2H), 1.39 (s, 9H); Anal. Calc'd for $C_{24}H_{27}ClN_4O_3$: C,63.36; H. 5.98; N, 12.31; Found: C, 63.34; H, 5.97; N, 12.22.

EXAMPLE A-442

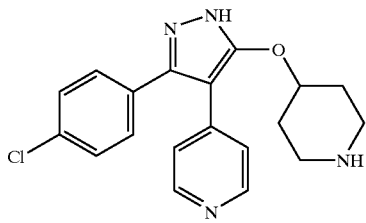

Example A-441 (130 mg, 0.28 mmol) was treated with concentrated HCl (0.5 mL) in ethanol (5 mL) for two hours. The solvent was removed in-vacuo and the resulting residue dissolved in ethanol and reconcentrated twice. The resulting solid was triturated with acetonitrile to afford a white solid. Yield: 119 mg (91%) tri-hydrochloride salt; mp 220.6–222.1° C.; ¹H-NMR (DMSO-d6/300 MHz) 13.25 (br s, 1H), 9.10 (br s, 2H), 8.67 (d, 2H), 7.75 (d, 2H), 7.60 (d, 2H), 7.50 (d, 2H), 5.04 (m, 1H), 3.17 (br d, 4H), 2.21 (m, 2H), 2.03 (m, 2H); Anal. Calc'd for $C_{19}H_{19}ClN_4O.3HCl$: C, 49.16; H, 4.78; N, 12.07. Found: C, 49.24; H, 4.72; N, 12.02.

EXAMPLE A-443

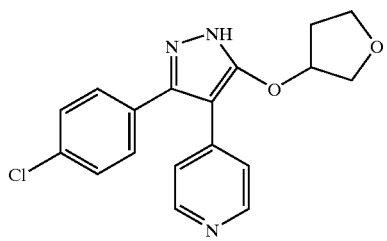

The above compound was prepared in a manner analogous to Example A-440 starting with (+/−)3-hydroxytetrahydrofuran. Recrystallized from ethanol. Yield: white crystalline solid, 57 mg (8%); mp>300° C.; ¹H-NMR (DMSO-d6/300 MHz) 12.65 (br s, 1H), 8.42 (d, 2H), 7.52 (d, 2H), 7.38 (d, 2H), 5.28 (m, 1H), 7.18 (d, 2H), 3.86 (m, 2H), 3.82 (m, 1H), 3.75 (m, 1H), 2.26–2.01 (br m, 2H); Anal. Calc'd for $C_{18}H_{16}ClN_3O_2$: C, 63.25; H, 4.72; N, 12.29. Found: C, 63.12; H, 4.51; N, 12.31.

EXAMPLE A-444

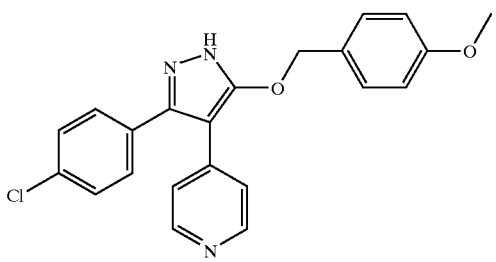

The above compound was prepared in a manner analogous to Example A-440 starting with p-methoxybenzyl alcohol. Yield: off-white solid, 252 mg (21%); mp=229.1–229.2° C.; ¹H-NMR (acetone-d6/300 MHz) 11.62 (br s, 1H), 8.40 (br s, 2H), 7.76 (s, 2H), 7.39 (m, 4H), 7.30 (br s, 2H), 6.87 (d, 2H), 5.27 (s, 2H), 3.77 (s, 3H); Anal. Calc'd for $C_{22}H_{18}ClN_3O_2 \cdot 0.25\ H_2O$: C, 66.67; H, 4.70; N, 10.60. Found: C, 66.79 ; H, 4.95 ; N, 10.54.

EXAMPLE A-445

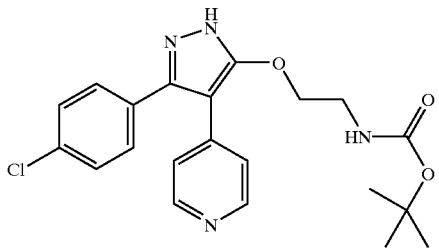

The above compound was prepared in a manner analogous to Example A-440 starting with N-tert-butoxycarbonyl-ethanolamine. Recrystallized from ethyl acetate/methanol. Yield: white solid, 75 mg (4%); mp>300° C.; ¹H-NMR (DMSO-d6/300 MHz) 12.60 (br s, 1H), 8.38 (d, 2H), 7.53 (d, 2H), 7.38 (d, 2H), 7.22 (d, 2H), 7.02 (t, 1H), 4.20 (t, 2H), 3.34 (m, 2H), 1.36 (s, 9H); ESHRMS m/z 415.1551 (M+H, $C_{21}H_{24}ClN_4O_3$ requires 415.1537)

EXAMPLE A-446

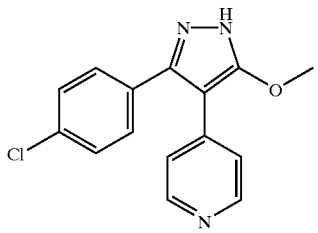

The above compound was prepared in a manner analogous to Example A-440 starting with methanol. Yield: off-white solid, 119 mg (14%); mp=265.3–265.3° C.; $^1$H-NMR (DMSO-d6/300 MHz) 12.61 (br s, 1H), 8.41 (d, 2H), 7.52 (d, 2H), 7.38 (d, 2H), 7.17 (d, 2H), 3.90 (s, 3H); ESHRMS m/z 286.0766 (M+H, $C_{15}H_{13}ClN_3O$ requires 286.0747); Anal. Calc'd for $Cl_{15}H_{12}ClN_3O \cdot 0.25 H2O$: C, 62.08; H, 4.34; N, 14.48. Found: C, 62.24; H, 4.11; N, 14.16.

EXAMPLE A-447

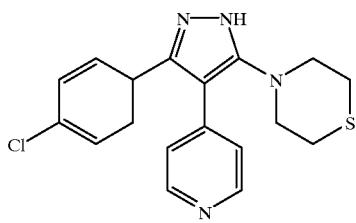

To the dithietane of Step 1 of Example A-341 (638 mg, 2 mmol) in toluene (15 mL) was added thiomorpholine (800 uL, 8 uL). The reaction mixture was heated to reflux for 6 hours, then cooled to room temperature and diluted with toluene (20 mL). The reaction mixture was then extracted twice with water (20 mL) and brine (20 mL). The organic solution was dried (MgSO$_4$), filtered, and concentrated to an oil. Hexane was added to the residue and heated to reflux, then decanted. The oil became semi-solid. The semi-solid was dissolved in tetrahydrofuran (10 mL) and potassium t-butoxide 1M in tetrahydrofuran (2 mL, 2 mmol) was added. This was followed by iodomethane (125 uL, 2 mmol). The reaction was stirred at room temperature for 1 hour, then quenched with water (20 mL). The reaction mixture was extracted with ethyl acetate (2×30 mL). The organic layers were pooled, washed with brine (20 mL) and dried (MgSO$_4$). Filtration and concentration produced an oil which was chased once with toluene to remove any ethyl acetate. The residue was dissolved in ethanol (10 mL) and hydrazine hydrate (97 uL, 2 mmol) was added. The reaction mixture was stirred at room temperature for 4 hours then partitioned between ethyl acetate and saturated sodium bicarbonate solution (30 mL each). The layers were separated and the aqueous layer extracted again with ethyl acetate (30 mL). The combined organic layers were washed with brine (20 mL) and dried (MgSO$_4$). Filtration and concentration produced an orange residue which was triturated with acetonitrile to generate a tan solid. Yield: 295 mg (43%); mp>300° C.; $^1$H NMR (DMSO-d6/300 MHz) 12.70 (br s, 1H), 8.47 (d, 2H), 7.46 (d, 2H), 7.26 (m, 4H), 3.13 (m, 4H), 2.62 (m, 4H); ESHRMS m/z 357.0942 (M+H, $C_{18}H_{18}ClN_4S$ requires 357.0941); Anal. Calc'd for $C_{18}H_{17}ClN_4S$: C, 60.58; H, 4.80; N, 15.70. Found: C, 60.32; H, 4.96; N, 15.60.

EXAMPLE A-448

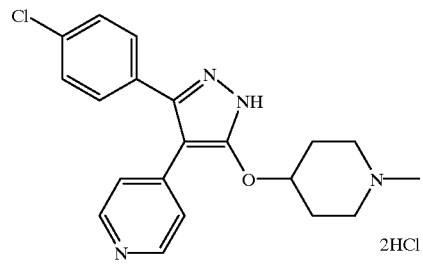

3-(4-chlorophenyl)-5-[(1-methylpiperidin-4-yl)-oxy]-4-pyridin-4-yl-1H-pyrazole

The compound of Example A-441 (455 mg, 1.5 mmol) was combined with 98% formic acid (6 mL) and heated to 100° C. After three hours, 37% formaldehyde (1.22 mL, 15 mmol) was added and the reaction was heated for an additional five hours at 100° C. The reaction mixture was allowed to cool to room temperature and filtered. The solution was diluted with water (15 mL) and extracted once with ethyl acetate (30 mL). The aqueous solution was then basified with 2.5 N sodium hydroxide to pH 8. The cloudy mixture was then extracted twice with 1:1 tetrahydrofuran-:ethyl acetate (30 mL). The organic layers were pooled and washed once with brine (25 mL), dried (MgSO$_4$), filtered and concentrated to an oil which solidified on standing. The solid was triturated with acetonitrile and collected by suction filtration. The solid was suspended in ethanol:water 2:1 (15 mL) and 1 mL of concentrated HCl was added. The solution was allowed to stir at room temperature for one hour, then filtered and concentrated. The residue was combined with ethanol (10 mL) and reconcentrated twice. The resulting solid was triturated with acetonitrile (10 mL) containing a small amount of ethanol (0.5 mL) to remove some colored impurities. The solid was collected by suction filtration, washed with acetonitrile and dried in-vacuo. Yield: 490 mg (88%); mp 255.9–256.8° C.; $^1$H NMR (D$_2$O/DMSO-d6/NaOD/300 MHz) 7.93 (d, 2H), 7.09 (s, 4H) 7.00 (d, 2H), 4.42 (m, 1H), 2.26 (br m, 2H,) 2.12 (br m, 2H), 1.92 (s, 3H), 1.68 (br m, 2 H), 1.57 (br m 2H); ESLRMS m/z 369 (M+H).

EXAMPLE A-449

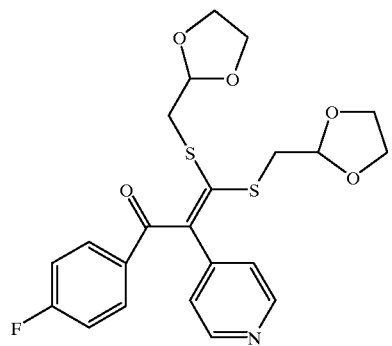

287

To the compound of Example C-1, infra, (4'-fluoro-1-(4-pyridyl)acetophenone, 14.0 g, 0.065 mol) in anhydrous tetrahydrofuran (200 mL) was added dropwise potassium t-butoxide (1M in tetrahydrofuran, 150 mL). The mixture was stirred 30 minutes. Carbon disulfide (4.2 mL, 0.07 mol) in tetrahydrofuran (25 mL) was added dropwise and stirred 15 minutes. 2-Bromomethyl-1,3-dioxolane (25.0 g, 0.15 mol) in tetrahydrofuran (25 mL) was added dropwise and contents were refluxed 10 hours. The mixture was allowed to cool and partitioned between ethyl acetate and water. The ethyl acetate layer was dried over $MgSO_4$ and concentrated in vacuo leaving a red oil (29.3 g). Chromatography on silica gel eluting with 25% ethyl acetate/hexanes gave the desired compound as a red oil, (5.5 g, 18% yield). $^1$H NMR ($CDCl^3$) 8.62–8.52 (m, 2H) 8.07–7.95 (m, 2H); 7.48–7.40 (m, 2H); 7.20–7.05 (m, 2H); 5.15–5.05 (m, 1H); 4.98–4.90 (m, 1H); 4.00–3.77 (m, 8H); 3.08 (d, J=6 Hz, 2H); 3.03 (d, J=6 Hz, 2H); ESHRMS m/z 464.0966 (M+H, $C_{22}H_{23}FNO_5S_2$ requires 464.1001); Anal. Calc'd for: $C_{22}H_{22}FNO_5S_2$ (0.1 $H_2O$): C, 56.79; H, 4.81; N, 3.01. Found: C, 56.45; H, 4.71; N, 3.02.

EXAMPLE A-450

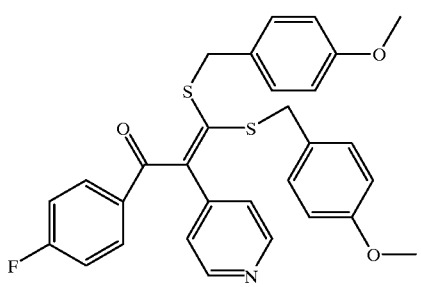

To the compound of Example C-1, infra, (4'-fluoro-1-(4-pyridyl)acetophenone, 7.0 g, 0.0325 mol) in anhydrous tetrahydrofuran (200 mL) was added dropwise potassium t-butoxide (1M in tetrahydrofuran, 75 mL). The mixture was stirred 30 minutes. Carbon disulfide (2.1 mL, 0.035 mol) in tetrahydrofuran (25 mL)was added dropwise and stirred 15 minutes. 4-Methoxybenzyl chloride (10.2 mL, 0.075 mol) in tetrahydrofuran (10 mL) was added dropwise and contents were stirred overnight. The contents were partitioned between ethyl acetate and water. The ethyl acetate layer was dried over $MgSO_4$ and concentrated in vacuo leaving a red oil (19.1 g). Chromatography on silica gel eluting with 25% ethyl acetate/hexanes gave the desired as a white solid (11.8 g, 68% yield). Recrystallization from ethyl acetate/hexanes gave the desired as colorless crystals: mp 118.5–120.6° C.; $^1$H NMR ($CDCl_3$) 8.43 (d, J=7 Hz, 2H); 7.62–7.52 (m, 2H) 7.20–6.72 (m, 12H); 3.98 (d, J=6 Hz, 4H); 3.83 (s, 3H); 3.81 (s, 3H); ESHRMS m/z 532.1408 (M+H, $C_{30}H_{27}FNO_3S_2$ requires 532.1416); Anal. Calc'd for: $C_{30}H_{26}FNO_3S_2$ (0.5 $H_2O$): C, 66.65; H, 5.03; N, 2.59. Found: C, 66.34; H, 4.96; N, 2.55.

288

EXAMPLE A-451

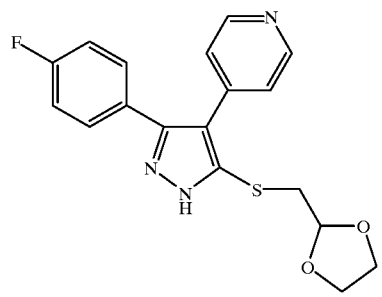

The compound of Example A-449 (4.0 g, 9.2 mmol) and hydrazine monohydrate (2.2 mL, 46 mmol) were refluxed in ethanol (100 mL) for three hours. The mixture was allowed to cool and stand overnight. A yellow precipitate was filtered to give the desired product as a yellow solid, (1.34 g, 41% yield); mp 202.1–205.4° C.; $^1$H NMR (DMSO-d6) 13.5 (br s, 1H); 8.55–8.45 (m, 2H); 7.40–7.12 (m, 6H); 5.01 (s, 1H); 3.92–3.70 (m, 4H); 3.13 (s, 2H); ESHRMS m/z 358.1025 (M+H, $C_{18}H_{17}FN_3O_2S$ requires 358.1025); Anal. Calc'd for: $C_{18}H_{16}FN_3O_2S$: C, 60.49; H, 4.51; N, 11.76. Found: C, 60.26; H, 4.55 N, 11.87.

EXAMPLE A-452

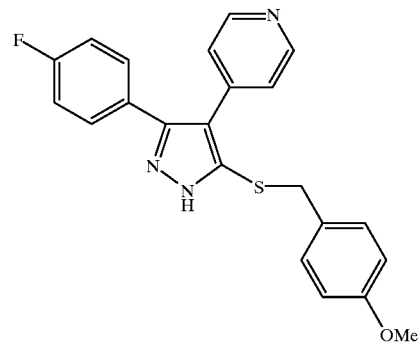

The above compound was prepared similarly to the compound of Example A-451 starting with the compound prepared in Example A-450. The desired product was obtained as a white solid (2.15 g, 49% yield); mp 214.7–215.8° C.; $^1$H NMR (DMSO-d6+approx. 10% TFA) 8.70 (d, 2H); 7.60 (d, 2H); 7.42–7.38 (m, 2H); 7.30–7.20 (m, 2H); 6.70 (d, 2H); 4.10 (s, 2H); 3.68 (s, 3H); ESHRMS m/z 392.1225 (M+H, $C_{22}H_{19}FN_3OS$ requires 392.1232); Anal. Calc'd for: $C_{22}H_{18}FN_3OS$: C, 67.50; H, 4.63; N, 10.73. Found: C, 67.46; H, 4.67 N, 10.77.

EXAMPLE A-453

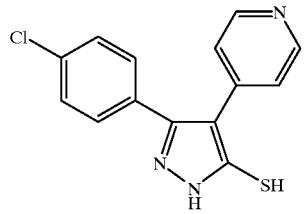

The compound prepared in step 1 of Example A-341 (50 g, 0.156 mol) and anhydrous hydrazine (25 mL, 0.8 mol) were refluxed in ethanol (500 mL) for five hours. The mixture was allowed to cool and the precipitate filtered to afford the desired product as a yellow-orange solid (21.8 g). The filtrate was diluted with water (200 mL) and a second crop was obtained as a yellow-orange solid (18.0 g). The pH of the filtrate was adjusted to pH 8 with 3N HCl and the precipitated solid filtered to give more desired as a yellow-orange solid (2.0 g). The product was obtained in 93% yield. mp 266.3–268.9° C.; $^1$H NMR (DMSO-d6) 13.80 (br, 1H); 12.20 (br s, 1H); 8.32 (s, 4H); 7.50–7.30 (m, 4H); ESHRMS m/z 288.0358 (M+H, $C_{14}H_{11}ClN_3S$ requires 288.0362); Anal. Calc'd for: $C_{14}H_{10}ClN_3S$ (0.4 H$_2$O): C, 57.01; H, 3.69; N, 14.25. Found: C, 56.95; H, 3.50 N, 14.14.

EXAMPLE A-454

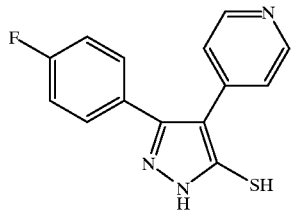

The above compound was prepared similarly to the compound of Example A-453. mp 261.3–263.9° C.; $^1$H NMR (DMSO-d6) 11.55 (br s, 1H); 8.25–8.13 (m, 2H); 7.61–7.50 (m, 2H); 7.36–7.20 (m, 2H); 7.19–7.05 (m, 2H); ESHRMS m/z 272.0691 (M+H, $C_{14}H_{11}FN_3S$ requires 272.0657); Anal. Calc'd for: $C14H_{10}FN_3S$ (0.25 H$_2$O): C, 60.97; H, 3.84; N, 15.24. Found: C, 61.05; H, 3.64 N, 15.12.

EXAMPLE A-455

To the compound prepared in Example A-453 (100 mg, 0.35 mmol) in methanol (2 mL) was added 0.5 M sodium methoxide (0.7 mL, 0.35 mmol). The mixture was stirred for 15 minutes and filtered to remove some small particles. The filtrate was concentrated in vacuo, dissolved in water and concentrated in vacuo leaving the desired product as a white solid. $^1$H NMR (DMSO-d6) 11.60 (br s, 1H); 8.20 (d, 2H); 7.60–7.50 (m, 2H); 7.40–7.20 (m, 4H); Anal. Calc'd for: $C_{14}H_9ClN_3NaS$ (2.5 H2O): C, 47.40; H, 3.98; N, 11.84. Found: C, 47.39; H, 3.33; N, 11.50.

EXAMPLE A-456

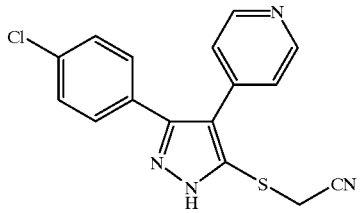

[3-(4-chlorophenyl)-4-pyridin-4-yl-1H-pyrazole-5-yl]thio]-acetonitrile

To the compound prepared in Example A-453 (584 mg, 2.0 mmol) and bromoacetonitrile (140 ul, 2.0 mmol) in dimethylformamide (5 mL) was added anhydrous potassium carbonate (276 mg, 2.0 mmol). The contents were stirred overnight, then partitioned between ethyl acetate and water. The ethyl acetate layer was dried over MgSO$_4$ and concentrated in vacuo leaving a tan solid. The solid was triturated with methanol and filtered to give the desired as a off-white solid (369 mg, 56% yield). mp 230.0–230.5° C.; $^1$H NMR (DMSO-d6) 13.90 (br s, 1H); 8.58 (d, 2H); 7.60–7.13 (m, 6H); 4.10 (s, 2H); ESHRMS m/z 327.0482 (M+H, $C_{16}H_{12}ClN_4S$ requires 327.0471); Anal. Calc'd for: $C_{16}H_{11}C_{11}N_4S$ (0.3 H$_2$O): C, 57.85, H, 3.52; N, 16.87. Found C, 57.88; H, 3.31; N, 16.77.

EXAMPLE A-457

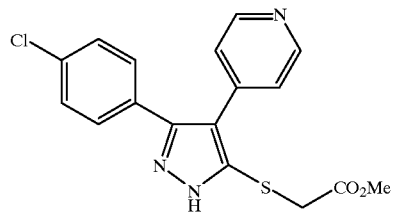

The above compound was prepared similarly to the compound of Example A-456 except that when the contents were partitioned between ethyl acetate and water, an insoluble solid was filltered to give the desired product as a white solid (2.16 g). A second crop (1.68 g) of desired product gave a total yield of 61%. mp 192.8–195.2° C.; $^1$H NMR (DMSO-d6+approximately 10% TFA) 9.80 (d, 2H); 7.80 (d, 2H); 7.52–7.34 (m, 4H); 3.92 (s, 2H); 3.57 (s, 3H); ESHRMS m/z 360.05735 (M+H, $C_{17}H_{14}ClN1_3O_2S$ requires 360.05732); Anal. Calc'd for: $C_{17}H_{14}ClN_3O_2S$ (0.25 H$_2$O): C, 56.05, H, 4.01; N, 11.53. Found C, 56.10; H, 3.72; N, 11.51.

EXAMPLE A-458

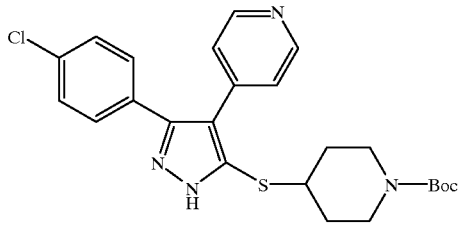

The compound prepared in Example A-453 (1.2 g, 4.2 mmol), potassium carbonate (630 mg, 4.6 mmol), N-tert-butoxycarbonyl-4-bromo piperidine (1.2 g, 4.5 mmol) were heated in dimethylformamide (15 mL) at 105° C. for three hours. Contents were allowed to cool and partitioned between ethyl acetate and water. The ethyl acetate layer was dried over MgSO$_4$ and concentrated in vacuo. The residue was triturated with ethyl acetate and filtered to give the desired as a white solid (1.2 g, 61% yield). mp 220.9–221.0° C.; $^1$H NMR (DMSO-d6) 13.70 (br, 1H); 8.60–8.50 (m, 2H); 7.58–7.10 (m, 6H); 3.80–3.60 (m, 2H); 3.40–3.20 (m, 1H); 3.00–2.63 (m, 2H); 2.00–1.53 (m, 2H); 1.50–1.05 (m, 2H); 1.40 (s, 9H); ESHRMS m/z 471.1605 (M+H, $C_{24}H_{28}ClN_4OS$ requires 471.1622); Anal. Calc'd for: $C_{24}H_{27}ClN_4OS$ (0.5 H$_2$O): C, 60.05; H, 5.88; N, 11.67. Found: C, 60.04; H, 5.57; N, 11.31.

EXAMPLE A-459

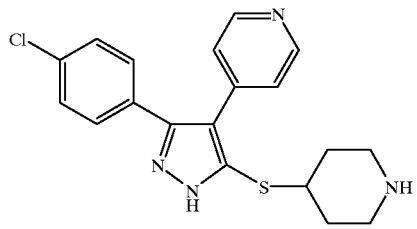

3-(4-chlorophenyl)-5-[(piperidin-4-yl)-thio]-4-pyridin-4-yl-1H-pyrazole

The compound prepared in Example A-458 (5.0 g, 11 mmol), and TFA (30 mL) were mixed in methylene chloride (50 mL) and stirred overnight. The mixture was concentrated in vacuo leaving a pale yellow oil which was dissolved in water. The pH was adjusted with 2.5 N sodium hydroxide to pH 9, precipitating a white solid which was filtered to give the desired product as a white solid (3.7 g, 93% yield). mp 211.1–211.2° C.; $^1$H NMR (DMSO-d6) 13.80 (br, 1H); 8.55 (d, 2H); 8.40 (br, 1H); 7.50–7.15 (m, 6H); 3.50–3.00 (m, 3H); 3.00–2.80 (m, 2H); 2.05–1.80 (m, 2H); 1.65–1.42 (m, 2H); ESHRMS m/z 371.1103 (M+H, $C_{19}H_{20}ClN_4S$ requires 371.1097); Anal. Calc'd for: $C_{19}H_{19}ClN_4S$ ($H_2O$): C, 58.68; H, 5.44; N, 14.41. Found: C, 58.86; H, 5.28; N, 14.25.

EXAMPLE A-460

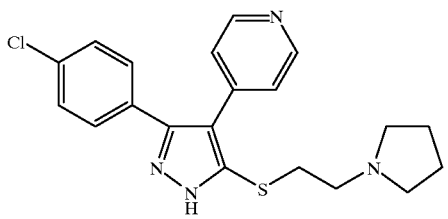

To 1-(2-chloroethyl)pyrrolidine hydrochloride (306 mg, 1.8 mmol) in methanol (10 mL) was added 0.5 M sodium methoxide (7.0 mL, 3.6 mmol). The mixture was stirred 10 minutes and the compound of Example A-453 (500 mg, 1.8 mmol) added. The contents were refluxed one hour, allowed to cool and partitioned between ethyl acetate and water. The ethyl acetate layer was dried over MgSO$_4$ and concentrated in vacuo leaving a light amber solid. The solid was recrystallized from methanol (15 mL) to give the desired product as a white solid (213 mg, 33% yield). mp 189.9–190.1° C.; $^1$H NMR (DMSO-d6) 13.65 (br, 1H); 8.52 (d, 2H); 7.42 (d, 2H); 7.38–7.10 (m, 4H); 3.10–2.93 (m, 2H); 2.63–2.51 (m, 2H); 2.38 (br s, 4H); 1.70–1.52 (m, 4H); ESHRMS m/z 385.1262 (M+H, $C_{20}H_{22}ClN_4S$ requires 385.1254); Anal. Calc'd for: $C_{20}H_{21}ClN_4S$: C, 62.41, H, 5.50; N, 14.56. Found C, 62.22; H, 5.62; N, 14.48.

EXAMPLE A-461

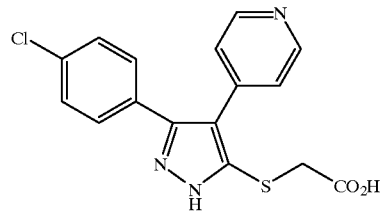

Method A: The compound prepared in Example A-457 (1.3 g, 3.6 mmol) in methanol (10 mL), 2.5N sodium hydroxide (4 mL) and water (10 mL) were stirred overnight. The mixture was concentrated in vacuo to remove the methanol and the aqueous solution left was made acidic to pH 6 with 3N HCl, precipitating a solid. The solid was extracted into ethyl acetate, dried over MgSO$_4$ and concentrated in vacuo leaving light tan crystals (205 mg). Brine was added to the aqueous layer precipitating more solid. The solid did not extract into ethyl acetate, but was filtered to give more desired product as a light tan powder (529 mg). Total yield was 61% yield. $^1$H NMR (DMSO-d6+10% TFA) 8.80 (d, 2H); 7.83 (d, 2H); 7.55–7.35 (m, 4H); 3.87 (s, 2H).

Method B: The compound prepared in Example A-457 (3.8 g, 11 mmol) and 3N HCl (30 mL) were reluxed for three hours. The mixture was allowed to cool and concentrated in vacuo. The residue was mixed with CH$_3$CN (50 mL). Upon standing overnight, pale yellow crystals grew and were filtered to give the desired product as the HCl salt (2.9 g, 69% yield). $^1$H NMR (DMSO-d6) 8.79 (d, 2H); 7.75 (d, 2H); 7.51–7.38 (m, 4H); 3.88 (s, 2H); ESHRMS m/z 346.0435 (M+H, $C_{17}H_{16}ClN_4OS$ requires 346.0417); Anal. Calc'd for: $C_{16}H_{12}ClN_3O_2S$ (HCl, 0.5 H2O): C, 49.12; H, 3.61; N, 10.74. Found: C, 49.36; H, 3.48; N, 10.72.

EXAMPLE A-462

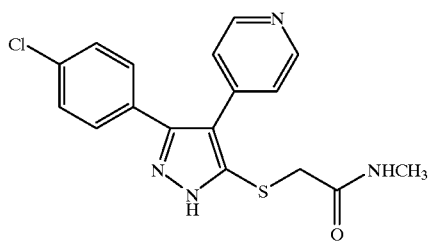

The compound prepared in Example A-457 (400 mg, 11 mmol) and a 2M solution of methyl amine in tetrahydrofuran (25 mL) were refluxed for three hours. The mixture was stirred overnight at room temperature before filtering to give the desired as a light amber solid (335 mg, 85% yield). mp 284.0–288.4° C.; $^1$H NMR (DMSO-d6) 13.58 (br, 1H); 8.60–8.45 (m, 2H); 7.98 (br s, 1H); 7.55–7.12 (m, 6H); 3.60 (s, 2H); 2.46 (s, 3H); ESHRMS m/z 359.0733 (M+H, $C_{17}H_{16}ClN_4OS$ requires 359.0745); Anal. Calc'd for: $C_{17}H_{15}ClN_4OS$: C, 56.90; H, 4.21; N, 15.61. Found: C, 56.74; H, 4.11; N, 15.17.

EXAMPLE A-463

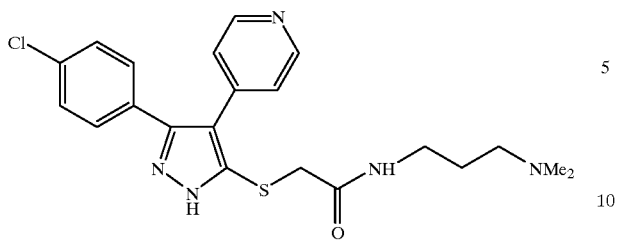

The compound prepared in Example A-457 (415 mg, 12 mmol) and N,N-dimethylaminopropylamine were refluxed in methanol (25 mL) for three hours. The mixture was stirred overnight at room temperature before concentrating in vacuo leaving a solid. The solid was triturated with ethyl acetate and filtered to give the desired as a white solid (256 mg, 50% yield). mp 168.8– 169.5° C.; $^1$H NMR (DMSO-d6) 13.80 (br, 1H); 8.55–8.50 (m 2H); 8.02 (t, 1H); 7.50–7.40 (m, 6H); 3.61 (s, 2H); 3.30–2.98 (m, 2H); 2.14–2.10 (m, 2H); 2.04 (s, 6H); 1.50–1.40 (m, 2H); ESHRMS m/z 430.1472 (M+H, $C_{21}H_{25}ClN_{12}OS$ requires 430.1468); Anal. Calc'd for: $C_{21}H_{24}ClN_5OS$ (0.5 $H_2O$): C, 57.46; H, 5.74; N, 15.95. Found: C, 57.71; H, 5.56; N, 16.12.

EXAMPLE A-464

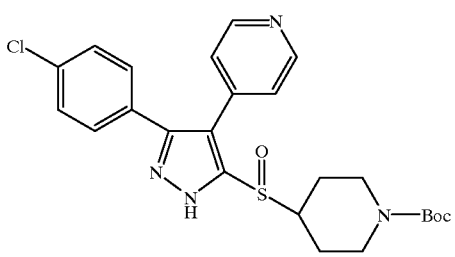

To the compound prepared in Example A-458 (1.0 g, 2.1 mmol) in methylene chloride (25 mL) was added meta-chloroperbenzoic acid (425 mg, 2.1 mmol). The mixture was stirred 15 minutes and chromatographed on silica gel (20 g) eluting with ethyl acetate. The desired product precipitated out of the ethyl acetate elutant upon standing and was filtered to give the desired product as a white solid (958 mg, 93% yield). mp 215.8–215.9° C.; $^1$H NMR (DMSO-d6) 14.34 (br s, 1H); 8.57–8.54 (m, 2H); 7.51–7.25 (m, 6H); 4.00–3.82 (m, 2H); 3.60–3.40 (m, 1H); 2.85–2.70 (m, 2H); 2.10–1.95 (m, 1H); 1.56–1.10 (m, 3H); 1.36 (s, 9H); ESHRMS m/z 487.1580 (M+H, $C_{17}H_{16}ClN_4OS$ requires 487.1571); Anal. Calc'd for: $C_{24}H_{27}ClN_{12}O_3S$: C, 59.19; H, 5.59; N, 11.50. Found: C, 59.00; H, 5.76; N, 11.46.

EXAMPLE A-465

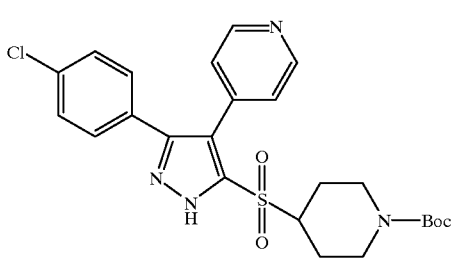

To the compound prepared in Example A-458 (320 mg, 0.68 mmol) in ethanol (5 mL) was added an aqueous solution of potassium peroxymonosulfate (420 mg, 0.68 mmol). The mixture was stirred two hours and extracted into ethyl acetate which was dried over $MgSO_4$ and concentrated in vacuo leaving a white solid. The solid was triturated with methanol and filtered to give the desired as a white solid (90 mg, 26% yield). mp 228.0–230.8° C.; $^1$H NMR (DMSO-d6) 8.61 (d, 2H); 7.48 (d, 2H); 7.31–7.20 (m, 4H); 4.05–3.90 (m, 2H); 3.54–3.35 (m, 1H); 2.85–2.60 (m, 2H); 1.92–1.80 (m, 2H); 1.48–1.25 (m, 2H); 1.32 (s, 9H); ESHRMS m/z 503.1541 (M+H, $C_{24}H_{27}ClN_4O_4S$ requires 503.1520); Anal. Calc'd for: $C_{24}H_{27}ClN_4O_4S$ ($H_2O$): C, 56.30; H, 5.51; N, 10.94. Found: C, 56.41; H, 5.78; N, 10.54.

EXAMPLE A-466

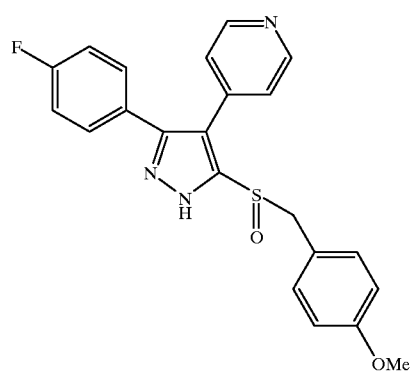

The above compound was prepared similarly to the compound of Example A-464. After chromatography the solid obtained was recrystallized from $CH_3CN$ to give the desired product as white crystals (64 mg, 33% yield). mp 189.5–189.5° C.; $^1$H NMR (DMSO-d6) 14.28 (br s, 1H); 8.50 (d, 2H); 7.40–7.20 (m, 4H); 7.20–7.05 (m, 4H); 6.85 (d, 2H); 4.41 (s, 2H); 3.70 (s, 3H); ESHRMS m/z 408.1168 (M+H, $C_{22}H_{19}FN_3O_2S$ requires 408.1182); Anal. Calc'd for: $C_{22}H_{18}FN_3O_2S$: C, 64.85; H, 4.45; N, 10.31. Found: C, 64.44; H, 4.34; N, 10.70.

EXAMPLE A-467

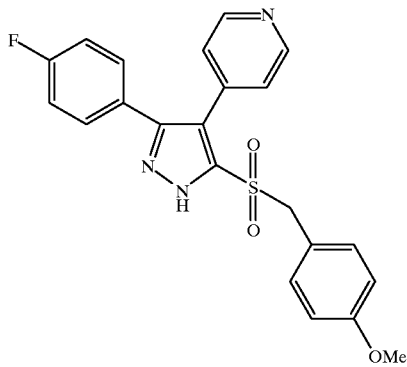

To the compound prepared in Example A-466 (1.2 g, 2.5 mmol) in methylene chloride (50 mL) was added meta-chloroperbenzoic acid (1.0 g, 5.0 mmol). The mixture was stirred 1.5 hours and filtered a white solid (620 mg) which was inorganic salts. The filtrate was chromatographed on silica gel (20 g) eluting with ethyl acetate to give the desired product as a white solid (98 mg, 9% yield). mp 241.9–242.0° C.; $^1$H NMR (DMSO-d6) 8.48–8.40 (m, 2H); 7.33–6.80 (m, 10H); 4.55 (s, 2H); 3.72 (s, 3H); ESHRMS m/z 424.1143 (M+H, $C_{24}H_{27}ClN_4O_4S$ requires 424.1131); Anal. Calc'd for: $C_{22}H_{18}FN_3O_3S$: C, 62.40; H, 4.28; N, 9.92. Found: C, 62.14; H, 4.42; N, 9.68.

EXAMPLE A-468

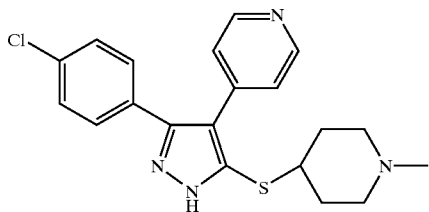

3-(4-chlorophenyl)-5-[(1-methylpiperidin-4-yl)-thio]-4-pyridin-4-yl-1H-pyrazole

The compound prepared in Example A-458 (5.0 g, 0.01 mol) and formic acid (96%, 7 mL) were heated at 100° C. for one hour. The mixture was allowed to cool to about 50° C. and formaldehyde (37%, 13 mL) was added. The contents were heated at 80° C. for two hours. The contents were allowed to cool, diluted with water (200 mL) and made basic to pH 11 with 2.5N sodium hydroxide, precipitating a white solid. The solid was filtered and recrystallized from methanol to give the desired as a white solid (174 mg. 33% yield). mp 227.7–227.7° C.; $^1$H NMR (DMSO-d6) 13.70 (br s, 1H); 8.56–8.48 (m, 2H); 7.50–7.15 (m, 6H); 3.10–2.92 (m, 1H); 2.63–2.50 (m, 2H); 2.05 (s, 3H); 1.95–1.65 (m, 4H); 1.50–1.30 (m, 2H); ESHRMS m/z 385.1233 (M+H, $C_{20}H_{22}ClN_4S$ requires 385.1254); Anal. Calc'd for: $C_{20}H_{21}ClN_4S$: C, 62.41; H, 5.50; N, 14.56. Found: C, 62.40; H, 5.80; N, 14.61.

EXAMPLE A-469

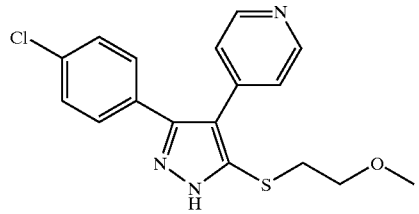

3-(4-chlorophenyl)-5-[(2-methoxyethyl)-thio]-4-pyridin-4-yl-1H-pyrazole

The above compound was prepared similarly to the compound of Example A-456 using bromoethyl methyl ether except contents were heated at 70° C. for one hour before partitioning between ethyl acetate and water. The crude product was recrystallized from methanol/ethyl acetate to give the desired product as a white solid (210 mg, 35% yield). mp 189.2–190.2° C.; $^1$H NMR (DMSO-d6) 8.60–8.45 (m, 2H); 7.60–7.10 (m, 6H); 3.60–2.85 (m, 7H); ESHRMS m/z 346.0799) M+H, $C_{17}H_{17}ClN_3OS$ requires 346.0781); Anal. Calc'd for: $C_{17}H_{16}ClN_3OS$ ($H_2O$): C, 58.73; H, 4.70; N, 12.09. Found: C, 58.67; H, 4.86; N, 12.03.

EXAMPLE A-470

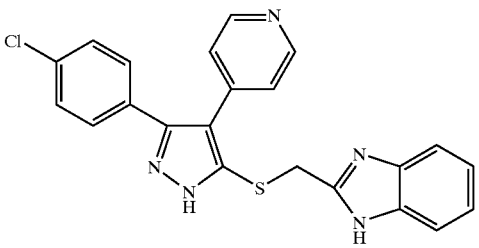

The above compound was prepared similarly to the compound of Example A-456 using 2-chloromethylbenzimidazole except contents were heated at 70° C. for one hour before partitioning between ethyl acetate and water. An insoluble solid was filtered from the two layers and triturated with methanol to give the desired product as a light amber solid (292 mg, 40% yield). mp 257.7–257.7° C.; $^1$H NMR (DMSO-d6) 13.75 (br s, 1H); 12.30 (br s, 1H); 8.55–8.30 (m, 2H); 7.65–6.90 (m, 10H); 4.40 (br s, 2H); ESHRMS m/z 418.0895 (M+H, $C_{22}H_{17}ClN_5S$ requires 418.0893); Anal. Calc'd for: $C_{22}H_{16}ClN_5S$ (0.75 $H_2O$): C, 61.25; H, 4.09; N, 16.23. Found: C, 61.27; H, 3.90; N, 15.92.

EXAMPLE A-471

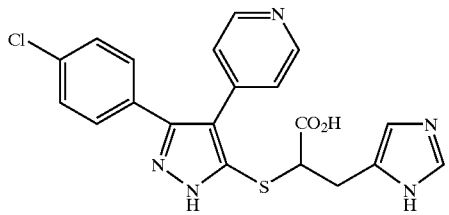

The above compound was prepared similarly to the compound of Example A-456 using DL-alpha-bromo-beta-(5- imidazolyl)propionic acid except the mixture was heated at 70° C. for one hour. The mixture contained an insoluble solid which was diluted with water and the pH was adjusted with 3N HCl to pH 7. The mixture was filtered and triturated with methanol to give the desired product as a white solid (1.5 g, 81% yield). mp 163.0–165.5° C.; $^1$H NMR (DMSO-d6+approx. 10% TFA) 8.92 (d, 1H); 8.83–8.75 (m, 2H); 7.80 (d, 2H); 7.55–7.30 (m, 5H); 4.20–4.05 (m, 1H); 3.25–3.00 (m, 2H). ESHRMS m/z 426.0799 (M+H, $C_{20}H_{17}ClN_5O_2S$ requires 426.0791); Anal. Calc'd for: $C_{20}H_{16}ClN_5O_2S$ (1.8 $H_2O$): C, 52.41 H, 4.31; N, 15.28. Found: C, 52.68; H, 4.58; N, 15.37.

EXAMPLE A-472

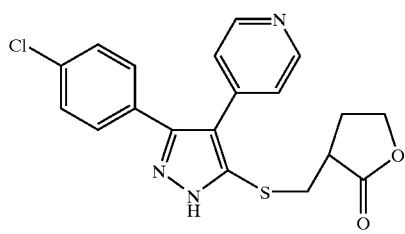

To the compound prepared in Example A-453 (264 mg, 0.9 mmol) and alpha-methylenebutyrolactone (0.08 mL, 0.9 mmol) in ethanol was added a drop of triethylamine. The mixture was stirred overnight. The resulting solid was filtered and triturated with methanol to give the desired product as a pale yellow solid (181 mg, 51% yield). mp 224.2–225.9° C.; $^1$H NMR (DMSO-d6+approx. 10% TFA) 8.80 (d, 2H); 7.80 (d, 2H); 7.53–7.33 (m, 4H); 4.30–4.05 (m, 2H); 3.50–3.40 (m, 1H); 3.15–2.90 (m, 2H); 2.32–2.20 (m, 1H) 2.10–1.90 (m, 1H); ESHRMS m/z 386.0760 (M+H, $C_{19}H_{17}ClN_3O_2S$ requires 386.0730); Anal. Calc'd for: $C_{19}H_{16}ClN_3O_2S$: C, 59.14 H, 4.18; N, 10.89. Found: C, 58.97; H, 4.21; N, 10.96.

EXAMPLE A-473

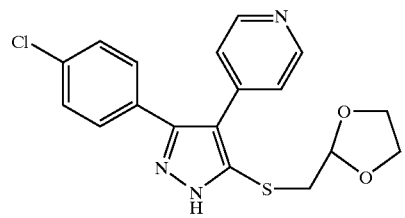

The above compound was prepared similarly to the compound of Example A-456 using 2-bromomethyl-1,3-dioxolane except the mixture was heated at 80° C. for two hours. The mixture was diluted with water and filtered to give a white solid (502 mg). The solid was recrystallized from ethanol to give the desired product as off-white crystals (280 mg, 43% yield). mp 197.0–198.2° C.; $^1$H NMR (DMSO-d6) 13.60 (br s, 1H); 8.60–8.45 (m, 2H); 7.60–7.10 (m, 6H); 5.15–4.85 (m, 1H); 3.95–3.62 (m, 4H); 3.40–2.95 (m, 2H); ESHRMS m/z 374.0741 (M+H, $C_{18}H_{17}ClN_3O_2S$ requires 374.0730); Anal. Calc'd for: $C_{18}H_{16}ClN_3O_2S$: C, 57.83 H, 4.31; N, 11.24. Found: C, 57.69; H, 4.41; N, 11.15.

EXAMPLE A-474

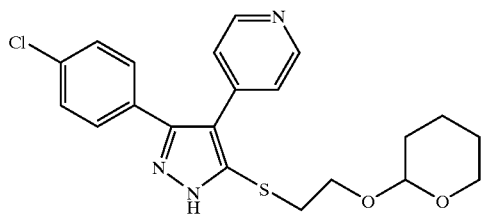

The above compound was prepared similarly to the compound of Example A-456 using 2-(2-bromoethoxy) tetrahydro-2H-pyran except that the mixture was heated at 80° C. for four hours. The mixture was allowed to cool and partitioned between ethyl acetate and water. The ethyl acetate layer was dried over $MgSO_4$ and concentrated in vacuo leaving a solid (737 mg). The solid was recrystallized from ethanol to give the desired product as pale yellow crystals (281 mg, 39% yield). mp 163.2–163.5° C.; $^1$H NMR (DMSO-d6) 13.80–13.70 (m, 1H), 8.60–8.42 (br s, 1H); 7.60–7.10 (m, 6H); 4.60–4.30 (m, 1H); 3.90–2.90 (m, 6H); 1.70–1.20 (m, 6H); ESHRMS m/z 416.1200 (M+H, $C_{21}H_{23}ClN_3O_2S$ requires 416.1198); Anal. Calc'd for: $C_{21}H_{22}ClN_3O_2S$: C, 60.64 H, 5.33; N, 10.10. Found: C, 60.49; H, 5.71; N, 9.96.

EXAMPLE A-475

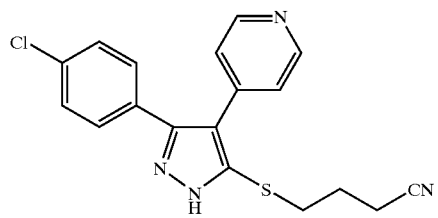

The above compound was prepared similarly to the compound of Example A-456 using 4-bromobutyronitrile except the mixture was heated at 55° C. for one hour. The mixture was diluted with water (75 mL) and filtered to give a white solid (567 mg). The solid was recrystallized from methanol to give the desired product as white crystals (333 mg, 54% yield). mp 216.7–216.9° C.; $^1$H NMR (DMSO-d6+approx. 10% TFA) 8.80–8.75 (m, 2H); 7.83–7.75 (m, 2H); 7.50–7.35 (m, 4H); 3.10–3.00 (m, 2H); 2.60–2.45 (m, 2H); 1.95–1.80 (m, 2H); ESHRMS m/z 355.0818 (M+H, $C_{18}H_{16}ClN_4S$ requires 355.0784); Anal. Calc'd for: $C_{18}H_{15}ClN_4S$ (0.5 $H_2O$): C, 59.42 H, 4.43; N, 15.40. Found: C, 59.64; H, 4.11; N, 15.44.

EXAMPLE A-476

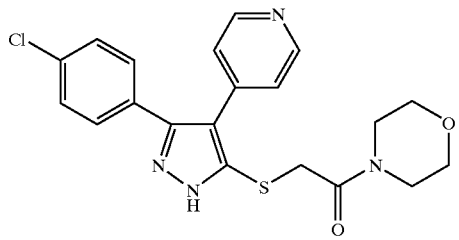

The compound prepared in Example A-461 (416 mg, 1.1 mmol), morpholine (4 mL), O-benzotriazol-1-yl-N,N,N',N'- tetramethyluronium tetrafluoroborate (481 mg, 1.5 mmol) and dimethylformamide (10 mL) were stirred overnight. The mixture was diluted with water (75 mL) and the resulting solid was filtered (363 mg). The solid was recrystallized from ethanol to give the desired product as a white solid (219 mg, 48% yield). mp 215.4–215.5° C.; $^1$H NMR (DMSO-d6) 13.70–13.60 (m, 1H); 8.60–8.50 (m, 2H); 7.50–7.10 (m, 6H); 3.93–3.80 (m, 2H); 3.60–3.20 (m, 8H); ESHRMS m/z 415.0995 (M+H, $C_{20}H_{20}ClN_4O_2S$ requires 415.1001); Anal. Calc'd for: $C_{20}H_{19}ClN_4O_2S$: C, 57.90 H, 4.62; N, 13.50. Found: C, 57.87; H, 4.86; N, 13.53.

EXAMPLE A-477

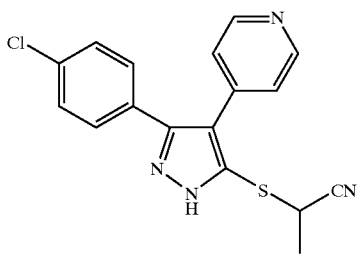

The above compound was prepared similarly to the compound of Example A-456 using 2-bromopropionitrile except the mixture was heated at 70° C. for one hour. The mixture was diluted with water (75 mL) and filtered to give an off-white solid (662 mg). The solid was recrystallized from methanol to give the desired product as a white solid (220 mg, 37% yield). mp 211.1–212.8° C.; $^1$H NMR (DMSO-d6+approx. 10% TFA) 8.87–8.80 (m, 2H); 7.90–7.80 (m, 2H); 7.55–7.45 (m, 6H); 4.42 (q, 1H); 1.50 (d, 3H); ESHRMS m/z 341.0628 (M+H, $C_{18}H_{16}ClN_4S$ requires 341.0628); Anal. Calc'd for: $C_{17}H_{13}ClN_4S$: C, 59.91 H, 3.84; N, 16.44. Found: C, 59.64; H, 4.01; N, 16.18.

EXAMPLE A-478

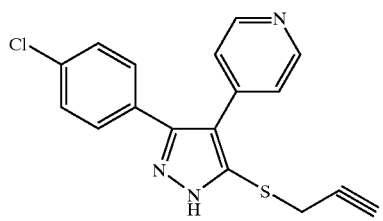

The above compound was prepared similarly to the compound of Example A-456 using propargyl bromide. The mixture was diluted with water (75 mL) and filtered to give a pale yellow solid (577 mg). The solid was triturated with methanol to give the desired product as a white solid (388 mg, 68% yield). mp 212.7–213.2° C.; $^1$H NMR (DMSO-d6+approx. 10% TFA) 8.80 (d, J=6.8 Hz, 2H); 7.82 (d, J=6.8 Hz, 2H); 7.50–7.35 (m, 4H); 3.81 (d, J=2.6 Hz, 2H); 3.05 (t, J=2.6 Hz, 1H); ESHRMS m/z 326.0533 (M+H, $C_{17}H_{13}ClN_3S$ requires 326.0519); Anal. Calc'd for: $C_{17}H_{12}ClN_3S$ (0.2 $H_2O$): C, 61.98 H, 3.79; N, 12.76. Found: C, 61.89; H, 3.45; N, 12.67.

EXAMPLE A-479

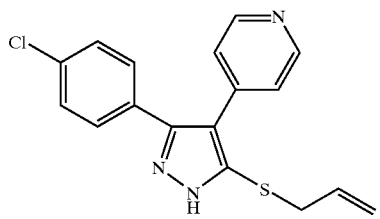

The above compound was prepared similarly to the compound of Example A-456 using allyl bromide. The mixture was diluted with water (75 mL) and filtered to give a pale yellow solid (509 mg). The solid was recrystallized from methanol to give the desired product as a pale yellow solid (187 mg, 33% yield). mp 207.3–208.1° C.; $^1$H NMR (DMSO-d6+approx. 10% TFA) 8.80 (d, 2H); 7.80 (d, 2H); 7.50–7.30 (m, 4H); 5.90–5.70 (m, 1H); 5.10–4.95 (m, 2H); 3.62 (d, 2H); ESHRMS m/z 328.0693 (M+H, $C_{17}H_{15}ClN_3S$ requires 328.0675); Anal. Calc'd for: $C_{17}H_{14}ClN_3S$ (0.1 $H_2O$): C, 61.94 H, 4.34; N, 12.75. Found: C, 61.83; H, 4.21; N, 12.76.

EXAMPLE A-480

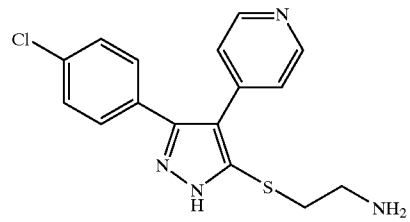

The above compound was prepared similarly to the compound of Example A-456 using 2-bromoethylamine except two equivalents of potassium carbonate were used. The mixture was diluted with water (75 mL) and filtered to give a pale yellow solid (509 mg). The solid was recrystallized from methanol to give the desired product as a pale yellow solid (262 mg, 45% yield). mp 186.8–187.8° C.; $^1$H NMR (DMSO-d6+approx. 10% TFA) 8.85–8.75 (m, 2H); 8.90 (br s, 2H); 8.85–8.75 (m, 2H); 7.55–7.35 (m, 4H); 3.30–3.00 (m, 4H); ESHRMS m/z 331.0779 (M+H, $C_{16}H_{16}ClN_4S$ requires 331.0784); Anal. Calc'd for: $C_{16}H_{15}ClN_4S$ (0.5 $H_2O$): C, 56.55; H, 4.75; N, 16.49. Found: C, 56.28; H, 4.38; N, 16.20.

EXAMPLE A-481

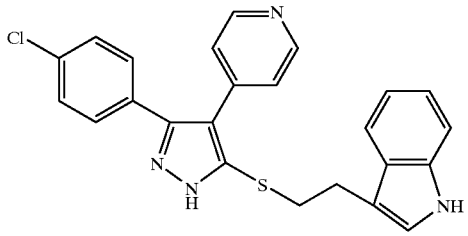

The above compound was prepared similarly to the compound of Example A-456 using 3-(2-bromoethyl)indole. The mixture was diluted with water (75 mL) and filtered to give a pale yellow solid (752 mg). The solid was triturated with methanol to give the desired product as a white solid (682 mg, 91% yield). mp 211.9–213.2° C.; $^1$H NMR (DMSO-d6+approx. 10% TFA) 10.80 (s, 1H); 8.72 (d, 2H); 7.71 (d, 2H); 7.55–7.35 (m, 5H); 7.29 (d, 1H); 7.12–6.88 (m, 3H); 3.40–3.30 (m, 2H); 3.05–2.95 (m, 2H); ESHRMS m/z 431.1095 (M+H, $C_{24}H_{20}ClN_4S$ requires 431.1097); Anal. Calc'd for: $C_{24}H_{19}ClN_4S$ (0.15 $H_2O$): C, 66.47 H, 4.49; N, 12.92. Found: C, 66.44; H, 4.51; N, 12.84.

EXAMPLE A-482

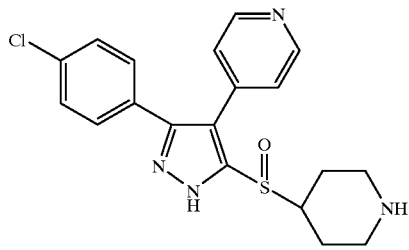

The compound of Example A-464 (464 mg, 0.95 mmol) and TFA (8 mL) were mixed in methylene chloride (10 mL) and stirred overnight. The mixture was concentrated in vacuo and the residue was partitioned between ether and water. The aqueous layer was made basic to pH 10 with 2.5N sodium hydroxide and extracted with ethyl acetate (2×100 mL). Upon standing overnight, a solid precipitated from the aqueous layer and was filtered to give the desired product as a white solid (183 mg, 50% yield). mp 189.1–190.8° C.; $^1$H NMR (DMSO-d6+approx. 10% TFA) 8.85 (d, 2H); 8.80–8.60 (m 1H); 8.45–8.25 (m, 1H); 7.90 (d, 2H); 7.55–7.30 (m, 4H); 3.65–3.20 (m 3H); 3.10–2.80 (m 2H); 2.20–2.00 (m, 1H); 1.90–1.50 (m, 3H); ESHRMS m/z 387.1032 (M+H, $C_{19}H_{20}ClN_4OS$ requires 387.1046); Anal. Calc'd for: $C_{19}H_{20}ClN_4OS$ (2 $H_2O$): C, 53.96 H, 5.48; N, 13.25. Found: C, 53.75; H, 4.99; N, 13.21.

EXAMPLE A-483

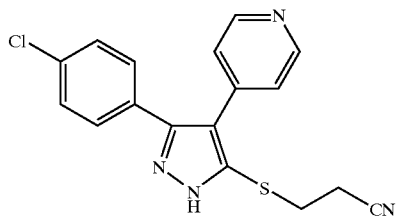

The above compound was prepared similarly to the compound of Example A-456 using 3-bromopropionitrile. The mixture was diluted with water (75 mL) and extracted into ethyl acetate, which was dried over $MgSO_4$ and concentrated in vacuo leaving an orange waxy solid (523 mg). The solid was dissolved in $CH_3CN$ and filtered through a pad of silica gel and eluted with ethyl acetate to give a white solid. The solid was triturated with ethyl acetate and filtered to give the desired product as a white solid (76 mg, 13% yield). mp 205.7–206.5° C.; $^1$H NMR (DMSO-d6+approx. 10% TFA) 8.80 (d, 2H); 7.80 (d, 2H); 7.55–7.35 (m, 4H); 3.30–3.20 (m, 2H); 2.90–2.80 (m, 2H); ESHRMS m/z 341.0639 (M+H, $C_{19}H_{20}ClN_4OS$ requires 341.0628); Anal. Calc'd for: $C_{17}H_{13}ClN_4S$ (0.25 $H_2O$): C, 59.13 H. 3.94; N, 16.22. Found: C, 59.03; H, 3.93; N, 15.90.

EXAMPLE A-484

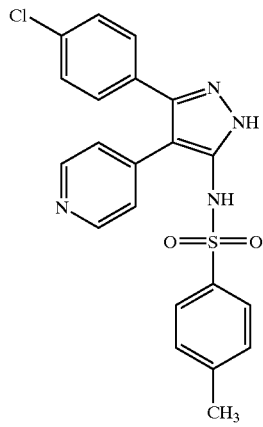

A solution of 5-amino-3-(4-chlorophenyl)-4-(pyridin-4-yl)-pyrazole (200 mg, 0.74 mmol) and toluene sulfonyl chloride (564 mg, 2.94 mmol, prepared as set forth in Example A-427) in pyridine (5 mL) was stirred at 100° C. for two days. The mixture was concentrated in vacuo to a brown residue. The residue was chromatographed on a silica gel column eluting with 10% methanol/dichloromethane. The fractions containing the desired product were combined and concentrated to a yellow solid which was washed with diethyl ether and filtered to afford 78 mg (25%) of the desired sulfonamide as a white solid. m.p.284.3–284.4° C. $^1$H NMR (DMSO/300 MHz) δ13.33 (brs, 0.8H), 9.94 (brs, 0.75H), 8.48 (brs, 1.75H), 8.22 (brs, 0.3H), 7.63 (d, 1.7H), 7.47 (d, 1.85H), 7.24 (m, 6.45H), 7.02 (brs, 0.25H), 6.81 (brs, 0.20H). ESLRMS m/z 425 (M+H). ESHRMS m/z 425.0848 (M+H, $C_{21}H_{18}N_4ClS$ requires 425.0839).

EXAMPLE A-485

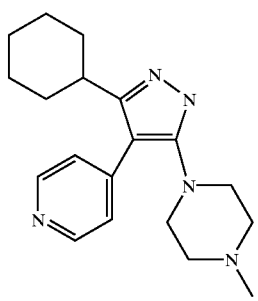

1-[cyclohexyl-4-(4-pyridinyl)-1H-pyrazol-3-yl]-4-methylpiperazine mp>300° C. (decomposed). $^1$H NMR ($CD_3OD$/300 MHz) 8.50 (d, 2H, J=6.0 Hz), 7.51 (d, 2H, J=5.8 Hz), 2.99–2.93, (m, 4H), 2.52–2.48 (m, 4H), 3.04–3.02 (m, 4H), 2.96 (s, 3H), 2.54–2.49 (m, 1H), 2.31–2.26 (m, 4H), 1.84–1.33 (m, 10H). FABLRMS m/z 326 (M+H).

Additional compounds of the present invention which could be prepared using one or more of the reaction schemes set forth in this application include, but are not limited to, the following:

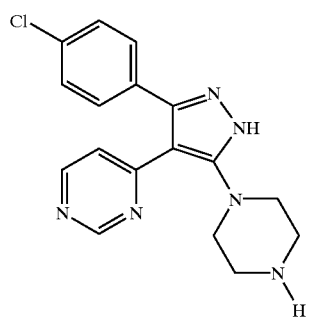

4-[3-(4-chlorophenyl)-5-
(1-piperazinyl)-1H-pyrazol-
4-yl]pyrimidine;

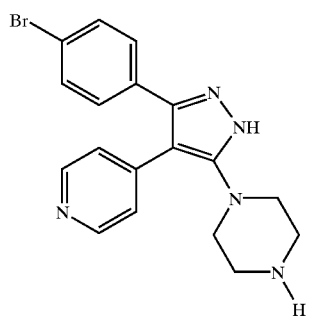

1-[5-(4-bromophenyl)-4-
(4-pyridinyl)-1H-pyrazol-3-yl]piperazine;

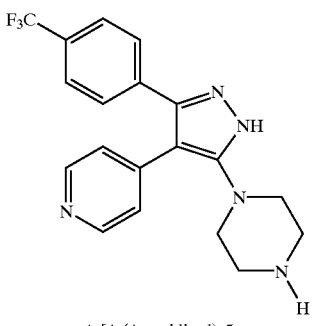

1-[4-(4-pyridinyl)-5-
[4-(trifluoromethyl)phenyl]-
1H-pyrazol-3-yl]piperazine;

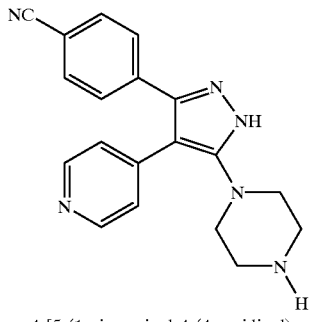

4-[5-(1-piperazinyl-4-(4-pyridinyl)
-1H-pyrazol-3-yl]benzonitrile;

-continued

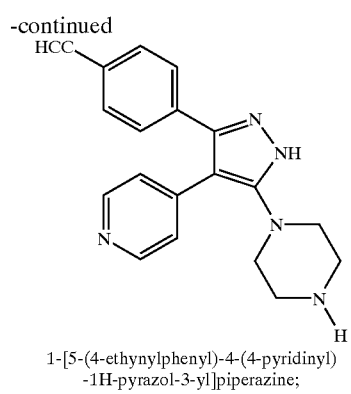

1-[5-(4-ethynylphenyl)-4-(4-pyridinyl)
-1H-pyrazol-3-yl]piperazine;

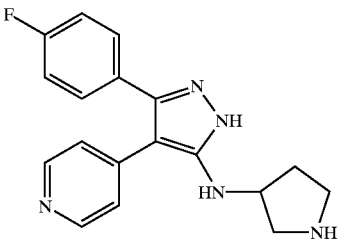

5-(4-fluorophenyl)-4-
(4-pyridinyl)-N-3-pyrrolidinyl-
1H-pyrazol-3-amine;

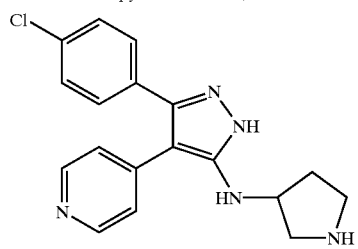

5-(4-chlorophenyl)-4-
(4-pyridinyl)-N-3-pyrrolidinyl-
1H-pyrazol-3-amine;

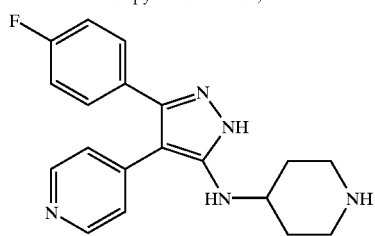

N-[5-(4-fluorophenyl)-4-
(4-pyridinyl)-1H-pyrazol-3-yl]
-4-piperidinamine;

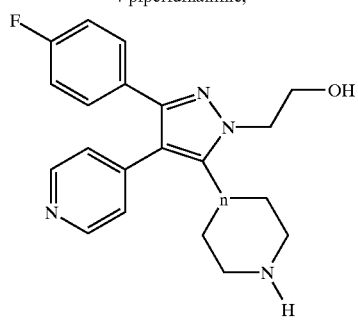

3-(4-fluorophenyl)-5-
(1-piperazinyl)-4-
(4-pyridinyl)-1H-pyrazole-
1-ethanol;

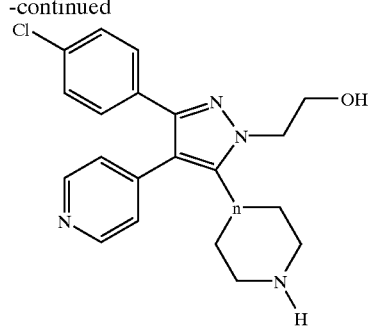

3-(4-chlorophenyl)-5-
(1-piperazinyl)-4-
(4-pyridinyl)-1H-pyrazole-
1-ethanol;

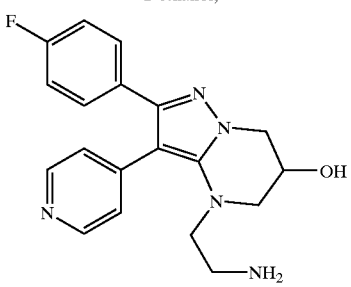

4-[2-aminoethyl]-2-(4-fluoro
phenyl)-4,5,6,7-tetrahydro-
3-(4-pyridinyl)pyrazolo
[1,5-a]pyrimidin-6-ol;

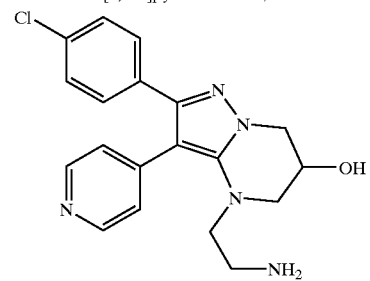

4-[2-aminoethyl]-2-(4-chloro
phenyl)-4,5,6,7-tetrahydro-
3-(4-pyridinyl)pyrazolo
[1,5-a]pyrimidin-6-ol;

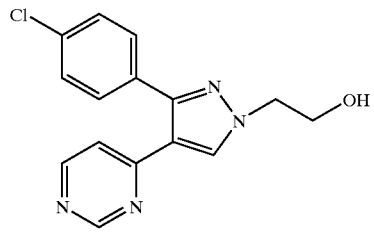

3-(4-chlorophenyl)-4-(4-pyrimidinyl)-
1H-pyrazole-1-ethanol;

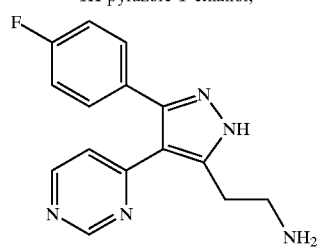

5-(4-fluorophenyl)-4-(4-pyrimidinyl)-
1H-pyrazole-3-ethanamine;

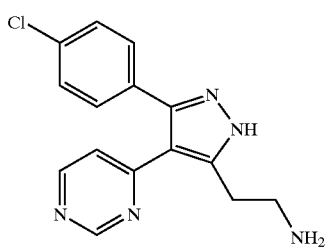

5-(4-chlorophenyl)-4-(4-pyrimidinyl)-
1H-pyrazole-3-ethanamine;

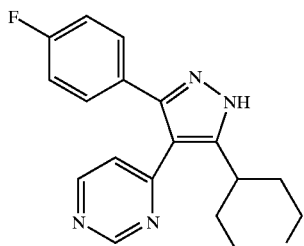

4-[3-(4-fluorophenyl)-5-(4-piperidinyl)-
1H-pyrazol-4-yl]pyrimidine;

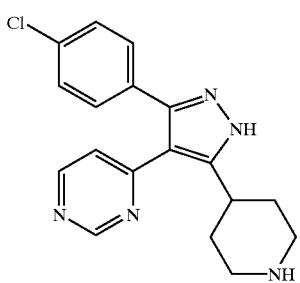

4-(3-(4-chlorophenyl)-5-(4-piperidinyl)-
1H-pyrazol-4-yl]pyrimidine;

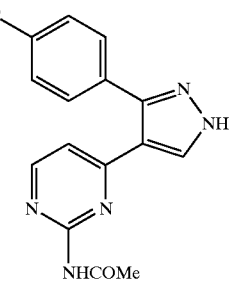

N-[4-(3-(4-fluorophenyl)-1H-pyrazol-4-yl]-
2-pyrimidinyl]acetamide;

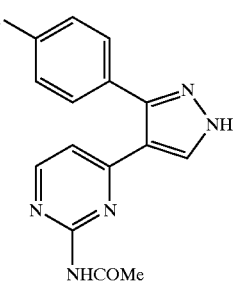

N-[4-(3-(4-chlorophenyl)-1H-pyrazol-4-yl]-
2-pyrimidinyl]acetamide;

-continued

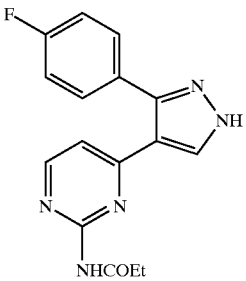

N-[4-(3-(4-fluorophenyl)-1H-pyrazol-4-yl]-
2-pyrimidinylpropanamide;

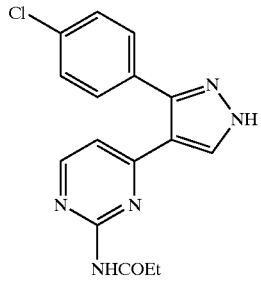

N-[4-(3-(4-fluorophenyl)-1H-pyrazol-4-yl]-
2-pyrimidinylpropanamide;

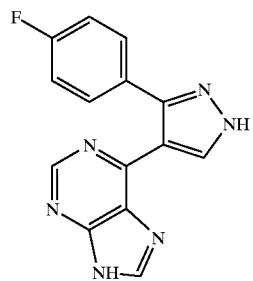

6-[3-(4-fluorophenyl)-1H-pyrazol-4-yl]-1H-purine;

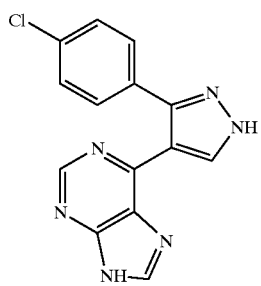

6-[3-(4-chlorophenyl)-1H-pyrazol-4-yl]-1H-purine;

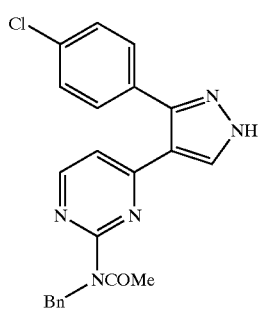

N-[4-[3-(4-chlorophenyl)-1H-pyrazol-4-yl]-
2-pyrimidinyl]-N-(phenylmethyl)acetamide;

-continued

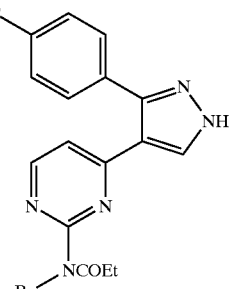

N-[4-[3-(4-fluorophenyl)-1H-pyrazol-4-yl]-
2-pyrimidinyl]-N-(phenylmethyl)propanamide;

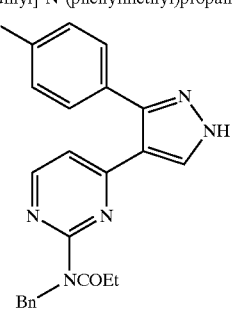

N-[4-[3-(4-chlorophenyl)-1H-pyrazol-4-yl]-
2-pyrimidinyl]-N-(phenylmethyl)propanamide;

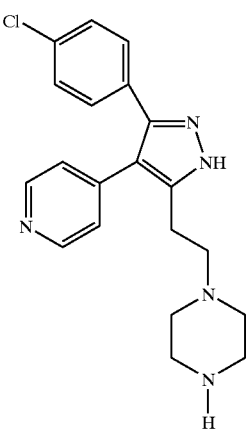

1-[2-[5-(4-chlorophenyl)-4-(4-pyridinyl)-1H-
pyrazol-3-yl]ethyl]piperazine

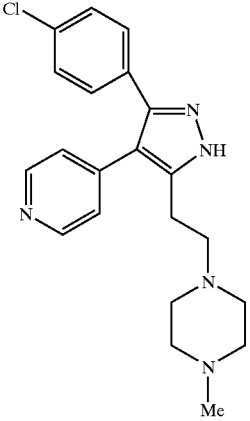

1-[2-[5-(4-chlorophenyl)-4-(4-pyridinyl)-1H-
pyrazol-3-yl]ethyl]-4-methylpiperazine

309
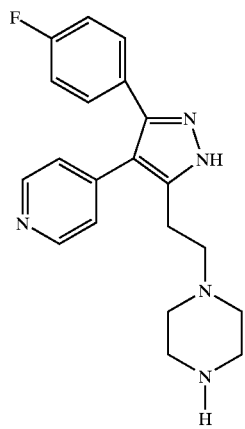
1-[2-[5-(4-fluorophenyl)-4-(4-pyridinyl)-1H-pyrazol-3-yl]ethyl]piperazine
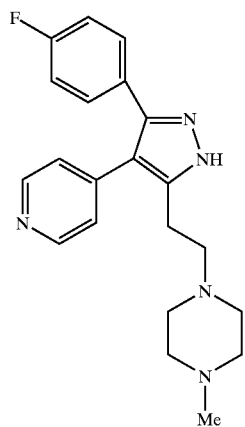
1-[2-[5-(4-fluorophenyl)-4-(4-pyridinyl)-1H-pyrazol-3-yl]ethyl]-4-methylpiperazine
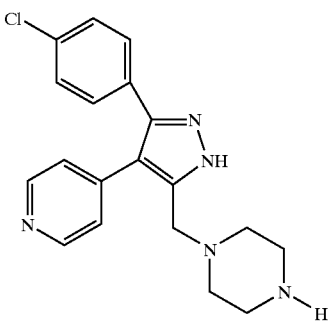
1-[(5-(4-chlorophenyl)-4-(4-pyridinyl)-1H-pyrazol-3-yl]methyl piperazine
310
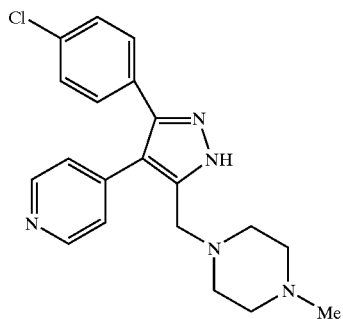
1-[[5-(4-chlorophenyl)-4-(4-pyridinyl)-1H-pyrazol-3-yl]methyl]-4-methylpiperazine
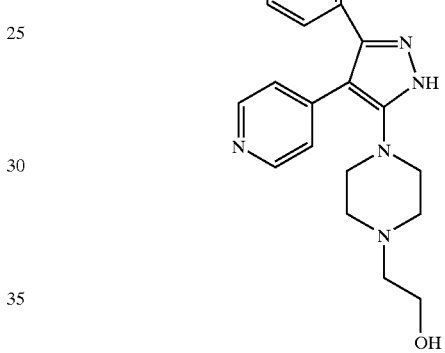
4-[5-(4-chlorophenyl)-4-(4-pyridinyl)-1H-pyrazol-3-yl]-1-piperazineethanol
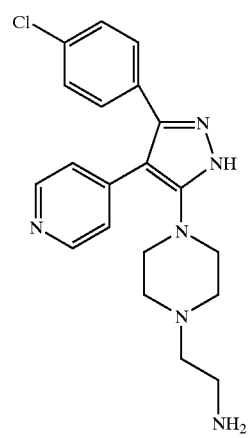
4-[5-(4-chlorophenyl)-4-(4-pyridinyl)-1H-pyrazol-3-yl]-1-piperazineethanamine

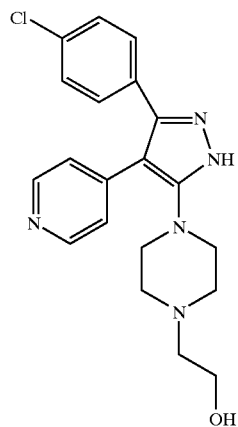
4-[5-[4-fluorophenyl)-4-(4-pyridinyl)-1H-pyrazol-3-yl]-1-piperazineethanol
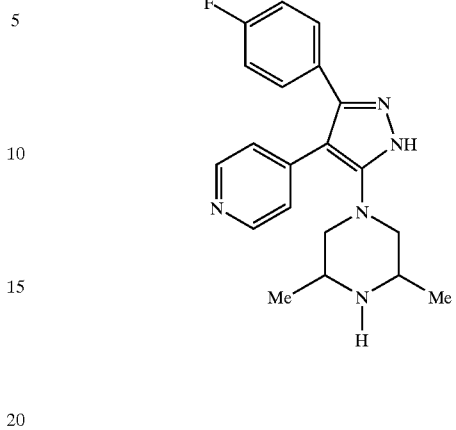
1-[5-(4-fluorophenyl)-4-(4-pyridinyl)-1H-pyrazol-3-yl]-3,5-dimethylpiperazine
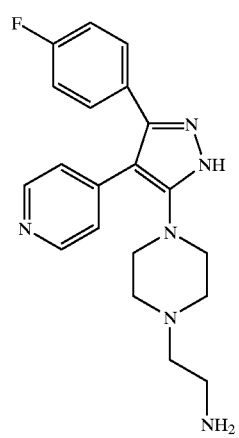
4-[5-(4-fluorophenyl)-4-(4-pyridinyl)-1H-pyrazol-3-yl]-1-piperazineethanamine
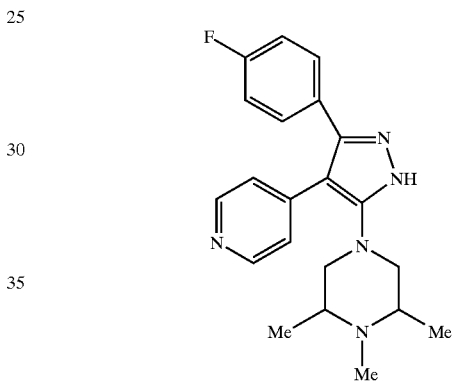
4-[5-(4-fluorophenyl)-4-(4-pyridinyl)-1H-pyrazol-3-yl]1-1,2,6-trimethylpiperazine
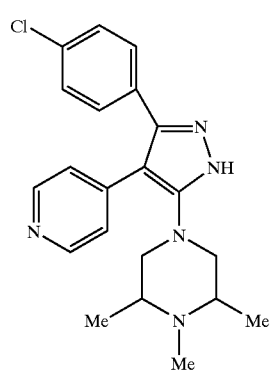
4-[5-(4-chlorophenyl)-4-(4-pyridinyl)-1H-pyrazol-3-yl]-1,2,6-trimethylpiperazine
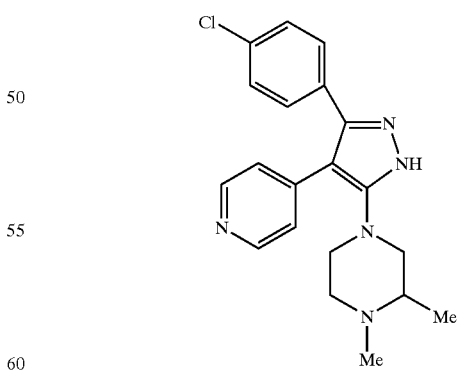
4-[5-(4-chlorophenyl)-4-(4-pyridinyl)-1H-pyrazol-3-yl]-1,2-dimethylpiperazine

313

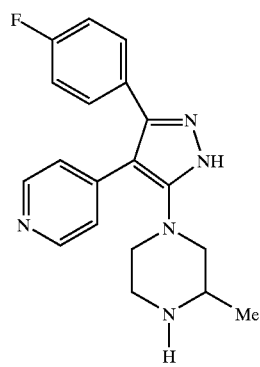

1-[5-(4-fluorophenyl)-4-(4-pyridinyl)-1H-pyrazol-3-yl]-3-methylpiperazine

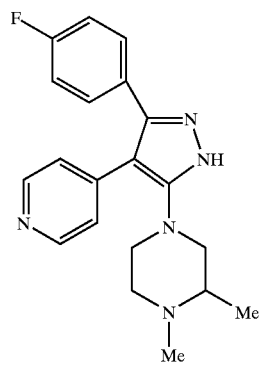

4-[5-(4-fluorophenyl)-4-(4-pyridinyl)-1H-pyrazol-3-yl]-1,2-dimethylpiperazine

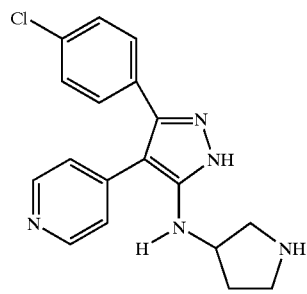

5-(4-chlorophenyl)-4-(4-pyridinyl)-N-3-pyrrolidinyl-1H-pyrazol-3-amine

314

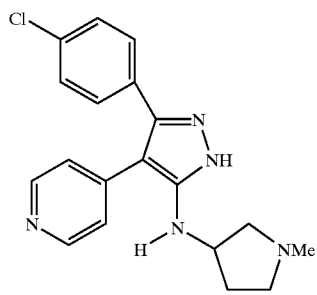

5-(4-chlorophenyl)-N-(1-methyl-3-pyrrolidinyl)-4-(4-pyridinyl)-1H-pyrazol-3-amine

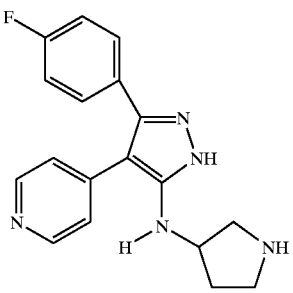

5-(4-fluorophenyl)-4-(4-pyridinyl)-N-3-pyrrolidinyl-1H-pyrazol-3-amine

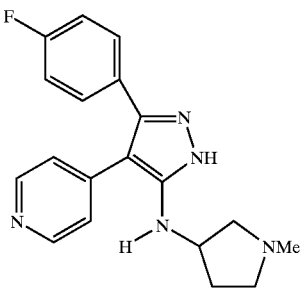

5-(4-fluorophenyl)-N-(1-methyl-3-pyrrolidinyl)-4-(4-pyridinyl)-1H-pyrazol-3-amine

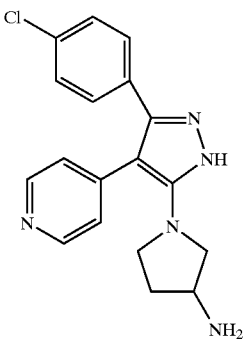

1-[5-(4-chlorophenyl)-4-(4-pyridinyl)-1H-pyrazol-3-yl]-3-pyrrolidinamine

315

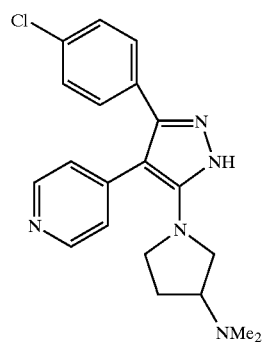

1-[5-(4-chlorophenyl)-4-(4-pyridinyl)-1H-pyrazol-3-yl]-N,N-dimethyl-3-pyrrolidinamine

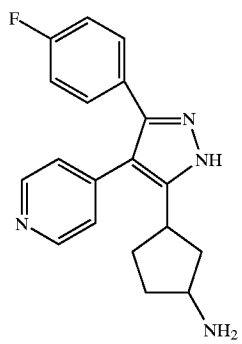

1-[5-(4-fluorophenyl)-4-(4-pyridinyl)-1H-pyrazol-3-yl]-3-pyrrolidinamine

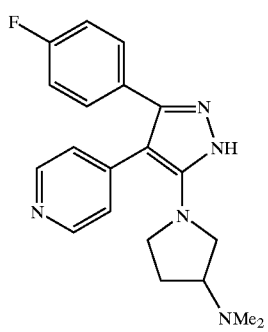

1-[5-(4-fluorophenyl)-4-(4-pyridinyl)-1H-pyrazol-3-yl]-N,N-dimethyl-3-pyrrolidinamine

316

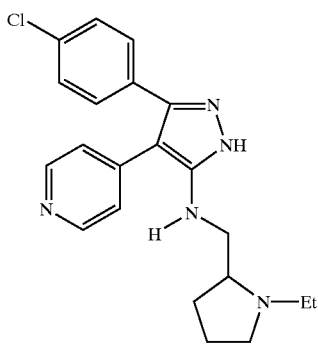

5-(4-chlorophenyl)-N-[(1-ethyl-2-pyrrolidinyl)methyl]-4-(4-pyridinyl)-1H-pyrazol-3-amine

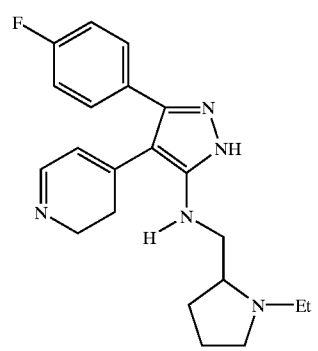

5-(4-fluorophenyl)-N-[(1-ethyl-2-pyrrolidinyl)methyl]-4-(4-pyridinyl)-1H-pyrazol-3-amine

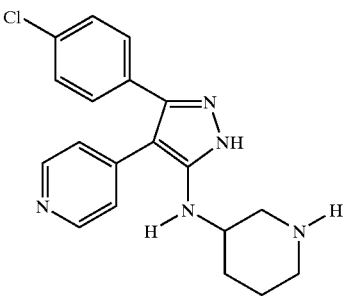

N-[5-(4-chlorophenyl)-4-(4-pyridinyl)-1H-pyrazol-3-yl]-3-methyl-3piperidinamine

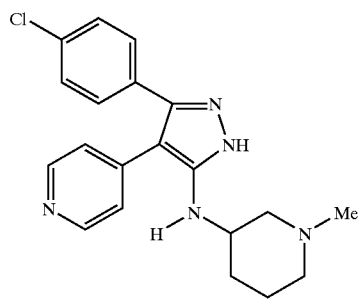

N-[5-(4-chlorophenyl)-4-(4-pyridinyl)-1H-pyrazol-
3-yl]-1-methyl-3-piperidinamine

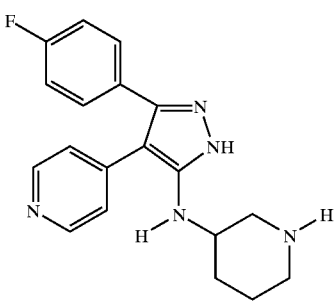

N-[5-(4-fluorophenyl)-4-(4-pyridinyl)-1H-pyrazol-3-
yl]-3-piperidinamine

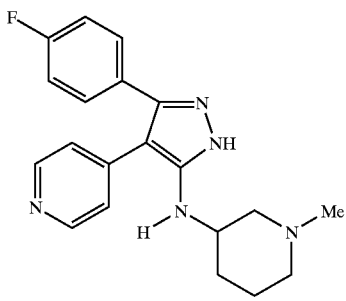

N-[5-(4-fluorophenyl)-4-(4-pyridinyl)-1H-pyrazol-3-
yl]-1-methyl-3-piperidinamine

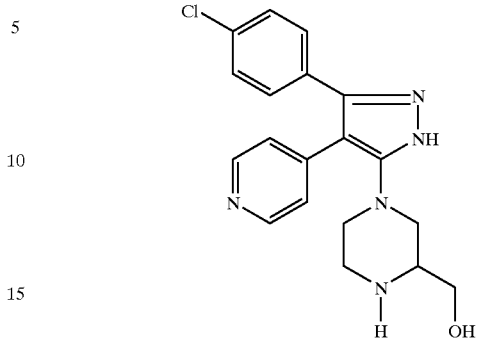

4-[5-(4-chlorophenyl)-4-(4-pyridinyl)-1H-pyrazol-3-
yl]-2-piperazinemethanol

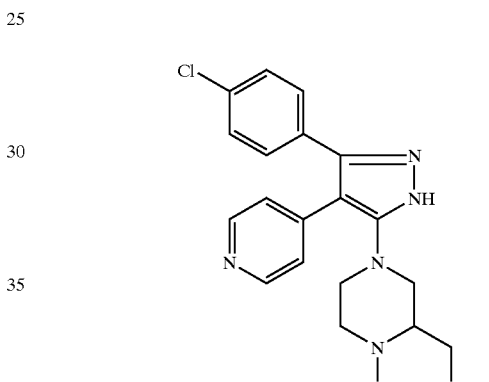

4-[5-(4-chlorophenyl)-4-(4-pyridinyl)-1H-pyrazol-3-
yl]-2-piperazinemethanamine

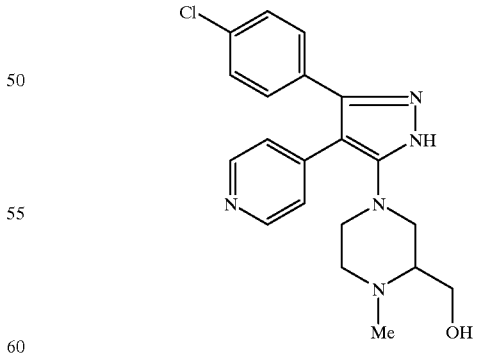

4-[5-(4-chlorophenyl)-4-(4-pyridinyl)-1H-pyrazol-3-
yl]-1-methyl-2-piperazinemethanol

319

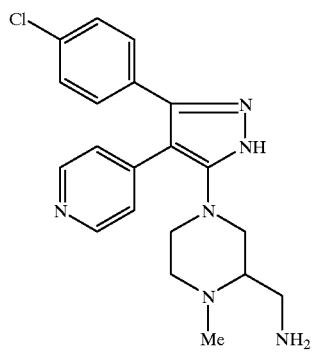

4-[5-(4-chlorophenyl)-4-(4-pyridinyl)-1H-pyrazol-3-yl]-1-methyl-2-piperazinemethanamine

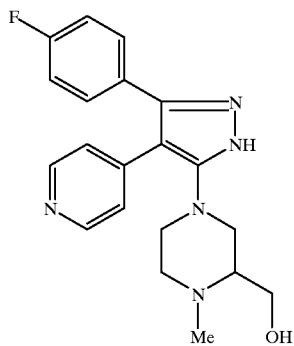

4-[5-(4-fluorophenyl)-4-(4-pyridinyl)-1H-pyrazol-3-yl]-2-piperazinemethanol

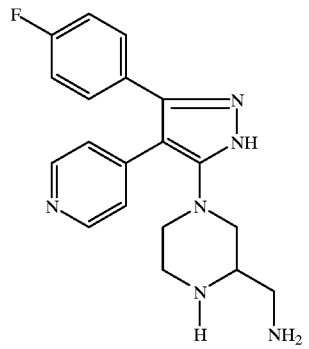

4-[5-(4-fluorophenyl)-4-(4-pyridinyl)-1H-pyrazol-3-yl]-2-piperazinemethanamine

320

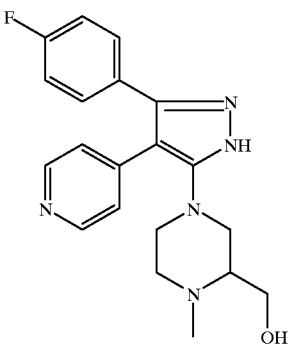

4-[5-(4-fluorophenyl)-4-(4-pyridinyl)-1H-pyrazol-3-yl]-1-methyl-2-piperazinemethanol

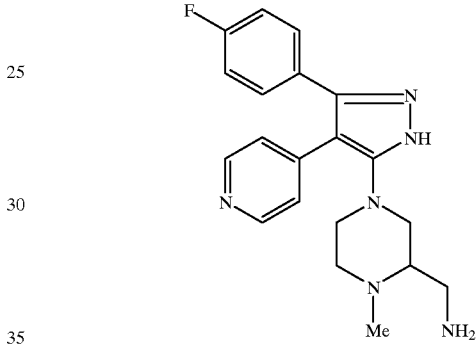

4-[5-(4-fluorophenyl)-4-(4-pyridinyl)-1H-pyrazol-3-yl]-1-methyl-2-piperazinemethanamine

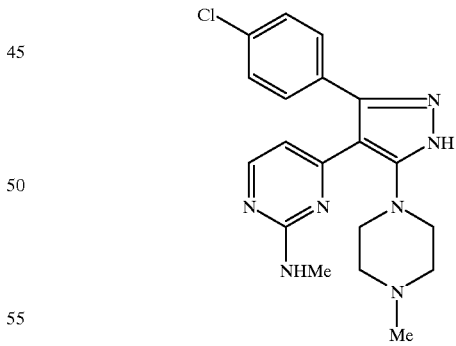

4-[3-(4-chlorophenyl)-5-(4-methyl-1-piperazinyl)-1H-pyrazol-4-yl]-N-methyl-2-pyrimidinamine

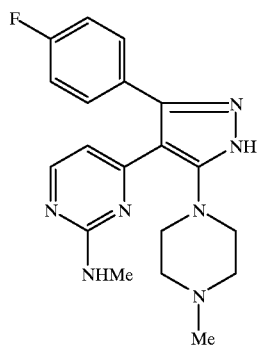

4-[3-(4-fluorophenyl)-5-(4-methyl-1-piperazinyl)-
1H-pyrazol-4-yl]-N-methyl-2-pyrimidinamine

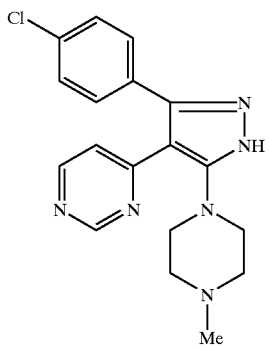

4-[3-(4-chlorophenyl)-5-(4-methyl-1-piperazinyl)-
1H-pyrazol-4-yl]pyrimidine

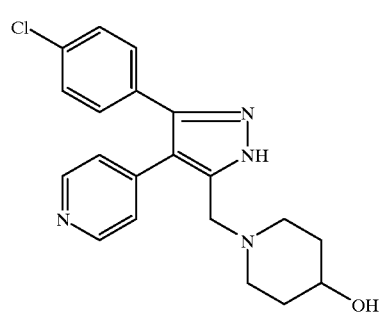

1-[[5-(4-chlorophenyl)-4-(4-pyridinyl)-1H-pyrazol-
3-yl]methyl]-4-piperidinol

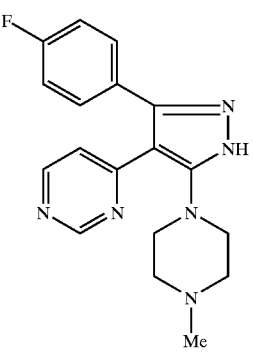

4-[3-(4-fluorophenyl)-5-(4-methyl-1-piperazinyl)-
1H-pyrazol-4-yl]pyrimidine

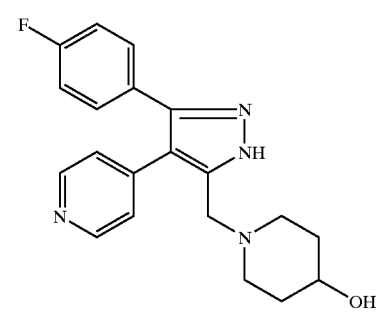

1-[[5-(4-fluorophenyl)-4-(4-pyridinyl)-1H-pyrazol-
3-yl]methyl-4-piperidinol

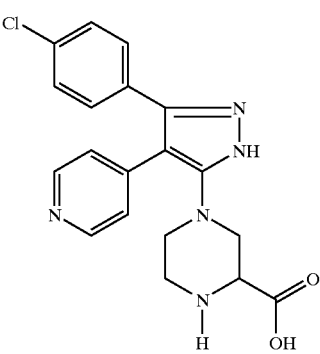

4-[5-(4-chlorophenyl)-4-(4-pyridinyl)-1H-pyrazol-3-
yl]-2-piperazinecarboxylic acid

323

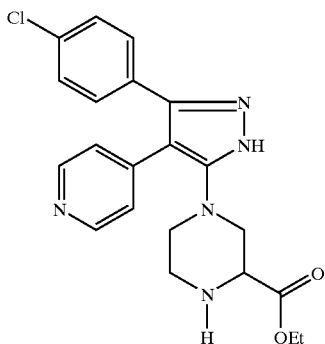

ethyl 4-[5[-(4-chlorophenyl)-4-(4-pyridinyl)-1H-
pyrazol-3-yl]-2-piperazinecarboxylate

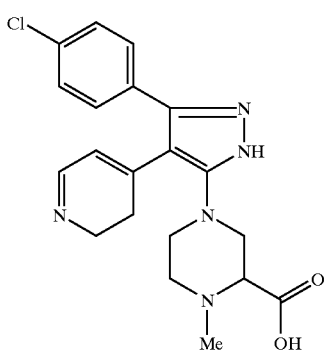

4-[5-(4-chlorophenyl)-4-(4-pyridinyl)-1H-pyrazol-3-
yl]-1-methyl-2-piperazinecarboxylic acid

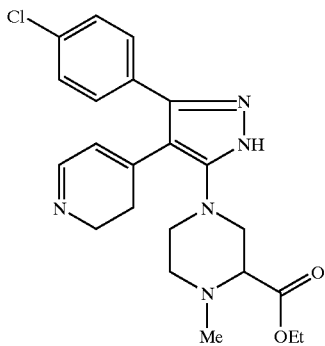

ethyl 4-[5-(4-chlorophenyl)-4-(4-pyridinyl)-1H-
pyrazol-3-yl]-1-methyl-2-piperazinecarboxylate

324

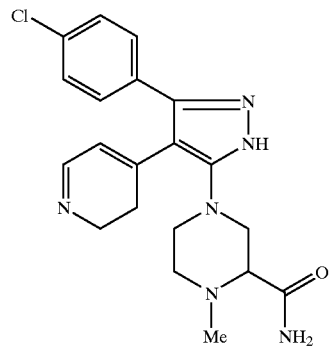

4-[5-(4-chlorophenyl)-4-(4-pyridinyl)-1H-pyrazol-3-
yl]-1-methyl-2-piperazinecarboxamide

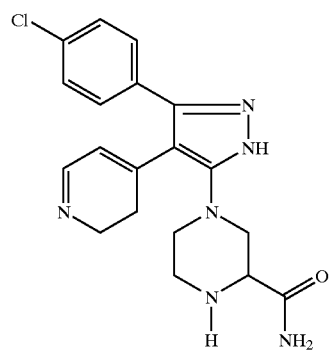

4-[5-(4-chlorophenyl)-4-(4-pyridinyl)-1H-pyrazol-3-
yl]-2-piperazinecarboxamide

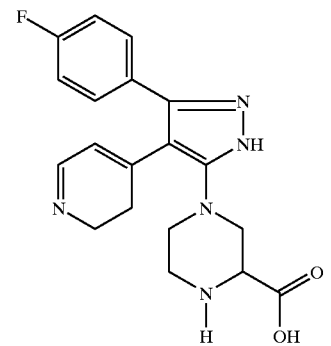

4-[5-(4-fluorophenyl)-4-(4-pyridinyl)-1H-pyrazol-3-
yl]-2-piperazinecarboxylic acid

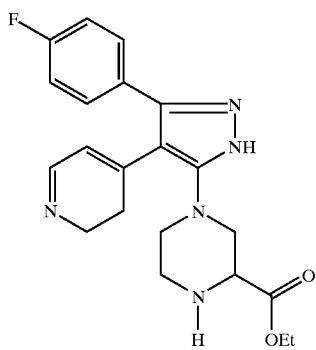

ethyl 4-[5-(4-fluorophenyl)-4-(4-pyridinyl)-1H-
pyrazol-3-yl]-2-piperazinecarboxylate

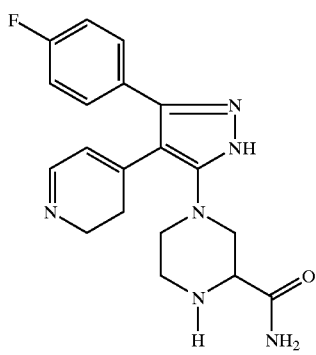

4-[5-(4-fluorophenyl)-4-(4-pyridinyl)-1H-pyrazol-3-
yl]-2-piperazinecarboxamide

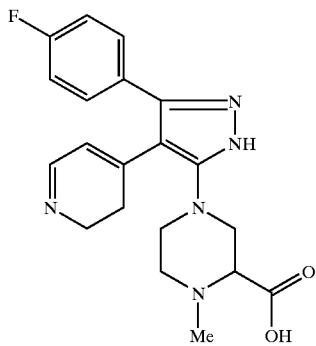

4-[5-(4-fluorophenyl)-4-(4-pyridinyl)-1H-pyrazol-3-
yl]-1-methyl-2-piperazinecarboxylic acid

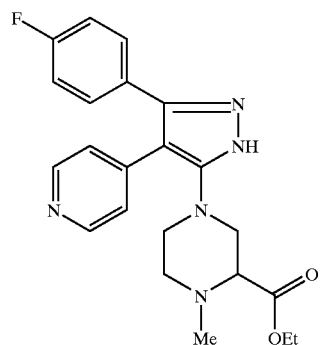

ethyl 4-[5-(4-fluorophenyl)-4-(4-pyridinyl)-1H-
pyrazol-3-yl]-1-methyl-2-piperazinecarboxylate

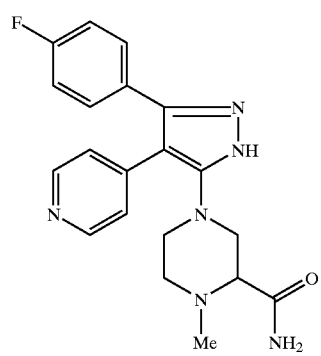

4-[5-(4-fluorophenyl)-4-(4-pyridinyl)-1H-pyrazol-3-
yl]-1-methyl-2-piperazinecarboxamide

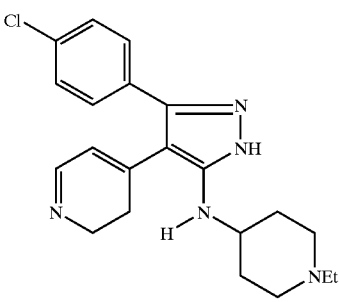

N-[5-(4-chlorophenyl)-4-(4-pyridinyl)-1H-pyrazol-
3-yl]-1-ethyl-4-piperidinamine

327

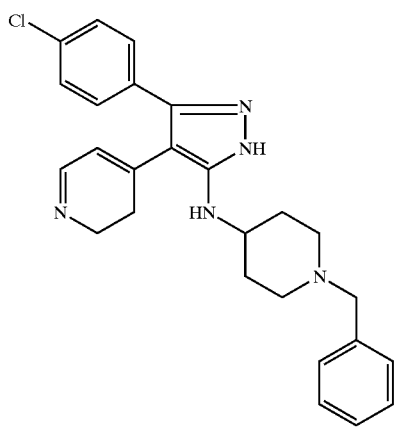

N-[5-(4-chlorophenyl)-4-(4-pyridinyl)-1H-pyrazol-
3-yl]-1-(phenylmethyl)-4-piperidinamine

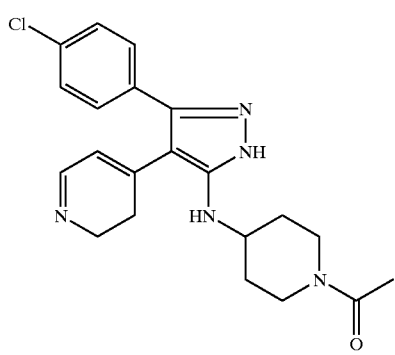

1-acetyl-N-[5-(4-chlorophenyl)-4-(4-pyridinyl)-1H-
pyrazol-3-yl]-4-piperidinamine

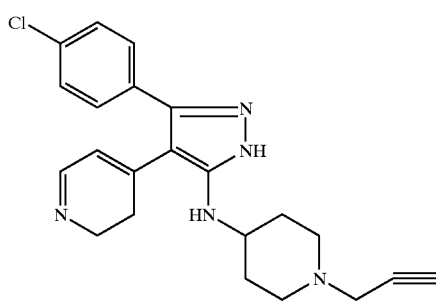

N-[5-(4-chlorophenyl)-4-(4-pyridinyl)-1H-pyrazol-
3-yl]-1-(2-propynyl)-4-piperidinamine

328

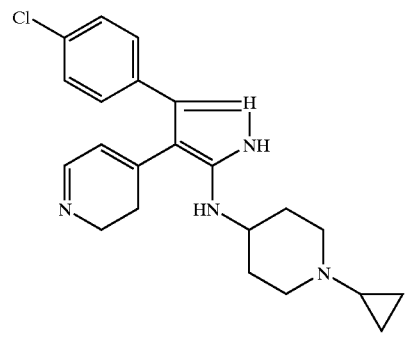

N-[5-(4-chlorophenyl)-4-(4-pyridinyl)-1H-pyrazol-
3-yl]-1-cyclopropyl-4-piperidinamine

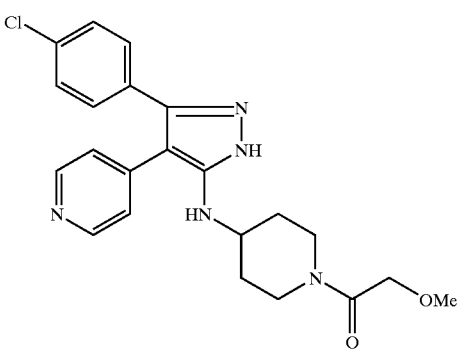

N-[5-(4-chlorophenyl)-4-(4-pyridinyl)-1H-pyrazol-
3-yl]-1-(methoxyacetyl)-4-piperidinamine

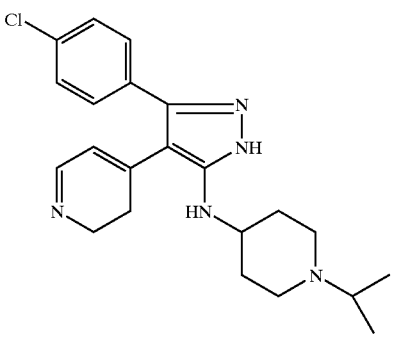

N-[5-(4-chlorophenyl)-4-(4-pyridinyl)-1H-pyrazol-
3-yl]-1-(methylethyl)-4-piperidinamine

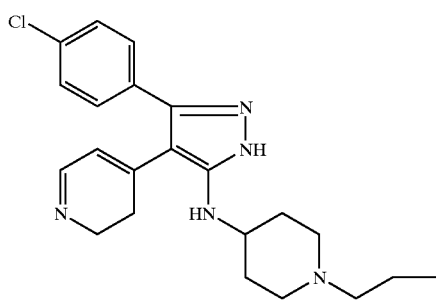
N-[5-(4-chlorophenyl)-4-(4-pyridinyl)-1H-pyrazol-3-yl]-1-propyl-4-piperidinamine
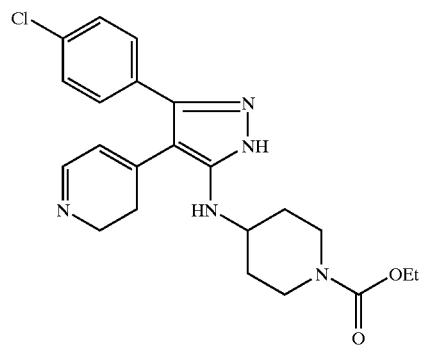
ethyl 4-([5-(4-chlorophenyl)-4-(4-pyridinyl)-1H-pyrazol-3-yl]amino]-1-piperidinecarboxylate
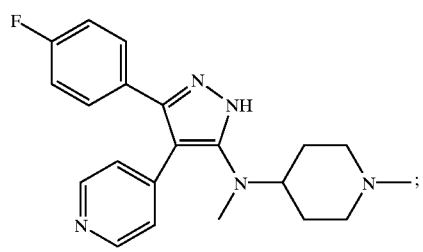
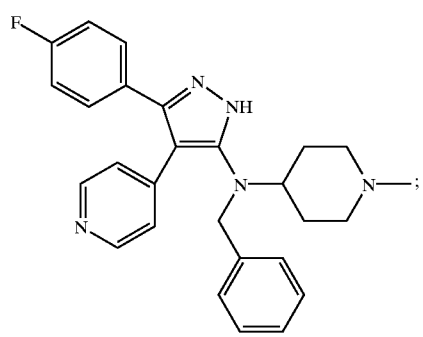
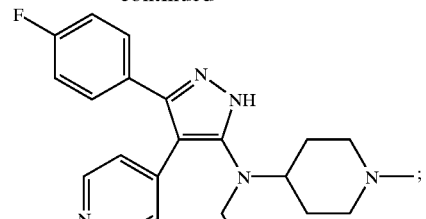
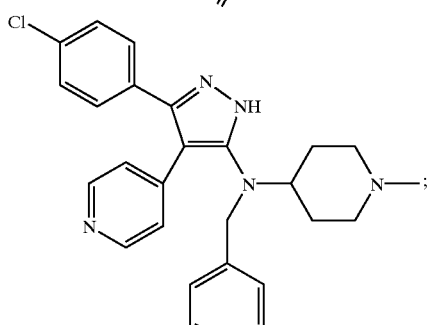
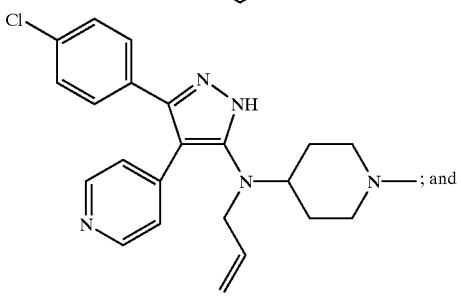
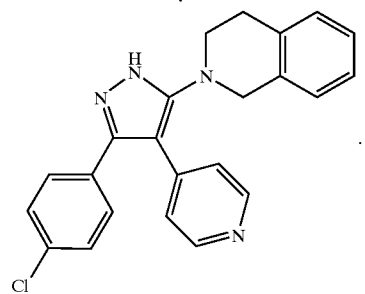
Additional compounds of specific interest include the compounds of Tables 3-3, 3-4, 3-5 and 3-6:
TABLE 3-3
| $R^2$ | $R^5$ | $R^{12}$ |
|---|---|---|
| 4-piperidinyl | methyl | m- or p-fluoro |
| 4-piperidinyl | ethyl | m- or p-fluoro |

TABLE 3-3-continued

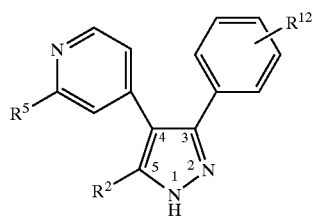

| R² | R⁵ | R¹² |
|---|---|---|
| 4-piperidinyl | amino | m- or p-fluoro |
| 4-piperidinyl | methylamino | m- or p-fluoro |
| 4-piperidinyl | dimethylamino | m- or p-fluoro |
| 4-piperidinyl | ethylamino | m- or p-fluoro |
| 4-piperidinyl | diethylamino | m- or p-fluoro |
| 4-piperidinyl | propylamino | m- or p-fluoro |
| 4-piperidinyl | dipropylamino | m- or p-fluoro |
| 4-piperidinyl | hydroxyethylamino | m- or p-fluoro |
| 4-piperidinyl | 1-hydroxy-1,1-dimethylethyl | m- or p-fluoro |
| 4-piperidinyl | methoxyethylamino | m- or p-fluoro |
| 4-piperidinyl | methyl | m- or p-chloro |
| 4-piperidinyl | ethyl | m- or p-chloro |
| 4-piperidinyl | amino | m- or p-chloro |
| 4-piperidinyl | methylamino | m- or p-chloro |
| 4-piperidinyl | dimethylamino | m- or p-chloro |
| 4-piperidinyl | ethylamino | m- or p-chloro |
| 4-piperidinyl | diethylamino | m- or p-chloro |
| 4-piperidinyl | propylamino | m- or p-chloro |
| 4-piperidinyl | dipropylamino | m- or p-chloro |
| 4-piperidinyl | hydroxyethylamino | m- or p-chloro |
| 4-piperidinyl | 1-hydroxy-1,1-dimethylethyl | m- or p-chloro |
| 4-piperidinyl | methoxyethylamino | m- or p-chloro |
| 4-piperidinyl | methyl | m- or p-methyl |
| 4-piperidinyl | ethyl | m- or p-methyl |
| 4-piperidinyl | amino | m- or p-methyl |
| 4-piperidinyl | methylamino | m- or p-methyl |
| 4-piperidinyl | dimethylamino | m- or p-methyl |
| 4-piperidinyl | ethylamino | m- or p-methyl |
| 4-piperidinyl | diethylamino | m- or p-methyl |
| 4-piperidinyl | propylamino | m- or p-methyl |
| 4-piperidinyl | dipropylamino | m- or p-methyl |
| 4-piperidinyl | hydroxyethylamino | m- or p-methyl |
| 4-piperidinyl | 1-hydroxy-1,1-dimethylethyl | m- or p-methyl |
| 4-piperidinyl | methoxyethylamino | m- or p-methyl |
| 4-piperazinyl | methyl | m- or p-fluoro |
| 4-piperazinyl | ethyl | m- or p-fluoro |
| 4-piperazinyl | amino | m- or p-fluoro |
| 4-piperazinyl | methylamino | m- or p-fluoro |
| 4-piperazinyl | dimethylamino | m- or p-fluoro |
| 4-piperazinyl | ethylamino | m- or p-fluoro |
| 4-piperazinyl | diethylamino | m- or p-fluoro |
| 4-piperazinyl | propylamino | m- or p-fluoro |
| 4-piperazinyl | dipropylamino | m- or p-fluoro |
| 4-piperazinyl | hydroxyethylamino | m- or p-fluoro |
| 4-piperazinyl | 1-hydroxy-1,1-dimethylethyl | m- or p-fluoro |
| 4-piperazinyl | methoxyethylamino | m- or p-fluoro |
| 4-piperazinyl | methyl | m- or p-chloro |
| 4-piperazinyl | ethyl | m- or p-chloro |
| 4-piperazinyl | amino | m- or p-chloro |
| 4-piperazinyl | methylamino | m- or p-chloro |
| 4-piperazinyl | dimethylamino | m- or p-chloro |
| 4-piperazinyl | ethylamino | m- or p-chloro |
| 4-piperazinyl | diethylamino | m- or p-chloro |
| 4-piperazinyl | propylamino | m- or p-chloro |
| 4-piperazinyl | dipropylamino | m- or p-chloro |
| 4-piperazinyl | hydroxyethylamino | m- or p-chloro |
| 4-piperazinyl | 1-hydroxy-1,1-dimethylethyl | m- or p-chloro |
| 4-piperazinyl | methoxyethylamino | m- or p-chloro |
| 4-piperazinyl | methyl | m- or p-methyl |
| 4-piperazinyl | ethyl | m- or p-methyl |
| 4-piperazinyl | amino | m- or p-methyl |
| 4-piperazinyl | methylamino | m- or p-methyl |
| 4-piperazinyl | dimethylamino | m- or p-methyl |
| 4-piperazinyl | ethylamino | m- or p-methyl |
| 4-piperazinyl | diethylamino | m- or p-methyl |
| 4-piperazinyl | propylamino | m- or p-methyl |
| 4-piperazinyl | dipropylamino | m- or p-methyl |
| 4-piperazinyl | hydroxyethylamino | m- or p-methyl |
| 4-piperazinyl | 1-hydroxy-1,1-dimethylethyl | m- or p-methyl |
| 4-piperazinyl | methoxyethylamino | m- or p-methyl |
| aminocyclohexyl | methyl | m- or p-fluoro |
| aminocyclohexyl | ethyl | m- or p-fluoro |
| aminocyclohexyl | amino | m- or p-fluoro |
| aminocyclohexyl | methylamino | m- or p-fluoro |
| aminocyclohexyl | dimethylamino | m- or p-fluoro |
| aminocyclohexyl | ethylamino | m- or p-fluoro |
| aminocyclohexyl | diethylamino | m- or p-fluoro |
| aminocyclohexyl | propylamino | m- or p-fluoro |
| aminocyclohexyl | dipropylamino | m- or p-fluoro |
| aminocyclohexyl | hydroxyethylamino | m- or p-fluoro |
| aminociohexyl | 1-hydroxy-1,1-dimethylethyl | m- or p-fluoro |
| aminocyclohexyl | methoxyethylamino | m- or p-fluoro |
| aminocyclohexyl | methyl | m- or p-chloro |
| aminocyclohexyl | ethyl | m- or p-chloro |
| aminocyclohexyl | amino | m- or p-chloro |
| aminocyclohexyl | methylamino | m- or p-chloro |
| aminocyclohexyl | dimethylamino | m- or p-chloro |
| aminocyclohexyl | ethylamino | m- or p-chloro |
| aminocyclohexyl | diethylamino | m- or p-chloro |
| aminocyclohexyl | propylamino | m- or p-chloro |
| aminocyclohexyl | dipropylamino | m- or p-chloro |
| aminocyclohexyl | hydroxyethylamino | m- or p-chloro |
| aminocyclohexyl | 1-hydroxy-1,1-dimethylethyl | m- or p-chloro |
| aminocyclohexyl | methoxyethylamino | m- or p-chloro |
| aminocyclohexyl | methyl | m- or p-methyl |
| aminocyclohexyl | ethyl | m- or p-methyl |
| aminocyclohexyl | amino | m- or p-methyl |
| aminocyclohexyl | methylamino | m- or p-methyl |
| aminocyclohexyl | dimethylamino | m- or p-methyl |
| aminocyclohexyl | ethylamino | m- or p-methyl |
| aminocyclohexyl | diethylamino | m- or p-methyl |
| aminocyclohexyl | propylamino | m- or p-methyl |
| aminocyclohexyl | dipropylamino | m- or p-methyl |
| aminocyclohexyl | hydroxyethylamino | m- or p-methyl |
| aminocyclohexyl | 1-hydroxy-1,1-dimethylethyl | m- or p-methyl |
| aminocyclohexyl | methoxyethylamino | m- or p-methyl |

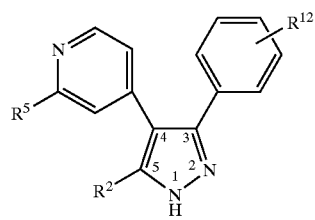

Still other compounds of specific interest include those compounds of Table 3-3 modified as follows:

(1) The 4-piperidinyl moiety is replaced with a 1-, 2- or 3-piperidinyl moiety; and/or (2) The 4-piperidinyl, 3-piperidinyl, 2-piperidinyl or piperazinyl ring is substituted at a nitrogen ring atom with methyl, ethyl, isopropyl, cyclopropyl, propargyl, benzyl, hydroxyethyl, methoxyethyl, or methoxyacetyl; and/or (3) The 1-piperidinyl ring is substituted at a carbon ring atom with methylamino, dimethylamino, ethylamino, diethylamino, isopropylamino, cyclopropylamino, propargylamino, benzylamino, hydroxyethylamino, methoxyethylamino, or methoxyacetylamino; and/or (4) The amino group of the aminocyclohexyl is replaced with methylamino, dimethylamino, ethylamino, diethylamino, isopropylamino, methoxyethylamino, or methoxyacetylamino; and/or (5) A linking group selected from the group consisting of methylene, —S—, —O—, and —NH— separates the piperidinyl, piperazinyl or cyclohexyl moiety from the pyrazole nucleus.

TABLE 3-4

| $R^4$ | $R^3$ | $R^{200}$ | $R^{201}$ |
|---|---|---|---|
| 4-pyridyl | 4-methylphenyl | H | O |
| 4-pyridyl | 4-methylphenyl | $CH_3$ | O |
| 4-pyrimidyl | 4-methylphenyl | H | O |
| 4-pyrimidyl | 4-methylphenyl | $CH_3$ | O |
| 4-pyridyl | 4-methylphenyl | H | S |
| 4-pyridyl | 4-methylphenyl | $CH_3$ | S |
| 4-pyrimidyl | 4-methylphenyl | H | S |
| 4-pyrimidyl | 4-methylphenyl | $CH_3$ | S |
| 4-pyridyl | 3-methylphenyl | H | O |
| 4-pyridyl | 3-methylphenyl | $CH_3$ | O |
| 4-pyrimidyl | 3-methylphenyl | H | O |
| 4-pyrimidyl | 3-methylphenyl | $CH_3$ | O |
| 4-pyridyl | 3-methylphenyl | H | S |
| 4-pyridyl | 3-methylphenyl | $CH_3$ | S |
| 4-pyrimidyl | 3-methylphenyl | H | S |
| 4-pyrimidyl | 3-methylphenyl | $CH_3$ | S |

TABLE 3-5

| $R^4$ | n | X |
|---|---|---|
| 4-chlorophenyl | 1 | S |
| 4-chlorophenyl | 2 | SO |
| 4-chlorophenyl | 2 | $SO_2$ |
| 4-chlorophenyl | 2 | $CH_2$ |
| 4-chlorophenyl | 2 | $CHCH_3$ |
| 4-chlorophenyl | 2 | CHOH |
| 4-chlorophenyl | 1 | $CH_2$ |
| 4-chlorobenzyl | 2 | $NCH_3$ |
| 2-chlorophenyl | 2 | $NCH_3$ |
| 3,4-methylenedioxyphenyl | 2 | $NCH_3$ |
| cyclohexyl | 2 | $NCH_3$ |
| 2-thienyl | 2 | $NCH_3$ |
| 5-chloro-2-thienyl | 2 | $NCH_3$ |
| 4-propynylphenyl | 2 | $NCH_3$ |
| 4-methylsulfoxylphenyl | 2 | $NCH_3$ |
| 4-methylsulfonylphenyl | 2 | $NCH_3$ |
| 2-(1-methyl-5-chloro)indolyl | 2 | $NCH_3$ |

TABLE 3-6

| $R^4$ | $R^3$ | $R^{400}$ |
|---|---|---|
| p-Cl phenyl | 4-pyridyl | —$SO_2CH_3$ |
| p-Cl phenyl | 4-pyridyl | —$CH_2CN$ |
| p-Cl phenyl | 4-pyridyl | —$CH_2$-(1,3-dioxolan-2-yl) |
| p-Cl phenyl | 2-(methylthio)pyrimidin-4-yl | H |

Biological Evaluation p38 Kinase Assay

Cloning of Human P38a

The coding region of the human p38a cDNA was obtained by PCR-amplification from RNA isolated from the human monocyte cell line THP.1. First strand cDNA was synthesized from total RNA as follows: 2 μg of RNA was annealed to 100 ng of random hexamer primers in a 10 μl reaction by heating to 70° C. for 10 minutes followed by 2 minutes on ice. cDNA was then synthesized by adding 1 μl of RNAsin (Promega, Madison Wis.), 2 μl of 50 mM dNTP's, 4 μl of 5×buffer, 2 μl of 100 mM DTT and 1 μl (200 U) of Superscript II™ AMV reverse transcriptase. Random primer, dNTP's and Superscript™ reagents were all purchased from Life-Technologies, Gaithersburg, Mass. The reaction was incubated at 42° C. for 1 hour. Amplification of p38 cDNA was performed by aliquoting 5 μl of the reverse transcriptase reaction into a 100 μl PCR reaction containing the following: 80 μl $dH_2O$, 2 μl 50 mM dNTP's, 1 μl each of forward and reverse primers (50 pmol/μl), 10 μl of 10×buffer and 1 μl Expand™ polymerase (Boehringer Mannheim). The PCR primers incorporated Bam HI sites onto the 5' and 3' end of the amplified fragment, and were purchased from Genosys. The sequences of the forward and reverse primers were 5'-GATCGAGGATTCATGTCTCAGGAGAGGCCCA-3' and 5' GATCGAGGATTCTCAGGACTCCATCTCTTC-3' respectively. The PCR amplification was carried out in a DNA Thermal Cycler (Perkin Elmer) by repeating 30 cycles of 94° C. for 1 minute, 60° C. for 1 minute and 68° C. for 2 minutes. After amplification, excess primers and unincorporated dNTP's were removed from the amplified fragment with a Wizard™ PCR prep (Promega) and digested with Bam HI (New England Biolabs). The Bam HI digested fragment was ligated into BamHI digested PGEX 2T plasmid DNA (PharmaciaBiotech) using T-4 DNA ligase (New England Biolabs) as described by T. Maniatis, *Molecular Cloning: A Laboratory Manual,* 2nd ed. (1989). The ligation reaction was transformed into chemically competent *E. coli* DH10B cells purchased from Life-Technologies following the manufacturer's instructions. Plasmid DNA was isolated from the resulting bacterial colonies using a Promega Wizard™ miniprep kit. Plasmids containing the appropriate Bam HI fragment were sequenced in a DNA Thermal Cycler (Perkin Elmer) with Prism™ (Applied Biosystems Inc.). cDNA clones were identified that coded for both human p38a isoforms (Lee et al. Nature 372, 739). One of the clones which contained the cDNA for p38a-2 (CSBP-2) inserted in the cloning site of PGEX 2T, 3' of the GST coding region was designated pMON 35802. The sequence obtained for this clone is an exact match of the cDNA clone reported by Lee et al. This expression plasmid allows for the production of a GST-p38a fusion protein.

Expression of Human p38a

GST/p38a fusion protein was expressed from the plasmid pMON 35802 in $E.$ $coli$, stain DH10B (Life Technologies, Gibco-BRL). Overnight cultures were grown in Luria Broth (LB) containing 100 mg/ml ampicillin. The next day, 500 ml of fresh LB was inoculated with 10 ml of overnight culture, and grown in a 2 liter flask at 37° C. with constant shaking until the culture reached an absorbance of 0.8 at 600 nm. Expression of the fusion protein was induced by addition of isopropyl b-D-thiogalactosidse (IPTG) to a final concentration of 0.05 mM. The cultures were shaken for three hours at room temperature, and the cells were harvested by centrifugation. The cell pellets were stored frozen until protein purification.

Purification of P38 Kinase-α

All chemicals were from Sigma Chemical Co. unless noted. Twenty grams of $E.$ $coli$ cell pellet collected from five 1 L shake flask fermentations was resuspended in a volume of PBS (140 mM NaCl, 2.7 mM KCl, 10 mM $Na_2HPO_4$, 1.8 mM KH2PO4, pH 7.3) up to 200 ml. The cell suspension was adjusted to 5 mM DTT with 2 M DTT and then split equally into five 50 ml Falcon conical tubes. The cells were sonnicated (Ultrasonics model W375) with a 1 cm probe for 3×1 minutes (pulsed) on ice. Lysed cell material was removed by centrifugation (12,000×g, 15 minutes) and the clarified supernatant applied to glutathione-sepharose resin (Pharmacia).

Glutathione-Sepharose Affinity Chromatography

Twelve ml of a 50% glutathione sepharose-PBS suspension was added to 200 ml clarified supernatant and incubated batchwise for 30 minutes at room temperature. The resin was collected by centrifugation (600×g, 5 min) and washed with 2×150 ml PBS/1% Triton X-100, followed by 4×40 ml PBS. To cleave the p38 kinase from the GST-p38 fusion protein, the glutathione-sepharose resin was resuspended in 6 ml PBS containing 250 units thrombin protease (Pharmacia, specific activity >7500 units/mg) and mixed gently for 4 hours at room temperature. The glutathione-sepharose resin was removed by centrifugation (600×g, 5 min) and washed 2×6 ml with PBS. The PBS wash fractions and digest supernatant containing p38 kinase protein were pooled and adjusted to 0.3 mM PMSF.

Mono Q Anion Exchange Chromatography

The thrombin-cleaved p38 kinase was further purified by FPLC-anion exchange chromatography. Thrombin-cleaved sample was diluted 2-fold with Buffer A (25 mM HEPES, pH 7.5, 25 mM beta-glycerophosphate, 2 mM DTT, 5% glycerol) and injected onto a Mono Q HR 10/10 (Pharmacia) anion exchange column equilibrated with Buffer A. The column was eluted with a 160 ml 0.1 M-0.6 M NaCl/Buffer A gradient (2 ml/minute flowrate). The p38 kinase peak eluting at 200 mM NaCl was collected and concentrated to 3–4 ml with a Filtron 10 concentrator (Filtron Corp.).

Sephacryl S100 Gel Filtration Chromatography

The concentrated Mono Q- p38 kinase purified sample was purified by gel filtration chromatography (Pharmacia HiPrep 26/60 Sephacryl S100 column equilibrated with Buffer B (50 mM HEPES, pH 7.5, 50 mM NaCl, 2 mM DTT, 5% glycerol)). Protein was eluted from the column with Buffer B at a 0.5 ml/minute flowrate and protein was detected by absorbance at 280 nm. Fractions containing p38 kinase (detected by SDS-polyacrylamide gel electrophoresis) were pooled and frozen at −80° C. Typical purified protein yields from 5 L $E.$ $coli$ shake flasks fermentations were 35 mg p38 kinase.

In Vitro Assay

The ability of compounds to inhibit human p38 kinase alpha was evaluated using two in vitro assay methods. In the first method, activated human p38 kinase alpha phosphorylates a biotinylated substrate, PHAS-I (phosphorylated heat and acid stable protein-insulin inducible), in the presence of gamma $^{32}$P-ATP ($^{32}$P-ATP). PHAS-I was biotinylated prior to the assay and provides a means of capturing the substrate which is phosphorylated during the assay. p38 Kinase was activated by MKK6. Compounds were tested in 10 fold serial dilutions over the range of 100 μM to 0.001 μM using 1% DMSO. Each concentration of inhibitor was tested in triplicate.

All reactions were carried out in 96 well polypropylene plates. Each reaction well contained 25 mM HEPES pH 7.5, 10 mM magnesium acetate and 50 μM unlabeled ATP. Activation of p38 was required to achieve sufficient signal in the assay. Biotinylated PHAS-I was used at 1–2 pg per 50 μl reaction volume, with a final concentration of 1.5 μM. Activated human p38 kinase alpha was used at 1 μg per 50 μl reaction volume representing a final concentration of 0.3 μM. Gamma $^{32}$P-ATP was used to follow the phosphorylation of PHAS-I. $^{32}$P-ATP has a specific activity of 3000 Ci/mmol and was used at 1.2 μCi per 50 μl reaction volume. The reaction proceeded either for one hour or overnight at 30° C.

Following incubation, 20 μl of reaction mixture was transferred to a high capacity streptavidin coated filter plate (SAM-streptavidin-matrix, Promega) prewetted with phosphate buffered saline. The transferred reaction mix was allowed to contact the streptavidin membrane of the Promega plate for 1–2 minutes. Following capture of biotinylated PHAS-I with $^{32}$P incorporated, each well was washed to remove unincorporated $^{32}$P-ATP three times with 2M NaCl, three washes of 2M NaCl with 1% phosphoric, three washes of distilled water and finally a single wash of 95% ethanol. Filter plates were air dried and 20 μl of scintillant was added. The plates were sealed and counted. Results are shown in Table 4.

A second assay format was also employed that is based on p38 kinase alpha induced phosphorylation of EGFRP (epidermal growth factor receptor peptide, a 21 mer) in the presence of $^{33}$P-ATP. Compounds were tested in 10 fold serial dilutions over the range of 100 μM to 0.001 μM in 10% DMSO. Each concentration of inhibitor was tested in triplicate. Compounds were evaluated in 50 μl reaction volumes in the presence of 25 mM Hepes pH 7.5, 10 mM magnesium acetate, 4% glycerol, 0.4% bovine serum albumin, 0.4 mM DTT, 50 μM unlabeled ATP, 25 μg EGFRP (200M), and 0.05 uCi gamma $^{33}$P-ATP. Reactions were initiated by addition of 0.09 μg of activated, purified human GST-p38 kinase alpha. Activation was carried out using GST-MKK6 (5:1,p38:MKK6) for one hour at 30° C. in the presence of 50 μM ATP. Following incubation for 60 minutes at room temperature, the reaction was stopped by addition of 150 μl of AG 1×8 resin in 900 mM sodium formate buffer, pH 3.0 (1 volume resin to 2 volumes buffer). The mixture was mixed three times with pipetting and the resin was allowed to settle. A total of 50 μl of clarified solution head volume was transferred from the reaction wells to Microlite-2 plates. 150 μl of Microscint 40 was then added to each well of the Microlite plate, and the plate was sealed, mixed, and counted.

TABLE 4

| Example | p38 kinase IC$_{50}$ (μM) |
|---|---|
| 1 | 4.6 |
| 2 | 1.5 |
| 8 | <0.1 |
| 16 | 3.8 |
| 23 | 1.5 |
| 25 | 2.6 |
| 26 | 0.7 |
| 28 | 0.3 |
| 33 | 2.5 |
| 34 | 8.0 |
| 36 | 12.1 |
| 38 | 0.8 |
| 39 | 1.1 |
| 40 | 1.3 |
| 42 | 0.3 |
| 43 | <0.1 |
| 44 | <0.1 |
| 45 | <0.1 |
| 46 | <0.1 |
| 47 | 3.2 |
| 48 | 1.8 |
| 50 | 2.3 |
| 51 | <0.1 |
| 52 | 0.1 |
| 53 | 0.9 |
| 54 | 0.7 |
| 55 | 6.4 |
| 143 | <0.1 |

TNF Cell Assays

Method of Isolation of Human Peripheral Blood Mononuclear Cells

Human whole blood was collected in Vacutainer tubes containing EDTA as an anticoagulant. A blood sample (7 ml) was carefully layered over 5 ml PMN Cell Isolation Medium (Robbins Scientific) in a 15 ml round bottom centrifuge tube. The sample was centrifuged at 450–500×g for 30–35 minutes in a swing out rotor at room temperature. After centrifugation, the top band of cells were removed and washed 3 times with PBS w/o calcium or magnesium. The cells were centrifuged at 400×g for 10 minutes at room temperature. The cells were resuspended in Macrophage Serum Free Medium (Gibco BRL) at a concentration of 2 million cells/ml.

LPS Stimulation of Human PBMs

PBM cells (0.1 ml, 2 million/ml) were co-incubated with 0.1 ml compound (10–0.41 μM, final concentration) for 1 hour in flat bottom 96 well microtiter plates. Compounds were dissolved in DMSO initially and diluted in TCM for a final concentration of 0.1% DMSO. LPS (Calbiochem, 20 ng/ml, final concentration) was then added at a volume of 0.010 ml. Cultures were incubated overnight at 37° C. Supernatants were then removed and tested by ELISA for TNF-a and IL1-b. Viability was analyzed using MTS. After 0.1 ml supernatant was collected, 0.020 ml MTS was added to remaining 0.1 ml cells. The cells were incubated at 37° C. for 2–4 hours, then the O.D. was measured at 490–650 nM.

Maintenance and Differentiation of the U937 Human Histiocytic Lymphoma Cell Line U937 cells (ATCC) were propagated in RPMI 1640 containing 10% fetal bovine serum, 100 IU/ml penicillin, 100 μg/ml streptomycin, and 2 mM glutamine (Gibco). Fifty million cells in 100 ml media were induced to terminal monocytic differentiation by 24 hour incubation with 20 ng/ml phorbol 12-myristate 13-acetate (Sigma). The cells were washed by centrifugation (200×g for 5 min) and resuspended in 100 ml fresh medium. After 24–48 hours, the cells were harvested, centrifuged, and resuspended in culture medium at 2 million cells/ml.

LPS Stimulation of TNF Production by U937 Cells

U937 cells (0.1 ml, 2 million/ml) were incubated with 0.1 ml compound (0.004–50 μM, final concentration) for 1 hour in 96 well microtiter plates. Compounds were prepared as 10 mM stock solutions in DMSO and diluted in culture medium to yield a final DMSO concentration of 0.1% in the cell assay. LPS (*E coli,* 100 ng/ml final concentration) was then added at a volume of 0.02 ml. After 4 hour incubation at 37° C., the amount of TNF-α released in the culture medium was quantitated by ELISA. Inhibitory potency is expressed as IC50 (μM). Results of these TNF Cell Assays are shown in Table 5.

TNF Inhibition: Human Whole Blood Assay

Human peripheral blood is obtained in heparinized tubes. A 190 μL aliquot of blood is placed in each well of a 96 well u-bottom plate. A compound or control vehicle (phosphate buffered saline with dimethylsulfoxide and ethanol) is added to the blood in 10 μL aliquots for serial dilutions providing final concentrations of 25, 5, 1 and 0.25 μM. The final dimethylsulfoxide and ethanol concentrations are 0.1% and 1.5%, respectively. After one hour of incubation at 37° C., 10 mL of lipopolysaccharide (*Salmonella typhosa*, Sigma) in phosphate buffered saline is added resulting in a final concentration of 10 mg/mL. After four to five hours of incubation at 37° C., the supernatants are harvested and assayed at 1:10 or 1:20 dilutions for human TNF using ELISA.

TABLE 5

| Example | Human PBM Assay IC50 (μM) | U937 Cell Assay IC50 (μM) |
|---|---|---|
| 1 | 0.5 | |
| 2 | 1.6 | 0.578 |
| 4 | 0.1 | 0.222 |
| 5 | | 0.274 |
| 7 | 0.2 | 0.201 |
| 8 | <0.1 | |
| 9 | 0.4 | |
| 10 | 0.7 | 1.687 |
| 12 | 8.5 | |
| 13 | 4.8 | |
| 14 | 1.2 | |
| 17 | 1.1 | |
| 19 | 0.3 | 0.484 |
| 20 | | 1.089 |
| 21 | | 0.077 |
| 22 | 3.2 | |
| 24 | 8.2 | |
| 26 | <0.1 | 0.029 |
| 27 | 2.7 | |
| 28 | 0.1 | |
| 29 | 2.2 | |
| 30 | 2.6 | |
| 31 | 0.8 | 1.053 |
| 32 | | 2.696 |
| 33 | 0.4 | |
| 34 | 0.5 | |
| 35 | 0.7 | |
| 36 | 1.4 | |
| 37 | 1.5 | 0.099 |
| 38 | 0.2 | 0.208 |
| 39 | 0.7 | 0.244 |
| 40 | 0.4 | |

TABLE 5-continued

| Example | Human PBM Assay IC50 (μM) | U937 Cell Assay IC50 ((μM) |
|---|---|---|
| 41 | 1.0 | |
| 42 | 0.7 | |
| 43 | <0.1 | 0.243 |
| 44 | 0.4 | 0.477 |
| 45 | <0.1 | 0.04 |
| 46 | | 0.329 |
| 47 | | 2.359 |
| 48 | 2.2 | 0.522 |
| 49 | 6.8 | |
| 50 | 0.9 | |
| 51 | | 0.074 |
| 54 | 0.2 | 0.13 |
| 55 | <0.1 | 0.228 |
| 143 | | 0.301 |

Rat Assay

The efficacy of the novel compounds in blocking the production of TNF also was evaluated using a model based on rats challenged with LPS. Male Harlen Lewis rats [Sprague Dawley Co.] were used in this model. Each rat weighed approximately 300 g and was fasted overnight prior to testing. Compound administration was typically by oral gavage (although intraperitoneal, subcutaneous and intravenous administration were also used in a few instances) 1 to 24 hours prior to the LPS challenge. Rats were administered 30 μg/kg LPS [*Salmonella typhosa*, Sigma Co.] intravenously via the tail vein. Blood was collected via heart puncture 1 hour after the LPS challenge. Serum samples were stored at −20° C. until quantitative analysis of TNF-α by Enzyme Linked-Immuno-Sorbent Assay ("ELISA") [Biosource]. Additional details of the assay are set forth in Perretti, M., et al., *Br. J. Pharmacol.* (1993), 110, 868–874, which is incorporated by reference in this application.

Mouse Assay

Mouse Model Of LPS-Induced TNF Alpha Production

TNF alpha was induced in 10–12 week old BALB/c female mice by tail vein injection with 100 ng lipopolysaccharide (from *S. Typhosa*) in 0.2 ml saline. One hour later mice were bled from the retroorbital sinus and TNF concentrations in serum from clotted blood were quantified by ELISA. Typically, peak levels of serum TNF ranged from 2–6 ng/ml one hour after LPS injection.

The compounds tested were administered to fasted mice by oral gavage as a suspension in 0.2 ml of 0.5% methylcellulose and 0.025% Tween 20 in water at 1 hour or 6 hours prior to LPS injection. The 1 hour protocol allowed evaluation of compound potency at Cmax plasma levels whereas the 6 hour protocol allowed estimation of compound duration of action. Efficacy was determined at each time point as percent inhibition of serum TNF levels relative to LPS injected mice that received vehicle only.

Additional results obtained using the above-described assays are set forth in Table 6 below. p38 assay and U937 cell assay results are expressed as IC$_{50}$ (μm). Mouse-LPS assay results are expressed as percent inhibition.

TABLE 6

| Example | p38[1] | p38[2] | U937 | mLPS 8 h | mLPS 6 h dose | mLPS 1 h, 30 mpk |
|---|---|---|---|---|---|---|
| A-212 | 0.49 | 0.74 | 0.0967 | 20 | 10 | 93 |
| A-208 | 0.104 | 0.049 | 0.1896 | 98 | 30 | 97 |
| A-227 | | 0.06 | | | | 96 |
| A-228 | 0.76 | 0.339 | 0.4173 | 32 | 30 | 92 |
| A-229 | | 1.4 | 0.4622 | 76 | | 91 |
| A-230 | 0.42 | 0.178 | | | | 96 |
| A-231 | | 0.174 | 0.3225 | 86 | 30 | 94 |
| A-232 | | 0.048 | | | | 96 |
| A-233 | | 0.044 | | | | 53 |
| A-234 | | 0.103 | | | | |
| A-235 | | 0.104 | | | | 56 |
| A-236 | | 0.237 | | | | 94 |
| A-237 | | 0.093 | 0.087 | | | 60 |
| A-238 | | 0.177 | 0.4016 | | | |
| A-239 | | 0.034 | | 51 | 30 | 87 |
| A-240 | | 0.961 | | 78 | 30 | 85 |
| A-241 | | 0.338 | | 79 | 30 | 87 |
| A-242 | | 0.047 | | 95 | 30 | 87 |
| A-243 | | 0.729 | | | | 82 |
| A-244 | | 0.099 | | | | |
| A-245 | | <0.001 | 0.0337 | | | 65 |
| A-246 | 0.403 | 0.592 | 0.4952 | | | |
| A-247 | | <0.01 | 0.166 | | | |
| A-249 | | 0.432 | | 73 | 30 | 86 |
| A-250 | | 2.873 | | | | |
| A-251 | | 0.637 | | 32 | | 87 |
| A-252 | | 0.774 | 1.197 | 48 | 30 | 75 |
| A-253 | | <0.001 | 0.0044 | | | 61 |
| A-254 | | 0.081 | 0.1411 | | | |
| A-215 | | 2.34 | 0.2976 | 38 | 30 | 80 |
| A-256 | | 0.813 | 0.4562 | | | |
| A-257 | 1.081 | <.01 | 0.5167 | | | |
| A-213 | | 0.22 | | | | 57 |
| A-258 | | 0.48 | 1.2083 | | | 68 |
| A-259 | | 0.17 | 0.7574 | | | 62 |
| A-210 | 0.16 | | 0.1983 | 85 | 30 | 93 |
| A-260 | | 0.23 | 1.2821 | 47 | 30 | 79 |
| A-214 | | 0.06 | 1.4006 | | | 70 |
| A-261 | | 0.008 | 0.2542 | 48 | 30 | 92 |
| A-216 | | 0.018 | 1.8287 | 27 | 30 | 91 |
| A-262 | | <0.1 | 0.3267 | | | 45 |
| A-263 | <0.01 | <0.1 | 0.5434 | | | 49 |
| A-264 | | | 0.2594 | | | 61 |
| A-265 | | <0.1 | 0.6016 | | | 32 |
| A-266 | | | 0.5393 | | | 0 |
| A-267 | | 0.43 | 2.6681 | | | 80 |
| A-268 | | <0.01 | 0.0074 | | | 11 |
| A-217 | 0.697 | | 0.3486 | | | 9 |
| A-269 | | | >10 uM | | | 51 |
| A-270 | | 0.015 | 0.3466 | | | 53 |
| A-271 | | 0.216 | 4.2144 | | | 68 |
| A-272 | 0.073 | | 0.583 | | | −8 |
| A-273 | 6.98 | | >10 | | | 43 |
| A-274 | <0.1 | | 0.92 | 21 | 30 | |
| A-275 | 10.142 | | >10 | | | |
| A-276 | 0.176 | | 0.45 | −24 | 30 | |
| A-277 | 0.026 | | | 33 | 30 | |
| A-278 | 0.285 | | 2.3 | 62 | 30 | |
| A-279 | 0.005 | | 0.7 | 64 | 30 | |
| A-280 | 0.134 | | | 15 | 30 | |
| A-281 | 0.053 | | | 22 | 30 | |
| A-218 | 0.044 | | | 18 | 30 | |
| A-282 | 0.045 | | 0.0973 | 30 | 30 | |
| A-283 | <0.1 | | 0.7998 | −20 | 30 | |
| A-284 | 0.98 | | 0.5088 | −1 | | |
| A-285 | <0.1 | | 0.1795 | 11 | 30 | |
| A-286 | 0.057 | | 0.09 | 29 | 30 | |
| A-287 | 0.041 | | 0.27 | −24 | 30 | |
| A-288 | 0.017 | | 0.3 | 40 | 30 | |
| A-289 | <0.1 | | 0.14 | 44 | 30 | |
| A-290 | | | 6.0191 | 4 | 30 | |
| A-291 | 0.388 | | 1.1309 | 36 | 30 | |
| A-292 | 1.15 | | >10 | | | |
| A-293 | 0.73 | | | | | |
| A-294 | 0.015 | | 0.5 | 61 | 30 | |

TABLE 6-continued

| Example | p38[1] | p38[2] | U937 | mLPS 8 h | mLPS 6 h dose | mLPS 1 h, 30 mpk |
|---|---|---|---|---|---|---|
| A-295 | 7.66 | | >10 | | 94 | 30 |
| A-296 | 26 | | | | | |
| A-297 | 0.52 | | | 0.17 | 89 | 30 |

[1]p38α in vitro assay results based on PHAS-I assay procedure
[2]p38α in vitro assay results based on EGFRP assay procedure Induction And Assessment Of Collagen-Induced Arthritis In Mice Arthritis was induced in mice according to the procedure set forth in J. M. Stuart, Collagen Autoimmune Arthritis, *Annual Rev. Immunol.* 2:199 (1984), which is incorporated herein by reference. Specifically, arthritis was induced in 8–12 week old DBA/1 male mice by injection of 50 μg of chick type II collagen (CII) (provided by Dr. Marie Griffiths, Univ. of Utah, Salt Lake City, Utah) in complete Freund's adjuvant (Sigma) on day 0 at the base of the tail. Injection volume was 100 μl. Animals were boosted on day 21 with 50 μg of CII in incomplete Freund's adjuvant (100 μl volume). Animals were evaluated several times each week for signs of arthritis. Any animal with paw redness or swelling was counted as arthritic. Scoring of arthritic paws was conducted in accordance with the procedure set forth in Wooley et al., Genetic Control of Type II Collagen Induced Arthritis in Mice: Factors Influencing Disease Suspectibility and Evidence for Multiple MHC Associated Gene Control., *Trans. Proc.,* 15:180 (1983). Scoring of severity was carried out using a score of 1–3 for each paw (maximal score of 12/mouse). Animals displaying any redness or swelling of digits or the paw were scored as 1. Gross swelling of the whole paw or deformity was scored as 2. Ankylosis of joints was scored as 3. Animals were evaluated for 8 weeks. 8–10 animals per group were used.

Preparation And Administration Of Compounds

The compounds tested on mice having collagen-induced arthritis were prepared as a suspension in 0.5% methylcelluose (Sigma, St. Louis, Mo.), 0.025% Tween 20 (Sigma). The compound suspensions were administered by oral gavage in a volume of 0.1 ml b.i.d. Administration began on day 20 post collagen injection and continued daily until final evaluation on day 56. Scoring of arthritic paws was conducted as set forth above. Assay results are set forth in Table 7.

TABLE 7

| Compound | % Inhibition of Arthritis |
|---|---|
| A-210 | 58.5 @ 15 mpk |
| A-172 | 49.3 @ 100 mpk |
| A-189 | 51.6 @ 30 mpk |
| A-208 | 97.5 @ 60 mpk |
| A-208 | 75.0 @ 60 mpk |

Additional results for selected compounds obtained using the above-described assays are set forth in Tables 8, 9 and 10 below:

TABLE 8

| Example | Rat LPS Assay % Inhibition (Dose in mg/kg) | TNF Inhibition- Human Whole Blood Assay (μM) | p38α Kinase Assay $IC_{50}$ in μM (% DMSO) |
|---|---|---|---|
| A-313, Step 1 | | | 1.34 (1) |
| A-313, Step 3 | 96.0 (20.0) | 0.12 | 0.036 (1) |
| | | | 0.37 (10) |
| A-314, Step 1 | | | 0.85 (1) |
| | | | 0.37 (10) |
| A-314, Step 2 | 0 (1.0) | 0.47 | 0.032 (10) |
| | 53.0 (5.0) | | |
| | 85.0 (20.0) | | |
| A-315 | | 1.75 | 0.049 (10) |
| A-317 | 58.0 (3.0) | 0.45 | 0.07 (10) |
| | 10.0 (3.0) | | 0.11 (10) |
| | 69.0 (10.0) | | |
| A-318 | 54.0 (3.0) | 0.167 | 0.29 (1) |
| | | | 0.58 (10) |
| | | | 0.37 (10) |
| | | | 0.6 (10) |
| A-319 | 62.0 (3.0) | >25.0 | 6.06 (1) |
| | | | 0.13 (10) |
| A-320 | 1.0 (3.0) | | 0.27 (1) |
| | | | 0.05 (10) |
| | | | 0.15 (10) |
| A-321 (dihydrate) | | >25.0 | 0.77 (1) |
| A-321 (monosodium salt dihydrate) | 14.0 (3.0) | | |
| A-322 | 51.5 (3.0) | 4.2 | 0.15 (10) |
| | | | 0.25 (10) |
| A-323 | 40.0 (30.0) | | 0.39 (10) |
| | 54.0 (30.0) | | |
| A-324 | 44.0 (3.0) | | 0.08 (10) |
| A-325 | 25.0 (3.0) | 0.057 | 0.021 (1) |
| | 11.0 (30.0) | | <0.1 (10) |
| A-326 | 0 (10.0) | >25.0 | 0.97 (10) |
| A-327 | 83.0 (20.0) | 0.18 | 0.15 (10) |
| A-328 | | | 0.012 (1) |
| A-331 | 13.0 (20.0) | | >100 (1) |
| | | | 0.64 (10) |
| A-332 | 33.0 (1.0) | 0.45 | 0.04 (1) |
| | 26.0 (3.0) | | 0.04 (10) |
| | 25.0 (5.0) | | 0.015 (10) |
| | −85.0 (10.0) | | <0.1 (10) |
| A-333 | 69.0 (5.0) | 0.585 | 0.052 (10) |
| A-334 | 95.0 (20.0) | 0.22 | 0.07 (10) |
| | 57.0 (5.0) | | |
| | 36.0 (1.0) | | |
| A-335 | | >25.0 | 89.9 (10) |
| A-336 | | | 1.16 (10) |
| A-337 | | >25.0 | 1.35 (10) |
| A-338 | | 0.059 | 0.018 (10) |
| A-339 | | 0.056 | 0.052 (10) |
| A-342 | 98.0 (20.0) | 0.31 | 0.012 (10) |
| A-343 | 96.0 (20.0) | | 0.016 (10) |

TABLE 9

| Example | Rat LPS Assay % Inhibition (Dose in mg/kg) | TNF Inhibition- Human Whole Blood Assay (μM) | p38α Kinase Assay $IC_{50}$ in μM (10% DMS0) |
|---|---|---|---|
| A-350 | 65 (20) | | |
| A-351 | 0 (20) | 0.49 | 0.27 |
| A-352 | 36 (20) | 9.8 | 0.13 |
| A-353 | 49 (20) | 5.3 | 0.037 |
| A-354 | 0 (20) | 25 | 0.22 |
| A-355 | 0 (20) | 0.095 | 0.05 |
| A-356 | 73 (20) | 5.3 | <0.01 |

TABLE 9-continued

| Example | Rat LPS Assay % Inhibition (Dose in mg/kg) | TNF Inhibition- Human Whole Blood Assay ($\mu$M) | p38$\alpha$ Kinase Assay IC$_{50}$ in $\mu$M (10% DMS0) |
|---|---|---|---|
| A-357 | 74 (20) | 0.25 | 0.12 |
| A-358 | 71 (20) | 4 | 0.23 |
| A-359 | 70 (20) | 1 | 0.3 |
| A-360 | 95 (20) | 0.5 | 0.06 |
|  | 14 (5) |  |  |
|  | 0 (1) |  |  |
| A-361 | 9 (20) | 1 |  |
| A-362 | 0 (20) | 5.5 | 0.69 |
| A-363 | 6 (20) | 25 | 1.5 |
| A-364 | 79 (20) | 0.255 | 0.49 |
| A-365 | 95 (20) | 0.057 | 0.032 |
|  | 50 (5) |  |  |
|  | 12 (1) |  |  |
| A-366 | 92 (20) | 0.29 | 0.041 |
|  | DR: 6 (1) |  | 0.06 |
|  | 45 (5) |  | 0.04 |
|  | 97 (20) |  |  |
| A-368 | 88 (20) | 0.66 | 0.042 |
|  | DR: 28 (1) |  |  |
|  | 41 (5) |  |  |
|  | 97 (20) |  |  |
| A-369 | 94 (20) | 0.84 | 0.019 |
|  | 52 (5) |  | 0.011 |
|  |  |  | 0.0027 |
| A-370 | 90 (20) | 1.92 | 0.16 |
|  | 46 (5) |  |  |
| A-371 | 52 (20) | 25 | 7.9 |
| A-372 | 56 (20) | 21 | 0.53 |
| A-374 | 88 (20) | 0.31 | 0.38 |
|  | 0 (5) |  |  |
|  | 3 (1) |  |  |
| A-375 | 43 (20) | 28% | 2.3 |
| A-376 | 24 (20) | 1 | 0.032 |
| A-377 | 84 (20) | 0.67 | 0.004 |
|  | DR: 32 (1) |  | 0.0019 |
|  | 67 (5) |  |  |
|  | 96 (20) |  |  |
| A-378 | 73 (10) | 49% | 6.2 |
| A-379 | 61 (10) | 44% | 0.19 |
| A-380 | 85 (30) | 32% | 0.85 |
|  | 62 (10) |  |  |
|  | 33 (3) |  |  |
| A-385 |  |  | 0.18 |
|  |  |  | 1.25 |
| A-386 | 91 (20) | 0.16 | 0.016 |
| A-387 | 83 (20) | 0.11 | 0.005 |
| A-388 | 97 (20) | 0.34 | 0.21 |
|  | 67 (5) |  |  |

TABLE 10

| Example | Rat LPS Assay % Inhibition (Dose in mg/kg @ 4.0 hours) | TNF Inhibition- Human Whole Blood Assay ($\mu$M) | p38$\alpha$ Kinase Assay IC$_{50}$ ($\mu$M) (10% DMS0; @ 1.0 hour) |
|---|---|---|---|
| A-389, Step 4 | 55.0 (5.0) 94.0 (20.0) |  | 0.16 |
| A-389, Step 1 |  |  | 1.72 |
| A-390 |  | >25.0 | 15.1 |
| A-391 | 53.0 (20.0) | >25.0 | 4.83 |
| A-392 |  |  | 29.7 |
| A-393 |  |  | 2.32 |
| A-394 |  |  | 9.11 |
| A-395 |  |  | >100 |
| A-397 |  |  | 30.0 |
| A-398 |  | >25.0 | 45.6 |
| A-399 |  |  | 22.9 |
| A-400 |  | >25.0 | 4.77 |
| A-401 |  |  | 21.2 |
| A-402 |  |  | 28.9 |
| A-403 |  | >25.0 | 4.89 |
| A-404 |  | >25.0 | 4.13 |
| A-405 |  | >25.0 | 4.85 |
| A-406 |  | >25.0 | 7.24 |
| A-407 | 21.0 (5.0) 82.0 (20.0) | 3.86 | 0.18 |
| A-408 | 20.0 (5.0) 49.0 (20.0) | 11.7 | 5.59 |
| A-409 | 41.0 (5.0) 89.0 (20.0) | 5.27 | 0.21 |
| A-410 | 11.0 (5.0) 0 (20.0) |  | 0.21 |
| A-411 | 40.0 (5.0) 0 (20.0) |  | 3.37 |
| A-412 | 0 (5.0) 0 (20.0) |  | 2.15 |
| A-413 | 45.0 (5.0) 85.0 (20.0) | 6.51 | 0.91 |
| A-414 | 3.0 (5.0) 14.0 (20.0) | 11.2 | 9.51 |
| A-415 | 17.0 (5.0) 84.0 (84.0) |  | 0.51 |
| A-416 |  | 5.07 | 0.041 |
| A-417 | 40.0 (5.0) 70.0 (20.0) | 12.0 | 0.19 |
| A-418 |  |  | 0.12 |
| A-419 | 24.0 (5.0) 58.0 (10.0) |  | 1.31 |
| A-420 | 47.0 (5.0) 91.0 (20.0) |  | 0.32 |
| A-427 | 56.0 (5.0) 77.0 (20.0) | 24.1 | 0.19 |
| A-428 |  | 0.68 | 0.4 |
| A-429 |  |  | 56.3 |
| A-430 |  |  | >100 |
| A-434 |  |  | 5.84 |
| A-435 | 10.0 (1.0) 0 (5.0) 14.0 (20.0) | >25.0 | 0.35 |
| A-436 |  | 4.61 | 2.81 |
| A-437 |  | >25.0 | 7.76 |
| A-438 | 49.0 (20.0) | >25.0 | 0.56 |
| A-439 | 58.0 (5.0) 93.0 (20.0) | 5.63 | 0.15 |
| A-440 |  |  |  |
| A-441 | 14.0 (5.0) 62.0 (20.0) | >25.0 | 1.21 |
| A-442 | 51.0 (1.0) 56.0 (5.0) 92.0 (20.0) | 0.16 | 0.022 |
| A-443 |  | 4.89 | 0.47 |
| A-444 |  |  | 6.99 |
| A-445 |  | >25.0 | 1.08 |
| A-446 |  | 3.38 | 0.9 |
| A-447 |  | >25.0 | 0.77 |
| A-448 | 73.0 (5.0) 97.0 (20.0) | 0.12 | 0.084 |
| A-449 |  |  | 59.0 |
| A-450 |  |  | >100 |
| A-451 |  | 15.0 | 0.078 |
| A-452 |  | 0.24 | 2.87 |
| A-454 |  |  | 8.41 |
| A-453 |  |  | 10.2 |
| A-455 |  |  | 12.9 |
| A-456 | 36.0 (1.0) 48.0 (5.0) 53.0 (20.0) | 0.98 | 0.12 |
| A-457 |  | >25.0 | 0.4 |

TABLE 10-continued

| Example | Rat LPS Assay % Inhibition (Dose in mg/kg @ 4.0 hours) | TNF Inhibition- Human Whole Blood Assay ($\mu$M) | p38$\alpha$ Kinase Assay IC$_{50}$ ($\mu$M) (10% DMSO; @ 1.0 hour) |
|---|---|---|---|
| A-458 | | >25.0 | 8.7 |
| A-459 | 0 (1.0) 54.0 (5.0) 80.0 (20.0) | 0.26 | 0.027 |
| A-459 (salt) | | 0.28 | 0.1 |
| A-460 | | 8.91 | 1.84 |
| A-461 | | | 30.6 |
| A-462 | | >25.0 | 1.66 |
| A-463 | | >25.0 | 1.66 |
| A-464 | | | >100 |
| A-465 | | | >100 |
| A-466 | | | 20.1 |
| A-467 | | | 21.4 |
| A-468 | 46.0 (1.0) 50.0 (5.0) 94.0 (20.0) | | 0.3 |
| A-469 | 51.0 (5.0) 68.0 (20.0) | 7.17 | 0.095 |
| A-470 | | | 10.4 |
| A-471 | | | 4.92 |
| A-472 | | >25.0 | 0.39 |
| A-473 | 58.0 (20.0) | 0.56 | 0.17 |
| A-474 | 59.0 (20.0) | 1.47 | 0.11 |
| A-475 | | 5.11 | 0.28 |
| A-476 | 35.0 (20.0) | 0.97 | 1.01 |
| A-477 | | | 0.34 |
| A-478 | | 0.49 | 0.18 |
| A-479 | | 2.97 | 0.072 |
| A-480 | | 0.16 | 0.11 |
| A-481 | | >25.0 | 0.2 |
| A-482 | 15.0 (20.0) | 0.69 | 1.62 |
| A-483 | | 0.51 | 0.3 |

Also embraced within this invention is a class of pharmaceutical compositions comprising the active compounds of this invention in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The active compounds and composition may, for example, be administered orally, intravascularly (IV), intraperitoneally, subcutaneously, intramuscularly (IM) or topically. For oral administration, the pharmaceutical composition may be in the form of, for example, a tablet, hard or soft capsule, lozenges, dispensable powders, suspension or liquid. The pharmaceutical composition is preferably made in the form of a dosage unit containing a particular amount of the active ingredient. Examples of such dosage units are tablets or capsules. The active ingredient may also be administered by injection (IV, IM, subcutaneous or jet) as a composition wherein, for example, saline, dextrose, or water may be used as a suitable carrier. The pH of the composition may be adjusted, if necessary, with suitable acid, base, or buffer. Suitable bulking, dispersing, wetting or suspending agents, including mannitol and PEG 400, may also be included in the composition. A suitable parenteral composition can also include a compound formulated as a sterile solid substance, including lyophilized powder, in injection vials. Aqueous solution can be added to dissolve the compound prior to injection. The amount of therapeutically active compounds that are administered and the dosage regimen for treating a disease condition with the compounds and/or compositions of this invention depends on a variety of factors, including the age, weight, sex and medical condition of the subject, the severity of the inflammation or inflammation related disorder, the route and frequency of administration, and the particular compound employed, and thus may vary widely. The pharmaceutical compositions may contain active ingredients in the range of about 0.1 to 1000 mg, preferably in the range of about 7.0 to 350 mg. A daily dose of about 0.01 to 100 mg/kg body weight, preferably between about 0.1 and about 50 mg/kg body weight and most preferably between about 0.5 to 30 mg/kg body weight, may be appropriate. The daily dose can be administered in one to four doses per day. In the case of skin conditions, it may be preferable to apply a topical preparation of compounds of this invention to the affected area two to four times a day. For disorders of the eye or other external tissues, e.g., mouth and skin, the formulations are preferably applied as a topical gel, spray, ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used. Formulations suitable for topical administration to the eye also include eye drops wherein the active ingredients are dissolved or suspended in suitable carrier, especially an aqueous solvent for the active ingredients. The anti-inflammatory active ingredients are preferably present in such formulations in a concentration of 0.5 to 20%, advantageously 0.5 to 10% and particularly about 1.5% w/w. For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

All patent documents listed herein are incorporated by reference.

Although this invention has been described with respect to specific embodiments, the details of these embodiments are not to be construed as limitations.

Description of Parallel Array Synthesis Methodology Utilized to Prepare Compounds of Examples B-i, B-ii, and B-iii Scheme B-1 describes the parallel array reaction blocks that were utilized to prepare compounds of Examples B-0001 through B-1574, and by analogy could also be used to prepare compounds of Examples B-1575 through B-2269. Parallel reactions were performed in multi-chamber reaction blocks. A typical reaction block is capable of performing 48 parallel reactions, wherein a unique compound is optionally prepared in each reaction vessel B1. Each reaction vessel B1 is made of either polypropylene or pyrex glass and contains a frit B2 toward the base of the vessel. Each reaction vessel is connected to the reaction block valve assembly plate B3 via leur-lock attachment or through a threaded connection. Each vessel valve B4 is either opened or closed by controlling the leur-lock position or by the opening or closing of levers B5 within a valve assembly plate row. Optionally, solutions can be either drained or maintained above the vessel frits by leaving the valves in the opened position and controlling the back pressure beneath the valve assembly plate by control of inert gas flow through the inert gas inlet valve B6. The parallel reactions that are performed in these reaction blocks are allowed to progress by incubation in a jacketed, temperature controlled shaking station. Temperature control of the reaction chambers is effected by passing a heat-transfer liquid through jacketed aluminum plates that make contact with the reaction block mantle B7. Mixing is effected at the shaking station by either vertical orbital shaking of the up-right reaction block or by lateral shaking of the reaction block tilted on its side.

Functionalized resins are optionally added to each reaction vessel B1 during the course of reaction or at the conclusion of the reaction. These functionalized resins enable the rapid purification of each reaction vessel product. Vacuum filtration of the reaction block apparatus by opening of the vacuum valve B8 allows purified products to be separated from resin-sequestered non-product species. Valve B8 is located on the bottom reaction block chamber B10 which houses the quadrant collection vial racks B11. The desired products are obtained as filtrates in unique collection vials B9. Removal of solvent from these collection vials affords desired products.

Scheme B-1

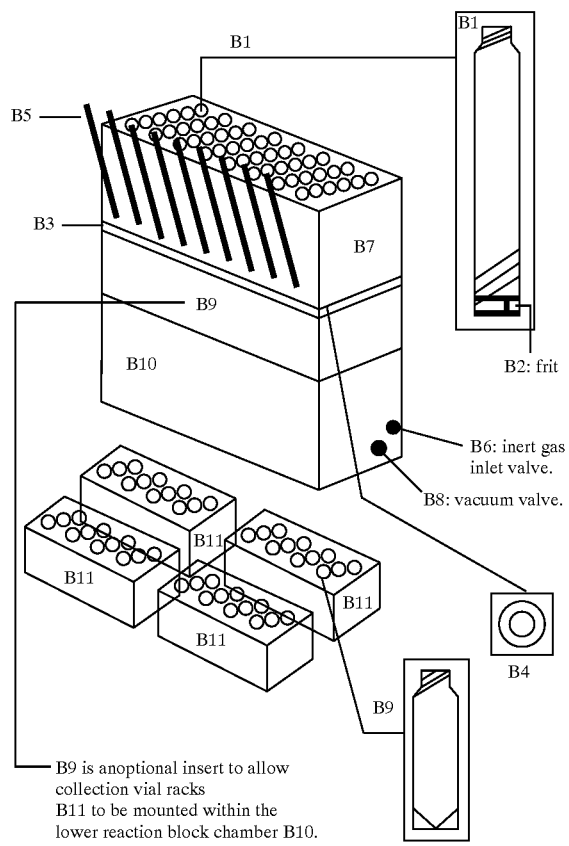

B9 is an optional insert to allow collection vial racks B11 to be mounted within the lower reaction block chamber B10.

Scheme B-2 illustrates the various utilizations of functionalized resins to purify reaction vessel products B22 prior to filtration from the fritted vessels B1 into collection vials B9. Said functionalized resins perform as 1) resin-bound reagents B12, which give rise to resin-bound reagent byproducts B13; 2) sequestrants B14 or B15 of excess solution-phase reactants B16 or B17, respectively. Solution-phase reactants B16 and B17 contain inherent reactive functionality $rf_1$ and $rf_2$ which enable their chemoselective sequestration by the complementary reactive functionality -$Crf_1$ and -$Crf_2$ attached to resins B14 and B15; 3) sequestrants B18 of solution-phase byproducts B19. Byproduct B19 contains molecular recognition functionality -$mr_2$ which enables its chemoselective sequestration by the complementary functionality -$Cmr_2$ attached to resin B18; 4) reaction-quenching resins B20 which give rise to quenched resins B21. Resin B20 contains functionality -Q which mediates reaction quenching (for instance, proton transfer) of product B22 to form a desired isolable form of product B22. Upon performing reaction quench, the resin B20 is converted to resin B21 wherein -q represents the spent functionality on resin B21 ; 5) sequestrants B23 of chemically-tagged reagents B24 and their corresponding reagent byproducts B25. The soluble reagent B24 contains a bifunctional chemical group, -tag, which is inert to the reaction conditions but is used to enable the post-reaction tary functionality attached to resin B18. Similar use of the bifunctional sequestration-enabling-reagent B29 transforms B19 into the more readily sequestrable species B30. The imparted molecular recognition functionality, mr, present in B30 is readily sequestered by the complementary functionality, Cmr, IS attached to resin B31. In some reactions, multiple sequestration resins are utilized simultaneously to perform reaction purifications. Even resins containing incompatible (mutually reactive) functional groups can be used simultaneously because these resins scavenge complementary functionalized solution phase reactants, reagents, or byproducts from solution phase faster than resin cross-neutralization. Similarly, resins containing mutually reactive or neutralizing reaction-quenching functionality are able to quench solution phase reactants, products, or byproducts faster than resin cross-neutralization.

Scheme B-2

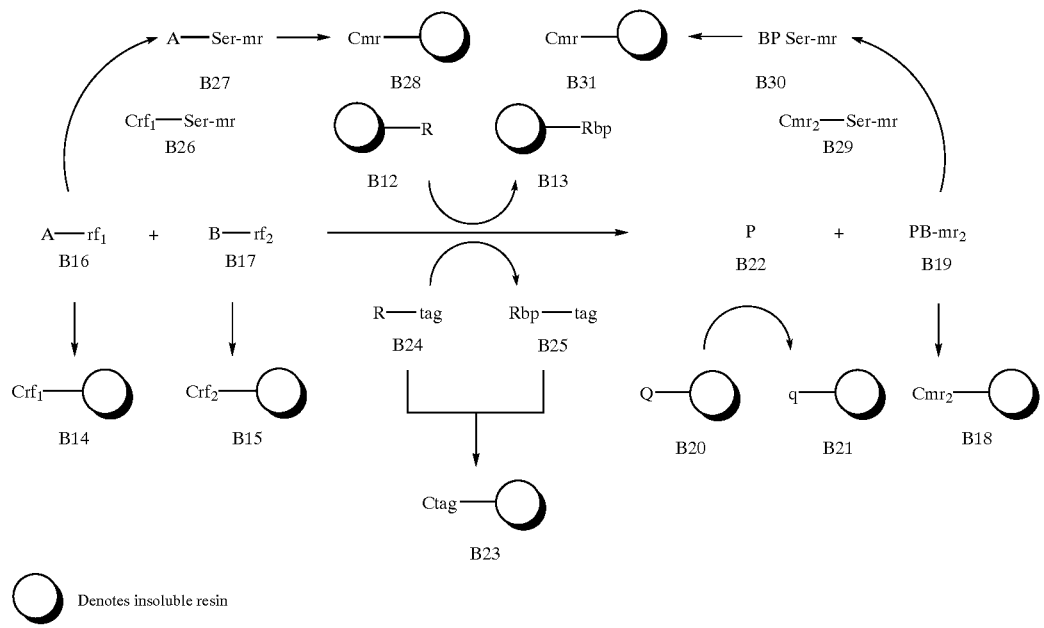

sequestration of B24 by the complementary functionality -Ctag attached to resin B23. Additionally, the soluble reagent byproduct B25, formed during the course of reaction, contains the same chemical function -tag that also enables its sequestration by resin B23. Additionally, some reactants B16, particularly sterically-hindered reactants and/or electron deficient nucleophiles, contain poorly sequestrable functionality (rf1 in this case is a poorly sequestable functionality). These poorly sequestable reactants B16 can be transformed in situ to more robustly sequestrable species B27 through their reaction with sequestration-enabling-reagents B26. B26 contain highly reactive, complementary functionality $Crf_1$ which reacts with B16 to form B27 in situ. The bifunctional molecular recognition functionality, mr, contained within B26 is also present on the in situ derivatized B27. Both B26 and B27 are sequestered by the complementary molecular recognition functionality attached to resin B28. By analogy, some reactions contain poorly sequestable byproducts B19, wherein the molecular recognition functionality $mr_2$ in this case is not able to mediate the direct sequestration of B19 by the complemen- Scheme B3 describes the modular robotics laboratory environment that was utilized to prepare compounds of Examples B0001 through Bxxxx. Chemicals that are utilized in the robotics laboratory are weighed and then dissolved or suspended into solvents at Station #1 (Automated Chemistry Prep Station). Thus, solutions or suspensions of known molarity are prepared for use at the other robotics workstations. Station #1 also optionally bar-code labels each chemical solution so that its identity can be read by bar-code scanning at this and other robotics workstations.

Reactions are initiated at the modular Stations #2 and #2 DUP. Station #2DUP is defined as a duplicate of Station #2 and is used to increase capacity within the robotics laboratory. A reaction block is mounted at Station #2 or #2 DUP. Also, racks containing reactants, reagents, solvents, and resin slurries are also mounted at Station #2 or #2 DUP. Under the control of a chemical informatics mapping file, reactions are initiated by the transfer of reactant solutions, reagent solutions, solvents, and/or resin slurries into each mounted reaction block vessel. The transfer of known volumes of solutions, suspensions, or solvents is mediated by syringes which control a one-up septum piercing/argon purging cannula, a wide-bore resin slurry-despensing cannula, or by a six-up cannula which can simultaneously deliver volumes to a row of six reaction vessels. The reaction block and/or chemical solution racks may be optionally cooled below room temperature during the chemical solution transfer operations. After the transfer of chemical solutions and solvents has been performed by Station#2 or #2DUP, incubation of the reaction block may occur while the reaction block is mounted at the robot station. Preferably, however, the reaction block is removed after all volume transfers are complete and the reaction block is brought to ambient temperature. The reaction block is transferred off-line to either a vertical- or lateral shaking Incubator Station #5.

The Automated weighing/archival Station #3 performs the functions of weighing empty collection vials (to obtain tare weights of collection vials) and also performs the functions of weighing collection vials containing filtered, purified products (to obtain gross weights of collection vials). After product-containing collection vials have been weighed (gross weight determinations) at workstation #3, the collection vial products are optionally redissolved into an organic solvent at workstation #3. Transfer of solvents is accomplished with syringes which control a mounted one-up septum-piercing/argon purging cannula. Each product-containing collection vial is prepared as a solution of known molarity as directed and recorded by the chemical informatics system. These product solutions may be subsequently mounted at Station #2 or #2DUP for subsequent reaction steps or taken to Station #7 or #7DUP for analytical processing.

Rapid solvent evaporation of product-containing collection vials is accomplished by mounting the collection racks at Savant Automated Solvent Evaporation Stations #4, #4 DUP, or #4 TRIP, wherein #4DUP and #4TRIP are defined as a duplicate and a triplicate of Station #4 to increase the capacity for solvent removal within the robotics laboratory. Commercially available solvent removal stations were purchased from the Savant Company (model #SC210A speed-vac unit equipped with model # RVT4104 vapor trap and model #VN100 vapornet cryopump).

Stations #7 and #7DUP perform analytical processing functions. Station #7DUP is defined as a duplicate of Station #7 to increase capacity within the robotics laboratory. Product-containing collection racks are mounted at either of these stations. Each product-containing collection vial is then prepared as a solution of known molarity as directed and recorded by the chemical informatics mapping file. Optionally, this dissolution function is performed by prior processing of the collection vial rack at Station #3 as described above. Station#7 or #7DUP, under the control of the chemical informatics mapping file, transfers aliquots of each product vial into unique and identifable microtiter plate wells that are utilized to perform analytical determinations. One such microtiter plate is prepared at Station #7 or #7DUP for subsequent utilization at the Automated HPLC/Mass Spectrometer Station #8 or #8DUP. Station #8DUP is a duplicate of Station #8 to increase the analytical capacity of the robotics laboratory. Stations #8 and #8DUP are commercially available benchtop LC/Mass spec units purchased from Hewlett Packard (model HP1100 HPLC connected to HP1100 MSD (G1946A) mass spectrometer; this unit is also equipped with a model#G1322A solvent degasser, model #G1312A binary pump, a model #G1316A column heater, and a model #G1315A diode array detector. The HP unit has been interfaced with a commercially available autosampler rack (Gilson Company #215 autosampler). Station #8 or #8DUP is utilized for the determination of product purity and identity by performing high performance liquid chromatography (HPLC) and companion atmospheric pressure chemi-ionization (APCI) or electrospray mass spectrometry for molecular weight determination.

Another microtiter plate is prepared at Station #7 or #7DUP for subsequent utilization at a commercially available flow-probe Varian NMR spectrometer Station #10 (Varian Instruments flow probe NMR, 300 MHz, interfaced with a commercially available Gilson 215 autosampler). Proton, $^{13}$-Carbon, and/or $^{19}$-Fluorine NMR spectra are determined at this Station #10.

Other microtiter plates are optionally mounted at Station #7 or #7DUP for the purpose of preparing product-containing plates for biological assays. Aliquots of product-containing collection vials are transferred to these biological assay microtiter plates under the control of the chemical informatics mapping file. Identity and amount of each transferred product is recorded by the chemical informatics system for retrieval by biologists who perform the biological assaying of products.

The Fourier Transfrom InfraRed (FT-IR) Spectrometer Station #11 is utilized to analyze resins for the identity of organic functional groups chemically attached to these resins. The resins, as mentioned above, contain chemical functionality utilized as reagents, chemoselective sequestrants, or reaction quenching media for the workup and purification of the crude product mixtures contained within reaction block vessels. The robotics laboratory utilizes a commercially available FT-IR spectrometer purchased from Nicolet Instruments (model # MagnaIR 560 interfaced with an InspectIR microscope for resin mounting and positioning).

Scheme B-3

The lines interconnecting the modular Stations denote the transfer of chemical racks, reaction blocks, and/or collection vial racks from one modular Station to another.

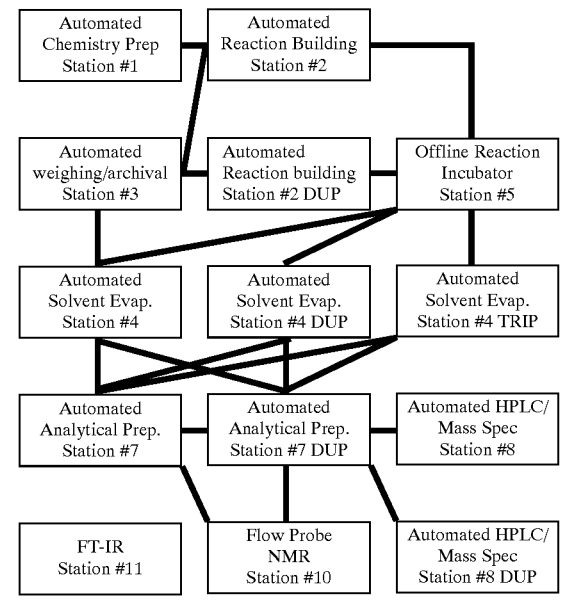

The ChemLib IT system is a composite of software running on the client's desktop and software running on a remote server.

The ChemLib IT system is a client/server software application developed to support and document the data handling flow in the robotics laboratory described above. This IT system integrates the chemist with the robotics synthesis laboratory and manages the data generated by this processes.

The software running on the server warehouses all the electronic data for the robotics chemistry unit. This server, a Silicon Graphics IRIX station v6.2, runs the database software, Oracle 7 v7.3.3.5.0, that warehouses the data. Connection from the client's desktop to the server is provided by Oracle's TCP/IP Adapter v2.2.2.1.0 and SQL*Net v2.2.2.1.0A. SQL*Net is Oracle's network interface that allows applications running on the client's desktop to access data in Oracles' database. The client's desktop is Microsoft Windows 95. The ChemLib IT system client software is composed of Omnis7 v3.5 and Microsoft Visual C++vS.0. This composition on the client side is what is herein referred to as ChemLib. ChemLib communicates with the server for its data via Oracle's PL/SQL v2.3.3.4.0. These PL/SQL calls within ChemLib creates a network socket connection to Oracle's SQL*Net driver and the TCP/IP Adapter thereby allowing access to the data on the server.

A "library" is defined as a composite number of wells, where each well defines a single compound. ChemLib defines a library in a module called the Electronic Spreadsheet. The Electronic Spreadsheet is then a composite of n-number of wells containing the components that are required to synthesize the compound that exist in each these well(s).

The chemist begins by populating the Electronic Spreadsheet with those components required for the compound synthesis. The identity and the availability of these components are defined in the Building Block Catalog module of ChemLib. The Building Block Catalog is a catalog of a listing of all reagents, solvents, peripherals available in the robotics laboratory. Upon selecting the components for each compound we also declare the quantity of each component to be utilized. The quantity of each component can be identified by its molarity and volumetric amounts (ul) or by it's solid state form (mg). Therefore a well in the Electronic Spreadsheet defines a compound that is identified by its components and the quantity of each of these components.

The assembly or the synthesis of these components for each compound in the Electronic Spreadsheet is defined in the WS Sequence module of ChemLib. The Define WS Sequence module identifies the synthesis steps to be performed at the robotics workstations and any activities to be performed manually or off-line from the robotics workstation. With this module we identify which components from the Electronic Spreadsheet and the activity that should be performed with this component in the robotics laboratory. In the Define WS Sequence module the chemist chooses from a list of activities to be performed in the robotics laboratory and assembles them in the order in which they are to occur. The ChemLib system takes these set of activities identified, and with the component data in the Electronic Spreadsheet assembles and reformats these instructions into terminology for the robotics workstation use. This robotics terminology is stored in a 'sequence' file on a common server that is accessible by the robotics workstation.

The robotics workstation performs the synthesis in a reaction block apparatus as described. Each well in the Electronic Spreadsheet is tracked and mapped to a unique location in the reaction block apparatus on the robotics workstation. The compound or product synthesized at the robotics workstation in the reaction block is then captured into collection vials.

The collection vials are first tarred then grossed on the robotics workstation after collecting their products from the reaction block. These weights (tare and gross) are recorded into the ChemLib system with the Tare/Gross Session module. The Tare/Gross Session module then calculates the product or compound yields and its final mass.

Preparation of the compound for analytical analysis and a, screening is defined by the Analytical WS Setup module in ChemLib. The Analytical WS Setup module identifies the dilution factor for each well in the Electronic Spreadsheet, based on the compound's product yield and the desired molar concentration. This identifies the quantity, in uL, to be transferred at the robotics workstation, to a specific location on the MTP (microtiter plate) to be sent for analysis and/or biological assaying. The mass spectrometric and HPLC results for each well are recorded and scored into the ChemLib system.

The Dilute/Archive WS module further identifies each compound by mapping the compound's well from the Electronic Spreadsheet to a specific MX block location for long term storage and archival as part of the registration process.

All communications between ChemLib and the robotics workstations are by ASCII files. These files are placed on a server by the ChemLib system that is accessible by the robotics workstations. Reports generated by the robotics workstations are also placed on the server where the ChemLib system can read these files to record the data generated. Each robotics workstation consists of robotics hardware by Bohdan Automation, Inc. Mundelein, Ill., and a PC currently running Microsoft Windows for Workgroup v3.11 and Ethernet software. The robotics workstation PC is logged into the network for one-way communication that allows the workstation to access the server for file access only.

General Scheme B4

Scaffold C-i with a primary amine functionality contained within the $R^4$ substituent is reacted in spatially addressed, parallel array reaction block vessels with excess of electrophiles $R^7$—Q wherein Q is chloro, bromo, or an acid activating group including but not limited to N-hydroxysuccinimide. $R^7$—Q includes acid chlorides, alkyl chloroformates, sulfonyl chlorides, activated esters of carboxylic acids, activated carbamates, and isocyanates. Reaction of scaffold C-i with $R^7$—Q is effected in the presence of a tertiary amine base at room temperature in a mixture of a polar aprotic solvent and/or a halogenated solvent. As illustrated in Scheme B-4 the products of the general formulae B-i are isolated in purified form by addition of a carbonyl-functionalized resin B32 which covalently sequesters any unreacted primary amine scaffold C-i as resin-bound adduct B35, and also by the addition of a primary amine-functionalized resin B33 which covalently sequesters any remaining electrophile $R^7$—Q from each reaction mixture as resin-bound adduct B34. Resin B33 also sequesters the HQ byproduct from the reaction mixture by proton transfer from solution-phase Base-HQ. Incubation at room temperature, filtration, rinsing of the resin cake, and concentration of the filtrates affords purified products B-i filtered away from resin-bound adducts B32, B33, B34, B35, and B36.

Scheme B-4

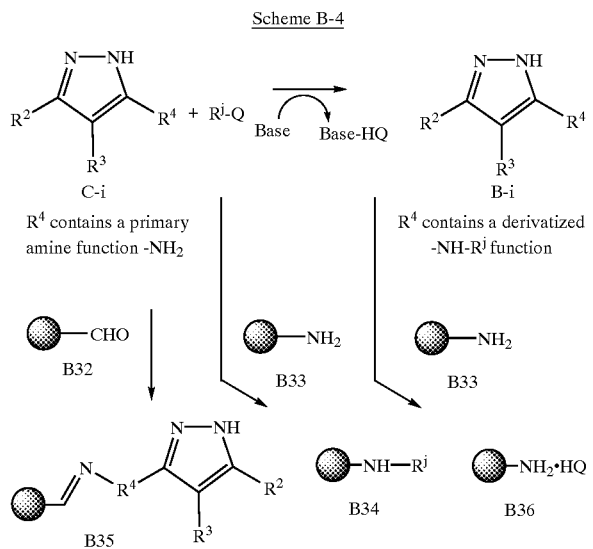

Scheme B-5 specifically illustrates the derivatization of the primary amine-containing scaffold C1 to afford the desired products B-i in a parallel array synthesis format. In a parallel array synthesis reaction block, individual reaction products are prepared in each of multiple reaction block vessels in a spatially addressed format. A solution of the desired primary amine-containing scaffold C1 (limiting amount,) in dimethylformamide (DMF) is added to the reaction vessels followed by a 4.0 fold stoichiometric excess solution of N-methylmorpholine in DMF. To each reaction vessel is then added the electrophiles: either a 2.0 fold stoichiometric excess when $R^J$—Q is an acid chloride or alkyl chloroformate, or a 1.5 fold stoichiometric excess when $R^J$—Q is a sulfonyl chloride, or a 1.25 stoichiometric excess when $R^J$—Q is an isocyanate. Excess electrophiles and N-methylmorpholine were used to effect more rapid and/or more complete conversion of scaffold C1 to products B-0001–B-0048 compared to reactions that do not utilize stoichiometric excesses of electrophiles and N-methylmorpholine. The reaction mixtures are incubated at ambient temperature for 2–3 h. Each reaction vessel is then charged with a large excess (15–20 fold stoichiometric excess) of the amine-functionalized resin B33 and the aldehyde-functionalized resin B32. The resin-charged reaction block is shaken vertically for 14–20 h on an orbital shaker at ambient temperature to allow optimum agitation of the resin-containing vessel mixtures. The excess electrophiles $R^J$—Q and any unreacted scaffold amine C1 are removed from the reaction medium as insoluble adducts B34 and B37 respectively. In addition the N-methylmorpholine hydrochloride salt formed during the course of the reaction is also neutralized to its free base form by proton transfer reaction to the amine-functionalized resin B33. Simple filtration of the insoluble resin-adducts B32, B33, B34, B36, and B37, rinsing of the resin cake with dichloroethane, and evaporation of the filtrates affords the desired products B-i in purified form.

Scheme B-5

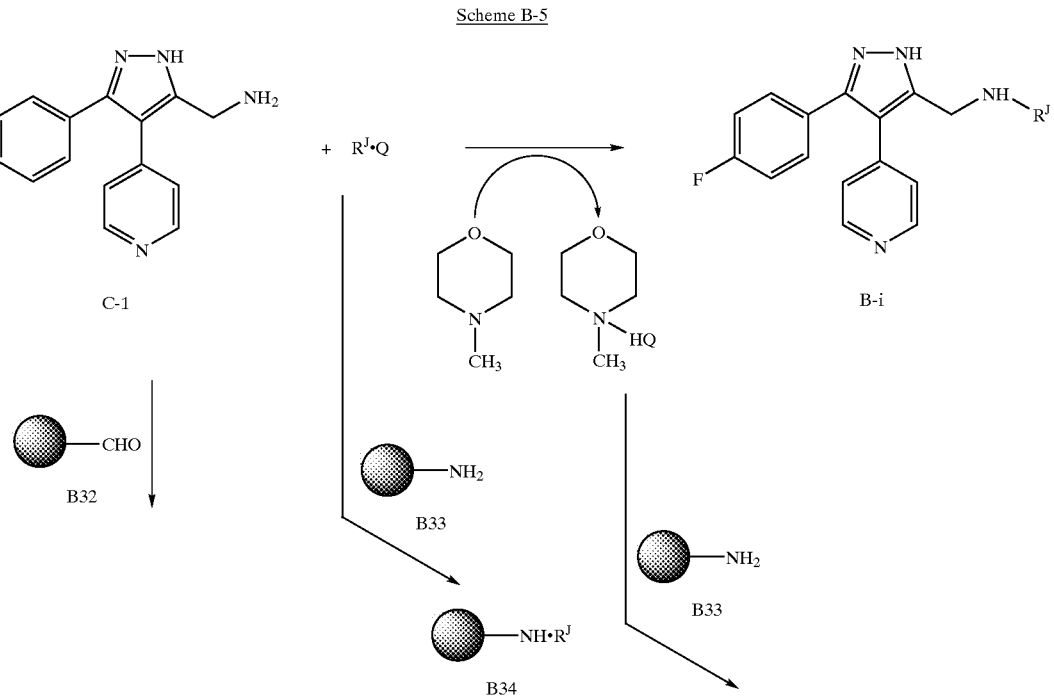

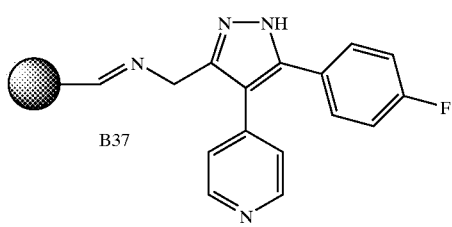

B37

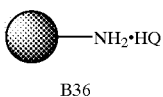

B36

Scheme B-6 illustrates a general synthetic method involving the parallel array reaction of a scaffold C-ii containing a secondary amine functionality within the definition of the $R^4$ substituent. Each reaction vessel is charged with the secondary amine-containing scaffold C-ii, followed by the introduction of a stoichiometric excess of an optionally unique electrophile $R^L$—Q into each vessel, wherein Q is chloro, bromo, or an acid activating group including but not limited to N-hydroxysuccinimide. $R^L$—Q includes acid chlorides, alkyl chloroformates, sulfonyl chlorides, activated esters of carboxylic acids, activated carbamates, and isocyanates. Reaction of scaffold C-ii with $R^L$—Q is effected in the presence of tertiary amine base at room temperature or elevated temperature in a mixture of a polar aprotics solvent and/or a halogenated solvent. After solution-phase reactions have progressed to afford crude product mixtures in each vessel, the products B-ii are isolated in purified form by the addition of the isocyanate-functionalized resin B38 which covalently sequesters remaining secondary amine scaffold C-ii as resin-bound adduct B39, and also by the addition of the primary amine-functionalized resin B33 which covalently sequesters remaining electrophile $R^L$—Q from each reaction vessel as resin-bound adducts B40. Resin B33 also sequesters the HQ byproduct in each vessel as B36, formed by proton transfer from solution-phase Base·HQ. Incubation with these resins, either simultaneously or sequentially, followed by filtration, rinsing, and concentration of the filtrates affords purified products B-ii filtered away from resin-adducts B33, B36, B38, B39, and B40.

Scheme B-6

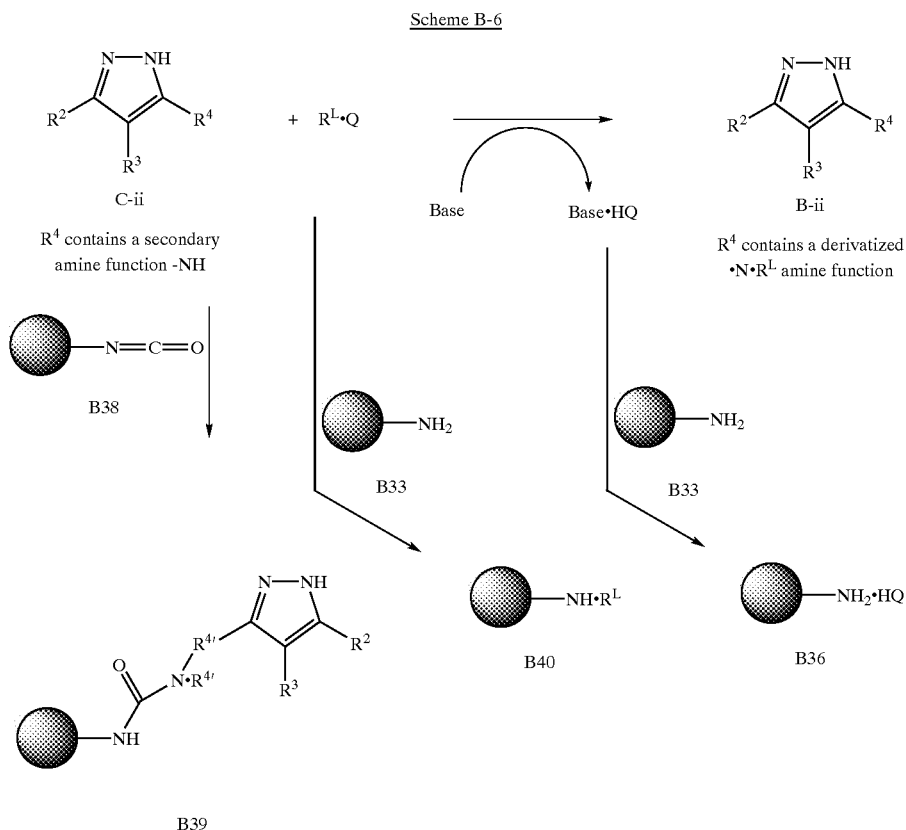

Scheme B-7 illustrates the conversion of the secondary-amine containing scaffold C-2 to the desired products B-ii. In a parallel array synthesis reaction block, individual reaction products are prepared in each of 48 multiple reaction block vessels. A solution of the scaffold C-2 (limiting amount) in dimethylformamide (DMF) is added to the reaction vessels followed by a 4.0-fold stoichiometric excess solution of N-methylmorpholine in DMF. To each reaction vessel is then added an electrophile $R^L$—Q as a dichloroethane (DCE) solution: either a 2.0 fold stoichiometric excess is used when $R^L$—Q is an acid chloride or alkyl chloroformate, or a 1.5 fold stoichiometric excess when $R^L$—Q is a sulfonyl chloride, or a 1.25 fold stoichiometric excess when $R^L$—Q is an isocyanate. The reaction mixtures are incubated at ambient temperature for 2–6 h. Each reaction vessel is then charged with a large excess (15–20 fold stoichiometric excess) of the amine-functionalized resin B33 and the isocyanate-functionalized resin B32. The resin-charged reaction block is shaken vertically for 14–20 h on an orbital shaker at ambient temperature to allow optimum agitation of the resin-containing vessel mixtures. The excess electrophiles $R^L$—Q and unreacted scaffold amine C-2 are removed from the reaction medium as insoluble adducts B40 and B39, respectively. Resin B33 also sequesters the HQ byproduct in each vessel as B36, formed by proton transfer from solution-phase Base-HQ. Incubation with these resins, followed by filtration and rinsing with solvent mixtures of DMF and/or DCE, affords purified product solutions in collection vials filtered away from resin-adducts B33, B36, B38, B39, and B40. Concentration of filtrates affords purified products B-ii.

Scheme B-7

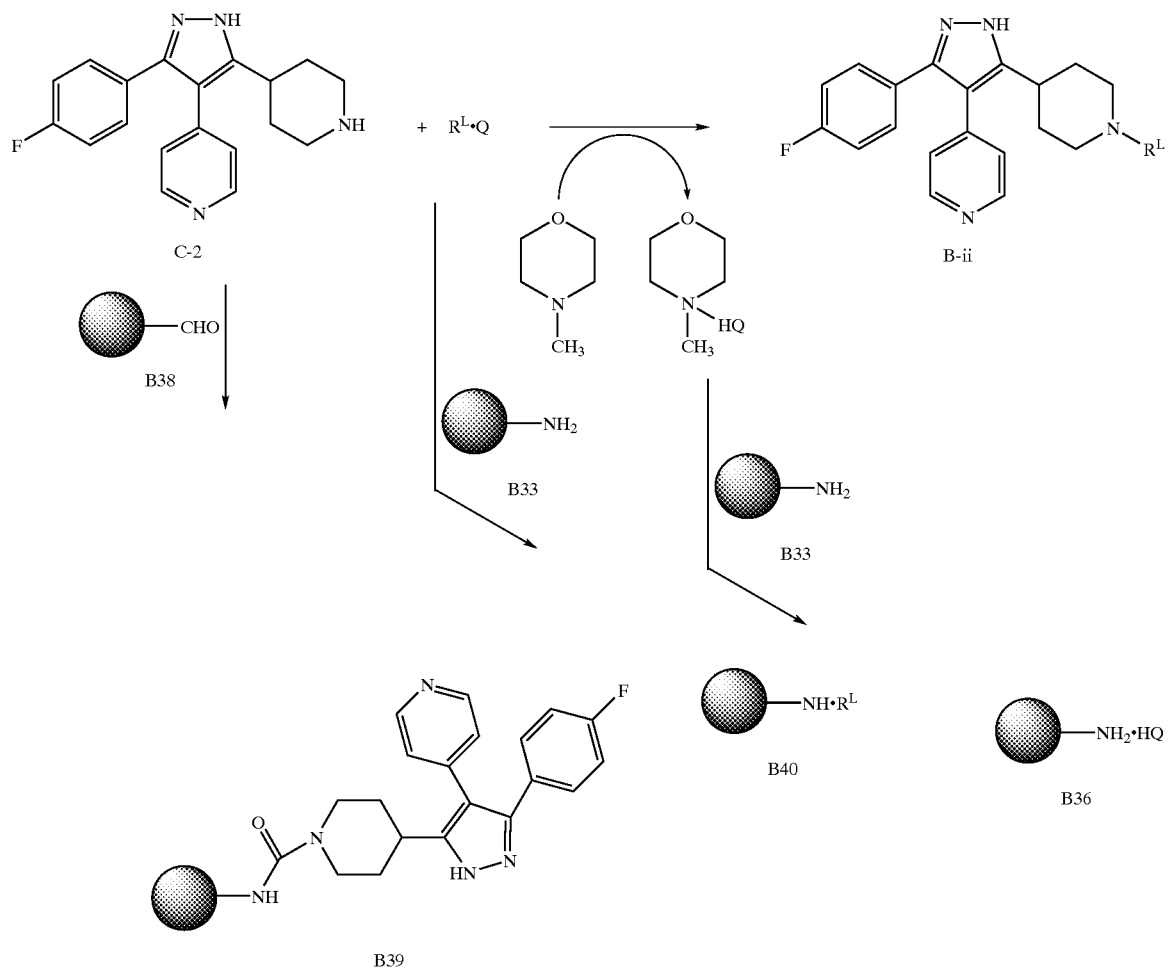

Scheme B-8 illustrates another general synthetic method involving the parallel array reaction of a scaffold C-ii containing a secondary amine functionality within the definition of the $R^4$ substituent. Each reaction vessel is charged with the secondary amine-containing scaffold C-ii, followed by the introduction of a stoichiometric excess of an optionally unique electrophile $R^L$—Q into each vessel. Reaction of scaffold C-ii with $R^L$—Q is effected in the presence of tertiary amine base at room temperature or elevated temperature in a mixture of a polar aprotic solvent and/or a halogenated solvent. Excess electrophiles and N-methylmorpholine are used to effect more rapid and/or more complete conversion of scaffold C-ii to products B-ii compared to reactions that do not utilize stoichiometric excesses of electrophiles and N-methylmorpholine. The reaction mixtures are incubated at ambient temperature for 2–8 h. Each reaction vessel is then charged with the sequestration-enabling reagent phenylsulfonylisocyanate B41. This reagent B41 reacts with remaining secondary amine scaffold C-ii, converting C-ii to the in situ-derivatized compound B42. Subsequent incubation of these vessel mixtures with a large excess (15–20 fold stoichiometric excess) of the amine-functionalized resin B33 sequesters the solution-phase species $R^L$—Q, HQ, B41, and B42 as the resin-bound adducts B40, B36, B44, and B43, respectively. The resin-charged reaction block is shaken vertically for 14–20 h on an orbital shaker at ambient temperature to allow optimum agitation of the resin-containing vessel mixtures. Filtration of the insoluble resin-adducts B33, B36, B40, B43 and B44 and subsequent rinsing of the vessel resin-bed with DMF and/or DCE affords filtrates containing the purified products B-ii. Concentration of the filtrates affords the purified products B-ii.

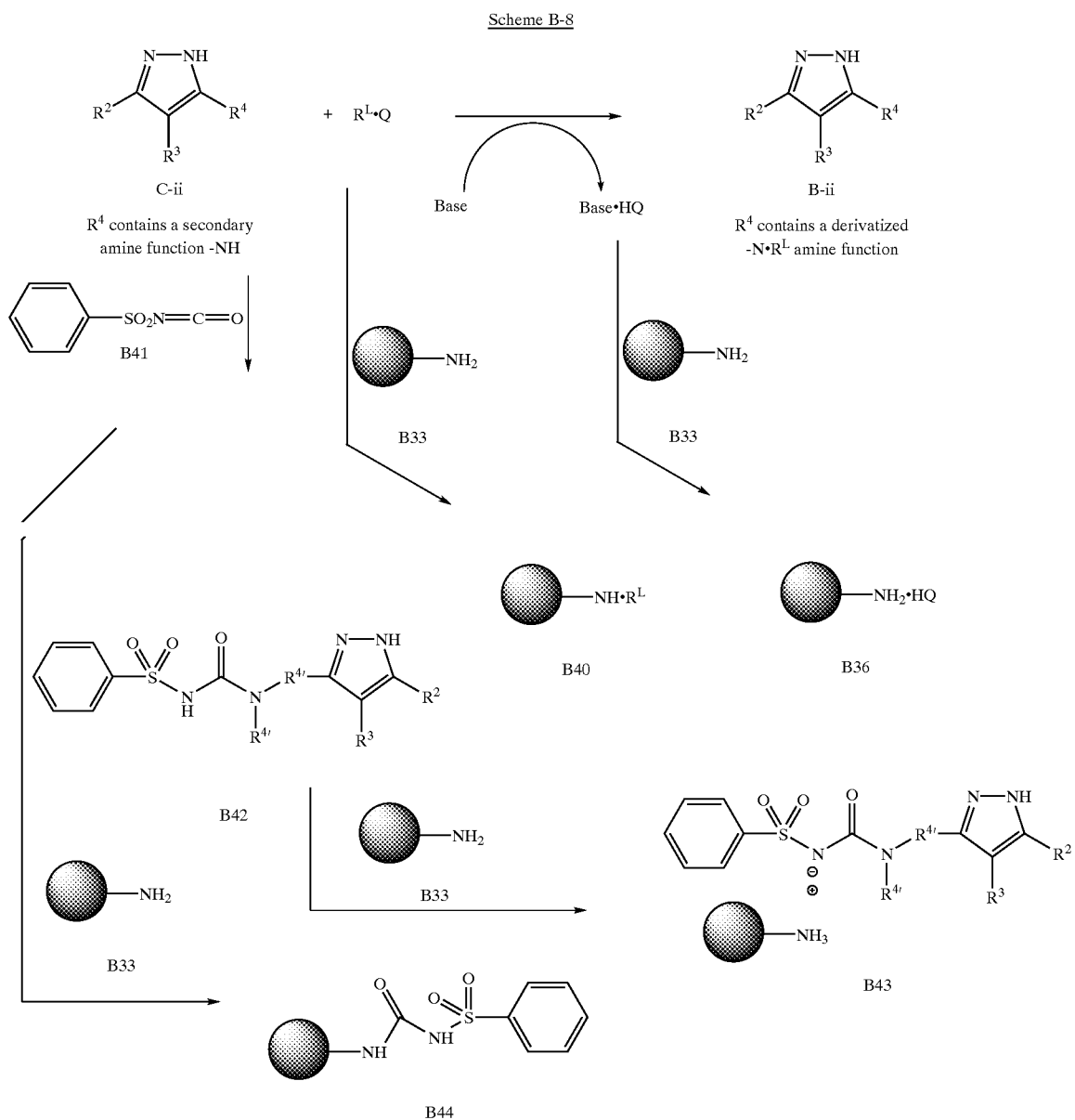

Scheme B-9 illustrates the method of Scheme B-8 using scaffold C-2. A solution of the scaffold C-2 (limiting amount) in dimethylformamide (DMF) is added to the reaction vessels followed by a 4.0-fold stoichiometric excess solution of N-methylmorpholine in DMF. To each reaction vessel is then added an electrophile $R^L$—Q as a dichloroethane (DCE) solution: either a 2.0 fold stoichiometric excess is used when $R^L$—Q is an acid chloride or alkyl chloroformate, or a 1.5 fold stoichiometric excess when $R^L$—Q is a sulfonyl chloride, or a 1.25 fold stoichiometric excess when $R^L$—Q is an isocyanate. The reaction mixtures are incubated at ambient temperature for 2–6 h. After solution-phase reactions have progressed to afford crude product mixtures, each reaction vessel is then charged with a dichloroethane solution of the sequestration-enabling reagent phenylsulfonylisocyanate B41. This reagent B41 reacts with remaining secondary amine scaffold C-2, converting C-2 to the in situ-derivatized compound B45. Subsequent incubation of these vessel mixtures with a large excess (15–20 fold stoichiometric excess) of the amine-functionalized resin B33 sequesters the solution-phase species $R^L$—Q, HQ, B41, and B45 as the resin-bound adducts B40, B36, B44, and B46, respectively. The resin-charged reaction block is shaken vertically for 20 h on an orbital shaker at ambient temperature to allow optimum agitation of the resin-containing vessel mixtures. Filtration of the insoluble resin- adducts B33, B36, B40, B44, and B46 and subsequent rinsing of the vessel resin-bed with DCE affords filtrates containing the purified products B-ii. Concentration of the filtrates affords the purified products B-ii.

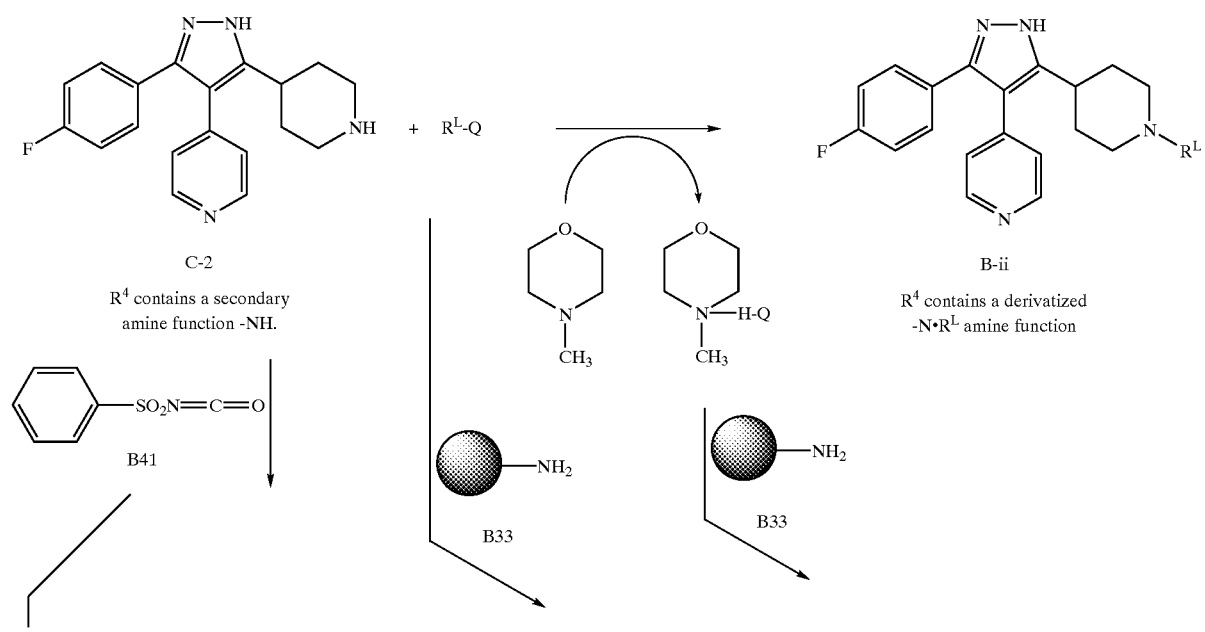

Scheme B-9

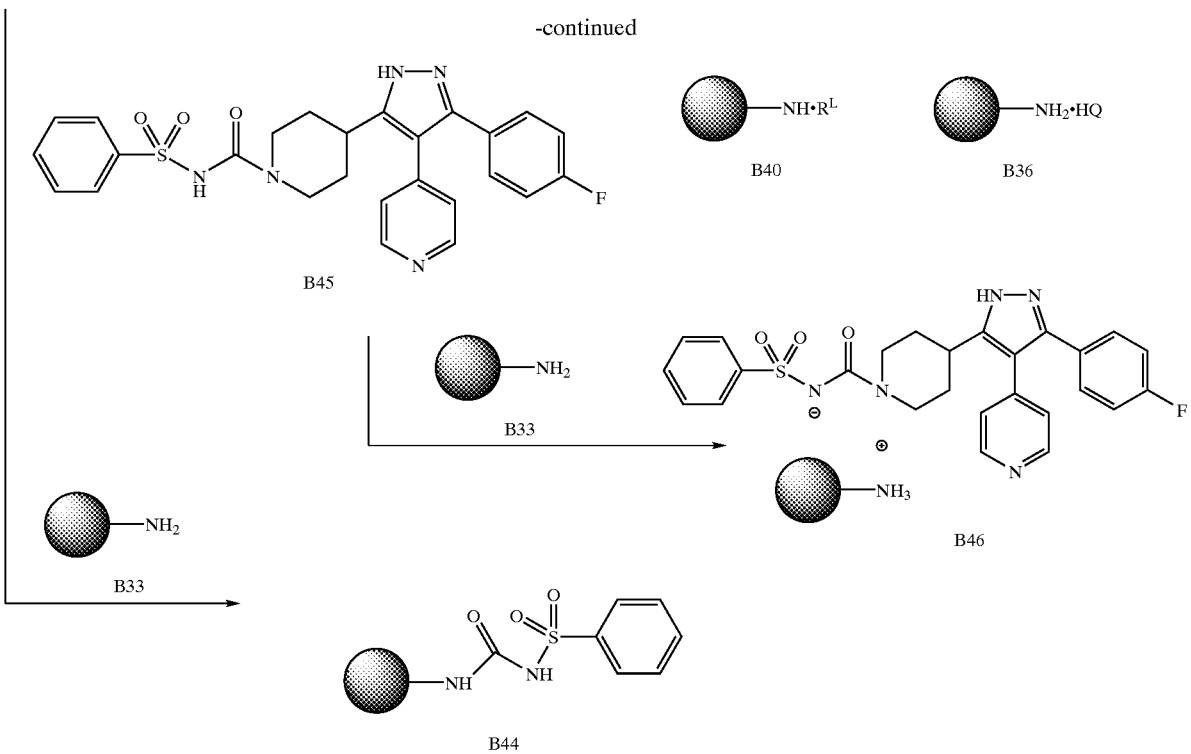

Another general method for the parallel array reaction block synthesis is illustrated in Scheme B-10 for the derivatization of the carboxylic acid-containing scaffold C-iii. Scaffold C-iii with a free carboxylic acid functionality is reacted in spatially addressed, parallel array reaction block vessels with excesses of optionally different primary or secondary amines B47 in the presence of the polymer-bound carbodiimide reagent B48 and a tertiary amine base in a mixture of a polar aprotic solvent and/or a halogenated solvent. After filtration of each crude vessel product misture away from resins B48 and B49, each reaction mixture is purified by treatment with the sequestration-enabling-reagent B50 (tetra-fluorophthalic anhydride). The reagent B50 reacts with remaining excess amine B47 to afford the in situ-derivatized intermediates B51 which contain carboxylic acid molecular recognition functionality. Subsequent incubation of each reaction mixture with a 15–20-fold stoichiometric excess of the primary amine-functonalized resin B33 sequesters B51, B50, and any remaining acid scaffold C-iii as resin-bound adducts B52, B53, and B54, respectively. Filtration of soluton-phase products B-iii away from these resin-bound adducts and rinsing of the resin beds with a polar aprotic solvent and/or halogenated solvent affords filtrates containing purified products B-iii. Concentration of the filtrates affords purified B-iii.

Scheme B-10

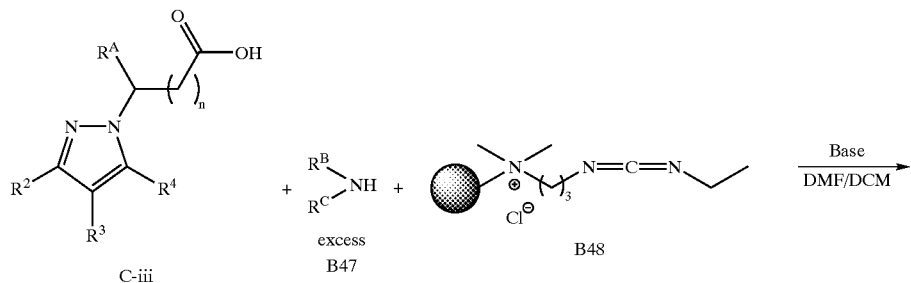

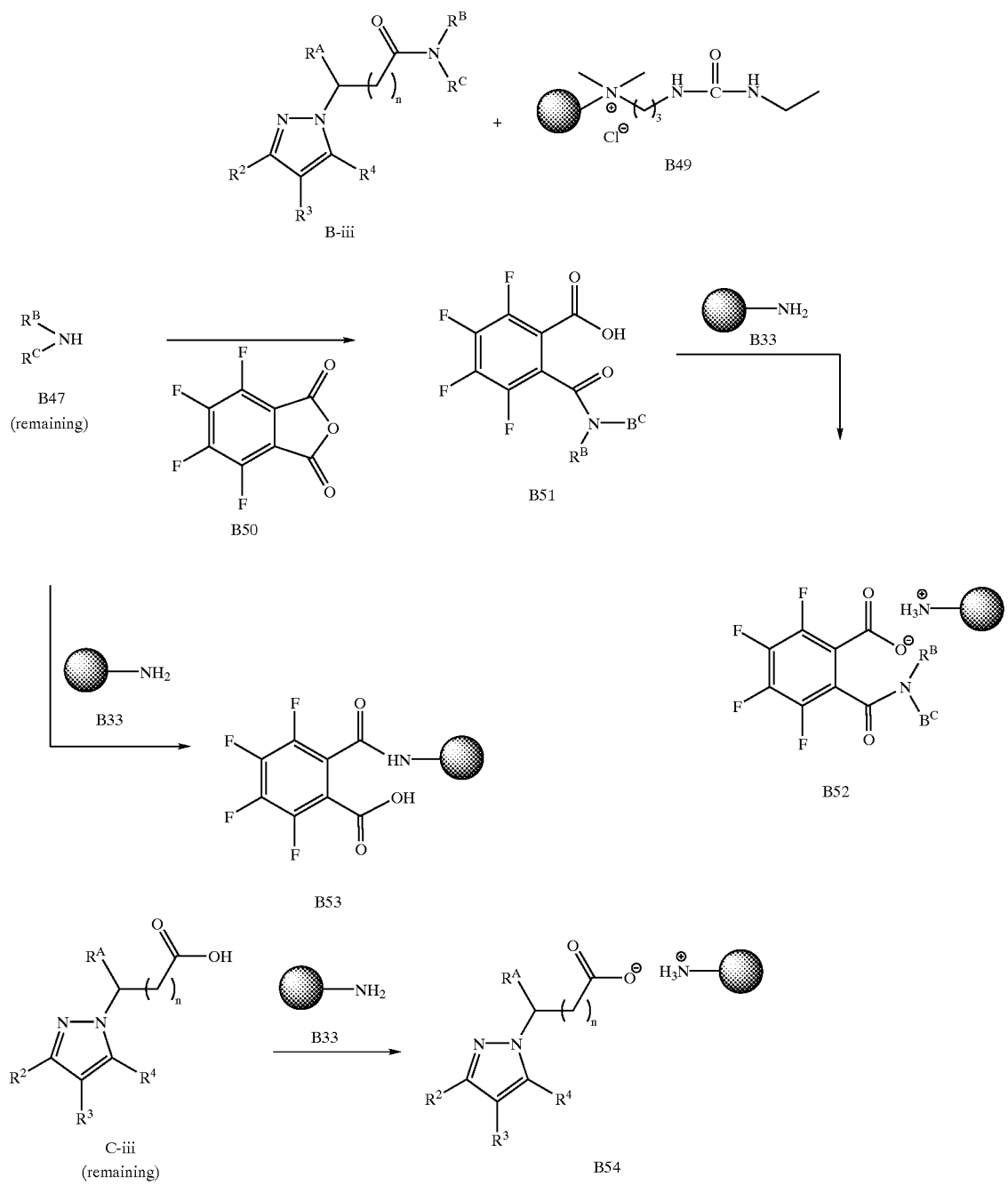

Scheme B-11 illustrates the conversion of the acid containing scaffold C-49 to the desired amide products B-iii in a parallel synthesis format. A limiting amount of the scaffold C-49 is added as a solution in dimethylformamide to each reaction vessel containing the polymer bound carbodiimide reagent B48 (5 fold stoichiometric excess). A solution of pyridine (4 fold stoichiometric excess) in dichloromethane is added to this slurry, followed by addition of an excess amount of a dimethylformamide solution of a unique amine B47 (1.5 fold stoichiometric excess) to each vessel. The parallel reaction block is then agitated vertically on an orbital shaker for 16–18 h at ambient temperature and filtered to separate the solution phase product mixture away from resin-bound reagent B48 and resin-bound reagent byproduct B49. The resulting solutions (filtrates) containing a mixture of the desired amide products B-iii, excess amines B47 and any unreacted acid containing scaffold C-49, are treated with tetrafluorophthalic anhydride B50. B50 converts the excess amines B47 in each filtrate vessel to its respective sequestrable half acid form B51. After two h incubation time, an excess of the amine-functionalized resin B33 and dichloromethane solvent are added to each reaction vessel. The amine-containing resin B33 converts B51, any remaining B50, and any remaining C-49 to their resin-bound adducts B52, B53, and B55, respectively. The resin-charged reaction block is shaken vertically for 16 h on an orbital shaker at ambient temperature to allow optimum agitation of the resin-containing vessel mixtures. Filtration of the insoluble resin-adducts B33, B52, B53, and B55 and subsequent rinsing of the vessel resin-bed with dimethyl- formamide affords filtrates containing the purified products B-iii. Concentration of the filtrates affords the purified products B-iii.
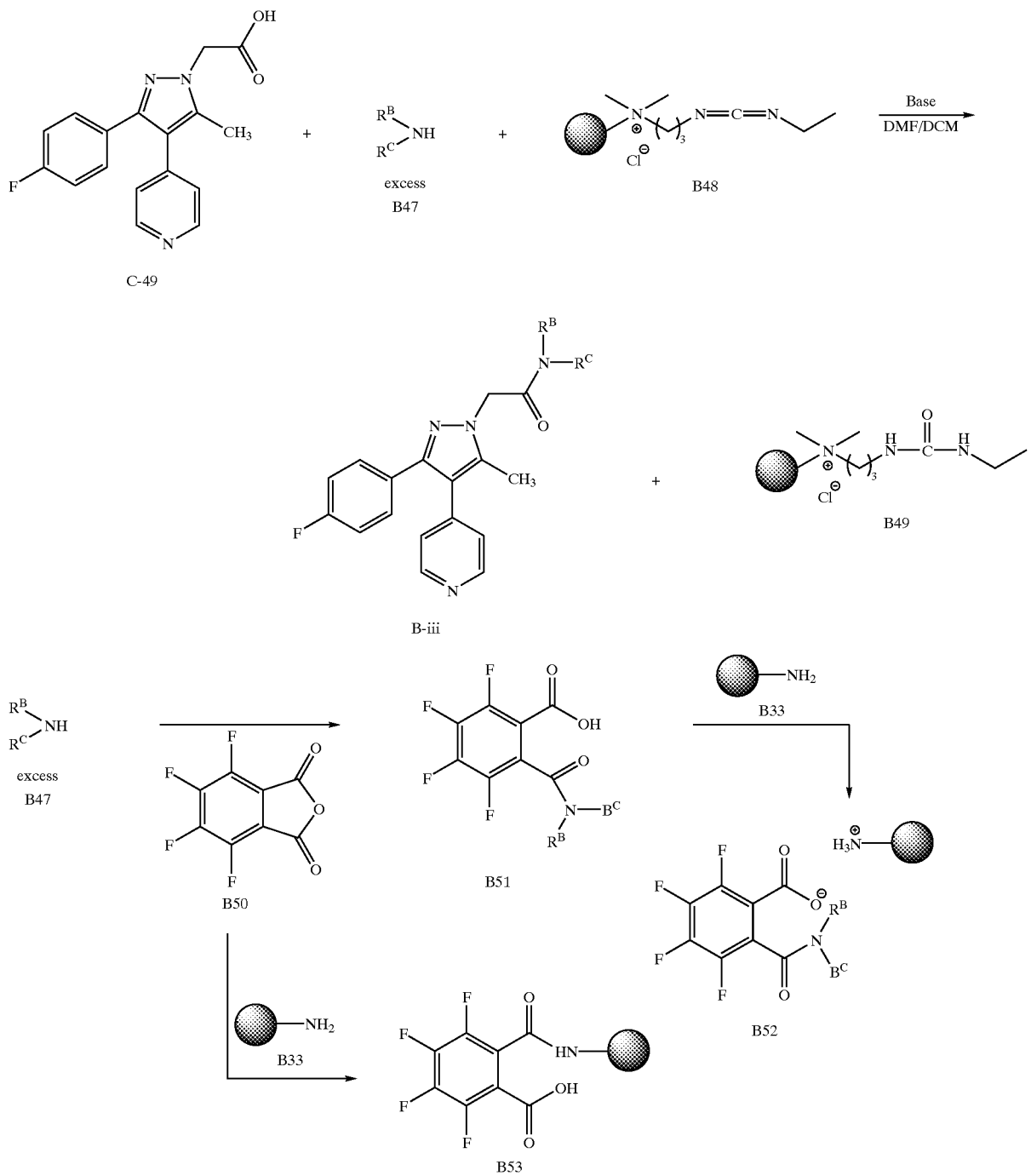
Scheme B-11

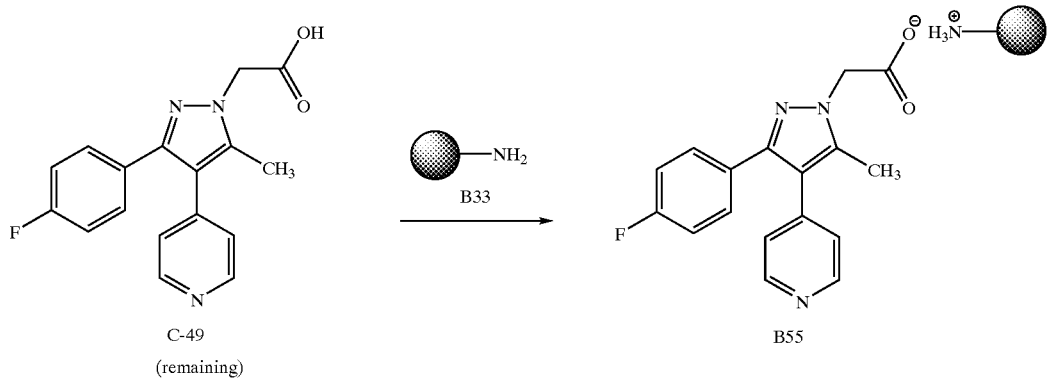

Although Schemes B-1 through B-11 describe the use of parallel array chemical library technology to prepare compounds of general formulae B-i, B-ii, and B-iii, it is noted that one with ordinary skill in the art of classical synthetic organic chemistry would be able to prepare B-i, B-ii, and B-iii by conventional means (one compound prepared at a time in conventional glassware and purified by conventional means such as chromatography and/or crystallization).

A general synthesis of pyridylpyrazole scaffolds C-i, C-ii, and C-iii is depicted in Scheme C-1.

Step A: Picoline is treated with a base chosen from but not limited to n-butyllithium (n-BuLi), lithium di-iso-propylamide (LDA), lithium hexamethyldisilazide (LiHMDS), potassium t-butoxide (tBuOK), or sodium hydride (NaH) in an organic solvent such as tetrahydrofuran (THF), diethyl ether, t-butyl methyl ether, t-BuOH or dioxane from −78° C. to 50° C. for a period of time from 10 minutes to 3 hours. The metallated picoline solution is then added to a solution of ester B56. The reaction is allowed to stir from 30 minutes to 48 hours during which time the temperature may range from −20° C. to 120° C. The mixture is then poured into water and extracted with an organic solvent. After drying and removal of solvent the pyridyl monoketone B57 is isolated as a crude solid which can be purified by crystallization and/or chromatography.

Step B: A solution of the pyridyl monoketone B57 in ether, THF, tBuOH, or dioxane is added to a base chosen from but not limited to n-BuLi, LDA, LiHMDS, tBuOK, or NaH contained in hexane, THF, diethyl ether, t-butyl methyl ether, or t-BuOH from −78° C. to 50° C. for a period of time from ranging from 10 minutes to 3 hours. An appropriately substituted activated ester or acid halide derived from $R^4$—$CO_2H$ is then added as a solution in THF, ether, or dioxane to the monoketone anion of B57 while the temperature is maintained between −50° C. and 50° C. The resulting mixture is allowed to stir at the specified temperature for a period of time from 5 minutes to three hours. The resulting pyridyl diketone intermediate B58 is utilized without purification in Step C.

Step C: The solution containing the pyridyl diketone B58 is quenched with water and the pH is adjusted to between 4 and 8 utilizing an inorganic or organic acid chosen from HOAc, $H_2SO4$, HCl, or $HNO_3$. The temperature during this step is maintained between −20° C. and room temperature. Hydrazine or hydrazine hydrate was then added to the mixture while maintaining the temperature between −20° C. and 40° C. for a period of 30 minutes to three hours. The mixture is then poured into water and extracted with an organic solvent. The pyridyl pyrazole C-i or C-ii is obtained as a crude solid which is purified by chromatography or crystallization.

Step: D In some cases the pyridyl pyrazole C-i or C-ii is alkylated with Q—$C(R^A)$—$(CH2)_n CO_2$alkyl wherein Q is halogen. C-i or C-ii is treated with a base chosen from NaH, NaOEt, KOtBu, or $NEt_3$ in an organic solvent such as THF, methylene chloride, dioxane, or DMF at temperatures between −20° C. and 150° C. and reaction times between 30 minutes and 12 hours. The resulting alkylated pyridyl pyrazole ester is then hydrolyzed to the acid by treament with NaOH or LiOH in acueous/alcohol solvent mixtures or in THF/water solvent mixtures. Alternatively, the ester function is removed by treatment with an organic or inorganic acid if the alkyl residue is t-butyl. Acidification, followed by extraction with an organic solvent affords C-iii which may be purified by chromatography or crystallography. In some cases, regioisomeric alkylated products C-iv are also formed. The desired C-iii can be separated away from C-iv by chromatographic purification or by fractional crystallization.

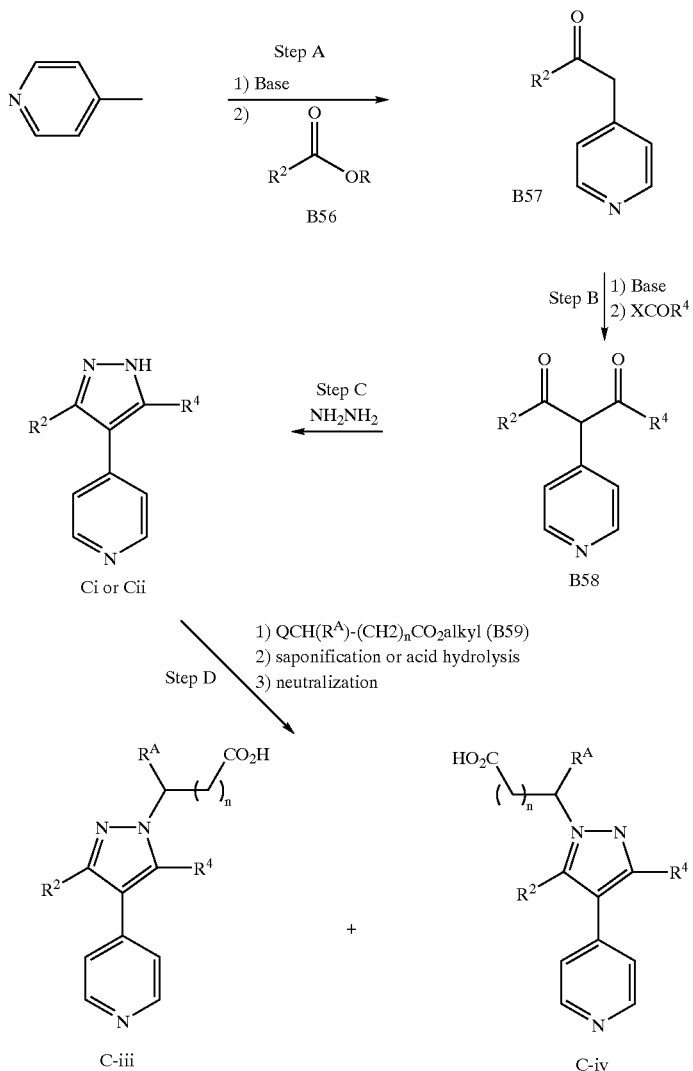

A synthesis of pyridylpyrazole scaffold C-1 is depicted in Scheme C-2

Step A: Picoline is added to a solution of LiHMDS in THF at room temperature over a time period ranging from 30 minutes to 1 hour. The resulting solution is stirred for an additional 30 minutes to 1 hour at room temperature. This solution is then added to neat ethyl p-fluorobenzoate B60 at room temperature over 1–2 h. The mixture is then allowed to stir at room temperature for 16–24 h. Equal portions of water and ethyl acetate are then added to the reaction and the mixture is partitioned in an extraction funnel. The organic layer is dried, filtered, and evaporated to give an oily solid. Hexanes are then added and the solid is filtered and washed with cold hexanes leaving the pyridyl monoketone B61 for use in Step B.

Step B: The pyridyl monoketone B61 is added as a solution in THF to a flask maintained at room temperature which contains t-BuOK in a THF/t-BuOH cosolvent. A yellow precipitate forms and stirring at room temperature is continued for 1–3 h. After this time, N-Cbz-protected glycine N-hydroxysuccinimide B62 is added dropwise at room temperature as a solution in THF over 1–3 h. This solution,-containing crude diketone B63, is used directly in Step C.

Step C:. The solution from step C is treated with water and the pH is adjusted to between 6 and 7 with acetic acid. Hydrazine hydrate is then added dropwise to the mixture as a solution in water over 30 minutes to 1 h at room temperature. Water and ethyl acetate are then added to the flask and the mixture is then partitioned in a separatory funnel. The organic layer is dried, filtered, and evaported to give a crude oil which is purified by silica gel chromatography, giving rise to purified C-1Cbz.

Step: D The Cbz protecting group contained in compound C-1Cbz is cleaved using hydrogen gas under pressure and Pd-C in methanol solvent. The resulting amine C-1 is obtained by filtration and concentration.

Scheme C-2

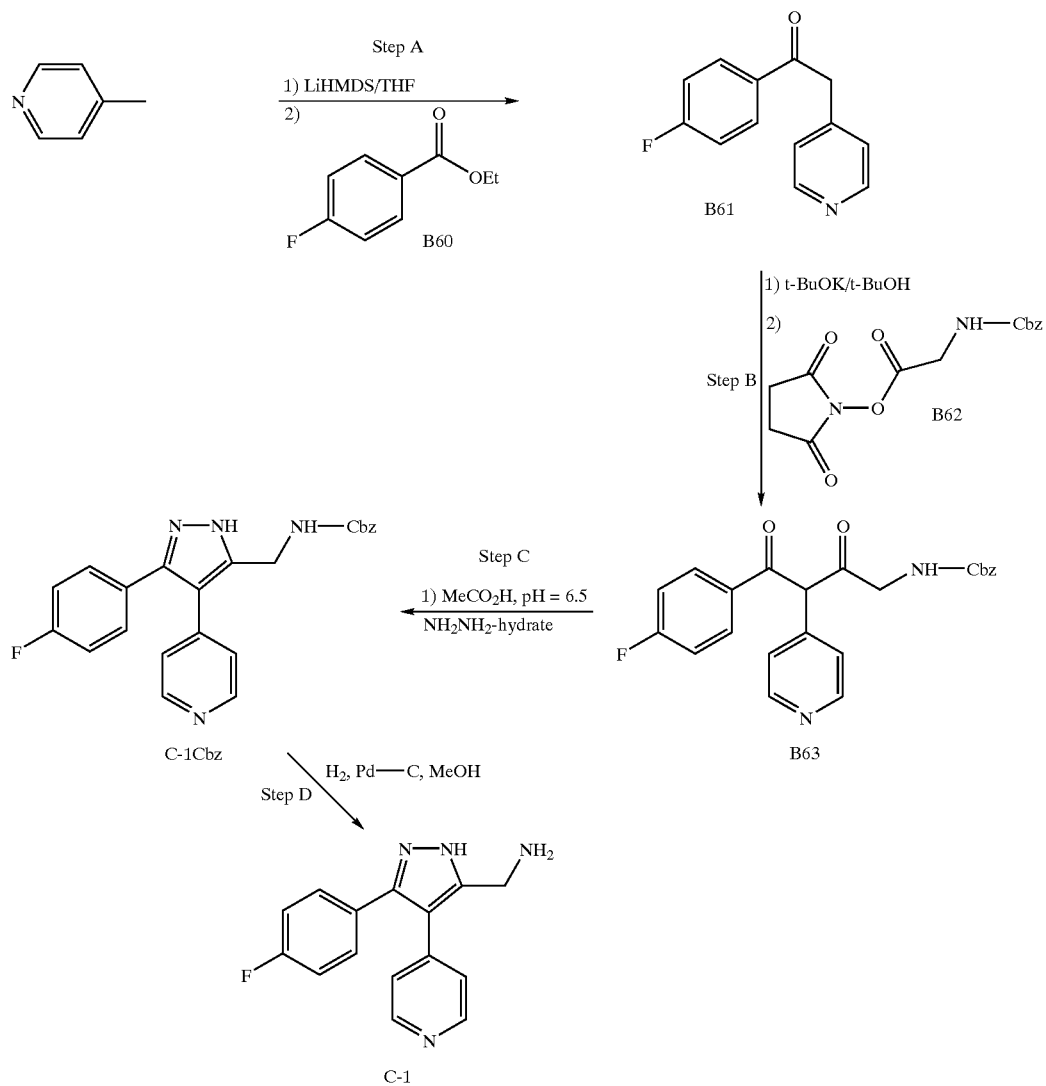

A number of pyridyl pyrazole scaffolds of type C-v are prepared as shown in Scheme C-3.

Step A: Picoline is treated with a base chosen from but not limited to n-BuLi, LDA, LiHMDS, tBuOK, or NaH in an organic solvent such as THF, ether, t-BuOH or dioxane from −78° C. to 50° C. for a period of time from 10 minutes to 3 hours. The metallated picoline solution is then added to a solution of an appropriately activated ester analog of a carboxylic acid $CbzNR^H$—$(CH_2)_n CR^F(R^G)$—$CO_2H$ or $BocNR^H$—$(CH_2)_n CR^F(R^G)$—$CO_2H$, preferably but not limited to the N-hydroxysuccinimide B64. The reaction is allowed to stir from 30 minutes to 48 hours during which time the temperature may range from −20° C. to 120° C. The mixture is then poured into water and extracted with an organic solvent. After drying and removal of solvent the pyridyl monoketone B65 is isolated as a crude solid which can be purified by crystallization and/or chromatography.

Step B: A solution of the pyridyl monoketone B65 in ether, THF, tBuOH, or dioxane is added to a base chosen from but not limited to n-BuLi, LDA, LiHMDS, tBuOK, or NaH contained in hexane, THF, ether, dioxane, or tBuOH from −78° C. to 50° C. for a period of time from 10 minutes to 3 hours. The anion sometimes precipitates as a yellow solid. An appropriately substituted activated ester such as the N-hydroxysuccinimide B66 is then added as a solution in THF, ether, or dioxane to the monoketone anion while the temperature is maintained between −50° C. and 50° C. The resulting mixture is allowed to stir at the specified temperature for a period of time from ranging from 5 minutes to 3 hours. The resulting pyridyl diketone intermediate B67 is utilized without further purification in Step C.

Step C: The solution containing the pyridyl diketone B67 is quenched with water and the pH is adjusted to between 4 and 8 utilizing an inorganic or organic acid chosen from HOAc, $H_2SO_4$, HCl, or $HNO_3$. The temperature during this step is maintained between −20° C. and room temperature. Hydrazine or hydrazine hydrate is then added to the mixture while maintaining the temperature between −20° C. and 40° C. for a period of 30 minutes to three hours. The mixture is then poured into water and extracted with an organic solvent. The pyridyl pyrazole C-vBoc or C-vCbz is obtained as a crude solid which is purified by chromatography or crystallization.

Step: D The carbamate protecting groups from C-vBoc or C-vCbz are removed to afford the scaffolds C-v containing either a free primary amine ($R^H$ is hydrogen) or a free secondary amine ($R^H$ not equal to hydrogen). The Boc protecting carbamate groups are cleaved utilizing 1:1 trifluoroacetic acid (TFA)/methylene chloride at room temperature for several hours. The CBZ carbamate protecting groups are cleaved using hydrogen gas under pressure and Pd-C in an alcoholic solvent. The resulting amines C-v are then optionally crystallized or purified by chromatography.

ranging from 1–24 h. Solvent is then evaporated and the resulting imine B69 is used in step B without further purification.

Step B: The pyridylpyrazole imine B69 is dissolved in THF and stirred under nitrogen at temperatures ranging from −78 to −20° C. A base such as LDA, n-BuLi, or LiHMDS is added dropwise to the mixture which is then stirred for an

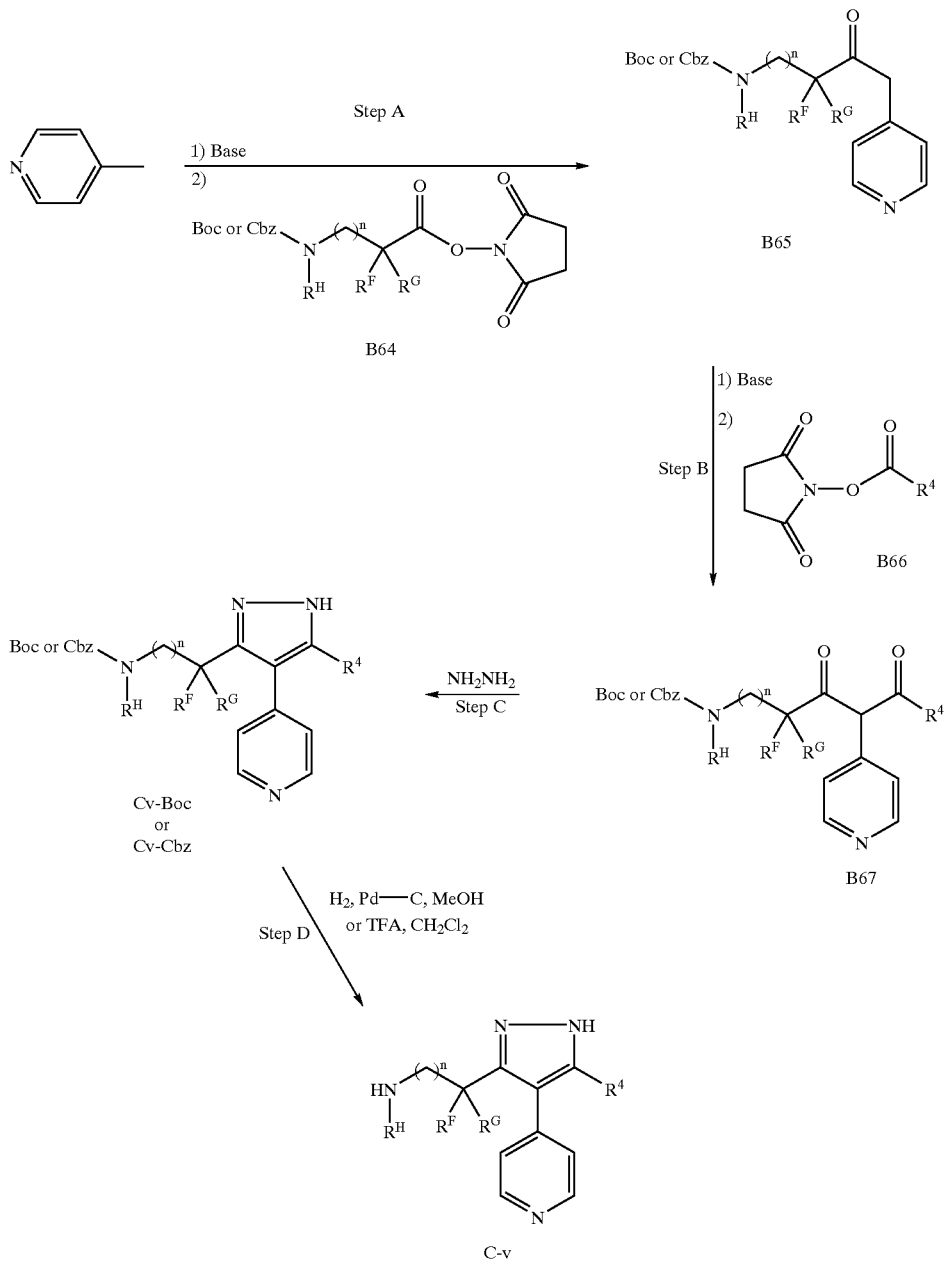

Scheme C-3

The synthesis of scaffolds C-vi is accomplished as shown in Scheme C-4.

Step A: A Boc protected pyridylpyrazole B68 is treated with benzaldehyde in methylene chloride at room temperature in the presence of a drying agent for a period of time additional 10 minutes to 3 h. Two-five equivalents of an alklyating agent $R^F$—Q are then added to the mixture and stirring is continued for several hours. The mixture is then quenched with acid and allowed to warm to room temperature and stirred several hours until cleavage of the Boc and the imine functions is complete. The pH is adjusted to 12 and then the mixture is extracted with an organic solvent, which is dried and evaporated. The crude pyridylpyrazole is then crystallized and/or chromatographed to give C-vi.

Scheme C-4

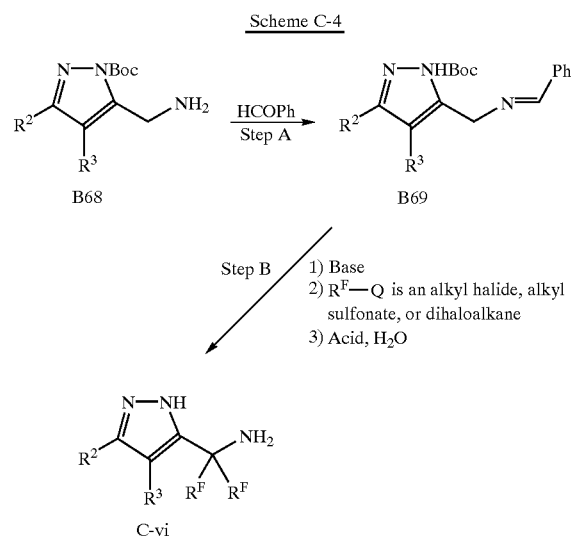

The synthesis of maleimide-containing scaffolds C-vii is accomplished as shown in Scheme C-5.

The maleimide pyrazole scaffolds C-vii are synthesized as depicted in scheme C-5. Condensation reaction of a primary amine H₂N—R with a maleic anhydride B70 that is substituted at position 3 with either a bromo, chloro, or triflate group generates compound B71. The formed maleimide derivative B71 then reacts with an acetophenone derivative B72 in the presence of a Pd(O) catalyst and base to afford compound B73. The methylene position of B73 is then acylated with an acid anhydride B74 or an activated acid ester B75, forming the di-ketone derivative B76. The di-ketone B76 condenses with hydrazine to afford the desired maleimide pyrazole scaffold C-vii.

Scheme C-5

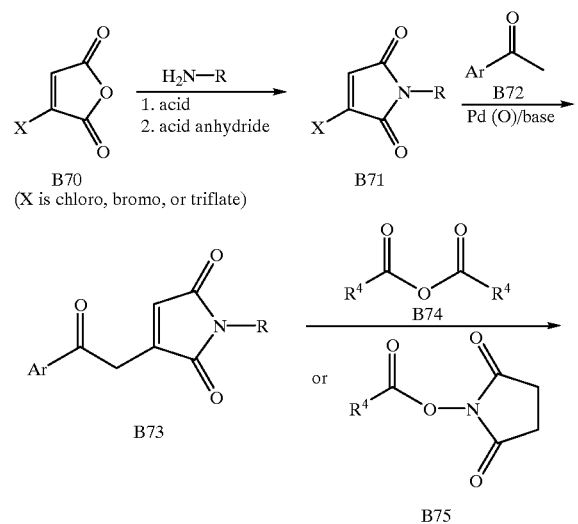

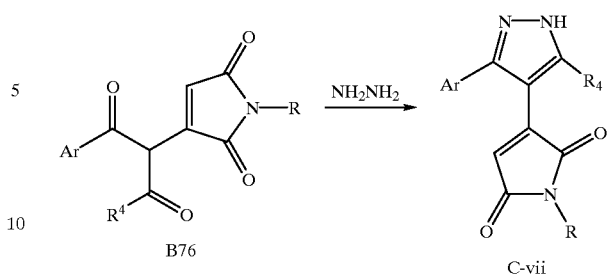

Scheme C-6 illustrates the synthesis of the maleimide pyrazole scaffold C-63 wherein $R^4$ is hydrogen. The synthesis starts with the condensation reaction of bromomaleic anhydride B77 with 2,4-dimethoxybenzylamine in acetic acid and acetic anhydride, giving rise to intermediate B78. The maleimide B78 is then treated with 4'-fluoroacetophenone in the presence of catalytic amount Pd₂(dba)₃ and sodium t-butoxide to form the fluoroacetophenone substituted maleimide B79. The B79 is treated with tert-butoxybis(dimethylamino)methane to yield the a-ketoenamine 80. The a-ketoenamine B80 is condensed with hydrazine to form the maleimide pyrazole skeleton B81. The 2,4-dimethoxybenzyl group protecting group is optionally removed with ceric ammonium nitrate (CAN) to give compound C-63.

Scheme C-6

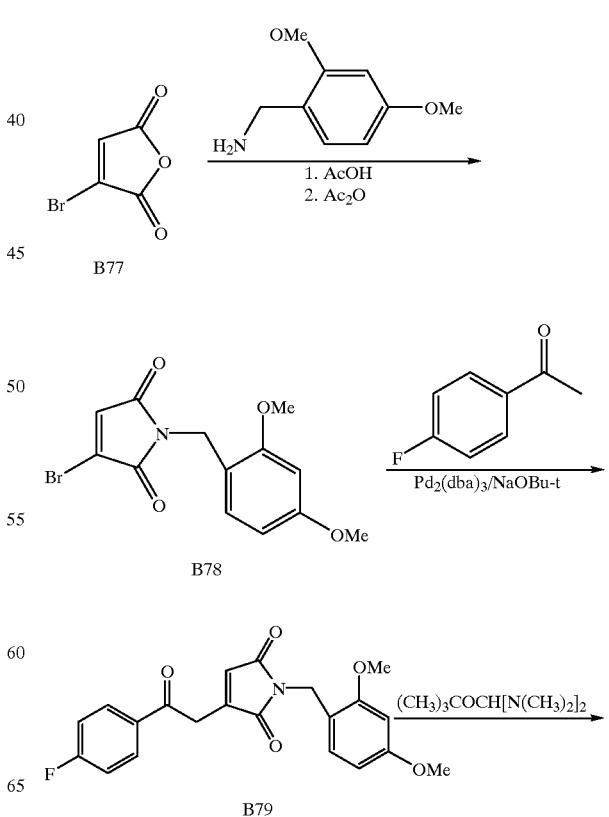

381
-continued

382
-continued

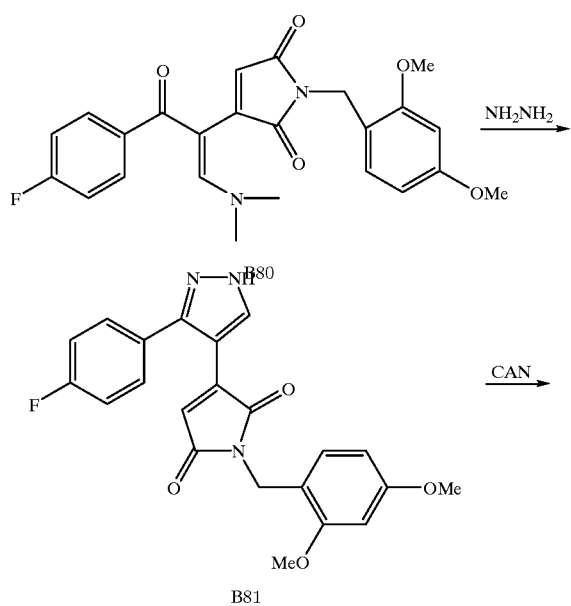

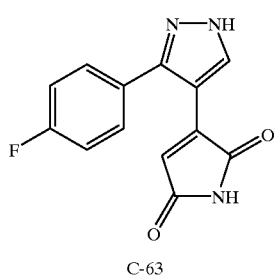

C-63

Scheme C-7 illustrates the synthesis of maleimide-containing scaffolds C-64 and C-65. These scaffolds C-49 and C-50 are synthesized according to the general methods illustrated in Scheme C-5 and exemplified with the utilization of N-hydroxysuccinimides B82 and B83 to afford the maleimide-containing pyrazoles B86 and B87, respectively. Optional removal of the 2,4-dimethoxybenzyl groups with CAN and subsequent removal of the Boc-protecting groups with trifluoroacetic acid (TFA) affords the scaffolds C-64 and C-65.

Scheme C-7

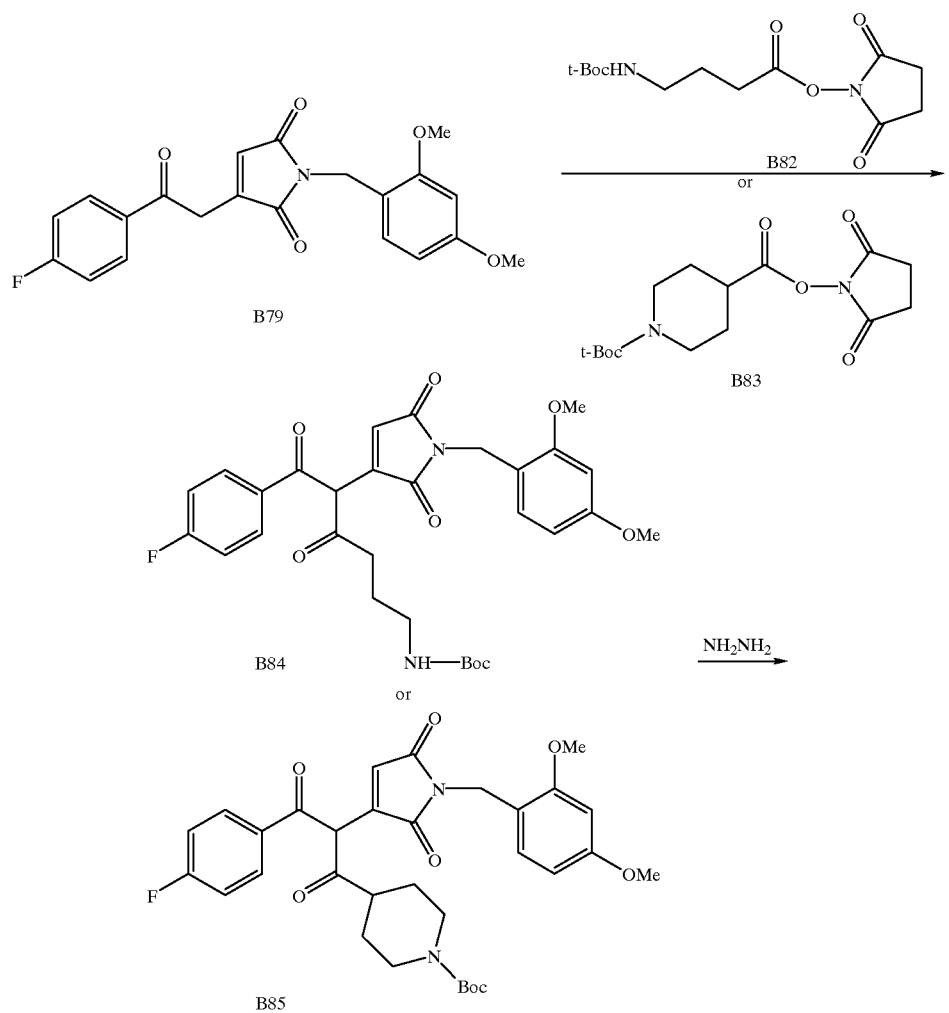

-continued

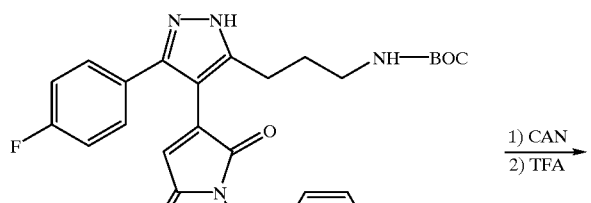

B86

1) CAN
2) TFA →

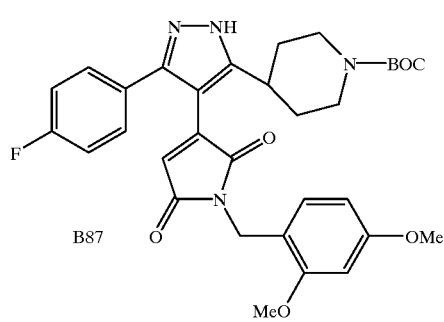

B87

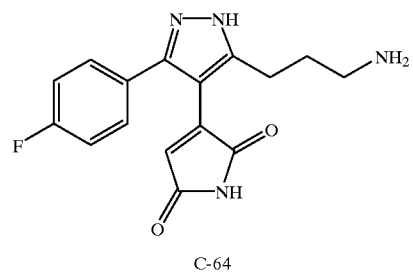

C-64

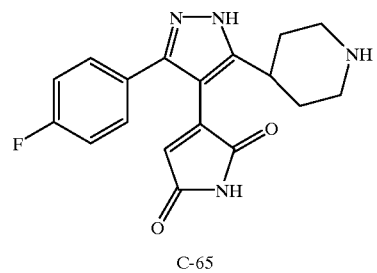

C-65

The various functionalized resins and sequestration-enabling-reagents utilized to prepare and purify parallel reaction mixtures are more fully described below, including their commercial source or literature reference to their preparation.

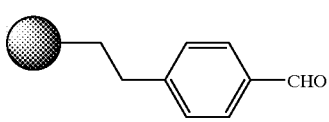

B32

4-benzyloxybenzaldehyde functionalized polystyrene.
Novabiochem cat. #01-64-0182

-continued

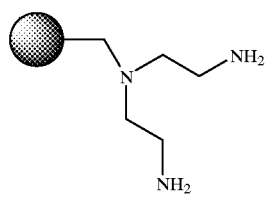

B33

Prepared as reported in D.L. Flynn et al,
J. American Chemical Society (1997) 119, 4874-4881.

385
-continued

B38
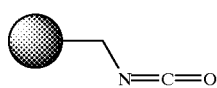
Methylisocyanate functionalized polystyrene.
Novabiochem cat. #01-64-0169

B48
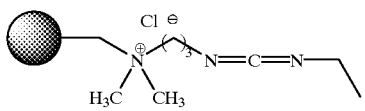
Polymer bound EDC, prepared as reported
by M.C. Desai et al, Tetrahedron Letters
(1993) 34, 7685.

B41
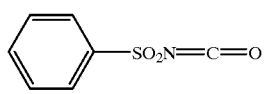
Benzenesulfonylisocyanate, purchased from
Aldrich Chemical Company. Cat. #23,229-7

B50
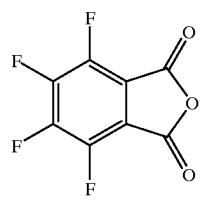
Tetra-fluorophthalic anhydride, purchased
from Aldrich Chemical Company. Cat. #33,901-6

Experimental Procedure for the Parallel Synthesis of a Series of Amides, Carbamates, Ureas and Sulfonamides B-0001 Through B-0048 from Scaffold C-1

386
EXAMPLES B-0001 THROUGH B-0048

To each reaction vessel (polypropylene syringe tubes fitted with a porous frit, closed at the bottom) of a parallel reaction apparatus was added 200 uL of dimethylformamide. A stock solution of the scaffold amine C-1 in dimethylformamide (0.1 M, 500 uL) was added to each reaction vessel followed by the addition of a stock solution of N-methylmorpholine in dimethylformamide (1.0 M., 200 uL). A stock solution of each of the electrophiles was then added to the appropriate reaction vessels: a) 500 uL of a 0.2 M solution of the acid chlorides in dichloroethane or b) 500 uL of a 0.2 M solution of the chloroformates in dichloroethane or c) 313 uL of a 0.2 M solution of the isocyanates in dichloroethane or d) 375 uL of a 0.2 M solution of the sulfonyl chlorides in dichloroethane. The parallel reaction apparatus was then orbitally shaken (Labline Benchtop orbital shaker) at 200 RPM at ambient temperature (23–30° C.) for a period of 2–3 h, under a gentle flow of nitrogen. At this time each reaction vessel was treated with approximately 250 mg of polyamine resin B33 (4.0 meq N/g resin) and approximately 100 mg of polyaldehyde resin B32 (2.9 mmol/g resin). Each reaction vessel was diluted with 1 mL dimethylformamide and 1 mL dichloroethane and the orbital shaking was continued at 200 RPM for a period of 14–20 h at ambient temperature. Each reaction vessel was then opened and the desired solution phase products separated from the insoluble quenched byproducts by filtration and collected in individual conical vials. Each vessel was rinsed twice with dichloroethane (1 mL) and the rinsings were also collected. The solutions obtained were then evaporated to dryness in a Savant apparatus (an ultracentrifuge equipped with high vacuum, scalable temperature settings and a solvent trap to condense the volatile solvent vapors). The resulting amide, carbamate, urea and sulfonamide products were then weighed and characterized. The yields and analytical data for the products obtained using this method are shown below.

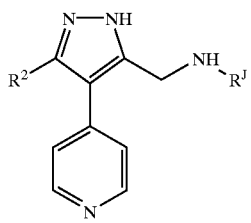

| Example # | $R^2$ | $R^J$ | % Yield | Calcd. Mass Spec | Observed Mass Spec (M + H) |
|---|---|---|---|---|---|
| B-0001 | F-phenyl | 4-ethynylbenzoyl | 85 | 397 | 398 |
| B-0002 | F-phenyl | 2-phenylcyclopropanecarbonyl | 94 | 412 | 413 |

-continued
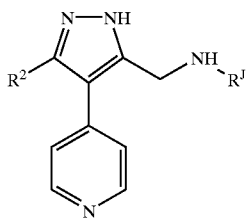
| Example # | R² | R^J | % Yield | Calcd. Mass Spec | Observed Mass Spec (M + H) |
|---|---|---|---|---|---|
| B-0003 | 4-F-C6H4 | -C(O)CH2OCH3 | 91 | 340 | 341 |
| B-0004 | 4-F-C6H4 | -C(O)CH2OC(O)CH3 | 79 | 368 | 369 |
| B-0005 | 4-F-C6H4 | -C(O)-(2-I-C6H4) | 92 | 498 | 499 |
| B-0006 | 4-F-C6H4 | -C(O)CH2OCH2Ph | 92 | 416 | 417 |
| B-0007 | 4-F-C6H4 | -C(O)-(4-Br-C6H4) | 86 | 450 | 451 |
| B-0008 | 4-F-C6H4 | -C(O)-(4-Ph-C6H4) | 86 | 448 | 449 |
| B-0009 | 4-F-C6H4 | -C(O)OCH2CH(CH3)2 | 83 | 368 | 369 |
| B-0010 | 4-F-C6H4 | -C(O)CH(CH3)2 | 86 | 338 | 339 |

-continued
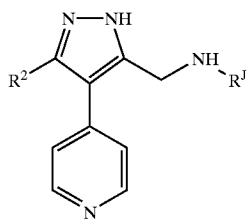
| Example # | R² | R^J | % Yield | Calcd. Mass Spec | Observed Mass Spec (M + H) |
|---|---|---|---|---|---|
| B-0011 | 4-F-C₆H₄ | 2-methoxybenzoyl | 92 | 402 | 403 |
| B-0012 | 4-F-C₆H₄ | 4-pentylbenzoyl | 74 | 442 | 443 |
| B-0013 | 4-F-C₆H₄ | 2-(2,5-dimethoxyphenyl)acetyl | 91 | 446 | 447 |
| B-0014 | 4-F-C₆H₄ | pentanoyl | 84 | 352 | 353 |
| B-0015 | 4-F-C₆H₄ | heptanoyl | 94 | 380 | 381 |
| B-0016 | 4-F-C₆H₄ | 2-(trifluoromethyl)benzoyl | 89 | 440 | 441 |
| B-0017 | 4-F-C₆H₄ | 4-iodobenzoyl | 83 | 498 | 499 |

-continued
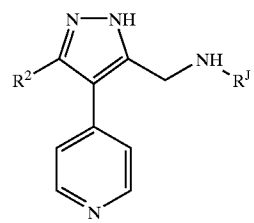
| Example # | R² | R^J | % Yield | Calcd. Mass Spec | Observed Mass Spec (M + H) |
|---|---|---|---|---|---|
| B-0018 | 4-F-phenyl | -C(O)CH₂C(O)-(1H-indol-3-yl) | 24 | 439 | 440 |
| B-0019 | 4-F-phenyl | -C(O)-(2,4,6-trichlorophenyl) | 89 | 474 | 475 |
| B-0020 | 4-F-phenyl | -C(O)-(3,5-dichlorophenyl) | 90 | 440 | 441 |
| B-0021 | 4-F-phenyl | -C(O)-(4-methylphenyl) | 85 | 386 | 387 |
| B-0022 | 4-F-phenyl | -C(O)-(4-nitrophenyl) | 35 | 417 | 418 |
| B-0023 | 4-F-phenyl | -C(O)-(3-cyanophenyl) | 94 | 397 | 398 |
| B-0024 | 4-F-phenyl | -C(O)-(2-nitrophenyl) | 87 | 417 | 418 |

-continued
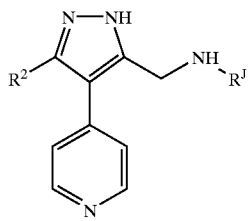
| Example # | R² | R^J | % Yield | Calcd. Mass Spec | Observed Mass Spec (M + H) |
|---|---|---|---|---|---|
| B-0025 | 4-F-phenyl | -C(O)C(O)OMe | 5 | 354 | — |
| B-0026 | 4-F-phenyl | 2,3,4-trifluorobenzoyl | 87 | 426 | 427 |
| B-0027 | 4-F-phenyl | -C(O)CH=C(Me)₂ | 89 | 350 | 351 |
| B-0028 | 4-F-phenyl | 4-(OCF₃)benzoyl | 92 | 456 | 457 |
| B-0029 | 4-F-phenyl | benzothiophene-2-carbonyl | 89 | 428 | 429 |
| B-0030 | 4-F-phenyl | 2,4,6-triisopropylbenzoyl | 37 | 498 | 499 |
| B-0031 | 4-F-phenyl | 5-nitrofuran-2-carbonyl | 18 | 407 | 408 |

-continued
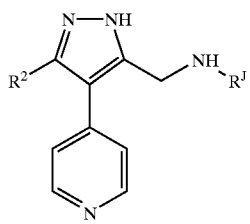
| Example # | R² | R^J | % Yield | Calcd. Mass Spec | Observed Mass Spec (M + H) |
|---|---|---|---|---|---|
| B-0032 | 4-F-phenyl | -C(O)-CH(Ph)₂ | 86 | 462 | 463 |
| B-0033 | 4-F-phenyl | -C(O)-O-CH₂-CH=CH₂ | 3 | 352 | — |
| B-0034 | 4-F-phenyl | -C(O)-CH₂-(3,4-dimethoxyphenyl) | 92 | 446 | 447 |
| B-0035 | 4-F-phenyl | tosyl-NH-CH(CH₂Ph)-CH(OH)- | 28 | 569 | 570 |
| B-0036 | 4-F-phenyl | -C(O)-CH₂-(4-methoxyphenyl) | 93 | 416 | 417 |
| B-0037 | 4-F-phenyl | -C(O)-(1-naphthyl) | 91 | 422 | 423 |
| B-0038 | 4-F-phenyl | -C(O)-CH₂-CH₂-(cyclopentenyl) | 84 | 390 | 393 |

-continued
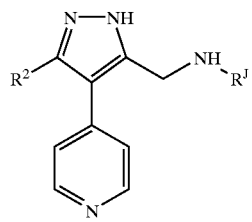
| Example # | R² | R^J | % Yield | Calcd. Mass Spec | Observed Mass Spec (M + H) |
|---|---|---|---|---|---|
| B-0039 | 4-F-phenyl | 4-methoxybenzoyl | 87 | 402 | 403 |
| B-0040 | 4-F-phenyl | (3-methoxyphenyl)acetyl | 92 | 416 | 417 |
| B-0041 | 4-F-phenyl | 4-butoxybenzoyl | 75 | 444 | 445 |
| B-0042 | 4-F-phenyl | 4-fluorobenzoyl | 54 | 390 | 391 |
| B-0043 | 4-F-phenyl | 2-acetoxy-2-methylpropanoyl | 80 | 396 | 397 |
| B-0044 | 4-F-phenyl | acetyl | 81 | 310 | 311 |
| B-0045 | 4-F-phenyl | 3,4-difluorobenzoyl | 91 | 408 | 409 |
| B-0046 | 4-F-phenyl | 2,2-bis(trifluoromethyl)-3,3,3-trifluoropropanoyl | 25 | 464 | 465 |

-continued

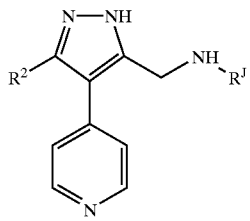

| Example # | R² | R^J | % Yield | Calcd. Mass Spec | Observed Mass Spec (M + H) |
|---|---|---|---|---|---|
| B-0047 | 4-F-phenyl | -C(O)-CH(Et)-O-phenyl | 88 | 430 | 431 |
| B-0048 | 4-F-phenyl | -C(O)-CH(Et)-phenyl | 95 | 414 | 415 |

By analogy to the procedure identified above for the preparation of Examples B0001-B0048, the following examples B-0049 through B-1573 were prepared.

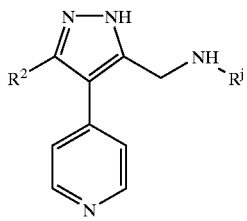

| Example# | R² | R^J | % Yield | Calcd. Mass Spec | Observed Mass Spec (M + H) |
|---|---|---|---|---|---|
| B-0049 | 4-F-phenyl | -C(O)-(2,4,6-trimethylphenyl) | 85 | 414 | 415 |
| B-0050 | 4-F-phenyl | -C(O)-CH₂-(2-F-5-CF₃-phenyl) | 9 | 458 | 459 |

-continued
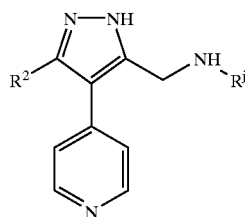
| Example# | R² | Rʲ | % Yield | Calcd. Mass Spec | Observed Mass Spec (M + H) |
|---|---|---|---|---|---|
| B-0051 | 4-F-C₆H₄ | 2,4,6-trifluorobenzoyl | 91 | 426 | 427 |
| B-0052 | 4-F-C₆H₄ | 6-chloropyridine-3-carbonyl | 79 | 407 | 408 |
| B-0053 | 4-F-C₆H₄ | 2-chloropyridine-3-carbonyl | 92 | 407 | 408 |
| B-0054 | 4-F-C₆H₄ | isoxazole-5-carbonyl | 92 | 363 | 364 |
| B-0055 | 4-F-C₆H₄ | 3-(2-F-6-Cl-phenyl)-5-methylisoxazole-4-carbonyl | 86 | 505 | 506 |
| B-0056 | 4-F-C₆H₄ | 3-(2-Cl-phenyl)-5-methylisoxazole-4-carbonyl | 86 | 487 | 488 |
| B-0057 | 4-F-C₆H₄ | 2-propylpentanoyl | 83 | 394 | 395 |

-continued
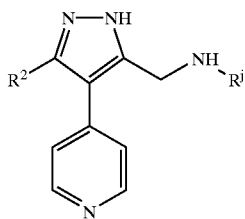
| Example# | R² | RJ | % Yield | Calcd. Mass Spec | Observed Mass Spec (M + H) |
|---|---|---|---|---|---|
| B-0058 | 4-F-phenyl | 3-chloro-benzothiophene-2-carbonyl | 86 | 462 | 463 |
| B-0059 | 4-F-phenyl | 2-ethoxy-naphthalene-1-carbonyl | 92 | 466 | 467 |
| B-0060 | 4-F-phenyl | 3-(trifluoromethoxy)benzoyl | 74 | 456 | 457 |
| B-0061 | 4-F-phenyl | 2-fluoro-4-(trifluoromethyl)benzoyl | 35 | 458 | 459 |
| B-0062 | 4-F-phenyl | 4-fluoro-2-(trifluoromethyl)benzoyl | 94 | 458 | 459 |
| B-0063 | 4-F-phenyl | benzoyl | 87 | 372 | 373 |
| B-0064 | 4-F-phenyl | nonanoyl | 5 | 394 | 395 |

-continued
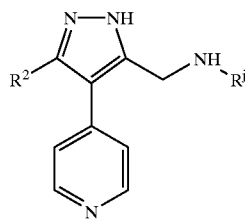
| Example# | R² | Rʲ | % Yield | Calcd. Mass Spec | Observed Mass Spec (M + H) |
|---|---|---|---|---|---|
| B-0065 | 4-F-C₆H₄ | 3-(chloromethyl)benzoyl | 87 | 420 | 395 |
| B-0066 | 4-F-C₆H₄ | cyclobutanoyl | 89 | 350 | 351 |
| B-0067 | 4-F-C₆H₄ | 3-methylbenzoyl | 92 | 386 | 387 |
| B-0068 | 4-F-C₆H₄ | 3,4-dimethoxybenzoyl | 89 | 432 | 433 |
| B-0069 | 4-F-C₆H₄ | 3-fluorobenzoyl | 37 | 390 | 391 |
| B-0070 | 4-F-C₆H₄ | 2,6-dimethoxybenzoyl | 18 | 432 | 433 |
| B-0071 | 4-F-C₆H₄ | 3,4-dichlorobenzoyl | 86 | 440 | 441 |

-continued
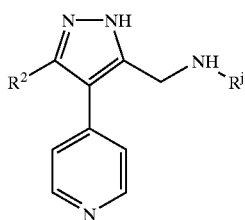
| Example# | R² | R^J | % Yield | Calcd. Mass Spec | Observed Mass Spec (M + H) |
|---|---|---|---|---|---|
| B-0072 | 4-F-C₆H₄ | 3,5-dimethoxybenzoyl | 3 | 432 | 433 |
| B-0073 | 4-F-C₆H₄ | 3-bromobenzoyl | 92 | 450 | 451 |
| B-0074 | 4-F-C₆H₄ | 2-fluorobenzoyl | 28 | 390 | 391 |
| B-0075 | 4-F-C₆H₄ | 3-methoxybenzoyl | 93 | 402 | 403 |
| B-0076 | 4-F-C₆H₄ | 3-phenylpropanoyl | 91 | 400 | 401 |
| B-0077 | 4-F-C₆H₄ | methyl 4-oxobutanoate | 84 | 382 | 383 |
| B-0078 | 4-F-C₆H₄ | methyl 5-oxopentanoate | 87 | 396 | 397 |
| B-0079 | 4-F-C₆H₄ | cyclopentanecarbonyl | 92 | 364 | 365 |

-continued
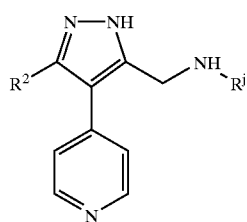
| Example# | R² | R^J | % Yield | Calcd. Mass Spec | Observed Mass Spec (M + H) |
|---|---|---|---|---|---|
| B-0080 | 4-F-phenyl | -C(O)CH2O-(2-NO2-phenyl) | 75 | 447 | 448 |
| B-0081 | 4-F-phenyl | -C(O)CH2CH2SCH3 | 54 | 370 | 371 |
| B-0082 | 4-F-phenyl | -C(O)-(4-CO2CH3-phenyl) | 80 | 430 | 431 |
| B-0083 | 4-F-phenyl | -C(O)CH(CH3)OC(O)CH3 | 81 | 382 | 383 |
| B-0084 | 4-F-phenyl | -C(O)CH2O-menthyl | 91 | 464 | 465 |
| B-0085 | 4-F-phenyl | -C(O)-(3,4,5-trimethoxyphenyl) | 25 | 462 | 463 |
| B-0086 | 4-F-phenyl | -C(O)-(2,4-dimethoxyphenyl) | 88 | 432 | 433 |

-continued
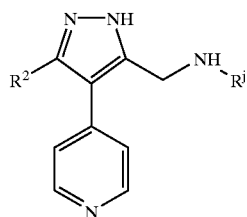
| Example# | R² | Rʲ | % Yield | Calcd. Mass Spec | Observed Mass Spec (M + H) |
|---|---|---|---|---|---|
| B-0087 | 4-F-C₆H₄ | -C(O)-CH(CH₃)-O-C₆H₅ | 95 | 416 | 417 |
| B-0088 | 4-F-C₆H₄ | -C(O)-(CH₂)₆-C(O)-OCH₃ |  | 438 | 439 |
| B-0089 | 4-F-C₆H₄ | -C(O)-cyclopropyl |  | 336 | 337 |
| B-0090 | 4-F-C₆H₄ | -C(O)-(3-acetoxyphenyl) |  | 444 | 445 |
| B-0091 | 4-F-C₆H₄ | -C(O)-CH₂-C(O)-OCH₃ |  | 368 | 369 |
| B-0092 | 4-F-C₆H₄ | -C(O)-(2-(benzoyloxymethyl)phenyl) |  | 506 | 507 |
| B-0093 | 4-F-C₆H₄ | -C(O)-CH₂-O-(4-Cl-C₆H₄) |  | 436 | 437 |
| B-0094 | 4-F-C₆H₄ | -C(O)-(N-trifluoroacetyl-pyrrolidin-2-yl) |  | 461 | 462 |

-continued
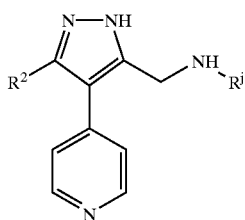
| Example# | R² | RJ | % Yield | Calcd. Mass Spec | Observed Mass Spec (M + H) |
|---|---|---|---|---|---|
| B-0095 | 4-F-C6H4 | 2,5-difluorobenzoyl | | 408 | 409 |
| B-0096 | 4-F-C6H4 | ethyl 4-oxopentanoate | | 410 | 411 |
| B-0097 | 4-F-C6H4 | 2-acetamido-4-methylthiazol-5-ylsulfonyl | 14 | 486 | 487 |
| B-0098 | 4-F-C6H4 | 4-acetamidophenylsulfonyl | 8 | 465 | — |
| B-0099 | 4-F-C6H4 | 4-methoxyphenylsulfonyl | 75 | 464 | 465 |
| B-0100 | 4-F-C6H4 | butylsulfonyl | 72 | 388 | 389 |
| B-0101 | 4-F-C6H4 | phenylsulfonyl | 23 | 408 | 409 |
| B-0102 | 4-F-C6H4 | 4-chloro-3-nitrophenylsulfonyl | 37 | 487 | 488 |

-continued
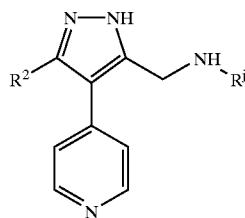
| Example# | R² | Rʲ | % Yield | Calcd. Mass Spec | Observed Mass Spec (M + H) |
|---|---|---|---|---|---|
| B-0103 | 4-F-C₆H₄ | 2-sulfonyl-4,6-dichlorophenol | 11 | 492 | 493 |
| B-0104 | 4-F-C₆H₄ | 4-F-C₆H₄-SO₂- | 59 | 426 | 427 |
| B-0105 | 4-F-C₆H₄ | Et-SO₂- | 79 | 360 | 361 |
| B-0106 | 4-F-C₆H₄ | iPr-SO₂- | 56 | 374 | 375 |
| B-0107 | 4-F-C₆H₄ | Me-SO₂- | 33 | 346 | 347 |
| B-0108 | 4-F-C₆H₄ | 2-(methoxycarbonyl)phenyl-SO₂- | 12 | 466 | 467 |
| B-0109 | 4-F-C₆H₄ | 2,4,6-trimethylphenyl-SO₂- | 65 | 450 | 451 |
| B-0110 | 4-F-C₆H₄ | 2-naphthyl-SO₂- | 55 | 458 | 459 |

-continued
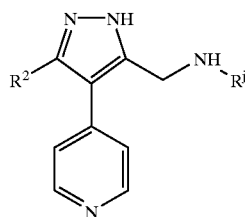
| Example# | R² | Rʲ | % Yield | Calcd. Mass Spec | Observed Mass Spec (M + H) |
|---|---|---|---|---|---|
| B-0111 | 4-F-phenyl | 1-naphthylsulfonyl | 41 | 458 | 459 |
| B-0112 | 4-F-phenyl | (2-nitrobenzyl)sulfonyl | 19 | 467 | 468 |
| B-0113 | 4-F-phenyl | 2-nitrophenylsulfonyl | 78 | 453 | 454 |
| B-0114 | 4-F-phenyl | 3-nitrophenylsulfonyl | 14 | 453 | 454 |
| B-0115 | 4-F-phenyl | 4-nitrophenylsulfonyl | 33 | 453 | — |
| B-0116 | 4-F-phenyl | 8-quinolinylsulfonyl | 11 | 459 | 487 |
| B-0117 | 4-F-phenyl | 4-methoxyphenylsulfonyl | 77 | 438 | 439 |
| B-0118 | 4-F-phenyl | 4-methylphenylsulfonyl | 52 | 422 | 423 |

-continued
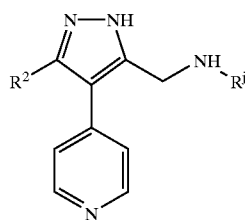
| Example# | R² | Rʲ | % Yield | Calcd. Mass Spec | Observed Mass Spec (M + H) |
|---|---|---|---|---|---|
| B-0119 | 4-F-phenyl | -SO₂-CH=CH-phenyl (cis) | 82 | 434 | 435 |
| B-0120 | 4-F-phenyl | -SO₂-CH₂-phenyl | 49 | 422 | 423 |
| B-0121 | 4-F-phenyl | -SO₂-(2-thienyl) | 64 | 414 | 415 |
| B-0122 | 4-F-phenyl | -SO₂-(5-dimethylamino-naphthalen-1-yl) | 87 | 501 | 502 |
| B-0123 | 4-F-phenyl | -SO₂-(4-isopropylphenyl) | 100 | 450 | 451 |
| B-0124 | 4-F-phenyl | -SO₂-(2-methyl-3-chlorophenyl) | 87 | 456 | 457 |
| B-0125 | 4-F-phenyl | -SO₂-(n-decyl) | 45 | 472 | 473 |

-continued
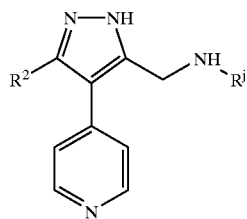
| Example# | R² | Rʲ | % Yield | Calcd. Mass Spec | Observed Mass Spec (M + H) |
|---|---|---|---|---|---|
| B-0126 | 4-F-phenyl | 2,4-dichlorophenylsulfonyl | 100 | 476 | 477 |
| B-0127 | 4-F-phenyl | 2-cyanophenylsulfonyl | 100 | 433 | 434 |
| B-0128 | 4-F-phenyl | 4,5-dichlorothien-2-ylsulfonyl | 100 | 482 | — |
| B-0129 | 4-F-phenyl | 4-butoxyphenylsulfonyl | 96 | 480 | 481 |
| B-0130 | 4-F-phenyl | 2,5-dimethoxyphenylsulfonyl | 93 | 468 | 469 |
| B-0131 | 4-F-phenyl | 3,4-dimethoxyphenylsulfonyl | 90 | 468 | 469 |
| B-0132 | 4-F-phenyl | 4-ethylphenylsulfonyl | 78 | 436 | 437 |

-continued
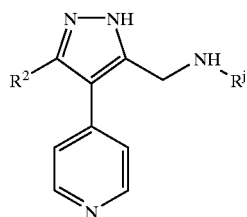
| Example# | R² | RJ | % Yield | Calcd. Mass Spec | Observed Mass Spec (M + H) |
|---|---|---|---|---|---|
| B-0133 | 4-F-C₆H₄ | 2-F-C₆H₄-SO₂- | 76 | 426 | 427 |
| B-0134 | 4-F-C₆H₄ | 2,4-diF-C₆H₃-SO₂- | 87 | 444 | 445 |
| B-0135 | 4-F-C₆H₄ | 3,4-diCl-C₆H₃-SO₂- | 67 | 476 | 477 |
| B-0136 | 4-F-C₆H₄ | 4,5-diBr-thien-2-yl-SO₂- | 100 | 570 | — |
| B-0137 | 4-F-C₆H₄ | 4-OMe-2,3,6-triMe-C₆H-SO₂- | 35 | 480 | 481 |
| B-0138 | 4-F-C₆H₄ | naphtho[oxadiazole]-SO₂- | 60 | 500 | — |
| B-0139 | 4-F-C₆H₄ | 5-(N,N-di-n-Bu-amino)-naphth-1-yl-SO₂- | 73 | 585 | 586 |
| B-0140 | 4-F-C₆H₄ | 4-vinyl-C₆H₄-SO₂- | 62 | 434 | 459 |

-continued

| Example# | R² | Rᴶ | % Yield | Calcd. Mass Spec | Observed Mass Spec (M + H) |
|---|---|---|---|---|---|
| B-0141 | 4-F-phenyl | 4-methoxy-2-nitrophenylsulfonyl | 100 | 483 | 484 |
| B-0142 | 4-F-phenyl | n-octylsulfonyl | 90 | 444 | 445 |
| B-0143 | 4-F-phenyl | 4-(trifluoromethoxy)phenylsulfonyl | 61 | 492 | 493 |
| B-0144 | 4-F-phenyl | 5-chlorothiophen-2-ylsulfonyl | 49 | 448 | 449 |
| B-0145 | 4-F-phenyl | (3-(methylthio)phenyl)aminocarbonyl | 48 | 433 | 434 |
| B-0146 | 4-F-phenyl | benzoylaminocarbonyl | 32 | 415 | 416 |

-continued
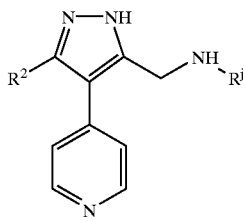
| Example# | R² | R^J | % Yield | Calcd. Mass Spec | Observed Mass Spec (M + H) |
|---|---|---|---|---|---|
| B-0147 | 4-F-phenyl | methionine ethyl ester amide | 67 | 471 | 472 |
| B-0148 | 4-F-phenyl | -C(O)NH-CH(CH₂F)-C(O)-C(O)-CH₂CH₃ | 79 | 465 | — |
| B-0149 | 4-F-phenyl | -C(O)NH-iPr | 65 | 353 | 354 |
| B-0150 | 4-F-phenyl | -C(O)NH-(4-Cl-phenyl) | 53 | 465 | 466 |
| B-0151 | 4-F-phenyl | -C(O)NH-CH₂-phenyl | 68 | 401 | 402 |

-continued
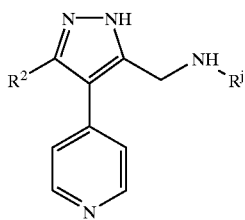
| Example# | R² | R^J | % Yield | Calcd. Mass Spec | Observed Mass Spec (M + H) |
|---|---|---|---|---|---|
| B-0152 | 4-F-phenyl | ethyl carbamoyl-CH₂- | 39 | 383 | — |
| B-0153 | 4-F-phenyl | trans-2-phenylcyclopropyl amide | 96 | 427 | 428 |
| B-0154 | 4-F-phenyl | 3-(ethoxycarbonyl)phenyl amide | 44 | 459 | 460 |
| B-0155 | 4-F-phenyl | 4-phenoxyphenyl amide | 74 | 479 | 480 |
| B-0156 | 4-F-phenyl | 4-butoxyphenyl amide | 44 | 459 | 460 |

-continued
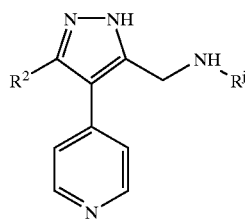
| Example# | R² | Rʲ | % Yield | Calcd. Mass Spec | Observed Mass Spec (M + H) |
|---|---|---|---|---|---|
| B-0157 | 4-F-phenyl | -C(O)NH-CH₂CH₂-phenyl | 72 | 415 | 416 |
| B-0158 | 4-F-phenyl | -C(O)NH-(2-CO₂Me-phenyl) | 96 | 445 | 446 |
| B-0159 | 4-F-phenyl | -C(O)NH-CH₂CH₂-C(O)OEt | 97 | 411 | 412 |
| B-0160 | 4-F-phenyl | -C(O)NH-(3-OMe-phenyl) | 49 | 417 | 418 |
| B-0161 | 4-F-phenyl | -NH-C(O)-(4-CO₂Et-phenyl) | 93 | 459 | 460 |

-continued
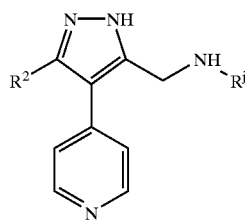
| Example# | R² | Rʲ | % Yield | Calcd. Mass Spec | Observed Mass Spec (M + H) |
|---|---|---|---|---|---|
| B-0162 | 4-F-phenyl | 2-F-phenyl-NHC(O)- | 91 | 405 | 406 |
| B-0163 | 4-F-phenyl | 4-CF₃-phenyl-NHC(O)- | 94 | 455 | 456 |
| B-0164 | 4-F-phenyl | 3,5-diCl-phenyl-NHC(O)- | 84 | 455 | 456 |
| B-0165 | 4-F-phenyl | ethyl alaninate amide | 52 | 411 | 412 |
| B-0166 | 4-F-phenyl | 2-OMe-phenyl-NHC(O)- | 72 | 417 | 418 |
| B-0167 | 4-F-phenyl | 2,4-diOMe-phenyl-NHC(O)- | 66 | 447 | 448 |

-continued
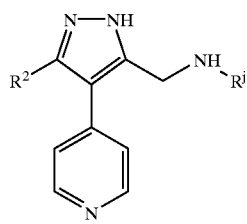
| Example# | R² | Rʲ | % Yield | Calcd. Mass Spec | Observed Mass Spec (M + H) |
|---|---|---|---|---|---|
| B-0168 | 4-F-phenyl | N-(2,6-dimethylphenyl)amide | 27 | 415 | 416 |
| B-0169 | 4-F-phenyl | N-(2-ethylphenyl)amide | 91 | 415 | 416 |
| B-0170 | 4-F-phenyl | N-allylamide | 8 | 351 | 352 |
| B-0171 | 4-F-phenyl | 1-naphthyl ketone | 10 | 437 | 438 |
| B-0172 | 4-F-phenyl | N-(4-trifluoromethoxyphenyl)amide | 62 | 471 | 472 |
| B-0173 | 4-F-phenyl | N-(3,4-dichlorophenyl)amide | 40 | 455 | 456 |

-continued
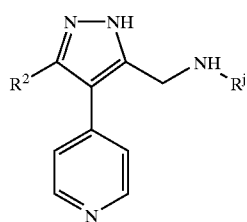
| Example# | R² | R? | % Yield | Calcd. Mass Spec | Observed Mass Spec (M + H) |
|---|---|---|---|---|---|
| B-0174 | 4-F-C₆H₄ | -C(O)NH-(4-F-C₆H₄) | 92 | 405 | 406 |
| B-0175 | 4-F-C₆H₄ | -C(O)NH-C₆H₅ | 96 | 387 | 388 |
| B-0176 | 4-F-C₆H₄ | -C(O)NH-CH(CH₃)-C₆H₅ | 25 | 415 | 416 |
| B-0177 | 4-F-C₆H₄ | -C(O)NH-CH₂-C(O)O-CH₂CH₃ | 100 | 397 | 398 |
| B-0178 | 4-F-C₆H₄ | -C(O)NH-(4-iPr-C₆H₄) | 34 | 429 | 430 |
| B-0179 | 4-F-C₆H₄ | -C(O)NH-(2-iPr-C₆H₄) | 72 | 429 | 430 |

-continued
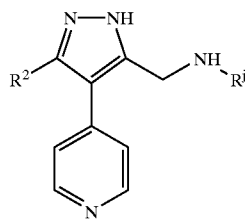
| Example# | R² | Rᴊ | % Yield | Calcd. Mass Spec | Observed Mass Spec (M + H) |
|---|---|---|---|---|---|
| B-0180 | 4-F-C₆H₄ | -C(O)NH-(4-phenyl)C₆H₄ | 91 | 463 | 464 |
| B-0181 | 4-F-C₆H₄ | -C(O)NH-(2-phenyl)C₆H₄ | 100 | 463 | 464 |
| B-0182 | 4-F-C₆H₄ | -C(O)NH-(2,5-dimethoxy)C₆H₃ | 50 | 447 | 448 |
| B-0183 | 4-F-C₆H₄ | -C(O)NH-(2,5-dichloro)C₆H₃ | 22 | 455 | 456 |
| B-0184 | 4-F-C₆H₄ | -C(O)NH-CH(CH₃)(1-naphthyl) | 63 | 465 | 466 |

-continued
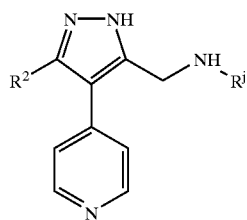
| Example# | R² | Rʲ | % Yield | Calcd. Mass Spec | Observed Mass Spec (M + H) |
|---|---|---|---|---|---|
| B-0185 | 4-F-phenyl | 2-(OCF₃)phenyl-NH-C(O)- | 65 | 471 | 472 |
| B-0186 | 4-F-phenyl | 2,4,6-trimethylphenyl-NH-C(O)- | 42 | 429 | 430 |
| B-0187 | 4-F-phenyl | 2,5-dimethoxyphenyl-NH-C(O)- | 62 | 481 | 482 |
| B-0188 | 4-F-phenyl | Val-OEt amide | 98 | 439 | 440 |
| B-0189 | 4-F-phenyl | Leu-OEt amide | 21 | 453 | 454 |
| B-0190 | 4-F-phenyl | 4-methoxyphenyl-NH-C(O)- | 57 | 417 | 418 |

-continued
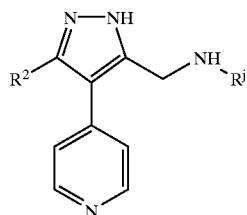
| Example# | R² | Rʲ | % Yield | Calcd. Mass Spec | Observed Mass Spec (M + H) |
|---|---|---|---|---|---|
| B-0191 | 4-F-phenyl | 3,4,5-trimethoxyphenyl-NH-C(O)- | 24 | 477 | 478 |
| B-0192 | 4-F-phenyl | 2,3-dichlorophenyl-NH-C(O)- | 35 | 455 | 456 |
| B-0193 | 4-F-phenyl | thiophene-2-C(O)- | 42 | 378 | 379 |
| B-0194 | 4-F-phenyl | prolyl (S) | 65 | 365 | 366 |
| B-0195 | 4-F-phenyl | N-Fmoc-prolyl | 93 | 587 | 588 |
| B-0196 | 4-F-phenyl | prolyl (R) | 82 | 365 | 366 |

-continued
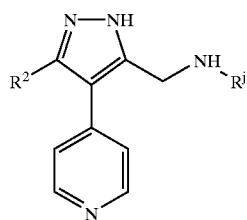
| Example# | R² | Rʲ | % Yield | Calcd. Mass Spec | Observed Mass Spec (M + H) |
|---|---|---|---|---|---|
| B-0197 | 4-F-C₆H₄ | Fmoc-proline carbonyl | 100 | 587 | 588 |
| B-0198 | 4-F-C₆H₄ | 2-pyridyl-C(O)- | 86 | 373 | 374 |
| B-0199 | 4-F-C₆H₄ | 4-pyridyl-C(O)- | 81 | 373 | 374 |
| B-200 | 4-F-C₆H₄ | 3-pyridyl-C(O)- | 78 | 373 | 374 |
| B-0201 | 4-F-C₆H₄ | t-Bu-C(O)- | 95 | 352 | 353 |
| B-0202 | 4-F-C₆H₄ | PhO-CH(CH₃)-C(O)- | 100 | 416 | 417 |
| B-0203 | 4-F-C₆H₄ | n-PrO-C(O)- | 69 | 354 | 355 |
| B-0204 | 4-F-C₆H₄ | EtO-C(O)- | 93 | 340 | 341 |

-continued
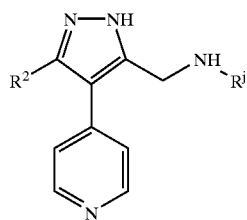
| Example# | R² | Rʲ | % Yield | Calcd. Mass Spec | Observed Mass Spec (M + H) |
|---|---|---|---|---|---|
| B-0205 | 4-F-C₆H₄- | -C(O)-O-iPr | 94 | 354 | 355 |
| B-0206 | 4-F-C₆H₄- | -C(O)-quinoxalin-2-yl | 79 | 424 | 425 |
| B-0207 | 4-F-C₆H₄- | -C(O)-O-Me | 82 | 326 | 327 |
| B-0208 | 4-F-C₆H₄- | -C(O)-thiophen-2-yl | 88 | 378 | 379 |
| B-0209 | 4-F-C₆H₄- | -C(O)-furan-2-yl | 83 | 362 | 363 |
| B-0210 | 4-F-C₆H₄- | -C(O)-CF₃ | 100 | 364 | 365 |
| B-0211 | 4-F-C₆H₄- | -C(O)-NH-Me | 60 | 325 | 326 |
| B-0212 | 4-F-C₆H₄- | -C(O)-NH-Et | 79 | 339 | 340 |
| B-0213 | 4-F-C₆H₄- | -C(O)-NH-nPr | 71 | 353 | 354 |

-continued
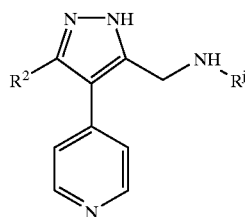
| Example# | R² | Rʲ | % Yield | Calcd. Mass Spec | Observed Mass Spec (M + H) |
|---|---|---|---|---|---|
| B-0214 | 4-F-C₆H₄ | –C(O)NH₂ | 77 | 311 | 312 |
| B-0215 | 4-F-C₆H₄ | –C(O)N(CH₃)₂ | 24 | 353 | 354 |
| B-0216 | 4-F-C₆H₄ | –C(O)-morpholinyl | | 339 | 340 |
| B-0217 | 4-F-C₆H₄ | –C(O)-pyrrolidinyl | | 381 | 382 |
| B-0218 | 4-F-C₆H₄ | –C(O)N(CH₃)Ph | | 365 | 366 |
| B-0219 | 4-F-C₆H₄ | –C(O)NH-CH(CH₃)Ph | | 401 | 402 |
| B-0220 | 4-F-C₆H₄ | –CH(CH₃)C(O)N(Et)₂ | | 415 | 416 |
| B-0221 | 4-F-C₆H₄ | –SO₂CF₃ | | 367 | 368 |
| B-0222 | 4-F-C₆H₄ | 4-methyl-2-(acetylamino)thiazol-5-ylsulfonyl | 96 | 486 | 487 |

-continued
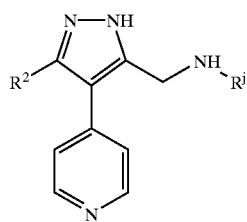
| Example# | R² | RJ | % Yield | Calcd. Mass Spec | Observed Mass Spec (M + H) |
|---|---|---|---|---|---|
| B-0223 | 4-F-phenyl | 4-(acetamido)phenylsulfonyl | 100 | 465 | 466 |
| B-0224 | 4-F-phenyl | 4-bromophenylsulfonyl | 75 | 486 | 509a |
| B-0225 | 4-F-phenyl | 4-chlorophenylsulfonyl | 100 | 442 | 443 |
| B-0226 | 4-F-phenyl | camphorsulfonyl | 88 | 482 | 483 |
| B-0227 | 4-F-phenyl | camphorsulfonyl | 73 | 482 | 483 |
| B-0228 | 4-F-phenyl | 2-carboxyphenylsulfonyl | 37 | 452 | — |
| B-0229 | 4-F-phenyl | 2,5-dichlorophenylsulfonyl | 100 | 476 | 477 |

-continued
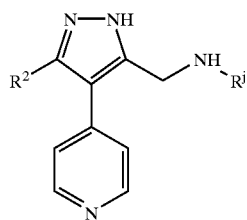
| Example# | R² | Rʲ | % Yield | Calcd. Mass Spec | Observed Mass Spec (M + H) |
|---|---|---|---|---|---|
| B-0230 | 4-F-phenyl | 2,3-diCl-phenylsulfonyl | 94 | 476 | 477 |
| B-0231 | 4-F-phenyl | 2-Cl-4-F-phenylsulfonyl | 100 | 460 | 461 |
| B-0232 | 4-F-phenyl | 2-Me-5-F-phenylsulfonyl | 90 | 440 | 441 |
| B-0233 | 4-F-phenyl | 2,6-diCl-phenylsulfonyl | 99 | 476 | 477 |
| B-0234 | 4-F-phenyl | 2-Br-phenylsulfonyl | 100 | 486 | 487,489 |
| B-0235 | 4-F-phenyl | 3-Br-phenylsulfonyl | 89 | 486 | 487,489 |
| B-0236 | 4-F-phenyl | 2-CF₃-phenylsulfonyl | 100 | 476 | 477 |
| B-0237 | 4-F-phenyl | 4-CF₃-phenylsulfonyl | 100 | 476 | 477 |

-continued
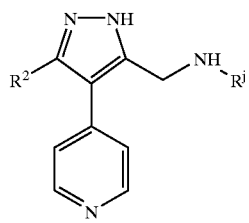
| Example# | R² | Rʲ | % Yield | Calcd. Mass Spec | Observed Mass Spec (M + H) |
|---|---|---|---|---|---|
| B-0238 | 4-F-C₆H₄ | 3-methylphenylsulfonyl | 92 | 438 | — |
| B-0239 | 4-F-C₆H₄ | 3-chlorophenylsulfonyl | 100 | 442 | 443 |
| B-0240 | 4-F-C₆H₄ | 2-chlorophenylsulfonyl | 100 | 442 | 443 |
| B-0241 | 4-F-C₆H₄ | 3,5-dichlorophenylsulfonyl | 100 | 476 | 477 |
| B-0242 | 4-F-C₆H₄ | 3-chloro-4-fluorophenylsulfonyl | 100 | 460 | 461 |
| B-0243 | 4-F-C₆H₄ | 2-chloro-6-methylphenylsulfonyl | 87 | 456 | 457 |
| B-0244 | 4-F-C₆H₄ | 2,5-dimethylphenylsulfonyl | 100 | 436 | 437 |
| B-0245 | 4-F-C₆H₄ | 2-methylphenylsulfonyl | 100 | 422 | 423 |

-continued
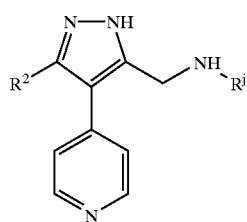
| Example# | R² | RJ | % Yield | Calcd. Mass Spec | Observed Mass Spec (M + H) |
|---|---|---|---|---|---|
| B-0246 | 4-F-C6H4 | 2-methoxy-5-methylphenylsulfonyl | 100 | 452 | 453 |
| B-0247 | 4-F-C6H4 | 3-CF3-phenylsulfonyl | 100 | 476 | 477 |
| B-0248 | 4-F-C6H4 | camphorsulfonyl | 73 | 468 | — |
| B-0249 | 4-F-C6H4 | 5-bromo-2-methoxyphenylsulfonyl | 100 | 516 | 517,519 |
| B-0250 | 4-F-C6H4 | 2-naphthylsulfonyl | 72 | 458 | — |
| B-0251 | 4-F-C6H4 | 3,5-dimethylisoxazol-4-ylsulfonyl | 100 | 427 | 428 |
| B-0252 | 4-F-C6H4 | benzo[1,2,5]oxadiazol-4-ylsulfonyl | 100 | 450 | 451 |

-continued
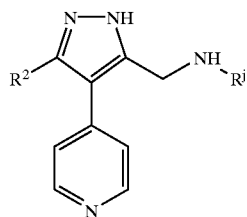
| Example# | R² | RJ | % Yield | Calcd. Mass Spec | Observed Mass Spec (M + H) |
|---|---|---|---|---|---|
| B-0253 | 4-F-C₆H₄ | 5-chloro-2-methoxyphenyl sulfonyl | 100 | 472 | 473 |
| B-0254 | 4-F-C₆H₄ | 4-cyanophenyl sulfonyl | 100 | 433 | 434 |
| B-0255 | 4-F-C₆H₄ | 5-(benzamidomethyl)thien-2-yl sulfonyl | 84 | 547 | 548 |
| B-0256 | 4-F-C₆H₄ | biphenyl-4-yl sulfonyl | 100 | 484 | 507a |
| B-0257 | 4-F-C₆H₄ | 2,2,5,7,8-pentamethylchroman-6-yl sulfonyl | 85 | 534 | 535 |
| B-0258 | 4-F-C₆H₄ | 5-(pyridin-2-yl)thien-2-yl sulfonyl | 100 | 491 | 492 |
| B-0259 | 4-F-C₆H₄ | 4-(phenylsulfonyl)thien-2-yl sulfonyl | 100 | 554 | 555 |

-continued
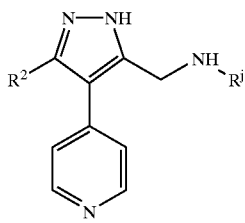
| Example# | R² | Rʲ | % Yield | Calcd. Mass Spec | Observed Mass Spec (M + H) |
|---|---|---|---|---|---|
| B-0260 | 4-F-C₆H₄ | 2-methyl-5-(methylsulfonyl)phenylsulfonyl | 91 | 500 | 501 |
| B-0261 | 4-F-C₆H₄ | 3-(methylsulfonyl)phenylsulfonyl | 100 | 486 | 487 |
| B-0262 | 4-F-C₆H₄ | 5-(isoxazol-3-yl)thiophen-2-ylsulfonyl | 100 | 481 | 482 |
| B-0263 | 4-F-C₆H₄ | 5-(phenylsulfonyl)thiophen-2-ylsulfonyl | 100 | 554 | 555 |
| B-0264 | 4-F-C₆H₄ | N,N-dimethylsulfamoyl | 75 | 375 | 376 |
| B-0265 | 4-F-C₆H₄ | isoquinolin-5-ylsulfonyl | 71 | 459 | 460 |
| B-0266 | 4-F-C₆H₄ | 1-methyl-1H-imidazol-4-ylsulfonyl | 100 | 412 | 413 |

-continued

| Example# | R² | Rʲ | % Yield | Calcd. Mass Spec | Observed Mass Spec (M + H) |
|---|---|---|---|---|---|
| B-0267 | 4-F-C₆H₄ | 2-methylbenzoyl | 100 | 386 | 387 |
| B-0268 | 4-F-C₆H₄ | 4-chlorobenzoyl | 89 | 406 | 407 |
| B-0269 | 4-F-C₆H₄ | 4-methylbenzoyl | 84 | 386 | 387 |
| B-0270 | 4-F-C₆H₄ | 3-(trifluoromethyl)benzoyl | 92 | 440 | 441 |
| B-0271 | 4-F-C₆H₄ | benzo[b]thiophene-2-carbonyl | 98 | 428 | 429 |
| B-0272 | 4-F-C₆H₄ | 2,4,6-triisopropylbenzoyl | 57 | 498 | 499 |
| B-0273 | 4-F-C₆H₄ | 3,5-dichlorobenzoyl | 100 | 440 | 441 |

-continued

| Example# | R² | Rʲ | % Yield | Calcd. Mass Spec | Observed Mass Spec (M + H) |
|---|---|---|---|---|---|
| B-0274 | 4-F-C₆H₄ | 3-CN-C₆H₄-C(O)- | 94 | 397 | 398 |
| B-0275 | 4-F-C₆H₄ | 1-naphthyl-C(O)- | 90 | 422 | 423 |
| B-0276 | 4-F-C₆H₄ | 3,4-diF-C₆H₃-C(O)- | 100 | 408 | 409 |
| B-0277 | 4-F-C₆H₄ | 3,5-diF-C₆H₃-C(O)- | 88 | 408 | 409 |
| B-0278 | 4-F-C₆H₄ | 2,3,6-triF-C₆H₂-C(O)- | 100 | 426 | 427 |
| B-0279 | 4-F-C₆H₄ | 2,3-diCl-C₆H₃-C(O)- | 54 | 440 | 441 |
| B-0280 | 4-F-C₆H₄ | 2,4,6-triMe-C₆H₂-C(O)- | 79 | 414 | 415 |

-continued
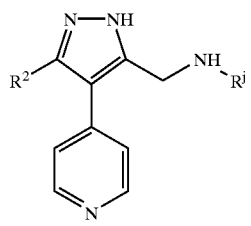
| Example# | R² | R^J | % Yield | Calcd. Mass Spec | Observed Mass Spec (M + H) |
|---|---|---|---|---|---|
| B-0281 | 4-F-C₆H₄ | 2-F-5-CF₃-C₆H₃-C(O)- | 82 | 458 | 459 |
| B-0282 | 4-F-C₆H₄ | 2,4,6-triF-C₆H₂-C(O)- | 89 | 426 | 427 |
| B-0283 | 4-F-C₆H₄ | 2-F-4-CF₃-C₆H₃-C(O)- | 90 | 458 | 459 |
| B-0284 | 4-F-C₆H₄ | 2-F-6-CF₃-C₆H₃-C(O)- | 100 | 458 | 459 |
| B-0285 | 4-F-C₆H₄ | 2-F-3-CF₃-C₆H₃-C(O)- | 94 | 458 | 459 |
| B-0286 | 4-F-C₆H₄ | 2-CF₃-4-F-C₆H₃-C(O)- | 100 | 458 | 459 |
| B-0287 | 4-F-C₆H₄ | 3-CF₃-4-F-C₆H₃-C(O)- | 96 | 458 | 459 |

-continued
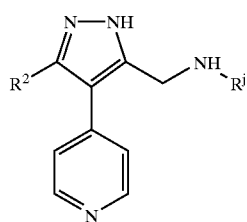
| Example# | R² | Rʲ | % Yield | Calcd. Mass Spec | Observed Mass Spec (M + H) |
|---|---|---|---|---|---|
| B-0288 | 4-F-C₆H₄ | 3-CF₃-5-F-C₆H₃-C(O)- | 100 | 458 | 459 |
| B-0289 | 4-F-C₆H₄ | 2-Cl-C₆H₄-C(O)- | 96 | 406 | 407 |
| B-0290 | 4-F-C₆H₄ | 3-CH₃-C₆H₄-C(O)- | 96 | 386 | 387 |
| B-0291 | 4-F-C₆H₄ | 2,4-diCl-C₆H₃-C(O)- | 95 | 440 | 441 |
| B-0292 | 4-F-C₆H₄ | 3-F-C₆H₄-C(O)- | 94 | 390 | 391 |
| B-0293 | 4-F-C₆H₄ | 2,3-diF-C₆H₃-C(O)- | 100 | 408 | 409 |
| B-0294 | 4-F-C₆H₄ | 2,6-diCl-C₆H₃-C(O)- | 100 | 440 | 441 |

-continued
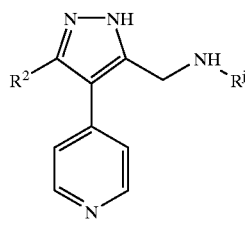
| Example# | R² | Rʲ | % Yield | Calcd. Mass Spec | Observed Mass Spec (M + H) |
|---|---|---|---|---|---|
| B-0295 | 4-F-C₆H₄ | 2,5-diF-C₆H₃-C(O)- | 91 | 408 | 409 |
| B-0296 | 4-F-C₆H₄ | 2,4,5-triF-C₆H₂-C(O)- | 96 | 426 | 427 |
| B-0297 | 4-F-C₆H₄ | 2-F-C₆H₄-C(O)- | 88 | 390 | 391 |
| B-0298 | 4-F-C₆H₄ | 2,6-diF-C₆H₃-C(O)- | 95 | 408 | 409 |
| B-0299 | 4-F-C₆H₄ | 2,4-diF-C₆H₃-C(O)- | 90 | 408 | 409 |
| B-0300 | 4-F-C₆H₄ | 3-Cl-C₆H₄-C(O)- | 95 | 406 | 407 |
| B-0301 | 4-F-C₆H₄ | 2-Br-C₆H₄-C(O)- | 99 | 450 | 451,453 |
| B-0302 | 4-F-C₆H₄ | 4-CF₃-C₆H₄-C(O)- | 94 | 440 | 441 |

-continued
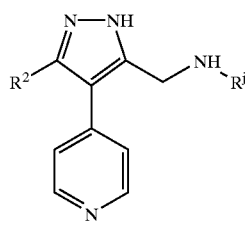
| Example# | R² | R^J | % Yield | Calcd. Mass Spec | Observed Mass Spec (M + H) |
|---|---|---|---|---|---|
| B-0303 | 4-F-phenyl | 2-thienyl-C(O)- | 100 | 378 | 379 |
| B-0304 | 4-F-phenyl | 3,5-dimethylisoxazol-4-yl-C(O)- | 100 | 391 | 392 |
| B-0305 | 3-Cl-phenyl | CH₃-C(O)- | 70 | 326 | 327 |
| B-0306 | 3-Cl-phenyl | CH₃CH₂-C(O)- | 59 | 340 | 341 |
| B-0307 | 3-Cl-phenyl | (CH₃)₂CH-C(O)- | 59 | 354 | 355 |
| B-0308 | 3-Cl-phenyl | (CH₃)₃C-C(O)- | 60 | 368 | 369 |
| B-0309 | 3-Cl-phenyl | cyclopropyl-C(O)- | 61 | 352 | 353 |
| B-0310 | 3-Cl-phenyl | cyclobutyl-C(O)- | 61 | 366 | 367 |

-continued
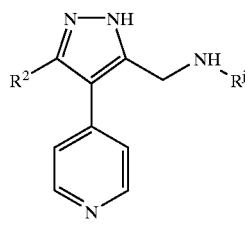
| Example# | R² | Rʲ | % Yield | Calcd. Mass Spec | Observed Mass Spec (M + H) |
|---|---|---|---|---|---|
| B-0311 | 3-Cl-phenyl | -C(O)CH₂OCH₃ | 65 | 356 | 357 |
| B-0312 | 3-Cl-phenyl | -C(O)OCH₃ | 75 | 342 | 343 |
| B-0313 | 3-Cl-phenyl | -C(O)OCH₂CH₃ | 68 | 356 | 357 |
| B-0314 | 3-Cl-phenyl | -C(O)OCH(CH₃)₂ | 31 | 370 | 371 |
| B-0315 | 3-Cl-phenyl | -C(O)OCH₂CH(CH₃)₂ | 61 | 384 | 385 |
| B-0316 | 3-Cl-phenyl | -C(O)OCH₂CH=CH₂ | 75 | 368 | 369 |
| B-0317 | 3-Cl-phenyl | -C(O)OCH₂C≡CH | 62 | 366 | 367 |
| B-0318 | 3-Cl-phenyl | -C(O)phenyl | 52 | 388 | 389 |

-continued
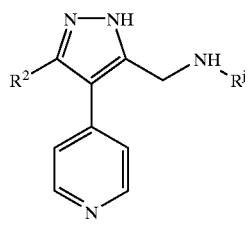
| Example# | R² | RJ | % Yield | Calcd. Mass Spec | Observed Mass Spec (M + H) |
|---|---|---|---|---|---|
| B-0319 | 3-Cl-phenyl | 2,6-diF-benzoyl | 53 | 424 | 425 |
| B-0320 | 3-Cl-phenyl | 2,4-diF-benzoyl | 50 | 424 | 425 |
| B-0321 | 3-Cl-phenyl | 2,4,6-triF-benzoyl | 54 | 442 | 443 |
| B-0322 | 3-Cl-phenyl | 2-CF₃-6-F-benzoyl | 64 | 474 | 475 |
| B-0323 | 3-Cl-phenyl | 2-CF₃-4-F-benzoyl | 58 | 474 | 475 |
| B-0324 | 3-Cl-phenyl | 2-Cl-benzoyl | 60 | 422 | 423 |
| B-0325 | 3-Cl-phenyl | 3-Cl-benzoyl | 64 | 422 | 423 |

-continued
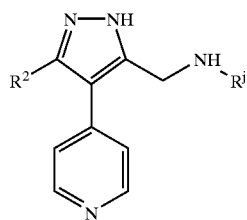
| Example# | R² | Rʲ | % Yield | Calcd. Mass Spec | Observed Mass Spec (M + H) |
|---|---|---|---|---|---|
| B-0326 | 3-Cl-phenyl | C(=O)-(4-Cl-phenyl) | 58 | 422 | 423 |
| B-0327 | 3-Cl-phenyl | C(=O)-(2-furyl) | 63 | 378 | 379 |
| B-0328 | 3-Cl-phenyl | C(=O)-(2-pyridyl) | 68 | 389 | 390 |
| B-0329 | 3-Cl-phenyl | S(=O)₂-CH₃ | 63 | 362 | 363 |
| B-0330 | 3-Cl-phenyl | S(=O)₂-Et | 48 | 376 | 377 |
| B-0331 | 3-Cl-phenyl | S(=O)₂-phenyl | 66 | 424 | 425 |
| B-0332 | 3-Cl-phenyl | S(=O)₂-(4-F-phenyl) | 61 | 442 | 443 |
| B-0333 | 3-Cl-phenyl | S(=O)₂-(4-Cl-phenyl) | 60 | 458 | 459 |

-continued
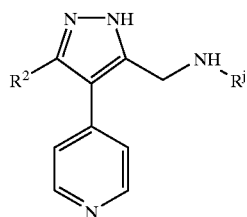
| Example# | R² | Rʲ | % Yield | Calcd. Mass Spec | Observed Mass Spec (M + H) |
|---|---|---|---|---|---|
| B-0334 | 3-Cl-phenyl | 4-Br-phenylsulfonyl | 55 | 502 | 503 |
| B-0335 | 3-Cl-phenyl | 4-OMe-phenylsulfonyl | 60 | 454 | 455 |
| B-0336 | 3-Cl-phenyl | 4-phenyl-phenylsulfonyl | 100 | 500 | 501 |
| B-0337 | 3-Cl-phenyl | 3-Cl-phenylsulfonyl | 65 | 458 | — |
| B-0338 | 3-Cl-phenyl | 3-Br-phenylsulfonyl | 69 | 502 | 503 |
| B-0339 | 3-Cl-phenyl | 3-Me-phenylsulfonyl | 69 | 454 | — |
| B-0340 | 3-Cl-phenyl | 3-CF₃-phenylsulfonyl | 77 | 492 | 493 |
| B-0341 | 3-Cl-phenyl | 2-Cl-phenylsulfonyl | 64 | 458 | 459 |

-continued
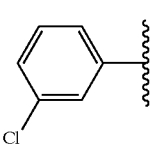
| Example# | R² | Rʲ | % Yield | Calcd. Mass Spec | Observed Mass Spec (M + H) |
|---|---|---|---|---|---|
| B-0342 | 3-Cl-phenyl | sulfonyl-CH₂-phenyl | 41 | 438 | — |
| B-0343 | 3-Cl-phenyl | sulfonyl-(2-thienyl) | 63 | 430 | 431 |
| B-0344 | 3-Cl-phenyl | sulfonyl-(5-Cl-2-thienyl) | 96 | 464 | 465 |
| B-0345 | 3-Cl-phenyl | sulfonyl-(5-(2-pyridyl)-2-thienyl) | 62 | 507 | 508 |
| B-0346 | 3-Cl-phenyl | sulfonyl-(5-(3-isoxazolyl)-2-thienyl) | 56 | 497 | 498 |
| B-0347 | 3-Cl-phenyl | C(O)NHCH₃ | 61 | 341 | 342 |
| B-0348 | 3-Cl-phenyl | C(O)NH-allyl | 3 | 367 | — |
| B-0349 | 3-Cl-phenyl | C(O)NH-phenyl | 57 | 403 | 404 |

-continued
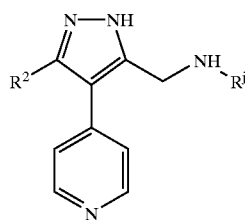
| Example# | R² | Rʲ | % Yield | Calcd. Mass Spec | Observed Mass Spec (M + H) |
|---|---|---|---|---|---|
| B-0350 | 3-Cl-C₆H₄- | -C(O)NH-(3-Br-C₆H₄) | 57 | 481 | 482 |
| B-0351 | 3-Cl-C₆H₄- | -C(O)N(CH₃)₂ | 31 | 355 | 356 |
| B-0352 | 3-Cl-C₆H₄- | -C(O)-morpholinyl | 51 | 397 | 398 |
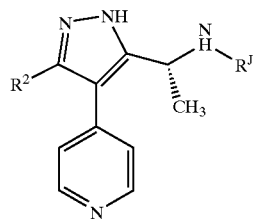
| Example # | R² | Rʲ | % Yield | Calcd. Mass Spec | Observed Mass Spec (M + H) |
|---|---|---|---|---|---|
| B-0353 | 4-F-C₆H₄- | -C(O)CH₂-OC(O)CH₃ | 71 | 382 | 383 |
| B-0354 | 4-F-C₆H₄- | -C(O)-(2-I-C₆H₄) | 35 | 512 | 513 |

-continued
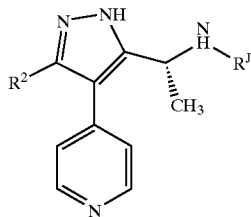
| Example # | R² | R^J | % Yield | Calcd. Mass Spec | Observed Mass Spec (M + H) |
|---|---|---|---|---|---|
| B-0355 | 4-F-C₆H₄- | -C(O)-CH(CH₃)₂ | 37 | 352 | 353 |
| B-0356 | 4-F-C₆H₄- | -C(O)-(4-F-C₆H₄) | 57 | 404 | 405 |
| B-0357 | 4-F-C₆H₄- | -C(O)-O-CH₂-CH=CH₂ | 88 | 366 | 367 |
| B-0358 | 4-F-C₆H₄- | -C(O)-C(CH₃)₂-O-C(O)-CH₃ | 88 | 410 | 411 |
| B-0359 | 4-F-C₆H₄- | -C(O)-CH₃ | 100 | 324 | 325 |
| B-0360 | 4-F-C₆H₄- | -C(O)-cyclobutyl | 56 | 364 | 365 |
| B-0361 | 4-F-C₆H₄- | -C(O)-cyclopropyl | 70 | 350 | 351 |
| B-0362 | 4-F-C₆H₄- | -C(O)-(3-Br-C₆H₄) | 100 | 464 | 465 |

-continued
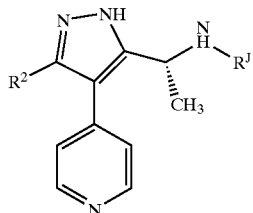
| Example # | R² | Rᴶ | % Yield | Calcd. Mass Spec | Observed Mass Spec (M + H) |
|---|---|---|---|---|---|
| B-0363 | 4-F-C₆H₄ | 4-I-C₆H₄-C(O)- | 73 | 512 | 513 |
| B-0364 | 4-F-C₆H₄ | isoxazol-5-yl-C(O)- | 88 | 377 | 378 |
| B-0365 | 4-F-C₆H₄ | CH₃C(O)O-CH(CH₃)-C(O)- | 70 | 396 | 397 |
| B-0366 | 4-F-C₆H₄ | CH₃O-CH₂-C(O)- | 100 | 354 | 355 |
| B-0367 | 4-F-C₆H₄ | 2-OMe-C₆H₄-C(O)- | 71 | 416 | 417 |
| B-0368 | 4-F-C₆H₄ | 2-CF₃-C₆H₄-C(O)- | 86 | 454 | 455 |
| B-0369 | 4-F-C₆H₄ | 2,3,4-triF-C₆H₂-C(O)- | 40 | 440 | 441 |

-continued
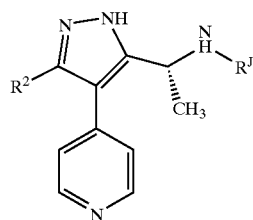
| Example # | R² | R^J | % Yield | Calcd. Mass Spec | Observed Mass Spec (M + H) |
|---|---|---|---|---|---|
| B-0370 | 4-F-phenyl | 4-methyl-3-oxopent-3-en-2-yl (prenyl ketone) | 94 | 364 | 365 |
| B-0371 | 4-F-phenyl | 3,4-dimethoxyphenylacetyl | 88 | 460 | 461 |
| B-0372 | 4-F-phenyl | 4-methoxyphenylacetyl | 69 | 430 | 431 |
| B-0373 | 4-F-phenyl | 3-methoxyphenylacetyl | 100 | 430 | 431 |
| B-0374 | 4-F-phenyl | 4-methylbenzoyl | 75 | 400 | 401 |
| B-0375 | 4-F-phenyl | benzoyl | 74 | 386 | 387 |
| B-0376 | 4-F-phenyl | cyclopentylcarbonyl | 53 | 378 | 379 |
| B-0377 | 4-F-phenyl | pyridin-3-ylcarbonyl | 71 | 387 | 388 |

-continued
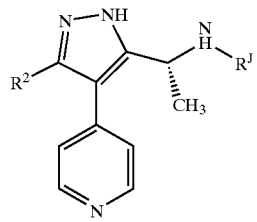
| Example # | R² | R^J | % Yield | Calcd. Mass Spec | Observed Mass Spec (M + H) |
|---|---|---|---|---|---|
| B-0378 | 4-F-C6H4 | 4-pyridyl-C(O)- | 69 | 387 | 388 |
| B-0379 | 4-F-C6H4 | 2-pyridyl-C(O)- | 66 | 387 | 388 |
| B-0380 | 4-F-C6H4 | 3-MeO-C6H4-C(O)- | 85 | 416 | 417 |
| B-0381 | 4-F-C6H4 | PhO-CH(CH3)-C(O)- | 93 | 430 | 431 |
| B-0382 | 4-F-C6H4 | iBuO-C(O)- | 84 | 382 | 383 |
| B-0383 | 4-F-C6H4 | 4-MeC6H4SO2NH-CH(CH2Ph)-C(O)- | 74 | 583 | 584 |

-continued
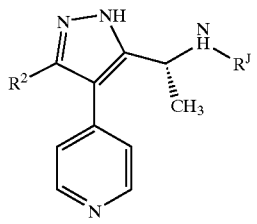
| Example # | R² | R^J | % Yield | Calcd. Mass Spec | Observed Mass Spec (M + H) |
|---|---|---|---|---|---|
| B-0384 | 4-F-C₆H₄ | 2-quinoxalinyl-C(O)- | 63 | 438 | 439 |
| B-0385 | 4-F-C₆H₄ | 4-F-C₆H₄-SO₂- | 83 | 440 | 441 |
| B-0386 | 4-F-C₆H₄ | C₆H₅-SO₂- | 99 | 422 | 423 |
| B-0387 | 4-F-C₆H₄ | iPr-SO₂- | 47 | 388 | 389 |
| B-0388 | 4-F-C₆H₄ | (E)-PhCH=CH-SO₂- | 100 | 448 | 449 |
| B-0389 | 4-F-C₆H₄ | PhCH₂-SO₂- | 71 | 436 | 437 |
| B-0390 | 4-F-C₆H₄ | 2,4-F₂-C₆H₃-SO₂- | 100 | 458 | 459 |
| B-0391 | 4-F-C₆H₄ | CF₃-SO₂- | 45 | 414 | 415 |

-continued
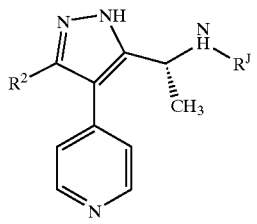
| Example # | R² | R^J | % Yield | Calcd. Mass Spec | Observed Mass Spec (M + H) |
|---|---|---|---|---|---|
| B-0392 | 4-F-C₆H₄ | 2-F-C₆H₄-SO₂- | 100 | 440 | 441 |
| B-0393 | 4-F-C₆H₄ | n-Pr-SO₂- | 75 | 388 | 389 |
| B-0394 | 4-F-C₆H₄ | n-Bu-SO₂- | 92 | 402 | 403 |
| B-0395 | 4-F-C₆H₄ | Et-SO₂- | 87 | 374 | 375 |
| B-0396 | 4-F-C₆H₄ | Me-SO₂- | 86 | 360 | 361 |
| B-0397 | 4-F-C₆H₄ | 4-MeO-C₆H₄-SO₂- | 81 | 452 | 453 |
| B-0398 | 4-F-C₆H₄ | 2-thienyl-SO₂- | 88 | 428 | 429 |
| B-0399 | 4-F-C₆H₄ | 4-Me-C₆H₄-SO₂- | 99 | 436 | 437 |
| B-0400 | 4-F-C₆H₄ | 3,4-(MeO)₂-C₆H₃-SO₂- | 82 | 482 | 483 |

-continued
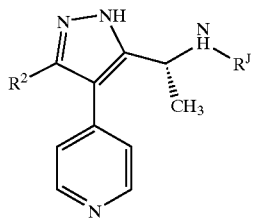
| Example # | R² | R^J | % Yield | Calcd. Mass Spec | Observed Mass Spec (M + H) |
|---|---|---|---|---|---|
| B-0401 | 4-F-C6H4 | C(O)NH-iPr | 94 | 367 | 368 |
| B-0402 | 4-F-C6H4 | C(O)NH2 | 73 | 325 | 326 |
| B-0403 | 4-F-C6H4 | C(O)NH-CH2-Ph | 91 | 415 | 416 |
| B-0404 | 4-F-C6H4 | C(O)-pyrrolidinyl | 41 | 379 | 380 |
| B-0405 | 4-F-C6H4 | C(O)-morpholinyl | 88 | 395 | 396 |
| B-0406 | 4-F-C6H4 | C(O)NH-(4-F-C6H4) | 100 | 419 | 420 |
| B-0407 | 4-F-C6H4 | C(O)N(CH3)2 | 52 | 353 | 354 |
| B-0408 | 4-F-C6H4 | C(O)NHCH3 | 83 | 339 | 340 |

-continued
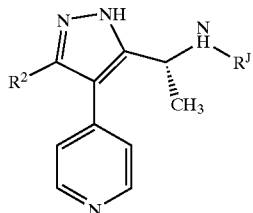
| Example # | R² | R^J | % Yield | Calcd. Mass Spec | Observed Mass Spec (M + H) |
|---|---|---|---|---|---|
| B-0409 | 4-F-C₆H₄ | N-methyl-N-phenyl amide | 74 | 415 | 416 |
| B-0410 | 4-F-C₆H₄ | 2-fluoroanilide | 100 | 419 | 420 |
| B-0411 | 4-F-C₆H₄ | 2,6-dimethylanilide | 94 | 429 | 430 |
| B-0412 | 4-F-C₆H₄ | N-allyl amide | 91 | 365 | 366 |
| B-0413 | 4-F-C₆H₄ | N-propyl amide | 79 | 367 | 368 |
| B-0414 | 4-F-C₆H₄ | N-(α-methylbenzyl) amide | 85 | 429 | 430 |
| B-0415 | 4-F-C₆H₄ | anilide | 82 | 401 | 402 |

-continued
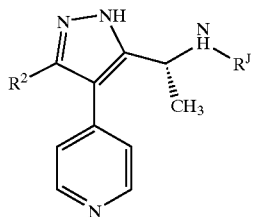
| Example # | R² | R^J | % Yield | Calcd. Mass Spec | Observed Mass Spec (M + H) |
|---|---|---|---|---|---|
| B-0416 | 4-F-phenyl | -C(O)NH-CH₂CH₂-phenyl | 93 | 429 | 430 |
| B-0417 | 4-F-phenyl | -C(O)NH-CH(CH₃)-phenyl | 97 | 429 | 430 |
| B-0418 | 4-F-phenyl | -C(O)NH-(3-F-phenyl) | 100 | 419 | 420 |
| B-0419 | 4-F-phenyl | -C(O)NH-(4-OMe-phenyl) | 100 | 431 | 432 |
| B-0420 | 4-F-phenyl | -C(O)N(Et)₂ | 36 | 381 | 382 |
| B-0421 | 4-F-phenyl | -C(O)NHEt | 96 | 353 | 354 |

-continued
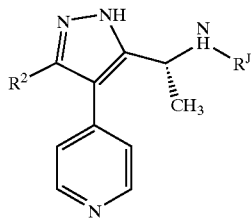
| Example # | R² | R^J | % Yield | Calcd. Mass Spec | Observed Mass Spec (M + H) |
|---|---|---|---|---|---|
| B-0422 | 4-F-phenyl | -C(O)NH-(2,4-dimethoxyphenyl) | 100 | 461 | 462 |
| B-0423 | 4-F-phenyl | -C(O)CH₂-(2-thienyl) | 100 | 406 | 407 |
| B-0424 | 4-F-phenyl | -C(O)C(CH₃)₃ | 76 | 366 | 367 |
| B-0425 | 4-F-phenyl | -C(O)O-n-propyl | 21 | 368 | 369 |
| B-0426 | 4-F-phenyl | -C(O)O-ethyl | 100 | 354 | 355 |
| B-0427 | 4-F-phenyl | -C(O)-(S)-prolinyl | 100 | 379 | 380 |
| B-0428 | 4-F-phenyl | -C(O)-(R)-prolinyl | 100 | 379 | 380 |
| B-0429 | 4-F-phenyl | -C(O)O-isopropyl | 86 | 368 | 369 |

-continued
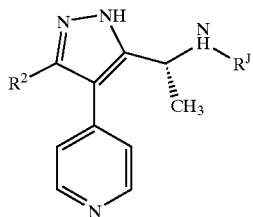
| Example # | R² | R^J | % Yield | Calcd. Mass Spec | Observed Mass Spec (M + H) |
|---|---|---|---|---|---|
| B-0430 | 4-F-phenyl | 5-(methylsulfonyl)-4-methyl-2-acetamido-thiazole | 51 | 500 | 501 |
| B-0431 | 4-F-phenyl | 4-acetamidophenylsulfonyl | 76 | 479 | 480 |
| B-0432 | 4-F-phenyl | 4-bromophenylsulfonyl | 90 | 500 | 501 |
| B-0433 | 4-F-phenyl | 4-chlorophenylsulfonyl | 96 | 456 | 457 |
| B-0434 | 4-F-phenyl | camphorsulfonyl | 75 | 496 | 497 |
| B-0435 | 4-F-phenyl | camphorsulfonyl (isomer) | 52 | 496 | 497 |
| B-0436 | 4-F-phenyl | 3,5-dichloro-2-hydroxyphenylsulfonyl | 73 | 506 | |

-continued
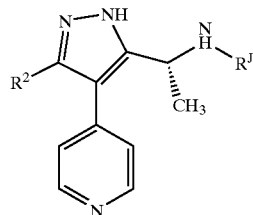
| Example # | R² | R^J | % Yield | Calcd. Mass Spec | Observed Mass Spec (M + H) |
|---|---|---|---|---|---|
| B-0437 | 4-F-phenyl | 2-(HOOC)-phenyl-SO₂- | 19 | 466 | |
| B-0438 | 4-F-phenyl | 2,5-diCl-phenyl-SO₂- | 100 | 490 | 491 |
| B-0439 | 4-F-phenyl | 2,4,6-triMe-phenyl-SO₂- | 67 | 464 | 465 |
| B-0440 | 4-F-phenyl | naphth-2-yl-SO₂- | 96 | 472 | 473 |
| B-0441 | 4-F-phenyl | naphth-1-yl-SO₂- | 87 | 472 | 473 |
| B-0442 | 4-F-phenyl | (2-NO₂-phenyl)CH₂-SO₂- | 72 | 481 | 482 |
| B-0443 | 4-F-phenyl | quinolin-8-yl-SO₂- | 66 | 473 | 474 |

-continued

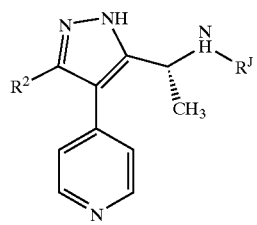

| Example # | R² | R^J | % Yield | Calcd. Mass Spec | Observed Mass Spec (M + H) |
|---|---|---|---|---|---|
| B-0444 | 4-F-phenyl | naphthalen-1-yl sulfonyl with 5-N(CH₃)₂ | 80 | 515 | 516 |
| B-0445 | 4-F-phenyl | 2,3-dichlorophenyl sulfonyl | 94 | 490 | 491 |
| B-0446 | 4-F-phenyl | 4-isopropylphenyl sulfonyl | 84 | 464 | 465 |
| B-0447 | 4-F-phenyl | 3-chloro-2-methylphenyl sulfonyl | 89 | 470 | 471 |
| B-0448 | 4-F-phenyl | 2,4-dichlorophenyl sulfonyl | 100 | 490 | 491 |
| B-0449 | 4-F-phenyl | 3-chloro-5-fluorophenyl sulfonyl | 100 | 474 | 475 |
| B-0450 | 4-F-phenyl | 2-cyanophenyl sulfonyl | 100 | 447 | 448 |
| B-0451 | 4-F-phenyl | 3-fluoro-6-methylphenyl sulfonyl | 100 | 454 | 455 |

-continued
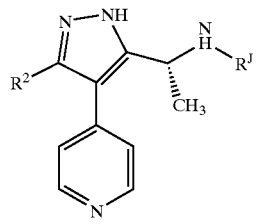
| Example # | R² | R^J | % Yield | Calcd. Mass Spec | Observed Mass Spec (M + H) |
|---|---|---|---|---|---|
| B-0452 | 4-F-phenyl | 4,5-dichlorothiophene-2-sulfonyl | 95 | 496 | 497 |
| B-0453 | 4-F-phenyl | 2,6-dichlorophenylsulfonyl | 100 | 490 | 491 |
| B-0454 | 4-F-phenyl | 2-bromophenylsulfonyl | 100 | 500 | 501 |
| B-0455 | 4-F-phenyl | 3-bromophenylsulfonyl | 96 | 500 | 501 |
| B-0456 | 4-F-phenyl | 4-butoxyphenylsulfonyl | 89 | 494 | 495 |
| B-0457 | 4-F-phenyl | 2,5-dimethoxyphenylsulfonyl | 93 | 482 | 483 |
| B-0458 | 4-F-phenyl | 2-CF₃-phenylsulfonyl | 100 | 490 | 491 |
| B-0459 | 4-F-phenyl | 4-CF₃-phenylmethylsulfonyl | 100 | 490 | 491 |

-continued
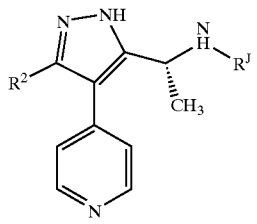
| Example # | R² | R^J | % Yield | Calcd. Mass Spec | Observed Mass Spec (M + H) |
|---|---|---|---|---|---|
| B-0460 | 4-F-C6H4 | 4-ethylphenyl sulfonyl | 93 | 450 | 451 |
| B-0461 | 4-F-C6H4 | 3-methylphenyl sulfonyl | 84 | 452 | 453 |
| B-0462 | 4-F-C6H4 | 3-chlorophenyl sulfonyl | 96 | 456 | 457 |
| B-0463 | 4-F-C6H4 | 2-chlorophenyl sulfonyl | 66 | 456 | 457 |
| B-0464 | 4-F-C6H4 | 3,5-dichlorophenyl sulfonyl | 69 | 490 | 491 |
| B-0465 | 4-F-C6H4 | 3,4-dichlorophenyl sulfonyl | 86 | 490 | 491 |
| B-0466 | 4-F-C6H4 | 3-chloro-4-fluorophenyl sulfonyl | 78 | 474 | 475 |
| B-0467 | 4-F-C6H4 | 2-chloro-6-methylphenyl sulfonyl | 78 | 470 | 471 |

-continued
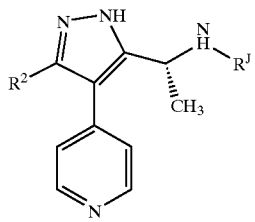
| Example # | R² | R^J | % Yield | Calcd. Mass Spec | Observed Mass Spec (M + H) |
|---|---|---|---|---|---|
| B-0468 | 4-F-C6H4 | 2,5-dimethylphenylsulfonyl | 91 | 450 | 451 |
| B-0469 | 4-F-C6H4 | 2-methylphenylsulfonyl | 85 | 436 | 437 |
| B-0470 | 4-F-C6H4 | 2-methoxy-5-methylphenylsulfonyl | 99 | 466 | 467 |
| B-0471 | 4-F-C6H4 | 3-(trifluoromethyl)phenylsulfonyl | 100 | 490 | 491 |
| B-0472 | 4-F-C6H4 | camphorsulfonyl | 37 | 482 | 483 |
| B-0473 | 4-F-C6H4 | 5-chlorothiophen-2-ylsulfonyl | 92 | 462 | 463 |
| B-0474 | 4-F-C6H4 | 5-bromo-2-methoxyphenylsulfonyl | 99 | 530 | 532 |

-continued
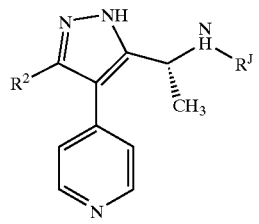
| Example # | R² | R^J | % Yield | Calcd. Mass Spec | Observed Mass Spec (M + H) |
|---|---|---|---|---|---|
| B-0475 | 4-F-C6H4 | naphthalen-2-ylsulfonyl | 55 | 472 | 473 |
| B-0476 | 4-F-C6H4 | (3,5-dimethylisoxazol-4-yl)sulfonyl | 89 | 441 | 442 |
| B-0477 | 4-F-C6H4 | benzo[1,2,5]oxadiazol-4-ylsulfonyl | 79 | 464 | 465 |
| B-0478 | 4-F-C6H4 | (2,5-dimethoxyphenyl)sulfonyl | 92 | 486 | 487 |
| B-0479 | 4-F-C6H4 | (4-cyanophenyl)sulfonyl | 97 | 447 | 448 |
| B-0480 | 4-F-C6H4 | 5-(benzamidomethyl)thiophen-2-ylsulfonyl | 75 | 561 | 562 |
| B-0481 | 4-F-C6H4 | biphenyl-4-ylsulfonyl | 74 | 498 | 499 |

-continued

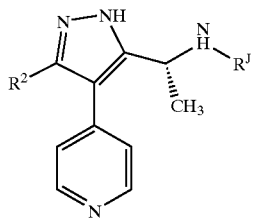

| Example # | R² | R^J | % Yield | Calcd. Mass Spec | Observed Mass Spec (M + H) |
|---|---|---|---|---|---|
| B-0482 | 4-F-phenyl | 2,2,5,7,8-pentamethylchroman-6-ylsulfonyl | 57 | 548 | 549 |
| B-0483 | 4-F-phenyl | 5-(pyridin-2-yl)thiophen-2-ylsulfonyl | 83 | 505 | 506 |
| B-0484 | 4-F-phenyl | 4-(phenylsulfonyl)thiophen-2-ylsulfonyl | 100 | 568 | 569 |
| B-0485 | 4-F-phenyl | 5-(isoxazol-3-yl)thiophen-2-ylsulfonyl | 100 | 495 | 496 |
| B-0486 | 4-F-phenyl | 1-methylimidazol-4-ylsulfonyl | 100 | 426 | 427 |
| B-0487 | 4-F-phenyl | N,N-dimethylsulfamoyl | 32 | 389 | 390 |
| B-0488 | 4-F-phenyl | 5-(phenylsulfonyl)thiophen-2-ylsulfonyl | 100 | 568 | 569 |

-continued
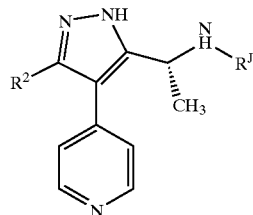
| Example # | R² | R^J | % Yield | Calcd. Mass Spec | Observed Mass Spec (M + H) |
|---|---|---|---|---|---|
| B-0489 | 4-F-phenyl | 2-(methylsulfonyl)phenylsulfonyl | 91 | 500 | 501 |
| B-0490 | 4-F-phenyl | isoquinolin-5-ylsulfonyl | 40 | 473 | 474 |
| B-0491 | 4-F-phenyl | 2-methyl-5-(methylsulfonyl)phenylsulfonyl | 73 | 514 | 515 |
| B-0492 | 4-F-phenyl | 2-methylbenzoyl | 89 | 400 | 401 |
| B-0493 | 4-F-phenyl | 4-chlorobenzoyl | 100 | 420 | 421 |
| B-0494 | 4-F-phenyl | 4-methylbenzoyl | 100 | 400 | 401 |
| B-0495 | 4-F-phenyl | 3-(trifluoromethyl)benzoyl | 100 | 454 | 455 |

-continued
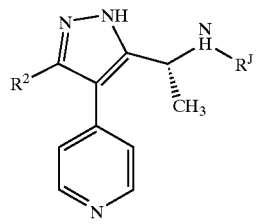
| Example # | R² | R^J | % Yield | Calcd. Mass Spec | Observed Mass Spec (M + H) |
|---|---|---|---|---|---|
| B-0496 | 4-F-phenyl | 2-benzothiophene-C(O)- | 100 | 442 | 443 |
| B-0497 | 4-F-phenyl | 2,4,6-triisopropylphenyl-C(O)- | 50 | 512 | 513 |
| B-0498 | 4-F-phenyl | 3,5-dichlorophenyl-C(O)- | 100 | 454 | 455 |
| B-0499 | 4-F-phenyl | 3-cyanophenyl-C(O)- | 98 | 411 | 412 |
| B-0500 | 4-F-phenyl | naphthalen-1-yl-C(O)- | 100 | 436 | 437 |
| B-0501 | 4-F-phenyl | 3,4-difluorophenyl-C(O)- | 100 | 422 | 423 |
| B-0502 | 4-F-phenyl | 3,5-difluorophenyl-C(O)- | 100 | 422 | 423 |

-continued
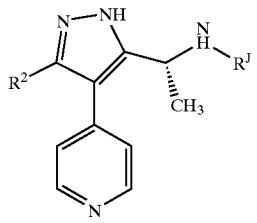
| Example # | R² | R<sup>J</sup> | % Yield | Calcd. Mass Spec | Observed Mass Spec (M + H) |
|---|---|---|---|---|---|
| B-0503 | 4-F-C₆H₄ | 2,3,6-trifluorobenzoyl | 92 | 440 | 441 |
| B-0504 | 4-F-C₆H₄ | 2,3-dichlorobenzoyl | 67 | 454 | 455 |
| B-0505 | 4-F-C₆H₄ | 2,4,6-trimethylbenzoyl | 68 | 428 | 429 |
| B-0506 | 4-F-C₆H₄ | 2-fluoro-5-(trifluoromethyl)benzoyl | 98 | 472 | 473 |
| B-0507 | 4-F-C₆H₄ | 2,4,6-trifluorobenzoyl | 82 | 440 | 441 |
| B-0508 | 4-F-C₆H₄ | 2-fluoro-4-(trifluoromethyl)benzoyl | 99 | 472 | 473 |
| B-0509 | 4-F-C₆H₄ | 2-fluoro-6-(trifluoromethyl)benzoyl | 100 | 472 | 473 |

-continued
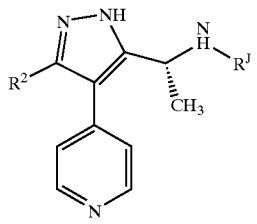
| Example # | R² | R^J | % Yield | Calcd. Mass Spec | Observed Mass Spec (M + H) |
|---|---|---|---|---|---|
| B-0510 | 4-F-C₆H₄ | 2-F-3-CF₃-C₆H₃-C(O)- | 96 | 472 | 473 |
| B-0511 | 4-F-C₆H₄ | 2-CF₃-4-F-C₆H₃-C(O)- | 100 | 472 | 473 |
| B-0512 | 4-F-C₆H₄ | 3-CF₃-4-F-C₆H₃-C(O)- | 100 | 472 | 473 |
| B-0513 | 4-F-C₆H₄ | 3-CF₃-5-F-C₆H₃-C(O)- | 100 | 472 | 473 |
| B-0514 | 4-F-C₆H₄ | 2-Cl-C₆H₄-C(O)- | 100 | 420 | 421 |
| B-0515 | 4-F-C₆H₄ | 3-CH₃-C₆H₄-C(O)- | 100 | 400 | 401 |
| B-0516 | 4-F-C₆H₄ | 2,4-Cl₂-C₆H₃-C(O)- | 100 | 454 | 455 |

-continued
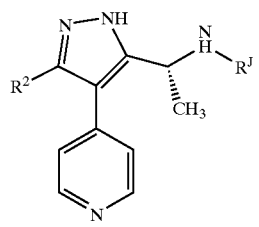
| Example # | R² | R^J | % Yield | Calcd. Mass Spec | Observed Mass Spec (M + H) |
|---|---|---|---|---|---|
| B-0517 | 4-F-C6H4 | 3-F-C6H4-C(O)- | 100 | 404 | 405 |
| B-0518 | 4-F-C6H4 | 2,3-diF-C6H3-C(O)- | 99 | 422 | 423 |
| B-0519 | 4-F-C6H4 | 2,6-diCl-C6H3-C(O)- | 100 | 454 | 455 |
| B-0520 | 4-F-C6H4 | 2,5-diF-C6H3-C(O)- | 98 | 422 | 423 |
| B-0521 | 4-F-C6H4 | 2,4,5-triF-C6H2-C(O)- | 99 | 440 | 441 |
| B-0522 | 4-F-C6H4 | 2-F-C6H4-C(O)- | 88 | 404 | 405 |
| B-0523 | 4-F-C6H4 | 2,6-diF-C6H3-C(O)- | 100 | 422 | 423 |
| B-0524 | 4-F-C6H4 | 2,4-diF-C6H3-C(O)- | 100 | 422 | 423 |

-continued
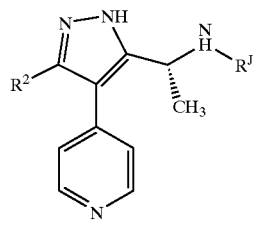
| Example # | R² | R^J | % Yield | Calcd. Mass Spec | Observed Mass Spec (M + H) |
|---|---|---|---|---|---|
| B-0525 | 4-F-C₆H₄ | 3-Cl-C₆H₄-C(O)- | 100 | 420 | 421 |
| B-0526 | 4-F-C₆H₄ | 2-Br-C₆H₄-C(O)- | 100 | 464 | 465 |
| B-0527 | 4-F-C₆H₄ | 4-CF₃-C₆H₄-C(O)- | 100 | 454 | 455 |
| B-0528 | 4-F-C₆H₄ | 2-thienyl-C(O)- | 100 | 392 | 393 |
| B-0529 | 4-F-C₆H₄ | 3,5-dimethylisoxazol-4-yl-C(O)- | 94 | 405 | 406 |

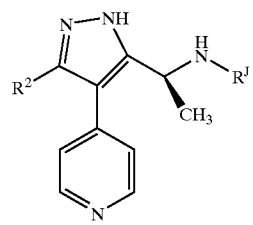
| Example # | R² | R^J | % Yield | Calcd. Mass Spec | Observed Mass Spec (M + H) |
|---|---|---|---|---|---|
| B-0530 | 4-F-C₆H₄ | -C(O)CH₂OC(O)CH₃ | 67 | 382 | 383 |
| B-0531 | 4-F-C₆H₄ | -C(O)(2-I-C₆H₄) | 66 | 512 | 513 |
| B-0532 | 4-F-C₆H₄ | -C(O)CH(CH₃)₂ | 37 | 352 | 353 |
| B-0533 | 4-F-C₆H₄ | -C(O)(4-I-C₆H₄) | 56 | 404 | 405 |
| B-0534 | 4-F-C₆H₄ | -C(O)O-CH₂CH=CH₂ | 100 | 366 | 367 |
| B-0535 | 4-F-C₆H₄ | -C(O)C(CH₃)₂OC(O)CH₃ | 100 | 410 | 411 |
| B-0536 | 4-F-C₆H₄ | -C(O)CH₃ | 41 | 324 | 325 |
| B-0537 | 4-F-C₆H₄ | -C(O)(cyclobutyl) | 100 | 364 | 365 |

-continued
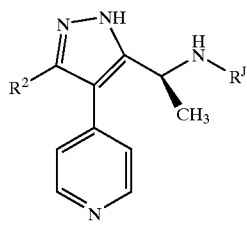
| Example # | R² | R^J | % Yield | Calcd. Mass Spec | Observed Mass Spec (M + H) |
|---|---|---|---|---|---|
| B-0538 | 4-F-C₆H₄ | cyclopropyl-C(O)- | 29 | 350 | 351 |
| B-0539 | 4-F-C₆H₄ | 3-Br-C₆H₄-C(O)- | 70 | 464 | 465 |
| B-0540 | 4-F-C₆H₄ | 4-SH-C₆H₄-C(O)- | 50 | 512 | 513 |
| B-0541 | 4-F-C₆H₄ | isoxazol-5-yl-C(O)- | 61 | 377 | 378 |
| B-0542 | 4-F-C₆H₄ | CH₃C(O)O-CH(CH₃)-C(O)- | 61 | 396 | 397 |
| B-0543 | 4-F-C₆H₄ | CH₃O-CH₂-C(O)- | 59 | 354 | 355 |
| B-0544 | 4-F-C₆H₄ | 2-OMe-C₆H₄-C(O)- | 45 | 416 | 417 |

-continued
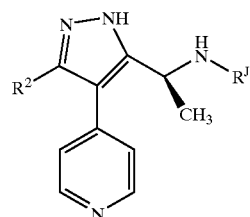
| Example # | R² | R^J | % Yield | Calcd. Mass Spec | Observed Mass Spec (M + H) |
|---|---|---|---|---|---|
| B-0545 | 4-F-phenyl | 2-(CF₃)-benzoyl | 100 | 454 | 455 |
| B-0546 | 4-F-phenyl | 2,3,4-trifluorobenzoyl | 44 | 440 | 441 |
| B-0547 | 4-F-phenyl | 4-methyl-3-pentenoyl | 64 | 364 | 365 |
| B-0548 | 4-F-phenyl | (3,4-dimethoxyphenyl)acetyl | 89 | 460 | 461 |
| B-0549 | 4-F-phenyl | (4-methoxyphenyl)acetyl | 100 | 430 | 431 |
| B-0550 | 4-F-phenyl | (3-methoxyphenyl)acetyl | 100 | 430 | 431 |
| B-0551 | 4-F-phenyl | 4-methylbenzoyl | 81 | 400 | 401 |
| B-0552 | 4-F-phenyl | benzoyl | 38 | 386 | 387 |

-continued
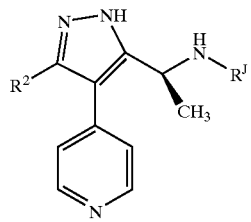
| Example # | R² | Rᴶ | % Yield | Calcd. Mass Spec | Observed Mass Spec (M + H) |
|---|---|---|---|---|---|
| B-0553 | 4-F-phenyl | cyclopentyl-C(O)- | 31 | 378 | 379 |
| B-0554 | 4-F-phenyl | 3-pyridyl-C(O)- | 100 | 387 | 388 |
| B-0555 | 4-F-phenyl | 4-pyridyl-C(O)- | 66 | 387 | 388 |
| B-0556 | 4-F-phenyl | 2-pyridyl-C(O)- | 32 | 387 | 388 |
| B-0557 | 4-F-phenyl | 3-methoxyphenyl-C(O)- | 70 | 416 | 417 |
| B-0558 | 4-F-phenyl | phenoxy-CH(CH₃)-C(O)- | 57 | 430 | 431 |
| B-0559 | 4-F-phenyl | isobutyl-O-C(O)- | 74 | 382 | 383 |

-continued
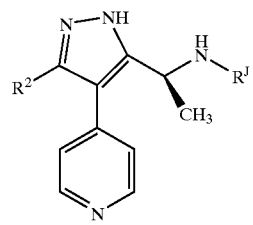
| Example # | R² | R^J | % Yield | Calcd. Mass Spec | Observed Mass Spec (M + H) |
|---|---|---|---|---|---|
| B-0560 | 4-F-C6H4 | tosyl-N-benzyl-α-amino ketone | 36 | 583 | 584 |
| B-0561 | 4-F-C6H4 | quinoxaline-2-carbonyl | 51 | 438 | 439 |
| B-0562 | 4-F-C6H4 | 4-F-phenylsulfonyl | 88 | 440 | 441 |
| B-0563 | 4-F-C6H4 | phenylsulfonyl | 68 | 422 | 423 |
| B-0564 | 4-F-C6H4 | isopropylsulfonyl | 47 | 388 | 389 |
| B-0565 | 4-F-C6H4 | styrylsulfonyl | 100 | 448 | 449 |
| B-0566 | 4-F-C6H4 | benzylsulfonyl | 76 | 436 | 437 |

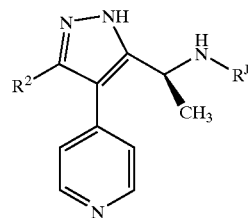
| Example # | R² | Rᴶ | % Yield | Calcd. Mass Spec | Observed Mass Spec (M + H) |
|---|---|---|---|---|---|
| B-0567 | 4-F-C₆H₄ | 2,4-difluorophenylsulfonyl | 99 | 458 | 459 |
| B-0568 | 4-F-C₆H₄ | CF₃-sulfonyl | 45 | 414 | 415 |
| B-0569 | 4-F-C₆H₄ | 2-fluorophenylsulfonyl | 88 | 440 | 441 |
| B-0570 | 4-F-C₆H₄ | n-propylsulfonyl | 61 | 388 | 389 |
| B-0571 | 4-F-C₆H₄ | n-butylsulfonyl | 58 | 402 | 403 |
| B-0572 | 4-F-C₆H₄ | ethylsulfonyl | 75 | 374 | 375 |
| B-0573 | 4-F-C₆H₄ | methylsulfonyl | 72 | 360 | 361 |
| B-0574 | 4-F-C₆H₄ | 4-methoxyphenylsulfonyl | 97 | 452 | 453 |
| B-0575 | 4-F-C₆H₄ | 2-thienylsulfonyl | 71 | 428 | 429 |
| B-0576 | 4-F-C₆H₄ | 4-methylphenylsulfonyl | 88 | 436 | 437 |

-continued
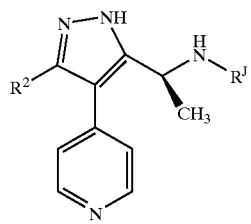
| Example # | R² | R^J | % Yield | Calcd. Mass Spec | Observed Mass Spec (M + H) |
|---|---|---|---|---|---|
| B-0577 | 4-F-phenyl | 3,4-dimethoxyphenylsulfonyl | 72 | 482 | 483 |
| B-0578 | 4-F-phenyl | C(O)NH-iPr | 89 | 367 | 368 |
| B-0579 | 4-F-phenyl | C(O)NH₂ | 100 | 325 | 326 |
| B-0580 | 4-F-phenyl | C(O)NH-benzyl | 75 | 415 | 416 |
| B-0581 | 4-F-phenyl | C(O)-pyrrolidinyl | 44 | 379 | 380 |
| B-0582 | 4-F-phenyl | C(O)-morpholinyl | 75 | 395 | 396 |
| B-0583 | 4-F-phenyl | C(O)NH-(4-F-phenyl) | 80 | 419 | 420 |
| B-0584 | 4-F-phenyl | C(O)N(CH₃)₂ | 57 | 353 | 354 |

-continued
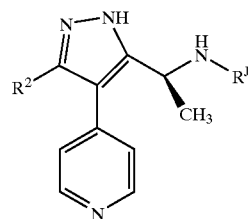
| Example # | R² | R^J | % Yield | Calcd. Mass Spec | Observed Mass Spec (M + H) |
|---|---|---|---|---|---|
| B-0585 | 4-F-phenyl | -C(O)NHCH₃ | 83 | 339 | 340 |
| B-0586 | 4-F-phenyl | -C(O)N(CH₃)Ph | 71 | 415 | 416 |
| B-0587 | 4-F-phenyl | -C(O)NH(2-F-phenyl) | 100 | 419 | 420 |
| B-0588 | 4-F-phenyl | -C(O)NH(2,6-dimethylphenyl) | 94 | 429 | 430 |
| B-0589 | 4-F-phenyl | -C(O)NH-allyl | 78 | 365 | 366 |
| B-0590 | 4-F-phenyl | -C(O)NH-propyl | 82 | 367 | 368 |
| B-0591 | 4-F-phenyl | -C(O)NH-(S)-CH(CH₃)Ph | 72 | 429 | 430 |

-continued
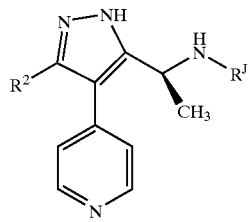
| Example # | R² | R^J | % Yield | Calcd. Mass Spec | Observed Mass Spec (M + H) |
|---|---|---|---|---|---|
| B-0592 | 4-F-phenyl | -C(O)NH-phenyl | 82 | 401 | 402 |
| B-0593 | 4-F-phenyl | -C(O)NH-CH2CH2-phenyl | 88 | 429 | 430 |
| B-0594 | 4-F-phenyl | -C(O)NH-CH(CH3)-phenyl | 100 | 429 | 430 |
| B-0595 | 4-F-phenyl | -C(O)NH-(3-F-phenyl) | 99 | 419 | 420 |
| B-0596 | 4-F-phenyl | -C(O)NH-(4-OMe-phenyl) | 93 | 431 | 432 |
| B-0597 | 4-F-phenyl | -C(O)N(Et)2 | 40 | 381 | 382 |

-continued
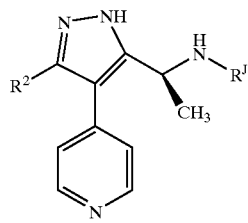
| Example # | R² | R^J | % Yield | Calcd. Mass Spec | Observed Mass Spec (M + H) |
|---|---|---|---|---|---|
| B-0598 | 4-F-phenyl | ethylaminocarbonyl | 93 | 353 | 354 |
| B-0599 | 4-F-phenyl | (2,4-dimethoxyphenyl)aminocarbonyl | 100 | 461 | 462 |
| B-0600 | 4-F-phenyl | thiophen-2-ylmethylcarbonyl | 98 | 406 | 407 |
| B-0601 | 4-F-phenyl | tert-butylcarbonyl | 66 | 366 | 367 |
| B-0602 | 4-F-phenyl | propoxycarbonyl | 25 | 368 | 369 |
| B-0603 | 4-F-phenyl | ethoxycarbonyl | 90 | 354 | 355 |
| B-0604 | 4-F-phenyl | prolinyl | 86 | 379 | 380 |
| B-0605 | 4-F-phenyl | prolinyl | 87 | 379 | 380 |

-continued

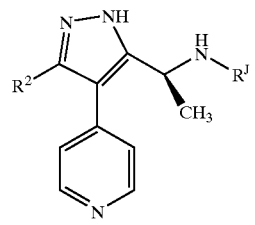

| Example # | R² | R^J | % Yield | Calcd. Mass Spec | Observed Mass Spec (M + H) |
|---|---|---|---|---|---|
| B-0606 | 4-F-phenyl | isopropyl ester group | 72 | 368 | 369 |
| B-0607 | 4-F-phenyl | 4-methyl-2-(acetylamino)thiazol-5-yl sulfonyl | 34 | 500 | 501 |
| B-0608 | 4-F-phenyl | 4-(acetylamino)phenylsulfonyl | 100 | 479 | 480 |
| B-0609 | 4-F-phenyl | 4-bromophenylsulfonyl | 82 | 500 | 501 |
| B-0610 | 4-F-phenyl | 4-chlorophenylsulfonyl | 100 | 456 | 457 |
| B-0611 | 4-F-phenyl | camphorsulfonyl | 76 | 496 | 497 |
| B-0612 | 4-F-phenyl | camphorethylsulfonyl | 69 | 496 | 497 |
| B-0613 | 4-F-phenyl | 3,5-dichloro-2-hydroxyphenylsulfonyl | 61 | 506 | |

-continued
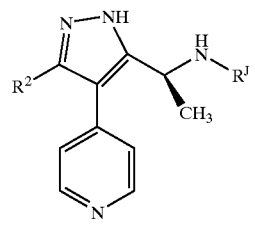
| Example # | R² | R^J | % Yield | Calcd. Mass Spec | Observed Mass Spec (M + H) |
|---|---|---|---|---|---|
| B-0614 | 4-F-C₆H₄ | 2-(HOOC)C₆H₄-SO₂- | 18 | 466 | |
| B-0615 | 4-F-C₆H₄ | 2,5-Cl₂-C₆H₃-SO₂- | 100 | 490 | 491 |
| B-0616 | 4-F-C₆H₄ | 2,4,6-trimethyl-C₆H₂-SO₂- | 77 | 464 | 465 |
| B-0617 | 4-F-C₆H₄ | 2-naphthyl-SO₂- | 93 | 472 | 473 |
| B-0618 | 4-F-C₆H₄ | 1-naphthyl-SO₂- | 84 | 472 | 473 |
| B-0619 | 4-F-C₆H₄ | 2-NO₂-C₆H₄-CH₂-SO₂- | 71 | 481 | 482 |
| B-0620 | 4-F-C₆H₄ | 8-quinolinyl-SO₂- | 89 | 473 | 474 |

-continued

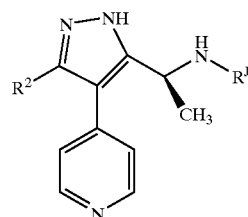

| Example # | R² | Rᴶ | % Yield | Calcd. Mass Spec | Observed Mass Spec (M + H) |
|---|---|---|---|---|---|
| B-0621 | 4-F-C₆H₄ | 5-(dimethylamino)naphthalen-1-yl sulfonyl | 68 | 515 | 516 |
| B-0622 | 4-F-C₆H₄ | 2,3-dichlorophenylsulfonyl | 70 | 490 | 491 |
| B-0623 | 4-F-C₆H₄ | 4-isopropylphenylsulfonyl | 92 | 464 | 465 |
| B-0624 | 4-F-C₆H₄ | 3-chloro-2-methylphenylsulfonyl | 98 | 470 | 471 |
| B-0625 | 4-F-C₆H₄ | 2,4-dichlorophenylsulfonyl | 96 | 490 | 491 |
| B-0626 | 4-F-C₆H₄ | 3-chloro-5-fluoropyridinylsulfonyl | 100 | 474 | 475 |
| B-0627 | 4-F-C₆H₄ | 2-cyanophenylsulfonyl | 100 | 447 | 448 |
| B-0628 | 4-F-C₆H₄ | 3-fluoro-6-methylphenylsulfonyl | 64 | 454 | 455 |

-continued

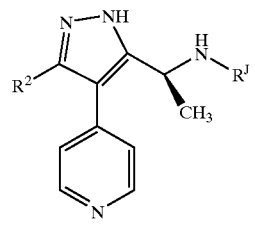

| Example # | R² | R^J | % Yield | Calcd. Mass Spec | Observed Mass Spec (M + H) |
|---|---|---|---|---|---|
| B-0629 | 4-F-phenyl | sulfonyl-4,5-dichlorothiophene | 100 | 496 | 497 |
| B-0630 | 4-F-phenyl | sulfonyl-2,6-dichlorophenyl | 85 | 490 | 491 |
| B-0631 | 4-F-phenyl | sulfonyl-2-bromophenyl | 75 | 500 | 501 |
| B-0632 | 4-F-phenyl | sulfonyl-3-bromophenyl | 83 | 500 | 501 |
| B-0633 | 4-F-phenyl | sulfonyl-4-butoxyphenyl | 58 | 494 | 495 |
| B-0634 | 4-F-phenyl | sulfonyl-2,5-dimethoxyphenyl | 63 | 482 | 483 |
| B-0635 | 4-F-phenyl | sulfonyl-2-(trifluoromethyl)phenyl | 95 | 490 | 491 |
| B-0636 | 4-F-phenyl | sulfonyl-4-(trifluoromethyl)phenyl | 100 | 490 | 491 |

-continued
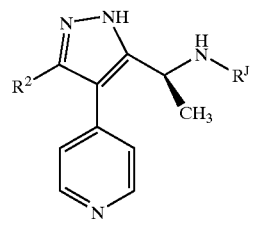
| Example # | R² | R^J | % Yield | Calcd. Mass Spec | Observed Mass Spec (M + H) |
|---|---|---|---|---|---|
| B-0637 | 4-F-C₆H₄ | SO₂-(4-ethylphenyl) | 91 | 450 | 451 |
| B-0638 | 4-F-C₆H₄ | SO₂-(3-methylphenyl) | 96 | 436 | 437 |
| B-0639 | 4-F-C₆H₄ | SO₂-(3-chlorophenyl) | 100 | 456 | 457 |
| B-0640 | 4-F-C₆H₄ | SO₂-(2-chlorophenyl) | 100 | 456 | 457 |
| B-0641 | 4-F-C₆H₄ | SO₂-(3,5-dichlorophenyl) | 88 | 490 | 491 |
| B-0642 | 4-F-C₆H₄ | SO₂-(3,4-dichlorophenyl) | 99 | 490 | 491 |
| B-0643 | 4-F-C₆H₄ | SO₂-(3-chloro-4-fluorophenyl) | 92 | 474 | 475 |
| B-0644 | 4-F-C₆H₄ | SO₂-(2-chloro-6-methylphenyl) | 100 | 470 | 471 |

-continued
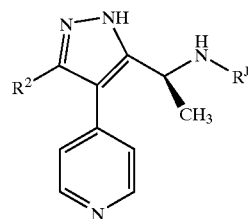
| Example # | R² | R^J | % Yield | Calcd. Mass Spec | Observed Mass Spec (M + H) |
|---|---|---|---|---|---|
| B-0645 | 4-F-C6H4 | 2,5-dimethylphenylsulfonyl | 92 | 450 | 451 |
| B-0646 | 4-F-C6H4 | 2-methylphenylsulfonyl | 100 | 436 | 437 |
| B-0647 | 4-F-C6H4 | 2-methoxy-5-methylphenylsulfonyl | 90 | 466 | 467 |
| B-0648 | 4-F-C6H4 | 3-trifluoromethylphenylsulfonyl | 94 | 490 | 491 |
| B-0649 | 4-F-C6H4 | camphorsulfonyl | 57 | 482 | |
| B-0650 | 4-F-C6H4 | 5-chlorothiophen-2-ylsulfonyl | 82 | 462 | 463 |
| B-0651 | 4-F-C6H4 | 5-bromo-2-methoxyphenylsulfonyl | 100 | 530 | 531 |

-continued
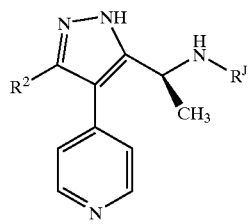
| Example # | R² | R^J | % Yield | Calcd. Mass Spec | Observed Mass Spec (M + H) |
|---|---|---|---|---|---|
| B-0652 | 4-F-phenyl | 2-naphthylsulfonyl | 53 | 472 | |
| B-0653 | 4-F-phenyl | (3,5-dimethylisoxazol-4-yl)sulfonyl | 84 | 441 | 442 |
| B-0654 | 4-F-phenyl | benzo[1,2,5]oxadiazol-4-ylsulfonyl | 92 | 464 | 465 |
| B-0655 | 4-F-phenyl | (5-chloro-2-methoxyphenyl)sulfonyl | 100 | 486 | 487 |
| B-0656 | 4-F-phenyl | (4-cyanophenyl)sulfonyl | 98 | 447 | 448 |
| B-0657 | 4-F-phenyl | [5-(benzoylaminomethyl)thien-2-yl]sulfonyl | 85 | 561 | 562 |
| B-0658 | 4-F-phenyl | (biphenyl-4-yl)sulfonyl | 92 | 498 | 499 |

-continued
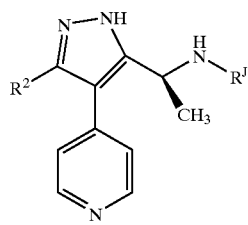
| Example # | R² | RJ | % Yield | Calcd. Mass Spec | Observed Mass Spec (M + H) |
|---|---|---|---|---|---|
| B-0659 | 4-F-phenyl | sulfonyl-2,2,5,7,8-pentamethylchroman | 46 | 548 | 549 |
| B-0660 | 4-F-phenyl | sulfonyl-thiophene-pyridine | 80 | 505 | 506 |
| B-0661 | 4-F-phenyl | sulfonyl-thiophene-sulfonyl-phenyl | 100 | 568 | 569 |
| B-0662 | 4-F-phenyl | sulfonyl-thiophene-isoxazole | 98 | 495 | 496 |
| B-0663 | 4-F-phenyl | sulfonyl-N-methylimidazole | 74 | 426 | 427 |
| B-0664 | 4-F-phenyl | sulfonyl-N,N-dimethyl | 30 | 389 | 390 |
| B-0665 | 4-F-phenyl | sulfonyl-thiophene-sulfonyl-phenyl | 100 | 568 | 569 |

-continued
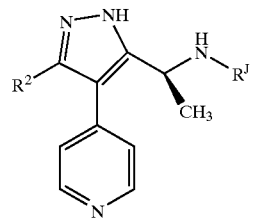
| Example # | R² | R^J | % Yield | Calcd. Mass Spec | Observed Mass Spec (M + H) |
|---|---|---|---|---|---|
| B-0666 | 4-F-phenyl | 2-(methylsulfonyl)phenylsulfonyl | 93 | 500 | 501 |
| B-0667 | 4-F-phenyl | isoquinolin-5-ylsulfonyl | 54 | 473 | 474 |
| B-0668 | 4-F-phenyl | 4-methyl-2-(methylsulfonyl)phenylsulfonyl | 66 | 514 | 515 |
| B-0669 | 4-F-phenyl | 2-methylbenzoyl | 65 | 400 | 401 |
| B-0670 | 4-F-phenyl | 4-chlorobenzoyl | 45 | 420 | 421 |
| B-0671 | 4-F-phenyl | 4-methylbenzoyl | 43 | 400 | 401 |
| B-0672 | 4-F-phenyl | 3-(trifluoromethyl)benzoyl | 45 | 454 | 455 |

-continued
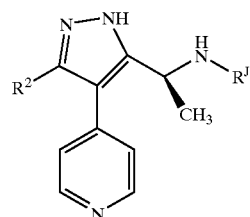
| Example # | R² | Rᴶ | % Yield | Calcd. Mass Spec | Observed Mass Spec (M + H) |
|---|---|---|---|---|---|
| B-0673 | 4-F-phenyl | benzothiophene-2-carbonyl | 41 | 442 | 443 |
| B-0674 | 4-F-phenyl | 2,4,6-triisopropylbenzoyl | 16 | 512 | 513 |
| B-0675 | 4-F-phenyl | 3,5-dichlorobenzoyl | 39 | 454 | 455 |
| B-0676 | 4-F-phenyl | 3-cyanobenzoyl | 34 | 411 | 412 |
| B-0677 | 4-F-phenyl | naphthalene-1-carbonyl | 46 | 436 | 437 |
| B-0678 | 4-F-phenyl | 3,4-difluorobenzoyl | 37 | 422 | 423 |
| B-0679 | 4-F-phenyl | 3,5-difluorobenzoyl | 34 | 422 | 423 |

-continued
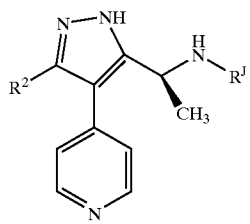
| Example # | R² | R^J | % Yield | Calcd. Mass Spec | Observed Mass Spec (M + H) |
|---|---|---|---|---|---|
| B-0680 | 4-F-phenyl | 2,3,6-trifluorobenzoyl | 60 | 440 | 441 |
| B-0681 | 4-F-phenyl | 2,3-dichlorobenzoyl | 31 | 454 | 455 |
| B-0682 | 4-F-phenyl | 2,4,6-trimethylbenzoyl | 37 | 428 | 429 |
| B-0683 | 4-F-phenyl | 2-fluoro-5-(trifluoromethyl)benzoyl | 46 | 472 | 473 |
| B-0684 | 4-F-phenyl | 2,3,5-trifluorobenzoyl | 50 | 440 | 441 |
| B-0685 | 4-F-phenyl | 2-fluoro-4-(trifluoromethyl)benzoyl | 44 | 472 | 473 |
| B-0686 | 4-F-phenyl | 2-(trifluoromethyl)-6-fluorobenzoyl | 66 | 472 | 473 |

-continued
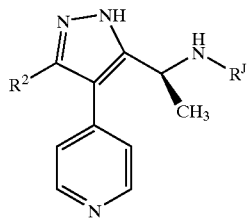
| Example # | R² | R^J | % Yield | Calcd. Mass Spec | Observed Mass Spec (M + H) |
|---|---|---|---|---|---|
| B-0687 | 4-F-C6H4 | 2-F-3-CF3-C6H3-C(O)- | 57 | 472 | 473 |
| B-0688 | 4-F-C6H4 | 2-CF3-4-F-C6H3-C(O)- | 52 | 472 | 473 |
| B-0689 | 4-F-C6H4 | 3-CF3-4-F-C6H3-C(O)- | 42 | 472 | 473 |
| B-0690 | 4-F-C6H4 | 3-CF3-5-F-C6H3-C(O)- | 34 | 472 | 473 |
| B-0691 | 4-F-C6H4 | 2-Cl-C6H4-C(O)- | 52 | 420 | 421 |
| B-0692 | 4-F-C6H4 | 3-CH3-C6H4-C(O)- | 41 | 400 | 401 |

-continued
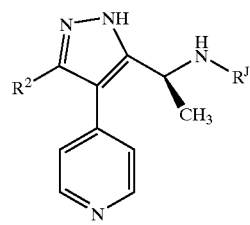
| Example # | R² | R^J | % Yield | Calcd. Mass Spec | Observed Mass Spec (M + H) |
|---|---|---|---|---|---|
| B-0693 | 4-F-phenyl | 2,4-dichlorobenzoyl | 56 | 454 | 455 |
| B-0694 | 4-F-phenyl | 3-fluorobenzoyl | 38 | 404 | 405 |
| B-0695 | 4-F-phenyl | 2,3-difluorobenzoyl | 43 | 422 | 423 |
| B-0696 | 4-F-phenyl | 2,6-dichlorobenzoyl | 57 | 454 | 455 |
| B-0697 | 4-F-phenyl | 2,5-difluorobenzoyl | 51 | 422 | 423 |
| B-0698 | 4-F-phenyl | 2,4,5-trifluorobenzoyl | 59 | 440 | 441 |
| B-0699 | 4-F-phenyl | 2-fluorobenzoyl | 46 | 404 | 405 |

-continued
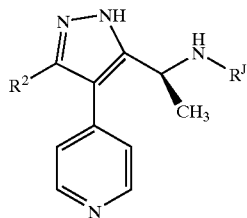
| Example # | R² | R^J | % Yield | Calcd. Mass Spec | Observed Mass Spec (M + H) |
|---|---|---|---|---|---|
| B-0700 | 4-F-C₆H₄ | 2,6-difluorobenzoyl | 47 | 422 | 423 |
| B-0701 | 4-F-C₆H₄ | 2,4-difluorobenzoyl | 46 | 422 | 423 |
| B-0702 | 4-F-C₆H₄ | 3-chlorobenzoyl | 43 | 420 | 421 |
| B-0703 | 4-F-C₆H₄ | 2-bromobenzoyl | 57 | 464 | 465 |
| B-0704 | 4-F-C₆H₄ | 4-trifluoromethylbenzoyl | 44 | 454 | 455 |
| B-0705 | 4-F-C₆H₄ | 2-thienylcarbonyl | 33 | 392 | 393 |
| B-0706 | 4-F-C₆H₄ | 3,5-dimethylisoxazol-4-ylcarbonyl | 35 | 405 | 406 |

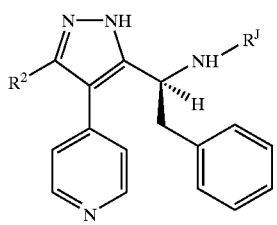
| Example # | R² | R^J | % Yield | Calcd. Mass Spec | Observed Mass Spec (M + H) |
|---|---|---|---|---|---|
| B-0707 | 4-F-C6H4 | 4-F-C6H4-SO2- | 76 | 516 | 517 |
| B-0708 | 4-F-C6H4 | C6H5-SO2- | 61 | 498 | 499 |
| B-0709 | 4-F-C6H4 | iPr-SO2- | 37 | 464 | 465 |
| B-0710 | 4-F-C6H4 | (E)-PhCH=CH-SO2- | 76 | 524 | 525 |
| B-0711 | 4-F-C6H4 | PhCH2-SO2- | 75 | 512 | 513 |
| B-0712 | 4-F-C6H4 | 2,4-diF-C6H3-SO2- | 91 | 534 | 535 |
| B-0713 | 4-F-C6H4 | CF3-SO2- | 42 | 490 | 491 |
| B-0714 | 4-F-C6H4 | 2-F-C6H4-SO2- | 87 | 516 | 517 |
| B-0715 | 4-F-C6H4 | n-Pr-SO2- | 60 | 464 | 465 |

-continued
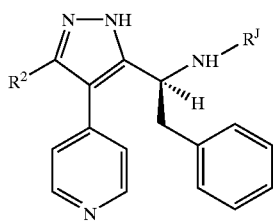
| Example # | R² | Rᴶ | % Yield | Calcd. Mass Spec | Observed Mass Spec (M + H) |
|---|---|---|---|---|---|
| B-0716 | 4-F-C₆H₄ | -SO₂-nBu | 59 | 478 | 479 |
| B-0717 | 4-F-C₆H₄ | -SO₂-Et | 61 | 450 | 451 |
| B-0718 | 4-F-C₆H₄ | -SO₂-Me | 65 | 436 | 437 |
| B-0719 | 4-F-C₆H₄ | -SO₂-(4-OMe-C₆H₄) | 84 | 528 | 529 |
| B-0720 | 4-F-C₆H₄ | -SO₂-(2-thienyl) | 69 | 504 | 505 |
| B-0721 | 4-F-C₆H₄ | -SO₂-(4-Me-C₆H₄) | 63 | 512 | 513 |
| B-0722 | 4-F-C₆H₄ | -SO₂-(3,4-diOMe-C₆H₃) | 88 | 558 | 559 |
| B-0723 | 4-F-C₆H₄ | -C(O)NH-iPr | 68 | 443 | 444 |
| B-0724 | 4-F-C₆H₄ | -C(O)NH₂ | 75 | 401 | 402 |

-continued
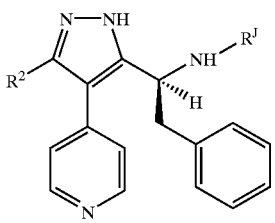
| Example # | R² | R^J | % Yield | Calcd. Mass Spec | Observed Mass Spec (M + H) |
|---|---|---|---|---|---|
| B-0725 | 4-F-C6H4 | -C(O)NH-CH2-Ph | 83 | 491 | 492 |
| B-0726 | 4-F-C6H4 | -C(O)-pyrrolidinyl | 24 | 455 | 456 |
| B-0727 | 4-F-C6H4 | -C(O)-morpholinyl | 67 | 471 | 472 |
| B-0728 | 4-F-C6H4 | -C(O)NH-C6H4-4-F | 89 | 495 | 496 |
| B-0729 | 4-F-C6H4 | -C(O)N(CH3)2 | 38 | 429 | 430 |
| B-0730 | 4-F-C6H4 | -C(O)NHCH3 | 76 | 415 | 416 |
| B-0731 | 4-F-C6H4 | -C(O)N(CH3)Ph | 60 | 491 | 492 |

-continued
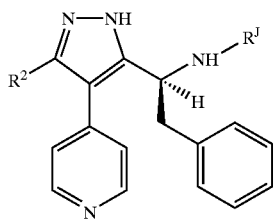
| Example # | R² | R^J | % Yield | Calcd. Mass Spec | Observed Mass Spec (M + H) |
|---|---|---|---|---|---|
| B-0732 | 4-F-C₆H₄ | 2-F-C₆H₄-NH-C(O)- | 86 | 495 | 496 |
| B-0733 | 4-F-C₆H₄ | 2,6-diMe-C₆H₃-NH-C(O)- | 81 | 505 | 506 |
| B-0734 | 4-F-C₆H₄ | allyl-NH-C(O)- | 87 | 441 | 442 |
| B-0735 | 4-F-C₆H₄ | n-Pr-NH-C(O)- | 83 | 443 | 444 |
| B-0736 | 4-F-C₆H₄ | (R)-α-methylbenzyl-NH-C(O)- | 91 | 505 | 506 |
| B-0737 | 4-F-C₆H₄ | Ph-NH-C(O)- | 9 | 477 | — |
| B-0738 | 4-F-C₆H₄ | PhCH₂CH₂-CHF-C(O)- | 87 | 505 | 506 |

-continued
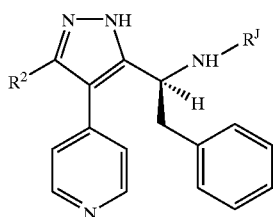
| Example # | R² | RJ | % Yield | Calcd. Mass Spec | Observed Mass Spec (M + H) |
|---|---|---|---|---|---|
| B-0739 | 4-F-phenyl | -C(O)NH-CH(CH₃)-phenyl | 82 | 505 | 506 |
| B-0740 | 4-F-phenyl | -C(O)NH-(3-F-phenyl) | 85 | 495 | 496 |
| B-0741 | 4-F-phenyl | -C(O)NH-(4-OMe-phenyl) | 68 | 507 | 508 |
| B-0742 | 4-F-phenyl | -C(O)N(Et)₂ | 14 | 457 | — |
| B-0743 | 4-F-phenyl | -C(O)NH-Et | 77 | 429 | 430 |
| B-0744 | 4-F-phenyl | -C(O)NH-(2,4-diOMe-phenyl) | 86 | 537 | 538 |
| B-0745 | 4-F-phenyl | -C(O)-CH₂-(2-thienyl) | 82 | 482 | 483 |

-continued
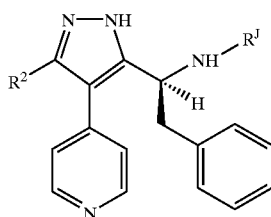
| Example # | R² | R^J | % Yield | Calcd. Mass Spec | Observed Mass Spec (M + H) |
|---|---|---|---|---|---|
| B-0746 | 4-F-C6H4 | C(O)C(CH3)3 | 74 | 442 | 443 |
| B-0747 | 4-F-C6H4 | C(O)O-n-propyl | 83 | 444 | 445 |
| B-0748 | 4-F-C6H4 | C(O)OEt | 94 | 430 | 431 |
| B-0749 | 4-F-C6H4 | (S)-prolyl | 100 | 455 | 456 |
| B-0750 | 4-F-C6H4 | (R)-prolyl | 100 | 455 | 456 |
| B-0751 | 4-F-C6H4 | C(O)O-i-Pr | 48 | 444 | 445 |

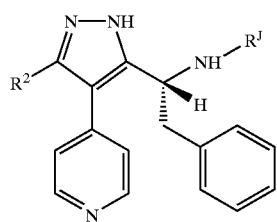
| Example # | R² | R^J | % Yield | Calcd. Mass Spec | Observed Mass Spec (M + H) |
|---|---|---|---|---|---|
| B-0752 | 4-F-C₆H₄ | 4-F-C₆H₄-SO₂- | 84 | 516 | 517 |
| B-0753 | 4-F-C₆H₄ | C₆H₅-SO₂- | 67 | 498 | 499 |
| B-0754 | 4-F-C₆H₄ | iPr-SO₂- | 31 | 464 | 465 |
| B-0755 | 4-F-C₆H₄ | (E)-PhCH=CH-SO₂- | 85 | 524 | 525 |
| B-0756 | 4-F-C₆H₄ | PhCH₂-SO₂- | 77 | 512 | 513 |
| B-0757 | 4-F-C₆H₄ | 2,4-F₂-C₆H₃-SO₂- | 57 | 534 | 535 |
| B-0758 | 4-F-C₆H₄ | CF₃-SO₂- | 36 | 490 | 491 |
| B-0759 | 4-F-C₆H₄ | 2-F-C₆H₄-SO₂- | 79 | 516 | 517 |
| B-0760 | 4-F-C₆H₄ | n-Pr-SO₂- | 53 | 464 | 465 |

-continued

| Example # | R² | R^J | % Yield | Calcd. Mass Spec | Observed Mass Spec (M + H) |
|---|---|---|---|---|---|
| B-0761 | 4-F-C₆H₄ | -SO₂-n-Bu | 50 | 478 | 479 |
| B-0762 | 4-F-C₆H₄ | -SO₂-Et | 60 | 450 | 451 |
| B-0763 | 4-F-C₆H₄ | -SO₂-Me | 75 | 436 | 437 |
| B-0764 | 4-F-C₆H₄ | -SO₂-(4-MeO-C₆H₄) | 43 | 528 | 529 |
| B-0765 | 4-F-C₆H₄ | -SO₂-(2-thienyl) | 75 | 504 | 505 |
| B-0766 | 4-F-C₆H₄ | -SO₂-(4-Me-C₆H₄) | 67 | 512 | 513 |
| B-0767 | 4-F-C₆H₄ | -SO₂-(3,4-diMeO-C₆H₃) | 43 | 558 | 559 |
| B-0768 | 4-F-C₆H₄ | -C(O)NH-iPr | 78 | 443 | 444 |
| B-0769 | 4-F-C₆H₄ | -C(O)NH₂ | 76 | 401 | 402 |

-continued
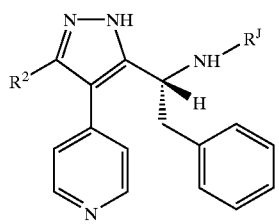
| Example # | R² | R^J | % Yield | Calcd. Mass Spec | Observed Mass Spec (M + H) |
|---|---|---|---|---|---|
| B-0770 | 4-F-C₆H₄ | -C(O)-NH-CH₂-C₆H₅ | 57 | 491 | 492 |
| B-0771 | 4-F-C₆H₄ | -C(O)-pyrrolidine | 14 | 455 | 456 |
| B-0772 | 4-F-C₆H₄ | -C(O)-morpholine | 72 | 471 | 472 |
| B-0773 | 4-F-C₆H₄ | -C(O)-NH-C₆H₄-4-F | 100 | 495 | 496 |
| B-0774 | 4-F-C₆H₄ | -C(O)-N(CH₃)₂ | 41 | 429 | 430 |
| B-0775 | 4-F-C₆H₄ | -C(O)-NH-CH₃ | 91 | 415 | 416 |
| B-0776 | 4-F-C₆H₄ | -C(O)-N(CH₃)-C₆H₅ | 64 | 491 | 492 |

-continued
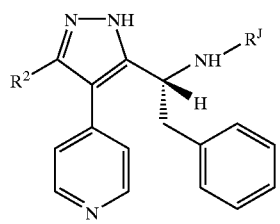
| Example # | R² | R$^J$ | % Yield | Calcd. Mass Spec | Observed Mass Spec (M + H) |
|---|---|---|---|---|---|
| B-0777 | 4-F-C₆H₄ | 2-F-C₆H₄-NH-C(O)- | 90 | 495 | 496 |
| B-0778 | 4-F-C₆H₄ | 2,6-diMe-C₆H₃-NH-C(O)- | 19 | 505 | 506 |
| B-0779 | 4-F-C₆H₄ | allyl-NH-C(O)- | 79 | 441 | 442 |
| B-0780 | 4-F-C₆H₄ | n-propyl-NH-C(O)- | 40 | 443 | 444 |
| B-0781 | 4-F-C₆H₄ | (S)-α-methylbenzyl-NH-C(O)- | 93 | 505 | 506 |
| B-0782 | 4-F-C₆H₄ | Ph-NH-C(O)- | 57 | 477 | 478 |
| B-0783 | 4-F-C₆H₄ | PhCH₂CH₂-NH-C(O)- | 99 | 505 | 506 |

-continued
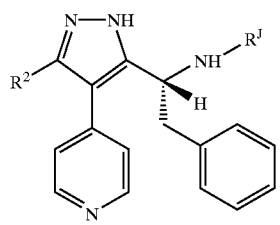
| Example # | R² | R^J | % Yield | Calcd. Mass Spec | Observed Mass Spec (M + H) |
|---|---|---|---|---|---|
| B-0784 | 4-F-C6H4 | -C(O)NH-CH(CH3)-Ph | 100 | 505 | 506 |
| B-0785 | 4-F-C6H4 | -C(O)NH-(3-F-C6H4) | 92 | 495 | 496 |
| B-0786 | 4-F-C6H4 | -C(O)NH-(4-MeO-C6H4) | 91 | 507 | 508 |
| B-0787 | 4-F-C6H4 | -C(O)N(Et)2 | 15 | 457 | 458 |
| B-0788 | 4-F-C6H4 | -C(O)NH-Et | 48 | 429 | 430 |
| B-0789 | 4-F-C6H4 | -C(O)NH-(2,4-diMeO-C6H3) | 91 | 537 | 538 |
| B-0790 | 4-F-C6H4 | -C(O)CH2-(2-thienyl) | 93 | 482 | 483 |

-continued
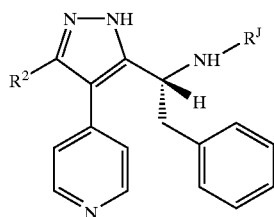
| Example # | R² | R^J | % Yield | Calcd. Mass Spec | Observed Mass Spec (M + H) |
|---|---|---|---|---|---|
| B-0791 | 4-F-C6H4 | C(O)C(CH3)3 | 76 | 442 | 443 |
| B-0792 | 4-F-C6H4 | C(O)O-n-propyl | 96 | 444 | 445 |
| B-0793 | 4-F-C6H4 | C(O)OEt | 54 | 430 | 431 |
| B-0794 | 4-F-C6H4 | (S)-prolyl | 100 | 455 | 456 |
| B-0795 | 4-F-C6H4 | (R)-prolyl | 100 | 455 | 456 |
| B-0796 | 4-F-C6H4 | C(O)O-iPr | 94 | 444 | 445 |
| B-0797 | 4-F-C6H4 | C(O)CH2OC(O)CH3 | 90 | 458 | 459 |
| B-0798 | 4-F-C6H4 | C(O)-(2-I-C6H4) | 90 | 588 | 589 |

-continued
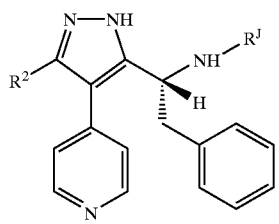
| Example # | R² | R^J | % Yield | Calcd. Mass Spec | Observed Mass Spec (M + H) |
|---|---|---|---|---|---|
| B-0799 | 4-F-C₆H₄ | isobutyryl | 82 | 428 | 429 |
| B-0800 | 4-F-C₆H₄ | 4-F-C₆H₄-C(O)- | 92 | 480 | 481 |
| B-0801 | 4-F-C₆H₄ | allyloxycarbonyl | 82 | 442 | 443 |
| B-0802 | 4-F-C₆H₄ | 2-acetoxy-2-methylpropanoyl | 95 | 486 | 487 |
| B-0803 | 4-F-C₆H₄ | acetyl | 89 | 400 | 401 |
| B-0804 | 4-F-C₆H₄ | cyclobutylcarbonyl | 87 | 440 | 441 |
| B-0805 | 4-F-C₆H₄ | cyclopropylcarbonyl | 100 | 426 | 427 |
| B-0806 | 4-F-C₆H₄ | 3-Br-C₆H₄-C(O)- | 99 | 540 | 541 |

-continued
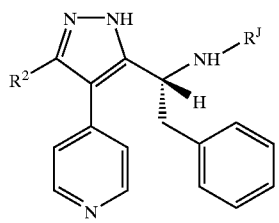
| Example # | R² | R^J | % Yield | Calcd. Mass Spec | Observed Mass Spec (M + H) |
|---|---|---|---|---|---|
| B-0807 | 4-F-C₆H₄ | 4-I-C₆H₄-C(O)- | 96 | 588 | 589 |
| B-0808 | 4-F-C₆H₄ | isoxazol-5-yl-C(O)- | 82 | 453 | 454 |
| B-0809 | 4-F-C₆H₄ | CH₃CH(OAc)-C(O)- | 92 | 472 | 473 |
| B-0810 | 4-F-C₆H₄ | CH₃OCH₂-C(O)- | 98 | 430 | 431 |
| B-0811 | 4-F-C₆H₄ | 2-MeO-C₆H₄-C(O)- | 88 | 492 | 493 |
| B-0812 | 4-F-C₆H₄ | 2-CF₃-C₆H₄-C(O)- | 81 | 530 | 531 |
| B-0813 | 4-F-C₆H₄ | 2,3,4-triF-C₆H₂-C(O)- | 98 | 516 | 517 |

-continued
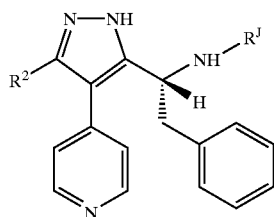
| Example # | R² | R^J | % Yield | Calcd. Mass Spec | Observed Mass Spec (M + H) |
|---|---|---|---|---|---|
| B-0814 | 4-F-phenyl | 4-methyl-3-oxopent-3-en-2-yl | 100 | 440 | 441 |
| B-0815 | 4-F-phenyl | 2-(3,4-dimethoxyphenyl)acetyl | 100 | 536 | 537 |
| B-0816 | 4-F-phenyl | 2-(4-methoxyphenyl)acetyl | 99 | 506 | 507 |
| B-0817 | 4-F-phenyl | 2-(3-methoxyphenyl)acetyl | 98 | 506 | 507 |
| B-0818 | 4-F-phenyl | 4-methylbenzoyl | 86 | 476 | 477 |
| B-0819 | 4-F-phenyl | benzoyl | 90 | 462 | 463 |
| B-0820 | 4-F-phenyl | cyclopentylcarbonyl | 91 | 454 | 455 |
| B-0821 | 4-F-phenyl | pyridin-3-ylcarbonyl | 69 | 463 | 464 |

-continued

| Example # | R² | Rᴶ | % Yield | Calcd. Mass Spec | Observed Mass Spec (M + H) |
|---|---|---|---|---|---|
| B-0822 | 4-F-phenyl | 4-pyridyl-C(O)- | 79 | 463 | 464 |
| B-0823 | 4-F-phenyl | 2-pyridyl-C(O)- | 79 | 463 | 464 |
| B-0824 | 4-F-phenyl | 3-methoxyphenyl-C(O)- | 82 | 492 | 493 |
| B-0825 | 4-F-phenyl | PhO-CH(CH₃)-C(O)- | 100 | 506 | 507 |
| B-0826 | 4-F-phenyl | iBuO-C(O)- | 97 | 458 | 459 |
| B-0827 | 4-F-phenyl | Tos-NH-CH(CH₂Ph)-C(O)- | 100 | 659 | 660 |

-continued

| Example # | R² | R^J | % Yield | Calcd. Mass Spec | Observed Mass Spec (M + H) |
|---|---|---|---|---|---|
| B-0828 | 4-F-phenyl | quinoxaline-2-carbonyl | 97 | 514 | 515 |
| B-0829 | 4-F-phenyl | -C(O)CH₂CH₂C(O)CH₃ | 63 | 458 | 459 |
| B-830 | 4-F-phenyl | 2-iodobenzoyl | 70 | 588 | 589 |
| B-0831 | 4-F-phenyl | isobutyryl | 100 | 428 | 429 |
| B-0832 | 4-F-phenyl | 4-fluorobenzoyl | 81 | 480 | 481 |
| B-0833 | 4-F-phenyl | allyloxycarbonyl | 73 | 442 | 443 |
| B-0834 | 4-F-phenyl | -C(O)C(CH₃)₂CH₂C(O)CH₃ | 79 | 486 | 487 |

-continued
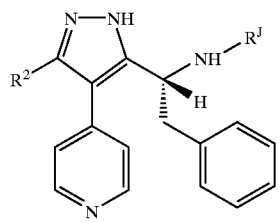
| Example # | R² | R^J | % Yield | Calcd. Mass Spec | Observed Mass Spec (M + H) |
|---|---|---|---|---|---|
| B-0835 | 4-F-C6H4 | acetyl | 5 | 400 | 401 |
| B-0836 | 4-F-C6H4 | cyclobutylcarbonyl | 28 | 440 | 441 |
| B-0837 | 4-F-C6H4 | cyclopropylcarbonyl | 81 | 426 | 427 |
| B-0838 | 4-F-C6H4 | 3-bromobenzoyl | 84 | 540 | 541 |
| B-0839 | 4-F-C6H4 | 4-iodobenzoyl | 80 | 588 | 589 |
| B-0840 | 4-F-C6H4 | isoxazol-5-ylcarbonyl | 71 | 453 | 454 |
| B-0841 | 4-F-C6H4 | (S)-2-acetoxypropanoyl | 55 | 472 | 473 |
| B-0842 | 4-F-C6H4 | methoxyacetyl | 71 | 430 | 431 |

-continued

| Example # | R² | R^J | % Yield | Calcd. Mass Spec | Observed Mass Spec (M + H) |
|---|---|---|---|---|---|
| B-0843 | 4-F-phenyl | 2-methoxybenzoyl | 68 | 492 | 493 |
| B-0844 | 4-F-phenyl | 2-(trifluoromethyl)benzoyl | 61 | 530 | 531 |
| B-0845 | 4-F-phenyl | 2,3,4-trifluorobenzoyl | 84 | 516 | 517 |
| B-0846 | 4-F-phenyl | 4-methyl-3-pentenoyl | 87 | 440 | 441 |
| B-0847 | 4-F-phenyl | (3,4-dimethoxyphenyl)acetyl | 86 | 536 | 537 |
| B-0848 | 4-F-phenyl | (4-methoxyphenyl)acetyl | 79 | 506 | 507 |
| B-0849 | 4-F-phenyl | (3-methoxyphenyl)acetyl | 81 | 506 | 507 |

-continued
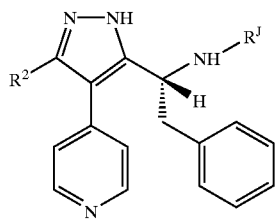
| Example # | R² | R^J | % Yield | Calcd. Mass Spec | Observed Mass Spec (M + H) |
|---|---|---|---|---|---|
| B-0850 | 4-F-phenyl | 4-methylbenzoyl | 69 | 476 | 477 |
| B-0851 | 4-F-phenyl | benzoyl | 83 | 462 | 463 |
| B-0852 | 4-F-phenyl | cyclopentylcarbonyl | 77 | 454 | 455 |
| B-0853 | 4-F-phenyl | pyridine-3-carbonyl | 87 | 463 | 464 |
| B-0854 | 4-F-phenyl | pyridine-4-carbonyl | 73 | 463 | 464 |
| B-0855 | 4-F-phenyl | pyridine-2-carbonyl | 92 | 463 | 464 |
| B-0856 | 4-F-phenyl | 3-methoxybenzoyl | 75 | 492 | 493 |

-continued
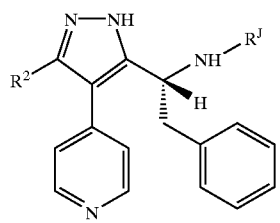
| Example # | R² | R^J | % Yield | Calcd. Mass Spec | Observed Mass Spec (M + H) |
|---|---|---|---|---|---|
| B-0857 | 4-F-C6H4 | -CH(CH3)-C(O)-O-Ph | 86 | 506 | 507 |
| B-0858 | 4-F-C6H4 | -CH2-C(O)-O-CH2CH(CH3)2 | 84 | 458 | 459 |
| B-0859 | 4-F-C6H4 | -CH(CH2Ph)-C(O)-NH-S(O)2-Ph | 80 | 659 | 660 |
| B-0860 | 4-F-C6H4 | -C(O)-quinoxalin-2-yl | 94 | 514 | 515 |

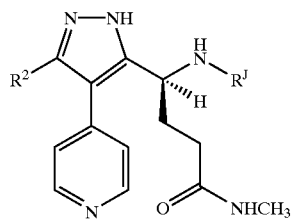
| Example # | R² | R^J | % Yield | Calcd. Mass Spec | Observed Mass Spec (M + H) |
|---|---|---|---|---|---|
| B-0861 | 4-F-phenyl | 2-iodobenzoyl | 84 | 583 | 584 |
| B-0862 | 4-F-phenyl | 4-fluorobenzoyl | 96 | 475 | 476 |
| B-0863 | 4-F-phenyl | isobutyryl | 69 | 423 | 424 |
| B-0864 | 4-F-phenyl | allyloxycarbonyl | 86 | 437 | 438 |
| B-0865 | 4-F-phenyl | acetyl | 62 | 395 | — |
| B-0866 | 4-F-phenyl | cyclopropanecarbonyl | 81 | 421 | 422 |
| B-0867 | 4-F-phenyl | 3-bromobenzoyl | 100 | 535 | 536 |
| B-0868 | 4-F-phenyl | 4-iodobenzoyl | 89 | 583 | 584 |

-continued

[Structure: pyrazole with R² at 3-position, 4-pyridyl at 4-position, and at 5-position a CH(NHR^J) group bearing a CH2CH2C(O)NHCH3 chain]

| Example # | R² | R^J | % Yield | Calcd. Mass Spec | Observed Mass Spec (M + H) |
|---|---|---|---|---|---|
| B-0869 | 4-F-C6H4 | isoxazol-5-yl-C(O)- | 100 | 448 | 449 |
| B-0870 | 4-F-C6H4 | CH3OCH2-C(O)- | 100 | 425 | 426 |
| B-0871 | 4-F-C6H4 | 2-methoxyphenyl-C(O)- | 100 | 487 | 486 |
| B-0872 | 4-F-C6H4 | (3-methoxyphenyl)CH2-C(O)- | 78 | 501 | 502 |
| B-0873 | 4-F-C6H4 | 4-methylphenyl-C(O)- | 78 | 471 | 472 |
| B-0874 | 4-F-C6H4 | 2-fluorophenyl-C(O)- | 92 | 475 | 476 |
| B-0875 | 4-F-C6H4 | pyridin-4-yl-C(O)- | 37 | 458 | 459 |

-continued

| Example # | R² | R^J | % Yield | Calcd. Mass Spec | Observed Mass Spec (M + H) |
|---|---|---|---|---|---|
| B-0876 | 4-F-C₆H₄ | benzylsulfonyl | 69 | 507 | 508 |
| B-0877 | 4-F-C₆H₄ | ethylsulfonyl | 70 | 445 | 446 |
| B-0878 | 4-F-C₆H₄ | methylsulfonyl | 91 | 431 | 432 |
| B-0879 | 4-F-C₆H₄ | 2-F-C₆H₄-sulfonyl | 92 | 511 | 512 |
| B-0880 | 4-F-C₆H₄ | N-methylcarbamoyl | 89 | 410 | 411 |
| B-0881 | 4-F-C₆H₄ | (2-F-phenyl)carbamoyl | 84 | 490 | 491 |
| B-0882 | 4-F-C₆H₄ | (2,6-dimethylphenyl)carbamoyl | 85 | 500 | 501 |
| B-0883 | 4-F-C₆H₄ | N-ethylcarbamoyl | 85 | 424 | 425 |

-continued
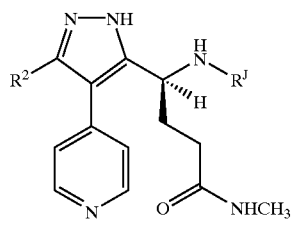
| Example # | R² | R^J | % Yield | Calcd. Mass Spec | Observed Mass Spec (M + H) |
|---|---|---|---|---|---|
| B-0884 | 4-F-C6H4 | -C(O)-NH-(2,4-dimethoxyphenyl) | 86 | 532 | 533 |
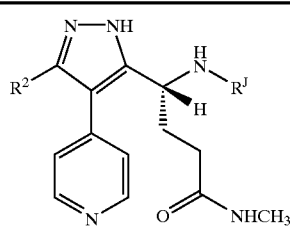
| Example # | R² | R^J | % Yield | Calcd. Mass Spec | Observed Mass Spec (M + H) |
|---|---|---|---|---|---|
| B-0885 | 4-F-C6H4 | -C(O)-(2-iodophenyl) | 51 | 583 | — |
| B-0886 | 4-F-C6H4 | -C(O)-(4-fluorophenyl) | 97 | 475 | — |
| B-0887 | 4-F-C6H4 | -C(O)-CH(CH3)2 | 29 | 423 | 424 |
| B-0888 | 4-F-C6H4 | -C(O)-O-CH2-CH=CH2 | 82 | 437 | 438 |
| B-0889 | 4-F-C6H4 | -C(O)-CH3 | 93 | 395 | 396 |

-continued

| Example # | R² | Rʲ | % Yield | Calcd. Mass Spec | Observed Mass Spec (M + H) |
|---|---|---|---|---|---|
| B-0890 | 4-F-phenyl | C(O)-cyclopropyl | 91 | 421 | 422 |
| B-0891 | 4-F-phenyl | C(O)-(3-Br-phenyl) | 43 | 535 | 536 |
| B-0892 | 4-F-phenyl | C(O)-(4-I-phenyl) | 62 | 583 | 584 |
| B-0893 | 4-F-phenyl | C(O)-isoxazol-5-yl | 95 | 448 | 449 |
| B-0894 | 4-F-phenyl | C(O)-CH₂-OCH₃ | 100 | 425 | 426 |
| B-0895 | 4-F-phenyl | C(O)-(2-OMe-phenyl) | 76 | 487 | 488 |
| B-0896 | 4-F-phenyl | C(O)-CH₂-(3-OMe-phenyl) | 62 | 501 | 502 |
| B-0897 | 4-F-phenyl | C(O)-(4-Me-phenyl) | 80 | 471 | 472 |

-continued

| Example # | R² | RJ | % Yield | Calcd. Mass Spec | Observed Mass Spec (M + H) |
|---|---|---|---|---|---|
| B-0898 | 4-F-phenyl | 2-F-benzoyl | 79 | 475 | 476 |
| B-0899 | 4-F-phenyl | pyridin-4-yl-carbonyl | 70 | 458 | 459 |
| B-0900 | 4-F-phenyl | benzylsulfonyl | 62 | 507 | 508 |
| B-0901 | 4-F-phenyl | ethylsulfonyl | 43 | 445 | 446 |
| B-0902 | 4-F-phenyl | methylsulfonyl | 93 | 431 | 432 |
| B-0903 | 4-F-phenyl | 2-F-phenylsulfonyl | 100 | 511 | 512 |
| B-0904 | 4-F-phenyl | N-methylcarbamoyl | 95 | 410 | 411 |
| B-0905 | 4-F-phenyl | (2-F-phenyl)aminocarbonyl | 89 | 490 | 491 |

-continued
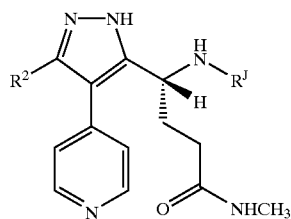
| Example # | R² | R<sup>J</sup> | % Yield | Calcd. Mass Spec | Observed Mass Spec (M + H) |
|---|---|---|---|---|---|
| B-0906 | 4-F-phenyl | -C(O)NH-(2,6-dimethylphenyl) | 69 | 500 | 501 |
| B-0907 | 4-F-phenyl | -C(O)NH-ethyl | 28 | 424 | 425 |
| B-0908 | 4-F-phenyl | -C(O)NH-(2,4-dimethoxyphenyl) | 64 | 532 | 533 |
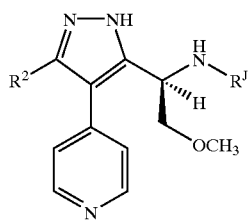
| Example # | R² | R<sup>J</sup> | % Yield | Calcd. Mass Spec | Observed Mass Spec (M + H) |
|---|---|---|---|---|---|
| B-0909 | 4-F-phenyl | -C(O)-(2-iodophenyl) | 83 | 542 | 543 |
| B-0910 | 4-F-phenyl | -C(O)-(4-fluorophenyl) | 80 | 434 | 435 |

-continued
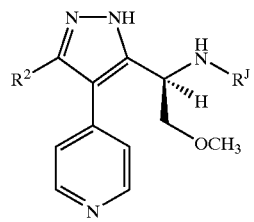
| Example # | R² | R^J | % Yield | Calcd. Mass Spec | Observed Mass Spec (M + H) |
|---|---|---|---|---|---|
| B-0911 | 4-F-phenyl | isopropyl C(O)- | 91 | 382 | 383 |
| B-0912 | 4-F-phenyl | allyloxycarbonyl-CH- | 100 | 396 | 397 |
| B-0913 | 4-F-phenyl | CH₃C(O)- | 94 | 354 | 355 |
| B-0914 | 4-F-phenyl | cyclopropyl-C(O)- | 95 | 380 | 381 |
| B-0915 | 4-F-phenyl | 3-Br-phenyl-C(O)- | 98 | 494 | 495 |
| B-0916 | 4-F-phenyl | 4-I-phenyl-C(O)- | 84 | 542 | 543 |
| B-0917 | 4-F-phenyl | isoxazol-5-yl-C(O)- | 79 | 407 | 408 |
| B-0918 | 4-F-phenyl | CH₃OCH₂C(O)- | 89 | 384 | 385 |

-continued
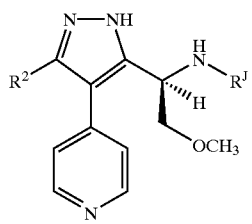
| Example # | R² | R^J | % Yield | Calcd. Mass Spec | Observed Mass Spec (M + H) |
|---|---|---|---|---|---|
| B-0919 | 4-F-phenyl | 2-methoxybenzoyl | 91 | 446 | 447 |
| B-0920 | 4-F-phenyl | (3-methoxyphenyl)acetyl | 99 | 460 | 461 |
| B-0921 | 4-F-phenyl | 4-methylbenzoyl | 84 | 430 | 431 |
| B-0922 | 4-F-phenyl | 2-fluorobenzoyl | 81 | 434 | 435 |
| B-0923 | 4-F-phenyl | isonicotinoyl | 76 | 417 | 418 |
| B-0924 | 4-F-phenyl | benzylsulfonyl | 70 | 466 | 467 |
| B-0925 | 4-F-phenyl | ethylsulfonyl | 64 | 404 | 405 |
| B-0926 | 4-F-phenyl | methylsulfonyl | 47 | 390 | 391 |

-continued
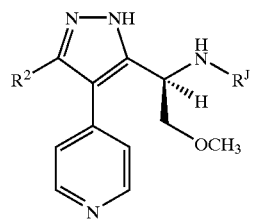
| Example # | R² | R^J | % Yield | Calcd. Mass Spec | Observed Mass Spec (M + H) |
|---|---|---|---|---|---|
| B-0927 | 4-F-C6H4 | 2-F-C6H4-SO2- | 89 | 470 | 471 |
| B-0928 | 4-F-C6H4 | -C(O)NHCH3 | 53 | 369 | 370 |
| B-0929 | 4-F-C6H4 | -C(O)NH-(2-F-C6H4) | 100 | 449 | 450 |
| B-0930 | 4-F-C6H4 | -C(O)NH-(2,6-diMe-C6H3) | 14 | 459 | 460 |
| B-0931 | 4-F-C6H4 | -C(O)NH-Et | 41 | 383 | 384 |
| B-0932 | 4-F-C6H4 | -C(O)NH-(2,4-diOMe-C6H3) | 94 | 491 | 492 |

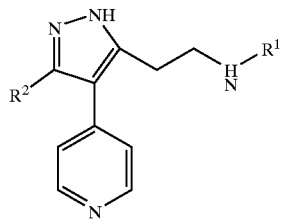
| Example# | R² | R^J | % Yield | Calcd. Mass Spec | Observed Mass Spec (M + H) |
|---|---|---|---|---|---|
| B-0933 | 4-F-C₆H₄ | 3-(methylthio)phenyl acetamide | 48 | 447 | 448 |
| B-0934 | 4-F-C₆H₄ | benzoylaminoacetyl | 44 | 429 | 430 |
| B-0935 | 4-F-C₆H₄ | methionine ethyl ester amide | 33 | 485 | 486 |
| B-0936 | 4-F-C₆H₄ | 8,9-dioxoundecanoyl | 30 | 479 | — |
| B-0937 | 4-F-C₆H₄ | N-isopropyl acetamide | 68 | 367 | 368 |
| B-0938 | 4-F-C₆H₄ | 4-bromophenyl acetamide | 72 | 479 | 480 |

-continued
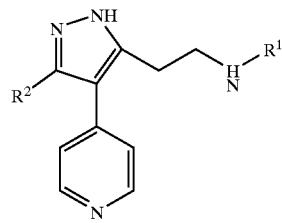
| Example# | R² | R^J | % Yield | Calcd. Mass Spec | Observed Mass Spec (M + H) |
|---|---|---|---|---|---|
| B-0939 | 4-F-phenyl | benzylaminocarbonyl (C(O)NHCH₂Ph) | 76 | 415 | 416 |
| B-0940 | 4-F-phenyl | ethoxycarbonylamino-methyl | 36 | 397 | 398 |
| B-0941 | 4-F-phenyl | (2-phenylcyclopropyl)aminocarbonyl | 41 | 441 | 442 |
| B-0942 | 4-F-phenyl | 3-(ethoxycarbonyl)phenyl-aminocarbonyl | 27 | 473 | 474 |
| B-0943 | 4-F-phenyl | 4-phenoxyphenyl-aminocarbonyl | 55 | 493 | 494 |
| B-0944 | 4-F-phenyl | 4-butoxyphenyl-aminocarbonyl | 53 | 473 | 474 |

-continued
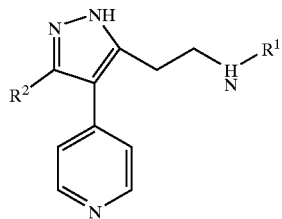
| Example# | R² | RJ | % Yield | Calcd. Mass Spec | Observed Mass Spec (M + H) |
|---|---|---|---|---|---|
| B-0945 | 4-F-phenyl | -C(O)NH-CH₂CH₂-phenyl | 82 | 429 | 430 |
| B-0946 | 4-F-phenyl | -C(O)NH-(2-CO₂Me-phenyl) | 100 | 459 | 460 |
| B-0947 | 4-F-phenyl | -C(O)NH-CH₂CH₂-CO₂Et | 60 | 425 | 426 |
| B-0948 | 4-F-phenyl | -C(O)NH-(3-OMe-phenyl) | 100 | 431 | 432 |
| B-0949 | 4-F-phenyl | -C(O)NH-(4-CO₂Et-phenyl) | 98 | 473 | 474 |
| B-0950 | 4-F-phenyl | -C(O)NH-(2-F-phenyl) | 64 | 419 | 420 |
| B-0951 | 4-F-phenyl | -C(O)NH-(4-CF₃-phenyl) | 100 | 469 | 470 |

-continued
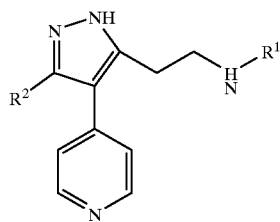
| Example# | R² | R¹ | % Yield | Calcd. Mass Spec | Observed Mass Spec (M + H) |
|---|---|---|---|---|---|
| B-0952 | 4-F-phenyl | -C(O)NH-(3,5-dichlorophenyl) | 61 | 469 | 470 |
| B-0953 | 4-F-phenyl | -C(O)-NH-CH(CH₃)-C(O)OEt | 67 | 425 | 426 |
| B-0954 | 4-F-phenyl | -C(O)NH-(2-methoxyphenyl) | 62 | 431 | 432 |
| B-0955 | 4-F-phenyl | -C(O)NH-(2,4-dimethoxyphenyl) | 39 | 461 | 462 |
| B-0956 | 4-F-phenyl | -C(O)NH-(2,6-dimethylphenyl) | 66 | 429 | 430 |
| B-0957 | 4-F-phenyl | -C(O)NH-(2-ethylphenyl) | 93 | 429 | 430 |
| B-0958 | 4-F-phenyl | -C(O)NH-allyl | 86 | 365 | 366 |

-continued
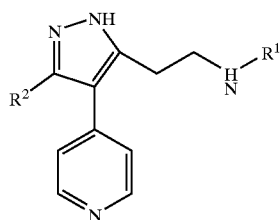
| Example# | R² | RJ | % Yield | Calcd. Mass Spec | Observed Mass Spec (M + H) |
|---|---|---|---|---|---|
| B-0959 | 4-F-phenyl | naphthalen-1-yl-NH-C(O)- | 73 | 451 | 452 |
| B-0960 | 4-F-phenyl | 4-(OCF₃)-phenyl-NH-C(O)- | 98 | 485 | 486 |
| B-0961 | 4-F-phenyl | 3,4-diCl-phenyl-NH-C(O)- | 100 | 469 | 470 |
| B-0962 | 4-F-phenyl | 4-F-phenyl-NH-C(O)- | 100 | 419 | 420 |
| B-0963 | 4-F-phenyl | phenyl-NH-C(O)- | 83 | 401 | 402 |
| B-0964 | 4-F-phenyl | (R)-PhCH(CH₃)-NH-C(O)- | 38 | 429 | 430 |
| B-0965 | 4-F-phenyl | EtO₂C-CH₂-NH-C(O)- | 90 | 411 | 412 |

-continued

| Example# | R² | R^J | % Yield | Calcd. Mass Spec | Observed Mass Spec (M + H) |
|---|---|---|---|---|---|
| B-0966 | 4-F-phenyl | -C(O)NH-(4-isopropylphenyl) | 76 | 443 | 444 |
| B-0967 | 4-F-phenyl | -C(O)NH-(2-isopropylphenyl) | 100 | 443 | 444 |
| B-0968 | 4-F-phenyl | -C(O)NH-(4-biphenyl) | 100 | 477 | 478 |
| B-0969 | 4-F-phenyl | -C(O)NH-(2-biphenyl) | 77 | 477 | 478 |
| B-0970 | 4-F-phenyl | -C(O)NH-(2,5-dimethoxyphenyl) | 38 | 461 | 462 |
| B-0971 | 4-F-phenyl | -C(O)NH-(2,5-dichlorophenyl) | 95 | 469 | 470 |

-continued
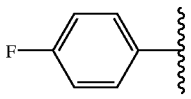
| Example# | R² | R³ | % Yield | Calcd. Mass Spec | Observed Mass Spec (M + H) |
|---|---|---|---|---|---|
| B-0972 | 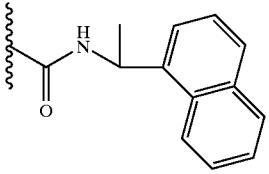 | 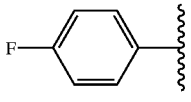 | 98 | 479 | 480 |
| B-0973 | 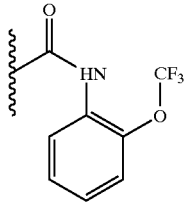 | 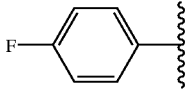 | 96 | 485 | 486 |
| B-0974 | 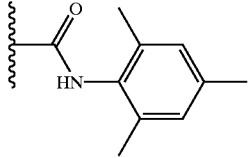 | 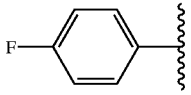 | 74 | 443 | 444 |
| B-0975 | 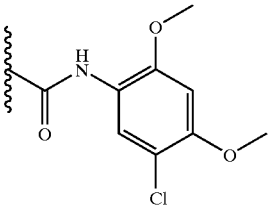 | 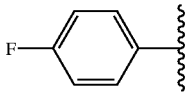 | 100 | 495 | 496 |
| B-0976 | 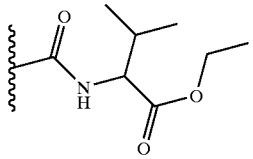 | 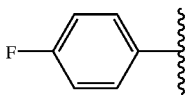 | 70 | 453 | 454 |
| B-0977 | | 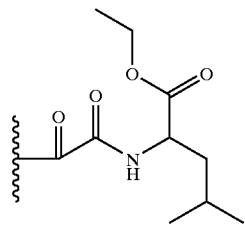 | 100 | 467 | 468 |

-continued
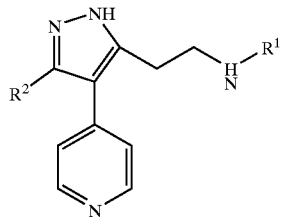
| Example# | R² | R¹ | % Yield | Calcd. Mass Spec | Observed Mass Spec (M + H) |
|---|---|---|---|---|---|
| B-0978 | 4-F-phenyl | 4-methoxyphenyl-NH-C(O)-CH- | 91 | 431 | 432 |
| B-0979 | 4-F-phenyl | 3,4,5-trimethoxyphenyl-NH-C(O)-CH- | 54 | 491 | 492 |
| B-0980 | 4-F-phenyl | 2,3-dichlorophenyl-NH-C(O)-CH- | 65 | 469 | 470 |
| B-0981 | 4-F-phenyl | -CH-C(O)-CH₂-O-C(O)-CH₃ | 78 | 382 | 383 |
| B-0982 | 4-F-phenyl | 2-methylphenyl-C(O)-CH- | 82 | 512 | 513 |
| B-0983 | 4-F-phenyl | -CH-C(O)-CH(CH₃)₂ | 94 | 352 | 353 |

-continued
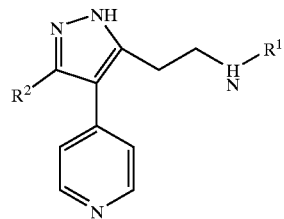
| Example# | R² | R¹ | % Yield | Calcd. Mass Spec | Observed Mass Spec (M + H) |
|---|---|---|---|---|---|
| B-0984 | 4-F-C₆H₄ | 4-methylbenzoyl | 81 | 404 | 405 |
| B-0985 | 4-F-C₆H₄ | allyloxycarbonyl | 84 | 366 | 367 |
| B-0986 | 4-F-C₆H₄ | 2-acetoxy-2-methylpropanoyl | 80 | 410 | 411 |
| B-0987 | 4-F-C₆H₄ | acetyl | 85 | 324 | 325 |
| B-0988 | 4-F-C₆H₄ | cyclobutanecarbonyl | 91 | 364 | 365 |
| B-0989 | 4-F-C₆H₄ | cyclopropanecarbonyl | 88 | 350 | 351 |
| B-0990 | 4-F-C₆H₄ | 3-bromobenzoyl | 68 | 464 | 465 |
| B-0991 | 4-F-C₆H₄ | 4-iodobenzoyl | 86 | 512 | 513 |

-continued
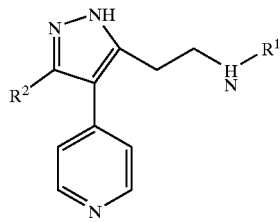
| Example# | R² | R^J | % Yield | Calcd. Mass Spec | Observed Mass Spec (M + H) |
|---|---|---|---|---|---|
| B-0992 | 4-F-C₆H₄ | isoxazol-5-yl carbonyl | 79 | 377 | 378 |
| B-0993 | 4-F-C₆H₄ | (S)-2-acetoxypropanoyl | 81 | 396 | 397 |
| B-0994 | 4-F-C₆H₄ | methoxyacetyl | 100 | 354 | 355 |
| B-0995 | 4-F-C₆H₄ | 2-methoxybenzoyl | 75 | 416 | 417 |
| B-0996 | 4-F-C₆H₄ | 2-trifluoromethylbenzoyl | 65 | 454 | 455 |
| B-0997 | 4-F-C₆H₄ | 2,3,4-trifluorobenzoyl | 64 | 440 | 441 |
| B-0998 | 4-F-C₆H₄ | 3-methyl-2-butenoyl | 81 | 364 | 365 |

-continued
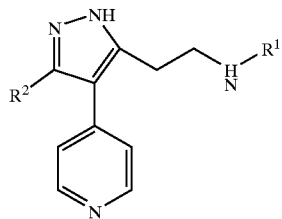
| Example# | R² | R^J | % Yield | Calcd. Mass Spec | Observed Mass Spec (M + H) |
|---|---|---|---|---|---|
| B-0999 | 4-F-phenyl | 3,4-dimethoxybenzyl ketone | 79 | 460 | 461 |
| B-1000 | 4-F-phenyl | 4-methoxybenzyl ketone | 84 | 430 | 431 |
| B-1001 | 4-F-phenyl | 3-methoxybenzyl ketone | 78 | 430 | 431 |
| B-1002 | 4-F-phenyl | 4-methylbenzoyl | 85 | 400 | 401 |
| B-1003 | 4-F-phenyl | benzoyl | 83 | 386 | 387 |
| B-1004 | 4-F-phenyl | cyclopentylcarbonyl | 87 | 378 | 379 |
| B-1005 | 4-F-phenyl | 3-pyridylcarbonyl | 57 | 387 | 388 |

-continued
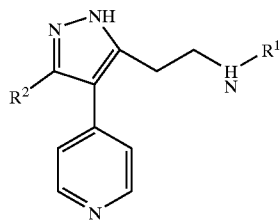
| Example# | R² | R¹ | % Yield | Calcd. Mass Spec | Observed Mass Spec (M + H) |
|---|---|---|---|---|---|
| B-1006 | 4-F-phenyl | 4-pyridyl carbonyl | 80 | 387 | 388 |
| B-1007 | 4-F-phenyl | 2-pyridyl carbonyl | 54 | 387 | 388 |
| B-1008 | 4-F-phenyl | 3-methoxyphenyl carbonyl | 64 | 416 | 417 |
| B-1009 | 4-F-phenyl | 1-phenoxyethyl carbonyl | 81 | 430 | 431 |
| B-1010 | 4-F-phenyl | isobutoxy carbonyl | 81 | 382 | 383 |
| B-1011 | 4-F-phenyl | N-tosyl-phenylalanyl | 66 | 583 | 584 |

-continued
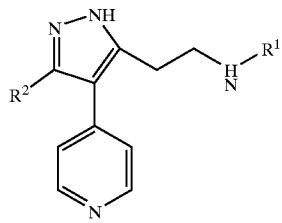
| Example# | R² | R^J | % Yield | Calcd. Mass Spec | Observed Mass Spec (M + H) |
|---|---|---|---|---|---|
| B-1012 | 4-F-phenyl | quinoxaline-2-carbonyl | 69 | 438 | 439 |
| B-1013 | 4-F-phenyl | 4-F-phenylsulfonyl | 53 | 440 | 441 |
| B-1014 | 4-F-phenyl | phenylsulfonyl | 61 | 422 | 423 |
| B-1015 | 4-F-phenyl | isopropylsulfonyl | 47 | 388 | 389 |
| B-1016 | 4-F-phenyl | (E)-styrylsulfonyl | 74 | 448 | 449 |
| B-1017 | 4-F-phenyl | benzylsulfonyl | 63 | 436 | 437 |
| B-1018 | 4-F-phenyl | 2,4-difluorophenylsulfonyl | 82 | 458 | 459 |
| B-1019 | 4-F-phenyl | trifluoromethylsulfonyl | 41 | 414 | 415 |

-continued
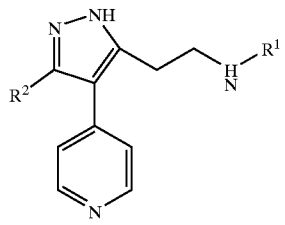
| Example# | R² | R^J | % Yield | Calcd. Mass Spec | Observed Mass Spec (M + H) |
|---|---|---|---|---|---|
| B-1020 | 4-F-C₆H₄ | 2-F-C₆H₄-SO₂- | 100 | 440 | 441 |
| B-1021 | 4-F-C₆H₄ | n-Pr-SO₂- | 1D0 | 388 | 389 |
| B-1022 | 4-F-C₆H₄ | n-Bu-SO₂- | 74 | 402 | 403 |
| B-1023 | 4-F-C₆H₄ | Et-SO₂- | 76 | 374 | 375 |
| B-1024 | 4-F-C₆H₄ | Me-SO₂- | 73 | 360 | 361 |
| B-1025 | 4-F-C₆H₄ | 4-MeO-C₆H₄-SO₂- | 100 | 452 | 453 |
| B-1026 | 4-F-C₆H₄ | 2-thienyl-SO₂- | 95 | 428 | 429 |
| B-1027 | 4-F-C₆H₄ | 4-Me-C₆H₄-SO₂- | 98 | 436 | 437 |
| B-1028 | 4-F-C₆H₄ | 3,4-(MeO)₂-C₆H₃-SO₂- | 100 | 482 | 483 |

-continued
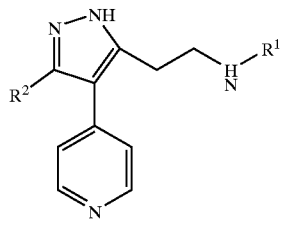
| Example# | R² | R^J | % Yield | Calcd. Mass Spec | Observed Mass Spec (M + H) |
|---|---|---|---|---|---|
| B-1029 | 4-F-phenyl | -C(O)NH-iPr | 98 | 367 | 368 |
| B-1030 | 4-F-phenyl | -C(O)NH₂ | 88 | 325 | 326 |
| B-1031 | 4-F-phenyl | -C(O)NH-CH₂-Ph | 97 | 415 | 416 |
| B-1032 | 4-F-phenyl | -C(O)-pyrrolidinyl | 64 | 379 | 380 |
| B-1033 | 4-F-phenyl | -C(O)-morpholinyl | 83 | 395 | 396 |
| B-1034 | 4-F-phenyl | -C(O)NH-(4-F-phenyl) | 67 | 419 | 420 |
| B-1035 | 4-F-phenyl | -C(O)N(CH₃)₂ | 73 | 353 | 354 |
| B-1036 | 4-F-phenyl | -C(O)NHCH₃ | 79 | 339 | 340 |

-continued
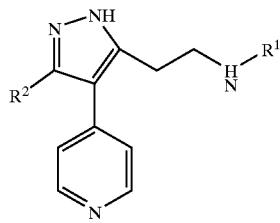
| Example# | R² | Rᴊ | % Yield | Calcd. Mass Spec | Observed Mass Spec (M + H) |
|---|---|---|---|---|---|
| B-1037 | 4-F-C₆H₄ | N-methyl-N-phenyl amide | 78 | 415 | 416 |
| B-1038 | 4-F-C₆H₄ | N-(2-fluorophenyl) amide | 100 | 419 | 420 |
| B-1039 | 4-F-C₆H₄ | N-(2,6-dimethylphenyl) amide | 95 | 429 | 430 |
| B-1040 | 4-F-C₆H₄ | N-allyl amide | 91 | 365 | 366 |
| B-1041 | 4-F-C₆H₄ | N-propyl amide | 88 | 367 | 368 |
| B-1042 | 4-F-C₆H₄ | N-((R)-1-phenylethyl) amide | 78 | 429 | 430 |
| B-1043 | 4-F-C₆H₄ | N-phenyl amide | 79 | 401 | 402 |

-continued
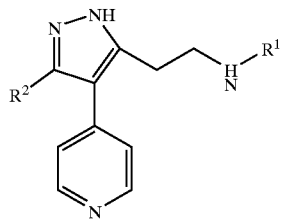
| Example# | R² | R^J | % Yield | Calcd. Mass Spec | Observed Mass Spec (M + H) |
|---|---|---|---|---|---|
| B-1044 | 4-F-C₆H₄ | -C(O)NH-CH₂CH₂-Ph | 93 | 429 | 430 |
| B-1045 | 4-F-C₆H₄ | -C(O)NH-CH(CH₃)-Ph (S) | 100 | 429 | 430 |
| B-1046 | 4-F-C₆H₄ | -C(O)NH-(3-F-C₆H₄) | 94 | 419 | 420 |
| B-1047 | 4-F-C₆H₄ | -C(O)NH-(4-Cl-C₆H₄) | 100 | 431 | 432 |
| B-1048 | 4-F-C₆H₄ | -C(O)N(Et)₂ | 58 | 381 | 382 |
| B-1049 | 4-F-C₆H₄ | -C(O)NH-Et | 97 | 353 | 354 |

-continued
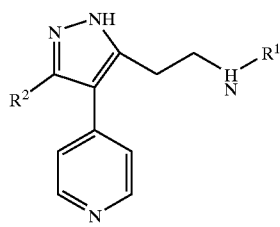
| Example# | R² | R¹ | % Yield | Calcd. Mass Spec | Observed Mass Spec (M + H) |
|---|---|---|---|---|---|
| B-1050 | 4-F-phenyl | -C(O)NH-(2,4-dimethoxyphenyl) | 100 | 461 | 462 |
| B-1051 | 4-F-phenyl | -C(O)CH₂-(2-thienyl) | 88 | 406 | 407 |
| B-1052 | 4-F-phenyl | -C(O)C(CH₃)₃ | 82 | 366 | 367 |
| B-1053 | 4-F-phenyl | -C(O)O-n-propyl | 21 | 368 | |
| B-1054 | 4-F-phenyl | -C(O)O-ethyl | 98 | 354 | 355 |
| B-1055 | 4-F-phenyl | -C(O)-(S)-pyrrolidinyl | 100 | 379 | 380 |
| B-1056 | 4-F-phenyl | -C(O)-(R)-pyrrolidinyl | 85 | 379 | 380 |
| B-1057 | 4-F-phenyl | -C(O)O-isopropyl | 30 | 368 | 369 |

-continued
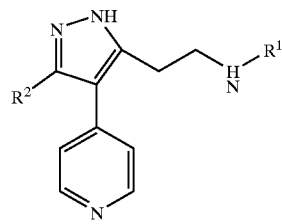
| Example# | R² | R^J | % Yield | Calcd. Mass Spec | Observed Mass Spec (M + H) |
|---|---|---|---|---|---|
| B-1058 | 4-F-C₆H₄ | methyl-acetamido-thiazolyl sulfonyl | 35 | 500 | 501 |
| B-1059 | 4-F-C₆H₄ | 4-acetamidophenyl sulfonyl | 77 | 479 | 480 |
| B-1060 | 4-F-C₆H₄ | 4-bromophenyl sulfonyl | 37 | 500 | 501 |
| B-1061 | 4-F-C₆H₄ | 4-chlorophenyl sulfonyl | 86 | 456 | 457 |
| B-1062 | 4-F-C₆H₄ | camphor sulfonyl | 58 | 496 | 497 |
| B-1063 | 4-F-C₆H₄ | camphor ethylsulfonyl | 59 | 496 | 497 |
| B-1064 | 4-F-C₆H₄ | 3,5-dichloro-2-hydroxyphenyl sulfonyl | 58 | 506 | — |

-continued
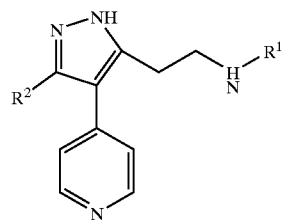
| Example# | R² | Rᴶ | % Yield | Calcd. Mass Spec | Observed Mass Spec (M + H) |
|---|---|---|---|---|---|
| B-1065 | 4-F-phenyl | 2-(carboxy)phenylsulfonyl | 24 | 466 | — |
| B-1066 | 4-F-phenyl | 2,5-dichlorophenylsulfonyl | 100 | 490 | 491 |
| B-1067 | 4-F-phenyl | 2,4,6-trimethylphenylsulfonyl | 74 | 464 | 465 |
| B-1068 | 4-F-phenyl | 2-naphthylsulfonyl | 79 | 472 | 473 |
| B-1069 | 4-F-phenyl | 1-naphthylsulfonyl | 97 | 472 | 473 |
| B-1070 | 4-F-phenyl | (2-nitrobenzyl)sulfonyl | 54 | 481 | 482 |
| B-1071 | 4-F-phenyl | 8-quinolinylsulfonyl | 67 | 473 | 474 |

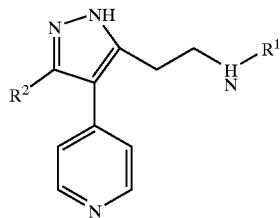
| Example# | R² | R^J | % Yield | Calcd. Mass Spec | Observed Mass Spec (M + H) |
|---|---|---|---|---|---|
| B-1072 | 4-F-C₆H₄ | naphthyl-sulfonyl-N(CH₃)₂ | 35 | 515 | 516 |
| B-1073 | 4-F-C₆H₄ | 2,3-diCl-C₆H₃-sulfonyl | 100 | 490 | 491 |
| B-1074 | 4-F-C₆H₄ | 4-isopropyl-C₆H₄-sulfonyl | 100 | 464 | 465 |
| B-1075 | 4-F-C₆H₄ | 2-methyl-3-Cl-C₆H₃-sulfonyl | 100 | 470 | 471 |
| B-1076 | 4-F-C₆H₄ | 4-Cl-2-methyl-C₆H₃-sulfonyl | 93 | 490 | 491 |
| B-1077 | 4-F-C₆H₄ | 2-Cl-4-F-C₆H₃-sulfonyl | 100 | 474 | 475 |
| B-1078 | 4-F-C₆H₄ | 2-cyano-C₆H₄-sulfonyl | 80 | 447 | 448 |
| B-1079 | 4-F-C₆H₄ | 3-F-C₆H₄-sulfonyl | 85 | 454 | 455 |

-continued

[Structure: pyrazole core with R² at position 3, 4-pyridyl at position 4, and -CH₂CH₂-NH-R¹ at position 5]

| Example# | R² | R¹ | % Yield | Calcd. Mass Spec | Observed Mass Spec (M + H) |
|---|---|---|---|---|---|
| B-1080 | 4-F-phenyl | sulfonyl-(4,5-dichlorothien-2-yl) | 100 | 496 | 497 |
| B-1081 | 4-F-phenyl | sulfonyl-(2,6-dichlorophenyl) | 100 | 490 | 491 |
| B-1082 | 4-F-phenyl | sulfonyl-(2-bromophenyl) | 100 | 500 | 501 |
| B-1083 | 4-F-phenyl | sulfonyl-(3-bromophenyl) | 93 | 500 | 501 |
| B-1084 | 4-F-phenyl | sulfonyl-(4-butoxyphenyl) | 81 | 494 | 495 |
| B-1085 | 4-F-phenyl | sulfonyl-(2,5-dimethoxyphenyl) | 93 | 482 | 483 |
| B-1086 | 4-F-phenyl | sulfonyl-(2-CF₃-phenyl) | 92 | 490 | 491 |
| B-1087 | 4-F-phenyl | sulfonyl-(4-CF₃-phenyl) | 100 | 490 | 491 |

-continued
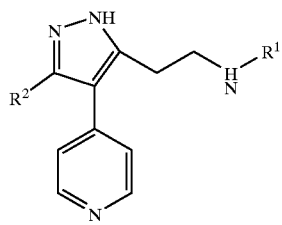
| Example# | R² | R¹ | % Yield | Calcd. Mass Spec | Observed Mass Spec (M + H) |
|---|---|---|---|---|---|
| B-1088 | 4-F-C₆H₄ | -SO₂-(4-ethylphenyl) | 97 | 450 | 451 |
| B-1089 | 4-F-C₆H₄ | -SO₂-(3-methylphenyl) | 100 | 436 | 437 |
| B-1090 | 4-F-C₆H₄ | -SO₂-(3-chlorophenyl) | 100 | 456 | 457 |
| B-1091 | 4-F-C₆H₄ | -SO₂-(2-chlorophenyl) | 100 | 456 | 457 |
| B-1092 | 4-F-C₆H₄ | -SO₂-(3,5-dichlorophenyl) | 96 | 490 | 491 |
| B-1093 | 4-F-C₆H₄ | -SO₂-(3,4-dichlorophenyl) | 100 | 490 | 491 |
| B-1094 | 4-F-C₆H₄ | -SO₂-(3-chloro-4-fluorophenyl) | 100 | 474 | 475 |
| B-1095 | 4-F-C₆H₄ | -SO₂-(2-methyl-6-chlorophenyl) | 81 | 470 | 471 |

-continued
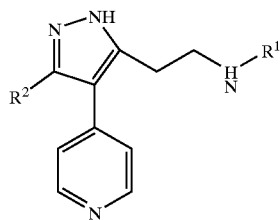
| Example# | R² | Rᴶ | % Yield | Calcd. Mass Spec | Observed Mass Spec (M + H) |
|---|---|---|---|---|---|
| B-1096 | 4-F-C₆H₄ | 2,5-dimethylphenylsulfonyl | 77 | 450 | 451 |
| B-1097 | 4-F-C₆H₄ | 2-methylphenylsulfonyl | 100 | 436 | 437 |
| B-1098 | 4-F-C₆H₄ | 4-methyl-2-(methylthio)phenylsulfonyl | 93 | 466 | 467 |
| B-1099 | 4-F-C₆H₄ | 3-(trifluoromethyl)phenylsulfonyl | 100 | 490 | 491 |
| B-1100 | 4-F-C₆H₄ | camphorsulfonyl | 47 | 482 | — |
| B-1101 | 4-F-C₆H₄ | 5-chlorothiophen-2-ylsulfonyl | 64 | 462 | 463 |
| B-1102 | 4-F-C₆H₄ | 5-bromo-2-methoxyphenylsulfonyl | 98 | 530 | 531 |

-continued
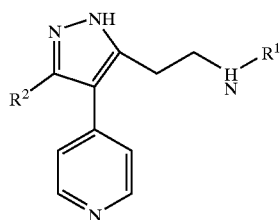
| Example# | R² | RJ | % Yield | Calcd. Mass Spec | Observed Mass Spec (M + H) |
|---|---|---|---|---|---|
| B-1103 | 4-F-phenyl | 2-naphthylsulfonyl | 65 | 472 | — |
| B-1104 | 4-F-phenyl | 3,5-dimethylisoxazol-4-ylsulfonyl | 88 | 441 | 442 |
| B-1105 | 4-F-phenyl | benzo[1,2,5]oxadiazol-4-ylsulfonyl | 100 | 464 | 465 |
| B-1106 | 4-F-phenyl | 5-chloro-2-methoxyphenylsulfonyl | 91 | 486 | 487 |
| B-1107 | 4-F-phenyl | 4-cyanobenzoyl | 96 | 447 | 448 |
| B-1108 | 4-F-phenyl | 5-(benzamidomethyl)thiophen-2-ylsulfonyl | 55 | 561 | 562 |
| B-1109 | 4-F-phenyl | biphenyl-4-ylsulfonyl | 100 | 498 | 499 |

-continued

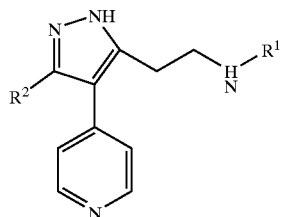

| Example# | R² | RJ | % Yield | Calcd. Mass Spec | Observed Mass Spec (M + H) |
|---|---|---|---|---|---|
| B-1110 | 4-F-phenyl | sulfonyl-2,2,5,7,8-pentamethylchroman | 73 | 548 | 549 |
| B-1111 | 4-F-phenyl | sulfonyl-(5-(pyridin-2-yl)thiophen-2-yl) | 94 | 505 | 506 |
| B-1112 | 4-F-phenyl | sulfonyl-(4-(phenylsulfonyl)thiophen-2-yl) | 100 | 568 | 569 |
| B-1113 | 4-F-phenyl | sulfonyl-(5-(isoxazol-3-yl)thiophen-2-yl) | 100 | 495 | 496 |
| B-1114 | 4-F-phenyl | sulfonyl-(1-methyl-1H-imidazol-4-yl) | 73 | 426 | 427 |
| B-1115 | 4-F-phenyl | sulfonyl-N,N-dimethyl | 30 | 389 | 390 |
| B-1116 | 4-F-phenyl | sulfonyl-(5-(phenylsulfonyl)thiophen-2-yl) | 100 | 568 | 569 |

-continued
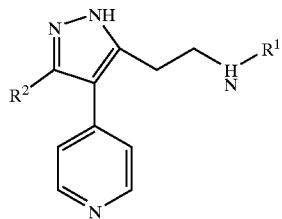
| Example# | R² | RJ | % Yield | Calcd. Mass Spec | Observed Mass Spec (M + H) |
|---|---|---|---|---|---|
| B-1117 | 4-F-C₆H₄ | 2-(methylsulfonyl)phenylsulfonyl | 83 | 500 | 501 |
| B-1118 | 4-F-C₆H₄ | isoquinoline-5-carbonyl | 55 | 473 | — |
| B-1119 | 4-F-C₆H₄ | 2-methyl-5-(methylsulfonyl)phenylsulfonyl | 70 | 514 | 515 |
| B-1120 | 4-F-C₆H₄ | 2-methylbenzoyl | 84 | 400 | 401 |
| B-1121 | 4-F-C₆H₄ | 4-chlorobenzoyl | 86 | 420 | 421 |
| B-1122 | 4-F-C₆H₄ | 4-methylbenzoyl | 90 | 400 | 401 |
| B-1123 | 4-F-C₆H₄ | 3-(trifluoromethyl)benzoyl | 100 | 454 | 455 |

-continued
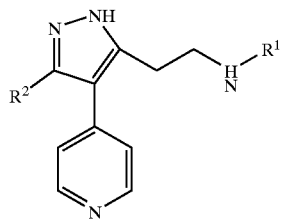
| Example# | R² | R^J | % Yield | Calcd. Mass Spec | Observed Mass Spec (M + H) |
|---|---|---|---|---|---|
| B-1124 | 4-F-phenyl | benzothiophene-2-carbonyl | 91 | 442 | 443 |
| B-1125 | 4-F-phenyl | 2,4,6-triisopropylbenzoyl | 50 | 512 | 513 |
| B-1126 | 4-F-phenyl | 3,5-dichlorobenzoyl | 85 | 454 | 455 |
| B-1127 | 4-F-phenyl | 3-cyanobenzoyl | 93 | 411 | 412 |
| B-1128 | 4-F-phenyl | naphthalene-1-carbonyl | 87 | 436 | 437 |
| B-1129 | 4-F-phenyl | 3,4-difluorobenzoyl | 78 | 422 | 423 |

-continued
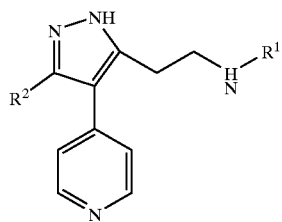
| Example# | R² | Rʲ | % Yield | Calcd. Mass Spec | Observed Mass Spec (M + H) |
|---|---|---|---|---|---|
| B-1130 | 4-F-phenyl | 3,5-difluorobenzoyl | 96 | 422 | 423 |
| B-1131 | 4-F-phenyl | 2,3,6-trifluorobenzoyl | 84 | 440 | 441 |
| B-1132 | 4-F-phenyl | 2,3-dichlorobenzoyl | 77 | 454 | 455 |
| B-1133 | 4-F-phenyl | 2,4,6-trimethylbenzoyl | 62 | 428 | 429 |
| B-1134 | 4-F-phenyl | 2-fluoro-4-trifluoromethylbenzoyl | 91 | 472 | 473 |
| B-1135 | 4-F-phenyl | 2,4,6-trifluorobenzoyl | 85 | 440 | 441 |
| B-1136 | 4-F-phenyl | 2-fluoro-4-trifluoromethylbenzoyl | 82 | 472 | 473 |

-continued
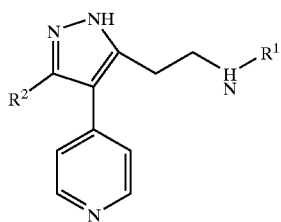
| Example# | R² | RJ | % Yield | Calcd. Mass Spec | Observed Mass Spec (M + H) |
| --- | --- | --- | --- | --- | --- |
| B-1137 | 4-F-phenyl | 2-CF₃,6-F-benzoyl | 95 | 472 | 473 |
| B-1138 | 4-F-phenyl | 2-F,3-CF₃-benzoyl | 100 | 472 | 473 |
| B-1139 | 4-F-phenyl | 2-CF₃,4-F-benzoyl | 100 | 472 | 473 |
| B-1140 | 4-F-phenyl | 3-CF₃,4-F-benzoyl | 92 | 472 | 473 |
| B-1141 | 4-F-phenyl | 3-CF₃,5-F-benzoyl | 100 | 472 | 473 |
| B-1142 | 4-F-phenyl | 2-Cl-benzoyl | 88 | 420 | 421 |
| B-1143 | 4-F-phenyl | 3-methyl-benzoyl | 90 | 400 | 401 |

-continued
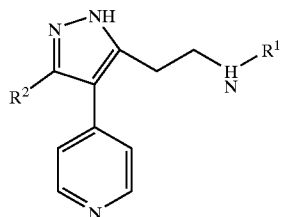
| Example# | R² | Rᴊ | % Yield | Calcd. Mass Spec | Observed Mass Spec (M + H) |
|---|---|---|---|---|---|
| B-1144 | 4-F-phenyl | 2,4-dichlorobenzoyl | 87 | 454 | 455 |
| B-1145 | 4-F-phenyl | 3-F-benzoyl | 93 | 404 | 405 |
| B-1146 | 4-F-phenyl | 2,3-difluorobenzoyl | 90 | 422 | 423 |
| B-1147 | 4-F-phenyl | 2,6-dichlorobenzoyl | 100 | 454 | 455 |
| B-1148 | 4-F-phenyl | 2,5-difluorobenzoyl | 87 | 422 | 423 |
| B-1149 | 4-F-phenyl | 2,4,5-trifluorobenzoyl | 87 | 440 | 441 |
| B-1150 | 4-F-phenyl | 2-F-benzoyl | 90 | 404 | 405 |

-continued
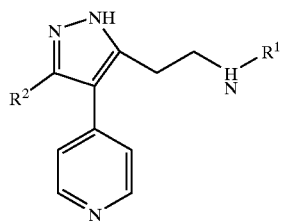
| Example# | R² | R¹ | % Yield | Calcd. Mass Spec | Observed Mass Spec (M + H) |
|---|---|---|---|---|---|
| B-1151 | 4-F-C₆H₄ | 2,6-diF-C₆H₃-C(O)- | 82 | 422 | 423 |
| B-1152 | 4-F-C₆H₄ | 2,4-diF-C₆H₃-C(O)- | 85 | 422 | 423 |
| B-1153 | 4-F-C₆H₄ | 3-Cl-C₆H₄-C(O)- | 90 | 420 | 421 |
| B-1154 | 4-F-C₆H₄ | 2-Br-C₆H₄-C(O)- | 78 | 464 | 465 |
| B-1155 | 4-F-C₆H₄ | 4-CF₃-C₆H₄-C(O)- | 79 | 454 | 455 |
| B-1156 | 4-F-C₆H₄ | 2-thienyl-C(O)- | 95 | 392 | 393 |
| B-1157 | 4-F-C₆H₄ | 3,5-dimethylisoxazol-4-yl-C(O)- | 81 | 405 | 406 |

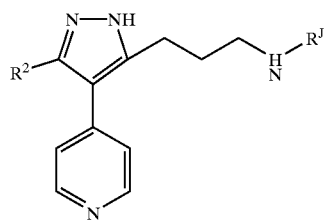
| Example # | R² | R^J | % Yield | Calcd. Mass Spec | Observed Mass Spec (M + H) |
|---|---|---|---|---|---|
| B-1158 | 4-F-C6H4 | -C(O)CH2-O-C(O)CH3 | 54 | 396 | 397 |
| B-1159 | 4-F-C6H4 | -C(O)-(2-I-C6H4) | 42 | 526 | 527 |
| B-1160 | 4-F-C6H4 | -C(O)CH(CH3)2 | 27 | 366 | 367 |
| B-1161 | 4-F-C6H4 | -C(O)-(4-F-C6H4) | 58 | 418 | 419 |
| B-1162 | 4-F-C6H4 | -C(O)-O-CH2CH=CH2 | 62 | 380 | 381 |
| B-1163 | 4-F-C6H4 | -C(O)C(CH3)2-O-C(O)CH3 | 58 | 424 | 425 |
| B-1164 | 4-F-C6H4 | -C(O)CH3 | 67 | 338 | 339 |
| B-1165 | 4-F-C6H4 | -C(O)-cyclobutyl | 66 | 378 | 379 |
| B-1166 | 4-F-C6H4 | -C(O)-cyclopropyl | 65 | 364 | 365 |

-continued

| Example # | R² | Rᴶ | % Yield | Calcd. Mass Spec | Observed Mass Spec (M + H) |
|---|---|---|---|---|---|
| B-1167 | 4-F-phenyl | 3-Br-benzoyl | 64 | 478 | 479 |
| B-1168 | 4-F-phenyl | 4-I-benzoyl | 76 | 526 | 527 |
| B-1169 | 4-F-phenyl | isoxazol-5-yl-carbonyl | 70 | 391 | 392 |
| B-1170 | 4-F-phenyl | (S)-2-acetoxypropanoyl | 76 | 410 | 411 |
| B-1171 | 4-F-phenyl | methoxyacetyl | 82 | 368 | 369 |
| B-1172 | 4-F-phenyl | 2-methoxybenzoyl | 73 | 430 | 431 |
| B-1173 | 4-F-phenyl | 2-CF₃-benzoyl | 74 | 468 | 469 |

-continued
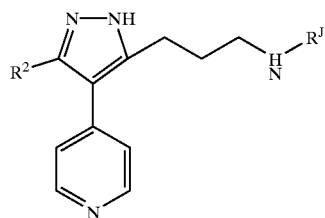
| Example # | R² | R^J | % Yield | Calcd. Mass Spec | Observed Mass Spec (M + H) |
|---|---|---|---|---|---|
| B-1174 | 4-F-phenyl | 2,3,4-trifluorobenzoyl | 83 | 454 | 455 |
| B-1175 | 4-F-phenyl | 4-methyl-3-pentenoyl | 76 | 378 | 379 |
| B-1176 | 4-F-phenyl | (3,4-dimethoxyphenyl)acetyl | 96 | 474 | 475 |
| B-1177 | 4-F-phenyl | (4-methoxyphenyl)acetyl | 94 | 444 | 445 |
| B-1178 | 4-F-phenyl | (3-methoxyphenyl)acetyl | 90 | 444 | 445 |
| B-1179 | 4-F-phenyl | 4-methylbenzoyl | 57 | 414 | 415 |
| B-1180 | 4-F-phenyl | benzoyl | 75 | 400 | 401 |
| B-1181 | 4-F-phenyl | cyclopentylcarbonyl | 66 | 392 | 393 |

-continued
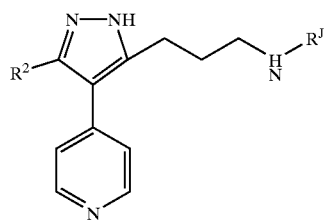
| Example # | R² | R^J | % Yield | Calcd. Mass Spec | Observed Mass Spec (M + H) |
|---|---|---|---|---|---|
| B-1182 | 4-F-C6H4 | 3-pyridyl-C(O)- | 74 | 401 | 402 |
| B-1183 | 4-F-C6H4 | 4-pyridyl-C(O)- | 62 | 401 | 402 |
| B-1184 | 4-F-C6H4 | 2-pyridyl-C(O)- | 51 | 401 | 402 |
| B-1185 | 4-F-C6H4 | 3-MeO-C6H4-C(O)- | 90 | 430 | 431 |
| B-1186 | 4-F-C6H4 | PhO-CH(CH3)-C(O)- | 86 | 444 | 445 |
| B-1187 | 4-F-C6H4 | iBuO-C(O)- | 74 | 396 | 397 |

-continued

| Example # | R² | R^J | % Yield | Calcd. Mass Spec | Observed Mass Spec (M + H) |
|---|---|---|---|---|---|
| B-1188 | 4-F-C₆H₄ | N-tosyl phenylalanyl carbonyl | 76 | 597 | 598 |
| B-1189 | 4-F-C₆H₄ | quinoxaline-2-carbonyl | 60 | 452 | 453 |
| B-1190 | 4-F-C₆H₄ | 4-fluorophenylsulfonyl | 44 | 454 | 455 |
| B-1191 | 4-F-C₆H₄ | phenylsulfonyl | 47 | 436 | 437 |
| B-1192 | 4-F-C₆H₄ | isopropylsulfonyl | 50 | 402 | 403 |
| B-1193 | 4-F-C₆H₄ | (E)-styrylsulfonyl | 62 | 462 | 463 |
| B-1194 | 4-F-C₆H₄ | benzylsulfonyl | 49 | 450 | 451 |

-continued
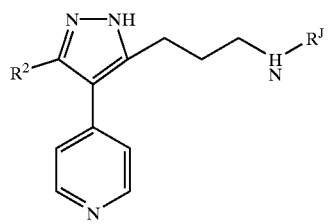
| Example # | R² | RJ | % Yield | Calcd. Mass Spec | Observed Mass Spec (M + H) |
|---|---|---|---|---|---|
| B-1195 | 4-F-C6H4 | 2,4-diF-C6H3-SO2- | 61 | 472 | 473 |
| B-1196 | 4-F-C6H4 | CF3-SO2- | 52 | 428 | 429 |
| B-1197 | 4-F-C6H4 | 2-F-C6H4-SO2- | 54 | 454 | 455 |
| B-1198 | 4-F-C6H4 | n-Pr-SO2- | 44 | 402 | 403 |
| B-1199 | 4-F-C6H4 | n-Bu-SO2- | 67 | 416 | 417 |
| B-1200 | 4-F-C6H4 | Et-SO2- | 45 | 388 | 389 |
| B-1201 | 4-F-C6H4 | Me-SO2- | 52 | 374 | 375 |
| B-1202 | 4-F-C6H4 | 4-MeO-C6H4-SO2- | 100 | 466 | 467 |
| B-1203 | 4-F-C6H4 | 2-thienyl-SO2- | 91 | 442 | 443 |
| B-1204 | 4-F-C6H4 | 4-Me-C6H4-SO2- | 100 | 450 | 451 |

-continued
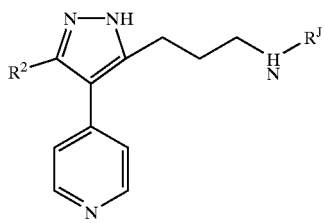
| Example # | R² | R^J | % Yield | Calcd. Mass Spec | Observed Mass Spec (M + H) |
|---|---|---|---|---|---|
| B-1205 | 4-F-C6H4 | 3,4-dimethoxyphenylsulfonyl | 83 | 496 | 497 |
| B-1206 | 4-F-C6H4 | C(O)NH-iPr | 97 | 381 | 382 |
| B-1207 | 4-F-C6H4 | C(O)NH2 | 100 | 339 | 340 |
| B-1208 | 4-F-C6H4 | C(O)NHCH2Ph | 90 | 429 | 430 |
| B-1209 | 4-F-C6H4 | C(O)-pyrrolidinyl | 69 | 393 | 394 |
| B-1210 | 4-F-C6H4 | C(O)-morpholinyl | 35 | 409 | 410 |
| B-1211 | 4-F-C6H4 | C(O)NH-(4-F-C6H4) | 100 | 433 | 434 |
| B-1212 | 4-F-C6H4 | C(O)N(CH3)2 | 83 | 367 | 368 |

-continued

[Structure: pyrazole core with R² at 3-position, 4-pyridyl at 4-position, and propyl-NH-R^J chain at 5-position]

| Example # | R² | R^J | % Yield | Calcd. Mass Spec | Observed Mass Spec (M + H) |
|---|---|---|---|---|---|
| B-1213 | 4-F-phenyl | -C(O)NHCH₃ | 78 | 353 | 354 |
| B-1214 | 4-F-phenyl | -C(O)N(CH₃)(phenyl) | 68 | 429 | 430 |
| B-1215 | 4-F-phenyl | -C(O)NH(2-F-phenyl) | 65 | 433 | 434 |
| B-1216 | 4-F-phenyl | -C(O)NH(2,6-diMe-phenyl) | 91 | 443 | 444 |
| B-1217 | 4-F-phenyl | -C(O)NH-allyl | 99 | 379 | 380 |
| B-1218 | 4-F-phenyl | -C(O)NH-propyl | 92 | 381 | 382 |
| B-1219 | 4-F-phenyl | -C(O)NH-CH(CH₃)phenyl | 74 | 443 | 444 |
| B-1220 | 4-F-phenyl | -C(O)NH-phenyl | 67 | 415 | 416 |

-continued
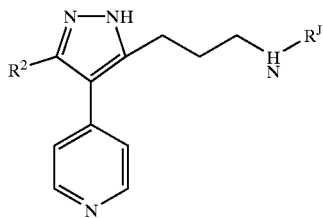
| Example # | R² | R^J | % Yield | Calcd. Mass Spec | Observed Mass Spec (M + H) |
|---|---|---|---|---|---|
| B-1221 | 4-F-phenyl | -C(O)NH-CH2CH2-phenyl | 14 | 443 | 444 |
| B-1222 | 4-F-phenyl | -C(O)NH-CH(CH3)-phenyl | 19 | 443 | 444 |
| B-1223 | 4-F-phenyl | -C(O)NH-(3-F-phenyl) | 71 | 433 | 434 |
| B-1224 | 4-F-phenyl | -C(O)NH-(4-OMe-phenyl) | 100 | 445 | 446 |
| B-1225 | 4-F-phenyl | -C(O)N(Et)2 | 75 | 395 | 396 |
| B-1226 | 4-F-phenyl | -C(O)NH-Et | 58 | 367 | 368 |

-continued
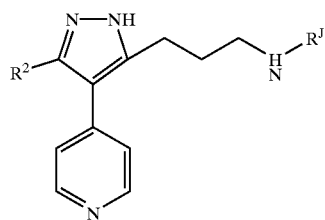
| Example # | R² | R^J | % Yield | Calcd. Mass Spec | Observed Mass Spec (M + H) |
|---|---|---|---|---|---|
| B-1227 | 4-F-phenyl | N-(2,4-dimethoxyphenyl)carbamoyl | 98 | 475 | 476 |
| B-1228 | 4-F-phenyl | (thiophen-2-yl)acetyl | 71 | 420 | 421 |
| B-1229 | 4-F-phenyl | pivaloyl | 85 | 380 | 381 |
| B-1230 | 4-F-phenyl | propoxycarbonyl | 10 | 382 | — |
| B-1231 | 4-F-phenyl | ethoxycarbonyl | 66 | 368 | 369 |
| B-1232 | 4-F-phenyl | (S)-prolyl | 100 | 393 | 394 |
| B-1233 | 4-F-phenyl | (R)-prolyl | 96 | 393 | 394 |
| B-1234 | 4-F-phenyl | isopropoxycarbonyl | 66 | 382 | 383 |

-continued

| Example # | R² | Rᴶ | % Yield | Calcd. Mass Spec | Observed Mass Spec (M + H) |
|---|---|---|---|---|---|
| B-1235 | 4-F-phenyl | sulfonyl-(4-methyl-2-acetamido-thiazol-5-yl) | 50 | 514 | 515 |
| B-1236 | 4-F-phenyl | sulfonyl-(4-acetamidophenyl) | 100 | 493 | 494 |
| B-1237 | 4-F-phenyl | sulfonyl-(4-bromophenyl) | 91 | 514 | 515 |
| B-1238 | 4-F-phenyl | sulfonyl-(4-chlorophenyl) | 100 | 470 | 471 |
| B-1239 | 4-F-phenyl | sulfonylmethyl-camphor | 71 | 510 | 511 |
| B-1240 | 4-F-phenyl | sulfonylethyl-camphor | 27 | 510 | 511 |
| B-1241 | 4-F-phenyl | sulfonyl-(2-hydroxy-3,5-dichlorophenyl) | 73 | 520 | |
| B-1242 | 4-F-phenyl | sulfonyl-(2-carboxyphenyl) | 26 | 480 | 481 |

-continued
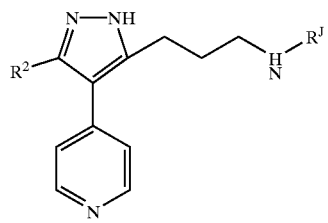
| Example # | R² | R^J | % Yield | Calcd. Mass Spec | Observed Mass Spec (M + H) |
|---|---|---|---|---|---|
| B-1243 | 4-F-phenyl | 2,5-dichlorophenyl sulfonyl | 100 | 504 | |
| B-1244 | 4-F-phenyl | 2,4,6-trimethylphenyl sulfonyl | 52 | 478 | 479 |
| B-1245 | 4-F-phenyl | 2-naphthyl sulfonyl | 100 | 486 | 487 |
| B-1246 | 4-F-phenyl | 1-naphthyl sulfonyl | 56 | 486 | 487 |
| B-1247 | 4-F-phenyl | (2-nitrobenzyl) sulfonyl | 43 | 495 | 496 |
| B-1248 | 4-F-phenyl | 8-quinolinyl sulfonyl | 61 | 487 | 468 |
| B-1249 | 4-F-phenyl | 5-(dimethylamino)naphthyl sulfonyl | 32 | 529 | 530 |

-continued

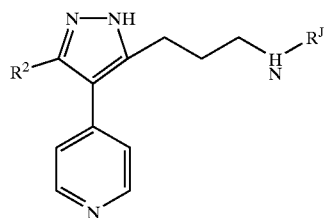

| Example # | R² | R^J | % Yield | Calcd. Mass Spec | Observed Mass Spec (M + H) |
|---|---|---|---|---|---|
| B-1250 | 4-F-phenyl | 2,3-dichlorophenylsulfonyl | 56 | 504 | 505 |
| B-1251 | 4-F-phenyl | 4-isopropylphenylsulfonyl | 58 | 478 | 479 |
| B-1252 | 4-F-phenyl | 3-chloro-2-methylphenylsulfonyl | 98 | 484 | 485 |
| B-1253 | 4-F-phenyl | 2,4-dichlorophenylsulfonyl | 59 | 504 | 505 |
| B-1254 | 4-F-phenyl | 2-chloro-4-fluorophenylsulfonyl | 100 | 488 | 489 |
| B-1255 | 4-F-phenyl | 2-cyanophenylsulfonyl | 96 | 461 | |
| B-1256 | 4-F-phenyl | 5-fluoro-2-methylphenylsulfonyl | 79 | 468 | 469 |
| B-1257 | 4-F-phenyl | 4,5-dichlorothiophen-2-ylsulfonyl | 63 | 510 | 511 |

-continued
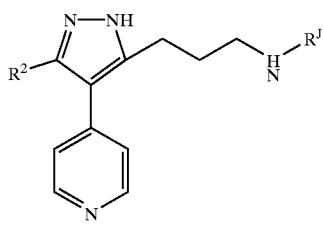
| Example # | R² | R^J | % Yield | Calcd. Mass Spec | Observed Mass Spec (M + H) |
|---|---|---|---|---|---|
| B-1258 | 4-F-phenyl | 2,6-dichlorophenylsulfonyl | 100 | 504 | 505 |
| B-1259 | 4-F-phenyl | 2-bromophenylsulfonyl | 95 | 514 | 515 |
| B-1260 | 4-F-phenyl | 3-bromophenylsulfonyl | 92 | 514 | 515 |
| B-1261 | 4-F-phenyl | 4-butoxyphenylsulfonyl | 98 | 508 | 509 |
| B-1262 | 4-F-phenyl | 2,5-dimethoxyphenylsulfonyl | 97 | 496 | 497 |
| B-1263 | 4-F-phenyl | 2-CF₃-phenylsulfonyl | 100 | 504 | 505 |
| B-1264 | 4-F-phenyl | 4-CF₃-phenylsulfonyl | 100 | 504 | 505 |
| B-1265 | 4-F-phenyl | 4-ethylphenylsulfonyl | 100 | 464 | 465 |

-continued

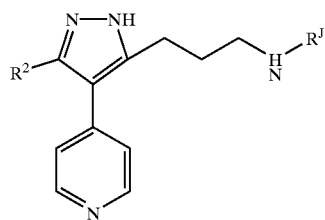

| Example # | R² | R^J | % Yield | Calcd. Mass Spec | Observed Mass Spec (M + H) |
|---|---|---|---|---|---|
| B-1266 | 4-F-phenyl | 3-methylphenylsulfonyl | 79 | 466 | 451 |
| B-1267 | 4-F-phenyl | 3-chlorophenylsulfonyl | 100 | 470 | 471 |
| B-1268 | 4-F-phenyl | 2-chlorophenylsulfonyl | 87 | 470 | 471 |
| B-1269 | 4-F-phenyl | 3,5-dichlorophenylsulfonyl | 100 | 504 | 505 |
| B-1270 | 4-F-phenyl | 3,4-dichlorophenylsulfonyl | 100 | 504 | 505 |
| B-1271 | 4-F-phenyl | 3-chloro-4-fluorophenylsulfonyl | 56 | 488 | 489 |
| B-1272 | 4-F-phenyl | 2-chloro-6-methylphenylsulfonyl | 98 | 484 | 485 |
| B-1273 | 4-F-phenyl | 2,5-dimethylphenylsulfonyl | 90 | 464 | 465 |

-continued
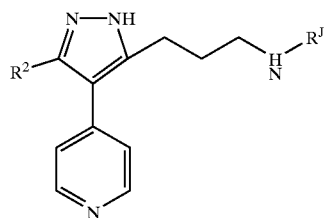
| Example # | R² | R^J | % Yield | Calcd. Mass Spec | Observed Mass Spec (M + H) |
|---|---|---|---|---|---|
| B-1274 | 4-F-C₆H₄ | 2-methylphenylsulfonyl | 87 | 450 | 451 |
| B-1275 | 4-F-C₆H₄ | 5-methyl-2-methoxyphenylsulfonyl | 94 | 480 | 481 |
| B-1276 | 4-F-C₆H₄ | 3-CF₃-phenylsulfonyl | 100 | 504 | 505 |
| B-1277 | 4-F-C₆H₄ | norbornanone-sulfonyl | 60 | 496 | 511 |
| B-1278 | 4-F-C₆H₄ | 5-chloroisothiazol-3-ylsulfonyl | 68 | 476 | 477 |
| B-1279 | 4-F-C₆H₄ | 2-methoxy-5-bromophenylsulfonyl | 100 | 544 | 545 |
| B-1280 | 4-F-C₆H₄ | 2-naphthylsulfonyl | 68 | 486 | — |

-continued

| Example # | R² | R^J | % Yield | Calcd. Mass Spec | Observed Mass Spec (M + H) |
|---|---|---|---|---|---|
| B-1281 | 4-F-phenyl | 3,5-dimethylisoxazol-4-ylsulfonyl | 98 | 455 | 456 |
| B-1282 | 4-F-phenyl | benzo[1,2,5]oxadiazol-4-ylsulfonyl | 100 | 478 | 479 |
| B-1283 | 4-F-phenyl | 5-chloro-2-methoxyphenylsulfonyl | 58 | 500 | 501 |
| B-1284 | 4-F-phenyl | 4-methylphenylsulfonyl | 58 | 461 | 462 |
| B-1285 | 4-F-phenyl | 5-(benzoylaminomethyl)thiophen-2-ylsulfonyl | 65 | 575 | 576 |
| B-1286 | 4-F-phenyl | biphenyl-4-ylsulfonyl | 87 | 512 | 513 |
| B-1287 | 4-F-phenyl | 2,2,5,7,8-pentamethylchroman-6-ylsulfonyl | 79 | 562 | 563 |

-continued

| Example # | R² | Rᴶ | % Yield | Calcd. Mass Spec | Observed Mass Spec (M + H) |
|---|---|---|---|---|---|
| B-1288 | 4-F-phenyl | sulfonyl-(thiophene-2-yl)-pyridine | 100 | 519 | 520 |
| B-1289 | 4-F-phenyl | sulfonyl-thiophene-phenylsulfonyl | 77 | 582 | 583 |
| B-1290 | 4-F-phenyl | sulfonyl-thiophene-isoxazole | 100 | 509 | 510 |
| B-1291 | 4-F-phenyl | sulfonyl-(N-methylimidazole) | 91 | 440 | 441 |
| B-1292 | 4-F-phenyl | sulfonyl-N,N-dimethyl | 35 | 403 | 404 |
| B-1293 | 4-F-phenyl | sulfonyl-thiophene-phenylsulfonyl | 73 | 582 | 583 |
| B-1294 | 4-F-phenyl | methylsulfonyl-phenyl-sulfonyl | 49 | 514 | 515 |

-continued
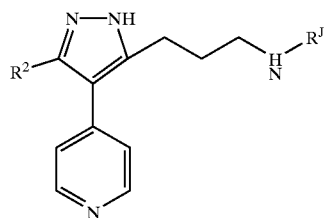
| Example # | R² | R^J | % Yield | Calcd. Mass Spec | Observed Mass Spec (M + H) |
|---|---|---|---|---|---|
| B-1295 | 4-F-C₆H₄ | isoquinoline-5-sulfonyl | 48 | 487 | — |
| B-1296 | 4-F-C₆H₄ | 2-methyl-5-(methylsulfonyl)phenylsulfonyl | 76 | 528 | 529 |
| B-1297 | 4-F-C₆H₄ | -C(O)NH-(CH₂)₃-imidazol-1-yl | 62 | 447 | 448 |
| B-1298 | 4-F-C₆H₄ | -C(O)NH-(CH₂)₂-piperidin-1-yl | 66 | 452 | 453 |
| B-1299 | 4-F-C₆H₄ | -C(O)NH-(CH₂)₃-(4-methylpiperazin-1-yl) | 65 | 479 | 431 |
| B-1300 | 4-F-C₆H₄ | -C(O)NH-(CH₂)₂-pyridin-3-yl | 71 | 444 | 445 |
| B-1301 | 4-F-C₆H₄ | -C(O)NH-CH₂-(4-dimethylaminophenyl) | 100 | 472 | 473 |

-continued
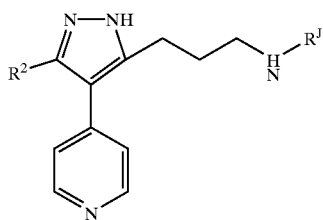
| Example # | R² | R^J | % Yield | Calcd. Mass Spec | Observed Mass Spec (M + H) |
|---|---|---|---|---|---|
| B-1302 | 4-F-C₆H₄ | -C(O)NH-CH₂CH₂-N(CH₃)₂ | 75 | 410 | 411 |
| B-1303 | 4-F-C₆H₄ | -C(O)NH-CH₂CH₂CH₂-N(CH₃)₂ | 74 | 424 | 425 |
| B-1304 | 4-F-C₆H₄ | -C(O)NH-CH₂-(2-pyridyl) | 11 | 430 | 431 |
| B-1305 | 4-F-C₆H₄ | -C(O)NH-CH₂CH₂-NH-C(O)CH₃ | 2 | 424 | — |
| B-1306 | 4-F-C₆H₄ | -C(O)NH-CH₂CH₂-(4-imidazolyl) | 30 | 433 | 434 |

-continued
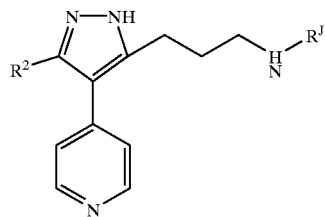
| Example # | R² | R^J | % Yield | Calcd. Mass Spec | Observed Mass Spec (M + H) |
|---|---|---|---|---|---|
| B-1307 | 4-F-phenyl | -C(O)NH-CH₂CH₂-(4-SO₂NH₂-phenyl) | 100 | 522 | 523 |
| B-1308 | 4-F-phenyl | -C(O)NH-CH₂-(4-SO₂NH₂-phenyl) | 100 | 508 | 509 |
| B-1309 | 4-F-phenyl | -C(O)NH-quinuclidinyl | 100 | 448 | 449 |
| B-1310 | 4-F-phenyl | -C(O)NH-CH₂-(3-pyridyl) | 26 | 430 | 431 |
| B-1311 | 4-F-phenyl | -C(O)NH-CH₂CH₂-OCH₃ | 45 | 397 | 398 |
| B-1312 | 4-F-phenyl | -C(O)NH-CH₂-(4-SO₂CH₃-phenyl) | 14 | 507 | 508 |

-continued
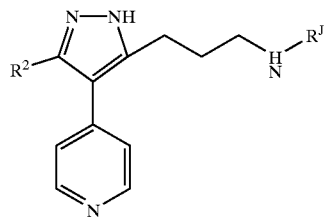
| Example # | R² | R^J | % Yield | Calcd. Mass Spec | Observed Mass Spec (M + H) |
|---|---|---|---|---|---|
| B-1313 | 4-F-C6H4 | C(O)NH-CH2CH2-(piperidin-1-yl) | 67 | 450 | 451 |
| B-1314 | 4-F-C6H4 | C(O)NH-CH2CH2-(pyridin-2-yl) | 69 | 444 | 445 |
| B-1315 | 4-F-C6H4 | C(O)NH-CH2CH2-(1-methylpyrrolidin-2-yl) | 57 | 450 | 451 |
| B-1316 | 4-F-C6H4 | C(O)NH-CH2-cyclopropyl | 75 | 393 | 394 |
| B-1317 | 4-F-C6H4 | C(O)NH-CH2CH2-(4-thio-phenyl) | 100 | 461 | 462 |
| B-1318 | 4-F-C6H4 | C(O)NH-CH2CH2CH2-(pyrrolidin-1-yl) | 31 | 450 | 451 |
| B-1319 | 4-F-C6H4 | C(O)NH-CH2CH2CH2-(2-oxopyrrolidin-1-yl) | 23 | 464 | 465 |

-continued

| Example # | R² | R^J | % Yield | Calcd. Mass Spec | Observed Mass Spec (M + H) |
|---|---|---|---|---|---|
| B-1320 | 4-F-phenyl | -C(O)-NH-(1-benzylpiperidin-4-yl) | 59 | 512 | 513 |
| B-1321 | 4-F-phenyl | -C(O)-(2-methylphenyl) | 63 | 414 | 415 |
| B-1322 | 4-F-phenyl | -C(O)-(4-chlorophenyl) | 45 | 434 | 435 |
| B-1323 | 4-F-phenyl | -C(O)-(4-methylphenyl) | 53 | 414 | 415 |
| B-1324 | 4-F-phenyl | -C(O)-(3-trifluoromethylphenyl) | 32 | 468 | 469 |
| B-1325 | 4-F-phenyl | -C(O)-(benzo[b]thiophen-2-yl) | 45 | 456 | 457 |
| B-1326 | 4-F-phenyl | -C(O)-(2,4,6-triisopropylphenyl) | 50 | 526 | 527 |

-continued
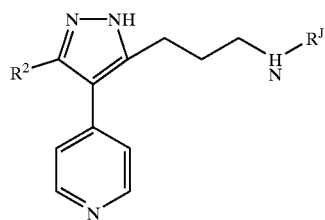
| Example # | R² | R^J | % Yield | Calcd. Mass Spec | Observed Mass Spec (M + H) |
|---|---|---|---|---|---|
| B-1327 | 4-F-phenyl | 3,5-dichlorobenzoyl | 55 | 468 | 469 |
| B-1328 | 4-F-phenyl | 3-cyanobenzoyl | 29 | 425 | 426 |
| B-1329 | 4-F-phenyl | 1-naphthoyl | 67 | 450 | 451 |
| B-1330 | 4-F-phenyl | 3,4-difluorobenzoyl | 59 | 436 | 437 |
| B-1331 | 4-F-phenyl | 3,5-difluorobenzoyl | 45 | 436 | 437 |
| B-1332 | 4-F-phenyl | 2,3,6-trifluorobenzoyl | 81 | 454 | 455 |
| B-1333 | 4-F-phenyl | 2,3-dichlorobenzoyl | 23 | 468 | 469 |

-continued
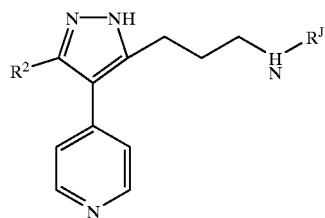
| Example # | R² | R^J | % Yield | Calcd. Mass Spec | Observed Mass Spec (M + H) |
|---|---|---|---|---|---|
| B-1334 | 4-F-phenyl | 2,4,6-trimethylbenzoyl | 53 | 442 | 443 |
| B-1335 | 4-F-phenyl | 2-fluoro-5-(trifluoromethyl)benzoyl | 81 | 486 | 487 |
| B-1336 | 4-F-phenyl | 2,4,6-trifluorobenzoyl | 69 | 454 | 455 |
| B-1337 | 4-F-phenyl | 2-fluoro-4-(trifluoromethyl)benzoyl | 67 | 486 | 487 |
| B-1338 | 4-F-phenyl | 2-fluoro-6-(trifluoromethyl)benzoyl | 39 | 486 | 487 |
| B-1339 | 4-F-phenyl | 2-fluoro-3-(trifluoromethyl)benzoyl | 61 | 486 | 487 |
| B-1340 | 4-F-phenyl | 4-fluoro-2-(trifluoromethyl)benzoyl | 49 | 486 | 487 |

-continued
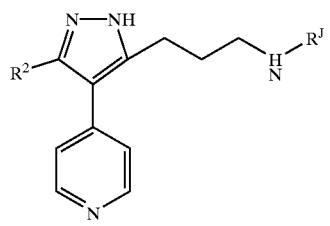
| Example # | R² | R^J | % Yield | Calcd. Mass Spec | Observed Mass Spec (M + H) |
|---|---|---|---|---|---|
| B-1341 | 4-F-C₆H₄ | 4-F-3-CF₃-benzoyl | 55 | 486 | 487 |
| B-1342 | 4-F-C₆H₄ | 3-F-5-CF₃-benzoyl | 51 | 486 | 487 |
| B-1343 | 4-F-C₆H₄ | 2-Cl-benzoyl | 72 | 434 | 435 |
| B-1344 | 4-F-C₆H₄ | 3-methylbenzoyl | 52 | 414 | 415 |
| B-1345 | 4-F-C₆H₄ | 3,5-diCl-benzoyl | 43 | 468 | 469 |
| B-1346 | 4-F-C₆H₄ | 3-F-benzoyl | 40 | 418 | 419 |
| B-1347 | 4-F-C₆H₄ | 2,3-diF-benzoyl | 67 | 436 | 437 |

-continued
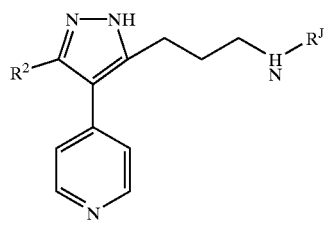
| Example # | R² | RJ | % Yield | Calcd. Mass Spec | Observed Mass Spec (M + H) |
|---|---|---|---|---|---|
| B-1348 | 4-F-C₆H₄ | 2,6-dichlorobenzoyl | 39 | 468 | 469 |
| B-1349 | 4-F-C₆H₄ | 2,5-difluorobenzoyl | 68 | 436 | 437 |
| B-1350 | 4-F-C₆H₄ | 2,4,5-trifluorobenzoyl | 73 | 454 | 455 |
| B-1351 | 4-F-C₆H₄ | 2-fluorobenzoyl | 54 | 418 | 419 |
| B-1352 | 4-F-C₆H₄ | 2,4-difluorobenzoyl | 77 | 436 | 437 |
| B-1353 | 4-F-C₆H₄ | 2,4-difluorobenzoyl | 66 | 436 | 437 |
| B-1354 | 4-F-C₆H₄ | 3-chlorobenzoyl | 58 | 434 | 435 |

-continued
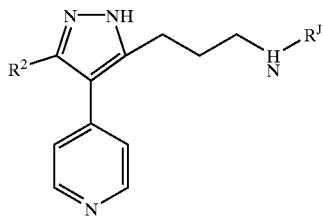
| Example # | R² | R^J | % Yield | Calcd. Mass Spec | Observed Mass Spec (M + H) |
|---|---|---|---|---|---|
| B-1355 | 4-F-phenyl | 2-Br-benzoyl | 77 | 478 | 479 |
| B-1356 | 4-F-phenyl | 4-CF₃-benzoyl | 50 | 468 | 469 |
| B-1357 | 4-F-phenyl | thiophene-2-carbonyl | 36 | 406 | 407 |
| B-1358 | 4-F-phenyl | 3,5-dimethylisoxazole-4-carbonyl | 39 | 419 | 420 |
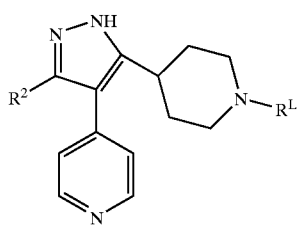
| Example # | R² | R^L | % Yield | Calcd. Mass Spec | Observed Mass Spec (M + H) |
|---|---|---|---|---|---|
| B-1359 | 4-F-phenyl | 2-I-benzoyl | 95 | 552 | 553 |

-continued
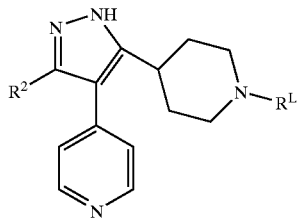
| Example # | R² | R^L | % Yield | Calcd. Mass Spec | Observed Mass Spec (M + H) |
|---|---|---|---|---|---|
| B-1360 | 4-F-C6H4 | 4-F-C6H4-C(O)- | 77 | 444 | 445 |
| B-1361 | 4-F-C6H4 | iPr-C(O)- | 100 | 392 | 393 |
| B-1362 | 4-F-C6H4 | allyl-O-C(O)- | 85 | 406 | 407 |
| B-1363 | 4-F-C6H4 | CH3-C(O)- | 100 | 364 | 365 |
| B-1364 | 4-F-C6H4 | cyclopropyl-C(O)- | 99 | 390 | 391 |
| B-1365 | 4-F-C6H4 | 3-Br-C6H4-C(O)- | 92 | 504 | 505 |
| B-1366 | 4-F-C6H4 | 4-I-C6H4-C(O)- | 100 | 552 | 553 |
| B-1367 | 4-F-C6H4 | isoxazol-5-yl-C(O)- | 100 | 417 | 418 |

-continued
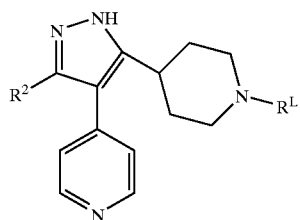
| Example # | R² | R^L | % Yield | Calcd. Mass Spec | Observed Mass Spec (M + H) |
|---|---|---|---|---|---|
| B-1368 | 4-F-C₆H₄ | -C(O)CH₂OCH₃ | 86 | 394 | 395 |
| B-1369 | 4-F-C₆H₄ | -C(O)-(2-OMe-C₆H₄) | 100 | 456 | 457 |
| B-1370 | 4-F-C₆H₄ | -C(O)CH₂-(3-OMe-C₆H₄) | 100 | 470 | 471 |
| B-1371 | 4-F-C₆H₄ | -C(O)-(4-Me-C₆H₄) | 77 | 440 | 441 |
| B-1372 | 4-F-C₆H₄ | -C(O)-(2-F-C₆H₄) | 100 | 444 | 445 |
| B-1373 | 4-F-C₆H₄ | -C(O)-(4-pyridyl) | 42 | 427 | 428 |
| B-1374 | 4-F-C₆H₄ | -SO₂CH₂-C₆H₅ | 60 | 476 | 477 |
| B-1375 | 4-F-C₆H₄ | -SO₂CH₂CH₃ | 94 | 414 | 415 |

-continued
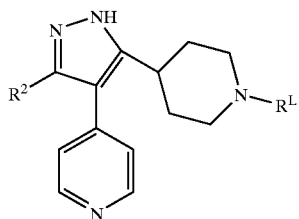
| Example # | R² | Rᴸ | % Yield | Calcd. Mass Spec | Observed Mass Spec (M + H) |
|---|---|---|---|---|---|
| B-1376 | 4-F-C₆H₄ | methylsulfonyl | 87 | 400 | 401 |
| B-1377 | 4-F-C₆H₄ | 2-F-C₆H₄-sulfonyl | 100 | 480 | 481 |
| B-1378 | 4-F-C₆H₄ | N-methylcarbamoyl | 95 | 379 | 380 |
| B-1379 | 4-F-C₆H₄ | N-(2-F-phenyl)carbamoyl | 93 | 459 | 460 |
| B-1380 | 4-F-C₆H₄ | N-(2,6-dimethylphenyl)carbamoyl | 89 | 469 | 470 |
| B-1381 | 4-F-C₆H₄ | N-ethylcarbamoyl | 84 | 393 | 394 |
| B-1382 | 4-F-C₆H₄ | N-(2,4-dimethoxyphenyl)carbamoyl | 85 | 501 | 502 |

-continued
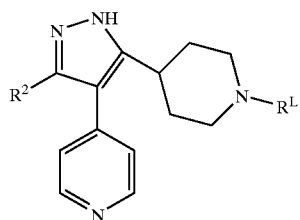
| Example # | R² | R^L | % Yield | Calcd. Mass Spec | Observed Mass Spec (M + H) |
|---|---|---|---|---|---|
| B-1383 | 4-F-C₆H₄ | 2-furanyl-C(O)- | 46 | 416 | 417 |
| B-1384 | 4-F-C₆H₄ | 2-thienyl-C(O)- | 56 | 432 | 433 |
| B-1385 | 4-F-C₆H₄ | phenyl-C(O)- | 59 | 426 | 427 |
| B-1386 | 4-F-C₆H₄ | 2-pyridyl-C(O)- | 50 | 427 | 428 |
| B-1387 | 4-F-C₆H₄ | 3-pyridyl-C(O)- | 12 | 427 | 428 |
| B-1388 | 4-F-C₆H₄ | 4-Br-C₆H₄-C(O)- | 66 | 504 | 505 |
| B-1389 | 4-F-C₆H₄ | 4-Cl-C₆H₄-C(O)- | 48 | 460 | 461 |
| B-1390 | 4-F-C₆H₄ | 4-CF₃-C₆H₄-C(O)- | 44 | 494 | 495 |
| B-1391 | 4-F-C₆H₄ | 4-OMe-C₆H₄-C(O)- | 50 | 456 | 457 |
| B-1392 | 4-F-C₆H₄ | 4-CN-C₆H₄-C(O)- | 47 | 451 | 452 |

-continued
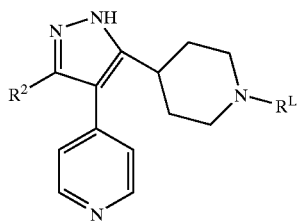
| Example # | R² | R^L | % Yield | Calcd. Mass Spec | Observed Mass Spec (M + H) |
|---|---|---|---|---|---|
| B-1393 | 4-F-C₆H₄ | 3-F-C₆H₄-C(O)- | 44 | 444 | 445 |
| B-1394 | 4-F-C₆H₄ | 3-Cl-C₆H₄-C(O)- | 52 | 460 | 461 |
| B-1395 | 4-F-C₆H₄ | 3-CH₃-C₆H₄-C(O)- | 77 | 440 | 441 |
| B-1396 | 4-F-C₆H₄ | 3-CN-C₆H₄-C(O)- | 58 | 451 | 452 |
| B-1397 | 4-F-C₆H₄ | 2-Cl-C₆H₄-C(O)- | 64 | 460 | 461 |
| B-1398 | 4-F-C₆H₄ | 2-Br-C₆H₄-C(O)- | 65 | 504 | 505 |
| B-1399 | 4-F-C₆H₄ | 2-CF₃-C₆H₄-C(O)- | 50 | 494 | 495 |

-continued
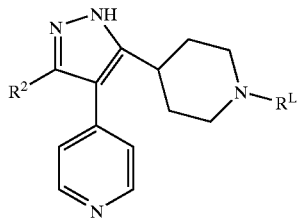
| Example # | R² | R^L | % Yield | Calcd. Mass Spec | Observed Mass Spec (M + H) |
|---|---|---|---|---|---|
| B-1400 | 4-F-C₆H₄ | 2-methylbenzoyl | 74 | 440 | 441 |
| B-1401 | 4-F-C₆H₄ | 2,6-difluorobenzoyl | 76 | 462 | 463 |
| B-1402 | 4-F-C₆H₄ | 2,5-difluorobenzoyl | 65 | 462 | 463 |
| B-1403 | 4-F-C₆H₄ | (3-methyl-5-methylisoxazol-4-yl)carbonyl | 64 | 445 | 446 |
| B-1404 | 4-F-C₆H₄ | 2-trifluoromethyl-6-fluorobenzoyl | 70 | 512 | 513 |
| B-1405 | 4-F-C₆H₄ | 5-trifluoromethyl-2-fluorobenzoyl | 57 | 512 | 513 |
| B-1406 | 4-F-C₆H₄ | 4-trifluoromethyl-2-fluorobenzoyl | 73 | 512 | 513 |

-continued
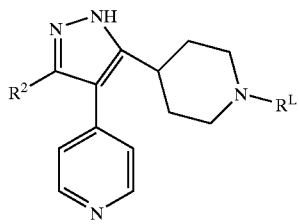
| Example # | R² | Rᴸ | % Yield | Calcd. Mass Spec | Observed Mass Spec (M + H) |
|---|---|---|---|---|---|
| B-1407 | 4-F-phenyl | 2-F, 3-CF₃-benzoyl | 80 | 512 | 513 |
| B-1408 | 4-F-phenyl | 4-F, 3-CF₃-benzoyl | 2 | 512 | 513 |
| B-1409 | 4-F-phenyl | 3-CF₃, 5-F-benzoyl | 62 | 512 | 513 |
| B-1410 | 4-F-phenyl | 4-F, 2-CF₃-benzoyl | 42 | 512 | 513 |
| B-1411 | 4-F-phenyl | 2,3-diF-benzoyl | 19 | 462 | 463 |
| B-1412 | 4-F-phenyl | 2,4-diF-benzoyl | 74 | 462 | 463 |
| B-1413 | 4-F-phenyl | 2,6-diCl-benzoyl | 75 | 494 | 495 |

-continued
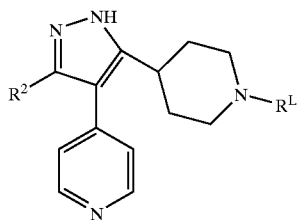
| Example # | R² | R^L | % Yield | Calcd. Mass Spec | Observed Mass Spec (M + H) |
|---|---|---|---|---|---|
| B-1414 | 4-F-phenyl | 3,4-difluorobenzoyl | 68 | 462 | 463 |
| B-1415 | 4-F-phenyl | 3,5-difluorobenzoyl | 48 | 462 | 463 |
| B-1416 | 4-F-phenyl | 2,3-dichlorobenzoyl | 48 | 494 | 495 |
| B-1417 | 4-F-phenyl | 2,4-dichlorobenzoyl | 57 | 494 | 495 |
| B-1418 | 4-F-phenyl | 3,4-dichlorobenzoyl | 49 | 494 | 495 |
| B-1419 | 4-F-phenyl | 3,5-dichlorobenzoyl | 39 | 494 | 495 |
| B-1420 | 4-F-phenyl | propanoyl | 72 | 378 | 379 |

-continued
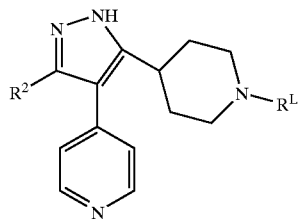
| Example # | R² | R^L | % Yield | Calcd. Mass Spec | Observed Mass Spec (M + H) |
|---|---|---|---|---|---|
| B-1421 | 4-F-C₆H₄ | -C(O)C(CH₃)₃ | 74 | 406 | 407 |
| B-1422 | 4-F-C₆H₄ | -C(O)OEt | 68 | 394 | 395 |
| B-1423 | 4-F-C₆H₄ | -C(O)O-nPr | 57 | 408 | 409 |
| B-1424 | 4-F-C₆H₄ | -C(O)O-iBu | 77 | 422 | 423 |
| B-1425 | 4-F-C₆H₄ | -C(O)O-iPr | 26 | 408 | 409 |
| B-1426 | 4-F-C₆H₄ | -C(O)O-allyl | 41 | 406 | 407 |
| B-1427 | 4-F-C₆H₄ | -C(O)O-propargyl | 37 | 404 | 405 |
| B-1428 | 4-F-C₆H₄ | -C(O)OCH₂Ph | 60 | 456 | 457 |
| B-1429 | 4-F-C₆H₄ | -C(O)CF₃ | 2 | 418 | 419 |

-continued
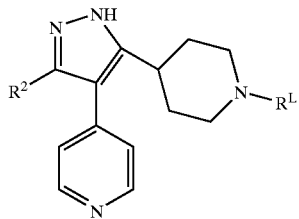
| Example # | R² | R^L | % Yield | Calcd. Mass Spec | Observed Mass Spec (M + H) |
|---|---|---|---|---|---|
| B-1430 | 4-F-phenyl | -SO₂-n-butyl | 61 | 442 | 443 |
| B-1431 | 4-F-phenyl | -SO₂-n-propyl | 64 | 428 | 429 |
| B-1432 | 4-F-phenyl | -SO₂-N(CH₃)₂ | 71 | 429 | 430 |
| B-1433 | 4-F-phenyl | -SO₂-phenyl | 74 | 462 | 463 |
| B-1434 | 4-F-phenyl | -SO₂-(1-methylimidazol-4-yl) | 88 | 466 | 467 |
| B-1435 | 4-F-phenyl | -SO₂-(3,5-dimethylisoxazol-4-yl) | 75 | 481 | 482 |
| B-1436 | 4-F-phenyl | -SO₂-(benzo[1,2,5]oxadiazol-4-yl) | 71 | 504 | 505 |
| B-1437 | 4-F-phenyl | -SO₂-(thiophen-2-yl) | 63 | 468 | 469 |
| B-1438 | 4-F-phenyl | -SO₂-(5-chlorothiophen-2-yl) | 78 | 502 | 503 |

-continued
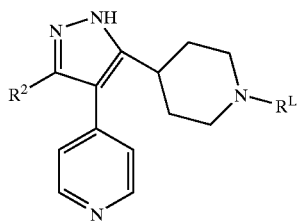
| Example # | R² | R^L | % Yield | Calcd. Mass Spec | Observed Mass Spec (M + H) |
|---|---|---|---|---|---|
| B-1439 | 4-F-phenyl | sulfonyl-thienyl-pyridyl | 70 | 545 | 546 |
| B-1440 | 4-F-phenyl | sulfonyl-thienyl-isoxazolyl | 62 | 535 | 536 |
| B-1441 | 4-F-phenyl | sulfonyl-thienyl-sulfonyl-phenyl | 82 | 608 | |
| B-1442 | 4-F-phenyl | sulfonyl-(N,N-dimethylamino)naphthyl | 79 | 555 | 556 |
| B-1443 | 4-F-phenyl | sulfonyl-isoquinolinyl | 28 | 513 | 514 |
| B-1444 | 4-F-phenyl | sulfonyl-2,5-dimethoxyphenyl | 75 | 522 | 523 |
| B-1445 | 4-F-phenyl | sulfonyl-5-chloro-2-methoxyphenyl | 74 | 526 | 527 |

-continued
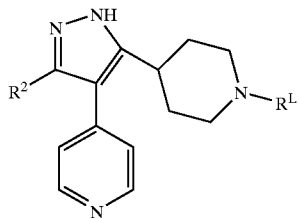
| Example # | R² | R^L | % Yield | Calcd. Mass Spec | Observed Mass Spec (M + H) |
|---|---|---|---|---|---|
| B-1446 | 4-F-C₆H₄ | 5-bromo-2-methoxyphenylsulfonyl | 70 | 570 | 571 |
| B-1447 | 4-F-C₆H₄ | 5-methoxy-2-methylphenylsulfonyl | 73 | 506 | 507 |
| B-1448 | 4-F-C₆H₄ | 2,3-dichlorophenylsulfonyl | 76 | 530 | 531 |
| B-1449 | 4-F-C₆H₄ | 2,4-dichlorophenylsulfonyl | 82 | 530 | 531 |
| B-1450 | 4-F-C₆H₄ | 2,5-dichlorophenylsulfonyl | 83 | 530 | 531 |
| B-1451 | 4-F-C₆H₄ | 2,6-dichlorophenylsulfonyl | 74 | 530 | 531 |
| B-1452 | 4-F-C₆H₄ | 3,4-dichlorophenylsulfonyl | 76 | 530 | 531 |

-continued
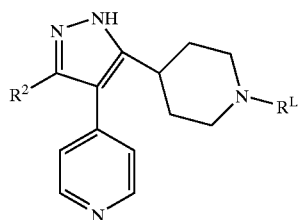
| Example # | R² | Rᴸ | % Yield | Calcd. Mass Spec | Observed Mass Spec (M + H) |
|---|---|---|---|---|---|
| B-1453 | 4-F-C₆H₄ | 3,5-diCl-C₆H₃-SO₂- | 73 | 530 | 531 |
| B-1454 | 4-F-C₆H₄ | 2,4-diF-C₆H₃-SO₂- | 81 | 498 | 499 |
| B-1455 | 4-F-C₆H₄ | 2,6-diF-C₆H₃-SO₂- | 83 | 498 | 499 |
| B-1456 | 4-F-C₆H₄ | 3,4-diF-C₆H₃-SO₂- | 78 | 498 | 499 |
| B-1457 | 4-F-C₆H₄ | 2-Cl-C₆H₄-SO₂- | 74 | 496 | 497 |
| B-1458 | 4-F-C₆H₄ | 2-Br-C₆H₄-SO₂- | 82 | 540 | 541 |
| B-1459 | 4-F-C₆H₄ | 2-Me-C₆H₄-SO₂- | 80 | 476 | 477 |
| B-1460 | 4-F-C₆H₄ | 3-CF₃-C₆H₄-SO₂- | 78 | 530 | 531 |

-continued
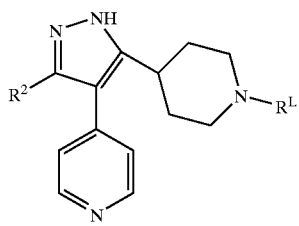
| Example # | R² | Rᴸ | % Yield | Calcd. Mass Spec | Observed Mass Spec (M + H) |
|---|---|---|---|---|---|
| B-1461 | 4-F-C₆H₄ | 2-CN-C₆H₄-SO₂- | 82 | 487 | 488 |
| B-1462 | 4-F-C₆H₄ | 2-(MeSO₂)-C₆H₄-SO₂- | 71 | 540 | 541 |
| B-1463 | 4-F-C₆H₄ | 2-(OCF₃)-C₆H₄-SO₂- | 78 | 546 | 547 |
| B-1464 | 4-F-C₆H₄ | 3-F-C₆H₄-SO₂- | 83 | 480 | 481 |
| B-1465 | 4-F-C₆H₄ | 3-Cl-C₆H₄-SO₂- | 84 | 496 | 497 |
| B-1466 | 4-F-C₆H₄ | 3-Br-C₆H₄-SO₂- | 80 | 540 | 541 |
| B-1467 | 4-F-C₆H₄ | 3-Me-C₆H₄-SO₂- | 79 | 476 | 477 |
| B-1468 | 4-F-C₆H₄ | 3-CF₃-C₆H₄-SO₂- | 79 | 530 | 531 |

-continued
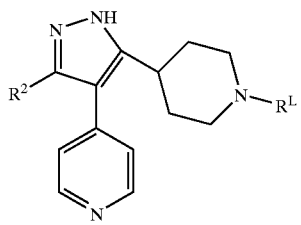
| Example # | R² | Rᴸ | % Yield | Calcd. Mass Spec | Observed Mass Spec (M + H) |
|---|---|---|---|---|---|
| B-1469 | 4-F-C₆H₄ | 3-CN-C₆H₄-SO₂ | 75 | 487 | 488 |
| B-1470 | 4-F-C₆H₄ | 4-F-C₆H₄-SO₂ | 80 | 480 | 481 |
| B-1471 | 4-F-C₆H₄ | 4-Cl-C₆H₄-SO₂ | 74 | 496 | 497 |
| B-1472 | 4-F-C₆H₄ | 4-Br-C₆H₄-SO₂ | 75 | 540 | 541 |
| B-1473 | 4-F-C₆H₄ | 4-CH₃-C₆H₄-SO₂ | 77 | 476 | 477 |
| B-1474 | 4-F-C₆H₄ | 4-CF₃-C₆H₄-SO₂ | 81 | 530 | 531 |
| B-1475 | 4-F-C₆H₄ | 4-CN-C₆H₄-SO₂ | 70 | 487 | 488 |

-continued
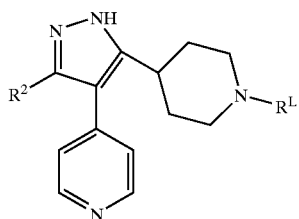
| Example # | R² | Rᴸ | % Yield | Calcd. Mass Spec | Observed Mass Spec (M + H) |
|---|---|---|---|---|---|
| B-1476 | 4-F-phenyl | 4-(methylsulfonyl)phenylsulfonyl | 54 | 540 | 541 |
| B-1477 | 4-F-phenyl | 4-(trifluoromethoxy)phenylsulfonyl | 79 | 546 | 547 |
| B-1478 | 4-F-phenyl | methoxyacetyl | 87 | 394 | 395 |
| B-1479 | 4-F-phenyl | 4-bromobenzoyl | 41 | 504 | 505 |
| B-1480 | 4-F-phenyl | 4-cyanobenzoyl | 87 | 451 | 452 |
| B-1481 | 4-F-phenyl | 2-furoyl | 18 | 416 | 417 |
| B-1482 | 4-F-phenyl | 2-pyridinylcarbonyl | 77 | 427 | 428 |

-continued
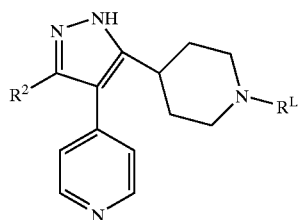
| Example # | R² | R^L | % Yield | Calcd. Mass Spec | Observed Mass Spec (M + H) |
|---|---|---|---|---|---|
| B-1483 | 4-F-phenyl | allyl carboxylate (-C(O)O-CH2-CH=CH2) | 74 | 406 | 407 |
| B-1484 | 4-F-phenyl | isobutyl carboxylate (-C(O)O-CH2-CH(CH3)2) | 82 | 422 | 423 |
| B-1485 | 4-F-phenyl | 4-Cl-benzoyl | 85 | 460 | 461 |
| B-1486 | 4-F-phenyl | pivaloyl (-C(O)-C(CH3)3) | 64 | 406 | 407 |
| B-1487 | 4-F-phenyl | isobutyryl (-C(O)-CH(CH3)2) | 71 | 392 | 393 |
| B-1488 | 4-F-phenyl | isonicotinoyl (4-pyridyl-C(O)-) | 82 | 427 | 428 |
| B-1489 | 4-F-phenyl | 4-F-benzoyl | 87 | 444 | 445 |
| B-1490 | 4-F-phenyl | 3,4-diF-benzoyl | 81 | 462 | 463 |

-continued
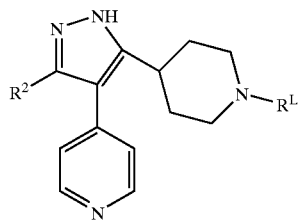
| Example # | R² | R^L | % Yield | Calcd. Mass Spec | Observed Mass Spec (M + H) |
|---|---|---|---|---|---|
| B-1491 | 4-F-phenyl | 3,5-difluorobenzoyl | 87 | 462 | 463 |
| B-1492 | 4-F-phenyl | acetyl | 69 | 364 | 365 |
| B-1493 | 4-F-phenyl | isoxazol-5-ylcarbonyl | 53 | 417 | 418 |
| B-1494 | 4-F-phenyl | benzoyl | 17 | 426 | 427 |
| B-1495 | 4-F-phenyl | 2-chlorobenzoyl | 79 | 460 | 461 |
| B-1496 | 4-F-phenyl | 3-fluorobenzoyl | 80 | 444 | 445 |
| B-1497 | 4-F-phenyl | 3-chlorobenzoyl | 82 | 460 | 461 |
| B-1498 | 4-F-phenyl | propionyl | 72 | 378 | 379 |

-continued
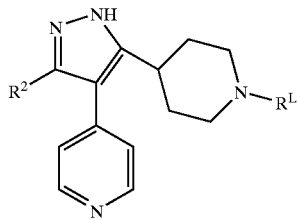
| Example # | R² | R^L | % Yield | Calcd. Mass Spec | Observed Mass Spec (M + H) |
|---|---|---|---|---|---|
| B-1499 | 4-F-C₆H₄ | -C(O)-2-thienyl | 70 | 432 | 433 |
| B-1500 | 4-F-C₆H₄ | -C(O)-cyclopropyl | 68 | 390 | 391 |
| B-1501 | 4-F-C₆H₄ | -C(O)O-ethyl | 63 | 394 | 395 |
| B-1502 | 4-F-C₆H₄ | -C(O)O-isopropyl | 78 | 408 | 409 |
| B-1503 | 4-F-C₆H₄ | -C(O)O-CH₂-C≡CH | 55 | 404 | 405 |
| B-1504 | 4-F-C₆H₄ | -C(O)CF₃ | 39 | 418 | 419 |
| B-1505 | 4-F-C₆H₄ | -SO₂-(4-Br-C₆H₄) | 69 | 540 | 541 |
| B-1506 | 4-F-C₆H₄ | -SO₂-C₆H₅ | 69 | 462 | 463 |

-continued
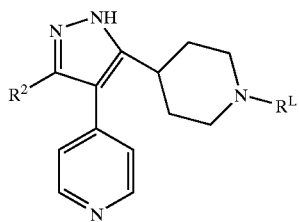
| Example # | R² | R^L | % Yield | Calcd. Mass Spec | Observed Mass Spec (M + H) |
|---|---|---|---|---|---|
| B-1507 | 4-F-C₆H₄ | 4-Cl-C₆H₄-SO₂- | 70 | 496 | 497 |
| B-1508 | 4-F-C₆H₄ | 4-F-C₆H₄-SO₂- | 65 | 480 | 481 |
| B-1509 | 4-F-C₆H₄ | Et-SO₂- | 56 | 414 | 415 |
| B-1510 | 4-F-C₆H₄ | Me-SO₂- | 62 | 400 | 401 |
| B-1511 | 4-F-C₆H₄ | 2-thienyl-SO₂- | 30 | 468 | 469 |
| B-1512 | 4-F-C₆H₄ | PhCH₂-SO₂- | 50 | 476 | 477 |
| B-1513 | 4-F-C₆H₄ | 3-Br-C₆H₄-SO₂- | 44 | 540 | 541 |
| B-1514 | 4-F-C₆H₄ | 4-CF₃-C₆H₄-SO₂- | 42 | 530 | 531 |

-continued
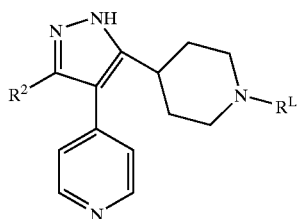
| Example # | R² | R^L | % Yield | Calcd. Mass Spec | Observed Mass Spec (M + H) |
|---|---|---|---|---|---|
| B-1515 | 4-F-C₆H₄ | 3-Cl-C₆H₄-SO₂- | 68 | 496 | 497 |
| B-1516 | 4-F-C₆H₄ | -SO₂-N(CH₃)₂ | 27 | 429 | 430 |
| B-1517 | 4-F-C₆H₄ | (1-methylimidazol-4-yl)-SO₂- | 92 | 466 | 467 |
| B-1518 | 4-F-C₆H₄ | -C(O)NHCH₃ | 33 | 379 | 380 |
| B-1519 | 4-F-C₆H₄ | -C(O)N(CH₃)₂ | 50 | 393 | 394 |
| B-1520 | 4-F-C₆H₄ | morpholine-C(O)- | 82 | 435 | 436 |
| B-1521 | 4-F-C₆H₄ | 4-CF₃-C₆H₄-NH-C(O)- | 86 | 509 | 510 |
| B-1522 | 4-F-C₆H₄ | allyl-NH-C(O)- | 12 | 405 | 406 |

-continued
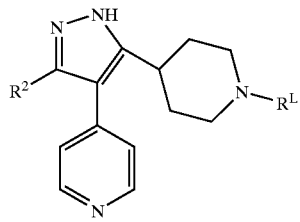
| Example # | R² | R^L | % Yield | Calcd. Mass Spec | Observed Mass Spec (M + H) |
|---|---|---|---|---|---|
| B-1523 | 4-F-phenyl | -C(O)NH-(3-F-phenyl) | 59 | 459 | 460 |
| B-1524 | 4-F-phenyl | -C(O)NH-(4-F-phenyl) | 81 | 459 | 460 |
| B-1525 | 4-F-phenyl | -C(O)-pyrrolidinyl | 57 | 419 | 420 |
| B-1526 | 3-Cl-phenyl | -C(O)CH₂OCH₃ | 73 | 410 | 411 |
| B-1527 | 3-Cl-phenyl | -C(O)-(4-Br-phenyl) | 66 | 520 | 521 |
| B-1528 | 3-Cl-phenyl | -C(O)-(4-CN-phenyl) | 91 | 467 | 468 |

-continued
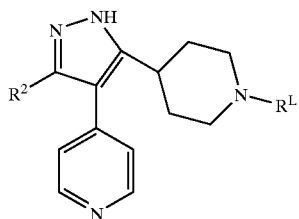
| Example # | R² | R^L | % Yield | Calcd. Mass Spec | Observed Mass Spec (M + H) |
|---|---|---|---|---|---|
| B-1529 | 3-Cl-phenyl | furan-2-carbonyl | 73 | 432 | 433 |
| B-1530 | 3-Cl-phenyl | pyridine-2-carbonyl | 91 | 443 | 444 |
| B-1531 | 3-Cl-phenyl | allyloxycarbonyl | 74 | 422 | 423 |
| B-1532 | 3-Cl-phenyl | isobutyloxycarbonyl | 68 | 438 | 439 |
| B-1533 | 3-Cl-phenyl | 4-Cl-benzoyl | 84 | 476 | 477 |
| B-1534 | 3-Cl-phenyl | pivaloyl | 72 | 422 | 423 |

-continued
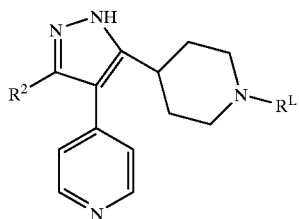
| Example # | R² | R^L | % Yield | Calcd. Mass Spec | Observed Mass Spec (M + H) |
|---|---|---|---|---|---|
| B-1535 | 3-Cl-C6H4 | isopropyl-C(O)- | 78 | 408 | 409 |
| B-1536 | 3-Cl-C6H4 | 4-pyridyl-C(O)- | 77 | 443 | 444 |
| B-1537 | 3-Cl-C6H4 | 4-F-C6H4-C(O)- | 86 | 460 | 461 |
| B-1538 | 3-Cl-C6H4 | 3,4-diF-C6H3-C(O)- | 74 | 478 | 479 |
| B-1539 | 3-Cl-C6H4 | 3,5-diF-C6H3-C(O)- | 85 | 478 | 479 |
| B-1540 | 3-Cl-C6H4 | CH3-C(O)- | 71 | 380 | 381 |

-continued
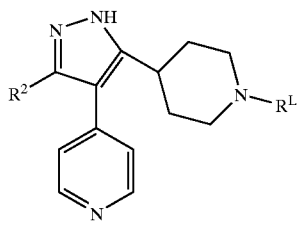
| Example # | R² | R^L | % Yield | Calcd. Mass Spec | Observed Mass Spec (M + H) |
|---|---|---|---|---|---|
| B-1541 | 3-Cl-C₆H₄ | isoxazol-5-yl-C(O)- | 71 | 433 | 434 |
| B-1542 | 3-Cl-C₆H₄ | C₆H₅-C(O)- | 89 | 442 | 443 |
| B-1543 | 3-Cl-C₆H₄ | 2-Cl-C₆H₄-C(O)- | 82 | 476 | 477 |
| B-1544 | 3-Cl-C₆H₄ | 3-F-C₆H₄-C(O)- | 76 | 460 | 461 |
| B-1545 | 3-Cl-C₆H₄ | 3-Cl-C₆H₄-C(O)- | 77 | 476 | 477 |
| B-1546 | 3-Cl-C₆H₄ | CH₃CH₂-C(O)- | 76 | 394 | 395 |

-continued
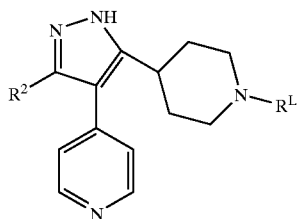
| Example # | R² | R^L | % Yield | Calcd. Mass Spec | Observed Mass Spec (M + H) |
|---|---|---|---|---|---|
| B-1547 | 3-Cl-C₆H₄ | 2-thienyl-C(O)- | 58 | 448 | 449 |
| B-1548 | 3-Cl-C₆H₄ | cyclopropyl-C(O)- | 83 | 406 | 407 |
| B-1549 | 3-Cl-C₆H₄ | EtO-C(O)- | 67 | 410 | 411 |
| B-1550 | 3-Cl-C₆H₄ | iPrO-C(O)- | 37 | 424 | 425 |
| B-1551 | 3-Cl-C₆H₄ | HC≡C-CH₂-O-C(O)- | 55 | 420 | 421 |
| B-1552 | 3-Cl-C₆H₄ | CF₃-C(O)- | 23 | 434 | 435 |

-continued
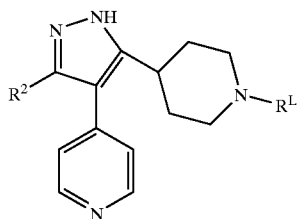
| Example # | R² | R^L | % Yield | Calcd. Mass Spec | Observed Mass Spec (M + H) |
|---|---|---|---|---|---|
| B-1553 | 3-Cl-phenyl | 4-Br-phenylsulfonyl | 83 | 556 | 557 |
| B-1554 | 3-Cl-phenyl | phenylsulfonyl | 84 | 478 | 479 |
| B-1555 | 3-Cl-phenyl | 4-Cl-phenylsulfonyl | 93 | 512 | 513 |
| B-1556 | 3-Cl-phenyl | 4-F-phenylsulfonyl | 83 | 496 | 497 |
| B-1557 | 3-Cl-phenyl | ethylsulfonyl | 62 | 430 | 431 |
| B-1558 | 3-Cl-phenyl | methylsulfonyl | 45 | 416 | 417 |

-continued
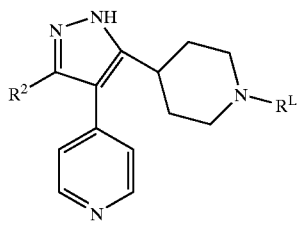
| Example # | R² | R^L | % Yield | Calcd. Mass Spec | Observed Mass Spec (M + H) |
|---|---|---|---|---|---|
| B-1559 | 3-Cl-C6H4 | sulfonyl-2-thienyl | 67 | 484 | 485 |
| B-1560 | 3-Cl-C6H4 | sulfonyl-CH2-phenyl | 16 | 492 | 493 |
| B-1561 | 3-Cl-C6H4 | sulfonyl-(3-Br-C6H4) | 84 | 556 | 557 |
| B-1562 | 3-Cl-C6H4 | sulfonyl-(4-CF3-C6H4) | 74 | 546 | 547 |
| B-1563 | 3-Cl-C6H4 | sulfonyl-(3-Cl-C6H4) | 72 | 512 | 513 |
| B-1564 | 3-Cl-C6H4 | sulfonyl-N(CH3)2 | 57 | 445 | 446 |

-continued
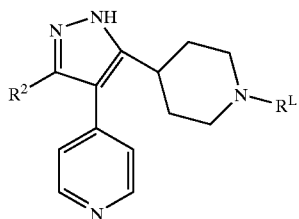
| Example # | R² | R^L | % Yield | Calcd. Mass Spec | Observed Mass Spec (M + H) |
|---|---|---|---|---|---|
| B-1565 | 3-Cl-C₆H₄ | 1-methylimidazol-4-ylsulfonyl | 64 | 482 | 483 |
| B-1566 | 3-Cl-C₆H₄ | C(O)NHCH₃ | 71 | 395 | 396 |
| B-1567 | 3-Cl-C₆H₄ | C(O)N(CH₃)₂ | 54 | 409 | 410 |
| B-1568 | 3-Cl-C₆H₄ | C(O)-morpholinyl | 76 | 451 | 452 |
| B-1569 | 3-Cl-C₆H₄ | C(O)NH-(4-CF₃-C₆H₄) | 70 | 525 | 526 |
| B-1570 | 3-Cl-C₆H₄ | C(O)NH-allyl | 79 | 421 | 422 |

-continued

| Example # | R² | R^L | % Yield | Calcd. Mass Spec | Observed Mass Spec (M + H) |
|---|---|---|---|---|---|
| B-1571 | 3-Cl-phenyl | -C(O)NH-(3-F-phenyl) | 60 | 475 | 476 |
| B-1572 | 3-Cl-phenyl | -C(O)NH-(4-F-phenyl) | 77 | 475 | 476 |
| B-1573 | 3-Cl-phenyl | -C(O)-pyrrolidinyl | 65 | 435 | 436 |

Proton NMR data for selected members from Examples B-0001 through B-1573 are shown in the following table.

| Plate ID | 1H NMR(solvent), d ppm |
|---|---|
| B-0120 | (DMF-d7) d 8.53(bd, J=4.99Hz, 2H), 7.44–7.24(m, 11H), 4.41(s, 2H)1 4.31(br, 2H) |
| B-0224 | (DMF-d7) d 8.56(bd, J=4.98Hz, 2H), 7.78–7.69(m, 4H), 7.39–7.19(m, 6H), 4.23(br, 2H) |
| B-0235 | (DMF-d7) d 8.47(br, 2H), 7.91–7.75(m, 3H), 7.57–7.53(m, 1H), 7.38–7.34(m, 2H), 7.21–7.13(m, 4H), 4.20(br, 2H) |
| B-0244 | (CDCl3/CD3OD) d 8.38(d, J=5.38 Hz, 1H), 7.62–7.32(m, 9H), 7.04–6.95(m, 4H), 6.86–6.80(m, 2H), 4.52(q, J=6.96 Hz, 1H), 1.40(d, J=6.88Hz, 3H) |
| B-0256 | (DMF-d7) d 8.45(bd, J=2.85, 2H), 7.87(br s, 4H), 7.76–7.75(m, 2H), 7.53–7.33(m, 5H), 7.18–7.13(br, 4H) |
| B-0426 | (DMF-d7), 1.32(br, 3H), 1.67(br, 3H), 4.17(br, 2H), 5.12(br, 1H), 7.50(m, 6H), 8.77(m, 2H), 13.54(br, 1H). |
| B-0438 | (DMSO), 1.14(t, J=6.9Hz, 3H), 4.54(m, 1 H), 6.99(br, 2H), 7.21(br, 4H), 7.45(s, 1H), 7.61(q, J=8.7Hz, 2H), 8.52(d, J=5.2Hz, 2H). |
| B-0466 | (DMF-d7), 1.61(brd, J=30.6Hz, 3H), 4.61(br, 1H), 7.25(m, 6H), 7.65(m, 3H), 8.59(br, 2H), 13.34(brd, J=34.8Hz, 1H). |
| B-0473 | (CD3OD), 1.53(d, J=7.2Hz, 3H), 4.59(q, J=7.2Hz, 1H), 6.88(d, J=4Hz, 1H), 7.09(m, 3H), 7.15(dd, J=4.4, 1.6Hz, 2H), 7.26(m, 2H), 8.46(d, J=6.0 Hz, 2H). |
| B-0477 | (DMF), 1.80(br, 3H), 2.35(s, 1H), 4.98(br, 1H), 7.38(m, 6H), 7.85(m, 2H), 8.45(br, 1H), 8.75(d, J=6.0Hz, 2H). |
| B-0479 | (Methanol-d4), 1.57(d, J=5.6Hz, 3H), 4.74(br, 1H), 7.23(m, 4H), 7.60(m, 2H), 7.81(m, 4H), 8.67(br, 2H). |

-continued

| Plate ID | 1H NMR(solvent), d ppm |
|---|---|
| B-0487 | (DMF), 1.78(s, 3H), 2.76(br, 6H), 4.85(br, 1H), 7.42(br, 2H), 7.54(br, 2H), 7.66(br, 3H), 8.82(s, 2H). |
| B-0566 | (CD3OD), 1.38(d, J=7.2Hz, 3H), 4.15(br, 2H), 4.50(br, 1H), 7.04(br, 2H), 7.18(br, 2H), 7.30(m, 7H), 8.45(m, 2H). |
| B-0569 | (CD3OD), 1.56(br, 3H), 4.66(q, J=6.7Hz, 1H), 7.17(m, 8H), 7.56(m, 2H), 8.47(s, 2H). |
| B-0574 | (Methanol-d4), 1.49(br, 3H), 3.86(br, 3H), 4.60(br, 1H), 6.92(br, 2H), 7.19(br, 2H), 7.31(br, 2H), 7.76(m, 4H), 8.60(br, 2H). |
| B-0639 | (DMF-d7), 1.58(brd, J=30.0Hz, 3H), 4.62(br, 1H), 7.25(m, 6H), 7.60(m, 4H), 8.59(br, 2H), 13.30(brd, J=12.3Hz). |
| B-0643 | 7.18(m, 2H), 7.32(dd, J=6.0, 4.4Hz, 1H), 7.70(dd, J=9.0, 5.8Hz, 1H), 8.43(dd, J=4.8, 3.2Hz, 2H). |
| B-0650 | (CD3OD), 1.58(br, 3H), 4.62(q, J=6.6Hz, 1H), 6.93(br, 1H), 7.17(m, 5H), 7.31(br, 2H), 8.51(br, 2H). |
| B-0656 | (CDCl3/CD3OD) d 8.48(d, J=5.30Hz, 2H), 7.72–7.59(m, 4H), 7.14–7.10(m, 2H), 7.03–6.97(m, 4H), 4.60(q, J=7.57Hz, 1H), 1.43(d, J=7.26Hz, 3H) |
| B-0663 | (CD3OD), 1.52(d, J=6.8 Hz, 3H), 3.75(s, 3H), 7.21(m, 2H), 7.42(m, 2H), 7.57(s, 1H), 7.76(s, 1H), 7.98(br, 2H), 8.76(br, 2H). |
| B-1165 | Hz, 2H), 3.06(m, 1H), 3.43(q, J=6.1Hz, 2H), 7.02(m, 2H), 7.14(m, 2H), 7.41(m, 2H), 8.59(d, J=5.6Hz, 2H). |
| B-1169 | =1.6Hz, 1H), 7.04(t, J=8.6Hz, 2H), 7.14(m, 2H), 7.36(m, 2H), 8.39(d, J=1.8 Hz, 1H), 8.60(m, 2H). |
| B-1171 | 6.83(br, 1H), 7.02(t, J=8.7Hz, 2H), 7.15(d, J=5.6Hz, 2H), 7.40(m, 2H), 8.59(d, J=5.0Hz, 2H). |
| B-1179 | (CDCl3), 1.94(br, 2H), 2.53(s, 3H), 2.85(t, J=6.2Hz, 2H), 3.65(br, 2H), 6.15(br, 1H), 7.04(m, 3H), 7.22(m, 3H), 7.41(br, 4H), 8.60(br, 2H). |
| B-1183 | (CDCl3), 2.00(br, 2H), 2.85(br, 2H), 3.64(br, 2H), 7.03(br, 3H), 7.17(br, 2H), 7.36(br, 2H), 7.66(br, 2H), 8.60(br, 2H), 8.77(br, 2H). |
| B-1194 | (DMSO), 1.76(br, 2H), 2.66(br, 2H), 2.91(br, 2H), 4.30(s, 2H), 7.18(br, 5H), 7.35(m, 6H), 8.54(d, J=5.8Hz, 2H). |
| B-1200 | (DMSO), 1.17(br, 3H), 1.76(br, 2H), 2.71(br, 2H), 2.97(br, 4H), 7.18(br, 4H), 7.36(br, 2H), 8.54(br, 2H). |
| B-1206 | (DMSO), 1.03(s, 6H), 1.68(br, 2H), 2.63(br, 2H), 3.00(br, 2H), 3.65(br, 1H), 5.69(m, 2H), 7.16(br, 4H), 7.35(br, 2H), 8.54(br, 2H). |
| B-1216 | (DMSO), 1.75(m, 2H), 2.14(s, 6H), 2.66(br, 2H), 3.10(br, 2H), 7.04(br, 3H), 7.18(br, 4H), 7.35(m, 2H), 7.47(br, 1H), 8.54(d, J=4.8Hz, 2H). |
| B-1226 | (DMF), 1.25(br, 3H), 2.01(br, 2H), 3.35(br, 4H), 6.20(s, 1H), 6.30(s, 1H), 7.42(br, 4H), 7.65(br, 2H), 8.77(s, 2H). |
| B-1360 | (DMSO-d6), 1.80(br, 4H), 2.82(br, 1H), 2.94(br, 1H), 3.10(br, 1H), 3.60(br, 1H), 4.54(br, 1H), 7.18(m, 4H), 7.30(m, 4H), 7.46(m, 2H), 8.54(br, 2H). |
| B-1361 | (DMSO-d6), 0.99(br, 6H), 1.73(br, 4H), 2.89(br, 2H), 3.03(m, 1H), 4.04(br, 2H), 4.44(m, 1H), 7.18(m, 4H), 7.30(m, 2H), 8.57(d, J=4.64Hz, 2H). |
| B-1363 | (DMSO-d6), 1.78(br, 4H), 2.01(s, 3H), 2.89(br, 1H), 3.05(br, 1H), 3.34(br, 1H), 3.85(br, 1H), 4.48(br, 1H), 7.12(br, 2H), 7.21(br, 2H), 7.30(br, 2H), 8.69(br, 2H). |
| B-1364 | (CDCl3), 0.78(dd, J=3.0, 2.9Hz, 2H), 1.00(s, 2H), 1.78(m, 1H), 1.86(b, 4H), 2.64(m, 1H), 2.99(m, 1H), 3.16(m, 1H), 4.33(br, 1H), 4.70(br, 1H), 6.99(m, 2H), 7.14(s, 2H), 7.29(m, 2H), 8.64(s, 2H). |
| B-1368 | (CDCl3), 1.89(s, 4H), 2.65(m, 1H), 2.96(m, 1H), 3.06(m, 1H), 3.43(s, 3H), 3.93(d, J=13.2Hz, 1H), 4.09(d, J=13.5Hz, 1H), 4.18(d, J=13.5Hz, 1H), 4.68(d, J=12.4Hz, 1H), 7.60(m, 2H), 7.12(s, 2H), 7.26(m, 2H), 8.63(s, 2H). |

By analogy to the procedure identified above for the preparation of Examples B0001-B0048, the following examples B-1574 through B-2269 are prepared.

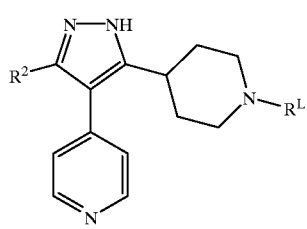

Examples B-1574 through B-1597 are prepared from Scaffold C-27

| Example # | R² | R^L |
|---|---|---|
| B-1574 | 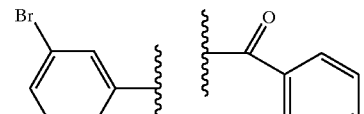 | |
| B-1575 | 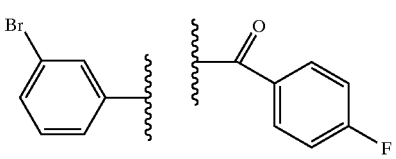 | |

-continued

| Example # | R² | R^L |
|---|---|---|
| B-1576 | Br-phenyl | isobutyryl (C(O)CH(CH3)2) |
| B-1577 | Br-phenyl | allyloxycarbonyl (C(O)OCH2CH=CH2) |
| B-1578 | Br-phenyl | acetyl (C(O)CH3) |
| B-1579 | Br-phenyl | cyclopropylcarbonyl |
| B-1580 | Br-phenyl | 3-bromobenzoyl |
| B-1581 | Br-phenyl | 4-iodobenzoyl |
| B-1582 | Br-phenyl | isoxazol-5-ylcarbonyl |
| B-1583 | Br-phenyl | methoxyacetyl (C(O)CH2OCH3) |
| B-1584 | Br-phenyl | 2-methoxybenzoyl |

-continued

| Example # | R² | R^L |
|---|---|---|
| B-1585 | Br-phenyl | (3-methoxyphenyl)acetyl |
| B-1586 | Br-phenyl | 4-methylbenzoyl |
| B-1587 | Br-phenyl | 2-fluorobenzoyl |
| B-1588 | Br-phenyl | pyridin-4-ylcarbonyl |
| B-1589 | Br-phenyl | 2-(benzyl)sulfonyl (cyclic) |
| B-1590 | Br-phenyl | ethylsulfonyl |
| B-1591 | Br-phenyl | methylsulfonyl |
| B-1592 | Br-phenyl | 2-fluorophenylsulfonyl |
| B-1593 | Br-phenyl | N-methylcarbamoyl |

-continued

| Example # | R² | R^L |
|---|---|---|
| B-1594 | 3-Br-phenyl | -C(O)NH-(2-F-phenyl) |
| B-1595 | 3-Br-phenyl | -C(O)NH-(2,6-dimethylphenyl) |
| B-1596 | 3-Br-phenyl | -C(O)NHEt |
| B-1597 | 3-Br-phenyl | -C(O)NH-(2,4-dimethoxyphenyl) |

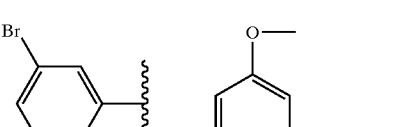

Examples B-1598 through B-1621 are prepared from Scaffold C-28

| Example # | R² | R^L |
|---|---|---|
| B-1598 | 3-methylphenyl | -C(O)-(2-I-phenyl) |
| B-1599 | 3-methylphenyl | -C(O)-(4-F-phenyl) |
| B-1600 | 3-methylphenyl | -C(O)CH(CH₃)₂ |
| B-1601 | 3-methylphenyl | -C(O)O-CH₂CH=CH₂ |
| B-1602 | 3-methylphenyl | -C(O)CH₃ |
| B-1603 | 3-methylphenyl | -C(O)-cyclopropyl |
| B-1604 | 3-methylphenyl | -C(O)-(3-Br-phenyl) |
| B-1605 | 3-methylphenyl | -C(O)-(4-I-phenyl) |
| B-1606 | 3-methylphenyl | -C(O)-isoxazol-5-yl |
| B-1607 | 3-methylphenyl | -C(O)CH₂OCH₃ |
| B-1608 | 3-methylphenyl | -C(O)-(2-methoxyphenyl) |

Examples B-1622 through B-1645 are prepared from Scaffold C-38
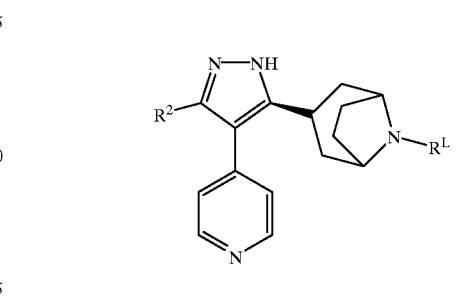

US 6,423,713 B1

-continued

| Example # | R² | R^L |
|---|---|---|
| B-1624 | 4-F-phenyl | -C(O)CH(CH₃)₂ |
| B-1625 | 4-F-phenyl | -C(O)O-CH₂CH=CH₂ |
| B-1626 | 4-F-phenyl | -C(O)CH₃ |
| B-1627 | 4-F-phenyl | -C(O)-cyclopropyl |
| B-1628 | 4-F-phenyl | -C(O)-(3-Br-phenyl) |
| B-1629 | 4-F-phenyl | -C(O)-(4-I-phenyl) |
| B-1630 | 4-F-phenyl | -C(O)-(isoxazol-5-yl) |
| B-1631 | 4-F-phenyl | -C(O)CH₂OCH₃ |
| B-1632 | 4-F-phenyl | -C(O)-(2-MeO-phenyl) |
| B-1633 | 4-F-phenyl | -C(O)CH₂-(3-MeO-phenyl) |

-continued

| Example # | R² | R^L |
|---|---|---|
| B-1634 | 4-F-phenyl | -C(O)-(4-Me-phenyl) |
| B-1635 | 4-F-phenyl | -C(O)-(2-F-phenyl) |
| B-1636 | 4-F-phenyl | -C(O)-(pyridin-4-yl) |
| B-1637 | 4-F-phenyl | benzosultam-S(O)₂- |
| B-1638 | 4-F-phenyl | -S(O)₂CH₂CH₃ |
| B-1639 | 4-F-phenyl | -S(O)₂CH₃ |
| B-1640 | 4-F-phenyl | -S(O)₂-(2-F-phenyl) |
| B-1641 | 4-F-phenyl | -C(O)NHCH₃ |
| B-1642 | 4-F-phenyl | -C(O)NH-(2-F-phenyl) |
| B-1643 | 4-F-phenyl | -C(O)NH-(2,6-diMe-phenyl) |

Examples B-1646 through B-1669 are prepared from Scaffold C-39
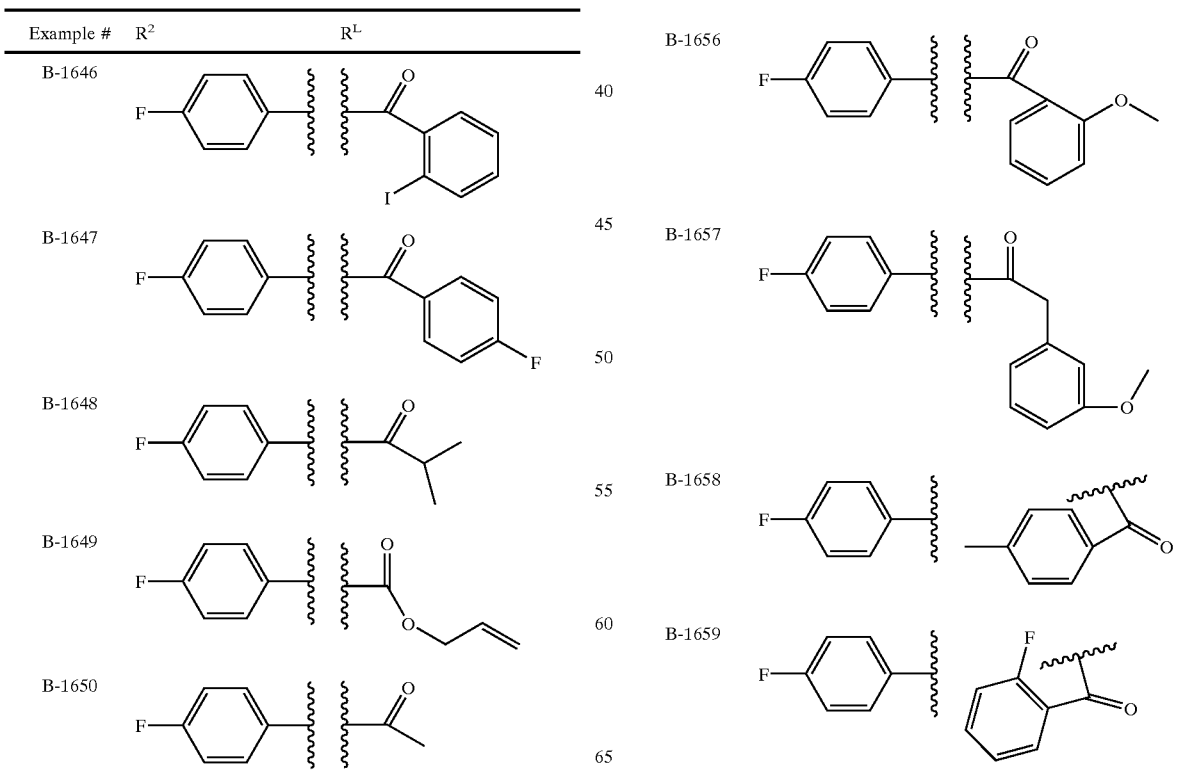

-continued

| Example # | R² | R^L |
|---|---|---|
| B-1660 | 4-F-phenyl | 4-pyridyl-C(=O)- |
| B-1661 | 4-F-phenyl | 2-(benzyl)sulfonyl |
| B-1662 | 4-F-phenyl | ethylsulfonyl |
| B-1663 | 4-F-phenyl | methylsulfonyl |
| B-1664 | 4-F-phenyl | 2-fluorophenylsulfonyl |
| B-1665 | 4-F-phenyl | -C(=O)NHCH₃ |
| B-1666 | 4-F-phenyl | -C(=O)NH(2-F-phenyl) |
| B-1667 | 4-F-phenyl | -C(=O)NH(2,6-dimethylphenyl) |
| B-1668 | 4-F-phenyl | -NHC(=O)-ethyl |
| B-1669 | 4-F-phenyl | 2,5-dimethoxyphenyl-NHC(=O)- |

Examples B-1670 through B-1693 are prepared from Scaffold C-65

| Example # | R² | R^L |
|---|---|---|
| B-1670 | 4-F-phenyl | 2-iodobenzoyl |
| B-1671 | 4-F-phenyl | 4-fluorobenzoyl |
| B-1672 | 4-F-phenyl | isopropyl-C(=O)- |
| B-1673 | 4-F-phenyl | -C(=O)O-allyl |
| B-1674 | 4-F-phenyl | acetyl |
| B-1675 | 4-F-phenyl | cyclopropyl-C(=O)- |
| B-1676 | 4-F-phenyl | 3-bromobenzoyl |
| B-1677 | 4-F-phenyl | 4-iodobenzoyl |

-continued

| Example # | R² | R^L |
|---|---|---|
| B-1678 | F-phenyl | isoxazol-5-yl carbonyl |
| B-1679 | F-phenyl | -C(O)CH₂OCH₃ |
| B-1680 | F-phenyl | 2-methoxyphenyl carbonyl |
| B-1681 | F-phenyl | -C(O)CH₂-(3-methoxyphenyl) |
| B-1682 | F-phenyl | 4-methylphenyl carbonyl |
| B-1683 | F-phenyl | 2-fluorophenyl carbonyl |
| B-1684 | F-phenyl | pyridin-4-yl carbonyl |
| B-1685 | F-phenyl | benzisothiazole-S,S-dioxide |
| B-1686 | F-phenyl | -SO₂Et |
| B-1687 | F-phenyl | -SO₂Me |

-continued

| Example # | R² | R^L |
|---|---|---|
| B-1688 | F-phenyl | 2-fluorophenylsulfonyl |
| B-1689 | F-phenyl | -C(O)NHCH₃ |
| B-1690 | F-phenyl | -C(O)NH-(2-fluorophenyl) |
| B-1691 | F-phenyl | -C(O)NH-(2,6-dimethylphenyl) |
| B-1692 | F-phenyl | -NHC(O)Et |
| B-1693 | F-phenyl | 2,4-dimethoxyphenyl-NHC(O)- |

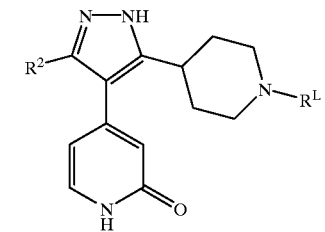

Examples B-1694 through B-1717 are prepared from Scaffold C-66

| Example # | R² | R^L |
|---|---|---|
| B-1694 | 4-F-phenyl | 2-iodobenzoyl |
| B-1695 | 4-F-phenyl | 4-fluorobenzoyl |
| B-1696 | 4-F-phenyl | isobutyryl |
| B-1697 | 4-F-phenyl | allyloxycarbonyl |
| B-1698 | 4-F-phenyl | acetyl |
| B-1699 | 4-F-phenyl | cyclopropanecarbonyl |
| B-1700 | 4-F-phenyl | 3-bromobenzoyl |
| B-1701 | 4-F-phenyl | 4-iodobenzoyl |
| B-1702 | 4-F-phenyl | isoxazol-5-ylcarbonyl |
| B-1703 | 4-F-phenyl | methoxyacetyl |
| B-1704 | 4-F-phenyl | 2-methoxybenzoyl |
| B-1705 | 4-F-phenyl | (3-methoxyphenyl)acetyl |
| B-1706 | 4-F-phenyl | 1-(4-methylphenyl)-1-oxo |
| B-1707 | 4-F-phenyl | 1-(2-fluorophenyl)-1-oxo |
| B-1708 | 4-F-phenyl | pyridin-4-ylcarbonyl |
| B-1709 | 4-F-phenyl | benzosultam |
| B-1710 | 4-F-phenyl | ethylsulfonyl |
| B-1711 | 4-F-phenyl | methylsulfonyl |
| B-1712 | 4-F-phenyl | 2-fluorophenylsulfonyl |
| B-1713 | 4-F-phenyl | N-methylcarbamoyl |

-continued

| Example # | R² | R^L |
|---|---|---|
| B-1714 | 4-F-phenyl | -C(O)NH-(2-F-phenyl) |
| B-1715 | 4-F-phenyl | -C(O)NH-(2,6-dimethylphenyl) |
| B-1716 | 4-F-phenyl | -C(O)NH-ethyl |
| B-1717 | 4-F-phenyl | -C(O)NH-(2,4-dimethoxyphenyl) |

Examples B-1718 through B-1741 are prepared from Scaffold C-69

| Example # | R² | R^L |
|---|---|---|
| B-1718 | 4-F-phenyl | -C(O)-(2-I-phenyl) |
| B-1719 | 4-F-phenyl | -C(O)-(4-F-phenyl) |

-continued

| Example # | R² | R^L |
|---|---|---|
| B-1720 | 4-F-phenyl | -C(O)-CH(CH₃)₂ |
| B-1721 | 4-F-phenyl | -C(O)O-CH₂CH=CH₂ |
| B-1722 | 4-F-phenyl | -C(O)CH₃ |
| B-1723 | 4-F-phenyl | -C(O)-cyclopropyl |
| B-1724 | 4-F-phenyl | -C(O)-(3-Br-phenyl) |
| B-1725 | 4-F-phenyl | -C(O)-(4-I-phenyl) |
| B-1726 | 4-F-phenyl | -C(O)-(isoxazol-5-yl) |
| B-1727 | 4-F-phenyl | -C(O)CH₂OCH₃ |
| B-1728 | 4-F-phenyl | -C(O)-(2-methoxyphenyl) |
| B-1729 | 4-F-phenyl | -C(O)CH₂-(3-methoxyphenyl) |

-continued

| Example # | R² | R^L |
|---|---|---|
| B-1730 | 4-F-phenyl | 4-methylbenzoyl |
| B-1731 | 4-F-phenyl | 2-fluorobenzoyl |
| B-1732 | 4-F-phenyl | pyridine-4-carbonyl |
| B-1733 | 4-F-phenyl | 2-(benzyl)sulfonyl |
| B-1734 | 4-F-phenyl | ethylsulfonyl |
| B-1735 | 4-F-phenyl | methylsulfonyl |
| B-1736 | 4-F-phenyl | 2-fluorophenylsulfonyl |
| B-1737 | 4-F-phenyl | N-methylcarbamoyl |
| B-1738 | 4-F-phenyl | N-(2-fluorophenyl)carbamoyl |
| B-1739 | 4-F-phenyl | N-(2,6-dimethylphenyl)carbamoyl |

-continued

| Example # | R² | R^L |
|---|---|---|
| B-1740 | 4-F-phenyl | N-ethylcarbamoyl |
| B-1741 | 4-F-phenyl | N-(2,4-dimethoxyphenyl)carbamoyl |

Examples B-1742 through B-1765 are prepared from Scaffold C-70

| Example # | R² | R^L |
|---|---|---|
| B-1742 | 4-F-phenyl | 2-iodobenzoyl |
| B-1743 | 4-F-phenyl | 4-fluorobenzoyl |
| B-1744 | 4-F-phenyl | isobutyryl |
| B-1745 | 4-F-phenyl | allyloxycarbonyl |
| B-1746 | 4-F-phenyl | acetyl |

| Example # | R² | Rᴸ |
|---|---|---|
| B-1747 | 4-F-phenyl | cyclopropyl ketone |
| B-1748 | 4-F-phenyl | 3-bromophenyl ketone |
| B-1749 | 4-F-phenyl | 4-iodophenyl ketone |
| B-1750 | 4-F-phenyl | isoxazol-5-yl ketone |
| B-1751 | 4-F-phenyl | methoxymethyl ketone |
| B-1752 | 4-F-phenyl | 2-methoxyphenyl ketone |
| B-1753 | 4-F-phenyl | (3-methoxyphenyl)acetyl |
| B-1754 | 4-F-phenyl | 4-methylbenzoyl |
| B-1755 | 4-F-phenyl | 2-fluorobenzoyl |
| B-1756 | 4-F-phenyl | pyridin-4-yl ketone |
| B-1757 | 4-F-phenyl | benzylsulfonyl |
| B-1758 | 4-F-phenyl | ethylsulfonyl |
| B-1759 | 4-F-phenyl | methylsulfonyl |
| B-1760 | 4-F-phenyl | 2-fluorophenylsulfonyl |
| B-1761 | 4-F-phenyl | N-methylcarbamoyl |
| B-1762 | 4-F-phenyl | N-(2-fluorophenyl)carbamoyl |
| B-1763 | 4-F-phenyl | N-(2,6-dimethylphenyl)carbamoyl |
| B-1764 | 4-F-phenyl | N-ethylcarbamoyl |

-continued
| Example # | R² | R^L |
|---|---|---|
| B-1765 |  |  |
Examples B-1766 through B-1789 are prepared from Scaffold C-71
| Example# | R² | R^L |
|---|---|---|
| B-1766 | | 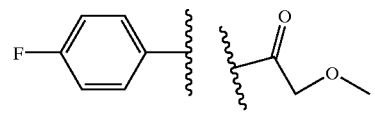 |
| B-1767 | | |
| B-1768 | | |
| B-1769 | | |
| B-1770 | | |
| B-1771 | | |
-continued
| Example# | R² | R^L |
|---|---|---|
| B-1772 | | 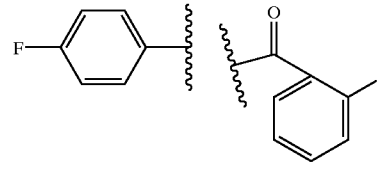 |
| B-1773 | | |
| B-1774 | | |
| B-1775 | | |
| B-1776 | | |
| B-1777 | | |
| B-1778 | | |
| B-1779 | | |
| B-1780 | | |

851

-continued

| Example# | R² | R^L |
|---|---|---|
| B-1781 | 4-F-phenyl | benzyl sulfonyl |
| B-1782 | 4-F-phenyl | ethylsulfonyl |
| B-1783 | 4-F-phenyl | methylsulfonyl |
| B-1784 | 4-F-phenyl | 2-fluorophenylsulfonyl |
| B-1785 | 4-F-phenyl | -C(O)NHCH₃ |
| B-1786 | 4-F-phenyl | -C(O)NH-(2-fluorophenyl) |
| B-1787 | 4-F-phenyl | -C(O)NH-(2,6-dimethylphenyl) |
| B-1788 | 4-F-phenyl | -CH₂CH₂NHC(O)- |
| B-1789 | 4-F-phenyl | -C(O)NH-(2,4-dimethoxyphenyl) |

852

Examples B-1790 through B-1813 are prepared from Scaffold C-72

| Example# | R² | R^L |
|---|---|---|
| B-1790 | 4-F-phenyl | -C(O)-(2-iodophenyl) |
| B-1791 | 4-F-phenyl | -C(O)-(4-fluorophenyl) |
| B-1792 | 4-F-phenyl | -C(O)-iPr |
| B-1793 | 4-F-phenyl | -C(O)O-allyl |
| B-1794 | 4-F-phenyl | -C(O)CH₃ |
| B-1795 | 4-F-phenyl | -C(O)-cyclopropyl |
| B-1796 | 4-F-phenyl | -C(O)-(3-bromophenyl) |
| B-1797 | 4-F-phenyl | -C(O)-(4-iodophenyl) |

-continued

| Example# | R² | R^L |
|---|---|---|
| B-1798 | 4-F-phenyl | C(=O)-isoxazol-5-yl |
| B-1799 | 4-F-phenyl | C(=O)CH₂OCH₃ |
| B-1800 | 4-F-phenyl | C(=O)-(2-methoxyphenyl) |
| B-1801 | 4-F-phenyl | C(=O)CH₂-(3-methoxyphenyl) |
| B-1802 | 4-F-phenyl | C(=O)-(4-methylphenyl) |
| B-1803 | 4-F-phenyl | C(=O)-(2-fluorophenyl) |
| B-1804 | 4-F-phenyl | C(=O)-(pyridin-4-yl) |
| B-1805 | 4-F-phenyl | SO₂CH₂-phenyl |
| B-1806 | 4-F-phenyl | SO₂CH₂CH₃ |
| B-1807 | 4-F-phenyl | SO₂CH₃ |

-continued

| Example# | R² | R^L |
|---|---|---|
| B-1808 | 4-F-phenyl | SO₂-(2-fluorophenyl) |
| B-1809 | 4-F-phenyl | C(=O)NHCH₃ |
| B-1810 | 4-F-phenyl | C(=O)NH-(2-fluorophenyl) |
| B-1811 | 4-F-phenyl | C(=O)NH-(2,6-dimethylphenyl) |
| B-1812 | 4-F-phenyl | C(=O)NHCH₂CH₃ |
| B-1813 | 4-F-phenyl | C(=O)NH-(2,4-dimethoxyphenyl) |

Examples B-1814 through B-1837 are prepared from Scaffold C-73

| Example# | R² | R^L |
|---|---|---|
| B-1814 | 4-F-phenyl | 2-iodobenzoyl |
| B-1815 | 4-F-phenyl | 4-fluorobenzoyl |
| B-1816 | 4-F-phenyl | isobutyryl |
| B-1817 | 4-F-phenyl | allyloxycarbonyl |
| B-1818 | 4-F-phenyl | acetyl |
| B-1819 | 4-F-phenyl | cyclopropylcarbonyl |
| B-1820 | 4-F-phenyl | 3-bromobenzoyl |
| B-1821 | 4-F-phenyl | 4-iodobenzoyl |
| B-1822 | 4-F-phenyl | isoxazol-5-ylcarbonyl |
| B-1823 | 4-F-phenyl | methoxyacetyl |
| B-1824 | 4-F-phenyl | 2-methoxybenzoyl |
| B-1825 | 4-F-phenyl | (3-methoxyphenyl)acetyl |
| B-1826 | 4-F-phenyl | 4-methylbenzoyl |
| B-1827 | 4-F-phenyl | 2-fluorobenzoyl |
| B-1828 | 4-F-phenyl | pyridin-4-ylcarbonyl |
| B-1829 | 4-F-phenyl | benzylsulfonyl |
| B-1830 | 4-F-phenyl | ethylsulfonyl |
| B-1831 | 4-F-phenyl | methylsulfonyl |
| B-1832 | 4-F-phenyl | 2-fluorophenylsulfonyl |

Examples B-1838 through B-1861 are prepared from Scaffold C-33
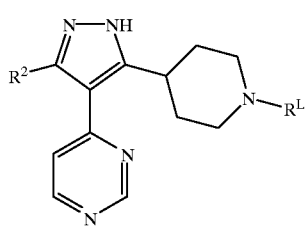

| Example# | R² | R^L |
|---|---|---|
| B-1849 | 4-F-phenyl | 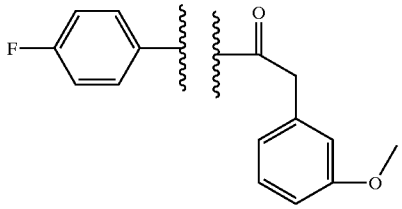 -CH₂-C(=O)- linked to 3-methoxyphenyl |
| B-1850 | 4-F-phenyl | 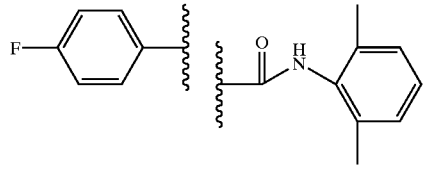 -C(=O)- linked to 4-methylphenyl |
| B-1851 | 4-F-phenyl | 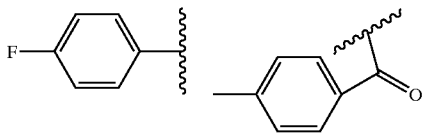 -C(=O)- linked to 2-fluorophenyl |
| B-1852 | 4-F-phenyl | 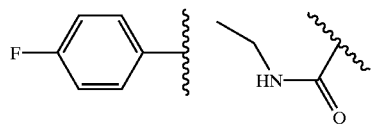 -C(=O)- linked to 4-pyridyl |
| B-1853 | 4-F-phenyl | 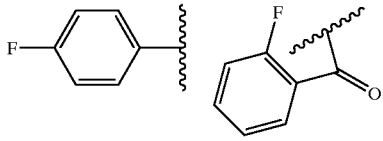 -S(=O)₂-CH₂-phenyl |
| B-1854 | 4-F-phenyl | 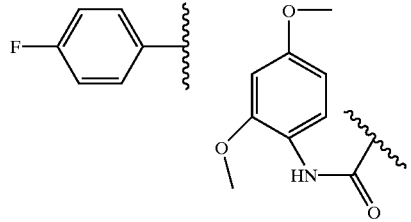 -S(=O)₂-ethyl |
| B-1855 | 4-F-phenyl | 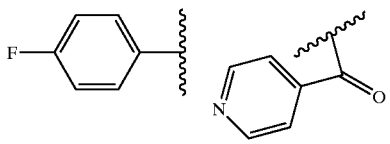 -S(=O)₂-methyl |
| B-1856 | 4-F-phenyl | 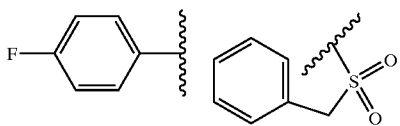 -S(=O)₂- linked to 2-fluorophenyl |
| B-1857 | 4-F-phenyl | 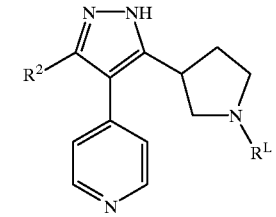 -C(=O)-NH-CH₃ |
| B-1858 | 4-F-phenyl | 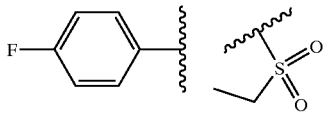 -C(=O)-NH- linked to 2-fluorophenyl |

| Example# | R² | R^L |
|---|---|---|
| B-1859 | 4-F-phenyl | 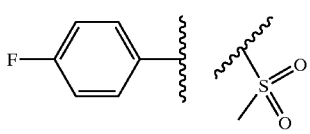 -C(=O)-NH- linked to 2,6-dimethylphenyl |
| B-1860 | 4-F-phenyl | 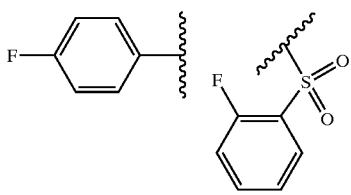 -C(=O)-NH-ethyl |
| B-1861 | 4-F-phenyl | 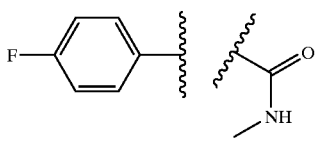 -C(=O)-NH- linked to 2,4-dimethoxyphenyl |

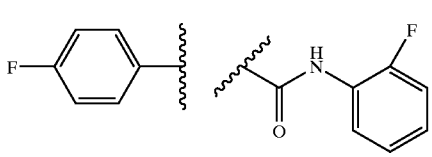

Examples B-1862 through B-1885 are prepared from Scaffold C-45

| Example # | R² | R^L |
|---|---|---|
| B-1862 | 4-F-phenyl | 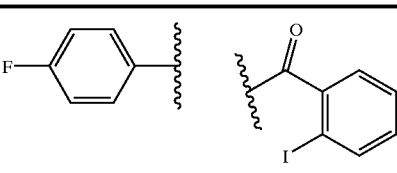 -C(=O)- linked to 2-iodophenyl |
| B-1863 | 4-F-phenyl | 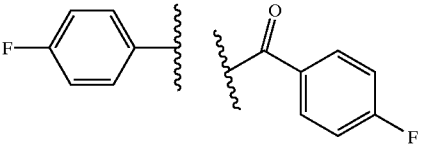 -C(=O)- linked to 4-fluorophenyl |
| B-1864 | 4-F-phenyl | 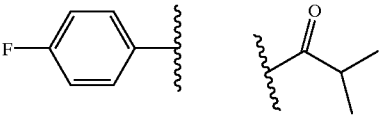 -C(=O)-CH(CH₃)₂ |

-continued

| Example # | R² | R^L |
|---|---|---|
| B-1865 | 4-F-phenyl | -C(=O)O-CH₂-CH=CH₂ (allyl ester) |
| B-1866 | 4-F-phenyl | -C(=O)CH₃ |
| B-1867 | 4-F-phenyl | -C(=O)-cyclopropyl |
| B-1868 | 4-F-phenyl | -C(=O)-(3-bromophenyl) |
| B-1869 | 4-F-phenyl | -C(=O)-(4-iodophenyl) |
| B-1870 | 4-F-phenyl | -C(=O)-(isoxazol-5-yl) |
| B-1871 | 4-F-phenyl | -C(=O)CH₂OCH₃ |
| B-1872 | 4-F-phenyl | -C(=O)-(2-methoxyphenyl) |
| B-1873 | 4-F-phenyl | -C(=O)CH₂-(3-methoxyphenyl) |

-continued

| Example # | R² | R^L |
|---|---|---|
| B-1874 | 4-F-phenyl | -C(=O)-(4-methylphenyl) |
| B-1875 | 4-F-phenyl | 7-fluoro-2-oxo-indan-1-yl |
| B-1876 | 4-F-phenyl | -C(=O)-(pyridin-4-yl) |
| B-1877 | 4-F-phenyl | -S(=O)₂-CH₂-phenyl |
| B-1878 | 4-F-phenyl | -S(=O)₂-CH₂CH₃ |
| B-1879 | 4-F-phenyl | -S(=O)₂-CH₃ |
| B-1880 | 4-F-phenyl | -S(=O)₂-(2-fluorophenyl) |
| B-1881 | 4-F-phenyl | -C(=O)NH-CH₃ |
| B-1882 | 4-F-phenyl | -C(=O)NH-(2-fluorophenyl) |
| B-1883 | 4-F-phenyl | -C(=O)NH-(2,6-dimethylphenyl) |

-continued

| Example # | R² | R^L |
|---|---|---|
| B-1884 | 4-F-phenyl | -NH-C(=O)-ethyl |
| B-1885 | 4-F-phenyl | 2,4-dimethoxyphenyl-NH-C(=O)- |

[Structure: pyrazole scaffold with R² at 3-position, 4-pyridyl at 4-position, and (3-piperidinyl with N-R^L) at 5-position; pyrazole NH]

Examples B-1886 through B-1909 prepared from Scaffold C-42

| Example # | R² | R^L |
|---|---|---|
| B-1886 | 4-F-phenyl | 2-iodobenzoyl |
| B-1887 | 4-F-phenyl | 4-fluorobenzoyl |
| B-1888 | 4-F-phenyl | isobutyryl |
| B-1889 | 4-F-phenyl | allyloxycarbonyl |
| B-1890 | 4-F-phenyl | acetyl (methyl ketone) |
| B-1891 | 4-F-phenyl | cyclopropylcarbonyl |
| B-1892 | 4-F-phenyl | 3-bromobenzoyl |
| B-1893 | 4-F-phenyl | 4-iodobenzoyl |
| B-1894 | 4-F-phenyl | isoxazol-5-ylcarbonyl |
| B-1895 | 4-F-phenyl | methoxyacetyl |
| B-1896 | 4-F-phenyl | 2-methoxybenzoyl |
| B-1897 | 4-F-phenyl | (3-methoxyphenyl)acetyl |
| B-1898 | 4-F-phenyl | 4-methylbenzoyl |
| B-1899 | 4-F-phenyl | 2-fluorobenzoyl |

-continued

| Example # | R² | R^L |
|---|---|---|
| B-1900 | 4-F-phenyl | 4-pyridyl-C(=O)- |
| B-1901 | 4-F-phenyl | PhCH₂-S(O)₂- |
| B-1902 | 4-F-phenyl | Et-S(O)₂- |
| B-1903 | 4-F-phenyl | Me-S(O)₂- |
| B-1904 | 4-F-phenyl | 2-F-phenyl-S(O)₂- |
| B-1905 | 4-F-phenyl | MeNH-C(=O)- |
| B-1906 | 4-F-phenyl | 2-F-phenyl-NH-C(=O)- |
| B-1907 | 4-F-phenyl | 2,6-dimethylphenyl-NH-C(=O)- |
| B-1908 | 4-F-phenyl | EtNH-C(=O)- |

-continued

| Example # | R² | R^L |
|---|---|---|
| B-1909 | 4-F-phenyl | 2,4-dimethoxyphenyl-NH-C(=O)- |

Examples B-1910 through B-1933 are prepared from Scaffold C-44

| Example # | R² | R^L |
|---|---|---|
| B-1910 | 4-F-phenyl | 2-I-phenyl-C(=O)- |
| B-1911 | 4-F-phenyl | 4-F-phenyl-C(=O)- |
| B-1912 | 4-F-phenyl | iPr-C(=O)- |
| B-1913 | 4-F-phenyl | allyl-O-C(=O)- |
| B-1914 | 4-F-phenyl | Me-C(=O)- |
| B-1915 | 4-F-phenyl | cyclopropyl-C(=O)- |

-continued

| Example # | R² | R^L |
|---|---|---|
| B-1916 | 4-F-phenyl | 3-bromobenzoyl |
| B-1917 | 4-F-phenyl | 4-iodobenzoyl |
| B-1918 | 4-F-phenyl | isoxazol-5-ylcarbonyl |
| B-1919 | 4-F-phenyl | methoxyacetyl |
| B-1920 | 4-F-phenyl | 2-methoxybenzoyl |
| B-1921 | 4-F-phenyl | (3-methoxyphenyl)acetyl (ketone) |
| B-1922 | 4-F-phenyl | 4-methylbenzoyl |
| B-1923 | 4-F-phenyl | 2-fluorobenzoyl |
| B-1924 | 4-F-phenyl | pyridin-4-ylcarbonyl |

-continued

| Example # | R² | R^L |
|---|---|---|
| B-1925 | 4-F-phenyl | benzylsulfonyl |
| B-1926 | 4-F-phenyl | ethylsulfonyl |
| B-1927 | 4-F-phenyl | methylsulfonyl |
| B-1928 | 4-F-phenyl | 2-fluorophenylsulfonyl |
| B-1929 | 4-F-phenyl | N-methylcarbamoyl-methyl |
| B-1930 | 4-F-phenyl | N-(2-fluorophenyl)carbamoyl-methyl |
| B-1931 | 4-F-phenyl | N-(2,6-dimethylphenyl)carbamoyl-methyl |
| B-1932 | 4-F-phenyl | N-ethylcarbamoyl-methyl |
| B-1933 | 4-F-phenyl | N-(2,4-dimethoxyphenyl)carbamoyl-methyl |

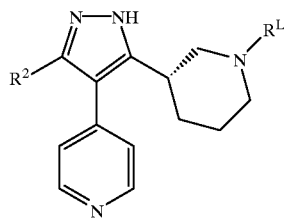
Examples B-1934 through B-1957 are prepared from Scaffold C-41

-continued

| Example # | R² | Rᴸ |
|---|---|---|
| B-1952 | 4-F-phenyl | 2-fluorophenylsulfonyl |
| B-1953 | 4-F-phenyl | N-methylcarbamoyl |
| B-1954 | 4-F-phenyl | N-(2-fluorophenyl)carbamoyl |
| B-1955 | 4-F-phenyl | N-(2,6-dimethylphenyl)carbamoyl |
| B-1956 | 4-F-phenyl | N-ethylcarbamoyl |
| B-1957 | 4-F-phenyl | N-(2,4-dimethoxyphenyl)carbamoyl |

| Example # | R² | Rᴸ |
|---|---|---|
| B-1958 | 4-F-phenyl | 2-iodobenzoyl |
| B-1959 | 4-F-phenyl | 4-fluorobenzoyl |
| B-1960 | 4-F-phenyl | isobutyryl |
| B-1961 | 4-F-phenyl | allyloxycarbonyl |
| B-1962 | 4-F-phenyl | acetyl |
| B-1963 | 4-F-phenyl | cyclopropanecarbonyl |
| B-1964 | 4-F-phenyl | 3-bromobenzoyl |
| B-1965 | 4-F-phenyl | 4-iodobenzoyl |
| B-1966 | 4-F-phenyl | isoxazole-5-carbonyl |
| B-1967 | 4-F-phenyl | methoxyacetyl |

Examples B-1958 through B-1981 are prepared from Scaffold C-43

-continued

| Example # | R² | R^L |
|---|---|---|
| B-1968 | 4-F-phenyl | 2-methoxybenzoyl |
| B-1969 | 4-F-phenyl | (3-methoxyphenyl)acetyl |
| B-1970 | 4-F-phenyl | 4-methylbenzoyl |
| B-1971 | 4-F-phenyl | 2-fluorobenzoyl |
| B-1972 | 4-F-phenyl | pyridin-4-ylcarbonyl |
| B-1973 | 4-F-phenyl | benzylsulfonyl |
| B-1974 | 4-F-phenyl | ethylsulfonyl |
| B-1975 | 4-F-phenyl | methylsulfonyl |
| B-1976 | 4-F-phenyl | (2-fluorophenyl)sulfonyl |
| B-1977 | 4-F-phenyl | N-methylcarbamoyl |

-continued

| Example # | R² | R^L |
|---|---|---|
| B-1978 | 4-F-phenyl | N-(2-fluorophenyl)carbamoyl |
| B-1979 | 4-F-phenyl | N-(2,6-dimethylphenyl)carbamoyl |
| B-1980 | 4-F-phenyl | N-ethylcarbamoyl |
| B-1981 | 4-F-phenyl | N-(2,4-dimethoxyphenyl)carbamoyl |

Examples B-1982 through B-2005 are prepared from Scaffold C-30

| Example # | R² | R^L |
|---|---|---|
| B-1982 | thien-3-yl | 2-iodobenzoyl |
| B-1983 | thien-3-yl | 4-fluorobenzoyl |

| Example # | R² | R^L |
|---|---|---|
| B-1984 | 3-thienyl | C(=O)CH(CH₃)₂ |
| B-1985 | 3-thienyl | CH₂C(=O)OCH₂CH=CH₂ |
| B-1986 | 3-thienyl | CH(CH₃)C(=O)CH₃ |
| B-1987 | 3-thienyl | C(=O)-cyclopropyl |
| B-1988 | 3-thienyl | C(=O)-(3-bromophenyl) |
| B-1989 | 3-thienyl | C(=O)-(4-iodophenyl) |
| B-1990 | 3-thienyl | C(=O)-(isoxazol-5-yl) |
| B-1991 | 3-thienyl | C(=O)CH₂OCH₃ |
| B-1992 | 3-thienyl | C(=O)-(2-methoxyphenyl) |
| B-1993 | 3-thienyl | C(=O)CH₂-(3-methoxyphenyl) |
| B-1994 | 3-thienyl | CH(CH₃)C(=O)-(4-methylphenyl) |
| B-1995 | 3-thienyl | CH(F)C(=O)-phenyl |
| B-1996 | 3-thienyl | CH(CH₃)C(=O)-(pyridin-4-yl) |
| B-1997 | 3-thienyl | S(=O)₂CH₂-phenyl |
| B-1998 | 3-thienyl | S(=O)₂CH₂CH₃ |
| B-1999 | 3-thienyl | CH(CH₃)S(=O)₂CH₃ |
| B-2000 | 3-thienyl | S(=O)₂-(2-fluorophenyl) |
| B-2001 | 3-thienyl | CH(CH₃)C(=O)NHCH₃ |
| B-2002 | 3-thienyl | CH(CH₃)C(=O)NH-(2-fluorophenyl) |

Examples B-2006 through B-2029 are prepared from Scaffold C-60

-continued
| Example # | R² | R^L |
|---|---|---|
| B-2018 | 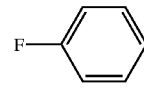 | 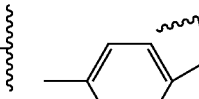 |
| B-2019 | 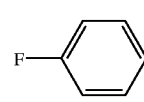 | 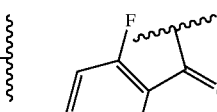 |
| B-2020 | 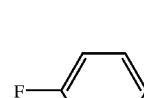 |  |
| B-2021 | 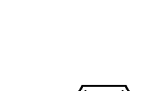 | 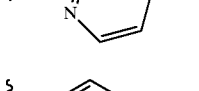 |
| B-2022 | 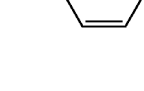 | 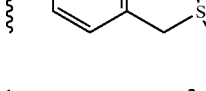 |
| B-2023 | 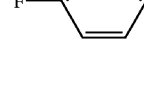 | 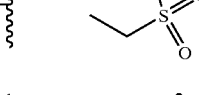 |
| B-2024 | 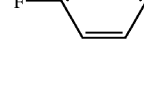 | 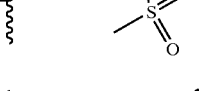 |
| B-2025 | 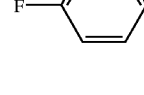 | 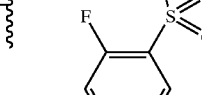 |
| B-2026 | 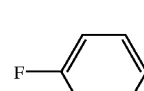 |  |
| B-2027 | 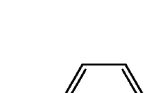 | 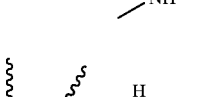 |
-continued
| Example # | R² | R^L |
|---|---|---|
| B-2028 | 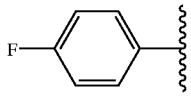 | 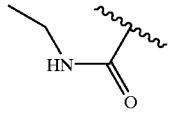 |
| B-2029 | 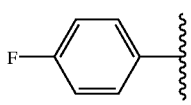 | 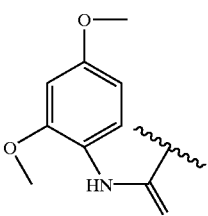 |
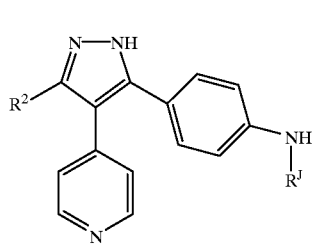
Examples B-2030 through B-2053 are prepared from Scaffold C-36
| Example # | R² | R^L |
|---|---|---|
| B-2030 | 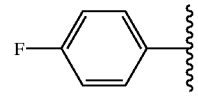 | 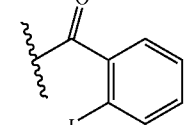 |
| B-2031 | 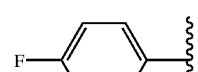 | 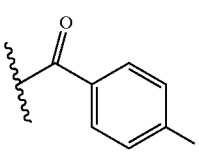 |
| B-2032 | 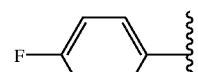 | 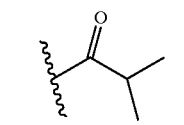 |
| B-2033 | 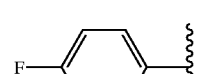 | 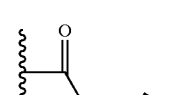 |
| B-2034 | 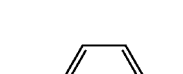 | 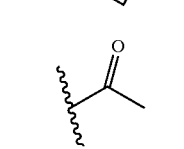 |

-continued

| Example # | R² | R^L |
|---|---|---|
| B-2035 | 4-F-C6H4 | cyclopropyl C(=O) |
| B-2036 | 4-F-C6H4 | 3-Br-C6H4-C(=O) |
| B-2037 | 4-F-C6H4 | 4-I-C6H4-C(=O) |
| B-2038 | 4-F-C6H4 | isoxazol-5-yl-C(=O) |
| B-2039 | 4-F-C6H4 | CH3OCH2C(=O) |
| B-2040 | 4-F-C6H4 | 2-MeO-C6H4-C(=O) |
| B-2041 | 4-F-C6H4 | 3-MeO-C6H4-CH2-C(=O) |
| B-2042 | 4-F-C6H4 | 4-Me-C6H4-C(=O) |
| B-2043 | 4-F-C6H4 | 2-F-C6H4-C(=O) |

-continued

| Example # | R² | R^L |
|---|---|---|
| B-2044 | 4-F-C6H4 | pyridin-4-yl-C(=O) |
| B-2045 | 4-F-C6H4 | PhCH2SO2 |
| B-2046 | 4-F-C6H4 | EtSO2 |
| B-2047 | 4-F-C6H4 | MeSO2 |
| B-2048 | 4-F-C6H4 | 2-F-C6H4-SO2 |
| B-2049 | 4-F-C6H4 | MeNHC(=O) |
| B-2050 | 4-F-C6H4 | 2-F-C6H4-NHC(=O) |
| B-2051 | 4-F-C6H4 | 2,6-diMe-C6H3-NHC(=O) |
| B-2052 | 4-F-C6H4 | EtNHC(=O) |

| Example # | R² | R^L |
|---|---|---|
| B-2053 | 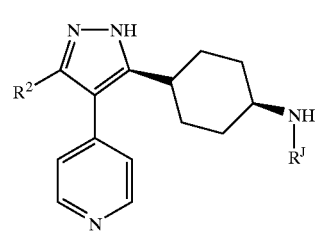 | |
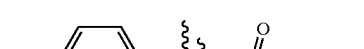
Examples B-2054 through B-2077 are prepared from Scaffold C-34
| Example# | R² | R^J |
|---|---|---|
| B-2054 | 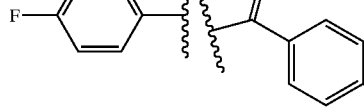 | |
| B-2055 | | |
| B-2056 | 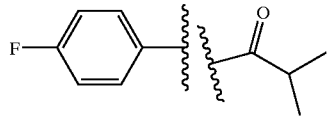 | |
| B-2057 | 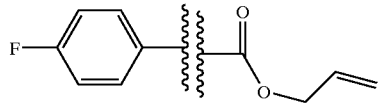 | |
| B-2058 | 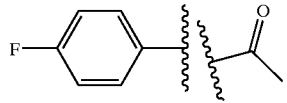 | |
| B-2059 | 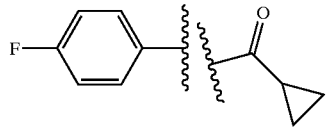 | |
| Example# | R² | R^J |
|---|---|---|
| B-2060 | 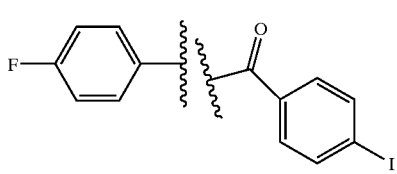 | |
| B-2061 | 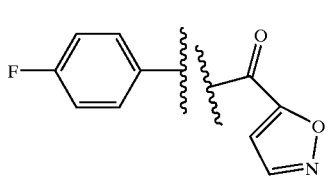 | |
| B-2062 | 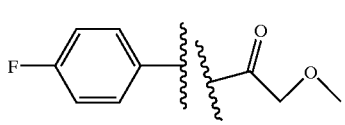 | |
| B-2063 | | |
| B-2064 | 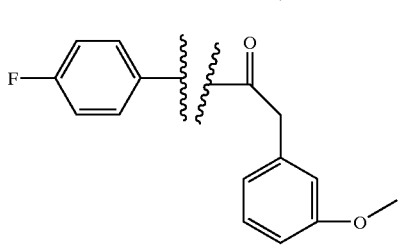 | |
| B-2065 | | |
| B-2066 | 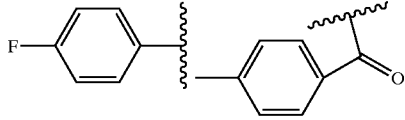 | |
| B-2067 | 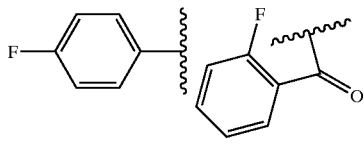 | |
| B-2068 | 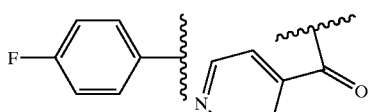 | |

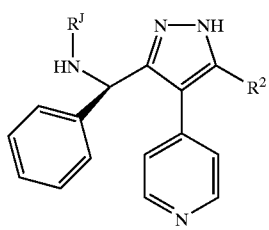

Examples B-2078 through B-2101 are prepared from Scaffold C-57

| Example# | R² | R^J |
|---|---|---|
| B-2069 | 4-F-C₆H₄ | benzyl methylsulfonyl group |
| B-2070 | 4-F-C₆H₄ | methylsulfonyl |
| B-2071 | 4-F-C₆H₄ | methylsulfonyl |
| B-2072 | 4-F-C₆H₄ | 2-fluorophenylsulfonyl |
| B-2073 | 4-F-C₆H₄ | N-methylcarboxamide |
| B-2074 | 4-F-C₆H₄ | N-(2-fluorophenyl)carboxamide |
| B-2075 | 4-F-C₆H₄ | N-(2,6-dimethylphenyl)carboxamide |
| B-2076 | 4-F-C₆H₄ | 2-aminoethylcarbonyl |
| B-2077 | 4-F-C₆H₄ | N-(2,4-dimethoxyphenyl)carboxamide |
| B-2078 | H | 2-iodobenzoyl |
| B-2079 | H | 4-fluorobenzoyl |
| B-2080 | H | isobutyryl |
| B-2081 | H | allyloxycarbonyl |
| B-2082 | H | acetyl |
| B-2083 | H | cyclopropylcarbonyl |
| B-2084 | H | 3-bromobenzoyl |
| B-2085 | H | 4-iodobenzoyl |

-continued
| Example# | R² | RJ |
|---|---|---|
| B-2086 | H | 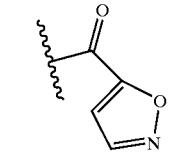 |
| B-2087 | H | 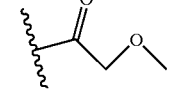 |
| B-2088 | H | 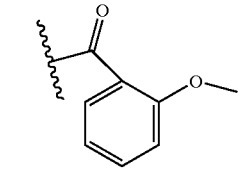 |
| B-2089 | H | 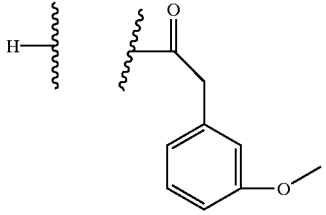 |
| B-2090 | H | 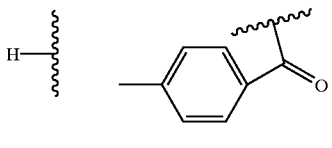 |
| B-2091 | H | 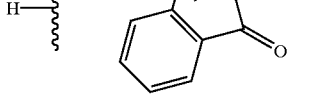 |
| B-2092 | H | 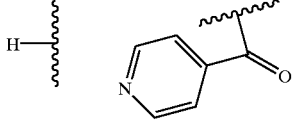 |
| B-2093 | H | 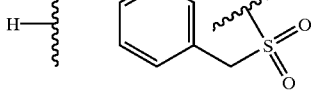 |
| B-2094 | H | 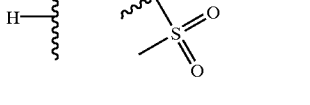 |
| B-2095 | H | 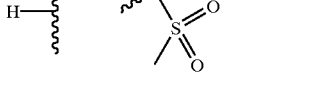 |
-continued
| Example# | R² | RJ |
|---|---|---|
| B-2096 | H | 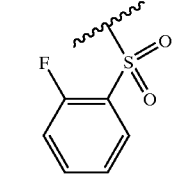 |
| B-2097 | H | 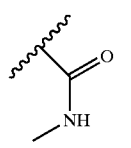 |
| B-2098 | H | 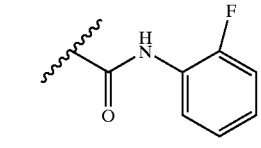 |
| B-2099 | H | 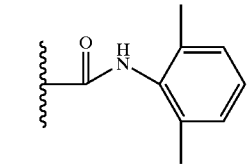 |
| B-2100 | H | 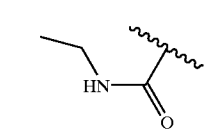 |
| B-2101 | H | 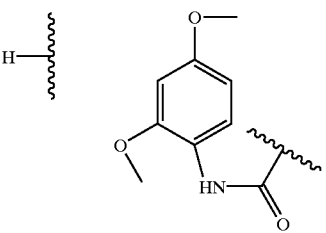 |
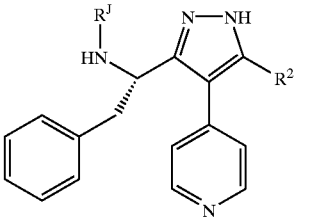
Examples B-2102 through B-2125 are prepared from Scaffold C-52

| Example# | R² | R^J |
|---|---|---|
| B-2102 | H– | –C(=O)-(2-I-C₆H₄) |
| B-2103 | H– | –C(=O)-(4-F-C₆H₄) |
| B-2104 | H– | –C(=O)-CH(CH₃)₂ |
| B-2105 | H– | –C(=O)-O-CH₂-CH=CH₂ |
| B-2106 | H– | –C(=O)-CH₃ |
| B-2107 | H– | –C(=O)-cyclopropyl |
| B-2108 | H– | –C(=O)-(3-Br-C₆H₄) |
| B-2109 | H– | –C(=O)-(4-I-C₆H₄) |
| B-2110 | H– | –C(=O)-(isoxazol-5-yl) |
| B-2111 | H– | –C(=O)-CH₂-O-CH₃ |

-continued

| Example# | R² | R^J |
|---|---|---|
| B-2112 | H– | –C(=O)-(2-OMe-C₆H₄) |
| B-2113 | H– | –C(=O)-CH₂-(3-OMe-C₆H₄) |
| B-2114 | H– | –C(=O)-(4-Me-C₆H₄) |
| B-2115 | H– | –C(=O)-(2-F-C₆H₄) |
| B-2116 | H– | –C(=O)-(pyridin-4-yl) |
| B-2117 | H– | –S(=O)₂-CH₂-C₆H₅ |
| B-2118 | H– | –S(=O)₂-CH₃ |
| B-2119 | H– | –S(=O)₂-CH₃ |
| B-2120 | H– | –S(=O)₂-(2-F-C₆H₄) |

Examples B-2126 through B-2149 are prepared from Scaffold C-56
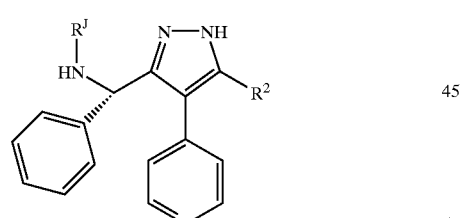

-continued

| Example# | R² | R^J |
|---|---|---|
| B-2137 | H— | (3-methoxyphenyl)acetyl ketone group |
| B-2138 | H— | (4-methylphenyl) ketone group |
| B-2139 | H— | (2-fluorophenyl) ketone group |
| B-2130 | H— | (pyridin-4-yl) ketone group |
| B-2141 | H— | benzylsulfonyl group |
| B-2142 | H— | methylsulfonyl group |
| B-2143 | H— | methylsulfonyl group |
| B-2144 | H— | (2-fluorophenyl)sulfonyl group |
| B-2145 | H— | N-methylcarbamoyl group |
| B-2146 | H— | N-(2-fluorophenyl)carbamoyl group |

-continued

| Example# | R² | R^J |
|---|---|---|
| B-2147 | H— | N-(2,6-dimethylphenyl)carbamoyl group |
| B-2148 | H— | N-ethylcarbamoyl group |
| B-2149 | H— | N-(2,4-dimethoxyphenyl)carbamoyl group |

Examples B-2150 through B-2173 are prepared from Scaffold C-32

| Example# | R² | R^J |
|---|---|---|
| B-2150 | 4-F-C₆H₄ | (2-iodophenyl) ketone group |
| B-2151 | 4-F-C₆H₄ | (4-fluorophenyl) ketone group |
| B-2152 | 4-F-C₆H₄ | isopropyl ketone group |
| B-2153 | 4-F-C₆H₄ | allyloxycarbonyl group |

| Example# | R² | Rᴊ |
|---|---|---|
| B-2154 | 4-F-phenyl | -C(O)CH₃ |
| B-2155 | 4-F-phenyl | -C(O)-cyclopropyl |
| B-2156 | 4-F-phenyl | -C(O)-(3-Br-phenyl) |
| B-2157 | 4-F-phenyl | -C(O)-(4-I-phenyl) |
| B-2158 | 4-F-phenyl | -C(O)-(isoxazol-5-yl) |
| B-2159 | 4-F-phenyl | -C(O)CH₂OCH₃ |
| B-2160 | 4-F-phenyl | -C(O)-(2-methoxyphenyl) |
| B-2161 | 4-F-phenyl | -C(O)CH₂-(3-methoxyphenyl) |
| B-2162 | 4-F-phenyl | -(4-C(O)-phenyl) |
| B-2163 | 4-F-phenyl | -C(O)-(2-F-phenyl) |
| B-2164 | 4-F-phenyl | -C(O)-(pyridin-4-yl) |
| B-2165 | 4-F-phenyl | -CH₂-phenyl-SO₂- |
| B-2166 | 4-F-phenyl | -SO₂CH₃ |
| B-2167 | 4-F-phenyl | -S(O)CH₃ |
| B-2168 | 4-F-phenyl | -SO₂-(2-F-phenyl) |
| B-2169 | 4-F-phenyl | -C(O)NHCH₃ |
| B-2170 | 4-F-phenyl | -C(O)NH-(2-F-phenyl) |
| B-2171 | 4-F-phenyl | -C(O)NH-(2,6-dimethylphenyl) |
| B-2172 | 4-F-phenyl | -CH₂NHC(O)- |

-continued

| Example# | R² | Rᴶ |
|---|---|---|
| B-2173 | 4-F-phenyl | 2,4-dimethoxy-phenyl-NHC(O)CH(-)- |

(structure with pyrazole, maleimide, and propylamine linker shown)

Examples 2174 through B-2197 are prepared from Scaffold C-64

| Example# | R² | Rᴶ |
|---|---|---|
| B-2174 | 4-F-phenyl | 2-iodobenzoyl |
| B-2175 | 4-F-phenyl | 4-fluorobenzoyl |
| B-2176 | 4-F-phenyl | isobutyryl |
| B-2177 | 4-F-phenyl | allyloxycarbonyl |
| B-2178 | 4-F-phenyl | acetyl |
| B-2179 | 4-F-phenyl | cyclopropanecarbonyl |

-continued

| Example# | R² | Rᴶ |
|---|---|---|
| B-2180 | 4-F-phenyl | 3-bromobenzoyl |
| B-2181 | 4-F-phenyl | 4-iodobenzoyl |
| B-2182 | 4-F-phenyl | isoxazole-5-carbonyl |
| B-2183 | 4-F-phenyl | methoxyacetyl |
| B-2184 | 4-F-phenyl | 2-methoxybenzoyl |
| B-2185 | 4-F-phenyl | (3-methoxyphenyl)acetyl |
| B-2186 | 4-F-phenyl | 4-methylbenzoyl |
| B-2187 | 4-F-phenyl | 2-fluorobenzoyl |
| B-2188 | 4-F-phenyl | pyridine-4-carbonyl |

| Example# | R² | Rᴊ |
|---|---|---|
| B-2189 | 4-F-phenyl | benzyl-SO₂- |
| B-2190 | 4-F-phenyl | -S(O)₂CH₃ |
| B-2191 | 4-F-phenyl | -S(O)₂CH₃ |
| B-2192 | 4-F-phenyl | 2-F-phenyl-SO₂- |
| B-2193 | 4-F-phenyl | -C(O)NHCH₃ |
| B-2194 | 4-F-phenyl | -C(O)NH(2-F-phenyl) |
| B-2195 | 4-F-phenyl | -C(O)NH(2,6-diMe-phenyl) |
| B-2196 | 4-F-phenyl | -CH₂NHC(O)- |
| B-2197 | 4-F-phenyl | 2,4-diMeO-phenyl-NHC(O)- |

Examples B-2198 through B-2221 are prepared from Scaffold C-22

| Example# | R² | Rᴊ |
|---|---|---|
| B-2198 | 4-F-phenyl | -C(O)(2-I-phenyl) |
| B-2199 | 4-F-phenyl | -C(O)(4-F-phenyl) |
| B-2200 | 4-F-phenyl | -C(O)CH(CH₃)₂ |
| B-2201 | 4-F-phenyl | -C(O)O-allyl |
| B-2202 | 4-F-phenyl | -C(O)CH₃ |
| B-2203 | 4-F-phenyl | -C(O)-cyclopropyl |
| B-2204 | 4-F-phenyl | -C(O)(3-Br-phenyl) |
| B-2205 | 4-F-phenyl | -C(O)(4-I-phenyl) |

-continued

| Example# | R² | Rᴶ |
|---|---|---|
| B-2206 | 4-F-phenyl | 5-isoxazolyl-C(O)- |
| B-2207 | 4-F-phenyl | -C(O)CH₂OCH₃ |
| B-2208 | 4-F-phenyl | 2-methoxyphenyl-C(O)- |
| B-2209 | 4-F-phenyl | -C(O)CH₂-(3-methoxyphenyl) |
| B-2210 | 4-F-phenyl | 4-(C(O)-)phenyl- |
| B-2211 | 4-F-phenyl | 2-F-phenyl-C(O)- |
| B-2212 | 4-F-phenyl | 4-pyridyl-C(O)- |
| B-2213 | 4-F-phenyl | phenyl-CH₂-SO₂- |
| B-2214 | 4-F-phenyl | -CH₂-SO₂-CH₃ |
| B-2215 | 4-F-phenyl | -SO₂-CH₃ |

-continued

| Example# | R² | Rᴶ |
|---|---|---|
| B-2216 | 4-F-phenyl | 2-F-phenyl-SO₂- |
| B-2217 | 4-F-phenyl | -C(O)NHCH₃ |
| B-2218 | 4-F-phenyl | -C(O)NH-(2-F-phenyl) |
| B-2219 | 4-F-phenyl | -C(O)NH-(2,6-dimethylphenyl) |
| B-2220 | 4-F-phenyl | -CH₂NHC(O)- |
| B-2221 | 4-F-phenyl | 2,4-dimethoxyphenyl-NHC(O)- |

Examples B-2222 through B-2245 are prepared from Scaffold C-29

| Example# | R² | Rᴶ |
|---|---|---|
| B-2222 | 3-thienyl | C(=O)-(2-iodophenyl) |
| B-2223 | 3-thienyl | C(=O)-(4-fluorophenyl) |
| B-2224 | 3-thienyl | C(=O)-CH(CH₃)₂ |
| B-2225 | 3-thienyl | C(=O)-O-CH₂-CH=CH₂ |
| B-2226 | 3-thienyl | C(=O)-CH₃ |
| B-2227 | 3-thienyl | C(=O)-cyclopropyl |
| B-2228 | 3-thienyl | C(=O)-(3-bromophenyl) |
| B-2229 | 3-thienyl | C(=O)-(4-iodophenyl) |
| B-2230 | 3-thienyl | C(=O)-(isoxazol-5-yl) |
| B-2231 | 3-thienyl | C(=O)-CH₂-O-CH₃ |

-continued

| Example# | R² | Rᴶ |
|---|---|---|
| B-2232 | 3-thienyl | C(=O)-(2-methoxyphenyl) |
| B-2233 | 3-thienyl | C(=O)-CH₂-(3-methoxyphenyl) |
| B-2234 | 3-thienyl | C(=O)-(4-methylphenyl) |
| B-2235 | 3-thienyl | C(=O)-(2-fluorophenyl) |
| B-2236 | 3-thienyl | C(=O)-(pyridin-4-yl) |
| B-2237 | 3-thienyl | S(=O)₂-CH₂-phenyl |
| B-2238 | 3-thienyl | S(=O)₂-CH₃ |
| B-2239 | 3-thienyl | S(=O)₂-CH₃ |
| B-2240 | 3-thienyl | S(=O)₂-(2-fluorophenyl) |

-continued

| Example# | R² | R^J |
|---|---|---|
| B-2241 | thiophen-3-yl | -C(O)NHCH₃ |
| B-2242 | thiophen-3-yl | -C(O)NH-(2-fluorophenyl) |
| B-2243 | thiophen-3-yl | -C(O)NH-(2,6-dimethylphenyl) |
| B-2244 | thiophen-3-yl | -CH₂CH₂NHC(O)- |
| B-2245 | thiophen-3-yl | -C(O)NH-(2,4-dimethoxyphenyl) |

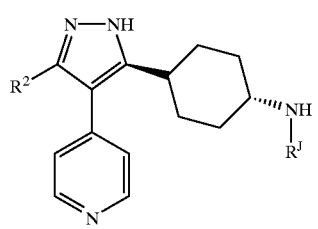

Examples B-2246 through B-2269 are prepared from Scaffold C-35

| Example# | R² | R^J |
|---|---|---|
| B-2246 | 4-fluorophenyl | -C(O)-(2-iodophenyl) |

-continued

| Example# | R² | R^J |
|---|---|---|
| B-2247 | 4-fluorophenyl | -C(O)-(4-fluorophenyl) |
| B-2248 | 4-fluorophenyl | -C(O)CH(CH₃)₂ |
| B-2249 | 4-fluorophenyl | -C(O)O-allyl |
| B-2250 | 4-fluorophenyl | -C(O)CH₃ |
| B-2251 | 4-fluorophenyl | -C(O)-cyclopropyl |
| B-2252 | 4-fluorophenyl | -C(O)-(3-bromophenyl) |
| B-2253 | 4-fluorophenyl | -C(O)-(4-iodophenyl) |
| B-2254 | 4-fluorophenyl | -C(O)-(isoxazol-5-yl) |
| B-2255 | 4-fluorophenyl | -C(O)CH₂OCH₃ |
| B-2256 | 4-fluorophenyl | -C(O)-(2-methoxyphenyl) |

EXAMPLES B-2270 THROUGH B-2317

In a parallel array reaction block containing 48 fritted vessels, each reaction vessel was charged with 250 mg of polymer bound carbodiimide B48 (1.0 mmol/g resin) and a solution of the acid-containing scaffold C-49 in dimethylformamide (0.1 M, 500 uL). To each slurry was added a solution of pyridine in dichloromethane (0.2 M, 1000 uL) followed by a solution of a unique amine B47 (0.2 M, 375 uL) in dimethylformamide. The reaction mixtures were agitated on a Labline benchtop orbital shaker at 250 RPM for 16–20 h at ambient temperature. The reaction mixtures were filtered into conical vials and the polymer was washed with 1.5 mL of dimethylformamide and 2.0 mL of dichloromethane. The filtrates were evaporated to dryness in a Savant apparatus and dimethylformamide (350 uL) was added to each conical vial to dissolve the residue. A solution of tetrafluorophthalic anhydride (1.0 M, 150 uL) in dimethylformamide was added to the reconstituted conical vials and the mixture incubated for 2 hours at ambient temperature. Polyamine polymer B33 (4.0 meq N/g resin, 250 mg) and 1.0 mL dichloromethane was then added to the reaction mixture in each conical vial. After agitating the reaction mixtures for 16 h at 250 RPM on an orbital shaker at ambient temperature, the mixtures were filtered through a polypropylene syringe tube fitted with a porous frit. The polymers were washed twice with dimethylformamide (1.0 mL each) and the filtrates and washings collected in conical vials. The filtrates were evaporated to dryness and weighed to afford the desired amide products B-2270 through B-2317 as oils or solids. The analytical data and yields for the products prepared in this manner are listed below.

| | R² | [NRBRC amide] | Yield | Calcd. Mass Spec. | Observed Mass Spec M + H |
|---|---|---|---|---|---|
| B-2270 | 4-F-phenyl | -C(O)NH-propyl | 12 | 352 | 353 |
| B-2271 | 4-F-phenyl | -C(O)NH-CH₂CH₂-(4-F-phenyl) | 39 | 432 | 433 |
| B-2272 | 4-F-phenyl | -C(O)NH-CH₂-phenyl | 26 | 400 | — |
| B-2273 | 4-F-phenyl | -C(O)NH-CH₂CH₂CH₂-O-ethyl | 14 | 396 | 397 |
| B-2274 | 4-F-phenyl | -C(O)NH-CH₂-(2-Cl-phenyl) | 30 | 434 | 435 |
| B-2275 | 4-F-phenyl | -C(O)NH-CH₂-(4-NMe₂-phenyl) | 43 | 443 | — |
| B-2276 | 4-F-phenyl | -C(O)NH-CH₂-cyclopropyl | 35 | 364 | 365 |

-continued

| R² | [N(R^B)(R^C)C(O)- group] | Yield | Calcd. Mass Spec. | Observed Mass Spec M + H |
|---|---|---|---|---|
| B-2277 | 4-F-phenyl | -C(O)NH-CH₂-CH(phenyl)₂ | 33 | 490 | — |
| B-2278 | 4-F-phenyl | -C(O)NH-CH₂-(2,4-dimethoxyphenyl) | 53 | 460 | 461 |
| B-2279 | 4-F-phenyl | -C(O)NH-CH₂CH₂-(2-thienyl) | 10 | 420 | — |
| B-2280 | 4-F-phenyl | -C(O)NH-CH₂CH₂CH₂-(2-oxopyrrolidin-1-yl) | 7 | 435 | 436 |
| B-2281 | 4-F-phenyl | -C(O)NH-CH₂-(2-pyridyl) | 18 | 401 | 402 |
| B-2282 | 4-F-phenyl | -C(O)NH-CH₂-(2-furyl) | 22 | 390 | 413[a] [a]M + Na |

-continued

| | R² | [amide group] | Yield | Calcd. Mass Spec. | Observed Mass Spec M + H |
|---|---|---|---|---|---|
| B-2283 | 4-F-phenyl | –C(O)NH-CH₂-(tetrahydrofuran-2-yl) | 10 | 394 | 417[a]<br>[a]M + Na |
| B-2284 | 4-F-phenyl | –C(O)NH-CH₂CH₂-morpholine | 7 | 423 | — |
| B-2285 | 4-F-phenyl | –C(O)NH-CH₂-(naphth-1-yl) | 23 | 450 | — |
| B-2286 | 4-F-phenyl | –C(O)NH-CH₂CH₂-(4-phenoxyphenyl) | 4 | 506 | — |
| B-2287 | 4-F-phenyl | –C(O)NH-(CH₂)₆-N(CH₃)₂ | 5 | 437 | 438 |
| B-2288 | 4-F-phenyl | –C(O)NH-(CH₂)₃-pyrrolidin-1-yl | 8 | 435 | 436 |
| B-2289 | 4-F-phenyl | –C(O)NH-(CH₂)₃-(4-methylpiperazin-1-yl) | 4 | 450 | 451 |

-continued
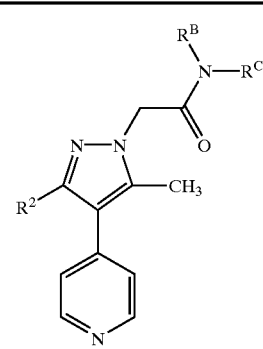
| R² | 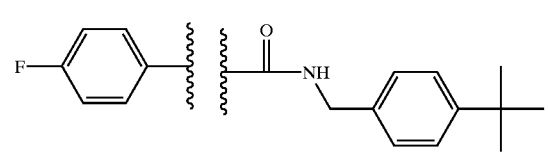 | Yield | Calcd. Mass Spec. | Observed Mass Spec M + H |
|---|---|---|---|---|
| B-2290 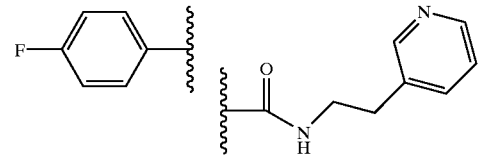 | | 9 | 456 | 457 |
| B-2291 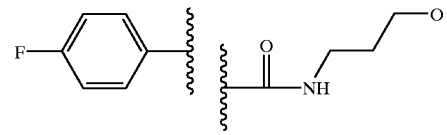 | | 9 | 415 | 416 |
| B-2292 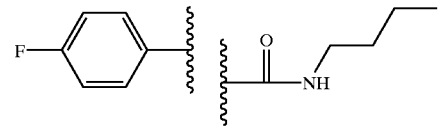 | | 5 | 368 | 369 |
| B-2293 | | 5 | 366 | 367 |
| B-2294 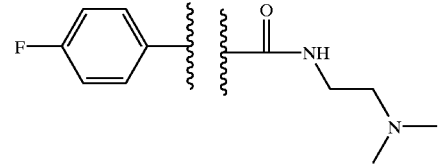 | | 5 | 381 | 382 |
| B-2295 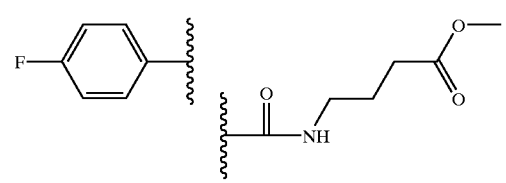 | | 16 | 410 | 411 |

-continued

| | R² | [amide group] | Yield | Calcd. Mass Spec. | Observed Mass Spec M + H |
|---|---|---|---|---|---|
| B-2296 | 4-F-phenyl | amide-CH₂CH₂-(5-methoxyindol-3-yl) | 4 | 483 | — |
| B-2297 | 4-F-phenyl | amide-CH₂-(3,4,5-trimethoxyphenyl) | 7 | 490 | — |
| B-2298 | 4-F-phenyl | amide-CH₂CH₂-C(O)-CH₂-(4-methoxynaphth-2-yl) | 4 | 537 | — |
| B-2299 | 4-F-phenyl | amide-CH₂CH₂-NH-SO₂-(4-methylphenyl) | 4 | 507 | 508 |
| B-2300 | 4-F-phenyl | amide-NH-(CH₂)₃-phenyl | 7 | 442 | — |

-continued
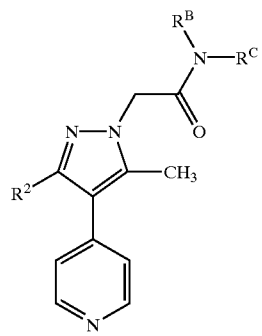
| | R² | ⸺N(R^B)(R^C) linker | Yield | Calcd. Mass Spec. | Observed Mass Spec M + H |
|---|---|---|---|---|---|
| B-2301 | 4-F-C₆H₄ | ⸺C(O)NH-CH₂CH₂-C(O)OCH₃ | 20 | 396 | 397 |
| B-2302 | 4-F-C₆H₄ | ⸺C(O)NH-CH₂CH₂-(4-NO₂-C₆H₄) | 30 | 459 | — |
| B-2303 | 4-F-C₆H₄ | ⸺C(O)NH-CH₂CH₂-(3,4-diCl-C₆H₃) | 6 | 482 | |
| B-2304 | 4-F-C₆H₄ | ⸺C(O)NH-CH₂CH₂CH₂-N(CH₃)₂ | 5 | 395 | 396 |
| B-2305 | 4-F-C₆H₄ | ⸺C(O)NH-CH₂-(3,5-diOMe-C₆H₃) | 10 | 460 | — |

-continued
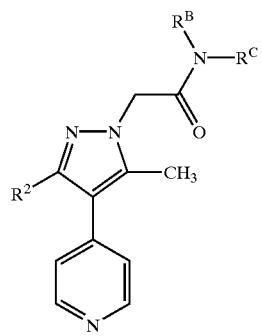
| | R² | ~N(R^B)(R^C) acyl group | Yield | Calcd. Mass Spec. | Observed Mass Spec M + H |
|---|---|---|---|---|---|
| B-2306 | 4-F-C₆H₄ | -C(O)NH-CH₂CH₂CH₂-S-cyclohexyl | 11 | 466 | 467 |
| B-2307 | 4-F-C₆H₄ | -C(O)NH-CH₂CH₂CH₂-pyrrolidinyl | 5 | 421 | 422 |
| B-2308 | 4-F-C₆H₄ | -C(O)NH-CH₂CH₂-(benzothiophen-3-yl) | 26 | 470 | — |
| B-2309 | 4-F-C₆H₄ | -C(O)NH-CH₂-C(O)O-C(CH₃)₃ | 24 | 424 | 425 |
| B-2310 | 4-F-C₆H₄ | -C(O)NH-CH₂-C≡CH | 9 | 348 | — |
| B-2311 | 4-F-C₆H₄ | -C(O)NH-Et | 21 | 338 | 339 |
| B-2312 | 4-F-C₆H₄ | -C(O)NH-CH₂CH₂-S-Et | 28 | 398 | 399 |

-continued

| R² | [RB/RC amide group] | Yield | Calcd. Mass Spec. | Observed Mass Spec M + H |
|---|---|---|---|---|
| B-2313 | 4-F-phenyl | —C(O)NH-CH₂CH₂CH₂-O-CH(CH₃)₂ | 6 | 410 | — |
| B-2314 | 4-F-phenyl | —C(O)NH-CH₂CH₂-CN | 15 | 363 | 364 |
| B-2315 | 4-F-phenyl | —C(O)NH-CH₂CH₂-(2-methoxyphenyl) | 11 | 444 | — |
| B-2316 | 4-F-phenyl | —C(O)NH-CH₂CH₂-(cyclohexenyl) | 11 | 418 | — |
| B-2317 | 4-F-phenyl | —C(O)NH-CH₂-C(O)-phenyl | 36 | 428 | — |

By analogy to the procedure identified above for the preparation of Examples B-2270 through B-2317, the following examples B-2318 through B-2461 were prepared.
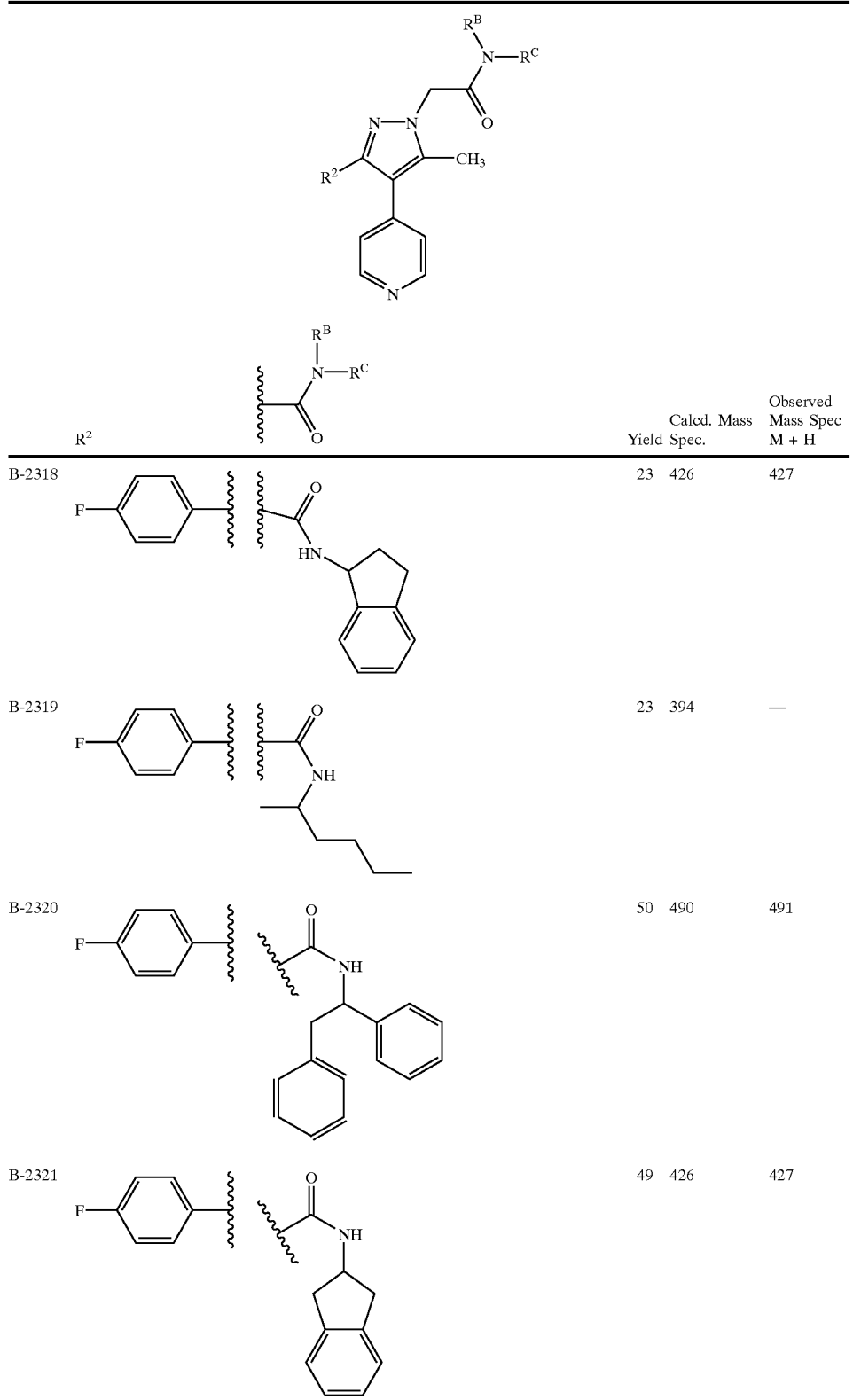

-continued

| | R² | ⟶N(R^B)(R^C)C(=O)– | Yield | Calcd. Mass Spec. | Observed Mass Spec M + H |
|---|---|---|---|---|---|
| B-2322 | 4-F-phenyl | NHCH(CH₃)CH₂CH₃ amide | 40 | 366 | 367 |
| B-2323 | 4-F-phenyl | NH-(2-oxotetrahydrothiophen-3-yl) amide | 68 | 410 | 411 |
| B-2324 | 4-F-phenyl | NH-CH(CO₂Me)CH₂CH₂SMe amide | 57 | 456 | 457 |
| B-2325 | 4-F-phenyl | NH-CH(CH₃)CH₂OMe amide | 41 | 382 | 383 |
| B-2326 | 4-F-phenyl | NH-(1,2,3,4-tetrahydronaphthalen-1-yl) amide | 71 | 440 | 441 |

-continued
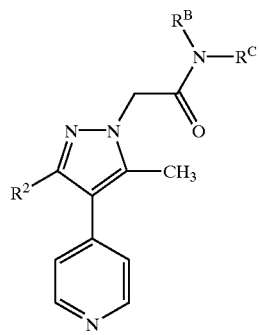
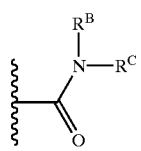
| R² | | Yield | Calcd. Mass Spec. | Observed Mass Spec M + H |
|---|---|---|---|---|
| B-2327 | 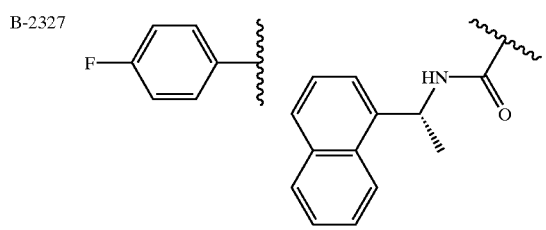 | 36 | 464 | 465 |
| B-2328 | 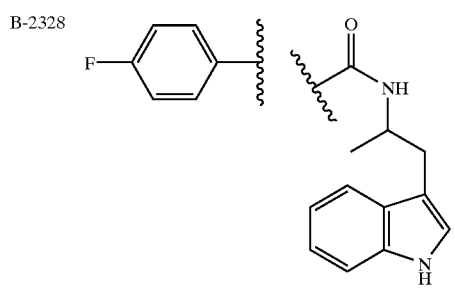 | 32 | 467 | 468 |
| B-2329 | 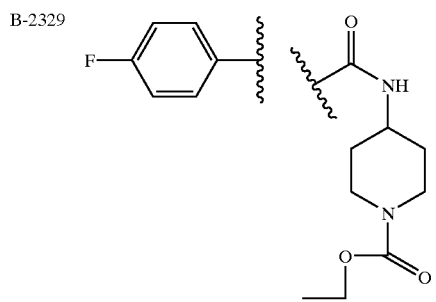 | 34 | 465 | 466 |
| B-2330 | 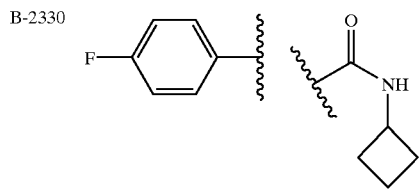 | 26 | 364 | 365 |

-continued
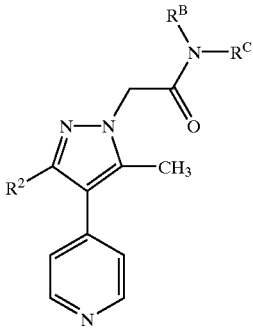
| | | | Yield | Calcd. Mass Spec. | Observed Mass Spec M + H |
|---|---|---|---|---|---|
| B-2331 | 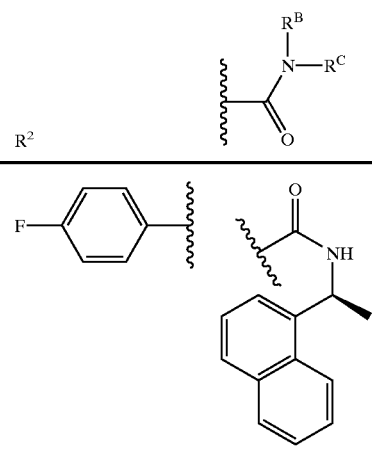 | | 38 | 464 | 465 |
| B-2332 | 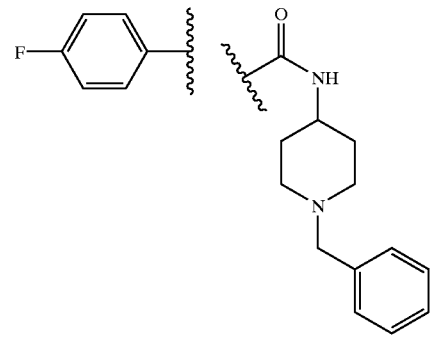 | | 33 | 483 | 484 |
| B-2333 | 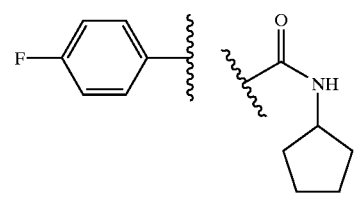 | | 36 | 378 | 379 |
| B-2334 | 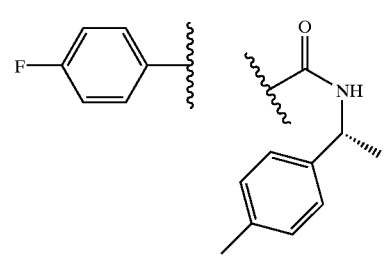 | | 44 | 428 | 429 |

-continued
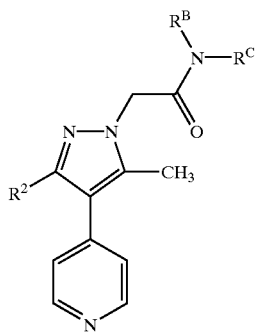
| R² | 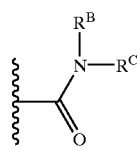 | Yield | Calcd. Mass Spec. | Observed Mass Spec M + H |
|---|---|---|---|---|
| B-2335 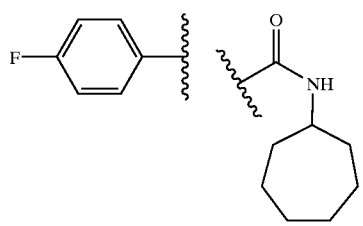 | | 27 | 406 | 407 |
| B-2336 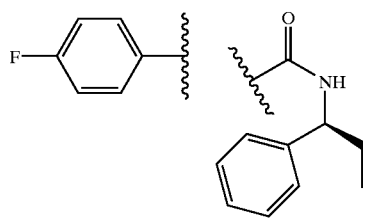 | | 41 | 428 | 429 |
| B-2337 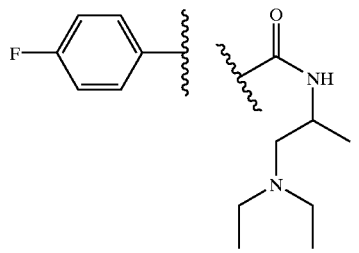 | | 27 | 423 | 424 |
| B-2338 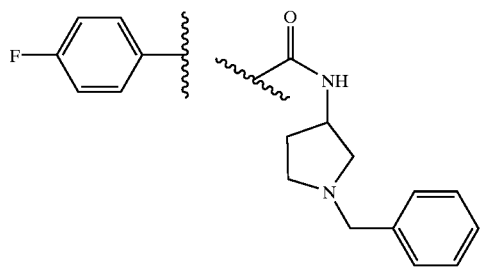 | | 33 | 469 | 470 |

-continued
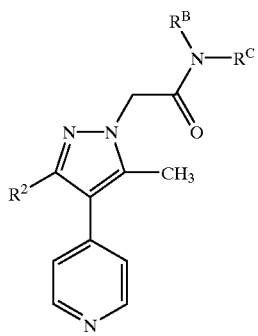
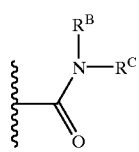
| R² | ⸺N(R^B)(R^C)C(=O)⸺ | Yield | Calcd. Mass Spec. | Observed Mass Spec M + H |
|---|---|---|---|---|
| B-2339 4-F-C₆H₄ | methyl 2-(benzylthiomethyl) ester amide | 52 | 518 | 519 |
| B-2340 4-F-C₆H₄ | 4-phenylbutan-2-yl amide | 64 | 442 | 443 |
| B-2341 4-F-C₆H₄ | cyclopropyl amide | 41 | 350 | 351 |
| B-2342 4-F-C₆H₄ | (S)-1-phenylethyl amide | 34 | 414 | 415 |

-continued
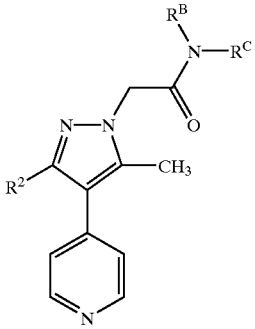
| | R² | 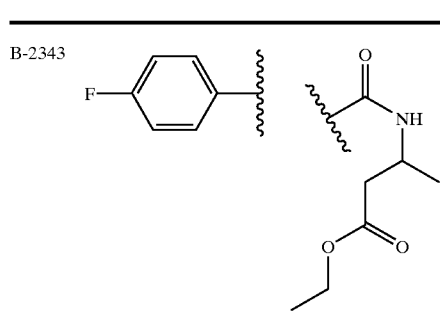 | Yield | Calcd. Mass Spec. | Observed Mass Spec M + H |
|---|---|---|---|---|---|
| B-2343 | 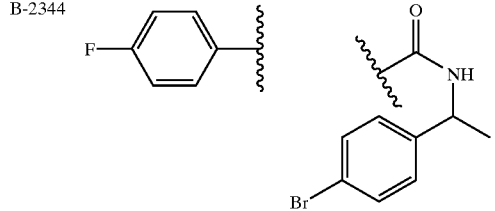 | | 29 | 424 | 425 |
| B-2344 | | | 33 | 492 | 493 |
| B-2345 | | | 30 | 420 | 421 |
| B-2346 | | 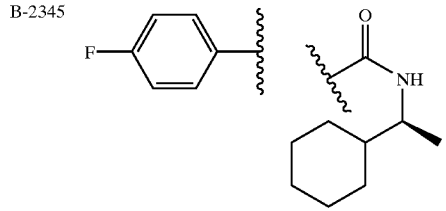 | 35 | 474 | 475 |
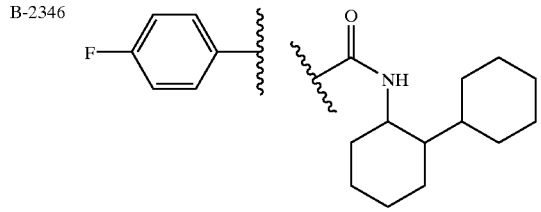

-continued

| | R² | ~N(RB)-C(=O)-~ | Yield | Calcd. Mass Spec. | Observed Mass Spec M + H |
|---|---|---|---|---|---|
| B-2347 | 4-F-phenyl | cyclohexyl-NH-C(=O)- | 34 | 392 | 393 |
| B-2348 | 4-F-phenyl | thiochroman-4-yl-NH-C(=O)- | 51 | 458 | 459 |
| B-2349 | 4-F-phenyl | (4-NO₂-benzyl, methyl ester)-NH-C(=O)- | 73 | 517 | 518 |
| B-2350 | 4-F-phenyl | (4-tert-butylcyclohexyl)-NH-C(=O)- | 22 | 448 | 449 |

-continued
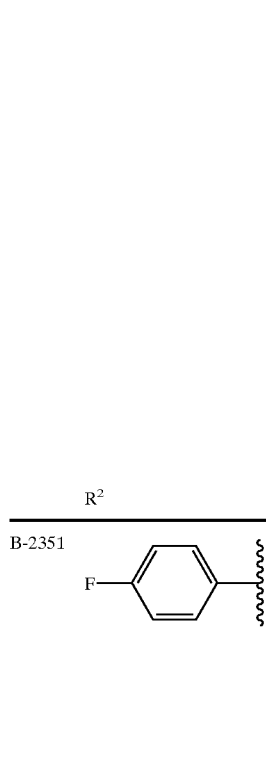
| | R² | 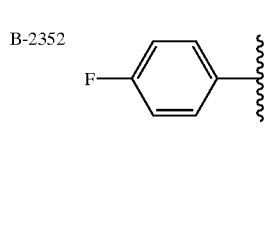 | Yield | Calcd. Mass Spec. | Observed Mass Spec M + H |
|---|---|---|---|---|---|
| B-2351 | 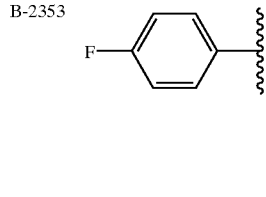 | 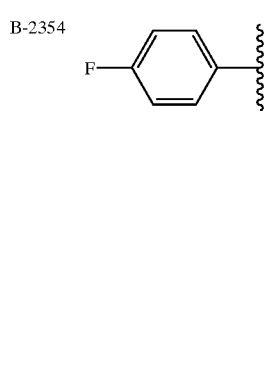 | 64 | 486 | 487 |
| B-2352 | | | 41 | 482 | 483 |
| B-2353 | | | 57 | 438 | 439 |
| B-2354 | | | 63 | 484 | 485 |

-continued

| | R² | ⟶N(R^B)(R^C)C(=O)- | Yield | Calcd. Mass Spec. | Observed Mass Spec M + H |
|---|---|---|---|---|---|
| B-2355 | 4-F-C₆H₄ | piperidin-4-yl-NH-C(=O)-CH< ; piperidine N-CH₂CH₂-(1H-indol-3-yl) | 28 | 536 | 537 |
| B-2356 | 4-F-C₆H₄ | (heptan-4-yl)NH-C(=O)-CH< | 29 | 408 | 409 |
| B-2357 | 4-F-C₆H₄ | (1,2-diethylpyrazolidin-4-yl)NH-C(=O)-CH< | 41 | 436 | 437 |
| B-2358 | 4-F-C₆H₄ | [1-methyl-2-(dipropylamino)ethyl]NH-C(=O)-CH< | 41 | 451 | 452 |

-continued
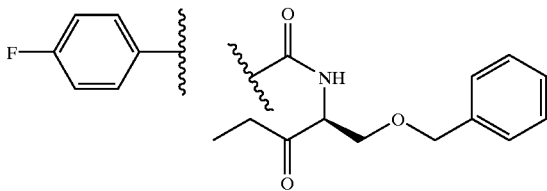
| R² | 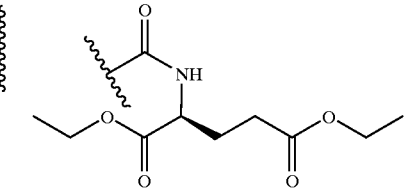 | Yield | Calcd. Mass Spec. | Observed Mass Spec M + H |
|---|---|---|---|---|
| B-2359 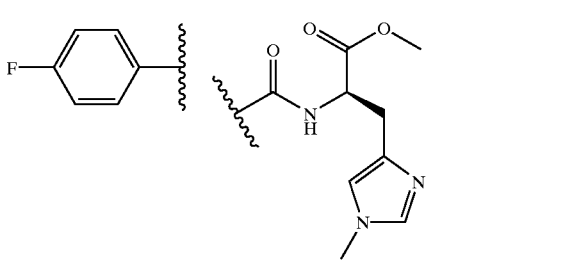 | | 57 | 502 | 503 |
| B-2360 | | 46 | 496 | 497 |
| B-2361 | | 13 | 476 | 477 |
| B-2362 | 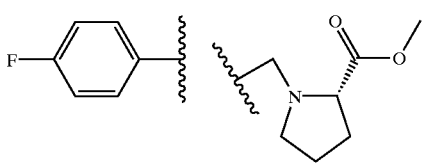 | 46 | 493 | 494 |

-continued

| R² | [RB-N-RC acyl group] | Yield | Calcd. Mass Spec. | Observed Mass Spec M + H |
|---|---|---|---|---|
| B-2363 4-F-phenyl | methyl alaninate amide | 57 | 396 | 397 |
| B-2364 4-F-phenyl | methyl leucinate amide | 61 | 438 | 439 |
| B-2365 4-F-phenyl | methyl valinate amide | 72 | 424 | 425 |

| | R² | NR^B R^C acyl group | Yield | Calcd. Mass Spec. | Observed Mass Spec M + H |
|---|---|---|---|---|---|
| B-2366 | 4-F-phenyl | morpholine amide | 34 | 380 | 381 |
| B-2367 | 4-F-phenyl | N-ethyl-N-(2-chloro-6-fluorobenzyl) amide | 52 | 480 | 481 |
| B-2368 | 4-F-phenyl | 4-ethylpiperazine amide | 35 | 407 | 407 |
| B-2369 | 4-F-phenyl | N-ethyl-N-(1-ethylpyrrolidin-3-yl) amide | 31 | 435 | 436 |
| B-2370 | 4-F-phenyl | N-methyl-N-benzyl amide | 33 | 414 | 415 |
| B-2371 | 4-F-phenyl | N,N-diethyl amide | 28 | 366 | 367 |

-continued
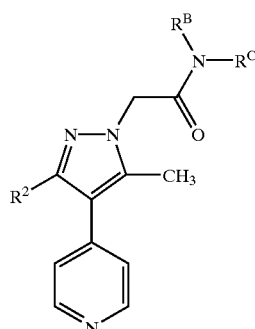
| | R² | ![N-RB,RC amide] | Yield | Calcd. Mass Spec. | Observed Mass Spec M + H |
|---|---|---|---|---|---|
| B-2372 | 4-F-phenyl | N,N-diisobutyl amide | 37 | 422 | 423 |
| B-2373 | 4-F-phenyl | N-allyl-N-cyclohexyl amide | 50 | 432 | 433 |
| B-2374 | 4-F-phenyl | N-methyl-N-(2-methoxyethyl) amide | 29 | 382 | 383 |
| B-2375 | 4-F-phenyl | N-methyl-N-(2-(dimethylamino)ethyl) amide | 35 | 395 | 396 |
| B-2376 | 4-F-phenyl | N-methyl-N-(2-phenylethyl) amide | 36 | 428 | 429 |

-continued
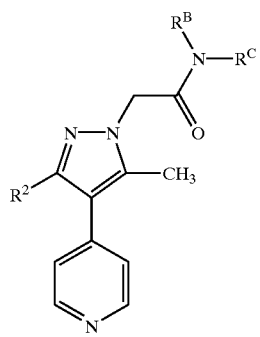
| R² | (structure) | Yield | Calcd. Mass Spec. | Observed Mass Spec M + H |
|---|---|---|---|---|
| B-2377 | 4-F-phenyl | NH-CH₂-C(O)O-tBu amide | 68 | 438 | 439 |
| B-2378 | 4-F-phenyl | N(iBu)(CH₂-2-furyl) amide | 55 | 446 | 447 |
| B-2379 | 4-F-phenyl | pyrrolidine amide | 33 | 364 | 365 |
| B-2380 | 4-F-phenyl | 4-acetylpiperazine amide | 51 | 421 | 422 |
| B-2381 | 4-F-phenyl | N(Et)(CH₂-4-pyridyl) amide | 52 | 429 | 430 |

-continued
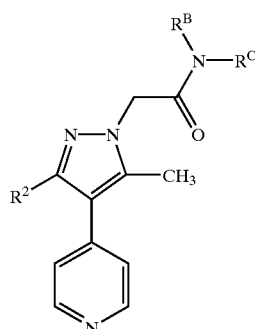
| R² | [acyl-N(R^B)R^C group] | Yield | Calcd. Mass Spec. | Observed Mass Spec M + H |
|---|---|---|---|---|
| B-2382 | 4-F-C₆H₄- ; acyl-N(4-methyl-1,4-diazepan-1-yl) | 48 | 407 | 408 |
| B-2383 | 4-F-C₆H₄- ; acyl-thiazolidin-3-yl | 53 | 382 | 383 |
| B-2384 | 4-F-C₆H₄- ; acyl-4-(pyrrolidin-1-ylmethyl)thiazolidin-3-yl | 38 | 447 | 448 |
| B-2385 | 4-F-C₆H₄- ; acyl-(1-Cbz-pyrrolidin-2-yl) | 59 | 498 | 450 |
| B-2386 | 4-F-C₆H₄- ; acyl-N(CH₃)(2-(pyridin-4-yl)ethyl) | 45 | 429 | 430 |

-continued

| | R² | ![RB,RC amide group] | Yield | Calcd. Mass Spec. | Observed Mass Spec M + H |
|---|---|---|---|---|---|
| B-2387 | 4-F-phenyl | N-methyl-N-[3-(dibenzosuberyl)propyl]amide | 74 | 558 | — |
| B-2388 | 4-F-phenyl | 2-[(1-methylpyrrolidin-2-yl)methyl]piperidin-1-yl amide | 53 | 475 | — |
| B-2389 | 4-F-phenyl | 3-[N-methyl-N-(tert-butoxycarbonyl)amino]pyrrolidin-1-yl amide | 33 | 493 | 494 |
| B-2390 | 4-F-phenyl | N-(pyridin-2-ylmethyl)-N-(ethoxycarbonylmethyl)amide | 53 | 487 | 488 |

-continued
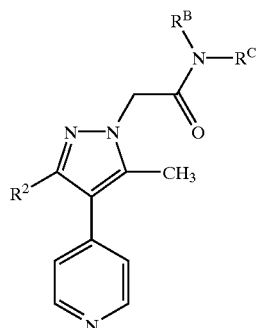
| R² | 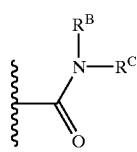 | Yield | Calcd. Mass Spec. | Observed Mass Spec M + H |
|---|---|---|---|---|
| B-2391 | | 30 | 435 | 436 |
| B-2392 | | 57 | 464 | 465 |
| B-2393 | | 50 | 418 | 419 |
| B-2394 | | 65 | 488 | 489 |
| B-2395 | | 59 | 437 | 438 |

-continued
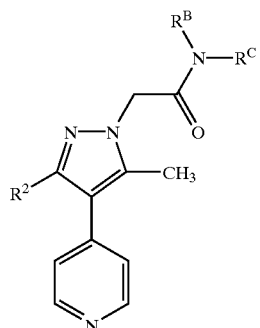
| R² | 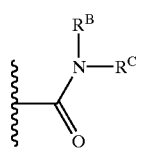 | Yield | Calcd. Mass Spec. | Observed Mass Spec M + H |
|---|---|---|---|---|
| B-2396 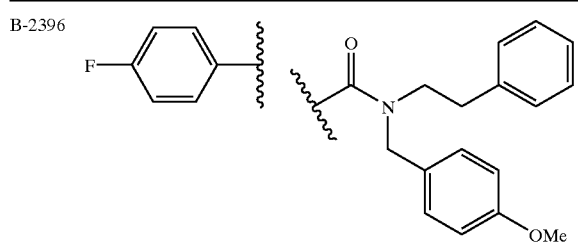 | | 34 | 534 | 535 |
| B-2397 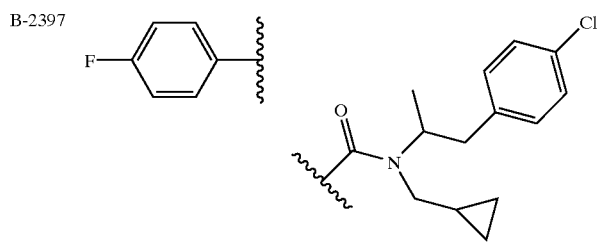 | | 32 | 516 | 517 |
| B-2398 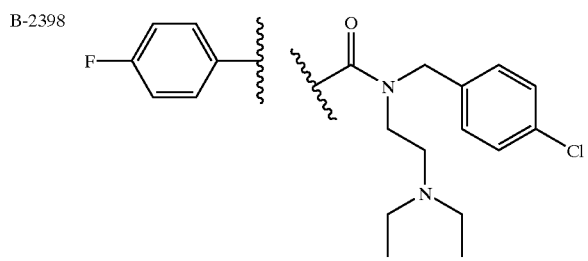 | | 81 | 533 | 534 |
| B-2399 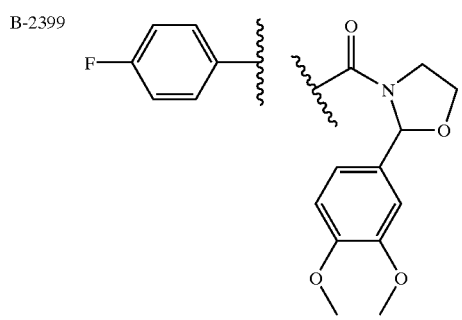 | | 55 | 502 | — |

-continued
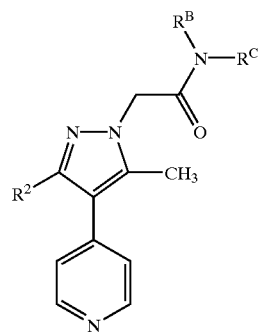
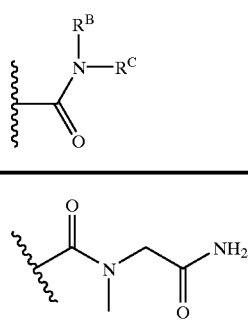
| R² | [acyl group] | Yield | Calcd. Mass Spec. | Observed Mass Spec M + H |
|---|---|---|---|---|
| B-2400 4-F-C₆H₄ | –C(O)–N(CH₃)–CH₂–C(O)NH₂ | 34 | 381 | 382 |
| B-2401 4-F-C₆H₄ | –C(O)–piperidinyl | 32 | 378 | 379 |
| B-2402 4-F-C₆H₄ | –C(O)–N(CH₂CH₂-2-pyridyl)(CH₂CH₂-phenyl) | 71 | 519 | 520 |
| B-2403 4-F-C₆H₄ | –C(O)–N(CH₂CH₂CN)(CH₂CH₂-3,4-dimethoxyphenyl) | 68 | 527 | 528 |

-continued
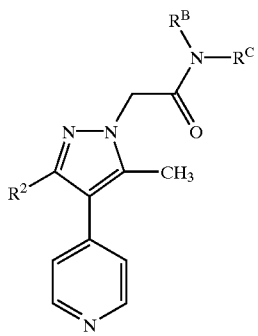
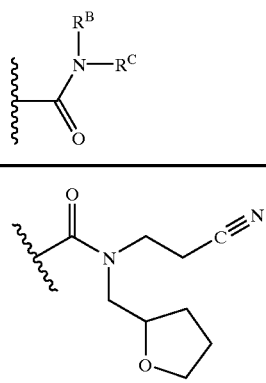
| R² | | Yield | Calcd. Mass Spec. | Observed Mass Spec M + H |
|---|---|---|---|---|
| B-2404 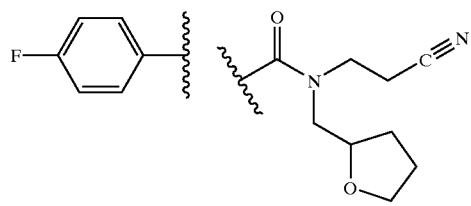 | | 62 | 447 | 448 |
| B-2405 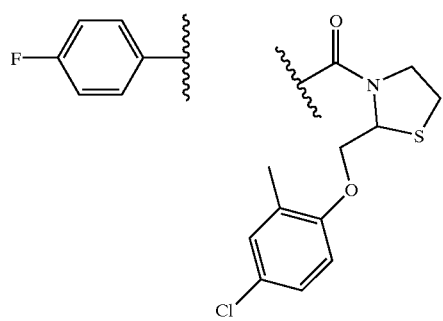 | | 71 | 536 | 537 |
| B-2406 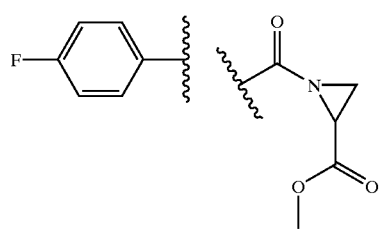 | | 47 | 394 | 395 |
| B-2407 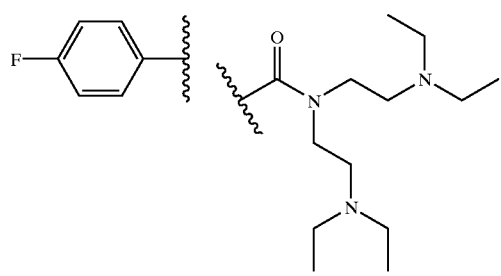 | | 65 | 508 | 509 |

-continued

| R² | ⸺N(R^B)(R^C) C(=O) group | Yield | Calcd. Mass Spec. | Observed Mass Spec M + H |
|---|---|---|---|---|
| B-2408 4-F-C₆H₄ | 2-acyl-6-methoxy-2,3,4,9-tetrahydro-1H-β-carboline | 34 | 495 | 496 |
| B-2409 4-F-C₆H₄ | 3-acyl-2-(2-furyl)thiazolidine | 47 | 448 | 449 |
| B-2410 4-F-C₆H₄ | 5-acyl-6-(4-chlorophenyl)-4,5,6,7-tetrahydrothieno[3,2-c]pyridine | 73 | 542 | 543 |

-continued
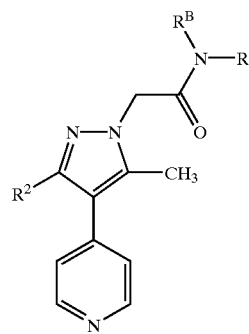
| | R² | [N-acyl group] | Yield | Calcd. Mass Spec. | Observed Mass Spec M + H |
|---|---|---|---|---|---|
| B-2411 | 4-F-C₆H₄ | piperidinyl-piperidine acyl | 81 | 489 | 490 |
| B-2412 | 4-F-C₆H₄ | N-methyl-N,N-dimethylamide acyl | 54 | 409 | 410 |
| B-2413 | 4-F-C₆H₄ | pyrrolidinyl-N-Me-N-Boc acyl | 37 | 493 | 494 |

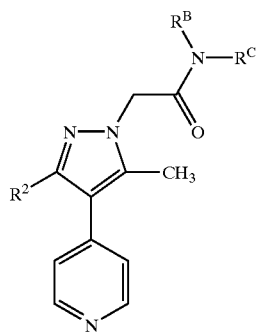
| | R² | 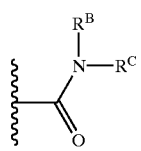 | Yield | Calcd. Mass Spec. | Observed Mass Spec M + H |
|---|---|---|---|---|---|
| B-2414 | 4-F-phenyl | acetamide-NH-(6-methoxybenzothiazol-2-yl) | 14 | 473 | 474 |
| B-2415 | 4-F-phenyl | acetamide-NH-(6-chloropyridin-3-yl) | 19 | 421 | 422 |
| B-2416 | 4-F-phenyl | acetamide-NH-phenyl | 13 | 386 | 387 |
| B-2417 | 4-F-phenyl | acetamide-NH-(2,6-dimethylphenyl) | 29 | 414 | 415 |
| B-2418 | 4-F-phenyl | acetamide-NH-(4-chlorophenyl) | 6 | 420 | 421 |

-continued

| | R² | [acyl group] | Yield | Calcd. Mass Spec. | Observed Mass Spec M + H |
|---|---|---|---|---|---|
| B-2419 | 4-F-C₆H₄ | -C(O)-NH-(2-CF₃-C₆H₄) | 10 | 454 | — |
| B-2420 | 4-F-C₆H₄ | -C(O)-NH-(2,6-diethyl-C₆H₃) | 5 | 442 | 443 |
| B-2421 | 4-F-C₆H₄ | -C(O)-NH-(2,6-diCl-C₆H₃) | 28 | 454 | 455 |
| B-2422 | 4-F-C₆H₄ | -C(O)-NH-(2-Cl-C₆H₄) | 47 | 420 | 421 |
| B-2423 | 4-F-C₆H₄ | -C(O)-NH-(4-Me-C₆H₄) | 53 | 400 | 401 |

-continued
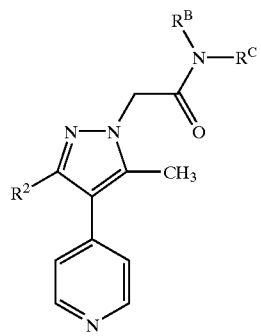
| R² | 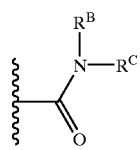 | Yield | Calcd. Mass Spec. | Observed Mass Spec M + H |
|---|---|---|---|---|
| B-2424 | | 15 | 400 | 401 |
| B-2425 | | 18 | 522 | 523 |
| B-2426 | | 38 | 464 | 465 |
| B-2427 | | 26 | 468 | 469 |

-continued
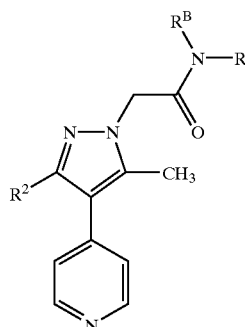
| R² | 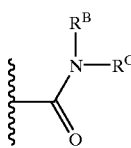 | Yield | Calcd. Mass Spec. | Observed Mass Spec M + H |
|---|---|---|---|---|
| B-2428 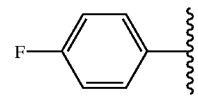 | 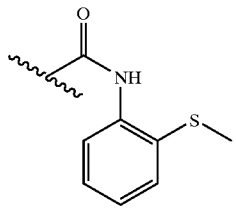 | 22 | 432 | 433 |
| B-2429 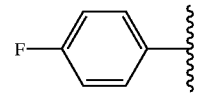 | 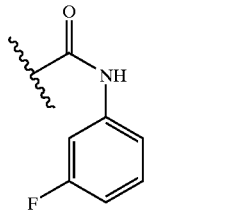 | 41 | 404 | 405 |
| B-2430 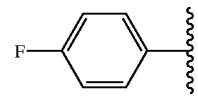 | 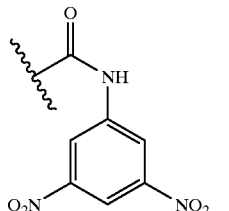 | 15 | 476 | 477 |
| B-2431 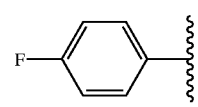 | 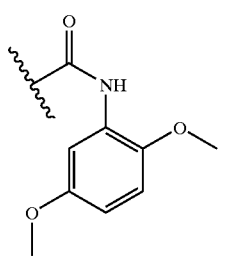 | 6 | 446 | 447 |

-continued
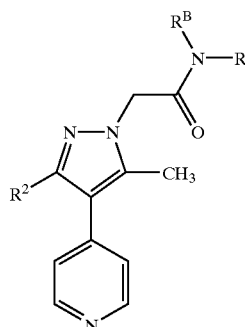
| R² | 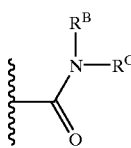 | Yield | Calcd. Mass Spec. | Observed Mass Spec M + H |
|---|---|---|---|---|
| B-2432 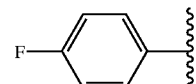 | 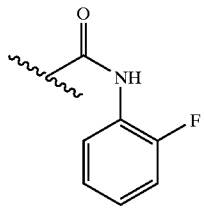 | 37 | 404 | 405 |
| B-2433 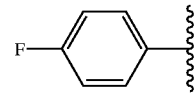 | 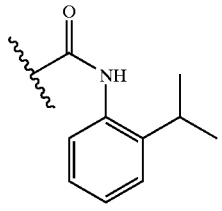 | 8 | 428 | 429 |
| B-2434 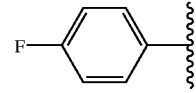 | 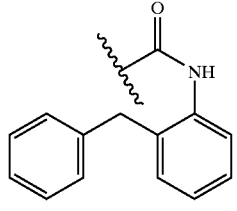 | 13 | 476 | 477 |
| B-2435 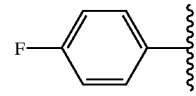 | 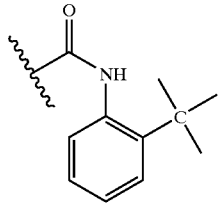 | 23 | 442 | 443 |

-continued
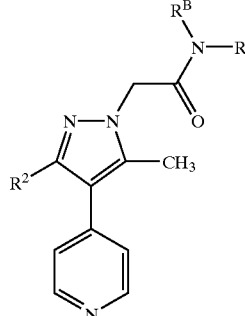
| R² | 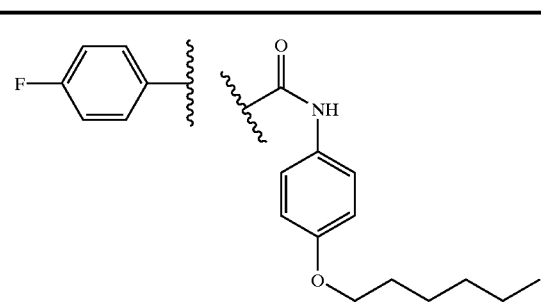 | Yield | Calcd. Mass Spec. | Observed Mass Spec M + H |
|---|---|---|---|---|
| B-2436 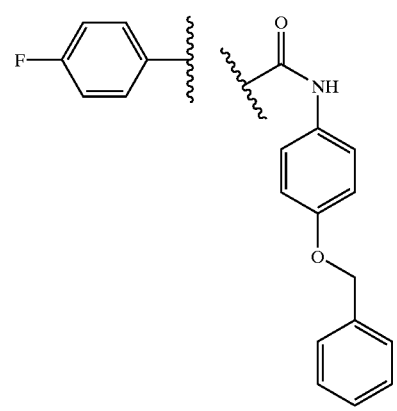 | 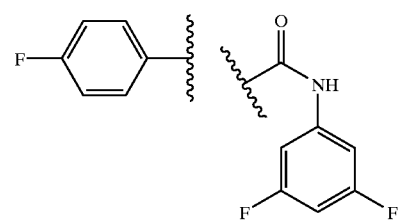 | 5 | 486 | 487 |
| B-2437 | | 4 | 492 | 493 |
| B-2438 | | 58 | 422 | 423 |

-continued
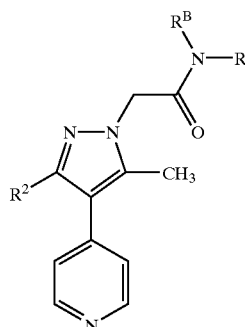
| | R² | 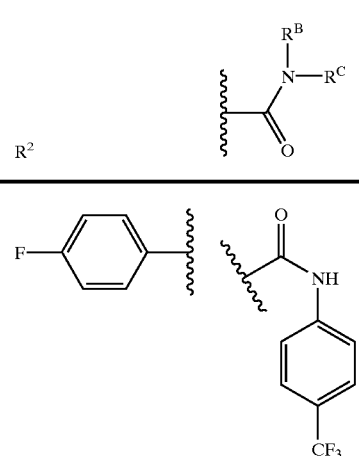 | Yield | Calcd. Mass Spec. | Observed Mass Spec M + H |
|---|---|---|---|---|---|
| B-2439 | 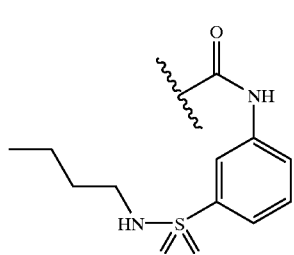 | | 12 | 454 | 455 |
| B-2440 | | | 8 | 521 | 522 |
| B-2441 | | 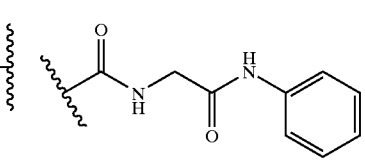 | 6 | 443 | 444 |
| B-2442 | | 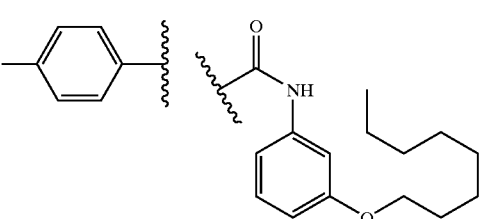 | 37 | 514 | 515 |

-continued

| | R² | [acyl group] | Yield | Calcd. Mass Spec. | Observed Mass Spec M + H |
|---|---|---|---|---|---|
| B-2443 | 4-F-phenyl | 2-(2,5-dimethylbenzoyl)phenyl-NH-C(O)- | 15 | 518 | |
| B-2444 | 4-F-phenyl | 4-[(3-methylphenoxy)carbonyl]phenyl-NH-C(O)- | 52 | 520 | |
| B-2445 | 4-F-phenyl | 4-[3-oxo-3-(pyridin-3-yl)propyl]phenyl-NH-C(O)- | 33 | 517 | 518 |
| B-2446 | 4-F-phenyl | 4-(difluoromethylsulfonyl)phenyl-NH-C(O)- | 70 | 500 | 501 |

-continued
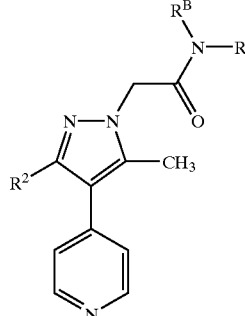
| R² | 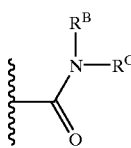 | Yield | Calcd. Mass Spec. | Observed Mass Spec M + H |
|---|---|---|---|---|
| B-2447 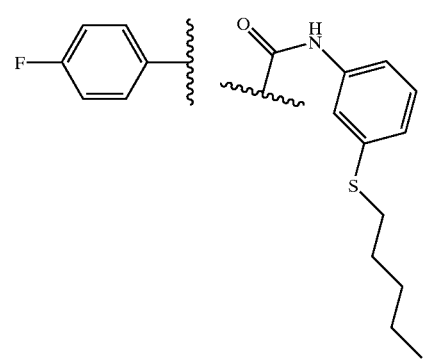 | | 56 | 488 | 489 |
| B-2448 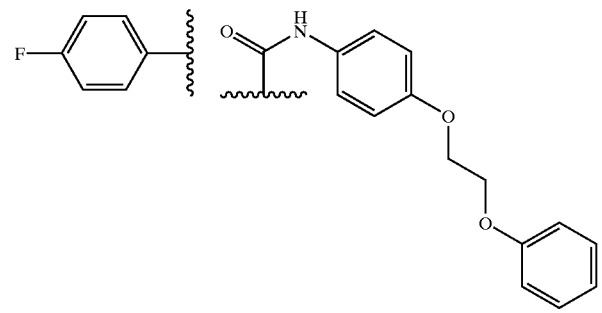 | | 51 | 522 | 523 |
| B-2449 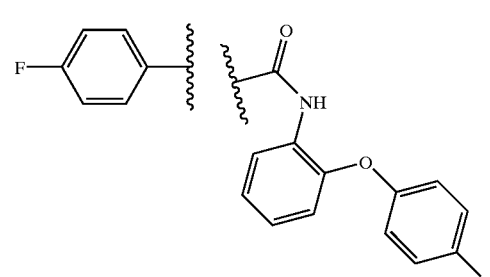 | | 19 | 512 | 513 |

-continued
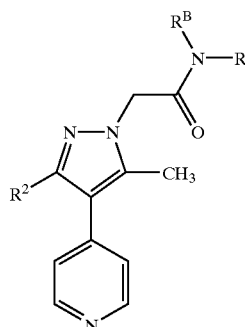
| R² | ![structure] | Yield | Calcd. Mass Spec. | Observed Mass Spec M + H |
|---|---|---|---|---|
| B-2450 | 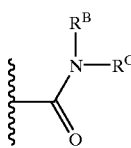 | 16 | 538 | 539 |
| B-2451 | 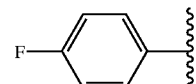 | 71 | 511 | 512 |
| B-2452 | 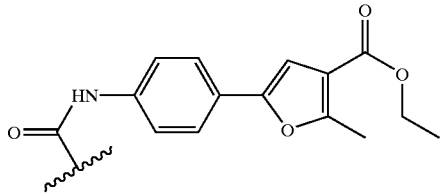 | 71 | 500 | 501 |
| B-2453 | 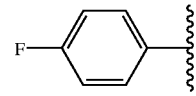 | 61 | 470 | — |

-continued
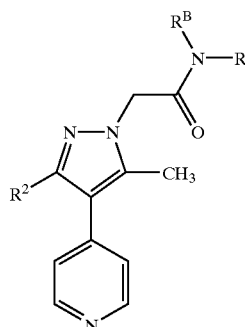
| R² | ⧜⧜N(R^B)(R^C)C(=O)⧜⧜ | Yield | Calcd. Mass Spec. | Observed Mass Spec M + H |
|---|---|---|---|---|
| B-2454 | 4-F-phenyl | NH-(2-isopropoxycarbonyl-phenyl)amide | 15 | 472 | 473 |
| B-2455 | 4-F-phenyl | NH-[4-(3-CF₃-pyrazol-1-yl)phenyl]amide | 39 | 520 | — |
| B-2456 | 4-F-phenyl | NH-[2-(N-(1-phenylethyl)carbamoyl)phenyl]amide | 51 | 533 | 534 |
| B-2457 | 4-F-phenyl | NH-[2-(5-nitro-pyridin-2-ylthio)phenyl]amide | 55 | 540 | — |

-continued
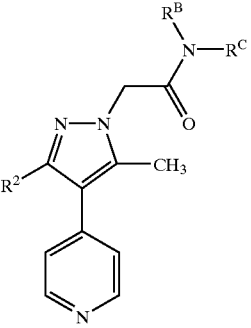
| R² | 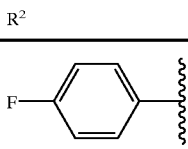 | Yield | Calcd. Mass Spec. | Observed Mass Spec M + H |
|---|---|---|---|---|
| B-2458 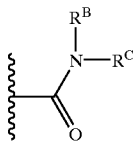 | | 22 | 488 | 489 |
| B-2459 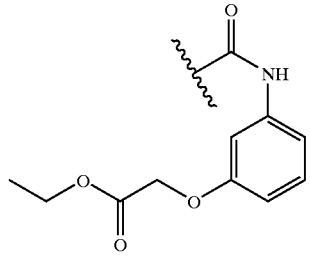 | | 8 | 486 | 487 |
| B-2460 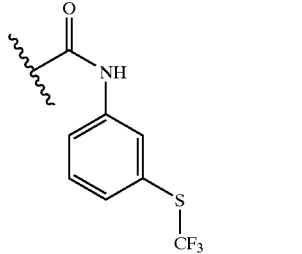 | | 13 | 534 | 535 |
| B-2461 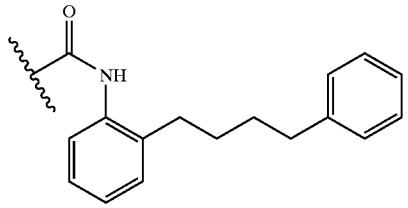 | 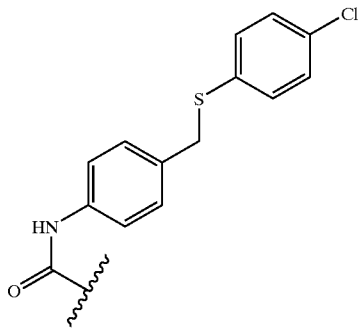 | 13 | 542 | — |

EXAMPLE C-1

5-aminomethyl-4-(4-pyridyl)-3-(4-fluorophenyl) pyrazole

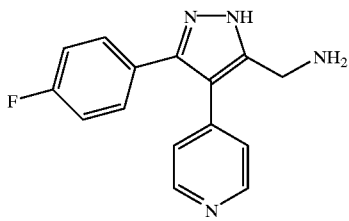

1-(4-fluorophenyl)-2-(4-pyridyl)-1-ethanone 4-picoline (40 g, 0.43 mol) was added to a LiHMDS solution (0.45 mol, 450 mL of a 1.0 M solution in THF) over 30 minutes at room temperature (a slight exotherm was observed) The resulting solution was stirred for 1 h. This solution was added to ethyl 4-fluorobenzoate (75.8 g, 0.45 mol. neat) over 1 h. The mixture was stirred overnight (16 h). Water (200 mL) was added and the mixture was extracted with EtOAc (2×200 mL). The organic layer was washed with brine (1×200 mL) and dried over $Na_2SO_4$. The organic layer was filtered and the solvent waS removed to leave oily solid. Hexane was added to the oil and the resulting solid was filtered and washed with hexane (cold). A yellow solid was isolated (50 g, 54%): $^1$H NMR ($CDCl_3$) δ8.58 (d, J=5.7 Hz, 2H), 8.02 (dd, J=5.5, 8.0, 2H), 7.12–7.21 (m, 4H), 4.23 (s, 2H); $^{19}$F NMR ($CDCl_3$) δ–104.38 (m); LC/MS, $t_r$=2.14 minutes (5 to 95% acetonitrile/water over 15 minutes at 1 mL/min, at 254 nm at 50° C.), M+H=216; High Resolution MS Calcd for $C_{23}H_{20}N_4O_2F$ (M+H): 216.0825. Found: 216.0830 (Δ mmu=0.5).

N-benzyloxycarbonyl-5-aminomethyl-4-(4-pyridyl)- 3-(4-fluorophenyl)pyrazole

A 3 L round bottom flask fitted with a mechanical stirrer, $N_2$ inlet and an addition funnel was was charged wtih 557 mL (0.56 mol) of 1 M t-BuOK in THF and 53 mL (0.56 mol) of t-BuOH. The ketone, 1 (60 g, 0.28 mol) was dissolved in 600 mL of THF and added to the stirred mixture at room temperature. A yellow precipitate formed and the mixture was stirred for 1 h. N-benzyloxycarbonyl-glycinyl N-hydroxysuccinimide (128.6 g, 0.42 mol) was dissolved in 600 mL of THF and added dropwise at r.t. over 1 h. The mixture was stirred for another 5 minutes and 150 mL of water was added. the pH was adjusted to 6.7 with 70 mL of AcOH. Hydrazine monohydrate (41 mL in 100 mL of water) was added via an addition funnel. The mixture was stirred for 1 h and was diluted with 500 mL of water and 500 mL of ethyl acetate. The biphasic mixture was transferred to a sep funnel and the layers were separated. The aqueous layer was extracted with EtOAc (3×300 mL). The organic layer was dried ($Na_2SO_4$), filtered and evaporated to leave 157 g of a crude reddish oil.

The oil was suspended in $CH_2Cl_2$ and filtered to remove any insoluble material (DCU, hydrazone of the monoketone). The solution was split into two portions and each portion was chromatographed (Biotage 75L, 3% EtOH/ $CH_2Cl_2$ then 6% EtOH/$CH_2Cl_2$). The appropriate fractions were concentrated (some contamination from the monoketone and the hydrazone) from each portion to leave a yellow solid. The solid was suspended in ethyl acetate and heated to boiling for 10 minutes. The solution was allowed to cool to R.T. overnight. The precipitate was filtered to give 30 g of a white solid (27% yield of 2): $^1$H NMR (DMF-$d_7$) δ13.36 (s, 1H), 8.57 (d, J=5.8 Hz, 2H), 7.16–7.52 (m, 11H), 5.11 (s, 2H), 4.48 (d, J=5.4 Hz, 2H); $^{19}$F NMR (DMF-$d_7$) δ–114.9 (m), –116.8 (m) (split fluorine signal is due to the pyrazole tautomers); LC/MS, $t_r$=3.52 minutes (5 to 95% acetonitrile/water over 15 minutes at 1 mL/min, at 254 nm at 50° C.), M+H=403; High Resolution MS Calcd for $C_{23}H_{20}N_4O_2F$ (M+H): 403.1570. Found: 403.1581 (Δ mmu=1.1).

5-aminomethyl-4-(4-pyridyl)-3-(4-fluorophenyl) pyrazole

To a 1 L Parr bottle was added 7 g (17.4 mmol) of 2 and 180 mL of MeOH and 90 mL of THF to give a clear solution. The bottle was purged with nitrogen and 1.5 g of 10% Pd/C (wet Degussa type E101) was added. The Parr bottle was pressured to 40 psi ($H_2$) and was agitated. Hydrogen uptake was 5 psi after 5 h. The bottle was repressured to 42 psi and was agitated overnight. The bottle was purged with N2 and was filtered through Celite. The Celite was washed with MeOH (3×50 mL) and the filtrate was concentrated to give 4.5 g of an off-white solid (94%). $^1$H NMR (DMSO-$d_6$) δ8.52 (d, J=4.63 Hz, 2H), 7.36 (dd, J=5.64, 8.1 Hz, 2H), 7.16–7.30 (m, 4H), 3.79 (s, 2H); $^{19}$F NMR (DMSO-$d_6$) δ–114.56 (m); LC/MS, $t_r$=1.21 minutes (5 to 95% acetonitrile/water over 15 minutes at 1 mL/min, at 254 nm at 50° C.), M+H=269 m/z; High Resolution MS Calcd for $C_{15}H_{14}N_4F$ (M+H): 269.1202. Found: 269.1229 (Δ mmu= 2.7).

The following pyridylpyrazoles (C-2 through C-21, Table C-1) were prepared according to the experimental procedure described above for example C-1.

TABLE C-1

| Example No. | Structure | MW, M + H Calculated Found | $^1$H NMR (solvent), ppm |
|---|---|---|---|
| C-2 | 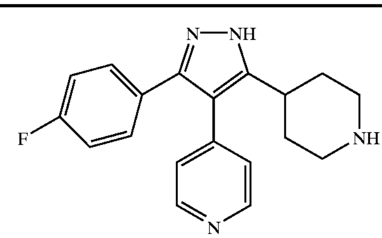 | 323.1672 323.1670 | (DMF-$d_7$): 8.77 (t, J= 4.4Hz, 2H), 7.60(m, 2H), 7.44(t, J=4.4Hz, 2H), 7.35(m, 2H), 3.22(bd, 2H), 3.01(septet, J=5.3 Hz, 1H), 2.74(m, 2H), 1.95(m, 4H) |

TABLE C-1-continued

| Example No. | Structure | MW, M + H Calculated Found | ¹H NMR (solvent), ppm |
|---|---|---|---|
| C-3 | 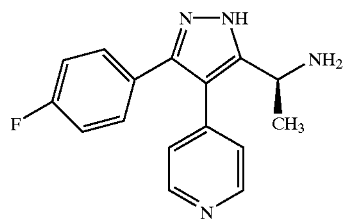 | 282.127 (M) 282.1245 (M, EI) | (DMF-d₇): 8.77(br s, 2H), 7.64–7.62(m, 2H), 7.50(br s, 2H), 7.38–7.34 (m, 2H), 4.40–4.37(m, 1H), 1.56(br s, 3H) |
| C-4 | 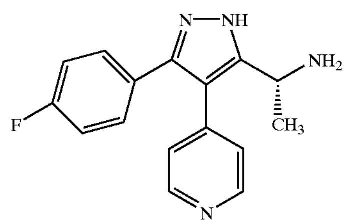 | 282.127 (M) 282.1147 (M, EI) | (DMF-d₇): 8.77(br s, 2H), 7.64–7.62(m, 2H), 7.50(br s, 2H), 7.38–7.35 (m, 2H), 4.40–4.37(m, 1H), 1.57(br s, 3H) |
| C-5 | 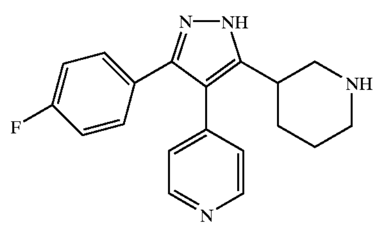 | 323.1672 323.1687 | (DMSO-d₆): 8.56(br, 2H), 7.32(m, 2H), 7.18(m, 4H), 2.91(m, 2H), 2.71 (m, 2H)1.88(m, 1H), 1.65 (m, 2H), 1.40(m, 2H) |
| C-6 | 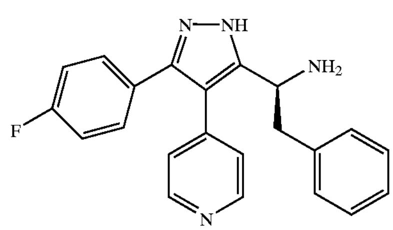 | 359 359 | (DMSO-d₆): 8.46(d, J= 4.6Hz, 2H), 7.32–7.13(m, 7H), 6.98–6.96(m, 4H), 4.06(t, J=7.0Hz, 1H), 2.98–2.95(m, 2H) |
| C-7 | 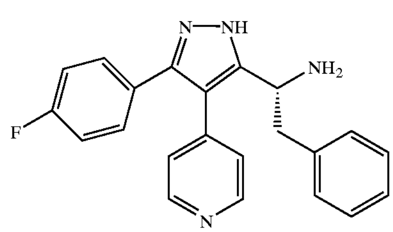 | 359 359 | (DMSO-d₆): 8.46(d, J= 5.4Hz, 2H), 7.32–7.28(m, 2H), 7.20–7.12(m, 5H), 6.98–6.96(m, 4H), 4.06 (t, J=7.0Hz, 1H), 2.98–2.94(m, 2H) |
| C-8 | 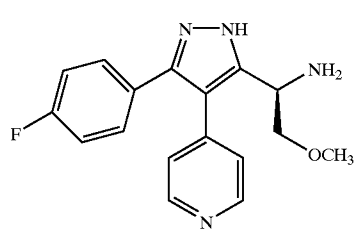 | 313.1465 313.1492 | (DMSO-d₆): 13.83(bs, 1H), 8.61(d, J=5.7Hz, 2H), 8.33(bs, 1H), 7.33 (m, 6H), 4.44(m, 1H), 3.63(m, 2H), 3.27(s, 3H) |

TABLE C-1-continued

| Example No. | Structure | MW, M + H Calculated Found | $^1$H NMR (solvent), ppm |
|---|---|---|---|
| C-9 | 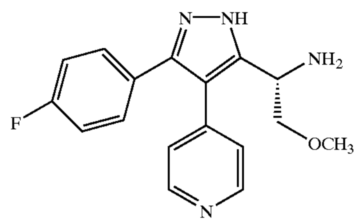 | 313.1465 313.1457 | (DMSO-d$_6$): 8.55(dd, J= 1.5, 4.4Hz,, 2H), 7.37–7.32(m, 2H), 7.26(dd, J= 1.6, 4.4Hz, 2H), 7.22–7.16(m, 2H), 4.06(t, J = 6.5Hz, 1H), 3.49(d, J = 6.6Hz, 2H), 3.20(s, 3H) |
| C-10 | 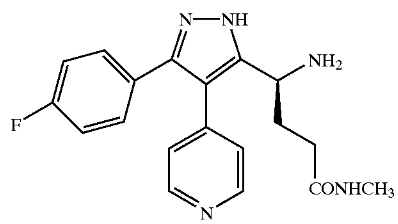 | 354 354 | (DMSO-d$_6$): 13.03(bs, 1H), 8.50(dd, J=1.6, 2.7 Hz, 2H), 7.58(bq, J=4.3 Hz, 1H), 7.3(m, 2H), 7.12–7.21(m, 4H), 3.77 (t, J=6.3Hz, 1H), 2.45 (d, J=4.5Hz, 3H), 1.97 (t, J=7.4Hz, 2H), 1.85 (dt, J=7.3, 7.1Hz, 2H) |
| C-11 | 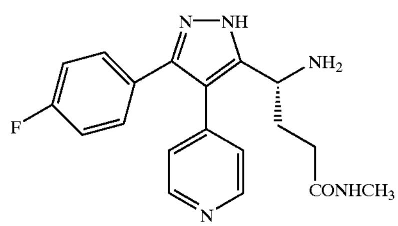 | 354 354 | (DMSO-d$_6$): 13.03(bs, 1H), 8.50(dd, J=1.6, 2.7 Hz, 2H), 7.58(bq, J=4.3 Hz, 1H), 7.3(m, 2H), 7.12–7.21(m, 4H), 3.77 (t, J=6.3Hz, 1H), 2.45 (d, J=4.5Hz, 3H), 1.97 (t, J=7.4Hz, 2H), 1.85 (dt, J=7.3, 7.1Hz, 2H) |
| C-12 | 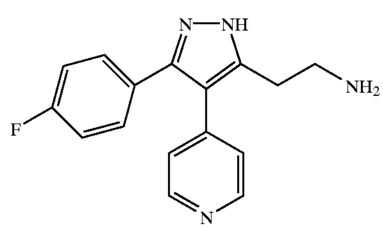 | 283.1359 283.1363 | (DMSO-d$_6$): 8.53(d, J= 5.0Hz, 2H), 7.37–7.32(m, 2H), 7.21–7.17(m, 4H), 2.83(d, J =6.0Hz, 2H), 2.77(d, J =6.0Hz, 2H) |
| C-13 | 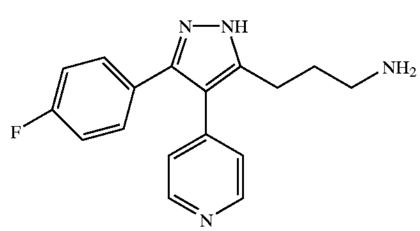 | 297.1515 297.1515 | (DMSO-d$_6$): 8.53(d, J= 5.4Hz, 2H), 7.34(dd, J= 5.8, 8.2Hz, 2H), 7.18 (dd, J=5.8, 9.8Hz, 4H), 2.68(t, J=7.3Hz, 2H), 2.52(m, 2H), 1.64(m, 2H) |
| C-14 | 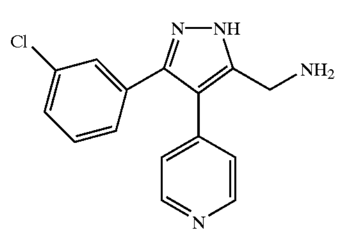 | 284.0829 284.0806 | (CD$_3$OD): 8.74(br, 2H), 7.77(br, 2H), 7.45–7.58 (m, 3H), 7.30–7.40(m, 1H), 4.43(s, 2H) |

TABLE C-1-continued

| Example No. | Structure | MW, M+H Calculated Found | ¹H NMR (solvent), ppm |
|---|---|---|---|
| C-15 | 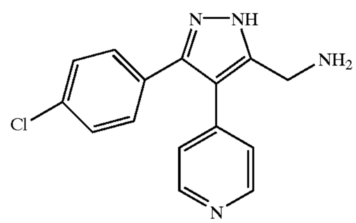 | 285 285 | (DMSO-d$_6$): 8.53(br, 2H), 7.56(br, 2H), 7.26(m, 4H), 3.75(br, 2H) |
| C-16 | 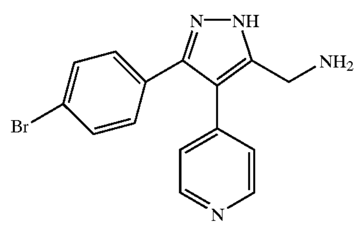 | 329, 331 329, 331 | (DMSO-d$_6$): 8.53(d, J= 4.4Hz, 2H), 7.42(d, J= 7.9Hz, 2H), 7.34(d, J = 8.5Hz, 2H), 7.24(d, J = 4.6Hz, 2H), 3.76(bs, 2H) |
| C-17 | 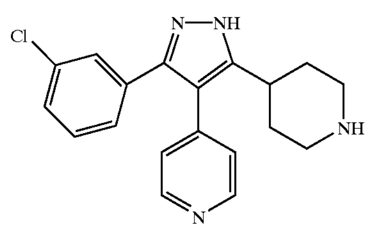 | 339 339 | (DMSO-d$_6$): 8.53(t, J = 4.3Hz, 2H), 7.33(m, 3H), 7.19(t, J=4.6Hz, 2H), 7.14(d, J=7.3Hz, 1H), 3.23(m, 2H), 2.88, (m, 3H), 1.92, (m, 3H), 1.70 (m, 1H) |
| C-18 | 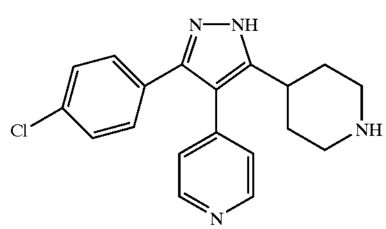 | 339 339 | (DMSO-d$_6$): 8.57(d, J= 4.6Hz, 2H), 7.41(d, J = 8.3Hz, 2H), 7.29(d, J = 8.5Hz, 2H), 7.20(d, J= 4.8Hz, 2H), 3.18(bd, 2H), 2.88(m, 1H), 2.76 (m, 2H), 1.82(br, 4H) |
| C-19 | 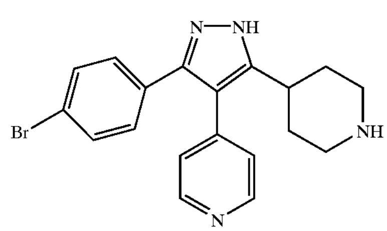 | 383, 385 383, 385 | (DMSO-d$_6$): 8.56(br, 2H), 7.52(br, 2H), 7.14–7.29 (m, 4H), 2.99(br, 2H), 2.71(br, 1H), 2.51(br, 2H), 1.68(br, 4H) |

The following pyridylpyrazoles (C-22 through C-40, Table C-2) are prepared utilizing the general schemes C-1 and C-2 and the experimental procedure described for example C-1 above.

TABLE C-2

| Cmpd. No. | Structure |
|---|---|
| C-22 | 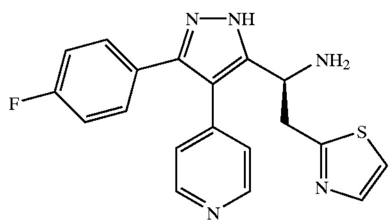 |
| C-23 | 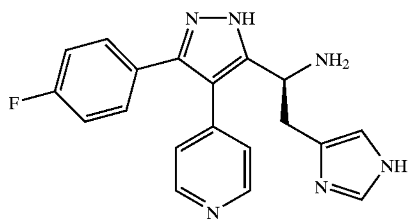 |
| C-24 | 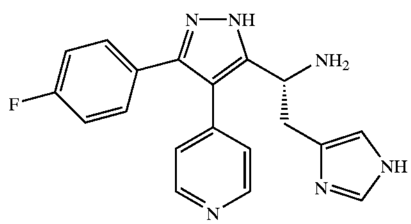 |
| C-25 | 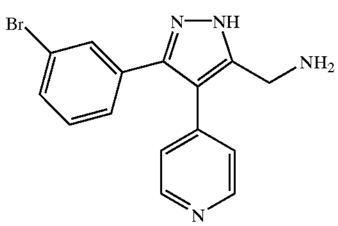 |
| C-26 | 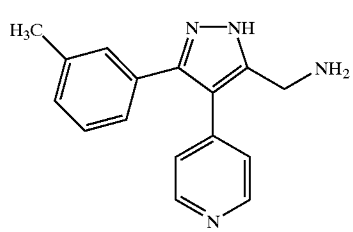 |
| C-27 | 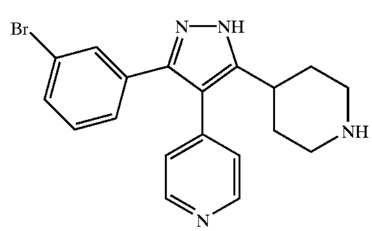 |

TABLE C-2-continued

| Cmpd. No. | Structure |
|---|---|
| C-28 | 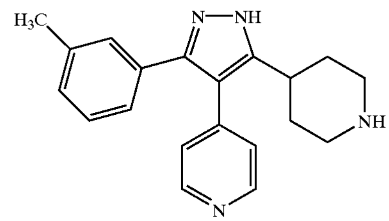 |
| C-29 | 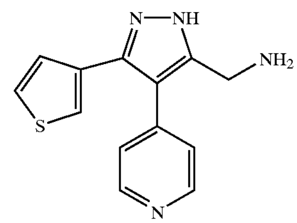 |
| C-30 | 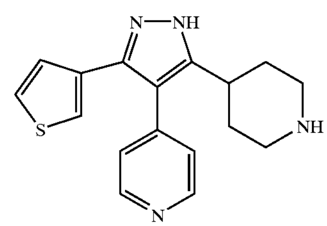 |
| C-31 | 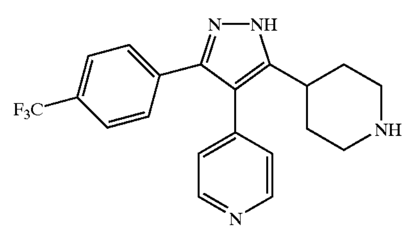 |
| C-32 | 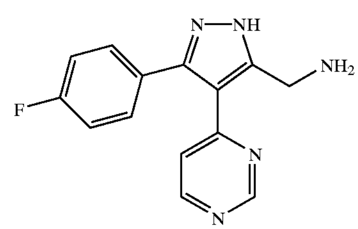 |
| C-33 | 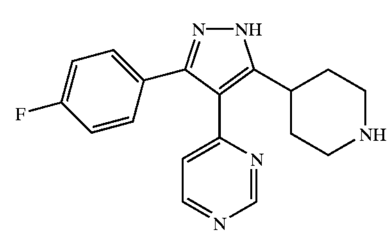 |

TABLE C-2-continued

| Cmpd. No. | Structure |
|---|---|
| C-34 | 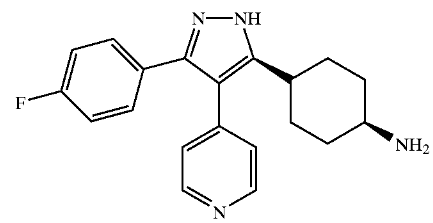 |
| C-35 | 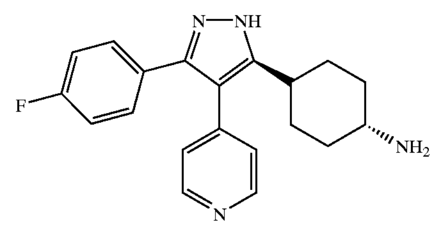 |
| C-36 | 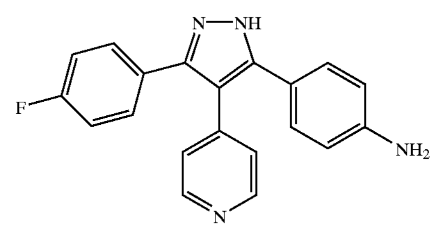 |
| C-37 | 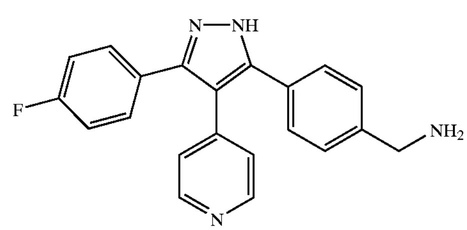 |
| C-38 | 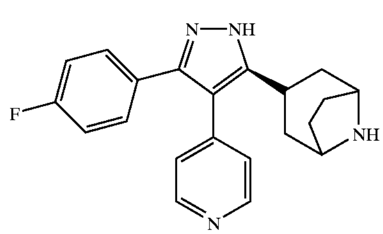 |
| C-39 | 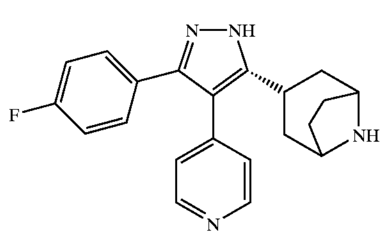 |
| C-40 | |
| C-41 | |
| C-42 | |
| C-43 | |
| C-44 | |
| C-45 | |

TABLE C-2-continued

| Cmpd. No. | Structure |
|---|---|
| C-46 | 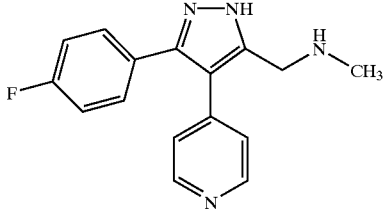 |
| C-47 | 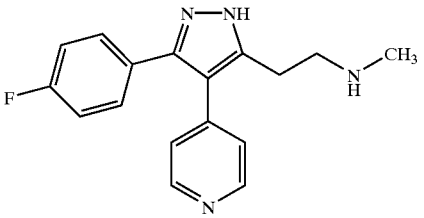 |
| C-48 | 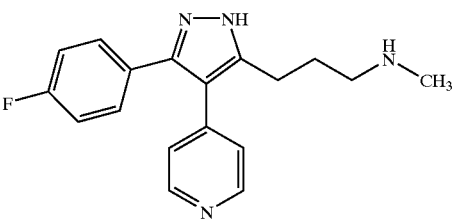 |

EXAMPLE C-49

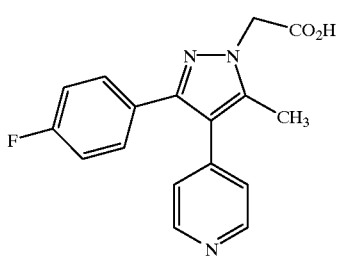

Step A

The pyrazole (2.60 g, 10.3 mmol) from example C-4 was suspended in 52 mL of dichloroethane and 52 mL of 2.5 M NaOH. Tetrabutylammonium hydroxide (0.5 mL of a 1 M aqueous solution) was added to the stirred mixture. To this mixture was added t-butyl bromoacetate (2.10 g, 10.8 mmol). The reaction mixture was stirred at room temperature for 4 h. The mixture was poured onto 200 mL of $CH_2Cl_2$ and 200 mL of $H_2O$. The phases were separated and the organic phase was washed with water (1×100 mL) and brine (1×100 mL). The organic layer was dried over $Na_2SO_4$ and was filtered. The solvent was removed to leave an off-white solid. This solid was triturated with hexane and the resulting solid isolated by filtration. The solid was washed with hexane to leave 3.4 g of a white solid (90%).

Step B

The alkylated pyrazole (3.7 g, 10.1 mmol) from Step A was treated with 57 mL of 4 N HCL in dioxane. The solution was stirred at room temperature for 4 h. The solvent was removed under reduced pressure and the residue was dissolved in THF. The solution was treated with propylene oxide (10.3 mmol) and was stirred for 1 h at room temperature. The solvent was removed to leave an oil. The residual solvent was chased with several portions of EtOH. The resulting solid was triturated with $Et_2O$ and the title compound Example C-49 was isolated by filtration to afford 3.0 g of an off-white solid (95%). Mass spec: M+H cald: 312; found 312. $^1$H NMR (DMSO-d6): 8.81 (d, J=6.4 Hz, 2H), 7.73 (d, J=5.8 Hz, 2H), 7.40 (m, 2H), 7.23 (t, J=8.5 Hz, 1H), 5.16 (s, 2H), 2.40 (s, 3H).

EXAMPLE C-50

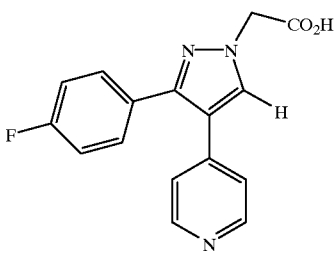

According to the procedure described above in Example C-49, Example C-50 was also prepared starting from 4-[3-(4-fluorophenyl)-1H-pyrazole-4-yl]pyridine. Mass spec: M+H cald: 298; found 298. $^1$H NMR (DMSO-d6): 8.75 (d, J=6.4 Hz, 2H), 8.68 (s, 1H), 7.78 (d, J=6.6 Hz, 2H), 7.52 (dd, J=5.4, 8.5 Hz, 2H), 7.31 (t, J=8.9 Hz, 2H), 5.16 (s, 2H).

EXAMPLE C-51

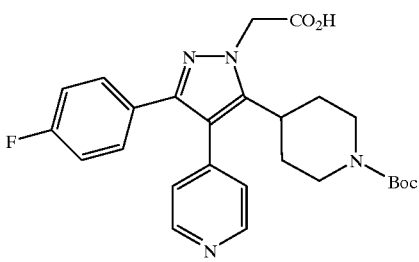

Starting with the N-Boc-piperidinyl analog of Example C-2, Example C-51 is also prepared according to the methods described in Scheme C-1.

EXAMPLE C-52

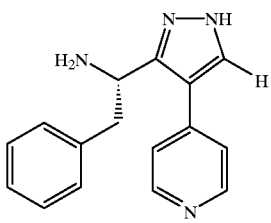

Step A: Picoline is treated with a base chosen from but not limited to n-BuLi, LDA, LiHMDS, tBuOK, or NaH in an organic solvent such as THF, ether, t-BuOH or dioxane from −78° C. to 50° C. for a period of time from 10 minutes to 3 hours. The picoline solution is then added to a solution of N-Cbz-(L)-phenylalaninyl N-hydroxysuccinimide. The reaction is allowed to stir from 30 minutes to 48 hours during which time the temperature may range from −20° C. to 120° C. The mixture is then poured into water and extracted with an organic solvent. After drying and removal of solvent the pyridyl monoketone is isolated as a crude solid which could be purified by crystallization and/or chromatography.

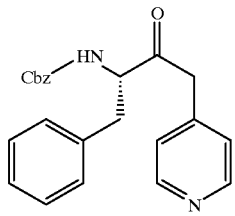

Step B: A solution of the pyridyl monoketone in ether, THF, tBuOH, or dioxane is added to a base chosen from but not limited to n-BuLi, LDA, LiHMDS, tBuOK, or NaH contained in hexane, THF, ether, dioxane, or tBuOH from −78° C. to 50° C. for a period of time from 10 minutes to 3 hours. Formyl acetic anhydride is then added as a solution in THF, ether, or dioxane to the monoketone anion while the temperature is maintained between −50° C. and 50° C. The resulting mixture is allowed to stir at the specified temperature for a period of time from 5 minutes to several hours. The resulting pyridyl diketone intermediate is utilized without purification in Step C.

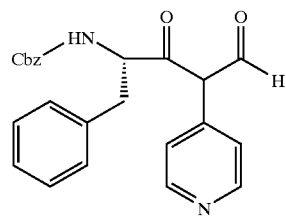

Step C: The solution containing the pyridyl diketone is quenched with water and the pH is adjusted to between 4 and 8 utilizing an inorganic or organic acid chosen from HOAc, $H_2SO_4$, HCl, or $HNO_3$. The temperature during this step is maintained between −20° C. and room temperature. Hydrazine or hydrazine hydrate is then added to the mixture while maintaining the temperature between −20° C. and 40° C. for a period of 30 minutes to several hours. The mixture is then poured into water and extracted with an organic solvent. The N-Cbz-protected pyridyl pyrazole is obtained as a crude solid which is purified by chromatography or crystallization.

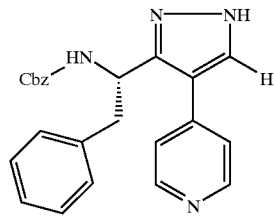

Step D: The CBZ protecting group is cleaved using hydrogen gas under pressure and Pd-C in an alcohol solvent, affording scaffold C-52 after filtration and concentration.

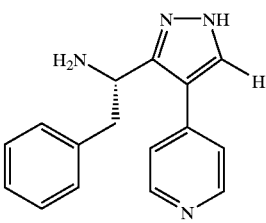

The following compounds C-53 through C-59 in Table C-3 are prepared according to the general procedure described above for the preparation of C-52.

TABLE C-3

| Example No. | Structure |
| --- | --- |
| C-53 | ![structure] |
| C-54 | ![structure] |
| C-55 | ![structure] |
| C-56 | ![structure] |
| C-57 | ![structure] |

TABLE C-3-continued

| Example No. | Structure |
|---|---|
| C-58 | 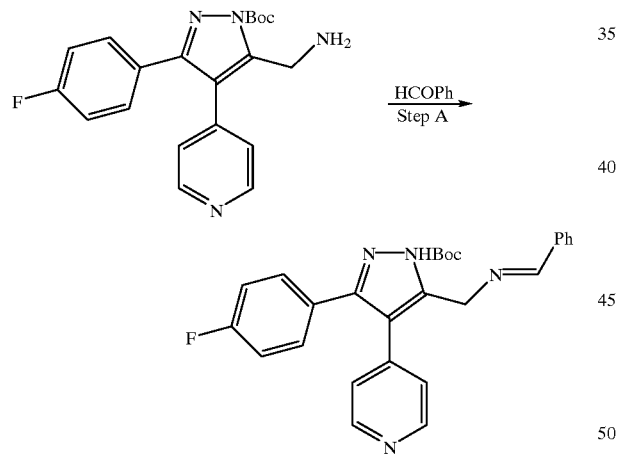 |
| C-59 | 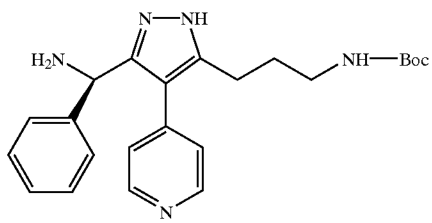 |

EXAMPLE C-60

Step A: A Boc protected pyridylpyrazole is treated with benzaldehyde in methylene chloride at room temperature in the presence of a drying agent for a period of time ranging from 1–24 h. Solvent is then evaporated and the resulting imine is used in step B without further purification.

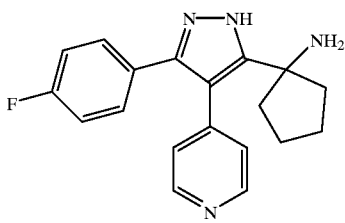

Step B: The pyridylpyrazole imine is dissolved in THF and stirred under nitrogen at temperatures ranging from −78 to −20° C. A base such as LDA, n-BuLi, or LiHMDS is added dropwise to the mixture which is then stirred for an additional 10 minutes to 3 h. Two equivalents of a methyl iodide are then added to the mixture and stirring is continued for several hours. The mixture is then quenched with acid and allowed to warm to room temperature and stirred several hours until cleavage of the Boc and the imine functions is complete. The pH is adjusted to 12 and then the mixture is extracted with an organic solvent, which is dried and evaporated. The crude pyridylpyrazole is then crystallized and/or chromatographed to give purified C-60.

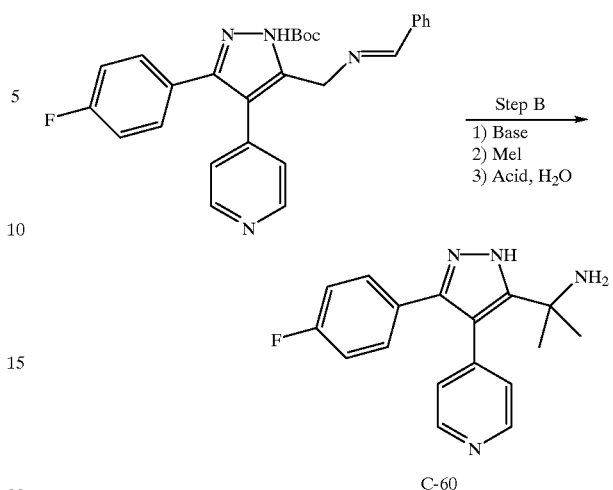

EXAMPLE C-61

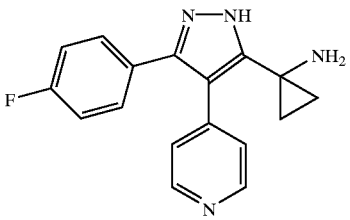

Example C-61 is prepared according to the method described in example C-60, substituting 1,4-dibromobutane for methyl iodide.

EXAMPLE C-62

Example C-62 is prepared according to the method described in example C-60, substituting 1,3-dibromoethane for methyl iodide.

EXAMPLE C-63

The synthesis of compound C-63 starts with the condensation reaction of bromomaleic anhydride B77 with 2,4-dimethoxybenzylamine in acetic acid and acetic anhydride. The maleimide B78 is then treated with 4'-fluoroacetophenone in the presence of catalytic amount $Pd_2(dba)_3$ and sodium t-butoxide to form the fluoroacetophenone substituted maleimide B79. B79 is then treated with tert-butoxybis(dimethylamino)methane to yield the a-ketoenamine B80. The a-ketoenamine B80 is condensed with hydrazine to form the N-protected maleimide pyrazole B81. The 2,4-dimethoxybenzyl group is cleaved with ceric ammonium nitrate (CAN) to give the title compound C-63.

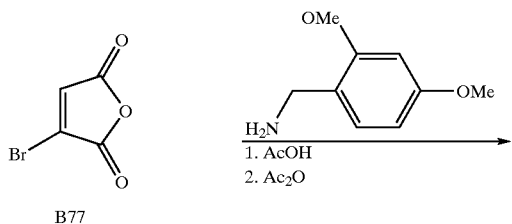

B77

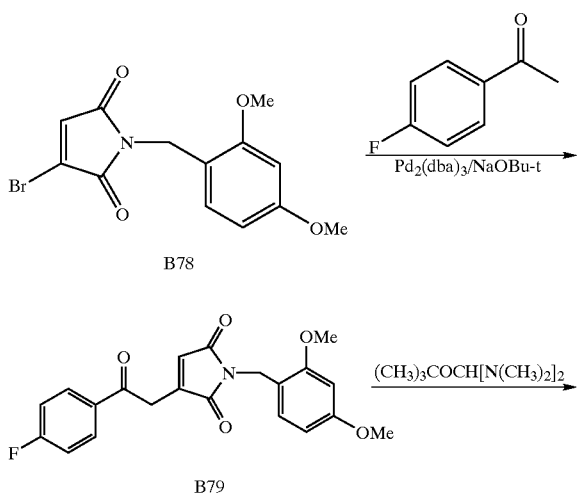

B78

B79

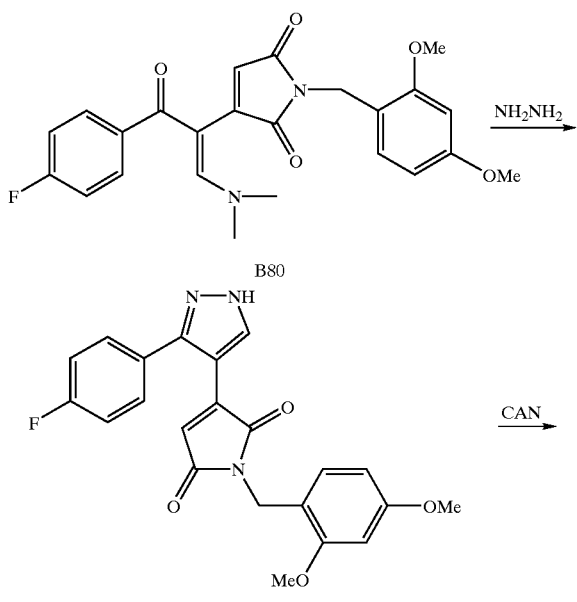

B80

B81

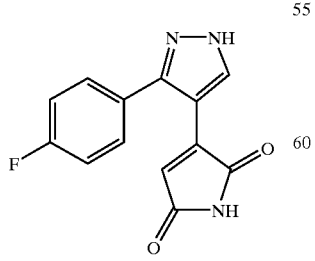

C-63

EXAMPLE C-64

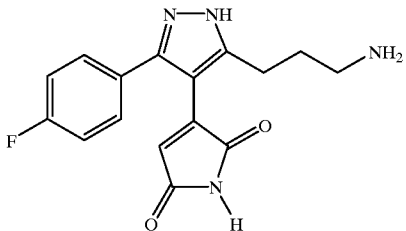

Using the method described in Schemes C-6 and C-7, Example 64 is prepared.

EXAMPLE C-65

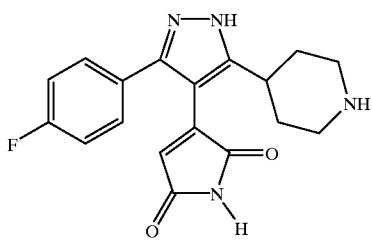

Using the method described in Schemes C-6 and C-7, Example 65 is prepared.

EXAMPLE C-66

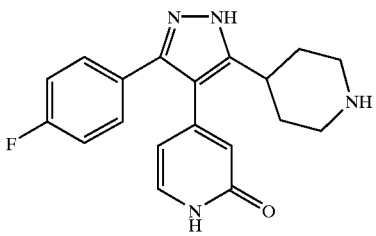

Using the method described in Schemes C-6 and C-7, Example C-66 is synthesized, substituting N-2,4-dimethoxybenzyl-4bromopyridone for B78.

EXAMPLE C-67

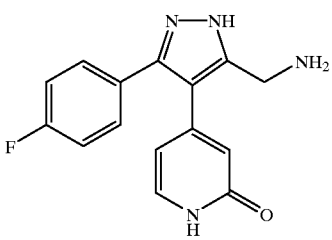

Using the method described in Schemes C-6 and C-7, Example C-67 is synthesized, substituting N-2,4-dimethoxybenzyl-4-bromopyridone for B78, and substituting N-Boc-glycyl N-hydroxysuccinimide for B82.

EXAMPLE C-68

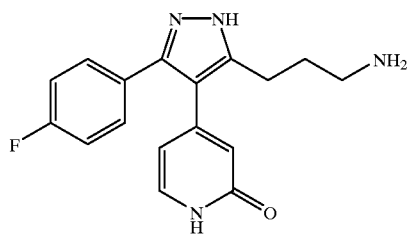

Using the method described in Schemes C-6 and C-7, Example C-68 is synthesized, substituting N-2,4-dimethoxybenzyl-4-bromopyridone for B78.

EXAMPLE C-69

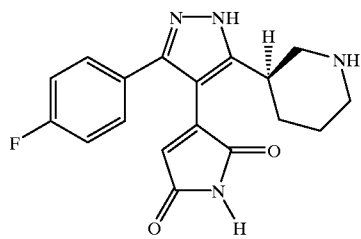

Using the method described in Schemes C-6 and C-7, Example 69 is prepared, substituting N-Boc-nipecotyl N-hydroxysuccinimide for B83.

EXAMPLE C-70

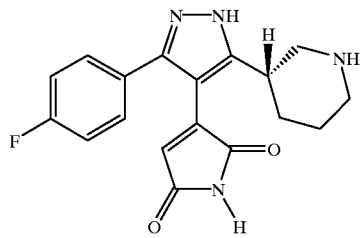

Using the method described in Schemes C-6 and C-7, Example 70 is prepared, substituting N-Boc-nipecotyl N-hydroxysuccinimide for B83.

EXAMPLE C-71

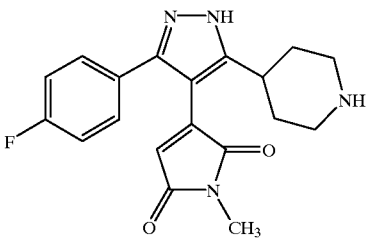

Using the method described in Schemes C-6 and C-7, Example 71 is prepared, substituting N-methyl-3-bromomaleimide for B78.

EXAMPLE C-72

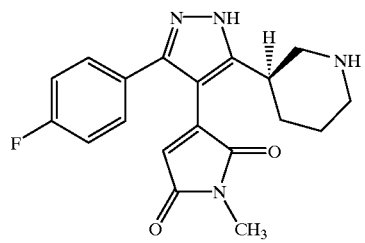

Using the method described in Schemes C-6 and C-7, Example 72 is prepared, substituting N-methyl-3-bromomaleimide for B78, and substituting N-Boc-nipecotyl N-hydroxysuccinimide for B83.

EXAMPLE C-73

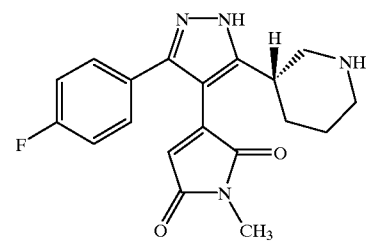

Using the method described in Schemes C-6 and C-7, Example 73 is prepared, substituting N-methyl-3-bromomaleimide for B78 and substituting N-Boc-nipecotyl N-hydroxysuccinimide for B83.

General Synthetic Procedures

Scheme C-8 illustrates a general method that can be used for the introduction of various groups on an unsubstituted nitrogen atom that is present as part of pyrazole (Cviii) with appropriately substituted aldehydes ($R_{302}CHO$) or ketones ($R_{302}COR_{303}$) in the presence of a reducing agent such as sodium cyanoborohydride or sodium triacetoxyborohydride affords the desired products (Cix). Typical conditions for the reductive alkylation include the use of an alcoholic solvent at temperatures ranging from 20° C. to 80° C. In Scheme C-8, $R_{302}$ and $R_{303}$ are selected from but not limited to alkyl, benzyl, substituted benzyl, arylalkyl, heteroarylalkyl.

Scheme C-8

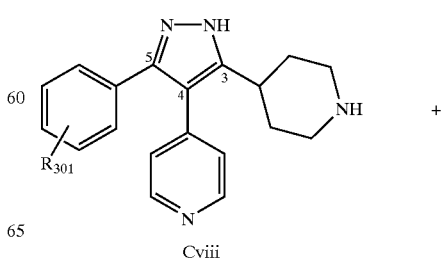

Cviii

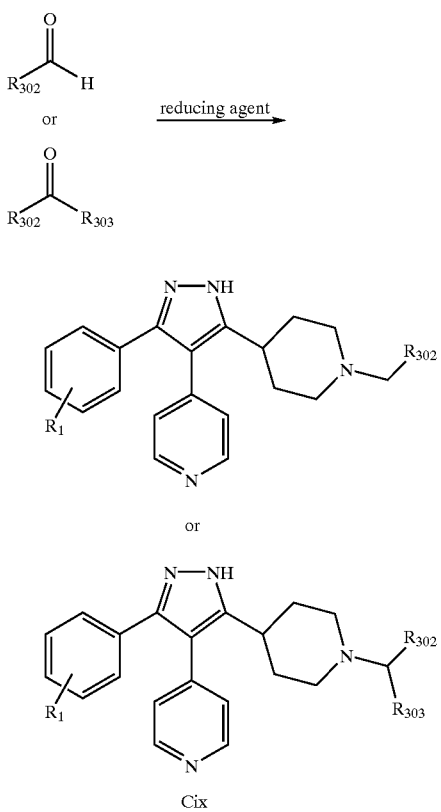

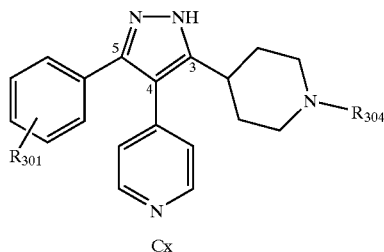

Cx

Typical conditions for the alkylation include reaction with the suitable base in a polar aprotic solvent such as acetonitrile, dimethylformamide, dimethylacetamide or dimethyl sulfoxide at temperatures ranging from 20° C. to 150° C. Typical $R_{304}$ substituents are selected from but are not limited to alkyl, substituted benzyl, heteroaromatic, substituted heteroalkyl and substituted heteroarylalkyl groups.

Compounds containing acyl, sulfonyl or ureidyl groups at the nitrogen atom can be prepared as shown in Scheme C-10. Treatment of the pyrazole Cviii with a suitable acylating agent in the presence of a base such as N-methylmorpholine, triethylamine, diisopropylethylamine or dimethylamino pyridine in an organic solvent such as dichloromethane, dichloroethane or dimethylformamide at temperatures ranging from 20° C. to 120° C. affords the desired acylated pyrazoles (Cxi). Suitable acylating agents include acid halides, activated esters of acids such as the N-hydroxysuccinimde esters, p-nitrophenyl esters, pentafluorophenyl esters, sulfonyl halides, isocyanates, and isothiocyanates.

Scheme C-9 illustrates another method for introduction of substituents on the unsubstituted nitrogen atom present as part of the C-3 position of the pyrazole (Cviii). Treatment of the pyrazole (Cviii) with a suitable alkylating agent ($R_{304}X$) such as an alkyl chloride, alkyl bromide, alkyl iodide or with an alkyl methanesulfonate or alkyl p-toluenesulfonate in the presence of a suitable base affords the desired alkylated pyrazoles (Cx). Examples of suitable bases include diisopropylethylamine, triethylamine, N-methylmorpholine, potassium carbonate and potassium bicarbonate.

Scheme C-9

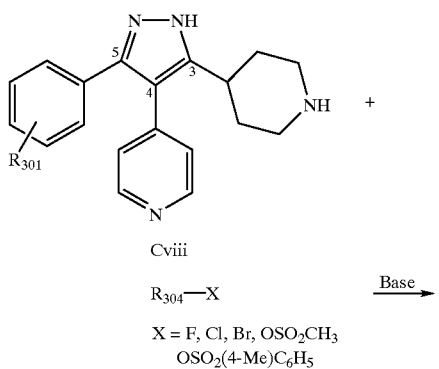

Cviii $R_{304}$—X $\xrightarrow{\text{Base}}$

X = F, Cl, Br, $OSO_2CH_3$
$OSO_2(4\text{-Me})C_6H_5$

Scheme C-10

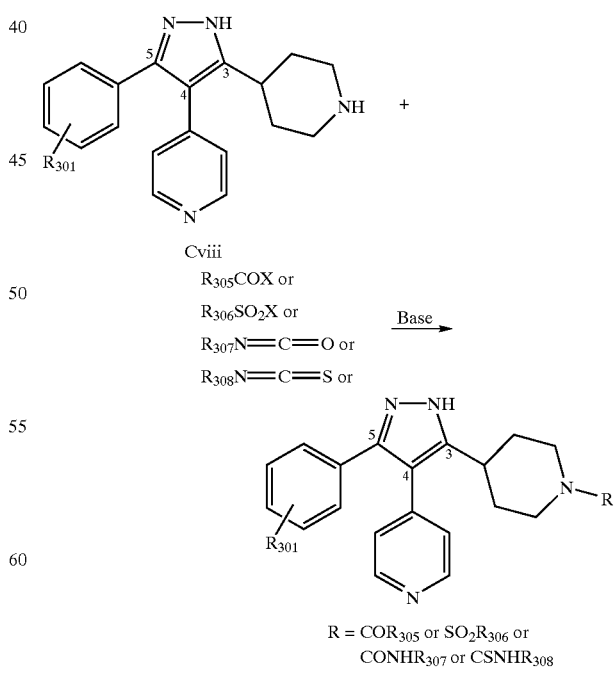

R = $COR_{305}$ or $SO_2R_{306}$ or
$CONHR_{307}$ or $CSNHR_{308}$

Cxi

A general synthesis of 2-substituted pyrimidinylpyrazole compounds of type Cxv is shown in Scheme C-11.

Step A

4-Methyl-2-methylmercaptopyrimidine is treated with a base selected from but not limited to n-BuLi, LDA, LiHMDS, t-BuOK, NaH in an organic solvent such as THF, ether, t-BuOH, dioxane from −78° C. to 50° C. for a period of time from 30 minutes to 5 hours. The resulting 4-methyl anion is then added to a solution of an appropriate ester B88. The reaction is allowed to stir from 30 minutes to 48 hours during which time the temperature may range from 0° C. to 100° C. The reaction mixture is then poured into water and extracted with an organic solvent. After drying and removal of solvent the desired monoketone B89 is isolated as a crude solid which can be recrystallized or purified by chromatography.

Step B

Monoketone B89 is treated with a base selected from but not limited to n-BuLi, LDA, LiHMDS, t-BuOK, NaH, $K_2CO_3$ or $Cs_2CO_3$ in an organic solvent such as THF, ether, t-BuOH, dioxane, toluene or DMF from −78° C. to 50° C. for a period of time from 30 minutes to 5 hours. A solution of an appropriately activated ester of a carboxylic acid $CbzNR^H-(CH_2)_nCR^F(R^G)-COOH$ or $BocNR^H-(CH_2)_nCR^F(R^G)-COOH$, preferably but not limited to the N-hydroxysuccinimide ester B90 is then added to the monoketone anion while maintaining the temperature between 0° C. to 100° C. The reaction is allowed to stir at the specified temperature for a period of time ranging from 30 minutes to 48 hours. The resulting pyrimidine diketone intermediate B91 is utilized without further purification in Step C.

Step C

The solution or suspension containing the diketone intermediate B91 is quenched with water and the pH adjusted to between 4 and 8 using an acid chosen from AcOH, $H_2SO_4$, HCl or $HNO_3$ while maintaining the temperature between 0° C. to 40° C. Hydrazine or hydrazine monohydrate is then added to the mixture while maintaining the temperature between 0° C. to 40° C. The mixture is stirred for a period of 30 minutes to 16 hours maintaining the temperature between 20° C. to 50° C., poured into water and extracted with an organic solvent. The pyrimidinyl pyrazole CxiiBoc or CxiiCbz is obtained as crude solid which is purified by chromatography or crystallization.

Step D

The 2-methylmercapto group in the pyrimidinyl pyrazole (CxiiBoc or CxiiCbz) is oxidized to the 2-methylsulfone (where n=2) or the 2-methylsulfoxide (where n=1) using either Oxone or m-chloroperbenzoic acid as an oxidizing agent in a suitable solvent at temperatures ranging from 25° C. to 100° C. Solvents of choice for the oxidation include dichloromethane, acetonitrile, tetrahydrofuran or hydroalcoholic mixtures. The 2-methylsulfone (n=2) or the 2-methylsulfoxide (n=1) (CxiiiBoc or CxiiiCbz) is purified by crystallization or chromatography.

Step E

The 2-methylsulfone/2-methylsulfoxide group in CxiiiBoc or CxiiiCBz is conveniently displaced with various amines or alkoxides at temperatures ranging from 20° C. to 200° C. in solvents that include but are not limited to dimethylformamide, acetonitrile, tetrahydrofuran and dioxane. The alkoxides can be generated from their alcohols by treatment with a base selected from but not limited to sodium hydride, lithium hexamethyldisilazide, potassium tertiary-butoxide in solvents such as tetrahydrofuran, dimethylformamide and dioxane at temperatures ranging from 0° C. to 100° C. The resulting 2-amino or 2-oxo derivatives (CxivBoc or CxivCbz) are purified by either chromatography or crystallization.

Step F

The carbamate protecting groups from CxivBoc or CxivCbz are removed to afford the desired compounds Cxv containing either a free primary amine ($R^H$ is hydrogen) or a free secondary amine ($R^H$ is not equal to hydrogen). The Boc protecting groups are cleaved utilizing either trifluoroacetic acid in methylene chloride or hydrochloric acid in dioxane at room temperature for several hours. The Cbz protecting groups are cleaved using hydrogen gas at atmospheric or higher pressures and a catalyst (palladium on charcoal) in an alcoholic solvent. The resulting amines Cxv are then crystallized or purified by chromatography.

Scheme C-11

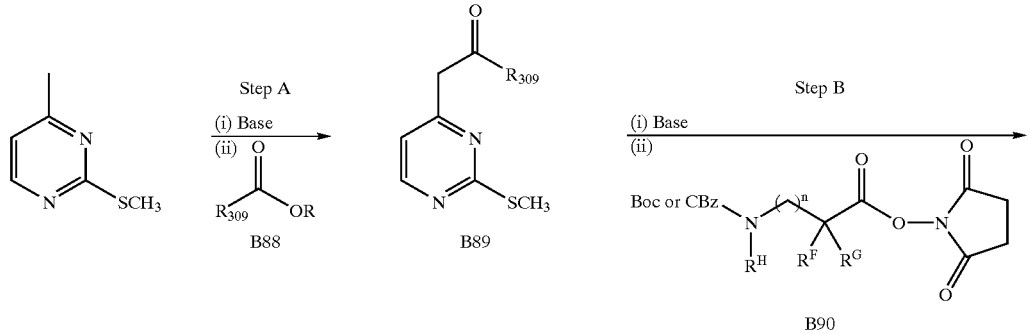

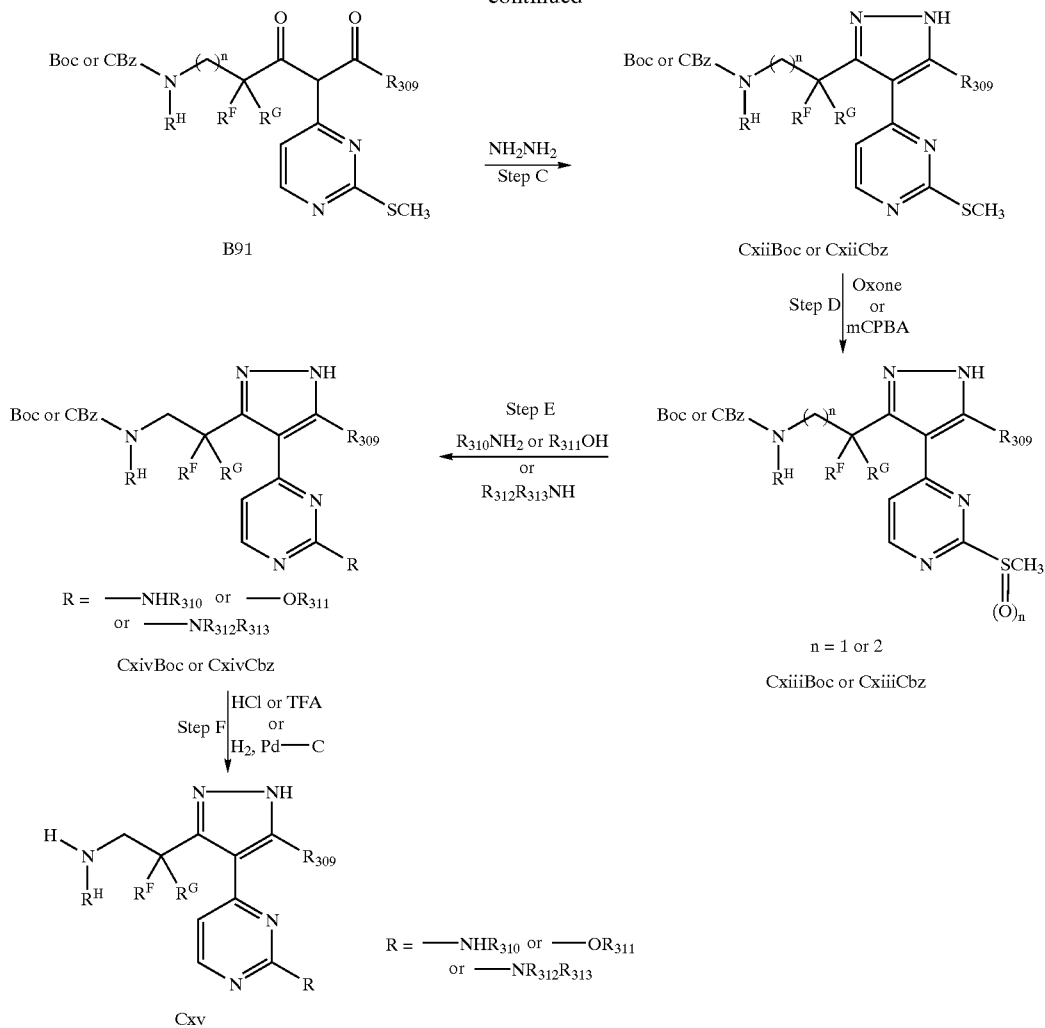

The following examples contain detailed descriptions of the methods of preparation of compounds that form part of the invention. These descriptions are presented for illustrative purposes only and are not intended as a restriction on the scope of the invention. All compounds showed NMR spectra consistant with their assigned structures.

EXAMPLE C-74

5-(4-piperidyl)-4-(4-pyridyl)-3-(4-chlorophenyl)pyrazole

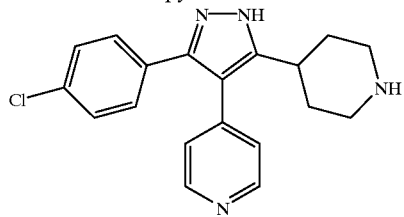

By following the method of Example C-1 and substituting methyl-4-chlorobenzoate for ethyl-4-fluorobenzoate and N-t-butoxycarbonyl-isonipecotyl N-hydroxysuccinimide for N-benyloxycarbonyl-glycinyl N-hydroxysuccinimide the title compound was prepared as the N-t-butoxycarbonyl protected compound. The deprotection of the N-t-butoxycarbonyl intermediate was accomplished with 4 N HCl in dioxane to afford the title compound as the hydrochloride salt: $^1$HNMR (d$_6$-DMSO) δ8.57 (d, J=4.83 Hz, 2 H), 7.41 (d, J=8.26 Hz, 2 H), 7.29 (d, J=8.26 Hz, 2 H), 7.20 (d, J=4.63 Hz, 2 H), 3.18 (bd, J=12.08 Hz, 2 H), 2.88 (m, 1 H), 2.76 (m, 2 H), 1.82 (bs, 4 H). MS (M+H): 339 (base peak).

EXAMPLE C-75

5-(N-methyl-4-piperidyl)-4-(4-pyridyl)-3-(4-chlorophenyl)pyrazole

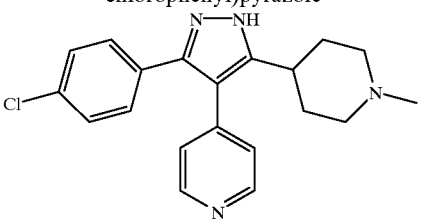

To a solution of 5-(4-piperidyl)-4-(4-pyridyl)-3-(4-chlorophenyl)pyrazole hydrochloride (Example C-74) (25 g, 61 mmol) in 140 mL of formic acid (96%) was added 50 g of formaldehyde (37%). The solution was stirred at 75° C.

for 48 h and was cooled to room temperature. The excess formic acid was removed under reduced pressure and the residue was dissolved in 100 mL of water. The solution was added to concentrated $NH_4OH/H_2O$ and the mixture was extracted with ethyl acetate (3×200 mL). The combined organic layers were washed with brine (1×250 mL) and was dried over $Na_2SO_4$. The solution was filtered and concentrated to leave a white solid. The solid was triturated with ether and was filtered to afford the title compound: MS (M+H): 353 (base peak).

EXAMPLE C-76

5-(N-acetyl-4-piperidyl)-4-(4-pyridyl)-3-(4-chlorophenyl)pyrazole

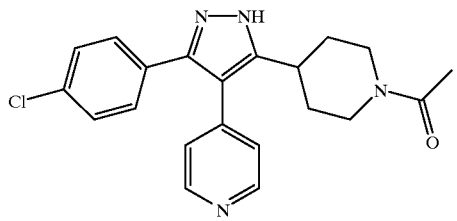

To a stirred suspension of 5-(4-piperidyl)-4-(4-pyridyl)-3-(4-chlorophenyl)pyrazole hydrochloride (Example C-74) (1 g, 2.4 mmol) in 24 mL of $CH_2Cl_2$ was added 4-dimethylamino pyridine (0.88 g, 7.2 mmol) and acetyl chloride (0.21 g, 2.6 mmol). The solution was stirred for 3 h and the solvent was removed under reduced pressure. The residue was treated with saturated $NH_4OH$ (20 mL) and the suspension was extracted with ethyl acetate (3×30 mL). The combined extracts were washed with brine (1×50 mL)), dried over $MgSO_4$, filtered and concentrated to leave a solid. The solid was triturated with ether and was filtered to leave the title compound: MS (M+H): 381 (base peak).

EXAMPLE C-77

5-(N-methoxyacetyl-4-piperidyl)-4-(4-pyridyl)-3-(4-chlorophenyl)pyrazole

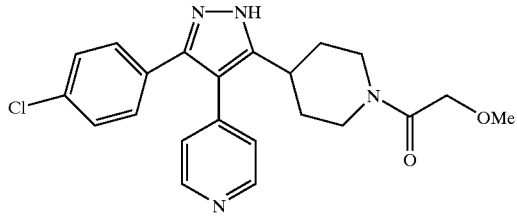

By following the method of Example C-76 and substituting methoxy acetyl chloride for acetyl chloride the title compound was prepared: $^1$HNMR (DMSO-$d_6$) δ8.75 (d, J=6.72 Hz, 2 H), 7.70 (d, J=6.72 Hz, 2 H), 7.38 (d, J=8.60 Hz, 2 H), 7.29 (dd, J=6.72, 1.88 Hz, 2 H), 4.40 (d, J=11.8 Hz, 1 H), 4.05 (m, 2 H), 3.70 (d, J=12.70 Hz, 1 H), 3.25 (s, 3 H), 3.0 (m, 2 H), 2.55 (m, 1 H), 1.7 (m, 4 H). MS (M+H): 411 (base peak).

EXAMPLE C-78

5-(N-methylsulfonyl-4-piperidyl)-4-(4-pyridyl)-3-(4-chlorophenyl)pyrazole

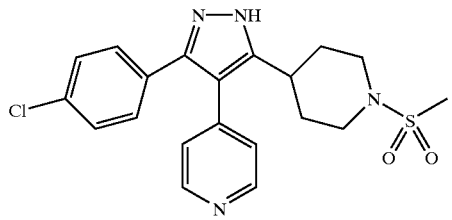

By following the method of Example C-76 and substituting methylsulfonyl chloride (2.0 equivalents) for acetyl chloride the title compound was prepared: $^1$HNMR (DMSO-$d_6$) δ8.70 (d, J=6.72 Hz, 2 H), 7.72 (d, J=6.72 Hz, 2 H), 7.38 (d, J=7.66 Hz, 2 H), 7.30 (dd, J=6.72, 1.88 Hz, 2 H), 3.58 (bd, J=11.8 Hz, 2 H), 2.87 (m, 1 H), 2.82 (s, 3 H), 2.72 (m, 2 H), 1.85 (m, 4 H). MS (M+H): 417 (base peak).

EXAMPLE C-79

5[N-methoxyethyl-4-piperidyl]-4-(4-pyridyl)-3-(4-chlorophenyl)pyrazole

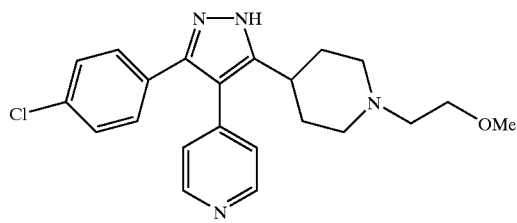

To a stirred suspension of 5-(4-piperidyl)-4-(4pyridyl)-3-(4-chlorophenyl)pyrazole hydrochloride (Example C-74) (500 mg, 1.2 mmol) in 12 mL of DMF was added Hunig's base (790 mg, 6.1 mmol) and 2-bromoethyl methyl ether (850 mg, 6.1 mmol). The solution was stirred at room temperature for 5 days. The solution was poured onto 2.5 N NaOH and was extracted with ethyl acetate (3×100 mL). The combined extracts were washed with water (3×100 mL) and brine (1×100 mL). The organic phase was dried over $Na_2SO_4$ and was filtered. The solvent was removed under reduced pressure to leave a solid. The solid was triturated and filtered to leave the title compound: $^1$HNMR (CDCl$_3$) δ8.63 (d, J=4.23 Hz, 2 H), 7.28 (m, 4 H), 7.14 (d, J=4.43 Hz, 2 H), 3.57 (t, J=5.24 Hz, 2 H), 3.38 (s, 3 H), 3.14 (bd, J=10.1 Hz, 2 H), 2.79 (m, 1 H), 2.68 (t, J=5.04, 2 H), 2.08 (m, 4 H), 1.92 (m, 2 H). MS (M+H): 397 (base peak).

EXAMPLE C-80

5-(N-allyl-4-piperidyl)-4-(4-pyridyl)-3-(4-chlorophenyl)pyrazole

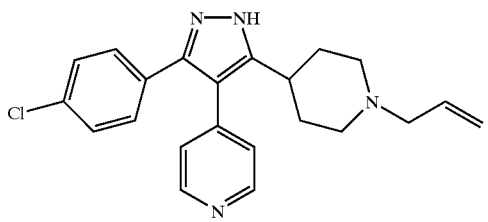

By following the method of example C-79 and substituting allyl bromide for 2-bromoethyl methyl ether the title compound was prepared: MS (M+H): 379 (base peak)

EXAMPLE C-81

5-(N-propargyl-4-piperidyl)-4-(4-pyridyl)-3-(4-chlorophenyl)pyrazole

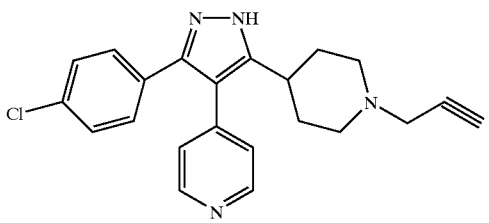

By following the method of example C-79 and substituting propargyl bromide for 2-bromoethyl methyl ether the title compound was prepared: MS (M+H): 377 (base peak)

EXAMPLE C-82

5-[N-(2-methylthiazolyl)-4-piperidyl]-4-(4-pyridyl)-3-(4-chlorophenyl)pyrazole

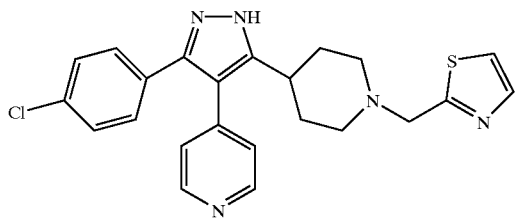

To a suspension of 5-(4-piperidyl)-4-(4-pyridyl)-3-(4-chlorophenyl)pyrazole hydrochloride (Example C-74) in 12 mL of MeOH was added trimethyl orthoformate (2.6 g, 24.4 mmol) and 2-thiazolecarboxaldehyde (1.4 g, 12.2 mmol). The suspension was stirred at room temperature for 2 h. To this mixture was added NaCNBH$_3$ (1.5 g, 24.4 mmol) and the resulting suspension was stirred at room temperature for 7 days. The mixture was poured onto 2.5 N NaOH and was extracted with ethyl acetate (2×100 mL). The combined extracts were washed with brine (1×100 mL), dried over Na$_2$SO$_4$, filtered and concentrated to leave a solid. This solid was triturated with ether and filtered to afford the title compound: MS (M+H): 436 (base peak).

EXAMPLE C-83

5-(4-piperidyl)-4-(4-pyridyl)-3-[4-(trifluoromethyl)phenyl]pyrazole

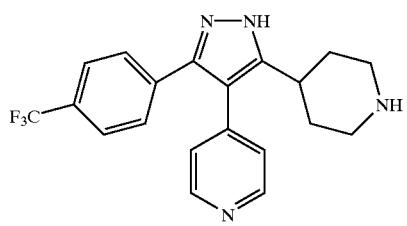

By following the method of Example C-1 and substituting methyl-4-(trifluoromethyl)benzoate for ethyl-4-fluorobenzoate and N-t-butoxycarbonyl-isonipecotyl N-hydroxysuccinimide for N-benyloxycarbonyl-glycinyl N-hydroxysuccinimide the title compound was prepared as the N-t-butoxycarbonyl protected compound. The deprotection of the N-t-butoxycarbonyl intermediate was accomplished with 4 N HCl in dioxane to afford the title compound as its hydrochloride salt: MS (M+H): 373 (base peak).

EXAMPLE C-84

5-(N-methyl-4-piperidyl)-4-(4-pyridyl)-3-[4-(trifluoromethyl)phenyl]pyrazole

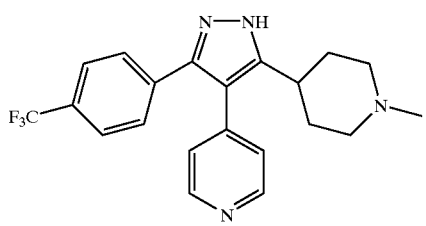

By following the method of Example C-75 and substituting 5-(4-piperidyl)-4-(4-pyridyl)-3-[4-(trifluoromethyl) phenyl]pyrazole hydrochloride (Example C-83) for 5-(4-piperidyl)-4-(4-pyridyl)-3-(4-chlorophenyl)pyrazole hydrochloride (Example C-74) the title compound was prepared: MS (M+H): 387 (base peak).

EXAMPLE C-85

5-[N-(2-propyl)-4-piperidyl]-4-(4-pyridyl)-3-[4-(trifluoromethyl)phenyl]pyrazole

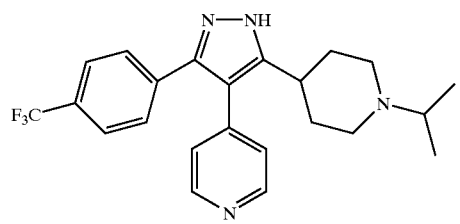

To a solution of 5-(4-piperidyl)-4-(4-pyridyl)-3-[4-(trifluoromethyl)phenyl]pyrazole (Example C-83) (300 mg, 0.7 mmol) in 50 mL of acetone was added 1 mL of AcOH and NaBH(OAc)$_3$ (15 g, 70.8 mmol). The mixture was warmed to reflux and was stirred for 5 days. The reaction mixture was poured onto 100 mL of 2.5 N NaOH and was extracted with ethyl acetate (2×100 mL). The extracts were combined and washed with brine (1×100 mL). The organic phase was dried over Na$_2$SO$_4$, filtered, and concentrated to afford the title compound: MS (M+H): 415 (base peak).

EXAMPLE C-86

5-(4-piperidyl)-4-(4-pyridyl)-3-[3-(trifluoromethyl)phenyl]pyrazole

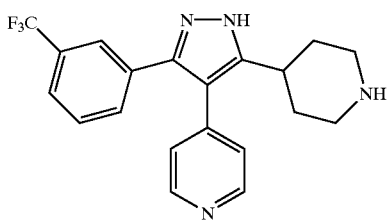

By following the method of Example C-1 and substituting methyl-3-(trifluoromethyl)benzoate for ethyl-4-fluorobenzoate and N-t-butoxycarbonyl-isonipecotyl N-hydroxysuccinimide for N-benyloxycarbonyl-glycinyl N-hydroxysuccinimide the title compound was prepared as the N-t-butoxycarbonyl protected compound. The deprotection of the N-t-butoxycarbonyl intermediate was accomplished with 4 N HCl in dioxane to afford the title compound as its hydrochloride salt: MS (M+H): 373 (base peak).the pyrazole C-3 substituent (Cviii). Treatment of the

EXAMPLE C-87

5-(N-methyl-4-piperidyl)-4-(4-pyridyl)-3-[3-(trifluoromethyl)phenyl]pyrazole

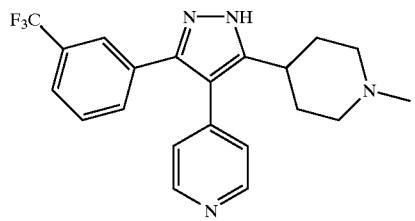

By following the method of Example C-75 and substituting 5-(4-piperidyl)-4-(4-pyridyl)-3-[3-(trifluoromethyl)phenyl]pyrazole hydrochloride (Example C-86) for 5-(4-piperidyl)-4-(4-pyridyl)-3-(4-chlorophenyl)pyrazole hydrochloride (Example C-74) the title compound was prepared: MS (M+H): 387 (base peak).

EXAMPLE C-88

5-(4-piperidyl)-4-(4-pyridyl)-3-(3-chlorophenyl)pyrazole

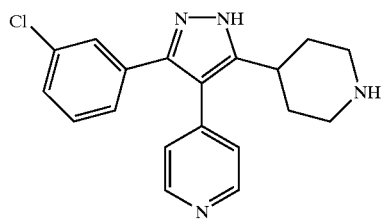

By following the method of Example C-1 and substituting methyl-3-chlorobenzoate for ethyl-4-fluorobenzoate and N-t-butoxycarbonyl-isonipecotyl N-hydroxysuccinimide for N-benyloxycarbonyl-glycinyl N-hydroxysuccinimide the title compound was prepared as the N-t-butoxycarbonyl protected compound. The deprotection of the N-t-butoxycarbonyl intermediate was accomplished with 4 N HCl in dioxane to afford the title compound: MS (M+H): 339 (base peak).

EXAMPLE C-89

5-(N-methyl-4-piperidyl)-4-(4-pyridyl)-3-(3-chlorophenyl)pyrazole

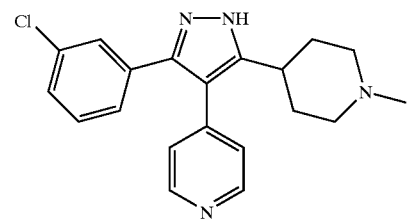

By following the method of Example C-75 and substituting 5-(4-piperidyl)-4-(4-pyridyl)-3-(3-chlorophenyl)pyrazole hydrochloride (Example C-88) for 5-(4-piperidyl)-4-(4-pyridyl)-3-(4-chlorophenyl)pyrazole hydrochloride (Example C-74) the title compound was prepared: MS (M+H): 353 (base peak).

EXAMPLE C-90

5-(3-piperidyl)-4-(4-pyridyl)-3-(4-fluorophenyl) pyrazole

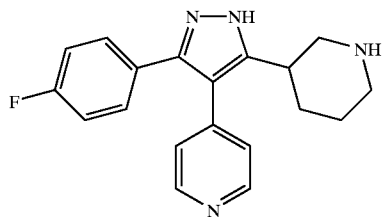

By following the method of Example C-1 and substituting N-t-butoxycarbonyl-nipecotyl N-hydroxysuccinimide for N-benyloxycarbonyl-glycinyl N-hydroxysuccinimide the title compound was prepared as the N-t-butoxycarbonyl protected compound. The deprotection of the N-t-butoxycarbonyl intermediate was accomplished with 4 N HCl in dioxane to afford the title compound as its hydrochloride salt: MS (M+H): 323 (base peak).

EXAMPLE C-91

5-(N-methyl-3-piperidyl)-4-(4-pyridyl)-3-(4-fluorophenyl)pyrazole

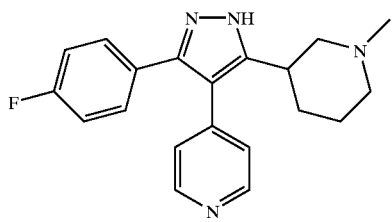

By following the method of Example C-75 and substituting 5-(3-piperidyl)-4-(4-pyridyl)-3-(4-fluorophenyl) pyrazole hydrochloride (Example C-90) for 5-(4-piperidyl)-4-(4-pyridyl)-3-(4-chlorophenyl)pyrazole hydrochloride (Example C-74) the title compound was prepared: MS (M+H): 337 (base peak).

EXAMPLE C-92

5-cis-(4-aminocyclohexyl)-4-(4-pyridyl)-3-(4-chlorophenyl)pyrazole

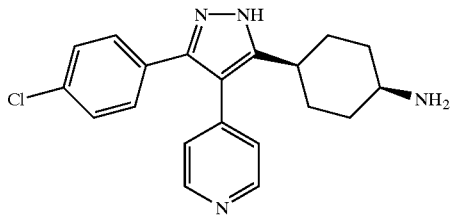

By following the method of Example C-1 and substituting methyl-4-chlorobenzoate for ethyl- 4-fluorobenzoate and N-t-butoxycarbonyl-cis-4-aminocyclohexanoyl N-hydroxysuccinimide for N-benyloxycarbonyl-glycinyl N-hydroxysuccinimide the title compound was prepared as the N-t-butoxycarbonyl protected compound. The deprotec-tion of the N-t-butoxycarbonyl intermediate was accomplished with 4 N HCl in dioxane to afford the title compound: $^1$HNMR ($d_6$-DMSO) δ8.56 (d, J=6.04 Hz, 2 H), 7.39 (d, J=8.66 Hz, 2 H), 7.31 (d, J=8.46 Hz, 2 H), 7.17 (d, J=5.84 Hz, 2 H), 3.05 (m, 1 H), 2.62 (m, 1 H), 1.99 (m, 2 H), 1.53 (m, 6 H). MS (M+H): 353 (base peak).

EXAMPLE C-93

5-cis-(4-N,N-dimetylaminocyclohexyl)-4-(4-pyridyl)-3-(4-chlorophenyl)pyrazole

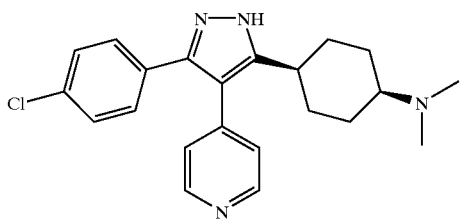

By following the method of Example C-75 and substituting 5-cis-(4-aminocyclohexyl)-4-(4-pyridyl)-3-(4-chlorophenyl)pyrazole (Example C-92) for 5-(4-piperidyl)-4-(4-pyridyl)-3-(4-chlorophenyl)pyrazole hydrochloride (Example C-74) the title compound was prepared: MS (M+H): 381 (base peak).

EXAMPLE C-94

5-[cis-4-N-(2-propyl)aminocyclohexyl]-4-(4-pyridyl)-3-(4-chlorophenyl)pyrazole

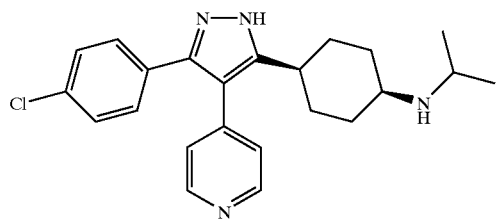

To a slurry of 5-cis-(4-aminocyclohexyl)-4-(4-pyridyl)-3-(4-chlorophenyl)pyrazole (Example C-92) (1.0 g, 2.8 mmol, 1.0 eq) in methylene chloride (28 mL) was added acetone (0.5 mL), acetic acid (0.5 mL) and solid sodium triacetoxyborohydride. The slurry was stirred for 5 h and the volatiles were removed. The residue was partitioned between 2.5 M NaOH (25 mL) and ethyl acetate (25 mL) and the aqueous layer was extracted with ethyl acetate (3×25 mL). The combined organic layer was washed with brine (50 mL), dried over $MgSO_4$ and evaporated. The residue was triturated with ether to yield the title compound as a white powder: $^1$HNMR ($d_6$-DMSO) δ8.56 (d, J=5.84 Hz, 2H), 7.40 (d, J=8.26 Hz, 2H), 7.30 (d, J=8.66 Hz, 2H), 7.18 (d, J=5.64 Hz, 2H), 2.95 (m, 2H), 2.72 (m, 1H), 1.90 (m, 2H), 1.73 (m, 2H), 1.55 (m, 4H), 1.07 (d, J=5.64 Hz, 6H). MS (M+H): 395 (base peak).

EXAMPLE C-95

5-cis-[4-N-(acetyl)aminocyclohexyl]-4-(4-pyridyl)-3-(4-chlorophenyl)pyrazole

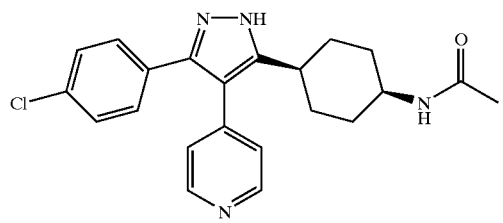

By following the method of Example C-76 and substituting 5-cis-(4-aminocyclohexyl)-4-(4-pyridyl)-3-(4-chlorophenyl)pyrazole (Example C-92) for 5-(4-piperidyl)-4-(4-pyridyl)-3-(4-chlorophenyl)pyrazole hydrochloride (Example C-74) the title compound was prepared: MS (M+H): 395 (base peak).

EXAMPLE C-96

5-cis-[4-N-(methoxyacetyl)aminocyclohexyl]-4-(4-pyridyl)-3-(4-chlorophenyl)pyrazole

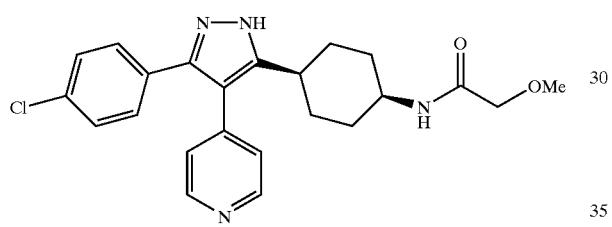

By following the method of Example C-76 and substituting 5-cis-(4-aminocyclohexyl)-4-(4-pyridyl)-3-(4-chlorophenyl)pyrazole (Example C-92) for 5-(4-piperidyl)-4-(4-pyridyl)-3-(4-chlorophenyl)pyrazole hydrochloride (Example C-74) and methoxy acetyl chloride for acetyl chloride the title compound was prepared: MS (M+H): 425 (base peak).

EXAMPLE C-97

5-cis-[4-N-(methylsulfonyl)aminocyclohexyl]-4-(4-pyridyl)-3-(4-chlorophenyl)pyrazole

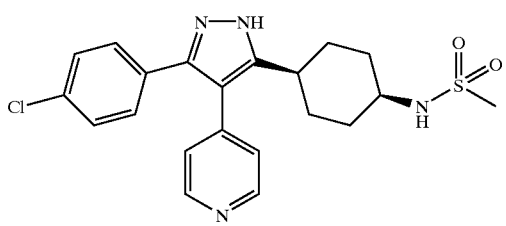

By following the method of Example C-76 and substituting 5-cis-(4-aminocyclohexyl)-4-(4-pyridyl)-3-(4-chlorophenyl)pyrazole (Example C-92) for 5-(4-piperidyl)-4-(4-pyridyl)-3-(4-chlorophenyl)pyrazole hydrochloride (Example C-74) and methylsulfonyl chloride for acetyl chloride the title compound was prepared: MS (M+H): 431 (base peak).

EXAMPLE C-98

5-cis-(4-aminocyclohexyl)-4-(4-pyridyl)-3-(4-fluorophenyl)pyrazole

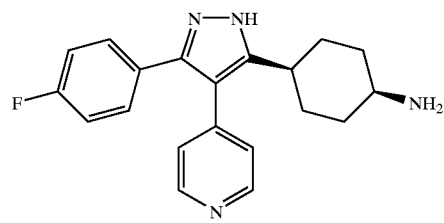

By following the method of Example C-1 and substituting N-t-butoxycarbonyl-cis-4-aminocyclohexanoyl N-hydroxysuccinimide for N-benyloxycarbonyl-glycinyl N-hydroxysuccinimide the title compound was prepared as the N-t-butoxycarbonyl protected compound. The deprotection of the N-t-butoxycarbonyl intermediate was accomplished with 4 N HCl in dioxane to afford the title compound: MS (M+H): 337 (base peak).

EXAMPLE C-99

5-(cis-4-N,N-dimethylaminocyclohexyl)-4-(4-pyridyl)-3-(4-fluorophenyl)pyrazole

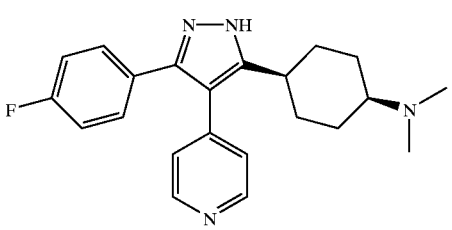

By following the method of Example C-75 and substituting 5-cis-(4-aminocyclohexyl)-4-(4-pyridyl)-3-(4-fluorophenyl)pyrazole (Example C-98) for 5-(4-piperidyl)-4-(4-pyridyl)-3-(4-chlorophenyl)pyrazole hydrochloride (Example C-74) the title compound was prepared: MS (M+H): 365 (base peak).

EXAMPLE C-100

5-cis-[4-N-(2-propyl)aminocyclohexyl]-4-(4-pyridyl)-3-(4-fluorophenyl)pyrazole

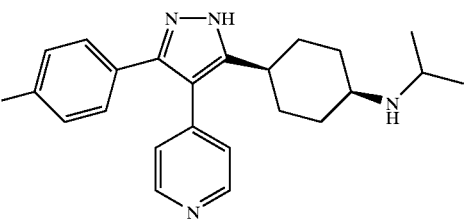

By following the method of Example C-94 and substituting cis-5-(4-aminocyclohexyl)-4-(4-pyridyl)-3-(4-fluorophenyl)pyrazole (Example C-98) for 5-(cis-4-n-(2-propyl)aminocyclohexyl)-4-(4-pyridyl)-3-(4-chlorophenyl)pyrazole (Example C-92) the title compound was prepared: MS (M+H): 379 (base peak).

EXAMPLE C-101

5-cis-(4-aminocyclohexyl)-4-(4-pyridyl)-3-[4-(trifluoromethyl)phenyl]pyrazole

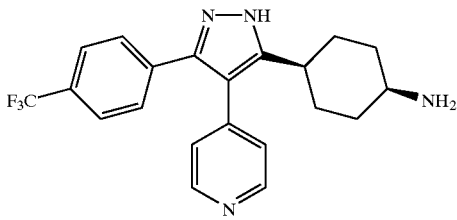

By following the method of Example C-1 and substituting methyl-4-(trifluoromethyl)benzoate for ethyl-4-fluorobenzoate and N-t-butoxycarbonyl-cis-4-aminocyclohexanoyl N-hydroxysuccinimide for N-benyloxycarbonyl-glycinyl N-hydroxysuccinimide the title compound was prepared as the N-t-butoxycarbonyl protected compound. The deprotection of the N-t-butoxycarbonyl intermediate was accomplished with 4 N HCl in dioxane to afford the title compound: MS (M+H): 387 (base peak).

EXAMPLE C-102

5-cis-(4-N,N-dimethylaminocyclohexyl)-4-(4-pyridyl)-3-[4-(trifluoromethyl)phenyl]pyrazole

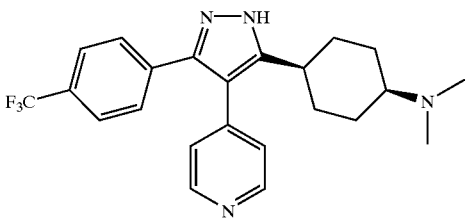

By following the method of Example C-75 and substituting 5-cis-(4-aminocyclohexyl)-4-(4-pyridyl)-3-[4-(trifluoromethyl)phenyl]pyrazole (Example C-101) for 5-(4-piperidyl)-4-(4-pyridyl)-3-(4-chlorophenyl)pyrazole hydrochloride (Example C-74) the title compound was prepared: MS (M+H): 415 (base peak).

EXAMPLE C-103

5-cis-(4-aminocyclohexyl)-4-(4-pyridyl)-3-[3-(trifluoromethyl)phenyl]pyrazole

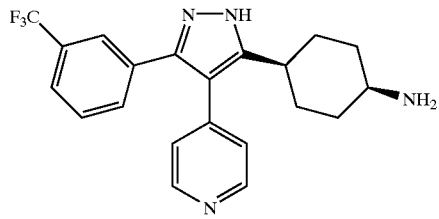

By following the method of Example C-1 and substituting methyl-3-(trifluoromethyl)benzoate for ethyl-4-fluorobenzoate and N-t-butoxycarbonyl-cis-4-aminocyclohexanoyl N-hydroxysuccinimide for N-benyloxycarbonyl-glycinyl N-hydroxysuccinimide the title compound was prepared as the N-t-butoxycarbonyl protected compound. The deprotection of the N-t-butoxycarbonyl intermediate was accomplished with 4 N HCl in dioxane to afford the title compound: MS (M+H): 387 (base peak).

EXAMPLE C-104

5-cis-(4-N,N-dimethylaminocyclohexyl)-4-(4-pyridyl)-3-[3-(trifluoromethyl)phenyl]pyrazole

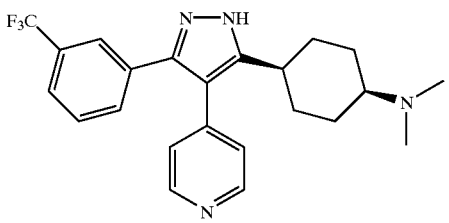

By following the method of Example C-75 and substituting 5-cis-(4-aminocyclohexyl)-4-(4-pyridyl)-3-(3-(trifluoromethyl)phenyl)pyrazole (Example C-103) for 5-(4-piperidyl)-4-(4-pyridyl)-3-(4-chlorophenyl)pyrazole hydrochloride (Example C-74) the title compound was prepared: MS (M+H): 415 (base peak).

EXAMPLE C-105

5-cis-(4-aminocyclohexyl)-4-(4-pyridyl)-3-(3-chlorophenyl)pyrazole

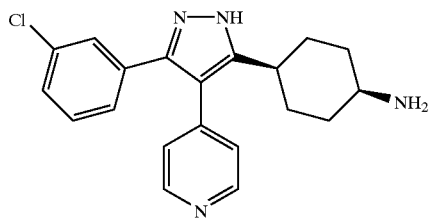

By following the method of Example C-1 and substituting methyl-3-chlorobenzoate for ethyl- 4-fluorobenzoate and N-t-butoxycarbonyl-cis-4-aminocyclohexanoyl N-hydroxysuccinimide for N-benyloxycarbonyl-glycinyl N-hydroxysuccinimide the title compound was prepared as the N-t-butoxycarbonyl protected compound. The deprotection of the N-t-butoxycarbonyl intermediate was accomplished with 4 N HCl in dioxane to afford the title compound: MS (M+H): 353 (base peak).

EXAMPLE C-106

5-cis-(4-N,N-dimethylaminocyclohexyl)-4-(4-pyridyl)-3-(3-chlorophenyl)pyrazole

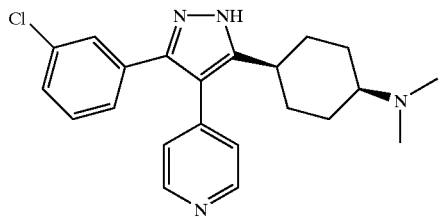

By following the method of Example C-75 and substituting 5-cis-(4-aminocyclohexyl)-4-(4-pyridyl)-3-(3-chlorophenyl)pyrazole hydrochloride (Example C-105) for 5-(4-piperidyl)-4-(4-pyridyl)-3-(4-chlorophenyl)pyrazole hydrochloride (Example C-74) the title compound was prepared: MS (M+H): 381 (base peak).

EXAMPLE C-107

5-(N-acetimido-4-piperidyl)-4-(4-pyridyl)-3-(4-fluorophenyl)pyrazole

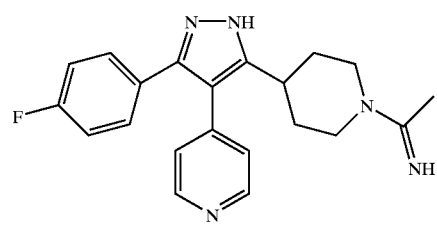

To a suspension of 5-(4-piperidyl)-4-(4-pyridyl)-3-(4-fluorophenyl)pyrazole (Example C-2) (0.11 g, 0.35 mmol) in 2 mL EtOH was added ethyl acetamidate hydrochloride (0.065 g, 0.53 mmol) and the mixture was refluxed for 30 minutes. The solution was left at 5–10° C. for 16 h and filtered to obtain the title compound as a white solid: MS (M+H): 364 (base peak).

EXAMPLE C-108

5-(N-carboxamidino-4-piperidyl)-4-(4-pyridyl)-3-(4-fluorophenyl)pyrazole

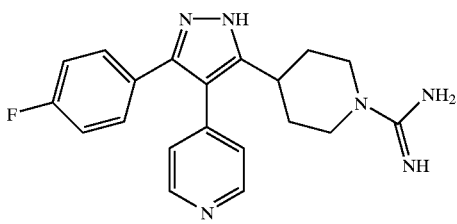

To a stirred suspension of 5-(4-piperidyl)-4-(4-pyridyl)-3-(4-fluorophenyl)pyrazole (C-2) (1.5 g, 4.7 mmol) in 47 mL of DMF was added Hunig's base (0.60 g, 4.7 mmol) and pyrazole carboxamide hydrochloride (0.68 g, 4.7 mmol). The slurry was allowed to stir at room temperature for 4 days. The reaction mixture was poured onto 300 mL of ether. The resulting precipitate was filtered to leave the title compound as the hydrochloride salt: MS (M+H): 365 (base peak).

EXAMPLE C-109

5-(N-cyclopropanoyl-4-piperidyl)-4-(4-pyridyl)-3-(4-chlorophenyl)pyrazole

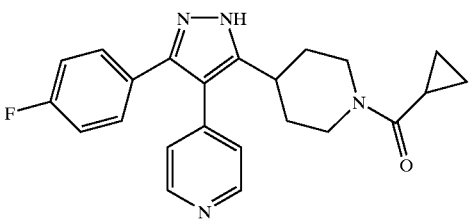

By following the method of Example C-76 and substituting cyclopropanoyl chloride for acetyl chloride the title compound was prepared: MS (M+H): 407 (base peak).

EXAMPLE C-110

5-[N-(2-fluoro)benzoyl-4-piperidyl]-4-(4-pyridyl)-3-(4-chlorophenyl)pyrazole

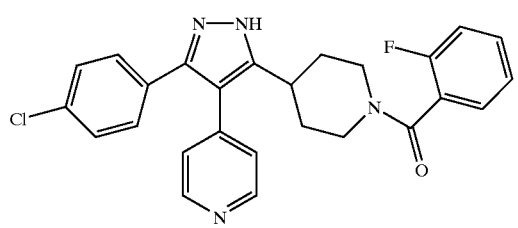

By following the method of Example C-76 and substituting 2-fluorobenzoyl chloride for acetyl chloride the title compound was prepared: MS (M+H): 461 (base peak).

EXAMPLE C-111

5-(N-methylsulfonyl-4-piperidyl)-4-(4-pyridyl)-3-(4-fluorophenyl)pyrazole

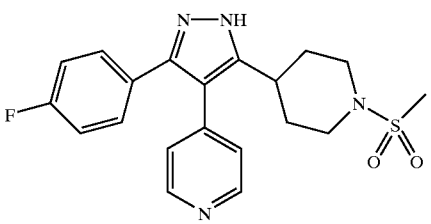

By following the method of Example C-76 and substituting 5-(4-piperidyl)-4-(4-pyridyl)-3-(4-fluorophenyl)pyrazole (Example C-2) for 5-(4-piperidyl)-4-(4-pyridyl)-3-(4-chlorophenyl)pyrazole (Example C-74) and methylsulfonyl chloride for acetyl chloride the title compound was prepared: MS (M+H): 401 (base peak).

EXAMPLE C-112

5-(N-methoxyacetyl-4-piperidyl)-4-(4-pyridyl)-3-(4-fluorophenyl)pyrazole

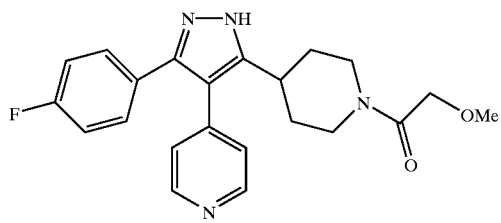

By following the method of Example C-76 and substituting 5-(4-piperidyl)-4-(4-pyridyl)-3-(4-fluorophenyl)pyrazole (Example C-2) for 5-(4-piperidyl)-4-(4-pyridyl)-3-(4-chlorophenyl)pyrazole (Example C-74) and methoxy acetyl chloride for acetyl chloride the title compound was prepared: MS (M+H): 395 (base peak).

EXAMPLE C-113

5-(N-acetyl-4-piperidyl)-4-(4-pyridyl)-3-(4-fluorophenyl)pyrazole

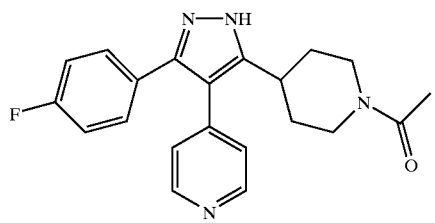

By following the method of Example C-76 and substituting 5-(4-piperidyl)-4-(4-pyridyl)-3-(4-fluorophenyl)pyrazole Example (C-2) for 5-(4-piperidyl)-4-(4-pyridyl)-3-(4-chlorophenyl)pyrazole Example (C-74) the title compound was prepared: MS (M+H): 365 (base peak).

EXAMPLE C-114

5-[2-(1,1-dimethyl)aminoethyl]-4-(4-pyridyl)-3-(4-fluorophenyl)pyrazole

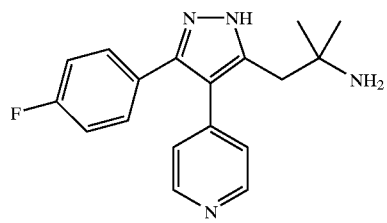

By following the method of Example C-1 and substituting N-t-butoxycarbonyl-2-amino-2,2-dimethylpropanoyl N-hydroxysuccinimide for N-benyloxycarbonyl-glycinyl N-hydroxysuccinimide the title compound was prepared as the N-t-butoxycarbonyl protected compound. The deprotection of the N-t-butoxycarbonyl intermediate was accomplished with 4 N HCl in dioxane to afford the title compound as the hydrochloride salt: MS (M+H): 327 (base peak).

EXAMPLE C-115

5-(methoxymethyl)-4-(4-pyridyl)-3-(4-chlorophenyl)pyrazole

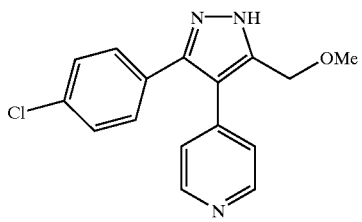

By following the method of Example C-1 and substituting methyl-4-chlorobenzoate for ethyl-4-fluorobenzoate and 2-methoxyacetyl N-hydroxysuccinimide for N-benyloxycarbonyl-glycinyl N-hydroxysuccinimide the title compound was prepared: MS (M+H): 300 (base peak).

EXAMPLE C-116

5-(4-aminobenzyl)-4-(4-pyridyl)-3-(4-chlorophenyl)pyrazole

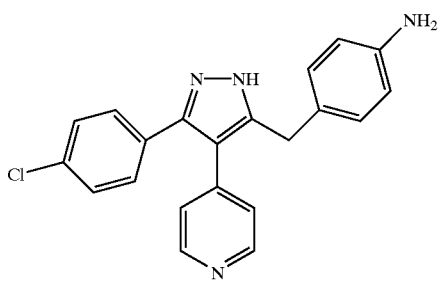

By following the method of Example C-1 and substituting methyl-4-chlorobenzoate for ethyl-4-fluorobenzoate and N-t-butoxycarbonyl-4-aminophenyl acetyl N-hydroxysuccinimide for N-benyloxycarbonyl-glycinyl N-hydroxysuccinimide the title compound was prepared as the N-t-butoxycarbonyl protected compound. The deprotection of the N-t-butoxycarbonyl intermediate was accomplished with 4 N HCl in dioxane to afford the title compound as the hydrochloride salt: MS (M+H): 361 (base peak).

EXAMPLE C-117

5-[4-(N,N-dimethyl)aminobenzyl]-4-(4-pyridyl)-3-(4-chlorophenyl)pyrazole

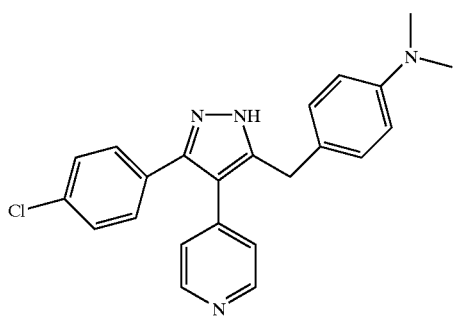

By following the method of Example C-75 and substituting 5-(4-aminobenzyl)-4-(4-pyridyl)-3-(4-chlorophenyl)

pyrazole (Example C-116) for 5-(4-piperidyl)-4-(4-pyridyl)-3-(4-chlorophenyl)pyrazole hydrochloride (Example C-74) the title compound was prepared: MS (M+H): 389 (base peak).

EXAMPLE C-118

5-[4-(N-acetyl)aminobenzyl]-4-(4-pyridyl)-3-(4-chlorophenyl)pyrazole

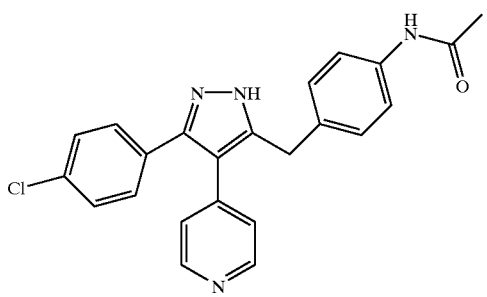

By following the method of Example C-76 and substituting 5-(4-aminobenzyl)-4-(4-pyridyl)-3-(4-chlorophenyl) pyrazole (Example C-116) for 5-(4-piperidyl)-4-(4-pyridyl)-3-(4-chlorophenyl)pyrazole hydrochloride (Example C-74) the title compound was prepared: MS (M+H): 403 (base peak).

EXAMPLE C-119

5-(N-methylaminomethyl)-4-(4-pyridyl)-3-(4-fluorophenyl)pyrazole

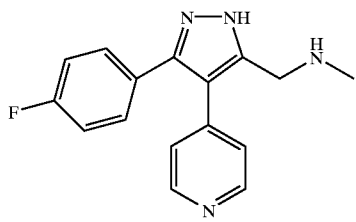

5-(N-formylaminomethyl)-4-(4-pyridyl)-3-(4-fluorophenyl)pyrazole. To a suspension of 5-aminomethyl-4-(4-pyridyl)-3-(4-fluorophenyl)pyrazole (Example C-1) (8.04 g, 30 mmol) in 120 mL dichloromethane was added p-nitrophenylformate (6.01 g, 36 mmol) as a solid. The suspension was stirred for 24 h at room temperature and the solvents removed under reduced pressure. The residue was triturated with ether and filtered to obtain the desired 5-(N-formylaminomethyl)-4-(4-pyridyl)-3-(4-fluorophenyl) pyrazole derivative as a white solid: MS (M+H): 297 (base peak).

5-(N-methylaminomethyl)-4-(4-pyridyl)-3-(4-fluorophenyl)pyrazole

To a suspension of 5-(N-formylaminomethyl)-4-(4-pyridyl)-3-(4-fluorophenyl) pyrazole (8.74 g, 29.5 mmol) in 90 mL anhydrous tetrahydrofuran was added a 1.0 M solution of borane in tetrahydrofuran (90 mL, 90 mmol) and the mixture was stirred at room temperature for 24 h. 1 N aqueous hydrochloric acid (100 mL) was then added to this mixture and the solution was refluxed for 5 hours and cooled to room temperature. The solution was extracted with ether (2×250 mL) and the pH of the aqueous layer adjusted to 9 by addition of concentrated ammonium hydroxide. The aqueous layers (pH~9) were then extracted with ethyl acetate (4×150 mL). The organic extracts were dried over sodium sulfate, filtered and evaporated to dryness under reduced pressure. The residue was triturated with acetonitrile and filtered to obtain the title compound as a white solid: MS (M+H): 283 (base peak).

EXAMPLE C-120

5-[N-(2-amino-2,2-dimethylacetyl)aminomethyl]-4-(4-pyridyl)-3-(4-fluorophenyl)pyrazole

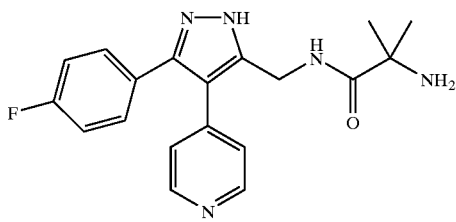

5-(N-t-butoxycarbonylaminomethyl)-4-(4-pyridyl)-3-(4-fluorophenyl)pyrazole

To a solution of 5-aminomethyl-4-(4-pyridyl)-3-(4-fluorophenyl)pyrazole (Example C-1) (0.27 g, 1 mmol) in anhydrous dimethylformamide (4 mL) was added N-tert-butoxycarbonyl aminoisobutyric acid N-hydroxysuccinimide ester (0.33 g, 1.1 mmol) and the mixture stirred at 40° C. for 24 h. The resulting solution was evaporated to dryness under reduced pressure. The residue was dissolved in dichloromethane (30 mL) and washed with a saturated solution of sodium bicarbonate (2×20 mL) and brine (20 mL). The organic layers were dried over sodium sulfate, filtered and evaporated under reduced pressure to dryness to afford 5-(N-t-butoxycarbonylaminomethyl)-4-(4-pyridyl)-3-(4-fluorophenyl)pyrazole as a white solid.

5-(N-(2-amino-2,2-dimethylacetyl)aminomethyl)-4-(4-pyridyl)-3-(4-fluorophenyl)pyrazole To a solution of the above compound in acetonitrile (2 mL) was added 1 mL of a 4.0 M solution of hydrochloric acid in dioxane. The reaction mixture was stirred at room temperature for 6 hours. The suspension was evaporated to dryness under reduced pressure. The resulting residue was stirred in acetonitrile (5 mL), filtered and dried in a vacuum dessicator to afford the title compound as a hydrochloride salt: MS (M+H): 354 (base peak).

EXAMPLE C-121

5-[N-(2-amino-2,2-dimethylacetyl)aminomethyl]-4-(4-pyridyl)-3-(4-chlorophenyl)pyrazole

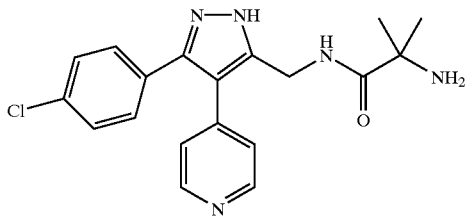

By following the method of Example C-120 and substituting 5-aminomethyl-4-(4-pyridyl)-3-(4-chlorophenyl)pyrazole (Example C-15) for 5-aminomethyl-4-(4-pyridyl)-3-(4-fluorophenyl)pyrazole (Example C-1) the title compound was prepared: MS (M+H): 370 (base peak).

EXAMPLE C-122

5-[4-N-(2-dimethylaminoacetyl)piperidyl]-4-(4-pyridyl)-3-(4-chlorophenyl)pyrazole

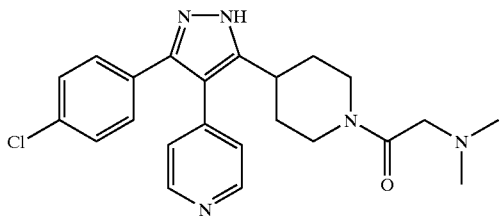

To a solution of N,N-dimethylglycine hydrochloride (0.28 g, 2 mmol) in dimethylformamide (4 mL) was added hydroxybenzotriazole (0.27 g, 2 mmol), N,N-diisopropylethyl amine (0.7 mL, 4 mmol) and polymer supported ethyl carbodimide (Example B-49) (1 g, 2.39 mmol). To this solution after 30 minutes at room temperature was added 5-(4-piperidyl)-4-(4-pyridyl)-3-(4-chlorophenyl)pyrazole hydrochloride (Example C-74), 0.41 g, 1 mmol). The suspension was agitated on a labtop orbital shaker for 24 h. The suspension was filtered, washed with dimethylformamide (2×5 mL) and the filtrates evaporated under high pressure. The residue was dissolved in dichloromethane (30 mL), washed with a saturated solution of sodium bicarbonate (50 mL) and brine (50 mL). The organic layers were dried over sodium sulfate, filtered and evaporated under high vacuum to afford the title compound as a white solid: MS (M+H): 424 (base peak).

EXAMPLE C-123

(S)-5-(2-pyrolidinyl)-4-(4-pyridyl)-3-(4-fluorophenyl)pyrazole

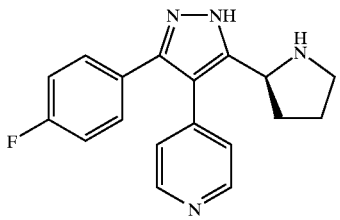

By following the method of Example C-1 and substituting (S)-N-t-butoxycarbonyl-prolinyl N-hydroxysuccinimide for N-benyloxycarbonyl-glycinyl N-hydroxysuccinimide the title compound was prepared as the N-t-butoxycarbonyl protected compound. The deprotection of the N-t-butoxycarbonyl intermediate was accomplished with 4 N HCl in dioxane to afford the title compound: MS (M+H): 309 (base peak).

EXAMPLE C-124

(S)-5-(N-methyl-2-pyrolidinyl)-4-(4-pyridyl)-3-(4-fluorophenyl)pyrazole

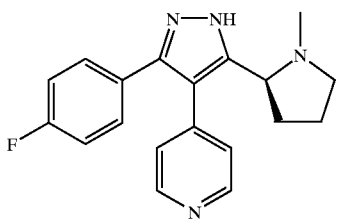

By following the method of Example C-75 and substituting (S)-5-(2-pyrolidinyl)-4-(4-pyridyl)-3-(4-fluorophenyl)pyrazole (Example C-123) for 5-(4-piperidyl)-4-(4-pyridyl)-3-(4-chlorophenyl)pyrazole hydrochloride (Example C-74) the title compound was prepared: MS (M+H): 323 (base peak).

EXAMPLE C-125

(R)-5-(2-pyrolidinyl)-4-(4-pyridyl)-3-(4-fluorophenyl)pyrazole

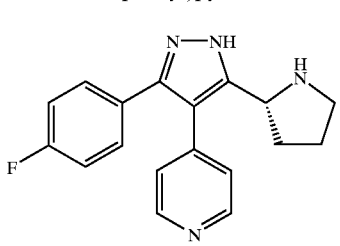

By following the method of Example C-1 and substituting (R)-N-t-butoxycarbonyl-prolinyl N-hydroxysuccinimide for N-benyloxycarbonyl-glycinyl N-hydroxysuccinimide the title compound was prepared as the N-t-butoxycarbonyl protected compound. The deprotection of the N-t-butoxycarbonyl intermediate was accomplished with 4 N HCl in dioxane to afford the title compound: MS (M+H): 309 (base peak).

EXAMPLE C-126

(R)-5-(N-methyl-2-pyrolidinyl)-4-(4-pyridyl)-3-(4-fluorophenyl)pyrazole

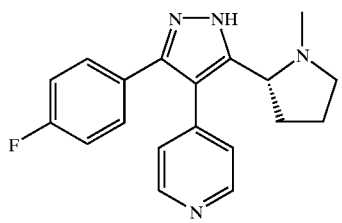

By following the method of Example C-75 and substituting (R)-5-(2-pyrolidinyl)-4-(4-pyridyl)-3-(4-fluorophenyl) pyrazole (Example C-125) for 5-(4-piperidyl)-4-(4-pyridyl)-3-(4-chlorophenyl)pyrazole hydrochloride (Example C-74) the title compound was prepared: MS (M+H): 323 (base peak).

EXAMPLE C-127

(R)-5-(3-piperidyl)-4-(4-pyridyl)-3-(4-fluorophenyl) pyrazole

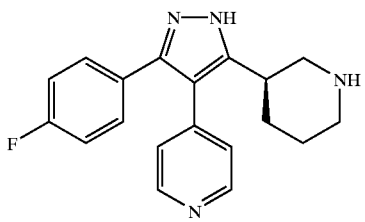

By following the method of Example C-1 and substituting (R)-N-t-butoxycarbonyl-nipecotyl N-hydroxysuccinimide for N-benyloxycarbonyl-glycinyl N-hydroxysuccinimide the title compound was prepared as the N-t-butoxycarbonyl protected compound. The deprotection of the N-t-butoxycarbonyl intermediate was accomplished with 4 N HCl in dioxane to afford the title compound: MS (M+H): 323 (base peak).

EXAMPLE C-128

(R)-5-(N-methyl-3-piperidyl)-4-(4-pyridyl)-3-(4-fluorophenyl)pyrazole

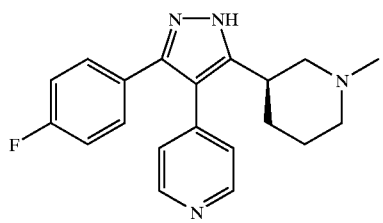

By following the method of Example C-75 and substituting (R)-5-(3-piperidyl)-4-(4-pyridyl)-3-(4-fluorophenyl) pyrazole (Example C-125) for 5-(4-piperidyl)-4-(4-pyridyl)-3-(4-chlorophenyl)pyrazole hydrochloride (Example C-74) the title compound was prepared: MS (M+H): 337 (base peak).

EXAMPLE C-129

2,2-dimethyl-4-[4-(4-pyridyl)-3-(4-chlorophenyl) pyrazolyl]butyric acid

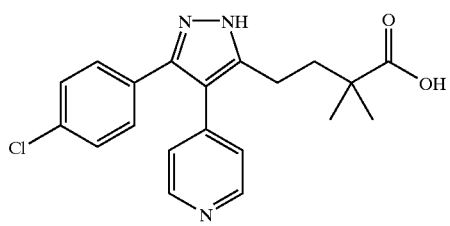

By following the method of Example C-1 and substituting methyl-4-chlorobenzoate for ethyl-4-fluorobenzoate and 2,2-dimethyl glutaric anhydride for N-benyloxycarbonyl-glycinyl N-hydroxysuccinimide the title compound was prepared: MS (M+H): 370 (base peak).

EXAMPLE C-130

4-[4-(4-pyridyl)-3-(4-fluorophenyl)pyrazolyl]butyric acid

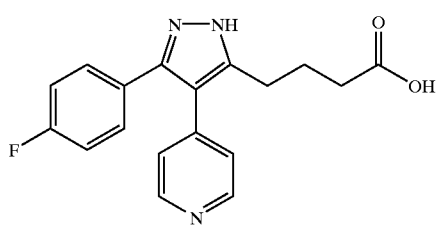

By following the method of Example C-1 and substituting glutaric anhydride for N-benzyloxycarbonyl-glycinyl N-hydroxysuccinimide the title compound was prepared: MS (M+H): 326 (base peak).

EXAMPLE C-131

4-[4-(4-pyridyl)-3-(4-fluorophenyl)pyrazolyl] butyramide

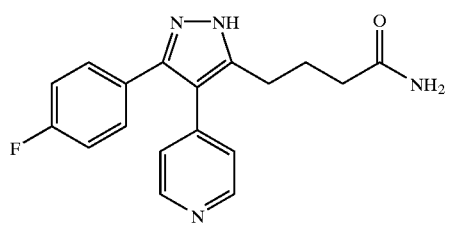

Methyl 4-(4-(4-pyridyl)-3-(4-fluorophenyl) pyrazolyl)butyrate

To a solution of 4-(4-(4-pyridyl)-3-(4-fluorophenyl) pyrazolyl)butyric acid (Example C-130) (40 g, 123 mmol) in 650 mL of MeOH was added 20 mL of concentrated $H_2SO_4$. The solution was stirred overnight at room temperature. The solution was concentrated and diluted with 200 mL of water. The solution was cooled with an ice/water bath and to the solution was added 150 mL of saturated NaHCO₃. The solution was neutralized further with 50% NaOH to pH 7. The resulting slurry was extracted with CH₂Cl₂ (3×250 mL). The combined extracts were washed with water (1×300 mL) and saturated NaHCO₃ (1×500 mL). The organic phase was dried over Na₂SO₄, filtered and concentrated to afford methyl 4-(4-(4-pyridyl)-3-(4-fluorophenyl)pyrazolyl) butyrate: MS (M+H): 340 (base peak).

4-(4-(4-pyridyl)-3-(4-fluorophenyl)pyrazolyl) butyramide

A solution of methyl 4-(4-(4-pyridyl)-3-(4-fluorophenyl) pyrazolyl)butyrate (39 g, 120 mmol) in 600 mL of MeOH was saturated with NH₃. The solution was periodically treated with additional NH₃ over a 24 h period. The solution was degassed with a stream of nitrogen and the solution was concentrated to leave a yellow solid. The solid was slurried in ether and filtered to leave the title compound: MS (M+H): 325 (base peak).

EXAMPLE C-132

5-[4-(1-hydroxy)butyl]-4-(4-pyridyl)-3-(4-fluorophenyl)pyrazole

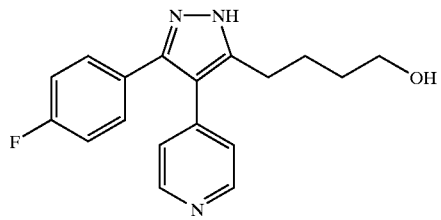

A stirred suspension of 4-(4-(4-pyridyl)-3-(4-fluorophenyl)pyrazolyl)butyric acid (Example C-130) (2 g, 6.15 mmol) in 100 ml of anhydrous ether was cooled to 0° C. under nitrogen. Lithium aluminum hydride (467 mg, 12.3 mmol) was added to this suspension slowly. After the addition was complete, the mixture was warmed to room temperature and stirred for additional 2 h. The reaction was quenched slowly with 1N KHSO₄, (80 ml). The mixture was transferred to a separatory funnel and the aqueous layer was removed. The aqueous layer was then made basic with K₂CO₃ (pH 8). The aqueous solution was extracted with ethyl acetate (2×100 mL). The combined ethyl acetate extracts were washed with water (1×100 mL), dried over MgSO₄, filtered and concentrated to give the title compound: MS (M+H): 312 (base peak).

EXAMPLE C-133

5-[4-(1,1-dimethyl-1-hydroxy)butyl]-4-(4-pyridyl)-3-(4-fluorophenyl)pyrazole

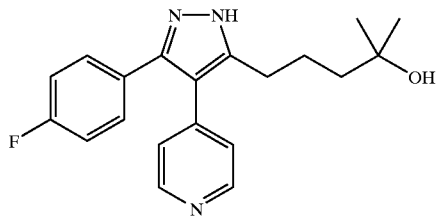

A solution of 4-(4-(4-pyridyl)-3-(4-fluorophenyl) pyrazolyl)butyric acid (Example C-130) (200 mg, 0.615 mmol) in 50 ml of MeOH was treated with 10 ml of 4 N HCl/dioxane. The reaction mixture was stirred for 5 hours and evaporated to dryness. To this residue was added 15 ml of 1N methyl magnesium bromide in butyl ether and 5 ml of anhydrous THF. The reaction was heated to reflux under nitrogen for 64 h.

The reaction was quenched with 20 ml of saturated ammonium chloride. This mixture was transferred to a separatory funnel and was extracted with 100 ml ethyl acetate (2×100 mL). The combined ethyl acetate extracts were washed with water (1×100 mL), dried over MgSO₄, filtered and concentrated to afford a crude oil. The crude oil was subjected to column chromatography by using 3.5% MeOH/CH₂Cl₂ followed by 6% MeOH/CH₂Cl₂ to give the title compound: MS (M+H): 340 (base peak).

EXAMPLE C-134

5-(4-(1-amino)butyl)-4-(4-pyridyl)-3-(4-fluorophenyl)pyrazole

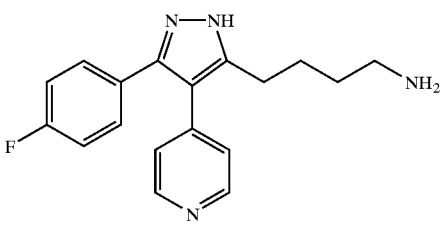

To a suspension of 4-(4-(4-pyridyl)-3-(4-fluorophenyl) pyrazolyl)butyramide (Example C-131) (2 g, 6.2 mmol) in 100 ml of anhydrous ether was added lithium aluminum hydride (467 mg, 12.3 mmol). After the addition was complete, the mixture was warmed to room temperature and stirred for additional 2 h. The reaction was quenched with 20 mL of ethyl acetate and was poured onto 100 mL of 2.5 N NaOH. The mixture was extracted with ethyl acetate (3×50 mL). The combined extracts were washed with brine (1×100 mL), dried over Na₂SO₄, filtered and concentrated to afford the title compound: MS (M+H): 311 (base peak).

EXAMPLE C-135

4-(4-(4-pyridyl)-3-(4-fluorophenyl)pyrazolyl) propionic acid

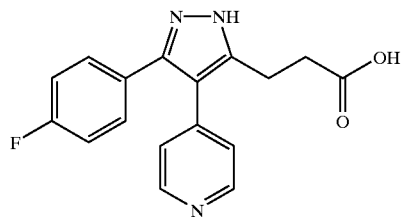

By following the method of Example C-1 and substituting succinic anhydride for N-benyloxycarbonyl-glycinyl N-hydroxysuccinimide the title compound was prepared: MS (M+H): 312 (base peak).

EXAMPLE C-136

5-(4-piperidyl)-4-(4-pyrimidyl)-3-(4-chlorophenyl) pyrazole

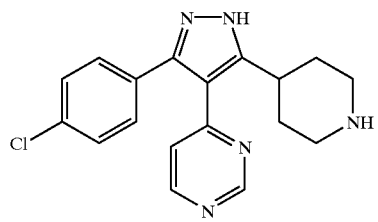

By following the method of Example C-1 and substituting methyl-4-chlorobenzoate for ethyl-4-fluorobenzoate, N-t-butoxycarbonyl-isonipecotyl N-hydroxysuccinimide for N-benyloxycarbonyl-glycinyl N-hydroxysuccinimide and 4-methylpyrimidine for 4-picoline the title compound was prepared as the N-t-butoxycarbonyl protected compound. The deprotection of the N-t-butoxycarbonyl intermediate was accomplished with 4 N HCl in dioxane to afford the title compound as the hydrochloride salt: $^1$H NMR (CDCl$_3$) δ9.2 (s, 1 H), 8.48 (d, J=5.19 Hz, 1 H), 7.31 (m, 4 H), 6.94 (d, J=4.79 Hz, 1 H), (3.69 (m, 3 H), 3.12 (m, 2 H), 2.3 (m, 3 H), 1.24 (m, 2 H). MS (M+H): 340 (base peak).

EXAMPLE C-137

5-(N-methyl-4-piperidyl)-4-(4-pyrimidyl)-3-(4-chlorophenyl)pyrazole

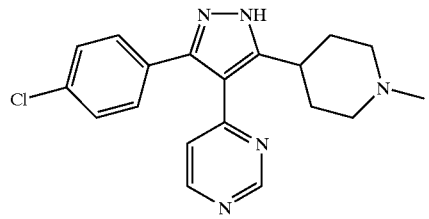

By following the method of Example C-75 and substituting 5-(4-piperidyl)-4-(4-pyrimidyl)-3-(4-chlorophenyl) pyrazole (Example C-136) for 5-(4-piperidyl)-4-(4-pyridyl)-3-(4-chlorophenyl)pyrazole hydrochloride (Example C-74) the title compound was prepared: $^1$H NMR (CDCl$_3$) δ9.2 (d, J=1.2 Hz, 1 H), 8.48 (d, J=5.59 Hz, 1 H), 7.31 (m, 4 H), 6.95 (dd, J=1.2, 5.6 Hz, 1 H), 3.39 (m, 1 H), 3.03 (d, J=11.6 Hz, 2 H), 2.38 (s, 3 H), 2.06 (m, 4 H), 1.24 (m, 2 H). MS (M+H): 354 (base peak).

EXAMPLE C-138

5-(N-acetyl-3-piperidyl)-4-(4-pyridyl)-3-(4-fluorophenyl)pyrazole

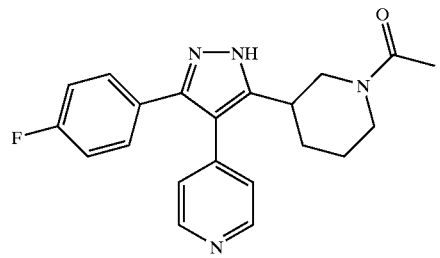

By following the method of Example C-76 and substituting 5-(3-piperidyl)-4-(4-pyridyl)-3-(4-fluorophenyl) pyrazole (C-90) for 5-(4-piperidyl)-4-(4-pyridyl)-3-(4-chlorophenyl)pyrazole (C-74) the title compound was prepared: MS (M+H): 365 (base peak).

EXAMPLE C-139

5-(N-methoxyacetyl-3-piperidyl)-4-(4-pyridyl)-3-(4-fluorophenyl)pyrazole

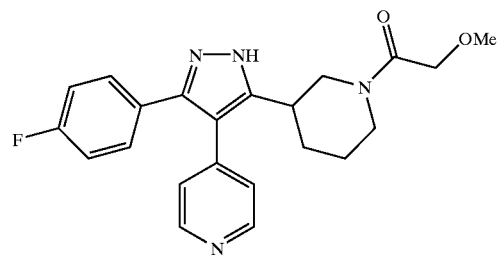

By following the method of Example C-76 and substituting 5-(3-piperidyl)-4-(4-pyridyl)-3-(4-fluorophenyl) pyrazole (C-90) for 5-(4-piperidyl)-4-(4-pyridyl)-3-(4-chlorophenyl)pyrazole (C-74) and methoxy acetyl chloride for acetyl chloride the title compound was prepared: MS (M+H): 395 (base peak).

Additional compounds of the present invention which could be prepared using one or more of the reaction schemes set forth in this application include, but are not limited to, the following:

EXAMPLE C-140

5-(4-N-t-butoxycarbonylpiperidinyl)-4-[4-(2-thiomethyl)pyrimidinyl]-3-(4-chlorophenyl)pyrazole

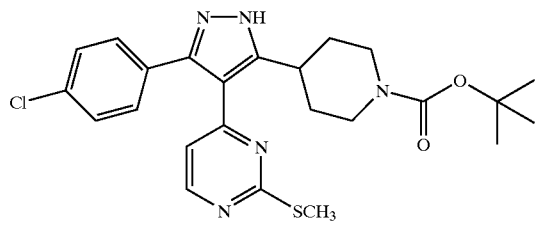

EXAMPLE C-141

5-(4-piperidinyl)-4-[4-(2-thiomethyl)pyrimidinyl]-3-(4-chlorophenyl)pyrazole

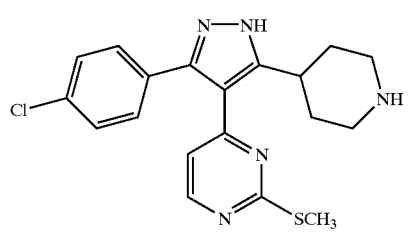

EXAMPLE C-142

5-(4-N-methylpiperidinyl)-4-[4-(2-thiomethyl)pyrimidinyl]-3-4-(chlorophenyl)pyrazole

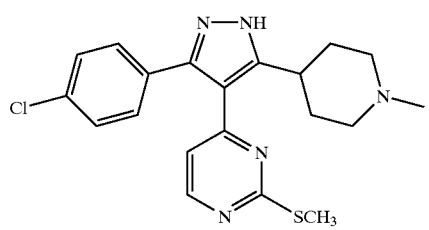

EXAMPLE C-143

5-(4-N-t-butoxycarbonylpiperidinyl)-4-[4-(2-methanesulfonyl)pyrimidinyl]-3-(4-chlorophenyl)pyrazole

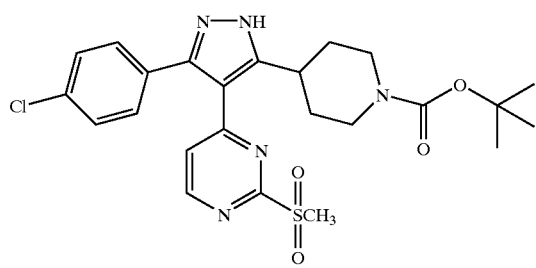

EXAMPLE C-144

5-(4-piperidinyl)-4-[4-(2-methanesulfonyl)pyrimidinyl]-3-(4 -chlorophenyl)pyrazole

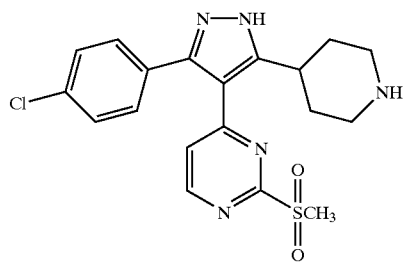

EXAMPLE C-145

5-(4-N-methylpiperidinyl)-4-[4-(2-methanesulfonfyl)pyrimidinyl]-3-(4-chlorophenyl)pyrazole

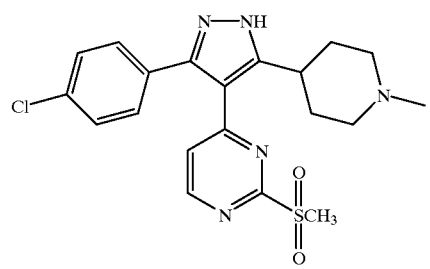

EXAMPLE C-146

5-(4-N-t-butoxycarbonylpiperidinyl)-4-[4-(2-amino)pyrimidinyl]-3-(4-chlorophenyl)pyrazole

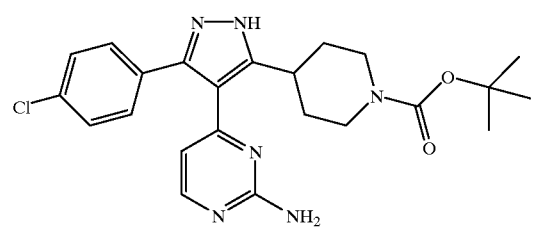

EXAMPLE C-147

5-(4-piperidinyl)-4-[4-(2-amino)pyrimidinyl]-3-(4-chlorophenyl)pyrazole

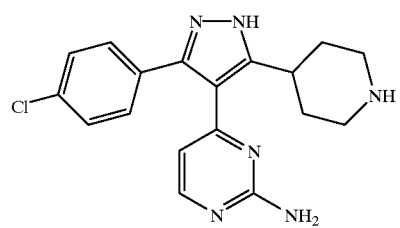

EXAMPLE C-148

5-(4-N-methylpiperidinyl)-4-[4-(2-amino)pyrimidinyl]-3-(4-chlorophenyl)pyrazole

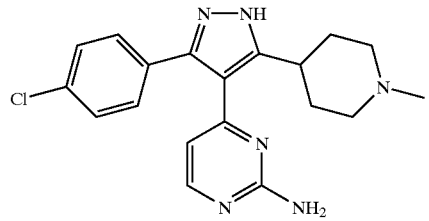

EXAMPLE C-149

5-(4-N-t-butoxycarbonylpiperidinyl)-4-[4-(2-methylamino)pyrimidinyl]-3-(4-chlorophenyl)pyrazole

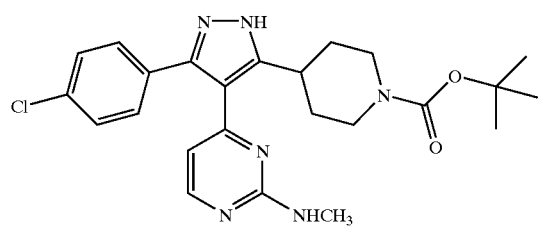

EXAMPLE C-150

5-(4-piperidinyl)-4-[4-(2-methylamino)pyrimidinyl]-3-(4-chlorophenyl)pyrazole

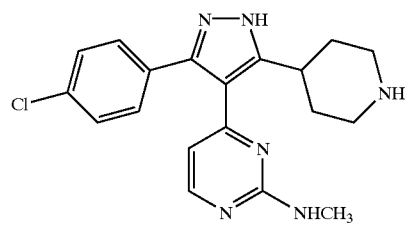

EXAMPLE C-151

5-(4-N-methylpiperidinyl)-4-[4-(2-methylamino)pyrimidinyl]-3-(4-chlorophenyl)pyrazole

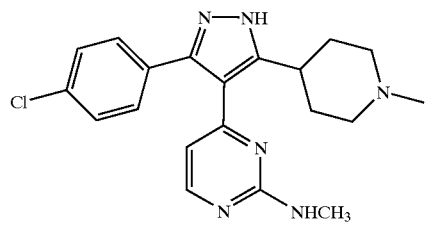

EXAMPLE C-152

5-(4-N-t-butoxycarbonylpiperidinyl)-4-[4-(2-isopropylamino)pyrimidinyl]-3-(4-chlorophenyl)pyrazole

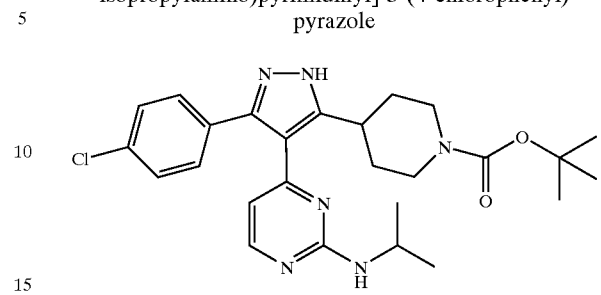

EXAMPLE C-153

5-(4-piperidinyl)-4-[4-(2-isopropylamino)pyrimidinyl]-3-(4-chlorophenyl)pyrazole

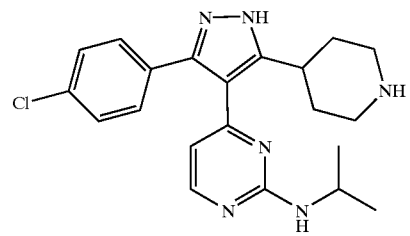

EXAMPLE C-154

5-(4-N-methylpiperidinyl)-4-[4-(2-isopropylamino)pyrimidinyl]-3-3-(4-chlorophenyl)pyrazole

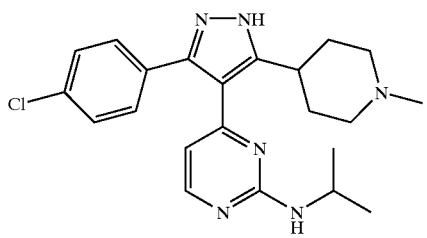

EXAMPLE C-155

5-(4-N-t-butoxycarbonylpiperidinyl)-4-[4-(2-(2-methoxyethylamino))pyrimidinyl]-3-(4-chlorophenyl)pyrazole

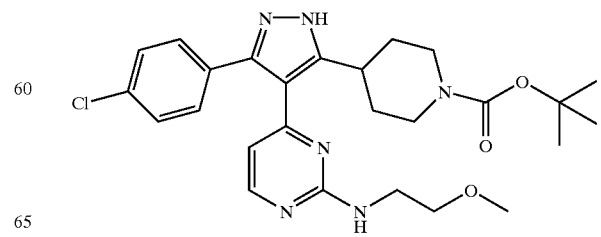

EXAMPLE C-156

5-(4-piperidinyl)-4-[4-(2-(2-methoxyethylamino))pyrimidinyl]-3-(4-chlorophenyl)pyrazole

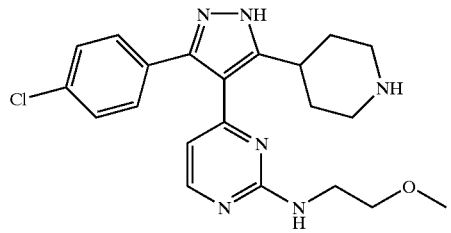

EXAMPLE C-157

5-(4-N-methylpiperidinyl)-4-[4-(2-(2-methoxyethylamino))pyrimidinyl]-3-(4-chlorophenyl)pyrazole

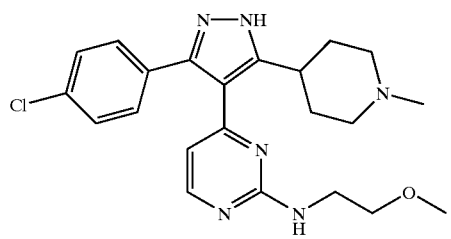

EXAMPLE C-158

5-(4-N-t-butoxycarbonylpiperidinyl)-4-[4-(2-methoxy)pyrimidinyl]-3-(4-chlorophenyl)pyrazole

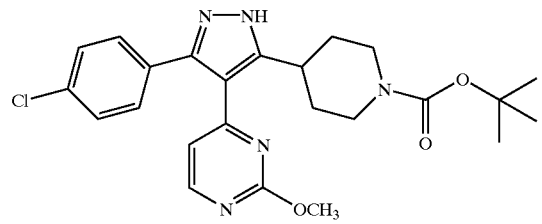

EXAMPLE C-159

5-(4-piperidinyl)-4-[4-(2-methoxy)pyrimidinyl]-3-(4-chlorophenyl)pyrazole

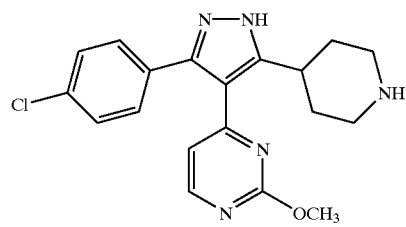

EXAMPLE C-160

5-(4-N-methylpiperidinyl)-4-[4-(2-methoxy)pyrimidinyl]-3-(4-chlorophenyl)pyrazole

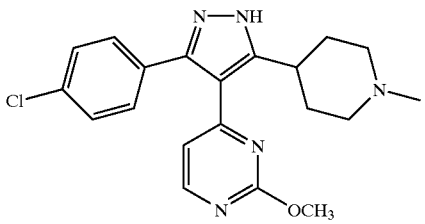

EXAMPLE C-161

5-(4-N-t-butoxycarbonylpiperidinyl)-4-[4-(2-isopropoxy)pyrimidinyl]-3-(4-chlorophenyl)pyrazole

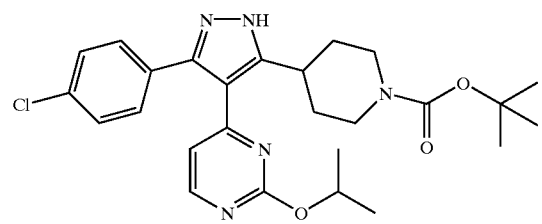

EXAMPLE C-162

5-(4-piperidinyl)-4-[4-(2-isopropoxy)pyrimidinyl]-3-(4-chlorophenyl)pyrazole

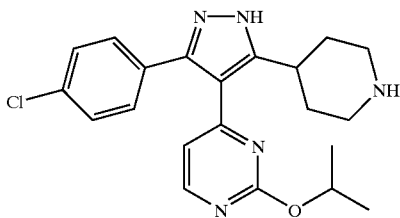

EXAMPLE C-163

5-(4-N-methylpiperidinyl)-4-[4-(2-isopropoxy)pyrimidinyl]-3-(4-chlorophenyl)pyrazole

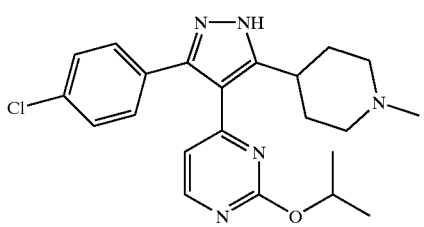

EXAMPLE C-164

5-(4-N-t-butoxycarbonylpiperidinyl)-4-[4-(2-(2-N,N-dimethylamino)ethoxy)pyrimidinyl]-3-(4-chlorophenyl)pyrazole

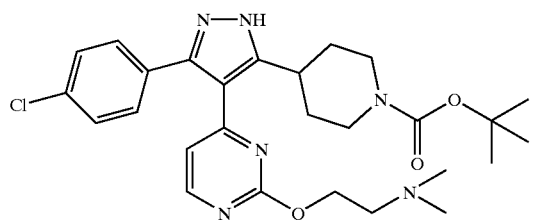

EXAMPLE C-165

5-(4-piperidinyl)-4-[4-(2-(2-N,N-dimethylamino)ethoxy)pyrimidinyl]-3-(4-chlorophenyl)pyrazole

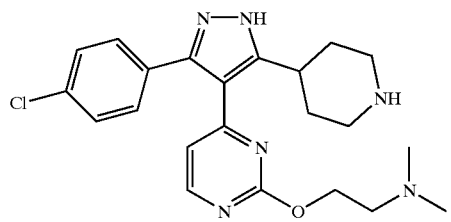

EXAMPLE C-166

5-(4-N-methylpiperidinyl)-4-[4-(2-(2-N,N-dimethylamino)ethoxy)pyrimidinyl]-3-(4-chlorophenyl)pyrazole

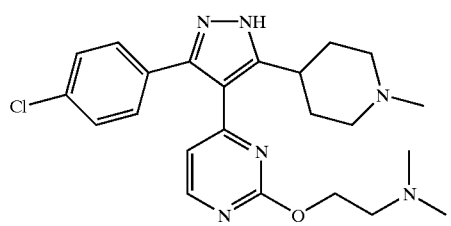

EXAMPLE C-167

5-(N-acetylhydroxylimido-4-piperidyl)-4-(4-pyridyl)-3-(4chlorophenyl)pyrazole

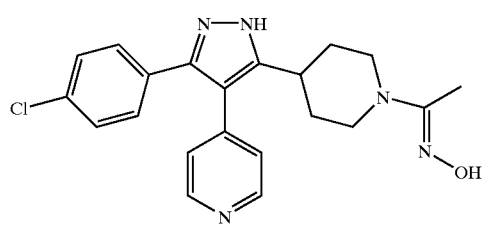

EXAMPLE C-168

5-(N-benzylhydroxylimido-4-piperidyl)-4-(4-pyridyl)-3-(4-chlorophenyl)pyrazole

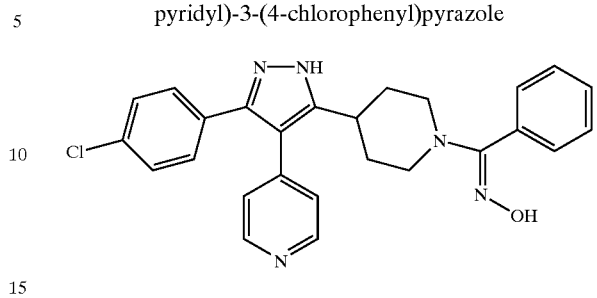

EXAMPLE C-169

5-(N-phenylacethydroxylimido-4-piperidyl)-4-(4-pyridyl)-3-(4-chlorophenyl)pyrazole

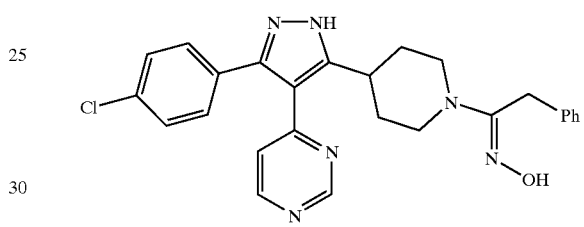

EXAMPLE C-170

5-[N-methyl-4-(3,4-dehydro)piperidyl]-4-(4-pyridyl)-3-(4-chlorophenyl)pyrazole

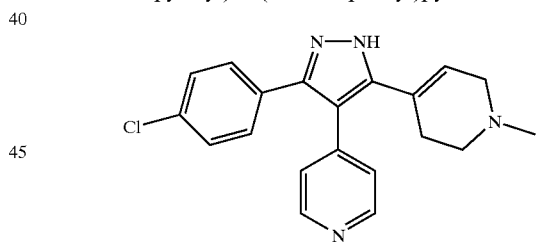

EXAMPLE C-171

5-[N-isopropyl-4-(3,4-dehydro)piperdyl]-4-(4-pyridyl)-3-(4-chlorophenyl)pyrazole

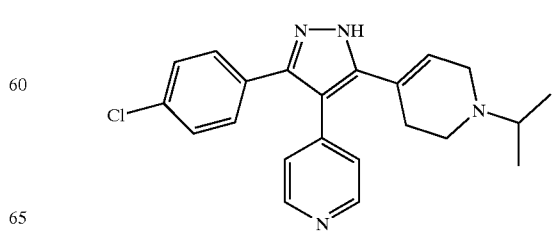

EXAMPLE C-172

5-[N-benzyl-4-(3,4-dehydro)piperidyl]-4-(4-pyridyl)-3-(4-chlorophenyl)pyrazole

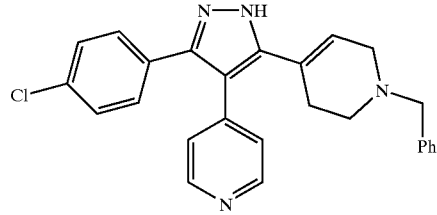

EXAMPLE C-173

5-[N-methyl-4-(4-fluoro)piperidyl]-4-(4-pyridyl)-3-(4-chlorophenyl)pyrazole

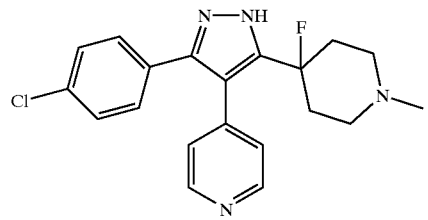

EXAMPLE C-174

5-[N-methyl-4-(4-hydroxy)piperidyl]-4-(4-pyridyl)-3-(4-chlorophenyl)pyrazole

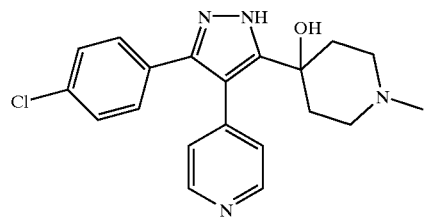

EXAMPLE C-175

5-[N-methyl-4-(4-methoxy)piperidyl]-4-(4-pyridyl)-3-(4-chlorophenyl)pyrazole

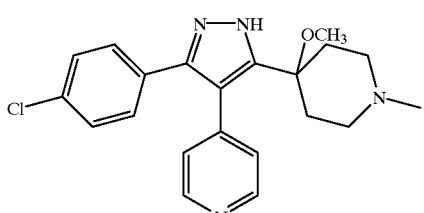

EXAMPLE C-176

5-[N-methyl-4-(2,5-tetramethyl-4-fluoro)piperidyl]-4-(4-pyridyl)-3-(4-chlorophenyl)pyrazole

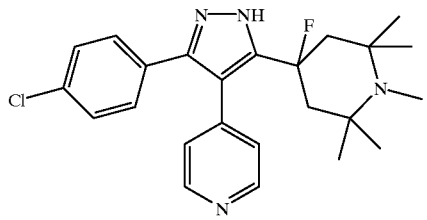

EXAMPLE C-177

5-[N-methyl-4-(2,5-tetramethyl-4-hydroxy)piperidyl]-4-(4-pyridyl)-3-(4-chlorophenyl)pyrazole

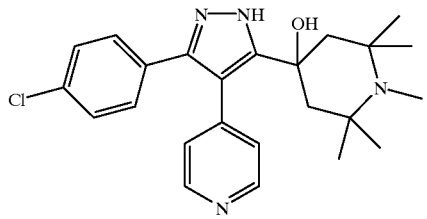

EXAMPLE C-178

5-[N-methyl-4-(2,5-tetramethyl-4-methoxy)piperidyl]-4-(4-pyridyl)-3-(4-chlorophenyl)pyrazole

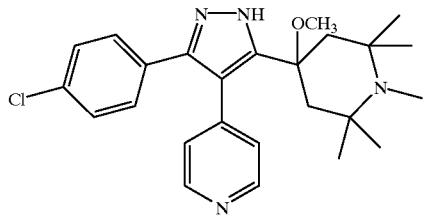

EXAMPLE C-179

5-[4-(3-fluoro)piperidyl]-4-(4-pyridyl)-3-(4-chlorophenyl)pyrazole

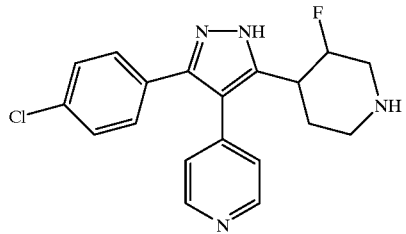

EXAMPLE C-180

5-[4-(N-methyl-3-fluoro)piperidyl]-4-(4-pyridyl)-3-(4-chlorophenyl)pyrazole

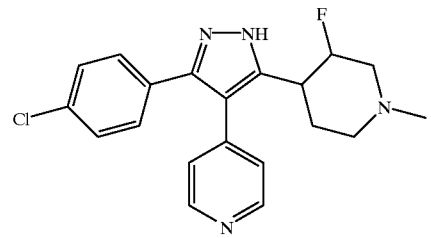

EXAMPLE C-181

5-[4-(N-isopropyl-3-fluoro)piperidyl]-4-(4-pyridyl)-3-(4-chlorophenyl)pyrazole

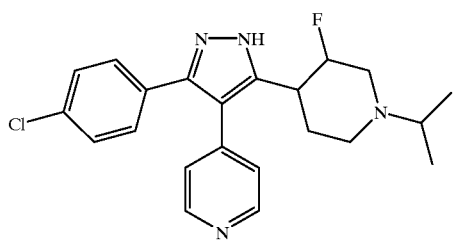

EXAMPLE C-182

5-[4-(N-benzyl-3-fluoro)piperidyl]-4-(4-pyridyl)-3-(4-chlorophenyl)pyrazole

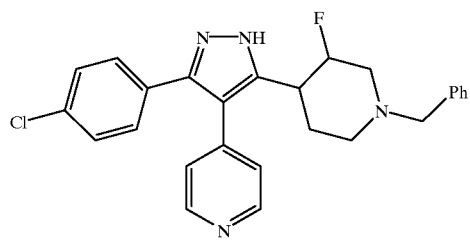

EXAMPLE C-183

5-[4-(N-acetyl-3-fluoro)piperidyl]-4-(4-pyridyl)-3-(4-chlorophenyl)pyrazole

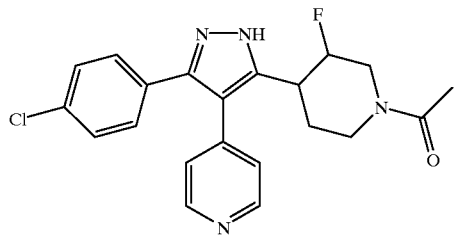

EXAMPLE C-184

5-[4-(2-oxo)piperidyl]-4-(4-pyridyl)-3-(4-chlorophenyl)pyrazole

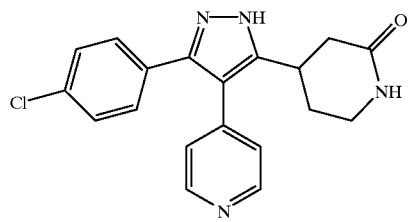

EXAMPLE C-185

5-[4-(N-methyl-2-oxo)piperidyl]-4-(4-pyridyl)-3-(4-chlorophenyl)pyrazole

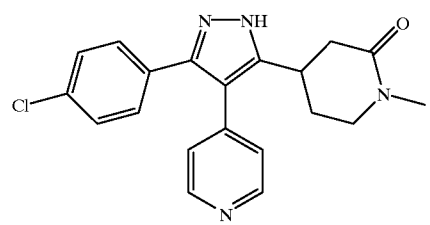

EXAMPLE C-186

5-[4-(N-isopropyl-2-oxo)piperidyl]-4-(4-pyridyl)-3-(4-chlorophenyl)pyrazole

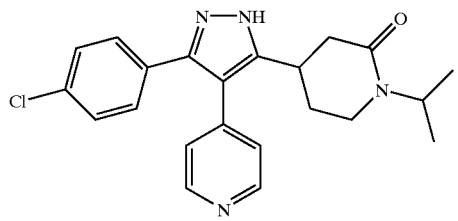

EXAMPLE C-187

5-[4-(N-benzyl-2-oxo)piperidyl]-4-(4-pyridyl)-3-(4-chlorophenyl)pyrazole

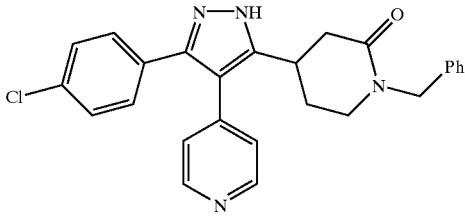

EXAMPLE C-188

5-[4-(N-acetyl-2-oxo)piperidyl]-4-(4-pyridyl)-3-(4-chlorophenyl)pyrazole

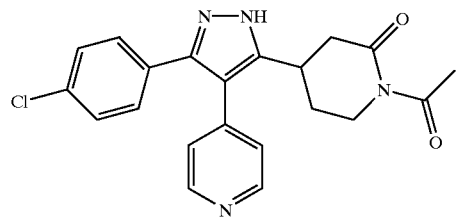

EXAMPLE C-189

5-[5-(2-oxo)piperidyl]-4-(4-pyridyl)-3-(4-chlorophenyl)pyrazole

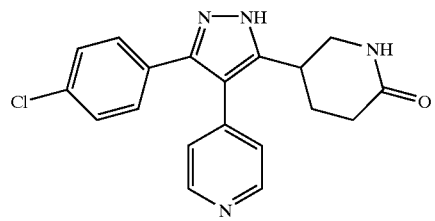

EXAMPLE C-190

5-[5-(N-methyl-2-oxo)piperidyl]-4-(4-pyridyl)-3-(4-chlorophenyl)pyrazole

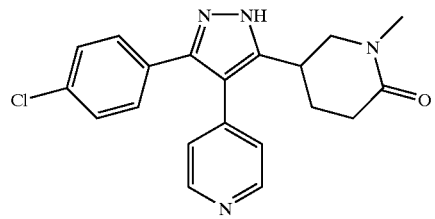

EXAMPLE C-191

5-[5-(N-isopropyl-2-oxo)piperidyl]-4-(4-pyridyl)-3-(4-chlorophenyl)pyrazole

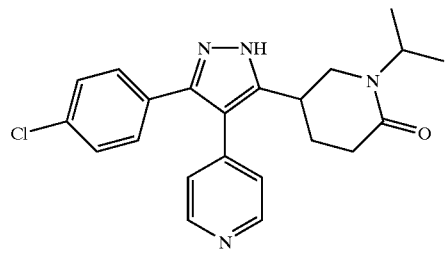

EXAMPLE C-192

5-[5-(N-benzyl-2-oxo)piperidyl]-4-(4-pyridyl)-3-(4-chlorophenyl)pyrazole

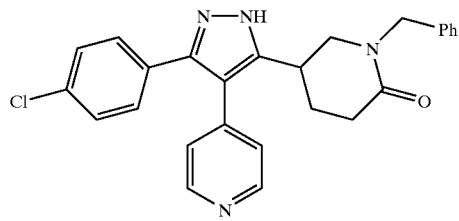

EXAMPLE C-193

5-[5-(N-acetyl-2-oxo)piperidyl]-4-(4-pyridyl)-3-(4-chlorophenyl)pyrazole

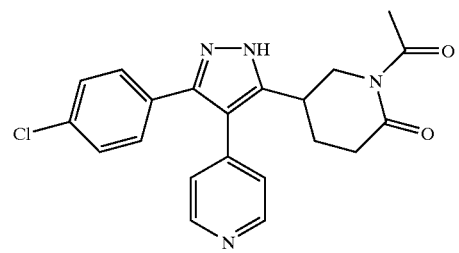

EXAMPLE C-194

5-(N-acethydroxylimido-3-piperidyl)-4-(4-pyridyl)-3-(4-chlorophenyl)pyrazole

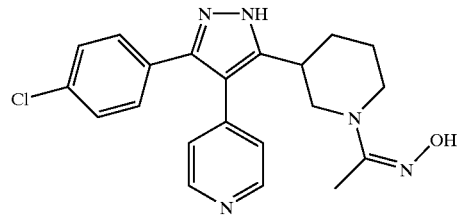

EXAMPLE C-195

5-(N-benzhydroxylimido-3-piperidyl)-4-(4-pyridyl)-3-(4-chlorophenyl)pyrazole

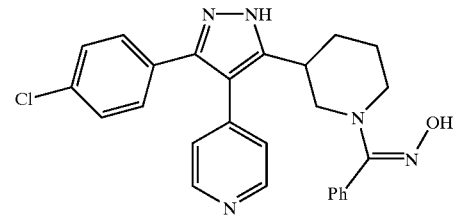

EXAMPLE C-196

5-(N-phenacethydroxylimido-3-piperidyl)-4-(4-pyridyl)-3-(4-chlorophenyl)pyrazole

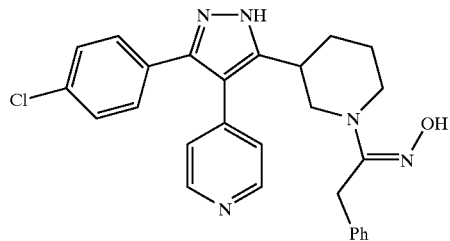

EXAMPLE C-197

5-(2-morpholinyl)-4-(4-pyridyl)-3-(4-chlorophenyl)pyrazole

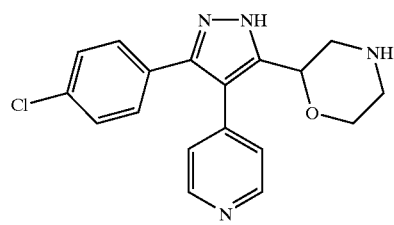

EXAMPLE C-198

5-(N-methyl-2-morpholinyl)-4-(4-pyridyl)-3-(4-chlorophenyl)pyrazole

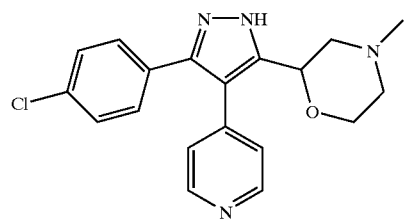

EXAMPLE C-199

5-(N-isopropyl-2-morpholinyl)-4-(4-pyridyl)-3-(4-chlorophenyl)pyrazole

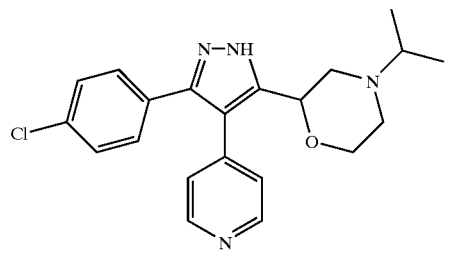

EXAMPLE C-200

5-(N-benzyl-2-morpholinyl)-4-(4-pyridyl)-3-(4-chlorophenyl)pyrazole

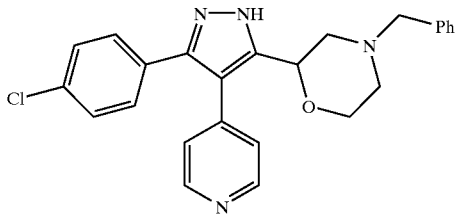

EXAMPLE C-201

5-(N-acetyl-2-morpholinyl)-4-(4-pyridyl)-3-(4-chlorophenyl)pyrazole

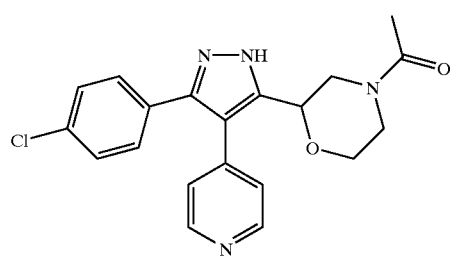

EXAMPLE C-202

5-[trans-4-(N-t-butoxycarbonylamino)methylcyclohexyl]-4-(4-pyridyl)-3-(4-chlorophenyl)pyrazole

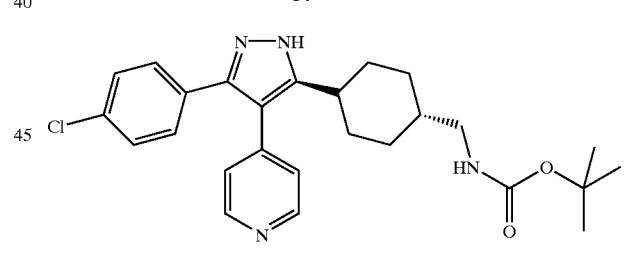

EXAMPLE C-203

5-(trans-4-aminomethylcyclohexyl)-4-(4-pyridyl)-3-(4-chlorophenyl)pyrazole

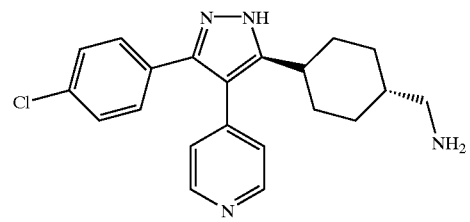

EXAMPLE C-204

5-[trans-4-(N-isopropylamino)methylcyclohexyl)-4-(4-pyridyl)-3-(4-chlorophenyl)pyrazole

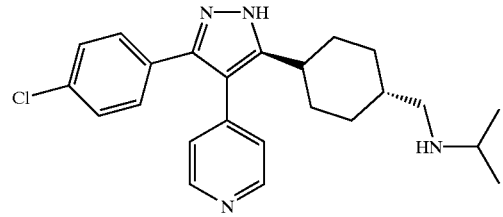

EXAMPLE C-205

5-[trans-4-(N,N-dimethylamino)methylcyclohexyl]-4-(4-pyridyl)-3-(4-chlorophenyl)pyrazole

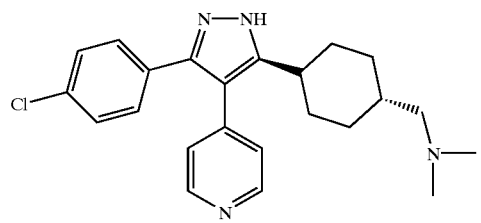

EXAMPLE C-206

5-[trans-4-(N-acetylamino)methylcyclohexyl)]-4-(4-pyridyl)-3-(4-chlorophenyl)pyrazole

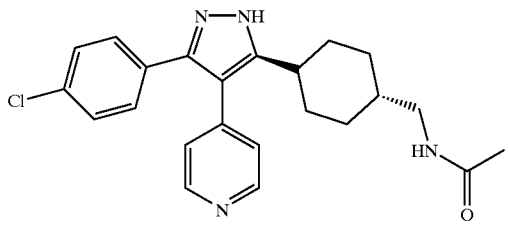

EXAMPLE C-207

5-[trans-4-(N-t-butoxycarbonylamino)cyclohexyl]-4-(4-pyridyl)-3-(4-chlorophenyl)pyrazole

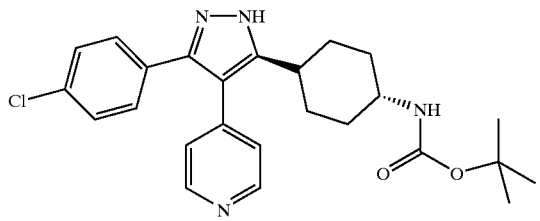

EXAMPLE C-208

5-(trans-4-aminocyclohexyl)-4-(4-pyridyl)-3-(4-chlorophenyl)pyrazole

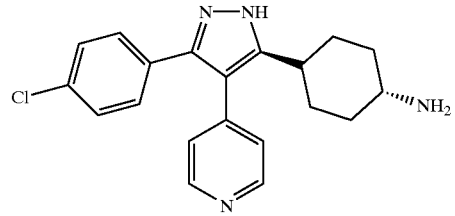

EXAMPLE C-209

5-[trans-4-(N,N-dimethylamino)cyclohexyl]-4-(4-pyridyl)-3-(4-chlorophenyl)pyrazole

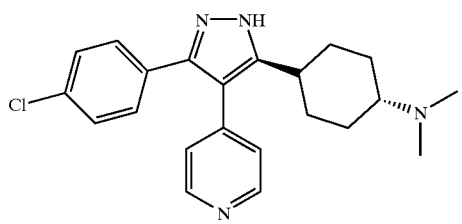

EXAMPLE C-210

5-[trans-4-(N-isopropylamino)cyclohexyl]-4-(4-pyridyl)-3-(4-chlorophenyl)pyrazole

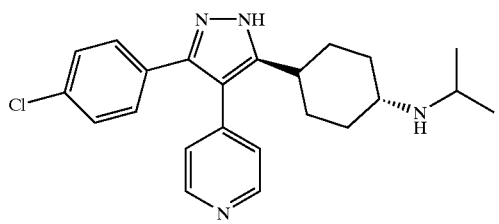

EXAMPLE C-211

5-[trans-4-(N-acetylamino)cyclohexyl]-4-(4-pyridyl)-3-(4-chlorophenyl)pyrazole

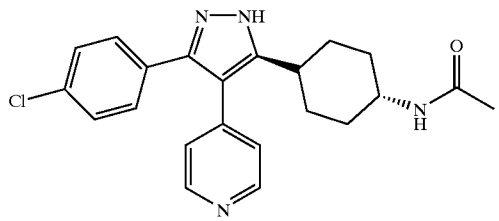

EXAMPLE C-212

5-[cis-4-(N-t-butoxycarbonyl)methylaminocyclohexyl)]-4-(4-pyridyl)-3-(4-chlorophenyl)pyrazole

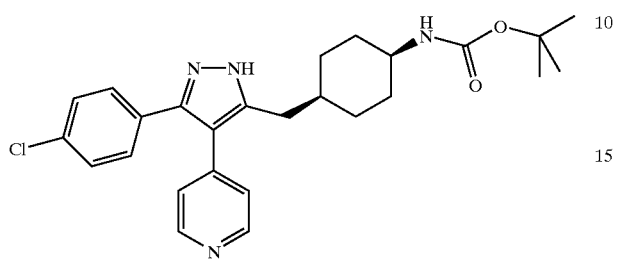

EXAMPLE C-213

5-(cis-4-methylaminocyclohexyl)-4-(4-pyridyl)-3-(4-chlorophenyl)pyrazole

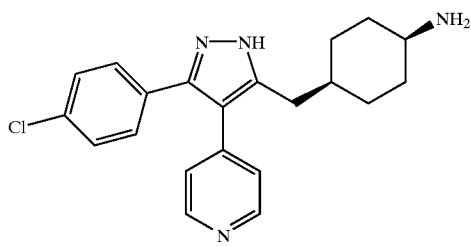

EXAMPLE C-214

5-[cis-4-(N,N-dimethyl)methylaminocyclohexyl)]-4-(4-pyridyl)-3-(4-chlorophenyl)pyrazole

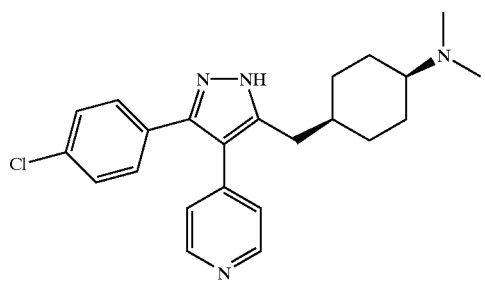

EXAMPLE C-215

5-[cis-4-(N-isopropyl)methylaminocyclohexyl)]-4-(4-pyridyl)-3-(4-chlorophenyl)pyrazole

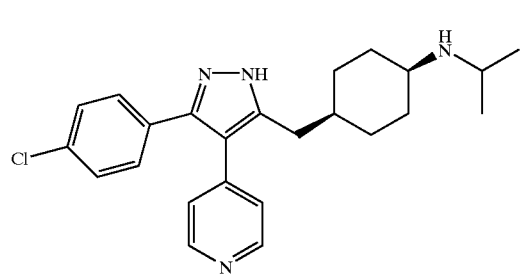

EXAMPLE C-216

5-[cis-4-(N-acetyl)methylaminocyclohexyl)]-4-(4-pyridyl)-3-(4-chlorophenyl)pyrazole

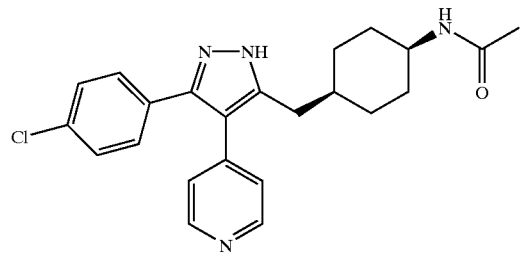

EXAMPLE C-217

5-[3-(1,1-dimethyl-1-(N-t-butoxycarbonylamino)propyl-4-(4-pyridyl)-3-(4-chlorophenyl)pyrazole

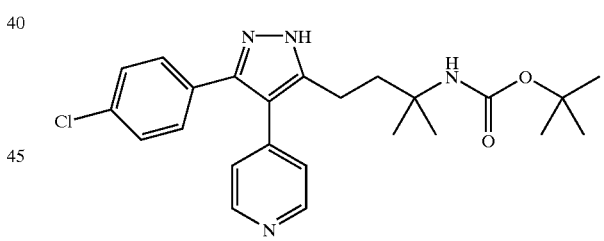

EXAMPLE C-218

5-[3-(1,1-dimethyl-1-amino)propyl-4-(4-pyridyl)-3-(4-chlorophenyl)pyrazole

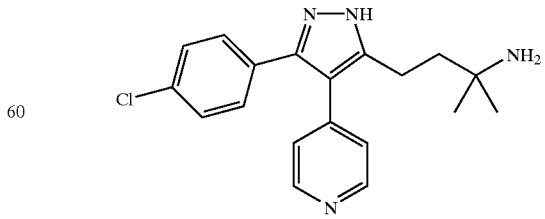

EXAMPLE C-219

5-[3-(1,1-dimethyl-1-(N,N-dimethylamino)propyl-4-(4-pyridyl)-3-(4-chlorophenyl)pyrazole

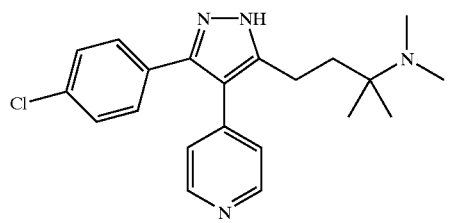

EXAMPLE C-220

5-[3-(1,1-dimethyl-1-(N-isopropylamnino)propyl-4-(4-pyridyl)-3-(4-chlorophenyl)pyrazole

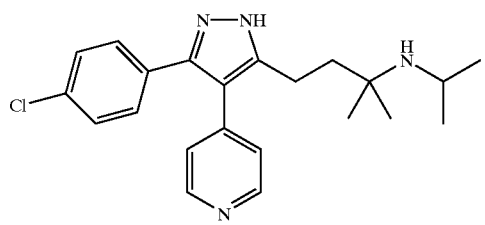

EXAMPLE C-221

5-[3-(1,1-dimethyl-1-(N-acetylamino)propyl-4-(4-pyridyl)-3-(4-chlorophenyl)pyrazole

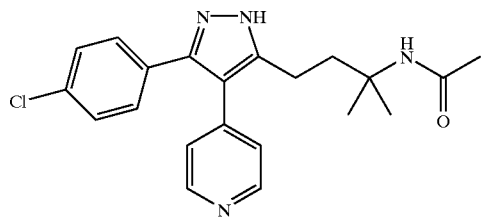

EXAMPLE C-222

5-[4-(1-carboxamidino)benzyl-4-(4-pyridyl)-3-(4-chlorophenyl)pyrazole

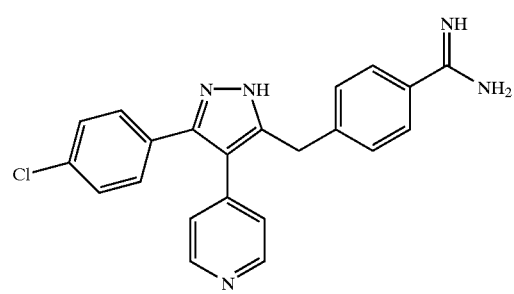

EXAMPLE C-223

5-[4-(1-N-methylcarboxamidino)benzyl-4-(4-pyridyl)-3-(4-chlorophenyl)pyrazole

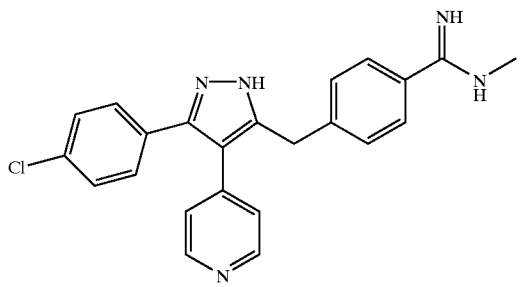

EXAMPLE C-224

5-[4-(1-N-benzylcarboxamidino)benzyl-4-(4-pyridyl)-3-(4-chlorophenyl)pyrazole

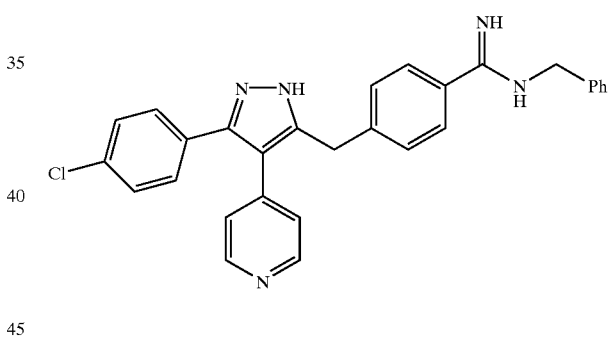

EXAMPLE C-225

5-[3-(1-carboxamidino)benzyl-4-(4-pyridyl)-3-(4-chlorophenyl)pyrazole

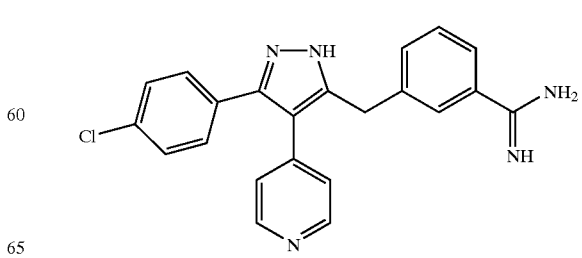

EXAMPLE C-226

5-[3-(1-N-methylcarboxamidino)benzyl-4-(4-pyridyl)-3-(4-chlorophenyl)pyrazole

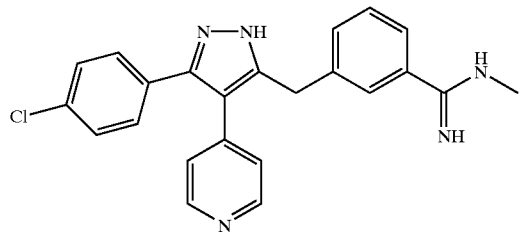

EXAMPLE C-227

5-[3-(1-N-benzylcarboxamidino)benzyl-4-(4-pyridyl)-3-(4-chlorophenyl)pyrazole

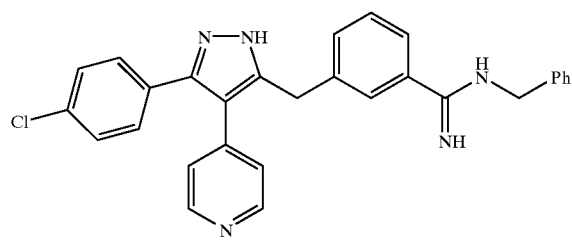

EXAMPLE C-228

5-[3-(N-t-butoxycarbonyl)aminobenzyl]-4-(4-pyridyl)-3-(4-chlorophenyl)pyrazole

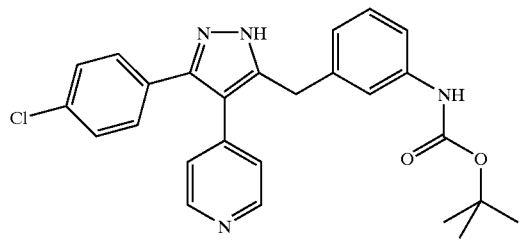

EXAMPLE C-229

5-(3-aminobenzyl)-4-(4-pyridyl)-3-(4-chlorophenyl)pyrazole

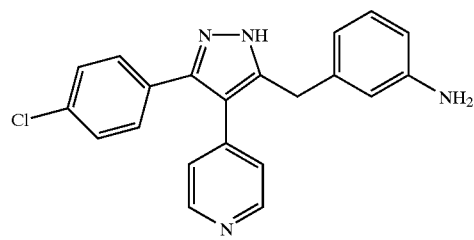

EXAMPLE C-230

5-[3-(N,N-dimethylamino)benzyl]-4-(4-pyridyl)-3-(4-chlorophenyl)pyrazole

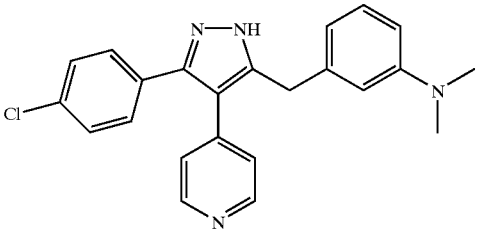

EXAMPLE C-231

5-[3-(N-isopropylamino)benzyl]-4-(4-pyridyl)-3-(4-chlorophenyl)pyrazole

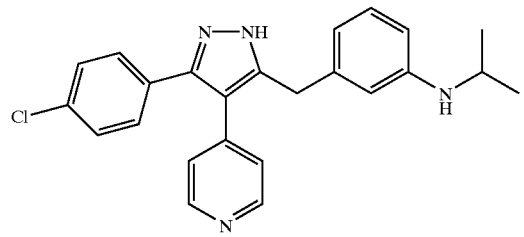

EXAMPLE C-232

5-[3-(N-benizylamino)benzyl]-4-(4-pyridyl)-3-(4-chlorophenyl)pyrazole

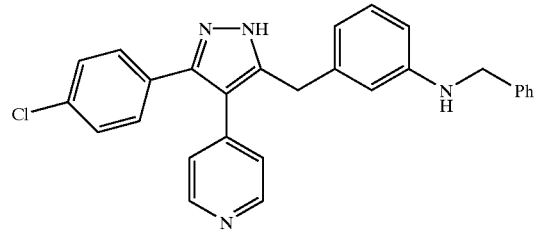

EXAMPLE C-233

5-[3-(N-acetylamino)benzyl]-4-(4-pyridyl)-3-(4-chlorophenyl)pyrazole

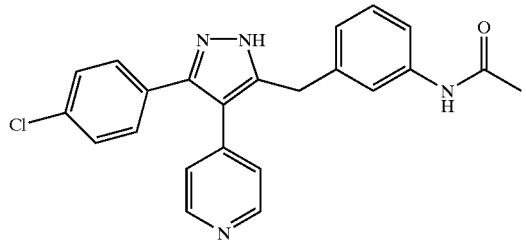

EXAMPLE C-234

5-[4-(2-amino)methylimidazolyl]-4-(4-pyridyl)-3-(4-chlorophenyl)pyrazole

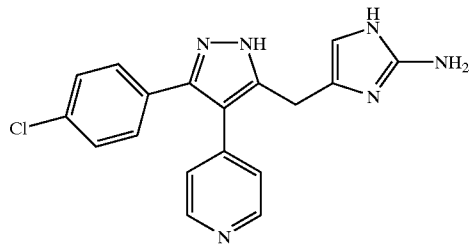

EXAMPLE C-235

5-[4-(2-N,N-dimethylamino)methylimidazolyl]-4-(4-pyridyl)-3-(4-chlorophenyl)pyrazole

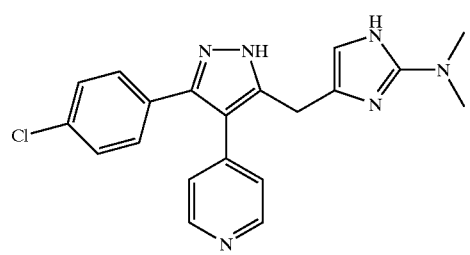

EXAMPLE C-236

5-[4-(2-N-isopropylamino)methylimidazolyl]-4-(4-pyridyl)-3-(4-chlorophenyl)pyrazole

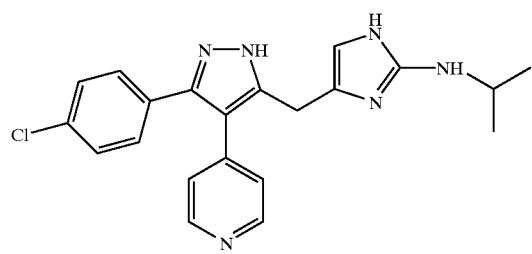

EXAMPLE C-237

5-[4-(2-N-benzylamino)methylimidazolyl]-4-(4-pyridyl)-3-(4-chlorophenyl)pyrazole

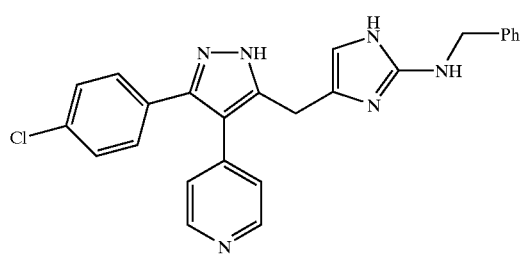

EXAMPLE C-238

5-[4-(2-N-acetylamino)methylimidazolyl]-4-(4-pyridyl)-3-(4-chlorophenyl)pyrazole

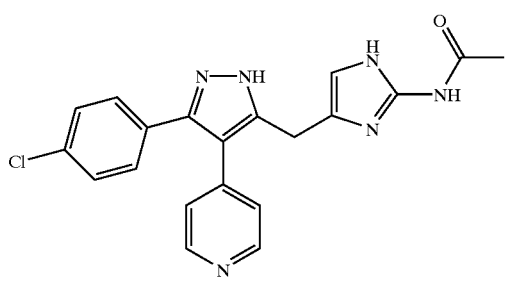

EXAMPLE C-239

5-[4-(2-amino)methloxazolyl]-4-(4-pyridyl)-3-(4-chlorophenyl)pyrazole

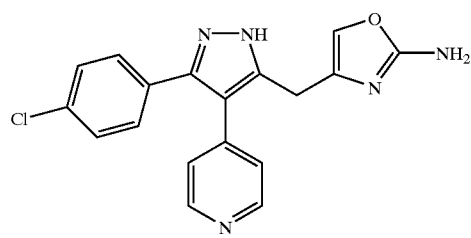

EXAMPLE C-240

5-[4-(2-N,N-dimethylamino)methyloxazolyl]-4-(4-pyridyl)-3-(4-chlorophenyl)pyrazole

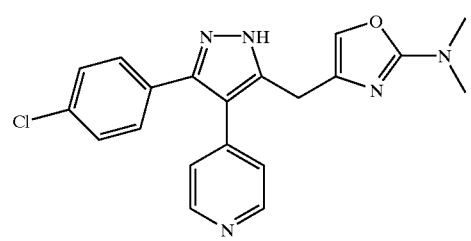

EXAMPLE C-241

5-[4-(2-N-isopropylamino)methyloxazolyl]-4-(4-pyridyl)-3-(4-chlorophenyl)pyrazole

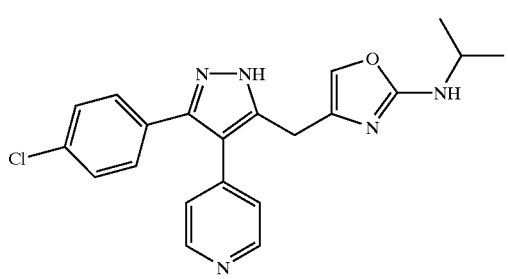

EXAMPLE C-242

5-[4-(2-N-benzylamino)methloxazolyl]-4-(4-pyridyl)-3-(4-chlorophenyl)pyrazole

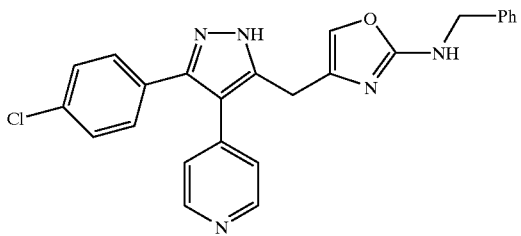

EXAMPLE C-243

5-[4-(2-N-acetylamino)methloxazolyl]-4-(4-pyridyl)-3-(4-chlorophenyl)pyrazole

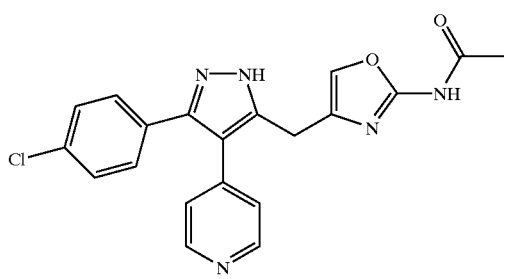

EXAMPLE C-244

5-[4-(2-amino)methylthiazolyl]-4-(4-pyridyl)-3-(4-chlorophenyl)pyrazole

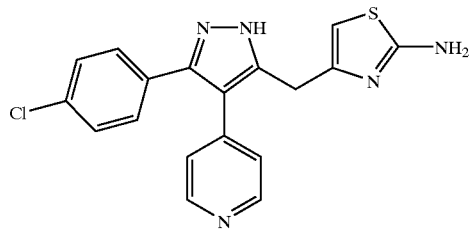

EXAMPLE C-245

5-[4-(2-N,N-dimethylamino)methylthiazolyl]-4-(4-pyridyl)-3-(4-chlorophenyl)pyrazole

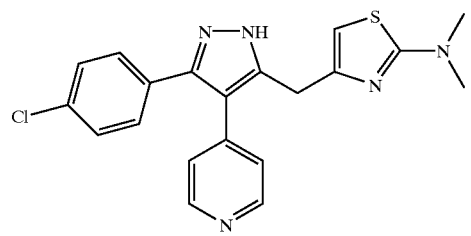

EXAMPLE C-246

5-[4-(2-N-isopropylamino)methylthiazolyl]-4-(4-pyridyl)-3-(4-chlorophenyl)pyrazole

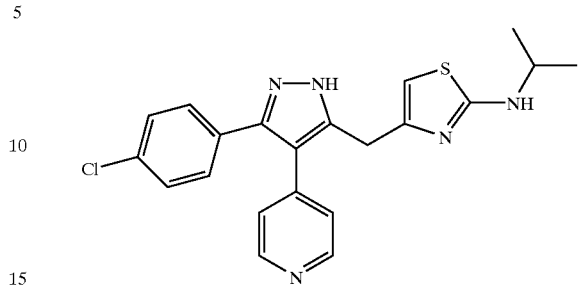

EXAMPLE C-247

5-[4-(2-N-benzylamino)methylthiazolyl]-4-(4-pyridyl)-3-(4-chlorophenyl)pyrazole

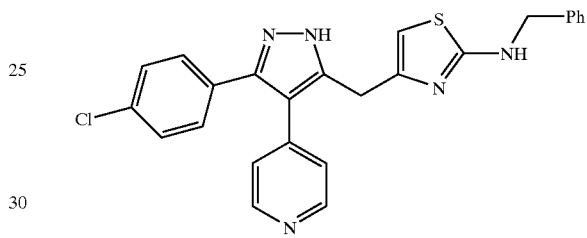

EXAMPLE C-248

5-[4-(2-N-acetylamino)methylthiazolyl]-4-(4-pyridyl)-3-(4-chlorophenyl)pyrazole

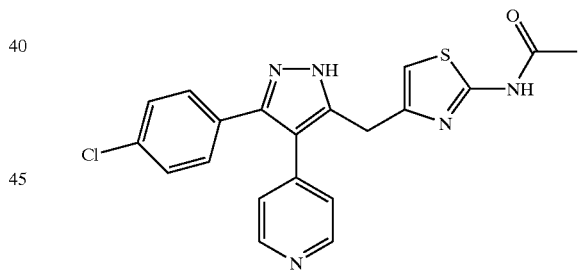

Biological data from compounds of Examples B-0001 through B-1573 and of Examples B-2270 through B-2462 are shown in the following tables.

In vitro P38-alpha kinase inhibitory data are shown in the column identified as:

"P38 alpha kinase $IC_{50}$, uM or % inhib @ conc. (uM)"

In vitro whole cell assay for measuring the ability of the compounds to inhibit TNF production in human U937 cells stimulated with LPS are shown in the column identified as:

"U937 Cell $IC_{50}$, uM or % inhib @ conc., (uM)"

In vivo assessment of the ability of the compounds to inhibit LPS-stimulated TNF release in the mouse is shown in the column identified as:

"Mouse LPS Model, % TNF inhib @ dose @ predose time"

wherein in the dose is milligram per kilogram (mpk) administered by oral gavage and the predose time indicates the number of hours before LPS challenge when the compound is administered.

In vivo assessment of the ability of the compounds to inhibit LPS-stimulated TNF release in the rat is shown in the column identified as:

"Rat LPS Model, % TNF inhib @ dose @ predose time" wherein in the dose is milligram per kilogram (mpk) administered by oral gavage and the predose time indicates the number of hours before LPS challenge when the compound is administered.

| Example # | P38 alpha kinase IC50, uM or % inhib @ conc. (uM) | U937 Cell IC50, uM or % inhib @ conc. (uM) | Mouse LPS Model % TNF inhib @ dose @ predose time | Rat LPS Model % inhib @ dose @ predose time |
|---|---|---|---|---|
| B-0001 | 53.0% @ 1.0 uM | 40.0% @ 1.0 uM | | |
| B-0002 | 71.0% @ 1.0 uM | 28.0% @ 10.0 uM | | |
| B-0003 | 70.0% @ 1.0 uM | 76.0% @ 10.0 uM | | |
| B-0004 | 80.0% @ 1.0 uM | 4.61 uM | | |
| B-0005 | 95.0% @ 1.0 uM | 2.91 uM | | |
| B-0006 | 82.0% @ 1.0 uM | 80% @ 10.0 uM | | |
| B-0007 | 74.0% @ 1.0 uM | 85.0% @ 10.0 uM | | |
| B-0008 | 42.0% @ 1.0 uM | 65.0% @ 10.0 uM | | |
| B-0009 | 0.04 uM | 0.72 uM | | |
| B-0010 | 0.52 uM | 0.65 uM | | |
| B-0011 | 0.03 uM | 4.47 uM | | |
| B-0012 | 30.0% @ 1.0 uM | 44.0% @ 1.0 uM | | |
| B-0013 | 70.0% @ 1.0 uM | 84.0% @ 10.0 uM | | |
| B-0014 | 79.0% @ 1.0 uM | 80.0% @ 10.0 uM | | |
| B-0015 | 82.0% @ 1.0 uM | 80.0% @ 10.0 uM | | |
| B-0016 | 94.0% @ 1.0 uM | 3.98 uM | | |
| B-0017 | 56.0% @ 1.0 uM | 79.0% @ 10.0 uM | | |
| B-0018 | 60.0% @ 1.0 uM | 59.0% @ 10.0 uM | | |
| B-0019 | 84.0% @ 1.0 uM | 100.0% @ 10.0 uM | | |
| B-0020 | 73.0% @ 1.0 uM | 81.0% @ 10.0 uM | | |
| B-0021 | 68.0% @ 1.0 uM | 76.0% @ 10.0 uM | | |
| B-0022 | 69.0% @ 1.0 uM | 44.0% @ 1.0 uM | | |
| B-0023 | 90.0% @ 1.0 uM | 77.0% @ 10.0 uM | | |
| B-0024 | 94.0% @ 1.0 uM | 52.0% @ 1.0 uM | | |
| B-0025 | 89.0% @ 1.0 uM | 79.0% @ 10.0 uM | | |
| B-0026 | 96.0% @ 1.0 uM | 3.27 uM | | |
| B-0027 | 94.0% @ 1.0 uM | 11.0 uM | | |
| B-0028 | 69.0% @ 1.0 uM | 45.0% @ 10.0 uM | | |
| B-0029 | 91.0% @ 1.0 uM | 58.0% @ 10.0 uM | | |
| B-0030 | 92.0% @ 1.0 uM | 75.0% @ 10.0 uM | | |
| B-0031 | 94.0% @ 1.0 uM | 100.0% @ 10.0 uM | | |
| B-0032 | 94.0% @ 1.0 uM | 78.0% @ 10.0 uM | | |
| B-0033 | 97.0% @ 1.0 uM | 10.0 uM | | |
| B-0034 | 95.0% @ 1.0 uM | 10.0 uM | | |
| B-0035 | 94.0% @ 1.0 uM | 10.0 uM | | |
| B-0036 | 92.0% @ 1.0 uM | 8.24 uM | | |
| B-0037 | 91.0% @ 1.0 uM | 86.0% @ 10.0 uM | | |
| B-0038 | 71.0% @ 1.0 uM | 84.0% @ 10.0 uM | | |
| B-0039 | 89.0% @ 1.0 uM | 72.0% @ 10.0 uM | | |
| B-0040 | 93.0% @ 1.0 uM | 2.3 uM | | |
| B-0041 | 65.0% @ 1.0 uM | 66.0% @ 10.0 uM | | |
| B-0042 | 94.0% @ 1.0 uM | 2.76 uM | | |
| B-0043 | 0.22 uM | 0.54 uM | | |
| B-0044 | 0.14 uM | 0.19 uM | | |
| B-0045 | 94.0% @ 1.0 uM | 1.01 uM | | |
| B-0046 | 96.0% @ 1.0 uM | 54.0% @ 1.0 uM | | |
| B-0047 | 94.0% @ 1.0 uM | 74.0% @ 10.0 uM | | |
| B-0048 | 94.0% @ 1.0 uM | 76.0% @ 10.0 uM | | |
| B-0049 | 88% @ 1.0 uM | 33.0% @ 1.0 uM | | |
| B-0050 | 73% @ 1.0 uM | 34.0% @ 1.0 uM | | |
| B-0051 | 3.3 uM | 2.15 uM | 47% @ 100 mpk @ −6 h | 79% @ 3 mpk @ −4 h |
| B-0052 | 92% @ 1.0 uM | 15.0% @ 1.0 uM | | |
| B-0053 | 95% @ 1.0 uM | 34.0% @ 1.0 uM | | |
| B-0054 | 90% @ 1.0 uM | 30.0% @ 1.0 uM | | |
| B-0055 | 93% @ 1.0 uM | >1.0 uM | | |
| B-0056 | 96% @ 1.0 uM | 21.0% @ 1.0 uM | | |
| B-0057 | 96% @ 1.0 uM | 29.0% @ 1.0 uM | | |
| B-0058 | 79% @ 1.0 uM | 18.0% @ 1.0 uM | | |
| B-0059 | 83% @ 1.0 uM | 35.0% @ 1.0 uM | | |
| B-0060 | 73% @ 1.0 uM | 22.0% @ 1.0 uM | | |
| B-0061 | 62% @ 1.0 uM | 27.0% @ 1.0 uM | | |
| B-0062 | 94% @ 1.0 uM | 36.0% @ 1.0 uM | | |
| B-0063 | 96% @ 1.0 uM | 40.0% @ 1.0 uM | | |
| B-0064 | 90% @ 1.0 uM | 4.0% @ 1.0 uM | | |
| B-0065 | 83% @ 1.0 uM | 21.0% @ 1.0 uM | | |
| B-0066 | 94% @ 1.0 uM | 28.0% @ 1.0 uM | | |
| B-0067 | 91% @ 1.0 uM | 1.0% @ 1.0 uM | | |
| B-0068 | 72% @ 1.0 uM | 22.0% @ 1.0 uM | | |

-continued

| Example # | P38 alpha kinase IC50, uM or % inhib @ conc. (uM) | U937 Cell IC50, uM or % inhib @ conc. (uM) | Mouse LPS Model % TNF inhib @ dose @ predose time | Rat LPS Model % inhib @ dose @ predose time |
|---|---|---|---|---|
| B-0069 | 96% @ 1.0 uM | 37.0% @ 1.0 uM | | |
| B-0070 | 92% @ 1.0 uM | 30.0% @ 1.0 uM | | |
| B-0071 | 86% @ 1.0 uM | 31.0% @ 1.0 uM | | |
| B-0072 | 77% @ 1.0 uM | 32.0% @ 1.0 uM | | |
| B-0073 | 91% @ 1.0 uM | 24.0% @ 1.0 uM | | |
| B-0074 | 92% @ 1.0 uM | 42.0% @ 1.0 uM | | |
| B-0075 | 91% @ 1.0 uM | 35.0% @ 1.0 uM | | |
| B-0076 | 58% @ 1.0 uM | 21.0% @ 1.0 uM | | |
| B-0077 | 0.8 uM | 10.0 uM | | |
| B-0078 | 80% @ 1.0 uM | 20.0% @ 1.0 uM | | |
| B-0079 | 93% @ 1.0 uM | 13.0% @ 1.0 uM | | |
| B-0080 | 73% @ 1.0 uM | 73.0% @ 1.0 uM | | |
| B-0081 | 92% @ 1.0 uM | 13.0% @ 1.0 uM | | |
| B-0082 | 47% @ 1.0 uM | 27.0% @ 1.0 uM | | |
| B-0083 | 0.22 uM | 6.51 uM | | |
| B-0084 | 56% @ 1.0 uM | 30.0% @ 1.0 uM | | |
| B-0085 | 83% @ 1.0 uM | 21.0% @ 1.0 uM | | |
| B-0086 | 91% @ 1.0 uM | 37.0% @ 1.0 uM | | |
| B-0087 | 0.55 uM | 2.26 uM | 38% @ 30 mpk @ −6 h | |
| B-0088 | 96% @ 1.0 uM | 9.0% @ 1.0 uM | | |
| B-0089 | 0.04 uM | 3.33 uM | | |
| B-0090 | 98% @ 1.0 uM | 52.0% @ 1.0 uM | | |
| B-0091 | 96% @ 1.0 uM | 40.0% @ 1.0 uM | | |
| B-0092 | 97% @ 1.0 uM | 34.0% @ 1.0 uM | | |
| B-0093 | 3.18 uM | 1.25 uM | 30% @ 30 mpk @ −6 h | |
| B-0094 | 96% @ 1.0 uM | 52.0% @ 1.0 uM | | |
| B-0095 | 98% @ 1.0 uM | 38.0% @ 1.0 uM | | |
| B-0096 | 91% @ 1.0 uM | 22.0% @ 1.0 uM | | |
| B-0097 | 72.0% @ 10.0 uM | 38.0% @ 1.0 uM | | |
| B-0098 | 66.0% @ 10.0 uM | 12.0% @ 1.0 uM | | |
| B-0099 | 43.0% @ 1.0 uM | >1.0 uM | | |
| B-0100 | 75.0% @ 1.0 uM | 5.0 uM | | |
| B-0101 | 71.0% @ 1.0 uM | 2.11 uM | | |
| B-0102 | 81.0% @ 1.0 uM | 15.0% @ 1.0 uM | | |
| B-0103 | 71.0% @ 1.0 uM | 6.0% @ 1.0 uM | | |
| B-0104 | 56.0% @ 1.0 uM | 2.78 uM | | |
| B-0105 | 78.0% @ 1.0 uM | 5.0 uM | | |
| B-0106 | 62.0% @ 1.0 uM | 5.0 uM | | |
| B-0107 | 0.27 uM | 5.0 uM | | |
| B-0108 | 61.0% @ 1.0 uM | 4.85 uM | | |
| B-0109 | 45.0% @ 1.0 uM | 19.0% @ 1.0 uM | | |
| B-0110 | 66.0% @ 1.0 uM | 13.0% @ 1.0 uM | | |
| B-0111 | 57.0% @ 1.0 uM | >1.0 uM | | |
| B-0112 | 97.0% @ 1.0 uM | 1.12 uM | | |
| B-0113 | 75.0% @ 1.0 uM | 43.0% @ 1.0 uM | | |
| B-0114 | 45.0% @ 1.0 uM | 3.92 uM | | |
| B-0115 | 47.0% @ 1.0 uM | 2.0% @ 1.0 uM | | |
| B-0116 | 73.0% @ 1.0 uM | 35.0% @ 1.0 uM | | |
| B-0117 | 0.46 uM | 1.78 uM | 30% @ 30 mpk @ −6 h | |
| B-0118 | 1.18 uM | 1.29 uM | | |
| B-0119 | 89.0% @ 10.0 uM | 2.78 uM | | |
| B-0120 | 0.008 uM | 0.21 uM | 77% @ 100 mpk @ −6 h | 70% @ 3 mpk @ −4 h |
| B-0121 | 79.0% @ 1.0 uM | 1.22 uM | | |
| B-0122 | 79.0% @ 10.0 uM | 2.0% @ 1.0 uM | | |
| B-0123 | 59.0% @ 1.0 uM | >1.0 uM | | |
| B-0124 | 73.0% @ 1.0 uM | 15.0% @ 1.0 uM | | |
| B-0125 | 70.0% @ 10.0 uM | 17.0% @ 1.0 uM | | |
| B-0126 | 66.0% @ 1.0 uM | 1.57 uM | | |
| B-0127 | 82.0% @ 1.0 uM | 0.96 uM | | |
| B-0128 | 78.0% @ 1.0 uM | 1.81 uM | | |
| B-0129 | 51.0% @ 1.0 uM | 31.0% @ 1.0 uM | | |
| B-0130 | 69.0% @ 1.0 uM | 58.0% @ 1.0 uM | | |
| B-0131 | 43.0% @ 1.0 uM | 46.0% @ 1.0 uM | | |
| B-0132 | 76.0% @ 1.0 uM | 8.0% @ 1.0 uM | | |
| B-0133 | 51.0% @ 1.0 uM | 42.0% @ 1.0 uM | | |
| B-0134 | 60.0% @ 1.0 uM | 2.17 uM | | |
| B-0135 | 78.0% @ 1.0 uM | 58.0% @ 1.0 uM | | |
| B-0136 | 77.0% @ 1.0 uM | 44.0% @ 1.0 uM | | |
| B-0137 | 41.0% @ 1.0 uM | 37.0% @ 1.0 uM | | |
| B-0138 | 50.0% @ 1.0 uM | 32.0% @ 1.0 uM | | |
| B-0139 | 54.0% @ 10.0 uM | 17.0% @ 1.0 uM | | |
| B-0140 | 67% @ 10.0 uM | 9.0% @ 1.0 uM | | |
| B-0141 | 78.0% @ 1.0 uM | 10.0% @ 1.0 uM | | |
| B-0142 | 86.0% @ 1.0 uM | 12.0% @ 1.0 uM | | |
| B-0143 | 42.0% @ 1.0 uM | 3.63 uM | | |

| Example # | P38 alpha kinase IC50, uM or % inhib @ conc. (uM) | U937 Cell IC50, uM or % inhib @ conc. (uM) | Mouse LPS Model % TNF inhib @ dose @ predose time | Rat LPS Model % inhib @ dose @ predose time |
|---|---|---|---|---|
| B-0144 | 86.0% @ 1.0 uM | 43.0% @ 1.0 uM | | |
| B-0145 | 54.0% @ 10.0 uM | 12.0% @ 1.0 uM | | |
| B-0146 | 77.0% @ 10.0 uM | 28.0% @ 1.0 uM | | |
| B-0147 | 44.0% @ 1.0 uM | 22.0% @ 1.0 uM | | |
| B-0148 | 51.0% @ 1.0 uM | >1.0 uM | | |
| B-0149 | 1.15 uM | 10.0 uM | | |
| B-0150 | 27.0% @ 10.0 uM | 35.0% @ 1.0 uM | | |
| B-0151 | 43.0% @ 1.0 uM | 30.0% @ 1.0 uM | | |
| B-0152 | 51.0% @ 1.0 uM | 24.0% @ 1.0 uM | | |
| B-0153 | 57.0% @ 1.0 uM | 21.0% @ 1.0 uM | | |
| B-0154 | 65.0% @ 10.0 uM | 14.0% @ 1.0 uM | | |
| B-0155 | 40.0% @ 10.0 uM | 26.0% @ 1.0 uM | | |
| B-0156 | 42.0% @ 10.0 uM | 13.0% @ 1.0 uM | | |
| B-0157 | 48.0% @ 10.0 uM | 9.0% @ 1.0 uM | | |
| B-0158 | 58.0% @ 10.0 uM | 39.0% @ 1.0 uM | | |
| B-0159 | 54.0% @ 10.0 uM | 5.0% @ 1.0 uM | | |
| B-0160 | 59.0% @ 10.0 uM | 26.0% @ 1.0 uM | | |
| B-0161 | 72.0% @ 10.0 uM | 13.0% @ 1.0 uM | | |
| B-0162 | 23% @ 1.0 uM | 2.05 uM | | |
| B-0163 | 20.0% @ 10.0 uM | 10.0% @ 1.0 uM | | |
| B-0164 | 37.0% @ 10.0 uM | 20.0% @ 1.0 uM | | |
| B-0165 | 70.0% @ 10.0 uM | 19.0% @ 1.0 uM | | |
| B-0166 | 45.0% @ 10.0 uM | 37.0% @ 1.0 uM | | |
| B-0167 | 40.0% @ 1.0 uM | 37.0% @ 1.0 uM | | |
| B-0168 | 44% @ 1.0 uM | 2.36 uM | | |
| B-0169 | 43.0% @ 1.0 uM | 21.0% @ 1.0 uM | | |
| B-0170 | 43.0% @ 1.0 uM | 30.0% @ 1.0 uM | | |
| B-0171 | 61.0% @ 10.0 uM | 21.0% @ 1.0 uM | | |
| B-0172 | 16.0% @ 10.0 uM | 11.0% @ 1.0 uM | | |
| B-0173 | 33.0% @ 10.0 uM | 48.0% @ 1.0 uM | | |
| B-0174 | 54.0% @ 10.0 uM | 43.0% @ 1.0 uM | | |
| B-0175 | 41.0% @ 10.0 uM | 31.0% @ 1.0 uM | | |
| B-0176 | 50.0% @ 1.0 uM | 30.0% @ 1.0 uM | | |
| B-0177 | 70.0% @ 10.0 uM | 27.0% @ 1.0 uM | | |
| B-0178 | 12.0% @ 10.0 uM | 35.0% @ 1.0 uM | | |
| B-0179 | 27.0% @ 10.0 uM | 37.0% @ 1.0 uM | | |
| B-0180 | 34.0% @ 10.0 uM | 23.0% @ 1.0 uM | | |
| B-0181 | 5.0% @ 1.0 uM | 2.0% @ 1.0 uM | | |
| B-0182 | 39.0% @ 10.0 uM | 40.0% @ 1.0 uM | | |
| B-0183 | 12.0% @ 10.0 uM | 34.0% @ 1.0 uM | | |
| B-0184 | 66.0% @ 10.0 uM | 17.0% @ 1.0 uM | | |
| B-0185 | 65.0% @ 10.0 uM | 25.0% @ 1.0 uM | | |
| B-0186 | 40.0% @ 1.0 uM | 25.0% @ 1.0 uM | | |
| B-0187 | 4.0% @ 10.0 uM | 14.0% @ 1.0 uM | | |
| B-0188 | 70.0% @ 10.0 uM | 35.0% @ 1.0 uM | | |
| B-0189 | 42.0% @ 10.0 uM | 9.0% @ 1.0 uM | | |
| B-0190 | 59.0% @ 10.0 uM | 31.0% @ 1.0 uM | | |
| B-0191 | 40.0% @ 1.0 uM | 29.0% @ 1.0 uM | | |
| B-0192 | 12.0% @ 10.0 uM | 47.0% @ 1.0 uM | | |
| B-0193 | 0.54 uM | 6% @ 1.0 uM | | |
| B-0194 | 1.31 uM | 22% @ 1.0 uM | | |
| B-0195 | 1.03 uM | 55% @ 1.0 uM | | |
| B-0196 | 2.24 uM | >1.0 uM | | |
| B-0197 | 2.0 uM | 14% @ 1.0 uM | | |
| B-0198 | 1.2 uM | 2% @ 1.0 uM | | |
| B-0199 | 1.34 uM | 3% @ 1.0 uM | | |
| B-0200 | 1.31 uM | 16% @ 1.0 uM | | |
| B-0201 | 0.29 uM | 59% @ 1.0 uM | | |
| B-0202 | 0.55 uM | 2.26 uM | | |
| B-0203 | 0.16 uM | 65% @ 1.0 uM | | |
| B-0204 | 0.21 uM | 48% @ 1.0 uM | | |
| B-0205 | 0.096 uM | 54% @ 1.0 uM | | |
| B-0206 | 5.76 uM | 14% @ 1.0 uM | | |
| B-0207 | 0.12 uM | 52% @ 1.0 uM | | |
| B-0208 | 0.067 uM | >1.0 uM | | |
| B-0209 | 0.29 uM | 8% @ 1.0 uM | | |
| B-0210 | 0.057 uM | 67% @ 1.0 uM | | |
| B-0211 | 0.25 uM | 30% @ 1.0 uM | | |
| B-0212 | 0.12 uM | 28% @ 1.0 uM | | |
| B-0213 | 0.31 uM | 39% @ 1.0 uM | | |
| B-0214 | 0.16 uM | 50% @ 1.0 uM | | |
| B-0215 | 0.11 uM | 51% @ 1.0 uM | | |
| B-0216 | 0.56 uM | >1.0 uM | | |
| B-0217 | 0.55 uM | >1.0 uM | | |
| B-0218 | 0.53 uM | 18% @ 1.0 uM | | |

-continued

| Example # | P38 alpha kinase IC50, uM or % inhib @ conc. (uM) | U937 Cell IC50, uM or % inhib @ conc. (uM) | Mouse LPS Model % TNF inhib @ dose @ predose time | Rat LPS Model % inhib @ dose @ predose time |
|---|---|---|---|---|
| B-0219 | 1.91 uM | 18% @ 1.0 uM | | |
| B-0220 | 0.13 uM | 40% @ 1.0 uM | | |
| B-0221 | 2.4 uM | >1.0 uM | | |
| B-0222 | 0.4 uM | 29.0% @ 1.0 uM | | |
| B-0223 | 0.2 uM | 1.0% @ 1.0 uM | | |
| B-0224 | <0.1 uM | 93.0% @ 1.0 uM | | |
| B-0225 | 0.047 uM | 37.0% @ 1.0 uM | | |
| B-0226 | 0.074 uM | 20.0% @ 1.0 uM | | |
| B-0227 | 0.045 uM | 1.0% @ 1.0 uM | | |
| B-0228 | 0.15 uM | 44.0% @ 1.0 uM | | |
| B-0229 | <0.1 uM | 61.0% @ 1.0 uM | | |
| B-0230 | 0.041 uM | 30.0% @ 1.0 uM | | |
| B-0231 | 0.055 uM | 40.0% @ 1.0 uM | | |
| B-0232 | 0.048 uM | 24.0% @ 1.0 uM | | |
| B-0233 | 0.095 uM | 43.0% @ 1.0 uM | | |
| B-0234 | 0.11 uM | 68.0% @ 1.0 uM | | |
| B-0235 | 1.31 uM | 90.0% @ 1.0 uM | | |
| B-0236 | 0.077 uM | 46.0% @ 1.0 uM | | |
| B-0237 | 0.13 uM | 60.0% @ 1.0 uM | | |
| B-0238 | 0.47 uM | 82.0% @ 1.0 uM | | |
| B-0239 | 5.73 uM | 84.0% @ 1.0 uM | | |
| B-0240 | 0.2 uM | 70.0% @ 1.0 uM | | |
| B-0241 | 0.1 uM | 45.0% @ 1.0 uM | | |
| B-0242 | <0.1 uM | 78.0% @ 1.0 uM | | |
| B-0243 | 0.039 uM | 53.0% @ 1.0 uM | | |
| B-0244 | 0.02 uM | 57.0% @ 1.0 uM | | |
| B-0245 | 0.13 uM | 24.0% @ 1.0 uM | | |
| B-0246 | <0.1 uM | >1.0 uM | | |
| B-0247 | 0.082 uM | 75.0% @ 1.0 uM | | |
| B-0248 | <0.1 uM | 11.0% @ 1.0 uM | | |
| B-0249 | <0.1 uM | 75.0% @ 1.0 uM | | |
| B-0250 | 0.28 uM | 36.0% @ 1.0 uM | | |
| B-0251 | 0.31 uM | 1.0% @ 1.0 uM | | |
| B-0252 | 0.041 uM | 54.0% @ 1.0 uM | | |
| B-0253 | 0.061 uM | 74.0% @ 1.0 uM | | |
| B-0254 | 0.12 uM | 59.0% @ 1.0 uM | | |
| B-0255 | 0.32 uM | 68.0% @ 1.0 uM | | |
| B-0256 | <0.1 uM | 88.0% @ 1.0 uM | | |
| B-0257 | 1.71 uM | 11.0% @ 1.0 uM | | |
| B-0258 | 0.37 uM | 63.0% @ 1.0 uM | | |
| B-0259 | 0.35 uM | 58.0% @ 1.0 uM | | |
| B-0260 | 0.56 uM | 23.0% @ 1.0 uM | | |
| B-0261 | 0.49 uM | 23.0% @ 1.0 uM | | |
| B-0262 | 0.41 uM | 89.0% @ 1.0 uM | | |
| B-0263 | 0.62 uM | 64.0% @ 1.0 uM | | |
| B-0264 | 0.14 uM | 18.0% @ 1.D uM | | |
| B-0265 | 0.92 uM | 24.0% @ 1.0 uM | | |
| B-0266 | 0.25 uM | 24.0% @ 1.0 uM | | |
| B-0267 | 0.48 uM | 11.0% @ 1.0 uM | | |
| B-0268 | 3.39 uM | 19.0% @ 1.0 uM | | |
| B-0269 | 9.81 uM | 19.0% @ 1.0 uM | | |
| B-0270 | 5.79 uM | 13.0% @ 1.0 uM | | |
| B-0271 | 7.55 uM | 12.0% @ 1.0 uM | | |
| B-0272 | 1.81 uM | 48.0% @ 1.0 uM | | |
| B-0273 | 5.03 uM | 13.0% @ 1.0 uM | | |
| B-0274 | 2.68 uM | 25.0% @ 1.0 uM | | |
| B-0275 | 2.67 uM | 33.0% @ 1.0 uM | | |
| B-0276 | 1.25 uM | 26.0% @ 1.0 uM | | |
| B-0277 | 0.68 uM | 34.0% @ 1.0 uM | | |
| B-0278 | 1.26 uM | 36.0% @ 1.0 uM | | |
| B-0279 | 1.39 uM | 33.0% @ 1.0 uM | | |
| B-0280 | 0.86 uM | 18.0% @ 1.0 uM | | |
| B-0281 | 7.37 uM | 24.0% @ 1.0 uM | | |
| B-0282 | 0.75 uM | 38.0% @ 1.0 uM | | |
| B-0283 | 6.66 uM | 29.0% @ 1.0 uM | | |
| B-0284 | 0.083 uM | 65.0% @ 1.0 uM | | |
| B-0285 | 4.57 uM | 29.0% @ 1.0 uM | | |
| B-0286 | 0.33 uM | 50.0% @ 1.0 uM | | |
| B-0287 | 4.0 uM | 22.0% @ 1.0 uM | | |
| B-0288 | 4.46 uM | 26.0% @ 1.0 uM | | |
| B-0289 | 0.15 uM | 55.0% @ 1.0 uM | | |
| B-0290 | 0.66 uM | 44.0% @ 1.0 uM | | |
| B-0291 | 1.33 uM | 20.0% @ 1.0 uM | | |
| B-0292 | 0.22 uM | 28.0% @ 1.0 uM | | |
| B-0293 | 0.66 uM | 53.0% @ 1.0 uM | | |

-continued

| Example # | P38 alpha kinase IC50, uM or % inhib @ conc. (uM) | U937 Cell IC50, uM or % inhib @ conc. (uM) | Mouse LPS Model % TNF inhib @ dose @ predose time | Rat LPS Model % inhib @ dose @ predose time |
|---|---|---|---|---|
| B-0294 | 0.68 uM | 45.0% @ 1.0 uM | | |
| B-0295 | 0.82 uM | 45.0% @ 1.0 uM | | |
| B-0296 | 8.03 uM | 36.0% @ 1.0 uM | | |
| B-0297 | 0.78 uM | 30.0% @ 1.0 uM | | |
| B-0298 | 0.58 uM | 48.0% @ 1.0 uM | | |
| B-0299 | 0.87 uM | 54.0% @ 1.0 uM | | |
| B-0300 | 0.78 uM | 32.0% @ 1.0 uM | | |
| B-0301 | 0.19 uM | 50.0% @ 1.0 uM | | |
| B-0302 | 4.02 uM | 24.0% @ 1.0 uM | | |
| B-0303 | 0.22 uM | 10.0% @ 1.0 uM | | |
| B-0304 | 0.56 uM | 28.0% @ 1.0 uM | | |
| B-0305 | | | | |
| B-0306 | | | | |
| B-0307 | | | | |
| B-0308 | | | | |
| B-0309 | | | | |
| B-0310 | | | | |
| B-0311 | | | | |
| B-0312 | | | | |
| B-0313 | | | | |
| B-0314 | | | | |
| B-0315 | | | | |
| B-0316 | | | | |
| B-0317 | | | | |
| B-0318 | | | | |
| B-0319 | | | | |
| B-0320 | | | | |
| B-0321 | | | | |
| B-0322 | | | | |
| B-0323 | | | | |
| B-0324 | | | | |
| B-0325 | | | | |
| B-0326 | | | | |
| B-0327 | | | | |
| B-0328 | | | | |
| B-0329 | | | | |
| B-0330 | | | | |
| B-0331 | | | | |
| B-0332 | | | | |
| B-0333 | | | | |
| B-0334 | | | | |
| B-0337 | | | | |
| B-0338 | | | | |
| B-0339 | | | | |
| B-0340 | | | | |
| B-0341 | | | | |
| B-0342 | | | | |
| B-0343 | | | | |
| B-0344 | | | | |
| B-0345 | | | | |
| B-0346 | | | | |
| B-0347 | | | | |
| B-0348 | | | | |
| B-0349 | | | | |
| B-0350 | | | | |
| B-0351 | | | | |
| B-0352 | | | | |
| B-0353 | 1.37 uM | 55% @ 1.0 uM | | |
| B-0354 | 1.0 uM | 0.66 uM | 51% @ 30 mpk @ −6 h | 54% @ 3 mpk @ −4 h |
| B-0355 | 0.75 uM | 40.0% @ 1.0 uM | | |
| B-0356 | 0.66 uM | 24.0% @ 1.0 uM | | |
| B-0357 | 1.46 uM | 0.66 uM | | |
| B-0358 | 0.37 uM | 17.0% @ 1.0 uM | | |
| B-0359 | 0.45 uM | 47.0% @ 1.0 uM | | |
| B-0360 | 1.6 uM | 19.0% @ 1.0 uM | | |
| B-0361 | 0.33 uM | 46.0% @ 1.0 uM | | |
| B-0362 | 0.52 uM | 27.0% @ 1.0 uM | | |
| B-0363 | 4.67 uM | 25.0% @ 1.0 uM | | |
| B-0364 | 1.44 uM | 27.0% @ 1.0 uM | | |
| B-0365 | 0.96 uM | 27.0% @ 1.0 uM | | |
| B-0366 | 0.7 uM | 46.0% @ 1.0 uM | | |
| B-0367 | 1.0 uM | 23.0% @ 1.0 uM | | |
| B-0368 | 1.0 uM | 0.64 uM | 37% @ 30 mpk @ −6 h | |
| B-0369 | 0.16 uM | 57.0% @ 1.0 uM | | |
| B-0370 | 0.65 uM | 28.0% @ 1.0 uM | | |

-continued

| Example # | P38 alpha kinase IC50, uM or % inhib @ conc. (uM) | U937 Cell IC50, uM or % inhib @ conc. (uM) | Mouse LPS Model % TNF inhib @ dose @ predose time | Rat LPS Model % inhib @ dose @ predose time |
|---|---|---|---|---|
| B-0371 | 0.49 uM | 28.0% @ 1.0 uM | | |
| B-0372 | 0.35 uM | 29.0% @ 1.0 uM | | |
| B-0373 | 0.45 uM | 18.0% @ 1.0 uM | | |
| B-0374 | 1.38 uM | 12.0% @ 1.0 uM | | |
| B-0375 | 1.0 uM | 19.0% @ 1.0 uM | | |
| B-0376 | 2.99 uM | 12.0% @ 1.0 uM | | |
| B-0377 | 1.29 uM | 36.0% @ 1.0 uM | | |
| B-0378 | 1.1 uM | 36.0% @ 1.0 uM | | |
| B-0379 | 0.53 uM | 24.0% @ 1.0 uM | | |
| B-0380 | 1.41 uM | 32.0% @ 1.0 uM | | |
| B-0381 | 0.22 uM | 47.0% @ 1.0 uM | | |
| B-0382 | 0.41 uM | 32.0% @ 1.0 uM | | |
| B-0383 | 1.43 uM | 10.0% @ 1.0 uM | | |
| B-0384 | 4.02 uM | 16.0% @ 1.0 uM | | |
| B-0385 | 0.057 uM | 0.9 uM | 30% @ 30 mpk@ −6 h | 0% @ 3 mpk @ −4 h |
| B-0386 | 0.13 uM | 54.0% @ 1.0 uM | | |
| B-0387 | 0.41 uM | 52.0% @ 1.0 uM | | |
| B-0388 | <0.1 uM | 36.0% @ 1.0 uM | | |
| B-0389 | 0.01 uM | 0.05 uM | | 62% @ 3 mpk @ −4 h |
| B-0390 | 0.089 uM | 55.0% @ 1.0 uM | | |
| B-0391 | 0.86 uM | 18.0% @ 1.0 uM | | |
| B-0392 | 0.13 uM | 57.0% @ 1.0 uM | | |
| B-0393 | 0.043 uM | 66.0% @ 1.0 uM | | |
| B-0394 | 0.13 uM | 45.0% @ 1.0 uM | | |
| B-0395 | 0.087 uM | 48.0% @ 1.0 uM | | |
| B-0396 | 0.097 uM | 0.44 uM | | |
| B-0397 | 0.17 uM | 41.0% @ 1.0 uM | | |
| B-0398 | 0.054 uM | 66.0% @ 1.0 uM | | |
| B-0399 | 0.14 uM | 39.0% @ 1.0 uM | | |
| B-0400 | 0.16 uM | 25.0% @ 1.0 uM | | |
| B-0401 | 0.46 uM | 52.0% @ 1.0 uM | | |
| B-0402 | 0.14 uM | 1.51 uM | | |
| B-0403 | 1.77 uM | 2.42 uM | | |
| B-0404 | 0.31 uM | 48.0% @ 1.0 uM | | |
| B-0405 | 0.79 uM | 30.0% @ 1.0 uM | | |
| B-0406 | 0.54 uM | 35.0% @ 1.0 uM | | |
| B-0407 | 0.76 uM | 27.0% @ 1.0 uM | | |
| B-0408 | 0.5 uM | 50.0% @ 1.0 uM | | |
| B-0409 | 0.53 uM | 30.0% @ 1.0 uM | | |
| B-0410 | 0.38 uM | 44.0% @ 1.0 uM | | |
| B-0411 | 0.62 uM | 50.0% @ 1.0 uM | | |
| B-0412 | 0.24 uM | 48.0% @ 1.0 uM | | |
| B-0413 | 0.18 uM | 55.0% @ 1.0 uM | | |
| B-0414 | 2.54 uM | 25.0% @ 1.0 uM | | |
| B-0415 | 0.42 uM | 43.0% @ 1.0 uM | | |
| B-0416 | 0.32 uM | 34.0% @ 1.0 uM | | |
| B-0417 | 0.91 uM | 28.0% @ 1.0 uM | | |
| B-0418 | 0.22 uM | 27.0% @ 1.0 uM | | |
| B-0419 | 0.85 uM | 41.0% @ 1.0 uM | | |
| B-0420 | 0.83 uM | 49.0% @ 1.0 uM | | |
| B-0421 | 0.46 uM | 57.0% @ 1.0 uM | | |
| B-0422 | <0.1 uM | 40.0% @ 1.0 uM | | |
| B-0423 | 0.18 uM | 33.0% @ 1.0 uM | | |
| B-0424 | 0.083 uM | 32.0% @ 1.0 uM | | |
| B-0425 | 0.26 uM | 54.0% @ 1.0 uM | | |
| B-0426 | 0.055 uM | 0.74 uM | | 41% @ 3 mpk @ −4 h |
| B-0427 | 0.63 uM | 39.0% @ 1.0 uM | | |
| B-0428 | 0.99 uM | 27.0% @ 1.0 uM | | |
| B-0429 | 0.27 uM | 45.0% @ 1.0 uM | | |
| B-0430 | 0.29 uM | 75.0% @ 1.0 uM | | |
| B-0431 | 0.21 uM | 64.0% @ 1.0 uM | | |
| B-0432 | <0.1 uM | 89.0% @ 1.0 uM | | |
| B-0433 | <0.1 uM | 92.0% @ 1.0 uM | | |
| B-0434 | 0.12 uM | 65.0% @ 1.0 uM | | |
| B-0435 | 0.3 uM | 61.0% @ 1.0 uM | | |
| B-0436 | 1.11 uM | 71.0% @ 1.0 uM | | |
| B-0437 | 0.58 uM | 59.0% @ 1.0 uM | | |
| B-0438 | <0.1 uM | 91.0% @ 1.0 uM | | |
| B-0439 | 2.12 uM | 65.0% @ 1.0 uM | | |
| B-0440 | 0.66 uM | 63.0% @ 1.0 uM | | |
| B-0441 | 0.8 uM | 58.0% @ 1.0 uM | | |
| B-0442 | <0.1 uM | 91.0% @ 1.0 uM | | |
| B-0443 | 2.01 uM | 71.0% @ 1.0 uM | | |
| B-0444 | 1.01 uM | 51.0% @ 1.0 uM | | |
| B-0445 | <0.1 uM | 83.0% @ 1.0 uM | | |

-continued

| Example # | P38 alpha kinase IC50, uM or % inhib @ conc. (uM) | U937 Cell IC50, uM or % inhib @ conc. (uM) | Mouse LPS Model % TNF inhib @ dose @ predose time | Rat LPS Model % inhib @ dose @ predose time |
|---|---|---|---|---|
| B-0446 | 0.78 uM | 80.0% @ 1.0 uM | | |
| B-0447 | 0.19 uM | 71.0% @ 1.0 uM | | |
| B-0448 | 0.4 uM | 79.0% @ 1.0 uM | | |
| B-0449 | 0.83 uM | 81.0% @ 1.0 uM | | |
| B-0450 | 0.26 uM | 81.0% @ 1.0 uM | | |
| B-0451 | 0.071 uM | 83.0% @ 1.0 uM | 42% @ 30 mpk @ −6 h | |
| B-0452 | 0.7 uM | 75.0% @ 1.0 uM | | |
| B-0453 | 0.47 uM | 75.0% @ 1.0 uM | | |
| B-0454 | 0.11 uM | 80.0% @ 1.0 uM | | |
| B-0455 | <0.1 uM | 95.0% @ 1.0 uM | | 36% @ 3 mpk % −4 h |
| B-0456 | 1.81 uM | 67.0% @ 1.0 uM | | |
| B-0457 | 0.089 uM | 81.0% @ 1.0 uM | | |
| B-0458 | 0.033 uM | 70.0% @ 1.0 uM | | |
| B-0459 | 0.099 uM | 76.0% @ 1.0 uM | | |
| B-0460 | 0.061 uM | 92.0% @ 1.0 uM | | |
| B-0461 | 0.025 uM | 96.0% @ 1.0 uM | | |
| B-0462 | <0.1 uM | 97.0% @ 1.0 uM | | |
| B-0463 | 0.052 uM | 95.0% @ 1.0 uM | | |
| B-0464 | <0.1 uM | 91.0% @ 1.0 uM | | |
| B-0465 | 0.084 uM | 98.0% @ 1.0 uM | | |
| B-0466 | <0.1 uM | 98.0% @ 1.0 uM | | 0% @ 3 mpk @ −4 h |
| B-0467 | <0.1 uM | 77.0% @ 1.0 uM | | |
| B-0468 | 0.031 uM | 93.0% @ 1.0 uM | | |
| B-0469 | 0.056 uM | 92.0% @ 1.0 uM | | |
| B-0470 | 0.063 uM | 92.0% @ 1.0 uM | | |
| B-0471 | 0.027 uM | 97.0% @ 1.0 uM | | |
| B-0472 | 0.19 uM | 54.0% @ 1.0 uM | | |
| B-0473 | 0.004 uM | 95.0% @ 1.0 uM | | |
| B-0474 | 0.024 uM | 86.0% @ 1.0 uM | | |
| B-0475 | 0.21 uM | 74.0% @ 1.0 uM | | |
| B-0476 | 0.56 uM | 69.0% @ 1.0 uM | | |
| B-0477 | 1.48 uM | 96.0% @ 1.0 uM | | |
| B-0478 | 0.034 uM | 87.0% @ 1.0 uM | | |
| B-0479 | 0.031 uM | 90.0% @ 1.0 uM | | 15% @ 3 mpk @ −4 h |
| B-0480 | 0.12 uM | 88.0% @ 1.0 uM | | |
| B-0481 | 0.014 uM | 95.0% @ 1.0 uM | | 56% @ 3 mpk @ −4 h |
| B-0482 | 0.97 uM | 68.0% @ 1.0 uM | | |
| B-0483 | 0.57 uM | 68.0% @ 1.0 uM | | |
| B-0484 | 0.28 uM | 62.0% @ 1.0 uM | | |
| B-0485 | 0.04 uM | 95.0% @ 1.0 uM | | |
| B-0486 | 0.24 uM | 80.0% @ 1.0 uM | | |
| B-0487 | 0.11 uM | 89.0% @ 1.0 uM | | 54% @ 3 mpk @ −4 h |
| B-0488 | 0.62 uM | 88.0% @ 1.0 uM | | |
| B-0489 | 0.3 uM | 80.0% @ 1.0 uM | | |
| B-0490 | 0.91 uM | 74.0% @ 1.0 uM | | |
| B-0491 | 0.43 uM | 66.0% @ 1.0 uM | | |
| B-0492 | 0.069 uM | 42.0% @ 1.0 uM | | |
| B-0493 | 0.3 uM | 36.0% @ 1.0 uM | | |
| B-0494 | 0.13 uM | 30.0% @ 1.0 uM | | |
| B-0495 | 0.12 uM | 25.0% @ 1.0 uM | | |
| B-0496 | 0.83 uM | 16.0% @ 1.0 uM | | |
| B-0497 | 0.44 uM | 31.0% @ 1.0 uM | | |
| B-0498 | 0.33 uM | 11.0% @ 1.0 uM | | |
| B-0499 | 0.39 uM | 37.0% @ 1.0 uM | | |
| B-0500 | 0.26 uM | 41.0% @ 1.0 uM | | |
| B-0501 | 0.049 uM | 52.0% @ 1.0 uM | | |
| B-0502 | 0.065 uM | 48.0% @ 1.0 uM | | |
| B-0503 | 0.16 uM | 73.0% @ 1.0 uM | | |
| B-0504 | 0.4 uM | 43.0% @ 1.0 uM | | |
| B-0505 | 0.28 uM | 44.0% @ 1.0 uM | | |
| B-0506 | 0.94 uM | 43.0% @ 1.0 uM | | |
| B-0507 | 0.18 uM | 75.0% @ 1.0 uM | | |
| B-0508 | 2.0 uM | 48.0% @ 1.0 uM | | |
| B-0509 | 0.1 uM | 86.0% @ 1.0 uM | | |
| B-0510 | 0.69 uM | 61.0% @ 1.0 uM | | |
| B-0511 | 0.007 uM | 90.0% @ 1.0 uM | | |
| B-0512 | 1.0 uM | 53.0% @ 1.0 uM | | |
| B-0513 | 0.72 uM | 52.0% @ 1.0 uM | | |
| B-0514 | 0.14 uM | 87.0% @ 1.0 uM | | |
| B-0515 | 0.42 uM | 61.0% @ 1.0 uM | | |
| B-0516 | 0.37 uM | 84.0% @ 1.0 uM | | |
| B-0517 | 0.094 uM | 52.0% @ 1.0 uM | | |
| B-0518 | 0.11 uM | 64.0% @ 1.0 uM | | |
| B-0519 | 0.043 uM | 87.0% @ 1.0 uM | | |
| B-0520 | 0.4 uM | 67.0% @ 1.0 uM | | |

-continued

| Example # | P38 alpha kinase IC50, uM or % inhib @ conc. (uM) | U937 Cell IC50, uM or % inhib @ conc. (uM) | Mouse LPS Model % TNF inhib @ dose @ predose time | Rat LPS Model % inhib @ dose @ predose time |
|---|---|---|---|---|
| B-0521 | 1.37 uM | 52.0% @ 1.0 uM | | |
| B-0522 | 0.15 uM | 75.0% @ 1.0 uM | | |
| B-0523 | 0.19 uM | 83.0% @ 1.0 uM | | |
| B-0524 | 0.4 uM | 77.0% @ 1.0 uM | | |
| B-0525 | 0.16 uM | 76.0% @ 1.0 uM | | |
| B-0526 | 0.031 uM | 87.0% @ 1.0 uM | | |
| B-0527 | 1.09 uM | 63.0% @ 1.0 uM | | |
| B-0528 | 0.14 uM | 70.0% @ 1.0 uM | | |
| B-0529 | 0.11 uM | 73.0% @ 1.0 uM | | |
| B-0530 | 5.53 uM | 45.0% @ 1.0 uM | | |
| B-0531 | 0.5 uM | 48.0% @ 1.0 uM | | |
| B-0532 | 0.45 uM | 1.01 uM | 41% @ 30 mpk @ −6 h | |
| B-0533 | 1.23 uM | 47.0% @ 1.0 uM | | |
| B-0534 | 0.41 uM | 54.0% @ 1.0 uM | | |
| B-0535 | 0.44 uM | 0.87 uM | | |
| B-0536 | 0.46 uM | 0.15 uM | | |
| B-0537 | 3.44 uM | 51.0% @ 1.0 uM | | |
| B-0538 | 1.13 uM | 45.0% @ 1.0 uM | | |
| B-0539 | 2.84 uM | 21.0% @ 1.0 uM | | |
| B-0540 | 3.62 uM | 54.0% @ 1.0 uM | | |
| B-0541 | 3.24 uM | 28.0% @ 1.0 uM | | |
| B-0542 | 1.55 uM | 50.0% @ 1.0 uM | | |
| B-0543 | 1.56 uM | 43.0% @ 1.0 uM | | |
| B-0544 | 1.12 uM | 27.0% @ 1.0 uM | | |
| B-0545 | 1.06 uM | 41.0% @ 1.0 uM | | |
| B-0546 | 1.04 uM | 18.0% @ 1.0 uM | | |
| B-0547 | 1.24 uM | 21.0% @ 1.0 uM | | |
| B-0548 | 1.77 uM | 28.0% @ 1.0 uM | | |
| B-0549 | 2.22 uM | 22.0% @ 1.0 uM | | |
| B-0550 | 2.41 uM | 14.0% @ 1.0 uM | | |
| B-0551 | 1.08 uM | 56.0% @ 1.0 uM | | |
| B-0552 | 0.13 uM | 46.0% @ 1.0 uM | | |
| B-0553 | 1.44 uM | 47.0% @ 1.0 uM | | |
| B-0554 | 2.58 uM | 20.0% @ 1.0 uM | | |
| B-0555 | 1.87 uM | 34.0% @ 1.0 uM | | |
| B-0556 | 0.49 uM | 39.0% @ 1.0 uM | | |
| B-0557 | 1.37 uM | 32.0% @ 1.0 uM | | |
| B-0558 | 0.85 uM | 33.0% @ 1.0 uM | | |
| B-0559 | 0.53 uM | 49.0% @ 1.0 uM | | |
| B-0560 | 2.57 uM | 31.0% @ 1.0 uM | | |
| B-0561 | 2.07 uM | 40.0% @ 1.0 uM | | |
| B-0562 | 0.22 uM | 0.3 uM | | 5% @ 3 mpk @ −4 h |
| B-0563 | 0.18 uM | 0.13 uM | | |
| B-0564 | 0.82 uM | 58% @ 1.0 uM | | |
| B-0565 | 0.23 uM | 0.59 uM | | |
| B-0566 | <0.1 uM | 0.17 uM | | 0% @ 3 mpk @ −4 h |
| B-0567 | 0.14 uM | 0.28 uM | | |
| B-0568 | 1.22 uM | 46.0% @ 1.0 uM | | |
| B-0569 | 0.15 uM | 0.26 uM | | |
| B-0570 | 0.27 uM | 46.0% @ 1.0 uM | | |
| B-0571 | 0.38 uM | 44.0% @ 1.0 uM | | |
| B-0572 | 0.27 uM | 41.0% @ 1.0 uM | | |
| B-0573 | 0.36 uM | 1.7 uM | | |
| B-0574 | 0.13 uM | 0.66 uM | | 37% @ 3 mpk @ −4 h |
| B-0575 | 0.032 uM | 0.17 uM | | |
| B-0576 | 0.068 uM | 0.39 uM | | 65% @ 3mpk @ −4 h |
| B-0577 | 0.091 uM | 66.0% @ 1.0 uM | | |
| B-0578 | 1.88 uM | 47.0% @ 1.0 uM | | |
| B-0579 | 0.11 uM | 79.0% @ 1.0 uM | | |
| B-0580 | 2.23 uM | 0.84 uM | | |
| B-0581 | 0.26 uM | 2.17 uM | | |
| B-0582 | 1.03 uM | 37.0% @ 1.0 uM | | |
| B-0583 | 3.93 uM | 26.0% @ 1.0 uM | | |
| B-0584 | 0.66 uM | 54.0% @ 1.0 uM | | |
| B-0585 | 0.83 uM | 79.0% @ 1.0 uM | 50% @ 30 mpk @ −6 h | |
| B-0586 | 0.81 uM | 51.0% @ 1.0 uM | | |
| B-0587 | 6.84 uM | 38% @ 1.0 uM | | |
| B-0588 | 12.8 uM | 42% @ 1.0 uM | | |
| B-0589 | 1.71 uM | 42% @ 1.0 uM | | |
| B-0590 | 1.57 uM | 38.0 uM | | |
| B-0591 | 3.59 uM | 29.0% @ 1.0 uM | | |
| B-0592 | 1.62 uM | 45.0% @ 1.0 uM | | |
| B-0593 | 1.22 uM | 36.0% @ 1.0 uM | | |
| B-0594 | — | 41.0% @ 1.0 uM | | |
| B-0595 | 2.42 uM | 22.0% @ 1.0 uM | | |

-continued

| Example # | P38 alpha kinase IC50, uM or % inhib @ conc. (uM) | U937 Cell IC50, uM or % inhib @ conc. (uM) | Mouse LPS Model % TNF inhib @ dose @ predose time | Rat LPS Model % inhib @ dose @ predose time |
|---|---|---|---|---|
| B-0596 | 20.0 uM | 41.0% @ 1.0 uM | | |
| B-0597 | 1.68 uM | 63.0% @ 1.0 uM | | |
| B-0598 | 2.12 uM | 50.0% @ 1.0 uM | | |
| B-0599 | 4.16 uM | 21.0% @ 1.0 uM | | |
| B-0600 | 0.002 uM | 28.0% @ 1.0 uM | | |
| B-0601 | 0.089 uM | 1.31 uM | 43% @ 3 mpk%–4 h | |
| B-0602 | 0.97 uM | 61.0% @ 1.0 uM | | |
| B-0603 | 0.09 uM | 51.0% @ 1.0 uM | | |
| B-0604 | 0.3 uM | 20.0% @ 1.0 uM | | |
| B-0605 | 0.18 uM | 47.0% @ 1.0 uM | | |
| B-0606 | 0.17 uM | 53.0% @ 1.0 uM | | |
| B-0607 | 2.79 uM | 70.0% @ 1.0 uM | | |
| B-0608 | 0.059 uM | 73.0% @ 1.0 uM | | |
| B-0609 | <0.1 uM | 87.0% @ 1.0 uM | | |
| B-0610 | <0.1 uM | 88.0% @ 1.0 uM | | |
| B-0611 | 0.65 uM | 60.0% @ 1.0 uM | | |
| B-0612 | 0.16 uM | 60.0% @ 1.0 uM | | |
| B-0613 | 0.17 uM | 76.0% @ 1.0 uM | | |
| B-0614 | 0.76 uM | 70.0% @ 1.0 uM | 0% @ 3 mpk @ 4 h | |
| B-0615 | 0.08 uM | 83.0% @ 1.0 uM | | |
| B-0616 | 0.38 uM | 87.0% @ 1.0 uM | | |
| B-0617 | 0.045 uM | 92.0% @ 1.0 uM | | |
| B-0618 | 0.37 uM | 80.0% @ 1.0 uM | | |
| B-0619 | <0.1 uM | 88.0% @ 1.0 uM | | |
| B-0620 | 1.59 uM | 58.0% @ 1.0 uM | | |
| B-0621 | 0.36 uM | 68.0% @ 1.0 uM | | |
| B-0622 | 0.076 uM | 78.0% @ 1.0 uM | | |
| B-0623 | 0.12 uM | 76.0% @ 1.0 uM | | |
| B-0624 | 0.085 uM | 54.0% @ 1.0 uM | | |
| B-0625 | 0.023 uM | 88.0% @ 1.0 uM | | |
| B-0626 | <0.1 uM | 85.0% @ 1.0 uM | | |
| B-0627 | 0.25 uM | 69.0% @ 1.0 uM | | |
| B-0628 | 0.023 uM | 72.0% @ 1.0 uM | | |
| B-0629 | 0.2 uM | 79.0% @ 1.0 uM | | |
| B-0630 | 0.06 uM | 77.0% @ 1.0 uM | | |
| B-0631 | 0.065 uM | 81.0% @ 1.0 uM | | |
| B-0632 | <0.1 uM | 79.0% @ 1.0 uM | | |
| B-0633 | 0.6 uM | 80.0% @ 1.0 uM | | |
| B-0634 | 0.6 uM | 40.0% @ 1.0 uM | | |
| B-0635 | 0.15 uM | 55.0% @ 1.0 uM | | |
| B-0636 | <0.1 uM | 86.0% @ 1.0 uM | | |
| B-0637 | 0.11 uM | 92.0% @ 1.0 uM | | |
| B-0638 | 0.25 uM | 89.0% @ 1.0 uM | | |
| B-0639 | 0.051 uM | 93.0% @ 1.0 uM | 50% @ 3 mpk @ −4 h | |
| B-0640 | 0.36 uM | 94.0% @ 1.0 uM | | |
| B-0641 | 0.58 uM | 65.0% @ 1.0 uM | | |
| B-0642 | 0.49 uM | 90.0% @ 1.0 uM | | |
| B-0643 | 0.069 uM | 85.0% @ 1.0 uM | 0% @ 3 mpk @ −4 h | |
| B-0644 | 0.058 uM | 89.0% @ 1.0 uM | | |
| B-0645 | 0.58 uM | 80.0% @ 1.0 uM | | |
| B-0646 | 0.26 uM | 94.0% @ 1.0 uM | | |
| B-0647 | 1.61 uM | 76.0% @ 1.0 uM | | |
| B-0648 | <0.1 uM | 83.0% @ 1.0 uM | | |
| B-0649 | 0.83 uM | 39.0% @ 1.0 uM | | |
| B-0650 | 0.006 uM | 95.0% @ 1.0 uM | 8% @ 3 mpk @ −4 h | |
| B-0651 | 1.78 uM | 81.0% @ 1.0 uM | | |
| B-0652 | 0.19 uM | 83.0% @ 1.0 uM | | |
| B-0653 | 2.01 uM | 74.0% @ 1.0 uM | | |
| B-0654 | 5.97 uM | 78.0% @ 1.0 uM | | |
| B-0655 | 1.25 uM | 76.0% @ 1.0 uM | | |
| B-0656 | 0.007 uM | 95.0% @ 1.0 uM | 28% @ 3 mpk @ −4 h | |
| B-0657 | 0.17 uM | 83.0% @ 1.0 uM | | |
| B-0658 | 1.14 uM | 91.0% @ 1.0 uM | | |
| B-0659 | 2.64 uM | 87.0% @ 1.0 uM | | |
| B-0660 | 0.088 uM | 92.0% @ 1.0 uM | | |
| B-0661 | <0.1 uM | 90.0% @ 1.0 uM | | |
| B-0662 | <0.1 uM | 95.0% @ 1.0 uM | | |
| B-0663 | 0.88 uM | 74.0% @ 1.0 uM | | |
| B-0664 | 0.39 uM | 80.0% @ 1.0 uM | | |
| B-0665 | 0.47 uM | 72.0% @ 1.0 uM | | |
| B-0666 | 0.17 uM | 73.0% @ 1.0 uM | | |
| B-0667 | 0.83 uM | 75.0% @ 1.0 uM | | |
| B-0668 | 0.27 uM | 78.0% @ 1.0 uM | | |
| B-0669 | 0.89 uM | 34.0% @ 1.0 uM | | |
| B-0670 | 3.15 uM | 32.0% @ 1.0 uM | | |

| Example # | P38 alpha kinase IC50, uM or % inhib @ conc. (uM) | U937 Cell IC50, uM or % inhib @ conc. (uM) | Mouse LPS Model % TNF inhib @ dose @ predose time | Rat LPS Model % inhib @ dose @ predose time |
|---|---|---|---|---|
| B-0671 | 6.38 uM | 36.0% @ 1.0 uM | | |
| B-0672 | 6.59 uM | 32.0% @ 1.0 uM | | |
| B-0673 | 8.54 uM | 48.0% @ 1.0 uM | | |
| B-0674 | 2.81 uM | 42.0% @ 1.0 uM | | |
| B-0675 | 5.42 uM | 3.0% @ 1.0 uM | | |
| B-0676 | 2.09 uM | 22.0% @ 1.0 uM | | |
| B-0677 | 1.63 uM | 25.0% @ 1.0 uM | | |
| B-0678 | 0.38 uM | 52.0% @ 1.0 uM | | |
| B-0679 | 0.062 uM | 45.0% @ 1.0 uM | | |
| B-0680 | 0.42 uM | 67.0% @ 1.0 uM | | |
| B-0681 | 1.96 uM | 17.0% @ 1.0 uM | | |
| B-0682 | 0.76 uM | 39.0% @ 1.0 uM | | |
| B-0683 | 13.0 uM | 32.0% @ 1.0 uM | | |
| B-0684 | 0.54 uM | 68.0% @ 1.0 uM | | |
| B-0685 | 15.4 uM | 33.0% @ 1.0 uM | | |
| B-0686 | 0.42 uM | 59.0% @ 1.0 uM | | |
| B-0687 | 10.1 uM | 15.0% @ 1.0 uM | | |
| B-0688 | 0.66 uM | 58.0% @ 1.0 uM | | |
| B-0689 | 14.6 uM | 27.0% @ 1.0 uM | | |
| B-0690 | 27.1 uM | 36.0% @ 1.0 uM | | |
| B-0691 | 0.16 uM | 48.0% @ 1.0 uM | | |
| B-0692 | 0.38 uM | 29.0% @ 1.0 uM | | |
| B-0693 | 0.39 uM | 28.0% @ 1.0 uM | | |
| B-0694 | 0.62 uM | 21.0% @ 1.0 uM | | |
| B-0695 | 0.23 uM | 32.0% @ 1.0 uM | | |
| B-0696 | 0.085 uM | 35.0% @ 1.0 uM | | |
| B-0697 | 0.45 uM | 44.0% @ 1.0 uM | | |
| B-0698 | 2.33 uM | 43.0% @ 1.0 uM | | |
| B-0699 | 0.34 uM | 31.0% @ 1.0 uM | | |
| B-0700 | 0.24 uM | 56.0% @ 1.0 uM | | |
| B-0701 | 0.39 uM | 45.0% @ 1.0 uM | | |
| B-0702 | 0.036 uM | 39.0% @ 1.0 uM | | |
| B-0703 | 0.12 uM | 39.0% @ 1.0 uM | | |
| B-0704 | 2.19 uM | 29.0% @ 1.0 uM | | |
| B-0705 | 0.44 uM | 21.0% @ 1.0 uM | | |
| B-0706 | 0.44 uM | 32.0% @ 1.0 uM | | |
| B-0707 | 1.7 uM | | | |
| B-0708 | 2.1 uM | | | |
| B-0709 | 0.84 uM | | | |
| B-0710 | 1.99 uM | | | |
| B-0711 | 1.99 uM | | | |
| B-0712 | 2.9 uM | | | |
| B-0713 | 4.3 uM | | | |
| B-0714 | 3.7 uM | | | |
| B-0715 | 3.2 uM | | | |
| B-0716 | 4.6 uM | | | |
| B-0717 | 4.3 uM | | | |
| B-0718 | 1.4 uM | | | |
| B-0719 | 3.4 uM | | | |
| B-0720 | 1.3 uM | | | |
| B-0721 | 3.8 uM | | | |
| B-0722 | 0.07 uM | >1.0 uM | | |
| B-0723 | 0.47 uM | | | |
| B-0724 | 0.06 uM | 17.0% @ 1.0 uM | | |
| B-0725 | 9.7 uM | | | |
| B-0726 | 1.4 uM | | | |
| B-0727 | 0.51 uM | | | |
| B-0728 | 20.0 uM | | | |
| B-0729 | 0.87 uM | | | |
| B-0730 | 0.25 uM | 11.0% @ 1.0 uM | | |
| B-0731 | 0.87 uM | >1.0 uM | | |
| B-0732 | 14.0 uM | | | |
| B-0733 | 32.0 uM | | | |
| B-0734 | 0.92 uM | | | |
| B-0735 | 1.0 uM | | | |
| B-0736 | 26.0 uM | | | |
| B-0737 | 2.6 uM | | | |
| B-0738 | 2.7 uM | | | |
| B-0739 | 4.1 uM | | | |
| B-0740 | 4.4 uM | | | |
| B-0741 | 26.0 uM | | | |
| B-0742 | 2.2 uM | | | |
| B-0743 | 1.2 uM | | | |
| B-0744 | 23.0 uM | | | |
| B-0745 | 6.0 uM | | | |

-continued

| Example # | P38 alpha kinase IC50, uM or % inhib @ conc. (uM) | U937 Cell IC50, uM or % inhib @ conc. (uM) | Mouse LPS Model % TNF inhib @ dose @ predose time | Rat LPS Model % inhib @ dose @ predose time |
|---|---|---|---|---|
| B-0746 | 0.01 uM | 22.0% @ 1.0 uM | | |
| B-0747 | 1.1 uM | | | |
| B-0748 | 1.2 uM | | | |
| B-0749 | 4.4 uM | | | |
| B-0750 | 0.92 uM | | | |
| B-0751 | 1.6 uM | | | |
| B-0752 | 0.33 uM | | | |
| B-0753 | 0.37 uM | | | |
| B-0754 | 0.55 uM | | | |
| B-0755 | 2.3 uM | | | |
| B-0756 | 0.94 uM | | | |
| B-0757 | 0.54 uM | 16.0% @ 1.0 uM | | |
| B-0758 | 1.5 uM | | | |
| B-0759 | 0.3 uM | | | |
| B-0760 | 0.01 uM | 13.0% @ 1.0 uM | | |
| B-0761 | <0.1 uM | | | |
| B-0762 | 0.13 uM | 5.0% @ 1.0 uM | | |
| B-0763 | 0.015 uM | 17.0% @ 1.0 uM | | |
| B-0764 | 0.67 uM | 26.0% @ 1.0 uM | | |
| B-0765 | 0.3 uM | 29.0% @ 1.0 uM | | |
| B-0766 | 0.95 uM | | | |
| B-0767 | 0.08 uM | | | |
| B-0768 | 1.4 uM | | | |
| B-0769 | 12.7 uM | | | |
| B-0770 | 2.3 uM | | | |
| B-0771 | 0.5 uM | | | |
| B-0772 | 0.8 uM | | | |
| B-0773 | 14.0 uM | | | |
| B-0774 | 1.5 uM | | | |
| B-0775 | 0.6 uM | >1.0 uM | | |
| B-0776 | 0.9 uM | >1.0 uM | | |
| B-0777 | 21.0 uM | | | |
| B-0778 | 51.0 uM | | | |
| B-0779 | 0.5 uM | | | |
| B-0780 | 1.1 uM | | | |
| B-0781 | 48.0 uM | | | |
| B-0782 | 22.0 uM | | | |
| B-0783 | 8.0 uM | | | |
| B-0784 | 7.0 uM | | | |
| B-0785 | 23.0 uM | | | |
| B-0786 | 24.0 uM | | | |
| B-0787 | 1.5 uM | | | |
| B-0788 | 1.2 uM | | | |
| B-0789 | 33.0 uM | | | |
| B-0790 | 1.0 uM | 4.0% @ 1.0 uM | | |
| B-0791 | 0.3 uM | >1.0 uM | | |
| B-0792 | 1.1 uM | | | |
| B-0793 | 0.3 uM | | | |
| B-0794 | 2.9 uM | 2.0% @ 1.0 uM | | |
| B-0795 | 1.9 uM | 11.0% @ 1.0 uM | | |
| B-0796 | 1.4 uM | | | |
| B-0797 | 1.04 uM | — | | |
| B-0798 | 1.73 uM | — | | |
| B-0799 | — | >1.0 uM | | |
| B-0800 | 1.01 uM | >1.0 uM | | |
| B-0801 | 0.67 uM | >1.0 uM | | |
| B-0802 | — | >1.0 uM | | |
| B-0803 | 0.057 uM | 53.0% @ 1.0 uM | | |
| B-0804 | 0.3 uM | 32.0% @ 1.0 uM | | |
| B-0805 | 0.71 uM | >1.0 uM | | |
| B-0806 | 3.28 uM | >1.0 uM | | |
| B-0807 | 10.8 uM | — | | |
| B-0808 | 3.09 uM | >1.0 uM | | |
| B-0809 | 1.22 uM | 7.0% @ 1.0 uM | | |
| B-0810 | 1.11 uM | >1.0 uM | | |
| B-0811 | 2.79 uM | 2.0% @ 1.0 uM | | |
| B-0812 | 2.12 uM | >1.0 uM | | |
| B-0813 | 3.02 uM | >1.0 uM | | |
| B-0814 | — | >1.0 uM | | |
| B-0815 | 2.11 uM | >1.0 uM | | |
| B-0816 | 3.46 uM | >1.0 uM | | |
| B-0817 | 3.07 uM | 33.0% @ 1.0 uM | | |
| B-0818 | 4.97 uM | >1.0 uM | | |
| B-0819 | 1.08 uM | >1.0 uM | | |
| B-0820 | 1.64 uM | 3.0% @ 1.0 uM | | |

-continued

| Example # | P38 alpha kinase IC50, uM or % inhib @ conc. (uM) | U937 Cell IC50, uM or % inhib @ conc. (uM) | Mouse LPS Model % TNF inhib @ dose @ predose time | Rat LPS Model % inhib @ dose @ predose time |
|---|---|---|---|---|
| B-0821 | 1.44 uM | — | | |
| B-0822 | 1.33 uM | — | | |
| B-0823 | 2.39 uM | >1.0 uM | | |
| B-0824 | 3.41 uM | — | | |
| B-0825 | — | — | | |
| B-0826 | 1.74 uM | — | | |
| B-0827 | 15.6 uM | — | | |
| B-0828 | 7.9 uM | — | | |
| B-0829 | 0.61 uM | 65.0% @ 1.0 uM | | |
| B-0830 | 0.54 uM | 34.0% @ 1.0 uM | | |
| B-0831 | 0.9 uM | >1.0 uM | | |
| B-0832 | 1.49 uM | — | | |
| B-0833 | 0.95 uM | 23.0% @ 1.0 uM | | |
| B-0834 | 1.25 uM | — | | |
| B-0835 | — | — | | |
| B-0836 | 1.24 uM | — | | |
| B-0837 | 1.96 uM | >1.0 uM | | |
| B-0838 | 3.1 uM | — | | |
| B-0839 | 4.3 uM | — | | |
| B-0640 | 0.63 uM | 47.0% @ 1.0 uM | | |
| B-0841 | 0.32 uM | 36.0% @ 1.0 uM | | |
| B-0842 | 0.74 uM | 63.0% @ 1.0 uM | | |
| B-0843 | 0.61 uM | >1.0 uM | | |
| B-0844 | 0.4 uM | 25.0% @ 1.0 uM | | |
| B-0845 | 1.78 uM | — | | |
| B-0846 | 1.8 uM | — | | |
| B-0847 | 0.73 uM | 21.0% @ 1.0 uM | | |
| B-0848 | 1.56 uM | — | | |
| B-0849 | 1.25 uM | — | | |
| B-0850 | 1.81 uM | — | | |
| B-0851 | 0.91 uM | 39.0% @ 1.0 uM | | |
| B-0852 | 1.02 uM | — | | |
| B-0853 | — | 38.0% @ 1.0 uM | | |
| B-0854 | — | 25.0% @ 1.0 uM | | |
| B-0855 | — | 8.0% @ 1.0 uM | | |
| B-0856 | — | 38.0% @ 1.0 uM | | |
| B-0857 | 6.25 uM | — | | |
| B-0858 | 2.1 uM | 48.0% @ 1.0 uM | | |
| B-0859 | 39.5 uM | — | | |
| B-0860 | 38.1 uM | — | | |
| B-0861 | 1.32 uM | 12.0% @ 1.0 uM | | |
| B-0862 | 2.15 uM | 4.0% @ 1.0 uM | | |
| B-0863 | 0.81 uM | 25.0% @ 1.0 uM | | |
| B-0864 | 0.39 uM | 40.% @ 1.0 uM | | |
| B-0865 | 0.66 uM | 46.0% @ 1.0 uM | | |
| B-0866 | 1.38 uM | 28.0% @ 1.0 uM | | |
| B-0867 | 0.62 uM | >1.0 uM | | |
| B-0868 | 3.28 uM | 8.0% @ 1.0 uM | | |
| B-0869 | 4.19 uM | >1.0 uM | | |
| B-0870 | 3.13 uM | >1.0 uM | | |
| B-0871 | 1.9 uM | >1.0 uM | | |
| B-0872 | 3.13 uM | 3.0% @ 1.0 uM | | |
| B-0873 | 6.92 uM | >1.0 uM | | |
| B-0874 | 1.92 uM | >1.0 uM | | |
| B-0875 | 2.13 uM | 8% @ 1.0 uM | | |
| B-0876 | 0.89 uM | >1.0 uM | | |
| B-0877 | 1.17 uM | 13.0% @ 1.0 uM | | |
| B-0878 | 0.65 uM | 19.0% @ 1.0 uM | | |
| B-0879 | 0.87 uM | 1.0% @ 1.0 uM | | |
| B-0880 | 0.15 uM | 40.0% @ 1.0 uM | | |
| B-0881 | 1.36 uM | >1.0 uM | | |
| B-0882 | 1.48 uM | 9% @ 1.0 uM | | |
| B-0883 | 1.06 uM | >1.0 uM | | |
| B-0884 | 1.89 uM | — | | |
| B-0885 | | | | |
| B-0886 | | | | |
| B-0887 | | | | |
| B-0888 | | | | |
| B-0889 | | | | |
| B-0890 | | | | |
| B-0891 | | | | |
| B-0892 | | | | |
| B-0893 | | | | |
| B-0894 | | | | |
| B-0895 | | | | |

-continued

| Example # | P38 alpha kinase IC50, uM or % inhib @ conc. (uM) | U937 Cell IC50, uM or % inhib @ conc. (uM) | Mouse LPS Model % TNF inhib @ dose @ predose time | Rat LPS Model % inhib @ dose @ predose time |
|---|---|---|---|---|
| B-0896 | | | | |
| B-0897 | | | | |
| B-0898 | | | | |
| B-0899 | | | | |
| B-0900 | | | | |
| B-0901 | | | | |
| B-0902 | | | | |
| B-0903 | | | | |
| B-0904 | | | | |
| B-0905 | | | | |
| B-0906 | | | | |
| B-0907 | | | | |
| B-0908 | | | | |
| B-0909 | | | | |
| B-0910 | | | | |
| B-0911 | | | | |
| B-0912 | | | | |
| B-0913 | | | | |
| B-0914 | | | | |
| B-0915 | | | | |
| B-0916 | | | | |
| B-0917 | | | | |
| B-0918 | | | | |
| B-0919 | | | | |
| B-0920 | | | | |
| B-0921 | | | | |
| B-0922 | | | | |
| B-0923 | | | | |
| B-0924 | | | | |
| B-0925 | | | | |
| B-0926 | | | | |
| B-0927 | | | | |
| B-0928 | | | | |
| B-0929 | | | | |
| B-0930 | | | | |
| B-0931 | | | | |
| B-0932 | | | | |
| B-0933 | 47.0% @ 1.0 uM | 37.0% @ 1.0 uM | | |
| B-0934 | 67.0% @ 1.0 uM | 36.0% @ 1.0 uM | | |
| B-0935 | 69.0% @ 1.0 uM | 54.0% @ 1.0 uM | | |
| B-0936 | 69.0% @ 1.0 uM | >1.0 uM | | |
| B-0937 | 64.0% @ 1.0 uM | 1.74 uM | | |
| B-0938 | 51.0% @ 1.0 uM | 29.0% @ 1.0 uM | | |
| B-0939 | 78.0% @ 1.0 uM | 14.0% @ 1.0 uM | | |
| B-0940 | 56.0% @ 1.0 uM | 22.0% @ 1.0 uM | | |
| B-0941 | 81.0% @ 1.0 uM | 25.0% @ 1.0 uM | | |
| B-0942 | 82.0% @ 1.0 uM | 2.0% @ 1.0 uM | | |
| B-0943 | 63.0% @ 10.0 uM | 24.0% @ 1.0 uM | | |
| B-0944 | 45.0% @ 1.0 uM | 27.0% @ 1.0 uM | | |
| B-0945 | 96.0% @ 1.0 uM | 0.93 uM | | |
| B-0946 | 76.0% @ 1.0 uM | 31.0% @ 1.0 uM | | |
| B-0947 | 69.0% @ 1.0 uM | 34.0% @ 1.0 uM | | |
| B-0948 | 68.0% @ 1.0 uM | 1.81 uM | | |
| B-0949 | 90.0% @ 1.0 uM | 17.0% @ 1.0 uM | | |
| B-0950 | 81.0% @ 1.0 uM | 0.58 uM | | |
| B-0951 | 82.0% @ 1.0 uM | 20.0% @ 1.0 uM | | |
| B-0952 | 44.0% @ 1.0 uM | 21.0% @ 1.0 uM | | |
| B-0953 | 63.0% @ 1.0 uM | 25.0% @ 1.0 uM | | |
| B-0954 | 62.0% @ 1.0 uM | 0.52 uM | | |
| B-0955 | 49.0% @ 1.0 uM | 0.54 uM | | |
| B-0956 | 56.0% @ 1.0 uM | 1.33 uM | | |
| B-0957 | 79.0% @ 1.0 uM | 22.0% @ 1.0 uM | | |
| B-0958 | 74.0% @ 1.0 uM | 0.38 uM | | |
| B-0959 | 83.0% @ 1.0 uM | 39.0% @ 1.0 uM | | |
| B-0960 | 48.0% @ 1.0 uM | 4.0% @ 1.0 uM | | |
| B-0961 | 79.0% @ 1.0 uM | 23.0% @ 1.0 uM | | |
| B-0962 | 85.0% @ 1.0 uM | 2.71 uM | | |
| B-0963 | 76.0% @ 1.0 uM | 39.0% @ 1.0 uM | | |
| B-0964 | 94.0% @ 1.0 uM | 5.0 uM | | |
| B-0965 | 74.0% @ 1.0 uM | 1.1 uM | | |
| B-0966 | 50.0% @ 1.0 uM | 5.0% @ 1.0 uM | | |
| B-0967 | 80.0% @ 1.0 uM | 29.0% @ 1.0 uM | | |
| B-0968 | 35.0% @ 1.0 uM | 26.0% @ 1.0 uM | | |
| B-0969 | 63.0% @ 1.0 uM | 35.0% @ 1.0 uM | | |
| B-0970 | 76.0% @ 10.0 uM | 0.88 uM | | |

-continued

| Example # | P38 alpha kinase IC50, uM or % inhib @ conc. (uM) | U937 Cell IC50, uM or % inhib @ conc. (uM) | Mouse LPS Model % TNF inhib @ dose @ predose time | Rat LPS Model % inhib @ dose @ predose time |
|---|---|---|---|---|
| B-0971 | 61.0% @ 1.0 uM | 39.0% @ 1.0 uM | | |
| B-0972 | 85.0% @ 1.0 uM | 2.0% @ 1.0 uM | | |
| B-0973 | 66.0% @ 10.0 uM | 48.0% @ 1.0 uM | | |
| B-0974 | 57.0% @ 1.0 uM | 47.0% @ 1.0 uM | | |
| B-0975 | 82.0% @ 1.0 uM | 32.0% @ 1.0 uM | | |
| B-0976 | 79.0% @ 1.0 uM | 36.0% @ 1.0 uM | | |
| B-0977 | 60.0% @ 1.0 uM | 26.0% @ 1.0 uM | | |
| B-0978 | 59.0% @ 1.0 uM | 36.0% @ 1.0 uM | | |
| B-0979 | 56.0% @ 10.0 uM | 23.0% @ 1.0 uM | | |
| B-0980 | 68.0% @ 1.0 uM | 31.0% @ 1.0 uM | | |
| B-0981 | 62.0% @ 1.0 uM | 57.0% @ 1.0 uM | | |
| B-0982 | 65.0% @ 1.0 uM | 23.0% @ 1.0 uM | | |
| B-0983 | 75.0% @ 1.0 uM | 0.8 uM | | |
| B-0984 | 60.0% @ 1.0 uM | 51.0% @ 1.0 uM | | |
| B-0985 | 86.0% @ 1.0 uM | 0.75 uM | | |
| B-0986 | 70.0% @ 1.0 uM | 71.0% @ 1.0 uM | | |
| B-0987 | 78.0% @ 1.0 uM | 79.0% @ 1.0 uM | | |
| B-0988 | 72.0% @ 1.0 uM | 65.0% @ 1.0 uM | | |
| B-0989 | 85.0% @ 1.0 uM | 0.85 uM | | |
| B-0990 | — | 26.0% @ 1.0 uM | | |
| B-0991 | 58.0% @ 1.0 uM | 33.0% @ 1.0 uM | | |
| B-0992 | 77.0% @ 1.0 uM | 45.0% @ 1.0 uM | | |
| B-0993 | 57.0% @ 1.0 uM | 73.0% @ 1.0 uM | | |
| B-0994 | 55.0% @ 1.0 uM | 43.0% @ 1.0 uM | | |
| B-0995 | 53.0% @ 1.0 uM | 14.0% @ 1.0 uM | | |
| B-0996 | 54.0% @ 1.0 uM | 27.0% @ 1.0 uM | | |
| B-0997 | 69.0% @ 1.0 uM | 22.0% @ 1.0 uM | | |
| B-0998 | 67.0% @ 1.0 uM | 25.0% @ 1.0 uM | | |
| B-0999 | 61.0% @ 1.0 uM | 24.0% @ 1.0 uM | | |
| B-1000 | 55.0% @ 1.0 uM | 42.0% @ 1.0 uM | | |
| B-1001 | 63.0% @ 1.0 uM | 31.0% @ 1.0 uM | | |
| B-1002 | 70.0% @ 1.0 uM | 41.0% @ 1.0 uM | | |
| B-1003 | 74.0% @ 1.0 uM | 29.0% @ 1.0 uM | | |
| B-1004 | 79.0% @ 1.0 uM | 45.0% @ 1.0 uM | | |
| B-1005 | 58.0% @ 1.0 uM | 23.0% @ 1.0 uM | | |
| B-1006 | 69.0% @ 1.0 uM | 38.0% @ 1.0 uM | | |
| B-1007 | 52.0% @ 1.0 uM | 34.0% @ 1.0 uM | | |
| B-1008 | 54.0% @ 1.0 uM | 23.0% @ 1.0 uM | | |
| B-1009 | 80.0% @ 1.0 uM | 55.0% @ 1.0 uM | | |
| B-1010 | 75.0% @ 1.0 uM | 1.0 uM | | |
| B-1011 | 72.0% @ 1.0 uM | 17.0% @ 1.0 uM | | |
| B-1012 | — | 20.0% @ 1.0 uM | | |
| B-1013 | 85.0% @ 1.0 uM | 7.0% @ 1.0 uM | | |
| B-1014 | 88.0% @ 1.0 uM | 20.0% @ 1.0 uM | | |
| B-1015 | 77.0% @ 1.0 uM | 34.0% @ 1.0 uM | | |
| B-1016 | 58.0% @ 1.0 uM | 10.0% @ 1.0 uM | | |
| B-1017 | 96.0% @ 1.0 uM | 58.0% @ 1.0 uM | | |
| B-1018 | 88.0% @ 1.0 uM | 34.0% @ 1.0 uM | | |
| B-1019 | 82.0% @ 1.0 uM | 66.0% @ 1.0 uM | | |
| B-1020 | 87.0% @ 1.0 uM | 36.0% @ 1.0 uM | | |
| B-1021 | 82.0% @ 1.0 uM | 35.0% @ 1.0 uM | | |
| B-1022 | 84.0% @ 1.0 uM | 53.0% @ 1.0 uM | | |
| B-1023 | 93.0% @ 1.0 uM | 70.0% @ 1.0 uM | | |
| B-1024 | 89.0% @ 1.0 uM | 57.0% @ 1.0 uM | | |
| B-1025 | 61.0% @ 1.0 uM | 23.0% @ 1.0 uM | | |
| B-1026 | 87.0% @ 1.0 uM | 53.0% @ 1.0 uM | | |
| B-1027 | 58.0% @ 1.0 uM | 18.0% @ 1.0 uM | | |
| B-1028 | 70.0% @ 1.0 uM | 17.0% @ 1.0 uM | | |
| B-1029 | 69.0% @ 1.0 uM | 54.0% @ 1.0 uM | | |
| B-1030 | 76.0% @ 1.0 uM | 60.0% @ 1.0 uM | | |
| B-1031 | 69.0% @ 1.0 uM | 42.0% @ 1.0 uM | | |
| B-1032 | 76.0% @ 1.0 uM | 37.0% @ 1.0 uM | | |
| B-1033 | 86.0% @ 1.0 uM | 34.0% @ 1.0 uM | | |
| B-1034 | 66.0% @ 1.0 uM | 39.0% @ 1.0 uM | | |
| B-1035 | 75.0% @ 1.0 uM | 52.0% @ 1.0 uM | | |
| B-1036 | 68.0% @ 1.0 uM | 68.0% @ 1.0 uM | | |
| B-1037 | — | 41.0% @ 1.0 uM | | |
| B-1038 | 57.0% @ 1.0 uM | 0.57 uM | | |
| B-1039 | — | 1.33 uM | | |
| B-1040 | 72.0% @ 1.0 uM | 0.38 uM | | |
| B-1041 | 70.0% @ 1.0 uM | 73.0% @ 1.0 uM | | |
| B-1042 | 79.0% @ 1.0 uM | 12.0% @ 1.0 uM | | |
| B-1043 | 64.0% @ 1.0 uM | 53.0% @ 1.0 uM | | |
| B-1044 | 94.0% @ 1.0 uM | 0.93 uM | | |
| B-1045 | 78.0% @ 1.0 uM | 25.0% @ 1.0 uM | | |

| Example # | P38 alpha kinase IC50, uM or % inhib @ conc. (uM) | U937 Cell IC50, uM or % inhib @ conc. (uM) | Mouse LPS Model % TNF inhib @ dose @ predose time | Rat LPS Model % inhib @ dose @ predose time |
|---|---|---|---|---|
| B-1046 | 72.0% @ 1.0 uM | 66.0% @ 1.0 uM | | |
| B-1047 | 72.0% @ 1.0 uM | 58.0% @ 1.0 uM | | |
| B-1048 | 67.0% @ 1.0 uM | 19.0% @ 1.0 uM | | |
| B-1049 | 67.0% @ 1.0 uM | 65.0% @ 1.0 uM | | |
| B-1050 | — | 0.54 uM | | |
| B-1051 | 68.0% @ 1.0 uM | 41% @ 1.0 uM | | |
| B-1052 | 69.0% @ 1.0 uM | 66% @ 1.0 uM | | |
| B-1053 | 78.0% @ 1.0 uM | 0.4 uM | | |
| B-1054 | 79.0% @ 1.0 uM | 55.0% @ 1.0 uM | | |
| B-1055 | 89.0% @ 1.0 uM | 63.0% @ 1.0 uM | | |
| B-1056 | 89.0% @ 1.0 uM | 0.76 uM | | |
| B-1057 | 85.0% @ 1.0 uM | 0.72 uM | | |
| B-1058 | 0.66 uM | 43.0% @ 1.0 uM | | |
| B-1059 | 0.18 uM | 24.0% @ 1.0 uM | | |
| B-1060 | 0.11 uM | 32.0% @ 1.0 uM | | |
| B-1061 | 0.03 uM | 19.0% @ 1.0 uM | | |
| B-1062 | <0.1 uM | 26.0% @ 1.0 uM | | |
| B-1063 | 0.16 uM | 44.0% @ 1.0 uM | | |
| B-1064 | 0.39 uM | 50.0% @ 1.0 uM | | |
| B-1065 | 0.56 uM | 40.0% @ 1.0 uM | | |
| B-1066 | <0.1 uM | 39.0% @ 1.0 uM | | |
| B-1067 | 1.6 uM | 32.0% @ 1.0 uM | | |
| B-1068 | 0.48 uM | 24.0% @ 1.0 uM | | |
| B-1069 | 0.22 uM | 27.0% @ 1.0 uM | | |
| B-1070 | <0.1 uM | 44.0% @ 1.0 uM | | |
| B-1071 | <0.1 uM | 48.0% @ 1.0 uM | | |
| B-1072 | 0.38 uM | 28.0% @ 1.0 uM | | |
| B-1073 | <0.1 uM | 21.0% @ 1.0 uM | | |
| B-1074 | 0.23 uM | 33.0% @ 1.0 uM | | |
| B-1075 | 0.03 uM | 29.0% @ 1.0 uM | | |
| B-1076 | 0.08 uM | 31.0% @ 1.0 uM | | |
| B-1077 | <0.1 uM | 38.0% @ 1.0 uM | | |
| B-1078 | 0.26 uM | 48.0% @ 1.0 uM | | |
| B-1079 | <0.1 uM | 40.0% @ 1.0 uM | | |
| B-1080 | 0.19 uM | 28.0% @ 1.0 uM | | |
| B-1081 | <0.1 uM | 37.0% @ 1.0 uM | | |
| B-1082 | <0.1 uM | 54.0% @ 1.0 uM | | |
| B-1083 | <0.1 uM | 23.0% @ 1.0 uM | | |
| B-1084 | 0.43 uM | 29.0% @ 1.0 uM | | |
| B-1085 | <0.1 uM | 29.0% @ 1.0 uM | | |
| B-1086 | <0.1 uM | 42.0% @ 1.0 uM | | |
| B-1087 | 0.05 uM | 32.0% @ 1.0 uM | | |
| B-1088 | 0.73 uM | 49.0% @ 1.0 uM | | |
| B-1089 | <0.1 uM | 39.0% @ 1.0 uM | | |
| B-1090 | <0.1 uM | 90.0% @ 1.0 uM | | |
| B-1091 | <1.0 uM | 73.0% @ 1.0 uM | | |
| B-1092 | 0.27 uM | 85.0% @ 1.0 uM | | |
| B-1093 | 0.33 uM | 36.0% @ 1.0 uM | | |
| B-1094 | 0.013 uM | 69.0% @ 1.0 uM | | |
| B-1095 | <0.1 uM | 70.0% @ 1.0 uM | | |
| B-1096 | <0.1 uM | 32.0% @ 1.0 uM | | |
| B-1097 | <0.1 uM | 44.0% @ 1.07 uM | | |
| B-1098 | <0.1 uM | 82.0% @ 1.0 uM | | |
| B-1099 | 0.26 uM | 74.0% @ 1.0 uM | | |
| B-1100 | 0.22 uM | 56.0% @ 1.0 uM | | |
| B-1101 | 0.026 uM | 82.0% @ 1.0 uM | | |
| B-1102 | 0.035 uM | 83.0% @ 1.0 uM | | |
| B-1103 | 0.094 uM | 90.0% @ 1.0 uM | | |
| B-1104 | 0.12 uM | 69.0% @ 1.0 uM | | |
| B-1105 | <0.1 uM | 84.0% @ 1.0 uM | | |
| B-1106 | <0.1 uM | 86.0% @ 1.0 uM | | |
| B-1107 | 0.057 uM | 84.0% @ 1.0 uM | | |
| B-1108 | 0.22 uM | 81.0% @ 1.0 uM | | |
| B-1109 | 0.054 uM | 80.0% @ 1.0 uM | | |
| B-1110 | 0.47 uM | 64.0% @ 1.0 uM | | |
| B-1111 | 0.19 uM | 64.0% @ 1.0 uM | | |
| B-1112 | 0.58 uM | 43.0% @ 1.0 uM | | |
| B-1113 | <0.1 uM | 72.0% @ 1.0 uM | | |
| B-1114 | 0.069 uM | 51.0% @ 1.0 uM | | |
| B-1115 | 0.024 uM | 89.0% @ 1.0 uM | | |
| B-1116 | 0.41 uM | 81.0% @ 1.0 uM | | |
| B-1117 | 0.13 uM | 73.0% @ 1.0 uM | | |
| B-1118 | 0.33 uM | 91.0% @ 1.0 uM | | |
| B-1119 | 0.35 uM | 80.0% @ 1.0 uM | | |
| B-1120 | 0.47 uM | 9.0% @ 1.0 uM | | |

| Example # | P38 alpha kinase IC50, uM or % inhib @ conc. (uM) | U937 Cell IC50, uM or % inhib @ conc. (uM) | Mouse LPS Model % TNF inhib @ dose @ predose time | Rat LPS Model % inhib @ dose @ predose time |
|---|---|---|---|---|
| B-1121 | 3.58 uM | 29.0% @ 1.0 uM | | |
| B-1122 | 1.84 uM | 32.0% @ 1.0 uM | | |
| B-1123 | 2.93 uM | 27.0% @ 1.0 uM | | |
| B-1124 | 1.49 uM | 52.0% @ 1.0 uM | | |
| B-1125 | 0.56 uM | 41.0% @ 1.0 uM | | |
| B-1126 | 1.5 uM | >1.0 uM | | |
| B-1127 | 0.71 uM | 7.0% @ 1.0 uM | | |
| B-1128 | 2.55 uM | 26.0% @ 1.0 uM | | |
| B-1129 | 1.07 uM | 46.0% @ 1.0 uM | | |
| B-1130 | 0.5 uM | 29.0% @ 1.0 uM | | |
| B-1131 | 0.076 uM | 34.0% @ 1.0 uM | | |
| B-1132 | 0.72 uM | 11.0% @ 1.0 uM | | |
| B-1133 | 0.38 uM | 33.0% @ 1.0 uM | | |
| B-1134 | 1.71 uM | 33.0% @ 1.0 uM | | |
| B-1135 | 0.23 uM | 38.0% @ 1.0 uM | | |
| B-1136 | 1.17 uM | 40.0% @ 1.0 uM | | |
| B-1137 | 0.038 uM | 35.0% @ 1.0 uM | | |
| B-1138 | 1.82 uM | >1.0 uM | | |
| B-1139 | 0.041 uM | 29.0% @ 1.0 uM | | |
| B-1140 | 1.68 uM | 39.0% @ 1.0 uM | | |
| B-1141 | 2.47 uM | 32.0% @ 1.0 uM | | |
| B-1142 | 0.11 uM | 37.0% @ 1.0 uM | | |
| B-1143 | 0.17 uM | 40.0% @ 1.0 uM | | |
| B-1144 | 0.44 uM | 72.0% @ 1.0 uM | | |
| B-1145 | 1.07 uM | 71.0% @ 1.0 uM | | |
| B-1146 | 0.47 uM | 61.0% @ 1.0 uM | | |
| B-1147 | 0.095 uM | 53.0% @ 1.0 uM | | |
| B-1148 | 0.43 uM | 61.0% @ 1.0 uM | | |
| B-1149 | 1.55 uM | 48.0% @ 1.0 uM | | |
| B-1150 | 0.47 uM | 75.0% @ 1.0 uM | | |
| B-1151 | 0.32 uM | 72.0% @ 1.0 uM | | |
| B-1152 | 0.73 uM | 53.0% @ 1.0 uM | | |
| B-1153 | 2.22 uM | 52.0% @ 1.0 uM | | |
| B-1154 | 0.085 uM | 46.0% @ 1.0 uM | | |
| B-1155 | 3.22 uM | 30.0% @ 1.0 uM | | |
| B-1156 | 0.27 uM | 78.0% @ 1.0 uM | | |
| B-1157 | 0.26 uM | 66.0% @ 1.0 uM | | |
| B-1158 | 74% @ 1.0 uM | 0.68 uM | 53% @ 30 mpk @ −6 h | |
| B-1159 | 66.0% @ 1.0 uM | 1.03 uM | 60% @ 30 mpk @ −6 h | |
| B-1160 | 79.0% @ 1.0 uM | 0.38 uM | | |
| B-1161 | 64.0% @ 1.0 uM | 0.93 uM | 40% @ 30 mpk @ −6 h | 45% @ 3 mpk @ −4 h |
| B-1162 | 79.0% @ 1.0 uM | 0.59 uM | 40% @ 30 mpk @ −6 h | |
| B-1163 | 74.0% @ 1.0 uM | 0.37 uM | | |
| B-1164 | — | 0.35 uM | | |
| B-1165 | 66.0% @ 1.0 uM | 0.99 uM | | |
| B-1166 | 77.0% @ 1.0 uM | 0.39 uM | 50% @ 30 mpk @ −6 h | 50% @ 3 mpk @ −4 h |
| B-1167 | 70.0% @ 1.0 uM | 1.06 uM | | |
| B-1168 | 66.0% @ 1.0 uM | 0.63 uM | | |
| B-1169 | 80.0% @ 1.0 uM | 0.11 uM | | |
| B-1170 | 82.0% @ 1.0 uM | 0.57 uM | | |
| B-1171 | 78.0% @ 1.0 uM | 0.23 uM | | |
| B-1172 | 68.0% @ 1.0 uM | 1.95 uM | | |
| B-1173 | 65.0% @ 1.0 uM | 62% @ 1.0 uM | | |
| B-1174 | 80.0% @ 1.0 uM | 0.86 uM | | |
| B-1175 | 72.0% @ 1.0 uM | 1.83 uM | | |
| B-1176 | 67.0% @ 1.0 uM | 67.0% @ 1.0 uM | | |
| B-1177 | 70.0% @ 1.0 uM | 1.16 uM | | |
| B-1178 | 92.0% @ 1.0 uM | 1.61 uM | | |
| B-1179 | 86.0% @ 1.0 uM | 0.41 uM | | |
| B-1180 | 78.0% @ 1.0 uM | 0.53 uM | | |
| B-1181 | 79.0% @ 1.0 uM | 66% @ 1.0 uM | | |
| B-1182 | 72.0% @ 1.0 uM | 0.65 uM | | |
| B-1183 | 77.0% @ 1.0 uM | 0.2 uM | | |
| B-1184 | 69.0% @ 1.0 uM | 0.63 uM | | |
| B-1185 | 71.0% @ 1.0 uM | 0.79 uM | | |
| B-1186 | 83.0% @ 1.0 uM | 60% @ 1.0 uM | | |
| B-1187 | 76.0% @ 1.0 uM | 1.89 uM | | |
| B-1188 | — | 36.0% @ 1.0 uM | | |
| B-1189 | 68.0% @ 1.0 uM | 0.83 uM | | |
| B-1190 | 78.0%@ 1.0 uM | 62.0% @ 1.0 uM | | |
| B-1191 | 74.0% @ 1.0 uM | 57.0% @ 1.0 uM | | |
| B-1192 | 84.0% @ 1.0 uM | 0.47 uM | | |
| B-1193 | 69.0% @ 1.0 uM | 65.0% @ 1.0 uM | | |
| B-1194 | 87.0% @ 1.0 uM | 0.58 uM | | |
| B-1195 | 52.0% @ 1.0 uM | 60.0% @ 1.0 uM | | |

-continued

| Example # | P38 alpha kinase IC50, uM or % inhib @ conc. (uM) | U937 Cell IC50, uM or % inhib @ conc. (uM) | Mouse LPS Model % TNF inhib @ dose @ predose time | Rat LPS Model % inhib @ dose @ predose time |
|---|---|---|---|---|
| B-1196 | 74.0% @ 1.0 uM | 68.0% @ 1.0 uM | | |
| B-1197 | 77.0% @ 1.0 uM | 45.0% @ 1.0 uM | | |
| B-1198 | 92.0% @ 1.0 uM | 0.46 uM | | |
| B-1199 | 87.0% @ 1.0 uM | 49.0% @ 1.0 uM | | |
| B-1200 | 95.0% @ 1.0 uM | 0.64 uM | | |
| B-1201 | 84.0% @ 1.0 uM | 0.51 uM | | |
| B-1202 | 71.0% @ 1.0 uM | 58.0% @ 1.0 uM | | |
| B-1203 | 84.0% @ 1.0 uM | 58.0% @ 1.0 uM | | |
| B-1204 | 68.0% @ 1.0 uM | 59.0% @ 1.0 uM | | |
| B-1205 | 74.0% @ 1.0 uM | 46.0% @ 1.0 uM | | |
| B-1206 | 81.0% @ 1.0 uM | 0.34 uM | | |
| B-1207 | 90.0% @ 1.0 uM | 58.0% @ 1.0 uM | | |
| B-1208 | 82.0% @ 1.0 uM | 51.0% @ 1.0 uM | | |
| B-1209 | 86.0% @ 1.0 uM | 55.0% @ 1.0 uM | | |
| B-1210 | 82.0% @ 1.0 uM | 57.0% @ 1.0 uM | | |
| B-1211 | 88.0% @ 1.0 uM | 59.0% @ 1.0 uM | | |
| B-1212 | 90.0% @ 1.0 uM | 57.0% @ 1.0 uM | | |
| B-1213 | 84.0% @ 1.0 uM | 0.62 uM | | |
| B-1214 | 76.0% @ 1.0 uM | 58.0% @ 1.0 uM | | |
| B-1215 | 86.0% @ 1.0 uM | 0.23 uM | | |
| B-1216 | 88.0% @ 1.0 uM | 0.18 uM | | |
| B-1217 | 87.0% @ 1.0 uM | 0.46 uM | | |
| B-1218 | 88.0% @ 1.0 uM | 76.0% @ 1.0 uM | | |
| B-1219 | 85.0% @ 1.0 uM | 37.0% @ 1.0 uM | | |
| B-1220 | 81.0% @ 1.0 uM | 53.0% @ 1.0 uM | | |
| B-1221 | 82.0% @ 1.0 uM | 44.0% @ 1.0 uM | | |
| B-1222 | 65.0% @ 1.0 uM | 9.0% @ 1.0 uM | | |
| B-1223 | 80.0% @ 1.0 uM | 61.0% @ 1.0 uM | | |
| B-1224 | 82.0% @ 1.0 uM | 74.0% @ 1.0 uM | | |
| B-1225 | 89.0% @ 1.0 uM | 73.0% @ 1.0 uM | | |
| B-1226 | 89.0% @ 1.0 uM | 0.18 uM | | |
| B-1227 | 83.0% @ 1.0 uM | 0.22 uM | | |
| B-1228 | 90.0% @ 1.0 uM | 0.72 uM | | |
| B-1229 | 87.0% @ 1.0 uM | 0.65 uM | | |
| B-1230 | 90.0% @ 1.0 uM | 0.25 uM | | |
| B-1231 | 94.0% @ 1.0 uM | 0.56 uM | | |
| B-1232 | 81.0% @ 1.0 uM | 54.0% @ 1.0 uM | | |
| B-1233 | 85.0% @ 1.0 uM | 0.36 uM | | |
| B-1234 | 89.0% @ 1.0 uM | 0.49 uM | | |
| B-1235 | 0.04 uM | 76.0% @ 1.0 uM | | |
| B-1236 | 0.1 uM | 53.0% @ 1.0 uM | | |
| B-1237 | 0.22 uM | 39.0% @ 1.0 uM | | |
| B-1238 | 0.14 uM | 16.0% @ 1.0 uM | | |
| B-1239 | <0.1 uM | 38.0% @ 1.0 uM | | |
| B-1240 | <0.1 uM | 59.0% @ 1.0 uM | | |
| B-1241 | 0.04 uM | 81.0% @ 1.0 uM | | |
| B-1242 | 0.08 uM | 83.0% @ 1.0 uM | | |
| B-1243 | 0.04 uM | 47.0% @ 1.0 uM | | |
| B-1244 | 0.26 uM | 44.0% @ 1.0 uM | | |
| B-1245 | 0.49 uM | 42.0% @ 1.0 uM | | |
| B-1246 | 0.27 uM | 40.0% @ 1.0 uM | | |
| B-1247 | <0.1 uM | 58.0% @ 1.0 uM | | |
| B-1248 | <0.1 uM | 68.0% @ 1.0 uM | | |
| B-1249 | 0.24 uM | 60.0% @ 1.0 uM | | |
| B-1250 | 0.14 uM | 18.0% @ 1.0 uM | | |
| B-1251 | 0.41 uM | 38.0% @ 1.0 uM | | |
| B-1252 | 0.17 uM | 46.0% @ 1.0 uM | | |
| B-1253 | 0.15 uM | 57.0% @ 1.0 uM | | |
| B-1254 | 0.15 uM | 68.0% @ 1.0 uM | | |
| B-1255 | 12.9 uM | 75.0% @ 1.0 uM | | |
| B-1256 | 0.12 uM | 41.0% @ 1.0 uM | | |
| B-1257 | 1.48 uM | 40.0% @ 1.0 uM | | |
| B-1258 | 0.07 uM | 56.0% @ 1.0 uM | | |
| B-1259 | <0.1 uM | 0.48 uM | | |
| B-1260 | 0.11 uM | 48.0% @ 1.0 uM | | |
| B-1261 | 0.74 uM | 44.0% @ 1.0 uM | | |
| B-1262 | <0.1 uM | 63.0% @ 1.0 uM | | |
| B-1263 | 1.05 uM | 57.0% @ 1.0 uM | | |
| B-1264 | 0.32 uM | 47.0% @ 1.0 uM | | |
| B-1265 | 0.43 uM | 51.0% @ 1.0 uM | | |
| B-1266 | <0.1 uM | 58.0% @ 1.0 uM | | |
| B-1267 | <0.1 uM | 73.0% @ 1.0 uM | | |
| B-1268 | <0.1 uM | 79.0% @ 1.0 uM | | |
| B-1269 | 0.46 uM | 84.0% @ 1.0 uM | | |
| B-1270 | 0.47 uM | 83.0% @ 1.0 uM | | |

-continued

| Example # | P38 alpha kinase IC50, uM or % inhib @ conc. (uM) | U937 Cell IC50, uM or % inhib @ conc. (uM) | Mouse LPS Model % TNF inhib @ dose @ predose time | Rat LPS Model % inhib @ dose @ predose time |
|---|---|---|---|---|
| B-1271 | 0.13 uM | 74.0% @ 1.0 uM | | |
| B-1272 | 0.014 uM | 38.0% @ 1.0 uM | | |
| B-1273 | <0.1 uM | 36.0% @ 1.0 uM | | |
| B-1274 | <0.1 uM | 41.0% @ 1.0 uM | | |
| B-1275 | <0.1 uM | 50.0% @ 1.0 uM | | |
| B-1276 | 0.062 uM | 11.0% @ 1.0 uM | | |
| B-1277 | <0.1 uM | 47.0% @ 1.0 uM | | |
| B-1278 | 0.12 uM | 85.0% @ 1.0 uM | | |
| B-1279 | <0.1 uM | 79.0% @ 1.0 uM | | |
| B-1280 | 0.039 uM | 83.0% @ 1.0 uM | | |
| B-1281 | <0.1 uM | 85.0% @ 1.0 uM | | |
| B-1282 | <0.1 uM | 75.0% @ 1.0 uM | | |
| B-1283 | <0.1 uM | 64.0% @ 1.0 uM | | |
| B-1284 | <0.1 uM | 75.0% @ 1.0 uM | | |
| B-1285 | 0.057 uM | 80.0% @ 1.0 uM | | |
| B-1286 | 0.15 uM | 78.0% @ 1.0 uM | | |
| B-1287 | 0.25 uM | 55.0% @ 1.0 uM | | |
| B-1288 | 0.15 uM | 74.0% @ 1.0 uM | | |
| B-1289 | 0.73 uM | 35.0% @ 1.0 uM | | |
| B-1290 | 0.26 uM | 75.0% @ 1.0 uM | | |
| B-1291 | 0.097 uM | 55.0% @ 1.0 uM | | |
| B-1292 | 0.01 uM | 74.0% @ 1.0 uM | | |
| B-1293 | 0.31 uM | 48.0% @ 1.0 uM | | |
| B-1294 | 0.013 uM | 54.0% @ 1.0 uM | | |
| B-1295 | 0.079 uM | 74.0% @ 1.0 uM | | |
| B-1296 | 0.038 uM | 48.0% @ 1.0 uM | | |
| B-1297 | 0.02 uM | >1.0 uM | | |
| B-1298 | 0.055 uM | 20.0% @ 1.0 uM | | |
| B-1299 | 0.091 uM | >1.0 uM | | |
| B-1300 | 0.071 uM | 18.0% @ 1.0 uM | | |
| B-1301 | 0.12 uM | 15.0% @ 1.0 uM | | |
| B-1302 | 0.023 uM | 11.0% @ 1.0 uM | | |
| B-1303 | 0.08 uM | >1.0 uM | | |
| B-1304 | 0.11 uM | 10.0% @ 1.0 uM | | |
| B-1305 | 0.64 uM | 9.0% @ 1.0 uM | | |
| B-1306 | 0.11 uM | >1.0 uM | | |
| B-1307 | 0.009 uM | 16.0% @ 1.0 uM | | |
| B-1308 | <0.1 uM | >1.0 uM | | |
| B-1309 | 0.045 uM | >1.0 uM | | |
| B-1310 | 0.12 uM | 11.0% @ 1.0 uM | | |
| B-1311 | 0.05 uM | 57.0% @ 1.0 uM | | |
| B-1312 | 0.35 uM | >1.0 uM | | |
| B-1313 | 0.035 uM | 37.0% @ 1.0 uM | | |
| B-1314 | 0.045 uM | 24.0% @ 1.0 uM | | |
| B-1315 | 0.055 uM | 12.0% @ 1.0 uM | | |
| B-1316 | 0.026 uM | 36.0% @ 1.0 uM | | |
| B-1317 | 0.019 uM | 9.0% @ 1.0 uM | | |
| B-1318 | <0.1 uM | 1.0% @ 1.0 uM | | |
| B-1319 | 0.24 uM | >1.0 uM | | |
| B-1320 | 0.047 uM | 43.0% @ 1.0 uM | | |
| B-1321 | 0.47 uM | 66.0% @ 1.0 uM | | |
| B-1322 | 0.12 uM | 87.0% @ 1.0 uM | | |
| B-1323 | 0.013 uM | 85.0% @ 1.0 uM | | |
| B-1324 | 0.16 uM | 83.0% @ 1.0 uM | | |
| B-1325 | 0.27 uM | 95.0% @ 1.0 uM | | |
| B-1326 | 0.092 uM | 84.0% @ 1.0 uM | | |
| B-1327 | 0.13 uM | 65.0% @ 1.0 uM | | |
| B-1328 | 0.032 uM | 86.0% @ 1.0 uM | | |
| B-1329 | 0.66 uM | 54.0% @ 1.0 uM | | |
| B-1330 | 0.053 uM | 85.0% @ 1.0 uM | | |
| B-1331 | 0.004 uM | 85.0% @ 1.0 uM | | |
| B-1332 | 0.007 uM | 81.0% @ 1.0 uM | | |
| B-1333 | 0.45 uM | 76.0% @ 1.0 uM | | |
| B-1334 | 0.13 uM | 73.0% @ 1.0 uM | | |
| B-1335 | 0.097 uM | 63.0% @ 1.0 uM | | |
| B-1336 | 0.072 uM | 83.0% @ 1.0 uM | | |
| B-1337 | 0.4 uM | 90.0% @ 1.0 uM | | |
| B-1338 | 0.18 uM | 73.0% @ 1.0 uM | | |
| B-1339 | 0.12 uM | 67.0% @ 1.0 uM | | |
| B-1340 | 0.043 uM | 63.0% @ 1.0 uM | | |
| B-1341 | 0.42 uM | 52.0% @ 1.0 uM | | |
| B-1342 | 0.25 uM | 59.0% @ 1.0 uM | | |
| B-1343 | 0.065 uM | 83.0% @ 1.0 uM | | |
| B-1344 | 0.014 uM | 86.0% @ 1.0 uM | | |
| B-1345 | 0.27 uM | 73.0% @ 1.0 uM | | |

-continued

| Example # | P38 alpha kinase IC50, uM or % inhib @ conc. (uM) | U937 Cell IC50, uM or % inhib @ conc. (uM) | Mouse LPS Model % TNF inhib @ dose @ predose time | Rat LPS Model % inhib @ dose @ predose time |
|---|---|---|---|---|
| B-1346 | 0.043 uM | 86.0% @ 1.0 uM | | |
| B-1347 | 0.021 uM | 84.0% @ 1.0 uM | | |
| B-1348 | 0.009 uM | 69.0% @ 1.0 uM | | |
| B-1349 | 0.037 uM | 86.0% @ 1.0 uM | | |
| B-1350 | 0.019 uM | 78.0% @ 1.0 uM | | |
| B-1351 | 0.068 uM | 78.0% @ 1.0 uM | | |
| B-1352 | 0.013 uM | 76.0% @ 1.0 uM | | |
| B-1353 | 0.062 uM | 80.0% @ 1.0 uM | | |
| B-1354 | 0.013 uM | 83.0% @ 1.0 uM | | |
| B-1355 | 0.07 uM | 75.0% @ 1.0 uM | | |
| B-1356 | 0.059 uM | 91.0% @ 1.0 uM | | |
| B-1357 | 0.18 uM | 84.0% @ 1.0 uM | | |
| B-1358 | 0.16 uM | 76.0% @ 1.0 uM | | |
| B-1359 | 0.005 | 84.0% @ 1.0 uM | | |
| B-1360 | 0.11 | 0.15 uM | | 54% @ 3 mpk @ −4 h |
| B-1361 | 0.03 | 0.29 uM | | |
| B-1362 | 0.003 | 0.29 uM | | |
| B-1363 | 0.009 | 0.28 uM | 51.0% @ 30 mpk @ −6 H | 53% @ 3 mpk @ −4 h |
| B-1364 | 0.009 | 0.27 uM | 53.0% @ 30 mpk @ −6.0 H | 17% @ 3 mpk @ −4 h |
| B-1365 | 0.17 | 88.0% @ 1.0 uM | | |
| B-1366 | 0.04 | 0.27 uM | | |
| B-1367 | <0.1 | 0.22 uM | | |
| B-1368 | 0.031 | 0.33 uM | 44.0% @ 30 mpk @ − | |
| B-1369 | <0.1 | 0.29 uM | | |
| B-1370 | <0.1 | 0.77 uM | | |
| B-1371 | 0.06 | 83.0% @ 1.0 uM | | |
| B-1372 | <0.1 | 0.41 uM | 48.0% @ 30 mpk @ − | |
| B-1373 | 0.016 | 0.17 uM | | |
| B-1374 | <0.1 | 0.28 uM | | |
| B-1375 | 0.01 | 0.25 uM | | |
| B-1376 | 0.009 | 0.26 uM | 3.0% @ 30 mpk @ −6 H | |
| B-1377 | 0.12 | 5.0 uM | | |
| B-1378 | 0.02 | 1.04 uM | | |
| B-1379 | <0.1 | 0.092 uM | | |
| B-1380 | <0.1 | 0.26 uM | | |
| B-1381 | 0.055 | 0.73 uM | | |
| B-1382 | <0.1 | 0.44 uM | | |
| B-1383 | 0.0012 | 0.15 uM | | |
| B-1384 | 0.57 | 0.37 uM | | |
| B-1385 | <0.1 | 0.11 uM | | |
| B-1386 | <0.1 | 0.25 uM | | |
| B-1387 | <0.1 | 0.1 uM | | |
| B-1388 | 0.57 | 1.38 uM | | |
| B-1389 | 0.06 | 0.57 uM | | |
| B-1390 | <0.1 | 71.0% @ 1.0 uM | | |
| B-1391 | 0.016 uM | 82.0% @ 1.0 uM | | |
| B-1392 | 0.059 uM | 82.0% @ 1.0 uM | | |
| B-1393 | 3.17 uM | 80.0% @ 1.0 uM | | |
| B-1394 | 0.32 uM | 78.0% @ 1.0 uM | | |
| B-1395 | 1.48 | 61.0% @ 1.0 uM | | |
| B-1396 | 1.55 | 73.0% @ 1.0 uM | | |
| B-1397 | 0.92 | 85.0% @ 1.0 uM | | |
| B-1398 | 0.67 | 83.0% @ 1.0 uM | | |
| B-1399 | 0.14 | 74.0% @ 1.0 uM | | |
| B-1400 | 0.024 | 83.0% @ 1.0 uM | | |
| B-1401 | 0.033 | 75.0% @ 1.0 uM | | |
| B-1402 | 0.12 | 76.0% @ 1.0 uM | | |
| B-1403 | 4.54 | 71% @ 1.0 uM | | |
| B-1404 | 0.6 | 70% @ 1.0 uM | | |
| B-1405 | 0.28 | 70% @ 1.0 uM | | |
| B-1406 | 1.39 | 56.0% @ 1.0 uM | | |
| B-1407 | 0.4 | 71.0% @ 1.0 uM | | |
| B-1408 | 0.27 | 69.0% @ 1.0 uM | | |
| B-1409 | <0.1 | 72.0% @ 1.0 uM | | |
| B-1410 | <0.1 | 69% @ 1.0 uM | | |
| B-1411 | <0.1 | 81.0% @ 1.0 uM | | |
| B-1412 | 0.097 | 80.0% @ 1.0 uM | | |
| B-1413 | 0.016 | 78.0% @ 1.0 uM | | |
| B-1414 | 0.025 | 83.0% @ 1.0 uM | | |
| B-1415 | 1.41 | 79.0% @ 1.0 uM | | |
| B-1416 | 0.14 | 81.0% @ 1.0 uM | | |
| B-1417 | 0.069 | 69.0% @ 1.0 uM | | |
| B-1418 | 1.01 | 82.0% @ 1.0 uM | | |
| B-1419 | 0.3 | 84.0% @ 1.0 uM | | |
| B-1420 | <0.1 | 82.0% @ 1.0 uM | | |

| Example # | P38 alpha kinase IC50, uM or % inhib @ conc. (uM) | U937 Cell IC50, uM or % inhib @ conc. (uM) | Mouse LPS Model % TNF inhib @ dose @ predose time | Rat LPS Model % inhib @ dose @ predose time |
|---|---|---|---|---|
| B-1421 | 0.014 | 75.0% @ 1.0 uM | | |
| B-1422 | 0.58 | 68.0% @ 1.0 uM | | |
| B-1423 | 1.58 | 84.0% @ 1.0 uM | | |
| B-1424 | 0.86 | 76.0% @ 1.0 uM | | |
| B-1425 | 0.09 | 83.0% @ 1.0 uM | | |
| B-1426 | 0.19 | 80.0% @ 1.0 uM | | |
| B-1427 | <0.1 | 84.0% @ 1.0 uM | | |
| B-1428 | <0.1 | 86.0% @ 1.0 uM | | |
| B-1429 | <0.1 | 87.0% @ 1.0 uM | | |
| B-1430 | 0.75 uM | 35.0% @ 1.0 uM | | |
| B-1431 | 0.36 uM | 58.0% @ 1.0 uM | | |
| B-1432 | 0.11 uM | 51.0% @ 1.0 uM | | |
| B-1433 | 0.26 uM | 21.0% @ 1.0 uM | | |
| B-1434 | 0.19 uM | 28.0% @ 1.0 uM | | |
| B-1435 | 1.8 uM | 45.0% @ 1.0 uM | | |
| B-1436 | 1.0 uM | 20.0% @ 1.0 uM | | |
| B-1437 | 0.3 uM | 23.0% @ 1.0 uM | | |
| B-1438 | 2.01 uM | 27.0% @ 1.0 uM | | |
| B-1439 | 1.7 uM | 17.0% @ 1.0 uM | | |
| B-1440 | 0.87 uM | 3.0% @ 1.0 uM | | |
| B-1441 | 1.95 uM | 66.0% @ 1.0 uM | | |
| B-1442 | 1.54 uM | 18.0% @ 1.0 uM | | |
| B-1443 | 0.014 uM | 83.0% @ 1.0 uM | | |
| B-1444 | 0.3 uM | 24.0% @ 1.0 uM | | |
| B-1445 | 0.43 uM | 27.0% @ 1.0 uM | | |
| B-1446 | 0.77 uM | 36.0% @ 1.0 uM | | |
| B-1447 | 0.5 uM | 34.0% @ 1.0 uM | | |
| B-1448 | 1.43 uM | 22.0% @ 1.0 uM | | |
| B-1449 | 1.61 uM | 50.0% @ 1.0 uM | | |
| B-1450 | 2.1 uM | 49.0% @ 1.0 uM | | |
| B-1451 | 2.88 uM | 50% @ 1.0 uM | | |
| B-1452 | 2.41 uM | 47.0% @ 1.0 uM | | |
| B-1453 | 2.53 uM | 49.0% @ 1.0 uM | | |
| B-1454 | 1.6 uM | 12.0% @ 1.0 uM | | |
| B-1455 | 1.21 uM | 8.0% @ 1.0 uM | | |
| B-1456 | 1.29 uM | >1.0 uM | | |
| B-1457 | 0.43 um | 43.0% @ 1.0 uM | | |
| B-1458 | 0.95 uM | 65.0% @ 1.0 uM | | |
| B-1459 | 0.67 uM | 46.0% @ 1.0 uM | | |
| B-1460 | 0.96 uM | 29.0% @ 1.0 uM | | |
| B-1461 | 0.4 uM | 39.0% @ 1.0 uM | | |
| B-1462 | 0.22 uM | 50.0% @ 1.0 uM | | |
| B-1463 | 2.34 uM | 26.0% @ 1.0 uM | | |
| B-1464 | 1.18 uM | 27.0% @ 1.0 uM | | |
| B-1465 | 3.23 uM | 31.0% @ 1.0 uM | | |
| B-1466 | 1.69 uM | >1.0 uM | | |
| B-1467 | 1.22 uM | 1.0% @ 1.0 uM | | |
| B-1468 | 1.61 uM | 10.0% @ 1.0 uM | | |
| B-1469 | 0.37 uM | 14.0% @ 1.0 uM | | |
| B-1470 | 0.6 uM | 28.0% @ 1.0 uM | | |
| B-1471 | 0.85 uM | 25.0% @ 1.0 uM | | |
| B-1472 | 0.93 uM | 12.0% @ 1.0 uM | | |
| B-1473 | 1.24 uM | 14.0% @ 1.0 uM | | |
| B-1474 | 1.23 uM | 31.0% @ 1.0 uM | | |
| B-1475 | 2.1 uM | 24.0% @ 1.0 uM | | |
| B-1476 | 0.047 uM | 42.0% @ 1.0 uM | | |
| B-1477 | 2.5 uM | 34.0% @ 1.0 uM | | |
| B-1478 | | | | |
| B-1479 | | | | |
| B-2270 | 0.72 uM | 31% @ 10.0 uM | | |
| B-2271 | 0.93 uM | 38% @ 10.0 uM | | |
| B-2272 | 0.26 uM | 53.0% @ 10.0 uM | | |
| B-2273 | 1.92 uM | 39.0% @ 10.0 uM | | |
| B-2274 | 0.26 uM | 59.0% @ 10.0 uM | | |
| B-2275 | 2.16 uM | 53.0% @ 10.0 uM | | |
| B-2276 | 11.5 uM | 37.0% @ 10.0 uM | | |
| B-2277 | 14.9 uM | 44.0% @ 10.0 uM | | |
| B-2278 | 0.8 uM | 51.0% @ 10.0 uM | | |
| B-2279 | 0.32 uM | 36.0% @ 10.0 uM | | |
| B-2280 | 0.4 uM | 57.0% @ 10.0 uM | | |
| B-2281 | 0.81 uM | 60.0% @ 10.0 uM | | |
| B-2282 | 0.91 uM | 41.0% @ 10.0 uM | | |
| B-2283 | 0.04 uM | 53.0% @ 10.0 uM | | |
| B-2284 | 4.61 uM | 62.0% @ 10.0 uM | | |
| B-2285 | 2.29 uM | 49.0% @ 10.0 uM | | |

| Example # | P38 alpha kinase IC50, uM or % inhib @ conc. (uM) | U937 Cell IC50, uM or % inhib @ conc. (uM) | Mouse LPS Model % TNF inhib @ dose @ predose time | Rat LPS Model % inhib @ dose @ predose time |
|---|---|---|---|---|
| B-2286 | 0.017 uM | 0.78 uM | 25% @ 30 mpk @ −1 h | |
| B-2287 | 2.56 uM | 61.0% @ 10.0 uM | | |
| B-2288 | 6.51 uM | 46.0% @ 10.0 uM | | |
| B-2289 | 3.0 uM | 30.0% @ 10.0 uM | | |
| B-2290 | 2.37 uM | 59.0% @ 10.0 uM | | |
| B-2291 | 0.019 uM | 41% @ 10.0 uM | | |
| B-2292 | 8.82 uM | 57.0% @ 10.0 uM | | |
| B-2293 | 2.11 uM | 56.0% @ 10.0 uM | | |
| B-2294 | 1.68 uM | 50.0% @ 10.0 uM | | |
| B-2295 | 1.79 uM | 56.0% @ 10.0 uM | | |
| B-2296 | 17.3 uM | 63.0% @ 10.0 uM | | |
| B-2297 | 3.59 uM | 57.0% @ 10.0 uM | | |
| B-2298 | 0.29 uM | 4.22 uM | | |
| B-2299 | 1.97 uM | 62.0% @ 10.0 uM | | |
| B-2300 | 0.07 uM | 43.0% @ 10.0 uM | | |
| B-2301 | 0.18 uM | 44.0% @ 10.0 uM | | |
| B-2302 | 1.0 uM | 58.0% @ 1.0 uM | | |
| B-2303 | 0.011 uM | 54.0% @ 10.0 uM | | |
| B-2304 | 1.41 uM | 50.0% @ 10.0 uM | | |
| B-2305 | 0.54 uM | 60.0% @ 10.0 uM | | |
| B-2306 | 5.88 uM | 39.0% @ 10.0 uM | | |
| B-2307 | 2.29 uM | 69.0% @ 10.0 uM | | |
| B-2308 | 0.66 uM | 56.0% @ 10.0 uM | | |
| B-2309 | 0.29 uM | 47.0% @ 10.0 uM | | |
| B-2310 | 0.12 uM | 1.2 uM | 50% @ 30 mpk @ −6 h | |
| B-2311 | 7.18 uM | 60% @ 10.0 uM | | |
| B-2312 | 2.93 uM | 43.0% @ 10.0 uM | | |
| B-2313 | 42.3 uM | 58.0% @ 10.0 uM | | |
| B-2314 | 11.0 uM | 66.0% @ 10.0 uM | | |
| B-2315 | 0.49 uM | 36.0% @ 10.0 uM | | |
| B-2316 | 0.46 uM | 58.0% @ 10.0 uM | | |
| B-2317 | 1.0 uM | 60.0% @ 10.0 uM | | |
| B-2318 | 73.0% @ 10.0 uM | 25.0% @ 10.0 uM | | |
| B-2319 | 75.0% @ 10.0 uM | 40.0% @ 10.0 uM | | |
| B-2320 | 44.0% @ 10.0 uM | 35.0% @ 10.0 uM | | |
| B-2321 | 69.0% @ 10.0 uM | 27.0% @ 10.0 uM | | |
| B-2322 | 76.0% @ 10.0 uM | 38.0% @ 10.0 uM | | |
| B-2323 | 69.0% @ 10.0 uM | 46.0% @ 10.0 uM | | |
| B-2324 | 58.0% @ 10.0 uM | 36.0% @ 10.0 uM | | |
| B-2325 | 60.0% @ 10.0 uM | 51.0% @ 10.0 uM | | |
| B-2326 | 76.0% @ 10.0 uM | 33.0% @ 10.0 uM | | |
| B-2327 | 76.0% @ 10.0 uM | 23.0% @ 10.0 uM | | |
| B-2328 | 65.0% @ 10.0 uM | 28.0% @ 10.0 uM | | |
| B-2329 | 72.0% @ 10.0 uM | 53.0% @ 10.0 uM | | |
| B-2330 | 81.0% @ 10.0 uM | 37.0% @ 10.0 uM | | |
| B-2331 | 74.0% @ 10.0 uM | 44.0% @ 10.0 uM | | |
| B-2332 | 70.0% @ 10.0 uM | 47.0% @ 10.0 uM | | |
| B-2333 | 58.0% @ 10.0 uM | 36.0% @ 10.0 uM | | |
| B-2334 | 81.0% @ 10.0 uM | 45.0% @ 10.0 uM | | |
| B-2335 | 82.0% @ 10.0 uM | 50.0% @ 10.0 uM | | |
| B-2336 | 48.0% @ 10.0 uM | 35.0% @ 10.0 uM | | |
| B-2337 | 46.0% @ 10.0 uM | 59.0% @ 10.0 uM | | |
| B-2338 | 73.0% @ 10.0 uM | 50.0% @ 10.0 uM | | |
| B-2339 | 84.0% @ 10.0 uM | >10.0 uM | | |
| B-2340 | 35.0% @ 10.0 uM | 12.0% @ 10.0 uM | | |
| B-2341 | 75.0% @ 10.0 uM | 50.0% @ 10.0 uM | | |
| B-2342 | 83.0% @ 10.0 uM | 46.0% @ 10.0 uM | | |
| B-2343 | 43.0% @ 10.0 uM | 27.0% @ 10.0 uM | | |
| B-2344 | 71.0% @ 10.0 uM | 50.0% @ 10.0 uM | | |
| B-2345 | 64.0% @ 10.0 uM | 38.0% @ 10.0 uM | | |
| B-2346 | 45.0% @ 10.0 uM | 48.0% @ 10.0 uM | | |
| B-2347 | 49.0% @ 10.0 uM | 50.0% @ 10.0 uM | | |
| B-2348 | 76.0% @ 10.0 uM | 48.0% @ 10.0 uM | | |
| B-2349 | 75.0% @ 10.0 uM | 27.0% @ 10.0 uM | | |
| B-2350 | 38.0% @ 10.0 uM | 56.0% @ 10.0 uM | | |
| B-2351 | 77.0% @ 10.0 uM | 1.0% @ 10.0 uM | | |
| B-2352 | 37.0% @ 10.0 uM | 19.0% @ 10.0 uM | | |
| B-2353 | 38.0% @ 10.0 uM | 33.0% @ 10.0 uM | | |
| B-2354 | 65.0% @ 10.0 uM | 25.0% @ 10.0 uM | | |
| B-2355 | 84.0% @ 10.0 uM | 50.0% @ 10.0 uM | | |
| B-2356 | 77.0% @ 10.0 uM | 45.0% @ 10.0 uM | | |
| B-2357 | 47.0% @ 10.0 uM | 41.0% @ 10.0 uM | | |
| B-2358 | 17.0% @ 10.0 uM | 52.0% @ 10.0 uM | | |
| B-2359 | 76.0% @ 10.0 uM | 35.0% @ 10.0 uM | | |
| B-2360 | 45.0% @ 10.0 uM | >10.0 uM | | |

-continued

| Example # | P38 alpha kinase IC50, uM or % inhib @ conc. (uM) | U937 Cell IC50, uM or % inhib @ conc. (uM) | Mouse LPS Model % TNF inhib @ dose @ predose time | Rat LPS Model % inhib @ dose @ predose time |
|---|---|---|---|---|
| B-2361 | 19.0% @ 10.0 uM | 46.0% @ 10.0 uM | | |
| B-2362 | 60% @ 10.0 uM | 39.0% @ 10.0 uM | | |
| B-2363 | 44.0% @ 10.0 uM | 1.0% @ 10.0 uM | | |
| B-2364 | 47.0% @ 10.0 uM | 4.0% @ 10.0 uM | | |
| B-2365 | 82.0% @ 10.0 uM | 43.0% @ 10.0 uM | | |
| B-2366 | 70.0% @ 10.0 uM | 59.0% @ 10.0 uM | | |
| B-2367 | 46.0% @ 10.0 uM | 40.0% @ 10.0 uM | | |
| B-2368 | 65.0% @ 10.0 uM | 55.0% @ 10.0 uM | | |
| B-2369 | 32.0% @ 10.0 uM | >10.0 uM | | |
| B-2370 | 73% @ 100.0 uM | 20.0% @ 10.0 uM | | |
| B-2371 | 54.0% @ 10.0 uM | 36.0% @ 10.0 uM | | |
| B-2372 | 55.0% @ 100.0 uM | >10.0 uM | | |
| B-2373 | 50.0% @ 100.0 uM | 6% @ 10.0 uM | | |
| B-2374 | 35.0% @ 10.0 uM | 20.0% @ 10.0 uM | | |
| B-2375 | 62.0% @ 100.0 uM | >10.0 uM | | |
| B-2376 | 32.0% @ 10.0 uM | 17.0% @ 10.0 uM | | |
| B-2377 | 34.0% @ 10.0 uM | 17.0% @ 10.0 uM | | |
| B-2378 | 48.0% @ 10.0 uM | 61.0% @ 10.0 uM | | |
| B-2379 | 73.0% @ 100.0 uM | 45.0% @ 1.0 uM | | |
| B-2380 | 81% @ 100.0 uM | 53.0% @ 10.0 uM | | |
| B-2381 | 68% @ 100.0 uM | 2.0% @ 10.0 uM | | |
| B-2382 | 51.0% @ 10.0 uM | 24.0% @ 10.0 uM | | |
| B-2383 | 63.0% @ 10.0 uM | 35.0% @ 10.0 uM | | |
| B-2384 | 49% @ 100.0 uM | 10.0% @ 10.0 uM | | |
| B-2385 | 79.0% @ 10.0 uM | 19.0% @ 10.0 uM | | |
| B-2386 | 38.0% @ 10.0 uM | 19.0% @ 10.0 uM | | |
| B-2387 | 50.0% @ 100.0 uM | >10.0 uM | | |
| B-2388 | 42.0% @ 10.0 uM | 24.0% @ 10.0 uM | | |
| B-2389 | 39.0 % @ 10.0 uM | 29.0% @ 10.0 uM | | |
| B-2390 | 34.0% @ 10.0 uM | 27.0% @ 1.0 uM | | |
| B-2391 | 40.0% @ 10.0 uM | 59.0% @ 10.0 uM | | |
| B-2392 | 63.0% @ 10.0 uM | 46.0% @ 10.0 uM | | |
| B-2393 | 43.0% @ 10.0 uM | >10.0 uM | | |
| B-2394 | 37.0% @ 10.0 uM | 22.0% @ 10.0 uM | | |
| B-2395 | 32.0% @ 10.0 uM | 28.0% @ 10.0 uM | | |
| B-2396 | 75.0% @ 10.0 uM | >10.0 uM | | |
| B-2397 | 83.0% @ 10.0 uM | 22.0% @ 10.0 uM | | |
| B-2398 | 55% @ 100.0 uM | 10.0% @ 10.0 uM | | |
| B-2399 | 69.0% @ 10.0 uM | 18.0% @ 10.0 uM | | |
| B-2400 | 60.0% @ 10.0 uM | 40.0% @ 10.0 uM | | |
| B-2401 | 78.0% @ 10.0 uM | 44.0% @ 10.0 uM | | |
| B-2402 | 43.0% @ 10.0 uM | 52.0% @ 10.0 uM | | |
| B-2403 | 72% @ 100.0 uM | 52.0% @ 10.0 uM | | |
| B-2404 | 58% @ 100.0 uM | 52.0% @ 10.0 uM | | |
| B-2405 | 47% @ 100.0 uM | >10.0 uM | | |
| B-2406 | 45.0% @ 10.0 uM | 24.0% @ 10.0 uM | | |
| B-2407 | 47% @ 10.0 uM | 27.0% @ 10.0 uM | | |
| B-2408 | 39.0% @ 10.0 uM | 10.0% @ 10.0 uM | | |
| B-2409 | 78.0% @ 10.0 uM | 26.0% @ 10.0 uM | | |
| B-2410 | 33.0% @ 10.0 uM | 32.0% @ 10.0 uM | | |
| B-2411 | 26% @ 100.0 uM | 13.0% @ 10.0 uM | | |
| B-2412 | 40.0% @ 10.0 uM | 31.0% @ 10.0 uM | | |
| B-2413 | 75.0% @ 10.0 uM | 37.0% @ 10.0 uM | | |
| B-2414 | 86.0% @ 10.0 uM | 38.0% @ 10.0 uM | | |
| B-2415 | 94.0% @ 10.0 uM | 50.0% @ 10.0 uM | | |
| B-2416 | 85.0% @ 10.0 uM | 43.0% @ 1.0 uM | | |
| B-2417 | 83.0% @ 10.0 uM | 18.0% @ 10.0 uM | | |
| B-2418 | 88.0% @ 10.0 uM | 34.0% @ 10.0 uM | | |
| B-2419 | 86.0% @ 10.0 uM | 66.0% @ 10.0 uM | | |
| B-2420 | 70.0% @ 10.0 uM | 34.0% @ 10.0 uM | | |
| B-2421 | 89.0% @ 10.0 uM | 38.0% @ 10.0 uM | | |
| B-2422 | 90.0% @ 10.0 uM | 17.0% @ 10.0 uM | | |
| B-2423 | 85.0% @ 10.0 uM | >10.0 uM | | |
| B-2424 | 86.0% @ 10.0 uM | 43.0% @ 10.0 uM | | |
| B-2425 | 79.0% @ 10.0 uM | 42.0% @ 10.0 uM | | |
| B-2426 | 88.0% @ 10.0 uM | 53.0% @ 10.0 uM | | |
| B-2427 | 87.0% @ 10.0 uM | 59.0% @ 10.0 uM | | |
| B-2428 | 82.0% @ 10.0 uM | 50.0% @ 10.0 uM | | |
| B-2429 | 92.0% @ 10.0 uM | 32.0% @ 10.0 uM | | |
| B-2430 | 90.0% @ 10.0 uM | 61.0% @ 10.0 uM | | |
| B-2431 | 85.0% @ 10.0 uM | 68.0% @ 10.0 uM | | |
| B-2432 | 86.0% @ 10.0 uM | 40.0% @ 10.0 uM | | |
| B-2433 | 94.0% @ 10.0 uM | 84.0% @ 10.0 uM | | |
| B-2434 | 92.0% @ 10.0 uM | 63.0% @ 10.0 uM | | |
| B-2435 | 84.0% @ 10.0 uM | 4.0% @ 10.0 uM | | |

-continued

| Example # | P38 alpha kinase IC50, uM or % inhib @ conc. (uM) | U937 Cell IC50, uM or % inhib @ conc. (uM) | Mouse LPS Model % TNF inhib @ dose @ predose time | Rat LPS Model % inhib @ dose @ predose time |
|---|---|---|---|---|
| B-2436 | 80.0% @ 10.0 uM | 54.0% @ 10.0 uM | | |
| B-2437 | 82.0% @ 10.0 uM | 41.0% @ 10.0 uM | | |
| B-2438 | 75.0% @ 10.0 uM | 40.0% @ 10.0 uM | | |
| B-2439 | 81.0% @ 10.0 uM | 44.0% @ 10.0 uM | | |
| B-2440 | 77.0% @ 10.0 uM | 78.0% @ 10.0 uM | | |
| B-2441 | 86.0% @ 10.0 uM | 46.0% @ 10.0 uM | | |
| B-2442 | 86.0% @ 10.0 uM | >10.0 uM | | |
| B-2443 | 84.0% @ 10.0 uM | 44.0% @ 10.0 uM | | |
| B-2444 | 89.0% @ 10.0 uM | 7.0% @ 10.0 uM | | |
| B-2445 | 94.0% @ 10.0 uM | 15.0% @ 10.0 uM | | |
| B-2446 | 90.0% @ 10.0 uM | 28.0% @ 10.0 uM | | |
| B-2447 | 94.0% @ 10.0 uM | >10.0 uM | | |
| B-2448 | 75.0% @ 10.0 uM | 30.0% @ 10.0 uM | | |
| B-2449 | 86.0% @ 10.0 uM | 42.0% @ 10.0 uM | | |
| B-2450 | 87.0% @ 10.0 uM | 46.0% @ 10.0 uM | | |
| B-2451 | 87.0% @ 10.0 uM | 45.0% @ 10.0 uM | | |
| B-2452 | 89.0% @ 10.0 uM | 33.0% @ 10.0 uM | | |
| B-2453 | 91.0% @ 10.0 uM | >10.0 uM | | |
| B-2454 | 88.0% @ 10.0 uM | 40.0% @ 10.0 uM | | |
| B-2455 | 87.0% @ 10.0 uM | 54.0% @ 10.0 uM | | |
| B-2456 | 86.0% @ 10.0 uM | 53.0% @ 10.0 uM | | |
| B-2457 | 90.0% @ 10.0 uM | 18.0% @ 10.0 uM | | |
| B-2458 | 83.0% @ 10.0 uM | 36.0% @ 10.0 uM | | |
| B-2459 | 82.0% @ 10.0 uM | 81.0% @ 10.0 uM | | |
| B-2460 | 80.0% @ 10.0 uM | 79.0% @ 10.0 uM | | |
| B-2461 | 67.0% @ 10.0 uM | 59.0% @ 10.0 uM | | |

Biological data from a number of compounds of Examples C-74 through C-139 are shown in the following tables.

In vitro P38-alpha kinase inhibitory data are shown in the column identified as:

"P38 alpha kinase IC50, $\mu M$"

In vitro human whole blood assay data for measuring the ability of the compounds to inhibit TNF production in human whole blood stimulated with LPS are shown in the column identified as:

"Human Whole Blood IC50, $\mu M$ or %Inhib@conc. ($\mu M$)"

In vivo assessment of the ability of the compounds to inhibit LPS-stimulated TNF release in the rat is shown in the column identified as:

"Rat LPS Model % Inhibition@dose@predose time"

wherein the dose is milligram per kilogram (mpk) administered by oral gavage and the predose time indicates the number of hours before LPS challenge when the compound is administered.

| Example # | P38 alpha kinase IC$_{50}$, $\mu M$ | Human Whole Blood IC$_{50}$, $\mu M$, or % Inhib @ conc. ($\mu M$) | Rat LPS Model % Inhibition @ dose @ predose time |
|---|---|---|---|
| C-74 | 0.037 | 0.56 | 54% @ 5 mpk @ −4 h |
| C-75 | 0.045 | 0.4 | 71% @ 5 mpk @ −4 h |
| C-76 | 0.07 | 3.24 | 66% @ 5 mpk @ −4 h |
| C-77 | 0.071 | 8.2 | 92% @ 5 mpk @ −4 h |
| C-78 | 0.068 | 10.5 | 87% @ 5 mpk @ −4 h |
| C-79 | 0.045 | 0.52 | 83% @ 5 mpk @ −4 h |
| C-80 | 0.008 | 51% @ 5 $\mu M$ | |
| C-81 | 0.037 | 40% @ 5 $\mu M$ | |
| C-82 | 0.15 | 7.31 | |
| C-83 | 0.24 | 1.23 | 25% @ 5 mpk @ −4 h |
| C-84 | 0.048 | 0.88 | 22% @ 5 mpk @ −4 h |
| C-85 | 0.57 | >25 | |
| C-86 | 0.007 | 0.19 | 66% @ 5 mpk @ −4 h |
| C-87 | 0.027 | 0.34 | |
| C-88 | 0.012 | 0.3 | 59% @ 5 mpk @ −4 h |
| C-89 | 0.039 | 0.12 | 27% @ 5 mpk @ −4 h |
| C-90 | 0.037 | 0.48 | |
| C-91 | 0.054 | 2.31 | 63% @ 5 mpk @ −4 h |
| C-92 | 0.024 | 0.28 | 66% @ 5 mpk @ −4 h |
| C-93 | 0.009 | 0.38 | 50% @ 5 mpk @ −4 h |
| C-94 | 0.02 | 0.27 | 73% @ 5 mpk @ −4 h |
| C-95 | 0.13 | 3.91 | 32% @ 5 mpk @ −4 h |
| C-96 | 0.077 | 2.1 | 38% @ 5 mpk @ −4 h |
| C-97 | 0.025 | 3.83 | 21% @ 5 mpk @ −4 h |
| C-98 | 0.016 | 0.64 | 78% @ 5 mpk @ −4 h |
| C-99 | 0.062 | 0.38 | 36% @ 5 mpk @ −4 h |
| C-100 | 0.027 | 0.27 | 44% @ 5 mpk @ −4 h |
| C-101 | 0.083 | 3.71 | 52% @ 5 mpk @ −4 h |
| C-102 | 0.29 | 7.56 | 72% @ 5 mpk @ −4 h |
| C-105 | 0.033 | 0.13 | 46% @ 5 mpk @ −4 h |
| C-106 | 0.026 | 0.44 | 23% @ 5 mpk @ −4 h |
| C-107 | 0.014 | 0.38 | 11% @ 5 mpk @ −4 h |
| C-108 | 0.02 | 0.73 | 0% @ 5 mpk @ −4 h |
| C-111 | 0.21 | 6.05 | 39% @ 5 mpk @ −4 h |
| C-112 | 0.54 | 6.36 | 89% @ 5 mpk @ −4 h |
| C-113 | 0.082 | 2.72 | 77% @ 5 mpk @ −4 h |
| C-114 | 0.11 | 1.73 | 39% @ 5 mpk @ −4 h |
| C-115 | 0.042 | 10.2 | 39% @ 5 mpk @ −4 h |
| C-116 | 0.429 | 0.50 | 53% @ 5 mpk @ −4 h |
| C-117 | 3.42 | 7.26 | 71% @ 5 mpk @ −4 h |
| C-118 | 0.298 | >25 | 39% @ 5 mpk @ −4 h |
| C-120 | 0.7 | 18.6 | 26% @ 5 mpk @ −4 h |
| C-121 | 0.11 | 15.3 | 39% @ 5 mpk @ −4 h |
| C-122 | 0.025 | | 55% @ 5 mpk @ −4 h |
| C-123 | 0.67 | >25.0 | |
| C-124 | 0.17 | 4.56 | 51% @ 20 mpk @ −4 h |
| C-125 | 7.22 | >25.0 | |
| C-126 | 0.71 | >25.0 | 6% @ 20 mpk @ −4 h |
| C-127 | 0.038 | 0.27 | 53% @ 5 mpk @ −4 h |
| C-128 | 0.09 | 2.22 | 63% @ 5 mpk @ −4 h |
| C-132 | 0.086 | 44% @ 5 $\mu M$ | |

-continued

| Example # | P38 alpha kinase IC$_{50}$, μM | Human Whole Blood IC$_{50}$, μM, or % Inhib @ conc. (μM) | Rat LPS Model % Inhibition @ dose @ predose time |
|---|---|---|---|
| C-133 | 0.16 | 4.54 | 55% @ 5 mpk @ −4 h |
| C-135 | 6.0 | | |
| C-136 | 0.032 | | |
| C-137 | 0.051 | | 58% @ 5 mpk @ −4 h |
| C-138 | 0.28 | 0.68 | 26% @ 5 mpk @ −4 h |
| C-139 | 0.2 | 3.66 | 46% @ 5 mpk @ −4 h |

What we claim is:

1. A compound or a pharmaceutically-acceptable salt or tautomer thereof, wherein:

the compound corresponds in structure to Formula IB:

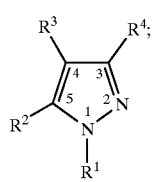

(IB)

as to $R^1$:

$R^1$ is selected from the group consisting of hydrido, alkyl, cycloalkyl, alkenyl, cycloalkenyl, alkynyl, cycloalkylalene, cycloalkenylalkylene, haloalkyl, haloalkenyl, haloalkyhyl, hydroxyalkyl, hydroxyalkenyl, hydroxyalkynyl, aralkyl, aralkenyl, aralkynyl, carboxy, carboxyalkyl, alkoxyalkyl, alkenotyalkyl, alkynoxyalkyl, aryloxyalkyl, alkoxyalkoxy, mercaptoalkyl, alkylthioalkylene, alkenylthioalkylene, alkylthioalkenylene, amino, aminoalkyl, alkylamino, alkenylamino, alkynylamino, arylamino, alkylsulfinyl, alkenylsulfinyl, alkynylsulfinyl, arylsulfinyl, alkylsulfonyl, alkenylsulfonyl, alkynylsulfonyl, arylsulfonyl, alkylaminoalkylene, alkylsulfonylalkylene, acyl, acyloxycarbonyl, alkoxycarbonylalkylene, aryloxycarbonylalkylene, alkoxycarbonylarylene, aryloxycarbonylarylene, alkylcarbonylalkylene, arylcarbonylalkylene, alkylcarbonylarylene, arylcarbonylarylene, alkylcarbonyloxyalkylene, arylcarbonyloxyalkylene, alkylcarbonyloxyarylene, and arylcarbonyloxyarylene, or $R^1$ has the formula:

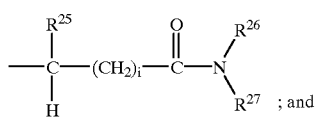

(II)

i is an integer from 0 to 9; and $R^{25}$ is selected from the group consisting of hydrogen, alkyl, aralkyl, alkoxyalkylene, aryloxyalkylene, aminoalkyl, alkylaminoalkyl, arylaminoalkyl, alkylcarbonylalkylene, and arylcarbonylalkflene; and $R^{26}$ is selected from the group consisting of hydrogen, alkyl, alkenyl, alkynyl, cycloalkylalkylene, aralkyl, alkoxycarbonylalkylene, and alkylaminoalkyl; and as to $R^{27}$:

$R^{27}$ is selected from the group consisting of alkyl, cycloalkyl, alkynyl, aryl, aralkyl, cycloalkylalkylene, cycloalkenylalkylene, cycloalkylarylene, cycloalkylcycloalkyl, alkylarylene, alkylaralkyl, aralkylaylene, alkoxyalkylene, alkoxyarylene, alkoxyaralkyl, alkoxyaitoxyarylene, aryloxyarylene, aralkoxyarylene, aryloxyaitoxyarylene, alkoxycarbonylalkylene, aminoalkyl, alkylaminoalkylene, arylaminocarbonylalkylene, alkoxyarylaminocarbonylalkylene, aminocarbonylalkylene, arylaminoalkylene, alkylaminocarbonylalkylene, arylcarbonylalkylene, alkoxycarbonylarylene, aryloxyctrbonylarylene, alkylaryloxycarbonylarylene, arylcarbonylarylene, alkylarylcarbonylarylene, alkoxycarbonylalkoxylarylene, alkylthioalkylene, cycloalkylthioalkylene, alkylthioarylene, aralkylthioarllene, arylthioalklylarylene, arylsulfonylaminoaaylene, alkylsulfonylarylene, and alkylaminosulfonylarylene, wherein:

the alkyl, cycloalkyl, aralkyl, alkoxyarylene, aryloxyarylene, arylaminocarbonylalkylene, aryloxycarbonylarylene, arylcarbonylarylene, alkylthioarylene, arylthioalklylarylene, or alkylsulfonylarylene may be optionally substituted with one or more radicals independently selected from the group consisting of alkyl, halo, haloalkyl, alkoxy, keto, amino, nito, and cyano, or $R^{27}$ is —$CHR^{28}R^{29}$; and $R^{28}$ is alkoxycarbonyl; and $R^{29}$ is selected from the group consisting of aralkyl, aralkoxyalkylene, alkoxycarbonylalkylene, alkylthioalkylene, and aralkylthioalkylene, wherein:

the aralkyl may be optionally substituted with one or more radicals independently selected from the group consisting of alkyl and nitro; and $R^2$ is selected from the group consisting of piperidinyl and piperazinyl, where in:

the piperidinyl or piperazinyl may be optionally substituted with one or more radicals independently selected from the group consisting of halo, keto, amino, alkyl, alkenyl, alkynyl, aryl, heterocyclyl, aralkyl, heterocyclylalkyl, epoxyalkyl, amino (hydroxyalkyl) carboxy, alkoxy, aryloxy, aralkoxy, haloalkyl, alkylamino, alkynylamino, alkylaminoalkylamino, heterocyalylalkylamino, alkylcarbonyl, alkoxycarbonyl, alkylsulfonyl, arylsulfonyl, and aralkylsulfonyl; and $R^3$ is pyridinyl, wherein:

the pyridinyl may be optionally substituted with one or more radicals independently selected from the group consisting of halo, alkyl, aralkyl, aralkenyl, carboxy, carboxyalkyl, alkoxy, aryloxy, alkylthio, arylthio, arylsulfinyl, arylsulfonyl, aralkoxy amino, alkylamino, alkenylamino, alkynylamino, cycloalkylamino, cycloalkenylamino, arylamino, aminocarbonyl, cyano, hydroxy, hydroxyalkyl, alkoxycarbonyl, aryloxycarbonyl, alkoxycarbonylamino, alkoxyaralkylamino, alkylaminoalkylamino, hydroxyalkylamino, aralkylamino, nitro, alkylaminocarbonyl, alkylcarbonylamino, halosulfonyl, aminoalkyl, haloalkyl, alkylcarbonyl, hydrazinyl, alkylhydrazinyl, arylhydrazinyl, and —$NR^{44}R^{45}$; and $R^{44}$ is selected from the group consisting of alkylcarbonyl and amino; and $R^{45}$ from the group consisting of alkyl and alkyl; and $R^4$ is phenyl, wherein:
the phenyl may be optionally substituted with one or more radicals independently selected from the group consisting of halo, alkyl, alenyl, alkynyl, aryl, alkylthio, arylthio, alkylthioalkylene, arylthioalkylene, alkylsulfmylalkylene, arylsulfinylalkylene, alkylsulfonylalkylene, arylsulfonylalkylene, alkoxy, aryloxy, aralkoxy, aminocarbonyl, alkylarninocarbonyl, arylaminocarbonyl, alkoxycarbonyl, aryloxycarbonyl, haloalkyl, amino, cyan, nitro, alkylamino, arylamino, alkylaminoalkylene, arylaminoalkylene, aminoalkylamino, and hydroxy.

2. A compound, salt, or tautomer according to claim 1, wherein $R^1$ is hydrido.

3. A compound, salt, or tautomer according to claim 1, wherein:
as to $R^1$:
$R^1$ is selected from the group consisting of hydrido, lower alkyl, lower cycloalkyl, lower alkenyl, lower alkynyl, lower cycloalkylalkylene, lower haloalkyl, lower hydroxyalkyl, lower aralkyl, lower alkoxyalkyl, lower mercaptoalkyl, lower alkylthioalkylene, amino, lower alkylamino, lower arylamino, and lower alkylaminoalkylene, or $R^1$ has the following formula:

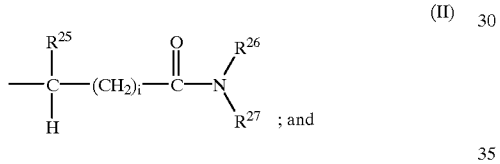

(II)

i is 0, 1, or 2; and $R^{25}$ is selected from the group consisting of hydrogen, lower alkyl, lower phenylalkyl, lower alkoxyalkylene, lower phenoxyalkylene, lower aminoalkyl, lower alkylaminoalkyl, lower phenoxyaminoalkyl, lower alkylcarbonylalkylene, and lower phenoxycarbonyla-lkylene; and $R^{26}$ is selected from the group consisting of hydrogen, lower alkyl, lower alkenyl, lower alkynyl, lower cycloalkylalkylene, lower phenylalkyl, lower alkoxycarbonylalkylene, and lower alkylaminoalkyl; and as to $R^{27}$:

$R^{27}$ is selected from the group consisting of lower alkyl, lower cycloalkyl, lower alkynyl, phenyl, biphenyl, naphthyl, lower phenylalkyl, lower cycloalkylalkylene, lower cycloalkenylalkylene, lower cycloalkylarylene, lower cycloalkylcycloalkyl, lower alkylphenylene, lower alkylphenylalkyl, lower phenylalkylphenylene, lower alkoxyalkylene, lower alkoxyphenylene, lower alkoxyphenylalkyl, lower alkoxyalkoxyphenylene, lower phenoxyphenylene, lower phenylalkoxyphenylene, lower phenoxyalkoxyphenylene, lower alkoxycarbonylalkylene, lower aminoalkyl, lower alkylaminoalkylene, lower phenylarninocarbonylalkylene, lower alkoxyphenylaminocarbonylalkylene, lower aminocarbonylalkylene, arylaminocarbonylalkylene, lower alkylaminocarbonylalkylene, lower phenylcarbonylalkylene, lower alkoxycarbonylphenylene, lower phenoxycarbonylphenylene, lower alkylphenoxycarbonylphenylene, lower phenylcarbonylphenylene, lower alkylphenylcarbonylphenylene, lower alkoxycarbonylalkoxylphenylene, lower alkylthioalkylene, cycloalkylthioalkylene, lower alkylthiophenylene, lower phenylalkylthiophenylene, lower phenylthioalklylphenylene, lower phenylsulfonylaminoalkylene, lower alkylsulfonylphenylene, and lower alkylaminosulfonylphenylene, wherein:
the lower alkyl, lower cycloalkyl, phenyl, biphenyl, naphthyl, lower phenylalkyl, lower alkoxyphenylene, lower phenoxyphenylene, lower phenylaminocarbonylalkylene, lower phenoxycarbonylphenylene, lower phenylcarbonylphenylene, lower alkylthiophenylene, lower phenylthioalklylphenylene, or lower alkylsulfo-nylphenylene may be optionally substituted with one or more radicals independently selected from the group consisting of lower alkyl, halo, lower haloalkyl, lower alkoxy, keto, amino, nitro, and cyano, or $R^{27}$ is —$CHR^{46}R^{47}$; and $R^{46}$ is lower alkoxycarbonyl; and $R^{47}$ is selected from the group consisting of lower phenylalkyl, lower phenylalkoxyalkylene, lower alkoxycarbonylalkylene, lower alkylthioalkylene, and lower phenylalkylthioalkylene, wherein:
the phenylalkyl may be optionally substituted with one or more radicals independently selected from the group consisting of lower alkyl and nitro; and $R^2$ is selected from the group consisting of piperidinyl land piperazinyl, wherein:
the piperidinyl or piperazinyl may be optionally substituted with one or more radicals independently selected from the group consisting of halo, keto, lower alkyl, lower alkynyl, phenyl, heterocyclyl, lower phenylalkyl, lower heterocyclylalkyl, lower epoxyalkyl, carboxy, lower alkoxy, lower aryloxy, lower phenylalkoxy, lower haloalkyl, lower alkylanino, lower alkylaminoalkylamino, lower alkynylamino, lower amino(hydroxyalkyl), lower heterocyclylalkylamino, lower alkylcarbonyl, lower alkoxycarbonyl, lower alkylsulfonyl, lower phenylalkylsulfonyl, and phenylsulfonyl; and $R^3$ is pyridinyl, wherein:
the pyridinyl may be optionally substituted with one or more radicals independently selected from the group consisting of lower alkylthio, halo, lower alkyl, lower aralkyl, lower phenylalkenyl, carboxy, cyano, lower alkoxycarbonyl, aminocarbonyl, lower alkylcarbonylamino, lower haloalkyl, hydroxy, lower alkoxy, amino, lower cycloalkylamino, lower alkylamino, lower alkenlamino, lower alkynylamino, lower aminoalkyl, arylamino, lower aralkylamino, nitro, halosulfonyl, lower alkylcarbonyl, lower alkoxycarbonylamino, lower alkoxyphenylalkylamino, lower alkylaminoalkylamino, lower hydroxyalkylamino, lower alkylaminocarbonyl, lower alkoxyphenylalkylamino, hydrazinyl, lower alkylhydrazinyl, and —$NR^{62}R^{63}$; and $R^{62}$ is selected from the group consisting of lower alkylcarbonyl and amino; and $R^{63}$ is selected from the group consisting of lower alkyl and lower phenylalkyl; and $R^4$ is phenyl, wherein:
  the phenyl may be optionally substituted with one or more radicals independently selected from the group consisting of lower alkylthio, halo, lower alkyl, lower alkynyl, lower alkoxy, lower aryloxy, lower aralkoxy, lower haloalkyl, amino, cyano, nitro, lower alkylamino, and hydroxy.

4. A compound, salt, or tautomer according to claim 3, wherein $R^1$ is selected from the group consisting of hydrido, methyl, and ethyl.

5. A compound, salt, or tautomer according to claim 3, wherein $R^1$ is hydrido.

6. A compound, salt, or tautomer according to claim 3, wherein:
  $R^1$ is selected from the group consisting of hydrido, methyl, ethyl, propyl, isopropyl, tert-butyl, isobutyl, fluoromethyl, difluororethyl, trifluoromethyl, chloromethyl, dichloromethyl, trichloroethyl, pentafluoroethyl, beptafluoropropyl, difluorochloromethyl, dichlorofluoromethyl, difluoroethyl, difluoropropyl, dichloroethyl, dichloropropyl, ethenyl, propenyl, ethynyl, propargyl, 1-prolynyl, 2-propynyl, benzyl, phenylethyl, methoxymethyl, ethoxyrnethyl, amino, methylamino, dimethylamino, phenylamino, methylaminomethyl, dimethylaminomethyl, methylaminoethyl, dimethylaminoethyl, ethylaminoethyl, diethylaminoethyl, cyclopropyl, cyclopentyl, cyclohexyl, cyclohexylmethyl, hydroxymethyl, hydroxyethy, mercaptomethyl, and methylthiomethyl; and $R^2$ is selected from the group consisting of piperidinyl and piperazinyl, wherein:
    the piperazinyl or piperidinyl may be optionally substituted with one or more radicals independently selected from the group consisting of fluoro, chloro, bromo, keto, methyl, ethyl, isopropyl, tert-butyl, isobutyl, benzyl, carboxy, methoxy, ethoxy, phenoxy, benzyloxy, trifluoromethyl, fluoromethyl, difluoromethyl, dimethylamino, methoxycarbonyl, ethoxycarbonyl, and 1,1-dimethylethylcarbonyl; and $R^3$ is pyridinyl, wherein:
    the pyridinyl may be optionally substituted with one or more radicals independently selected from the group consisting of methylthio, fluoro, chloro, bromo, methyl, ethyl, isopropyl, tert-butyl, isobutyl, cyano, methoxycarbonyl, ethoxycarbonyl, aminocarbonyl, methylcarbonylamino, trifluoromethyl, difluoromethyl, fluoromethyl, trichloromethyl, dichloromethyl, chloromethyl, hydroxy, fluorophenylmethyl, fluorophenylethyl, chlorophenylmethyl, chlorophenylethyl, fluorophenylethenyl, chlorophenylethenyl, carboxy, methoxy, ethoxy, propyloxy, n-butoxy, methylamino, ethylamino, dimethylamino, diethylamino, 2-methylbutylamino, propargylamino, aminomethyl, aminoethyl, N-methyl-N-phenylamino, phenylamino, diphenylamino, benzylamino, phenethylamino, cyclopropylamino, nitro, chlorosulfonyl, amino, methylcarbonyl, methoxycarbonylamino, ethoxycarbonylamino, methoxyphenylmethylamino, N,N-dimethylaminoethylamino, hydroxypropylamino, hydroxyethylamino, (1-ethyl-2-hydroxy) ethylamino, phenylmethylamino, fluorophenylmethylamino, fluorophenylethylamino, methylaminocarbonyl, ethylaminocarbonyl, methylcarbonyl, methoxyphenylmethylamino, hydrazinyl, 1-methyl-hydrazinyl, and —$NR^{62}R^{63}$; and $R^{62}$ is selected from the group consisting of methylcarbonyl and amino; and $R^{63}$ is selected from the group consisting of methyl, ethyl and phenylmethyl; and $R^4$ is phenyl, wherein:
    the phenyl may be optionally substituted with one or more radicals independently selected from the group consisting of methylthio, methylsulfinyl, methylsulfonyl, fluoro, chloro, bromo, methyl, ethyl, isopropyl, tert-butyl, isobutyl, ethynyl, methoxy, ethoxy, phenoxy, benzyloxy, trifluoromethyl, fluoromethyl, difluoromethyl, amino, cyano, nitro, dimethylamino, aid hydroxy.

7. A compound, salt, or tautomer according to claim 6, wherein $R^1$ is selected from the group consisting of hydrido, methyl, and ethyl.

8. A compound, salt, or tautomer according to claim 6, wherein $R^1$ is hydrido.

9. A compound, salt, or tautomer according to claim 6, wherein $R^1$ is selected from the group consisting of methyl and ethyl.

10. A compound, salt, or tautomer according to claim 6, wherein:
  $R^1$ is selected from the group consisting of hydrido, methyl, ethyl, propargyl, hydroxyethyl, dimethylaminoethyl, and diethylaminoethyl; and $R^2$ is selected from the group consisting of piperidinyl and piperazinyl, wherein:
    the piperidinyl or piperazinyl may be optionally substituted with one or more radicals independently selected from the group consisting of fluoro, chloro, bromo, methyl, ethyl, and trifluoromethyl; and $R^3$ is pyridinyl, wherein:
    the pyridinyl may be optionally substituted with one or more radicals independently selected from the group consisting of fluoro, bromo, methyl, cyano, methoxycarbonyl, aminocarbonyl, benzyl, phenethyl, acetyl, hydroxyl, methoxy, dimethylamino, benzylamino, phenethylamino, aminomethyl, amino, hydroxy, and methylcarbonyl; and $R^4$ is phenyl, wherein:
    the phenyl may be optionally substituted with one or more radicals independently selected from the group consisting of methylthio, fluoro, chloro, bromo, methyl, ethyl, methtxy, ethoxy, phenoxy, benzyloxy, trifluoromethyl, nitro, dimethylamino, and hydroxy.

11. A compound, salt, or tautomer according to claim 10, wherein:
  $R^1$ is selected from the group consisting of hydrido and methyl; and $R^2$ is selected from the group consisting of piperidinyl and piperazinyl, wherein:
    the piperidinyl or piperazinyl may be optionally substituted with one or more radicals independently selected from the group consisting of fluoro, chloro, bromo, methyl, ethyl, and trifluoromethyl; and $R^3$ is pyridinyl, wherein:
    the pyridinyl may be optionally substituted with one or more radicals independently selected from the group consisting of fluoro, bromo, methyl, cyano, methoxycarbonyl, aminocarbonyl, benzyl, phenethyl, acetyl, hydroxyl, methoxy, dimethyamino, benzylamino, phenethylamino, aminomethyl, amino, hydroxy, and methylcarbonyl; and $R^4$ is selected from the group consisting of phenyl, wherein;
the phenyl may be optionally substituted with one or more radicals independently selected from the group consisting of methylthio, fluoro, chloro, bromo, methyl, ethyl, methoxy, ethoxy, phenoxy, benzyloxy, trifluoromethyl, nitro, dimethylamino, and hydroxy, 12. A compound, salt, or tautomer according to claim 3, wherein:

$R^1$ is selected from the group consisting of hydrido, methyl, ethyl, propyl, isopropyl, tert-butyl, isobutyl, fluoromethyl, difluoromethyl, trifluoromethyl, chloromethyl, dichloromethyl, trichloroethyl, pentafluoroethyl, heptafluoropropyl, difluorochloromethyl dichlorofluoromethyl, difluoroethyl, difluoropropyl, dichloroethyl, dichloropropyl, ethenyl, propenyl, ethynyl, propargyl, 1-propynyl, 2-propynyl, benzyl, phenylethyl, metioxymethyl, ethoxymethyl, amino, methylamino, dimethylamino, phenylamino, methylaminomethyl, methylaminomethyl, methylaminoethyl, dimethylaminoethyl, ethylaminoethyl, diethylaminoethyl, cyclopropyl, cyclopentyl, cyclohexyl, cyclohexylmethyl, hydroxymethyl, hydroxyethyl, mercaptomethyl, and methylthiomethyl; and $R^2$ is selected from the group consisting of:

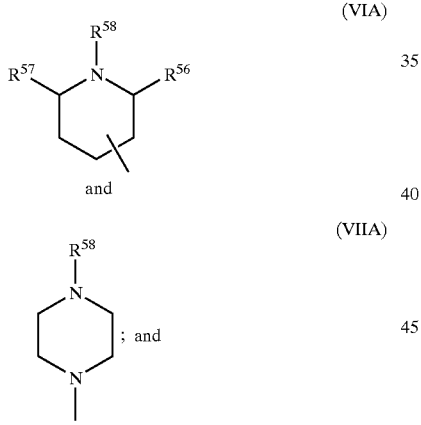

and $R^{56}$ is hydrogen or lower alkyl; and
$R^{57}$ is hydrogen or lower alkyl; and
$R^{58}$ is selected from the group consisting of hydrogen, lower alkyl, lower phenylalkyl, phenyl, biphenyl, naphthyl, lower heterocyclyl, lower heterocyclylalkyl, lower alkoxycarbonyl, lower alkylsulfonyl, lower phenylalkylsulfonyl, lower phenylsulfonyl, —C(O)$R^{59}$, —SO$_2$R$^{60}$, and —C(O)NHR$^{61}$; and
$R^{59}$ is selected from the group consisting of lower alkyl, lower haloalkyl, lower cycloalkyl, phenyl, biphenyl, naphthyl, lower heterocyclyl, lower alkylphenylene, lower phenylalkyl, lower alkylheterocyclyl, lower alkoxy, lower alkenoxy, lower phenylalkoxy, lower alkoxyalkylene, lower alkoxyphenylene, and lower alkoxyphenylalkyl, wherein:
the phenyl, biphenyl, naphthyl, lower heterocyclyl, or lower phenylalkyl may be optionally substituted with one or more radicals independently selected from the group consisting of lower alkyl, halo, hydroxy, lower haloalkyl, lower alkoxy, lower haloalkoxy, keto, amino, nitro, and cyano; and $R^{60}$ is selected from the group consisting of lower alkyl, phenyl, biphenyl, naphthyl, lower heterocyclyl, lower alkylphenylene, lower alkylheterocyclyl, lower phenylalkyl, lower heterocyclylheterocyclyl, lower alkoxyphenylene, lower alkylamino, lower alkylamin phenylene, lower alkylsulfonylphenylene, and lower phenylsulfonylheterocyclyl, wherein:
the phenyl, biphenyl, naphthyl, lower heterocyclyl, or lower phenylalkyl may be optionally substituted with one or more radicals independently selected from the group consisting of lower alkyl, halo, hydroxy, lower haloalkyl, lower alkoxy, lower haloalkoxy, keto, amino, nitro, and cyano; and $R^{61}$ is selected from the group consisting of lower alkyl, phenyl, biphenyl, napthyl, lower alkylphenylene, and lower alkoxyphenylene, wherein:
the phenyl, biphenyl, or napthyl may be optionally substituted with one or more radicals independently selected from the group consisting of lower alkyl, halo, hydroxy, loser haloalkyl, lower alkoxy, lower haloalkoxy, keto, amine, nitro, and cyano; and $R^3$ is pyridinyl, wherein:
the pyridinyl may be optionally substituted with one or more radicals independently selected from the group consisting of methylthio, methylsulfinyl, methylsulfonyl, fluoro, chloro, bromo, aminosulfonyl, methyl, ethyl, isopropyl, tert-butyl, isobutyl, cyano, methoxycarbonyl, ethoxycarbonyl, aminocarbonyl, methylcarbonylamino, trifluoromethyl, difluoromethyl, fluoromethyl, trichloromethyl, dichloromethyl, chloromethyl, hydroxy, fluorophenylmethyl, fluorophenylethyl, chlorophenylmethyl, chlorophenylethyl, fluorophenylithenyl, chlorophenylethenyl, carboxy, methoxy, ethoxy, proprloxy, n-butoxy, methylamino, ethylamino, dimethylamino, dilthylamino, 2-methylbutylamino, propargylamino, aminomethyl, aminoethyl, N-methyl-N-phenylamino, phenylamino, diphenylamino, benzylamino, phenethylamino, cyclopropylamino, nitro, chlorosulfonyl, amino, methylcarbonyl, methoxycarbonylamino, ethoxycarbonylamino, methoxyphenylmethylamino, N,N-dimethylaminoethylamino, hydroxypropylamino, hydroxyethylamino, (1-ethyl-2-hydroxy) ethylamino, phenylmethylamino, fluorophenylmethylamino, fluorophenylethylamino, methylaminocarbonyl, ethylaminocarbonyl, methylcarbonyl, methoxyphenylmethylamino, hydrazinyl, 1-methyl-hydrazinyl, and —NR$^{62}$R$^{63}$; and $R^{62}$ is selected from the group consisting of methylcaronyl and amino; and $R^{63}$ is selected from the group consisting of methyl, ethyl and phenylmethyl; and $R^4$ is phenyl, wherein:
the phenyl may be optionally substituted with one or more radicals independently selected from the group consisting of methylthio, methylsulfinyl, methylsulfonyl, fluoro, chloro, bromo, methyl, ethyl, isopropyl, tert-butyl, isobutyl, ethynyl, methoxy, ethoxy, phenoxy, benzyloxy, trifluoromethyl, fluoromethyl, difluoromethyl, amino, cyano, nitro, dimethylamino, and hydroxy.

13. A compound, salt, or tautomer according to claim 12, wherein $R^1$ is hydrido.

14. A compound, salt, or tautomer according to claim 12, wherein $R^1$ is selected from the group consisting of methyl and ethyl.

15. A compound, salt, or tautomer according to claim 12, wherein:
$R^1$ is selected from the group consisting of hydrido, methyl, ethyl, propargyl, hydroxyethyl, dimethylaminoethyl, and diethylaminoethyl; and
$R^2$ is selected from the group consisting of

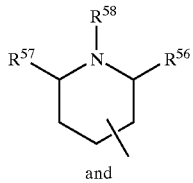

(VIA)

and

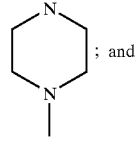

; and (VIIA)

$R^{56}$ is hydrogen; and
$R^{57}$ is hydrogen; and
$R^{58}$ is selected from the group consisting of —C(O)$R^{59}$ and —SO$_2$$R^{60}$; and
$R^{59}$ is selected from the group consisting of lower alkyl, lower cycloalkyl, phenyl, lower alkylphenylene, and lower alkoxyalkylene, wherein:
the phenyl may be optionally substituted with one or more radicals independently selected from the group consisting of lower alkyl, halo, hydroxy, lower haloalkyl, lower alkoxy, lower haloalkoxy, keto, amino, nitro, and cyano; and
$R^{60}$ is selected from lower alkyl; and
$R^3$ is pyridinyl, wherein:
the pyridinyl may be optionally substituted with one or more radicals independently selected from the group consisting of fluoro, bromo, methyl, cyano, methoxycarbonyl, aminocarbonyl, benzyl, phenethyl, acetyl, hydroxyl, methoxy, dimethilamino, benzylamino, phenethylamino, aminomethyl, amino, hydroxy, and methylcarbonyl; and
$R^4$ is phenyl, wherein:
the phenyl may be optionally substituted with one or more radicals independently selected from the group consisting of methylthio, fluoro, chloro, bromo, methyl, ethyl, methoxy, ethoxy, phenoxy, benzyloxy, trifluoromethyl, nitro, dimethylamino, and hydroxy.

16. A compound, salt, or tautomer according to claim 6, wherein:
$R^1$ is selected from the group consisting of hydrido and methyl; and
$R^3$ is pyridinyl, wherein:
the pyridinyl may be optionally substituted with one or more radicals independently selected from the group consisting of fluoro, bromo, methyl, cyano, methoxycarbonyl, aminocarbonyl, benzyl, phenethyl, acetyl, hydroxyl, methoxy, dimethylamino, benzylamino, phenethylamino, aminomethyl, amino, hydroxy, and methylcarbonyl; and
$R^4$ is selected from phenyl, wherein:
the phenyl may be optionally substituted with one or more radicals independently selected from the group consisting of methylthio, fluoro, chloro, bromo, methyl, ethyl, methoxy, ethoxy, phenoxy, benzyloxy, trifluoromethyl, nitro, dimethylamino, and hydroxy.

17. A compound, salt, or tautomer according to claim 1, wherein:
the compound corresponds in structure to Formula IXA:

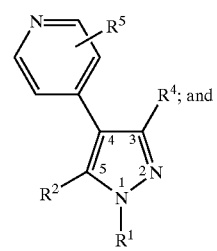

(IXA)

$R^1$ is selected from the group consisting of hydrido, lower alkyl, lower hydroxyalkyl, lower alkynyl, lower aralkyl, lower aminoalkyl and lower alkylaminoalkyl; and
$R^2$ is selected from the group consisting of piperidinyl and piperazinyl, wherein:
the piperidinyl or piperazinyl may be optionally substituted with one or more radicals independently selected from the group consisting of halo, lower alkyl, keto, aralkyl, carboxy, lower alkylaminoalkylamino, lower alkynylamino, lower heterocyclylalkylamino, lower alkylcarbonyl and lower alkoxycarbonyl; and
$R^4$ is phenyl, wherein:
the phenyl may be optionally substituted at a substitutable position with one or more radicals independently selected from the group consisting of halo, lower alkyl, lower alkoxy, aryloxy, lower aralkoxy, lower haloalkyl, lower alkylthio, lower alkylamino, nitro, and hydroxy; and
$R^5$ is selected from the group consisting of halo, amino, cyano, aminocarbonyl, lower alkyl, lower alkoxy, hydroxy, lower aminoalkyl, lower aralkyl, lower aralkyloxy, lower aralkylamino, lower alkoxycarbonyl, lower alkylamino, lower alkylcarbonyl, lower aralkenyl, carboxy, lower cycloalkylamino, lower alkoxycarbonylamino, lower alkoxyaralkylamino, lower alkylaminoalkylamino, lower alkylaminocarbonyl, lower alkoxyaralkylamino, hydrazinyl, lower alkylhydrazinyl, and —NR$^{62}$R$^{63}$; and
$R^{62}$ is selected from the group consisting of lower alkl-carbonyl and amino; and
$R^{63}$ is selected from the group consisting of lower alkyl and lower phenylalkyl.

18. A compound, salt, or tautomer according to claim 17, wherein $R^1$ is hydrido.

19. A compound, salt, or tautomer according to claim 17, wherein $R^1$ is lower alkyl.

20. A compound, salt, or tautomer according to claim 17, wherein $R^1$ is selected from the group consisting of hydrido, methyl, and ethyl.

21. A compound, salt, or tautomer according to claim 17, wherein:
$R^1$ is selected from the group consisting of hydrido, methyl, ethyl, hydroxyethyl, and propargyl; and
$R^2$ is selected from the group consisting of piperidinyl and piperazinyl, wherein:
the piperidinyl or piperazinyl may be optionally substituted with one or more radicals independently selected from the group consisting of fluoro, chloro, bromo, keto, methyl, ethyl, trifluoromethyl, benzyl, methoxy, methoxycarbonyl, ethoxycarbonyl, and (1,1-dimethyl)ethoxycarbonyl; and
$R^4$ is phenyl, wherein:
the phenyl may be optionally substituted with one or more radicals independently selected from the group consisting of methylthio, fluoro, chloro, bromo, methyl, ethyl, methoxy, ethoxy, phenoxy, benzyloxy, trifluoromethyl, nitro, dimethylamino, and hydroxy; and
$R^5$ is selected from the group consisting of fluoro, chloro, bromo, methyl, fluorophenylethyl, fluorophenylethenyl, cyano, methoxycarbonyl, aminocarbonyl, acetyl, hydroxy, carboxy, methoxy, methylamino, dimethylamino, 2-methylbutylamino, ethylamino, dimethylaminoethylamino, hydroxypropylamino, hydroxyethylamino, (1-ethyl-2-hydroxy)ethylamino, aminomethyl, cyclopropylamino, amino, hydroxy, methylcarbonyl, ethoxycarbonylamino, methoxyphenylmethylamino, phenylmethylamino, fluorophenylmethylamino, fluorophenylethylamino, methylaminocarbonyl, hydrazinyl, 1-methylhydrazinyl, and —NR$^{62}$R$^{63}$; and
$R^{62}$ is selected from the group consisting of methylcarbonyl and amino; and
$R^{63}$ is selected from the group consisting of methyl and benzyl.

22. A compound, salt, or tautomer according to claim 21, wherein $R^1$ is hydrido.

23. A compound, salt, or tautomer according to claim 21, wherein $R^1$ is lower alkyl.

24. A compound, salt, or tautomer according to claim 21, wherein $R^1$ is selected from, the group consisting of hydrido, methyl, and ethyl.

25. A compound, salt, or tautomer according to claim 1, wherein:
the compound corresponds in structure to Formula XA:

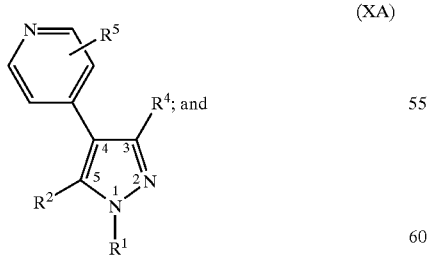

(XA)

$R^1$ is selected from the group consisting of lower alkyl, lower hydroxyalkyl, lower alkynyl, lower aminoalkyl, and lower alkylaminoalkyl; and
$R^2$ is selected from the group consisting of piperidinyl and piperazinyl, wherein:
the piperidinyl or piperazinyl may be optionally substituted with one or more radicals independently selected from the group consisting of halo, lower alkyl, keto, aralkyl, carboxy, lower alkylaminoalkylamino, lower alkynylamino, lower heterocyclylalkylamino, lower alkylcarbonyl and lower alkoxycarbonyl; and
$R^4$ is phenyl, wherein:
the phenyl may be optionally substituted with one or more radicals independently selected from the group consisting of halo, lower alkyl, lower alkoxy, aryloxy, lower aralkoxy, lower haloalkyl, lower alkylthio, lower alkylamino, nitro, and hydroxy; and
$R^5$ is selected from the group consisting of halo, amino, cyano, aminocarbonyl, lower alkyl, lower alkoxy, hydroxy, lower aminoalkyl, lower aralkyl, lower aralkyloxy, lower aralkylamino, lower alkoxycarbonyl, lower alkylamino, lower alkylcarbonyl, carboxy, lower cycloalkylamino, lower alkoxycarbonylamino, lower alkoxyaralkylamino, lower alkylaminoalkylamino, lower alkylaminocarbonyl, lower alkoxyaralkylamino, hydrazinyl, lower alkylhydrazinyl, and —NR$^{62}$R$^{63}$; and
$R^{62}$ is selected from the group consisting of lower alkylcarbonyl and amino; and
$R^{63}$ is selected from the group consisting of lower alkyl and lower phenylalkyl.

26. A compound, salt, or tautomer according to claim 25, wherein:
$R^1$ is selected from the group consisting of methyl, ethyl, hydroxyethyl, and propargyl; and
$R^2$ is selected from the group consisting of piperidinyl and piperazinyl, wherein:
the piperidinyl or piperazinyl may be optionally substituted with one or more radicals independently selected from the group consisting of fluoro, chloro, bromo, keto, methyl, ethyl, trifluoromethyl, benzyl, methoxy, methoxycarbonyl, ethoxycarbonyl, and (1,1-dimethyl)ethoxycarbonyl; and
$R^4$ is phenyl, wherein:
the phenyl may be optionally substituted with one or more radicals independently selected from the group consisting of methylthio, fluoro, chloro, bromo, methyl, ethyl, methoxy, ethoxy, phenoxy, benzyloxy, trifluoromethyl, nitro, dimethylamino, and hydroxy; and
$R^5$ is selected from the group consisting of fluoro, choro, bromo, methyl, fluorophenylethyl, fluorophenylethenyl, cyano, methoxycarbonyl, aminocarbonyl, acetyl, hydroxy, carboxy, methoxy, methylamino, dimethylamino, 2-methylbutylamino, ethylamino, dimethylaminoethylamino, hydroxypropylamino, hydroxythylamino, propargylamino, (1-ethyl-2-hydroxy)ethylamino, aminomethyl, cyclopropylamino, amino, hydroxy, methylcarbonyl, ethoxycarbonylamino, methoxyphenylmethylamino, phenylmethylamino, fluorophenylmethylamino, fluorophenylethylamino, methylaminocarbonyl, hydrazinyl, 1-methylhydrazinyl, and —NR$^{62}$R$^{63}$; and
$R^{62}$ is selected from methylcarbonyl and amino; and
$R^{63}$ is selected from methyl and benzyl.

27. A compound, salt, or tautomer according to claim 26, wherein $R^1$ is lower alkyl.

28. A compound, salt, or tautomer according to claim 26, wherein $R^1$ is selected from the group consisting of methyl and ethyl.

29. A compound, salt, or tautomer according to claim 25, wherein $R^1$ is lower alkyl.
30. A compound, salt, or tautomer according to claim 25, wherein $R^1$ is selected from the group consisting of methyl and ethyl.
31. A compound, salt, or tautomer according to claim 1, wherein the compound corresponds in structure to a formula selected from the group consisting of:
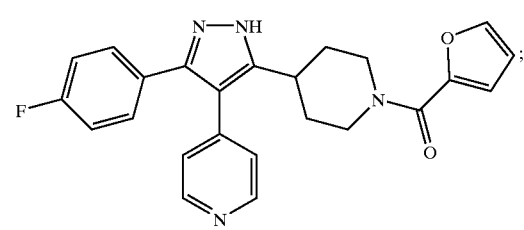
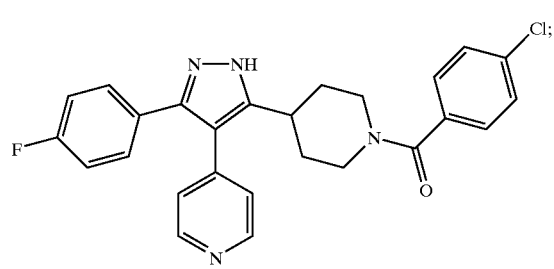
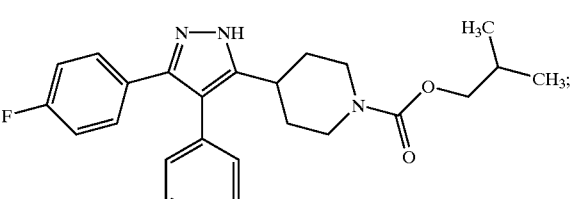
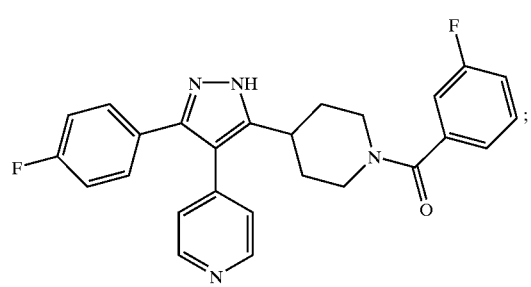
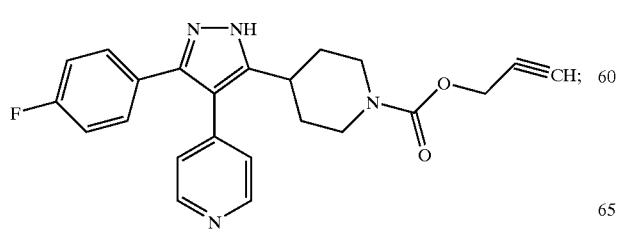
-continued
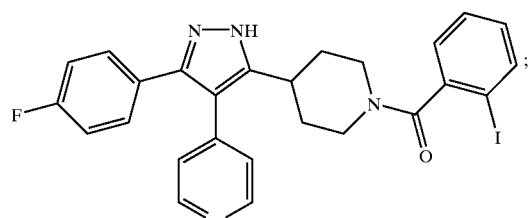
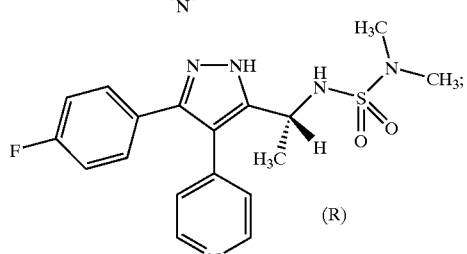
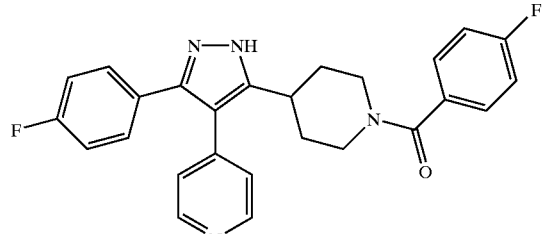
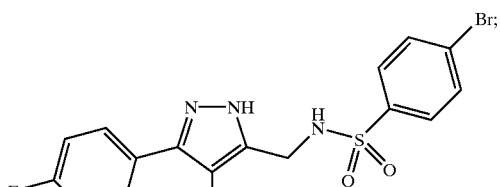
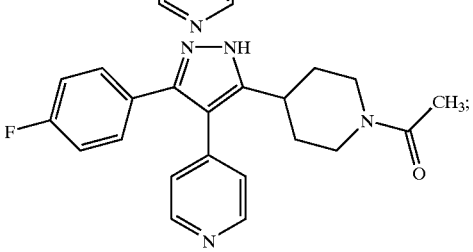

1137
-continued
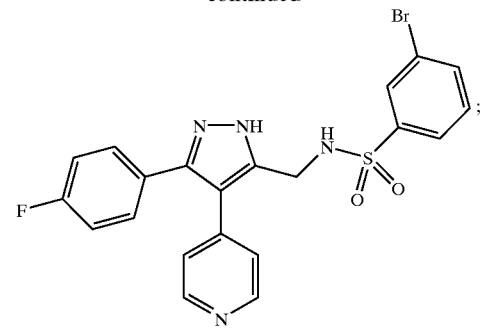
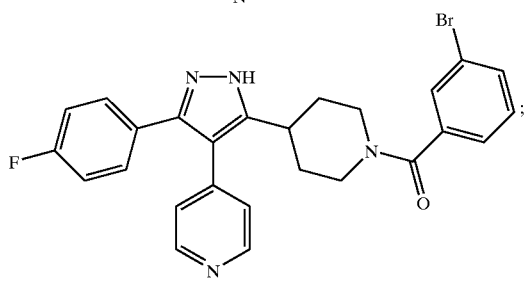
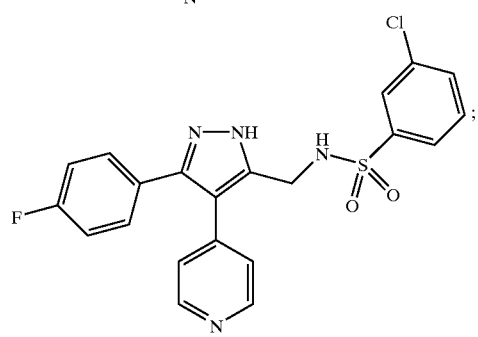
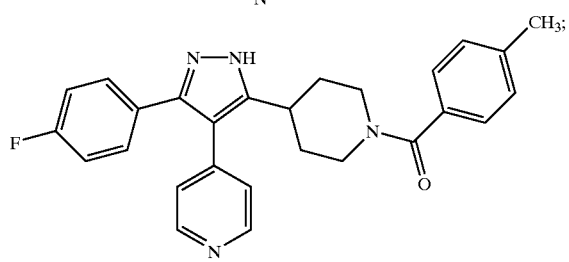
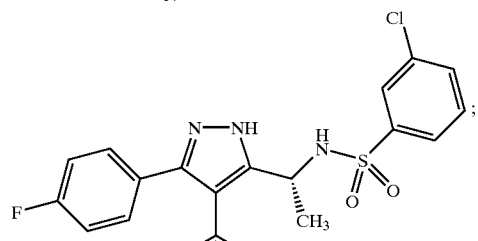
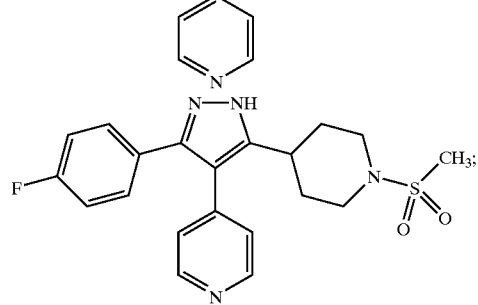
1138
-continued
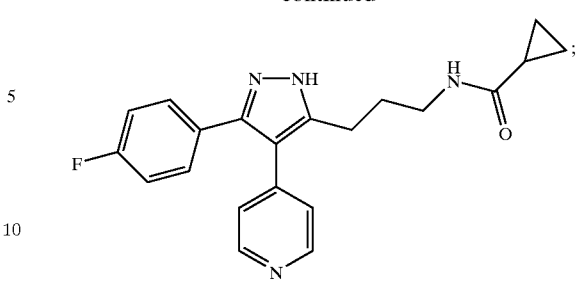
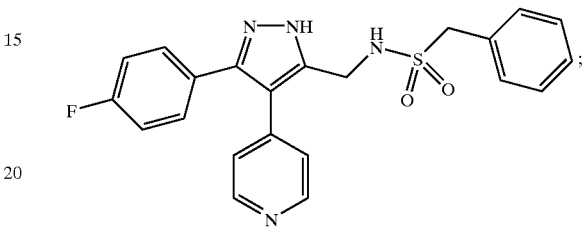
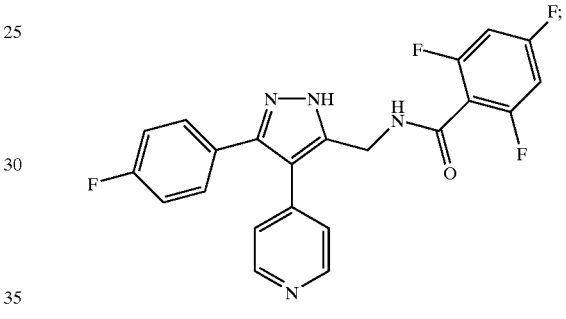
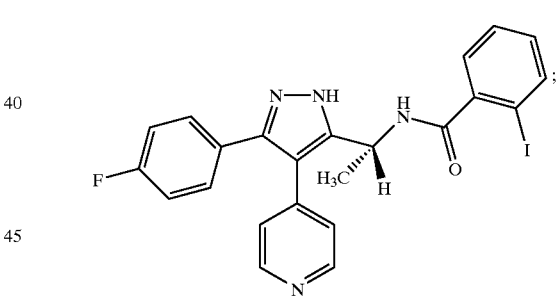
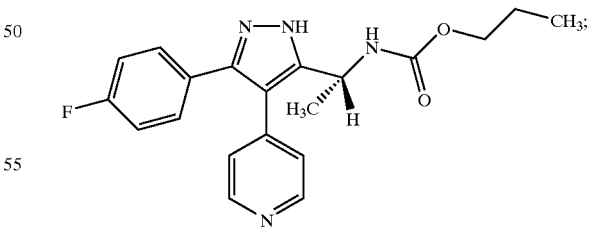
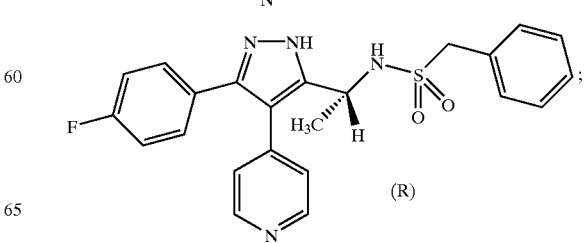

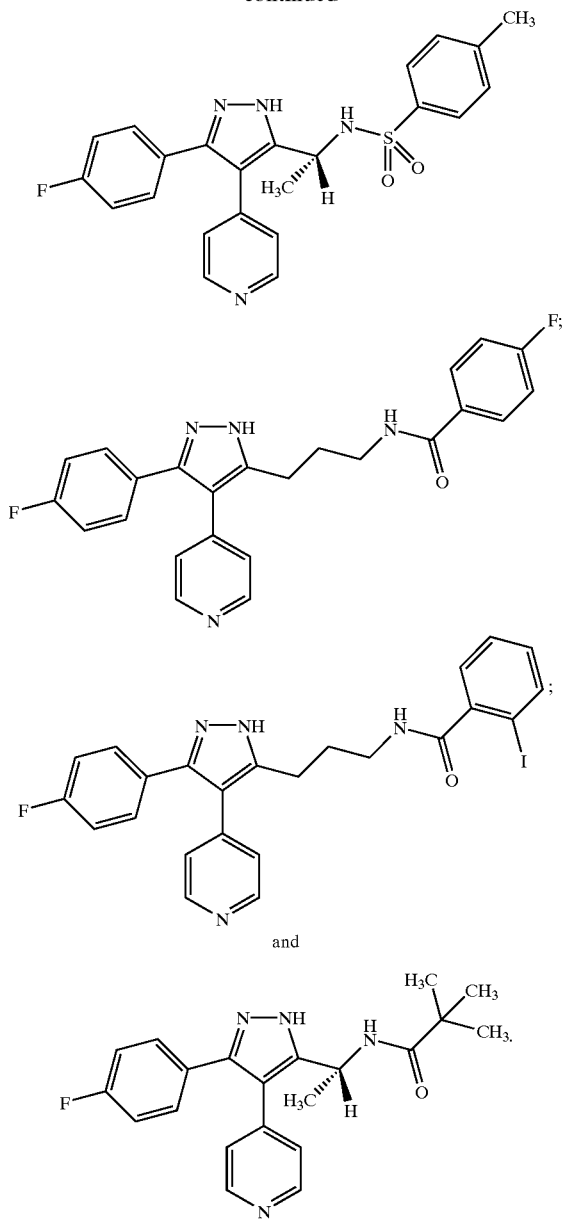

and

32. A compound, salt, or tautomer according to claim 1, wherein the compound is 4-[5-(4-fluorophenyl)-1-(2-propynyl)-1H-pyrazol-4-yl]pyridine.

33. A compound, salt, or tautomer according to claim 1, wherein the compound is 4-[3-(4-fluorophenyl)-1-(2-propynyl)-1H-pyrazol-4-yl]pyridine.

34. A compound, salt, or tautomer according to claim 1, wherein the compound is 3-(4-fluorophenyl)-4-(4-pyridinyl)-1H-pyrazole-1-ethanol.

35. A compound, salt, or tautomer according to claim 1, wherein the compound is 4-[3-(4-fluorophenyl)-1-methyl-1H-pyrazol-4-yl]-2-(1-methylhydrazino)pyridine.

36. A compound, salt, or tautomer according to claim 1, wherein the compound is 1-[5-(4-chlorophenyl)-4-(4-pyridinyl)-1H-pyrazol-3-yl]piperazine.

37. A compound, salt, or tautomer according to claim 1, wherein the compound is 4-[3-cyclopropyl-5-(4-fluorophenyl)-1H-pyrazol-4-yl]pyridine.

38. A compound, salt, or tautomer according to claim 1, wherein the compound is 4-[3-(4-fluorophenyl)-1H-pyrazol4-yl]pyridine.

39. A compound, salt, or tautomer according to claim 1, wherein the compound is 1-[5-(4-chlorophenyl)-4-(4-pyridinyl)-1H-pyrazol-3-yl]4-methylpiperazine.

40. A compound, salt, or tautomer according to claim 1, wherein the compound is 2-fluoro4-[3-(4-fluorophenyl)-1H-pyrazol-4-yl]pyridine.

41. A compound, salt, or tautomer according to claim 1, wherein the compound is 4-[3-(3,4-diflurophenyl)-1-methyl-1H-pyrazol-4-yl]pyridine.

42. A compound, salt, or tautomer according to claim 1, wherein the compound is 4-[3-(4-bromophenyl)-1H-pyrazol-4yl]pyridine.

43. A compound, salt, or tautomer according to claim 1, wherein the compound is 4-[3-(4-chlorophenyl)1H-pyrazol-4-yl]-2-fluoropyridine.

44. A compound, salt, or tautomer according to claim 1, wherein the compound is 4-[3-(1,3-benzodioxol 5-y)-1-methyl-1H-pyrazol-4-yl]pyridine.

45. A compound, salt, or tautomer according to claim 1, wherein the compound is 4-[3-(3-fluorophenyl)1-methyl-1H-pyrazol-4-yl]pyridine.

46. A compound, salt, or tautomer according to claim 1, wherein the compound is 4-[3-(3-fluorophenyl)-1-methyl-pyrazol-4-yl]pyridine.

47. A compound, salt, or tautomer according to claim 1, wherein the compound is 5-(4-fluorophenyl)-N-2-propynyl-4-(4-pyridinyl)-1H-pyrazol-3-amine.

48. A compound or a pharmaceutically-acceptable salt or tautomer thereof, wherein:

the compound corresponds in structure to Formula XIA:

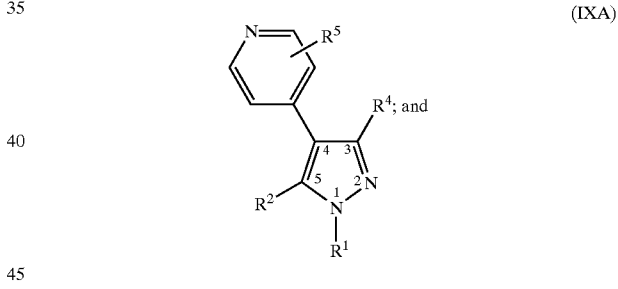

(IXA)

$R^1$ is selected from the group consisting of lower alkyl, lower hydroxyalkyl, lower alkynyl, lower aminoalkyl, and lower alkylaminoalkyl; and $R^2$ is selected from the group consisting of piperidinyl and piperazinyl, wherein:
the piperidinyl or piperazinyl may be optionally substituted with one or more radicals independently selected from the group consisting of halo, lower alkyl, keto, aralkyl, carboxy, lower alkylaminoalkylamino, lower alkynylamino, lower heterocyclylalkylamino, lower alkylcarbonyl and lower alkoxycarbonyl; and $R^4$ is phenyl, wherein:
the phenyl may be optionally substituted with one or more radicals independently selected from the group consisting of halo, lower alkyl, lower alkoxy, aryloxy, lower aralkoxy, lower haloalkyl, lower alkylthio, lower alkylamino, nitro, and hydroxy; and $R^5$ is selected from the group consisting of halo, amino, cyano, aminocarbonyl, lower alkyl, lower alkoxy, hydroxy, lower aminoalkyl, lower aralkyl, lower aralkyloxy, lower aralkylamino, lower alkoxycarbonyl, lower alkylamino, lower alkylcarbonyl, lower aralkenyl, carboxy, lower cycloalkylamino, lower alkoxycarbonylamino, lower alkoxyaralkylamino, lower alkylaminoalkylamino, lower alkylaminocarbonyl, lower alkoxyaralkylamino, hydrazinyl lower alkylhydrazinyl, and —NR$^{62}$R$^{63}$; and R$^{62}$ is selected from the group consisting of lower alkylcarbonyl and amino; and R$^{63}$ is selected from the group consisting of lower alkyl and lower phenylalkyl.

49. A compound, salt, or tautomer according to claim 48, wherein R$^1$ is lower alkyl.

50. A compound, salt, or tautomer according to claim 48, wherein R$^1$ is selected from the group consisting of methyl and ethyl.

51. A compound, salt, or tautomer according to claim 48, wherein:

R$^1$ is selected from the group consisting of methyl, ethyl, hydroxyethyl, and propargyl; and R$^2$ is selected from the group consisting of piperidinyl and piperazinyl, wherein:
  the piperidinyl or piperazinyl may be optionally substituted with one or more radicals independently selected from the group consisting of fluoro, chloro, bromo, keto, methyl, ethyl, trifluoromethyl, benzyl, methoxy, methoxycarbonyl, ethoxycarbonyl, and (1,1-dimethyl)ethoxycarbonyl; and R$^4$ is phenyl, wherein:
  the phenyl may be optionally substituted with one or more radicals independently selected from the group consisting of methylthio, fluoro, chloro, bromo, methyl, ethyl, methoxy, ethoxy, phenoxy, benzyloxy, trifluoromethyl, nitro, dimethylamino, and hydroxy; and R$^5$ is selected from the group consisting of fluoro, chloro, bromo, methyl, fluorophenylethyl, fluorophenylethenyl, cyano, methoxycarbonyl, aminocarbonyl, acetyl, hydroxy, carboxy, methoxy, methylamino, dimethylamino, 2-methylbutylamino, ethylamino, dimethylaminoethylamino, hydroxypropylamino, hydroxyethylamino, (1-ethyl-2-hydroxy)ethylamino, aminomethyl, cyclopropylamino, amino, hydroxy, methylcarbonyl, ethoxycarbonylamino, metboxyphenylmethylamino, phenylmethylamino, fluorophenylmethylamino, fluorophenylethylamino, methylaminocarbonyl, hydrazinyl, 1-methylhydrazinyl, and —NR$^{62}$R$^{63}$; and R$^{62}$ is selected from the group consisting of methylcarbonyl and amino; and R$^{63}$ is selected from the group consisting of methyl an benzyl.

52. A compound, salt, or tautomer according to claim 51, wherein R$^1$ is lower alkyl.

53. A compound, salt, or tautomer according to claim 51, wherein R$^1$ is selected from the group consisting of methyl and ethyl.

54. A compound or a pharmaceutically-acceptable salt or tautomer thereof, wherein:

the compound corresponds in structure to Formula IA-1:

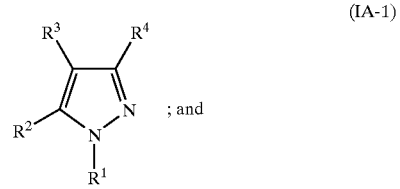

(IA-1)

; and as to R$^1$:

R$^1$ is selected from the group consisting of hydrido, hydroxy, alkyl, cycloalkyl, alkenyl, cycloalkenyl, alkynyl, cycloalkylalkylene, cycloalkenylalkylene, haloalkyl, haloalkenyl, haloalkynyl, hydroxyalkyl, hydroxyalkenyl, hydroxyalkynyl, aralkyl, aralkenyl, aralkynyl, carboxy, carboxyalkyl, alkoxyalkyl, alkenoxyalkyl, alkynoxyalkyl, aryloxyalkyl, alkoxyaryl, alkoxyalkoxy, mercaptoalkyl, alkylthioalkylene, alkenylthioalkylene, alkylthioalkenylene, amino, aminoalkyl, alkylamino, alkenylamino, alkynylamino, arylamino, alkylsulfinyl, alkenylsulfinyl, alkynylsulfinyl, arylsulfinyl, alkylsufonyl, alkenylsulfonyl, alkynylsulfonyl, arylsulfonyl, alkylaminoalkylene, alkylsulfonylalkylene, acyl, acyloxycarbonyl, alkoxycarbonylalkylene, aryloxycarbonylalkylene, alkoxycarbonylarylene, aryloxycarbonylarylene, alkylcarbonylalkylene, arylcarbonylalkylene, alkylcarbonylarylene, arylcarbonylarylene, alkylcarbonyloxyalkylene, arylcarbonyloxyalkylene, alkylcarbonyloxyarylene, and arylcarbonyloxyarylene, or R$^1$ has the formula:

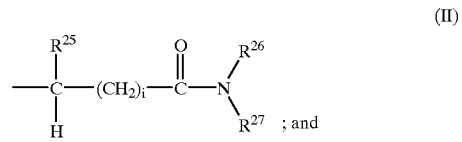

(II)

; and i is an integer from 0 to 9; and

R$^{25}$ is selected from the group consisting of hydrogen, alkyl, aralkyl, alkoxyalkylene, aryloxyalkylene, aminoalkyl, alkylaminoalkyl, arylaminoalkyl, alkylcarbonylalkylene, and arylcarbonylalkylene; and R$^{26}$ is selected from the group consisting of hydrogen, alkyl, alkenyl, alkynyl, cycloalkylalkylene, aralkyl, alkoxycarbonylalkylene, and alkylaminoalkyl; and as to R$^{27}$:

R$^{27}$ is selected from the group consisting of alkyl, cycloalkyl, alkynyl, aryl, aralkyl, cycloalkylalkylene, cycloalkenylalkylene, cycloalkylarylene, cycloalkylcycloalkyl, alkylarylene, alkylaralkyl, aralkylarylene, alkoxyalkylene, alkoxyarylene, alkoxyaralkyl, alkoxyalkoxyarylene, aryloxyarylene, araloxyarylene, aryloxyalkoxyarylene, alkoxycarbonylalkylene, aminoalkyl, alkylaminoalkylene, arylaminocarbonylalkylene, alkoxyarylaminocarbonylalkylene, aminocarbonylalkylene, arylaminocarbonylalkylene, alkylaminocarbonylalkylene, arylcarbonylalkylene, alkoxycarbonylarylene, aryloxycarbonylarylene, alkylaryloxycarbonylarylene, arylcarbonylarylene, alikylarylcarbonylarylene, alkoxycarbonylalkoxylarylene, alkylthioalkylene, cycloalkyltbioalkylene, alkylthioarylene, aralkylthioaylene, arylthioalklylarylene, arylsulfonylaminoalkylene, alkylsulfonylarylene, and alkylaminosulfonylarylene, wherein:
the alkyl, cycloalkyl, aralkyl, alkoxyarylene, aryloxyaryiene, arylaminocarbonylalkylene, aryloxycarbonylarylene, arylcarbonylarylene, alkylthioarylene, arylthioalklylarylene, or alkylsulfonylarylene may be optionally substituted with one or more radicals independently selected from the group consisting of alkyl, halo, haloalkyl, alkoxy, keto, amino, nitro, and cyano, or $R^{27}$ is —$CHR^{28}R^{29}$; and $R^{28}$ is alkoxycarbonyl; and $R^{29}$ is selected from the group consisting of aralkyl, aralkoxyalkylene, alkoxycarbonylalkylene, alkylthioalkylene, and aralkylthioalkylene, wherein:
the aralkyl may be optionally substituted with one or more radicals independently selected from the group consisting of alkyl and nitro; and as to $R^2$:

$R^2$ is selected from the group consisting of piperdinyl and piperazinyl, wherein:
the piperidinyl or piperazinyl is substituted with one or more radicals independently selected from the group consisting of epoxyalkyl, amino(hydroxyalkyl) carboxy, aryloxy, aralkoxy, alkynylamino, alkylaminoalkylamino, heterocyclylalkylamino, arylsulfonyl, and aralkylsulfonyl, or $R^2$ is -piperidinyl-$R^{201}$ or -piperazianyl-$R^{201}$; and $R^{201}$ represents one or more radicals selected from the group consisting of hydrido, halogen, hydroxy, carboxy, keto, alkyl, hydroxyalkyl, haloalkyl, cycloalkyl, alkenyl, alkynyl, aryl, heterocyclyl, aralkyl, heterocyclylalkylene, alkylcarbonyl, hydroxyalkylcarbonyl, cycloalkylcarbonyl, arylcarbonyl, haloarylcarbonyl, alkoxy, alkoxyalkylene, alkoxyarylene, alkoxycarbonyl, carboxyalkylcarbonyl, alkoxyalkylcarbonyl, heterocyclylalkylcarbonyl, alkylsulfonyl, alkylsulfonylalkylene, amino, aminoalkyl, alkylamino, aralkylamino, alkylaminoalkylene, aminocarbonyl, alkylcarbonylamino, alkylcarbonylaminoalkylene, alkylaminoalkylcarbonyl, alkylaminoalkylcarbonylamino, aminoalkylcarbonylaminoalkyl, alkoxycarbonylamino, alkoxyalkylcarbonylamino, alkoxycarbonylaminoalkylene, alkylimidocarbonyl, amidino, alkylamidino, aralkylamidino, guanidino, guanidinoalkylen, and alkylsulfonylamino; and $R^3$ is pyridinyl, wherein:
the pyridinyl may be optionally substituted with one or more radicals independently selected from the group consisting of halo, keto, alkyl, aralkyl, aralkenyl, carboxy, carboxyalkyl, alkoxy, aryloxy, alkylthio, arylthio, arylsulfinyl, arylsulfonyl, aralkoxy, amino, alkylamino, alkenylamino, alkynylamino, cycloalkylamino, cycloalkenylamino, arylamino, haloarylamino, aminocarbonyl, cyano, hydroxy, hydroxyalkyl, alkoxyalkylene, alkenoxyalkylene, aryloxyalkyl, alkoxyalkylamino, alkylaminoalkoxy, alkoxycarbonyl, aryloxycarbonyl, alkoxycarbonylamino, alkoxyarylamino, alkoxyaralkylamino, alkylsulfonylamino, alkylaminoalkylamino, hydroxyalkylamino, aralkylamino, aryl(hydroxyalkyl)amino, alkylaminoalkylaminoalkylamino, nitro, alkylaminocarbonyl, alkylcarbonylamino, haloalkylsulfonyl, aminoalkyl, haloalkyl, alkylcarbonyl, hydrazinyl, alkylhydrazinyl, arylhydrazinyl, and —$NR^{44}R^{45}$; and $R^{44}$ is selected from the group consisting of alkylcarbonyl and amino; and $R^{45}$ is selected from the group consisting of alkyl and aralkyl; and $R^4$ is phenyl, wherein:
the phenyl may be optionally substituted with one or more radicals independently selected from the group consisting of halo, alkyl, alkenyl, alkynyl, aryl, alkylthio, arylthio, alkylthioalkylene, arylthioalkylene, alkylsulfinylalkylene, arylsulfinylalkylene, alkylsulfonylalkylene, arylsulfonylalkylene, alkoxy, aryloxy, aralkoxy, aminocarbonyl, alkylaminocarbonyl, arylaminocarbonyl, alkoxycarbonyl, aryloxycarbonyl, haloalkyl, amino, cyano, nitro, alkylamino, arylamino, alkylaminoalkylene, arylaminolakylene, aminoalkylamino, and hydroxy.

55. A compound, salt, or tautomer according to claim 54, wherein:
as to $R^2$:
$R^2$ is piperidinyl that is substituted with one or more radicals independently selected from the group consisting of epoxyalkyl, amino(hydroxyalkyl) carboxy, aryloxy, aralkoxy, alkynylamino, alkylaminoalkylamino, heterocyclylalkylamino, arylsulfonyl, and aralkylsulfonyl, or $R^2$ is -piperidinyl-$R^{201}$ or -piperazinyl-$R^{201}$; and $R^{201}$ represents one or more radicals selected from the group consisting of hydrido, halogen, hydroxy, carboxy, keto, alkyl, hydroxyalkyl, haloalkyl, cycloalkyl, alkenyl, alkynyl, aryl, heterocyclyl, aralkyl, heterocyclylalkylene, alkylcarbonyl, hydroxyalkylcarbonyl, cycloalkylcarbonyl, arylcarbonyl, haloarylcarbonyl, alkoxy, alkoxyalkylene, alkoxyarylene, alkoxycarbonyl, carboxyalkylcarbonyl, alkoxyalkylcarbonyl, heterocyclylalkylcarbonyl, alkylsulfonyl, alkylsulfonylalkylene, amino, aminoalkyl, alkylamino, aralkylamino, alkylaminoalkylene, aminocarbonyl, alkylcarbonylamino, alkylcarbonylamnoalkylene, alkylaminoalkylcarbonyl, alkylaminoalkylcarbonylamino, aminoalkylcarbonylaminoalkyl, alkoxycarbonylamino, alkoxyalkylcarbonylamino, alkoxycarbonylaminoalkylene, alkylimidocarbonyl, amidino, alkylamidino, aralkylamidino, guanidino, guanidinoalkylene, and alkylsulfonylamino.

56. A compound, salt, or tautomer according to claim 54, wherein $R^2$ is piperidinyl that is substituted with one or more radicals independently selected from the group consisting of epoxyalkyl, amino(hydroxyalkyl) carboxy, aryloxy, aralkoxy, alkynylamino, alkylaminoalkylamino, heterocyclylalkylamino, arylsulfonyl, and aralkylsulfonyl.

57. A compound, salt, or tautomer according to claim 54, wherein:
$R^2$ is -piperidinyl-$R^{201}$ or -piperazinyl-$R^{201}$; and $R^{201}$ represents one or more radicals selected from the group consisting of hydrido, halogen, hydroxy, carboxy, keto, alkyl, hydroxyalkyl, haloalkyl, cycloalkyl, alkenyl, alkynyl, aryl, heteroclyl, aralkyl, heterocyclylalkylene, alkylcarbonyl, hydroxyalkylcarbonyl, cycloalkylcarbonyl, arylcarbonyl, haloarylcarbonyl, alkoxy, alkoxyalkylene, alkoxyarylene, alkoxycarbonyl, carboxyalkylcarbonyl, alkoxyalkylcarbonyl, heterocyclylalkylcarbonyl, alkylsulfonlyl, alkylsulfonylalkylene, amino, aminoalkyl, alkylamino, aralkylamino, alkylaminoalkylene, aminocarbonyl, alkylcarbonylamino, alkylcarbonylaminoalkylene, alkylaminoalkylcarbonyl, alkylaminoalkylcarbonylamino, aminoalkylcarbonylaminoalkyl, alkoxycarbonylamino, alkoxyalkylcarbonylamino, alkoxycarbonylaminoalkylene, alkylimidocarbonyl, amidino, alkylamidino, aralkylamidino, guanidino, guanidinoalkylene, and alkylsulfonylamino.

58. A compound, salt, or tautomer according to claim 54, wherein:
the compound corresponds in structure to Formula IA-2:

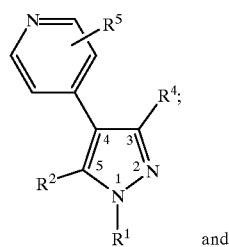

(IA-2)

and $R^1$ is selected from the group consisting of hydrido, lower alkyl, lower hydroxyalkyl, lower alkynyl, lower aralkyl, lower aminoalkyl and lower alkylaminoalkyl; and $R^2$ is -piperidinyl-$R^{201}$ or -piperazinyl-$R^{201}$; and $R^{201}$ represents one or more radicals selected from the group consisting of hydrido, halogen, hydroxy, carboxy, keto, lower alkyl, lower hydroxyalkyl, lower haloalkyl, lower cycloalkyl, lower alkenyl, lower alkynyl, aryl, heterocyclyl, lower aralkyl, lower heterocyclylalkylene, lower alkylcarbonyl, lower hydroxyalkylcarbonyl, lower cycloalkylcarbonyl, arylcarbonyl, haloarylcarbonyl, lower alkoxy, lower alkoxyalkylene, lower alkoxyarylene, lower alkoxycarbonyl, lower carboxyalkylcarbonyl, lower alkoxyalkylcarbonyl, lower heterocyclylalkylcarbonyl, lower alkylsulfonyl, lower alkylsulfonylalkylene, amino, lower aminoalkyl, lower alkylamino, lower aralkylamino, lower alkylaminoalkylene, aminocarbonyl, lower alkylcarbonylamino, lower alkylcarbonylaminoalkylene, lower alkylaminoalkylcarbonyl, lower alkylaminoalkylcarbonylamino, lower aminoalkylcarbonylaminoalkyl, lower alkoxycarbonylamino, lower alkoxyalkylcarbonylamino, lower alkoxycarbonylaminoalkylene, lower alkylimidocarbonyl, amidino, lower alkylamidino, lower aralkylamidino, guanidino, lower guanidinoalkylene, and lower alkylsulfonylamino; and $R^4$ is phenyl, wherein:
the phenyl may be optionally substituted at a substitutable position with one or more radicals independently selected from the group consisting of halo, lower alkyl, lower alkoxy, aryloxy, lower aralkoxy, lower haloalkyl, lower alkylthio, lower alkylamino, nitro, and hydroxy; and $R^5$ is selected from the group consisting of hydrido, halo, amino, cyano, aminocarbonyl, lower alkyl, lower alkoxy, hydroxy, lower aminoalkyl, lower aralkyl, lower aralkyloxy, lower aralkylamino, lower alkoxycarbonyl, lower alkylamino, lower hydroxyalkylamino, lower alkylcarbonyl, lower aralkenyl, carboxy, lower cycloalkylamino, lower hydroxycycloalkylamino, lower alkoxycarbonylamino, lower alkoxyaralkylamino, lower alkylaminoalkylamino, lower alkylaminocarbonyl, lower alkoxyaralkylamino, hydrazinyl, and lower alkylhydrazinyl, and —$NR^{62}R^{63}$; and $R^{62}$ is selected from the group consisting of lower alkylcarbonyl and amino; and $R^{63}$ is selected from the group consisting of lower alkyl and lower phenylalkyl.

59. A compound, salt, or tautomer according to claim 58, wherein at least one $R^{201}$ radical is attached to the distal nitrogen heteroatom or to a carbon ring atom adjacent to the distal nitrogen heteroatom of the piperidine or piperazine ring.

60. A compound, salt, or tautomer according to claim 58, wherein:
$R^1$ is selected from the group consisting of hydrido, methyl, ethyl, hydroxyethyl and propargyl; and $R^2$ is -piperidinyl-$R^{201}$ or -piperazinyl-$R^{201}$; and $R^{201}$ represents one or more radicals selected from the group consisting of hydrido, chloro, fluoro, bromo, iodo, hydroxy, carboxy, keto, methyl, ethyl, propyl, butyl, hydroxymethyl, hydroxyethyl, hydroxypropyl, hydroxybutyl, (1-hydroxy-1,1-dimethyl)ethyl, chloromethyl, chloroethyl, chloropropyl, chlorobutyl, fluoromethyl, fluoroethyl, fluoropropyl, fluorobutyl, cyclopropyl, cyclobutyl, cyclopentyl, cyclohexyl, ethenyl, propenyl, butenyl, ethynyl, propynyl, propargyl, butynyl, phenyl, benzyl, piperidinyl, piperazinyl, piperidinylmethylene, piperazinylmethylene, methoxy, ethoxy, propoxy, butoxy, methoxymethylene, methoxyethylene, methoxypropylene, ethoxyethylene, ethoxypropylene, propoxyethylene, propoxypropylene, methoxyphenylene, ethoxyphenylene, propoxyphenylene, methylcarbonyl, ethylcarbonyl, propylcarbonyl, cyclopropylcarbonyl, cyclobutylcarbonyl, cyclopentylcarbonyl, cyclohexylcarbonyl, benzoyl, chlorobenzoyl, fluorobenzoyl, hydroxymethylcarbonyl, hydroxyethylcarbonyl, hydroxypropylcarbonyl, carboxymeloylcarbonyl, carboxyethylcarbonyl, carboxypropylcarbonyl, methoxymethlcarbonyl, methoxyethylcarbonyl, methoxypropylcarbonyl, ethoxymethylcarbonyl, ethoxyethylcarbonyl, ethoxypropylcarbonyl, propoxymethylcarbonyl, propoxyethylcarbonyl, propoxypropylcarbonyl, methoxyphenylcarbonyl, ethoxyphenylcarbonyl, propoxyphenylcarbonyl, piperidinylmethylcarbonyl, piperazinylmethylcarbonyl, methylsulfonyl, ethylsulfonyl, methylsulfonylmethylene, amino, aminomethyl, aminoethyl, aminopropyl, N-rnethylamino, N,N-dimethylamino, N-ethylamino, N,N-diethylamino, N-propylamino, N,N-dipropylamino, phenylamino, benzylamino, methylaminomethylene, ethylaminomethylene, methylaminoethylene, ethylaminoethylene, aminocarbonyl, methylcarbonylamino, etylcarbonylaminol, methylaminomethylcarbonyl, ethylaminomethylcarbonyl, methylcarbonylaminomethylene, ethylcarbonylaminomethylene, aminomethylcarbonylaminocarbonylmethylene, methoxycarbonylamino, ethoxycarbonylamino, methoxymethylcarbonylamino, methoxyethylcarbonylamino, ethoxymethylcarbonylamino, ethoxyethylcarbonylamino, methoxycarbonylaminomethylene, ethoxycarbonylaminomethylene, methylimidocarbonyl, ethylimidocarbonyl, amidino, methylamidino, methylamidino, benzylamidino, guanidino, guanidinomethylene, guanidinoethylene, and methylsulfonylamino; and $R^4$ is phenyl, wherein:
the phenyl may be optionally substituted with one or more radicals independently selected from the group consisting of methylthio, fluoro, chloro, bromo, iodo, methyl, ethyl, methoxy, ethoxy, phenoxy, benzyloxy, trifluoromethyl, nitro, dimethylamino, and hydroxy; and $R^5$ is selected from the group consisting of hydrido, fluoro, chloro, bromo, iodo, hydroxy, methyl, ethyl, propyl, benzyl, fluorolphenylethyl, fluorophenylethenyl, cyano, carboxy, methoxy, methoxycarbonyl, aminocarbonyl, acetyl, methylamino, dimethylamino, 2-methylbutylamino, ethylamino, dimethylaminoethylamino, hydroxyethylamino, hydroxypropylamino, hydroxybutylamino, hydroxycyclopropylamino, hydroxycyclobutylamino, hydroxycyclopentylamino, hydroxycyclohexylamino, (1-ethyl-2-hydroxy)ethylamino, aminomethyl, cyclopropylamino, amino, hydroxy, ethoxycarbonylamino, methoxyphenylmethylamino, phenylmethylamino, fluorophenylmethylamino, fluorophenylethylamino, methylaminoethylamino, dimetbylaminoethylamino, methylaminopropylamino, dimethylaminopropylamino, methylaminobutylamino, dimethylaminobutylamino, methylaminopentylamino, dimethylaminopentylamino, ethylaminoethylamino, diethylaminoethylamino, ethylaminopropylamino, diethylaminopropylamino, ethylaminobutylamino, diethylaminobutylamino, ethylaminopentylamino, methylaminocarbonyl, methylcarbonyl, ethylcarbonyl, hydrazinyl, 1-methylhydrazinyl, and —$NR^{62}R^{63}$; and $R^{62}$ is selected from the group consisting of methylcarbonyl and amino; and $R^{63}$ is selected from the group consisting of methyl and benzyl.

61. A compound, salt, or tautomer according to claim 58, wherein:

$R^1$ is selected from the group consisting of hydrido, methyl, ethyl, hydroxyethyl, and propargyl; and $R^2$ is -piperidinyl-$R^{201}$; and $R^{201}$ represents one or more radicals selected from the group consisting of hydrido, chloro, fluoro, bromo, iodo, hydroxy, carboxy, keto, methyl, ethyl, propyl, butyl, hydroxymethyl, hydroxyethyl, hydroxypropyl, hydroxybutyl, (1-hydroxy-1,1-dimethyl)ethyl, chloromethyl, chloroethyl, chloropropyl, chlorobutyl, fluoromethyl, fluoroethyl, fluoropropyl, fluorobutyl, cyclopropyl, cyclobutyl, cyclopentyl, cyclohexyl, ethenyl, propenyl, butenyl, ethynyl, propynyl, propargyl, butynyl, phenyl, benzyl, piperidinyl, piperazinyl, piperidinylmethylene, piperazinylmethylene, methoxy, ethoxy, propoxy, butoxy, methoxymethylene, methoxyethylene, methoxypropylene, ethoxyethylene, ethoxypropylene, propoxyethylene, propoxtropylene, methoxyphenylene, ethoxyphenylene, propoxyphenylene, methylcarbonyl, ethylcarbonyl, propylcarbonyl, cyclopropylcarbonyl, cyclobutylcarbonyl, cyclopentylcarbonyl, cyclohexylcarbonyl, benzoyl, chlorobenzoyl, fluorobenzoyl, hydroxymethylcarbonyl, hydroxyethylcarbonyl, hydroxypropylcarbonyl, carboxymetylcarbonyl, carboxyethylcarbonyl, carboxypropylcarbonyl, methoxymethylcarbonyl, methoxyethylcarbonyl, methoxypropylcarbonyl, ethoxymethylcarbonyl, ethoxyethylcarbonyl, ethoxypropylcarbonyl, propoxymethylcarbonyl, propoxyethylcarbonyl, propoxypropylcarbonyl, methoxyphenylcarbonyl, ethoxyphenylcarbonyl, propoxyphenylcarbonyl, piperidinylmethylcarbonyl, piperazinylmethylcarbonyl, methylsulfonyl, ethylsulfonyl, methylsulfonylmethylene, amino, aminomethyl, aminoethyl, aminopropyl, N-methylamino, N,N-dimethylamino, N-ethylamino, N,N-diethylamino, N-propylamino, N,N-dipropylamino phenylamino, benzylamino, methylaminomethylene, ethylaminomethylene, metbylaminoethylene, ethylaminoethylene, aminocarbonyl, methylcarbonylamino, ethylcarbonylamino, methylaminomethylcarbonyl, ethylaminomethylcarbonyl, methylcarbonylaminomethylene, ethylcarbonylaminomethylene, aminometbylcarbonylaminocarbonylmethylene, methoxycarbonylamino, ethoxycarbonylamino, methoxymethylcarbonylamino, methoxyethylcarbonylamino, ethoxymethylcarbonylamino, ethoxyethylcarbonylamino, methoxycarbonylaminomethylene, ethoxycarbonylaminomethylene, methylimidocarbonyl, ethylimidocarbonyl, amidino, methylamidino, methylamidino, benzylamidino, guanidino, guanidinomethylene, guanidinoethylene, and methylsulfonylamino; and $R^4$ is phenyl, wherein:
the phenyl may be optionally substituted with one or more radicals independently selected from the group consisting of fluoro, chloro, methyl, ethyl, methoxy and ethoxy; and $R^5$ is selected fromn the group consisting of hydrido, fluoro, chloro, bromo, hydroxy, methyl, ethyl, propyl, benzyl, cyano, carboxy, methoxy, methoxycarbonyl, aminocarbonyl, acetyl, methylamino, dimethylamino, 2-methylbutylamino, ethylamino, dimethylaminoethylamino, hydroxyethylamino, hydroxypropylamino, hydroxybutylamino, hydroxycyclopropylamino, hydroxycyclobutylamino, hydroxycyclopentylamino, hydroxycyclohexylamino, (1-ethyl-2-hydroxy)ethylamino, aminomethyl, cyclopropylamino, amino, hydroxy, ethoxycarbonylamino, methoxyphenylmethylamino, phenylmethylamino, fluorophenylmethylamino, fluorophenylethylamino, methylaminoethylamino, dimethylaminoethylamino, methylaminopropylamino, dimethylaminopropylamino, methylaminobutylamino, dimethylaminobutylamino, methylaminopentylamino, dimethylaminopentylamino, ethylaminoethylamino, diethylaminoethylamino, ethylaminopropylamino, diethylaminopropylamino, ethylaminobutylamino, diethylaminobutylamino, ethylaminopentylamrino, methylaminocarbonyl, methylcarbonyl, and ethylcarbonyl.

62. A compound, salt, or tautomer according to claim 58, wherein:

$R^1$ is selected from the group consisting of hydrido, methyl, ethyl, hydroxyethyl, and propargyl; and $R^2$ is -piperidinyl-$R^{201}$; and $R^{201}$ represents one or more radicals selected from the group consisting of hydrido, chloro, fluoro, hydroxy, carboxy, keto, methyl, ethyl, propyl, hydroxymethyl, hydroxyethyl, hydroxypropyl, (1-hydroxy-1,1-dimethyl)ethyl, chloromethyl, chloroethyl, chloropropyl, fluoromethyl, fluororoethyl, fluoropropyl, phenyl, benzyl, piperidinyl, piperazinyl, piperidinylmethylene, piperazinylmethylene, methoxy, ethoxy, propoxy, methoxymethyl, methoxyetbyl, methoxypropyl, ethoxyethyl, ethoxypropyl, propoxyethyl, propoxypropyl, methoxyphenyl, ethoxyphenyl, propoxyphenyl, methylcarbonyl, ethylcarbonyl, propylcarbonyl, hydroxymethylcarbonyl, hydroxyethylcarbonyl, carboxymethylcarbonyl, carboxyethylcarbonyl, methoxymethylcarbonyl, methoxyethylcarbonyl, methoxypropylcarbonyl, ethoxymethylcarbonyl, ethoxyethIlcarbonyl, ethoxypropylcarbonyl, propoxymethylcarbonyl, propoxyethylcarbonyl, propoxypropylcarbonyl, methoxyphenylcarbonyl, ethoxyphenylcarbonyl, propoxyphenylcarbonyl, methylsulfonyl, ethylsulfonyl, metbylsulfonylmethylene, amino, aminomethyl, aminoethyl, aminopropyl, N-methylamino, N,N-dimethylamino, N-ethylamino, N,N-diethylamino, N-propylamino, N,N-dipropylamino, N-benzylamino, methylaminomethylene, aminocarbonyl, methoxycarbonylamino, ethoxycarbonylamino, and methylsulfonylamino; and $R^4$ is phenyl, wherein:
the phenyl may be optionally substituted with one or more radicals independently selected from the group consisting of fluoro, chloro, methyl, ethyl, methoxy and ethoxy; and $R^5$ is selected from the group consisting of hydrido, fluoro, chloro, bromo, hydroxy, methyl, ethyl, cyano, carboxy, methoxy, methoxycarbonyl, aminocarbonyl, acetyl, methylamino, dinethylamino, ethylamino, dimethylaminoethylamino, hydroxyethylamino, hydroxypropylamino, hydroxybutylamino, hydroxycyclopropylamino, hydroxycyclobutylamino, hydroxycyclopentylamino, hydroxycyclohexylamino, (1-ethyl-2-hydroxy)ethylamino, aminomethyl, cyclopropylamino, amino, ethoxycarbonylamino, methoxyphenylmethylamino, phenylmethylamino, fluorophenylmethylamino, fluorophenylethylamino, methylaminoethylamino, dimethylaminoethylamino, methylaminopropylamino, dimethylaminopropylamino, methylaminobutylamino, dimethylaminobutylamino, methylaminopentylamino, dimethylaminopentylamino, ethylaminoethylamino, diethylaminoethylamino, ethylaminopropylamino, diethylaminopropylamino, ethylaminobutylamino, diethylaminobutylamino, ethylaminopentylamino, methylaminocarbonyl, methylcarbonyl, and ethylcarbonyl.

63. A compound, salt, or tautomer according to claim 58, wherein:

$R^1$ is hydrido; and $R^2$ is -piperidinyl-$R^{201}$; and $R^{201}$ represents one or more radicals selected from the group consisting of hydrido, hydroxy, methyl, ethyl, propyl, hydroxymethyl, hydroxyethyl, hydroxypropyl, methoxymethyl, methoxyethyl, methoxypropyl, ethoxyethyl, ethoxypropyl, propoxyethyl, propoxypropyl, methoxyphenyl, ethoxyphenyl, propoxyphethyl, methylcarbonyl, ethylcarbonyl, propylcarbonyl, hydroxymethylcarbonyl, hydroxyethylcarbonyl, carboxymethylcarbonyl, carboxyethylcarbonyl, metboxymethylcarbonyl, methoxyethylcarbonyl, ethoxymethylcarbonyl, ethoxyethylcarbonyl, methoxyphenylcarbonyl, ethoxyphenylcarbonyl, methylsulfonyl, ethylsulfonyl, amino, aminomethyl, aminoethyl, aminopropyl, N-methylamino, N,N-dimethylamino, N-ethy amino, N,N-diethylamino, N-propylamino, N,N-dipropylamino, N-benzylamino, methylaminomethylene, aminocarbonyl, methoxyearbonylamino, and ethoxycarbonylamino; and $R^4$ is phenyl, wherein:
the phenyl may be optionally substituted with one or more radicals independently selected from the group consisting of fluoro, chloro, methyl, and methoxy; and $R^5$ is selected from the group consisting of hydrido, methylamino, dimethylamino, 2-methylbutylamino, ethylamino, dimethylaminoethylamino, hydroxypropylamino, hydroxyethylamino, hydroxypropylamino, hydroxybutylamino, hydroxycyclopropylamino, hydroxycyclobutylamino, hydroxycyclopentylamino, hydroxycyclohexylamino, (1-ethyl-2-hydroxy)ethylamino, aminomethyl, cyclopropylamino, amino, dimetbylaminoethylamino, dimethylaminopropylamino, dimethylaminobutylamino, dimethylaminopentylamino, diethylaminoethylamino, diethylaminopropylamino, diethylaminobutylamino, and diethylaminopentylamino.

64. A compound, salt, or tautomer according to claim 58, wherein:

$R^1$ is hydrido; and $R^2$ is -piperidinyl-$R^{201}$; and $R^{201}$ represents one or more radicals selected from the group consisting of hydrido, methyl, methoxyethyl, methylcarbonyl, hydroxymethylcarbonyl, methoxymethylcarbonyl, methylsulfonyl, amino, N,N-dimethylamino, and N,N-diethylamino; and $R^4$ is phenyl, wherein:
the phenyl may be optionally substituted with one or more radicals independently selected from the group consising of fluoro, chloro, methyl, and methoxy; and $R^5$ is selected from the group consisting of hydrido, hydroxypropylamino, hydroxycyclohexylamino, and diethylaminonethylamino.

65. A compound, salt, or tautomer according to claim 58, wherein:

$R^1$ is selected from the group consisting of hydrido, methyl, ethyl, ethyl, hydroxyethyl and propargyl; and $R^2$ is -piperazinyl-$R^{201}$; and $R^{201}$ represents one or more radicals selected from the group consisting of hydrido, chloro, fluoro, bromo, iodo, hydroxy; carboxy, keto, methyl, ethyl, propyl, butyl, hydroxymethyl, hydroxyethyl, hydroxypropyl, hydroxybutyl, (1-hydroxy-1,1-dimethyl)ethyl, chloromethyl, chloroethyl, chloropropyl, chlorobutyl, fluoromethyl, fluoroethyl, fluoropropyl, fluorobutyl, cyclopropyl, cyclobutyl, cyclopentyl, cyclohexyl, ethenyl, propenyl, butenyl, ethynyl, propynyl, propargyl, butynyl, phenyl, benzyl, piperidinyl, piperazinyl; piperidinylmethylene, piperazinylmethylene, methoxy, ethoxy, propoxy, butoxy, methoxymethylene, methoxyethylene, methoxypropylene, ethoxyethylene, ethoxypropylene, propoxyethylene, propoxypropylene, methoxyphenylene, ethoxyphenylene, propoxyphenylene, methylcarbonyl, ethylcarbonyl, propylcarbonyl, cyclopropylcarbonyl, cyclobutylcarbonyl, cyclopentylcarbonyl, cyclohexylcarbotyl, benzoyl, chlorobenzoyl, fluorobenzoyl, hydroxymethylcarbonyl, hydroxyethylcarbonyl, hydroxypropylcarbonyl, carboxymethylcarbonyl, carboxyethylcarbonyl, carboxypropylcarbonyl, methoxymethylcarbonyl, methoxyethylcarbonyl, methoxypropylcarbonyl, ethoxymeylcarbonyl, ethoxyethylcarbonyl, etboxypropylcarbonyl, propoxymethylcarbonyl, propoxyethylcarbonyl, propoxypropylcarbonyl, methoxyphenylcarbonyl, ethoxyphenylcarbonyl, propoxyphenylcarbonyl, piperidinylmethylcarbonyl, piperazinylmethylcarbonyl, methylsulfonyl, ethylsulfonyl, methylsulfonylmethylene, amino, aminomethyl, aminoethyl, aminopropyl, N-methylamino, N,N-dimethylamino, N-ethylamino, N,N-diethylamino, N-propylamino, N,N-dipropylamino, phenylamino, benzylamino, methylaminomethylene, ethylaminomethylene, methylaminoethylene, ethylaminoethylene, aminocarbonyl, methylcarbonylamino, ethylcarbonylamino, methylaminomethylcarbonyl, ethylaminomethylcarbonyl, methylcarbonylaminomethylene, ethylcarbonylaminomethylene, aminomethylcarbonylaminocarbonylmethylene, methoxycarbonylamino, ethoxycarbonylamino, methoxymethylcarbonylamino, methoxyethylcarbonylamino, ethoxymethylcarbonylamino, ethoxyethylcarbonylamino, methoxycarbonylaminomethylene, ethoxycarbonylaminomethylene, methylimidocarbonyl, ethylimidocarbonyl, amidino, methylamidino, methylamidino, benzylamidino, guanidino, guanidinomethylene, guanidinoethylene, and methylsulfonylamino; and $R^4$ is phenyl, wherein:
the phenyl may be optionally substituted with one or more radicals independently selected from the group consisting of fluoro, chloro, methyl, ethyl, methoxy, and ethoxy; and $R^5$ is selected from the group consisting of hydrido, fluoro, chloro, bromo, hydroxy, methyl, ethyl, ptopyl, benzyl, cyano, carboxy, methoxy, metboxycarbonyl, aminocarbonyl, acetyl, methylamino, dimethylamino, 2-methylbutylamino, ethylamino, dimethylaminoethylamino, hydroxyethylamino, hydroxypropylamino, hydroxybutylamino, hydroxycyclopropylamino, hydroxycyclobutylamino, hydroxycyclopentylamino, hydroxycyclohexylamino, (1-ethyl-2-hydroxy)ethylamino, aminomethyl, cyclopropylamino, amino, hydroxy, ethoxycarbonylamino, methoxyphenylmethylamino, phenylmethylamino, fluorophenylmethylamino, fluorophenylethylamino, methylaminoethylamino, dimethylaminoethylamino, methylaminopropylamino, dimethylaminopropylamino, methylaminobutylamino, dimethylaminobutylamino, methylaminopentylamino, dimethylaminopentylamino, ethylaminoethylamino, diethylaminoethylamino, ethylaminopropylamino, diethylaminopropylamino, ethylaminobutylamino, diethylaminobutylamino, ethylaminopentylamino, methylaminocarbonyl, methylcarbonyl, and ethylcarbonyl.

66. A compound, salt, or tautomer according to claim 58, wherein:

$R^1$ is selected from the group consisting of hydrido, methyl, ethyl, hydroxyethyl, and propargyl; and $R^2$ is -piperazinyl-$R^{201}$; and $R^{201}$ represents one or more radicals selected from the group consisting of hydrido, chloro, fluoro, bromo, hydroxy, carboxy, keto, methyl, ethyl, propyl, hydroxymethyl, hydroxyethyl, hydroxypropyl, (1-hydroxy-1,1-dimethyl)ethyl, chloromethyl, chloroethyl, chloropropyl, fluoromethyl, fluoroethyl, fluoropropyl, cyclopropyl, cyclobutyl, cyclopentyl, cyclohexyl, ethenyl, propenyl, butenyl, ethynyl, propynyl, propargyl, phenyl, benzyl, piperidinyl, piperazinyl, piperidinylmethylene, piperazinylmethylene, methoxy, ethoxy, propoxy, methoxymethylene, methoxyethylene, ethoxyethylene, methoxyphenylene, ethoxyphenylene, methylcarbonyl, ethylcarbonyl, propylcarbonyl, cyclopropylcarbonyl, cyclobutylcarbonyl, cyclopentylcarbonyl, cyclohexylcarbonyl, benzoyl, chloroblenzoyl, fluorobenzoyl, hydroxymethylcarbonyl, hydroxyethylcarbonyl, hydroxypropylcarbonyl, carboxymethylcarbonyl, carboxyethylcarbonyl, carboxypropylcarbonyl, methoxymethylcarbonyl, methoxyethylcarbonyl, methoxypropylcarbonyl, ethoxymethylcarbonyl, ethoxyethylcarbonyl, ethoxypropylcarbonyl, propoxymethylcarbonyl, propoxyethylcarbonyl, propoxypropylcarbonyl, methoxyphenylcarbonyl, ethoxyphenylcarbonyl, propoxyphenylcarbonyl, piperidinylmethylcarbonyl, piperazinylmethylcarbonyl, methylsulfonyl, ethylsulfonyl, methylsulfonylmethylene, amino, aminomethyl, aminoethyl, aminopropyl, N-methylamino, N,N-dimethylamino, N-ethylamino, N,N-diethylamino, N-propylamino, N,N-dipropylamino, phenylamino, benzylamino, methylaminomethylene, ethylaminomethylene, methylaminoethylene, ethylaminoethylene, aminocarbonyl, methylcarbonylamino, ethylcarbonylamino, methylaminomethylcarbonyl, ethylaminomethylcarbonyl, methylcarbonylaminomethylene, ethylcarbonylaminomethylene, aminomethylcarbonylaminocarbonylmethylene, methoxycarbonylamino, ethoxycarbonylamino, methoxymethylcarbonylamino, methoxyethylcarbonylamino, ethoxymethylcarbonylamino, ethoxyethylcarbonylamino, methoxycarbonylaminomethylene, ethoxycarbonylaminomethylene, and methylsulfonylamino; and $R^4$ is phenyl, wherein:
the phenyl may be optionally substituted with one or more radicals independently selected from the group consisting of fluoro, chloro, metbyl, ethyl, methoxy, and ethoxy; and $R^5$ is selected from the group consisting of hydrido, fluoro, chloro, bromo, hydroxy, methyl, ethyl, cyano, carboxy, methoxy, methoxycarbonyl, aminocarbonyl, acetyl, metbylamino, dimethylamino, ethylamino, dimethylaminoethylamino, hydroxyethylamino, hydroxypropylamino, hydroxybutylamino, hydroxycyclopropylamino, hydroxycyclobutylamino, hydroxycyclopentylamino, hydroxycyclohexylamino, (1-ethyl-2-hydroxy)ethylamino, aminomethyl, cyclopropylamiino, amino, ethoxycarbonylamino, methoxyphenylmethylamino, phenylmethylamino, fluorophenylmethylamino, fluorophenylethylamino, methylaminoethylamino, dimethylaminoethylamino, methylaminopropylamino, dimethylaminopropylamino, methylaminobutylamino, dimethylaminobutylamino, methylaminopentylamino, dimethylaminopentylamino, ethylaminoethylamino, diethylaminoethylamino, ethylaminopropylamino, diethylaminopropylamino, ethylaminobutylamino, diethylaminobutylamino, ethylaminopentylamino, methylaminocarbonyl, methylcarbonyl, and ethylcarbonyl.

67. A compound, salt, or tautomer according to claim 58, wherein:

$R^1$ is hydrido; and $R^2$ is -piperazinyl-$R^{201}$; and $R^{201}$ represents one or more radicals selected from the group consisting of hydrido, methyl, ethyl, propyl, cyclopropyl, cyclobutyl, cyclopentyl, cyclohexyl, ethynyl, propynyl, propargyl, phenyl, benzyl, piperidinyl, and piperazinyl; and $R^4$ is phenyl, wherein:
the phenyl may be optionally substituted with one or more radicals independently selected from the group consisting of fluoro, chloro, methyl, and methoxy; and $R^5$ is selected from the group consisting of hydrido, methylamino, dimethylamino, 2-methylbutylamino, ethylamino, dimethylaminoethylamino, hydroxypropylamino, hydroxyethylamino, hydroxypropylamino, hydroxybutylamino, hydroxycyclopropylamino, hydroxycyclobutylamino, hydroxycyclopentylamino, hydroxycyclohexylamino, (1-ethyl-2-hydroxy)ethylamino, aminomethyl, cyclopropylamino, amino, dimethylaminoethylamino, dimethylaminopropylamino, dimethylaminobutylamino, dimethylaminopentylamino, diethylaminoethylamino, diethylaminopropylamino, diethylaminobutylamino, and diethylaminopentylamino.

68. A compound, salt, or tautomer according to claim 58, wherein:

$R^1$ is hydrido; and $R^2$ is-piperazinyl-$R^{201}$; and $R^{201}$ represents one or more radicals selected from the group consisting of hydrido, methyl, cyclopropyl, propargyl, and benzyl; and $R^4$ is phenyl, wherein:
the phenyl may be optionally substituted with one or more radicals independently selected from the group consisting of fluoro, chloro, methyl, and methoxy; and $R^5$ is selected from the group consisting of hydrido, hydroxypropylamino, hydroxycyclohexylamino, and diethylaminoethylamino.

69. A pharmaceutical composition comprising:
a therapeutically-effective amount of a compound or salt of claim 54, and
a pharmaceutically acceptable carrier.

70. A pharmaceutical composition comprising:
a therapeutically-effective amount of a compound or salt of claim 55, and
a pharmaceutically acceptable carrier.

71. A pharmaceutical composition comprising:
a therapeutically-effective amount of a compound or salt of claim 58, and
a pharmaceutically acceptable carrier.

72. A pharmaceutical composition comprising:
a therapeutically-effective amount of a compound or salt of claim 61, and
a pharmaceutically acceptable carrier.

73. A pharmaceutical composition comprising:
a therapeutically-effective amount of a compound or salt claim 65 and
a pharmaceutically acceptable carrier.

74. A method of treating a tumor necrosis factor mediated disorder, the method comprising treating a subject having or susceptible to inflammation with a therapeutically-effective amount of a compound or salt of claim 54.

75. The method according to claim 74, wherein the tumor necrosis factor mediated disorder comprises a disorder selected from the group of disorders consisting of bone resorption, graft vs. host reaction, atherosclerosis, arthritis, osteoarthritis, rheumatoid arthritis, gout, psoriasis, topical inflammatory disorder state, adult respiratory distress syndrome, asthma, chronic pulmonary inflammatory disorder, cardiac reperfusion injury, renal reperfusion injury, thrombus, glomerulonephritis, Crohn's disorder, ulcerative colitis, inflammatory bowel disorder, and cachexia.

76. The method according to claim 74, wherein the tumor necrosis factor mediated disorder comprises inflammation.

77. The method according to claim 74, wherein the tumor necrosis factor mediated disorder comprises arthritis.

78. The method according to claim 74, wherein the tumor necrosis factor mediated disorder comprises asthma.

79. A method of treating a p38 kinase mediated disorder, the method comprising treating a subject having or susceptible to inflammation with a therapeutically-effective amount of compound or salt of claim 54.

80. The method according to claim 79, wherein the p38 kinase mediated disorder comprises a disorder selected from the group of disorders consisting of bone resorption, graft vs. host reaction, atherosclerosis, arthritis, osteoarthritis, rheumatoid arthritis, gout, psoriasis, topical inflammatory disorder state, adult respiratory distress syndrome, asthma, chronic pulmonary inflammatory disorder, cardiac reperfusion injury, renal reperfusion injury, thrombus, glomerulonephritis, Crohn's disorder, ulcerative colitis, inflamatory bowel disorder, and cachexia.

81. The method according to claim 79, wherein the p38 kinase mediated disorder comprises inflammation.

82. The method according to claim 79, wherein the p38 kinase mediated disorder comprises arthritis.

83. The method according to claim 79, wherein the p38 kinase mediated disorder comprises asthma.

84. A method of treating inflammation, the method comprising treating a subject having or susceptible to inflammation with a therapeutically-effective amount of a compound or salt of claim 54.

85. A method of treating arthritis, the method comprising treating a subject having or susceptible to arthritis with a therapeutically-effective amount of a compound or salt of claim 54.

86. A method of preparing a compound or a pharmaceutically-acceptable salt or tautomer thereof, wherein:

the method comprises cyclizing an acyl hydrazone of Formnula XX:

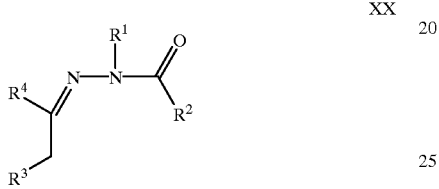

to form the substituted pyrazole of Formula IA-1; and the compound corresponds in structure to Formula IA-1:

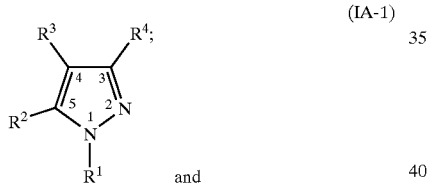

as to $R^1$:

$R^1$ is selected from the group consisting of hydrido, hydroxy, alkyl, cycloalkyl, alkenyl, cycloalkenyl, alkynyl, cycloalkylalkylene, cycloalkenylalkylene, haloalkyl, haloalkenyl, haloalkynyl, hydroxyalkyl, hydroxyalkenyl, hydroxyalkynyl, aralkyl, aralkenyl, aralkynyl, carboxy, carboxyalkyl, alkoxyalkyl, alkenoxyalkyl, alkynoxyalkyl, aryloxyalkyl, alkoxyaryl, alkoxyalkoxy, mercaptoalkyl, alkylthioalkylene, alkenylthioalkylene, alkylthioalkenylene, amino, aminoalkyl, alkylamino, alkenylamino, alkynylamino, arylamino, alkylsulfinyl, alkenylsulfinyl, alkynylsulfinyl, arylsulfinyl, alkylsulfonyl, alkenylsulfonyl, alkynylsulfonyl, arylsulfonyl, alkylaminoalkylene, alkylsulfonylalkylene, acyl, acyloxycarbonyl, alkoxycarbonylalkylene, aryloxycarbonylalkylene, alkoxycarbonylarylene, aryloxycarbonylarylene, alkylcarbonylalkylene, arylcarbonylalkylene, alkylcarbonylarylene, arylcarbonylarylene, alkylcarbonyloxyalkylene, arylcarbonyloxyalkylene, alkylcarbonyloxyarylene, and arylcarbonyloxyarylene, or $R^1$ has the formula:

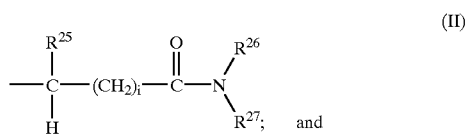

i is an integer from 0 to 9; and $R^{25}$ is selected from the group consisting of hydrogen, alkyl, aralkyl, alkoxyalkylene, aryloxyalkylene, aminoalkyl, alkylaminoalkyl, arylaminoalkyl, alkylcarbonylalkylene, and arylcarbonylalkyene; and $R^{26}$ is selected from the group consisting of hydrogen, alkyl, alkenyl, alkynyl, cycloalkylalkylene, aralkyl, alkoxycarbonylalkylene, and alkylaminoalkyl; and as to $R^{27}$:

$R^{27}$ is selected from the group consisting of alkyl, cycloalkyl, alkynyl, aryl, aralkyl, cycloalkylalkylene, cycloalkenylalkylene, cycloalkylarylene, cycloalkylcycloalkyl, alkylarylene, alkylaralkyl, aralkylarylene, alkoxyalkylene, alkoxyarylene, alkoxyaralkyl, alkoxyalkoxyarylene, aryloxyarylene, aralkoxyarylene, aryloxyalkoxyarylene, alkoxycarbonylalkylene, aminoalkyl, alkylaminoalkylene, arylaminocarbonylalkylene, alkoxyarylaminocarbonylalkylene, aminocarbonylalkylene, arylaminocarbonylalkylene, alkylaminocarbonylalkylene, arylcarbonylalkylene, alkoxycarbonylarylene, aryloxycarbonylarylene, alkylaryloxycarbonylarylene, arylcarbonylarylene, alkylarylcarbonylarylene, alkoxycarbonylalkoxylarylene, alkylthioalkylene, cycloalkylthioalkylene, alkylthioarylene, aralkylthioarylene, arylthioalklylarylene, arylsulfonylaminoalkylene, alkylsulfonylarylene, and alkylaminosulfonylarylene, wherein the alkyl, cycloalkyl, aralkyl, alkoxyarylene, aryloxyarylene, arylaminocarbonylarylene, aryloxycarbonylarylene, arylcarbonylarylene, alkyltbioarylene, arylthioalklylarylene, or alkylsulfonylarylene may be optionally substituted with one or more radicals independently selected from the group consisting of alkyl, halo, haloalkyl, alkoxy, keto, amino, nitro, and cyano, or $R^{27}$ is —$CHR^{28}R^{29}$; and $R^{28}$ is alkoxycarbonyl; and $R^{29}$ is selected from the group consisting of aralkyl, aralkoxyalkylene, alkoxycarbonylalkylene, alkylthioalkylene, and aralkylthioalkylene, wherein:
the aralkyl may be optionally substituted with one or more radicals independently selected from the group consisting of alkyl and nitro; and as to $R^2$:

$R^2$ is selected from the group consisting of piperidinyl and piperazinyl, wherein:
the piperidinyl or piperazinyl is substituted with one or more radicals independently selected from the group consisting of epoxyalkyl, amino(hydroxyalkyl) carboxy, aryloxy, aralkoxy, alkynylamino, alkylaminoalkylamino, heterocyclylalkylamino, arylsulfonyl, and aralkylsulfonyl, or $R^2$ is -piperidinyl-$R^{201}$ or -piperazinyl-$R^{201}$; and $R^{201}$ represents one or more radicals selected from the group consisting of hydrido, halogen, hydroxy, carboxy, keto, alkyl, hydroxyalkyl, haloalkyl, cycloalkyl, alkenyl, alkynyl, aryl, heterocyclyl, aralkyl, heterocyclylalkylene, alkylcarbonyl, hydroxyalkylcarbonyl, cycloalkylcarbonyl, arylcarbonyl, haloarylcarbonyl, alkoxy;, alkoxyalkylene, alkoxyarylene, alkoxycarbonyl, carboxyalkylcarbonyl, alkoxyalkylcarbonyl, heterocyclylalkylcarbonyl, alkylsulfonyl, alkylsulfonylalkylene, amino, aminoalkyl, alkylamino, aralkylamino, alkylaminoalkylene, aminocarbonyl, alkylcarbonylamino, alkylcarbonylaminoalkylene, alkylaminoalkylcarbonyl, alkylamoalkylcarbonylamino, aminoalkylcarbonylaminoalkyl, alkoxycarbonylamino, alkoxyalkylcarbonylamino, alkoxycarbonylaminoalkylene, alkylimidocarbonyl, amidino, alkylamidino, aralkylamidino, guanidino, guanidinoalkylene, and alkylsulfonylamino; and $R^3$ is pyridinyl, wherein:
the pyridinyl may be optionally substituted with one or more radicals independently selected from the group consisting of halo, keto, alkyl, aralkyl, aralkenyl, carboxy, carboxyalkyl, alkoxy, aryloxy, alkylthio, arylthio, arylsulfinyl, arylsulfonyl, aralkoxy, amino, alkylamino, alkenylamino, alkynylamino, cycloalkylamino, cycloalkenylamino, arylamino, haloarylamino, aminocarbonyl, cyano, hydroxy, hydroxyalkyl, alkoxyalkylene, alkenoxyalkylene, aryloxyalkyl, alkoxyalkylamino, alkylaminoalkoxy, alkoxycarbonyl, aryloxycarbonyl, alkoxycarbonylamino, alkoxyatylamino, alkoxyaralkylamino, alkylsulfonylamino, alkylaminoalkylamino, hydroxyalkylamino, aralkylamino, aryl(hydroxyalkyl)amino, alkylaminoalkylaminoalkylamino, nitro, alkylaminocarbonyl, alkylcarbonylamino, haloalkylsulfonyl, aminoalkyl, haloalkyl, alkylcarbonyl, hydrazinyl, alkylhydrazinyl, arylhydrazinyl, and —$NR^{44}R^{45}$; and $R^{44}$ is selected from the group consisting of alkylcarbonyl and amino; and $R^{45}$ is selected from the group consisting of alkyl and alkyl; and $R^4$ is phenyl, wherein:
the phenyl may be optionally substituted with one or more radicals independently selected from the group consisting of halo, alkyl, alkenyl, alkynyl, aryl, alkylthio, arylthio, alkylthioalkylene, arylthioalkylene, alkylsulfinylalkylene, arylsulfinylalkylene, alkylsulfonylalkylene, arylsulfonylalkylene, alkoxy, aryloxy, aralkoxy, aminocarbonyl, alkylaminocarbonyl, arylaminocarbonyl, alkoxycarbonyl, aryloxycarbonyl, haloalkyl, amino, cyano, nitro, alkylamino, arylamino, alkylaminoalkylene, arylaminoalkylene, aminoalkylamino, and hydroxy.

87. The process of claim 86, wherein the acyl hydrazone of Formula XX is formed by reaction of a keton, of Formula

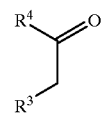

XXI with an acyl hydrazide of Formula XXII:

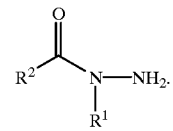

XXII

88. The process of claim 87, wherein the condensation is performed at a temperature of from about 25 to about 200° C.

* * * * *

UNITED STATES PATENT AND TRADEMARK OFFICE
CERTIFICATE OF CORRECTION

PATENT NO.    : 6,423,713 B1
DATED         : July 23, 2002
INVENTOR(S)   : Ashok S. Naraian et al.

It is certified that error appears in the above-identified patent and that said Letters Patent is hereby corrected as shown below:

<u>Title page,</u>
Item [75], Inventors, "Ashok S. Anantanarayan" should read as
-- Ashok S. Naraian --

Signed and Sealed this

First Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,423,713 B1
DATED : July 23, 2002
INVENTOR(S) : Ashok S. Naraian et al.

It is certified that error appears in the above-identified patent and that said Letters Patent is hereby corrected as shown below:

<u>Column 1123,</u>
Line 34, replace "alkenotyalkyl" with -- alkenoxyalkyl --;
Line 63, replace "arylcarbonylalkflene" with -- arylcarbonylalkylene --;

<u>Column 1124,</u>
Line 5, replace "aralkylaylene" with -- aralkylarylene --;
Line 6, replace "alkoxyaitoxyarylene" with -- alkoxyalkoxyarylene --;
Line 7, replace "aryloxyaitoxyarylene" with -- aryloxyalkoxyarylene --;
Line 18, replace "aralkylthioarllene" with -- aralkylthioarylene --;
Line 19, replace with "arylsulfonylaminoaaylene" with -- arylsulfonylaminoalkylene --;

<u>Column 1125,</u>
Line 5, replace "alenyl" with -- alkenyl --;
Line 7, replace "alkylsulfmylalkylene" with -- alkylsulfinylalkylene --; and
Line 10, replace "alkylarninocarbonyl" with -- alkylaminocarbonyl --;
Line 63, replace "phenylarninocarbonylalkylene" with
-- phenylaminocarbonylalkylene --;

<u>Column 1126,</u>
Line 36, replace "land" with -- and --;
Line 44, replace "alkylanino" with -- alkylamino --; and
Line 57, replace "alkenlamino" with -- alkenylamino --.

<u>Column 1127,</u>
Line 26, replace "ethoxyrnethyl" with -- ethoxymethyl --; and
Line 32, replace "hydroxyethy" with -- hydroxyethyl --.

<u>Column 1128,</u>
Line 53, replace "methtxy" with -- methoxy --.

<u>Column 1129,</u>
Line 20, insert a comma between "difluorochloromethyl" and "dichlorofluoromethyl";
Line 23, replace "metioxymethyl" with -- methoxymethyl --;

UNITED STATES PATENT AND TRADEMARK OFFICE
CERTIFICATE OF CORRECTION

PATENT NO.   : 6,423,713 B1
DATED        : July 23, 2002
INVENTOR(S)  : Ashok S. Naraian et al.

It is certified that error appears in the above-identified patent and that said Letters Patent is hereby corrected as shown below:

Column 1130,
Lines 9-10, replace "alkylamin phenylene" with -- alkylaminophenylene --;
Line 24, replace "loser" with -- lower --;
Line 25, replace "amine" with -- amino --;
Line 38, replace "fluorophenylithenyl" with -- fluorophenylethenyl --; and
Line 40, replace "dilthylamino" with -- diethylamino --.

Column 1131,
Line 52, replace "dimethilamino" with -- dimethylamino --.

Column 1134,
Line 53, replace "hydroxythylamino" with -- hydroxyethylamino --.

Column 1140,
Lines 2-3, replace "4-[3-(4-fluorophenyl)-1H-pyrazol4-yl]pyridine" with -- 4-[3-(4-fluorophenyl)-1H-pyrazol-4-yl]pyridine --.
Line 36, replace

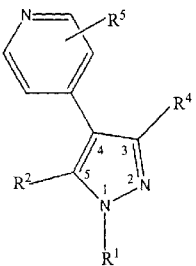

with:

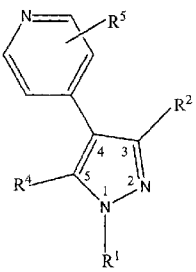

UNITED STATES PATENT AND TRADEMARK OFFICE
CERTIFICATE OF CORRECTION

PATENT NO.    : 6,423,713 B1
DATED         : July 23, 2002
INVENTOR(S)   : Ashok S. Naraian et al.

It is certified that error appears in the above-identified patent and that said Letters Patent is hereby corrected as shown below:

Column 1141,
Line 7, insert a comma between "hydrazinyl" and "lower".
Line 51, replace "metboxyphenylmethylamino" with -- methoxyphenylmethylamino --.

Column 1142,
Line 4, replace

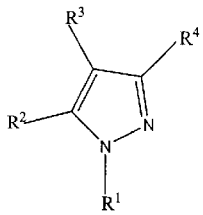

with:

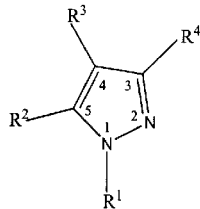

Column 1143,
Line 1, replace "alikylarylcarbonylarylene" with -- alkylarylcarbonylarylene --;
Line 3, replace "cycloalkyltbioalkylene" with -- cycloalkylthioalkylene --;
Line 4, replace "aralkylthioaylene" with -- aralkylthioarylene --;
Line 33, replace "-piperazianyl-$R^{201}$" with -- -piperazinyl-$R^{201}$ --; and
Line 53, replace "guanidinoalkylen" with -- guanidinoalkylene --.

Column 1144,
Line 48, replace "alkylcarbonylamnoalkylene" with -- alkylcarbonylaminoalkylene --.

UNITED STATES PATENT AND TRADEMARK OFFICE
CERTIFICATE OF CORRECTION

PATENT NO. : 6,423,713 B1
DATED : July 23, 2002
INVENTOR(S) : Ashok S. Naraian et al.

It is certified that error appears in the above-identified patent and that said Letters Patent is hereby corrected as shown below:

Column 1145,
Line 1, replace "heteroclyl" with -- heterocyclyl --.

Column 1146,
Line 53, replace "carboxymeloylcarbonyl" with -- carboxymethylcarbonyl --; and Column 1147,
Line 41, replace "dimetbylaminoethylamino" with -- dimethylaminoethylamino --.

Column 1148,
Line 8, replace "propoxtropylene" with -- propoxypropylene --;
Line 23, replace "piperidinylimethylcarbonyl" with -- piperidinylmethylcarbonyl --; and Column 1149,
Line 7, replace "ethylaminopentylamrino" with -- ethylaminopentylamino --.
Line 24, replace "methoxyetbyl" with -- methoxyethyl --;
Line 33, replace "ethoxyethIlcarbonyl" with -- ethoxyethylcarbonyl --; and
Line 53, replace "dinethylamino" with -- dimethylamino --.

Column 1150,
Line 23, replace "N-ethy amino" with -- N-ethylamino --; and
Line 43, replace "dimetbylaminoethylamino" with -- dimethylaminoethylamino --.

Column 1151,
Line 6, replace the semicolon between "hydroxy" and "carboxy" with a comma;
Line 14, replace the semicolon between "piperazinyl" and "piperidinylmethylene" with a comma;
Line 28, replace "ethoxymeylcarbonyl" with -- ethoxymethylcarbonyl --; and
Line 64, replace "ptopyl" with -- propyl --.

UNITED STATES PATENT AND TRADEMARK OFFICE
CERTIFICATE OF CORRECTION

PATENT NO.   : 6,423,713 B1
DATED         : July 23, 2002
INVENTOR(S)  : Ashok S. Naraian et al.

It is certified that error appears in the above-identified patent and that said Letters Patent is hereby corrected as shown below:

Column 1153,
Line 8, replace "metbyl" with -- methyl --;
Line 13, replace "metbylamino" with -- methylamino --; and
Line 19, replace "cyclopropylamiino" with -- cyclopropylamino --.

Column 1156,
Line 42, replace "alkyltbioarylene" with -- alkylthioarylene --.

Column 1158,
Line 37, replace "87" with -- 86 --.

Signed and Sealed this

Fourth Day of November, 2003

JAMES E. ROGAN
*Director of the United States Patent and Trademark Office*